United States Patent
Feng et al.

(10) Patent No.: US 12,162,893 B2
(45) Date of Patent: *Dec. 10, 2024

(54) TRICYCLIC PYRIDONES AND PYRIMIDONES

(71) Applicant: Erasca, Inc., San Diego, CA (US)

(72) Inventors: Jun Feng, San Diego, CA (US); Jean-Michel Vernier, San Diego, CA (US); Marcos Gonzalez-Lopez, San Diego, CA (US); Benjamin Jones, San Diego, CA (US); Nicholas A. Isley, San Diego, CA (US); Ping Chen, San Diego, CA (US)

(73) Assignee: ERASCA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/482,350

(22) Filed: Sep. 22, 2021

(65) Prior Publication Data

US 2022/0119409 A1    Apr. 21, 2022

Related U.S. Application Data

(60) Provisional application No. 63/259,894, filed on Dec. 18, 2020, provisional application No. 63/082,221, filed on Sep. 23, 2020.

(51) Int. Cl.
| | |
|---|---|
| C07D 513/06 | (2006.01) |
| A61K 31/429 | (2006.01) |
| A61K 31/542 | (2006.01) |
| A61K 31/554 | (2006.01) |
| A61P 35/00 | (2006.01) |
| C07D 498/16 | (2006.01) |

(52) U.S. Cl.
CPC .......... *C07D 498/16* (2013.01); *A61P 35/00* (2018.01); *C07D 513/06* (2013.01)

(58) Field of Classification Search
CPC .. C07D 513/06; A61K 31/429; A61K 31/542; A61K 31/554; A61P 35/00
See application file for complete search history.

(56) References Cited

U.S. PATENT DOCUMENTS

| | | |
|---|---|---|
| 10,280,172 B2 | 5/2019 | Li et al. |
| 10,414,757 B2 | 9/2019 | Li et al. |
| 10,633,381 B2 | 4/2020 | Blake et al. |
| 11,008,334 B2 | 5/2021 | Ostrem et al. |
| 2009/0099195 A1 | 4/2009 | Bayrakdarian et al. |
| 2019/0233440 A1 | 8/2019 | Planken et al. |
| 2019/0270743 A1 | 9/2019 | Marx et al. |
| 2019/0284144 A1 | 9/2019 | Li et al. |
| 2020/0331911 A1 | 10/2020 | Marx et al. |
| 2021/0122764 A1 | 4/2021 | Bharathan et al. |
| 2021/0130303 A1 | 5/2021 | Koltun et al. |
| 2021/0130326 A1 | 5/2021 | Aggen et al. |
| 2021/0130369 A1 | 5/2021 | Koltun et al. |
| 2021/0230162 A1 | 7/2021 | Zhao et al. |
| 2021/0355141 A1 | 11/2021 | Hoang et al. |
| 2023/0107642 A1* | 4/2023 | Feng ................ A61P 35/00 514/210.05 |

FOREIGN PATENT DOCUMENTS

| | | |
|---|---|---|
| CN | 110256421 A | 9/2019 |
| CN | 111484477 A | 8/2020 |
| CN | 112047937 A | 12/2020 |
| CN | 112047948 A | 12/2020 |
| CN | 112110918 A | 12/2020 |
| CN | 112159405 A | 1/2021 |
| CN | 112174950 A | 1/2021 |
| CN | 112225734 A | 1/2021 |
| CN | 112300153 A | 2/2021 |
| CN | 112430234 A | 3/2021 |
| CN | 112442029 A | 3/2021 |
| CN | 112552295 A | 3/2021 |
| CN | 112574199 A | 3/2021 |
| CN | 112574224 A | 3/2021 |
| CN | 112694475 A | 4/2021 |
| CN | 112707905 A | 4/2021 |
| CN | 112745335 A | 5/2021 |
| CN | 112778284 A | 5/2021 |

(Continued)

OTHER PUBLICATIONS

International Search Report and Written Opinion in International Application No. PCT/US2021/019804, mailed on May 19, 2021, 12 pages.
International Search Report and Written Opinion received for PCT Application No. PCT/US2021/064356, mailed on Feb. 23, 2022, 17 pages.
International Search Report and Written Opinion received for PCT Application No. PCT/US21/51601, mailed on Nov. 22, 2021, 11 pages.
International Search Report and Written Opinion received for PCT Patent International Application No. PCT/US2020/65966, mailed on Apr. 19, 2021, 18 pages.
"Targeting The Genetic and Immunological Drivers of Cancer", *Mirati Therapeutics, Presentation at investor event*, Sep. 20, 2021, 30 pages.

(Continued)

*Primary Examiner* — Brenda L Coleman

(74) *Attorney, Agent, or Firm* — Mintz, Levin, Cohn, Ferris, Glovsky and Popeo, P.C.

(57) ABSTRACT

A compound of Formula (I) is provided:

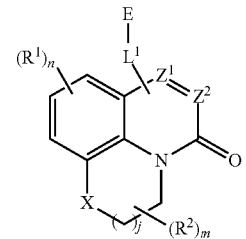

(I)

where the variables are defined herein.

4 Claims, No Drawings

Specification includes a Sequence Listing.

(56) References Cited

FOREIGN PATENT DOCUMENTS

| | | |
|---|---|---|
| CN | 112830928 A | 5/2021 |
| CN | 112851663 A | 5/2021 |
| CN | 112920183 A | 6/2021 |
| CN | 113004269 A | 6/2021 |
| CN | 113045565 A | 6/2021 |
| CN | 113045570 A | 6/2021 |
| CN | 113061132 A | 7/2021 |
| CN | 113105448 A | 7/2021 |
| CN | 113321654 A | 8/2021 |
| CN | 113527293 A | 10/2021 |
| CN | 113527294 A | 10/2021 |
| CN | 113563323 A | 10/2021 |
| CN | 113929681 A | 1/2022 |
| CN | 113980032 A | 1/2022 |
| CN | 113999226 A | 2/2022 |
| CN | 114057743 A | 2/2022 |
| CN | 114057744 A | 2/2022 |
| CN | 114380827 A | 4/2022 |
| CN | 114621244 A | 6/2022 |
| CN | 115073450 A | 9/2022 |
| WO | 2014/152588 A1 | 9/2014 |
| WO | 2015/054572 A1 | 4/2015 |
| WO | 2016/049524 A1 | 3/2016 |
| WO | 2016/049565 A1 | 3/2016 |
| WO | 2016/049568 A1 | 3/2016 |
| WO | 2016/164675 A1 | 10/2016 |
| WO | 2016/168540 A1 | 10/2016 |
| WO | 2017/015562 A1 | 1/2017 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/087528 A1 | 5/2017 |
| WO | 2017/100546 A1 | 6/2017 |
| WO | 2017/172979 A1 | 10/2017 |
| WO | 2017/201161 A1 | 11/2017 |
| WO | 2018/064510 A1 | 4/2018 |
| WO | 2018/068017 A1 | 4/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/206539 A1 | 11/2018 |
| WO | 2018/217651 A1 | 11/2018 |
| WO | 2018/218069 A1 | 11/2018 |
| WO | 2018/218070 A2 | 11/2018 |
| WO | 2018/218071 A1 | 11/2018 |
| WO | 2019/051291 A1 | 3/2019 |
| WO | 2019/099524 A1 | 5/2019 |
| WO | 2019/110751 A1 | 6/2019 |
| WO | 2019/141250 A1 | 7/2019 |
| WO | 2019/155399 A1 | 8/2019 |
| WO | 2019/213516 A1 | 11/2019 |
| WO | 2019/215203 A1 | 11/2019 |
| WO | 2019/217307 A1 | 11/2019 |
| WO | 2020/027083 A1 | 2/2020 |
| WO | 2020/027084 A1 | 2/2020 |
| WO | 2020/028706 A1 | 2/2020 |
| WO | 2020/035031 A1 | 2/2020 |
| WO | 2020/047192 A1 | 3/2020 |
| WO | 2020/068867 A1 | 4/2020 |
| WO | 2020/068873 A1 | 4/2020 |
| WO | 2020/086739 A1 | 4/2020 |
| WO | 2020/097537 A2 | 5/2020 |
| WO | 2020/106640 A1 | 5/2020 |
| WO | 2020/118066 A1 | 6/2020 |
| WO | 2020/165732 A1 | 8/2020 |
| WO | 2020/178282 A1 | 9/2020 |
| WO | 2020/233592 A1 | 11/2020 |
| WO | 2020/234103 A1 | 11/2020 |
| WO | 2020/236940 A1 | 11/2020 |
| WO | 2020/238791 A1 | 12/2020 |
| WO | 2020/239077 A1 | 12/2020 |
| WO | 2020/239123 A1 | 12/2020 |
| WO | 2021/023247 A1 | 2/2021 |
| WO | 2021/027911 A1 | 2/2021 |
| WO | 2021/027943 A1 | 2/2021 |
| WO | 2021/055728 A1 | 3/2021 |
| WO | 2021/058018 A1 | 4/2021 |
| WO | 2021/068898 A1 | 4/2021 |
| WO | 2021/081212 A1 | 4/2021 |
| WO | 2021/083167 A1 | 5/2021 |
| WO | 2021/084765 A1 | 5/2021 |
| WO | 2021/085653 A1 | 5/2021 |
| WO | 2021/088938 A1 | 5/2021 |
| WO | 2021/093758 A1 | 5/2021 |
| WO | 2021/097212 A1 | 5/2021 |
| WO | 2021/098859 A1 | 5/2021 |
| WO | 2021/104431 A1 | 6/2021 |
| WO | 2021/106230 A1 | 6/2021 |
| WO | 2021/118877 A1 | 6/2021 |
| WO | 2021/120045 A1 | 6/2021 |
| WO | 2021/120890 A1 | 6/2021 |
| WO | 2021/121330 A1 | 6/2021 |
| WO | 2021/121367 A1 | 6/2021 |
| WO | 2021/121371 A1 | 6/2021 |
| WO | 2021/139748 A1 | 7/2021 |
| WO | 2021/143693 A1 | 7/2021 |
| WO | 2021/147967 A1 | 7/2021 |
| WO | 2021/152149 A1 | 8/2021 |
| WO | 2021/155716 A1 | 8/2021 |
| WO | 2021/165456 A1 | 8/2021 |
| WO | 2021/168193 A1 | 8/2021 |
| WO | 2021/169963 A1 | 9/2021 |
| WO | 2021/169990 A1 | 9/2021 |
| WO | 2021/175199 A1 | 9/2021 |
| WO | 2021/180181 A1 | 9/2021 |
| WO | 2021/185233 A1 | 9/2021 |
| WO | 2021/190467 A1 | 9/2021 |
| WO | 2021/211864 A1 | 10/2021 |
| WO | 2021/216770 A1 | 10/2021 |
| WO | 2021/217019 A1 | 10/2021 |
| WO | 2021/219072 A1 | 11/2021 |
| WO | 2021/219090 A1 | 11/2021 |
| WO | 2021/228161 A1 | 11/2021 |
| WO | 2021/231526 A1 | 11/2021 |
| WO | 2021/239058 A1 | 12/2021 |
| WO | 2021/244603 A1 | 12/2021 |
| WO | 2021/245051 A1 | 12/2021 |
| WO | 2021/245055 A1 | 12/2021 |
| WO | 2021/248079 A1 | 12/2021 |
| WO | 2021/248082 A1 | 12/2021 |
| WO | 2021/248083 A1 | 12/2021 |
| WO | 2021/248090 A1 | 12/2021 |
| WO | 2021/248095 A1 | 12/2021 |
| WO | 2021/252339 A1 | 12/2021 |
| WO | 2021/259331 A1 | 12/2021 |
| WO | 2022/028492 A1 | 2/2022 |
| WO | 2022/037560 A1 | 2/2022 |
| WO | 2022/040469 A1 | 2/2022 |
| WO | 2022/047093 A1 | 3/2022 |
| WO | 2022/056307 A1 | 3/2022 |
| WO | 2022/067462 A1 | 4/2022 |
| WO | 2022/072783 A1 | 4/2022 |
| WO | 2022/081655 A1 | 4/2022 |
| WO | 2022/083569 A1 | 4/2022 |
| WO | 2022/083616 A1 | 4/2022 |
| WO | 2022/087371 A1 | 4/2022 |
| WO | 2022/087375 A1 | 4/2022 |
| WO | 2022/087624 A1 | 4/2022 |
| WO | 2022/089604 A1 | 5/2022 |
| WO | 2022/093856 A1 | 5/2022 |
| WO | 2022/109485 A1 | 5/2022 |
| WO | 2022/109487 A1 | 5/2022 |
| WO | 2022/111527 A1 | 6/2022 |
| WO | 2022/111644 A1 | 6/2022 |

(56) References Cited

FOREIGN PATENT DOCUMENTS

| | | |
|---|---|---|
| WO | 2022/115439 A1 | 6/2022 |
| WO | 2022/117748 A1 | 6/2022 |
| WO | 2022/161489 A1 | 8/2022 |
| WO | 2022/193982 A1 | 9/2022 |
| WO | 2022/198904 A1 | 9/2022 |
| WO | 2022/221528 A2 | 10/2022 |
| WO | 2022/222871 A1 | 10/2022 |
| WO | 2022/223037 A1 | 10/2022 |
| WO | 2022/232318 A1 | 11/2022 |
| WO | 2022/232320 A1 | 11/2022 |
| WO | 2022/251576 A1 | 12/2022 |

OTHER PUBLICATIONS

Bauer, R.A. "Covalent Inhibitors in Drug Discovery: From Accidental Discoveries to Avoided Liabilities and Designed Therapies", *Drug Discov. Today*, 2015, 20, 9, 1061-1073.

Briere et al. "The KRASG12C Inhibitor MRTX849 Reconditions the Tumor Immune Microenvironment and Leads to Durable Complete Responses in Combination with Anti-PD-1 Therapy in a Syngeneic Mouse Model", *AACR Meeting*, 2019, 1 page.

Cruz-Migoni et al. "Structure-Based Development of New RAS-Effector Inhibitors from a Combination of Active and Inactive RAS-Binding Compounds", *PNAS*, 2019, 116, 7, 2545-2550.

Database Genbank "MRTX-1257", Cas No. #2206736-04-09, 2 pages. 2020.

Database Genbank "MRTX-849", Cas No. #2326521-71-3, 2 pages. 2020.

Downward J. "Targeting RAS Signalling Pathways in Cancer Therapy", *Nat. Rev. Cancer.*, 2003, 3, 1, 11-22.

FDA "NDA/BLA Multi-disciplinary Review and Evaluation {NOA 214665}: LUMAKRAS™ (sotorasib)", 268 pages. 2020.

Fell et al. "Discovery of Tetrahydropyridopyrimidines as Irreversible Covalent Inhibitors of KRAS-G12C with In Vivo Activity", *ACS Med. Chem. Lett.*, 2018, 9, 12, 1230-1234.

Gill, Adrian "Discovery of Small Molecule Inhibitors of Oncogenic Mutants of Ras", *ACS Meeting*, 2019, 23 pages.

Hallin et al. 2019, "Insight Towards Therapeutic Susceptibility of KRAS Mutant Cancers from MRTX 1257: A Prototype Selective Inhibitors of Kras G12C", AACR Meeting, 1 Page.

Hallin et al. "Insight Towards Therapeutic Susceptibility of KRAS Mutant Cancers from MRTX1257, a Novel Kras G12C Mutant Selective Small Molecule Inhibitor", *AACR Annual Meeting*, 2019, 1 page.

Hallin et al. "The KRASG12C Inhibitor, MRTX849, Provides Insight Toward Therapeutic Susceptibility of KRAS Mutant Cancers in Mouse Models and Patients", *Cancer Discov.*, 2020, 10, 1, 54-71.

Kettle et al. "Covalent inhibitors of the GTPase KRASG12C: a review of the patent literature", *xpert Opin. Ther. Pat.*, 2020, 30, 2, 103-120.

Kettle et al. "Structure-Based Design and Pharmacokinetic Optimization of Covalent Allosteric Inhibitors of the Mutant GTPase KRAS G12C", *J. Med. Chem.*, 2020, 63, 9, 4468-4483.

Lanman et al. "Discovery of a Covalent Inhibitor of KRASG12C (AMG 510) for the Treatment of Solid Tumors", *J. Med. Chem.*, 2019, 63, 1, 52-65.

Lanman et al. "Discovery of AMG 510, A First-in-Human Covalent Inhibitor of KRASG12C for the Treatment of Solid Tumors", *J. Med. Chem.*, 2019, 79, 13_Supplement, 15 pages.

Lipford, J.R. "Pre-Clinical Development of AMG 510: The First Inhibitor of KRASG12C in Clinical Testing", *Presentation at AACR*, Mar. 31, 2018, 21 pages.

Marx et al. "Structure-Based Drug Discovery of MRTX1257, a Selective, Covalent KRAS G12C Inhibitor with Oral Activity in Animal Models of Cancer", *Mol. Cancer Res.*, 2020, 18, 5_Supplement, B30 (1 page).

Nnadi et al. "Novel K-Ras G12C Switch-II Covalent Binders Destabilize Ras and Accelerate Nucleotide Exchange", *J. Chem. Inf. Model.*, 2018, 58, 464-471.

Ostrem, J.M. "K-Ras (G12c) Inhibitors Allosterically Control GTP Affinity And Effector Interactions", *Nature*, 2013, 503, 7477, 548-551.

Reese et al. "Advancing a Portfolio of Novel, High-Potential Cancer Therapies", *Presentation at ASCO*, Jun. 3, 2019, 41 pages.

Sabari et al. "Activity of Adagrasib (MRTX849) in Patients with KRASG12c-Mutated NSCLC and Active, Untreated CNS Metastases in the KRYSTAL-1 Trial", *Presentation at ASCO*, Jun. 6, 2020, 40, 17_suppl, 21 pages.

Ukrainets et al. "4-Hydroxy-2-quinolones 122. 1-Hydroxy-3-oxo-5,6-dihydro-3H-pyrrolo[3,2, 1-ij]-quinoline-2-carboxylic acid hetarylamides as Potential Antitubercular Agents", *Chem. Heterocycl. Compd.*, 2007, 43, 7, 863-870.

Ukrainets et al. "4-Hydroxy-2-quinolones 138. Synthesis and Study of Structure-Biological Activity Relationships in a Series of 1-hydroxy-3-oxo-5,6-dihydro-3H-pyrrolo[3,2, 1-ij]quinoline-2-carboxylic acid anilides", *Chem. Heterocycl. Compd.*, 2007, 43, 1532-1539.

Ukrainets et al. "Synthesis And Diuretic Properties of N-Aryl-6-Hydroxy-2-Methyl-4-Oxo-2,4-Dihydro-1h-Pyrrolo [3,2, 1-lj]Quinoline-5-Carboxamides with Electron-Acceptor Substituents in the Anilide Fragment", *J. Org. Pharm. Chem.*, 2013, 11, 3, 6 pages.

Wang et al. "Deep Dive on KRAS G12C Inhibitor-Another Drug Class on The Horizon", *Barclays US*, Feb. 5, 2019, 28 pages.

\* cited by examiner

TRICYCLIC PYRIDONES AND PYRIMIDONES

CROSS-REFERENCE TO RELATED APPLICATIONS

This application claims the benefit of priority to U.S. provisional application Ser. No. 63/082,221, filed Sep. 23, 2020, and U.S. provisional application No. 63/259,894 entitled "Tricyclic Pyridones and Pyrimidones" filed Dec. 18, 2020, the contents of which are incorporated herein by reference in their entirety.

REFERENCE TO SEQUENCE LISTING

This application incorporates by reference a Computer Readable Form (CRF) of a Sequence Listing in ASCII text format submitted with this application, entitled 055745_502002US_SequenceListing_ST25.TXT, was created on Sep. 20, 2021, and is 8,686 bytes in size.

BACKGROUND

Embodiments herein relate to compounds and methods for the treatment of RAS-mediated disease. In particular, embodiments herein relate to compounds and methods for treating diseases such as cancer via targeting oncogenic mutants of the K-RAS isoform.

Ras proteins are small guanine nucleotide-binding proteins that act as molecular switches by cycling between active GTP-bound and inactive GDP-bound conformations. Ras signaling is regulated through a balance between activation by guanine nucleotide exchange factors (GEFs), most commonly son of sevenless (SOS), and inactivation by GTPase-activating proteins (GAPs) such as neurofibromin or p120GAP. The Ras proteins play an important role in the regulation of cell proliferation, differentiation, and survival. Dysregulation of the Ras signaling pathway is almost invariably associated with disease. Hyper-activating somatic mutations in Ras are among the most common lesions found in human cancer. Most of these mutations have been shown to decrease the sensitivity of Ras to GAP stimulation and decrease its intrinsic GTPase activity, leading to an increase in the active GTP-bound population. Although mutation of any one of the three Ras isoforms (K-Ras, N-Ras, or H-Ras) has been shown to lead to oncogenic transformation, K-Ras mutations are by far the most common in human cancer. For example, K-Ras mutations are known to be often associated with pancreatic, colorectal and non-small-cell lung carcinomas. Similarly, H-Ras mutations are common in cancers such as papillary thyroid cancer, lung cancers and skin cancers. Finally, N-Ras mutations occur frequently in hepatocellular carcinoma.

There is a need for effective Ras inhibitors, which may provide a new class of anticancer compounds. These and other advantages will be apparent to those skilled in the art based upon embodiments and disclosures herein.

SUMMARY

In some aspects, embodiments disclosed herein relate to compounds of Formula (I)

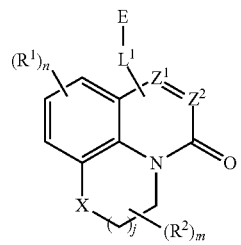

(I)

wherein:
X is O, $S(O)_p$ $CR^3R^4$, $NR^5$, or C(O), wherein p is an integer from 0 to 2;
j is an integer from 0 to 2;
$Z^1$ and $Z^2$ are independently $CR^6$ or N, with the proviso that at least one of $Z^1$ or $Z^2$
is $CR^6$ with $R^6$ being a bond to $L^1$;
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:
at least one $R^1$ is aryl, N-arylamino, N-aryl-N-alkylamino, aryloxy, arylthio, or heteroaryl, any of which is optionally substituted;
n is an integer from 1 to 3;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, and heteroaryl, any of which are optionally substituted; and
$R^6$ is selected from the group consisting of hydrogen, alkyl, haloakyl, cyano, halo, alkoxy, aryl, heteroaryl, trifluoromethyl and bond to $L^1$.

In some aspects, embodiments herein relate to methods of treating a subject with cancer associated with a G12C Kras mutation comprising administering to the subject a compound, as disclosed herein, in a pharmaceutically acceptable vehicle.

DETAILED DESCRIPTION

I. General

Disclosed herein are potent and selective tricyclic quinazoline-2-ones compounds, which have been found to be useful as inhibitors of oncogenic mutants of RAS proteins. Among various advantages, the compounds disclosed herein are selective for oncogenic RAS mutants over wild-type RAS proteins. Further, compounds disclosed herein may exhibit selectivity for oncogenic mutants of K-RAS over other mutated K-RAS proteins, as well as mutants of the N-RAS and H-RAS isoforms. In particular, the compounds disclosed herein may exhibit selectivity for K-RAS, N-RAS, and H-RAS mutants having a common G12C mutation. Also disclosed herein are pharmaceutical compositions comprising these compounds, and their application in the treatment of disease, such as cancer. Methods of inhibition of oncogenic mutant K-RAS, N-RAS, and H-RAS activity are also provided, as well as methods for the treatment of oncogenic mutant RAS-mediated diseases, especially those involving elevated levels of oncogenic mutated RAS, in particular cancer.

Disclosed herein is a class of compounds useful in treating oncogenic RAS-mediated disorders and conditions, defined by structural Formula (I):

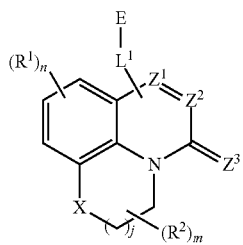

(I)

wherein:
X is O, $S(O)_p$, $CR^3R^4$, $NR^5$, or C(O), wherein p is an integer from 0 to 2;
j is an integer from 0 to 2;
$Z^1$ and $Z^2$ are independently $CR^6$ or N, with the proviso that at least one of $Z^1$ or $Z^2$ is $CR^6$ with $R^6$ being a bond to $L^1$; $Z^3$ is S or O;
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:
at least one $R^1$ is aryl, N-arylamino, N-aryl-N-alkylamino, aryloxy, arylthio, or heteroaryl, any of which is optionally substituted;
n is an integer from 1 to 3;
$R^2$ is selected from the group consisting of alkyl, alkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, and heteroaryl, any of which are optionally substituted; and
$R^6$ is selected from the group consisting of hydrogen, alkyl, haloakyl, cyano, halo, alkoxy, aryl, heteroaryl, trifluoromethyl and bond to $L^1$.

In further embodiments, compounds of the various embodiments disclosed herein have structural Formula (IIa):

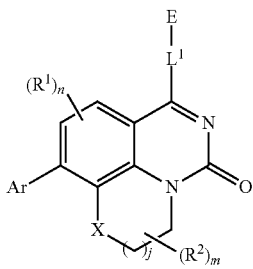

(IIa)

wherein:
X is O, $S(O)_p$, $CR^3R^4$, $NR^5$, or C(O), wherein p is an integer from 0 to 2;
j is an integer from 0 to 2;
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of hydrogen, alkyl, cyano, cycloalkyl, halo, haloalkyl, trifluoromethyl, and alkoxy;
n is an integer from 0 to 2;
$R^2$ is selected from the group consisting of alkyl, alkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, and heteroaryl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In further embodiments, compounds of the various embodiments disclosed herein have structural Formula (IIb):

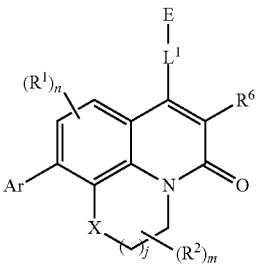

(IIa)

wherein:
X is O, $S(O)_p$, $CR^3R^4$, $NR^5$, or C(O), wherein p is an integer from 0 to 2;
j is an integer from 0 to 2;
$L^1$ is linking group comprising at least one nitrogen atom;
E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted;

$R^6$ is selected from the group consisting of hydrogen, alkyl, haloakyl, cyano, halo, alkoxy, aryl, heteroaryl, and trifluoromethyl; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

Compounds according to the various embodiments disclosed herein possess useful oncogenic mutant RAS inhibiting or modulating activity, and may be used in the treatment or prophylaxis of a disease or condition in which oncogenic mutant RAS plays an active role. Thus, in a broad aspect, embodiments disclosed herein also provide pharmaceutical compositions comprising one or more compounds disclosed herein together with a pharmaceutically acceptable carrier, as well as methods of making and using the compounds and compositions. Embodiments disclosed herein provide methods for selectively inhibiting the RAS that are oncogenic mutants having the G12C mutation. In some embodiments, there are provided methods for treating an oncogenic mutant K-RAS-mediated disorder in a subject, comprising administering to the subject a therapeutically effective amount of a compound or pharmaceutical composition according to the various embodiments disclosed herein. Related embodiments disclose the use of the compounds disclosed herein as therapeutic agents, for example, in treating cancer and other diseases involving elevated levels of oncogenic mutant K-RAS. The various embodiments disclosed herein also contemplate the use of the compounds disclosed herein for use in the manufacture of a medicament for the treatment of a disease or condition ameliorated by the inhibition of oncogenic mutant K-RAS. In some such embodiments, the disease or condition is cancer. Each of the aforementioned methods apply equally to the similar mutation in N-RAS and H-RAS bearing the G12C mutation.

Compounds of the various embodiments disclosed herein may be selective amongst the RAS oncogenic mutant forms in various ways. For example, compounds described herein may be selective for G12C mutants of K-RAS, N-RAS, or H-RAS. In certain embodiments, compounds of the various embodiments disclosed herein may be selective for K-RAS G12C over other K-RAS mutants and Wild Type K-RAS. Likewise, compounds of various embodiments disclosed herein may be selective for N-RAS and H-RAS bearing the same G12C mutation.

The various embodiments disclosed herein also relate to methods of inhibiting at least one RAS function comprising the step of contacting an oncogenic mutant RAS with a compound of Formula I, as described herein. The cell phenotype, cell proliferation, activity of the mutant RAS, change in biochemical output produced by active mutant RAS, expression of mutant RAS, or binding of mutant RAS with a natural binding partner may be affected. Such methods may be embrace modes of treatment of disease, biological assays, cellular assays, biochemical assays, or the like.

II. Definitions

A. General Definitions

As used herein, the terms below have the meanings indicated.

When ranges of number values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure, taking into account significant figures.

"A," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

B. Chemical Definitions

The following chemical functional group definitions are provided to give guidance in understanding their meaning and scope. Those skilled in the art will recognize that these functional groups are being used in a manner consistent with practice of the chemical arts. Any of the following chemical functional groups may be optionally substituted as defined below and each chemical functional group below may itself be an optional substitution.

The term "acyl," as used herein, alone or in combination, refers to a carbonyl (C=O) attached to an alkenyl, alkyl, aryl, cycloalkyl, heteroaryl, heterocycloalkyl, or any other moiety were the atom attached to the carbonyl is carbon. An "acetyl" group, which is a type of acyl, refers to a (—C(=O)CH₃) group. An "alkylcarbonyl" or "alkanoyl" group refers to an alkyl group attached to the parent molecular moiety through a carbonyl group. Examples of such groups include, without limitation, methylcarbonyl and ethylcarbonyl. Similarly, an "arylcarbonyl" or "aroyl" group refers to an aryl group attached to the parent molecular moiety through a carbonyl group. Examples of such groups include, without limitation, benzoyl and naphthoyl. Accordingly, generic examples of acyl groups include alkanoyl, aroyl, heteroaroyl, and so on. Specific examples of acyl groups include, without limitation, formyl, acetyl, acryloyl, benzoyl, trifluoroacetyl and the like.

The term "alkenyl," as used herein, alone or in combination, refers to a straight-chain or branched-chain hydrocarbon radical having one or more double bonds and containing from 2 to 20 carbon atoms. In certain embodiments, the alkenyl may comprise from 2 to 6 carbon atoms, or from 2 to 4 carbons, either of which may be referred to as "lower alkenyl." The term "alkenylene" refers to a carbon-carbon double bond system attached at two or more positions such as ethenylene (—CH═CH—). Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$, and so on up to 20 carbon atoms. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted. Unless otherwise specified, the term "alkenyl" may include "alkenylene" groups.

The term "alkoxy," as used herein, alone or in combination, refers to an alkyl ether radical, wherein the term alkyl is as defined below. Alkoxy groups may have the general formula: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, and the like. The alkoxy groups can be further optionally substituted as defined herein.

The term "alkyl," as used herein, alone or in combination, (sometimes abbreviated Alk) refers to a straight-chain or branched-chain alkyl radical containing from 1 to 20 carbon atoms. In certain embodiments, the alkyl may comprise from 1 to 10 carbon atoms. In further embodiments, the alkyl may comprise from 1 to 6 carbon atoms, or from 1 to 4 carbon atoms. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups. When the alkyl is methyl, it may be represented structurally as CH$_3$, Me, or just a single bond terminating with no end group substitution.

The term "alkylamino," as used herein, alone or in combination, refers to an alkyl group attached to the parent molecular moiety through an amino group. Suitable alkylamino groups may be mono- or dialkylated, forming groups such as, for example, N-methylamino (—NHMe), N-ethylamino (—NHEt), N,N-dimethylamino (—NMe$_2$), N,N-ethylmethylamino (—NMeEt) and the like. The term "aminoalkyl" refers to reverse orientation in which the amino group appears distal to the parent molecular moiety and attachment to the parent molecular moiety is through the alkyl group. For example, NH$_2$(CH$_2$)$_n$— describes an aminoalkyl group with a terminal amine at the end of an alkyl group attached to the parent molecular moiety. The two terms alkylamino and aminoalkyl can be combined to describe an "alkylaminoalkyl" group in which an alkyl group resides on a nitrogen atom distal to the parent molecular moiety, such as MeNH (CH$_2$)$_n$—. In a similar manner, an aryl group, as defined herein, may combine in a similar fashion providing an arylaminoalkyl group ArNH(CH$_2$)$_n$—. For additional clarity nomenclature may be provided where the group that is attached to nitrogen is indicated so by use of "N-" in the name, such as N-arylaminoalkyl, which is understood to mean that the aryl group is a substituent on the nitrogen atom of the aminoalkyl group, the alkyl being attached the parent molecular moiety.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (AlkS-) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like. Similarly, "arylthio" refers to arylthioether (ArS-) radical wherein the term aryl is as defined herein and wherein the sulfur may be singly or double oxidized.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted. Unless otherwise specified, the term "alkynyl" may include "alkynylene" groups.

The terms "amido," as used herein, alone or in combination, refer to an amino group as described below attached to the parent molecular moiety through a carbonyl group. The term "C-amido" as used herein, alone or in combination, refers to a —C(═O)N(R)$_2$ group where is R as defined herein. The term "N-amido" as used herein, alone or in combination, refers to RC(═O)N(R')— group, with R and R' as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —N(R)(R') or —N$^+$(R)(R')(R"), wherein R, R' and R" are independently selected from the group consisting of hydrogen, alkyl, acyl, heteroalkyl, aryl, cycloalkyl, heteroaryl, and heterocycloalkyl, any of which may themselves be optionally substituted.

The term "amino acid," as used herein, alone or in combination, means a substituent of the form —NRCH(R')

C(O)OH, wherein R is typically hydrogen, but may be cyclized with N (for example, as in the case of the amino acid proline), and R' is selected from the group consisting of hydrogen, alkyl, heteroalkyl, cycloalkyl, heterocycloalkyl, aryl, heteroaryl, amino, amido, cycloalkylalkyl, heterocycloalkylalkyl, arylalkyl, heteroarylalkyl, aminoalkyl, amidoalkyl, hydroxyalkyl, thiol, thioalkyl, alkylthioalkyl, and alkylthio, any of which may be optionally substituted. The term "amino acid" includes all naturally occurring amino acids as well as synthetic analogues.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$— derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid (oxygen) end, and which may be optionally substituted as defined herein.

The term "O-carbamyl" as used herein, alone or in combination, refers to a —OC(O)NRR', group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(=O)H] and in combination is a —C(=O)— group.

The term "carboxyl" or "carboxyl," as used herein, refers to —C(=O)OH, O-carboxy, C-carboxy, or the corresponding "carboxylate" anion, such as is in a carboxylic acid salt. An "O-carboxy" group refers to a RC(=O)O— group, where R is as defined herein. A "C-carboxy" group refers to a —C(=O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12 carbon atom ring members and which may optionally be a benzo fused ring system which is optionally substituted as defined herein. In some embodiments, a cycloalkyl may comprise from 3 to 7 carbon atoms, or from 5 to 7 carbon atoms. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term "electrophilic moiety," as used herein, is used in accordance with its plain ordinary chemical meaning and refers to a chemical group that is electrophilic. Exemplary electrophilic moieties include, without limitation, unsaturated carbonyl containing compounds such as acrylamides, acrylates, unsaturated (i.e., vinyl) sulfones or phosphates, epoxides, and vinyl epoxides.

The term "ester," as used herein, alone or in combination, refers to a carboxyl group bridging two moieties linked at carbon atoms (—CRR'C(=O)OCRR'—), where each R and R' are independent and defined herein.

The term "ether," as used herein, alone or in combination, typically refers to an oxy group bridging two moieties linked at carbon atoms. "Ether" may also include polyethers, such as, for example, —RO(CH$_2$)$_2$O(CH$_2$)$_2$O(CH$_2$)$_2$OR', —RO(CH$_2$)$_2$O(CH$_2$)$_2$OR', —RO(CH$_2$)$_2$OR', and —RO(CH$_2$)$_2$OH.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl, trihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized (i.e. bond to 4 groups). The heteroatom(s) O, N and S may be placed at any interior position of the heteroalkyl group. Up to two heteroatoms may be consecutive, such as, for example, —CH$_2$NHOCH$_3$. The term heteroalkyl may include ethers.

The term "heteroaryl," as used herein, alone or in combination, refers to 3 to 7 membered unsaturated heteromonocyclic rings, or fused polycyclic rings, each of which is 3 to 7 membered, in which at least one of the fused rings is unsaturated, wherein at least one atom is selected from the group consisting of O, S, and N. In some embodiments, a heteroaryl may comprise from 5 to 7 carbon atoms. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Non-limiting examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

The terms "heterocycloalkyl" and, interchangeably, "heterocycle," or "heterocyclyl" as used herein, alone or in combination, each refer to a saturated, partially unsaturated, or fully unsaturated monocyclic, bicyclic, or tricyclic heterocyclic radical containing at least one heteroatom as ring members, wherein each heteroatom may be independently selected from the group consisting of nitrogen, oxygen, and sulfur. In certain embodiments, a heterocycloalkyl may comprise from 1 to 4 heteroatoms as ring members. In further embodiments, a heterocycloalkyl may comprise from 1 to 2 heteroatoms ring members. In some embodiments, a heterocycloalkyl may comprise from 3 to 8 ring members in each ring. In further embodiments, a heterocycloalkyl may comprise from 3 to 7 ring members in each ring. In yet further embodiments, a heterocycloalkyl may comprise from 5 to 6 ring members in each ring. "Heterocycloalkyl" and "heterocycle" are intended to include sugars, sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycloalkyl groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, epoxy, isoindolinyl, morpholinyl, piperazinyl, pyrrolidinyl, tetrahydropyridinyl, piperidinyl, thiomorpholinyl, and the like. The heterocycloalkyl groups may be optionally substituted unless specifically prohibited.

"Heterocycloalkyl" may refer to a saturated ring system having from 3 to 12 ring members and from 1 to 5 heteroatoms of N, O and S. The heteroatoms can also be oxidized, such as, but not limited to, S(O) and S(O)$_2$. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, 4, or 5, or 1 to 2, 1 to 3, 1 to 4, 1 to 5, 2 to 3, 2 to 4, 2 to 5, 3 to 4 or 3 to 5. The heterocycloalkyl group can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. The heterocycloalkyl group can include groups such as aziridine, azetidine, pyrrolidine, piperidine, azepane, diazepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline, diazabicycloheptane, diazabicyclooctane, diazaspirooctane or diazaspirononane. Heterocycloalkyl groups can be unsubstituted or substituted. For example, heterocycloalkyl groups can be substituted with C1 6 alkyl or oxo (=O), among many others. Heterocycloalkyl groups can also include a double bond or a triple bond, such as, but not limited to dihydropyridine or 1,2,3,6-tetrahydropyridine.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

The term "hydrazinyl" as used herein, alone or in combination, refers to two amino groups joined by a single bond, i.e., —N----. In general, the hydrazinyl group has optional substitution on at least one NH hydrogen to confer stability.

The term "hydroxamic acid" or its ester as used herein, refers to —C(O)ON(R)O(R'), wherein R and R' are as defined herein, or the corresponding "hydroxamate" anion, including any corresponding hydroxamic acid salt.

The term "hydroxy," as used herein, alone or in combination, refers to OH.

The term "hydroxyalkyl," as used herein, alone or in combination, refers to a hydroxy group attached to the parent molecular moiety through an alkyl group. "Hydroxyalkyl" or "alkylhydroxy" refers to an alkyl group, as defined above, where at least one of the hydrogen atoms is replaced with a hydroxy group. As for the alkyl group, hydroxyalkyl or alkylhydroxy groups can have any suitable number of carbon atoms, such as $C_{1-6}$. Exemplary $C_{1-4}$ hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), 1,2-dihydroxyethyl, and the like.

The term "imino," as used herein, alone or in combination, refers to C=NR.

The term "iminohydroxy," as used herein, alone or in combination, refers to C=N(OH) and it O-ether C=N—OR.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "linking group," as used herein refers to any nitrogen containing organic fragment that serves to connect the pyrimidine or pyridone core of the compounds disclosed herein to the electrophilic moiety E, as defined herein. Exemplary linking groups include piperazines, aminoalkyls, alkyl- or aryl-based diamines, aminocycloalkyls, amine-containing spirocyclics, any of which may be optionally substituted as defined herein. In some embodiments, linking groups may comprise the substructure L-Q-L'-E wherein Q is a monocyclic 4 to 7 membered ring or a bicyclic, bridged, or fused, or spiro 6-11 membered ring, any of which optionally include one or more nitrogen atoms, E is the electrophilic group, L is bond, $C_{1-6}$ alkylene, —O—$C_{0-5}$ alkylene, —S—$C_{0-5}$ alkylene, or —NH—$C_{0-5}$ alkylene, and for $C_{2-6}$ alkylene, —O—$C_{2-5}$ alkylene, —S—$C_{2-5}$ alkylene, and NH—$C_{2-5}$ alkylene, one carbon atom of any of the alkylene groups can optionally be replaced with O, S, or NH; and L' is bond when Q comprises a nitrogen to link to E, otherwise L' is NR, where R is hydrogen or alkyl.

The term "lower," as used herein, alone or in combination, means containing from 1 to and including 6 carbon atoms, or from 1 to 4 carbon atoms.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphoamide" as used herein, alone or in combination, refers to a phosphate group [(OH)$_2$P(=O)O—] in which one or more of the hydroxyl groups has been replaced by nitrogen, amino, or amido.

The term "phosphonate" as used herein, alone or in combination, refers to a group of the form ROP(OR')(OR)O— wherein R and R' are selected from the group consisting of hydrogen, alkyl, acyl, heteroalkyl, aryl, cycloalkyl, heteroaryl, and heterocycloalkyl, any of which may themselves be optionally substituted. "Phosphonate" includes "phosphate [(OH)$_2$P(O)O—] and related phosphoric acid anions which may form salts.

The terms "sulfonate," "sulfonic acid," and "sulfonic," as used herein, alone or in combination, refers to the —SO$_3$H group and its anion as the sulfonic acid is used in salt formation or sulfonate ester where OH is replaced by OR, where R is not hydrogen, but otherwise is as defined herein, and typically being alkyl or aryl.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(=S)H and in combination is a —C(=S)— group.

The term "N-thiocarbamyl" refers to an ROC(=S)NR'— group, with R and R' as defined herein.

The term "O-thiocarbamyl" refers to a —OC(=S)NRR', group with R and R' as defined herein.

The term "thiocyanato" refers to a —CNS group.

The term "trihalomethanesulfonamido" refers to a X$_3$CS(=O)$_2$NR— group with X is a halogen and R as defined herein.

The term "trihalomethanesulfonyl" refers to a X$_3$CS(=O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent. A "null" group occurring between two other group may also be understood to be a collapsing of flanking groups. For example, if in —(CH$_2$)$_x$G$^1$G$^2$G$^3$, the element G$^2$ were null, said group would become —(CH$_2$)$_x$G$^1$G$^3$.

The term "optionally substituted" means the anteceding group or groups may be substituted or unsubstituted. Groups constituting optional substitution may themselves be optionally substituted. For example, where an alkyl group is embraced by an optional substitution, that alkyl group itself may also be optionally substituted. When substituted, the substituents of an "optionally substituted" group may include, without limitation, one or more substituents independently selected from the following groups or a particular designated set of groups, alone or in combination: alkyl, alkenyl, alkynyl, alkanoyl, heteroalkyl, heterocycloalkyl, haloalkyl, haloalkenyl, haloalkynyl, lower perhaloalkyl, perhaloalkoxy, cycloalkyl, phenyl, aryl, aryloxy, alkoxy, haloalkoxy, oxo, acyloxy, carbonyl, carboxyl, alkylcarbonyl, carboxyester, carboxamido, cyano, hydrogen, halogen, hydroxy, amino, alkylamino, arylamino, amido, nitro, thiol, alkylthio, haloalkylthio, perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, carbamate, and urea. Particular subsets of optional substitution include, without limitation: (1) alkyl, halo, and alkoxy; (2) alkyl and halo; (3) alkyl and alkoxy; (4) alkyl, aryl, and heteroaryl; (5) halo and alkoxy; and (6) hydroxyl, alkyl, halo, alkoxy, and cyano. Where an optional substitution comprises a heteroatom-hydrogen bond (—NH—, SH, OH), further optional substitution of the heteroatom hydrogen is contemplated and includes, without limitation optional substitution with alkyl, acyl, alkoxymethyl, alkoxyethyl, arylsulfonyl, alkyl sulfonyl, any of which are further optionally substituted. These subsets of optional substitutions are intended to be merely exemplary and any combination of 2 to 5, or 2 to 10, or 2 to 20 of the groups recited above up to all the group recited above and any subrange in between are contemplated. "Optionally substituted" may include any of the chemical functional groups defined hereinabove and throughout this disclosure. Two optional substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$).

The various optional substitutions need not be the same and any combination of optional substituent groups may be combined. For example, a carbon chain may be substituted with an alkyl group, a halo group, and an alkoxy group. Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, hydroxyl, halogen, alkyl, cycloalkyl, heteroalkyl, aryl, heteroaryl and heterocycloalkyl, any of which may be optionally substituted. Each such R and R' groups should be understood to be optionally substituted as defined herein. Each incidence of R and R' should be understood to be independent. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers, axial asymmetry (non-interchanging rotamers), or the like may exist in the compounds of the various embodiments disclosed herein. Such chirality may be designated by the symbols "R" or "S," depending on the configuration of substituents around the chiral carbon atom or the relevant axis. It should be understood that embodiments encompasses all stereochemical isomeric forms, including diasteromeric, enantiomeric, and epimeric forms, d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the various embodiments disclosed herein may exist as geometric isomers. The various embodiments disclosed herein includes all cis, trans, syn, anti, entgegen (E), and zusammen (Z) isomers as well as the appropriate mixtures thereof. Additionally, compounds may exist as tautomers, including keto-enol tautomers; all tautomeric isomers are embraced by the embodiments disclosed herein.

Additionally, the compounds of the various embodiments disclosed herein can exist in unsolvated as well as solvated forms with pharmaceutically acceptable solvents such as water, ethanol, and the like. In general, the solvated forms are considered equivalent to the unsolvated forms for the purposes of the various embodiments disclosed herein.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

1. Salts of Compounds

The compounds disclosed herein can exist as pharmaceutically acceptable salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002). It is understood that each of the compounds disclosed herein, and each embodiment of the compounds set forth herein, include pharmaceutically acceptable salts of such compounds.

The term "pharmaceutically acceptable salt," as used herein, represents salts or zwitterionic forms of the compounds disclosed herein which are water or oil-soluble or dispersible and pharmaceutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the various embodiments disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the various embodiments disclosed herein contemplates sodium, potassium, magnesium, and calcium salts of the compounds disclosed herein, and the like.

Basic addition salts can be prepared during the final isolation and purification of the compounds by reacting a carboxyl group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

C. Treatment-Related Definitions

The term "disease" as used herein is intended to be generally synonymous, and is used interchangeably with, the terms "disorder" and "condition" (as in medical condition), in that all reflect an abnormal condition of the body or of one of its parts that impairs normal functioning and is typically manifested by distinguishing signs and symptoms.

As used herein, the term "cancer" refers to all types of cancer, neoplasm or malignant tumors found in mammals (e.g., but not limited to, humans), including leukemia, lymphomas, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

"Ras associated cancer" (also referred to herein as "Ras related cancer") refers to a cancer caused by aberrant Ras activity or signaling. A "cancer associated with aberrant K-Ras activity" (also referred to herein as "K-Ras related cancer") is a cancer caused by aberrant K-Ras activity or signaling (e.g. a mutant K-Ras). K-Ras related cancers may include lung cancer, non-small cell lung cancer, breast cancer, leukemia, pancreatic cancer, colon cancer, colorectal cancer. Other cancers that are associated with aberrant activity of one or more of Ras, K-Ras, H-Ras, N-Ras, mutant K-Ras (including K-Ras G12C, K-Ras G12V, K-Ras G13C, K-Ras G12D, K-Ras G13D mutants), mutant N-Ras, and mutant H-Ras are well known in the art, including G12C in both N-Ras and H-Ras, and determining such cancers are within the skill of a person of skill in the art.

The term "administer (or administering) a Ras inhibitor" means administering a compound that inhibits the activity or level (e.g. amount) or level of a signaling pathway of one or more Ras proteins (e.g. a Ras inhibitor, K-Ras inhibitor, N-Ras inhibitor, H-Ras inhibitor, mutant K-Ras inhibitor, K-Ras G12C inhibitor, K-Ras G12V inhibitor, K-Ras G13C inhibitor, K-Ras G12D inhibitor, K-Ras G13D inhibitor) to a subject. Administration may include, without being limited by mechanism, allowing sufficient time for the Ras inhibitor to reduce the activity of one or more Ras proteins or for the Ras inhibitor to reduce one or more symptoms of a disease (e.g. cancer, wherein the Ras inhibitor may arrest the cell cycle, slow the cell cycle, reduce DNA replication, reduce cell replication, reduce cell growth, reduce metastasis, or cause cell death). The term "administer (or administering) a K-Ras inhibitor" means administering a compound that inhibits the activity or level (e.g. amount) or level of a signaling pathway of one or more K-Ras proteins (K-Ras, mutant K-Ras, K-Ras G12C, K-Ras G12V, K-Ras G12D, K-Ras G13C, K-Ras G13D). In embodiments, the administering does not include administration of any active agent other than the recited active agent.

The term "associated" or "associated with" in the context of a substance or substance activity or function associated with a disease (e.g. Ras (e.g., human K-Ras or human H-Ras) activity, a protein associated disease, a cancer associated with aberrant Ras activity, K-Ras associated cancer, mutant K-Ras associated cancer, activated K-Ras associated cancer, K-RasG12C associated cancer, K-Ras G12V associated cancer, K-Ras G13C associated cancer, K-Ras G12D associated cancer, K-Ras G13D associated cancer) means that the disease (e.g. cancer) is caused by (in whole or in part), or a symptom of the disease is caused by (in whole or in part) the substance or substance activity or function. For example, a cancer associated with aberrant Ras activity or function may be a cancer that results (entirely or partially) from aberrant Ras activity or function (e.g. enzyme activity, protein-protein binding, signaling pathway) or a cancer wherein a particular symptom of the disease is caused (entirely or partially) by aberrant Ras activity or function. As used herein, what is described as being associated with a disease, if a causative agent, could be a target for treatment of the disease. For example, a cancer associated with aberrant Ras activity or function or a Ras associated cancer, may be treated with a Ras modulator or Ras inhibitor, in the instance where increased Ras activity or function (e.g., signaling pathway activity) causes the cancer. For example, a cancer associated with K-Ras G12C may be a cancer that a subject with K-Ras G12C is at higher risk of developing as compared to a subject without K-Ras G12C. For example, a cancer associated with K-Ras G12V may be a cancer that a subject with K-Ras G12V is at higher risk of developing as compared to a subject without K-Ras G12V.

The term "Ras" refers to one or more of the family of human Ras GTPase proteins (e.g. K-Ras, H-Ras, N-Ras). The term "K-Ras" refers to the nucleotide sequences or proteins of human K-Ras (e.g. human K-Ras4A (NP_203524.1), human K-Ras4B (NP_004976.2), or both K-Ras4A and K-Ras4B). The term "K-Ras" includes both the wild-type form of the nucleotide sequences or proteins as well as any mutants thereof. In some embodiments, "K-Ras" is wild-type K-Ras. In some embodiments, "K-Ras" is one or more mutant forms. The term "K-Ras" XYZ refers to a nucleotide sequence or protein of a mutant K-Ras wherein the Y numbered amino acid of K-Ras that has an X amino acid in the wildtype instead has a Z amino acid in the mutant (e.g. K-Ras G12C has a G in wildtype protein but a C in the K-Ras G12C mutantprotein). In some embodiments K-Ras refers to K-Ras4A and K-Ras4B. In some embodiments, K-Ras refers to K-Ras4A. In some embodiments, K-Ras refers to K-Ras4B (e.g., NM_004985.4 or NP_004976.2). In some embodiments, K-Ras refers to the protein including (e.g., consisting of) the amino acid sequence below or including the sequence below with one or more mutations (e.g., G12C, G12V, or G13C):

```
                                      (SEQ ID NO: 1)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEK
```

In some embodiments, K-Ras refers to the protein including (e.g., consisting of) the amino acid sequence below or including (e.g., consisting of) the sequence below with one or more mutations (e.g., G12C, G12V, or G13C):

```
                                      (SEQ ID NO: 2)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEKMSKDGKKKKKKSKTKCVIM
```

1 mteyklvvvg aggvgksalt iqlignhfvd eydptiedsy rkqvvidget clldildtag 61 qeeysamrdq ymrtgegflc vfainntksf edihhyregi krvkdsedvp mvlvgnkcdl 121 psrtvdtkqa qdlarsygip fietsaktrq gvddafytlv reirkhkekm skdgkkkkkk 181 sktkcvim (SEQ ID NO:3)

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"K-RAS inhibitor" is used herein to refer to a compound that exhibits an $IC_{50}$ with respect to K-RAS activity of no more than about 100 mM and more typically not more than about 50 mM, as measured in the K-RAS assay described generally hereinbelow. "$IC_{50}$" is that concentration of inhibitor that reduces the activity of an enzyme (e.g., K-RAS) to half-maximal level. Compounds of the various embodiments disclosed herein have been discovered to exhibit inhibition against oncogenic mutant K-RAS isoforms. In some embodiments, compounds will exhibit an $IC_{50}$ with respect to oncogenic mutant K-RAS of no more than about 10 mM; in further embodiments, compounds will exhibit an $IC_{50}$ with respect to K-RAS of no more than about 5 mM; in yet further embodiments, compounds will exhibit an $IC_{50}$ with respect to K-RAS of not more than about 1 mM, as measured in the K-RAS assay described herein. In yet further embodiments, compounds will exhibit an $IC_{50}$ with respect to K-RAS of not more than about 200 nM. Without being bound by theory, in some embodiments, the K-RAS inhibitor is an irreversible inhibitor by way of covalent bond formation to the cysteine at the G12C mutation site.

The phrase "therapeutically effective" is intended to qualify the amount of active ingredients used in the treatment of a disease or disorder. This amount will achieve the goal of reducing or eliminating the disease or disorder.

As used herein, reference to "treatment" of a subject is intended to include prophylaxis. The term "subject" means all mammals, including humans. Examples of subjects include humans, cows, dogs, cats, goats, sheep, pigs, and rabbits. In some embodiments, the subject is a human.

The term "prodrug" refers to a compound that is made active in vivo through chemical reaction in vivo thereby releasing an active compound. Compounds disclosed herein can be modified to exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the active compound. Additionally, prodrugs can be converted to the active compounds by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the active compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound which is administered as an ester (the "prodrug"), which is then metabolically hydrolyzed to the carboxylic acid, as the active entity. Additional examples include peptidyl derivatives of a compound. The term "therapeutically acceptable prodrug," refers to those prodrugs or zwitterions which are suitable for use in contact with the tissues of subjects without undue toxicity, irritation, and allergic response, are commensurate with a reasonable benefit/risk ratio, and are effective for their intended use.

III. Compound Embodiments

A. Genus I—General

In some embodiments, there are provided compounds of Formula (I):

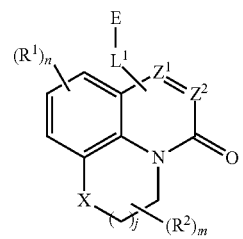

wherein:
X is O, $S(O)_p$, $CR^3R^4$, $NR^5$, or $C(O)$, wherein p is an integer from 0 to 2;
j is an integer from 0 to 2;
$Z^1$ and $Z^2$ are independently $CR^6$ or N, with the proviso that at least one of $Z^1$ or $Z^2$ is $CR^6$ with $R^6$ being a bond to $L^1$;
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:
at least one $R^1$ is aryl, N-arylamino, N-aryl-N-alkylamino, aryloxy, arylthio, or heteroaryl, any of which is optionally substituted;
n is an integer from 1 to 3;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, and heteroaryl, any of which are optionally substituted; and
$R^6$ is selected from the group consisting of hydrogen, alkyl, haloakyl, cyano, halo, alkoxy, aryl, heteroaryl, trifluoromethyl and bond to $L^1$.

In some embodiments, X is O.
In one or more of the preceding embodiments, j is 1.
In one or more of the preceding embodiments, m is 0. In one or more of the preceding embodiments, m is 1.
In one or more of the preceding embodiments, $Z^1$ is $CR^6$ with $R^6$ being a bond to $L^1$.
In one or more of the preceding embodiments, $Z^2$ is N.
In one or more of the preceding embodiments, $L^1$ is

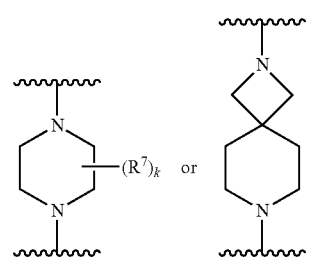

wherein k is an integer from 0 to 4; and each $R^7$ is independently selected from methyl, and cyanomethyl.

In one or more of the preceding embodiments, E is an acrylyl group having optional substitution R:

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a $C_2$-$C_6$ nitrogen containing heterocycle.

B. Genus II—General Pyrimidone

In some embodiments, there are provided compounds of Formula (IIa):

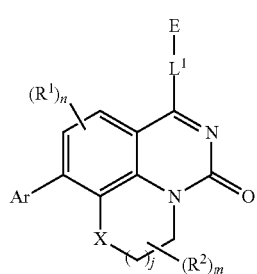

(IIa)

wherein:
X is O, S(O)$_p$, CR$^3$R$^4$, NR$^5$, or C(O), wherein p is an integer from 0 to 2;
j is an integer from 0 to 2;
$L^1$ is linking group comprising at least one nitrogen atom;
E is an electrophilic moiety, wherein E is bound to $L^1$ via the at least one nitrogen atom;
each $R^1$ is an optional substitution selected from the group consisting of alkyl, cyano, cycloalkyl, halo, haloalkyl, trifluoromethyl, and alkoxy;
n is an integer from 0 to 2;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, and heteroaryl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In some embodiments, X is O.

In one or more of the preceding embodiments, j is 1.

In one or more of the preceding embodiments, m is 0. In one or more of the preceding embodiments, m is 1.

In one or more of the preceding embodiments, $L^1$ is

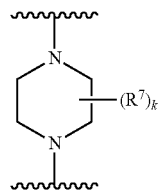

wherein k is an integer from 0 to 4; and each $R^7$ is independently selected from methyl, and cyanomethyl.

In one or more of the preceding embodiments, E is an acrylyl group having optional substitution R:

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a $C_2$-$C_6$ nitrogen containing heterocycle.

In one or more of the preceding embodiments, Ar creates axial asymmetry.

In one or more of the preceding embodiments, the compound is a single rotamer.

In one or more of the preceding embodiments, Ar is:

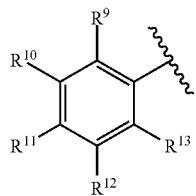

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

C. Genus III-Pyrimidone Unsubstituted Ring Fusion

In some embodiments, there are provided compounds of Formula (III):

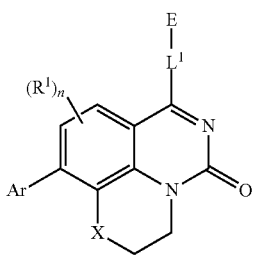

(III)

wherein:
X is O, $S(O)_p$, $CR^3R^4$, $NR^5$, or C(O), wherein p is an integer from 0 to 2;
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of hydrogen, alkyl, cyano, cycloalkyl, halo, haloalkyl, trifluoromethyl, and alkoxy;
n is an integer from 0 to 2;
$R^3$, $R^4$, and $R^5$ are each independently selected from the group consisting of hydrogen alkyl, halo, alkoxy, aryl, and heteroaryl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In one or more of the preceding embodiments, X is O.
In one or more of the preceding embodiments, $L^1$ is

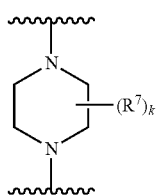

wherein k is an integer from 0 to 4; and each $R^7$ is independently selected from methyl and cyanomethyl;
In one or more of the preceding embodiments, E is an acrylyl group having optional substitution R:

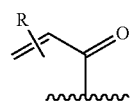

wherein R is selected from the group consisting of fluorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.
In one or more of the preceding embodiments, optional substitution comprises monofluorination.
In one or more of the preceding embodiments, Ar creates axial asymmetry.
In one or more of the preceding embodiments, the compound is a single rotamer.

In one or more of the preceding embodiments, Ar is:

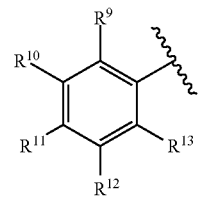

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

D. Genus IV-Pyrimidone Unsubstituted Morpholine Ring Fusion

In some embodiments, there are provided compounds of Formula (IV):

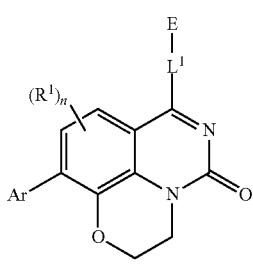

(IV)

wherein:
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of hydrogen, alkyl, cyano, cycloalkyl, halo, haloalkyl, trifluoromethyl, and alkoxy;
n is an integer from 0 to 2; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In some embodiments, $L^1$ is

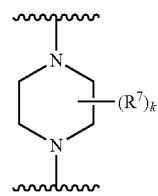

wherein k is an integer from 0 to 4; and each $R^7$ is independently selected from methyl, and cyanomethyl;
In one or more of the preceding embodiments, E is an acrylyl group having optional substitution R:

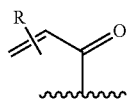

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle.

In one or more of the preceding embodiments, optional substitution comprises monofluorination.

In one or more of the preceding embodiments, Ar creates axial asymmetry.

In one or more of the preceding embodiments, the compound is a single rotamer.

In one or more of the preceding embodiments, Ar is:

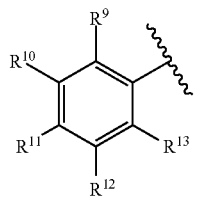

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.

E. Genus V-Pyrimidone Substituted Morpholine Ring Fusion

In some embodiments, there are provided compounds of Formula (V):

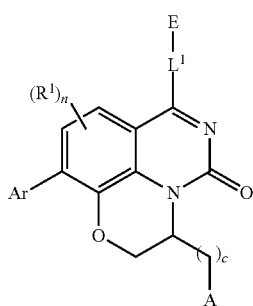

(V)

wherein:
L$^1$ is linking group comprising at least one nitrogen atom;
E is an electrophilic moiety, wherein E is bound to L$^1$ via the at least one nitrogen atom;
each R$^1$ is an optional substitution independently selected from the group consisting of alkyl, cyano, cycloalkyl, halo, haloalkyl, trifluoromethyl, and alkoxy;
n is an integer from 0 to 2;
c is an integer from 0 to 4;
A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In some embodiments, L$^1$ is

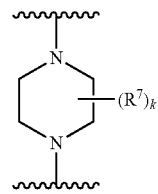

wherein k is an integer from 0 to 4; and each R$^7$ is independently selected from methyl and cyanomethyl;

In one or more of the preceding embodiments, E is an acrylyl group having optional substitution R:

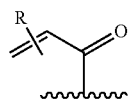

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle.

In one or more of the preceding embodiments, optional substitution comprises monofluorination.

In one or more of the preceding embodiments, Ar creates axial asymmetry.

In one or more of the preceding embodiments, the compound is a single rotamer.

In one or more of the preceding embodiments, Ar is:

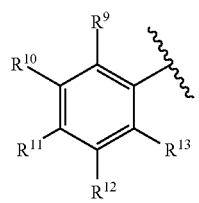

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.

F. Genus VI-Pyrimidone Acrylate Functionalized

In some embodiments, there are provided compounds of Formula (VI):

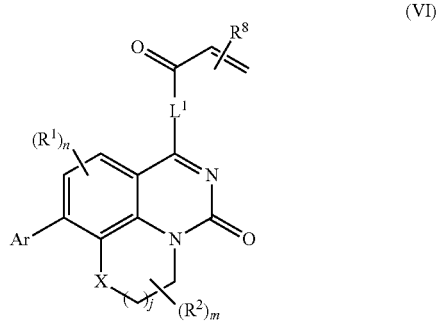

wherein:
- X is O, $S(O)_p$, $CR^3R^4$, $NR^5$, or C(O), wherein p is an integer from 0 to 2;
- j is an integer from 0 to 2;
- $L^1$ is linking group comprising at least one nitrogen atom;
- each $R^1$ is an optional substitution independently selected from the group consisting of alkyl, cyano, cycloalkyl, halo, haloalkyl, trifluoromethyl, and alkoxy; n is an integer from 0 to 2;
- $R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
- m is an integer from 0 to 6;
- $R^3$, $R^4$, and $R^5$ are each independently selected from the group consisting of hydrogen alkyl, halo, alkoxy, aryl, and heteroaryl, any of which are optionally substituted;
- $R^8$ is selected from the group consisting of fluorine, methyl, and $-CH_2NR^aR^b$, wherein $R^a$ and $R^b$ are independently selected from hydrogen or alkyl; or $R^a$ and $R^b$ combine to form a $C_2$-$C_6$ nitrogen containing heterocycle; and
- Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In some embodiments, X is O.
In one or more of the preceding embodiments, j is 1.
In one or more of the preceding embodiments, m is 0. In one or more of the preceding embodiments, m is 1.
In one or more of the preceding embodiments, $L^1$ is

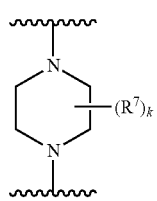

wherein k is an integer from 0 to 4; and each $R^7$ is independently selected from methyl and cyanomethyl;

In one or more of the preceding embodiments, Ar creates axial asymmetry.
In one or more of the preceding embodiments, the compound is a single rotamer.
In one or more of the preceding embodiments, Ar is:

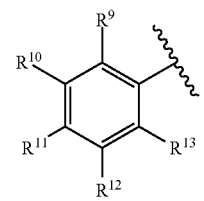

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

G. Genus VII-Pyrimidone Unsubstituted Morpholine Acrylate Functionalized

In some embodiments, there are provided compounds of Formula (VII):

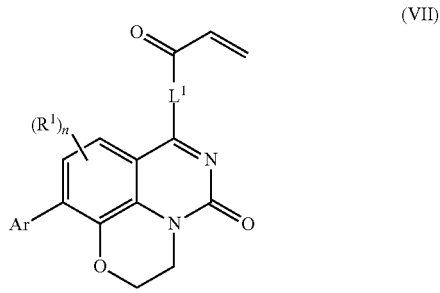

wherein:
- $L^1$ is linking group comprising at least one nitrogen atom;
- each $R^1$ is an optional substitution independently selected from the group consisting of alkyl, cyano, cycloalkyl, halo, haloalkyl, trifluoromethyl, and alkoxy;
- n is an integer from 0 to 2; and
- Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In some embodiments, $L^1$ is:

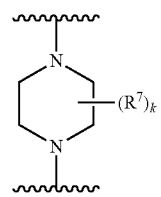

wherein k is an integer from 0 to 4; and each $R^7$ is independently selected from methyl and cyanomethyl;

In one or more of the preceding embodiments, Ar creates axial asymmetry.

In one or more of the preceding embodiments, the compound is a single rotamer.

In one or more of the preceding embodiments, Ar is:

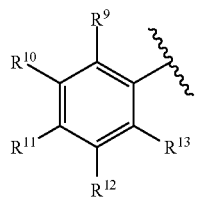

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

H. Genus VIII-Pyrimidone Substituted Morpholine Acrylate Functionalized

In some embodiments, there are provided compounds of Formula (VIII):

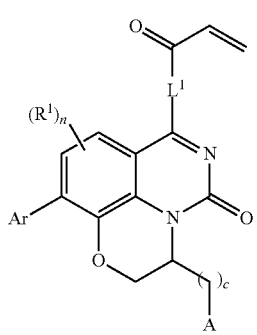

(VIII)

wherein:
$L^1$ is linking group comprising at least one nitrogen atom;
each $R^1$ is an optional substitution independently selected from the group consisting of alkyl, cyano, cycloalkyl, halo, haloalkyl, trifluoromethyl, and alkoxy;
n is an integer from 0 to 2;
c is an integer from 0 to 4;
A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In some embodiments, $L^1$ is

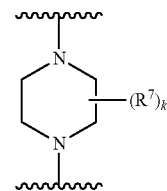

wherein k is an integer from 0 to 4; and each $R^7$ is independently selected from methyl and cyanomethyl;

In one or more of the preceding embodiments, Ar creates axial asymmetry.

In one or more of the preceding embodiments, the compound is a single rotamer.

In one or more of the preceding embodiments, Ar is:

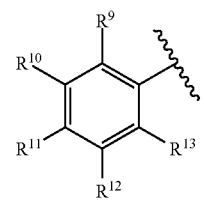

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^1$, and $R^{13}$ together combine to form a further fused ring that is an aromatic ring optionally comprising 1 to 3 heteroatoms independently selected from N, O or S, the further fused ring being optionally substituted.

I. Genus IX-Pyrimidone Heterocycle Linker Acrylate Functionalized

In some embodiments, there are provided compounds of Formula (IX):

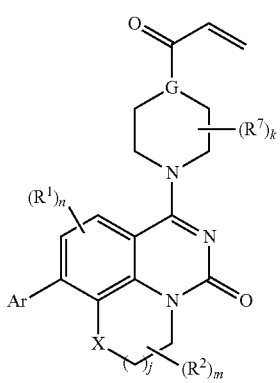

(IX)

wherein:
X is O, S(O)$_p$, CR$^3$R$^4$, NR$^5$, or C(O), wherein p is an integer from 0 to 2;
j is an integer from 0 to 2;
G is selected from the group consisting of N, CH, and

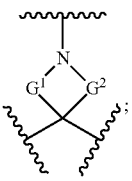

wherein G$^1$ and G$^2$ are independently (CH$_2$)$_q$, where q is 1 or 2;
each R$^1$ is an optional substitution independently selected from the group consisting of alkyl, cyano, cycloalkyl, halo, haloalkyl, trifluoromethyl, and alkoxy;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
n is an integer from 0 to 2;
R$^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
R$^3$, R$^4$, and R$^5$ are each independently selected from the group consisting of hydrogen alkyl, halo, alkoxy, aryl, and heteroaryl, any of which are optionally substituted;
wherein k is an integer from 0 to 4; and each R$^7$ is independently selected from methyl and cyanomethyl; and
wherein the acrylyl moiety linked to G is optionally substituted.

In some embodiments, X is O.
In one or more of the preceding embodiments, j is 1.
9 In one or more of the preceding embodiments, m is 0.
In one or more of the preceding embodiments, m is 1.
In one or more of the preceding embodiments, Ar creates axial asymmetry.
In one or more of the preceding embodiments, the compound is a single rotamer
In one or more of the preceding embodiments, Ar is:

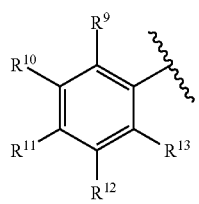

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.

J. Genus X-Pyrimidone Morpholine Fusion Heterocycle Linker Acrylate Functionalized In some embodiments, there are provided compounds of Formula (X):

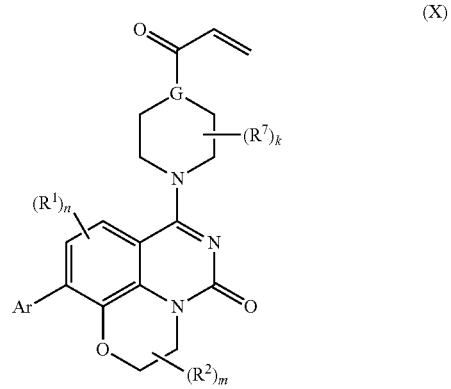

wherein:
G is selected from the group consisting of N, CH, and

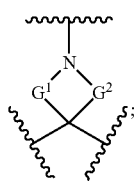

wherein G$^1$ and G$^2$ are independently (CH$_2$)$_q$, where q is 1 or 2;
each R$^1$ is an optional substitution independently is selected from the group consisting of alkyl, cyano, cycloalkyl, halo, haloalkyl, trifluoromethyl, and alkoxy;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
n is an integer from 0 to 2;
R$^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 4;
wherein k is an integer from 0 to 4; and each R$^7$ is independently selected from methyl, and cyanomethyl; and wherein the acrylyl moiety linked to G is optionally substituted.

In some embodiments, m is 0. In some embodiments, m is 1.

In one or more of the preceding embodiments, Ar creates axial asymmetry.

In one or more of the preceding embodiments, the compound is a single rotamer.

In one or more of the preceding embodiments, Ar is:

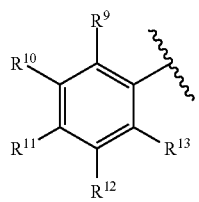

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

K. Genus XI-Pyrimidone Substituted Morpholine Heterocycle Linker Acrylate Functionalized In some embodiments, there are provided compounds of Formula (XI):

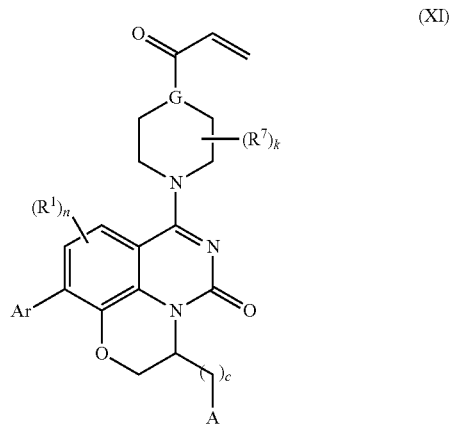

(XI)

wherein:

G is selected from the group consisting of N, CH, and

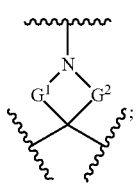

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

wherein k is an integer from 0 to 4; and each $R^7$ is independently selected from methyl, and cyanomethyl; and wherein the acrylyl moiety linked to G is optionally substituted.

In some embodiments, Ar creates axial asymmetry.

In one or more of the preceding embodiments, the compound is a single rotamer.

In one or more of the preceding embodiments, Ar is:

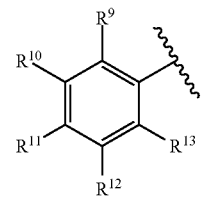

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

L. Genus XII-Pyrimidone Unsubstituted Morpholine Heterocycle Linker Acrylate Functionalized In some embodiments, there are provided compounds of Formula (XII):

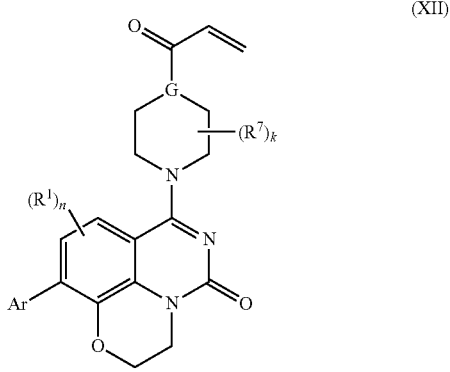

(XII)

wherein:

G is selected from the group consisting of N, CH, and

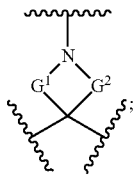

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

wherein k is an integer from 0 to 4; and each $R^7$ is independently selected from methyl, and cyanomethyl; and wherein the acrylyl moiety linked to G is optionally substituted.

In some embodiments, Ar creates axial asymmetry.

In one or more of the preceding embodiments, the compound is a single rotamer.

In one or more of the preceding embodiments, Ar is:

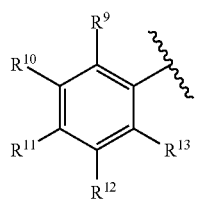

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

M. Genus XIII-Pyrimidone Unsubstituted Morpholine Piperazine Linker Acrylate Functionalized In some embodiments, there are provided compounds of Formula (XIII):

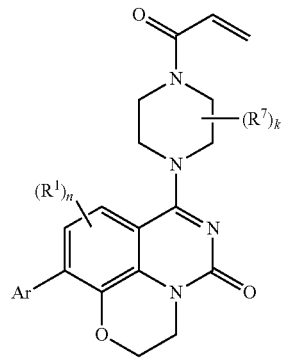

(XIII)

wherein:

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

wherein k is an integer from 0 to 4; each $R^7$ is independently selected from methyl and cyanomethyl; and wherein the acrylyl moiety linked to N is optionally substituted.

In some embodiments, Ar creates axial asymmetry.

In one or more of the preceding embodiments, the compound is a single rotamer.

In one or more of the preceding embodiments, Ar is:

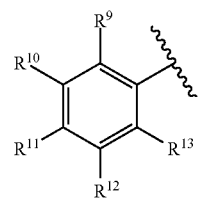

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

N. Genus XIV-Pyrimidone Substituted Morpholine Piperazine Linker Acrylate Functionalized In some embodiments, there are provided compounds of Formula (XIV):

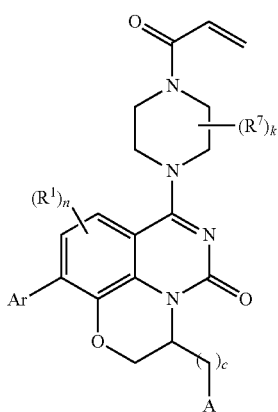

(XIV)

wherein:
  each $R^1$ is an optional substitution independently selected from the group consisting of alkyl, cyano, cycloalkyl, halo, haloalkyl, trifluoromethyl, and alkoxy;
  n is an integer from 0 to 2;
  Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
  c is an integer from 0 to 4;
  A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
  wherein k is an integer from 0 to 4; and each $R^7$ is independently selected from methyl, and cyanomethyl; and
  wherein the acrylyl moiety linked to N is optionally substituted.

In some embodiments, Ar creates axial asymmetry.

In one or more of the preceding embodiments, the compound is a single rotamer.

In one or more of the preceding embodiments, Ar is:

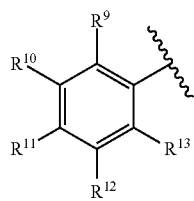

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

O. Genus XV-Pyrimidone Substituted Morpholine Substituted Piperazine Linker Acrylate Functionalized In some embodiments, there are provided compounds of Formula (XV):

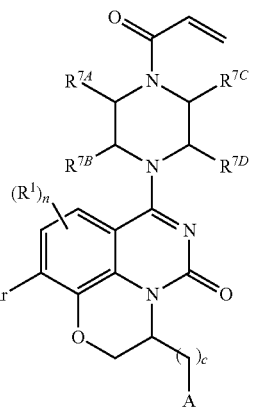

(XV)

wherein:
  each $R^1$ is an optional substitution independently selected from the group consisting of alkyl, cyano, cycloalkyl, halo, haloalkyl, trifluoromethyl, and alkoxy;
  n is an integer from 0 to 2;
  Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
  c is an integer from 0 to 4;
  A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
  $R^{7A}$, $R^{7B}$, $R^{7C}$, and $R^{7D}$ are independently selected from hydrogen, alkyl, and cyanoalkyl; and
  wherein the acrylyl moiety linked to N is optionally substituted.

In some embodiments, Ar creates axial asymmetry.

In one or more of the preceding embodiments, the compound is a single rotamer.

In one or more of the preceding embodiments, Ar is:

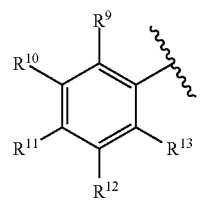

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

In one or more of the preceding embodiments, $R^{7B}$ is methyl.

In one or more of the preceding embodiments, a stereogenic center created by the $R^{7B}$ methyl group is in the R-configuration. In one or more of the preceding embodiments, a stereogenic center created by the $R^{7B}$ methyl group is in the S-configuration.

In one or more of the preceding embodiments, $R^{7C}$ is methyl.

In one or more of the preceding embodiments, a stereogenic center created by the $R^{7C}$ methyl group is in the R-configuration. In one or more of the preceding embodiments, a stereogenic center created by the $R^{7C}$ methyl group is in the S-configuration.

In one or more of the preceding embodiments, $R^{7D}$ is hydrogen.

In one or more of the preceding embodiments, $R^{1a}$ is cyanomethyl.

In one or more of the preceding embodiments, a stereogenic center created by the cyanomethyl group is in the R-configuration. In one or more of the preceding embodiments, a stereogenic center created by the cyanomethyl group is in the S-configuration.

P. Genus XVI-Pyrimidone Unsubstituted Morpholine Substituted Piperazine Linker Acrylate Functionalized In some embodiments, there are provided compounds of Formula (XVI):

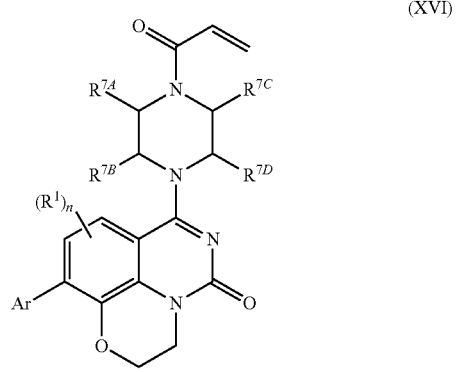

(XVI)

wherein:
  each $R^1$ is an optional substitution independently selected from the group consisting of alkyl, cyano, cycloalkyl, halo, haloalkyl, trifluoromethyl, and alkoxy;
  n is an integer from 0 to 2;
  Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

$R^{7A}$, $R^{7B}$, $R^{7C}$, and $R^{7D}$ are independently selected from hydrogen, alkyl, and cyanoalkyl; and wherein the acrylyl moiety linked to N is optionally substituted.

In some embodiments, Ar creates axial asymmetry.

In one or more of the preceding embodiments, the compound is a single rotamer.

In one or more of the preceding embodiments, Ar is:

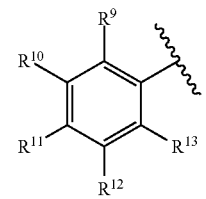

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

In one or more of the preceding embodiments, $R^{7B}$ is methyl.

In one or more of the preceding embodiments, a stereogenic center created by the $R^{7B}$ methyl group is in the R-configuration. In one or more of the preceding embodiments, a stereogenic center created by the $R^{7B}$ methyl group is in the S-configuration.

In one or more of the preceding embodiments, $R^{7C}$ is methyl.

In one or more of the preceding embodiments, a stereogenic center created by the $R^{7C}$ methyl group is in the R-configuration. In one or more of the preceding embodiments, a stereogenic center created by the $R^{7C}$ methyl group is in the S-configuration.

In one or more of the preceding embodiments, $R^{7D}$ is hydrogen.

In one or more of the preceding embodiments, $R^{1a}$ is cyanomethyl.

In one or more of the preceding embodiments, a stereogenic center created by the cyanomethyl group is in the R-configuration. In one or more of the preceding embodiments, a stereogenic center created by the cyanomethyl group is in the S-configuration.

Q. Genus XVII-Pyrimidone Morpholine Substituted Heterocycle Linker Arylated

In some embodiments, there are provided compounds of Formula (XVII):

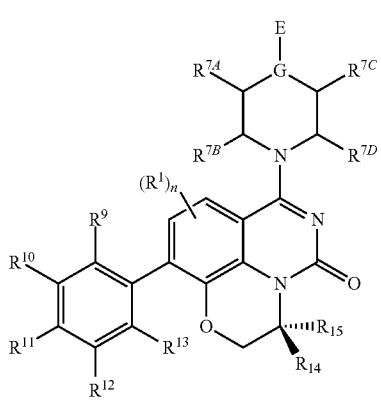

(XVII)

wherein:
E is an electrophilic moiety;
G is selected from the group consisting of N, CH, and

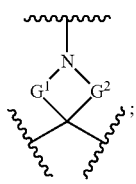

wherein $G^1$ and $G^2$ are independently $(CH_2)_q$, where q is 1 or 2;
each $R^1$ is an optional substitution independently selected from the group consisting of alkyl, cyano, cycloalkyl, halo, haloalkyl, trifluoromethyl, and alkoxy;
n is an integer from 0 to 2;
$R^{7A}$, $R^{7B}$, $R^{7C}$, and $R^{7D}$ are independently selected from hydrogen, alkyl, and cyanoalkyl;
wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.
wherein $R^{14}$ and $R^{15}$ are selected from the group consisting of hydrogen, hydroxyl, amino, N-alkylamino, dialkylamino, N-alkylamino alkyl, N,N-dialkylamino, N,N-dialkylamino alkyl, cycloalkylamino, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; with the proviso that one of $R^{14}$ or $R^{15}$ is hydrogen; and
wherein the acrylyl moiety linked to G is optionally substituted.

In some embodiments, the compound has axial asymmetry.

In one or more of the preceding embodiments, the compound is a single rotamer.

In one or more of the preceding embodiments, $R^{7B}$ is methyl.

In one or more of the preceding embodiments, a stereogenic center created by the $R^{7B}$ methyl group is in the R-configuration. In one or more of the preceding embodiments, a stereogenic center created by the $R^{7B}$ methyl group is in the S-configuration.

In one or more of the preceding embodiments, $R^{7C}$ is methyl.

In one or more of the preceding embodiments, a stereogenic center created by the $R^{7C}$ methyl group is in the R-configuration. In one or more of the preceding embodiments, a stereogenic center created by the $R^{7C}$ methyl group is in the S-configuration.

In one or more of the preceding embodiments, $R^{7D}$ is hydrogen.

In one or more of the preceding embodiments, $R^{7A}$ is cyanomethyl.

In one or more of the preceding embodiments, a stereogenic center created by the cyanomethyl group is in the R-configuration. In one or more of the preceding embodiments, a stereogenic center created by the cyanomethyl group is in the S-configuration.

1. Genus XVIIa-Rotamer Pyrimidone Morpholine Piperazine Linker Arylated

In one or more of the preceding embodiments, the compound is a single rotamer of Formula (XVIIa):

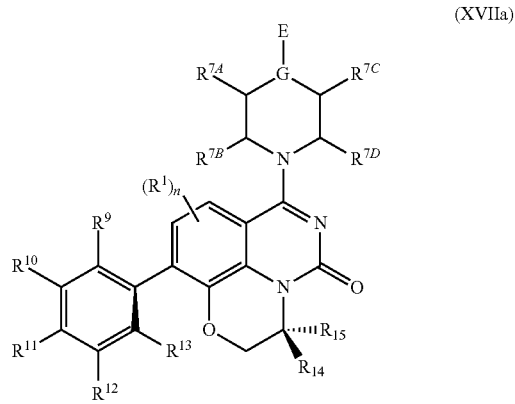

(XVIIa)

2. Genus XVIIb-Rotamer Pyrimidone Substituted Morpholine Substituted Heterocycle Linker Arylated In one or more of the preceding embodiments, the compound is a single rotamer of Formula (XVIIb):

R. Genus XVIII—Pyrimidone Unsubstituted Morpholine Piperazine Linker Acrylate Functionalized Arylated In some embodiments, there are provided compounds of Formula (XVIII):

(XVIII)

wherein:
- each $R^1$ is an optional substitution independently selected from the group consisting of alkyl, cyano, cycloalkyl, halo, haloalkyl, trifluoromethyl, and alkoxy;
- n is an integer from 0 to 2;
- $R^{7A}$, $R^{7B}$, $R^{7C}$, and $R^{7D}$ are independently selected from hydrogen, alkyl, and cyanoalkyl;
- wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.
- wherein the acrylyl moiety linked to N is optionally substituted.

In some embodiments, the compounds have axial asymmetry.

In one or more of the preceding embodiments, the compound is a single rotamer.

In one or more of the preceding embodiments, $R^{7B}$ is methyl.

In one or more of the preceding embodiments, a stereogenic center created by the $R^{7B}$ methyl group is in the R-configuration. In one or more of the preceding embodiments, a stereogenic center created by the $R^{7B}$ methyl group is in the S-configuration.

In one or more of the preceding embodiments, $R^{7C}$ is methyl.

In one or more of the preceding embodiments, a stereogenic center created by the $R^{7C}$ methyl group is in the R-configuration. In one or more of the preceding embodiments, a stereogenic center created by the $R^{7C}$ methyl group is in the S-configuration.

In one or more of the preceding embodiments, $R^{7D}$ is hydrogen.

In one or more of the preceding embodiments, $R^{7A}$ is cyanomethyl.

In one or more of the preceding embodiments, a stereogenic center created by the cyanomethyl group is in the R-configuration. In one or more of the preceding embodiments, a stereogenic center created by the cyanomethyl group is in the S-configuration.

S. Genus XIX— Pyrimidone Substituted Morpholine Substituted Piperazine Linker Acrylate Functionalized Arylated In some embodiments, there are provided compounds of Formula (XIX):

(XIX)

wherein * is a stereogenic center;
- each $R^1$ is an optional substitution independently selected from the group consisting of alkyl, cyano, cycloalkyl, halo, haloalkyl, trifluoromethyl, and alkoxy;
- n is an integer from 0 to 2;
- $R^{7A}$, $R^{7B}$, $R^{7C}$, and $R^{7D}$ are independently selected from hydrogen, alkyl, and cyanoalkyl;
- wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.
- c is an integer from 0 to 4;
- A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

wherein the acrylyl moiety linked to N is optionally substituted.

In some embodiments, the compounds have axial asymmetry.

1 In one or more of the preceding embodiments, the compound is a single rotamer.

In one or more of the preceding embodiments, $R^{7B}$ is methyl.

In one or more of the preceding embodiments, a stereogenic center created by the $R^{7B}$ methyl group is in the R-configuration. In one or more of the preceding embodiments, a stereogenic center created by the $R^{7B}$ methyl group is in the S-configuration.

In one or more of the preceding embodiments, $R^{7C}$ is methyl.

In one or more of the preceding embodiments, a stereogenic center created by the $R^{7C}$ methyl group is in the R-configuration. In one or more of the preceding embodiments, a stereogenic center created by the $R^{7C}$ methyl group is in the S-configuration.

In one or more of the preceding embodiments, $R^{7D}$ is hydrogen.

In one or more of the preceding embodiments, $R^{7A}$ is cyanomethyl.

In one or more of the preceding embodiments, a stereogenic center created by the cyanomethyl group is in the R-configuration. In one or more of the preceding embodiments, a stereogenic center created by the cyanomethyl group is in the S-configuration.

T. Genus XX— Pyridone Acrylate Functionalized Arylated

In some embodiments, there are provided compounds of Formula (XX):

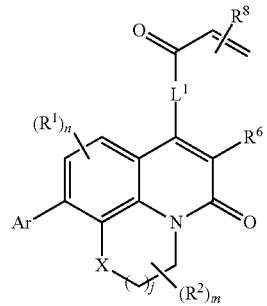

(XX)

wherein:
X is O, $S(O)_p$, $CR^3R^4$, $NR^5$, or C(O), wherein p is an integer from 0 to 2;
j is an integer from 0 to 2;
$L^1$ is linking group comprising at least one nitrogen atom;
each $R^1$ is an optional substitution independently selected from the group consisting of alkyl, cyano, cycloalkyl, halo, haloalkyl, trifluoromethyl, and alkoxy;
n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;
$R^3$, $R^4$, and $R^5$ are each independently selected from the group consisting of hydrogen alkyl, halo, alkoxy, aryl, and heteroaryl, any of which are optionally substituted;

$R^6$ is selected from the group consisting of hydrogen, alkyl, haloakyl, cyano, halo, alkoxy, aryl, heteroaryl, and trifluoromethyl;

$R^8$ is selected from the group consisting of fluorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In some embodiments, X is O.
In one or more of the preceding embodiments, j is 1.
In one or more of the preceding embodiments, m is 0. In one or more of the preceding embodiments, m is 1.
In one or more of the preceding embodiments, $L^1$ is

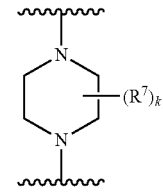

wherein k is an integer from 0 to 4; and each $R^7$ is independently selected from methyl and cyanomethyl;

In one or more of the preceding embodiments, Ar creates axial asymmetry.

In one or more of the preceding embodiments, the compound is a single rotamer.

In one or more of the preceding embodiments, Ar is:

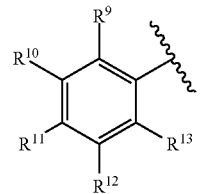

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

U. Linkers L¹
For each of the subgeneric structures disclosed hereinabove, L¹ can alternatively be selected from:
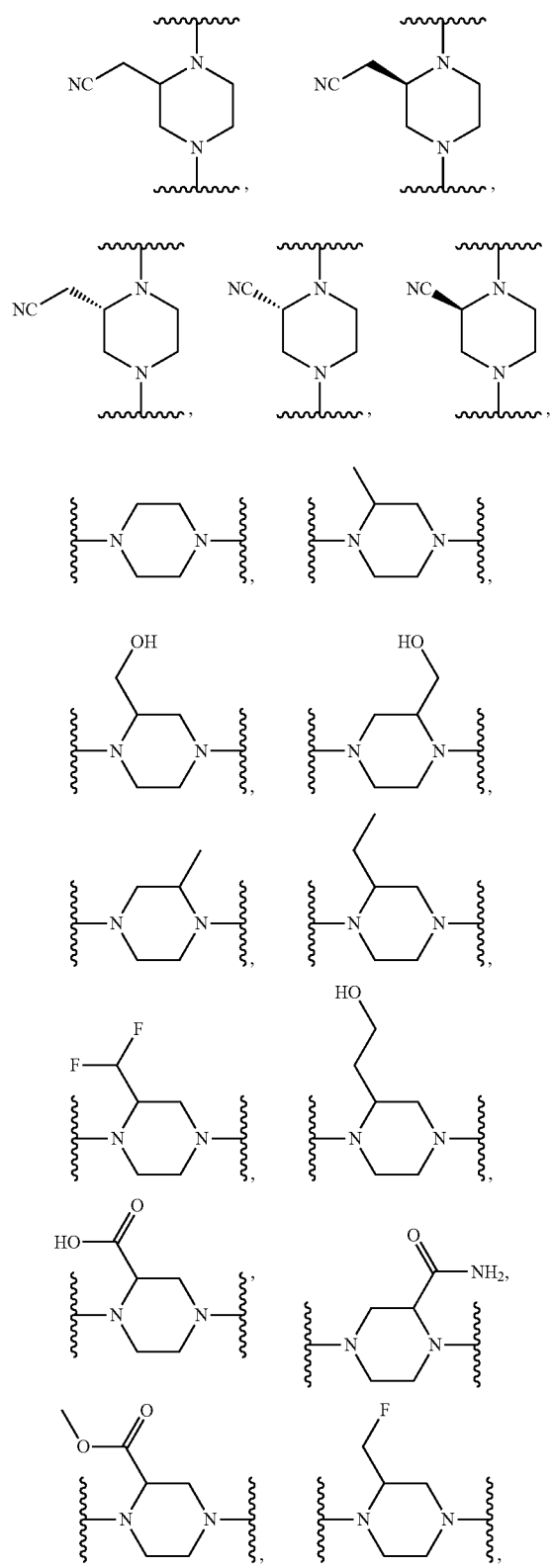
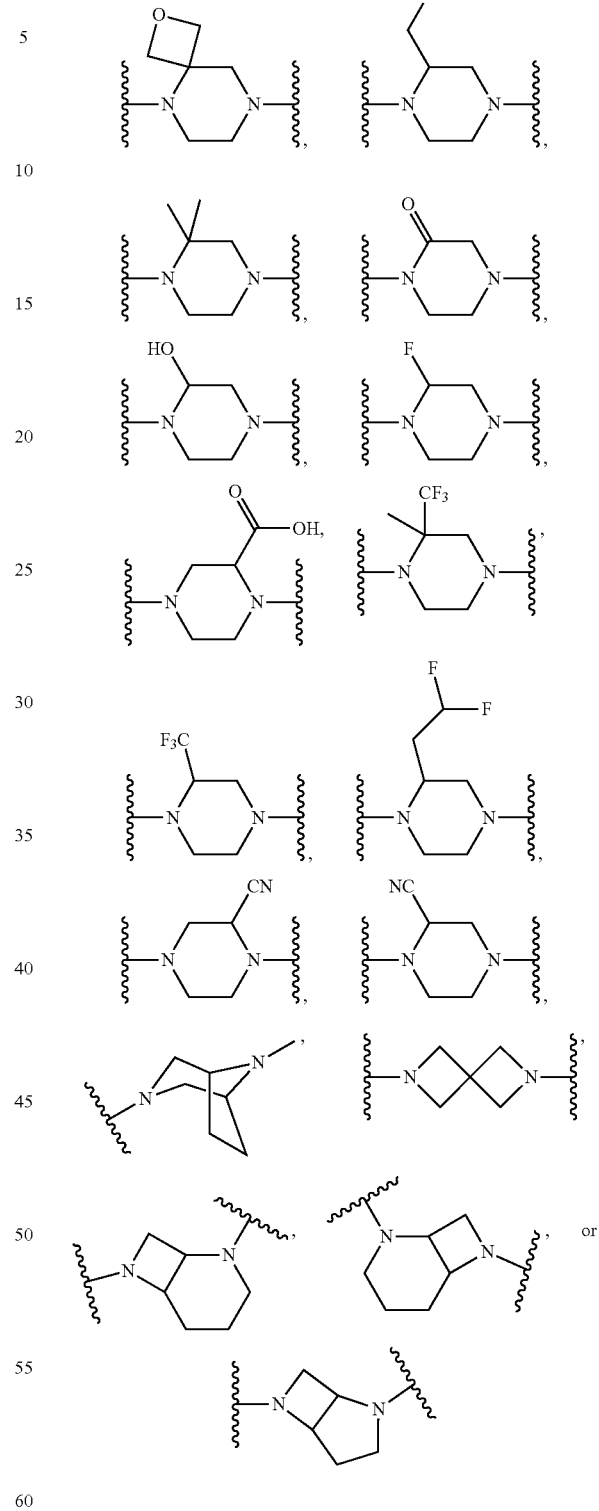
V. Electrophlic Moiety E
For each of the subgeneric structures disclosed hereinabove, electrophilic moiety E can alternatively be selected from:

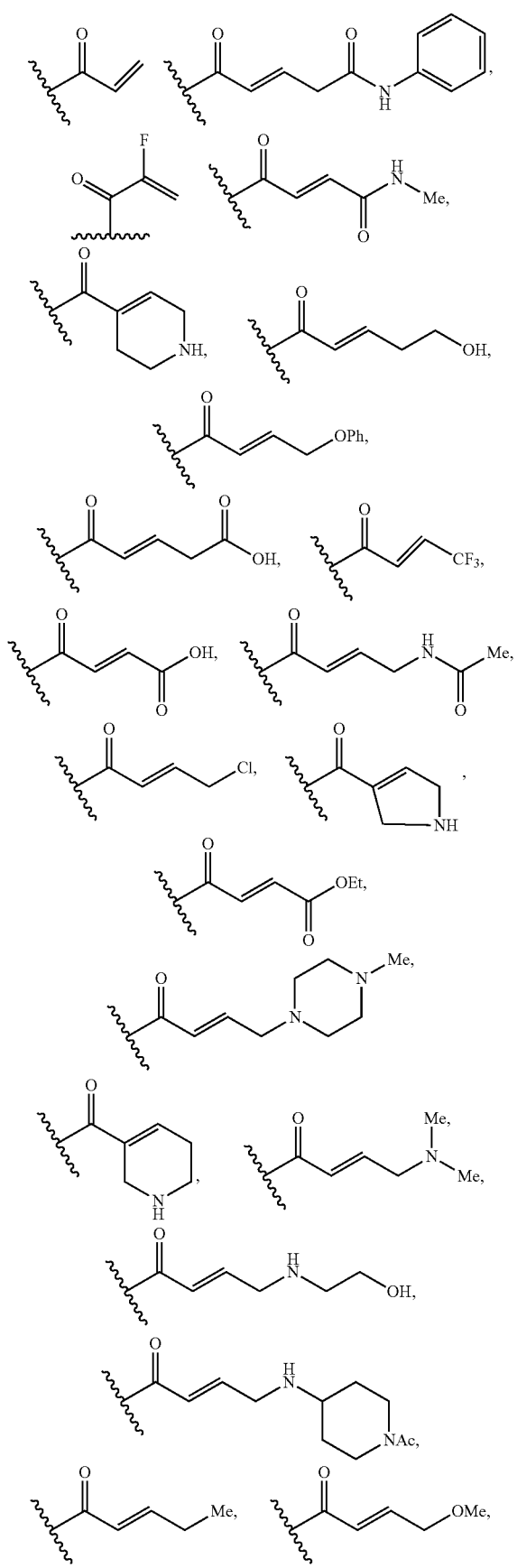
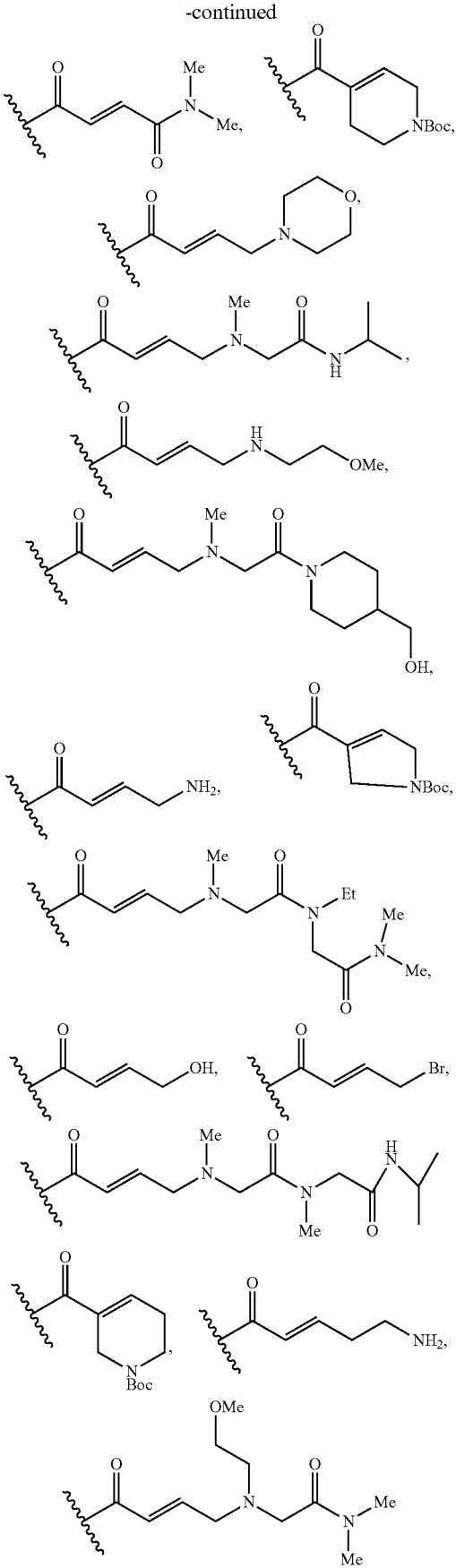

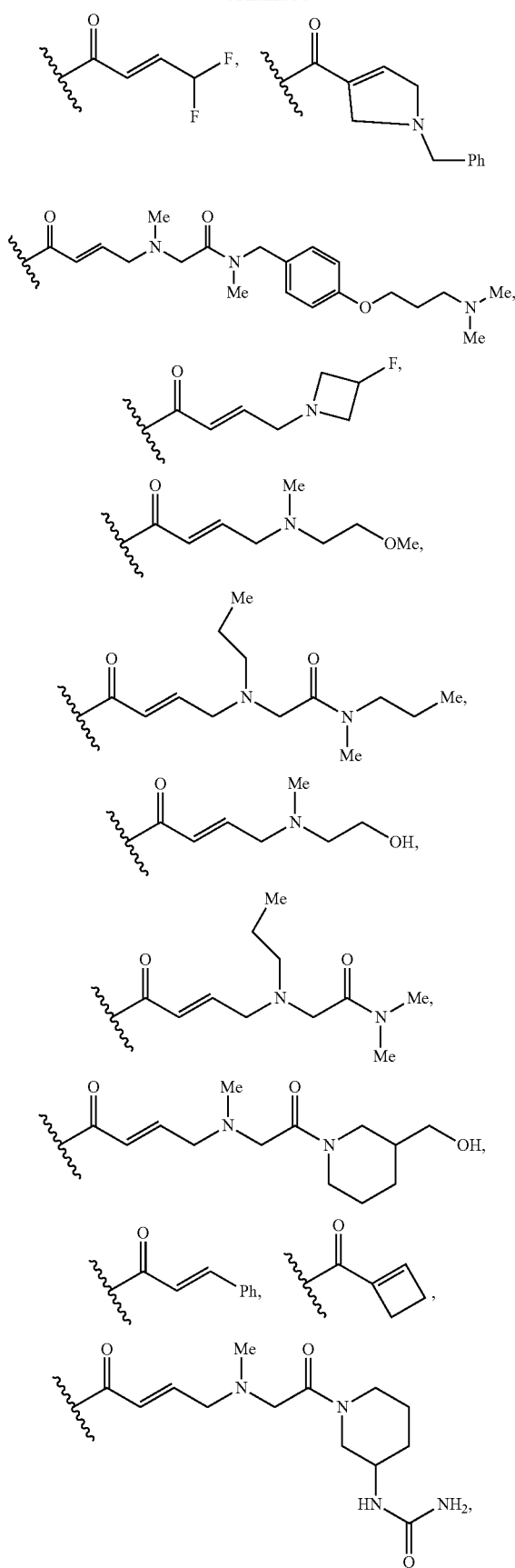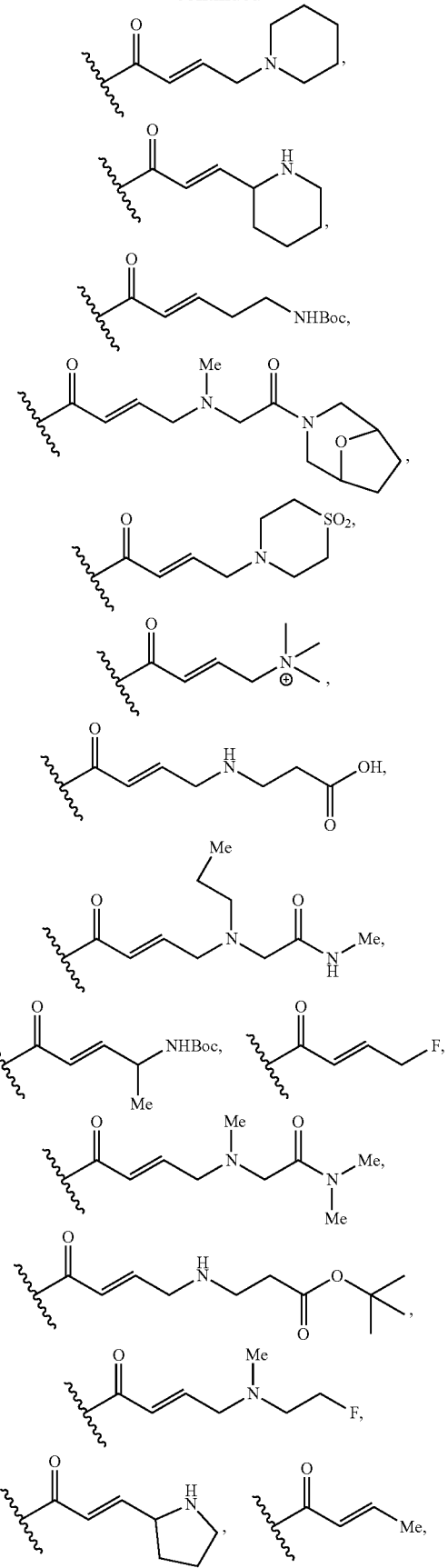

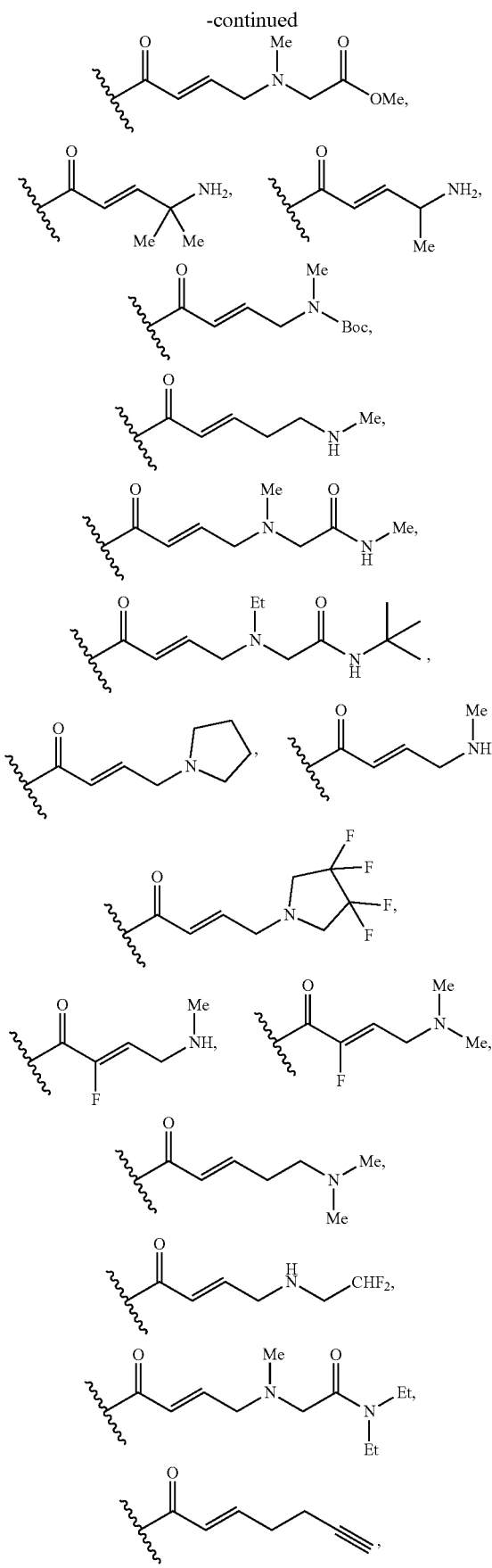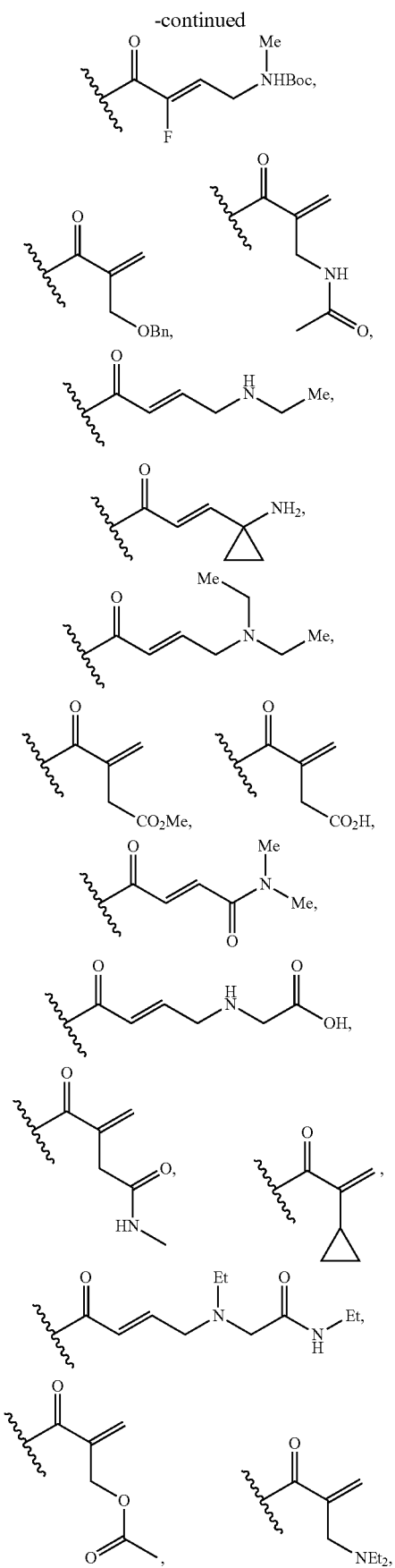

-continued
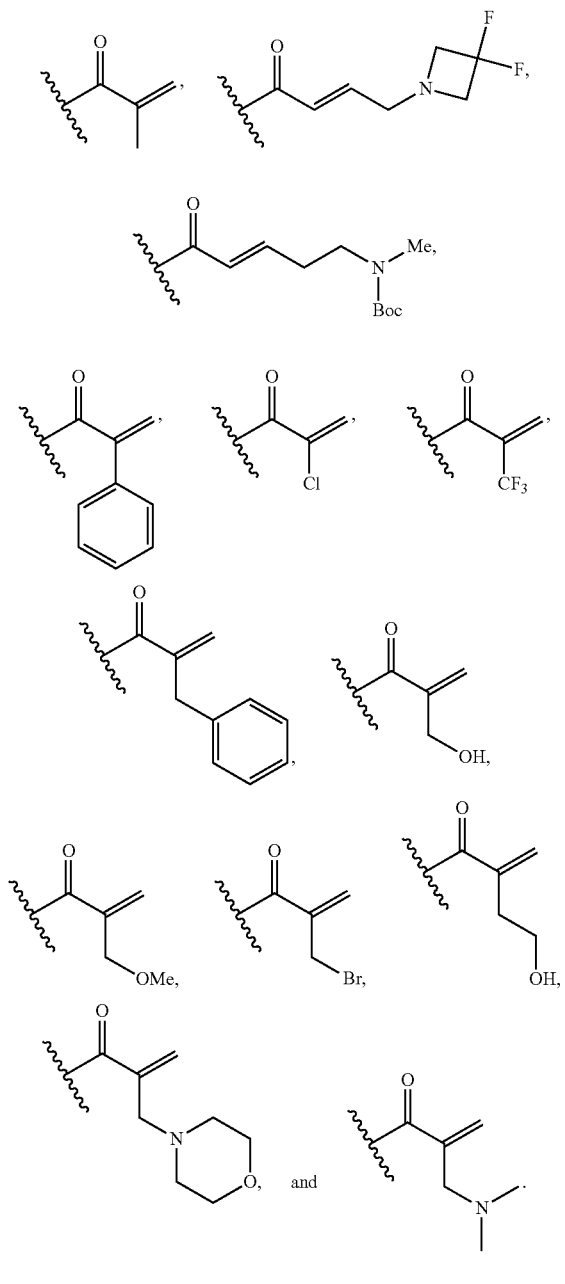
W. Linker-Electrophile Combination L¹-E
For each of the subgeneric structures disclosed hereinabove, L¹-E combined can alternatively be selected from:
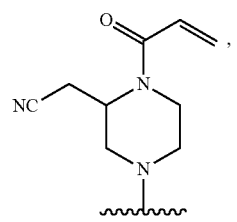 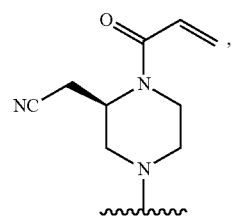
-continued
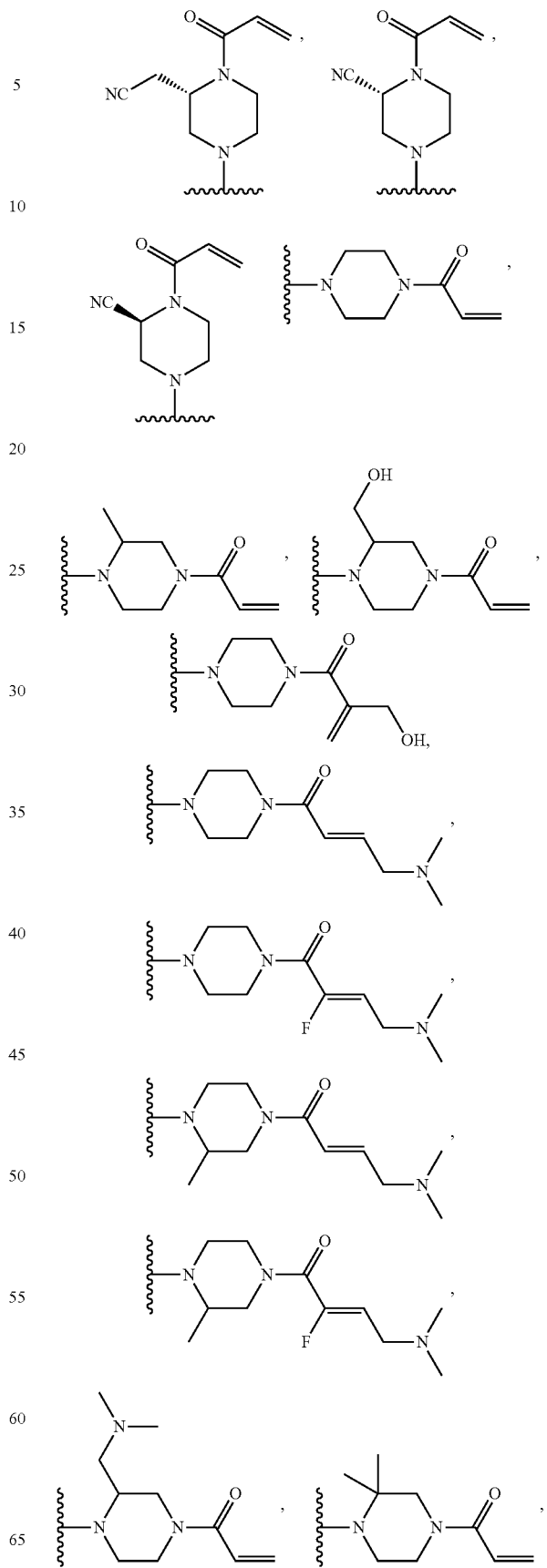

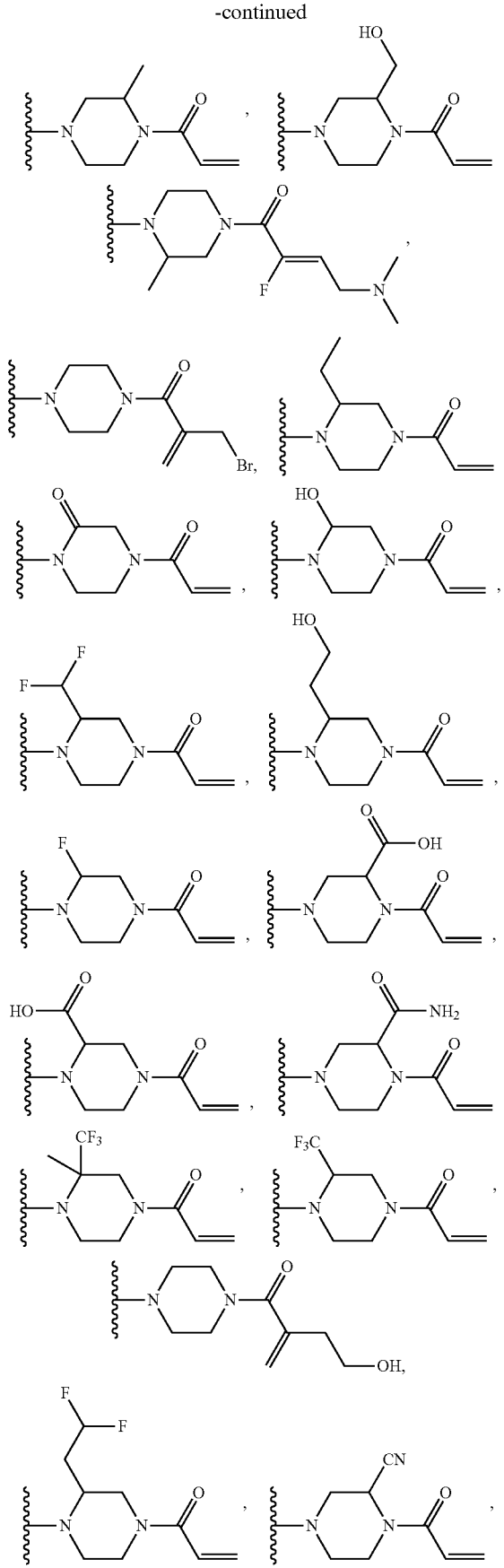
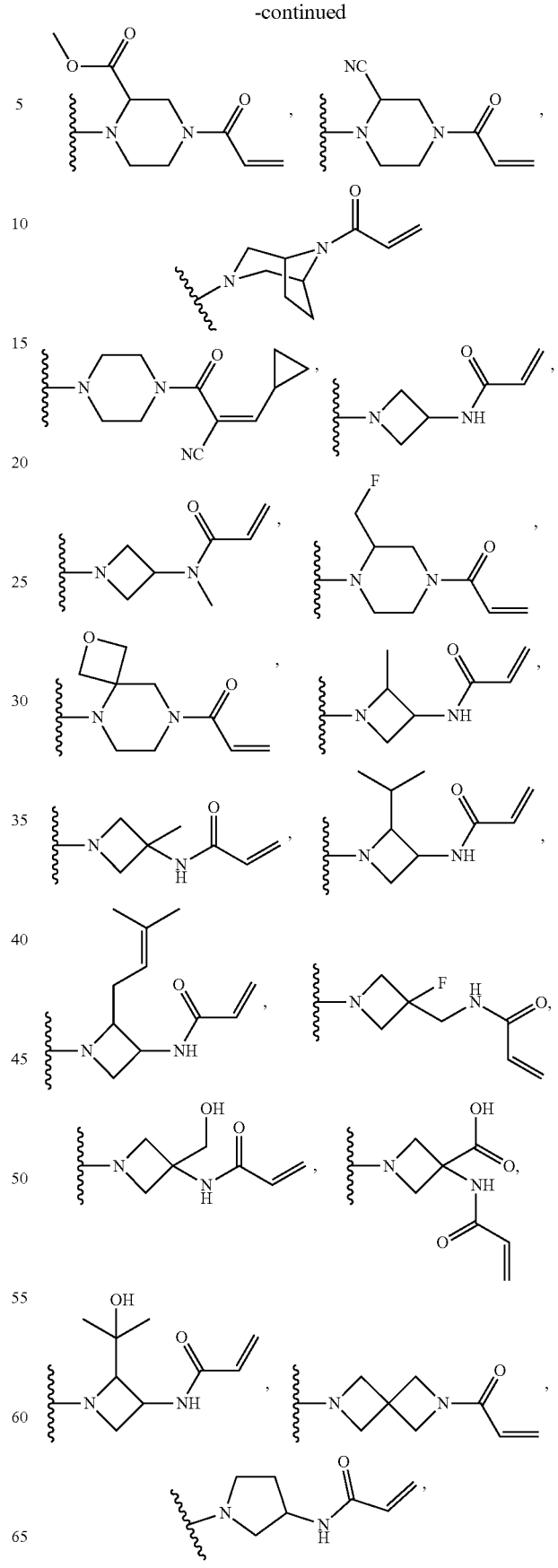

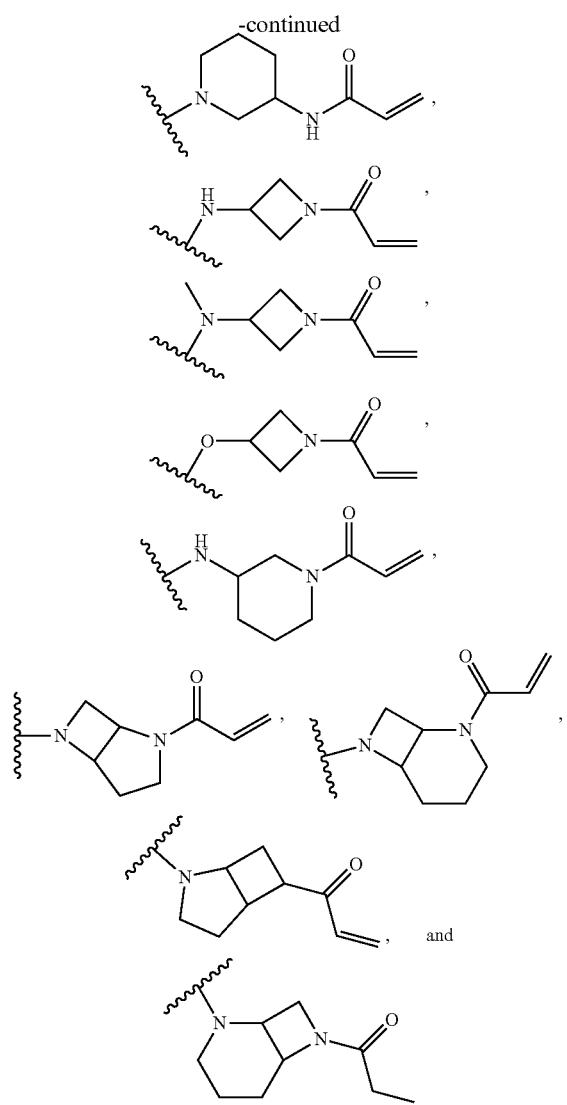

X. Aryl Groups Ar

For each of the subgeneric structures disclosed hereinabove, Ar can alternatively be selected from phenyl, naphthyl, pyridyl, indazolyl, indolyl, azaindolyl, indolinyl, benzotriazolyl, benzoxadiazolyl, imidazolyl, cinnolinyl, imdiazopyridyl, pyrazolopyridyl, quinolinyl, isoquinolinyl, quinazolinyl, quinazolinonyl, indolinonyl, isoindolinonyl, tetrahydronaphthyl, tetrahydroquinolinyl, or tetrahydroisoquinolinyl, any of which may be optionally substituted as defined herein.

For each of the subgeneric structures disclosed hereinabove, Ar can alternatively be selected from:

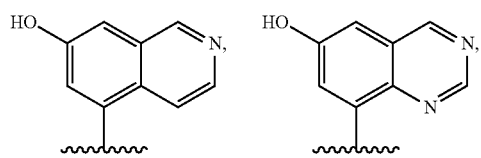

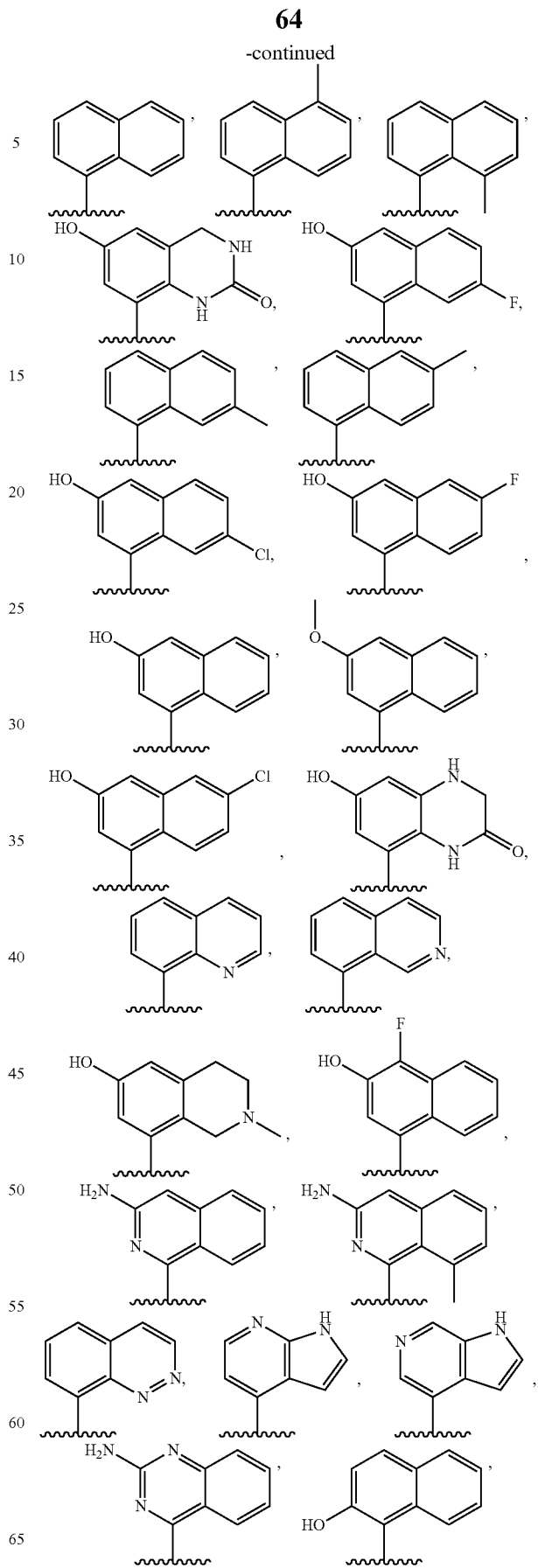

-continued
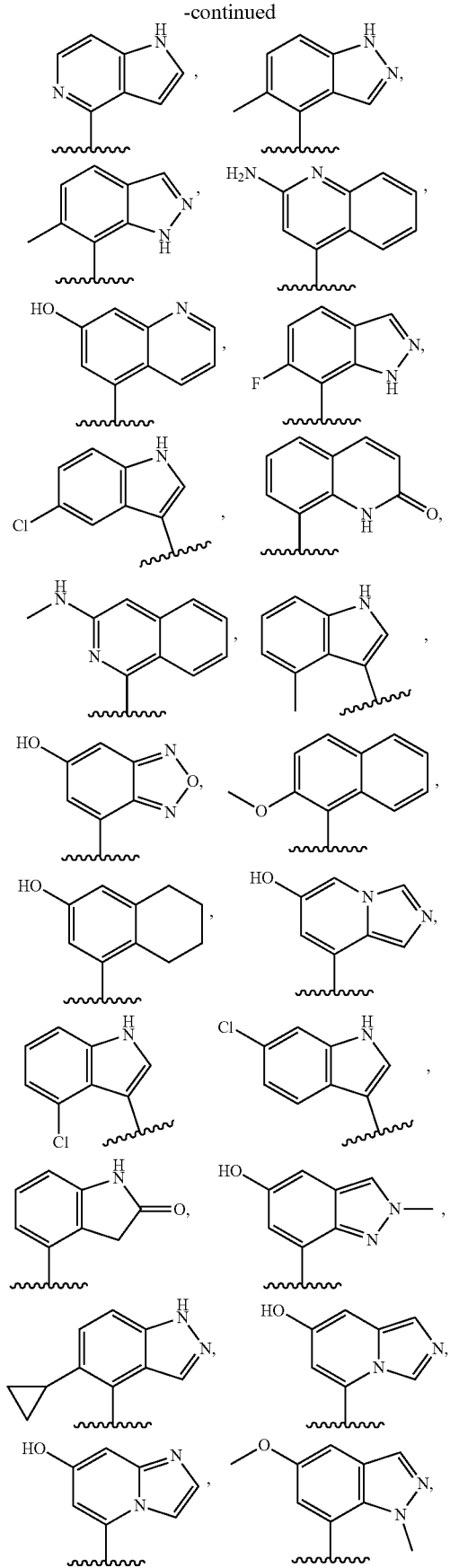
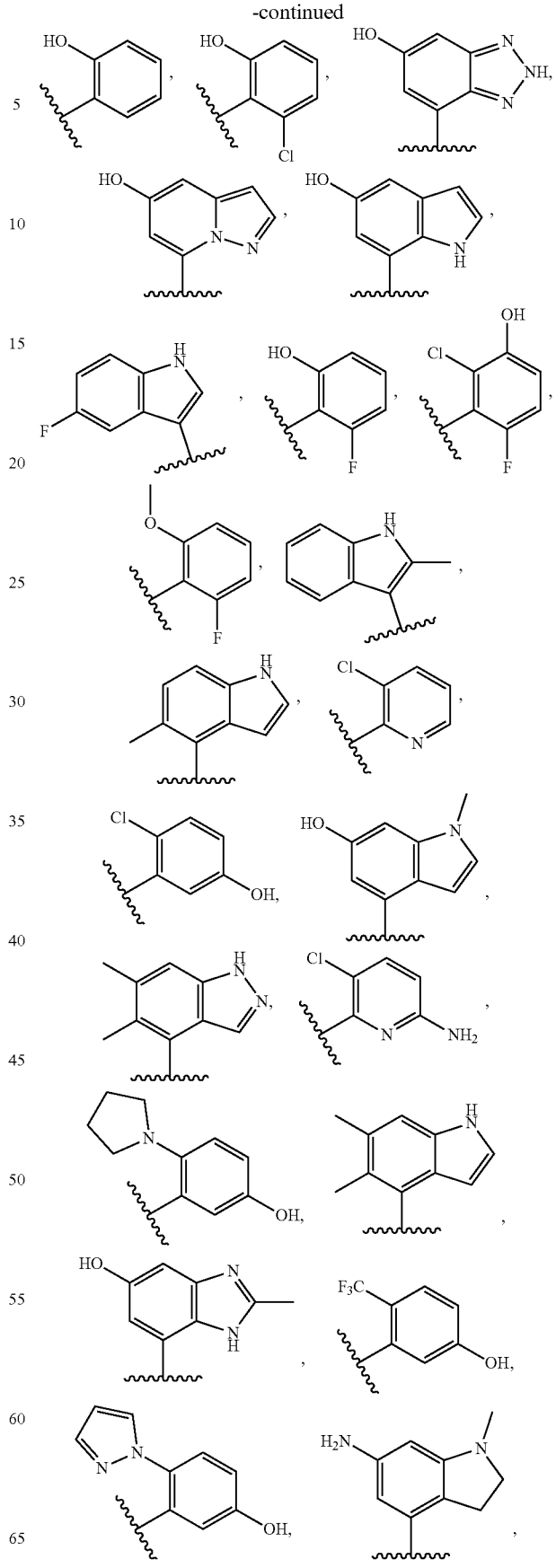

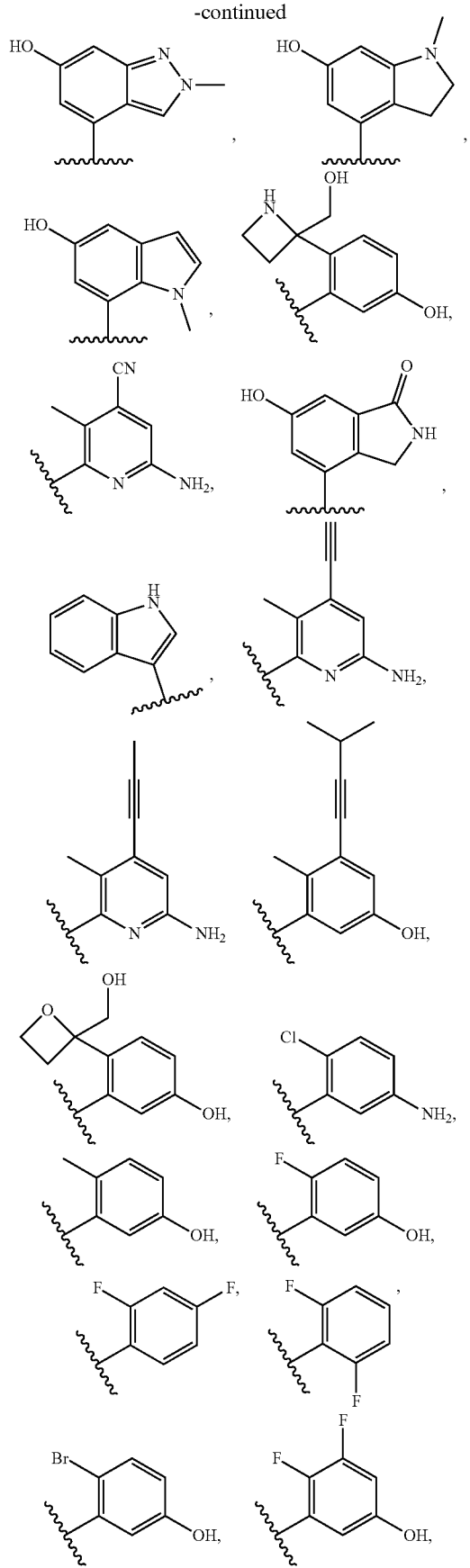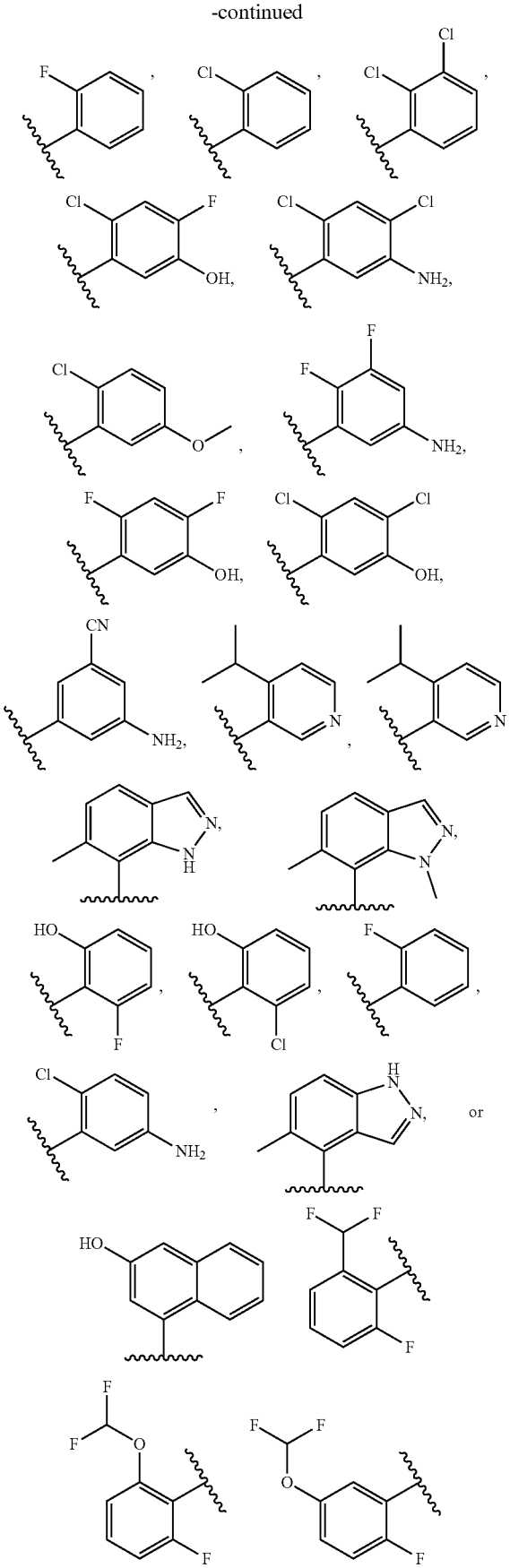

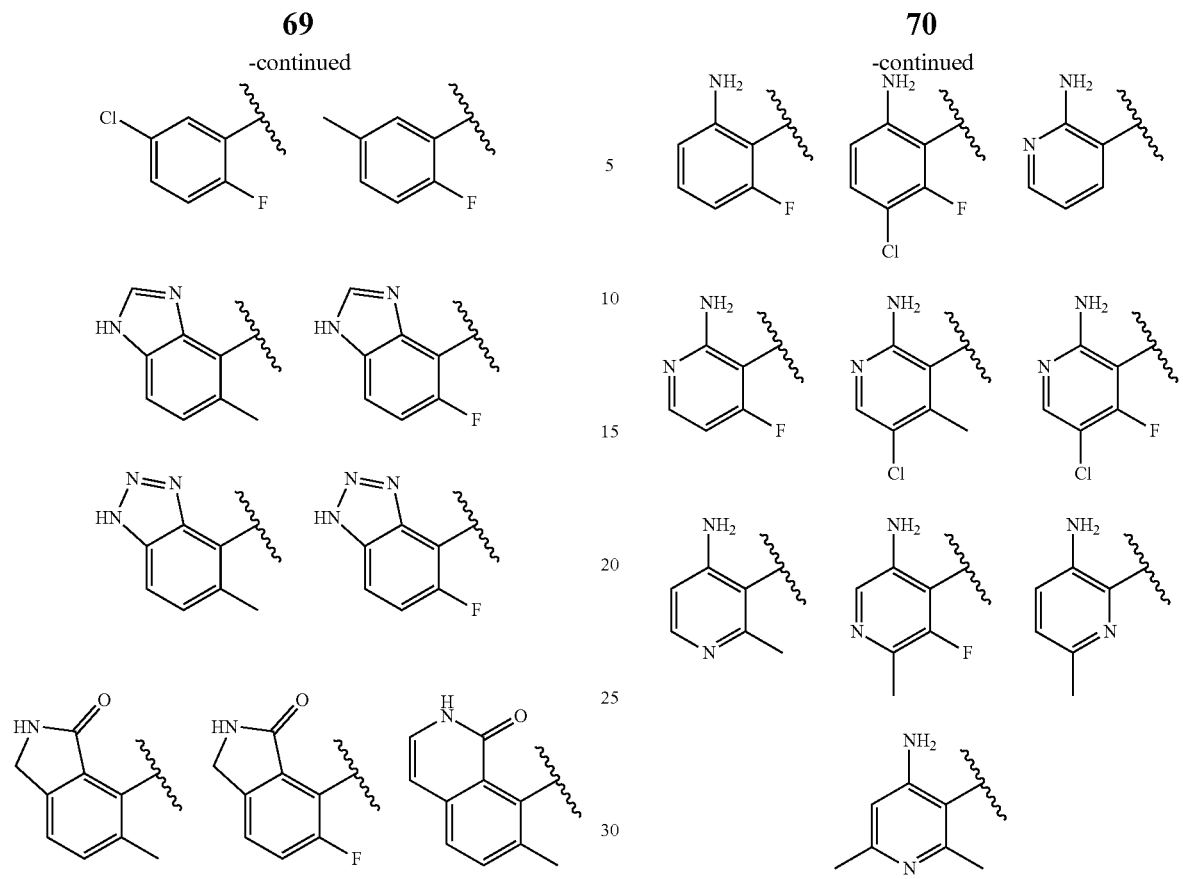

Y. Compound Tables

Embodiments disclosed herein are further illustrated by the following examples in Tables 1-4 and the Examples hereinbelow. The Tables indicate the compound number, structure, the observed mass spectral molecular weight peak, and covalent adduct formation (CAF) with a mutant G12C K-RAS after 60 minutes at a concentration of 10 micromolar.

TABLE 1

Pyrimidone Core-Morpholine Unsubstituted

| Example No. | Table Entry No. | Structure | [M + H]⁺ | % CAF (60 min) |
|---|---|---|---|---|
| 1 | 1-1 | 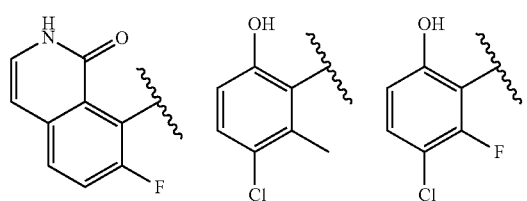 | 471.1 | 89 |

TABLE 1-continued
Pyrimidone Core-Morpholine Unsubstituted
| Example No. | Table Entry No. | Structure | [M + H]⁺ | % CAF (60 min) |
|---|---|---|---|---|
| 2 | 1-2 | 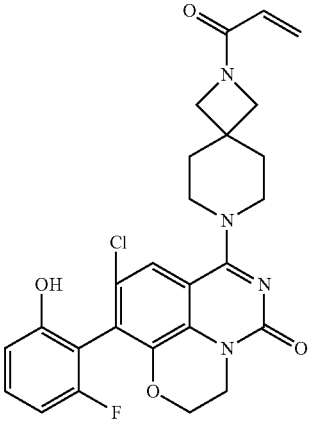 [SMILES: C=CC(=O)N1CC2(CCN(c3nc(=O)n4c5c(c(-c6c(O)cccc6F)c(Cl)cc35)OCC4)CC2)C1] | 511.2 | 42.5 |
| 3 | 1-3 | 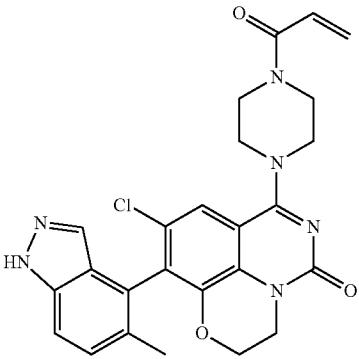 | 490.9 | 67.4 |
| 4 | 1-4 | 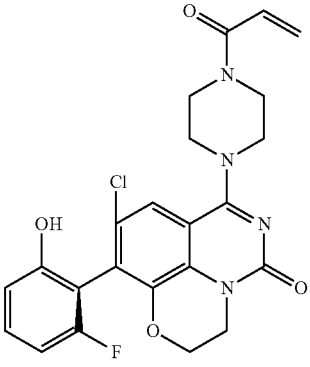 | 471.1 | ND |
| 5 | 1-5 | 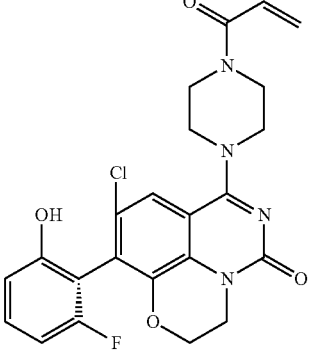 | 471.1 | 87.6 |

TABLE 1-continued

Pyrimidone Core-Morpholine Unsubstituted

| Example No. | Table Entry No. | Structure | [M + H]$^+$ | % CAF (60 min) |
|---|---|---|---|---|
| 6 | 1-6 | 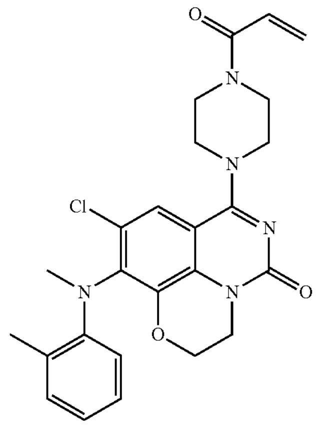 [SMILES: C=CC(=O)N1CCN(c2nc(=O)n3c4c(c(N(C)c5ccccc5C)c(Cl)cc24)OCC3)CC1] | 480.1 | 17.6 |
| 7 | 1-7 | 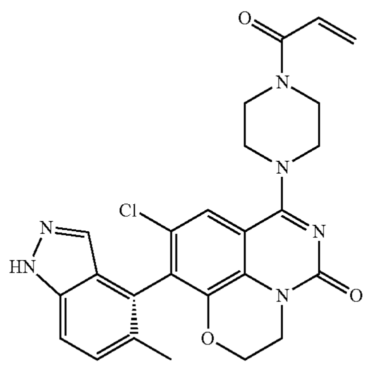 | 490.9 | 79.6 |
| 8 | 1-8 | 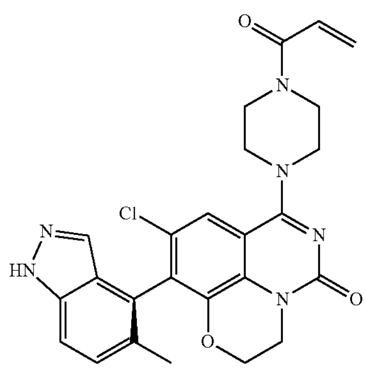 | 490.9 | 0 |
| 9 | 1-9 | 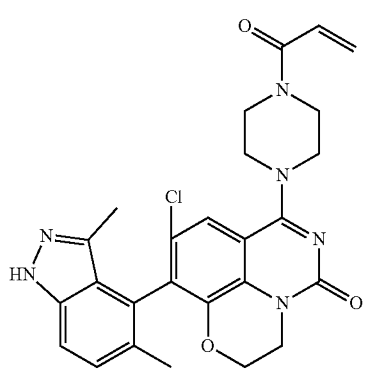 [SMILES: C=CC(=O)N1CCN(c2nc(=O)n3c4c(c(-c5c(C)ccc6[nH]nc(C)c56)c(Cl)cc24)OCC3)CC1] | 505.1 | 72.6 |

TABLE 1-continued

Pyrimidone Core-Morpholine Unsubstituted

| Example No. | Table Entry No. | Structure | [M + H]⁺ | % CAF (60 min) |
|---|---|---|---|---|
| 10 | 1-10 | 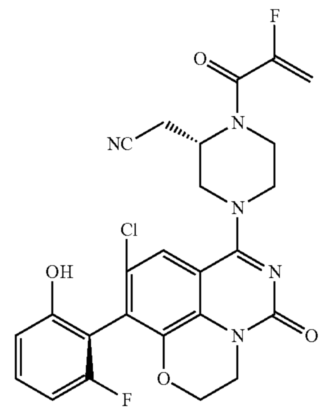 | 528.2 | 8.5 |
| 11 | 1-11 | 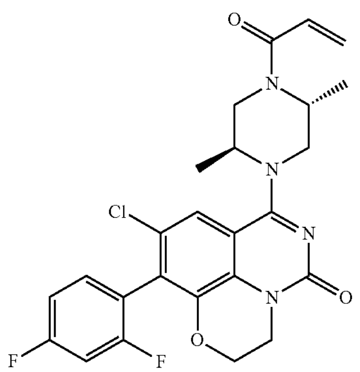 | 501.1 | 68 |
| 12 | 1-12 | 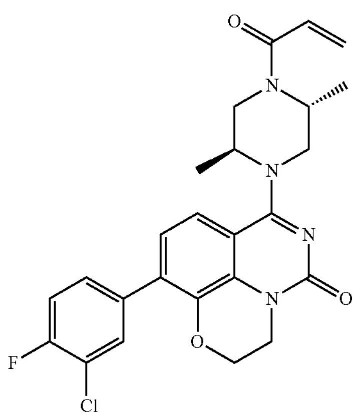 [SMILES: C=CC(=O)N1C[C@H](C)N(c2nc(=O)n3c4c(c(-c5ccc(F)c(Cl)c5)ccc24)OCC3)C[C@H]1C] | 483.1 | 0 |
| 13 | 1-13 | 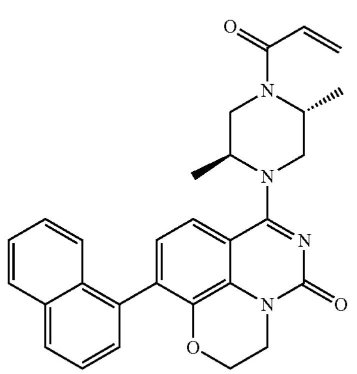 [SMILES: C=CC(=O)N1C[C@H](C)N(c2nc(=O)n3c4c(c(-c5cccc6ccccc56)ccc24)OCC3)C[C@H]1C] | 481.2 | 3 |

TABLE 1-continued

Pyrimidone Core-Morpholine Unsubstituted

| Example No. | Table Entry No. | Structure | [M + H]⁺ | % CAF (60 min) |
|---|---|---|---|---|
| 14 | 1-14 | 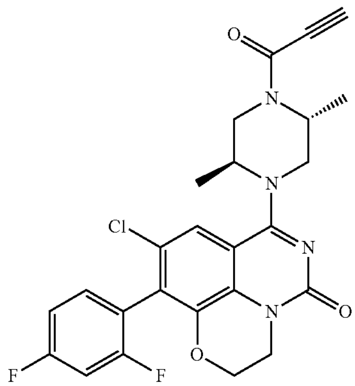 [SMILES: C#CC(=O)N1C[C@H](C)N(c2nc(=O)n3c4c(c(-c5ccc(F)cc5F)c(Cl)cc24)OCC3)C[C@H]1C] | 499.2 | 46 |
| 15 | 1-15 | 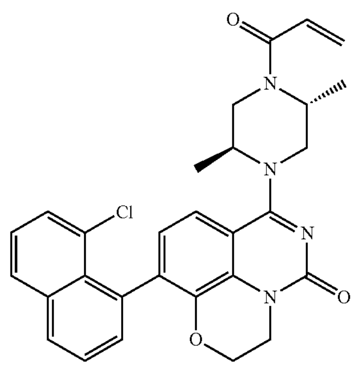 [SMILES: C=CC(=O)N1C[C@H](C)N(c2nc(=O)n3c4c(c(-c5cccc6cccc(Cl)c56)ccc24)OCC3)C[C@H]1C] | 515.2 | 0 |
| 16 | 1-16 | 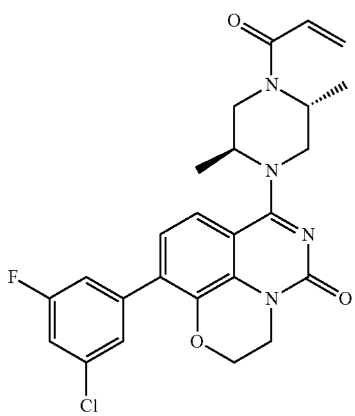 [SMILES: C=CC(=O)N1C[C@H](C)N(c2nc(=O)n3c4c(c(-c5cc(F)cc(Cl)c5)ccc24)OCC3)C[C@H]1C] | 483.1 | 0 |
| 17 | 1-17 | 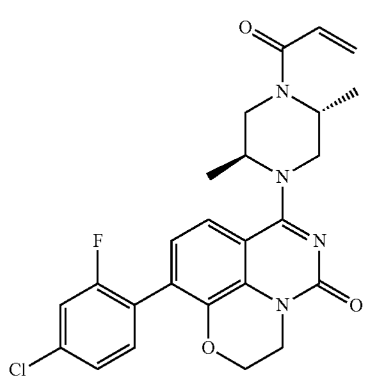 [SMILES: C=CC(=O)N1C[C@H](C)N(c2nc(=O)n3c4c(c(-c5ccc(Cl)cc5F)ccc24)OCC3)C[C@H]1C] | 483.1 | 2 |

TABLE 1-continued

Pyrimidone Core-Morpholine Unsubstituted

| Example No. | Table Entry No. | Structure | [M + H]⁺ | % CAF (60 min) |
|---|---|---|---|---|
| 18 | 1-18 | 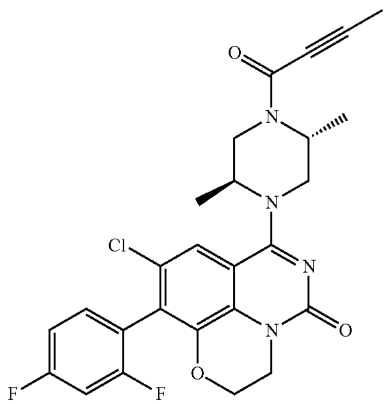 [SMILES: CC#CC(=O)N1C[C@H](C)N(c2nc(=O)n3c4c(c(-c5ccc(F)cc5F)c(Cl)cc24)OCC3)C[C@H]1C] | 513.1 | |
| 19c | 1-19 | 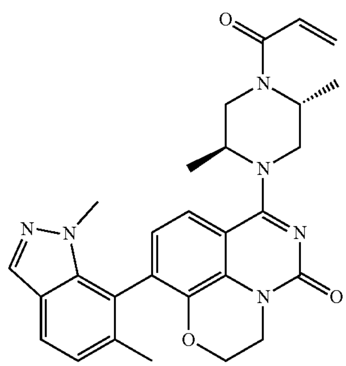 [SMILES: C=CC(=O)N1C[C@H](C)N(c2nc(=O)n3c4c(c(-c5c(C)ccc6cnn(C)c56)ccc24)OCC3)C[C@H]1C] | 499.3 | |

TABLE 2

Pyrimidone Core-Morpholine Substituted

| Example No. | Table Entry No. | Structure | [M + H]⁺ | % CAF (60 min) |
|---|---|---|---|---|
| 20 | 2-1 | 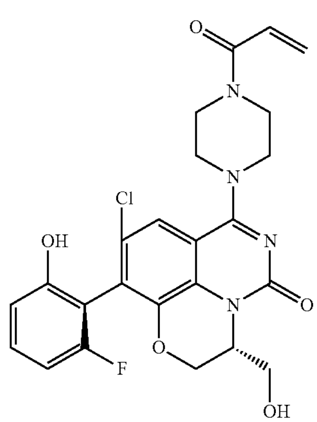 | 500.9 | 0 |

TABLE 2-continued
Pyrimidone Core-Morpholine Substituted
| Example No. | Table Entry No. | Structure | [M + H]⁺ | % CAF (60 min) |
|---|---|---|---|---|
| 21 | 2-2 | 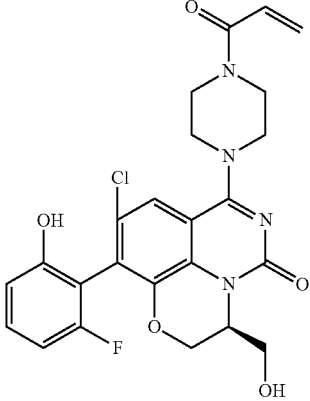 [SMILES: C=CC(=O)N1CCN(c2nc(=O)n3c4c(c(-c5c(O)cccc5F)c(Cl)cc24)OC[C@@H]3CO)CC1] | 500.9 | 72.8 |
| 22 | 2-3 | 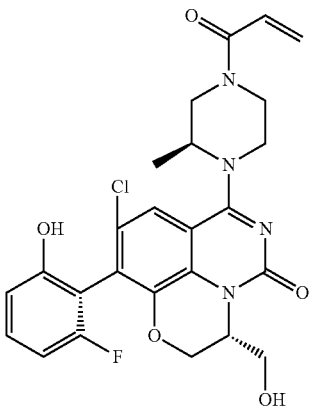 | 515.2 | 87.6 |
| 23 | 2-4 | 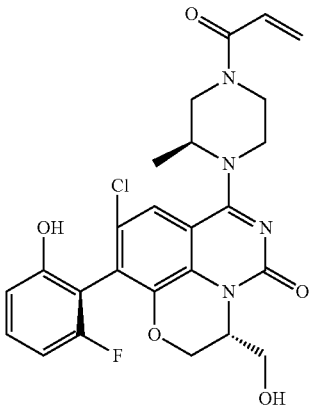 | 515.2 | 0 |

TABLE 2-continued

| | Pyrimidone Core-Morpholine Substituted | | | |
|---|---|---|---|---|
| Example No. | Table Entry No. | Structure | [M + H]⁺ | % CAF (60 min) |
| 24 | 2-5 | | 515.2 | 0 |
| 25 | 2-6 | | 515.2 | 84.7 |
| 26 | 2-7 | | 529.2 | 81.9 |

TABLE 2-continued

Pyrimidone Core-Morpholine Substituted

| Example No. | Table Entry No. | Structure | [M + H]⁺ | % CAF (60 min) |
|---|---|---|---|---|
| 27 | 2-8 | 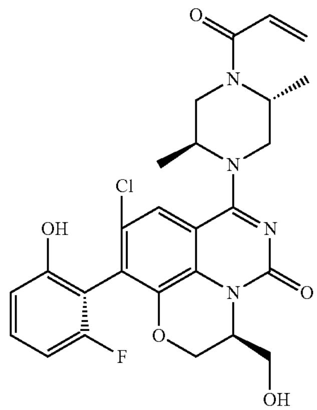 | 529.2 | 85.5 |
| 28 | 2-9 | 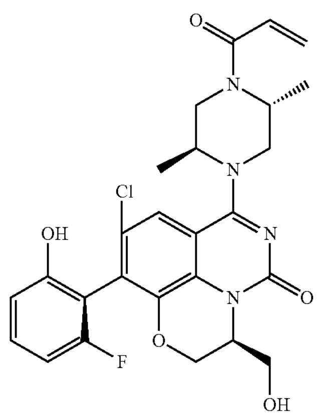 | 529.2 | 1.3 |
| 29 | 2-10 | 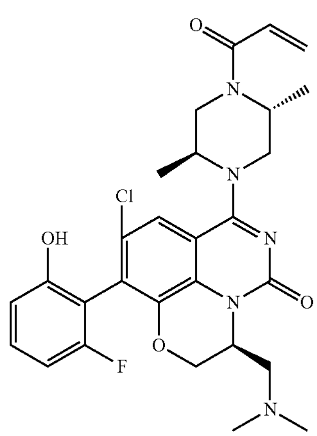 [SMILES: C=CC(=O)N1C[C@H](C)N(c2nc(=O)n3c4c(c(-c5c(O)cccc5F)c(Cl)cc24)OC[C@@H]3CN(C)C)C[C@H]1C] | 556.2 | 35.1 |

TABLE 2-continued

Pyrimidone Core-Morpholine Substituted

| Example No. | Table Entry No. | Structure | [M + H]$^+$ | % CAF (60 min) |
|---|---|---|---|---|
| 30 | 2-11 | 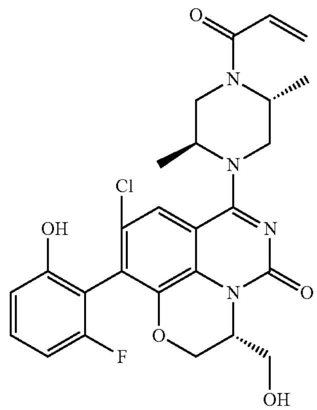 [SMILES: C=CC(=O)N1C[C@H](C)N(c2nc(=O)n3c4c(c(-c5c(O)cccc5F)c(Cl)cc24)OC[C@H]3CO)C[C@H]1C] | 529.2 | 68.1 |
| 31 | 2-12 | 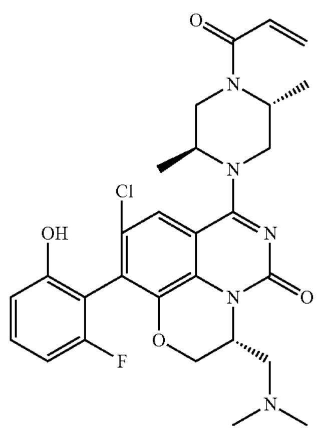 [SMILES: C=CC(=O)N1C[C@H](C)N(c2nc(=O)n3c4c(c(-c5c(O)cccc5F)c(Cl)cc24)OC[C@H]3CN(C)C)C[C@H]1C] | 556.3 | 86.6 |
| 32 | 2-13 | 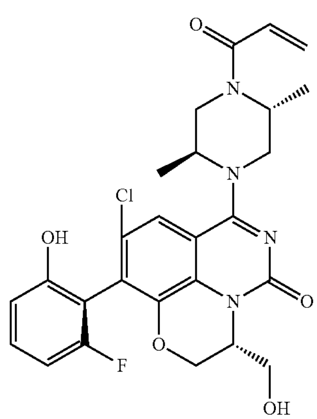 | 529.2 | 0 |

TABLE 2-continued

Pyrimidone Core-Morpholine Substituted

| Example No. | Table Entry No. | Structure | [M + H]⁺ | % CAF (60 min) |
|---|---|---|---|---|
| 33 | 2-13 | 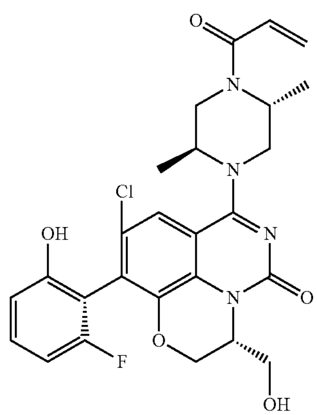 | 529.2 | 87.3 |
| 34 | 2-14 | 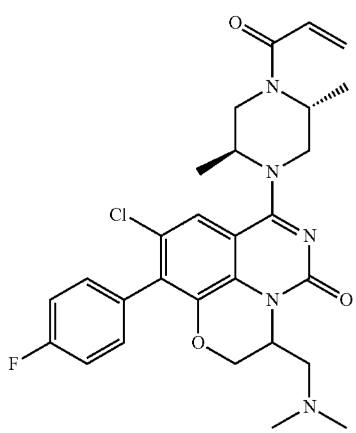 [SMILES: C=CC(=O)N1C[C@H](C)N(c2nc(=O)n3c4c(c(-c5ccc(F)cc5)c(Cl)cc24)OCC3CN(C)C)C[C@H]1C] | 540.2 | 77.4 |
| 35 | 2-15 | 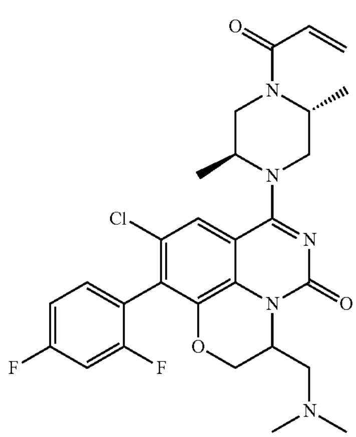 [SMILES: C=CC(=O)N1C[C@H](C)N(c2nc(=O)n3c4c(c(-c5ccc(F)cc5F)c(Cl)cc24)OCC3CN(C)C)C[C@H]1C] | 558.2 | 84.6 |

TABLE 2-continued

Pyrimidone Core-Morpholine Substituted

| Example No. | Table Entry No. | Structure | [M + H]⁺ | % CAF (60 min) |
|---|---|---|---|---|
| 36 | 2-16 | 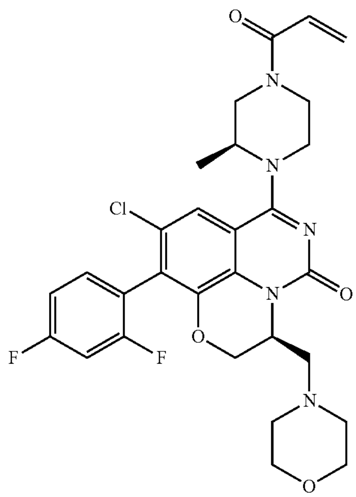 | 586.1 | |
| 37 | 2-17 | 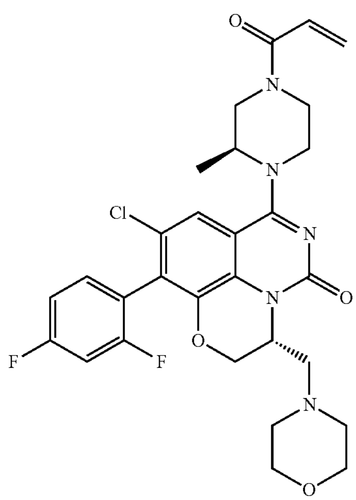 [SMILES: C=CC(=O)N1CCN(c2nc(=O)n3c4c(c(-c5ccc(F)cc5F)c(Cl)cc24)OC[C@H]3CN2CCOCC2)[C@@H](C)C1] | 586.1 | |

TABLE 3

Pyridone Core-Morpholine Unsubstituted

| Example No. | Table Entry No. | Structure | [M + H]⁺ | CAF |
|---|---|---|---|---|
| 38 | 1 | 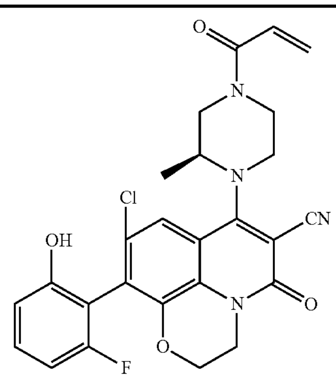 | 508.9 | 49.1 |

TABLE 3-continued

| Pyridone Core-Morpholine Unsubstituted | | | | |
|---|---|---|---|---|
| Example No. | Table Entry No. | Structure | [M + H]+ | CAF |
| 39 | 2 | | 508.9 | 0 |
| 40 | 3 | | 508.9 | 75.5 |
| 41 | 4 | | 523.2 | 22.3 |

TABLE 3-continued

Pyridone Core-Morpholine Unsubstituted

| Example No. | Table Entry No. | Structure | [M + H]⁺ | CAF |
|---|---|---|---|---|
| 42 | 5 | 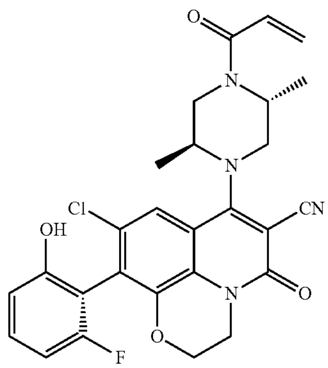 | 515.2 | 0 |
| 43 | 6 | 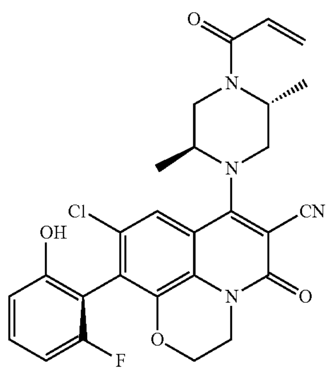 | 515.1 | 0 |
| 44 | 7 | 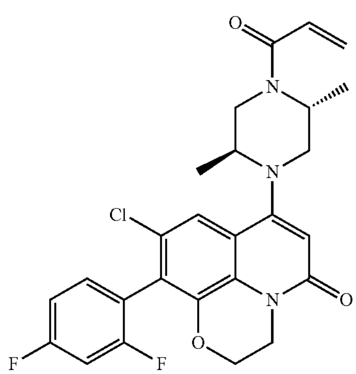 [SMILES: C=CC(=O)N1C[C@H](C)N(c2cc(=O)n3c4c(c(-c5ccc(F)cc5F)c(Cl)cc24)OCC3)C[C@H]1C] | 500.2 | 4.2 |
| 45 | 8 | 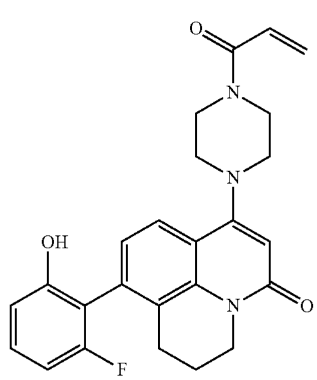 [SMILES: C=CC(=O)N1CCN(c2cc(=O)n3c4c(c(-c5c(O)cccc5F)ccc24)CCC3)CC1] | 434.2 | 1 |

TABLE 3-continued

| Pyridone Core-Morpholine Unsubstituted |||||
|---|---|---|---|---|
| Example No. | Table Entry No. | Structure | [M + H]⁺ | CAF |
| 46 | 9 | | 454.2 | 12 |
| 47 | 10 | | 436.2 | 2 |
| 48 | 11 | | 468.3 | 1 |

TABLE 4

| | | Pyridone Core-Morpholine Substituted | | |
|---|---|---|---|---|
| Example No. | Table Entry No. | Structure | [M + H]$^+$ | % CAF (60 min) |
| 49 | 1 | | — | 0 |
| 50 | 2 | | — | 3.7 |
| 51 | 3 | | — | 0 |

TABLE 4-continued

| | Pyridone Core-Morpholine Substituted | | | |
|---|---|---|---|---|
| Example No. | Table Entry No. | Structure | [M + H]⁺ | % CAF (60 min) |
| 52 | 4 | | — | 0 |
| 53 | 5 | | — | ND |
| 54 | 6 | | — | ND |

TABLE 4-continued

Pyridone Core-Morpholine Substituted

| Example No. | Table Entry No. | Structure | [M + H]⁺ | % CAF (60 min) |
|---|---|---|---|---|
| 55 | 7 | 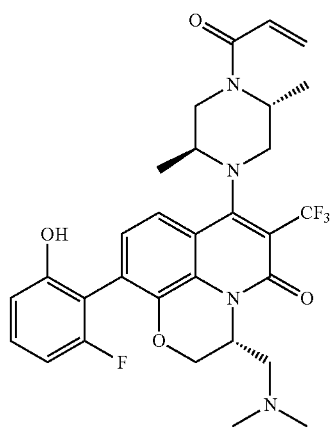 [SMILES: C=CC(=O)N1C[C@H](C)N(c2c(C(F)(F)F)c(=O)n3c4c(c(-c5c(O)cccc5F)ccc24)OC[C@H]3CN(C)C)C[C@H]1C] | — | ND |
| 56 | 8 | 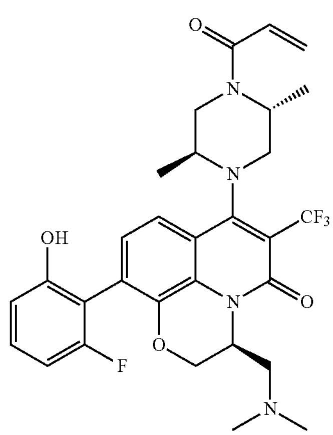 [SMILES: C=CC(=O)N1C[C@H](C)N(c2c(C(F)(F)F)c(=O)n3c4c(c(-c5c(O)cccc5F)ccc24)OC[C@@H]3CN(C)C)C[C@H]1C] | — | ND |
| 57 | 9 | 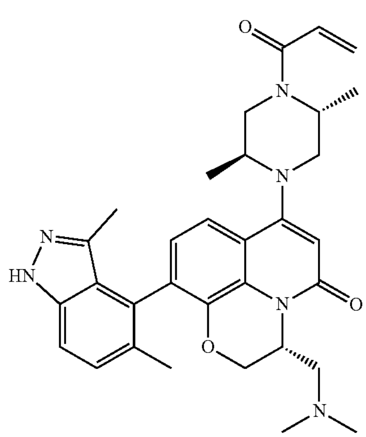 [SMILES: C=CC(=O)N1C[C@H](C)N(c2cc(=O)n3c4c(c(-c5c(C)ccc6[nH]nc(C)c56)ccc24)OC[C@H]3CN(C)C)C[C@H]1C] | — | ND |

TABLE 4-continued

Pyridone Core-Morpholine Substituted

| Example No. | Table Entry No. | Structure | [M + H]⁺ | % CAF (60 min) |
|---|---|---|---|---|
| 58 | 10 | 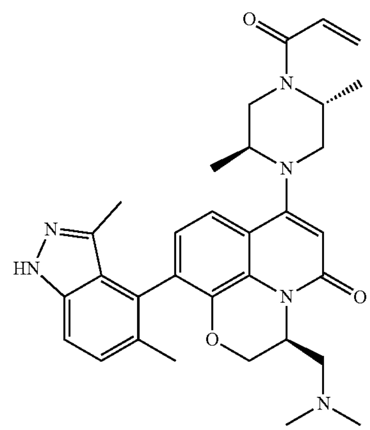 [SMILES: C=CC(=O)N1C[C@H](C)N(c2cc(=O)n3c4c(c(-c5c(C)ccc6[nH]nc(C)c56)ccc24)OC[C@@H]3CN(C)C)C[C@H]1C] | — | ND |
| 59 | 11 | 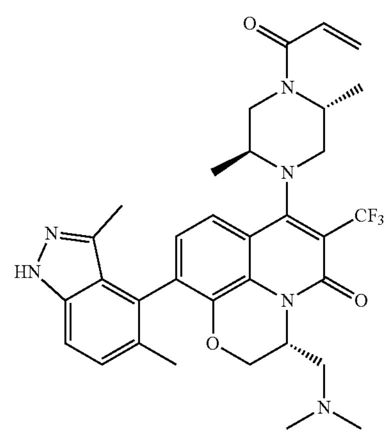 [SMILES: C=CC(=O)N1C[C@H](C)N(c2c(C(F)(F)F)c(=O)n3c4c(c(-c5c(C)ccc6[nH]nc(C)c56)ccc24)OC[C@H]3CN(C)C)C[C@H]1C] | — | ND |
| 60 | 12 | 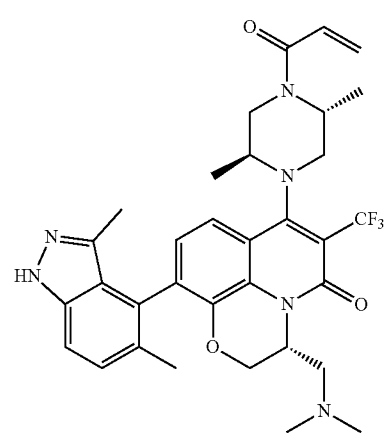 [SMILES: C=CC(=O)N1C[C@H](C)N(c2c(C(F)(F)F)c(=O)n3c4c(c(-c5c(C)ccc6[nH]nc(C)c56)ccc24)OC[C@H]3CN(C)C)C[C@H]1C] | — | ND |

TABLE 4-continued

Pyridone Core-Morpholine Substituted

| Example No. | Table Entry No. | Structure | [M + H]⁺ | % CAF (60 min) |
|---|---|---|---|---|
| 61 | 13 | 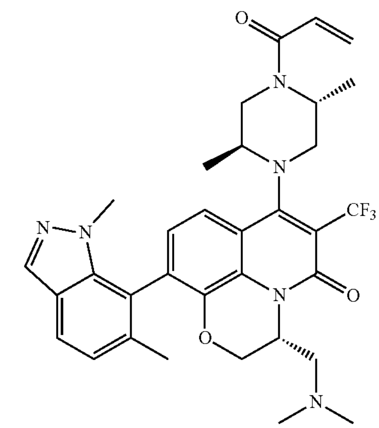 [SMILES: C=CC(=O)N1C[C@H](C)N(c2c(C(F)(F)F)c(=O)n3c4c(c(-c5c(C)ccc6cnn(C)c56)ccc24)OC[C@H]3CN(C)C)C[C@H]1C] | — | ND |
| 62 | 14 | 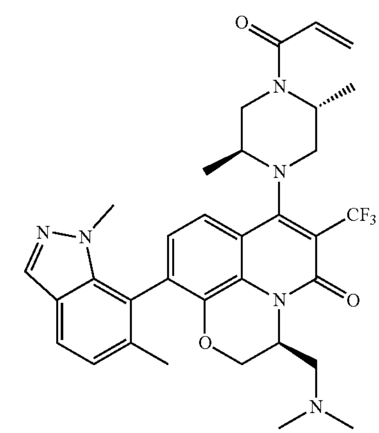 [SMILES: C=CC(=O)N1C[C@H](C)N(c2c(C(F)(F)F)c(=O)n3c4c(c(-c5c(C)ccc6cnn(C)c56)ccc24)OC[C@@H]3CN(C)C)C[C@H]1C] | — | ND |

TABLE 5

| Example No. | Structure | MW | % CAF @ 10 uM, 1 h | Name |
|---|---|---|---|---|
| 63 | 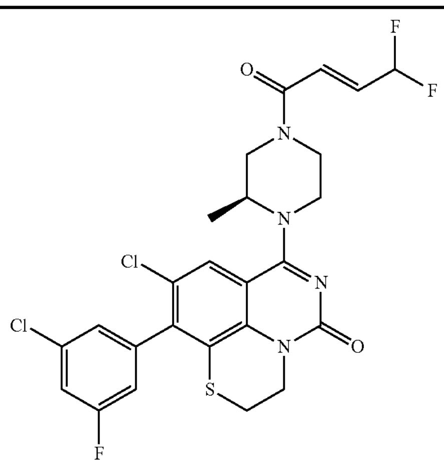 | 569.43 | 67 | (S,E)-9-chloro-10-(3-chloro-5-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 64 | 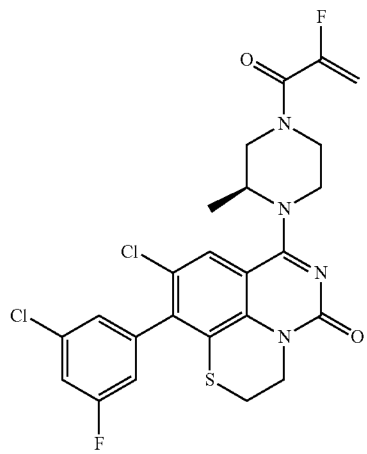 [SMILES: C=C(F)C(=O)N1CCN(c2nc(=O)n3c4c(c(-c5cc(F)cc(Cl)c5)c(Cl)cc24)SCC3)[C@@H](C)C1] | 537.41 | 75 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one |
| 65 | 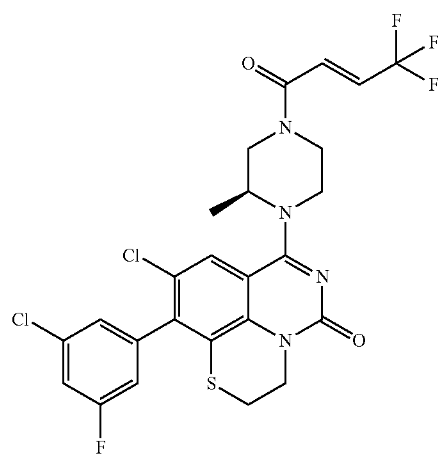 [SMILES: C[C@H]1CN(C(=O)/C=C/C(F)(F)F)CCN1c1nc(=O)n2c3c(c(-c4cc(F)cc(Cl)c4)c(Cl)cc13)SCC2] | 587.42 | 3 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one |
| 66 | 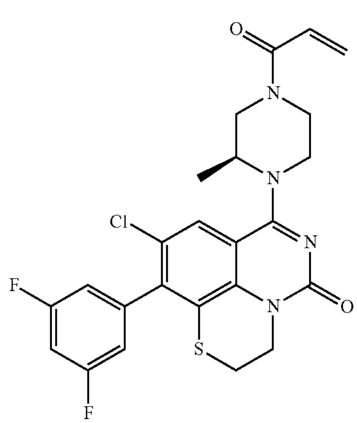 [SMILES: C=CC(=O)N1CCN(c2nc(=O)n3c4c(c(-c5cc(F)cc(F)c5)c(Cl)cc24)SCC3)[C@@H](C)C1] | 502.96 | 70 | (S)-7-(4-acryloyl-2-methylpiperazin-1-yl)-9-chloro-10-(3,5-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 67 | 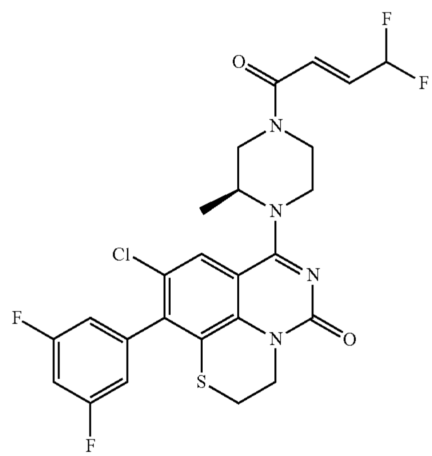 [SMILES: C[C@H]1CN(C(=O)/C=C/C(F)F)CCN1c1nc(=O)n2c3c(c(-c4cc(F)cc(F)c4)c(Cl)cc13)SCC2] | 552.97 | 91 | (S,E)-9-chloro-7-(4-(4,4-difluorobut-2-enoyl)-2-methylpiperazin-1-yl)-10-(3,5-difluorophenyl)-2,3-dihydro-5H-[1,4]thiazino[2,3,4-ij]quinazolin-5-one |
| 68 | 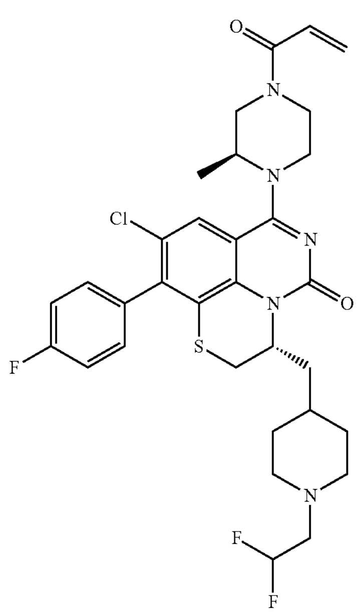 [SMILES: C=CC(=O)N1CCN(c2nc(=O)n3c4c(c(-c5ccc(F)cc5)c(Cl)cc24)SC[C@H]3CC2CCN(CC(F)F)CC2)[C@@H](C)C1] | 646.17 | 87 | (R)-7-((S)-4-acryloyl-2-methylpiperazin-1-yl)-9-chloro-3-((1-(2,2-difluoroethyl)piperidin-4-yl)methyl)-10-(4-fluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 69 | 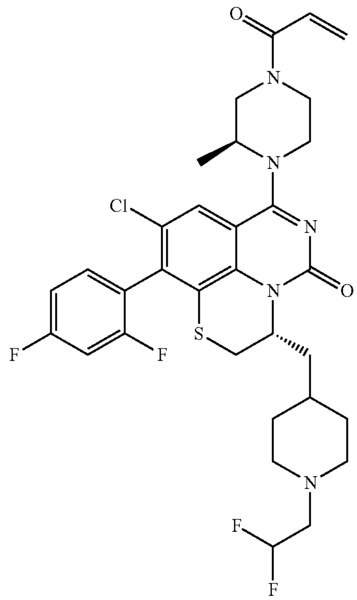 | 664.16 | 96 | (3R)-7-((S)-4-acryloyl-2-methylpiperazin-1-yl)-9-chloro-3-((1-(2,2-difluoroethyl)piperidin-4-yl)methyl)-10-(2,4-difluorophenyl)-2,3-dihydro-5H-[1,4]thiazino[2,3,4-ij]quinazolin-5-one |
| 70 | 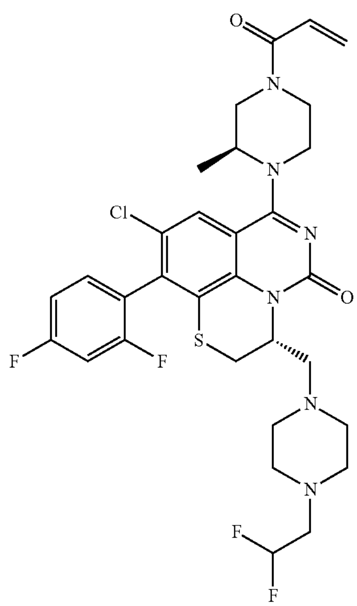 | 665.14 | 94 | (3R)-7-((S)-4-acryloyl-2-methylpiperazin-1-yl)-9-chloro-3-((4-(2,2-difluoroethyl)piperazin-1-yl)methyl)-10-(2,4-difluorophenyl)-2,3-dihydro-5H-[1,4]thiazino[2,3,4-ij]quinazolin-5-one |
| 71 | 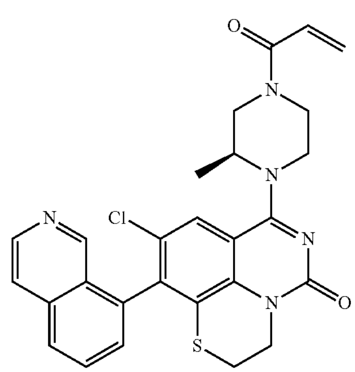 [SMILES: C=CC(=O)N1CCN(c2nc(=O)n3c4c(c(-c5cccc6ccncc56)c(Cl)cc24)SCC3)[C@@H](C)C1] | 518.03 | 87.8 | 7-((S)-4-acryloyl-2-methylpiperazin-1-yl)-9-chloro-10-(isoquinolin-8-yl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 72 | 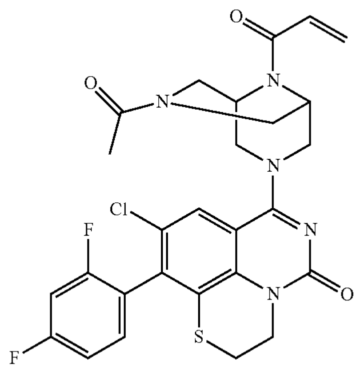 [SMILES: C=CC(=O)N1C2CN(C(C)=O)CC1CN(c1nc(=O)n3c4c(c(-c5ccc(F)cc5F)c(Cl)cc14)SCC3)C2] | 572.03 | 80.5 | 7-(7-acetyl-9-acryloyl-3,7,9-triazabicyclo[3.3.1]nonan-3-yl)-9-chloro-10-(2,4-difluorophenyl)-2,3-dihydro-5H-[1,4]oxazino[2,3,4-ij]quinazolin-5-one |
| 73 | 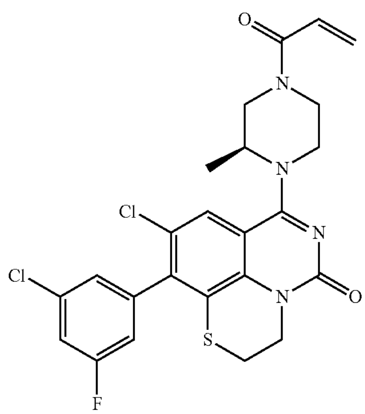 [SMILES: C=CC(=O)N1CCN(c2nc(=O)n3c4c(c(-c5cc(F)cc(Cl)c5)c(Cl)cc24)SCC3)[C@@H](C)C1] | 519.42 | 73 | (S)-7-(4-acryloyl-2-methylpiperazin-1-yl)-9-chloro-10-(3-chloro-5-fluorophenyl)-2,3-dihydro-5H-[1,4]thiazino[2,3,4-ij]quinazolin-5-one |
| 74 | 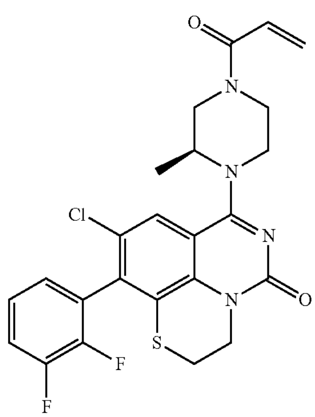 [SMILES: C=CC(=O)N1CCN(c2nc(=O)n3c4c(c(-c5cccc(F)c5F)c(Cl)cc24)SCC3)[C@@H](C)C1] | 502.96 | 95.6 | 7-((S)-4-acryloyl-2-methylpiperazin-1-yl)-9-chloro-10-(2,3-difluorophenyl)-2,3-dihydro-5H-[1,4]thiazino[2,3,4-ij]quinazolin-5-one |
| 75 | 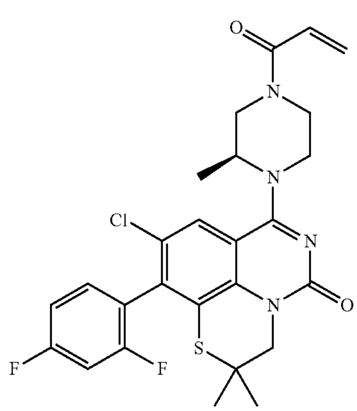 [SMILES: C=CC(=O)N1CCN(c2nc(=O)n3c4c(c(-c5ccc(F)cc5F)c(Cl)cc24)SC(C)(C)C3)[C@@H](C)C1] | 531.02 | 86.8 | 7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 76 | 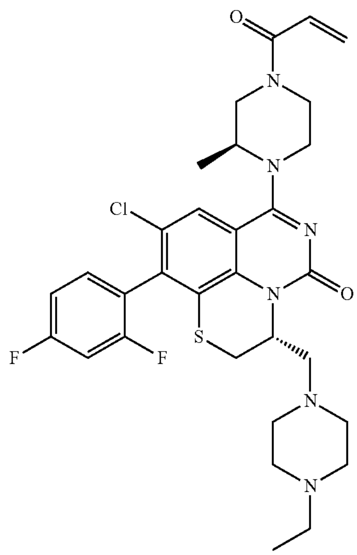 | 629.16 | 79.3 | (3R)-7-((S)-4-acryloyl-2-methylpiperazin-1-yl)-9-chloro-10-(2,4-difluorophenyl)-3-((4-ethylpiperazin-1-yl)methyl)-2,3-dihydro-5H-[1,4]thiazino[2,3,4-ij]quinazolin-5-one |
| 77 | 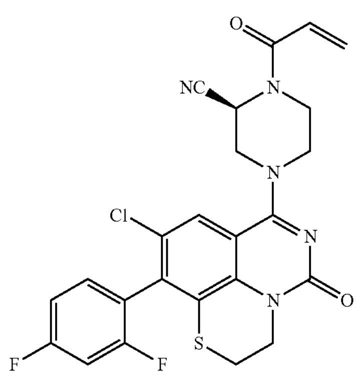 [SMILES: C=CC(=O)N1CCN(c2nc(=O)n3c4c(c(-c5ccc(F)cc5F)c(Cl)cc24)SCC3)C[C@H]1C#N] | 513.95 | 82 | (2S)-1-acryloyl-4-(9-chloro-10-(2,4-difluorophenyl)-5-oxo-2,3-dihydro-5H-[1,4]thiazino[2,3,4-ij]quinazolin-7-yl)piperazine-2-carbonitrile |
| 78 | 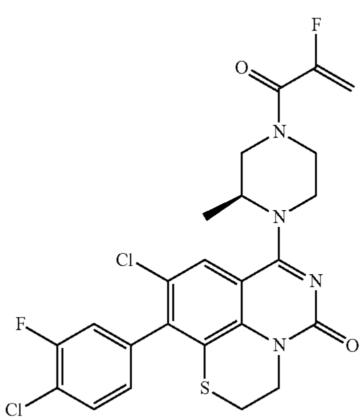 [SMILES: C=C(F)C(=O)N1CCN(c2nc(=O)n3c4c(c(-c5ccc(Cl)c(F)c5)c(Cl)cc24)SCC3)[C@@H](C)C1] | 537.41 | 6.7 | (S)-9-chloro-10-(4-chloro-3-fluorophenyl)-7-(4-(2-fluoroacryloyl)-2-methylpiperazin-1-yl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 79 | 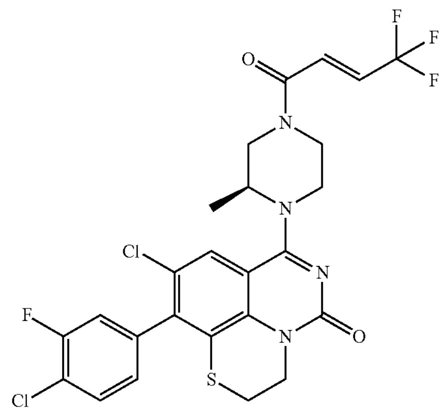 [SMILES: C[C@H]1CN(C(=O)/C=C/C(F)(F)F)CCN1c1nc(=O)n2c3c(c(-c4ccc(Cl)c(F)c4)c(Cl)cc13)SCC2] | 587.42 | 92 | (S,E)-9-chloro-10-(4-chloro-3-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one |
| 80 | 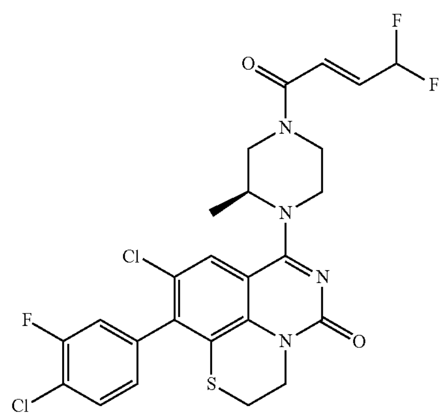 [SMILES: C[C@H]1CN(C(=O)/C=C/C(F)F)CCN1c1nc(=O)n2c3c(c(-c4ccc(Cl)c(F)c4)c(Cl)cc13)SCC2] | 569.43 | 93.5 | (S,E)-9-chloro-10-(4-chloro-3-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one |
| 81 | 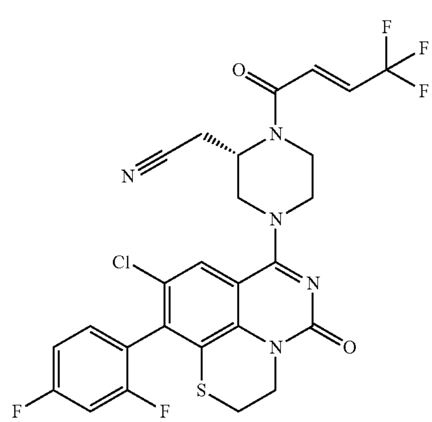 [SMILES: N#CC[C@H]1CN(c2nc(=O)n3c4c(c(-c5ccc(F)cc5F)c(Cl)cc24)SCC3)CCN1C(=O)/C=C/C(F)(F)F] | 595.97 | 89 | 2-((2S)-4-(9-chloro-10-(2,4-difluorophenyl)-5-oxo-2,3-dihydro-5H-[1,4]thiazino[2,3,4-ij]quinazolin-7-yl)-1-((E)-4,4,4-trifluorobut-2-enoyl)piperazin-2-yl)acetonitrile |

TABLE 5-continued

| Example No. | Structure | MW | % CAF @ 10 uM, 1 h | Name |
|---|---|---|---|---|
| 82 | 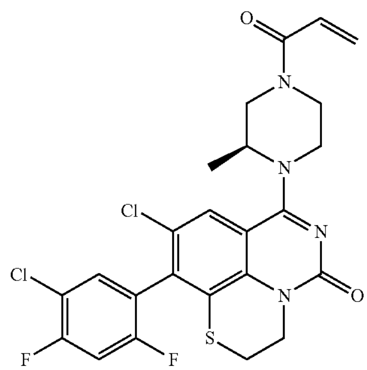 [SMILES: C=CC(=O)N1CCN(c2nc(=O)n3c4c(c(-c5cc(Cl)c(F)cc5F)c(Cl)cc24)SCC3)[C@@H](C)C1] | 537.41 | 85.8 | 7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one |
| 83 | 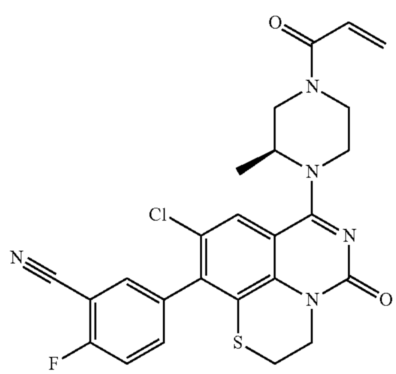 [SMILES: C=CC(=O)N1CCN(c2nc(=O)n3c4c(c(-c5ccc(F)c(C#N)c5)c(Cl)cc24)SCC3)[C@@H](C)C1] | 509.98 | 85.3 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluorobenzonitrile |
| 84 | 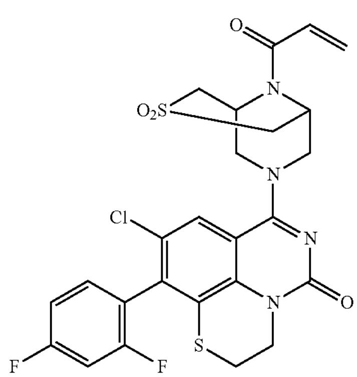 | 579.04 | 43.8 | 7-(9-acryloyl-3,3-dioxido-3-thia-7,9-diazabicyclo[3.3.1]nonan-7-yl)-9-chloro-10-(2,4-difluorophenyl)-2,3-dihydro-5H-[1,4]oxazino[2,3,4-ij]quinazolin-5-one |
| 85 | 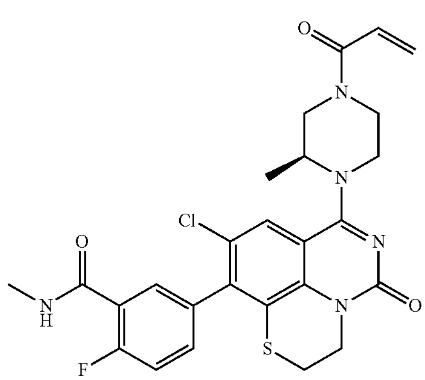 [SMILES: C=CC(=O)N1CCN(c2nc(=O)n3c4c(c(-c5ccc(F)c(C(=O)NC)c5)c(Cl)cc24)SCC3)[C@@H](C)C1] | 542.02 | 60.3 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluoro-N-methylbenzamide |

TABLE 5-continued

| Example No. | Structure | MW | % CAF @ 10 uM, 1 h | Name |
|---|---|---|---|---|
| 86 | 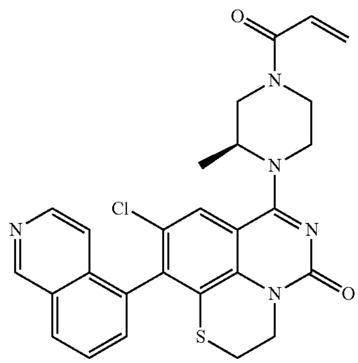 [SMILES: C=CC(=O)N1CCN(c2nc(=O)n3c4c(c(-c5cccc6cnccc56)c(Cl)cc24)SCC3)[C@@H](C)C1] | 518.03 | 76.1 | 7-((S)-4-acryloyl-2-methylpiperazin-1-yl)-9-chloro-10-(isoquinolin-5-yl)-2,3-dihydro-5H-[1,4]thiazino[2,3,4-ij]quinazolin-5-one |
| 87 | 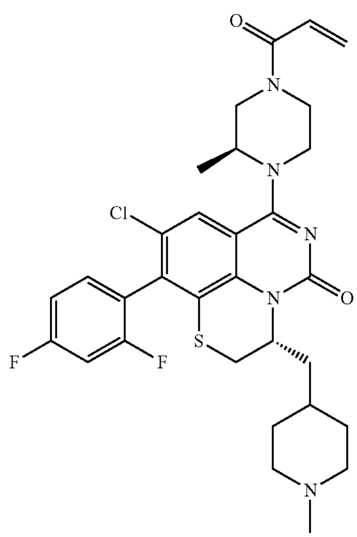 | 614.15 | 82.4 | (3R)-7-((S)-4-acryloyl-2-methylpiperazin-1-yl)-9-chloro-10-(2,4-difluorophenyl)-3-((1-methylpiperidin-4-yl)methyl)-2,3-dihydro-5H-[1,4]thiazino[2,3,4-ij]quinazolin-5-one |
| 88 | 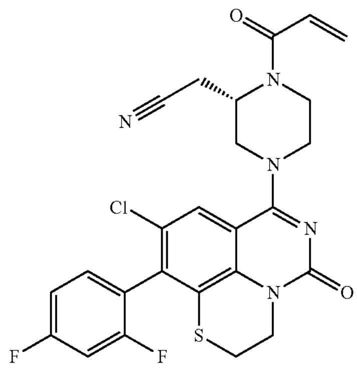 [SMILES: C=CC(=O)N1CCN(c2nc(=O)n3c4c(c(-c5ccc(F)cc5F)c(Cl)cc24)SCC3)C[C@@H]1CC#N] | 527.97 | 90.2 | 2-((2S)-1-acryloyl-4-(9-chloro-10-(2,4-difluorophenyl)-5-oxo-2,3-dihydro-5H-[1,4]thiazino[2,3,4-ij]quinazolin-7-yl)piperazin-2-yl)acetonitrile |

TABLE 5-continued

| Example No. | Structure | MW | % CAF @ 10 uM, 1 h | Name |
| --- | --- | --- | --- | --- |
| 89 | 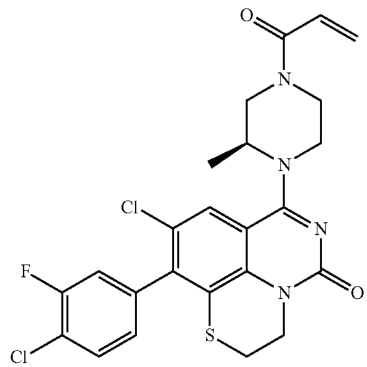 [SMILES: C=CC(=O)N1CCN(c2nc(=O)n3c4c(c(-c5ccc(Cl)c(F)c5)c(Cl)cc24)SCC3)[C@@H](C)C1] | 519.42 | 94.5 | (S)-7-(4-acryloyl-2-methylpiperazin-1-yl)-9-chloro-10-(4-chloro-3-fluorophenyl)-2,3-dihydro-5H-[1,4]thiazino[2,3,4-ij]quinazolin-5-one |
| 90 | 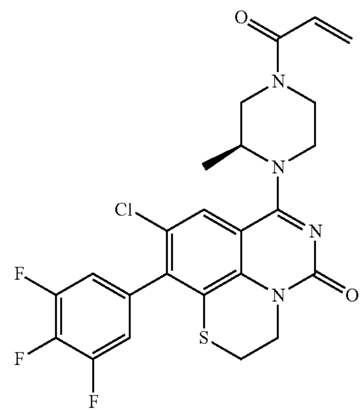 [SMILES: C=CC(=O)N1CCN(c2nc(=O)n3c4c(c(-c5cc(F)c(F)c(F)c5)c(Cl)cc24)SCC3)[C@@H](C)C1] | 520.95 | 78.8 | (S)-7-(4-acryloyl-2-methylpiperazin-1-yl)-9-chloro-10-(3,4,5-trifluorophenyl)-2,3-dihydro-5H-[1,4]thiazino[2,3,4-ij]quinazolin-5-one |
| 91 | 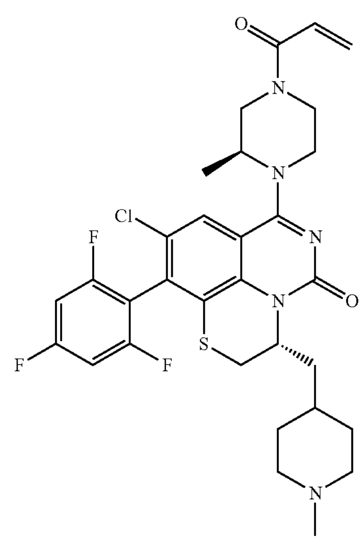 [SMILES: C=CC(=O)N1CCN(c2nc(=O)n3c4c(c(-c5c(F)cc(F)cc5F)c(Cl)cc24)SC[C@H]3CC2CCN(C)CC2)[C@@H](C)C1] | 632.14 | 94.8 | (R)-7-((S)-4-acryloyl-2-methylpiperazin-1-yl)-9-chloro-3-((1-methylpiperidin-4-yl)methyl)-10-(2,4,6-trifluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 92 | 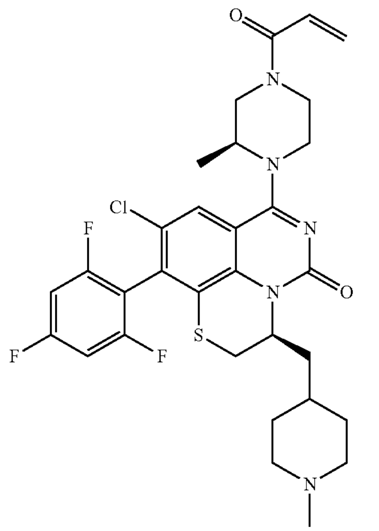 [SMILES: C=CC(=O)N1CCN(c2nc(=O)n3c4c(c(-c5c(F)cc(F)cc5F)c(Cl)cc24)SC[C@@H]3CC2CCN(C)CC2)[C@@H](C)C1] | 632.14 | 96.7 | (S)-7-((S)-4-acryloyl-2-methylpiperazin-1-yl)-9-chloro-3-((1-methylpiperidin-4-yl)methyl)-10-(2,4,6-trifluorophenyl)-2,3-dihydro-5H-[1,4]thiazino[2,3,4-ij]quinazolin-5-one |
| 93 | 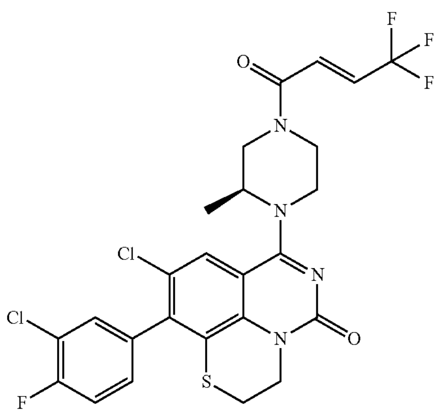 [SMILES: C[C@H]1CN(C(=O)/C=C/C(F)(F)F)CCN1c1nc(=O)n2c3c(c(-c4ccc(F)c(Cl)c4)c(Cl)cc13)SCC2] | 587.42 | 95 | (S,E)-9-chloro-10-(3-chloro-4-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one |
| 94 | 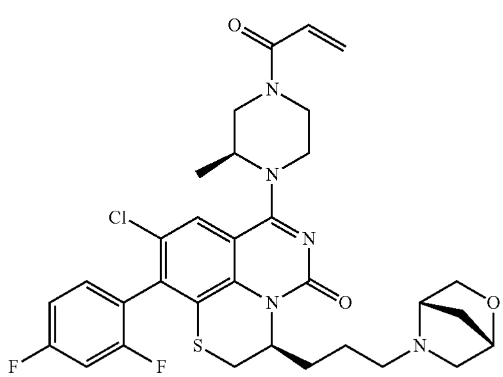 | 642.16 | 94.7 | (3S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 95 | 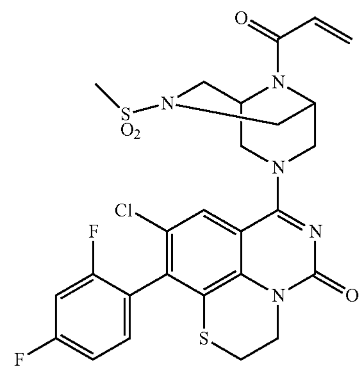 [SMILES: C=CC(=O)N1C2CN(c3nc(=O)n4c5c(c(-c6ccc(F)cc6F)c(Cl)cc35)SCC4)CC1CN(S(C)(=O)=O)C2] | 608.08 | 70.5 | 7-(9-acryloyl-7-(methylsulfonyl)-3,7,9-triazabicyclo[3.3.1]nonan-3-yl)-9-chloro-10-(2,4-difluorophenyl)-2,3-dihydro-5H-[1,4]thiazino[2,3,4-ij]quinazolin-5-one |
| 96 | 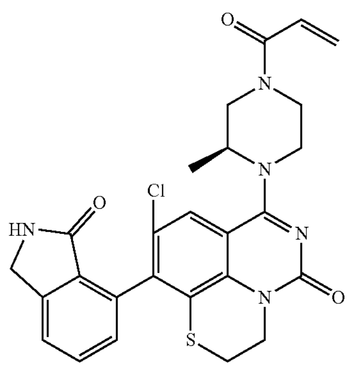 [SMILES: C=CC(=O)N1CCN(c2nc(=O)n3c4c(c(-c5cccc6c5C(=O)NC6)c(Cl)cc24)SCC3)[C@@H](C)C1] | 522.02 | 54 | 7-((S)-4-acryloyl-2-methylpiperazin-1-yl)-9-chloro-10-(3-oxoisoindolin-4-yl)-2,3-dihydro-5H-[1,4]thiazino[2,3,4-ij]quinazolin-5-one |
| 97 | 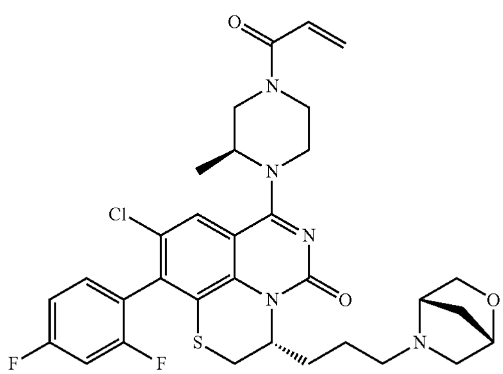 [SMILES: C=CC(=O)N1CCN(c2nc(=O)n3c4c(c(-c5ccc(F)cc5F)c(Cl)cc24)SC[C@H]3CCCN2C[C@@H]3C[C@H]2CO3)[C@@H](C)C1] | 642.16 | 96.5 | (3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |
| 98 | 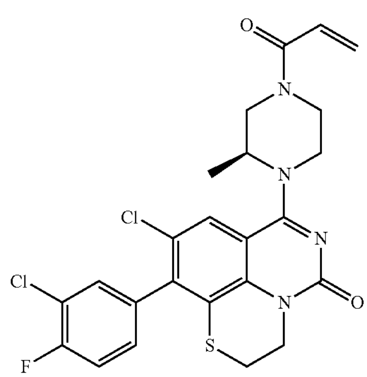 [SMILES: C=CC(=O)N1CCN(c2nc(=O)n3c4c(c(-c5ccc(F)c(Cl)c5)c(Cl)cc24)SCC3)[C@@H](C)C1] | 519.42 | 86.4 | (S)-7-(4-acryloyl-2-methylpiperazin-1-yl)-9-chloro-10-(3-chloro-4-fluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 99 | 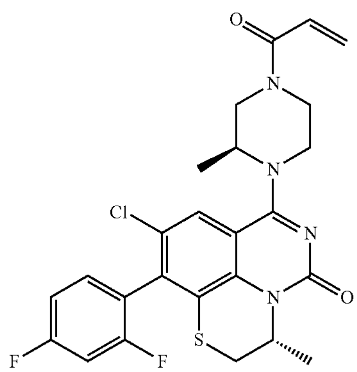 | 516.99 | 87.2 | (3R)-7-((S)-4-acryloyl-2-methylpiperazin-1-yl)-9-chloro-10-(2,4-difluorophenyl)-3-methyl-2,3-dihydro-5H-[1,4]thiazino[2,3,4-ij]quinazolin-5-one |
| 100 | 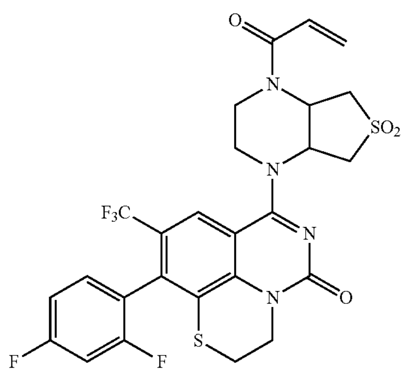 [SMILES: C=CC(=O)N1CCN(c2nc(=O)n3c4c(c(-c5ccc(F)cc5F)c(C(F)(F)F)cc24)SCC3)C2CS(=O)(=O)CC21] | 612.59 | 94 | 7-(4-acryloyl-6,6-dioxidohexahydrothieno[3,4-b]pyrazin-1(2H)-yl)-10-(2,4-difluorophenyl)-9-(trifluoromethyl)-2,3-dihydro-5H-[1,4]thiazino[2,3,4-ij]quinazolin-5-one |
| 101 | 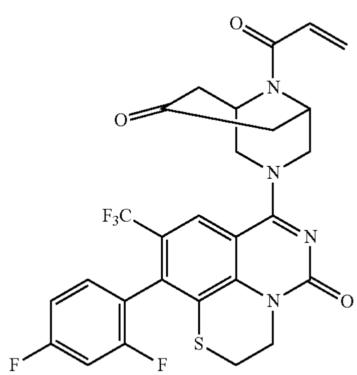 [SMILES: C=CC(=O)N1C2CC(=O)CC1CN(c1nc(=O)n3c4c(c(-c5ccc(F)cc5F)c(C(F)(F)F)cc14)SCC3)C2] | 576.54 | 96.5 | 7-(9-acryloyl-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one |
| 102 | 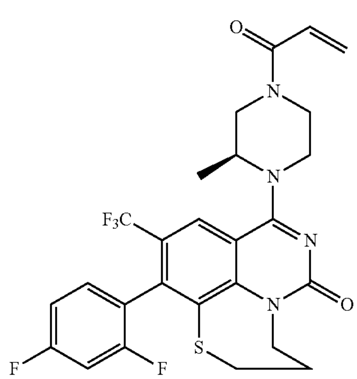 | 516.99 | 95.4 | 8-((S)-4-acryloyl-2-methylpiperazin-1-yl)-10-chloro-11-(2,4-difluorophenyl)-3,4-dihydro-2H,6H-[1,4]thiazepino[2,3,4-ij]quinazolin-6-one |

TABLE 5-continued

| Example No. | Structure | MW | % CAF @ 10 uM, 1 h | Name |
|---|---|---|---|---|
| 103 | 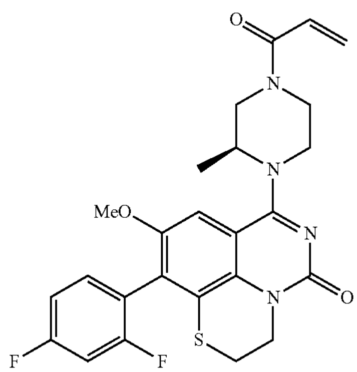 | 498.54 | 92.5 | 7-((S)-4-acryloyl-2-methylpiperazin-1-yl)-10-(2,4-difluorophenyl)-9-methoxy-2,3-dihydro-5H-[1,4]thiazino[2,3,4-ij]quinazolin-5-one |
| 104 | 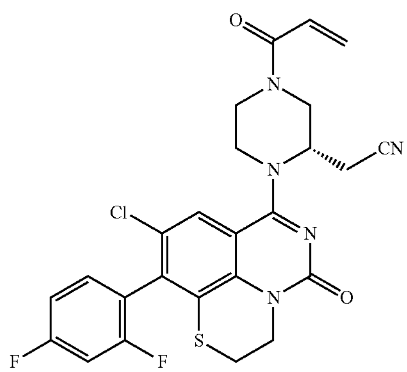 [SMILES: C=CC(=O)N1CCN(c2nc(=O)n3c4c(c(-c5ccc(F)cc5F)c(Cl)cc24)SCC3)[C@@H](CC#N)C1] | 527.97 | 94.4 | 2-((2S)-4-acryloyl-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile |
| 105 | 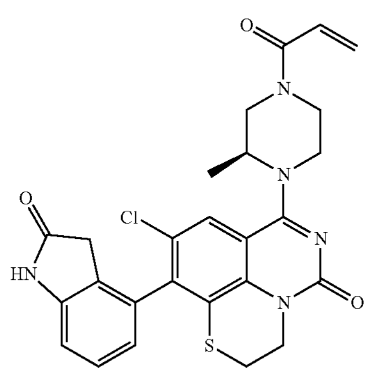 [SMILES: C=CC(=O)N1CCN(c2nc(=O)n3c4c(c(-c5cccc6c5CC(=O)N6)c(Cl)cc24)SCC3)[C@@H](C)C1] | 522.02 | 18.9 | 7-((S)-4-acryloyl-2-methylpiperazin-1-yl)-9-chloro-10-(2-oxoindolin-4-yl)-2,3-dihydro-5H-[1,4]thiazino[2,3,4-ij]quinazolin-5-one |
| 106 | 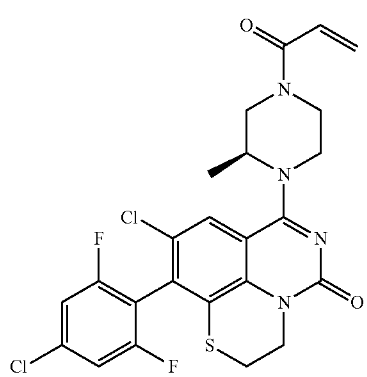 [SMILES: C=CC(=O)N1CCN(c2nc(=O)n3c4c(c(-c5c(F)cc(Cl)cc5F)c(Cl)cc24)SCC3)[C@@H](C)C1] | 537.41 | 45.2 | (S)-7-(4-acryloyl-2-methylpiperazin-1-yl)-9-chloro-10-(4-chloro-2,6-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 107 | 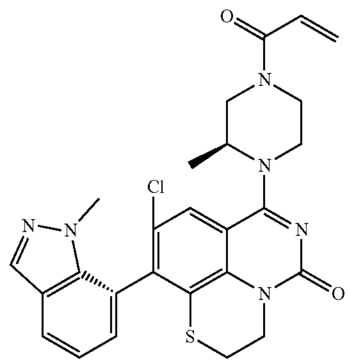 | 521.03 | 0 | (S)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one |
| 108 | 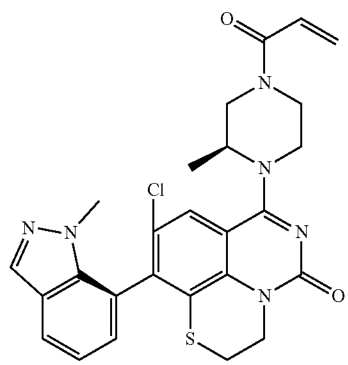 | 521.03 | 91.7 | (R)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one |
| 109 | 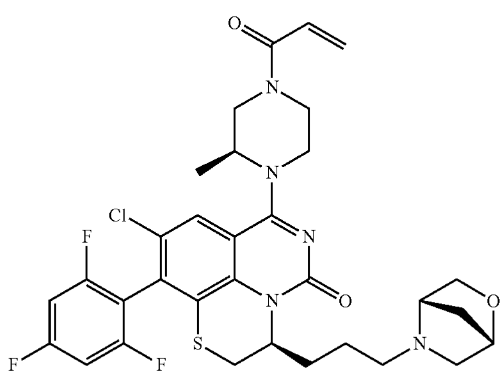 [SMILES: C=CC(=O)N1CCN(c2nc(=O)n3c4c(c(-c5c(F)cc(F)cc5F)c(Cl)cc24)SC[C@@H]3CCCN2C[C@@H]3C[C@H]2CO3)[C@@H](C)C1] | 660.15 | 96.9 | (S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2,3-dihydro-5H-[1,4]thiazino[2,3,4-ij]quinazolin-5-one |
| 110 | 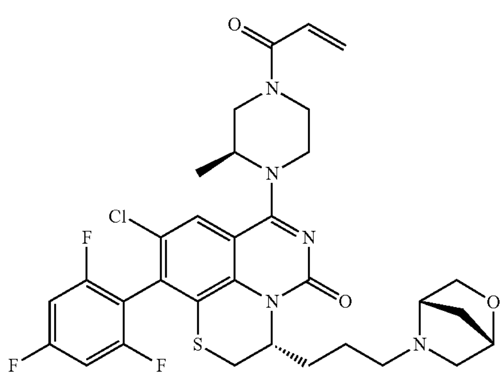 [SMILES: C=CC(=O)N1CCN(c2nc(=O)n3c4c(c(-c5c(F)cc(F)cc5F)c(Cl)cc24)SC[C@H]3CCCN2C[C@@H]3C[C@H]2CO3)[C@@H](C)C1] | 660.15 | 96.6 | (R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 111 | 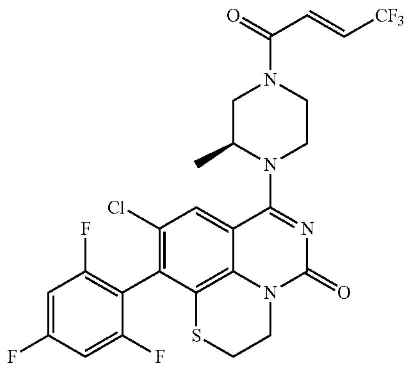 [SMILES: C[C@H]1CN(C(=O)/C=C/C(F)(F)F)CCN1c1nc(=O)n2c3c(c(-c4c(F)cc(F)cc4F)c(Cl)cc13)SCC2] | 588.95 | 95.2 | (S,E)-9-chloro-7-(2-methyl-4-(4,4,4-trifluorobut-2-enoyl)piperazin-1-yl)-10-(2,4,6-trifluorophenyl)-2,3-dihydro-5H-[1,4]thiazino[2,3,4-ij]quinazolin-5-one |
| 112 | 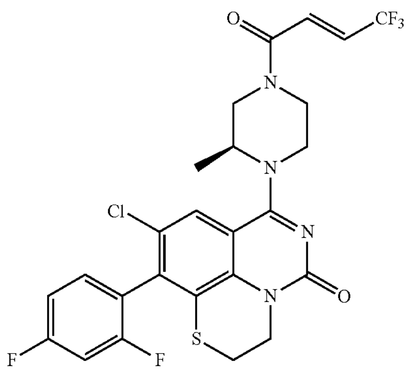 [SMILES: C[C@H]1CN(C(=O)/C=C/C(F)(F)F)CCN1c1nc(=O)n2c3c(c(-c4ccc(F)cc4F)c(Cl)cc13)SCC2] | 570.96 | 86.2 | 9-chloro-10-(2,4-difluorophenyl)-7-((S)-2-methyl-4-((E)-4,4,4-trifluorobut-2-enoyl)piperazin-1-yl)-2,3-dihydro-5H-[1,4]thiazino[2,3,4-ij]quinazolin-5-one |
| 113 | 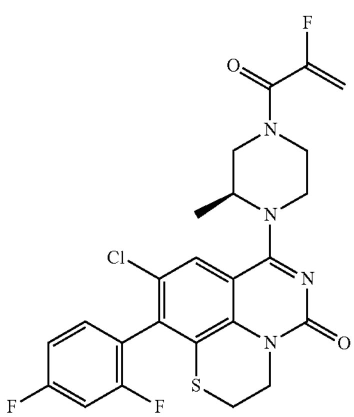 [SMILES: C=C(F)C(=O)N1CCN(c2nc(=O)n3c4c(c(-c5ccc(F)cc5F)c(Cl)cc24)SCC3)[C@@H](C)C1] | 520.95 | 21.7 | 9-chloro-10-(2,4-difluorophenyl)-7-((S)-4-(2-fluoroacryloyl)-2-methylpiperazin-1-yl)-2,3-dihydro-5H-[1,4]thiazino[2,3,4-ij]quinazolin-5-one |
| 114 | 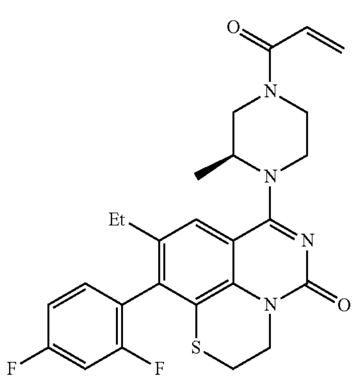 [SMILES: C=CC(=O)N1CCN(c2nc(=O)n3c4c(c(-c5ccc(F)cc5F)c(CC)cc24)SCC3)[C@@H](C)C1] | 496.57 | 92.8 | 7-((S)-4-acryloyl-2-methylpiperazin-1-yl)-10-(2,4-difluorophenyl)-9-ethyl-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 115 | 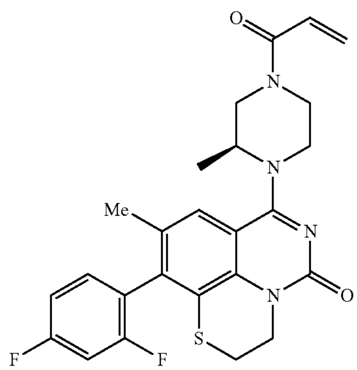 | 482.55 | 94.1 | 7-((S)-4-acryloyl-2-methylpiperazin-1-yl)-10-(2,4-difluorophenyl)-9-methyl-2,3-dihydro-5H-[1,4]thiazino[2,3,4-ij]quinazolin-5-one |
| 116 | 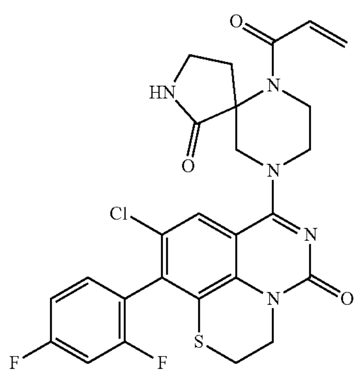 [SMILES: C=CC(=O)N1CCN(c2nc(=O)n3c4c(c(-c5ccc(F)cc5F)c(Cl)cc24)SCC3)CC12CCNC2=O] | 558 | 27.4 | 7-(6-acryloyl-1-oxo-2,6,9-triazaspiro[4.5]decan-9-yl)-9-chloro-10-(2,4-difluorophenyl)-2,3-dihydro-5H-[1,4]thiazino[2,3,4-ij]quinazolin-5-one |
| 117 | 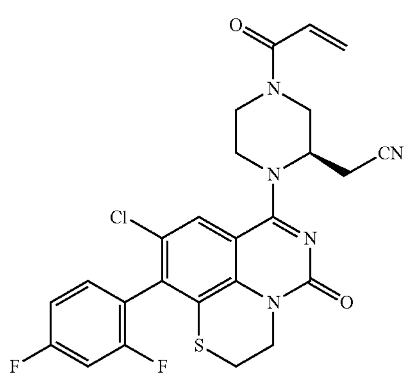 [SMILES: C=CC(=O)N1CCN(c2nc(=O)n3c4c(c(-c5ccc(F)cc5F)c(Cl)cc24)SCC3)[C@H](CC#N)C1] | 527.97 | 75.6 | 7-(6-acryloyl-1-oxo-2,6,9-triazaspiro[4.5]decan-9-yl)-9-chloro-10-(2,4-difluorophenyl)-2,3-dihydro-5H-[1,4]thiazino[2,3,4-ij]quinazolin-5-one |
| 118 | 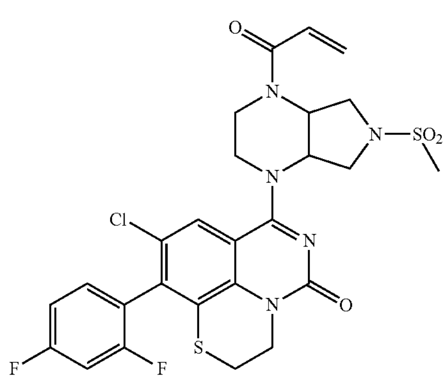 [SMILES: C=CC(=O)N1CCN(c2nc(=O)n3c4c(c(-c5ccc(F)cc5F)c(Cl)cc24)SCC3)C2CN(S(C)(=O)=O)CC21] | 608.08 | 48.3 | 7-(4-acryloyl-6-(methylsulfonyl)octahydro-1H-pyrrolo[3,4-b]pyrazin-1-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 119 | 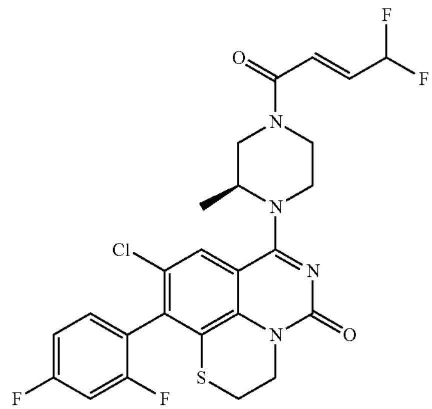 [SMILES: C[C@H]1CN(C(=O)/C=C/C(F)F)CCN1c1nc(=O)n2c3c(c(-c4ccc(F)cc4F)c(Cl)cc13)SCC2] | 552.97 | 97.1 | 9-chloro-7-((S)-4-((E)-4,4-difluorobut-2-enoyl)-2-methylpiperazin-1-yl)-10-(2,4-difluorophenyl)-2,3-dihydro-5H-[1,4]thiazino[2,3,4-ij]quinazolin-5-one |
| 120 | 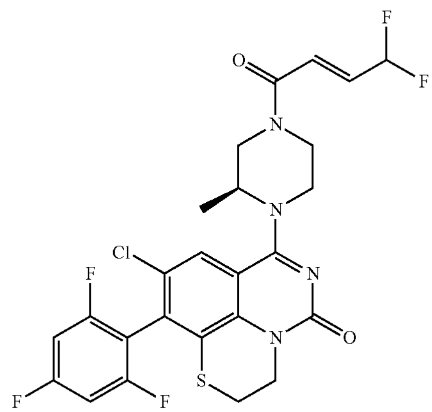 [SMILES: C[C@H]1CN(C(=O)/C=C/C(F)F)CCN1c1nc(=O)n2c3c(c(-c4c(F)cc(F)cc4F)c(Cl)cc13)SCC2] | 570.96 | 95.9 | (S,E)-9-chloro-7-(4-(4,4-difluorobut-2-enoyl)-2-methylpiperazin-1-yl)-10-(2,4,6-trifluorophenyl)-2,3-dihydro-5H-[1,4]thiazino[2,3,4-ij]quinazolin-5-one |
| 121 | 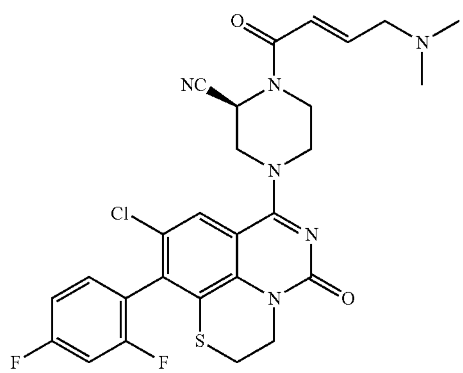 [SMILES: CN(C)C/C=C/C(=O)N1CCN(c2nc(=O)n3c4c(c(-c5ccc(F)cc5F)c(Cl)cc24)SCC3)C[C@H]1C#N] | 571.04 | 3.6 | (2S)-4-(9-chloro-10-(2,4-difluorophenyl)-5-oxo-2,3-dihydro-5H-[1,4]thiazino[2,3,4-ij]quinazolin-7-yl)-1-((E)-4-(dimethylamino)but-2-enoyl)piperazine-2-carbonitrile |
| 122 | 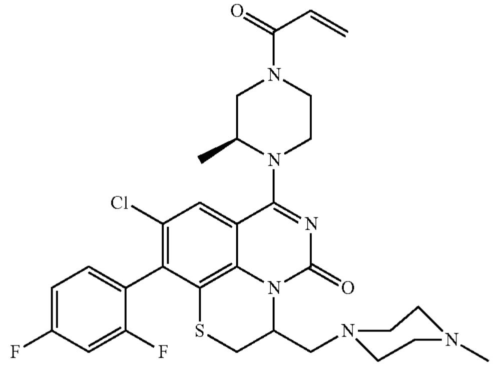 [SMILES: C=CC(=O)N1CCN(c2nc(=O)n3c4c(c(-c5ccc(F)cc5F)c(Cl)cc24)SCC3CN2CCN(C)CC2)[C@@H](C)C1] | 629.16 | 80.9 | 7-((S)-4-acryloyl-2-methylpiperazin-1-yl)-9-chloro-10-(2,4-difluorophenyl)-3-((4-ethylpiperazin-1-yl)methyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 123 | 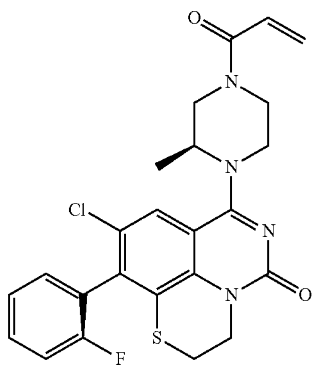 | 484.97 | 91.3 | (R)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one |
| 124 | 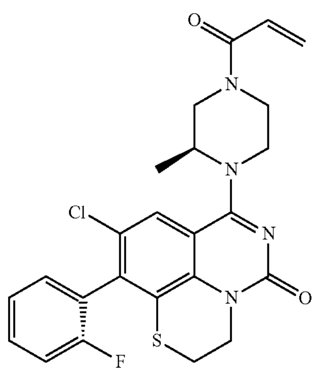 | 484.97 | 96 | (S)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one |
| 125 | 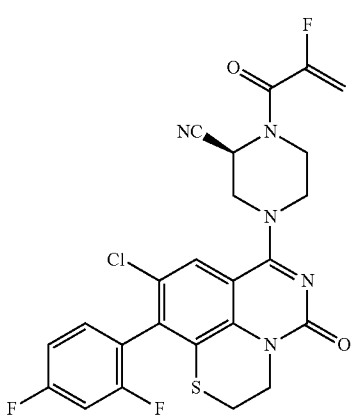 [SMILES: C=C(F)C(=O)N1CCN(c2nc(=O)n3c4c(c(-c5ccc(F)cc5F)c(Cl)cc24)SCC3)C[C@H]1C#N] | 531.94 | 94.5 | (2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl)piperazine-2-carbonitrile |
| 126 | 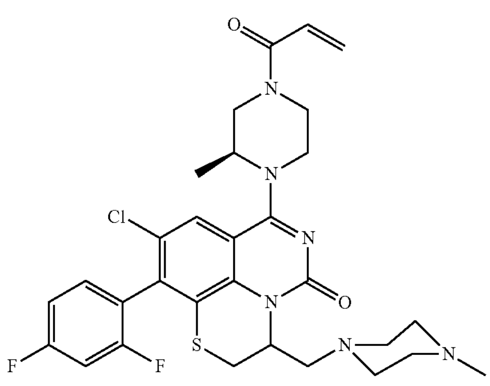 [SMILES: C=CC(=O)N1CCN(c2nc(=O)n3c4c(c(-c5ccc(F)cc5F)c(Cl)cc24)SCC3CN2CCN(C)CC2)[C@@H](C)C1] | 615.14 | 33.1 | 7-((S)-4-acryloyl-2-methylpiperazin-1-yl)-9-chloro-10-(2,4-difluorophenyl)-3-((4-methylpiperazin-1-yl)methyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 127 | 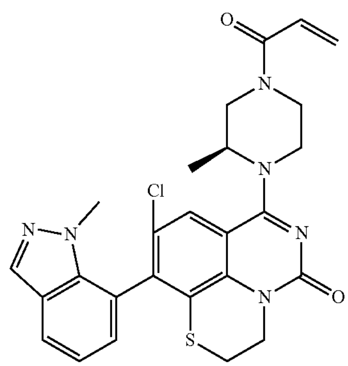 [SMILES: C=CC(=O)N1CCN(c2nc(=O)n3c4c(c(-c5cccc6cnn(C)c56)c(Cl)cc24)SCC3)[C@@H](C)C1] | 521.03 | 60 | 7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one |
| 128 | 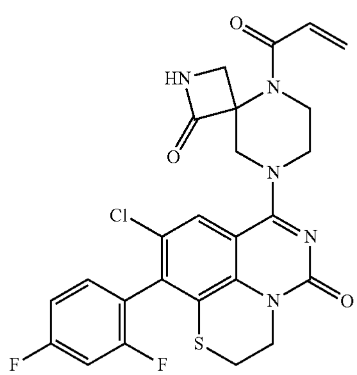 [SMILES: C=CC(=O)N1CCN(c2nc(=O)n3c4c(c(-c5ccc(F)cc5F)c(Cl)cc24)SCC3)CC12CNC2=O] | 543.97 | 62.7 | 7-(5-acryloyl-1-oxo-2,5,8-triazaspiro[3.5]nonan-8-yl)-9-chloro-10-(2,4-difluorophenyl)-2,3-dihydro-5H-[1,4]thiazino[2,3,4-ij]quinazolin-5-one |
| 129 | 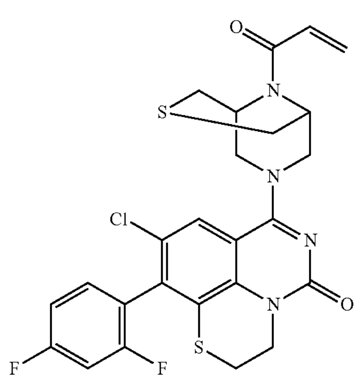 | 547.04 | 95.3 | 7-(9-acryloyl-3-thia-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one |
| 130 | 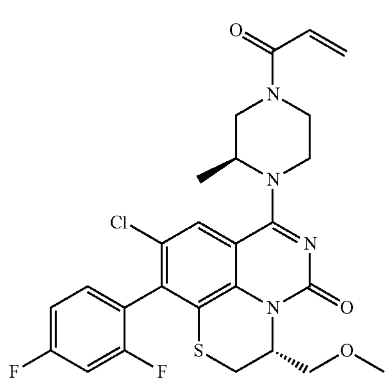 [SMILES: C=CC(=O)N1CCN(c2nc(=O)n3c4c(c(-c5ccc(F)cc5F)c(Cl)cc24)SC[C@H]3COC)[C@@H](C)C1] | 547.02 | 94.5 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 131 | 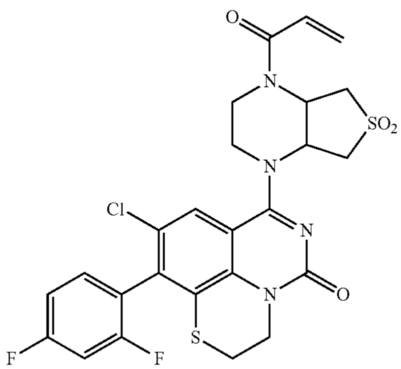 | 579.04 | 82.2 | 7-(4-acryloyl-6,6-dioxidohexahydrothieno[3,4-b]pyrazin-1(2H)-yl)-9-chloro-10-(2,4-difluorophenyl)-2,3-dihydro-5H-[1,4]thiazino[2,3,4-ij]quinazolin-5-one |
| 132 | 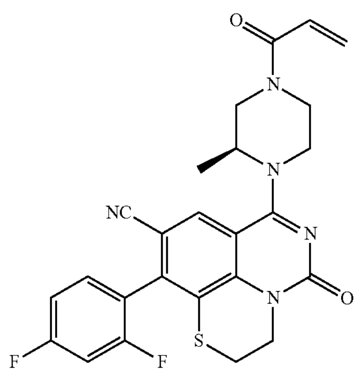 | 493.53 | 91.9 | 7-((S)-4-acryloyl-2-methylpiperazin-1-yl)-10-(2,4-difluorophenyl)-5-oxo-2,3-dihydro-5H-[1,4]thiazino[2,3,4-ij]quinazoline-9-carbonitrile |
| 133 | 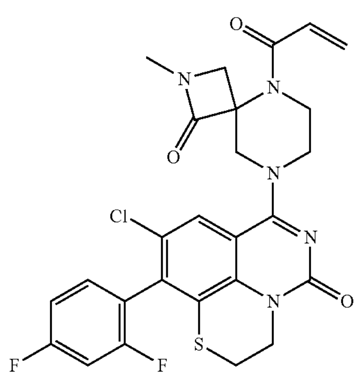 [SMILES: C=CC(=O)N1CCN(c2nc(=O)n3c4c(c(-c5ccc(F)cc5F)c(Cl)cc24)SCC3)CC12CN(C)C2=O] | 558 | 51.9 | 7-(5-acryloyl-2-methyl-1-oxo-2,5,8-triazaspiro[3.5]nonan-8-yl)-9-chloro-10-(2,4-difluorophenyl)-2,3-dihydro-5H-[1,4]thiazino[2,3,4-ij]quinazolin-5-one |
| 134 | 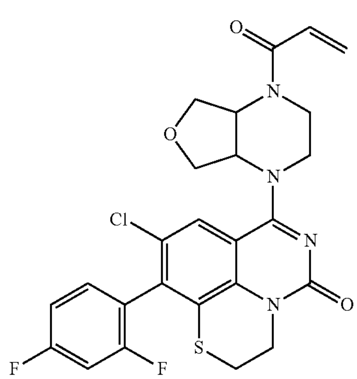 [SMILES: C=CC(=O)N1CCN(c2nc(=O)n3c4c(c(-c5ccc(F)cc5F)c(Cl)cc24)SCC3)C2COCC21] | 530.97 | 85 | 7-(4-acryloylhexahydrofuro[3,4-b]pyrazin-1(2H)-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 135 | 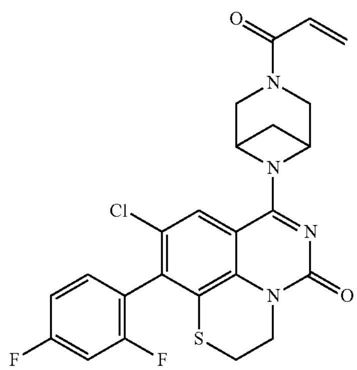 [SMILES: C=CC(=O)N1CC2CC(C1)N2c1nc(=O)n2c3c(c(-c4ccc(F)cc4F)c(Cl)cc13)SCC2] | 500.95 | 0 | 7-(3-acryloyl-3,6-diazabicyclo[3.1.1]heptan-6-yl)-9-chloro-10-(2,4-difluorophenyl)-2,3-dihydro-5H-[1,4]thiazino[2,3,4-ij]quinazolin-5-one |
| 136 | 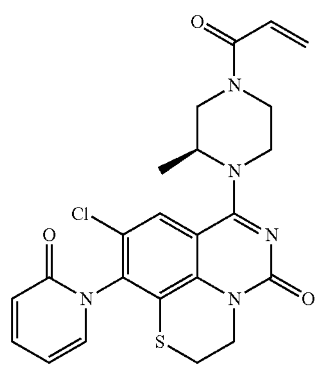 [SMILES: C=CC(=O)N1CCN(c2nc(=O)n3c4c(c(-n5ccccc5=O)c(Cl)cc24)SCC3)[C@@H](C)C1] | 483.97 | 89.4 | 7-((S)-4-acryloyl-2-methylpiperazin-1-yl)-9-chloro-10-(2-oxopyridin-1(2H)-yl)-2,3-dihydro-5H-[1,4]thiazino[2,3,4-ij]quinazolin-5-one |
| 137 | 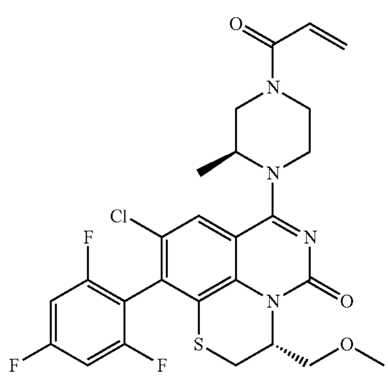 [SMILES: C=CC(=O)N1CCN(c2nc(=O)n3c4c(c(-c5c(F)cc(F)cc5F)c(Cl)cc24)SC[C@H]3COC)[C@@H](C)C1] | 565.01 | 86.8 | (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one |
| 138 | 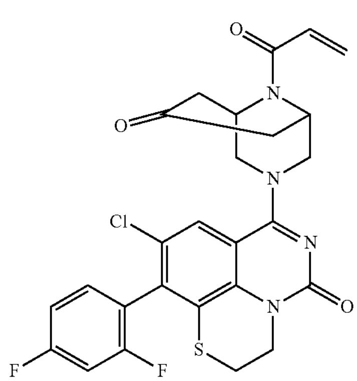 [SMILES: C=CC(=O)N1C2CC(=O)CC1CN(c1nc(=O)n3c4c(c(-c5ccc(F)cc5F)c(Cl)cc14)SCC3)C2] | 542.98 | 95.8 | 7-(9-acryloyl-7-oxo-3,9-diazabicyclo[3.3.1]nonan-3-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 139 | 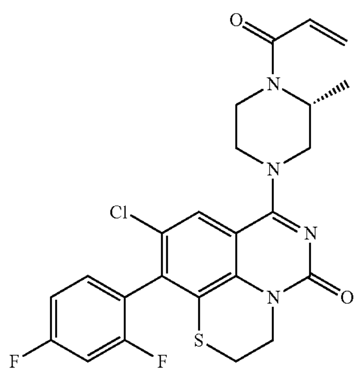 [SMILES: C=CC(=O)N1CCN(c2nc(=O)n3c4c(c(-c5ccc(F)cc5F)c(Cl)cc24)SCC3)C[C@H]1C] | 502.96 | 94.8 | 7-((R)-4-acryloyl-3-methylpiperazin-1-yl)-9-chloro-10-(2,4-difluorophenyl)-2,3-dihydro-5H-[1,4]thiazino[2,3,4-ij]quinazolin-5-one |
| 140 | 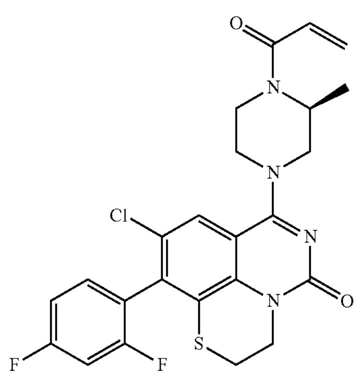 [SMILES: C=CC(=O)N1CCN(c2nc(=O)n3c4c(c(-c5ccc(F)cc5F)c(Cl)cc24)SCC3)C[C@@H]1C] | 502.96 | 90.6 | 7-((S)-4-acryloyl-3-methylpiperazin-1-yl)-9-chloro-10-(2,4-difluorophenyl)-2,3-dihydro-5H-[1,4]thiazino[2,3,4-ij]quinazolin-5-one |
| 141 | 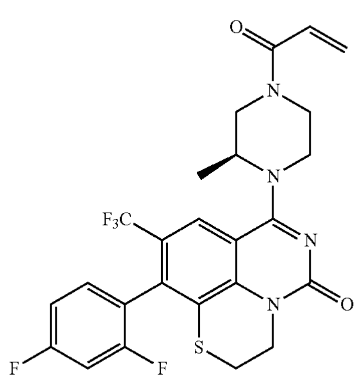 | 536.52 | 95.7 | 7-((S)-4-acryloyl-2-methylpiperazin-1-yl)-10-(2,4-difluorophenyl)-9-(trifluoromethyl)-2,3-dihydro-5H-[1,4]thiazino[2,3,4-ij]quinazolin-5-one |
| 142 | 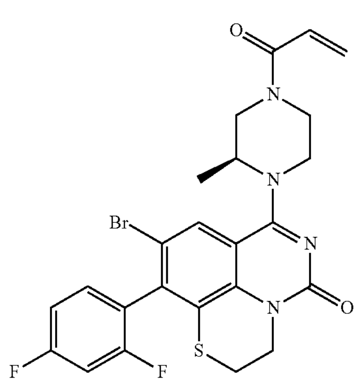 | 547.41 | 94.7 | 7-((S)-4-acryloyl-2-methylpiperazin-1-yl)-9-bromo-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 143 | 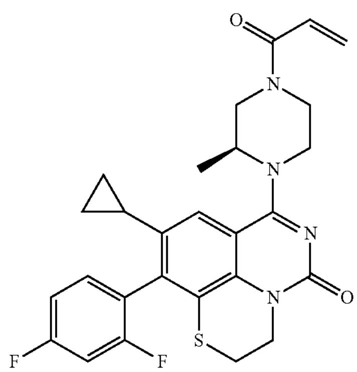 [SMILES: C=CC(=O)N1CCN(c2nc(=O)n3c4c(c(-c5ccc(F)cc5F)c(C5CC5)cc24)SCC3)[C@@H](C)C1] | 508.58 | 95.4 | 7-((S)-4-acryloyl-2-methylpiperazin-1-yl)-9-cyclopropyl-10-(2,4-difluorophenyl)-2,3-dihydro-5H-[1,4]thiazino[2,3,4-ij]quinazolin-5-one |
| 144 | 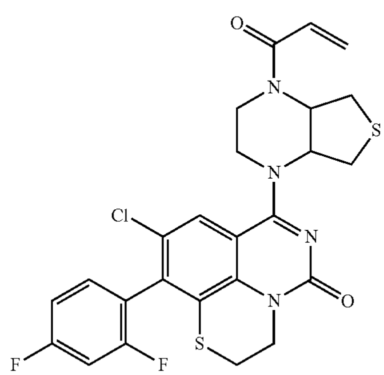 [SMILES: C=CC(=O)N1CCN(c2nc(=O)n3c4c(c(-c5ccc(F)cc5F)c(Cl)cc24)SCC3)C2CSCC21] | 547.04 | 64.9 | 7-(4-acryloylhexahydrothieno[3,4-b]pyrazin-1(2H)-yl)-9-chloro-10-(2,4-difluorophenyl)-2,3-dihydro-5H-[1,4]thiazino[2,3,4-ij]quinazolin-5-one |
| 145 | 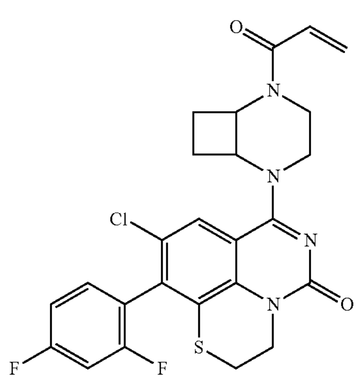 [SMILES: C=CC(=O)N1CCN(c2nc(=O)n3c4c(c(-c5ccc(F)cc5F)c(Cl)cc24)SCC3)C2CCC21] | 514.97 | 58 | 7-(5-acryloyl-2,5-diazabicyclo[4.2.0]octan-2-yl)-9-chloro-10-(2,4-difluorophenyl)-2,3-dihydro-5H-[1,4]thiazino[2,3,4-ij]quinazolin-5-one |
| 146 | 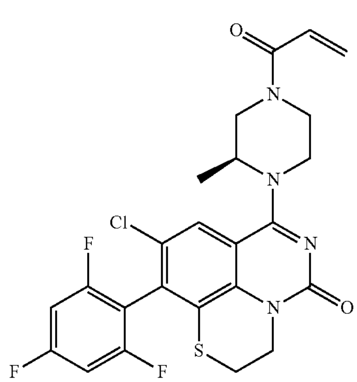 [SMILES: C=CC(=O)N1CCN(c2nc(=O)n3c4c(c(-c5c(F)cc(F)cc5F)c(Cl)cc24)SCC3)[C@@H](C)C1] | 520.95 | 90.7 | (S)-7-(4-acryloyl-2-methylpiperazin-1-yl)-9-chloro-10-(2,4,6-trifluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 147 | 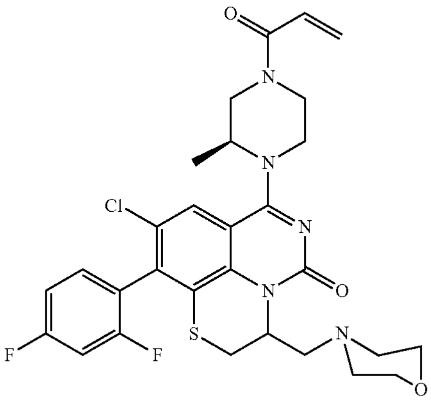 [SMILES: C=CC(=O)N1CCN(c2nc(=O)n3c4c(c(-c5ccc(F)cc5F)c(Cl)cc24)SCC3CN2CCOCC2)[C@@H](C)C1] | 602.1 | 44.6 | 7-((S)-4-acryloyl-2-methylpiperazin-1-yl)-9-chloro-10-(2,4-difluorophenyl)-3-(morpholinomethyl)-2,3-dihydro-5H-[1,4]thiazino[2,3,4-ij]quinazolin-5-one |
| 148 | 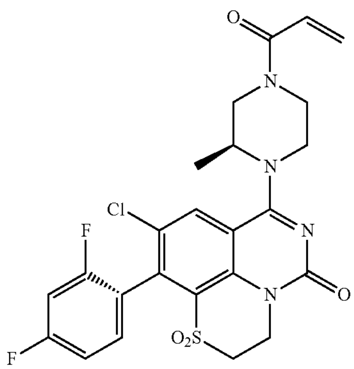 | 534.96 | 95.9 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide |
| 149 | 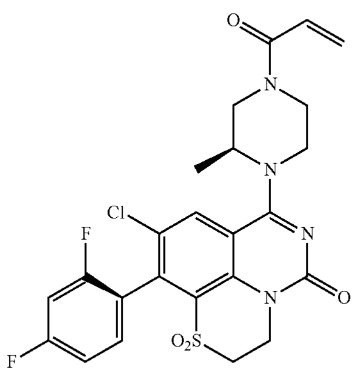 | 534.96 | 52.8 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide |
| 150 | 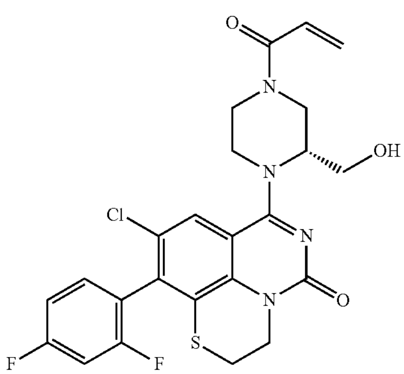 | 518.96 | 59.9 | 7-((R)-4-acryloyl-2-(hydroxymethyl)piperazin-1-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 151 | 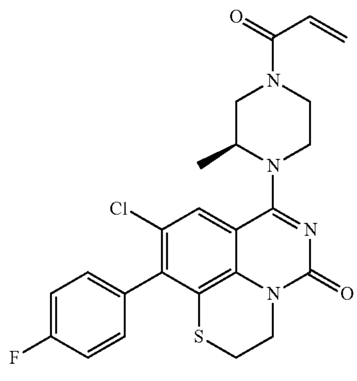 [SMILES: C=CC(=O)N1CCN(c2nc(=O)n3c4c(c(-c5ccc(F)cc5)c(Cl)cc24)SCC3)[C@@H](C)C1] | 484.97 | 94.1 | (S)-7-(4-acryloyl-2-methylpiperazin-1-yl)-9-chloro-10-(4-fluorophenyl)-2,3-dihydro-5H-[1,4]thiazino[2,3,4-ij]quinazolin-5-one |
| 152 | 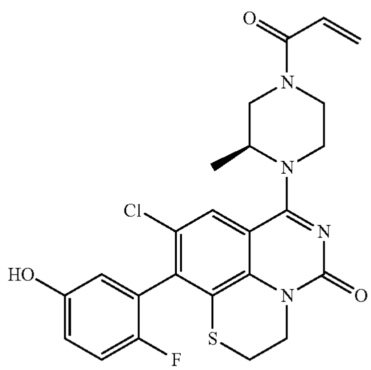 [SMILES: C=CC(=O)N1CCN(c2nc(=O)n3c4c(c(-c5cc(O)ccc5F)c(Cl)cc24)SCC3)[C@@H](C)C1] | 500.97 | 55.3 | 7-((S)-4-acryloyl-2-methylpiperazin-1-yl)-9-chloro-10-(2-fluoro-5-hydroxyphenyl)-2,3-dihydro-5H-[1,4]thiazino[2,3,4-ij]quinazolin-5-one |
| 153 | 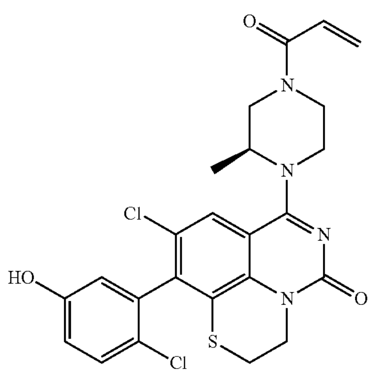 [SMILES: C=CC(=O)N1CCN(c2nc(=O)n3c4c(c(-c5cc(O)ccc5Cl)c(Cl)cc24)SCC3)[C@@H](C)C1] | 517.43 | 55.7 | 7-((S)-4-acryloyl-2-methylpiperazin-1-yl)-9-chloro-10-(2-chloro-5-hydroxyphenyl)-2,3-dihydro-5H-[1,4]thiazino[2,3,4-ij]quinazolin-5-one |
| 154 | 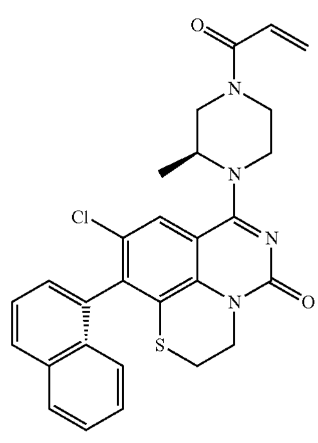 | 517.04 | 24 | (R)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 155 | 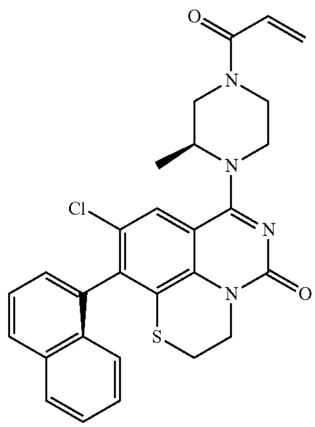 | 517.04 | 92.2 | (S)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one |
| 156 | 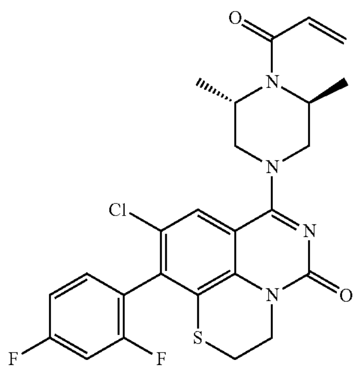 [SMILES: C=CC(=O)N1[C@@H](C)CN(c2nc(=O)n3c4c(c(-c5ccc(F)cc5F)c(Cl)cc24)SCC3)C[C@@H]1C] | 516.99 | 0 | 7-((3S,5S)-4-acryloyl-3,5-dimethylpiperazin-1-yl)-9-chloro-10-(2,4-difluorophenyl)-2,3-dihydro-5H-[1,4]thiazino[2,3,4-ij]quinazolin-5-one |
| 157 | 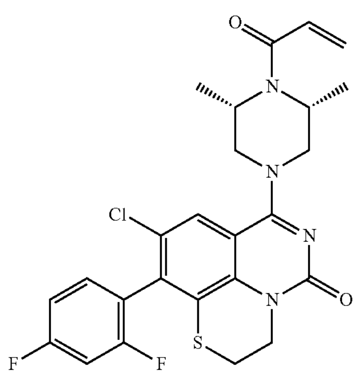 [SMILES: C=CC(=O)N1[C@H](C)CN(c2nc(=O)n3c4c(c(-c5ccc(F)cc5F)c(Cl)cc24)SCC3)C[C@@H]1C] | 516.99 | 95 | 7-((3R,5S)-4-acryloyl-3,5-dimethylpiperazin-1-yl)-9-chloro-10-(2,4-difluorophenyl)-2,3-dihydro-5H-[1,4]thiazino[2,3,4-ij]quinazolin-5-one |
| 158 | 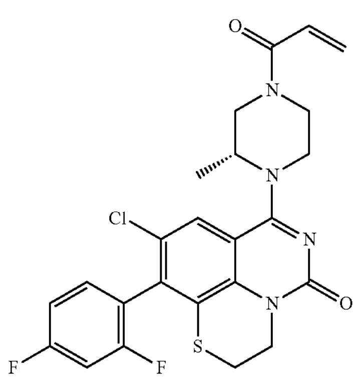 [SMILES: C=CC(=O)N1CCN(c2nc(=O)n3c4c(c(-c5ccc(F)cc5F)c(Cl)cc24)SCC3)[C@H](C)C1] | 502.96 | 64 | 7-((R)-4-acryloyl-2-methylpiperazin-1-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 159 | 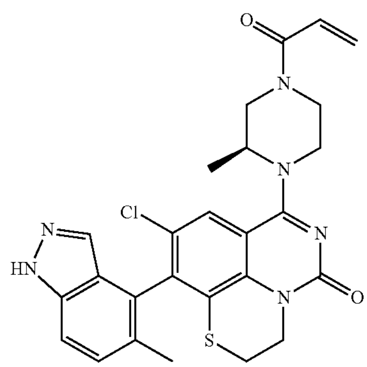 [SMILES: C=CC(=O)N1CCN(c2nc(=O)n3c4c(c(-c5c(C)ccc6[nH]ncc56)c(Cl)cc24)SCC3)[C@@H](C)C1] | 521.03 | 37.2 | 7-((S)-4-acryloyl-2-methylpiperazin-1-yl)-9-chloro-10-(5-methyl-1H-indazol-4-yl)-2,3-dihydro-5H-[1,4]thiazino[2,3,4-ij]quinazolin-5-one |
| 160 | 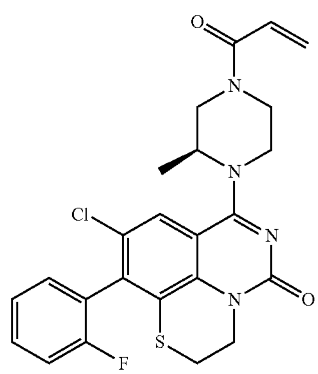 | 484.97 | 72.7 | 7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one |
| 161 | 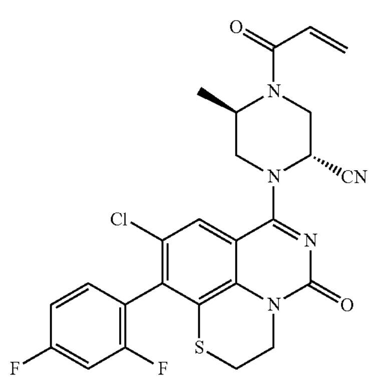 [SMILES: C=CC(=O)N1C[C@H](C#N)N(c2nc(=O)n3c4c(c(-c5ccc(F)cc5F)c(Cl)cc24)SCC3)C[C@H]1C] | 527.97 | 1 | (2R,5R)-4-acryloyl-1-(9-chloro-10-(2,4-difluorophenyl)-5-oxo-2,3-dihydro-5H-[1,4]thiazino[2,3,4-ij]quinazolin-7-yl)-5-methylpiperazine-2-carbonitrile |
| 162 | 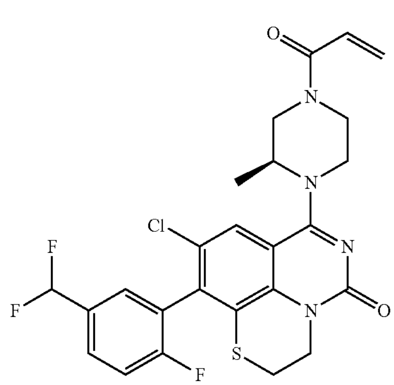 [SMILES: C=CC(=O)N1CCN(c2nc(=O)n3c4c(c(-c5cc(C(F)F)ccc5F)c(Cl)cc24)SCC3)[C@@H](C)C1] | 534.98 | 39 | 7-((S)-4-acryloyl-2-methylpiperazin-1-yl)-9-chloro-10-(5-(difluoromethyl)-2-fluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 163 | 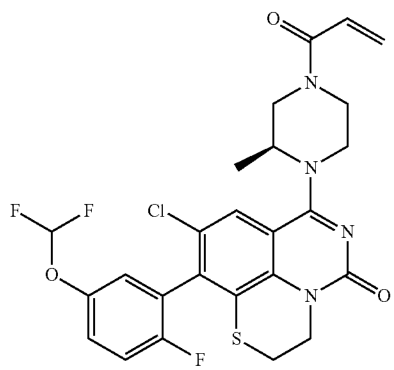 [SMILES: C=CC(=O)N1CCN(c2nc(=O)n3c4c(c(-c5cc(OC(F)F)ccc5F)c(Cl)cc24)SCC3)[C@@H](C)C1] | 550.98 | 41.4 | 7-((S)-4-acryloyl-2-methylpiperazin-1-yl)-9-chloro-10-(5-(difluoromethoxy)-2-fluorophenyl)-2,3-dihydro-5H-[1,4]thiazino[2,3,4-ij]quinazolin-5-one |
| 164 | 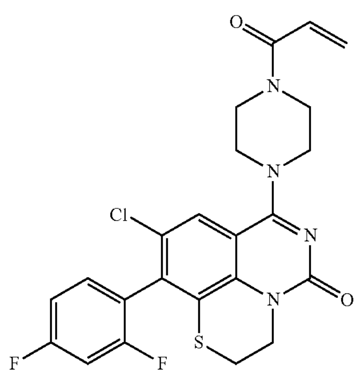 [SMILES: C=CC(=O)N1CCN(c2nc(=O)n3c4c(c(-c5ccc(F)cc5F)c(Cl)cc24)SCC3)CC1] | 488.94 | 95.1 | 7-(4-acryloylpiperazin-1-yl)-9-chloro-10-(2,4-difluorophenyl)-2,3-dihydro-5H-[1,4]thiazino[2,3,4-ij]quinazolin-5-one |
| 165 | 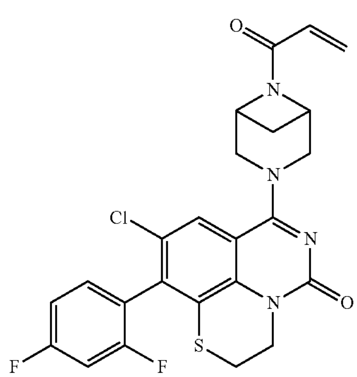 [SMILES: C=CC(=O)N1C2CC1CN(c1nc(=O)n3c4c(c(-c5ccc(F)cc5F)c(Cl)cc14)SCC3)C2] | 500.95 | 16.9 | 7-(6-acryloyl-3,6-diazabicyclo[3.1.1]heptan-3-yl)-9-chloro-10-(2,4-difluorophenyl)-2,3-dihydro-5H-[1,4]thiazino[2,3,4-ij]quinazolin-5-one |
| 166 | 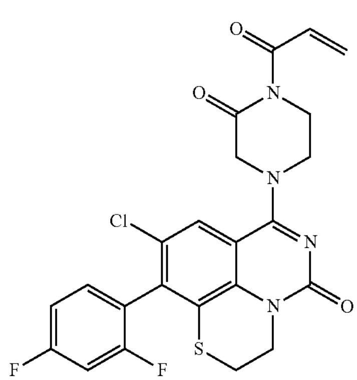 [SMILES: C=CC(=O)N1CCN(c2nc(=O)n3c4c(c(-c5ccc(F)cc5F)c(Cl)cc24)SCC3)CC1=O] | 502.92 | 65.5 | 7-(4-acryloyl-3-oxopiperazin-1-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 167 | 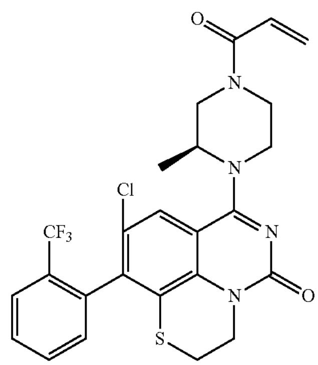 [SMILES: C=CC(=O)N1CCN(c2nc(=O)n3c4c(c(-c5ccccc5C(F)(F)F)c(Cl)cc24)SCC3)[C@@H](C)C1] | 534.98 | 69.8 | 7-((S)-4-acryloyl-2-methylpiperazin-1-yl)-9-chloro-10-(2-(trifluoromethyl)phenyl)-2,3-dihydro-5H-[1,4]thiazino[2,3,4-ij]quinazolin-5-one |
| 168 | 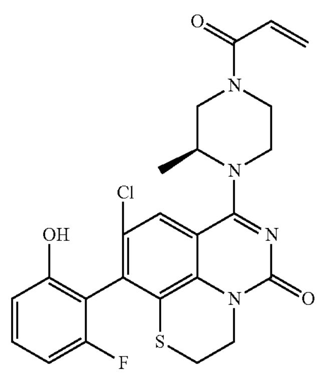 [SMILES: C=CC(=O)N1CCN(c2nc(=O)n3c4c(c(-c5c(O)cccc5F)c(Cl)cc24)SCC3)[C@@H](C)C1] | 500.97 | 30.6 | 7-((S)-4-acryloyl-2-methylpiperazin-1-yl)-9-chloro-10-(2-fluoro-6-hydroxyphenyl)-2,3-dihydro-5H-[1,4]thiazino[2,3,4-ij]quinazolin-5-one |
| 169 | 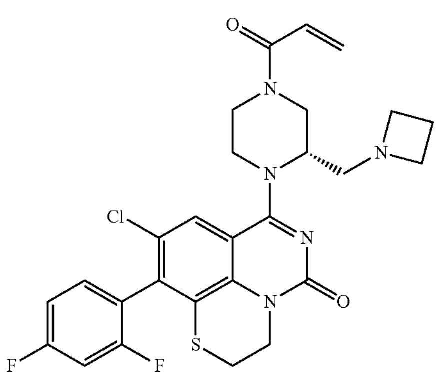 [SMILES: C=CC(=O)N1CCN(c2nc(=O)n3c4c(c(-c5ccc(F)cc5F)c(Cl)cc24)SCC3)[C@@H](CN2CCC2)C1] | 558.04 | 23.3 | 7-((S)-4-acryloyl-2-(azetidin-1-ylmethyl)piperazin-1-yl)-9-chloro-10-(2,4-difluorophenyl)-2,3-dihydro-5H-[1,4]thiazino[2,3,4-ij]quinazolin-5-one |
| 170 | 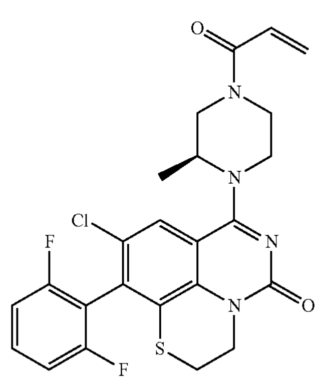 [SMILES: C=CC(=O)N1CCN(c2nc(=O)n3c4c(c(-c5c(F)cccc5F)c(Cl)cc24)SCC3)[C@@H](C)C1] | 502.96 | 75.9 | (S)-7-(4-acryloyl-2-methylpiperazin-1-yl)-9-chloro-10-(2,6-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 171 | 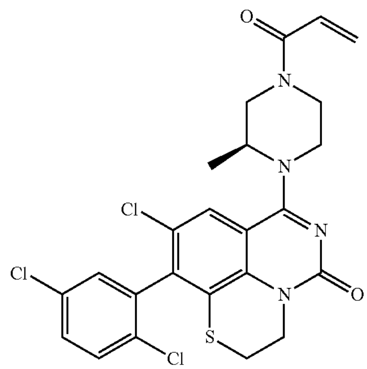 [SMILES: C=CC(=O)N1CCN(c2nc(=O)n3c4c(c(-c5cc(Cl)ccc5Cl)c(Cl)cc24)SCC3)[C@@H](C)C1] | 535.87 | 48.9 | 7-((S)-4-acryloyl-2-methylpiperazin-1-yl)-9-chloro-10-(2,5-dichlorophenyl)-2,3-dihydro-5H-[1,4]thiazino[2,3,4-ij]quinazolin-5-one |
| 172 | 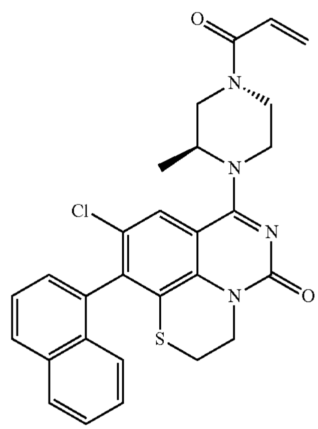 | 517.04 | 51.9 | 7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one |
| 173 | 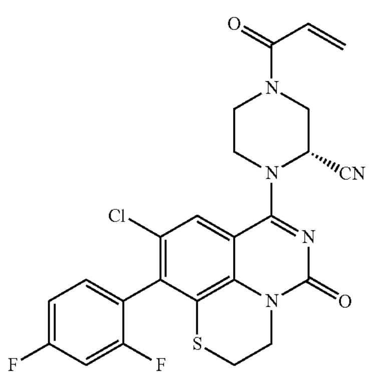 [SMILES: C=CC(=O)N1CCN(c2nc(=O)n3c4c(c(-c5ccc(F)cc5F)c(Cl)cc24)SCC3)[C@@H](C#N)C1] | 513.95 | 2.2 | (2R)-4-acryloyl-1-(9-chloro-10-(2,4-difluorophenyl)-5-oxo-2,3-dihydro-5H-[1,4]thiazino[2,3,4-ij]quinazolin-7-yl)piperazine-2-carbonitrile |
| 174 | 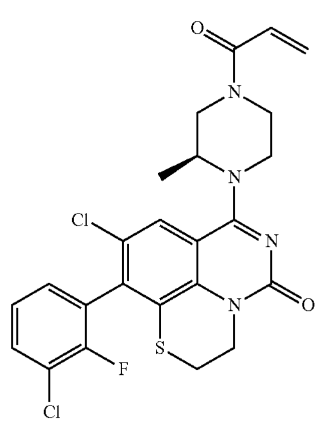 [SMILES: C=CC(=O)N1CCN(c2nc(=O)n3c4c(c(-c5cccc(Cl)c5F)c(Cl)cc24)SCC3)[C@@H](C)C1] | 519.42 | 93.8 | 7-((S)-4-acryloyl-2-methylpiperazin-1-yl)-9-chloro-10-(3-chloro-2-fluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 175 | 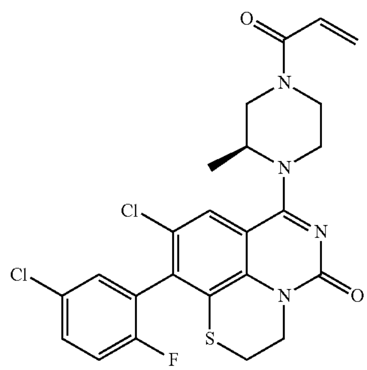 [SMILES: C=CC(=O)N1CCN(c2nc(=O)n3c4c(c(-c5cc(Cl)ccc5F)c(Cl)cc24)SCC3)[C@@H](C)C1] | 519.42 | 79.8 | 7-((S)-4-acryloyl-2-methylpiperazin-1-yl)-9-chloro-10-(5-chloro-2-fluorophenyl)-2,3-dihydro-5H-[1,4]thiazino[2,3,4-ij]quinazolin-5-one |
| 176 | 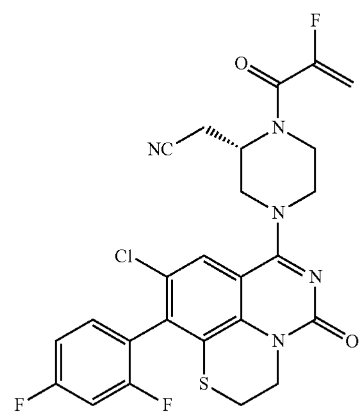 [SMILES: C=C(F)C(=O)N1CCN(c2nc(=O)n3c4c(c(-c5ccc(F)cc5F)c(Cl)cc24)SCC3)C[C@@H]1CC#N] | 545.96 | 40.5 | 2-((2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl)piperazin-2-yl)acetonitrile |
| 177 | 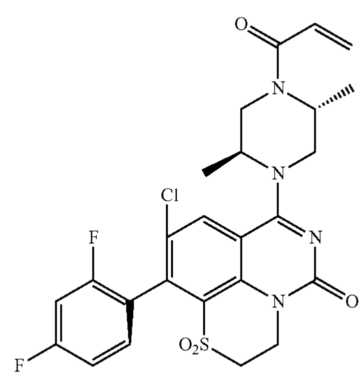 | 548.99 | 93.5 | (S)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide |
| 178 | 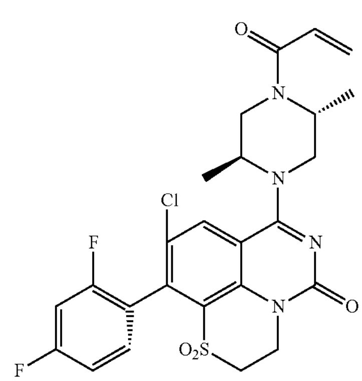 | 548.99 | 58.3 | (R)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide |

TABLE 5-continued

| Example No. | Structure | MW | % CAF @ 10 uM, 1 h | Name |
|---|---|---|---|---|
| 179 | 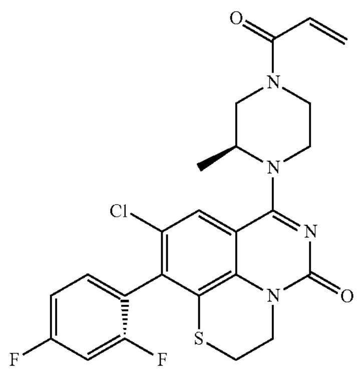 | 502.96 | 96 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |
| 180 | 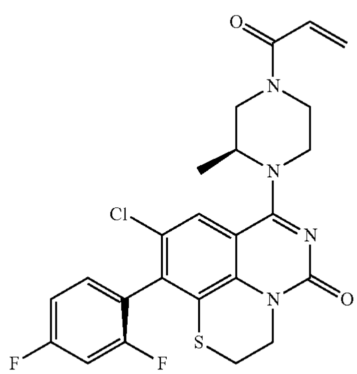 | 502.96 | 94.7 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |
| 181 | 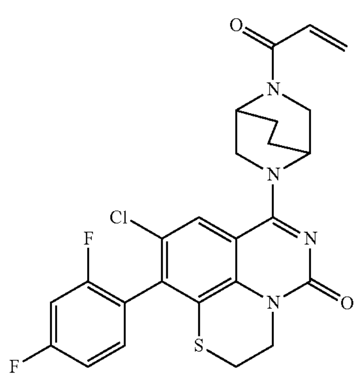 [SMILES: C=CC(=O)N1CC2CCC1CN2c1nc(=O)n2c3c(c(-c4ccc(F)cc4F)c(Cl)cc13)SCC2] | 517.97 | 28.7 | 7-(5-acryloyl-2,5-diazabicyclo[2.2.2]octan-2-yl)-9-chloro-10-(2,4-difluorophenyl)-2,3-dihydro-5H-[1,4]thiazino[2,3,4-ij]quinazolin-5-one |
| 182 | 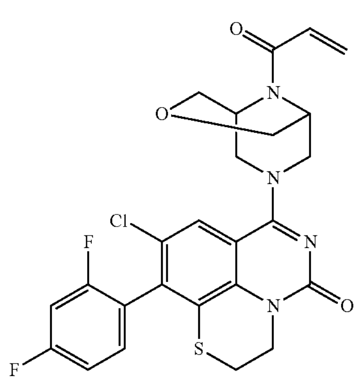 [SMILES: C=CC(=O)N1C2COCC1CN(c1nc(=O)n3c4c(c(-c5ccc(F)cc5F)c(Cl)cc14)SCC3)C2] | 530.97 | 94.4 | 7-(9-acryloyl-3-oxa-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 183 | 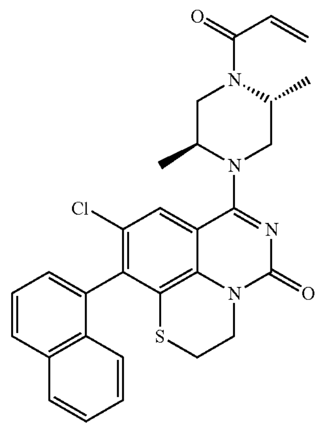 | 531.07 | 45.3 | 7-((2S,5R)-4-acryloyl-2,5-dimethylpiperazin-1-yl)-9-chloro-10-(naphthalen-1-yl)-2,3-dihydro-5H-[1,4]thiazino[2,3,4-ij]quinazolin-5-one |
| 184 | 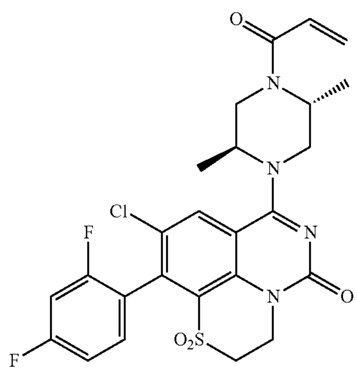 [SMILES: C=CC(=O)N1C[C@H](C)N(c2nc(=O)n3c4c(c(-c5ccc(F)cc5F)c(Cl)cc24)S(=O)(=O)CC3)C[C@H]1C] | 548.99 | 91.4 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide |
| 185 | 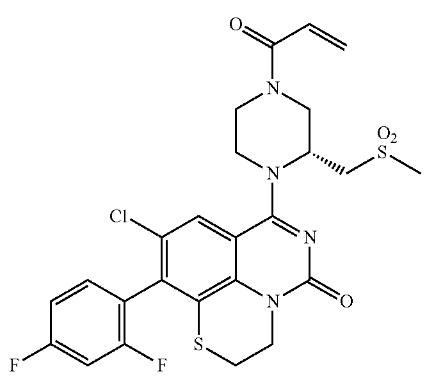 [SMILES: C=CC(=O)N1CCN(c2nc(=O)n3c4c(c(-c5ccc(F)cc5F)c(Cl)cc24)SCC3)[C@@H](CS(C)(=O)=O)C1] | 581.05 | 93.3 | 7-((R)-4-acryloyl-2-((methylsulfonyl)methyl)piperazin-1-yl)-9-chloro-10-(2,4-difluorophenyl)-2,3-dihydro-5H-[1,4]thiazino[2,3,4-ij]quinazolin-5-one |
| 186 | 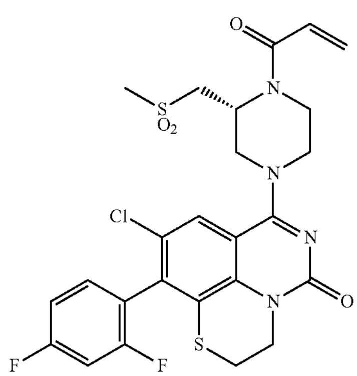 [SMILES: C=CC(=O)N1CCN(c2nc(=O)n3c4c(c(-c5ccc(F)cc5F)c(Cl)cc24)SCC3)C[C@@H]1CS(C)(=O)=O] | 581.05 | 92.6 | 7-((R)-4-acryloyl-3-((methylsulfonyl)methyl)piperazin-1-yl)-9-chloro-10-(2,4-difluorophenyl)-2,3-dihydro-5H-[1,4]thiazino[2,3,4-ij]quinazolin-5-one |

TABLE 5-continued

| Example No. | Structure | MW | % CAF @ 10 uM, 1 h | Name |
|---|---|---|---|---|
| 187 | 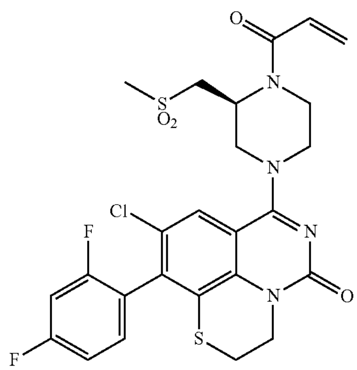 [SMILES: C=CC(=O)N1CCN(c2nc(=O)n3c4c(c(-c5ccc(F)cc5F)c(Cl)cc24)SCC3)C[C@H]1CS(C)(=O)=O] | 581.05 | 83.7 | 7-((S)-4-acryloyl-3-((methyl-sulfonyl)methyl)piperazin-1-yl)-9-chloro-10-(2,4-difluorophenyl)-2,3-dihydro-5H-[1,4]thiazino[2,3,4-ij]quinazolin-5-one |
| 188 | 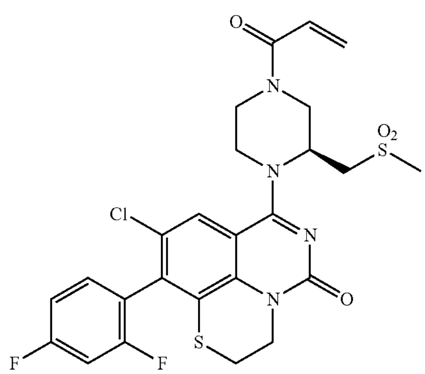 [SMILES: C=CC(=O)N1CCN(c2nc(=O)n3c4c(c(-c5ccc(F)cc5F)c(Cl)cc24)SCC3)[C@H](CS(C)(=O)=O)C1] | 581.05 | 89.2 | 7-((S)-4-acryloyl-2-((methyl-sulfonyl)methyl)piperazin-1-yl)-9-chloro-10-(2,4-difluorophenyl)-2,3-dihydro-5H-[1,4]thiazino[2,3,4-ij]quinazolin-5-one |
| 189 | 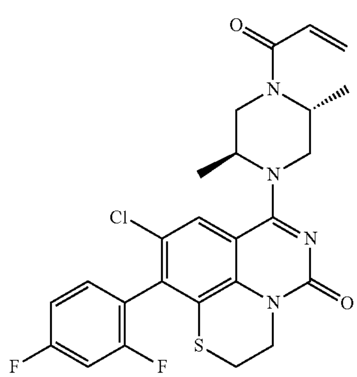 [SMILES: C=CC(=O)N1C[C@H](C)N(c2nc(=O)n3c4c(c(-c5ccc(F)cc5F)c(Cl)cc24)SCC3)C[C@H]1C] | 516.99 | 93.8 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one |
| 190 | 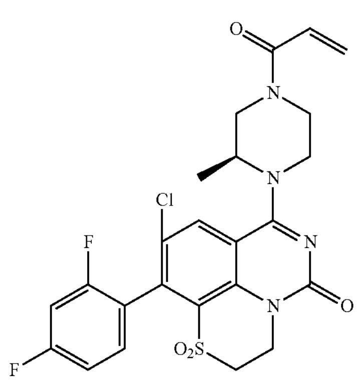 [SMILES: C=CC(=O)N1CCN(c2nc(=O)n3c4c(c(-c5ccc(F)cc5F)c(Cl)cc24)S(=O)(=O)CC3)[C@@H](C)C1] | 534.96 | 88.2 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide |

TABLE 5-continued

| Example No. | Structure | MW | % CAF @ 10 uM, 1 h | Name |
|---|---|---|---|---|
| 191 | 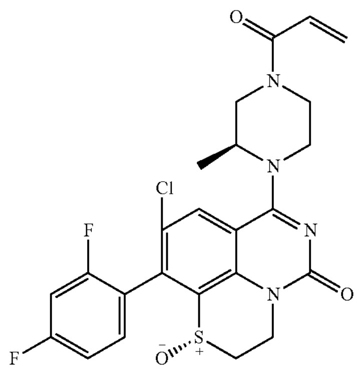 | 518.96 | 26.6 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide |
| 192 | 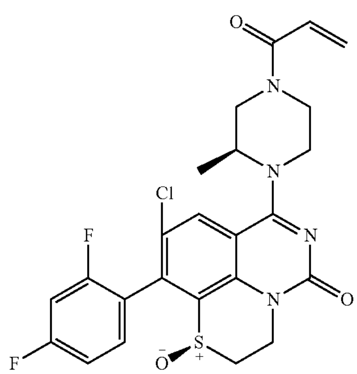 | 518.96 | 62.4 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide |
| 193 | 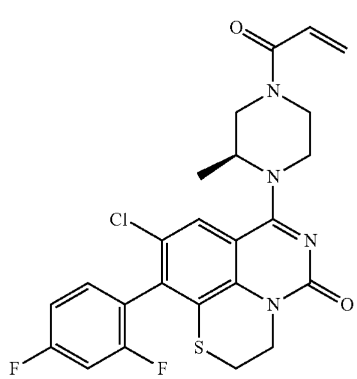 [SMILES: C=CC(=O)N1CCN(c2nc(=O)n3c4c(c(-c5ccc(F)cc5F)c(Cl)cc24)SCC3)[C@@H](C)C1] | 502.96 | 97 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |

TABLE 6

| Example No. | Structure | MW | % CAF @ 10 μM, 1 h | Name |
|---|---|---|---|---|
| 194 | 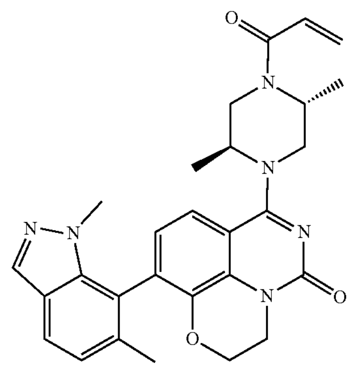 [SMILES: C=CC(=O)N1C[C@H](C)N(c2nc(=O)n3c4c(c(-c5c(C)ccc6cnn(C)c56)ccc24)OCC3)C[C@H]1C] | 498.58 | 2.5 | 7-((2S,5R)-4-acryloyl-2,5-dimethylpiperazin-1-yl)-10-(1,6-dimethyl-1H-indazol-7-yl)-2,3-dihydro-5H-[1,4]oxazino[2,3,4-ij]quinazolin-5-one |
| 195 | 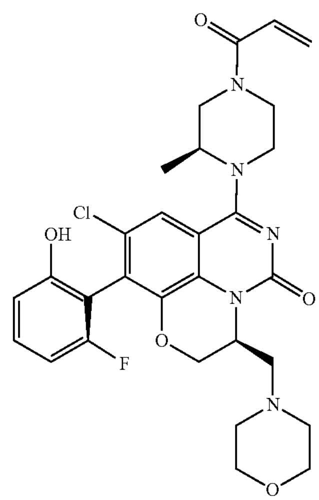 | 584.04 | 0 | (3S,10R)-7-((S)-4-acryloyl-2-methylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one |
| 196 | 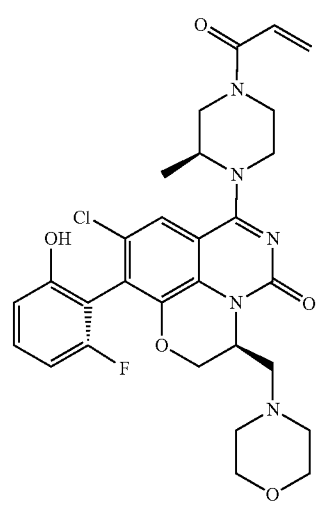 | 584.04 | 97.6 | (3S,10S)-7-((S)-4-acryloyl-2-methylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 197 | 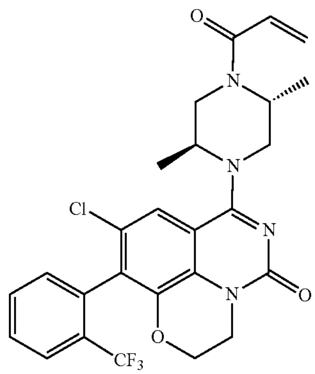 [SMILES: C=CC(=O)N1C[C@H](C)N(c2nc(=O)n3c4c(c(-c5ccccc5C(F)(F)F)c(Cl)cc24)OCC3)C[C@H]1C] | 532.94 | 0 | 7-((2S,5R)-4-acryloyl-2,5-dimethylpiperazin-1-yl)-9-chloro-10-(2-(trifluoromethyl)phenyl)-2,3-dihydro-5H-[1,4]oxazino[2,3,4-ij]quinazolin-5-one |
| 198 | 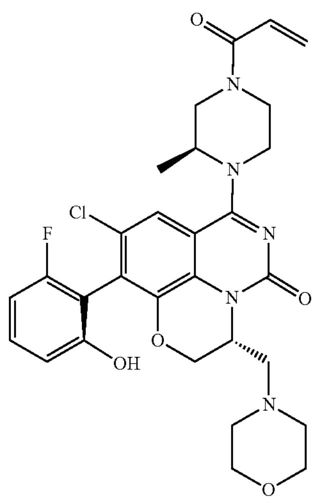 | 584.04 | 100 | (3R,10S)-7-((S)-4-acryloyl-2-methylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one |
| 199 | 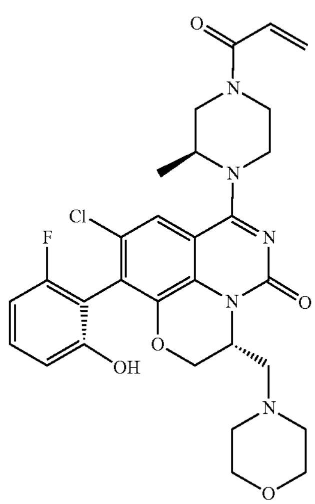 | 584.04 | 0 | (3R,10R)-7-((S)-4-acryloyl-2-methylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 200 | | 498.5 | 0 | 7-((2S,5R)-4-acryloyl-2,5-dimethylpiperazin-1-yl)-10-(2-(difluoromethyl)-6-fluorophenyl)-2,3-dihydro-5H-1,4]oxazino[2,3,4-ij]quinazolin-5-one |
| 201 | 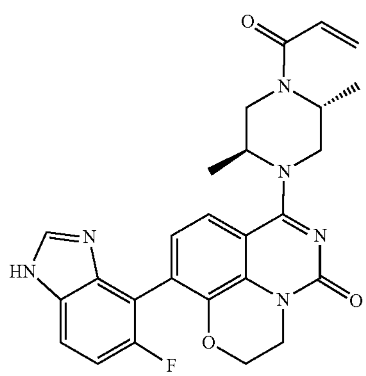 | 488.51 | 0 | 7-((2S,5R)-4-acryloyl-2,5-dimethylpiperazin-1-yl)-10-(5-fluoro-1H-benzo[d]imidazol-4-yl)-2,3-dihydro-5H-[1,4]oxazino[2,3,4-ij]quinazolin-5-one |
| 202 | 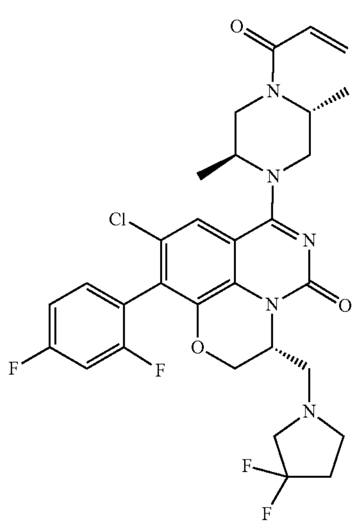 [SMILES: C=CC(=O)N1C[C@H](C)N(c2nc(=O)n3c4c(c(-c5ccc(F)cc5F)c(Cl)cc24)OC[C@H]3CN2CCC(F)(F)C2)C[C@H]1C] | 620.04 | 34.2 | (3R)-7-((2S,5R)-4-acryloyl-2,5-dimethylpiperazin-1-yl)-9-chloro-10-(2,4-difluorophenyl)-3-((3,3-difluoropyrrolidin-1-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 203 | 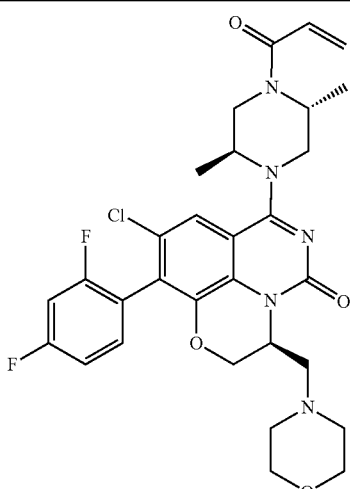 | 600.06 | 84.3 | (3S)-7-((2S,5R)-4-acryloyl-2,5-dimethylpiperazin-1-yl)-9-chloro-10-(2,4-difluorophenyl)-3-(morpholinomethyl)-2,3-dihydro-5H-[1,4]oxazino[2,3,4-ij]quinazolin-5-one |
| 204 | 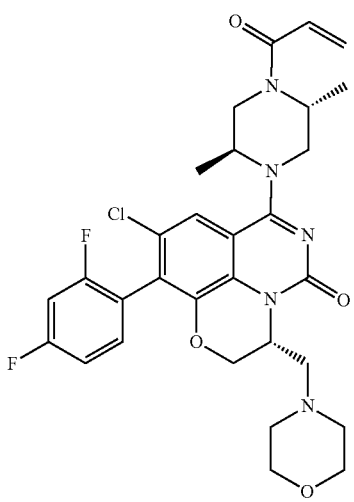 [SMILES: C=CC(=O)N1C[C@H](C)N(c2nc(=O)n3c4c(c(-c5ccc(F)cc5F)c(Cl)cc24)OC[C@H]3CN2CCOCC2)C[C@H]1C] | 600.06 | 82 | (3R)-7-((2S,5R)-4-acryloyl-2,5-dimethylpiperazin-1-yl)-9-chloro-10-(2,4-difluorophenyl)-3-(morpholinomethyl)-2,3-dihydro-5H-[1,4]oxazino[2,3,4-ij]quinazolin-5-one |
| 205 | 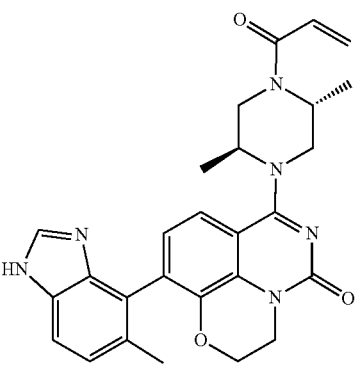 [SMILES: C=CC(=O)N1C[C@H](C)N(c2nc(=O)n3c4c(c(-c5c(C)ccc6[nH]cnc56)ccc24)OCC3)C[C@H]1C] | 484.55 | 4.3 | 7-((2S,5R)-4-acryloyl-2,5-dimethylpiperazin-1-yl)-10-(5-methyl-1H-benzo[d]imidazol-4-yl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 206 | 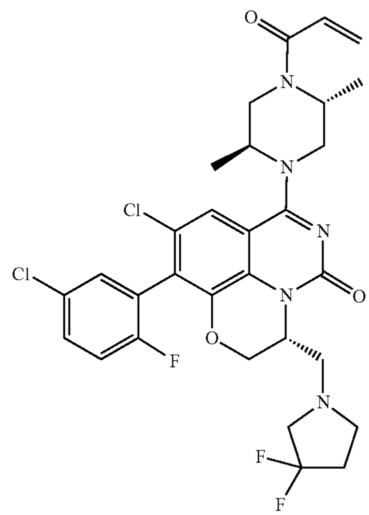 [SMILES: C=CC(=O)N1C[C@H](C)N(c2nc(=O)n3c4c(c(-c5cc(Cl)ccc5F)c(Cl)cc24)OC[C@H]3CN2CCC(F)(F)C2)C[C@H]1C] | 636.49 | 10.7 | (3R)-7-((2S,5R)-4-acryloyl-2,5-dimethylpiperazin-1-yl)-9-chloro-10-(5-chloro-2-fluorophenyl)-3-((3,3-difluoropyrrolidin-1-yl)methyl)-2,3-dihydro-5H-[1,4]oxazino[2,3,4-ij]quinazolin-5-one |
| 207 | 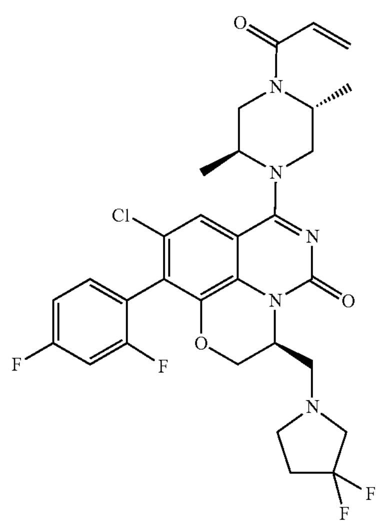 [SMILES: C=CC(=O)N1C[C@H](C)N(c2nc(=O)n3c4c(c(-c5ccc(F)cc5F)c(Cl)cc24)OC[C@@H]3CN2CCC(F)(F)C2)C[C@H]1C] | 620.04 | 85.6 | (3S)-7-((2S,5R)-4-acryloyl 2,5-dimethylpiperazin-1-yl)-9-chloro-10-(2,4-difluorophenyl)-3-((3,3-difluoropyrrolidin-1-yl)methyl)-2,3-dihydro-5H[1,4]oxazino[2,3,4-ij]quinazolin-5-one |
| 208 | 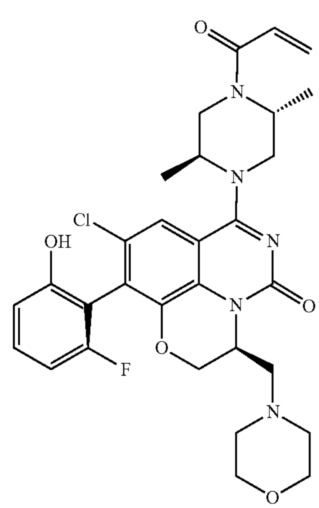 | 598.06 | 0 | (3R,10R)-7-((2S,5R)-4-acryloyl-2,5-dimethylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 209 | 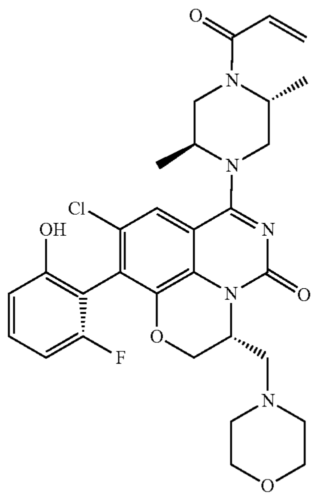 | 598.06 | 85 | (3R,10S)-7-((2S,5R)-4-acryloyl-2,5-dimethylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one |
| 210 | 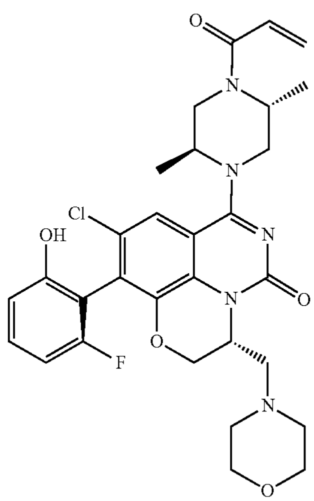 | 598.06 | 0 | (3R,10R)-7-((2S,5R)-4-acryloyl-2,5-dimethylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one |
| 211 | 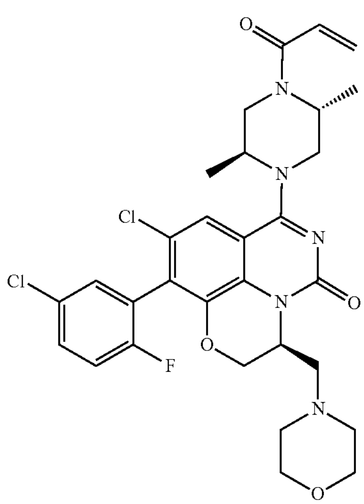 [SMILES: C=CC(=O)N1C[C@H](C)N(c2nc(=O)n3c4c(c(-c5cc(Cl)ccc5F)c(Cl)cc24)OC[C@@H]3CN2CCOCC2)C[C@H]1C] | 616.51 | 77.4 | (3S)-7-((2S,5R)-4-acryloyl-2,5-dimethylpiperazin-1-yl)-9-chloro-10-(5-chloro-2-fluorophenyl)-3-(morpholinomethyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 212 | 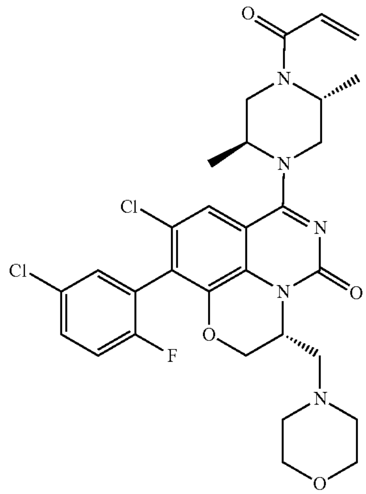 [SMILES: C=CC(=O)N1C[C@H](C)N(c2nc(=O)n3c4c(c(-c5cc(Cl)ccc5F)c(Cl)cc24)OC[C@H]3CN2CCOCC2)C[C@H]1C] | 616.51 | 59.8 | (3R)-7-((2S,5R)-4-acryloyl-2,5-dimethylpiperazin-1-yl)-9-chloro-10-(5-chloro-2-fluorophenyl)-3-(morpholinomethyl)-2,3-dihydro-5H-[1,4]oxazino[2,3,4-ij]quinazolin-5-one |
| 213 | 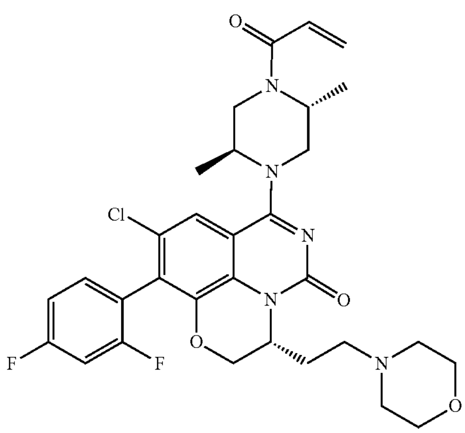 [SMILES: C=CC(=O)N1C[C@H](C)N(c2nc(=O)n3c4c(c(-c5ccc(F)cc5F)c(Cl)cc24)OC[C@H]3CCN2CCOCC2)C[C@H]1C] | 614.08 | 90.6 | (3R)-7-((2S,5R)-4-acryloyl-2,5-dimethylpiperazin-1-yl)-9-chloro-10-(2,4-difluorophenyl)-3-(2-morpholinoethyl)-2,3-dihydro-5H-[1,4]oxazino[2,3,4-ij]quinazolin-5-one |
| 214 | 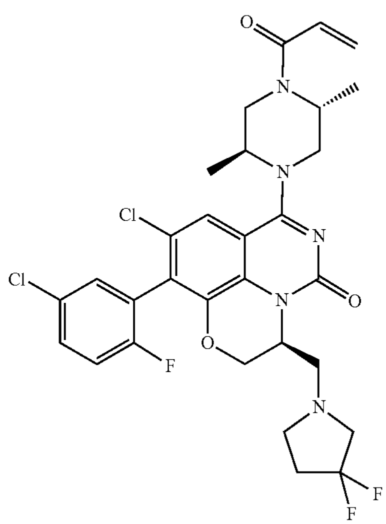 [SMILES: C=CC(=O)N1C[C@H](C)N(c2nc(=O)n3c4c(c(-c5cc(Cl)ccc5F)c(Cl)cc24)OC[C@@H]3CN2CCC(F)(F)C2)C[C@H]1C] | 636.49 | 60.9 | (3S)-7-((2S,5R)-4-acryloyl 2,5-dimethylpiperazin-1-yl)-9-chloro-10-(5-chloro-2-fluorophenyl)-3-((3,3-difluoropyrrolidin-1-yl)methyl)-2,3-dihydro-5H [1,4]oxazino[2,3,4-ij]quinazolin-5-one |

TABLE 6-continued

| Example No. | Structure | MW | % CAF @ 10 μM, 1 h | Name |
|---|---|---|---|---|
| 215 | 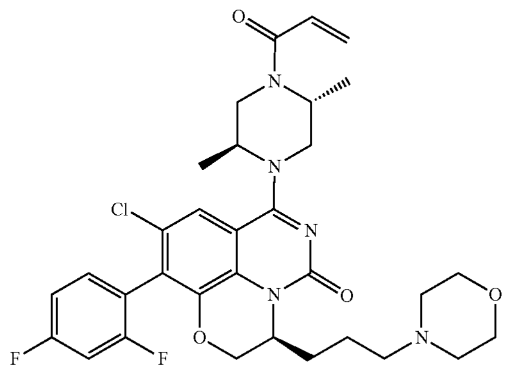 [SMILES: C=CC(=O)N1C[C@H](C)N(c2nc(=O)n3c4c(c(-c5ccc(F)cc5F)c(Cl)cc24)OC[C@@H]3CCCN2CCOCC2)C[C@H]1C] | 628.11 | 91.2 | (3S)-7-((2S,5R)-4-acryloyl-2,5-dimethylpiperazin-1-yl)-9-chloro-10-(2,4-difluorophenyl)-3-(3-morpholinopropyl)-2,3-dihydro-5H-[1,4]oxazino[2,3,4-ij]quinazolin-5-one |
| 216 | 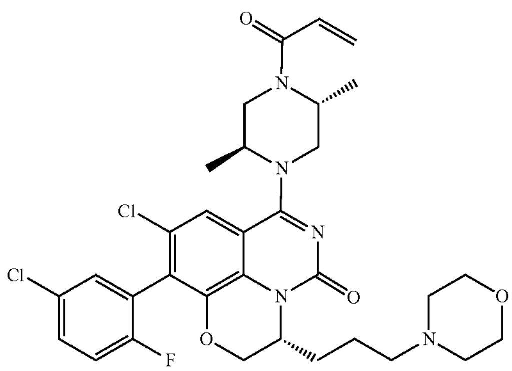 [SMILES: C=CC(=O)N1C[C@H](C)N(c2nc(=O)n3c4c(c(-c5cc(Cl)ccc5F)c(Cl)cc24)OC[C@H]3CCCN2CCOCC2)C[C@H]1C] | 644.56 | 73.8 | (3R)-7-((2S,5R)-4-acryloyl-2,5-dimethylpiperazin-1-yl)-9-chloro-10-(5-chloro-2-fluorophenyl)-3-(3-morpholinopropyl)-2,3-dihydro-5H-[1,4]oxazino[2,3,4-ij]quinazolin-5-one |
| 217 | 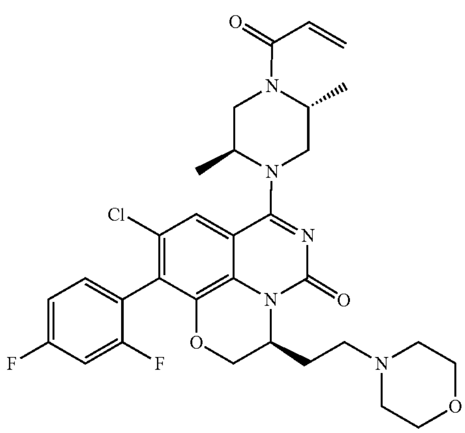 [SMILES: C=CC(=O)N1C[C@H](C)N(c2nc(=O)n3c4c(c(-c5ccc(F)cc5F)c(Cl)cc24)OC[C@@H]3CCN2CCOCC2)C[C@H]1C] | 614.08 | 83.4 | (3S)-7-((2S,5R)-4-acryloyl-2,5-dimethylpiperazin-1-yl)-9-chloro-10-(2,4-difluorophenyl)-3-(2-morpholinoethyl)-2,3-dihydro-5H-[1,4]oxazino[2,3,4-ij]quinazolin-5-one |
| 218 | 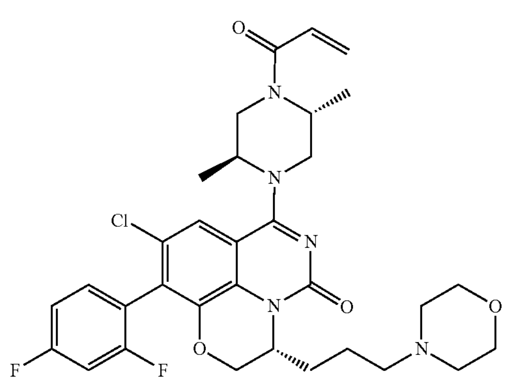 [SMILES: C=CC(=O)N1C[C@H](C)N(c2nc(=O)n3c4c(c(-c5ccc(F)cc5F)c(Cl)cc24)OC[C@H]3CCCN2CCOCC2)C[C@H]1C] | 628.11 | 95.6 | (3R)-7-((2S,5R)-4-acryloyl-2,5-dimethylpiperazin-1-yl)-9-chloro-10-(2,4-difluorophenyl)-3-(3-morpholinopropyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
| --- | --- | --- | --- | --- |
| 219 | 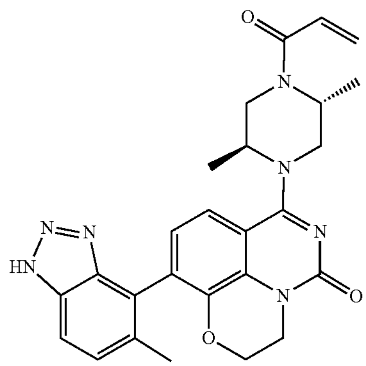 [SMILES: C=CC(=O)N1C[C@H](C)N(c2nc(=O)n3c4c(c(-c5c(C)ccc6[nH]nnc56)ccc24)OCC3)C[C@H]1C] | 485.54 | 0 | 7-((2S,5R)-4-acryloyl-2,5-dimethylpiperazin-1-yl)-10-(5-methyl-1H-benzo[d][1,2,3]triazol-4-yl)-2,3-dihydro-5H-[1,4]oxazino[2,3,4-ij]quinazolin-5-one |
| 220 | 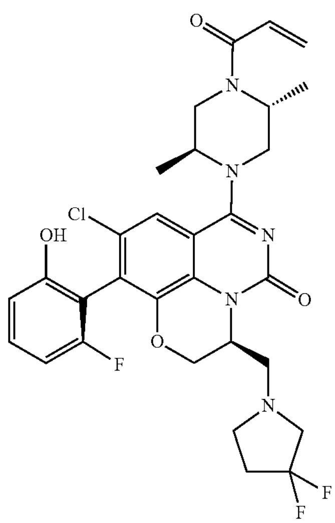 | 618.05 | 0 | (3S,10R)-7-((2S,5R)-4-acryloyl-2,5-dimethylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one |
| 221 | 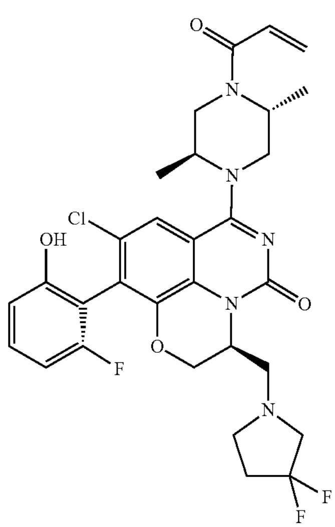 | 618.05 | 70.9 | (3S,10S)-7-((2S,5R)-4-acryloyl-2,5-dimethylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one |

TABLE 6-continued

| Example No. | Structure | MW | % CAF @ 10 µM, 1 h | Name |
|---|---|---|---|---|
| 222 | 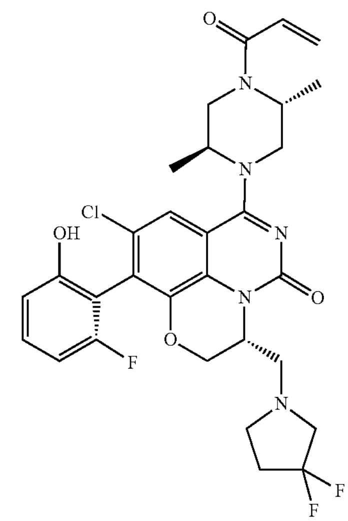 | 618.05 | 1.4 | (3R,10S)-7-((2S,5R)-4-acryloyl-2,5-dimethylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one |
| 223 | 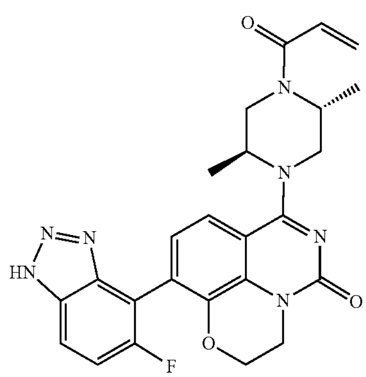 [SMILES: C=CC(=O)N1C[C@H](C)N(c2nc(=O)n3c4c(c(-c5c(F)ccc6[nH]nnc56)ccc24)OCC3)C[C@H]1C] | 489.5 | 0 | 7-((2S,5R)-4-acryloyl-2,5-dimethylpiperazin-1-yl)-10-(5-fluoro-1H-benzo[d][1,2,3]triazol-4-yl)-2,3-dihydro-5H-[1,4]oxazino[2,3,4-ij]quinazolin-5-one |
| 224 | 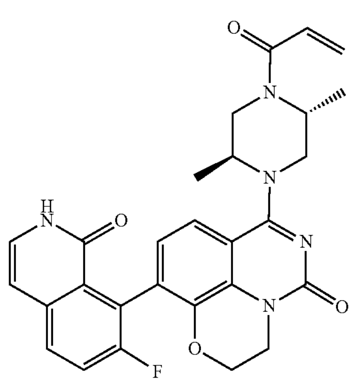 [SMILES: C=CC(=O)N1C[C@H](C)N(c2nc(=O)n3c4c(c(-c5c(F)ccc6cc[nH]c(=O)c56)ccc24)OCC3)C[C@H]1C] | 515.54 | 0 | 7-((2S,5R)-4-acryloyl-2,5-dimethylpiperazin-1-yl)-10-(7-fluoro-1-oxo-1,2-dihydroisoquinolin-8-yl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 225 | 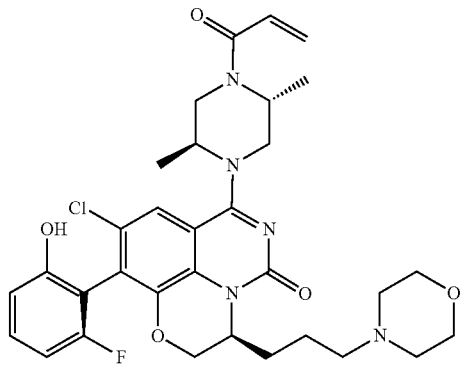 | 626.12 | 4.4 | (3S,10R)-7-((2S,5R)-4-acryloyl-2,5-dimethylpiperazin-1-yl)-9-chloro-10-(2-fluoro-6-hydroxyphenyl)-3-(3-morpholinopropyl)-2,3-dihydro-5H-[1,4]oxazino[2,3,4-ij]quinazolin-5-one |
| 226 | 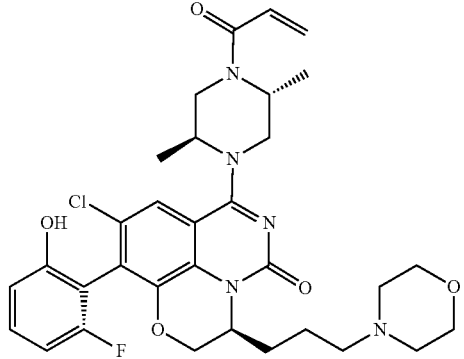 | 626.12 | 97.8 | (3S,10S)-7-((2S,5R)-4-acryloyl-2,5-dimethylpiperazin-1-yl)-9-chloro-10-(2-fluoro-6-hydroxyphenyl)-3-(3-morpholinopropyl)-2,3-dihydro-5H-[1,4]oxazino[2,3,4-ij]quinazolin-5-one |
| 227 | 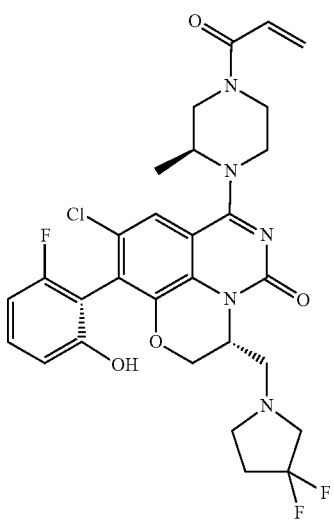 | 604.02 | 0 | (3R,10R)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 228 | 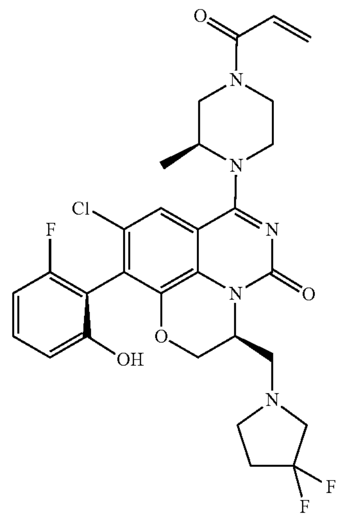 | 604.02 | 98 | (3S,10S)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one |
| 229 | 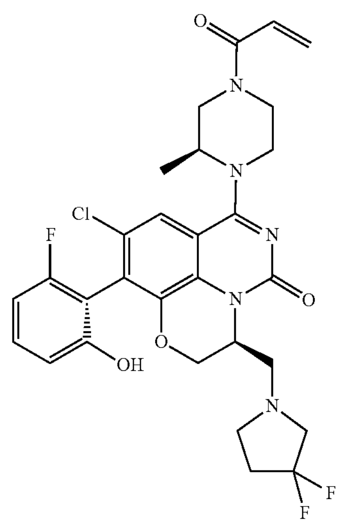 | 604.02 | 1.6 | (3S,10R)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one |
| 230 | 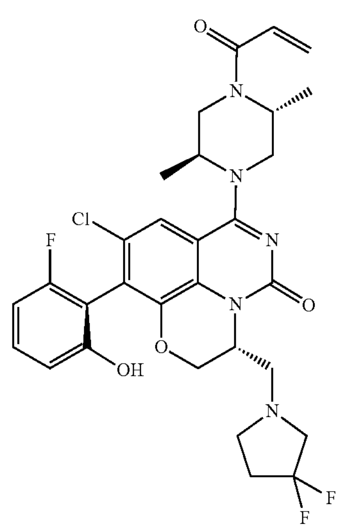 | 604.02 | 75.9 | (3R,10S)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 231 | 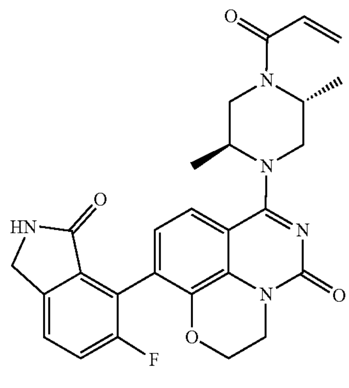 [SMILES: C=CC(=O)N1C[C@H](C)N(c2nc(=O)n3c4c(c(-c5c(F)ccc6c5C(=O)NC6)ccc24)OCC3)C[C@H]1C] | 503.52 | 0 | 7-((2S,5R)-4-acryloyl-2,5-dimethylpiperazin-1-yl)-10-(5-fluoro-3-oxoisoindolin-4-yl)-2,3-dihydro-5H-[1,4]oxazino[2,3,4-ij]quinazolin-5-one |
| 232 | 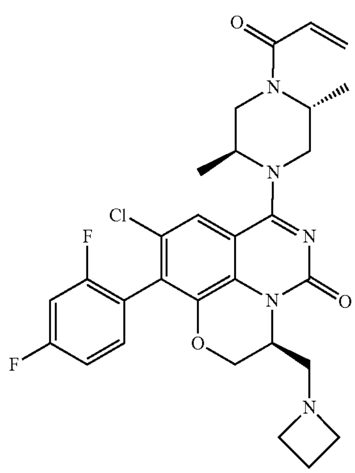 [SMILES: C=CC(=O)N1C[C@H](C)N(c2nc(=O)n3c4c(c(-c5ccc(F)cc5F)c(Cl)cc24)OC[C@@H]3CN2CCC2)C[C@H]1C] | 570.03 | 82.4 | (3S)-7-((2S,5R)-4-acryloyl-2,5-dimethylpiperazin-1-yl)-3-(azetidin-1-ylmethyl)-9-chloro-10-(2,4-difluorophenyl)-2,3-dihydro-5H-[1,4]oxazino[2,3,4-ij]quinazolin-5-one |
| 233 | 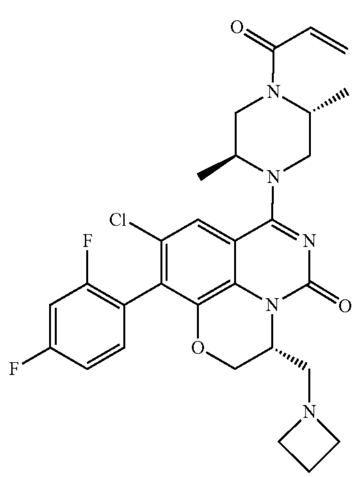 [SMILES: C=CC(=O)N1C[C@H](C)N(c2nc(=O)n3c4c(c(-c5ccc(F)cc5F)c(Cl)cc24)OC[C@H]3CN2CCC2)C[C@H]1C] | 570.03 | 76 | (3R)-7-((2S,5R)-4-acryloyl-2,5-dimethylpiperazin-1-yl)-3-(azetidin-1-ylmethyl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 234 | 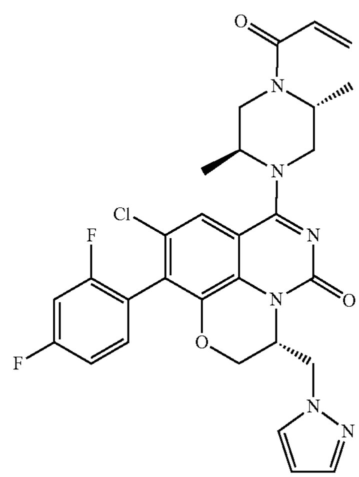 [SMILES: C=CC(=O)N1C[C@H](C)N(c2nc(=O)n3c4c(c(-c5ccc(F)cc5F)c(Cl)cc24)OC[C@H]3Cn2cccn2)C[C@H]1C] | 581.01 | 71.3 | (3R)-3-((1H-pyrazol-1-yl)methyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |
| 235 | 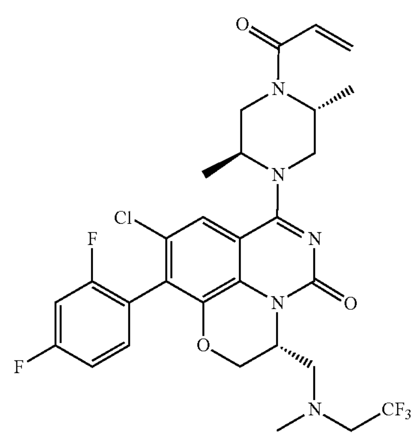 [SMILES: C=CC(=O)N1C[C@H](C)N(c2nc(=O)n3c4c(c(-c5ccc(F)cc5F)c(Cl)cc24)OC[C@H]3CN(C)CC(F)(F)F)C[C@H]1C] | 626.02 | 44.5 | (3R)-7-((2S,5R)-4-acryloyl-2,5-dimethylpiperazin-1-yl)-9-chloro-10-(2,4-difluorophenyl)-3-((methyl(2,2,2-trifluoroethyl)amino)methyl)-2,3-dihydro-5H-[1,4]oxazino[2,3,4-ij]quinazolin-5-one |
| 236 | 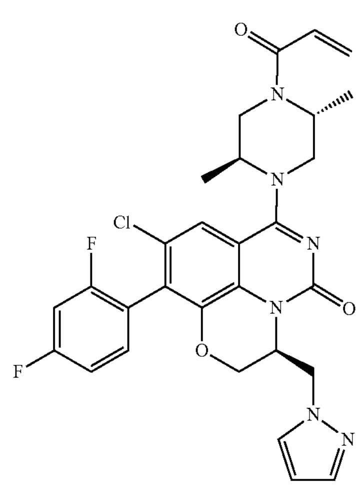 [SMILES: C=CC(=O)N1C[C@H](C)N(c2nc(=O)n3c4c(c(-c5ccc(F)cc5F)c(Cl)cc24)OC[C@@H]3Cn2cccn2)C[C@H]1C] | 581.01 | 60.9 | (3S)-3-((1H-pyrazol-1-yl)methyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 µM, 1 h | Name |
|---|---|---|---|---|
| 237 | 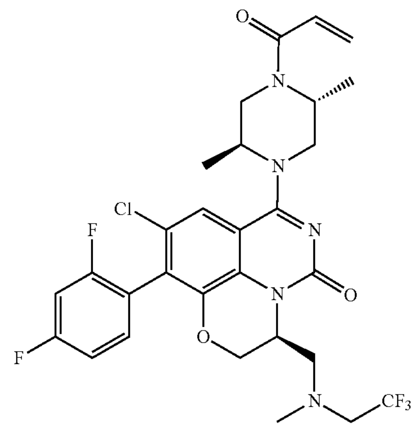 [SMILES: C=CC(=O)N1C[C@H](C)N(c2nc(=O)n3c4c(c(-c5ccc(F)cc5F)c(Cl)cc24)OC[C@@H]3CN(C)CC(F)(F)F)C[C@H]1C] | 626.02 | 78.5 | (3S)-7-((2S,5R)-4-acryloyl-2,5-dimethylpiperazin-1-yl)-9-chloro-10-(2,4-difluorophenyl)-3-((methyl(2,2,2-trifluoroethyl)amino)methyl)-2,3-dihydro-5H-[1,4]oxazino[2,3,4-ij]quinazolin-5-one |
| 238 | 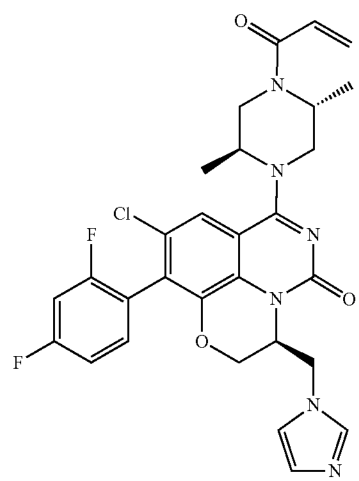 [SMILES: C=CC(=O)N1C[C@H](C)N(c2nc(=O)n3c4c(c(-c5ccc(F)cc5F)c(Cl)cc24)OC[C@@H]3Cn2ccnc2)C[C@H]1C] | 581.01 | 79.4 | (3S)-3-((1H-imidazol-1-yl)methyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |
| 239 | 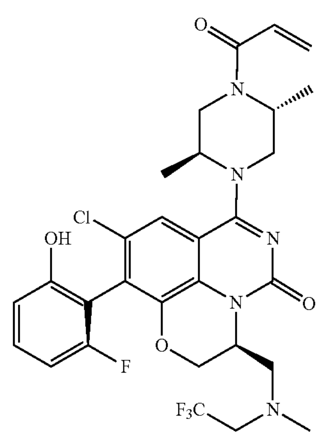 | 624.03 | 3 | (3S,10R)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2,3-dihydro-5H-[1,4]oxazino[2,3,4-ij]quinazolin-5-one |

TABLE 6-continued

| Example No. | Structure | MW | % CAF @ 10 µM, 1 h | Name |
|---|---|---|---|---|
| 240 | 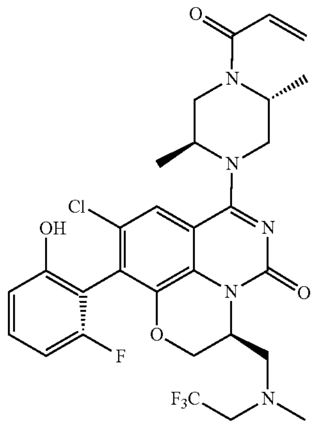 | 624.03 | 82.1 | (3S,10S)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2,3-dihydro-5H-[1,4]oxazino[2,3,4-ij]quinazolin-5-one |
| 241 | 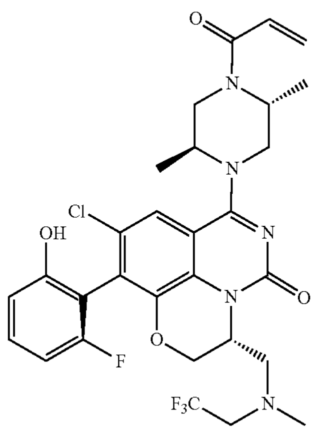 | 624.03 | 0 | (3R,10R)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2,3-dihydro-5H-[1,4]oxazino[2,3,4-ij]quinazolin-5-one |
| 242 | 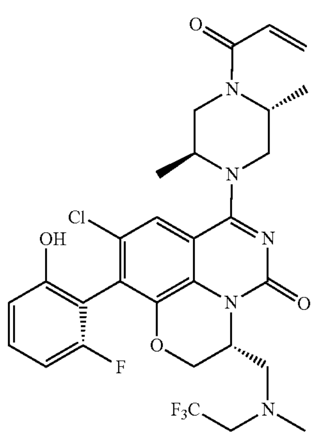 | 624.03 | 63.1 | (3R,10S)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
| --- | --- | --- | --- | --- |
| 243 | 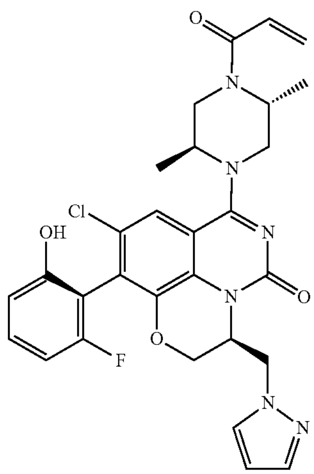 | 579.02 | 80.6 | (3S,10S)-7-((1H-pyrazol-1-yl)methyl)-7-((2S,5R)-4-acryloyl-2,5-dimethylpiperazin-1-yl)-9-chloro-10-(2-fluoro-6-hydroxyphenyl)-2,3-dihydro-5H-[1,4]oxazino[2,3,4-ij]quinazolin-5-one |
| 244 | 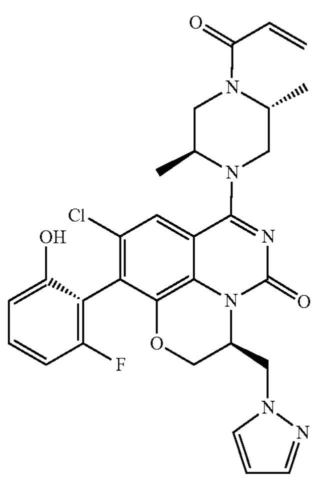 | 579.02 | 4.4 | (3S,10R)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2,3-dihydro-5H-[1,4]oxazino[2,3,4-ij]quinazolin-5-one |
| 245 | 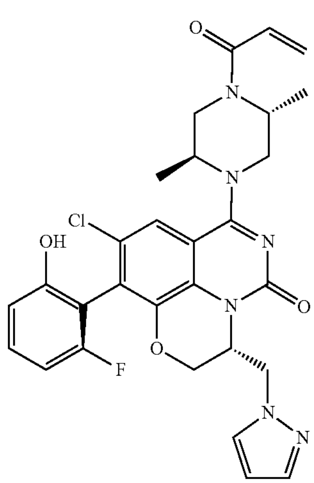 | 579.02 | 0 | (3R,10R)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 246 | 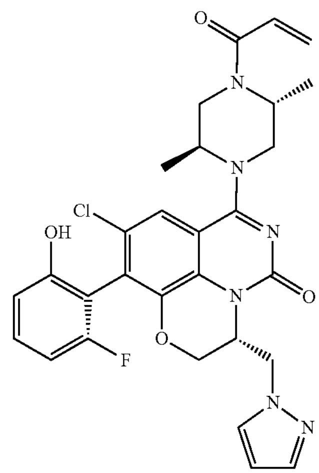 | 579.02 | 97.4 | (3R,10S)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2,3-dihydro-5H-[1,4]oxazino[2,3,4-ij]quinazolin-5-one |
| 247 | 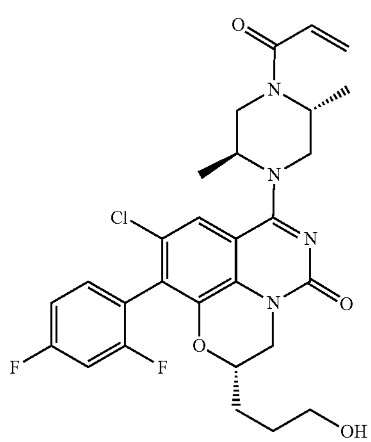 [SMILES: C=CC(=O)N1C[C@H](C)N(c2nc(=O)n3c4c(c(-c5ccc(F)cc5F)c(Cl)cc24)O[C@@H](CCCO)C3)C[C@H]1C] | 559 | 42.2 | (2S)-7-((2S,5R)-4-acryloyl-2,5-dimethylpiperazin-1-yl)-9-chloro-10-(2,4-difluorophenyl)-2-(3-hydroxypropyl)-2,3-dihydro-5H-[1,4]oxazino[2,3,4-ij]quinazolin-5-one |
| 248 | 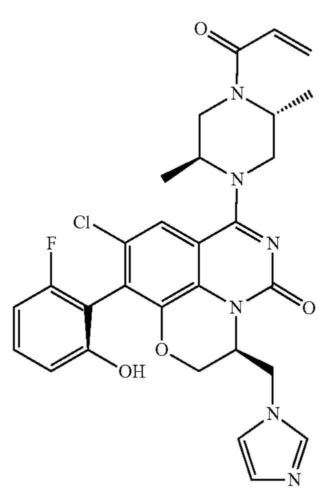 | 579.02 | 2.3 | (3S,10S)-3-((1H-imidazol-1-yl)methyl)-7-((2S,5R)-4-acryloyl-2,5-dimethylpiperazin-1-yl)-9-chloro-10-(2-fluoro-6-hydroxyphenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 249 | 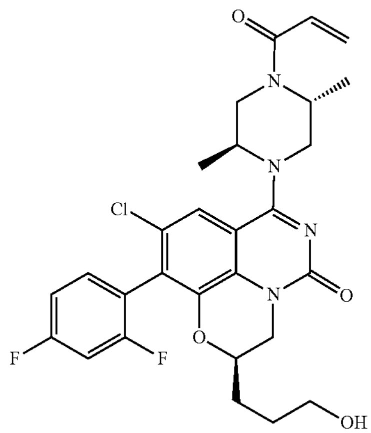 | 559 | 51.2 | (2R)-7-((2S,5R)-4-acryloyl-2,5-dimethylpiperazin-1-yl)-9-chloro-10-(2,4-difluorophenyl)-2-(3-hydroxypropyl)-2,3-dihydro-5H-[1,4]oxazino[2,3,4-ij]quinazolin-5-one |
| 250 | 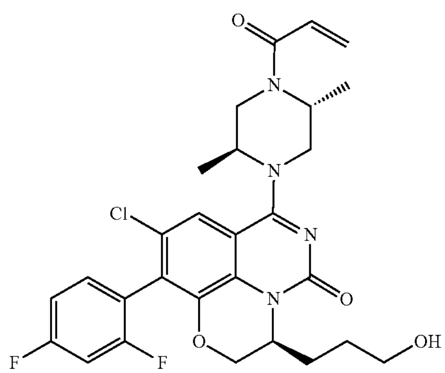 [SMILES: C=CC(=O)N1C[C@H](C)N(c2nc(=O)n3c4c(c(-c5ccc(F)cc5F)c(Cl)cc24)OC[C@@H]3CCCO)C[C@H]1C] | 559 | 70.1 | (3S)-7-((2S,5R)-4-acryloyl-2,5-dimethylpiperazin-1-yl)-9-chloro-10-(2,4-difluorophenyl)-3-(3-hydroxypropyl)-2,3-dihydro-5H-[1,4]oxazino[2,3,4-ij]quinazolin-5-one |
| 251 | 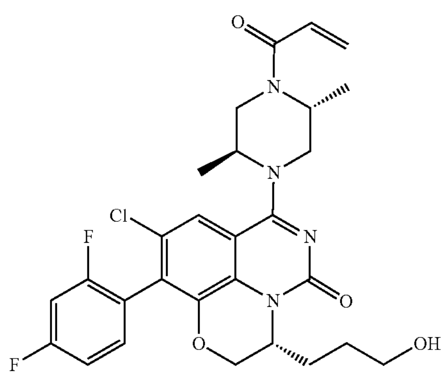 [SMILES: C=CC(=O)N1C[C@H](C)N(c2nc(=O)n3c4c(c(-c5ccc(F)cc5F)c(Cl)cc24)OC[C@H]3CCCO)C[C@H]1C] | 559 | 85.3 | (3R)-7-((2S,5R)-4-acryloyl-2,5-dimethylpiperazin-1-yl)-9-chloro-10-(2,4-difluorophenyl)-3-(3-hydroxypropyl)-2,3-dihydro-5H-[1,4]oxazino[2,3,4-ij]quinazolin-5-one |
| 252 | 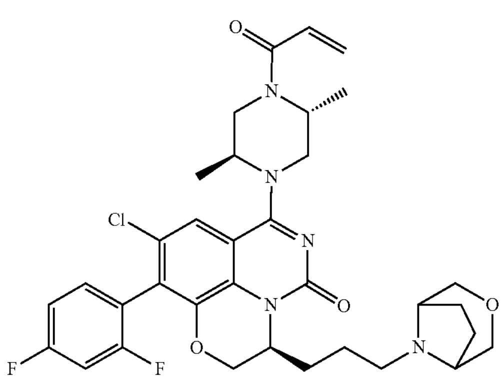 [SMILES: C=CC(=O)N1C[C@H](C)N(c2nc(=O)n3c4c(c(-c5ccc(F)cc5F)c(Cl)cc24)OC[C@@H]3CCCN2C3CCC2COC3)C[C@H]1C] | 654.15 | 60.5 | (3S)-3-(3-(3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 253 | 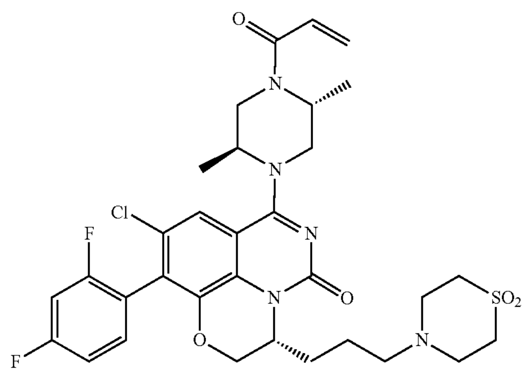 [SMILES: C=CC(=O)N1C[C@H](C)N(c2nc(=O)n3c4c(c(-c5ccc(F)cc5F)c(Cl)cc24)OC[C@H]3CCCN2CCS(=O)(=O)CC2)C[C@H]1C] | 676.17 | 87.6 | (3R)-7-((2S,5R)-4-acryloyl-2,5-dimethylpiperazin-1-yl)-9-chloro-10-(2,4-difluorophenyl)-3-(3-(1,1-dioxidothiomorpholino)propyl)-2,3-dihydro-5H-[1,4]oxazino[2,3,4-ij]quinazolin-5-one |
| 254 | 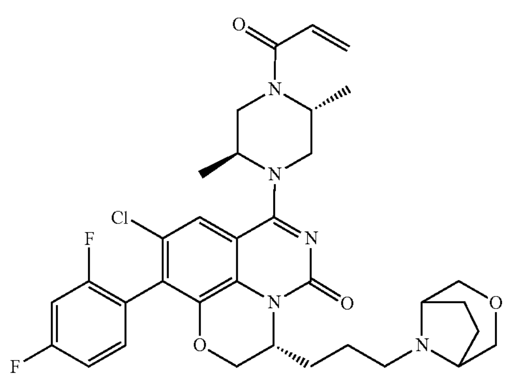 [SMILES: C=CC(=O)N1C[C@H](C)N(c2nc(=O)n3c4c(c(-c5ccc(F)cc5F)c(Cl)cc24)OC[C@H]3CCCN2C3CCC2COC3)C[C@H]1C] | 654.15 | 99.5 | (3R)-3-(3-(3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |
| 255 | 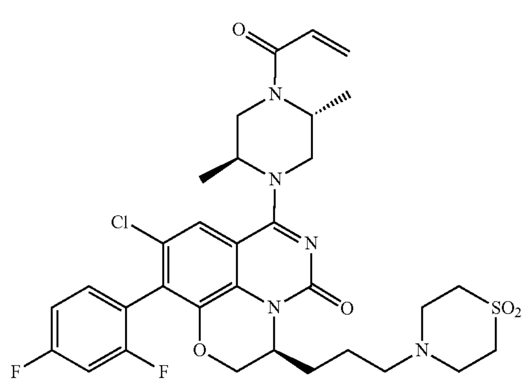 [SMILES: C=CC(=O)N1C[C@H](C)N(c2nc(=O)n3c4c(c(-c5ccc(F)cc5F)c(Cl)cc24)OC[C@@H]3CCCN2CCS(=O)(=O)CC2)C[C@H]1C] | 676.17 | 86.8 | (3S)-7-((2S,5R)-4-acryloyl-2,5-dimethylpiperazin-1-yl)-9-chloro-10-(2,4-difluorophenyl)-3-(3-(1,1-dioxidothiomorpholino)propyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 256 | 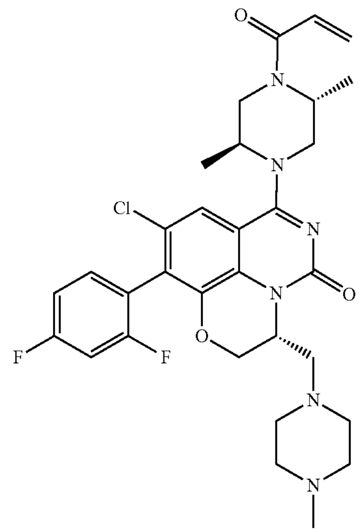 | 613.1 | 80.1 | (3R)-7-((2S,5R)-4-acryloyl-2,5-dimethylpiperazin-1-yl)-9-chloro-10-(2,4-difluorophenyl)-3-((4-methylpiperazin-1-yl)methyl)-2,3-dihydro-5H-[1,4]oxazino[2,3,4-ij]quinazolin-5-one |
| 257 | 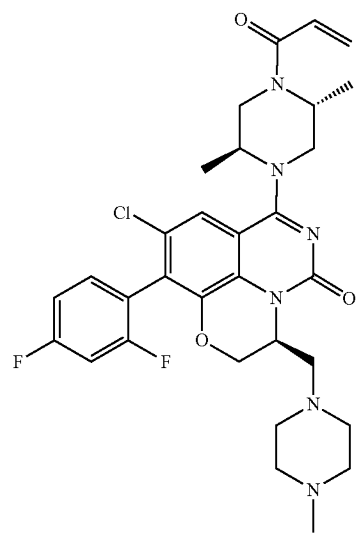 | 613.1 | 94.8 | (3S)-7-((2S,5R)-4-acryloyl-2,5-dimethylpiperazin-1-yl)-9-chloro-10-(2,4-difluorophenyl)-3-((4-methylpiperazin-1-yl)methyl)-2,3-dihydro-5H-[1,4]oxazino[2,3,4-ij]quinazolin-5-one |
| 258 | 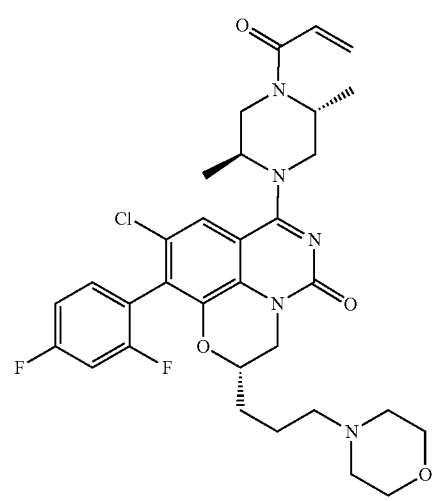 [SMILES: C=CC(=O)N1C[C@H](C)N(c2nc(=O)n3c4c(c(-c5ccc(F)cc5F)c(Cl)cc24)O[C@@H](CCCN2CCOCC2)C3)C[C@H]1C] | 628.11 | 17.7 | (2S)-7-((2S,5R)-4-acryloyl-2,5-dimethylpiperazin-1-yl)-9-chloro-10-(2,4-difluorophenyl)-2-(3-morpholinopropyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 259 | 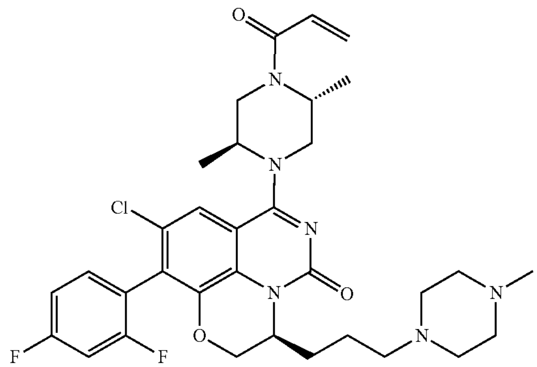 [SMILES: C=CC(=O)N1C[C@H](C)N(c2nc(=O)n3c4c(c(-c5ccc(F)cc5F)c(Cl)cc24)OC[C@@H]3CCCN2CCN(C)CC2)C[C@H]1C] | 641.15 | 90.2 | (3S)-7-((2S,5R)-4-acryloyl-2,5-dimethylpiperazin-1-yl)-9-chloro-10-(2,4-difluorophenyl)-3-(3-(4-methylpiperazin-1-yl)propyl)-2,3-dihydro-5H-[1,4]oxazino[2,3,4-ij]quinazolin-5-one |
| 260 | 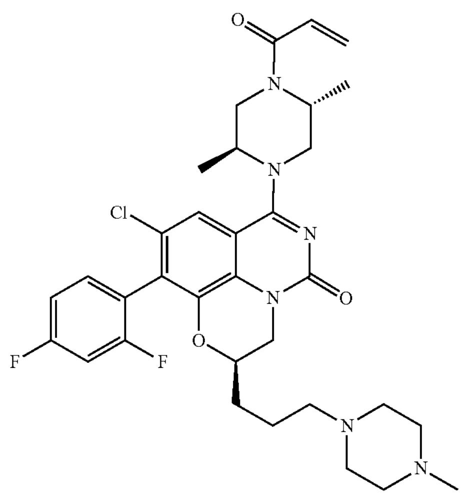 [SMILES: C=CC(=O)N1C[C@H](C)N(c2nc(=O)n3c4c(c(-c5ccc(F)cc5F)c(Cl)cc24)O[C@H](CCCN2CCN(C)CC2)C3)C[C@H]1C] | 641.15 | 48.4 | (2R)-7-((2S,5R)-4-acryloyl-2,5-dimethylpiperazin-1-yl)-9-chloro-10-(2,4-difluorophenyl)-2-(3-(4-methylpiperazin-1-yl)propyl)-2,3-dihydro-5H-[1,4]oxazino[2,3,4-ij]quinazolin-5-one |
| 261 | 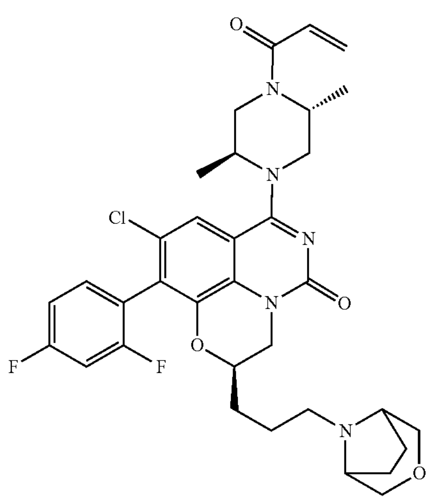 [SMILES: C=CC(=O)N1C[C@H](C)N(c2nc(=O)n3c4c(c(-c5ccc(F)cc5F)c(Cl)cc24)O[C@H](CCCN2C4CCC2COC4)C3)C[C@H]1C] | 654.15 | 21.1 | (2R)-2-(3-(3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 262 | 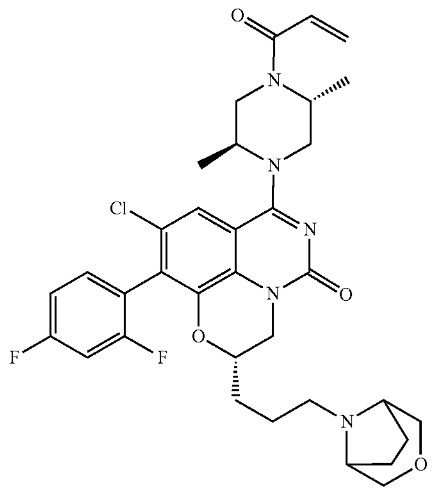 [SMILES: C=CC(=O)N1C[C@H](C)N(c2nc(=O)n3c4c(c(-c5ccc(F)cc5F)c(Cl)cc24)O[C@@H](CCCN2C4CCC2COC4)C3)C[C@H]1C] | 654.15 | 31.6 | (2S)-2-(3-(3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |
| 263 | 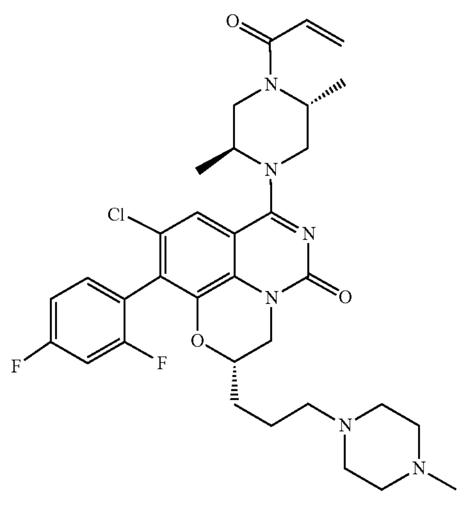 [SMILES: C=CC(=O)N1C[C@H](C)N(c2nc(=O)n3c4c(c(-c5ccc(F)cc5F)c(Cl)cc24)O[C@@H](CCCN2CCN(C)CC2)C3)C[C@H]1C] | 641.15 | 41.6 | (2S)-7-((2S,5R)-4-acryloyl-2,5-dimethylpiperazin-1-yl)-9-chloro-10-(2,4-difluorophenyl)-2-(3-(4-methylpiperazin-1-yl)propyl)-2,3-dihydro-5H-[1,4]oxazino[2,3,4-ij]quinazolin-5-one |
| 264 | 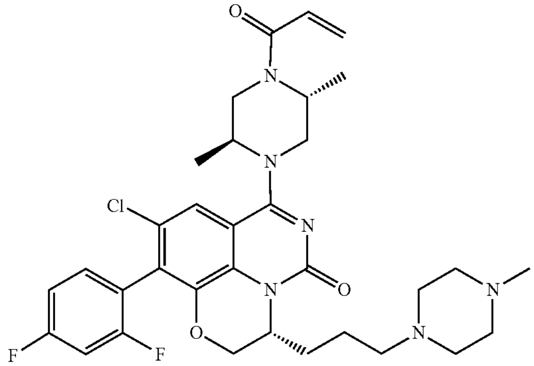 [SMILES: C=CC(=O)N1C[C@H](C)N(c2nc(=O)n3c4c(c(-c5ccc(F)cc5F)c(Cl)cc24)OC[C@H]3CCCN2CCN(C)CC2)C[C@H]1C] | 641.15 | 97.4 | (3R)-7-((2S,5R)-4-acryloyl-2,5-dimethylpiperazin-1-yl)-9-chloro-10-(2,4-difluorophenyl)-3-(3-(4-methylpiperazin-1-yl)propyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 265 | 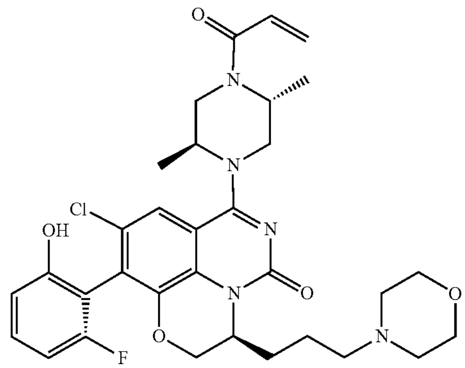 | 626.12 | 97.5 | (3S,10S)-7-((2S,5R)-4-acryloyl-2,5-dimethylpiperazin-1-yl)-9-chloro-10-(2-fluoro-6-hydroxyphenyl)-3-(3-morpholinopropyl)-2,3-dihydro-5H-[1,4]oxazino[2,3,4-ij]quinazolin-5-one |
| 266 | 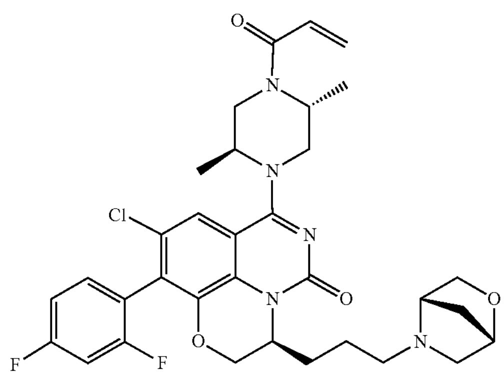 [SMILES: C=CC(=O)N1C[C@H](C)N(c2nc(=O)n3c4c(c(-c5ccc(F)cc5F)c(Cl)cc24)OC[C@@H]3CCCN2C[C@@H]3C[C@H]2CO3)C[C@H]1C] | 640.12 | 59.2 | (3S)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |
| 267 | 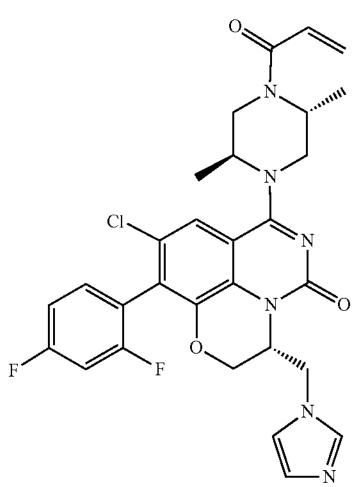 [SMILES: C=CC(=O)N1C[C@H](C)N(c2nc(=O)n3c4c(c(-c5ccc(F)cc5F)c(Cl)cc24)OC[C@H]3Cn2ccnc2)C[C@H]1C] | 581.01 | 13.6 | (3R)-3-((1H-imidazol-1-yl)methyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 268 | 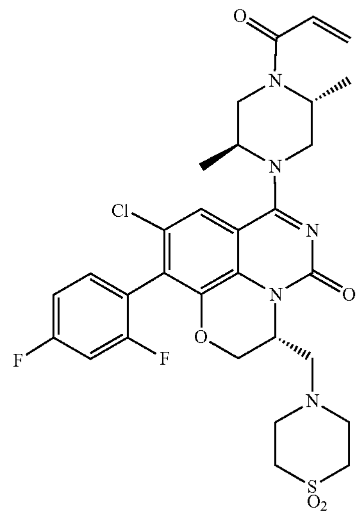 [SMILES: C=CC(=O)N1C[C@H](C)N(c2nc(=O)n3c4c(c(-c5ccc(F)cc5F)c(Cl)cc24)OC[C@H]3CN2CCS(=O)(=O)CC2)C[C@H]1C] | 648.12 | 68 | (3R)-7-((2S,5R)-4-acryloyl-2,5-dimethylpiperazin-1-yl)-9-chloro-10-(2,4-difluorophenyl)-3-((1,1-dioxidothiomorpholino)methyl)-2,3-dihydro-5H-[1,4]oxazino[2,3,4-ij]quinazolin-5-one |
| 269 | 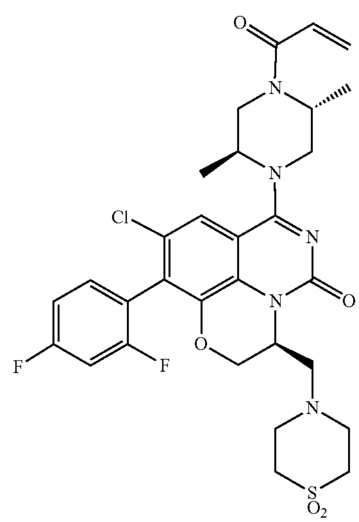 [SMILES: C=CC(=O)N1C[C@H](C)N(c2nc(=O)n3c4c(c(-c5ccc(F)cc5F)c(Cl)cc24)OC[C@@H]3CN2CCS(=O)(=O)CC2)C[C@H]1C] | 648.12 | 94.6 | (3S)-7-((2S,5R)-4-acryloyl-2,5-dimethylpiperazin-1-yl)-9-chloro-10-(2,4-difluorophenyl)-3-((1,1-dioxidothiomorpholino)methyl)-2,3-dihydro-5H-[1,4]oxazino[2,3,4-ij]quinazolin-5-one |
| 270 | 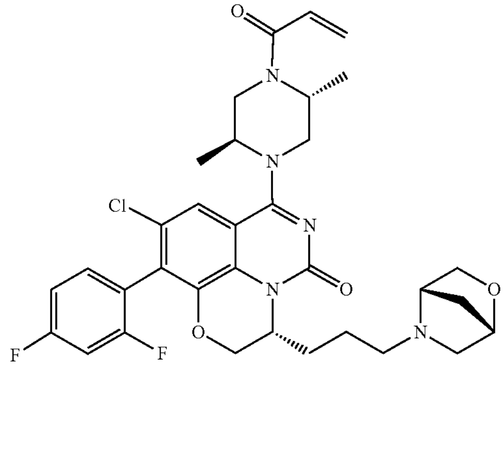 [SMILES: C=CC(=O)N1C[C@H](C)N(c2nc(=O)n3c4c(c(-c5ccc(F)cc5F)c(Cl)cc24)OC[C@H]3CCCN2C[C@@H]3C[C@H]2CO3)C[C@H]1C] | 640.12 | 96.4 | (3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 µM,1 h | Name |
|---|---|---|---|---|
| 271 | 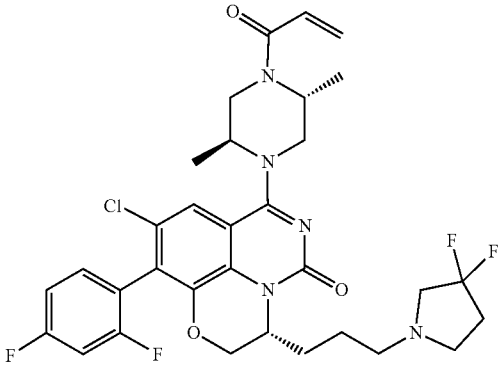 [SMILES: C=CC(=O)N1C[C@H](C)N(c2nc(=O)n3c4c(c(-c5ccc(F)cc5F)c(Cl)cc24)OC[C@H]3CCCN2CCC(F)(F)C2)C[C@H]1C] | 648.09 | 93.6 | (3R)-7-((2S,5R)-4-acryloyl-2,5-dimethylpiperazin-1-yl)-9-chloro-10-(2,4-difluorophenyl)-3-(3-(3,3-difluoropyrrolidin-1-yl)propyl)-2,3-dihydro-5H-[1,4]oxazino[2,3,4-ij]quinazolin-5-one |
| 272 | 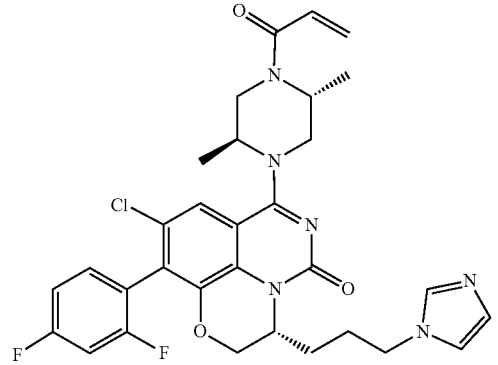 [SMILES: C=CC(=O)N1C[C@H](C)N(c2nc(=O)n3c4c(c(-c5ccc(F)cc5F)c(Cl)cc24)OC[C@H]3CCCn2ccnc2)C[C@H]1C] | 609.07 | 89.4 | (3R)-3-(3-(1H-imidazol-1-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |
| 273 | 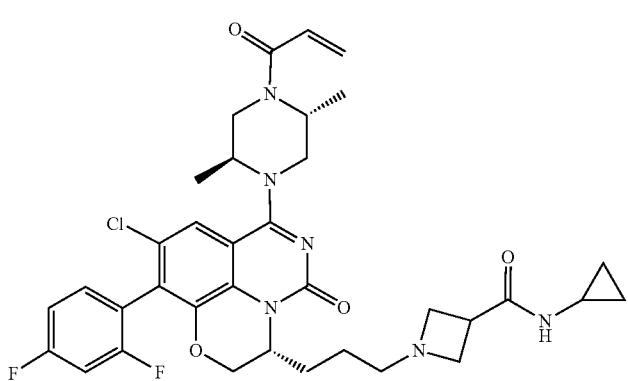 [SMILES: C=CC(=O)N1C[C@H](C)N(c2nc(=O)n3c4c(c(-c5ccc(F)cc5F)c(Cl)cc24)OC[C@H]3CCCN2CC(C(=O)NC3CC3)C2)C[C@H]1C] | 681.17 | 71.8 | (3S)-7-((2S,5R)-4-acryloyl-2,5-dimethylpiperazin-1-yl)-9-chloro-10-(2,4-difluorophenyl)-3-((4-methyl-2-oxopiperazin-1-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 274 | 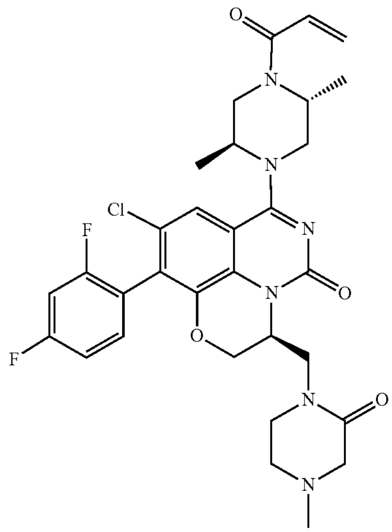 [SMILES: C=CC(=O)N1C[C@H](C)N(c2nc(=O)n3c4c(c(-c5ccc(F)cc5F)c(Cl)cc24)OC[C@@H]3CN2CCN(C)CC2=O)C[C@H]1C] | 627.08 | 67 | (3S)-7-((2S,5R)-4-acryloyl-2,5-dimethylpiperazin-1-yl)-9-chloro-10-(2,4-difluorophenyl)-3-((4-methyl-2-oxopiperazin-1-yl)methyl)-2,3-dihydro-5H-[1,4]oxazino[2,3,4-ij]quinazolin-5-one |
| 275 | 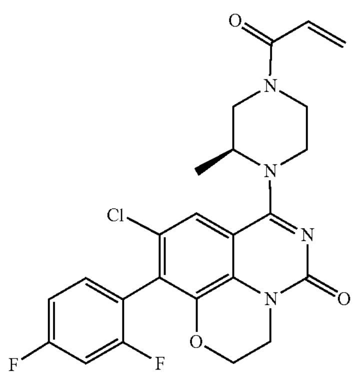 [SMILES: C=CC(=O)N1CCN(c2nc(=O)n3c4c(c(-c5ccc(F)cc5F)c(Cl)cc24)OCC3)[C@@H](C)C1] | 486.9 | 89.6 | 7-((S)-4-acryloyl-2-methylpiperazin-1-yl)-9-chloro-10-(2,4-difluorophenyl)-2,3-dihydro-5H-[1,4]oxazino[2,3,4-ij]quinazolin-5-one |
| 276 | 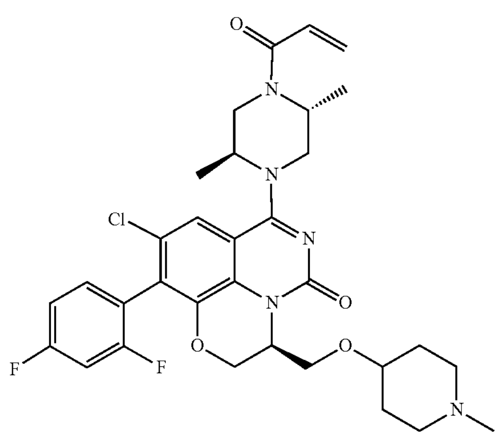 [SMILES: C=CC(=O)N1C[C@H](C)N(c2nc(=O)n3c4c(c(-c5ccc(F)cc5F)c(Cl)cc24)OC[C@@H]3COC2CCN(C)CC2)C[C@H]1C] | 628.11 | 73.5 | (3S)-7-((2S,5R)-4-acryloyl-2,5-dimethylpiperazin-1-yl)-9-chloro-10-(2,4-difluorophenyl)-3-(((1-methylpiperidin-4-yl)oxy)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 277 | 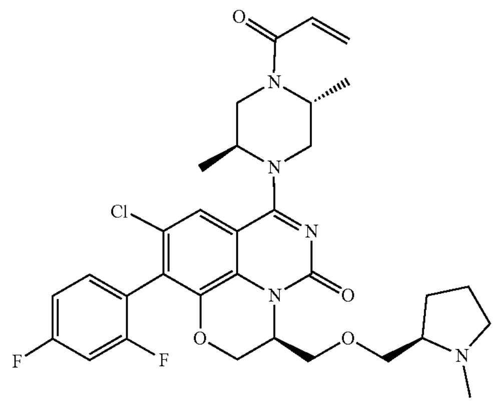 [SMILES: C=CC(=O)N1C[C@H](C)N(c2nc(=O)n3c4c(c(-c5ccc(F)cc5F)c(Cl)cc24)OC[C@@H]3COC[C@H]2CCCN2C)C[C@H]1C] | 628.11 | 76.9 | (3S)-7-((2S,5R)-4-acrloyl-2,5-dimethylpiperazin-1-yl)-9-chloro-10-(2,4-difluorophenyl)-3-((((R)-1-methylpyrrolidin-2-yl)methoxy)methyl)-2,3-dihydro-5H-[1,4]oxazino[2,3,4-ij]quinazolin-5-one |
| 278 | 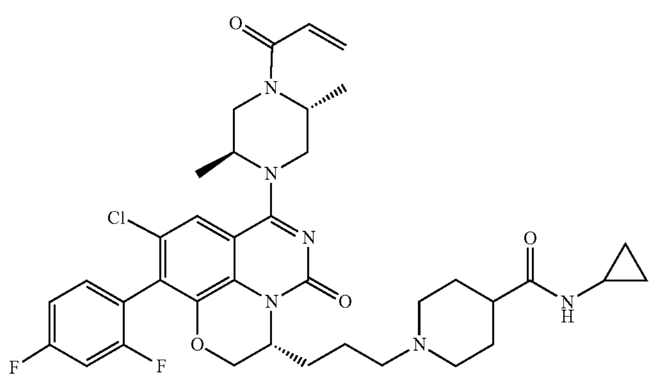 [SMILES: C=CC(=O)N1C[C@H](C)N(c2nc(=O)n3c4c(c(-c5ccc(F)cc5F)c(Cl)cc24)OC[C@H]3CCCN2CCC(C(=O)NC3CC3)CC2)C[C@H]1C] | 709.22 | 98.3 | (3R)-7-((2S,5R)-4-acryloyl-2,5-dimethylpiperazin-1-yl)-9-chloro-10-(2,4-difluorophenyl)-3-(3-(4-(prop-1-en-2-yl)piperidin-1-yl)propyl)-2,3-dihydro-5H-[1,4]oxazino[2,3,4-ij]quinazolin-5-one |
| 279 | 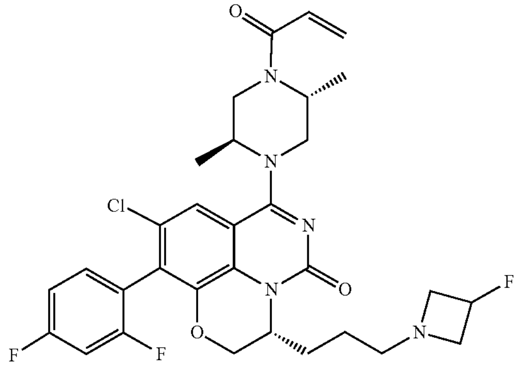 [SMILES: C=CC(=O)N1C[C@H](C)N(c2nc(=O)n3c4c(c(-c5ccc(F)cc5F)c(Cl)cc24)OC[C@H]3CCCN2CC(F)C2)C[C@H]1C] | 616.07 | 97.5 | (3R)-7-((2S,5R)-4-acryloyl-2,5-dimethylpiperazin-1-yl)-9-chloro-10-(2,4-difluorophenyl)-3-(3-(3-fluoroazetidin-1-yl)propyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 280 | 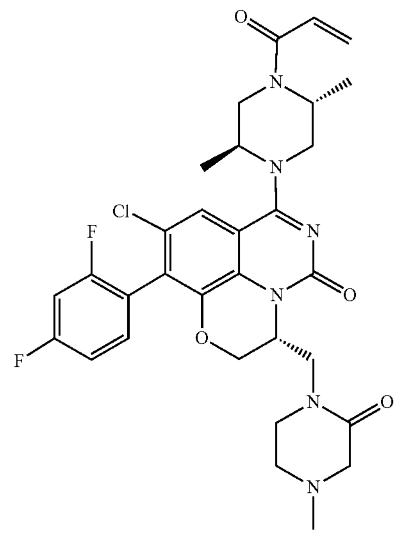 [SMILES: C=CC(=O)N1C[C@H](C)N(c2nc(=O)n3c4c(c(-c5ccc(F)cc5F)c(Cl)cc24)OC[C@H]3CN2CCN(C)CC2=O)C[C@H]1C] | 627.08 | 57.5 | (3R)-7-((2S,5R)-4-acryloyl-2,5-dimethylpiperazin-1-yl)-9-chloro-10-(2,4-difluorophenyl)-3-((4-methyl-2-oxopiperazin-1-yl)methyl)-2,3-dihydro-5H-[1,4]oxazino[2,3,4-ij]quinazolin-5-one |
| 281 | 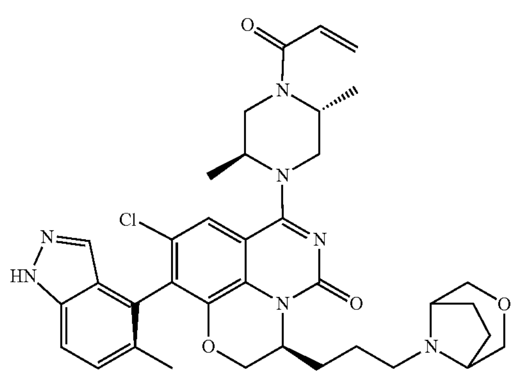 | 672.22 | 0 | (3S,10S)-3-(3-(3-oxa-8-azabicyclo[3.2.1]octan-8-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one |
| 282 | 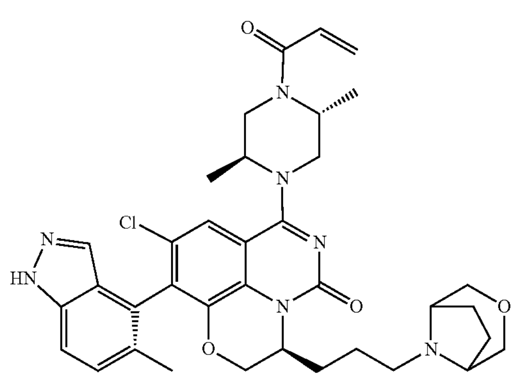 | 672.22 | 86 | (3S,10R)-3-(3-(3-oxa-8-azabicyclo[3.2.1]octan-8-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 283 | 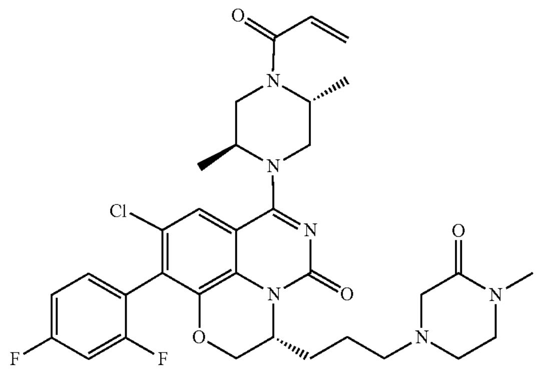 [SMILES: C=CC(=O)N1C[C@H](C)N(c2nc(=O)n3c4c(c(-c5ccc(F)cc5F)c(Cl)cc24)OC[C@H]3CCCN2CCN(C)C(=O)C2)C[C@H]1C] | 655.13 | 92.4 | (3R)-7-((2S,5R)-4-acryloyl-2,5-dimethylpiperazin-1-yl)-9-chloro-10-(2,4-difluorophenyl)-3-(3-(4-methyl-3-oxopiperazin-1-yl)propyl)-2,3-dihydro-5H-[1,4]oxazino[2,3,4-ij]quinazolin-5-one |
| 284 | 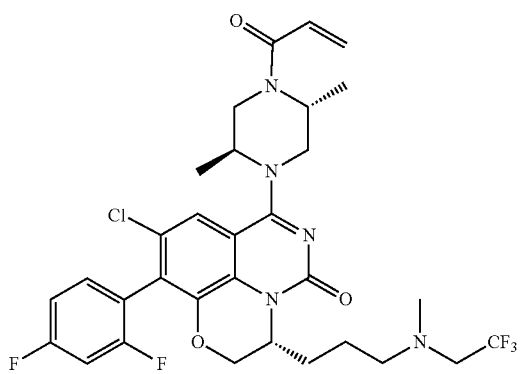 [SMILES: C=CC(=O)N1C[C@H](C)N(c2nc(=O)n3c4c(c(-c5ccc(F)cc5F)c(Cl)cc24)OC[C@H]3CCCN(C)CC(F)(F)F)C[C@H]1C] | 654.07 | 92.4 | (3R)-7-((2S,5R)-4-acryloyl-2,5-dimethylpiperazin-1-yl)-9-chloro-10-(2,4-difluorophenyl)-3-(3-(methyl(2,2,2-trifluoroethyl)amino)propyl)-2,3-dihydro-5H-[1,4]oxazino[2,3,4-ij]quinazolin-5-one |
| 285 | 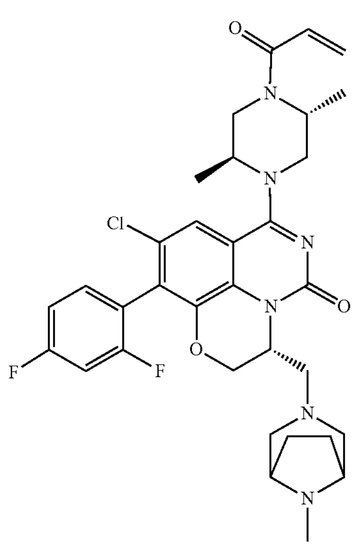 [SMILES: C=CC(=O)N1C[C@H](C)N(c2nc(=O)n3c4c(c(-c5ccc(F)cc5F)c(Cl)cc24)OC[C@H]3CN2CC3CCC(C2)N3C)C[C@H]1C] | 639.14 | 86.2 | (3R)-7-((2S,5R)-4-acryloyl-2,5-dimethylpiperazin-1-yl)-9-chloro-10-(2,4-difluorophenyl)-3-(((1R,5S)-8-methyl-3,8-diazabicyclo[3.2.1]octan-3-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 286 | 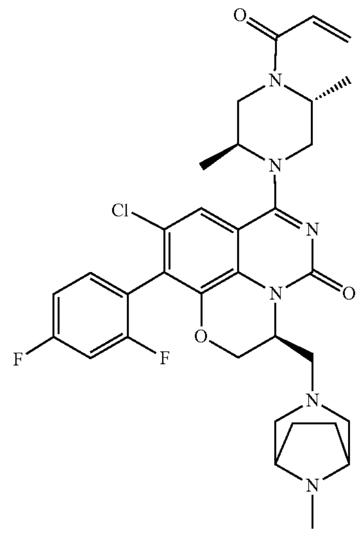 [SMILES: C=CC(=O)N1C[C@H](C)N(c2nc(=O)n3c4c(c(-c5ccc(F)cc5F)c(Cl)cc24)OC[C@@H]3CN2CC3CCC(C2)N3C)C[C@H]1C] | 639.14 | 91.6 | (3S)-7-((2S,5R)-4-acryloyl-2,5-dimethylpiperazin-1-yl)-9-chloro-10-(2,4-difluorophenyl)-3-(((1R,5S)-8-methyl-3,8-diazabicyclo[3.2.1]octan-3-yl)methyl)-2,3-dihydro-5H-[1,4]oxazino[2,3,4-ij]quinazolin-5-one |
| 287 | 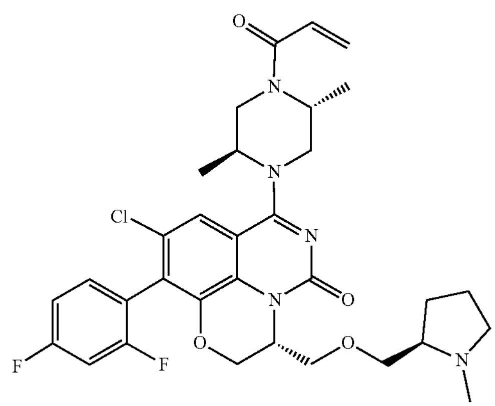 [SMILES: C=CC(=O)N1C[C@H](C)N(c2nc(=O)n3c4c(c(-c5ccc(F)cc5F)c(Cl)cc24)OC[C@H]3COC[C@H]2CCCN2C)C[C@H]1C] | 628.11 | 91.6 | (3S)-7-((2S,5R)-4-acryloyl-2,5-dimethylpiperazin-1-yl)-9-chloro-10-(2,4-difluorophenyl)-3-((((R)-1-methylpyrrolidin-2-yl)methoxy)methyl)-2,3-dihydro-5H-[1,4]oxazino[2,3,4-ij]quinazolin-5-one |
| 288 | 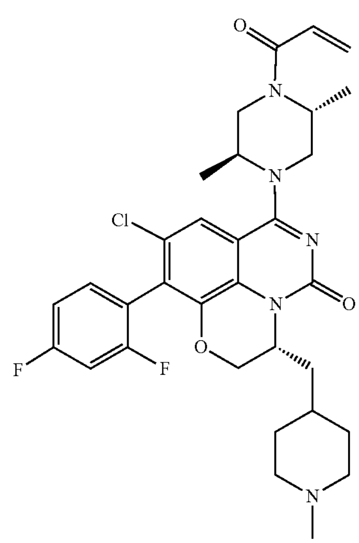 [SMILES: C=CC(=O)N1C[C@H](C)N(c2nc(=O)n3c4c(c(-c5ccc(F)cc5F)c(Cl)cc24)OC[C@H]3CC2CCN(C)CC2)C[C@H]1C] | 612.11 | 95.9 | (3R)-7-((2S,5R)-4-acryloyl-2,5-dimethylpiperazin-1-yl)-9-chloro-10-(2,4-difluorophenyl)-3-((1-methylpiperidin-4-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 289 | 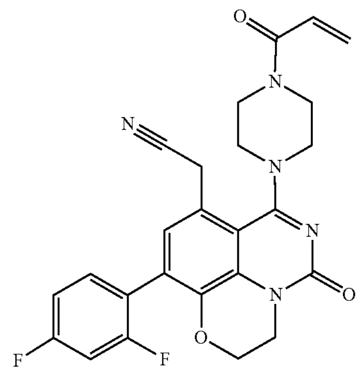 [SMILES: C=CC(=O)N1CCN(c2nc(=O)n3c4c(c(-c5ccc(F)cc5F)cc(CC#N)c24)OCC3)CC1] | 477.46 | 13.5 | 2-(7-(4-acryloylpiperazin-1-yl)-10-(2,4-difluorophenyl)-5-oxo-2,3-dihydro-5H-[1,4]oxazino[2,3,4-ij]quinazolin-8-yl)acetonitrile |
| 290 | 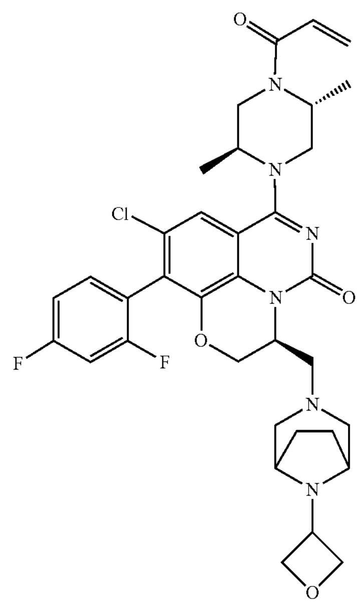 [SMILES: C=CC(=O)N1C[C@H](C)N(c2nc(=O)n3c4c(c(-c5ccc(F)cc5F)c(Cl)cc24)OC[C@@H]3CN2CC3CCC(C2)N3C2COC2)C[C@H]1C] | 681.17 | 92.6 | (3S)-7-((2S,5R)-4-acryloyl-2,5-dimethylpiperazin-1-yl)-9-chloro-10-(2,4-difluorophenyl)-3-(((1R,5S)-8-(oxetan-3-yl)-3,8-diazabicyclo[3.2.1]octan-3-yl)methyl)-2,3-dihydro-5H-[1,4]oxazino[2,3,4-ij]quinazolin-5-one |
| 291 | 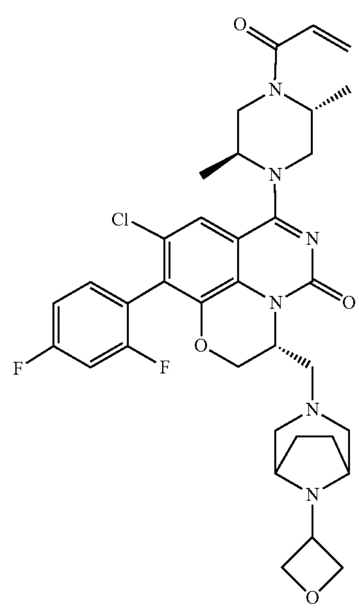 [SMILES: C=CC(=O)N1C[C@H](C)N(c2nc(=O)n3c4c(c(-c5ccc(F)cc5F)c(Cl)cc24)OC[C@H]3CN2CC3CCC(C2)N3C2COC2)C[C@H]1C] | 681.17 | 88.8 | (3R)-7-((2S,5R)-4-acryloyl-2,5-dimethylpiperazin-1-yl)-9-chloro-10-(2,4-difluorophenyl)-3-(((1R,5S)-8-(oxetan-3-yl)-3,8-diazabicyclo[3.2.1]octan-3-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 292 | 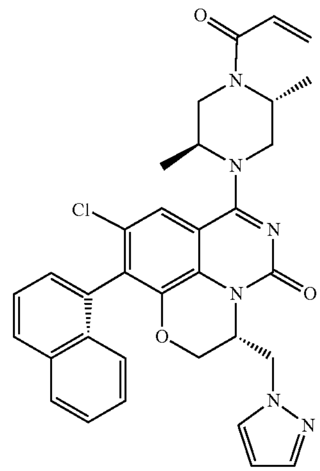 | 595.09 | 95 | (3R,10S)-3-((1H-pyrazol-1-yl)methyl)-7-((2S,5R)-4-acryloyl-2,5-dimethylpiperazin-1-yl)-9-chloro-10-(naphthalen-1-yl)methyl)-2,3-dihydro-5H-[1,4]oxazino[2,3,4-ij]quinazolin-5-one |
| 293 | 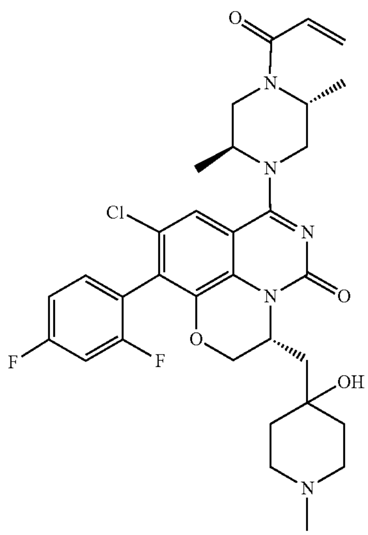 [SMILES: C=CC(=O)N1C[C@H](C)N(c2nc(=O)n3c4c(c(-c5ccc(F)cc5F)c(Cl)cc24)OC[C@H]3CC2(O)CCN(C)CC2)C[C@H]1C] | 628.11 | 82.4 | (3R)-7-((2S,5R)-4-acryloyl-2,5-dimethylpiperazin-1-yl)-9-chloro-10-(2,4-difluorophenyl)-3-((4-hydroxy-1-methylpiperidin-4-yl)methyl)-2,3-dihydro-5H-[1,4]oxazino[2,3,4-ij]quinazolin-5-one |
| 294 | 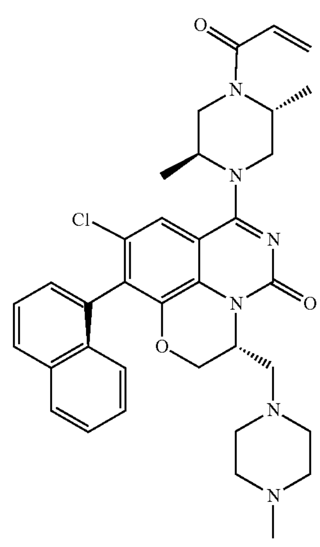 | 627.18 | 75.2 | (3R,10R)-7-((2S,5R)-4-acryloyl-2,5-dimethylpiperazin-1-yl)-9-chloro-3-((4-methylpiperazin-1-yl)methyl)-10-(naphthalen-1-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 295 | 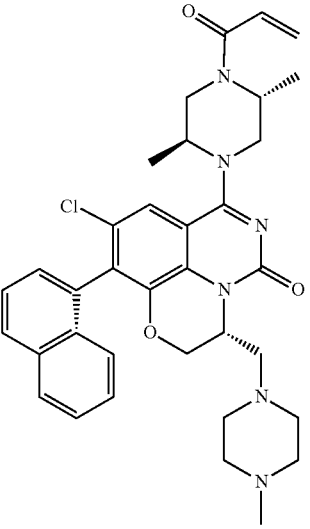 | 627.18 | 58.4 | (3R,10S)-7-((2S,5R)-4-acryloyl-2,5-dimethylpiperazin-1-yl)-9-chloro-3-((4-methylpiperazin-1-yl)methyl)-10-(naphthalen-1-yl)methyl)-2,3-dihydro-5H-[1,4]oxazino[2,3,4-ij]quinazolin-5-one |
| 296 | 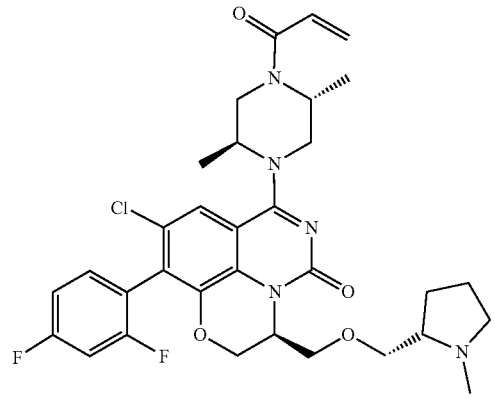 | 628.11 | 79.8 | (3S)-7-((2S,5R)-4-acryloyl-2,5-dimethylpiperazin-1-yl)-9-chloro-10-(2,4-difluorophenyl)-3-((((S)-1-methylpyrrolidin-2-yl)methoxy)methyl)-2,3-dihydro-5H-[1,4]oxazino[2,3,4-ij]quinazolin-5-one |
| 297 | 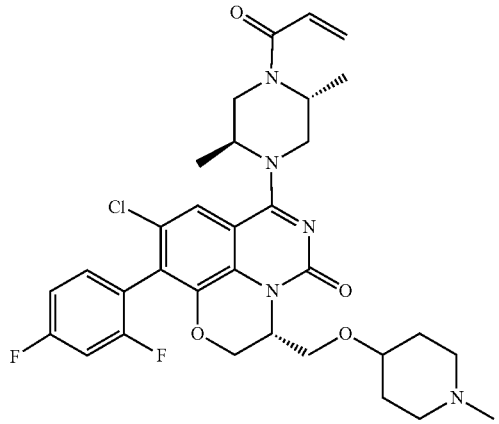 [SMILES: C=CC(=O)N1C[C@H](C)N(c2nc(=O)n3c4c(c(-c5ccc(F)cc5F)c(Cl)cc24)OC[C@H]3COC2CCN(C)CC2)C[C@H]1C] | 628.11 | 90.5 | (3R)-7-((2S,5R)-4-acryloyl-2,5-dimethylpiperazin-1-yl)-9-chloro-10-(2,4-difluorophenyl)-3-(((1-methylpiperidin-4-yl)oxy)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 298 | 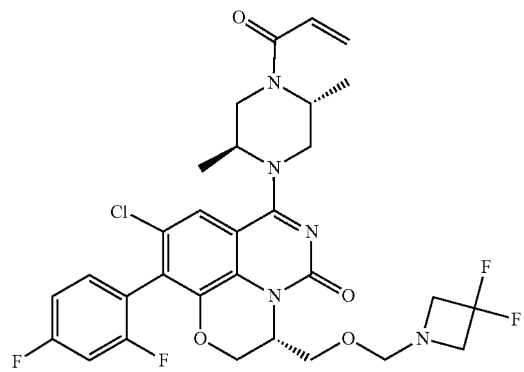 [SMILES: C=CC(=O)N1C[C@H](C)N(c2nc(=O)n3c4c(c(-c5ccc(F)cc5F)c(Cl)cc24)OC[C@H]3COCN2CC(F)(F)C2)C[C@H]1C] | 634.06 | 68 | (3R)-7-((2S,5R)-4-acryloyl-2,5-dimethylpiperazin-1-yl)-9-chloro-3-(3-(3,3-difluoroazetidin-1-yl)propyl)-10-(2,4-difluorophenyl)-2,3-dihydro-5H-[1,4]oxazino[2,3,4-ij]quinazolin-5-one |
| 299 | 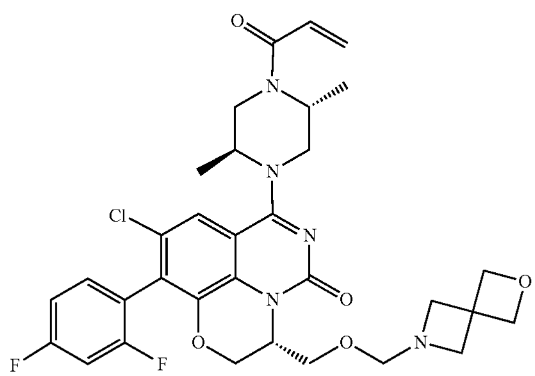 [SMILES: C=CC(=O)N1C[C@H](C)N(c2nc(=O)n3c4c(c(-c5ccc(F)cc5F)c(Cl)cc24)OC[C@H]3COCN2CC3(COC3)C2)C[C@H]1C] | 640.12 | 75.4 | (3R)-3-(3-(2-oxa-6-azaspiro[3.3]heptan-6-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |
| 300 | 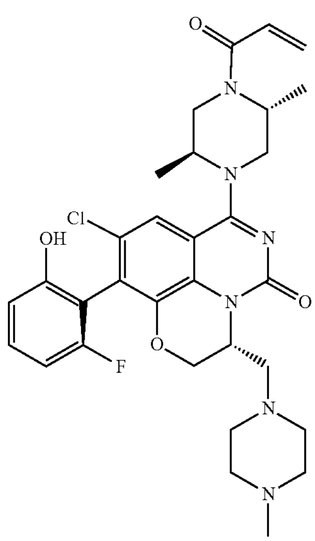 | 611.11 | 0 | (3R,10R)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 301 | 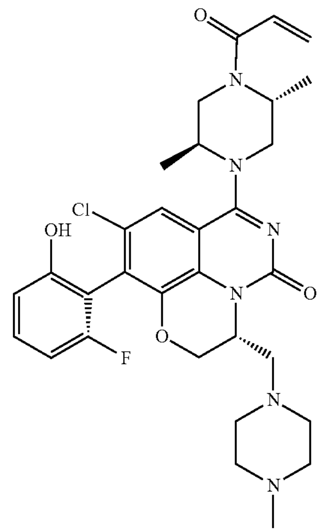 | 611.11 | 52.1 | (3R,10S)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one |
| 302 | 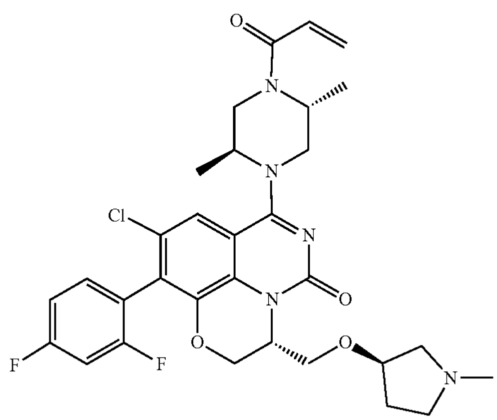 [SMILES: C=CC(=O)N1C[C@H](C)N(c2nc(=O)n3c4c(c(-c5ccc(F)cc5F)c(Cl)cc24)OC[C@H]3CO[C@@H]2CCN(C)C2)C[C@H]1C] | 614.08 | 45.8 | (3R)-7-((2S,5R)-4-acryloyl-2,5-dimethylpiperazin-1-yl)-9-chloro-10-(2,4-difluorophenyl)-3-((((R)-1-methylpyrrolidin-3-yl)oxy)methyl)-2,3-dihydro-5H-[1,4]oxazino[2,3,4-ij]quinazolin-5-one |
| 303 | 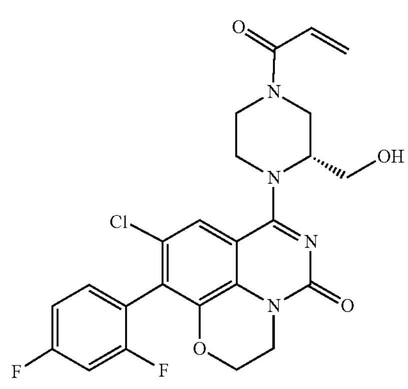 [SMILES: C=CC(=O)N1CCN(c2nc(=O)n3c4c(c(-c5ccc(F)cc5F)c(Cl)cc24)OCC3)[C@@H](CO)C1] | 502.9 | 15.4 | 7-((R)-4-acryloyl-2-(hydroxymethyl)piperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 304 | 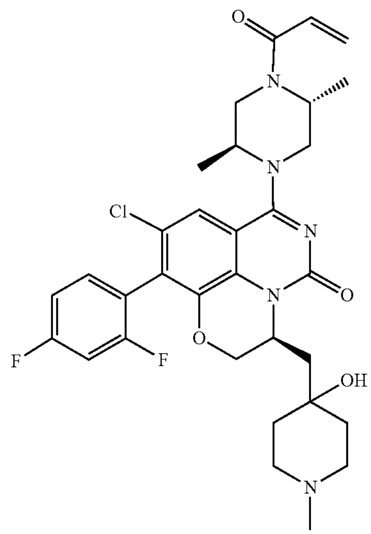 [SMILES: C=CC(=O)N1C[C@H](C)N(c2nc(=O)n3c4c(c(-c5ccc(F)cc5F)c(Cl)cc24)OC[C@@H]3CC2(O)CCN(C)CC2)C[C@H]1C] | 628.11 | 45.1 | (3S)-7-((2S,5R)-4-acryloyl-2,5-dimethylpiperazin-1-yl)-9-chloro-10-(2,4-difluorophenyl)-3-((4-hydroxy-1-methylpiperidin-4-yl)methyl)-2,3-dihydro-5H-[1,4]oxazino[2,3,4-ij]quinazolin-5-one |
| 305 | 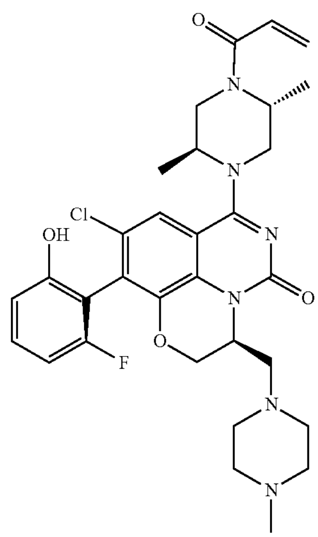 | 611.11 | 0 | (3S,10R)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one |
| 306 | 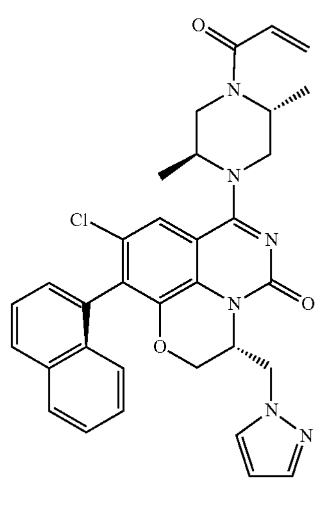 | 595.09 | 73.5 | (3R,10R)-3-((1H-pyrazol-1-yl)methyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 307 | 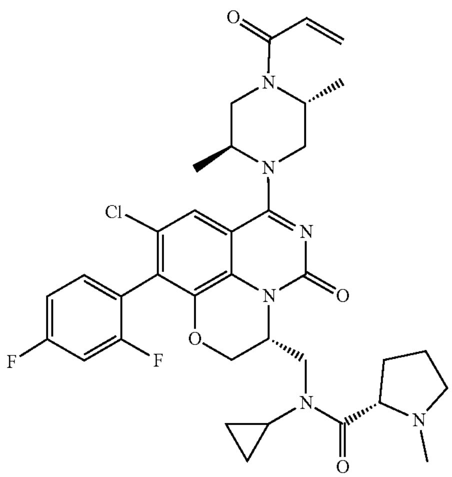 [SMILES: C=CC(=O)N1C[C@H](C)N(c2nc(=O)n3c4c(c(-c5ccc(F)cc5F)c(Cl)cc24)OC[C@H]3CN(C(=O)[C@@H]2CCCN2C)C2CC2)C[C@H]1C] | 681.17 | 51.1 | (2S)-N-(((3R)-7-((2S,5R)-4-acryloyl-2,5-dimethylpiperazin-1-yl)-9-chloro-10-(2,4-difluorophenyl)-5-oxo-2,3-dihydro-5H-[1,4]oxazino[2,3,4-ij]quinazolin-3-yl)methyl)-N-cyclopropyl-1-methylpyrrolidine-2-carboxamide |
| 308 | 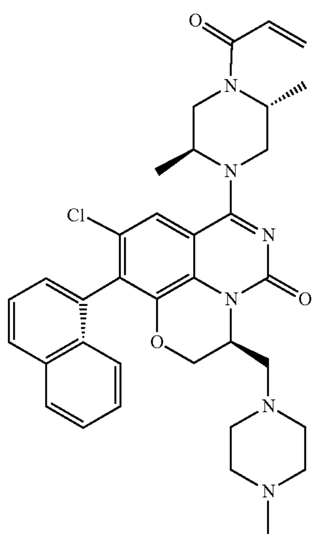 | 627.18 | 22.8 | (3S,10S)-7-((2S,5R)-4-acryloyl-2,5-dimethylpiperazin-1-yl)-9-chloro-3-((4-methylpiperazin-1-yl)methyl)-10-(naphthalen-1-yl)-2,3-dihydro-5H-[1,4]oxazino[2,3,4-ij]quinazolin-5-one |
| 309 | 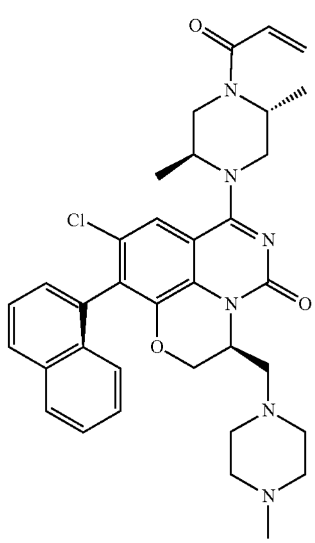 | 627.18 | 94.4 | (3S,10R)-7-((2S,5R)-4-acryloyl-2,5-dimethylpiperazin-1-yl)-9-chloro-3-((4-methylpiperazin-1-yl)methyl)-10-(naphthalen-1-yl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 310 | 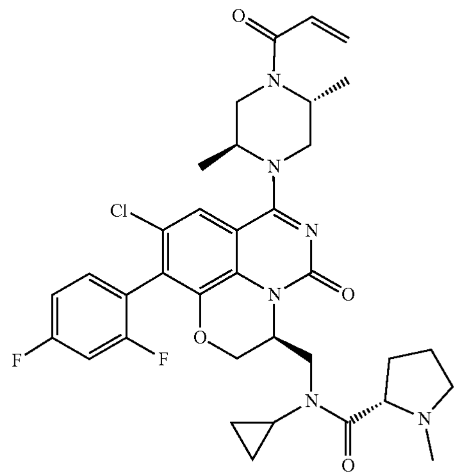 [SMILES: C=CC(=O)N1C[C@H](C)N(c2nc(=O)n3c4c(c(-c5ccc(F)cc5F)c(Cl)cc24)OC[C@@H]3CN(C(=O)[C@@H]2CCCN2C)C2CC2)C[C@H]1C] | 681.17 | 53.4 | (2S)-N-(((3S)-7-((2S,5R)-4-acryloyl-2,5-dimethylpiperazin-1-yl)-9-chloro-10-(2,4-difluorophenyl)-5-oxo-2,3-dihydro-5H-[1,4]oxazino[2,3,4-ij]quinazolin-3-yl)methyl)-N-cyclopropyl-1-methylpyrrolidine-2-carboxamide |
| 311 | 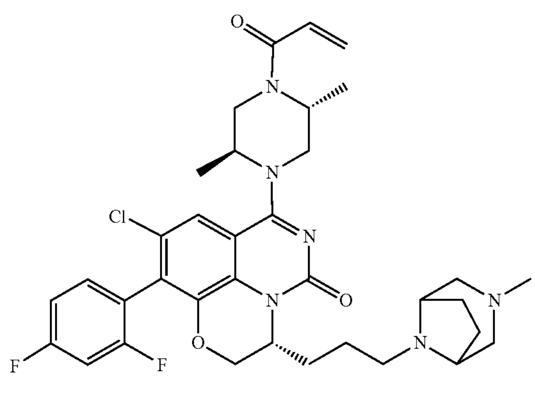 [SMILES: C=CC(=O)N1C[C@H](C)N(c2nc(=O)n3c4c(c(-c5ccc(F)cc5F)c(Cl)cc24)OC[C@H]3CCCN2C3CCC2CN(C)C3)C[C@H]1C] | 667.19 | 64.1 | (3R)-7-((2S,5R)-4-acryloyl-2,5-dimethylpiperazin-1-yl)-9-chloro-10-(2,4-difluorophenyl)-3-(3-(3-methyl-3,8-diazabicyclo[3.2.1]octan-8-yl)propyl)-2,3-dihydro-5H-[1,4]oxazino[2,3,4-ij]quinazolin-5-one |
| 312 | 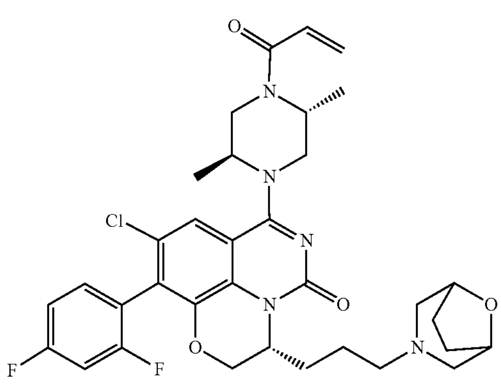 [SMILES: C=CC(=O)N1C[C@H](C)N(c2nc(=O)n3c4c(c(-c5ccc(F)cc5F)c(Cl)cc24)OC[C@H]3CCCN2CC3CCC(C2)O3)C[C@H]1C] | 654.15 | 68.2 | (3R)-3-(3-(8-oxa-3-azabicyclo[3.2.1]octan-3-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 313 | 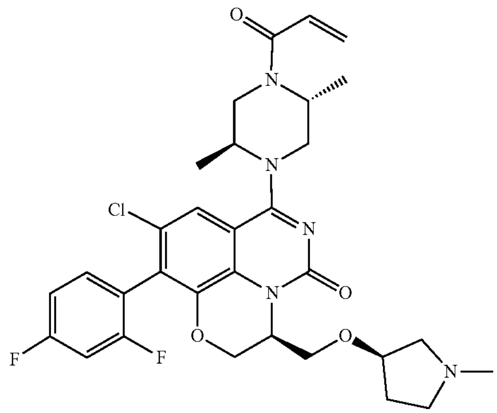 [SMILES: C=CC(=O)N1C[C@H](C)N(c2nc(=O)n3c4c(c(-c5ccc(F)cc5F)c(Cl)cc24)OC[C@@H]3CO[C@@H]2CCN(C)C2)C[C@H]1C] | 614.08 | 66.1 | (3S)-7-((2S,5R)-4-acryloyl-2,5-dimethylpiperazin-1-yl)-9-chloro-10-(2,4-difluorophenyl)-3-((((S)-1-methylpyrrolidin-3-yl)oxy)methyl)-2,3-dihydro-5H-[1,4]oxazino[2,3,4-ij]quinazolin-5-one |
| 314 | 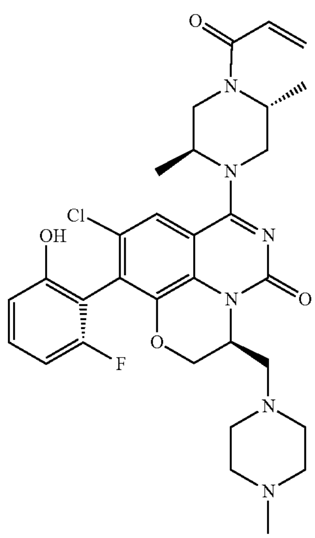 | 611.11 | 74.8 | (3S,10S)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one |
| 315 | 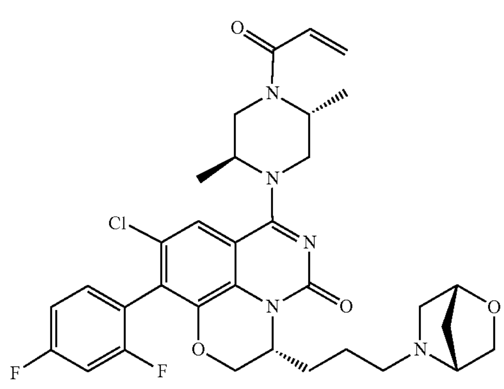 [SMILES: C=CC(=O)N1C[C@H](C)N(c2nc(=O)n3c4c(c(-c5ccc(F)cc5F)c(Cl)cc24)OC[C@H]3CCCN2C[C@H]3C[C@@H]2CO3)C[C@H]1C] | 640.12 | 89.8 | (3R)-3-(3-((1R,4R)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 316 | 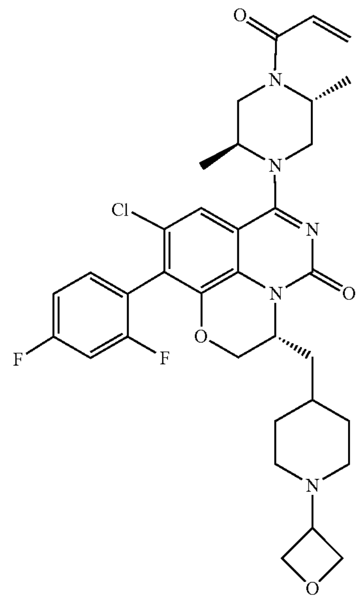 [SMILES: C=CC(=O)N1C[C@H](C)N(c2nc(=O)n3c4c(c(-c5ccc(F)cc5F)c(Cl)cc24)OC[C@H]3CC2CCN(C3COC3)CC2)C[C@H]1C] | 654.15 | 84.2 | (3R)-7-((2S,5R)-4-acryloyl-2,5-dimethylpiperazin-1-yl)-9-chloro-10-(2,4-difluorophenyl)-3-((1-(oxetan-3-yl)piperidin-4-yl)methyl)-2,3-dihydro-5H-[1,4]oxazino[2,3,4-ij]quinazolin-5-one |
| 317 | 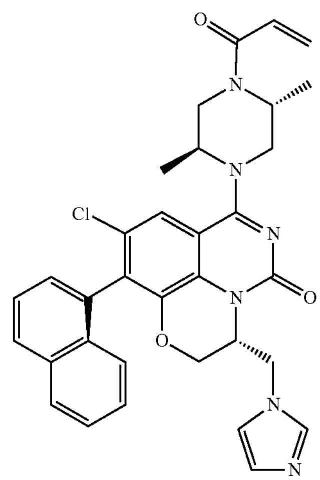 | 595.09 | 72.8 | (3R,10R)-3-((1H-imidazol-1-yl)methyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one |
| 318 | 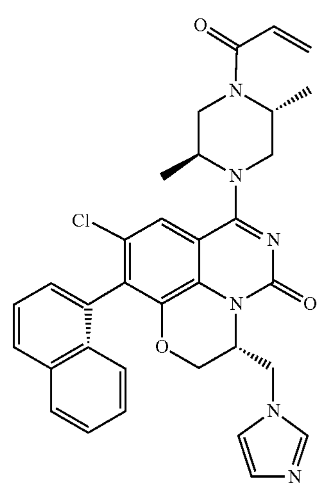 | 595.09 | 70.6 | (3R,10S)-3-((1H-imidazol-1-yl)methyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 319 | 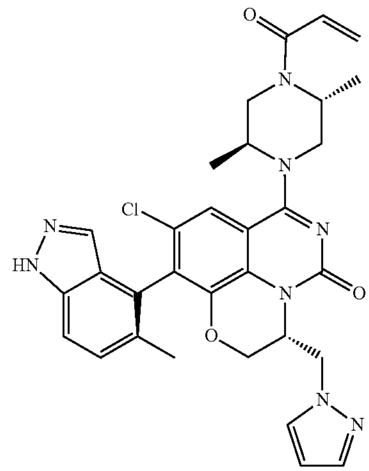 | 599.08 | 0 | (3R,10S)-3-((1H-pyrazol-1-yl)methyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one |
| 320 | 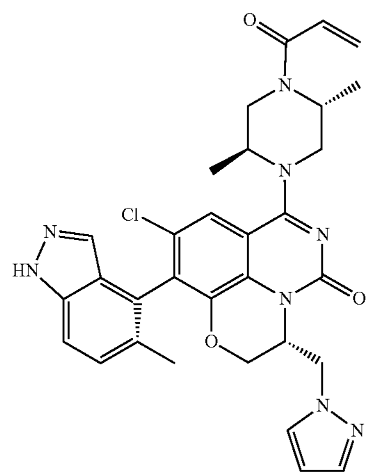 | 599.08 | 94.2 | (3R,10R)-3-((1H-pyrazol-1-yl)methyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one |
| 321 | 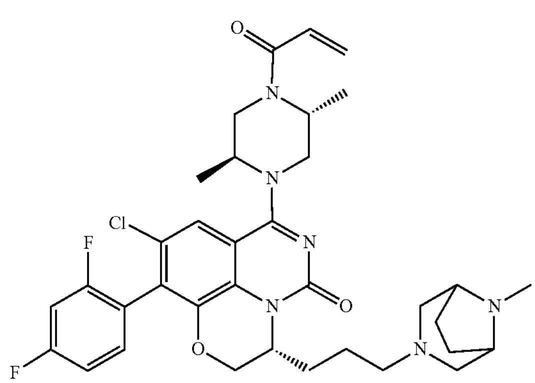 [SMILES: C=CC(=O)N1C[C@H](C)N(c2nc(=O)n3c4c(c(-c5ccc(F)cc5F)c(Cl)cc24)OC[C@H]3CCCN2CC3CCC(C2)N3C)C[C@H]1C] | 667.19 | 71.2 | (3R)-7-((2S,5R)-4-acryloyl-2,5-dimethylpiperazin-1-yl)-9-chloro-10-(2,4-difluorophenyl)-3-(3-(3-methyl-3,8-diazabicyclo[3.2.1]octan-8-yl)propyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 322 | 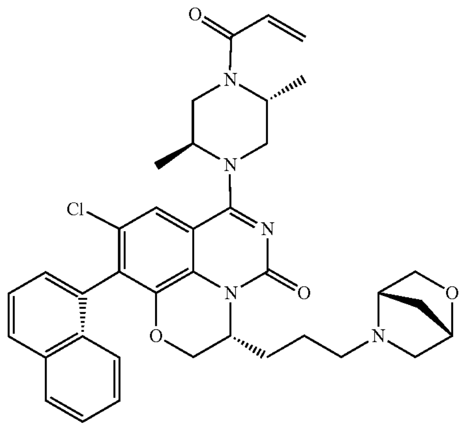 | 654.2 | 78.5 | (3R,10S)-3-(3-((1S,4S)-2-oxa-5-azabicyclo[3.2.1]heptan-5-yl)propyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one |
| 323 | 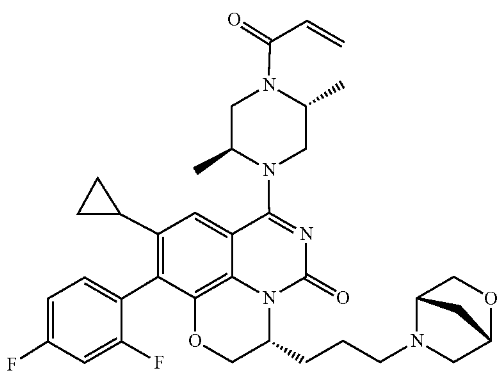 [SMILES: C=CC(=O)N1C[C@H](C)N(c2nc(=O)n3c4c(c(-c5ccc(F)cc5F)c(C5CC5)cc24)OC[C@H]3CCCN2C[C@@H]3C[C@H]2CO3)C[C@H]1C] | 645.74 | 81.1 | (3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-cyclopropyl-10-(2,4-difluorophenyl)-2,3-dihydro-5H-[1,4]oxazino[2,3,4-ij]quinazolin-5-one |
| 324 | 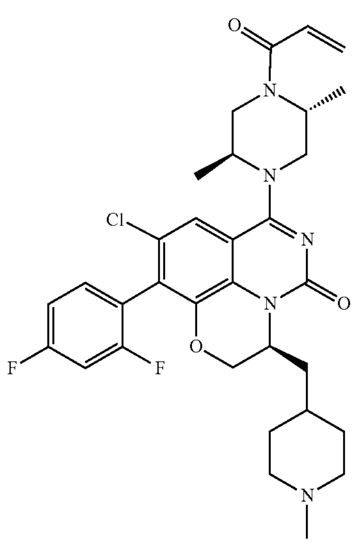 | 612.11 | 63.4 | (3S)-7-((2S,5R)-4-acryloyl-2,5-dimethylpiperazin-1-yl)-9-chloro-10-(2,4-difluorophenyl)-3-((1-methylpiperidin-4-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 325 | 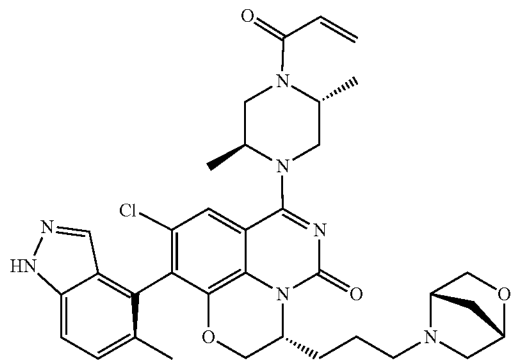 | 658.19 | 0 | (3R,10S)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one |
| 326 | 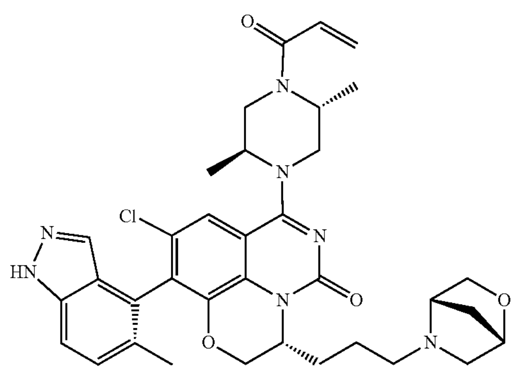 | 658.19 | 94.2 | (3R,10R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one |
| 327 | 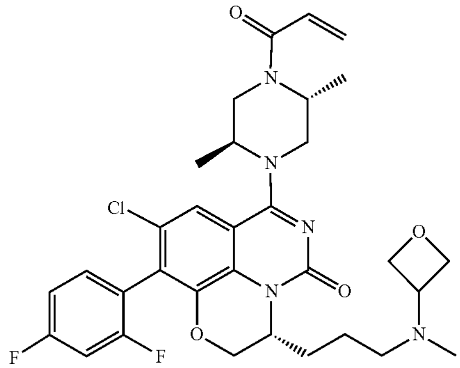 [SMILES: C=CC(=O)N1C[C@H](C)N(c2nc(=O)n3c4c(c(-c5ccc(F)cc5F)c(Cl)cc24)OC[C@H]3CCCN(C)C2COC2)C[C@H]1C] | 628.11 | 84.5 | (3R)-7-((2S,5R)-4-acryloyl-2,5-dimethylpiperazin-1-yl)-9-chloro-10-(2,4-difluorophenyl)-3-(3-(methyl(oxetan-3-yl)amino)propyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 328 | 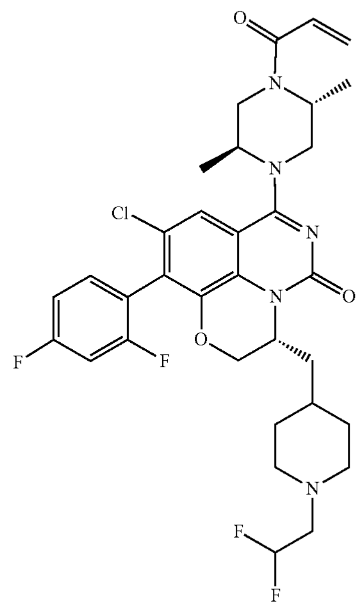 [SMILES: C=CC(=O)N1C[C@H](C)N(c2nc(=O)n3c4c(c(-c5ccc(F)cc5F)c(Cl)cc24)OC[C@H]3CC2CCN(CC(F)F)CC2)C[C@H]1C] | 662.12 | 87 | (3R)-7-((2S,5R)-4-acryloyl-2,5-dimethylpiperazin-1-yl)-9-chloro-3-((1-(2,2-difluoroethyl)piperidin-4-yl)methyl)-10-(2,4-difluorophenyl)-2,3-dihydro-5H-[1,4]oxazino[2,3,4-ij]quinazolin-5-one |
| 329 | 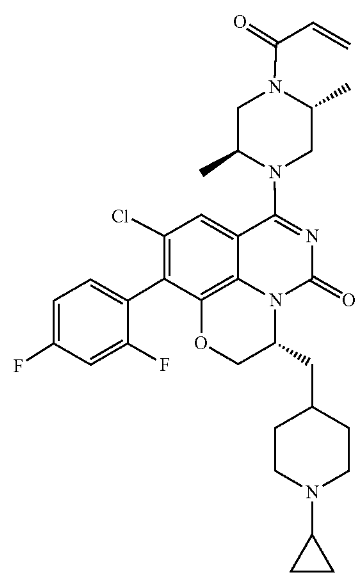 [SMILES: C=CC(=O)N1C[C@H](C)N(c2nc(=O)n3c4c(c(-c5ccc(F)cc5F)c(Cl)cc24)OC[C@H]3CC2CCN(C3CC3)CC2)C[C@H]1C] | 638.15 | 73.4 | (3R)-7-((2S,5R)-4-acryloyl-2,5-dimethylpiperazin-1-yl)-9-chloro-3-((1-cyclopropylpiperidin-4-yl)methyl)-10-(2,4-difluorophenyl)-2,3-dihydro-5H-[1,4]oxazino[2,3,4-ij]quinazolin-5-one |
| 330 | 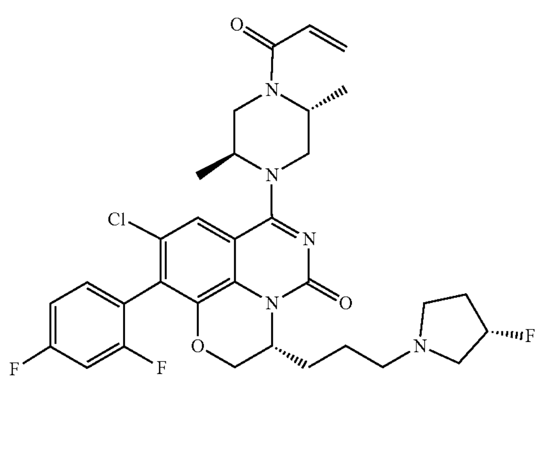 [SMILES: C=CC(=O)N1C[C@H](C)N(c2nc(=O)n3c4c(c(-c5ccc(F)cc5F)c(Cl)cc24)OC[C@H]3CCCN2CC[C@H](F)C2)C[C@H]1C] | 630.1 | 91.7 | (3R)-7-((2S,5R)-4-acryloyl-2,5-dimethylpiperazin-1-yl)-9-chloro-10-(2,4-difluorophenyl)-3-(3-((S)-3-fluoropyrrolidin-1-yl)propyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 331 | 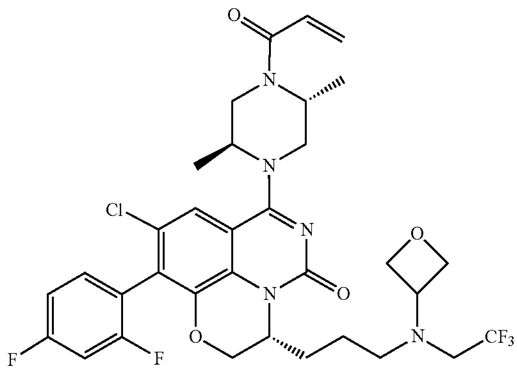 [SMILES: C=CC(=O)N1C[C@H](C)N(c2nc(=O)n3c4c(c(-c5ccc(F)cc5F)c(Cl)cc24)OC[C@H]3CCCN(CC(F)(F)F)C2COC2)C[C@H]1C] | 696.11 | 59.2 | (3R)-7-((2S,5R)-4-acryloyl-2,5-dimethylpiperazin-1-yl)-9-chloro-10-(2,4-difluorophenyl)-3-(3-(oxetan-3-yl(2,2,2-trifluoroethyl)amino)propyl)-2,3-dihydro-5H-[1,4]oxazino[2,3,4-ij]quinazolin-5-one |
| 332 | 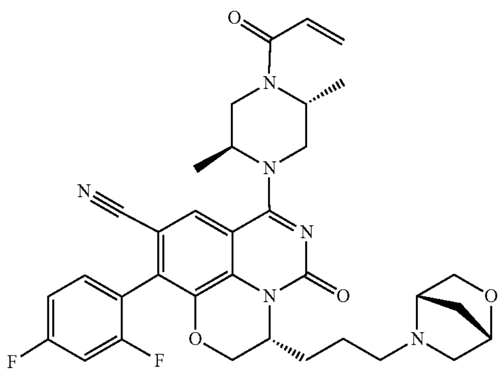 [SMILES: C=CC(=O)N1C[C@H](C)N(c2nc(=O)n3c4c(c(-c5ccc(F)cc5F)c(C#N)cc24)OC[C@H]3CCCN2C[C@@H]3C[C@H]2CO3)C[C@H]1C] | 630.68 | 56.9 | (3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-10-(2,4-difluorophenyl)-5-oxo-2,3-dihydro-5H-[1,4]oxazino[2,3,4-ij]quinazolin-9-carbonitrile |
| 333 | 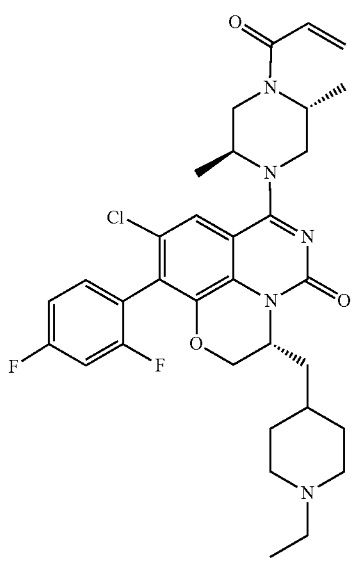 [SMILES: C=CC(=O)N1C[C@H](C)N(c2nc(=O)n3c4c(c(-c5ccc(F)cc5F)c(Cl)cc24)OC[C@H]3CC2CCN(CC)CC2)C[C@H]1C] | 626.14 | 83.9 | (3R)-7-((2S,5R)-4-acryloyl-2,5-dimethylpiperazin-1-yl)-9-chloro-10-(2,4-difluorophenyl)-3-((1-ethylpiperidin-4-yl)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 334 | 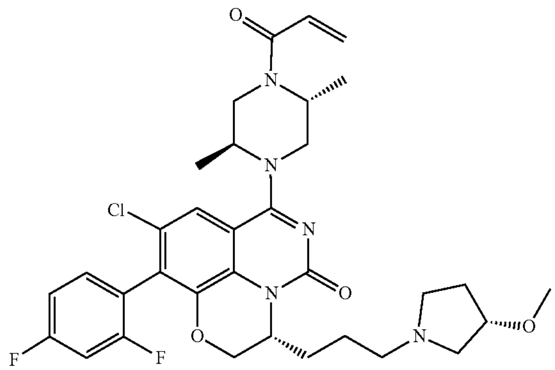 [SMILES: C=CC(=O)N1C[C@H](C)N(c2nc(=O)n3c4c(c(-c5ccc(F)cc5F)c(Cl)cc24)OC[C@H]3CCCN2CC[C@H](OC)C2)C[C@H]1C] | 642.14 | 84.6 | (3R)-7-((2S,5R)-4-acryloyl-2,5-dimethylpiperazin-1-yl)-9-chloro-10-(2,4-difluorophenyl)-3-(3-((S)-3-methoxypyrrolidin-1-yl)propyl)-2,3-dihydro-5H-[1,4]oxazino[2,3,4-ij]quinazolin-5-one |
| 335 | 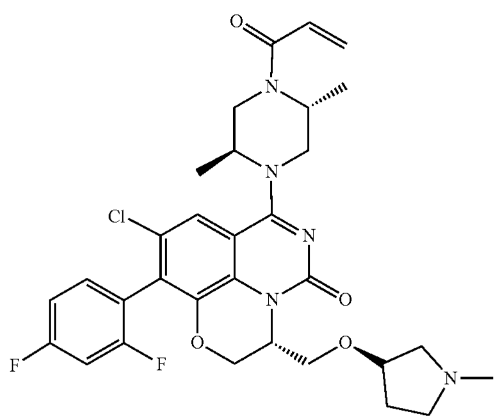 | 614.08 | 54.6 | (3R)-7-((2S,5R)-4-acryloyl-2,5-dimethylpiperazin-1-yl)-9-chloro-10-(2,4-difluorophenyl)-3-((((S)-1-methylpyrrolidin-3-yl)oxy)methyl)-2,3-dihydro-5H-[1,4]oxazino[2,3,4-ij]quinazolin-5-one |
| 336 | 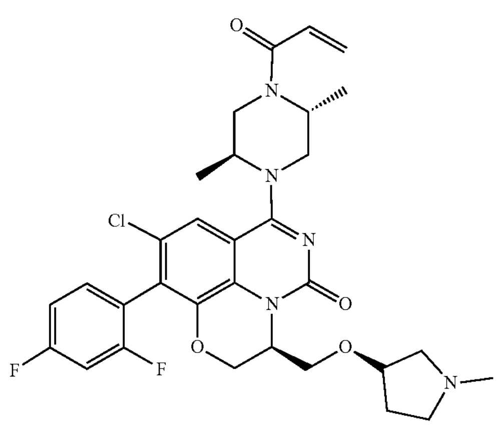 | 614.08 | 79 | (3S)-7-((2S,5R)-4-acryloyl-2,5-dimethylpiperazin-1-yl)-9-chloro-10-(2,4-difluorophenyl)-3-((((R)-1-methylpyrrolidin-3-yl)oxy)methyl)-2,3-dihydro-5H-[1,4]oxazino[2,3,4-ij]quinazolin-5-one |

TABLE 6-continued

| Example No. | Structure | MW | % CAF @ 10 μM, 1 h | Name |
|---|---|---|---|---|
| 337 | 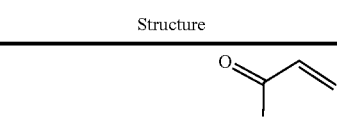 | 560.47 | 95.9 | 7-(9-acryloyl-7-oxo-3,9-diazabicyclo[3.3.1]nonan-3-yl)-10-(2,4-difluorophenyl)-9-(trifluoromethyl)-2,3-dihydro-5H-[1,4]oxazino[2,3,4-ij]quinazolin-5-one |

TABLE 7

| | | | | |
|---|---|---|---|---|
| 338 | 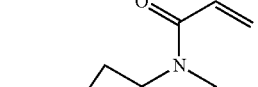 | 574.5 | 95.3 | 8-(9-acryloyl-7-oxo-3,9-diazabicyclo[3.3.1]nonan-3-yl)-11-(2,4-difluorophenyl)-10-(trifluoromethyl)-3,4-dihydro-2H,6H-[1,4]oxazepino[2,3,4-ij]quinazolin-6-one |
| 137 (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one | 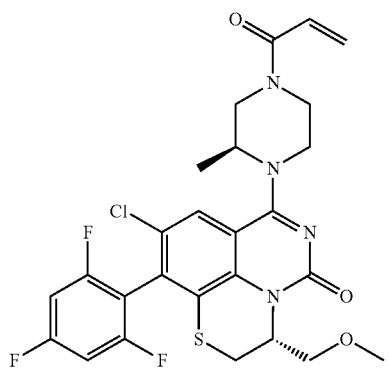 | 565.1 | 86.8 | |

TABLE 7-continued
| | | | | |
|---|---|---|---|---|
| 130 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one | 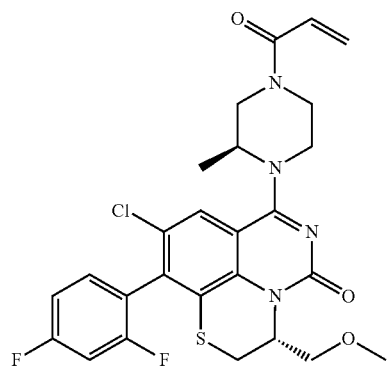 | 547.1 | 94.5 |
| 99 | (3R)-7-((S)-4-acryloyl-2-methylpiperazin-1-yl)-9-chloro-10-(2,4-difluorophenyl)-3-methyl-2H-[1,4]thiazino[2,3,4-ij]quinazolin-5(3H)-one | 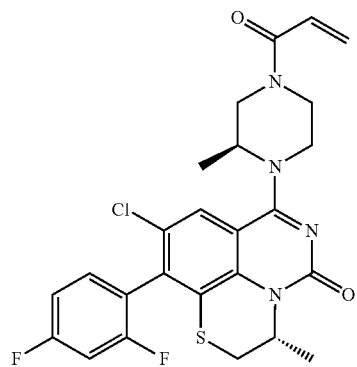 | 517.1 | 87.2 |
| 339 | (R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 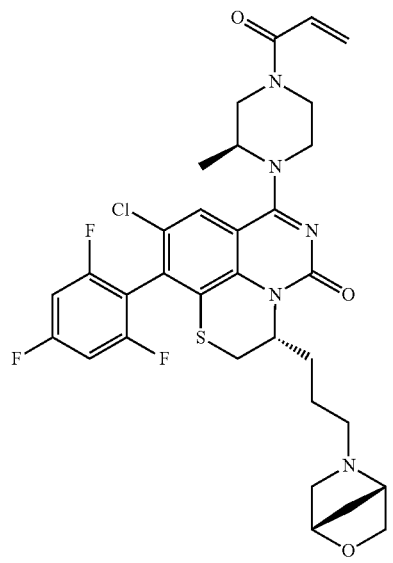 | 660.2 | 96.6 |

| | | | | |
|---|---|---|---|---|
| 340 | (S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 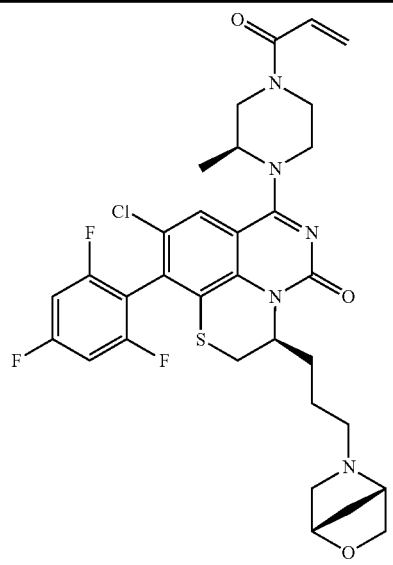 | 660.2 | 96.9 |
| 341 | (3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 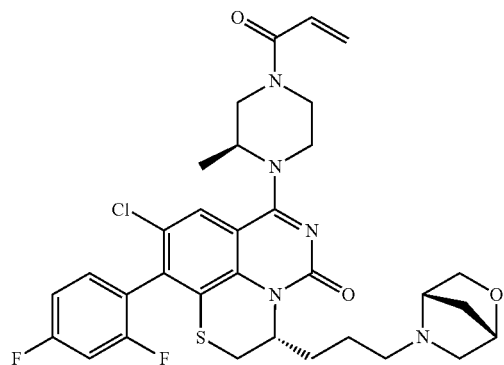 | 642.3 | 96.5 |
| 342 | (3S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 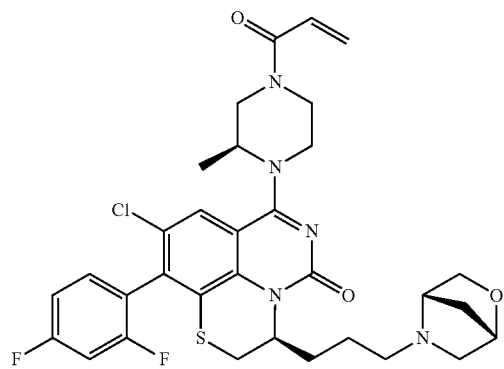 | 642.2 | 94.7 |

TABLE 7-continued

| 343 | (S)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 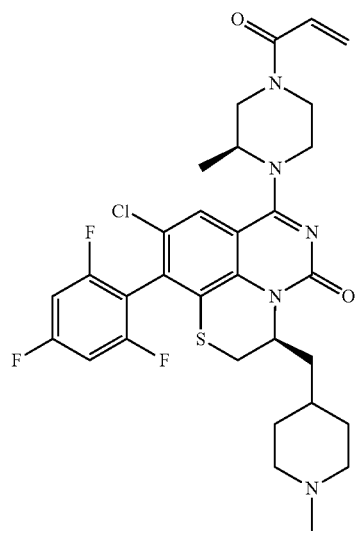 | 632.2 | 96.7 |
| 344 | (R)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 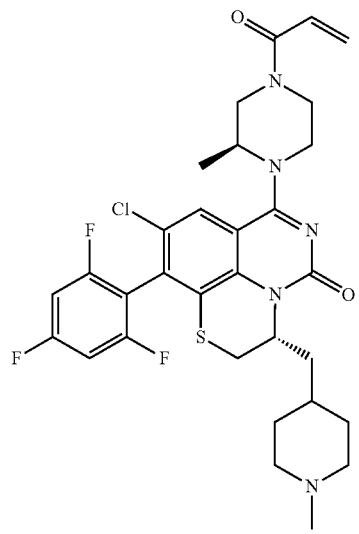 | 632.2 | 94.8 |
| 345 | (3R)-7-((S)-4-acryloyl-2-methylpiperazin-1-yl)-9-chloro-10-(2,4-difluorophenyl)-3-((1-methylpiperidin-4-yl)methyl)-2H-[1,4]thiazino[2,3,4-ij]quinazolin-5(3H)-one | 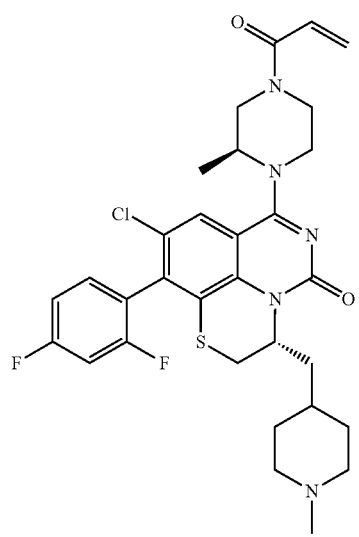 | 614.2 | 82.4 |

TABLE 7-continued
| 346 | (3R)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 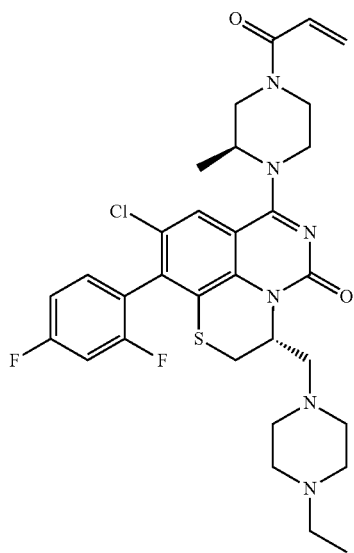 | 629.3 | 79.3 |
| 76 | 7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one | 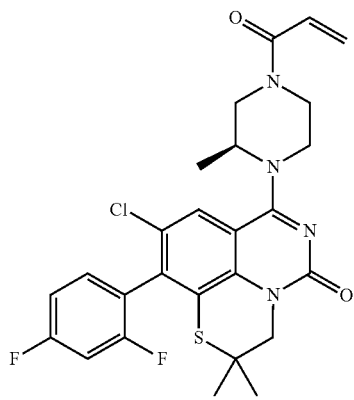 | 531.2 | 86.8 |
| 347 | (3R)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 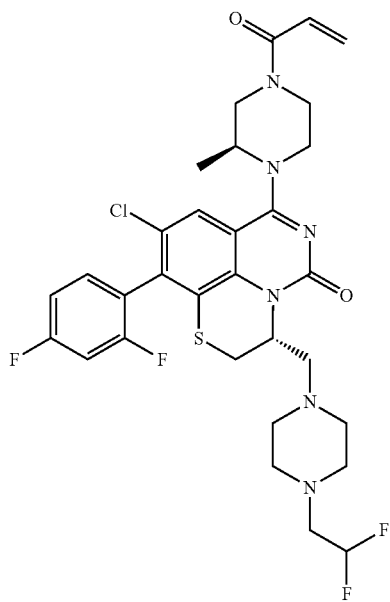 | 665.2 | 82.5 |

| | | | | |
|---|---|---|---|---|
| 348 | (3R)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 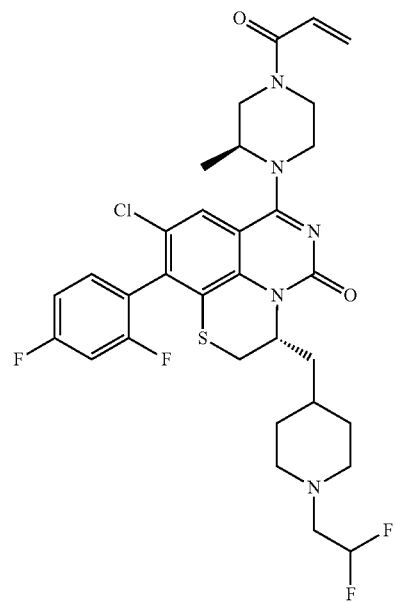 | 664.3 | 92 |
| 349 | (R)-7-((S)-4-acryloyl-2-methylpiperazin-1-yl)-9-chloro-3-((1-(2,2-difluoroethyl)piperidin-4-yl)methyl)-10-(4-fluorophenyl)-2H-[1,4]thiazino[2,3,4-ij]quinazolin-5(3H)-one | 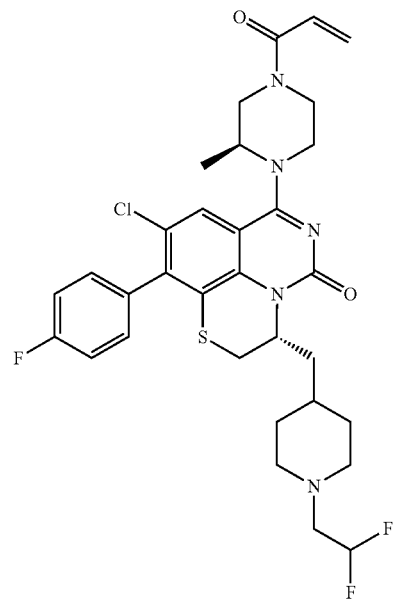 | 646.2 | 94 |

TABLE 7-continued
| 350 | (3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one | 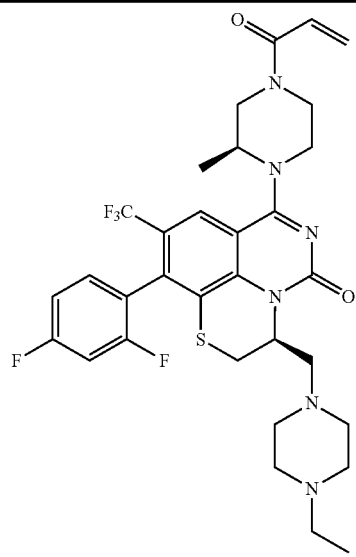 | 663.3 | 95 |
| --- | --- | --- | --- | --- |
| 351 | (S)-7-((S)-4-acryloyl-2-methylpiperazin-1-yl)-9-chloro-3-((4-ethylpiperazin-1-yl)methyl)-10-(2,4,6-trifluorophenyl)-2H-[1,4]thiazino[2,3,4-ij]quinazolin-5(3H)-one | 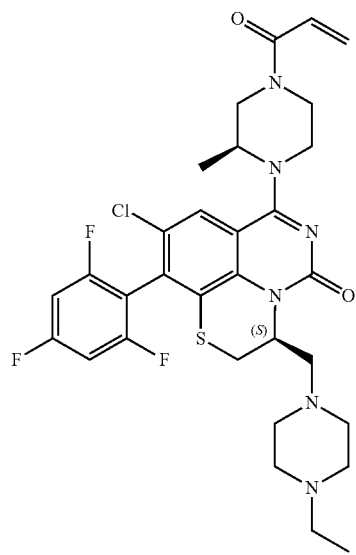 | 647.2 | 74 |

| | | | |
|---|---|---|---|
| 352 | (3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one | 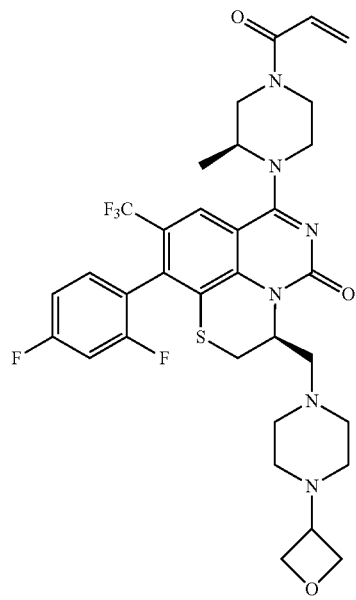 | 691.2  96 |
| 353 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one | 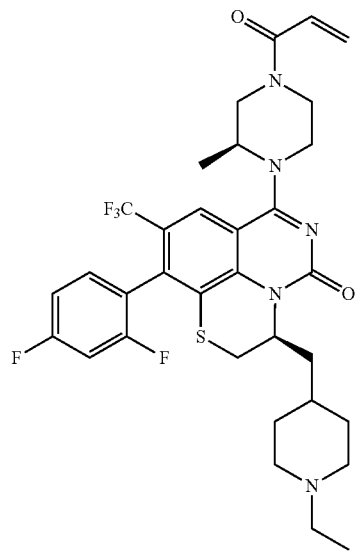 | 662.2  97 |

TABLE 7-continued
| | | | | |
|---|---|---|---|---|
| 354 | (3S)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 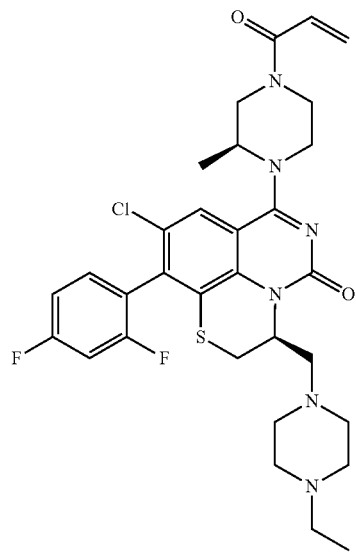 [SMILES: C=CC(=O)N1CCN(c2nc(=O)n3c4c(c(-c5ccc(F)cc5F)c(Cl)cc24)SC[C@@H]3CN2CCN(CC)CC2)[C@@H](C)C1] | 629.3 | 96 |
| 355 | (3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one | 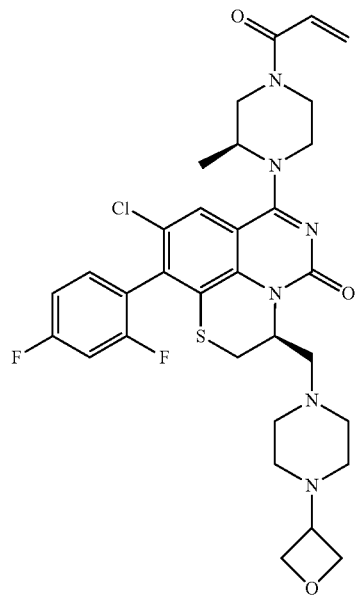 [SMILES: C=CC(=O)N1CCN(c2nc(=O)n3c4c(c(-c5ccc(F)cc5F)c(Cl)cc24)SC[C@@H]3CN2CCN(C3COC3)CC2)[C@@H](C)C1] | 657.3 | 96 |

TABLE 7-continued
| 356 | (3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 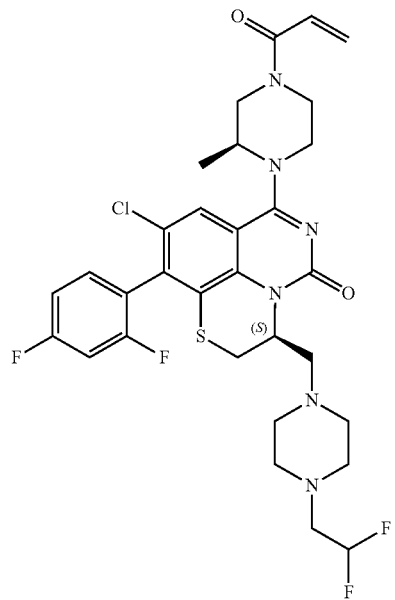 | 665.3 | 95 |
| 19 | (3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one | 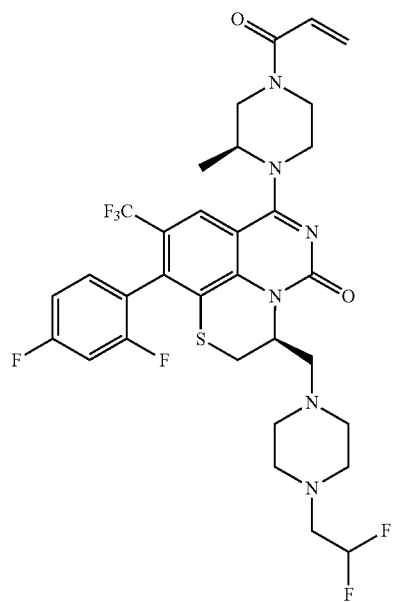 [SMILES: C=CC(=O)N1CCN(c2nc(=O)n3c4c(c(-c5ccc(F)cc5F)c(C(F)(F)F)cc24)SC[C@@H]3CN2CCN(CC(F)F)CC2)[C@@H](C)C1] | 699.6 | 96 |

In embodiments, there are provided further compounds:
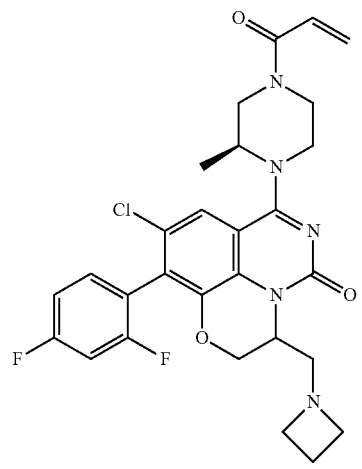
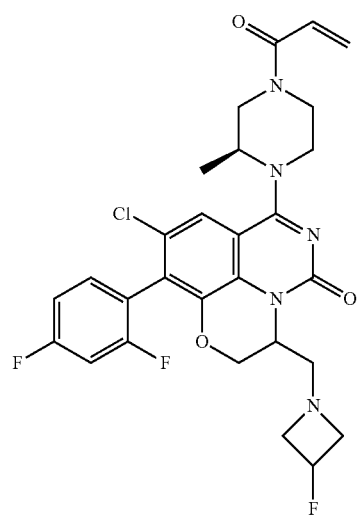
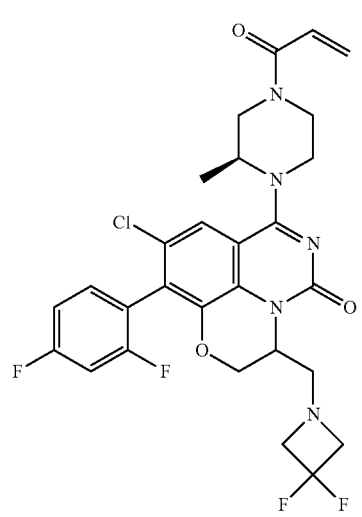
-continued
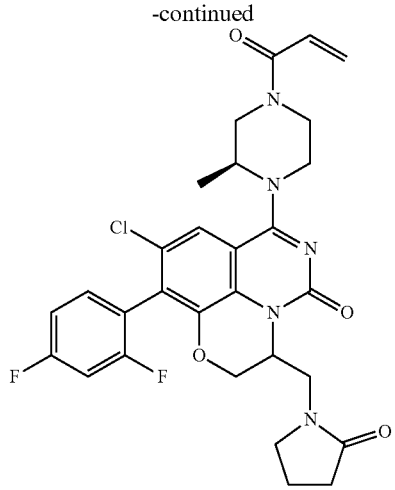
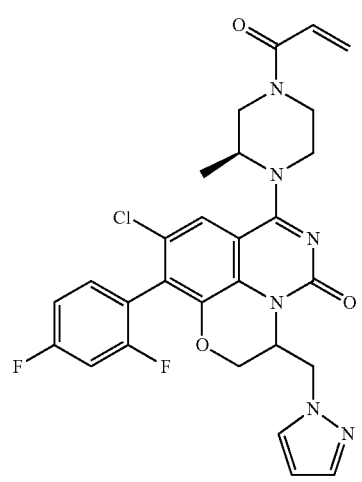
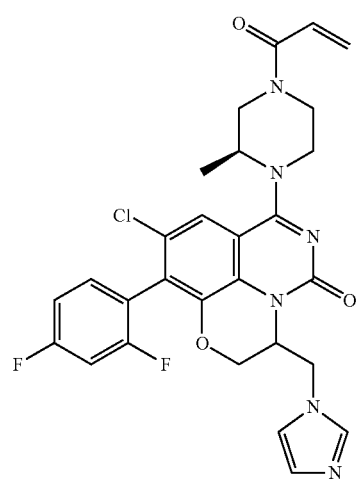

295
-continued
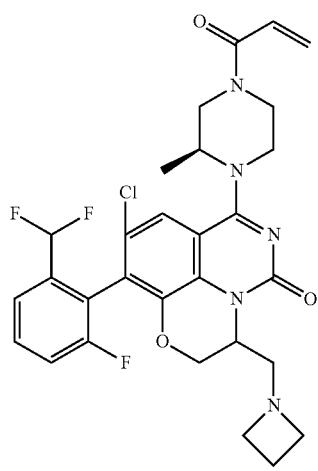
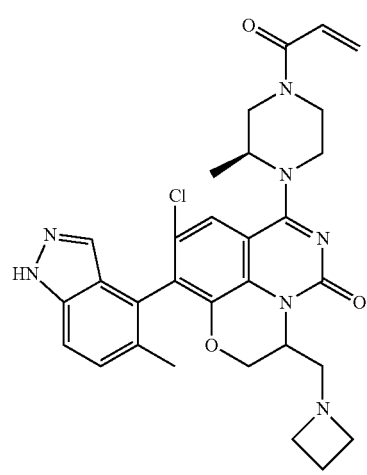
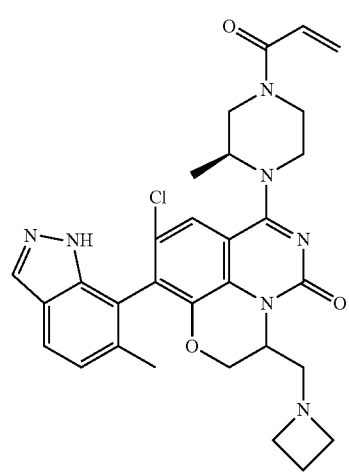
296
-continued
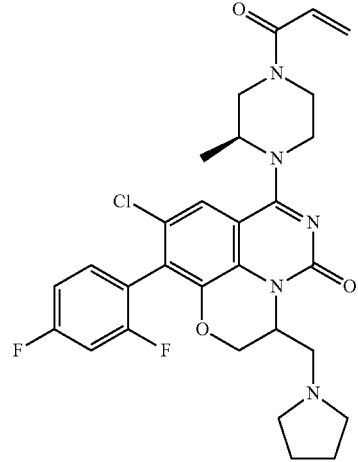
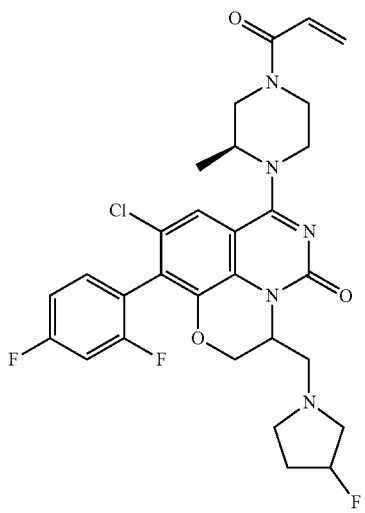
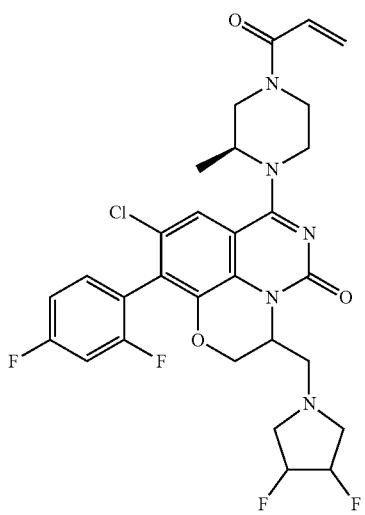

297
-continued
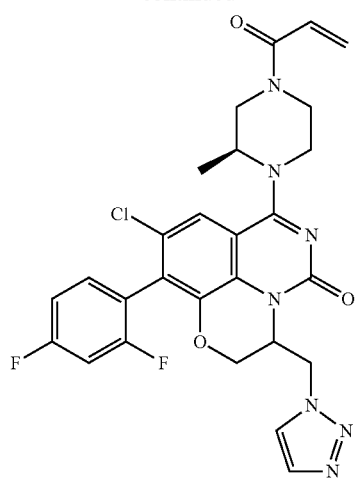
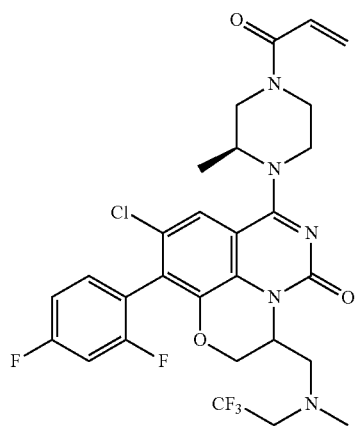
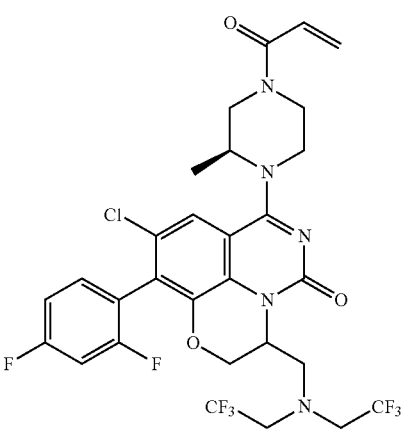
298
-continued
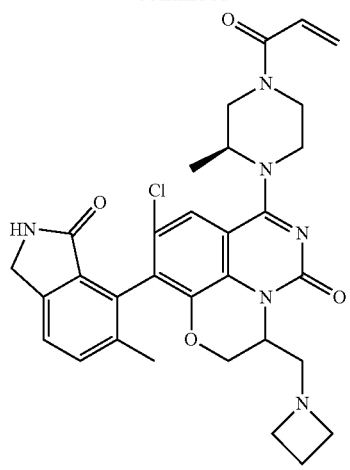
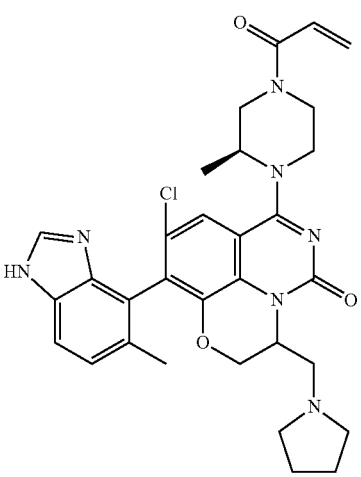
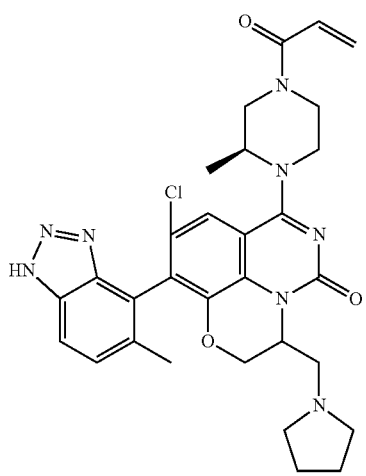

299
-continued
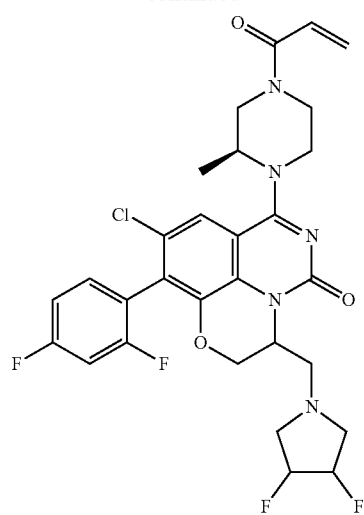
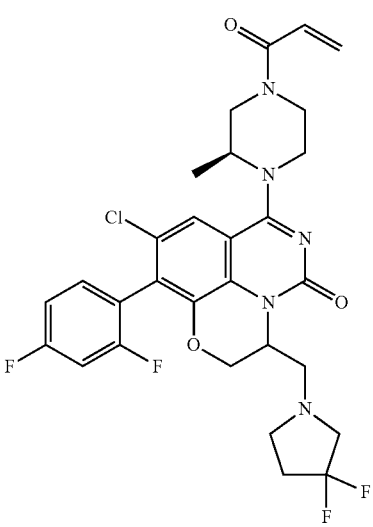
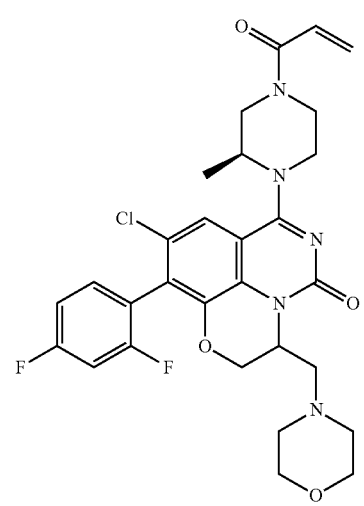
300
-continued
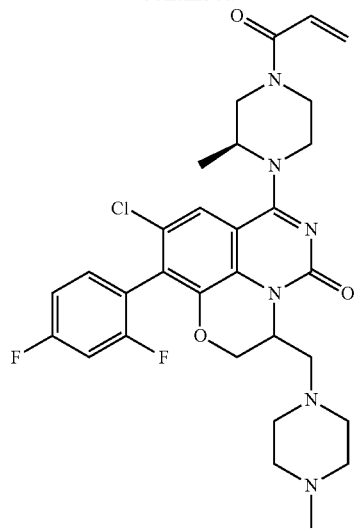
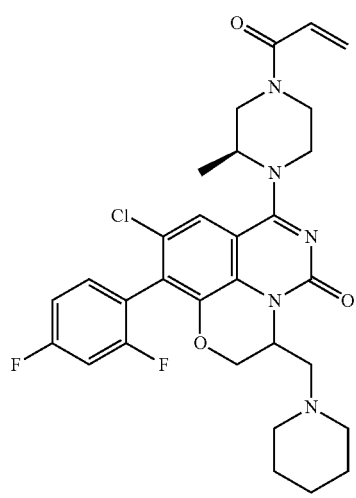
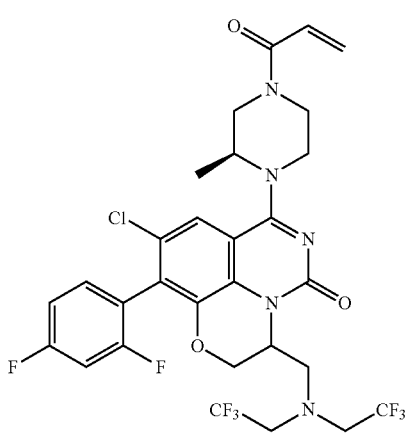

301
-continued
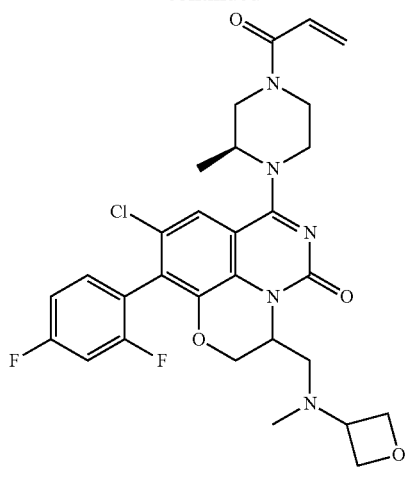
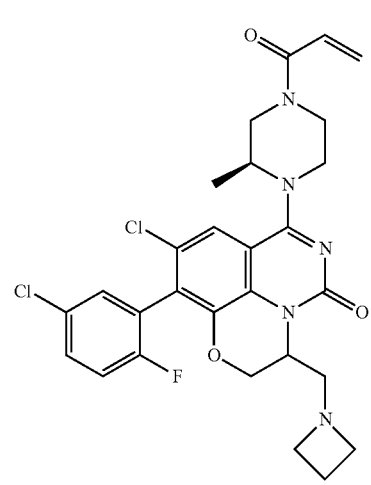
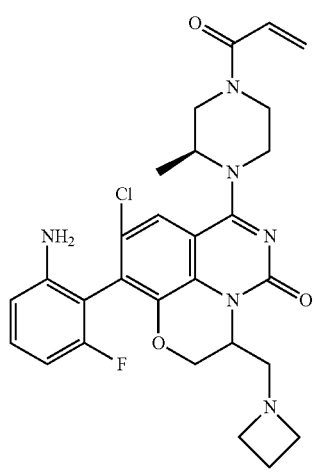
302
-continued
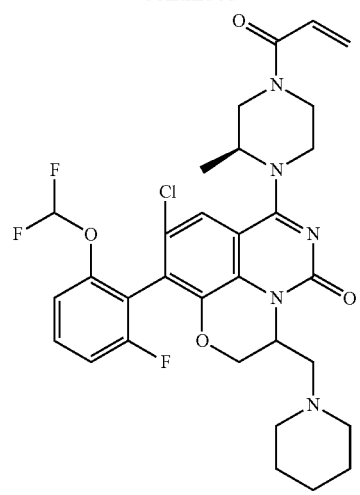
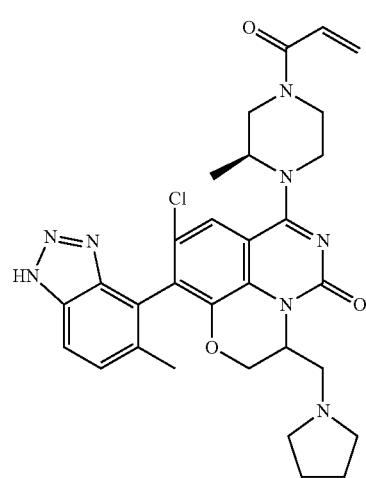
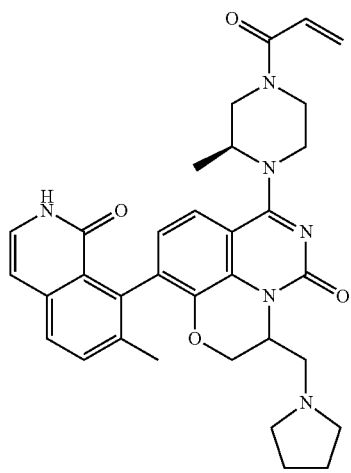

303
-continued
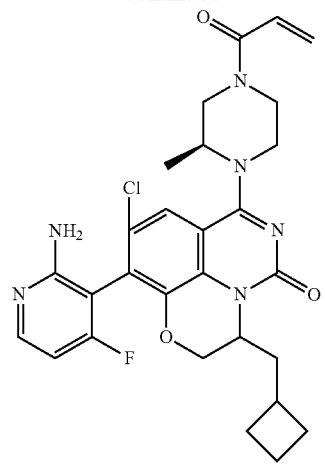
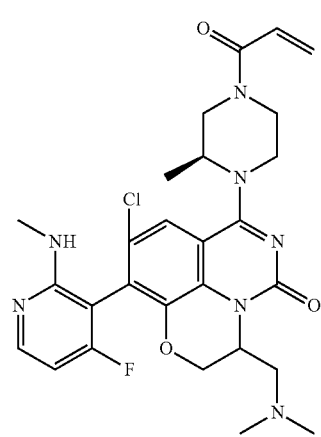
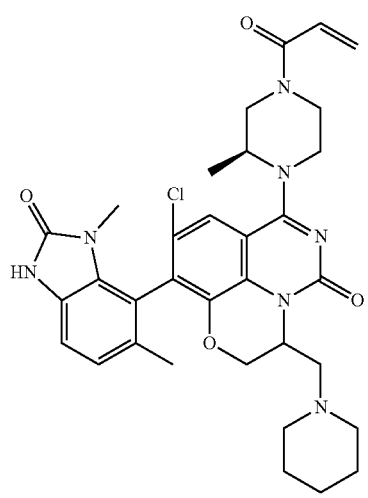
304
-continued
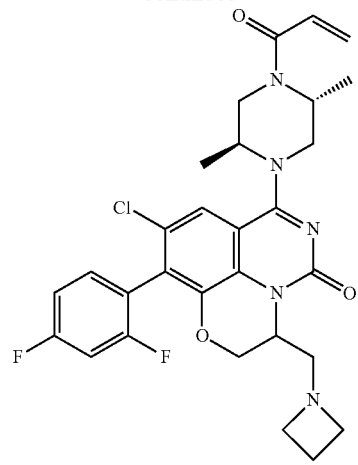
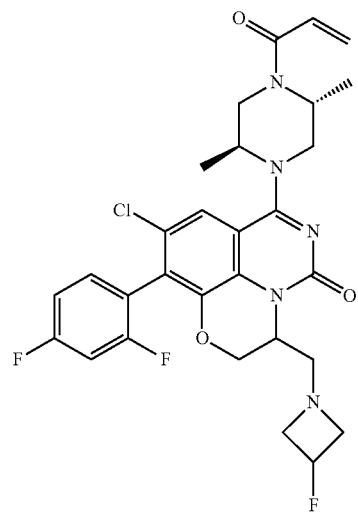
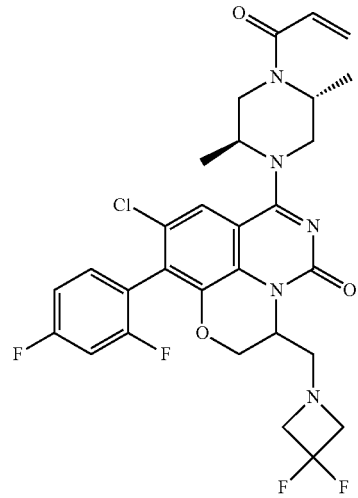

305
-continued
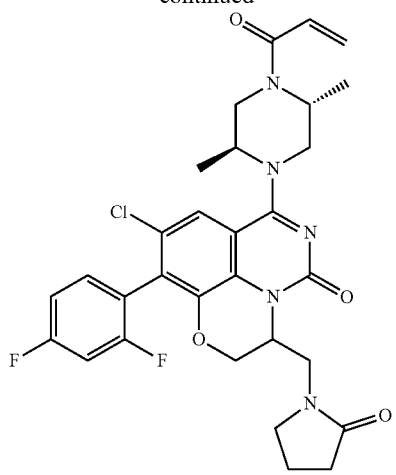
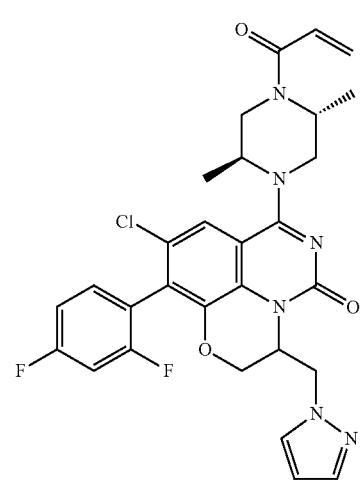
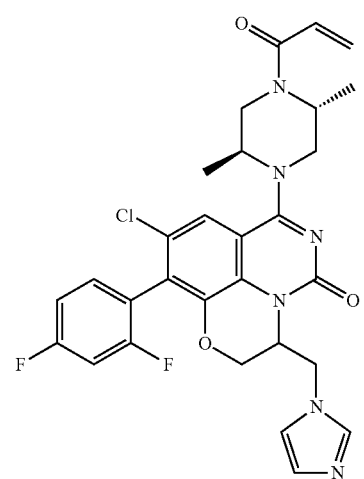
306
-continued
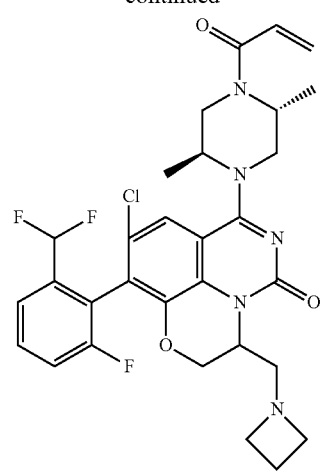
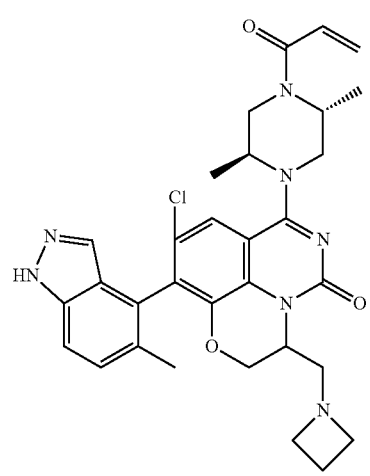
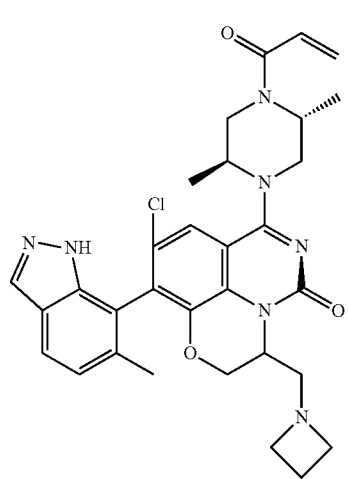

307
-continued
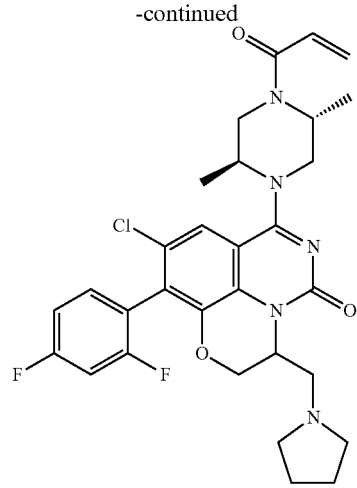
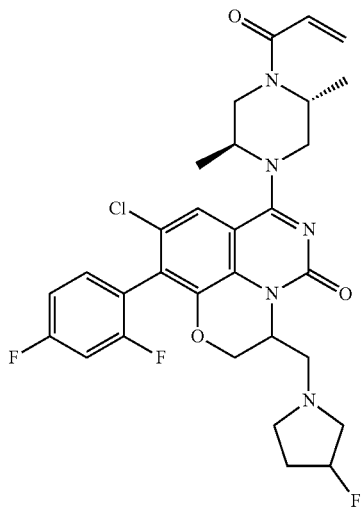
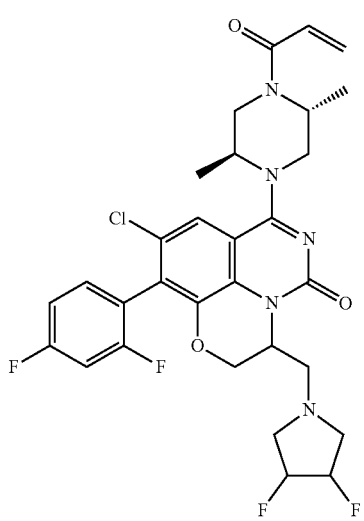
308
-continued
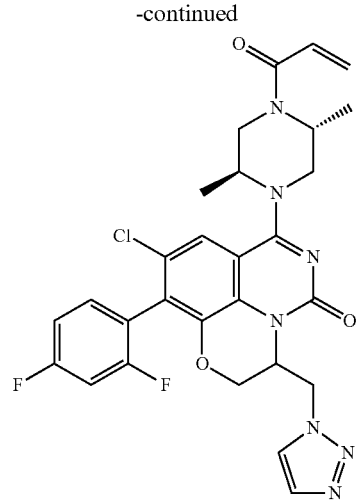
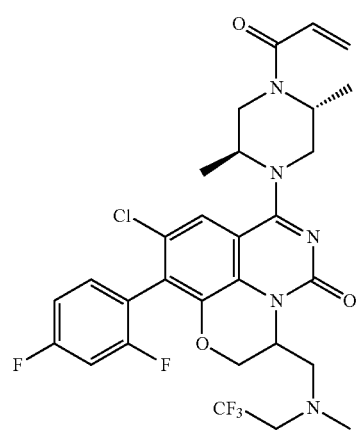
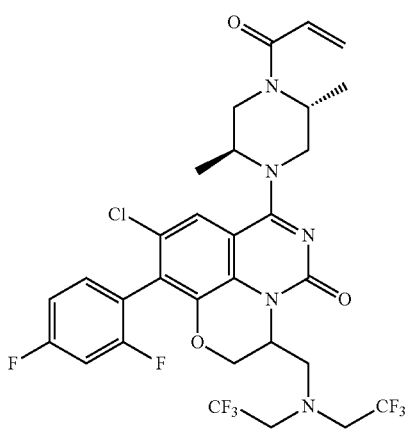

309
-continued
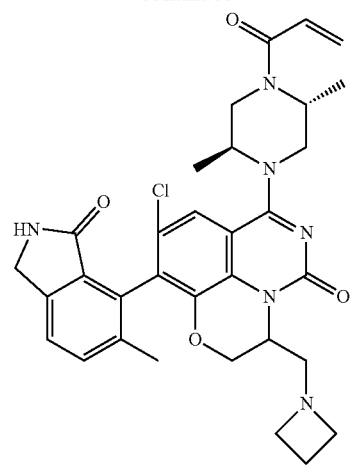
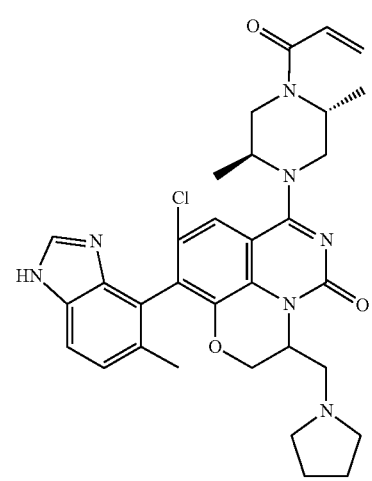
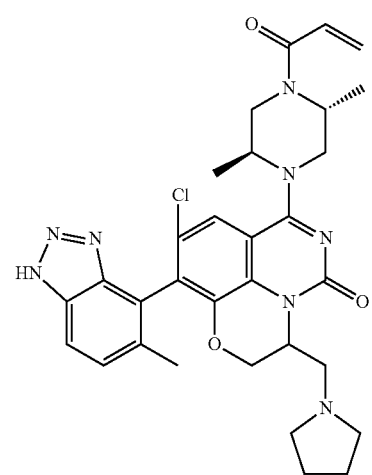
310
-continued
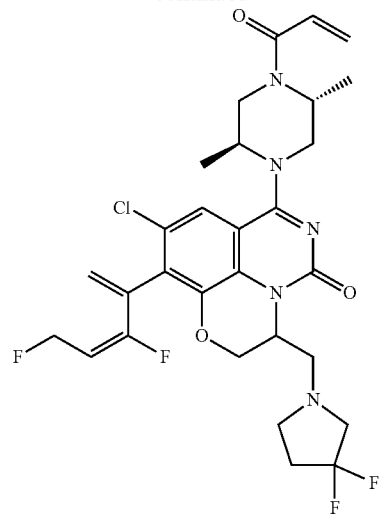
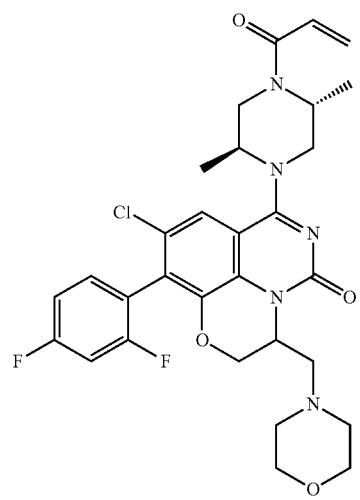
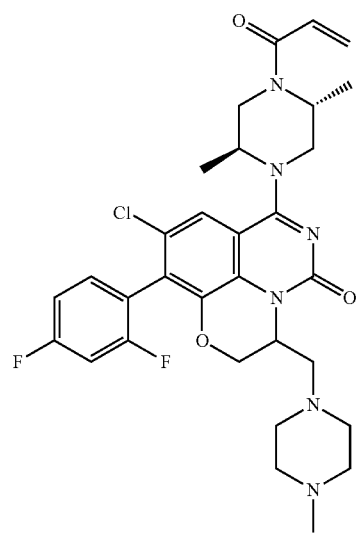

311
-continued
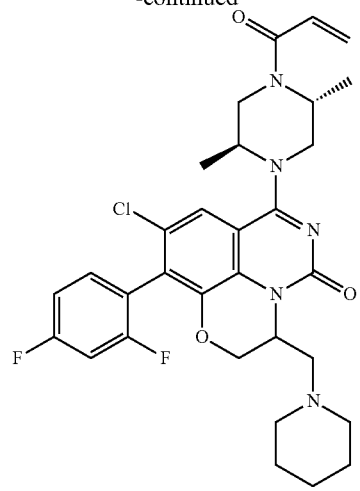
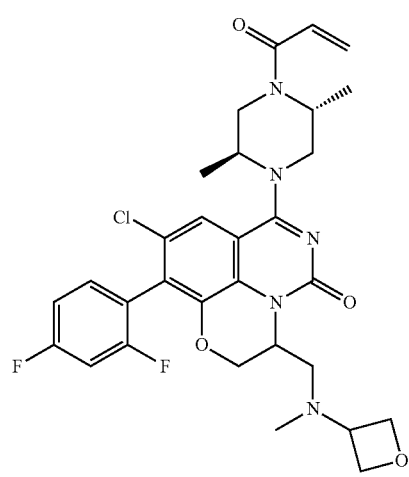
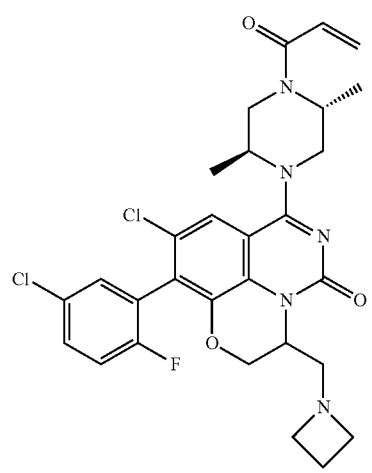
312
-continued
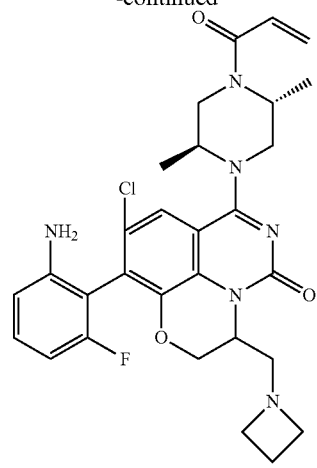
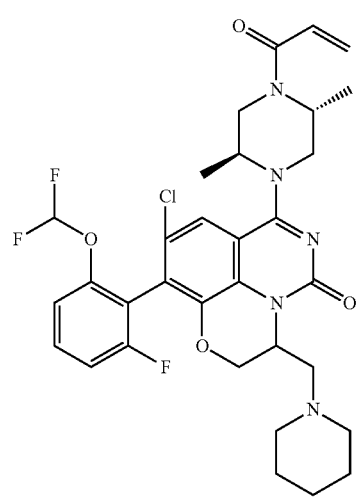
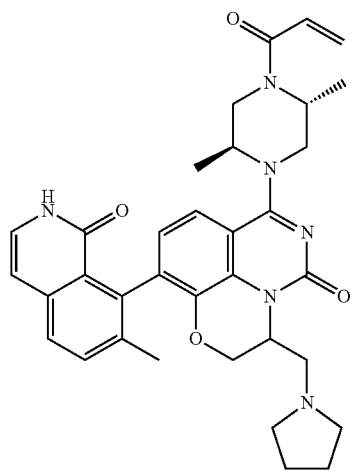

313
-continued
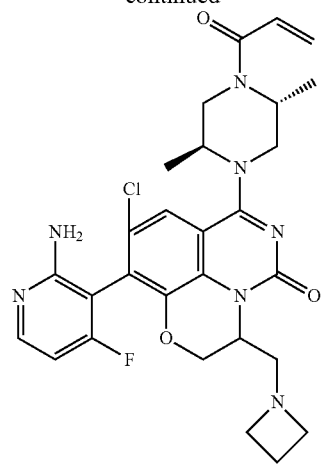
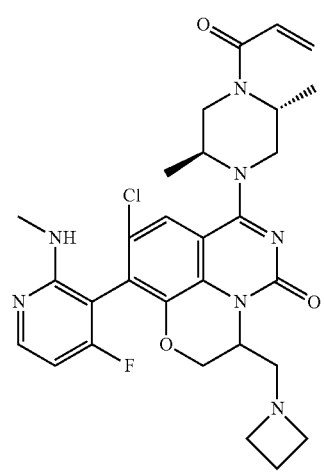
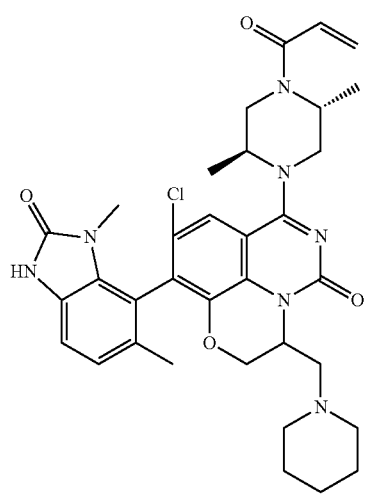
314
-continued
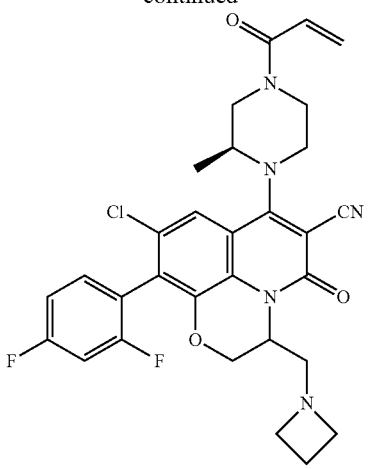
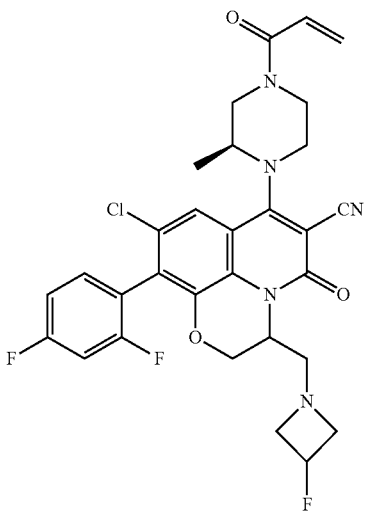
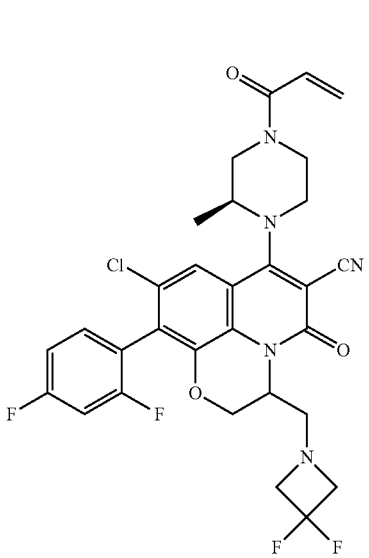

315
-continued
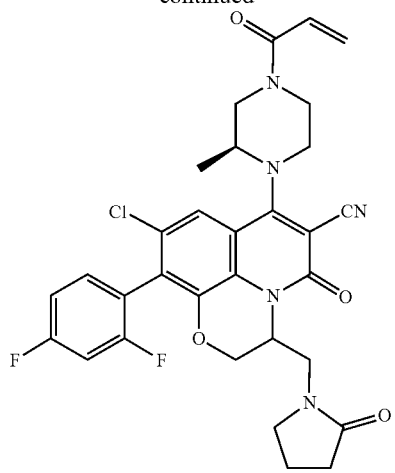
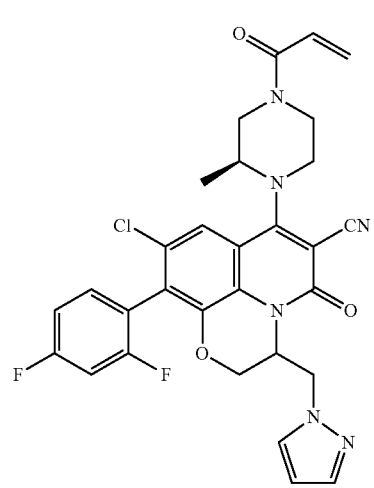
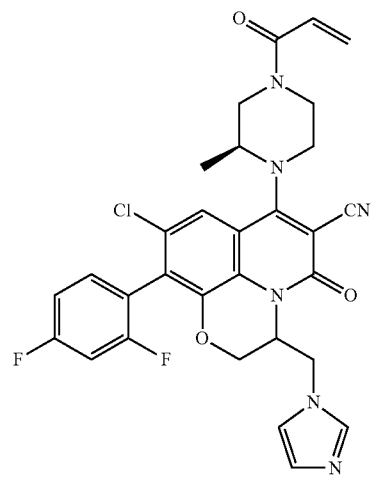
316
-continued
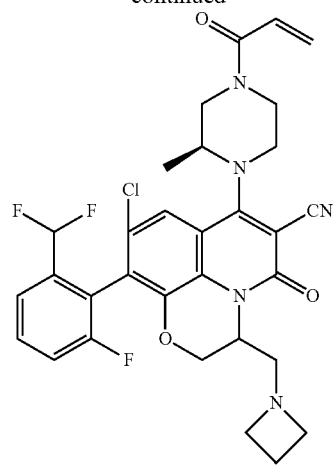
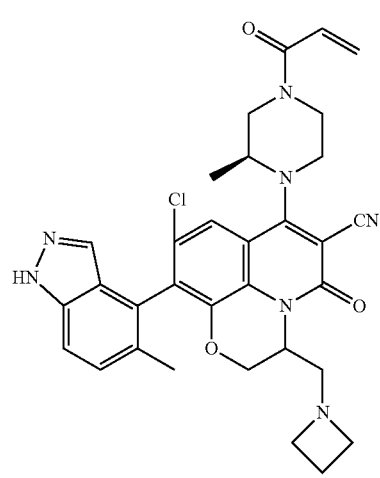
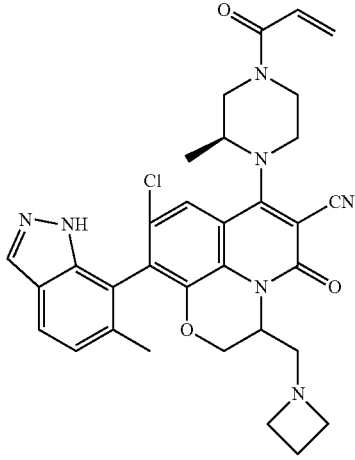

| 317 | 318 |
|---|---|
| 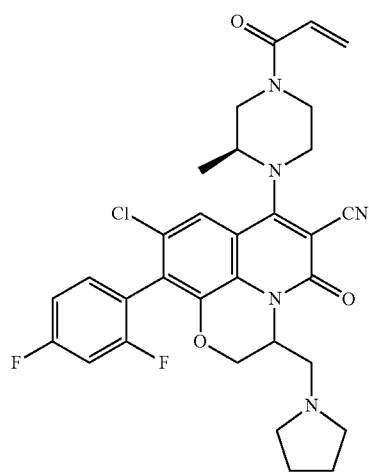 | -continued<br>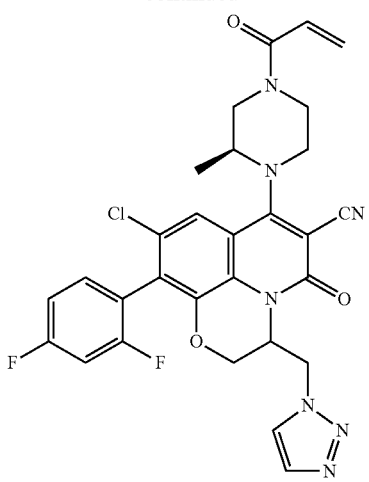 |
| 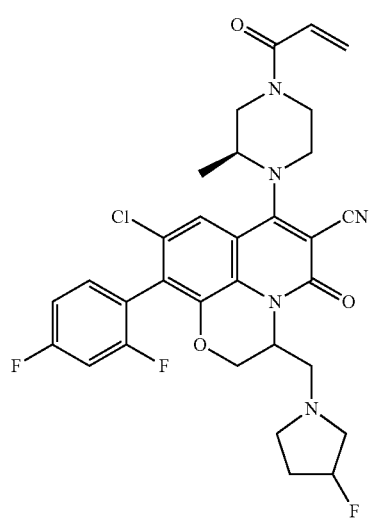 | 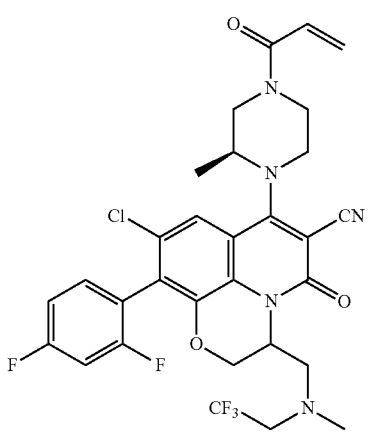 |
| 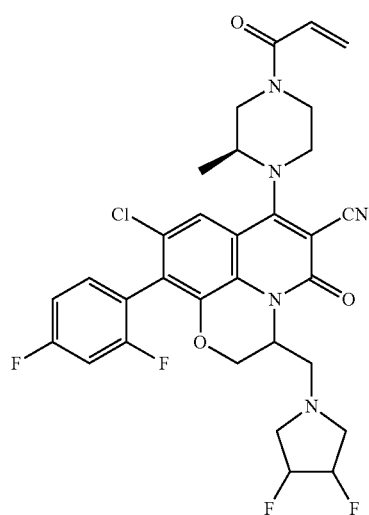 | 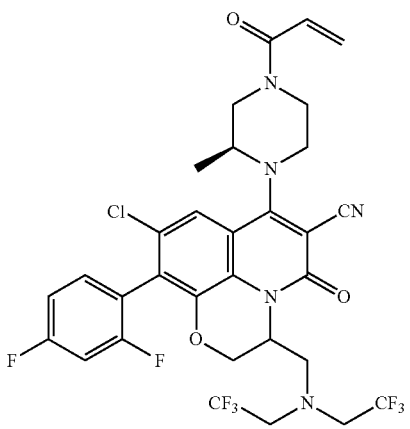 |

319
-continued
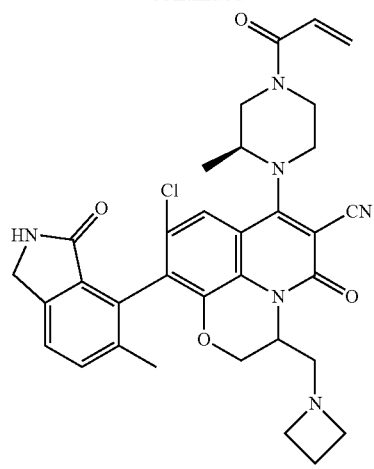
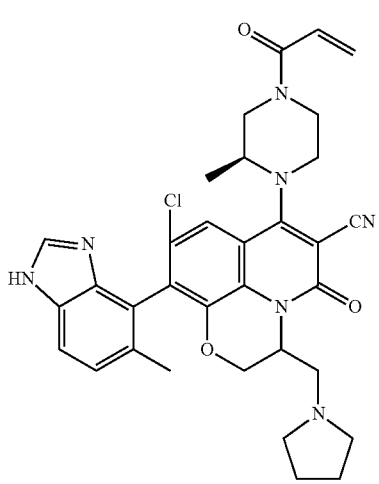
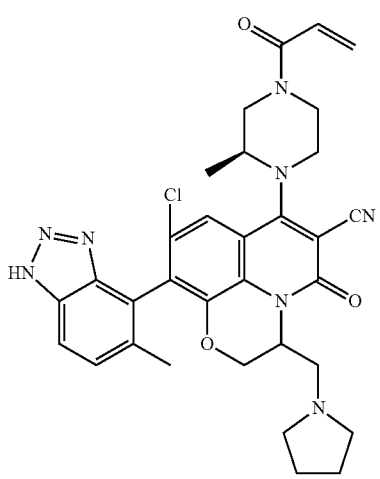
320
-continued
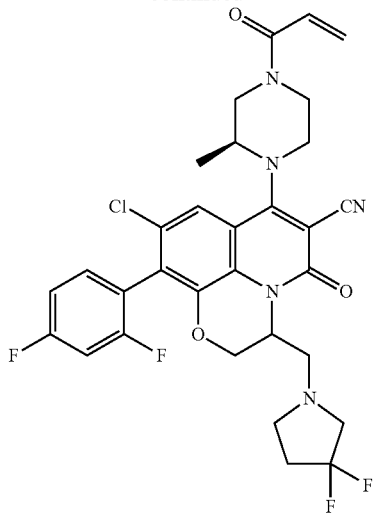
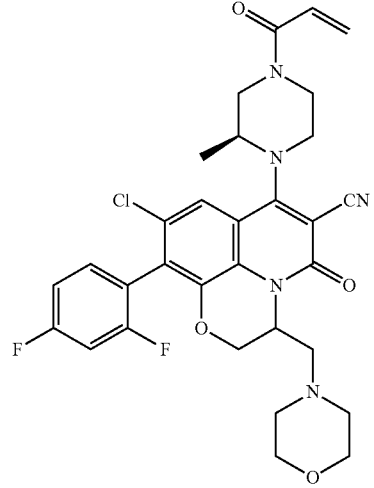
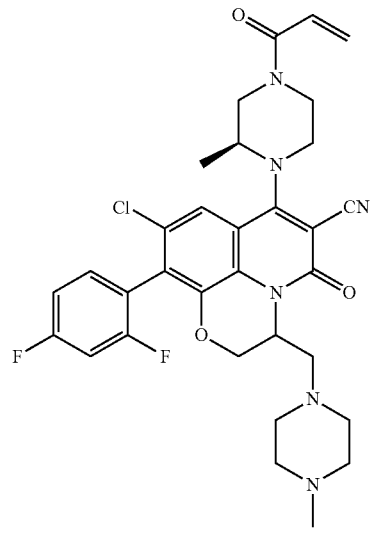

321
-continued
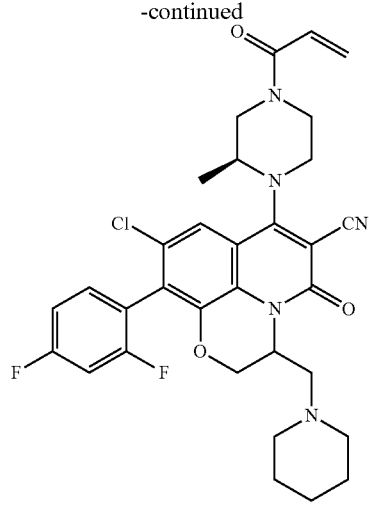
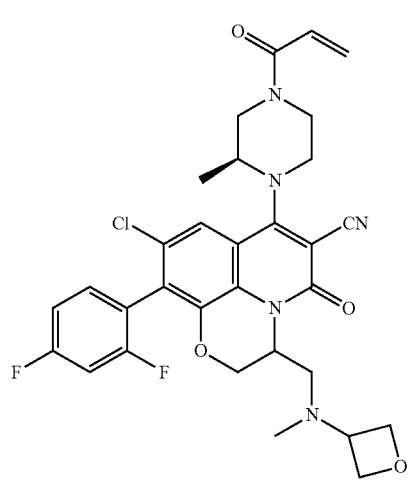
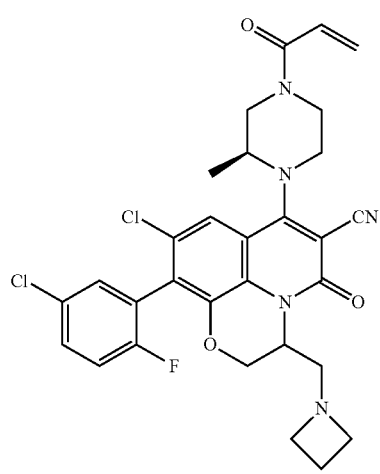
322
-continued
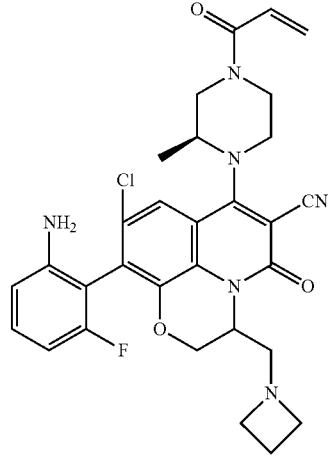
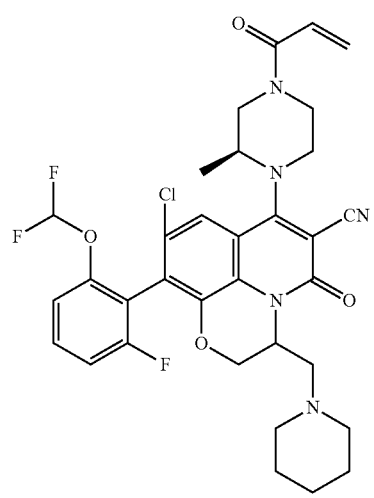
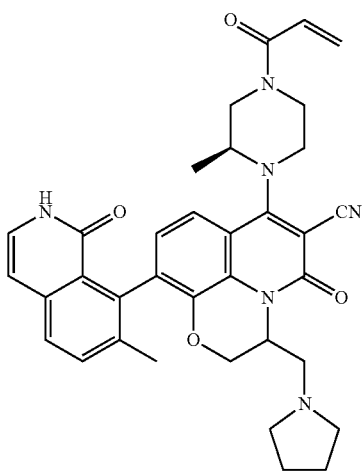

323
-continued
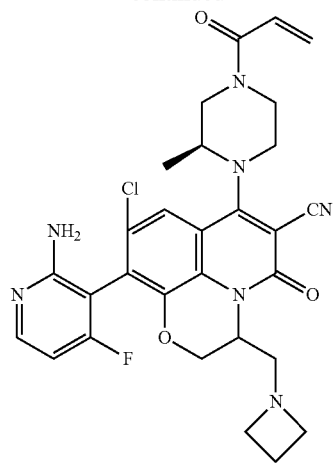
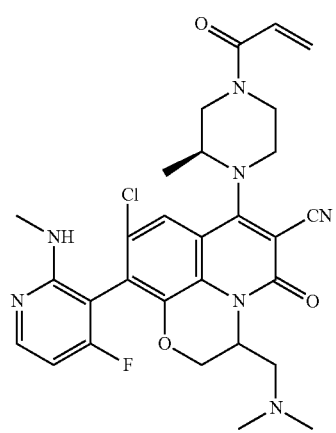
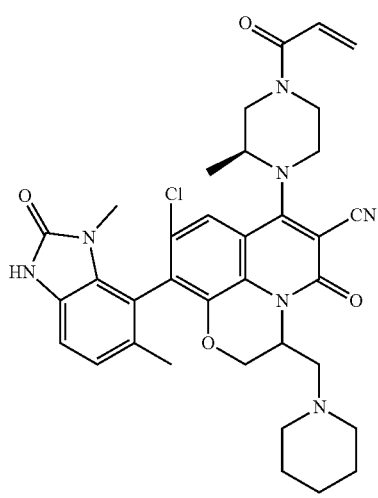
324
-continued
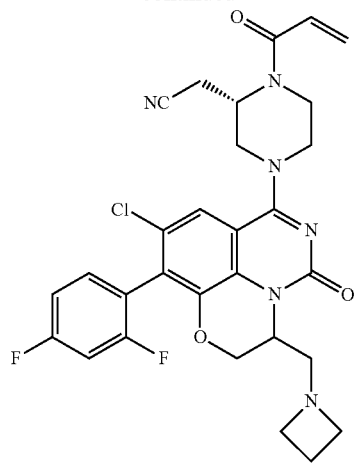
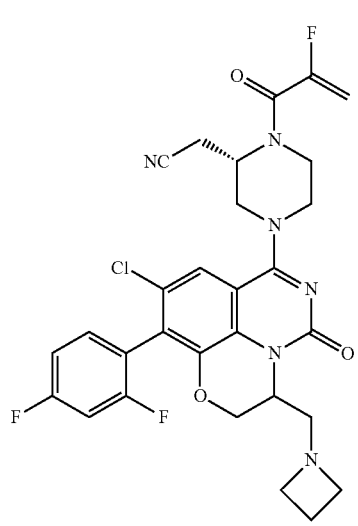
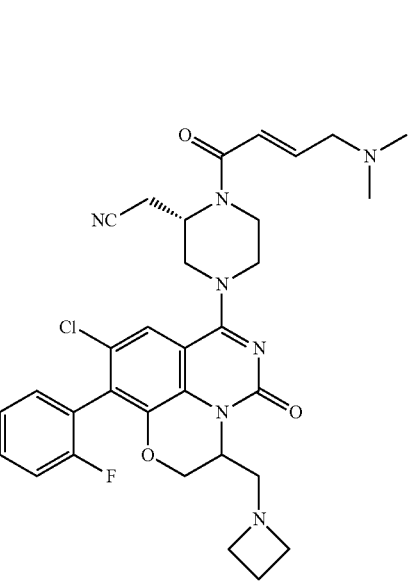

325
-continued
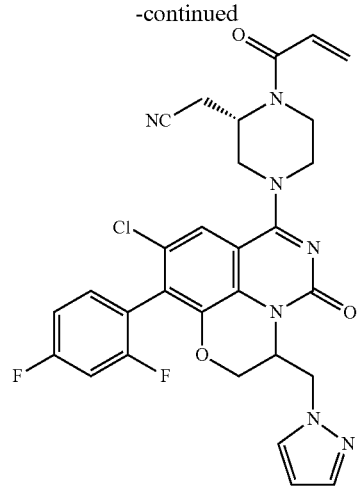
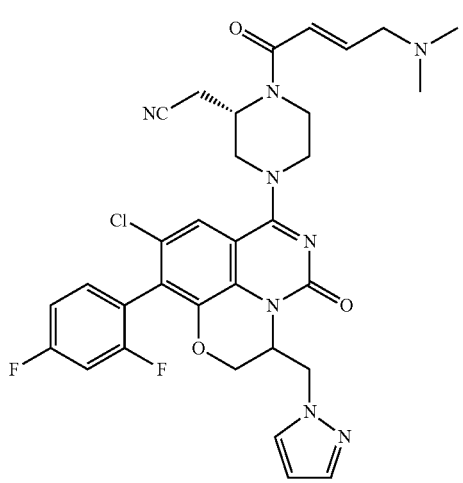
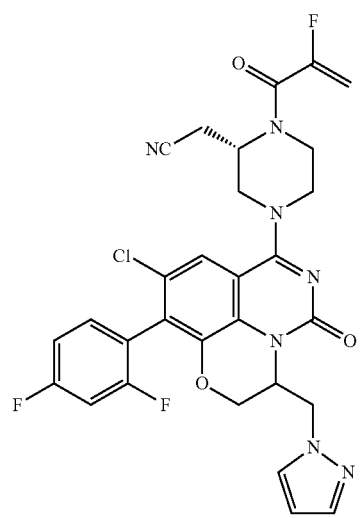
326
-continued
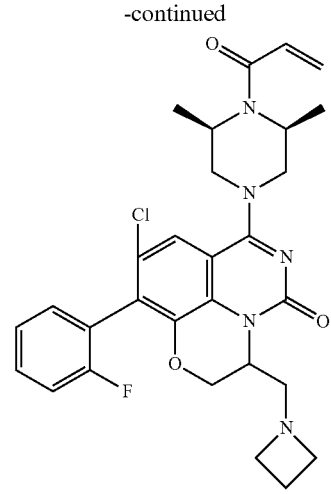
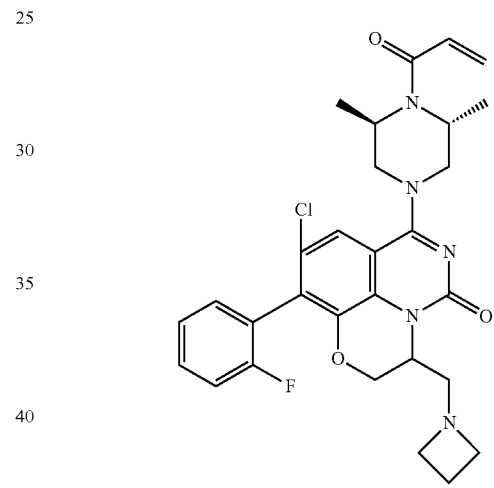
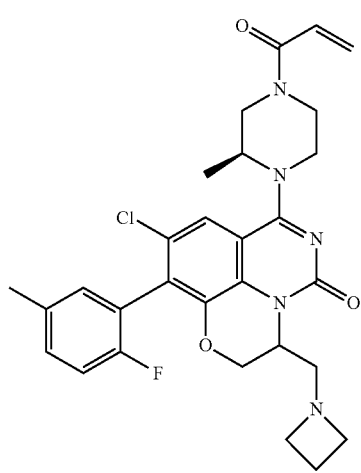

327
-continued
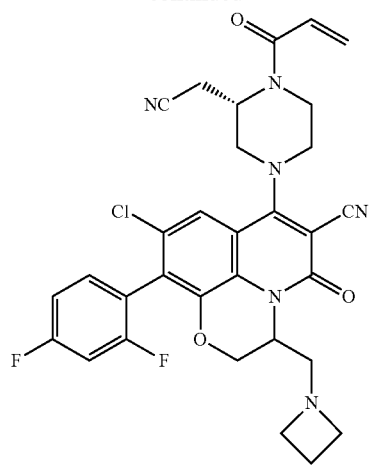
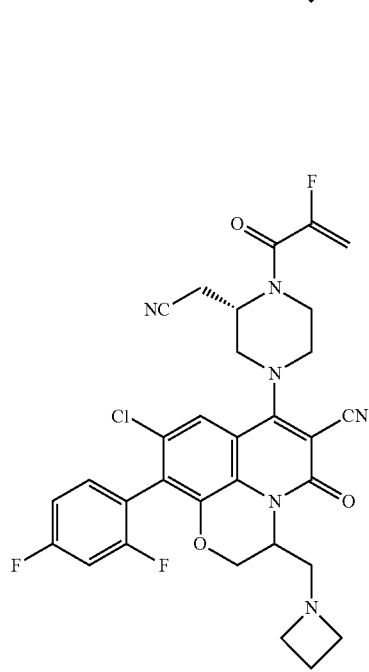
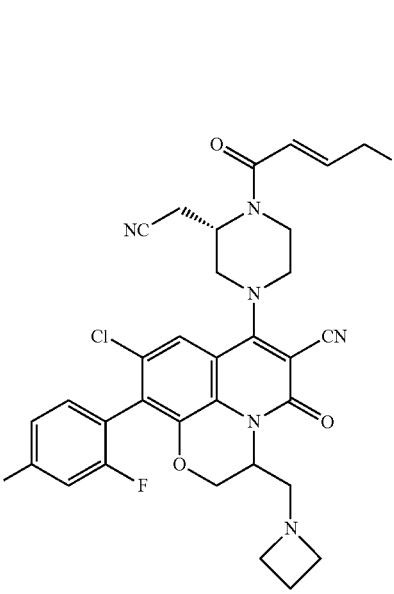
328
-continued
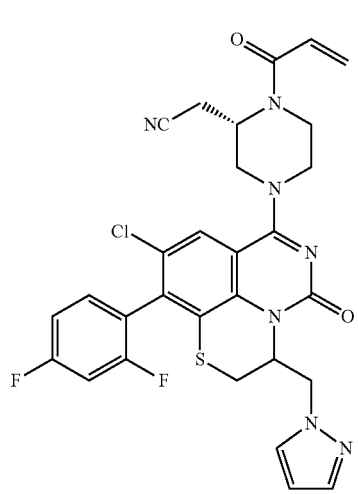
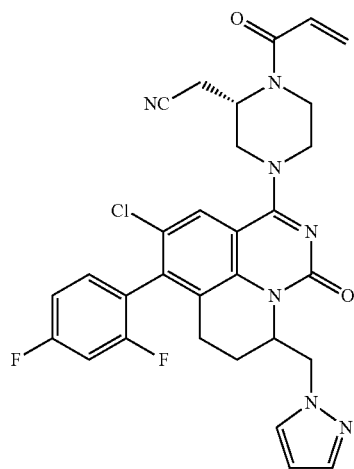

329
-continued
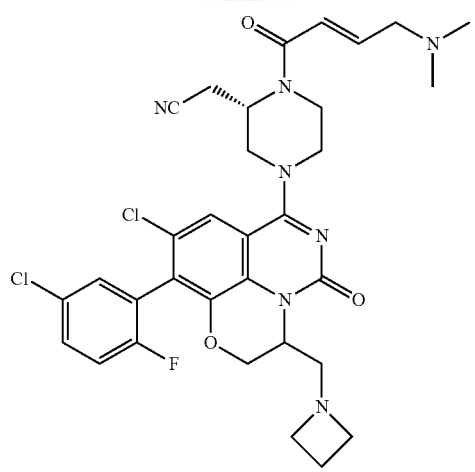
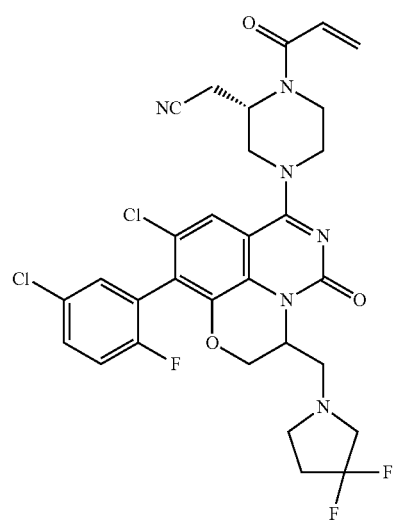
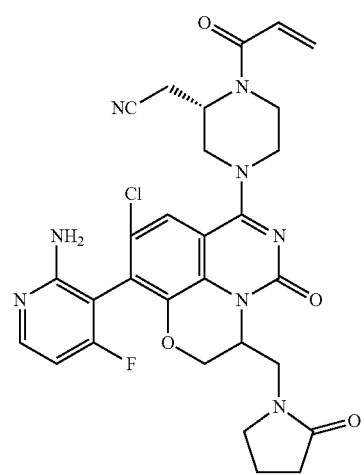
330
-continued
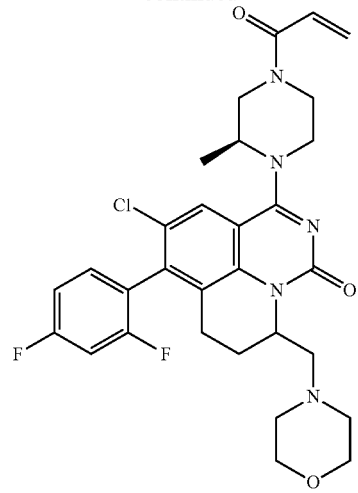
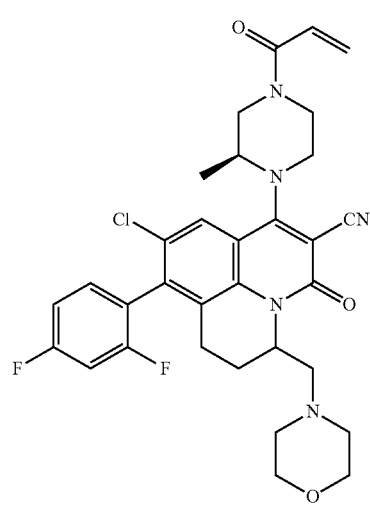
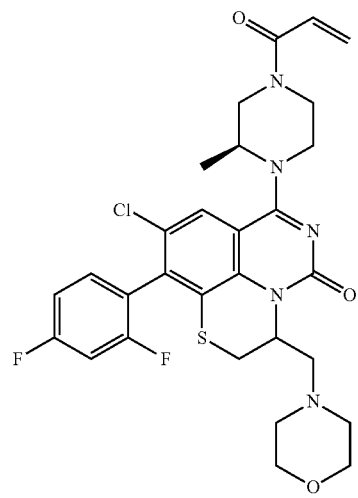

331
-continued
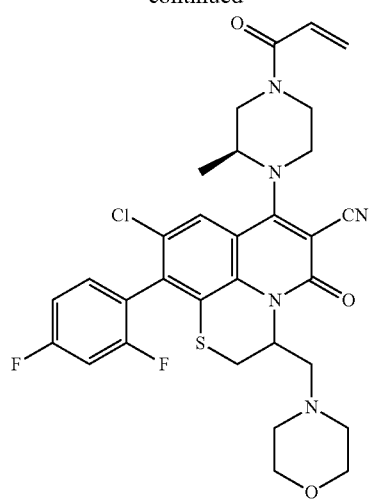
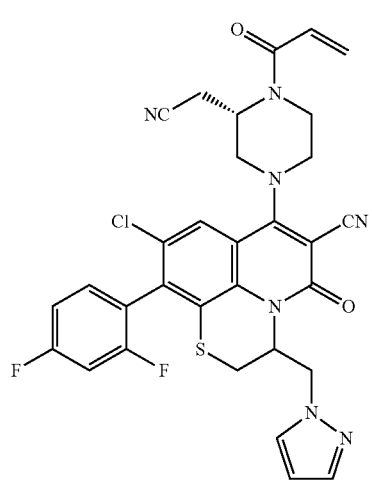
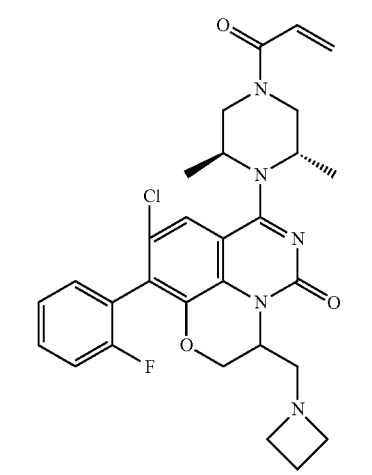
332
-continued
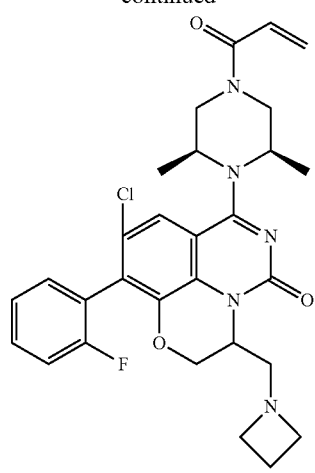
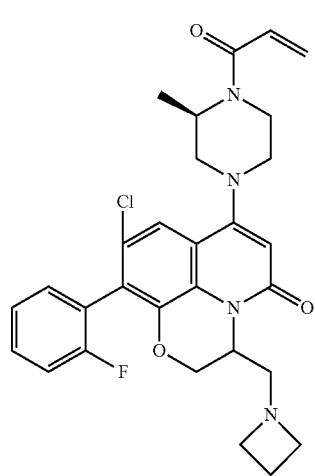
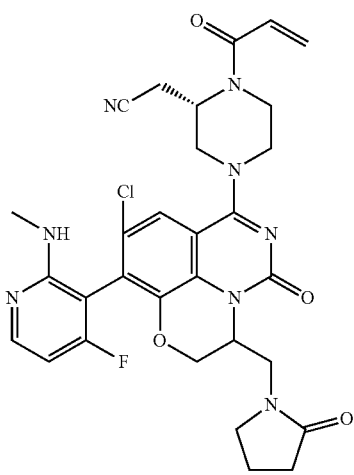

333
-continued
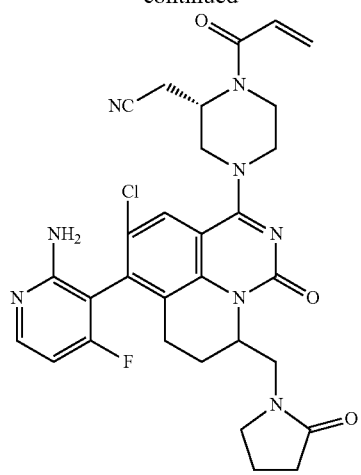
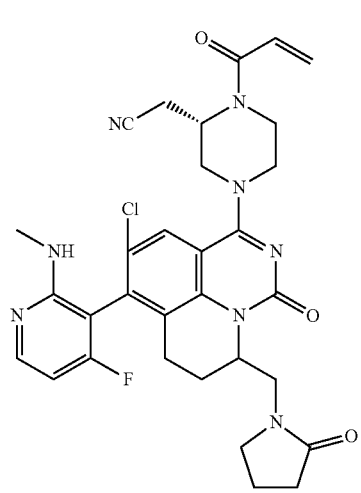
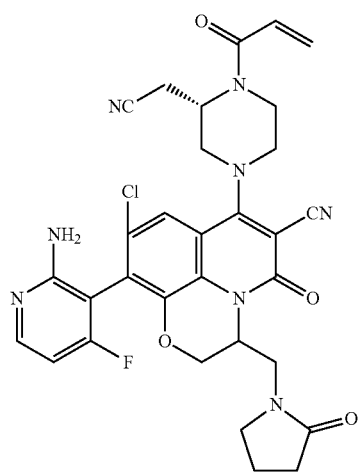
334
-continued
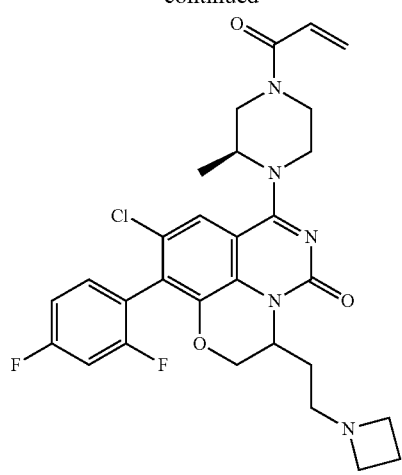
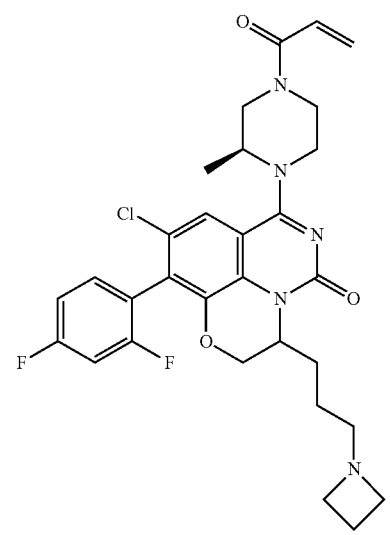
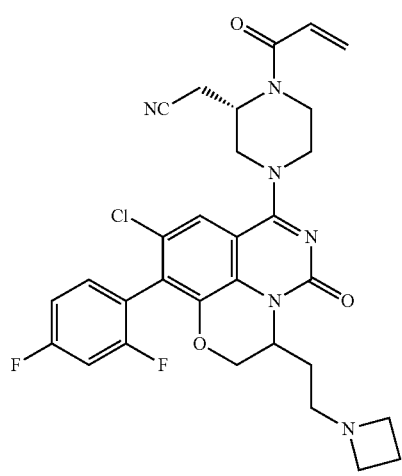

335
-continued
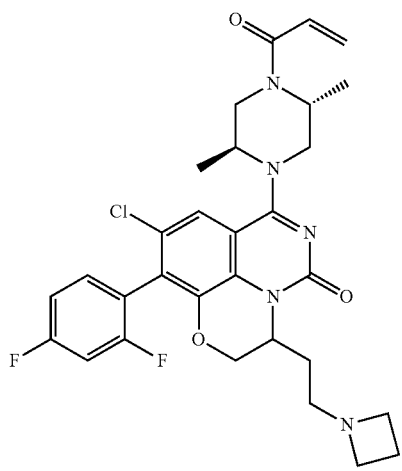
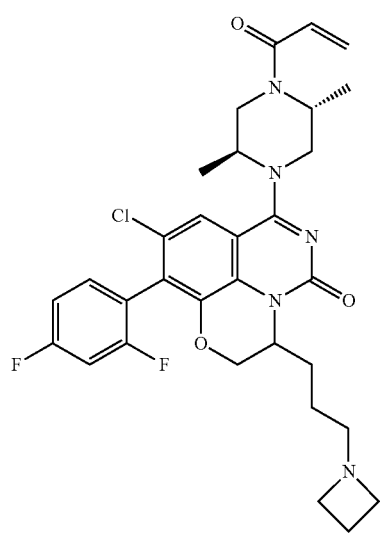
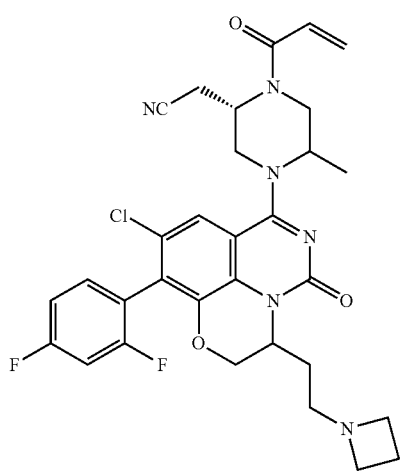
336
-continued
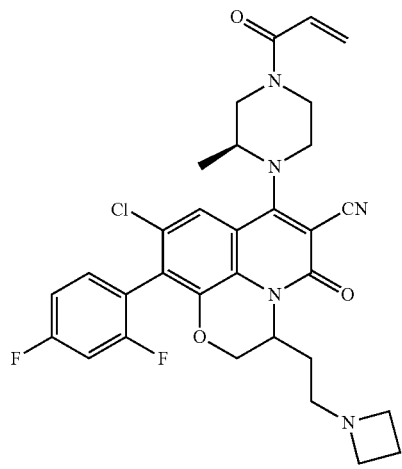
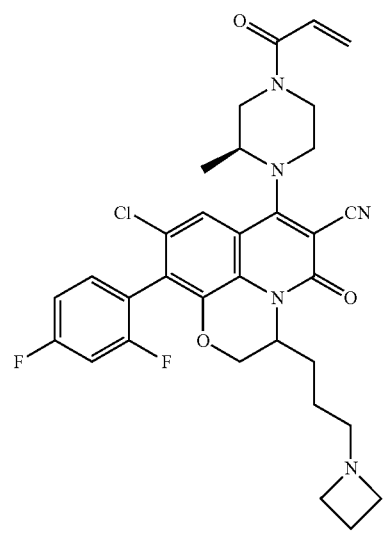
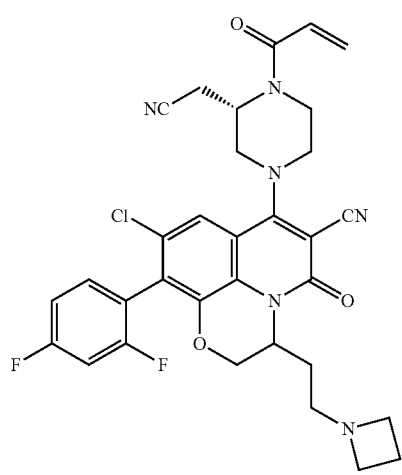

| 337 -continued | 338 -continued |
|---|---|
| 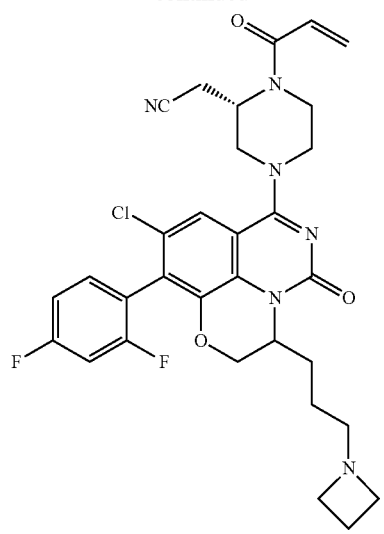 | 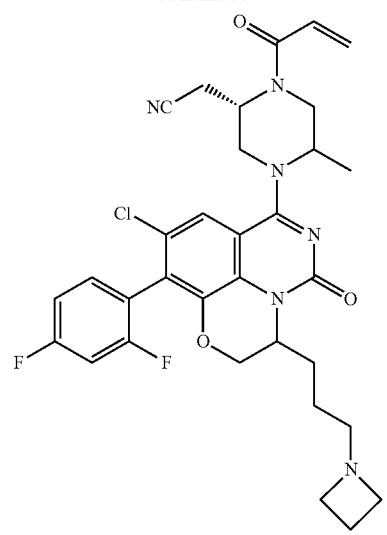 |
| 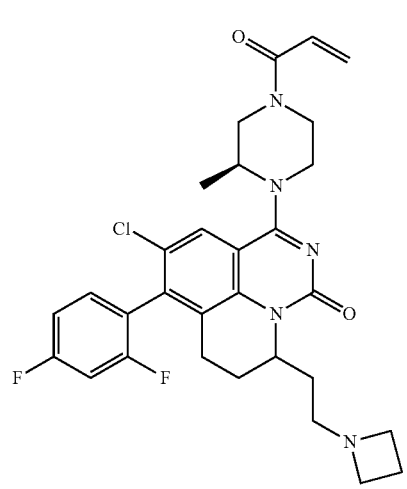 | 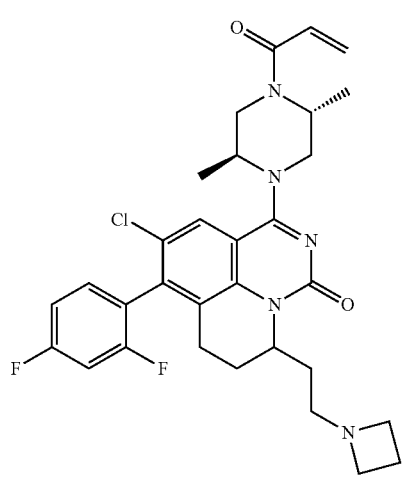 |
| 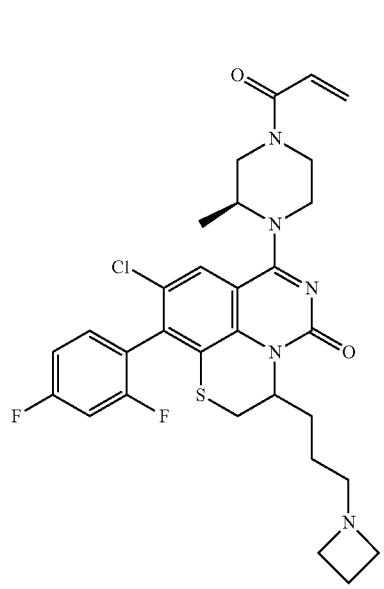 | 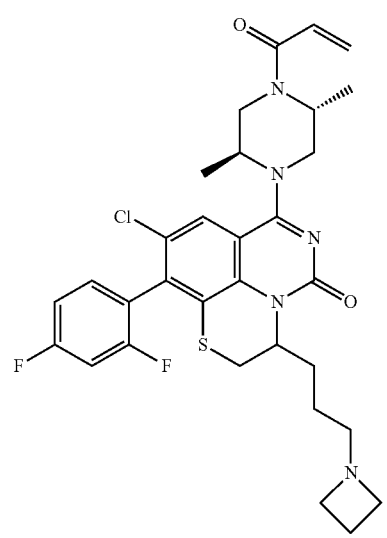 |

339
-continued
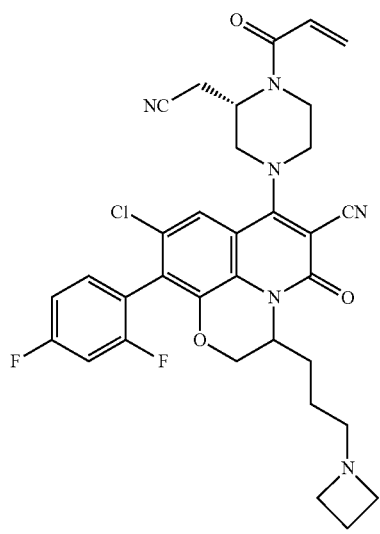
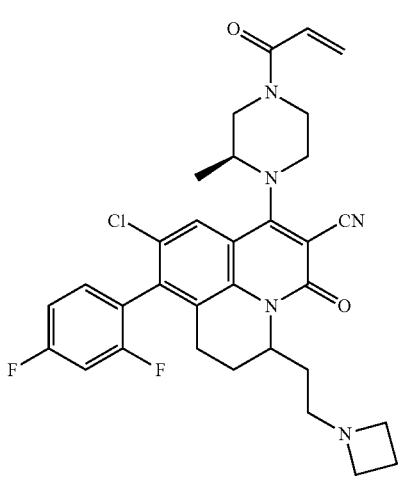
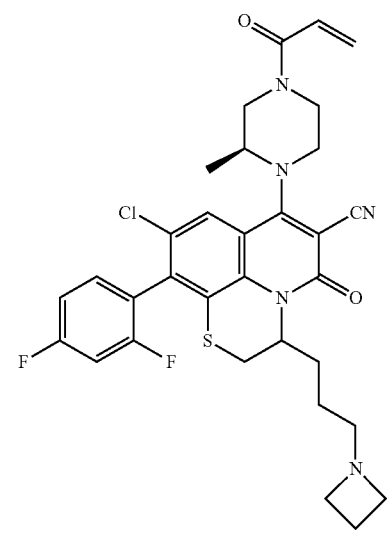
340
-continued
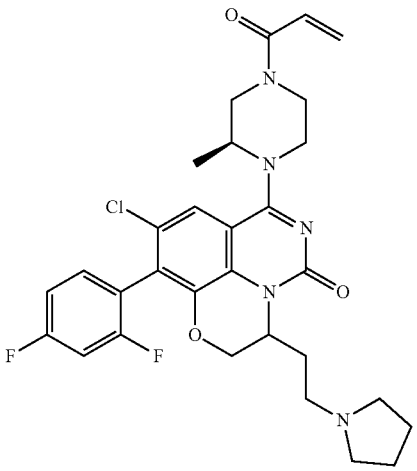
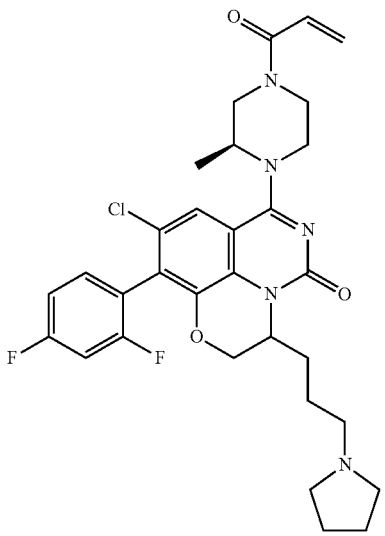
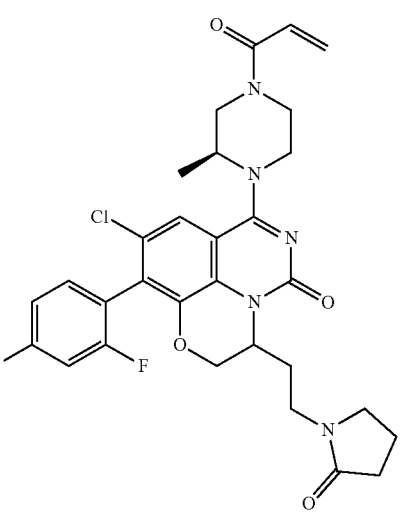

341
-continued
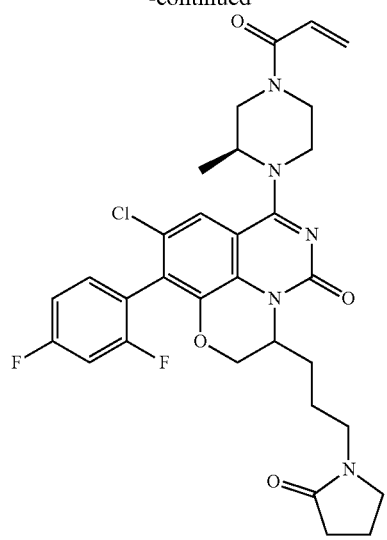
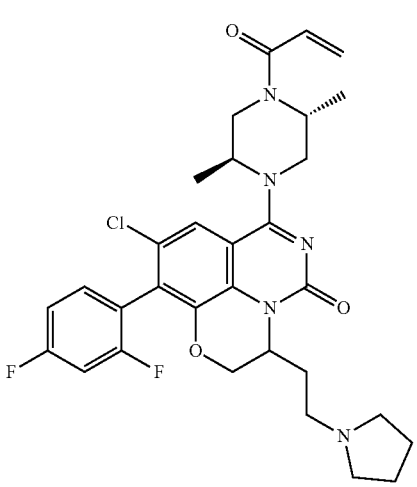
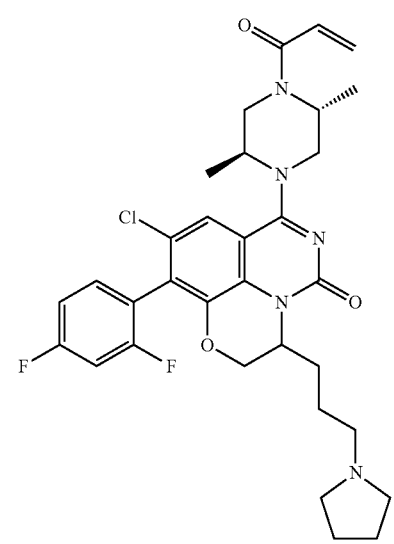
342
-continued
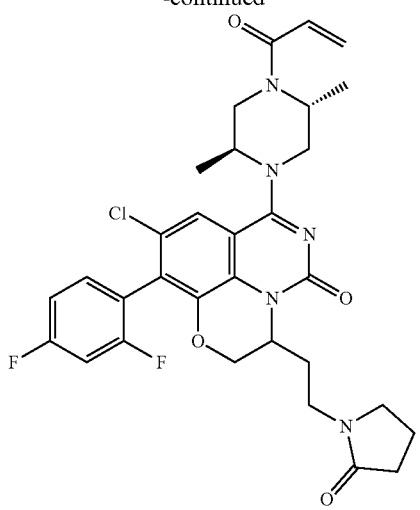
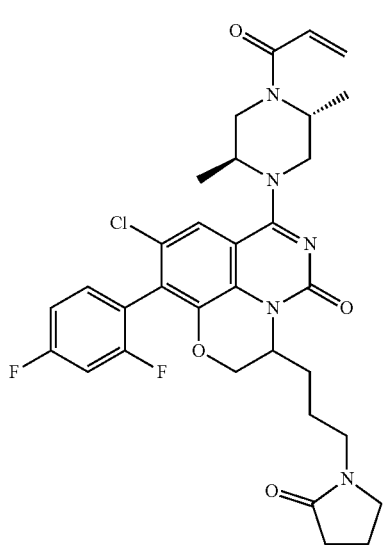
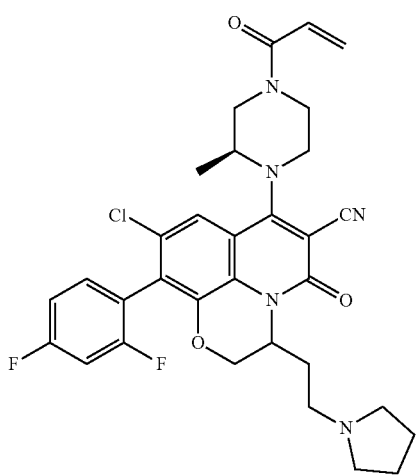

343
-continued
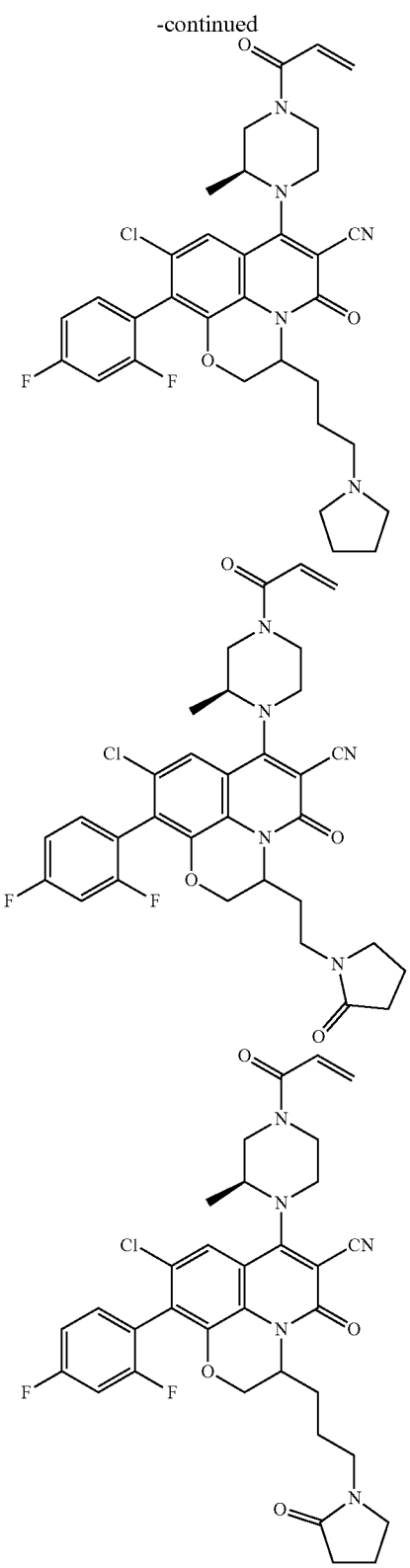
IV. General Synthetic Methods for Preparing Compounds
The following schemes can be used to practice the various embodiments disclosed herein. It will be understood that these schemes are merely exemplary and that they provide ready access to core structures with variable functionality.
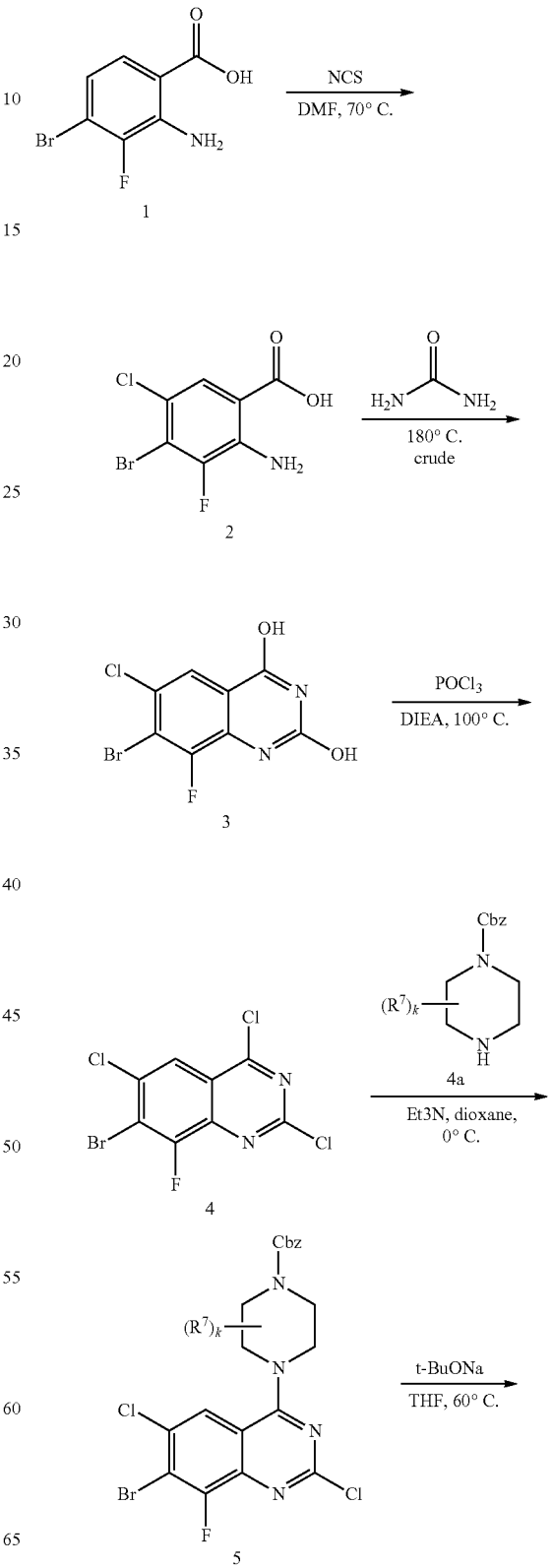

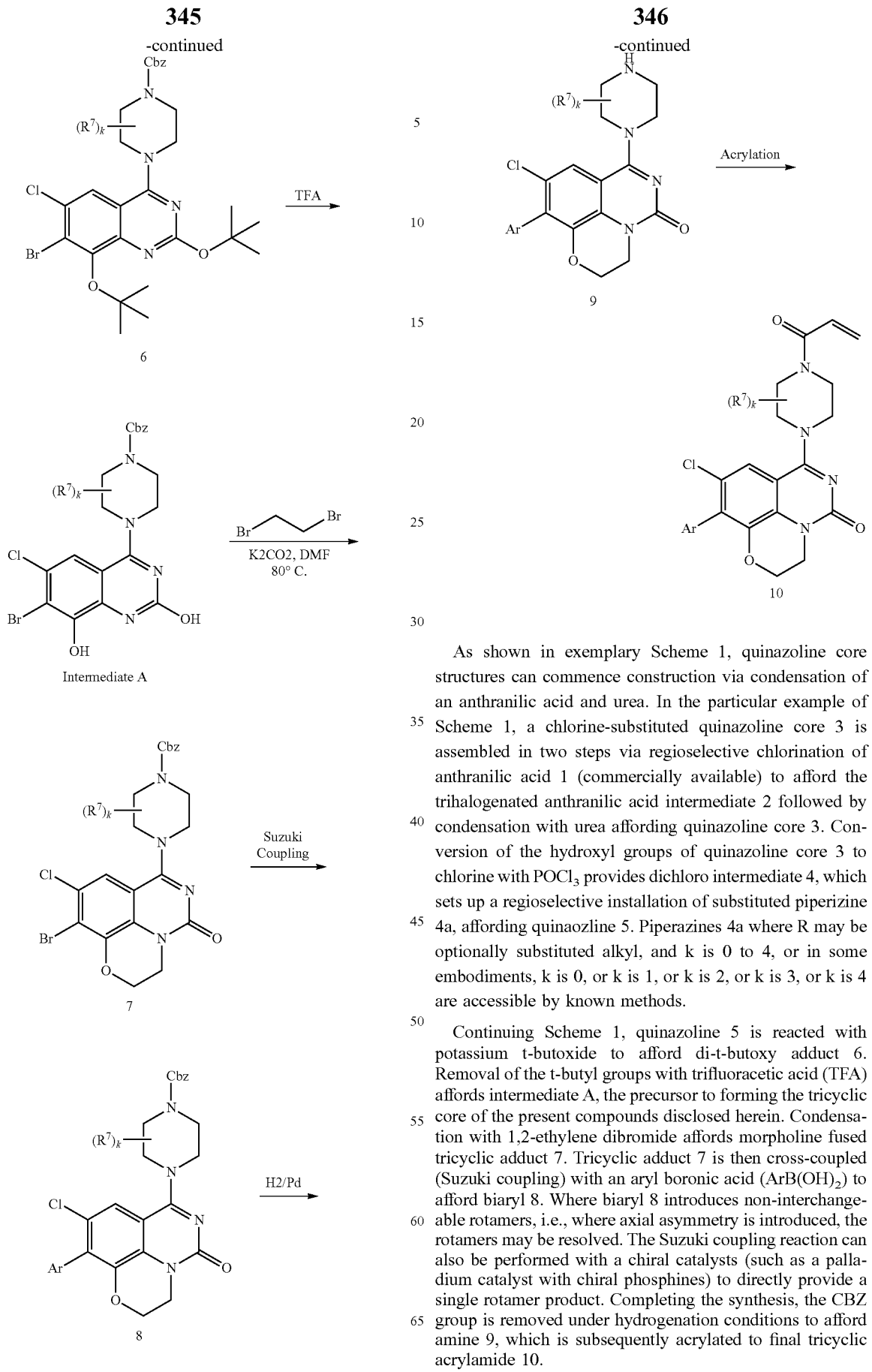

As shown in exemplary Scheme 1, quinazoline core structures can commence construction via condensation of an anthranilic acid and urea. In the particular example of Scheme 1, a chlorine-substituted quinazoline core 3 is assembled in two steps via regioselective chlorination of anthranilic acid 1 (commercially available) to afford the trihalogenated anthranilic acid intermediate 2 followed by condensation with urea affording quinazoline core 3. Conversion of the hydroxyl groups of quinazoline core 3 to chlorine with $POCl_3$ provides dichloro intermediate 4, which sets up a regioselective installation of substituted piperizine 4a, affording quinaozline 5. Piperazines 4a where R may be optionally substituted alkyl, and k is 0 to 4, or in some embodiments, k is 0, or k is 1, or k is 2, or k is 3, or k is 4 are accessible by known methods.

Continuing Scheme 1, quinazoline 5 is reacted with potassium t-butoxide to afford di-t-butoxy adduct 6. Removal of the t-butyl groups with trifluoracetic acid (TFA) affords intermediate A, the precursor to forming the tricyclic core of the present compounds disclosed herein. Condensation with 1,2-ethylene dibromide affords morpholine fused tricyclic adduct 7. Tricyclic adduct 7 is then cross-coupled (Suzuki coupling) with an aryl boronic acid $(ArB(OH)_2)$ to afford biaryl 8. Where biaryl 8 introduces non-interchangeable rotamers, i.e., where axial asymmetry is introduced, the rotamers may be resolved. The Suzuki coupling reaction can also be performed with a chiral catalysts (such as a palladium catalyst with chiral phosphines) to directly provide a single rotamer product. Completing the synthesis, the CBZ group is removed under hydrogenation conditions to afford amine 9, which is subsequently acrylated to final tricyclic acrylamide 10.

Scheme 2—Pyrimidone Core-Morpholine Substituted

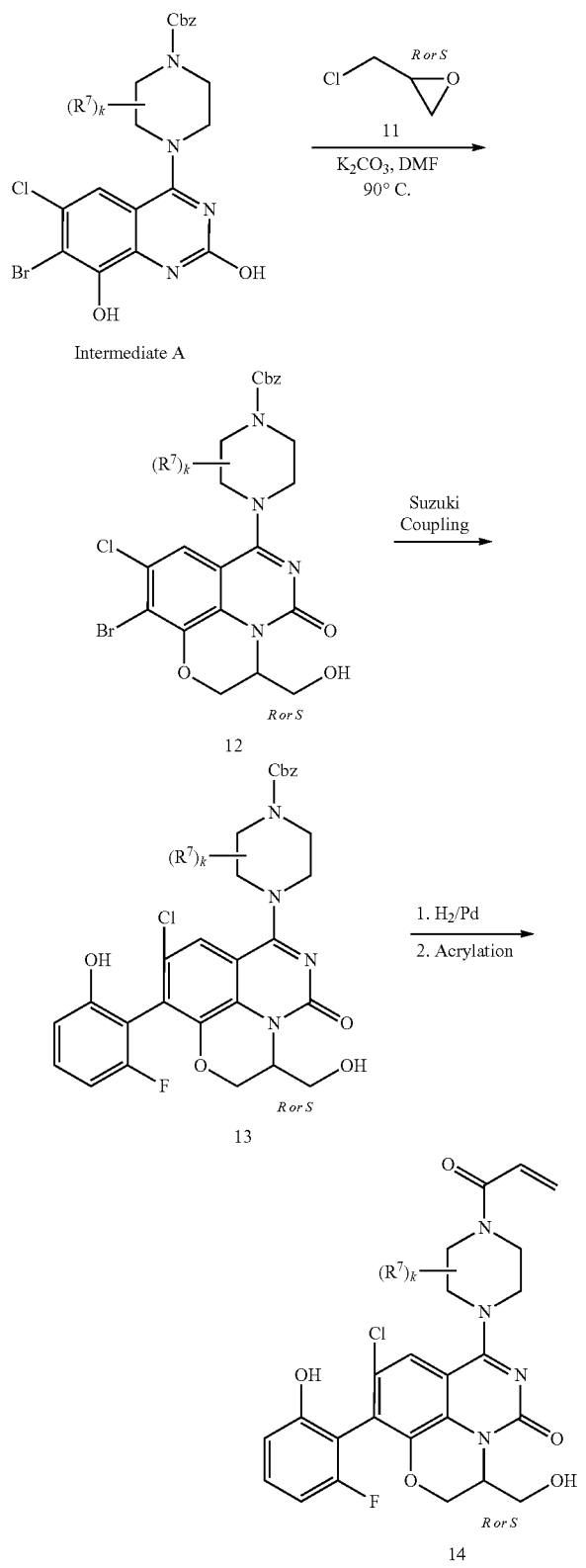

with Intermediate A (Schemes 1 and 2). As indicated in Scheme 2, condensation of Intermediate A with epoxide 11 (available in enantiomerically pure form via, for example, asymmetric epoxidation of allyl alcohol or other chiral starting material) affords morpholine-fused pyrmidone 12. Suzuki coupling with an aryl boronic acid as described above, affords biaryl 13. Removal of the CBZ protecting group and acrylation affords acrylamide 14. Intermediates 12 or 13 can potentially elaborate on the pendant hydroxyl moiety to access a host of functionalization at that position. For example, the hydroxyl can be converted to other functional groups including amines, azides or nitriles (to access cycloaddition chemistry), carboxylic acids and their derivatives (i.e., amides, esters, and the like). The extent of potential chemical conversions of the hydroxyl functionality in intermediates 12 or 13 will be apparent to those skilled in the art.

Other condensation partners besides ethylene dibromide (Scheme 1) and epoxides (Scheme 2) may be used. In some embodiments, condensation partners may comprise any organic reactant having two electrophilic portions including any combination of halide, epoxide, sulfonate, activated acids (e.g., acid halides, anhydrides), unsaturated acids, aldehydes, and the like. Scheme 3 below shows an exemplary synthetic process that employs a bis-sulfonate electrophile 17.

Scheme 3—Pyrimidone Core-Morpholine Substituted

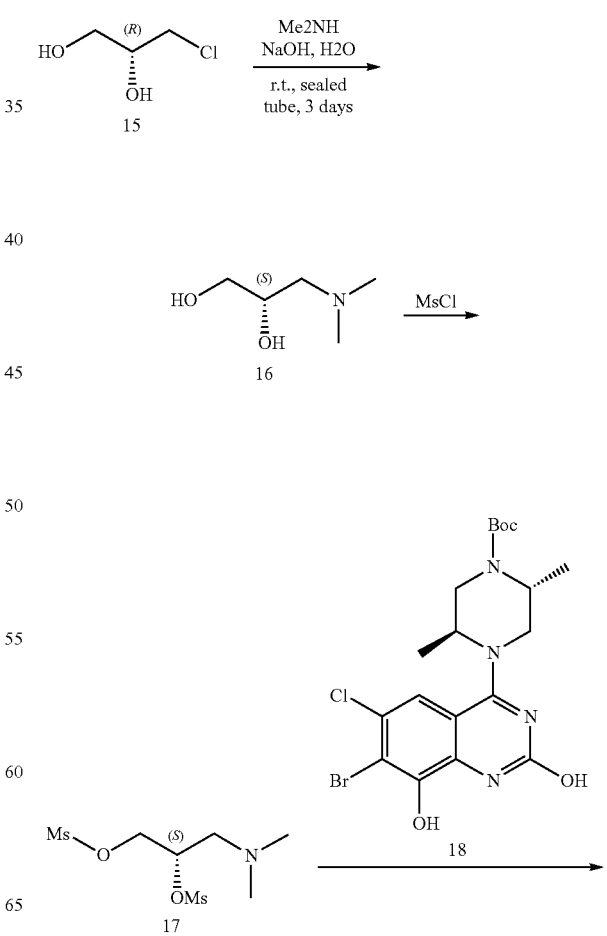

As shown in Scheme 2 above, the morophline moiety can be optionally substituted to include stereogenic centers and functional group handles by reaction of appropriate reagents

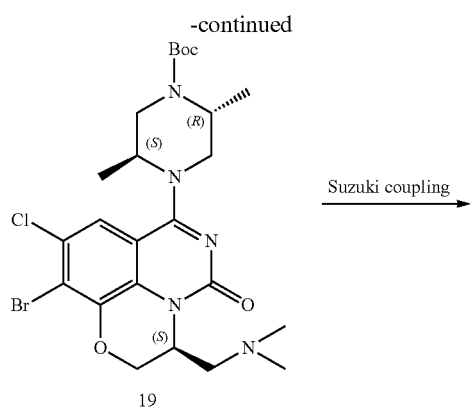

19

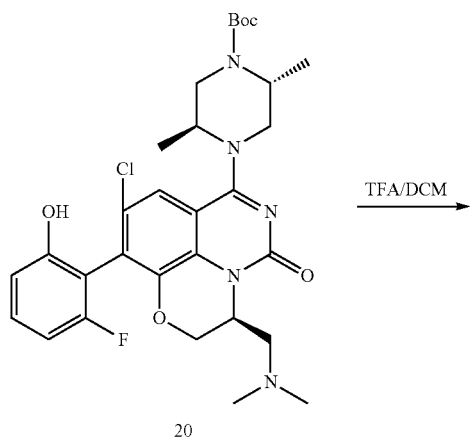

20

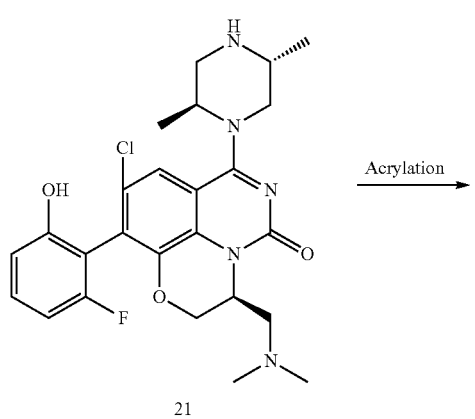

21

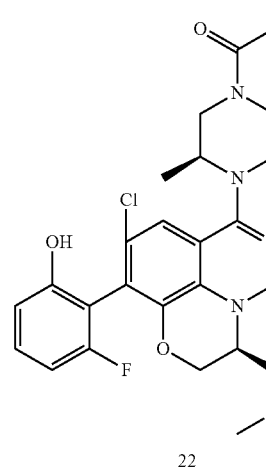

22

As shown in Scheme 3, readily available chloro diol 15 is reacted with dimethylamine to afford amine 16. Conversion to bis-mesylate 17 and condensation with quinazoline 18 provides morpholine fused quinazolien 19 having a pendant dimethylaminomethyl substitution on the morpholine ring.

Turning next to Scheme 4, the utility of the anthanilic acid starting point provides access to other heterocyclic systems such as quinolones, which in turn can be converted to pyridone-morpholine fused systems.

Scheme 4---Pyridone Core-Morpholine Unsubstituted

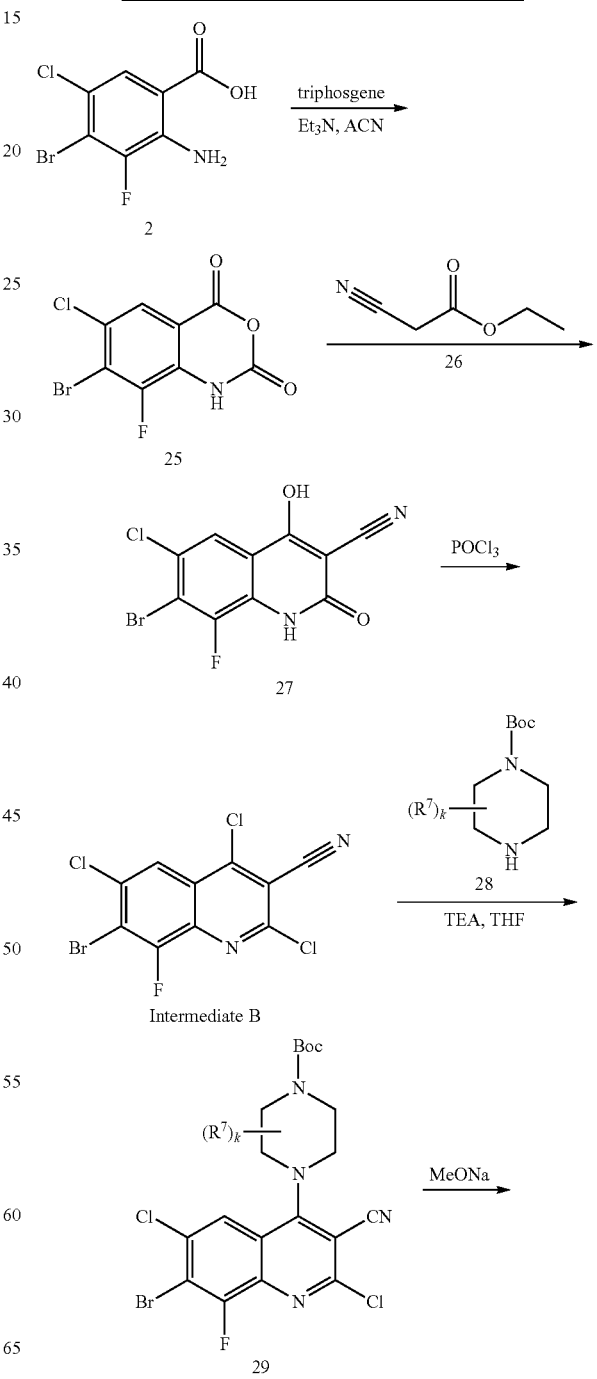

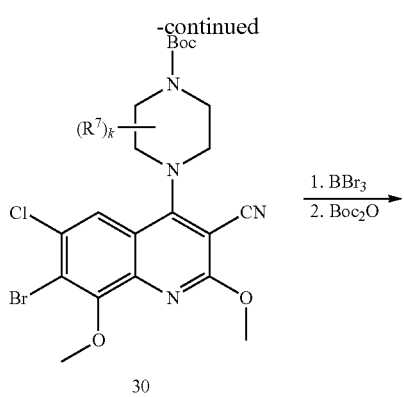

30

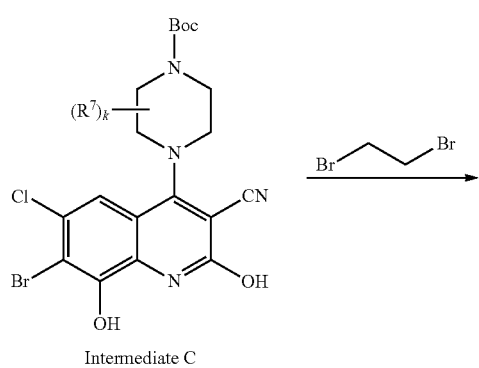

Intermediate C

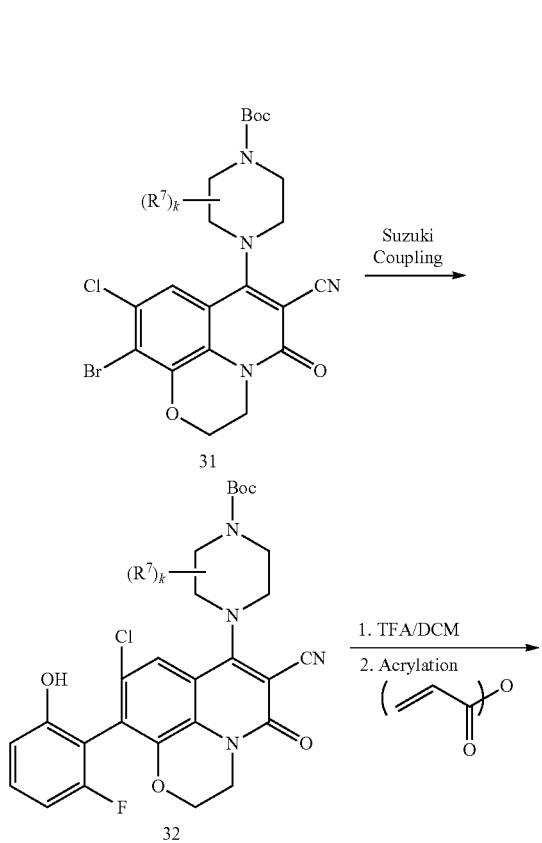

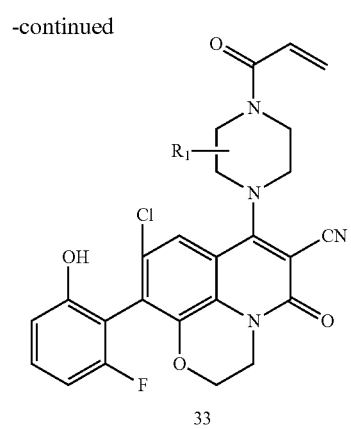

33

As shown in Scheme 4 above, anthranilic acid 2 (Scheme 1 supra) undergoes condensation with triphosgene to afford anhydride 25. Further condensation of anhydrided 25 with ethyl cyanoacetate provides cyano substituted pyridone 27. Conversion of pyridone 27 to dichloroquinoline Intermediate B is effected by reaction with $POCl_3$. Regioselective reaction with piperazine 28, provides piperazine-quinoline adduct 29. Adduct 29 is susceptible to $SN_{Ar}$ substitution by reaction with methoxide to provide bis-methylether 30. Demethylation with boron tribromide and reprotection of the piperazine amine with Boc anhydride provides Intermediate C, the precursor for morpholine fusion. Accordingly, Intermediate C is reacted with ethylene dibromide to afford morpholine-fused pyridone 31. Suzuki arylation with aryl boronic acids provides biaryl 32. Removal of the Boc protecting group and acrylation provides acrylamide 33.

Scheme 5---Pyridone Core-Morpholine Substituted

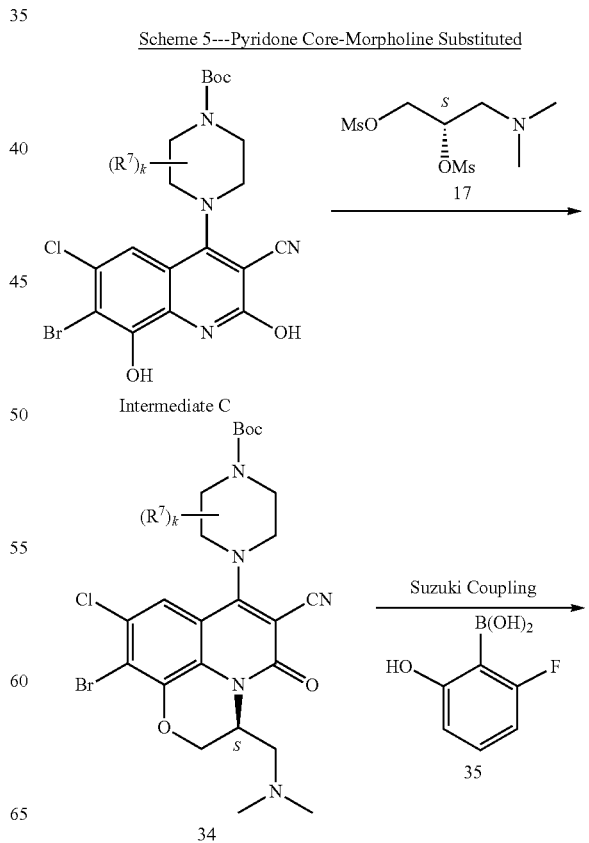

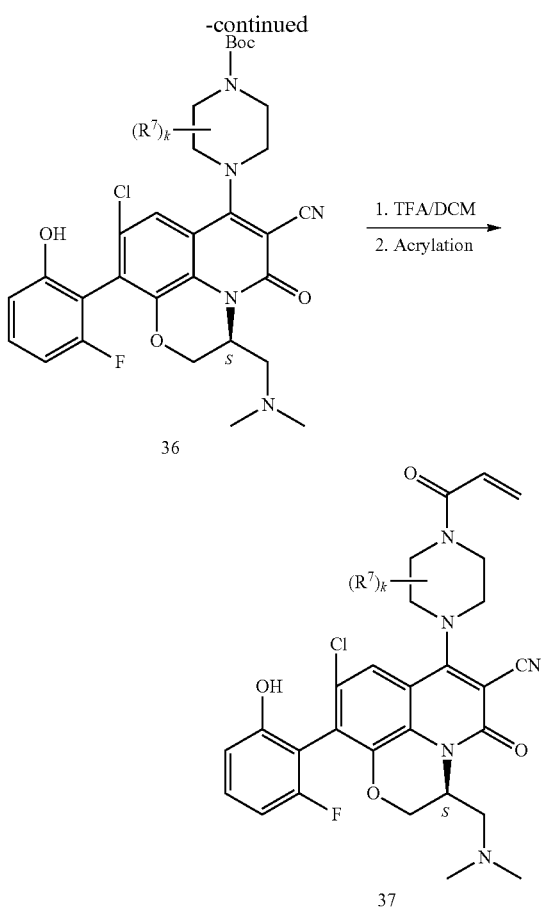

As shown in Scheme 5 above, Intermediate C (Scheme 4) can also be reacted with bis-mesylate 17 (Scheme 3) to provide morpholine fused pyridone 34. Suzuki couple with aryl boronic acid 35 provides biaryl 36. Boc deprotection and acrylation affords acrylamide 37.

V. Modes of Administration

While it may be possible for the compounds disclosed herein to be administered as the raw chemical, it is also possible to present them as a pharmaceutical composition (i.e., as a formulation). Accordingly, provided herein are pharmaceutical compositions which comprise one or more of the compounds disclosed herein, or one or more pharmaceutically acceptable salts, esters, prodrugs, amides, or solvates thereof, together with one or more pharmaceutically acceptable carriers and optionally one or more other therapeutic ingredients. The carrier(s) should be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The pharmaceutical compositions may include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The pharmaceutical composition may conveniently be presented in unit dosage form and may be prepared by any of the methods well known in the art of pharmacy. Typically, these methods include the step of bringing into association a compound disclosed herein or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Pharmaceutical compositions of the various embodiments disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical compositions that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores may be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds disclosed herein may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds disclosed herein may also be formulated in rectal compositions such as suppositories or retention enemas, e.g., containing conventional suppository bases such as cocoa butter, polyethylene glycol, or other glycerides.

Compounds disclosed herein may be administered topically, that is by non-systemic administration. This includes the application of a compound of the various embodiments disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Gels for topical or transdermal administration may comprise, generally, a mixture of volatile solvents, nonvolatile solvents, and water. In certain embodiments, the volatile solvent component of the buffered solvent system may include ($C_1$-$C_6$) alkyl alcohols, alkyl glycols and glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the pharmaceutical compositions described above may include other agents conventional in the art having regard to the type of formulation in question, for example those suitable for oral administration may include flavoring agents.

Dosage

The compounds disclosed herein may be administered orally or via injection at a dose of from 0.1 to 500 mg/kg per day. A common dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds disclosed herein can be administered in various modes, e.g. orally, topically, or by injection. The precise amount of compound administered to a subject will be the responsibility of the attendant physician. The specific dose level for any particular subject will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for cancer involving administration of one of the compounds described herein, increased therapeutic benefit may result by also providing the patient with another therapeutic agent for cancer. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound of the various embodiments disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

VI. Methods of Treatment

Thus, in another aspect, embodiments herein provide methods for treating K-RAS-mediated disorders in a human or animal subject in need of such treatment comprising administering to said subject an amount of a compound of the various embodiments disclosed herein effective to reduce or prevent said disorder in the subject in combination with at least one additional agent for the treatment of said disorder that is known in the art. In a related aspect, the various embodiments disclosed herein provides therapeutic compositions comprising at least one compound of the various embodiments disclosed herein in combination with one or more additional agents for the treatment of K-RAS-mediated disorders. In some such embodiments, the K-RAS-mediated disease is cancer and the K-RAS presents in an oncogenic mutated form.

Compounds disclosed herein may be useful in treating K-RAS-mediated disease, disorders and conditions. In some embodiments, the compounds disclosed herein may be used in treating cancer, as disclosed hereinabove. In some such embodiments, the type of cancer may depend on presentation of a particular type of oncogenic mutation of K-RAS. For example, in some embodiments oncogenic K-RAS mutations may be tied to human cancer of the pancreas, lung, and/or colon.

1. Combination Therapies

Compounds disclosed herein may be used in combination therapies. For example, the compounds disclosed herein may be used in combination with inhibitors of mammalian target of rapamycin (mTOR), insulin growth factor 1 receptor (IGF1R), and combinations thereof. Such combination therapies may be particularly suited to certain cancer types such as lung cancer. See Molinas-Arcas et al. *Sci. Trans. Med.* 18 Sep. 2019 11:510 eaaw7999 at stm.sciencemag.org/ content/11/510/eaaw7999. Compounds disclosed herein may be combined with modulators the ULK family of proteins, which regulate autophagy. Other compounds of interest in combination therapy include inhibitors of SHP2. Other SHP2 inhibitors include those disclosed in WO2016/203404, WO2018/136264, WO2018/057884, WO2019/067843, WO2019/183367, WO2016/203405, WO2019/051084, WO2018/081091, WO2019/165073, WO2017/216706, WO2018/218133, WO2019/183364, WO 2020061103, and WO2020061101. All references and patent applications, including compositions, methods of using, and methods of making compounds disclosed therein are incorporated herein by reference in their entirety.

In embodiments, compounds disclosed herein may be combined with an EGFR inhibitor. In embodiments, the EGFR inhibitor is selective for a mutant EGFR, including, without limitation, C797X, L718Q, G724S, S768I, G719X, L792X, G796X, T263P, A289D/V, G598V, and EGFRvIII high expression. In embodiments, the combination therapy with EGFR agents tracked by mutation and indication are shown in Table CT-1 below.

TABLE CT-1

| Mutation | Indication | EGFR agent |
|---|---|---|
| mEGFR | NSCLC | osimertinib |
| mEGFR | NSCLC | afatinib |
| mEGFR | NSCLC | erlotinib |
| mEGFR | NSCLC | gefitinib |
| mEGFR | NSCLC | lazertinib |
| mEGFR | NSCLC | nazartinib |
| mEGFR | NSCLC | dacomitinib |
| mEGFR | NSCLC | BLU-945 |
| mEGFR | NSCLC | icotinib |
| wtEGFR | Esophageal/CRC | cetuximab |
| wtEGFR | CRC | paninitumab |
| wtEGFR | NSCLC | amivantamab |
| wtHER2/wtEGFR | Breast cancer | lapatinib |
| wtHER2/wtEGFR | Breast cancer | neratinib |
| wtEGFR | NSCLC | zorifertinib |
| mEGFR | NSCLC | mobicertinib |

EGFR inhibitors include those disclosed in U.S. Pat. Nos. 5,747,498, 8,946,235, and 9,732,058, WO2002030926, US 20040048880, US20050165035, and WO2019067543. All patents and applications, including compositions, methods of using, and methods of making compounds disclosed therein are incorporated herein by reference in their entirety.

Other combination therapies based on target biomarkers are shown below in Table CT-2.

TABLE CT-2

| Biomarker(s) | Cancer Type | Target | Combination Agent |
|---|---|---|---|
| KRAS G12C | Solid tumors | KRAS G12C | AMG 510 |
| KRAS G12C | Solid tumors | KRAS G12C | MRTX849 |
| KRAS G12C | Solid tumors | KRAS G12C | GDC-6036 |
| BRAF V600E | CRC/NSCLC | BRAF V600E | encorafenib |
| BRAF V600E | CRC/NSCLC | BRAF V600E | dabrafenib |
| BRAF V600E | CRC/NSCLC | BRAF V600E and MEK | encorafenib and binimetinib |
| BRAF V600E | CRC/NSCLC | BRAF V600E and MEK | dabrafenib and trametinib |
| RB1 functional | Solid tumors | CDK4 and CDK6 | palbociclib |
| RB1 functional | Solid tumors | CDK4 and CDK6 | abemaciclib |
| RB1 functional | Solid tumors | CDK4 and CDK6 | ribociclib |
| RTK and/or RAS Driven | Solid tumors | SHP2 | TNO155 |
| RTK and/or RAS Driven | Solid tumors | SHP2 | RMC-4630 |
| RTK and/or RAS Driven | Solid tumors | SHP2 | JAB-3068 |
| RTK and/or RAS Driven | Solid tumors | SHP2 | JAB-3312 |
| RTK and/or RAS Driven | Solid tumors | SHP2 | RLY-1971 |
| RTK, RAS, BRAF, and/or MEK driven | Solid tumors | ERK | ulixertinib |
| RTK, RAS, BRAF, and/or MEK driven | Solid tumors | ERK | ASN007 |
| RTK, RAS, BRAF, and/or MEK driven | Solid tumors | ERK | LY3214996 |
| RTK, RAS, BRAF, and/or MEK driven | Solid tumors | ERK | LTT462 |
| RTK, RAS, and/or BRAF | Solid tumors | MEK | trametinib |
| RTK, RAS, and/or BRAF | Solid tumors | MEK | binimetinib |
| RTK, RAS, and/or BRAF | Solid tumors | MEK | cobimetinib |
| RTK, RAS, and/or BRAF | Solid tumors | MEK | selumetinib |
| MET-driven | Solid tumors | MET | capmatinib |
| MET-driven | Solid tumors | MET | crizotinib |
| MET-driven | Solid tumors | MET | savolitinib |

The second agent of the pharmaceutical combination formulation or dosing regimen may have complementary activities to the compounds disclosed herein such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound disclosed herein or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound disclosed herein may be administered with another therapeutic agent simultaneously or sequentially in separate unit dosage forms or together in a single unit dosage form. Accordingly, the present invention provides a single unit dosage form comprising a compound of Formulas I-XX, an additional therapeutic agent, and a pharmaceutically acceptable carrier, adjuvant, or vehicle.

The amount of both the compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound disclosed herein or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signalling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXO- TERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA©); ibandronate; CPT-11; topoisomerase inhibitor RFS 2000; difluoromethylomithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5 [[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; famesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lomoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound disclosed herein is administered in combination with a biologic agent, such as bevacizumab or panitumumab.

In certain embodiments, compounds disclosed herein, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

Embodiments

1. A compound of Formula (I)

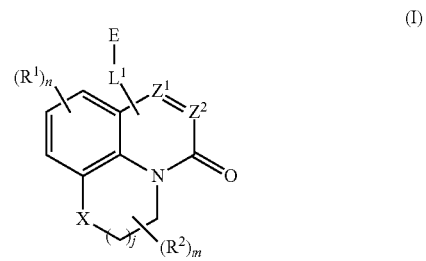

wherein:
X is O, $S(O)_p$, $CR^3R^4$, $NR^5$, or C(O), wherein p is an integer from 0 to 2;
j is an integer from 0 to 2;
$Z^1$ and $Z^2$ are independently $CR^6$ or N, with the proviso that at least one of $Z^1$ or $Z^2$ is $CR^6$ with $R^6$ being a bond to $L^1$;
$L^1$ is linking group comprising at least one nitrogen atom;
E is an electrophilic moiety, wherein E is bound to $L^1$ via the at least one nitrogen atom;
each $R^1$ is independently selected from the group consisting of acyl, alkyl, carboxamide, cyano, cycloalkyl, halo, haloalkyl, trifluoromethyl, alkoxy, aryl, heteroaryl, N-arylamino, N-aryl-N-alkylamino, aryloxy, cycloalkyl, heterocyclyl, and arylthio with the proviso that:
at least one $R^1$ is aryl, N-arylamino, N-aryl-N-alkylamino, aryloxy, arylthio, or heteroaryl, any of which is optionally substituted;
n is an integer from 1 to 3;
$R^2$ is selected from the group consisting of alkyl, alkylamino, dialkylamino, alkylamidoalkyl, arylamidoalkyl, alkylsulfonamidoalkyl, arylsulfonamidoalkyl, N-alkyl aminoalkyl, N,N-dialkyl aminoalkyl, amido, amido alkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, and heteroaryl, cycloalkyl, any of which are optionally substituted; and $R^6$ is selected from the group consisting of hydrogen, alkyl, haloakyl, cyano, halo, alkoxy, aryl, heteroaryl, trifluoromethyl and bond to $L^1$ and pharmaceutically acceptable salts thereof.
2. The compound wherein X is O.
3. The compound wherein j is 1.
4. The compound wherein m is 0.
5. The compound wherein m is 1.
6. The compound wherein $Z^1$ is $CR^6$ with $R^6$ being a bond to $L^1$.
7. The compound wherein $Z^2$ is N.
8. The compound wherein $L^1$ is

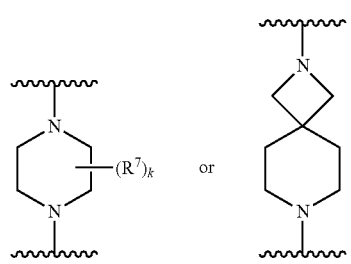

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl.
9. The compound wherein E is an acrylyl group having optional substitution R:

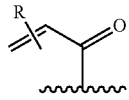

wherein R is selected from the group consisting of fluorine, chlorine, methyl, haloalkyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.
10. A compound of Formula (II):

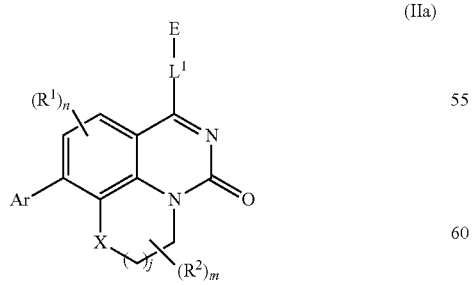

wherein:
X is O, $S(O)_p$, $CR^3R^4$, $NR^5$, or C(O), wherein p is an integer from 0 to 2;
j is an integer from 0 to 2;

$L^1$ is linking group comprising at least one nitrogen atom;
E is an electrophilic moiety, wherein E is bound to $L^1$ via the at least one nitrogen atom of $L^1$;
each $R^1$ is an optional substitution independently selected from the group consisting of alkyl, cyano, cycloalkyl, halo, haloalkyl, trifluoromethyl, and alkoxy;
n is an integer from 0 to 2;
$R^2$ is selected from the group consisting of alkyl, alkylamino, dialkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, alkylthio, sulfone, sulfonamide, oxo, halo, alkoxy, aryl, and heteroaryl, cycloalkyl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.
11. The compound wherein X is O.
12. The compound wherein j is 1.
13. The compound wherein m is 0.
14. The compound wherein m is 1.
15. The compound wherein $L^1$ is

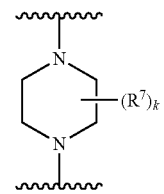

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R_j$ is H, methyl or trifluoromethyl.
16. The compound wherein E is an acrylyl group having optional substitution R:

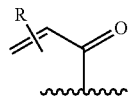

wherein R is selected from the group consisting of fluorine, chlorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.

17. The compound wherein Ar creates axial asymmetry.
18. The compound wherein the compound is a single rotamer.
19. The compound wherein Ar is:

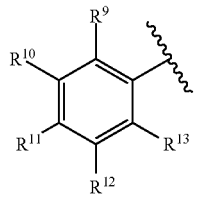

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, and cycloalkyl; or any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

20. A compound of Formula (III):

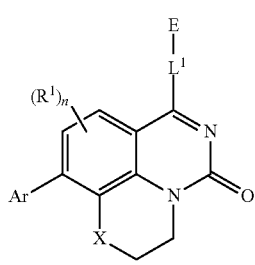

(III)

wherein:
X is O, $S(O)_p$, $CR^3R^4$, $NR^5$, or C(O), wherein p is an integer from 0 to 2;
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of alkyl, cyano, cycloalkyl, halo, haloalkyl, trifluoromethyl, and alkoxy;
n is an integer from 0 to 2;
$R^3$, $R^4$, and $R^5$ are each independently selected from the group consisting of hydrogen alkyl, halo, alkoxy, aryl, and heteroaryl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

21. The compound wherein X is O.
22. The compound wherein $L^1$ is

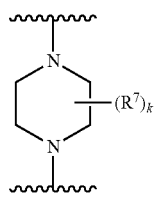

wherein k is an integer from 0 to 4; and each $R^7$ is independently selected from an alkyl group selected from methyl, ethyl, and propyl, any of which are optionally substituted with one or more fluorine atoms, —$CH_2(CH_3)C$=$CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl.

23. The compound wherein E is an acrylyl group having optional substitution R:

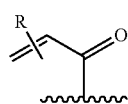

wherein R is selected from the group consisting of fluorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.

24. The compound wherein optional substitution R is monofluorination.
25. The compound wherein Ar creates axial asymmetry.
26. The compound wherein the compound is a single rotamer.
27. The compound wherein Ar is:

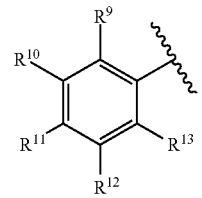

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

28. A compound of Formula (IV):

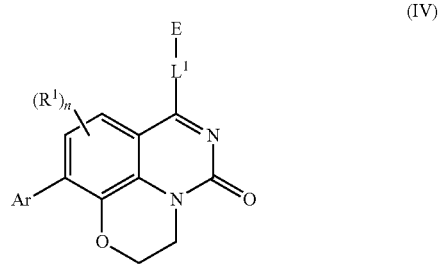

(IV)

wherein:

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy; n is an integer from 0 to 2; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

29. The compound wherein $L^1$ is

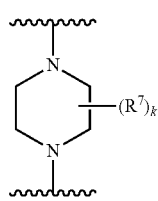

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl.

30. The compound wherein E is an acrylyl group having optional substitution R:

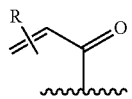

wherein R is selected from the group consisting of fluorine, methyl, and —$CH_2NR^aR^b$, wherein $R^a$ and $R^b$ are independently selected from hydrogen and alkyl; or $R^a$ and $R^b$ combine to form a $C_2$-$C_6$ nitrogen containing heterocycle.

31. The compound wherein optional substitution comprises monofluorination.

32. The compound wherein Ar creates axial asymmetry.

33. The compound wherein the compound is a single rotamer.

34. The compound wherein Ar is:

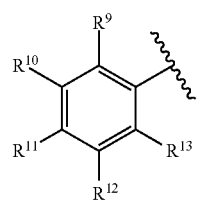

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.

35. A compound of Formula (V):

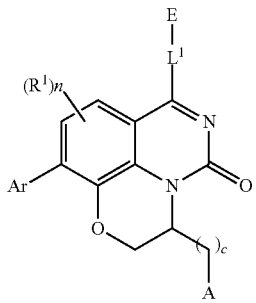

(V)

wherein:

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

36. The compound wherein $L^1$ is

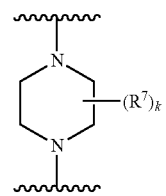

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl.

37. The compound wherein E is an acrylyl group having optional substitution R:

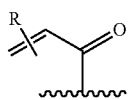

wherein R is selected from the group consisting of fluorine, methyl, haloalkyl, and —CH$_2$NR$^a$R$^b$, wherein R$^a$ and R$^b$ are independently selected from hydrogen and alkyl; or R$^a$ and R$^b$ combine to form a C$_2$-C$_6$ nitrogen containing heterocycle.

38. The compound wherein optional substitution comprises monofluorination.
39. The compound wherein Ar creates axial asymmetry.
40. The compound wherein the compound is a single rotamer.
41. The compound wherein Ar is:

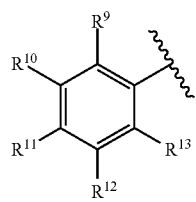

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.

42. A compound of Formula (VI):

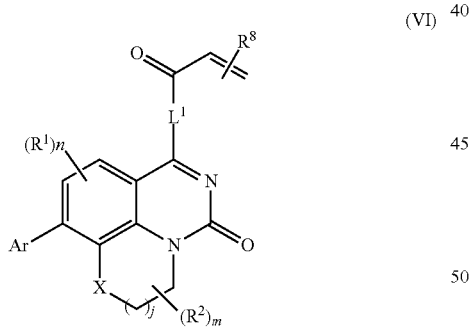

(VI)

wherein:
X is O, S(O)$_p$, CR$^3$R$^4$, NR$^5$, or C(O), wherein p is an integer from 0 to 2;
j is an integer from 0 to 2;
L$^1$ is linking group comprising at least one nitrogen atom;
each R$^1$ is an optional substitution independently selected from the group consisting of alkyl, cyano, cycloalkyl, halo, haloalkyl, trifluoromethyl, and alkoxy;
n is an integer from 0 to 2;
R$^2$ is selected from the group consisting of alkyl, alkylamino, dialkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
R$^3$, R$^4$, and R$^5$ are each independently selected from the group consisting of hydrogen alkyl, halo, alkoxy, aryl, and heteroaryl, any of which are optionally substituted;
R$^8$ is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

43. The compound wherein X is O.
44. The compound wherein j is 1.
45. The compound wherein m is 0.
46. The compound wherein m is 1.
47. The compound wherein L$^1$ is

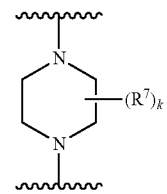

wherein k is an integer from 0 to 4; and each R$^7$ is independently selected from an alkyl group selected from methyl, ethyl, and propyl, any of which are optionally substituted with one or more fluorine atoms, —CH$_2$(CH$_3$)C═CF$_2$, cyano, propargyl, —CH$_2$C(O)V, wherein V is selected from methyl, OH, NHR$^i$ wherein R$^i$ is hydrogen or alkyl, and cyanomethyl; or any two R$^7$ may combine to form a fused-ring, spiro or bridging bicycle, wherein any one fused-ring or bridging atom is O, S, S═O, SO$_2$, or NR, wherein R$^j$ is H, methyl or trifluoromethyl.

48. The compound wherein Ar creates axial asymmetry.
49. The compound wherein the compound is a single rotamer.
50. The compound wherein Ar is:

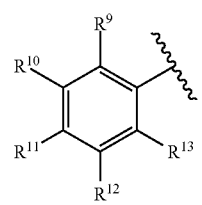

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^1$, and R$^{13}$ together combine to form a further fused ring that is an aromatic ring optionally comprising 1 to 3 heteroatoms independently selected from N, O or S, the further fused ring being optionally substituted.

51. A compound of Formula (VII):

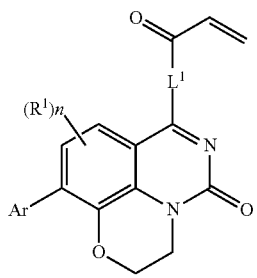

(VII)

wherein:
L¹ is linking group comprising at least one nitrogen atom;
each R¹ is an optional substitution independently selected from the group consisting of alkyl, cyano, cycloalkyl, halo, haloalkyl, trifluoromethyl, and alkoxy;
n is an integer from 0 to 2; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.
52. The compound wherein L¹ is

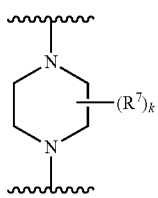

wherein k is an integer from 0 to 4; and each R⁷ is independently selected from an alkyl group selected from methyl, ethyl, and propyl, any of which are optionally substituted with one or more fluorine atoms, —CH₂(CH₃)C=CF₂, cyano, propargyl, —CH₂C(O)V, wherein V is selected from methyl, OH, NHRⁱ wherein Rⁱ is hydrogen or alkyl, and cyanomethyl; or any two R⁷ may combine to form a fused-ring, spiro or bridging bicycle, wherein any one fused-ring or bridging atom is O, S, S=O, SO₂, or NR, wherein Rʲ is H, methyl or trifluoromethyl.
53. The compound wherein Ar creates axial asymmetry.
54. The compound wherein the compound is a single rotamer.
55. The compound wherein Ar is:

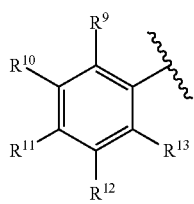

wherein R⁹, R¹⁰, R¹¹, R¹², and R¹³ are each independently selected from the group consisting of hydrogen, halo, alkyl, alkoxy, haloalkyl, trifluoromethyl, cycloalkyl and any two adjacent R⁹, R¹⁰, R¹¹, R¹², and R¹³ together combine to form a further fused ring that is an aromatic ring optionally comprising 1 to 3 heteroatoms independently selected from N, O or S, the further fused ring being optionally substituted.
56. A compound of Formula (VIII):

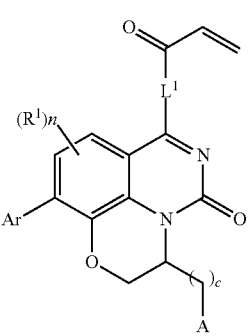

(VIII)

wherein:
L¹ is linking group comprising at least one nitrogen atom;
each R¹ is an optional substitution independently selected from the group consisting of alkyl, cyano, cycloalkyl, halo, haloalkyl, trifluoromethyl, and alkoxy;
n is an integer from 0 to 2;
c is an integer from 0 to 4;
A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.
57. The compound wherein L¹ is

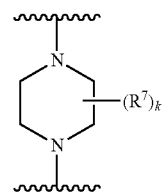

wherein k is an integer from 0 to 4; and each R⁷ is independently selected from an alkyl group selected from methyl, ethyl, and propyl, any of which are optionally substituted with one or more fluorine atoms, —CH₂(CH₃)C=CF₂, cyano, propargyl, —CH₂C(O)V, wherein V is selected from methyl, OH, NHRⁱ wherein Rⁱ is hydrogen or alkyl, and cyanomethyl; or any two R⁷ may combine to form a fused-ring, spiro or bridging bicycle, wherein any one fused-ring or bridging atom is O, S, S=O, SO₂, or NR, wherein Rʲ is H, methyl or trifluoromethyl.
58. The compound wherein Ar creates axial asymmetry.
59. The compound wherein the compound is a single rotamer.

60. The compound wherein Ar is:

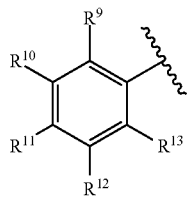

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.

61. A compound of Formula (IX):

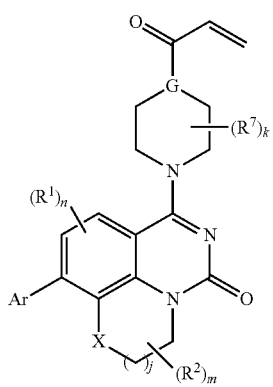

wherein:
X is O, $S(O)_p$, $CR^3R^4$, $NR^5$, or C(O), wherein p is an integer from 0 to 2;
j is an integer from 0 to 2;
G is selected from the group consisting of N, CH, and

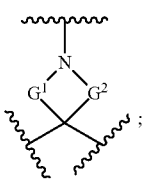

wherein $G^1$ and $G^2$ are independently $(CH_2)_q$, where q is 1 or 2;
each $R^1$ is an optional substitution independently selected from the group consisting of alkyl, cyano, cycloalkyl, halo, haloalkyl, trifluoromethyl, and alkoxy;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
n is an integer from 0 to 2;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, and heteroaryl, any of which are optionally substituted;
wherein k is an integer from 0 to 4; and each $R^7$ is independently selected from an alkyl group selected from methyl, ethyl, and propyl, any of which are optionally substituted with one or more fluorine atoms, $-CH_2(CH_3)C=CF_2$, cyano, propargyl, $-CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl; and
wherein the acrylyl moiety linked to G is optionally substituted.

62. The compound wherein X is O.
63. The compound wherein j is 1.
64. The compound wherein m is 0.
65. The compound wherein m is 1.
66. The compound wherein Ar creates axial asymmetry.
67. The compound wherein the compound is a single rotamer.
68. The compound wherein Ar is:

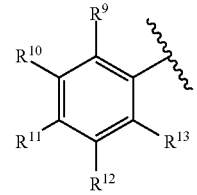

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

69. A compound of Formula (X):

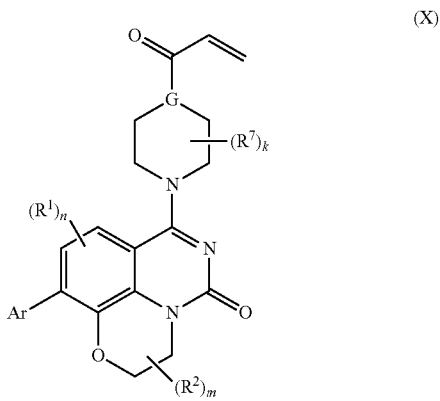

wherein:
G is selected from the group consisting of N, CH, and

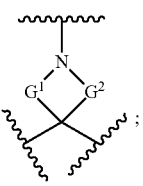

wherein $G^1$ and $G^2$ are $(CH_2)_q$, where each q is independently 1 or 2;
each $R^1$ is an optional substitution independently selected from the group consisting of alkyl, cyano, cycloalkyl, halo, haloalkyl, trifluoromethyl, and alkoxy;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
n is an integer from 0 to 2;
$R^2$ is selected from the group consisting of alkyl, alkylamino, dialkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 4;
wherein k is an integer from 0 to 4; and each $R^7$ is independently selected from an alkyl group selected from methyl, ethyl, and propyl, any of which are optionally substituted with one or more fluorine atoms, $-CH_2(CH_3)C=CF_2$, cyano, propargyl, $-CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl; and
wherein the acrylyl moiety linked to G is optionally substituted.
70. The compound wherein m is 0.
71. The compound wherein m is 1.
72. The compound wherein Ar creates axial asymmetry.
73. The compound wherein the compound is a single rotamer.
74. The compound wherein Ar is:

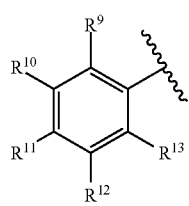

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.
75. A compound of Formula (XI):

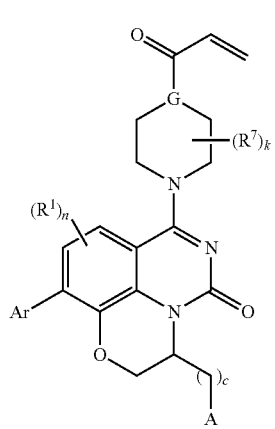

wherein:
G is selected from the group consisting of N, CH, and

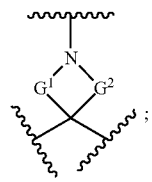

wherein $G^1$ and $G^2$ are independently $(CH_2)_q$, where q is 1 or 2;
each $R^1$ is an optional substitution independently selected from the group consisting of alkyl, cyano, cycloalkyl, halo, haloalkyl, trifluoromethyl, and alkoxy;
n is an integer from 0 to 2;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
c is an integer from 0 to 4;
A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
wherein k is an integer from 0 to 4; and each $R^7$ is independently selected from an alkyl group selected from methyl, ethyl, and propyl, any of which are optionally substituted with one or more fluorine atoms, $-CH_2(CH_3)C=CF_2$, cyano, propargyl, $-CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl; and wherein the acrylyl moiety linked to G is optionally substituted.

76. The compound wherein Ar creates axial asymmetry.
77. The compound wherein the compound is a single rotamer.
78. The compound wherein Ar is:

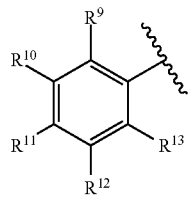

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

79. A compound of Formula (XII):

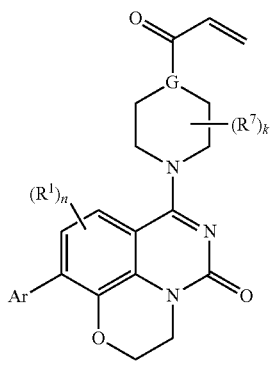

(XII)

wherein:
G is selected from the group consisting of N, CH, and

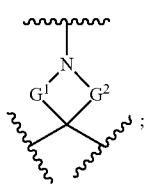

;

wherein $G^1$ and $G^2$ are independently $(CH_2)_q$, where q is 1 or 2;
each $R^1$ is an optional substitution independently selected from the group consisting of alkyl, cyano, cycloalkyl, halo, haloalkyl, trifluoromethyl, and alkoxy;
n is an integer from 0 to 2;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
wherein k is an integer from 0 to 4; and each $R^7$ is independently selected from an alkyl group selected from methyl, ethyl, and propyl, any of which are optionally substituted with one or more fluorine atoms, —$CH_2(CH_3)C$=$CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl; and wherein the acrylyl moiety linked to G is optionally substituted.

80. The compound wherein Ar creates axial asymmetry.
81. The compound wherein the compound is a single rotamer.
82. The compound wherein Ar is:

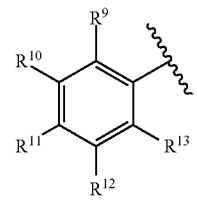

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

83. A compound of Formula (XIII):

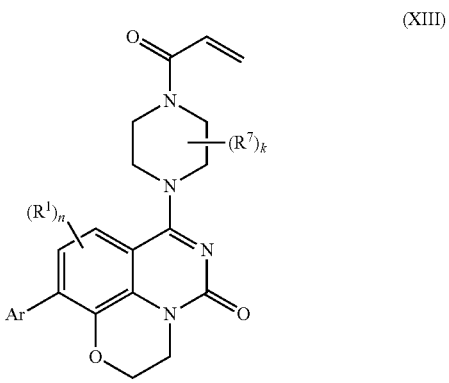

(XIII)

wherein:
each $R^1$ is an optional substitution independently selected from the group consisting of alkyl, cyano, cycloalkyl, halo, haloalkyl, trifluoromethyl, and alkoxy;
n is an integer from 0 to 2;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
wherein k is an integer from 0 to 4; and each $R^7$ is independently selected from an alkyl group selected from methyl, ethyl, and propyl, any of which are optionally substituted with one or more fluorine atoms, —$CH_2(CH_3)C$=$CF_2$, cyano, propargyl, —$CH_2C(O)V$, wherein V is selected from methyl, OH, NHR$^i$ wherein R$^i$ is hydrogen or alkyl, and cyanomethyl; or any two R$^7$ may combine to form a fused-ring, spiro or bridging bicycle, wherein any one fused-ring or bridging atom is O, S, S=O, SO$_2$, or NR, wherein R$^j$ is H, methyl or trifluoromethyl; and wherein the acrylyl moiety linked to N is optionally substituted.

84. The compound wherein Ar creates axial asymmetry.
85. The compound wherein the compound is a single rotamer.
86. The compound wherein Ar is:

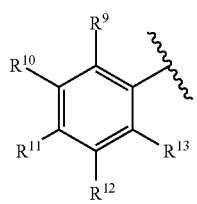

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.

87. A compound of Formula (XIV):

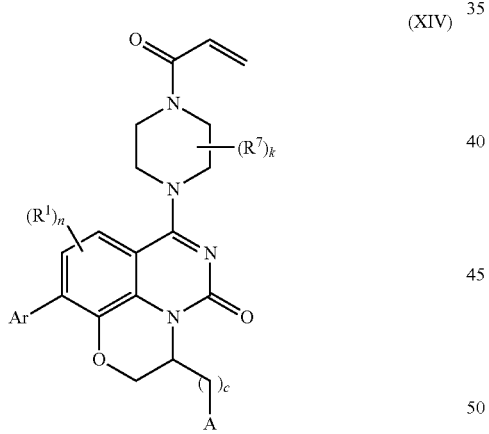

(XIV)

wherein:
each R$^1$ is an optional substitution independently selected from the group consisting of alkyl, cyano, cycloalkyl, halo, haloalkyl, trifluoromethyl, and alkoxy;
n is an integer from 0 to 2;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
c is an integer from 0 to 4;
A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

wherein k is an integer from 0 to 4; and each R$^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein R$^i$ is hydrogen or alkyl, and cyanomethyl; or any two R$^7$ may combine to form a fused-ring, spiro or bridging bicycle, wherein any one fused-ring or bridging atom is O, S, S=O, SO$_2$, or NR, wherein R$^j$ is H, methyl or trifluoromethyl; and wherein the acrylyl moiety linked to N is optionally substituted.

88. The compound wherein Ar creates axial asymmetry.
89. The compound wherein the compound is a single rotamer.
90. The compound wherein Ar is:

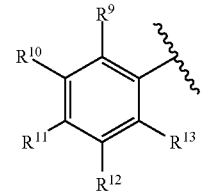

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.

91. A compound of Formula (XV):

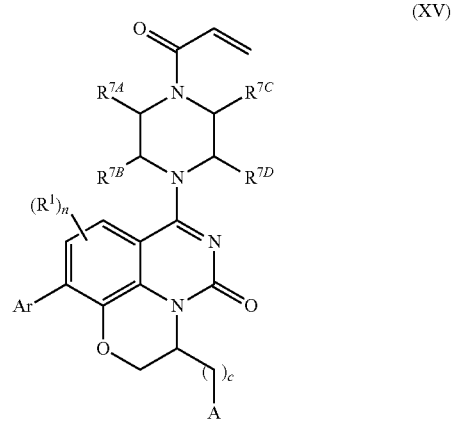

(XV)

wherein:
each R$^1$ is an optional substitution independently selected from the group consisting of alkyl, cyano, cycloalkyl, halo, haloalkyl, trifluoromethyl, and alkoxy;
n is an integer from 0 to 2;
Ar is aryl, N-arylamino, N-aryl-N-alkylamino, aryloxy, arylthio, heteroaryl, N-heteroarylamino, N-heteroaryl- N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

$R^{7A}$, $R^{7B}$, $R^{7C}$, and $R^{7D}$ are independently selected from hydrogen, alkyl, cyano, and cyanoalkyl; and wherein the acrylyl moiety linked to N is optionally substituted.

92. The compound wherein Ar creates axial asymmetry.

93. The compound wherein the compound is a single rotamer.

94. The compound wherein Ar is:

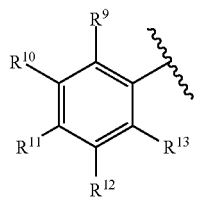

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

95. The compound wherein $R^{7B}$ is methyl.

96. The compound wherein a stereogenic center created by the $R^{7B}$ methyl group is in the R-configuration.

97. The compound wherein a stereogenic center created by the $R^{7B}$ methyl group is in the S-configuration.

98. The compound wherein $R^{7C}$ is methyl.

99. The compound wherein a stereogenic center created by the $R^{7C}$ methyl group is in the R-configuration.

100. The compound wherein a stereogenic center created by the $R^{7C}$ methyl group is in the S-configuration.

101. The compound wherein $R^{7D}$ is hydrogen.

102. The compound wherein $R^{7A}$ is cyanomethyl.

103. The compound wherein a stereogenic center created by the cyanomethyl group is in the R-configuration.

104. The compound wherein a stereogenic center created by the cyanomethyl group is in the S-configuration.

105. A compound of Formula (XVI):

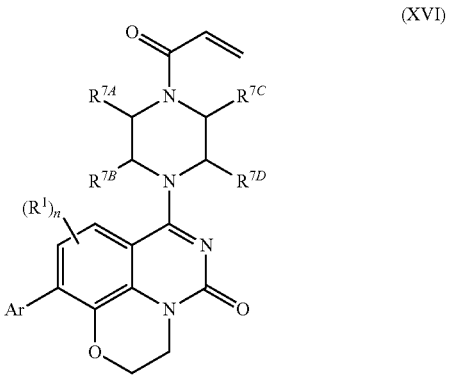

wherein:

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

$R^{7A}$, $R^{7B}$, $R^{7C}$, and $R^{7D}$ are independently selected from hydrogen, alkyl, cyano, and cyanoalkyl; and wherein the acrylyl moiety linked to N is optionally substituted.

106. The compound wherein Ar creates axial asymmetry.

107. The compound wherein the compound is a single rotamer.

108. The compound wherein Ar is:

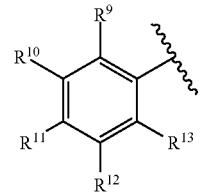

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

109. The compound wherein $R^{7B}$ is methyl.

110. The compound wherein a stereogenic center created by the $R^{7B}$ methyl group is in the R-configuration.

111. The compound wherein a stereogenic center created by the $R^{7B}$ methyl group is in the S-configuration.

112. The compound wherein $R^{7C}$ is methyl.

113. The compound wherein a stereogenic center created by the $R^{7C}$ methyl group is in the R-configuration.

114. The compound wherein a stereogenic center created by the $R^{7C}$ methyl group is in the S-configuration.

115. The compound wherein $R^{7D}$ is hydrogen.

116. The compound wherein $R^{1A}$ is cyanomethyl.

117. The compound wherein a stereogenic center created by the cyanomethyl group is in the R-configuration.

118. The compound wherein a stereogenic center created by the cyanomethyl group is in the S-configuration.

119. A compound of Formula (XVII):

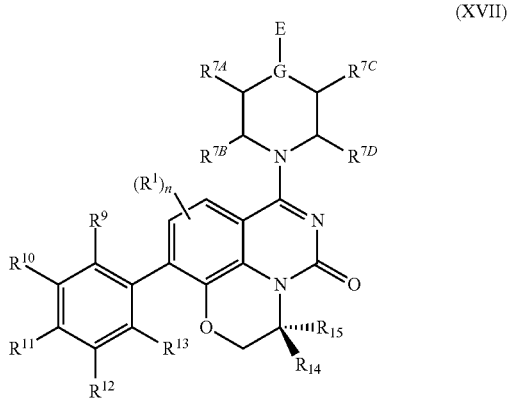

(XVII)

wherein:

E is an electrophilic moiety;

G is selected from the group consisting of N, CH, and

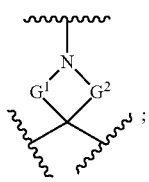

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

n is an integer from 0 to 2;

$R^{7A}$, $R^{7B}$, $R^{7C}$, and $R^{7D}$ are independently selected from hydrogen, alkyl, cyano, and cyanoalkyl;

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted;

wherein $R^{14}$ and $R^{15}$ are selected from the group consisting of hydrogen, hydroxyl, amino, N-alkylamino, dialkylamino, N-alkylamino alkyl, N,N-dialkylamino, N,N-dialkylamino alkyl, cycloalkylamino, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted, with the proviso that one of $R^{14}$ or $R^{15}$ is hydrogen; and wherein the acrylyl moiety linked to G is optionally substituted.

120. The compound having axial asymmetry.

121. The compound wherein the compound is a single rotamer.

122. The compound wherein $R^{7B}$ is methyl.

123. The compound wherein a stereogenic center created by the $R^{7B}$ methyl group is in the R-configuration.

124. The compound wherein a stereogenic center created by the $R^{7B}$ methyl group is in the S-configuration.

125. The compound wherein $R^{7C}$ is methyl.

126. The compound wherein a stereogenic center created by the $R^{7C}$ methyl group is in the R-configuration.

127. The compound wherein a stereogenic center created by the $R^{7C}$ methyl group is in the S-configuration.

128. The compound wherein $R^{7D}$ is hydrogen.

129. The compound wherein $R^{7A}$ is cyanomethyl.

130. The compound wherein a stereogenic center created by the cyanomethyl group is in the R-configuration.

131. The compound wherein a stereogenic center created by the cyanomethyl group is in the S-configuration.

132. The compound wherein the compound is a single rotamer of Formula (XVIIa):

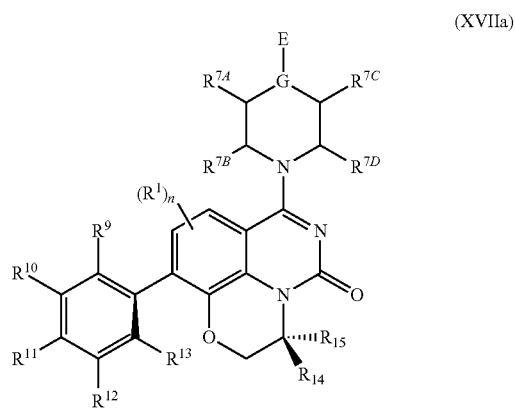

(XVIIa)

133. The compound wherein the compound is a single rotamer of Formula (XVIIb):

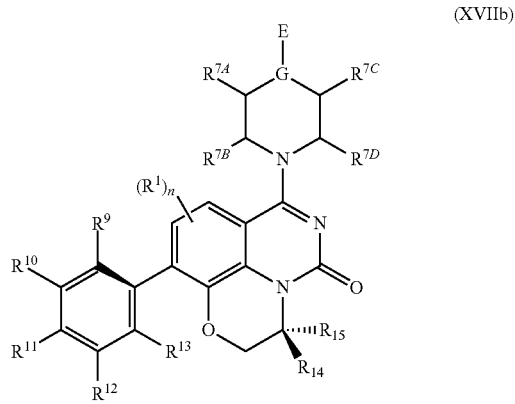

(XVIIb)

134. A compound of Formula (XVIII):

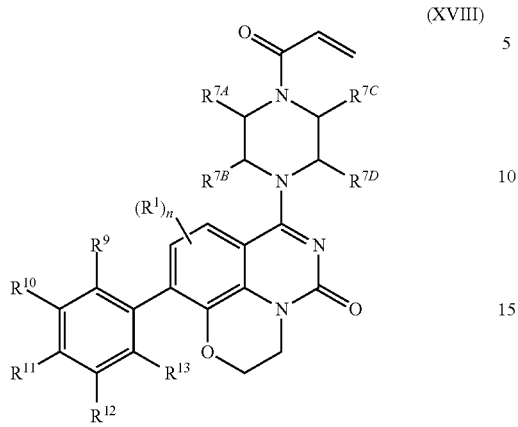

(XVIII)

wherein:
each $R^1$ is an optional substitution independently selected from the group consisting of alkyl, cyano, cycloalkyl, halo, haloalkyl, trifluoromethyl, and alkoxy;
n is an integer from 0 to 2;
$R^{7A}$, $R^{7B}$, $R^{7C}$, and $R^{7D}$ are independently selected from hydrogen, alkyl, cyano, and cyanoalkyl;
wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted; and
wherein the acrylyl moiety linked to N is optionally substituted.

135. The compound having axial asymmetry.
136. The compound wherein the compound is a single rotamer.
137. The compound wherein $R^{7B}$ is methyl.
138. The compound wherein a stereogenic center created by the $R^{7B}$ methyl group is in the R-configuration.
139. The compound wherein a stereogenic center created by the $R^{7B}$ methyl group is in the S-configuration.
140. The compound wherein $R^{7C}$ is methyl.
141. The compound wherein a stereogenic center created by the $R^{7C}$ methyl group is in the R-configuration.
142. The compound wherein a stereogenic center created by the $R^{7C}$ methyl group is in the S-configuration.
143. The compound wherein $R^{7D}$ is hydrogen.
144. The compound wherein $R^{7A}$ is cyanomethyl.
145. The compound wherein a stereogenic center created by the cyanomethyl group is in the R-configuration.
146. The compound wherein a stereogenic center created by the cyanomethyl group is in the S-configuration.

147. A compound of Formula (XIX):

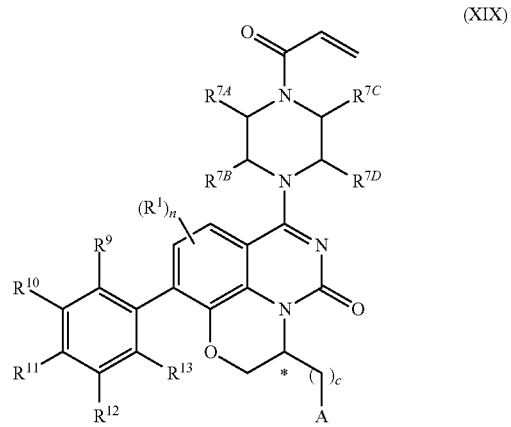

(XIX)

wherein * is a stereogenic center;
each $R^1$ is an optional substitution independently selected from the group consisting of alkyl, cyano, cycloalkyl, halo, haloalkyl, trifluoromethyl, and alkoxy;
n is an integer from 0 to 2;
$R^{7A}$, $R^{7B}$, $R^{7C}$, and $R^{7D}$ are independently selected from hydrogen, alkyl, cyano, and cyanoalkyl;
wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted;
c is an integer from 0 to 4;
A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and
wherein the acrylyl moiety linked to N is optionally substituted.

148. The compound having axial asymmetry.
149. The compound wherein the compound is a single rotamer.
150. The compound wherein $R^{7B}$ is methyl.
151. The compound wherein a stereogenic center created by the $R^{7B}$ methyl group is in the R-configuration.
152. The compound wherein a stereogenic center created by the $R^{7B}$ methyl group is in the S-configuration.
153. The compound wherein $R^{7C}$ is methyl.
154. The compound wherein a stereogenic center created by the $R^{7C}$ methyl group is in the R-configuration.
155. The compound wherein a stereogenic center created by the $R^{7C}$ methyl group is in the S-configuration.
156. The compound wherein $R^{7D}$ is hydrogen.
157. The compound o wherein $R^{7A}$ is cyanomethyl.
158. The compound wherein a stereogenic center created by the cyanomethyl group is in the R-configuration.
159. The compound wherein a stereogenic center created by the cyanomethyl group is in the S-configuration.

160. A compound of Formula (XX):

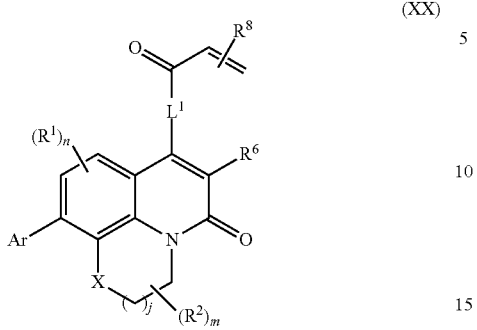

wherein:
X is O, S(O)$_p$, CR$^3$R$^4$, NR$^5$, or C(O), wherein p is an integer from 0 to 2;
j is an integer from 0 to 2;
L$^1$ is linking group comprising at least one nitrogen atom;
each R$^1$ is an optional substitution independently selected from the group consisting of alkyl, cyano, cycloalkyl, halo, haloalkyl, trifluoromethyl, and alkoxy;
n is an integer from 0 to 2;
R$^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
R$^3$, R$^4$, and R$^5$ are each independently selected from the group consisting of hydrogen alkyl, halo, alkoxy, aryl, and heteroaryl, any of which are optionally substituted;
R$^6$ is selected from the group consisting of hydrogen, alkyl, haloakyl, cyano, halo, alkoxy, aryl, heteroaryl, and trifluoromethyl;
R$^8$ is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.
161. The compound wherein X is O.
162. The compound wherein j is 1.
163. The compound wherein m is 0.
164. The compound wherein m is 1.
165. The compound wherein L$^1$ is

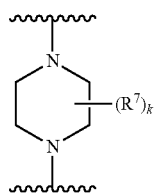

wherein k is an integer from 0 to 4; and each R$^7$ is independently selected from an alkyl group selected from methyl, ethyl, and propyl, any of which are optionally substituted with one or more fluorine atoms, —CH$_2$(CH$_3$)C═CF$_2$, cyano, propargyl, —CH$_2$C(O)V, wherein V is selected from methyl, OH, NHR$^i$ wherein R$^i$ is hydrogen or alkyl, and cyanomethyl; or any two R$^7$ may combine to form a fused-ring, spiro or bridging bicycle, wherein any one fused-ring or bridging atom is O, S, S═O, SO$_2$, or NR, wherein R$^j$ is H, methyl or trifluoromethyl.
166. The compound wherein Ar creates axial asymmetry.
167. The compound wherein the compound is a single rotamer.
168. The compound wherein Ar is:

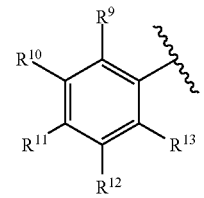

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.
169. A compound selected from Tables 1-7.
170. A method of modulating a G12C mutant K-Ras comprising contacting the G12C mutant K-Ras with a compound disclosed herein.
171. A method of treating a subject with cancer associated with a G12C Kras mutation comprising administering to the subject a compound disclosed herein in a pharmaceutically acceptable vehicle.
172. Use of a compound disclosed herein in the manufacture of a medicament for the treatment of cancer in a subject.
173. A compound of Formula (XXI)

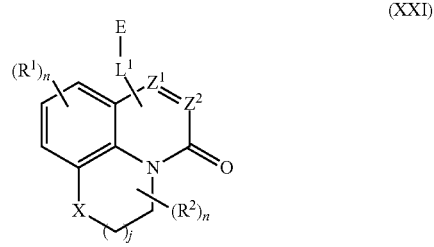

wherein:
X is S(O)$_p$, wherein p is an integer from 0 to 2;
j is an integer from 0 to 2;
Z$^1$ and Z$^2$ are independently CR$^6$ or N, with the proviso that at least one of Z$^1$ or Z$^2$ is CR$^6$ with R$^6$ being a bond to L$^1$;
L$^1$ is linking group comprising at least one nitrogen atom;
E is an electrophilic moiety, wherein E is bound to L$^1$ via the at least one nitrogen atom;
each R$^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:
at least one $R^1$ is aryl, N-arylamino, N-aryl-N-alkylamino, aryloxy, arylthio, or heteroaryl, any of which is optionally substituted;
n is an integer from 1 to 3;
$R^2$ is selected from the group consisting of alkyl, amino, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, hydroxy, aryl, aralkyl, heteroaryl, heteroarylalkyl, heterocyclyl, heterocyclylalkyl, and oxo any of which are optionally substituted; or two $R^2$ together with the carbon atom to which they are attached form a spirocycle or heterocycle.
m is an integer from 0 to 6; and
$R^6$ is selected from the group consisting of hydrogen, alkyl, haloakyl, cyano, halo, alkoxy, aryl, heteroaryl, trifluoromethyl and bond to $L^1$.
174. The compound wherein X is S.
175. The compound wherein X is S=O or $SO_2$.
176. The compound wherein j is 1.
177. The compound wherein m is 0.
178. The compound wherein m is 1.
179. The compound wherein $Z^1$ is $CR^6$ with $R^6$ being a bond to $L^1$.
180. The compound wherein $Z^2$ is N.
181. The compound wherein $L^1$ is

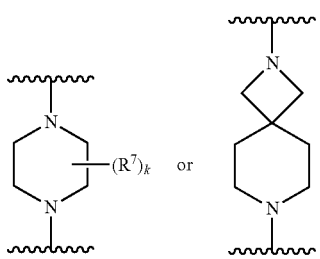

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl.
182. The compound wherein E is an acrylyl group having optional substitution R:

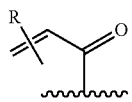

wherein R is selected from the group consisting of fluorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.

183. A compound of Formula (XXIIa):

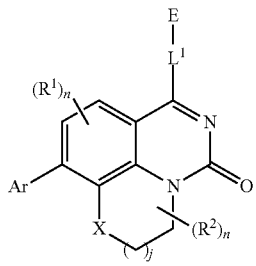

wherein:
X is $S(O)_p$, wherein p is an integer from 0 to 2;
j is an integer from 0 to 2;
$L^1$ is linking group comprising at least one nitrogen atom;
E is an electrophilic moiety, wherein E is bound to $L^1$ via the at least one nitrogen atom;
each $R^1$ is an optional substitution independently selected from the group consisting of alkyl, cyano, cycloalkyl, halo, haloalkyl, trifluoromethyl, and alkoxy;
n is an integer from 0 to 2;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.
184. The compound wherein X is S.
185. The compound wherein X is S=O or $SO_2$.
186. The compound wherein j is 1.
187. The compound wherein m is 0.
188. The compound wherein m is 1.
189. The compound wherein $L^1$ is

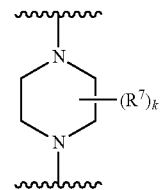

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl.

190. The compound wherein E is an acrylyl group having optional substitution R:

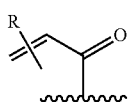

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle.

191. The compound wherein Ar creates axial asymmetry.

192. The compound wherein the compound is a single rotamer.

193. The compound wherein Ar is:

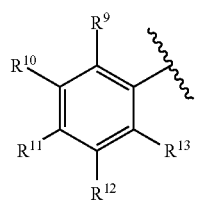

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R$^{12}$, and R$^{13}$ together combine to form a further fused ring that is an aromatic ring optionally comprising 1 to 3 heteroatoms independently selected from N, O or S, the further fused ring being optionally substituted.

194. A compound of Formula (XXIII):

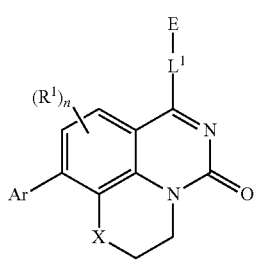

(XXIII)

wherein:
X is S(O)$_p$, wherein p is an integer from 0 to 2;
L$^1$ is linking group comprising at least one nitrogen atom;
E is an electrophilic moiety, wherein E is bound to L$^1$ via the at least one nitrogen atom;
each R$^1$ is an optional substitution independently selected from the group consisting of alkyl, cyano, cycloalkyl, halo, haloalkyl, trifluoromethyl, and alkoxy;
n is an integer from 0 to 2; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

195. The compound wherein X is S.

196. The compound wherein X is S=O or SO$_2$.

197. The compound wherein L$^1$ is

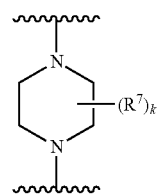

wherein k is an integer from 0 to 4; and each R$^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein R$^i$ is hydrogen or alkyl, and cyanomethyl; or any two R$^7$ may combine to form a fused-ring, spiro or bridging bicycle, wherein any one fused-ring or bridging atom is O, S, S=O, SO$_2$, or NR, wherein R$^j$ is H, methyl or trifluoromethyl.

198. The compound wherein E is an acrylyl group having optional substitution R:

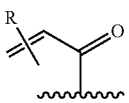

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle.

199. The compound wherein optional substitution comprises monofluorination.

200. The compound wherein Ar creates axial asymmetry.

201. The compound wherein the compound is a single rotamer.

202. The compound wherein Ar is:

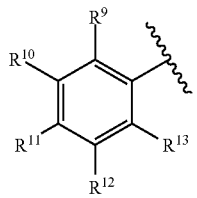

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R, and R$^{13}$ together combine to form a further fused ring that is an aromatic ring optionally comprising 1 to 3 heteroatoms independently selected from N, O or S, the further fused ring being optionally substituted.

203. A compound of Formula (XXIV):

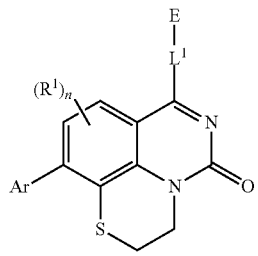

(XXIV)

wherein:

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy; n is an integer from 0 to 2; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

204. The compound wherein $L^1$ is

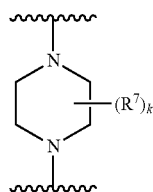

wherein k is an integer from 0 to 4; and each $R^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, SO$_2$, or NR, wherein $R^j$ is H, methyl or trifluoromethyl.

205. The compound wherein E is an acrylyl group having optional substitution R:

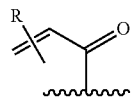

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle.

206. The compound wherein optional substitution R is monofluorination.

207. The compound wherein Ar creates axial asymmetry.

208. The compound wherein the compound is a single rotamer.

209. The compound wherein Ar is:

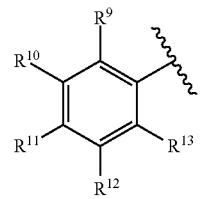

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

210. A compound of Formula (XXV):

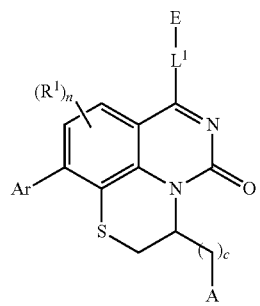

(XXV)

wherein:

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

211. The compound wherein $L^1$ is

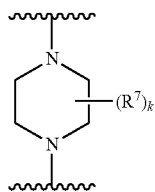

wherein k is an integer from 0 to 4; and each $R^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein R$^i$ is hydrogen or alkyl, and cyanomethyl; or any two $R^7$ may combine to form a fused-ring, spiro or bridging bicycle, wherein any one fused-ring or bridging atom is O, S, S=O, SO$_2$, or NR, wherein R$^j$ is H, methyl or trifluoromethyl.

212. The compound wherein E is an acrylyl group having optional substitution R:

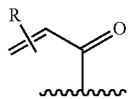

wherein R is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle.

213. The compound wherein optional substitution comprises monofluorination.

214. The compound wherein Ar creates axial asymmetry.

215. The compound wherein the compound is a single rotamer.

216. The compound wherein Ar is:

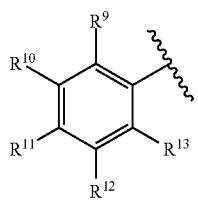

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.

217. A compound of Formula (XXVI):

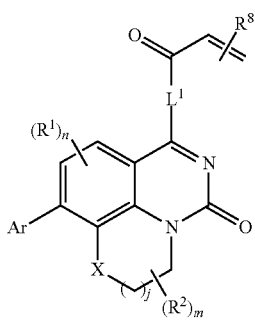

(XXVI)

wherein:
X is S(O)$_p$, wherein p is an integer from 0 to 2;
j is an integer from 0 to 2;
$L^1$ is linking group comprising at least one nitrogen atom; each $R^1$ is an optional substitution independently selected from the group consisting of alkyl, cyano, cycloalkyl, halo, haloalkyl, trifluoromethyl, and alkoxy;
n is an integer from 0 to 2;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^8$ is selected from the group consisting of fluorine, methyl, and —CH$_2$NR$^a$R$^b$, wherein R$^a$ and R$^b$ are independently selected from hydrogen or alkyl; or R$^a$ and R$^b$ combine to form a C$_2$-C$_6$ nitrogen containing heterocycle; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

218. The compound wherein X is S.
219. The compound wherein X is S=O or SO$_2$.
220. The compound wherein j is 1.
221. The compound wherein m is 0.
222. The compound wherein m is 1.
223. The compound wherein $L^1$ is

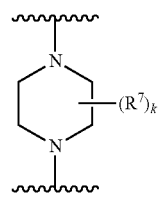

wherein k is an integer from 0 to 4; and each $R^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein R$^i$ is hydrogen or alkyl, and cyanomethyl; or any two $R^7$ may combine to form a fused-ring, spiro or bridging bicycle, wherein any one fused-ring or bridging atom is O, S, S=O, SO$_2$, or NR, wherein R$^j$ is H, methyl or trifluoromethyl.

224. The compound wherein Ar creates axial asymmetry.

225. The compound wherein the compound is a single rotamer.

226. The compound wherein Ar is:

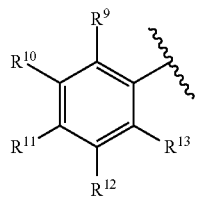

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R, and R$^{13}$ together combine to form a further fused ring that is an aromatic ring optionally comprising 1 to 3 heteroatoms independently selected from N, O or S, the further fused ring being optionally substituted.

227. A compound of Formula (XXVII):

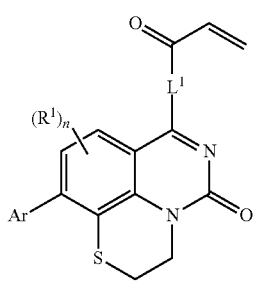

(XXVII)

wherein:
L$^1$ is linking group comprising at least one nitrogen atom;
each R$^1$ is an optional substitution independently selected from the group consisting of alkyl, cyano, cycloalkyl, halo, haloalkyl, trifluoromethyl, and alkoxy;
n is an integer from 0 to 2; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

228. The compound wherein L$^1$ is

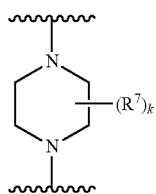

wherein k is an integer from 0 to 4; and each R$^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein R$^i$ is hydrogen or alkyl, and cyanomethyl; or any two R$^7$ may combine to form a fused-ring, spiro or bridging bicycle, wherein any one fused-ring or bridging atom is O, S, S=O, SO$_2$, or NR, wherein R$^j$ is H, methyl or trifluoromethyl.

229. The compound wherein Ar creates axial asymmetry.

230. The compound wherein the compound is a single rotamer.

231. The compound wherein Ar is:

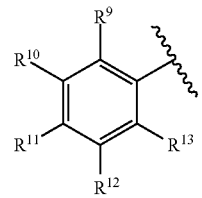

wherein R$^9$, R$^{10}$, R$^{11}$, R$^{12}$, and R$^{13}$ are each independently selected from the group consisting of hydrogen, halo, alkyl, alkoxy, haloalkyl, trifluoromethyl, cycloalkyl and any two adjacent R$^9$, R$^{10}$, R$^{11}$, R, and R$^{13}$ together combine to form a further fused ring that is an aromatic ring optionally comprising 1 to 3 heteroatoms independently selected from N, O or S, the further fused ring being optionally substituted.

232. A compound of Formula (XXVIII):

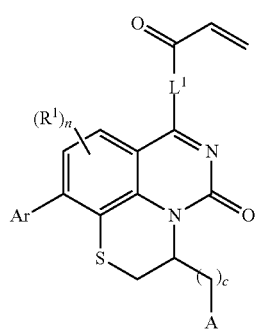

(XXVIII)

wherein:
L$^1$ is linking group comprising at least one nitrogen atom;
each R$^1$ is an optional substitution independently selected from the group consisting of alkyl, cyano, cycloalkyl, halo, haloalkyl, trifluoromethyl, and alkoxy;
n is an integer from 0 to 2;
c is an integer from 0 to 4;
A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

233. The compound wherein $L^1$ is

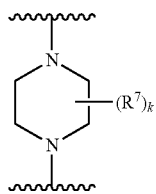

wherein k is an integer from 0 to 4; and each $R^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein R$^i$ is hydrogen or alkyl, and cyanomethyl; or any two $R^7$ may combine to form a fused-ring, spiro or bridging bicycle, wherein any one fused-ring or bridging atom is O, S, S=O, SO$_2$, or NR, wherein R$^j$ is H, methyl or trifluoromethyl.

234. The compound wherein Ar creates axial asymmetry.

235. The compound wherein the compound is a single rotamer.

236. The compound wherein Ar is:

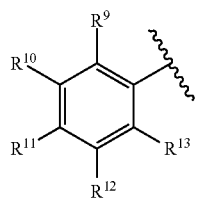

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

237. A compound of Formula (XXIX):

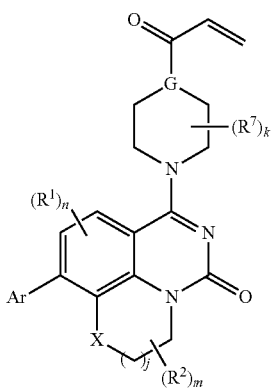

(XXIX)

wherein:
X is S(O)$_p$, wherein p is an integer from 0 to 2;
j is an integer from 0 to 2;
G is selected from the group consisting of N, CH, and

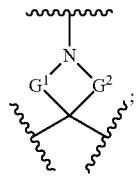

wherein $G^1$ and $G^2$ are independently (CH$_2$)$_q$, where q is 1 or 2;
each $R^1$ is an optional substitution independently selected from the group consisting of alkyl, cyano, cycloalkyl, halo, haloalkyl, trifluoromethyl, and alkoxy; Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
n is an integer from 0 to 2;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
wherein k is an integer from 0 to 4; and each $R^7$ is independently selected from an alkyl group selected from methyl, ethyl, and propyl, any of which are optionally substituted with one or more fluorine atoms, —CH$_2$(CH$_3$)C=CF$_2$, cyano, propargyl, —CH$_2$C(O)V, wherein V is selected from methyl, OH, NHR$^i$ wherein R$^i$ is hydrogen or alkyl, and cyanomethyl; or any two $R^7$ may combine to form a fused-ring, spiro or bridging bicycle, wherein any one fused-ring or bridging atom is O, S, S=O, SO$_2$, or NR, wherein R$^j$ is H, methyl or trifluoromethyl; and
wherein the acrylyl moiety linked to G is optionally substituted.

238. The compound wherein X is S.
239. The compound wherein X is S=O or SO$_2$.
240. The compound wherein j is 1.
241. The compound wherein m is 0.
242. The compound wherein m is 1.
243. The compound wherein Ar creates axial asymmetry.
244. The compound wherein the compound is a single rotamer.
245. The compound wherein Ar is:

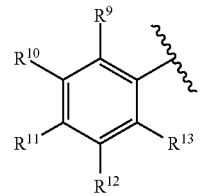

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.

246. A compound of Formula (XXX):

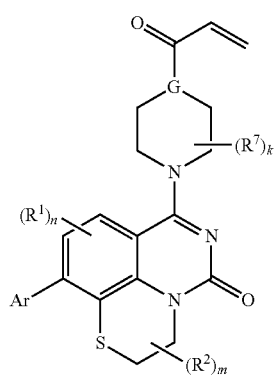

(XXX)

wherein:
G is selected from the group consisting of N, CH, and

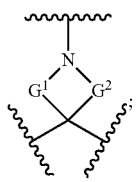

wherein $G^1$ and $G^2$ are independently $(CH_2)_q$, where q is 1 or 2;
each $R^1$ is an optional substitution independently selected from the group consisting of alkyl, cyano, cycloalkyl, halo, haloalkyl, trifluoromethyl, and alkoxy;
Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;
n is an integer from 0 to 2;
$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 4;
wherein k is an integer from 0 to 4; and each $R^7$ is independently selected from an alkyl group selected from methyl, ethyl, and propyl, any of which are optionally substituted with one or more fluorine atoms, —$CH_2(CH_3)C$=$CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl; and wherein the acrylyl moiety linked to G is optionally substituted.
247. The compound wherein m is 0.
248. The compound wherein m is 1.
249. The compound wherein Ar creates axial asymmetry.
250. The compound wherein the compound is a single rotamer.
251. The compound wherein Ar is:

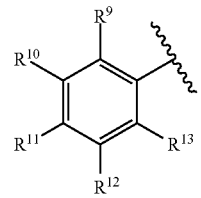

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

252. A compound of Formula (XXXI):

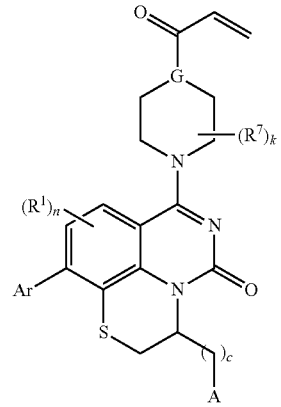

(XXXI)

wherein:
G is selected from the group consisting of N, CH, and

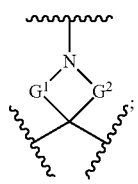

wherein $G^1$ and $G^2$ are independently $(CH_2)_q$, where q is 1 or 2;
each $R^1$ is an optional substitution independently selected from the group consisting of alkyl, cyano, cycloalkyl, halo, haloalkyl, trifluoromethyl, and alkoxy;
n is an integer from 0 to 2;
Ar is aryl, N-arylamino, N-aryl-N-alkylamino, aryloxy, arylthio, heteroaryl, N-heteroarylamino, N-heteroaryl- N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

wherein k is an integer from 0 to 4; and each $R^7$ is independently selected from an alkyl group selected from methyl, ethyl, and propyl, any of which are optionally substituted with one or more fluorine atoms, —$CH_2(CH_3)C$=$CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl; and wherein the acrylyl moiety linked to G is optionally substituted.

253. The compound wherein Ar creates axial asymmetry.

254. The compound wherein the compound is a single rotamer.

255. The compound wherein Ar is:

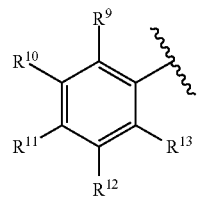

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.

256. A compound of Formula (XXXII):

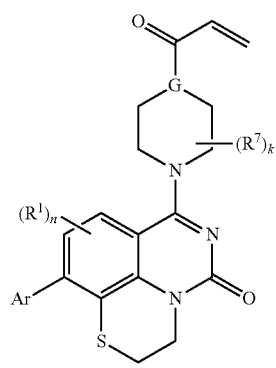

(XXXII)

wherein:

G is selected from the group consisting of N, CH, and

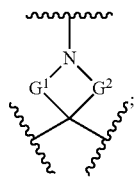

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

wherein k is an integer from 0 to 4; and each $R^7$ is independently selected from an alkyl group selected from methyl, ethyl, and propyl, any of which are optionally substituted with one or more fluorine atoms, —$CH_2(CH_3)C$=$CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or $NR^j$, wherein $R^j$ is H, methyl or trifluoromethyl; and wherein the acrylyl moiety linked to G is optionally substituted.

257. The compound wherein Ar creates axial asymmetry.

258. The compound wherein the compound is a single rotamer.

259. The compound wherein Ar is:

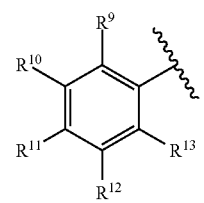

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

260. A compound of Formula (XXXIII):

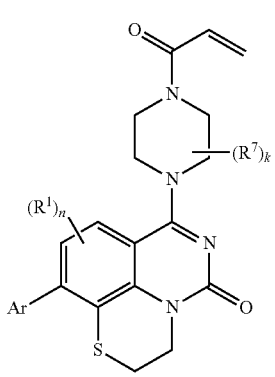

(XXXIII)

wherein:

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl; and wherein the acrylyl moiety linked to N is optionally substituted.

261. The compound wherein Ar creates axial asymmetry.

262. The compound wherein the compound is a single rotamer.

263. The compound wherein Ar is:

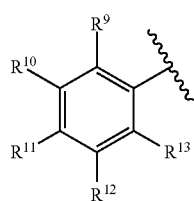

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.

264. A compound of Formula (XXXIV):

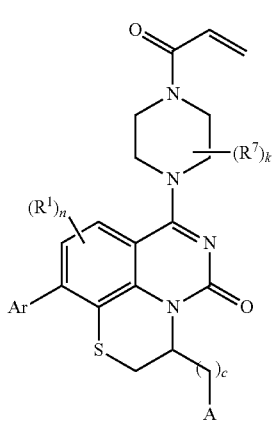

(XXXIV)

wherein:

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

wherein k is an integer from 0 to 4; and each $R^7$ is independently selected from an alkyl group selected from methyl, ethyl, and propyl, any of which are optionally substituted with one or more fluorine atoms, —$CH_2(CH_3)C=CF_2$, cyano, propargyl, —$CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or $NR^j$, wherein $R^j$ is H, methyl or trifluoromethyl; and wherein the acrylyl moiety linked to N is optionally substituted.

265. The compound wherein Ar creates axial asymmetry.

266. The compound wherein the compound is a single rotamer.

267. The compound wherein Ar is:

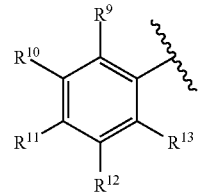

wherein R⁹, R¹⁰, R¹¹, R¹², and R¹³ are each independently selected from the group consisting of hydrogen, halo, alkyl, alkoxy, haloalkyl, trifluoromethyl, cycloalkyl and any two adjacent R⁹, R¹⁰, R¹¹, R¹², and R¹³ together combine to form a further fused ring that is an aromatic ring optionally comprising 1 to 3 heteroatoms independently selected from N, O or S, the further fused ring being optionally substituted.

268. A compound of Formula (XXXV):

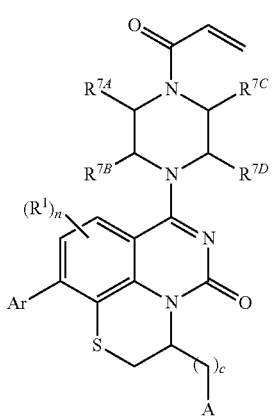

(XXXV)

wherein:

each R¹ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

R⁷ᴬ, R⁷ᴮ, R⁷ᶜ, and R⁷ᴰ are independently selected from hydrogen, alkyl, and cyanoalkyl; or any two R⁷ᴬ⁻ᴰ may combine to form a fused-ring or bridging bicycle, wherein any one fused-ring or bridging atom is O, S, S=O, or SO₂.and wherein the acrylyl moiety linked to N is optionally substituted.

269. The compound wherein Ar creates axial asymmetry.

270. The compound wherein the compound is a single rotamer.

271. The compound wherein Ar is:

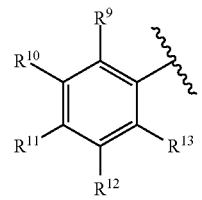

wherein R⁹, R¹⁰, R¹¹, R¹², and R¹³ are each independently selected from the group consisting of hydrogen, halo, alkyl, alkoxy, haloalkyl, trifluoromethyl, cycloalkyl and any two adjacent R⁹, R¹⁰, R¹¹, R¹², and R¹³ together combine to form a further fused ring that is an aromatic ring optionally comprising 1 to 3 heteroatoms independently selected from N, O or S, the further fused ring being optionally substituted.

272. The compound wherein R⁷ᴮ is methyl.

273. The compound wherein a stereogenic center created by the R⁷ᴮ methyl group is in the R-configuration.

274. The compound wherein a stereogenic center created by the R⁷ᴮ methyl group is in the S-configuration.

275. The compound wherein R⁷ᶜ is methyl.

276. The compound wherein a stereogenic center created by the R⁷ᶜ methyl group is in the R-configuration.

277. The compound wherein a stereogenic center created by the R⁷ᶜ methyl group is in the S-configuration.

278. The compound wherein R⁷ᴰ is hydrogen.

279. The compound wherein R⁷ᴬ is cyanomethyl.

280 The compound wherein a stereogenic center created by the cyanomethyl group is in the R-configuration.

281. The compound wherein a stereogenic center created by the cyanomethyl group is in the S-configuration.

282. A compound of Formula (XXXVI):

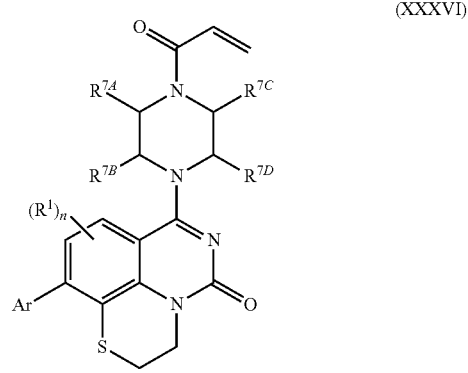

(XXXVI)

wherein:

each R¹ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

R⁷ᴬ, R⁷ᴮ, R⁷ᶜ, and R⁷ᴰ are independently selected from hydrogen, alkyl, and cyanoalkyl; or any two R⁷ᴬᴰ may combine to form a fused-ring or bridging bicycle, wherein any one fused-ring or bridging atom is O, S, S=O, or SO₂; and wherein the acrylyl moiety linked to N is optionally substituted.

283. The compound wherein Ar creates axial asymmetry.

284. The compound wherein the compound is a single rotamer.

285. The compound wherein Ar is:

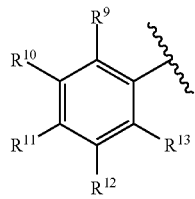

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, R, and $R^{13}$ together combine to form a further fused ring that is an aromatic ring optionally comprising 1 to 3 heteroatoms independently selected from N, O or S, the further fused ring being optionally substituted.

286. The compound wherein $R^{7B}$ is methyl.

287. The compound wherein a stereogenic center created by the $R^{7B}$ methyl group is in the R-configuration.

288. The compound wherein a stereogenic center created by the $R^{7B}$ methyl group is in the S-configuration.

289. The compound wherein $R^{7C}$ is methyl.

290. The compound wherein a stereogenic center created by the $R^{7C}$ methyl group is in the R-configuration.

291. The compound wherein a stereogenic center created by the $R^{7C}$ methyl group is in the S-configuration.

292. The compound wherein $R^{7D}$ is hydrogen.

293. The compound wherein $R^{7A}$ is cyanomethyl.

294. The compound wherein a stereogenic center created by the cyanomethyl group is in the R-configuration.

295. The compound wherein a stereogenic center created by the cyanomethyl group is in the S-configuration.

296. A compound of Formula (XXXVII):

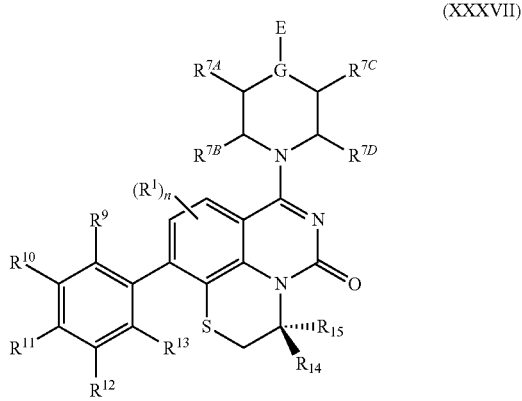

(XXXVII)

wherein:
E is an electrophilic moiety;
G is selected from the group consisting of N, CH, and

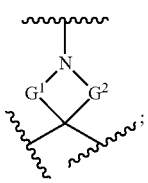

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

n is an integer from 0 to 2;

$R^{7A}$, $R^{7B}$, $R^{7C}$, and $R^{7D}$ are independently selected from hydrogen, alkyl, and cyanoalkyl; or any two $R^{7A}$-D may combine to form a fused-ring or bridging bicycle, wherein any one fused-ring or bridging atom is O, S, S=O, or $SO_2$.

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted;

wherein $R^{14}$ and $R^{15}$ are selected from the group consisting of hydrogen, hydroxyl, amino, N-alkylamino, dialkylamino, N-alkylamino alkyl, N,N-dialkylamino, N,N-dialkylamino alkyl, cycloalkylamino, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted, with the proviso that one of $R^{14}$ or $R^{15}$ is hydrogen; and wherein E is optionally substituted.

297. The compound having axial asymmetry.

298. The compound wherein the compound is a single rotamer.

299. The compound wherein $R^{7B}$ is methyl.

300. The compound wherein a stereogenic center created by the $R^{7B}$ methyl group is in the R-configuration.

301. The compound wherein a stereogenic center created by the $R^{7B}$ methyl group is in the S-configuration.

302. The compound wherein $R^{7C}$ is methyl.

303. The compound wherein a stereogenic center created by the $R^{7C}$ methyl group is in the R-configuration.

304. The compound wherein a stereogenic center created by the $R^{7C}$ methyl group is in the S-configuration.

305. The compound wherein $R^{7D}$ is hydrogen.

306. The compound wherein $R^{7A}$ is cyanomethyl.

307. The compound wherein a stereogenic center created by the cyanomethyl group is in the R-configuration.

308 The compound wherein a stereogenic center created by the cyanomethyl group is in the S-configuration.

309. The compound wherein the compound is a single rotamer of Formula (XXXVIIa):

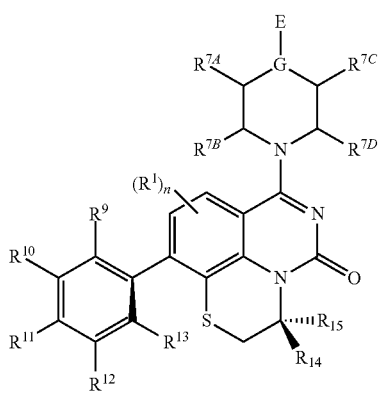

(XXXVIIa)

310. The compound wherein the compound is a single rotamer of Formula (XXXVIIb):

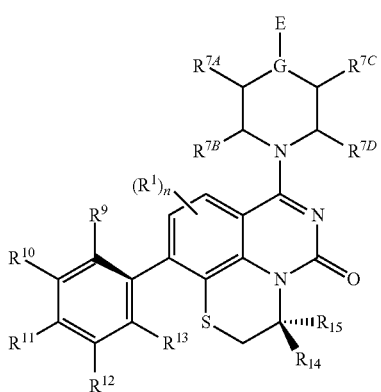

(XXXVIIb)

311. A compound of Formula (XXXVIII):

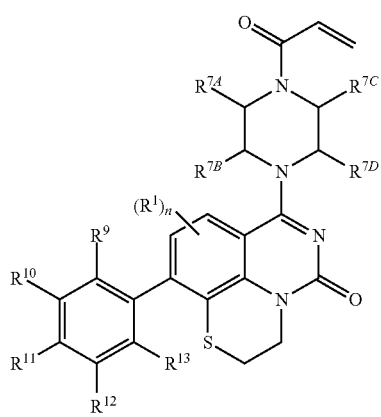

(XXXVIII)

wherein:
each $R^1$ is an optional substitution independently selected from the group consisting of alkyl, cyano, cycloalkyl, halo, haloalkyl, trifluoromethyl, and alkoxy;
n is an integer from 0 to 2;
$R^{7A}$, $R^{7B}$, $R^{7C}$, and $R^{7D}$ are independently selected from hydrogen, alkyl, and cyanoalkyl; or any two $R^{7A\text{-}D}$ may combine to form a fused-ring or bridging bicycle, wherein any one fused-ring or bridging atom is O, S, S=O, or $SO_2$.
wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.
wherein the acrylyl moiety linked to N is optionally substituted.
312. The compound having axial asymmetry.
313. The compound wherein the compound is a single rotamer.
314. The compound wherein $R^{7B}$ is methyl.
315. The compound wherein a stereogenic center created by the $R^{7B}$ methyl group is in the R-configuration.
316. The compound wherein a stereogenic center created by the $R^{7B}$ methyl group is in the S-configuration.
317. The compound wherein $R^{7C}$ is methyl.
318. The compound wherein a stereogenic center created by the $R^{7C}$ methyl group is in the R-configuration.
319. The compound wherein a stereogenic center created by the $R^{7C}$ methyl group is in the S-configuration.
320. The compound wherein $R^{7D}$ is hydrogen.
321. The compound wherein $R^{7A}$ is cyanomethyl.
322. The compound wherein a stereogenic center created by the cyanomethyl group is in the R-configuration.
323. The compound wherein a stereogenic center created by the cyanomethyl group is in the S-configuration.
324. A compound of Formula (XXXIX):

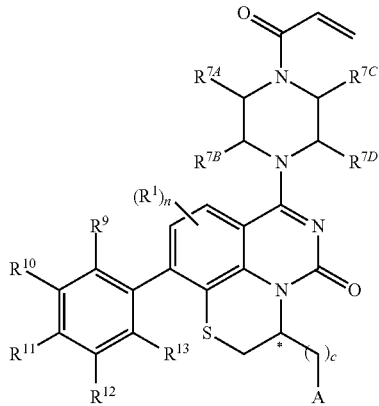

(XXXIX)

wherein * is a stereogenic center;
each $R^1$ is an optional substitution independently selected from the group consisting of alkyl, cyano, cycloalkyl, halo, haloalkyl, trifluoromethyl, and alkoxy;
n is an integer from 0 to 2;
$R^{7A}$, $R^{7B}$, $R^{7C}$, and $R^{7D}$ are independently selected from hydrogen, alkyl, and cyanoalkyl; or any two $R^{7A}$D may combine to form a fused-ring or bridging bicycle, wherein any one fused-ring or bridging atom is O, S, S=O, or $SO_2$.
wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and wherein the acrylyl moiety linked to N is optionally substituted.

325. The compound having axial asymmetry.

326. The compound wherein the compound is a single rotamer.

327. The compound wherein $R^{7B}$ is methyl.

328. The compound wherein a stereogenic center created by the $R^{7B}$ methyl group is in the R-configuration.

329. The compound wherein a stereogenic center created by the $R^{7B}$ methyl group is in the S-configuration.

330. The compound wherein $R^{7C}$ is methyl.

331. The compound wherein a stereogenic center created by the $R^{7C}$ methyl group is in the R-configuration.

332. The compound wherein a stereogenic center created by the $R^{7C}$ methyl group is in the S-configuration.

333. The compound wherein $R^{7D}$ is hydrogen.

334. The compound wherein $R^{7A}$ is cyanomethyl.

335. The compound wherein a stereogenic center created by the cyanomethyl group is in the R-configuration.

336. The compound wherein a stereogenic center created by the cyanomethyl group is in the S-configuration.

337. A compound of Formula (XL):

(XL)

wherein:

X is $S(O)_p$, wherein p is an integer from 0 to 2;

j is an integer from 0 to 2;

$L^1$ is linking group comprising at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^6$ is selected from the group consisting of hydrogen, alkyl, haloakyl, cyano, halo, alkoxy, aryl, heteroaryl, and trifluoromethyl;

$R^8$ is selected from the group consisting of fluorine, methyl, and $-CH_2NR^aR^b$, wherein $R^a$ and $R^b$ are independently selected from hydrogen or alkyl; or $R^a$ and $R^b$ combine to form a $C_2$-$C_6$ nitrogen containing heterocycle; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

338. The compound wherein X is S.

339. The compound wherein X is S=O or $SO_2$.

340. The compound wherein j is 1.

341. The compound wherein m is 0.

342. The compound wherein m is 1.

343. The compound wherein $L^1$ is wherein k is an integer from 0 to 4; and each $R^7$ is independently selected from an alkyl group selected from methyl, ethyl, and propyl, any of which are optionally substituted with one or more fluorine atoms, $-CH_2(CH_3)C=CF_2$, cyano, propargyl, $-CH_2C(O)V$, wherein V is selected from methyl, OH, $NHR^i$, wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or NR, wherein $R^j$ is H, methyl or trifluoromethyl.

344. The compound wherein Ar creates axial asymmetry.

345. The compound wherein the compound is a single rotamer.

346. The compound wherein Ar is:

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

347. The compound given by Formula XLI:

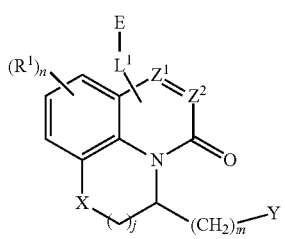

(XLI)

wherein:
Y is selected from the group consisting of hydrogen; N-linked heteroaromatic ring; N-linked azetidinyl optionally substituted with fluorine, CO—NR'R", or spiro-linked oxetane; $OR^a$; and $Z^3R^bR^c$;
R' and R" are independently hydrogen, alkyl or cycloalkyl;
$Z^3$ is CH, COH, or N;
m is an integer from 1 to 5;
$R^a$ is hydrogen, methyl, ethyl trifluoromethyl, heterocyclyl, or heterocyclylalkyl;
$R^b$ and R' are independently selected from alkyl, alkyl having one or more fluorine substitutions, cycloalkyl, oxetanyl, and N-methyl prolinyl; or $R^b$ and $R^c$ combine to form a cyclic structure A1:

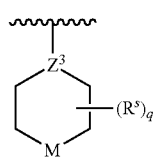

A1 wherein q is an integer from 1 to 4; M is selected from a bond, O, S, SO, $SO_2$, $CH_2$, NH, NMe, N-ethyl, N-oxetanyl, and N-cyclopropyl, wherein each C—H of each alkylene, alkyl or cycloalkyl group is independently optionally substituted with a fluorine atom; each $R^S$ is independently fluorine, oxo, alkoxy, or CO—NR'R", or any two $R^S$ combine to form a 1 to 3 carbon atom bridge, wherein the 1 to 3 carbon atom bridge is optionally substituted with one or more fluorine atoms; each R' and R" is independently hydrogen, alkyl or cycloalkyl; j is an integer from 0 to 2;
$Z^1$ and $Z^2$ are independently $CR^6$ or N, with the proviso that at least one of $Z^1$ or $Z^2$ is $CR^6$ with $R^6$ being a bond to $L^1$;
$L^1$ is linking group comprising at least one nitrogen atom;
E is an electrophilic moiety, wherein E is bound to $L^1$ via the at least one nitrogen atom;
each $R^1$ is independently selected from the group consisting of acyl, alkyl, carboxamide, cyano, cycloalkyl, halo, haloalkyl, trifluoromethyl, alkoxy, aryl, heteroaryl, N-arylamino, N-aryl-N-alkylamino, aryloxy, cycloalkyl, heterocyclyl, and arylthio with the proviso that at least one $R^1$ is aryl, N-arylamino, N-aryl-N-alkylamino, aryloxy, arylthio, or heteroaryl, any of which is optionally substituted;
n is an integer from 1 to 3;
m is an integer from 0 to 6;
$R^3$, $R^4$, and $R^5$ are each independently selected from the group consisting of hydrogen alkyl, halo, alkoxy, aryl, heteroaryl, and cycloalkyl, any of which are optionally substituted; and
$R^6$ is selected from the group consisting of hydrogen, alkyl, haloakyl, cyano, halo, alkoxy, aryl, heteroaryl, trifluoromethyl and bond to $L^1$, and pharmaceutically acceptable salts thereof.

348. The compound having the formula XLII

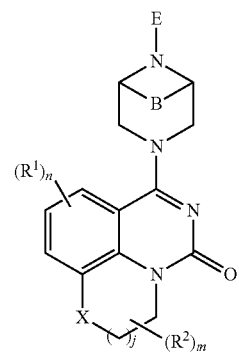

(XLII)

wherein:
X is O, $S(O)_p$, $CR^3R^4$, $NR^5$, or C(O), wherein p is an integer from 0 to 2;
j is an integer from 0 to 2;
B is bridging group comprising 1 to 3 carbon atoms, wherein any one carbon atom is optionally replaced by O, S, $SO_2$, or N-alkyl;
E is an electrophilic moiety;
each $R^1$ is independently selected from the group consisting of acyl, alkyl, carboxamide, cyano, cycloalkyl, halo, haloalkyl, trifluoromethyl, alkoxy, aryl, heteroaryl, N-arylamino, N-aryl-N-alkylamino, aryloxy, cycloalkyl, heterocyclyl, and arylthio with the proviso that:
at least one $R^1$ is aryl, N-arylamino, N-aryl-N-alkylamino, aryloxy, arylthio, or heteroaryl, any of which is optionally substituted;
n is an integer from 1 to 3;
$R^2$ is selected from the group consisting of alkyl, alkylamino, dialkylamino, alkylamidoalkyl, arylamidoalkyl, alkylsulfonamidoalkyl, arylsulfonamidoalkyl, N-alkyl aminoalkyl, N,N-dialkyl aminoalkyl, amido, amido alkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;
m is an integer from 0 to 6;
$R^3$, $R^4$, and $R^5$ are each independently selected from the group consisting of hydrogen alkyl, halo, alkoxy, aryl, heteroaryl, and cycloalkyl, any of which are optionally substituted, and pharmaceutically acceptable salts thereof.

349. A compound selected from Tables 1-7.
350. A method of modulating a G12C mutant K-Ras comprising contacting the G12C mutant K-Ras with a compound disclosed herein.
351. A method of treating a subject with cancer associated with a G12C Kras mutation comprising administering to the subject a compound disclosed herein in a pharmaceutically acceptable vehicle.
352. Use of a compound disclosed herein, in the manufacture of a medicament for the treatment of cancer in a subject.

353. A compound of Formula (XLIII) or pharmaceutically acceptable salt thereof:

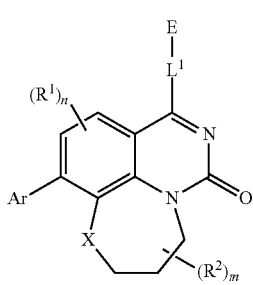

(XLIII)

wherein:
X is O or S;
L¹ is linking group comprising at least one nitrogen atom;
E is an electrophilic moiety, wherein E is bound to L¹ via the at least one nitrogen atom;
each R¹ is an optional substitution independently selected from the group consisting of alkyl, cyano, cycloalkyl, halo, haloalkyl, trifluoromethyl, and alkoxy;
Ar is selected from the group consisting of aryl, N-arylamino, N-aryl-N-alkylamino, aryloxy, arylthio, or heteroaryl, any of which is optionally substituted; n is an integer from 1 to 2;
each R² is independently selected from the group consisting optionally substituted aryl, optionally substituted heteroaryl, optionally substituted heterocyclyl, —CHR'R", —OR', —SR', and —NR',R"; wherein each R' or R" is selected from the group consisting of hydrogen, alkyl, alkoxy, alkoxyalkyl, hydroxy, cycloalkoxy, cyano, cyanoalkyl, amido, amidoalkyl, N-alkylamido, N-alkylamidoalkyl, N,N-dialkylamido, N,N-dialkylamidoalkyl, amino, aminoalkyl, N-alkyl amino, N-alkyl aminoalkyl, N,N-dialkylamino, and N,N-dialkylaminoalkyl, any of which are optionally substituted; or any two R' and R" combine to form 3-7-membered ring, optionally comprising 1 or 2 heteroatoms selected from N, O, or S; or any two R² combine to form a spirocycle comprising 0 to 2 heteroatoms selected from N, O, or S; and
m is an integer from 0 to 6.

354. The compound wherein m is 0-2.
355. The compound wherein m is 1 or 2.
356. The compound wherein L¹ is

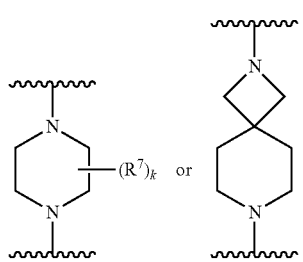

wherein k is an integer from 0 to 4; and each R⁷ is independently selected from methyl, and cyanomethyl, or any two R⁷ combine to form a bridge or spirocycle structure optionally comprising a heteroatom in the bridge or spirocycle selected from S, SO₂, 0 or N, and wherein the bridge or spirocycle structure is optionally substituted with oxo.

357. The compound wherein E is an acrylyl group having optional substitution R.

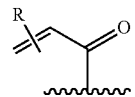

wherein R is selected from the group consisting of fluorine, methyl, and —CH₂NR$^a$R$^b$, wherein R$^a$ and R$^b$ are independently selected from hydrogen or alkyl; or R$^a$ and R$^b$ combine to form a C₂-C₆ nitrogen containing heterocycle.

358. The compound wherein X is S.
359. The compound wherein Ar is a phenyl optionally substituted with one or more alkyl, cycloalkyl, fluoro, chloro, bromo, iodo, trifluoromethyl or cyano.
360. A compound of Formula (XLIV) or pharmaceutically acceptable salt thereof:

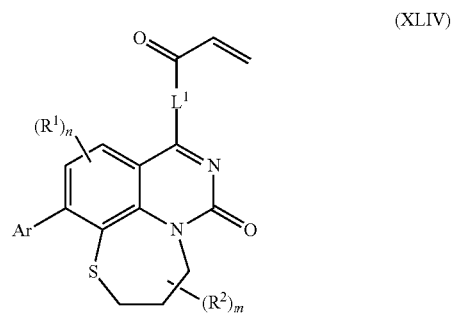

(XLIV)

wherein:
L¹ is linking group comprising at least one nitrogen atom;
each R¹ is an optional substitution independently selected from the group consisting of alkyl, cyano, cyclopropyl, halo, haloalkyl, trifluoromethyl, alkoxy, n is 1 or 2;
each R² is independently selected from the group consisting optionally substituted aryl, optionally substituted heteroaryl, optionally substituted heterocyclyl, —CHR'R", —OR', —SR', and —NR',R"; wherein each R' or R" is selected from the group consisting of hydrogen, alkyl, alkoxy, alkoxyalkyl, hydroxy, cycloalkoxy, cyano, cyanoalkyl, amido, amidoalkyl, N-alkylamido, N-alkylamidoalkyl, N,N-dialkylamido, N,N-dialkylamidoalkyl, amino, aminoalkyl, N-alkyl amino, N-alkyl aminoalkyl, N,N-dialkylamino, and N,N-dialkylaminoalkyl, any of which are optionally substituted; or any two R' and R" combine to form 3-7-membered ring, optionally comprising 1 or 2 heteroatoms selected from N, O, or S; or any two R² combine to form a spirocycle comprising 0 to 2 heteroatoms selected from N, O, or S;

m is 1 or 2; and

Ar is a phenyl group optionally substituted with one or more alkyl, cycloalkyl, fluoro, chloro, bromo, iodo, trifluoromethyl or cyano.

361. The compound wherein L¹ is

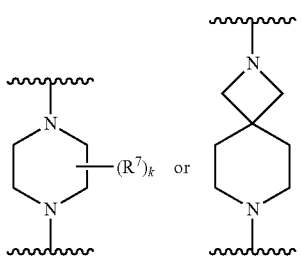

wherein k is an integer from 0 to 4; and each $R^7$ is independently selected from methyl, and cyanomethyl, or any two $R^7$ combine to form a bridge or spirocycle structure optionally comprising a heteroatom in the bridge or spirocycle selected from S, $SO_2$, O or N, and wherein the bridge or spirocycle structure is optionally substituted with oxo.

362. The compound wherein n is 1 and $R^1$ is ortho to Ar.

363. The compound wherein $R^1$ is chloro or trifluoromethyl.

364. The compound wherein Ar is a phenyl ring comprising 1 to 3 fluorine substitutions.

365. A compound of Formula (XLV) or pharmaceutically acceptable salt thereof:

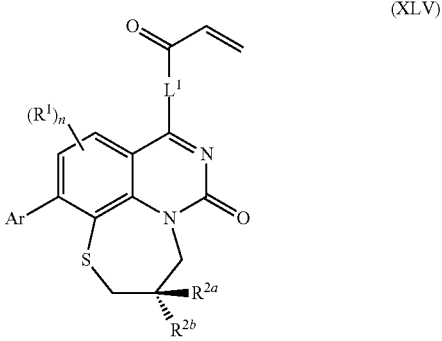

(XLV)

wherein:

L¹ is linking group comprising at least one nitrogen atom;

each $R^1$ is an optional substitution independently selected from the group consisting of alkyl, cyano, cyclopropyl, halo, haloalkyl, trifluoromethyl, alkoxy, n is 1 or 2;

$R^{2a}$ and $R^{2b}$ are independently selected from the group consisting of hydrogen, optionally substituted aryl, optionally substituted heteroaryl, optionally substituted heterocyclyl, —CHR'R", —OR', —SR', and —NR',R"; wherein each R' or R" is selected from the group consisting of hydrogen, alkyl, alkoxy, alkoxyalkyl, hydroxy, cycloalkoxy, cyano, cyanoalkyl, amido, amidoalkyl, N-alkylamido, N-alkylamidoalkyl, N,N-dialkylamido, N,N-dialkylamidoalkyl, amino, aminoalkyl, N-alkyl amino, N-alkyl aminoalkyl, N,N-dialkylamino, N,N-dialkylaminoalkyl, any of which are optionally substituted; or R' and R" combine to form 3-7-membered ring, optionally comprising 1 or 2 heteroatoms selected from N, O, or S, or $R^{2a}$ and $R^{2b}$ combine to form a spirocycle comprising 0 to 2 heteroatoms selected from N, O, or S; and Ar is a phenyl optionally substituted with one or more alkyl, cycloalkyl, fluoro, chloro, bromo, iodo, trifluoromethyl or cyano.

366. The compound wherein L¹ is

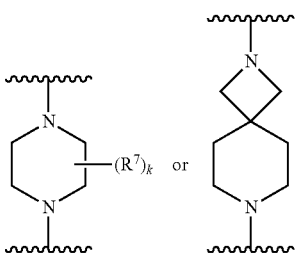

wherein k is an integer from 0 to 4; and each $R^7$ is independently selected from methyl, and cyanomethyl, or any two $R^7$ combine to form a bridge or spirocycle structure optionally comprising a heteroatom in the bridge or spirocycle selected from S, $SO_2$, O or N, and wherein the bridge or spirocycle structure is optionally substituted with oxo.

367. The compound wherein n is 1 and $R^1$ is ortho to Ar.

368. The compound wherein $R^1$ is chloro or trifluoromethyl.

369. The compound wherein Ar is a phenyl ring comprising 1 to 3 fluorine substitutions.

370. The compound wherein $R^{2a}$ is hydrogen and $R^{2b}$ is not hydrogen.

371. The compound wherein $R^{2a}$ is hydrogen and $R^{2b}$ is not hydrogen.

372. The compound wherein $R^{2a}$ and $R^{2b}$ combine to form a spirocyclic carbocycle or heterocycle.

373. The compound having the structure of formula XLVa or XLVb:

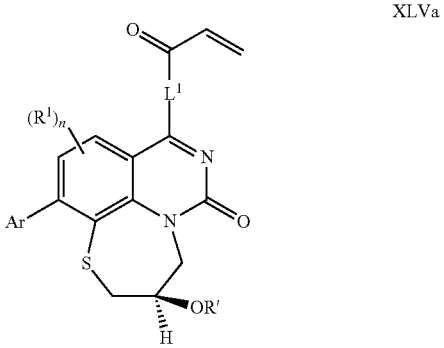

XLVa

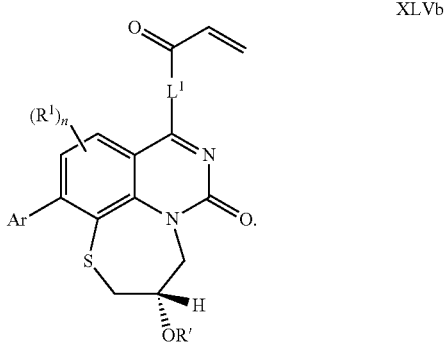

XLVb

374. The compound having the structure of formula XLVc or XLVd:
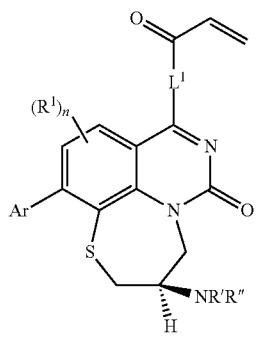
XLVc
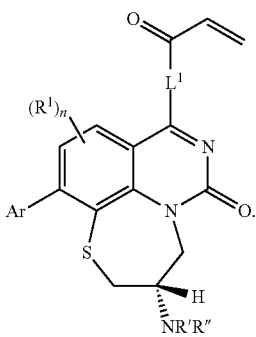
XLVd
375. The compound having the structure of formula XLVe or XLVf:
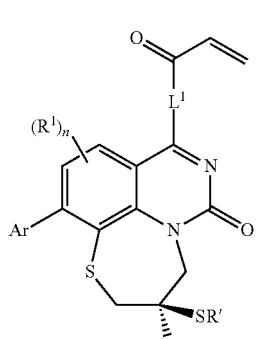
XLVe
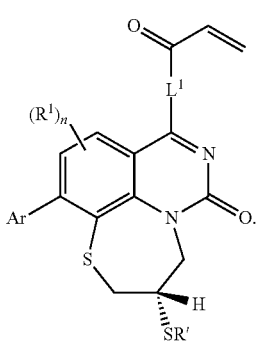
XLVf
376. The compound having the structure of formula XLVg or XLVh:
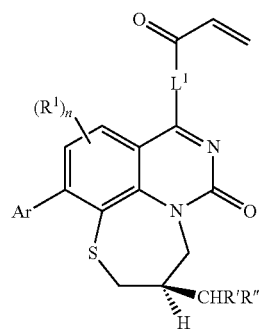
XLVg
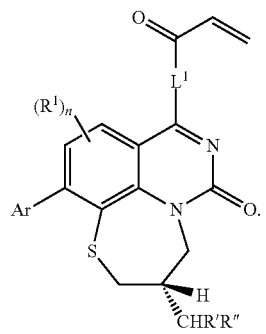
XLVh
377. A compounds selected from:
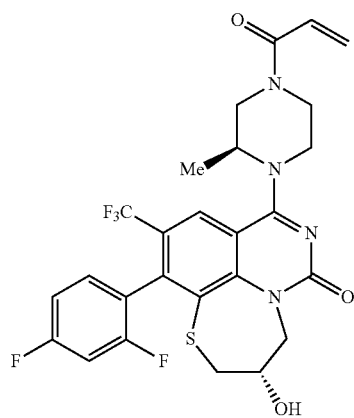
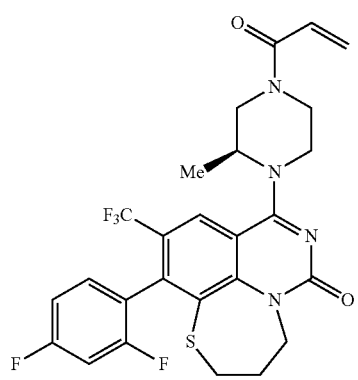

| 429 | 430 |
|---|---|
| -continued | -continued |
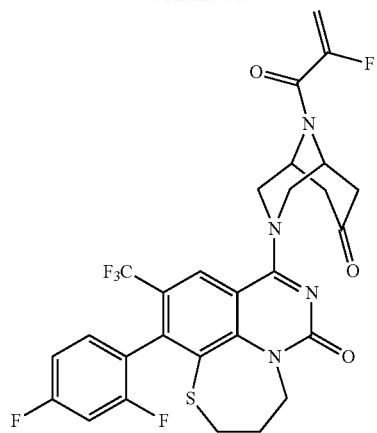
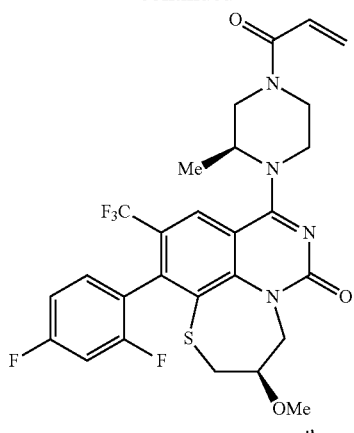
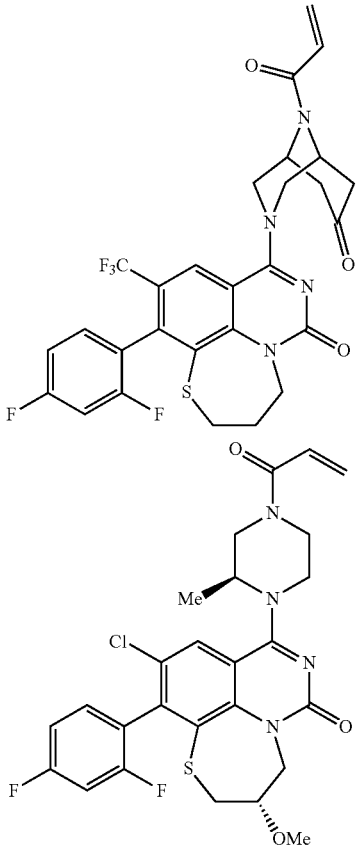
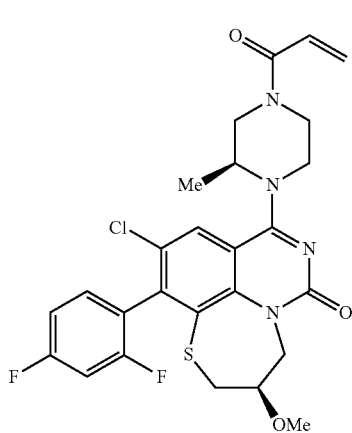

| 431 | 432 |
|---|---|
| -continued | -continued |
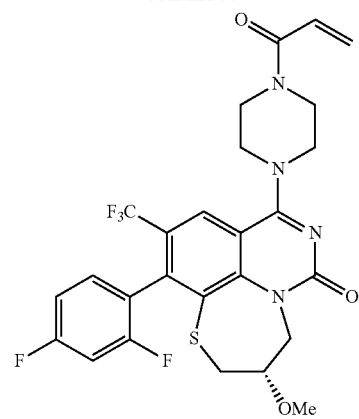
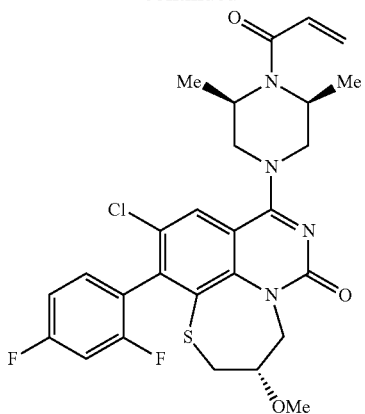
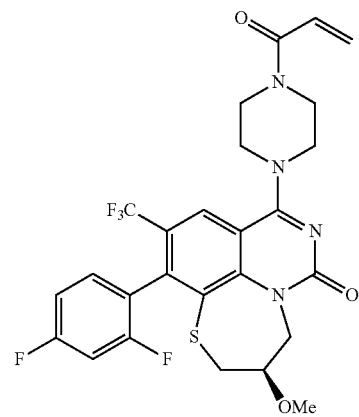
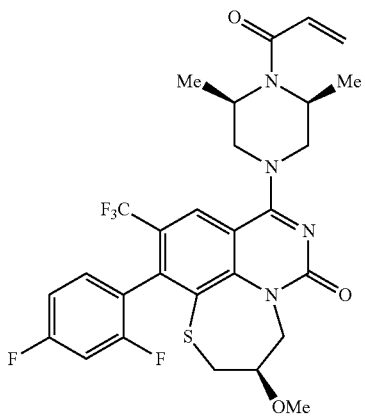
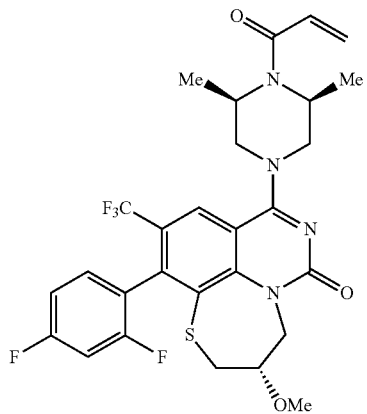
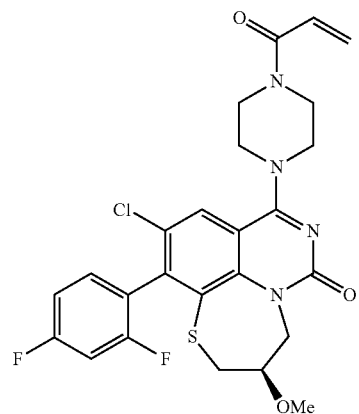
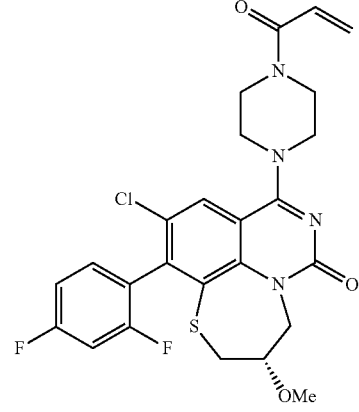
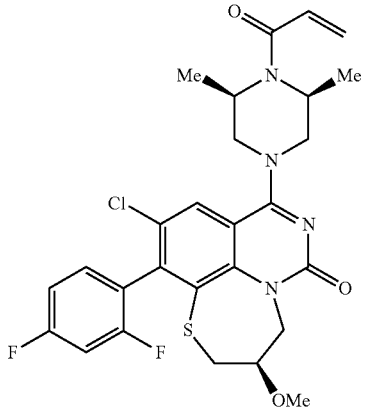

433
-continued
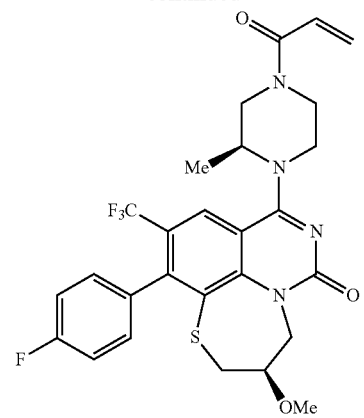
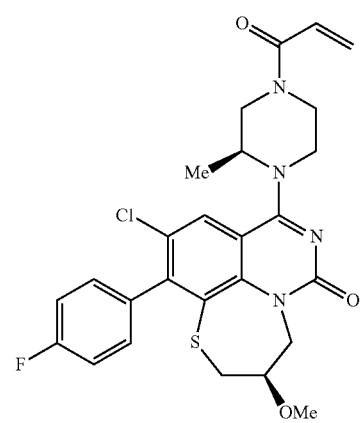
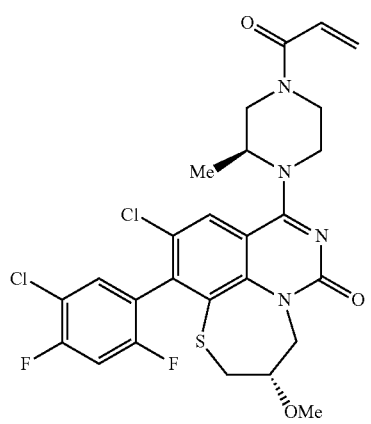
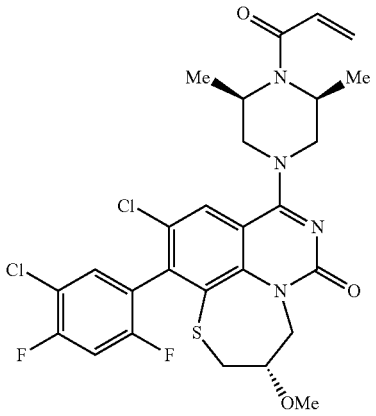
434
-continued
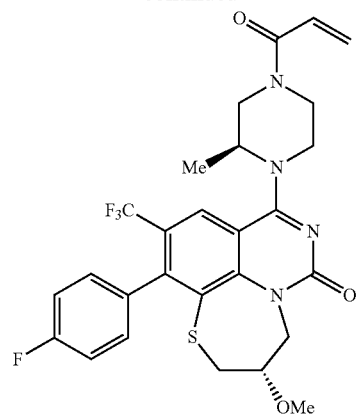
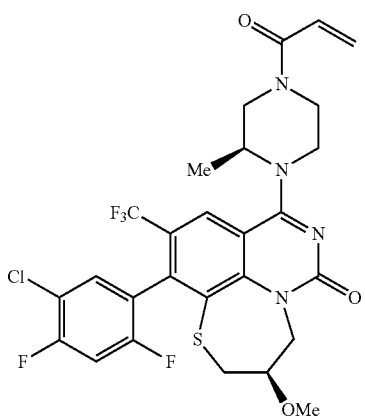
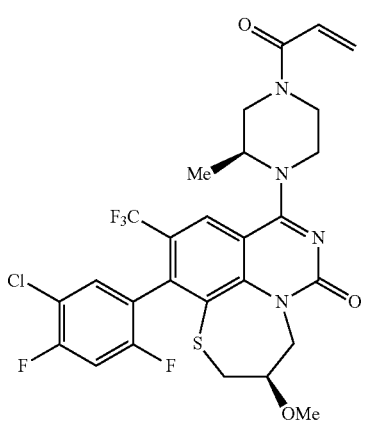
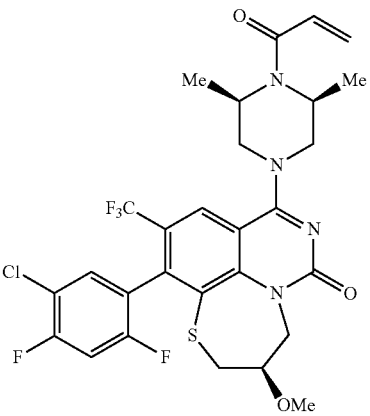

435
-continued
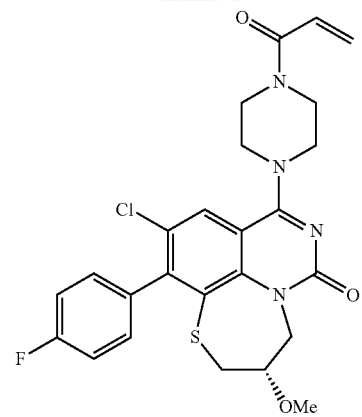
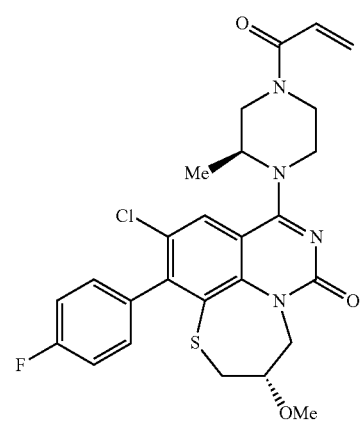
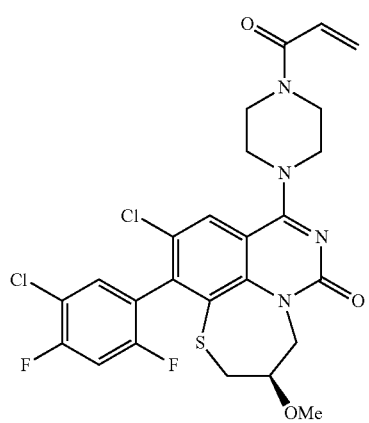
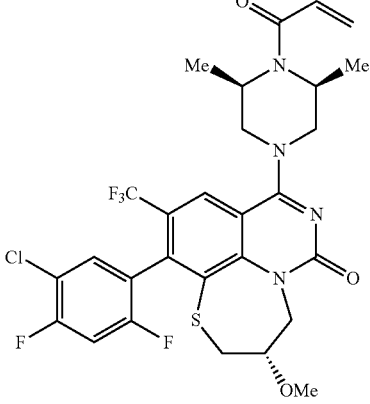
436
-continued
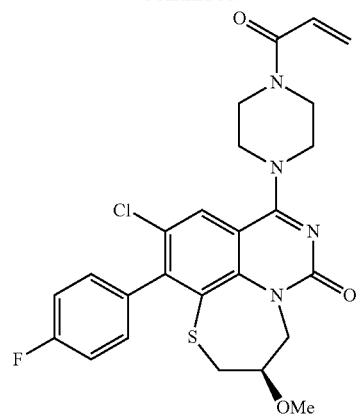
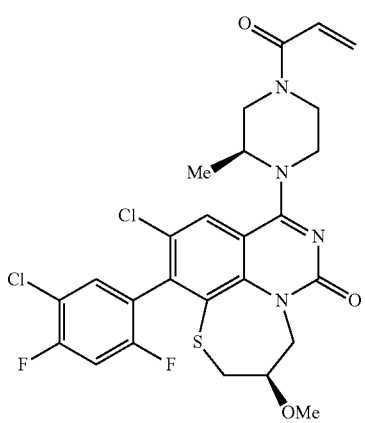
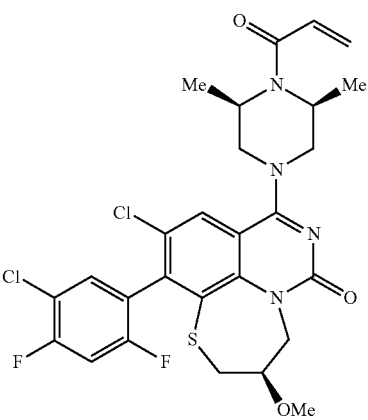
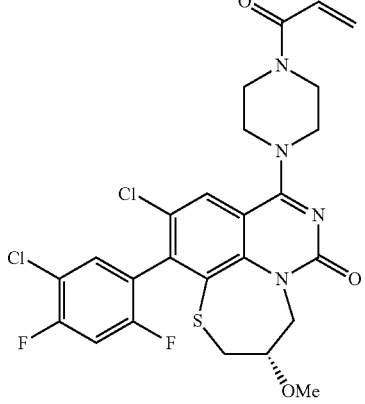

437
-continued
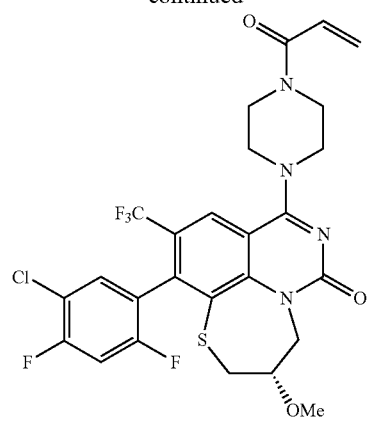

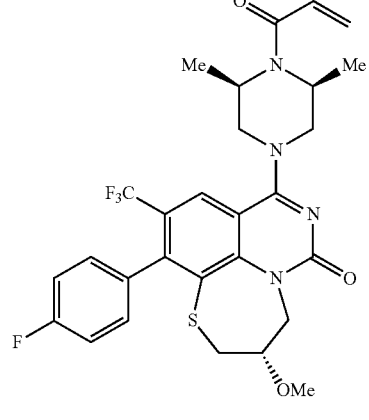
438
-continued
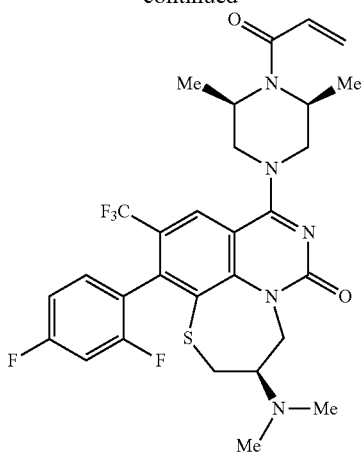
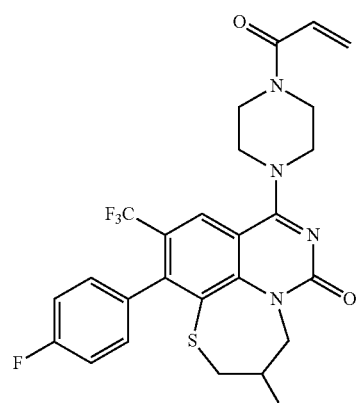
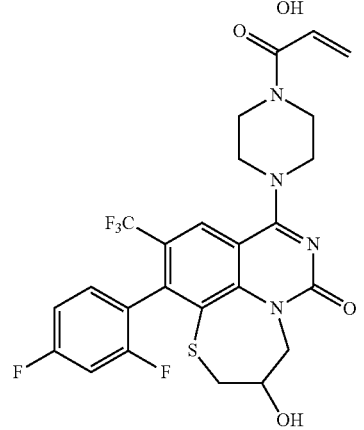
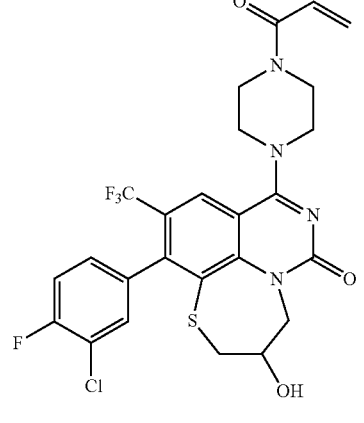

439
-continued
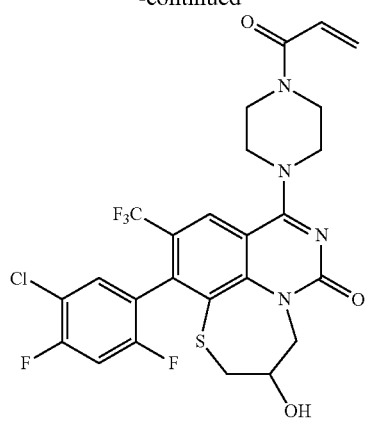
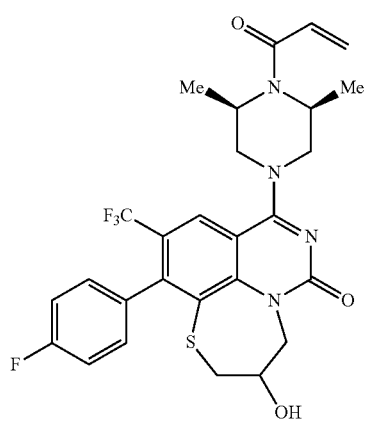
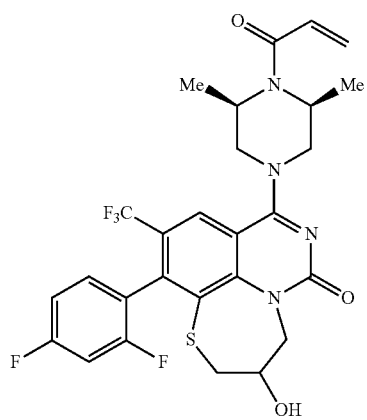
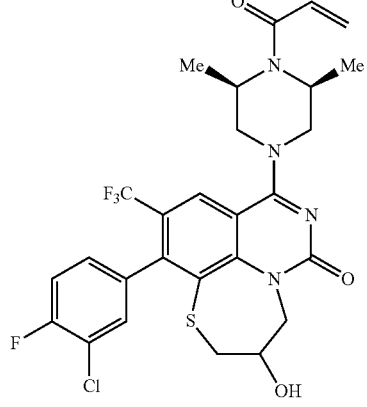
440
-continued
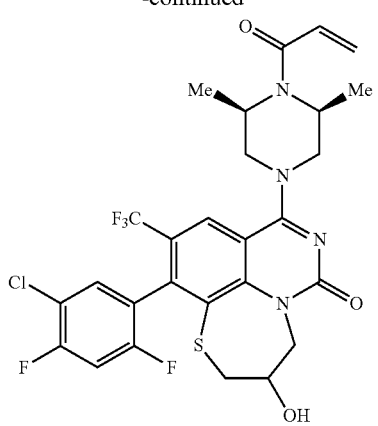
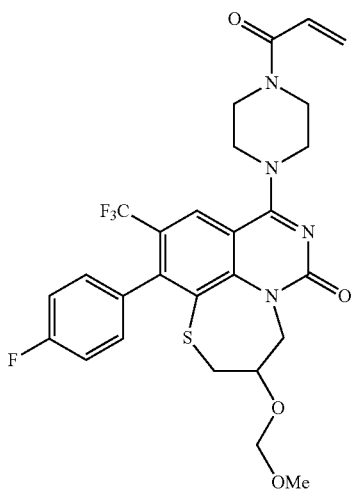
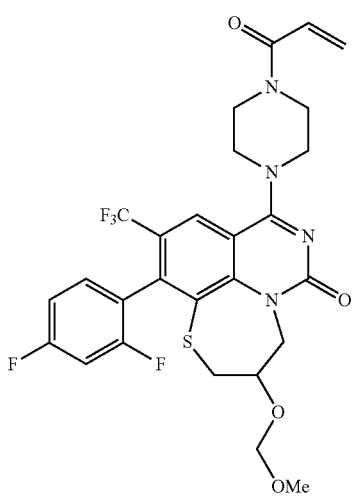

441
-continued
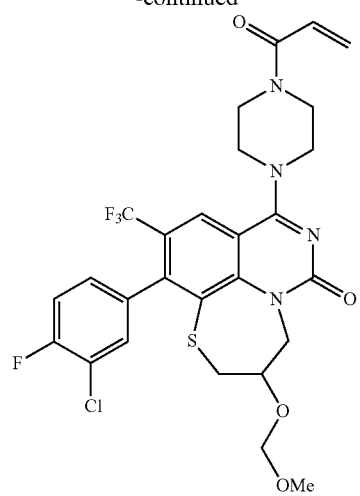
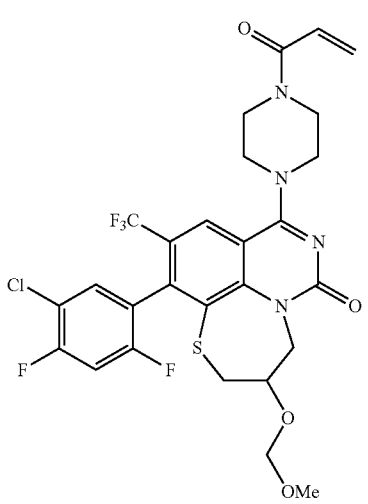 [SMILES: C=CC(=O)N1CCN(c2nc(=O)n3c4c(c(-c5cc(Cl)c(F)cc5F)c(C(F)(F)F)cc24)SCC(OC2CC2)C3)CC1]
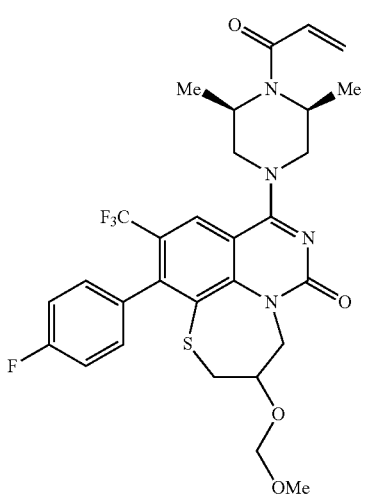
442
-continued
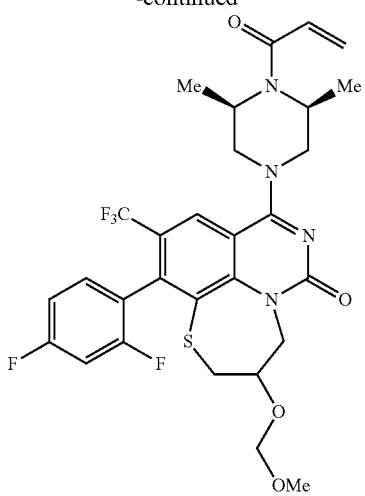
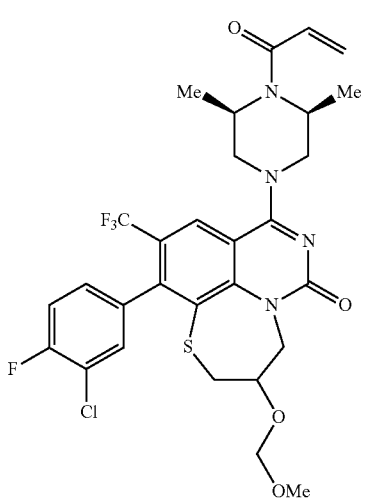
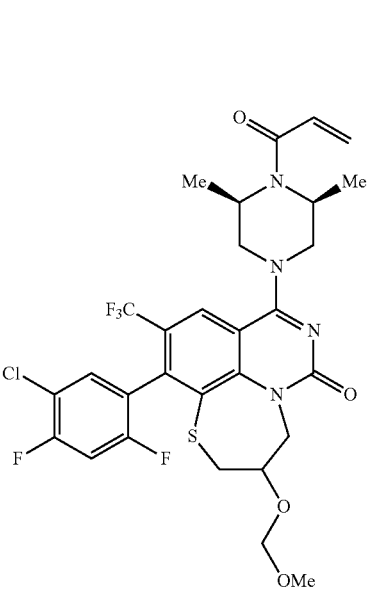

443
-continued
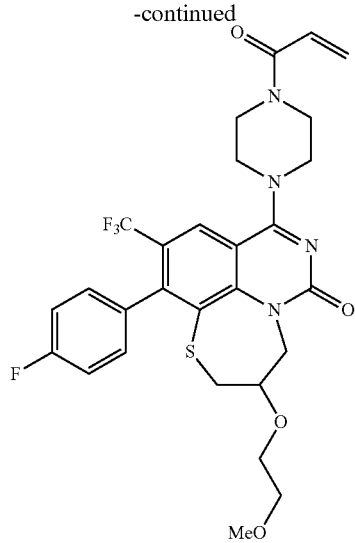
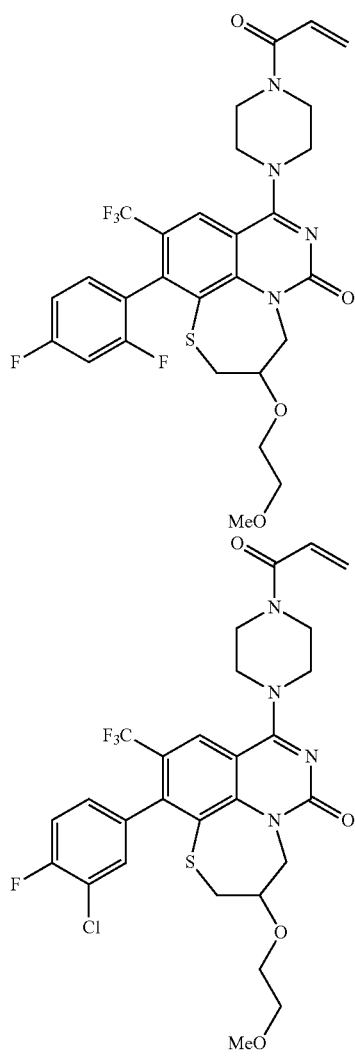
444
-continued
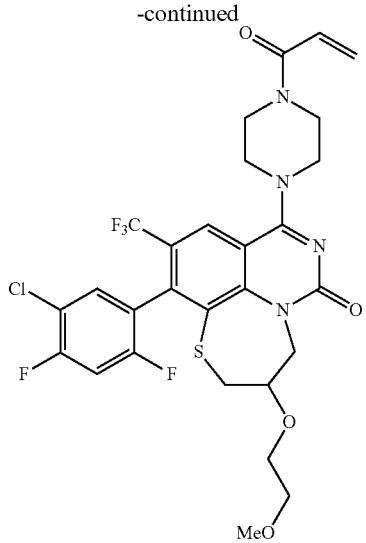
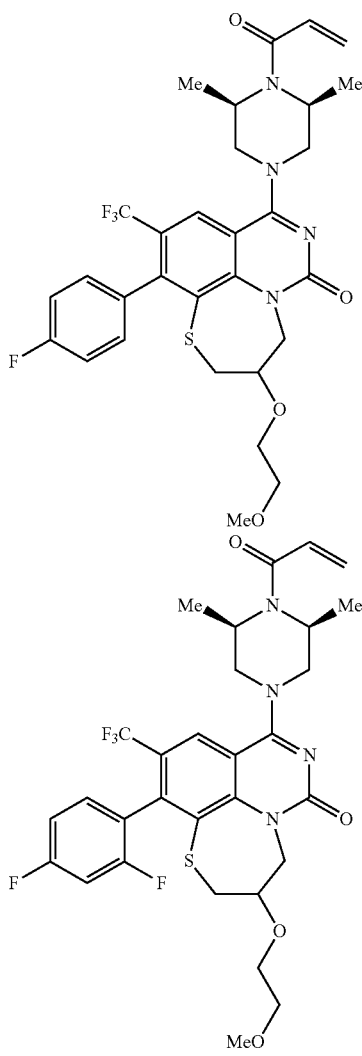

445
-continued
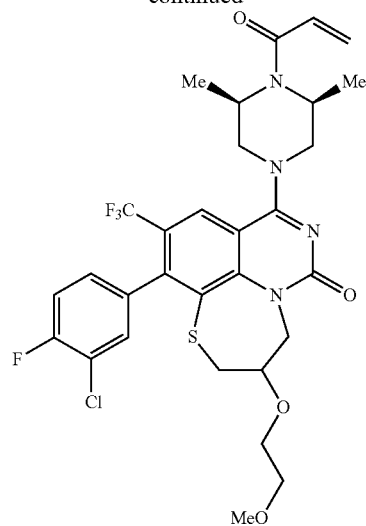
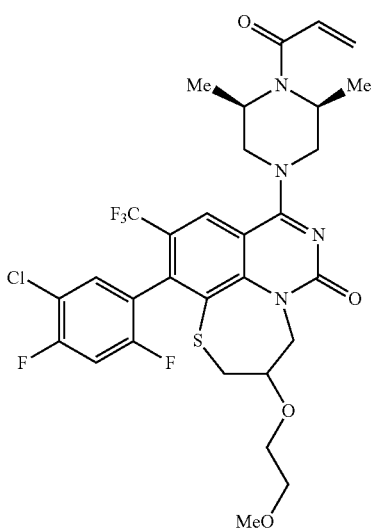
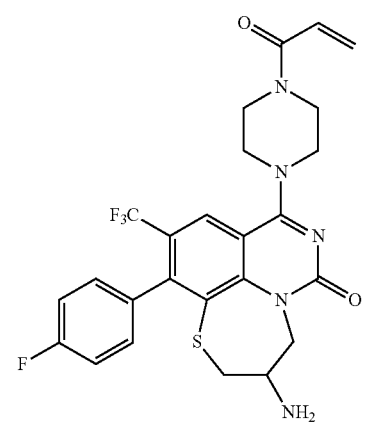
446
-continued
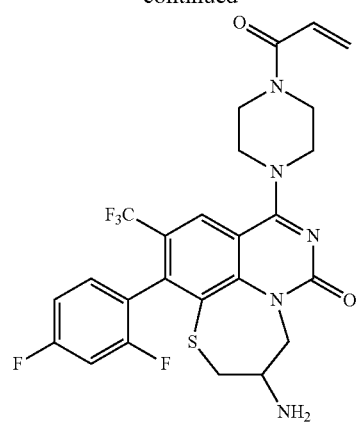
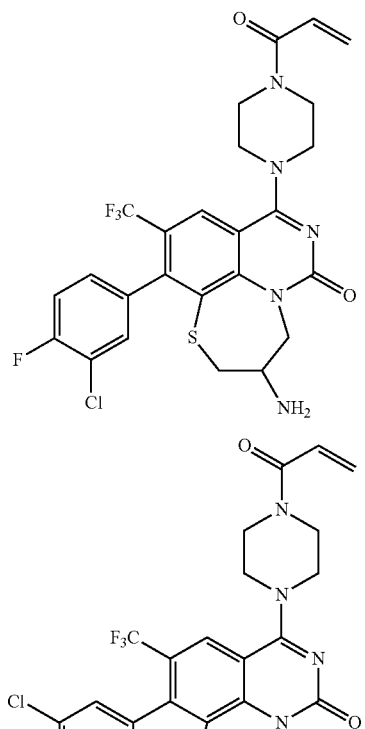
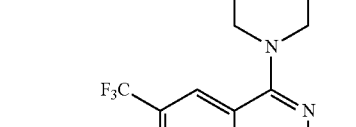
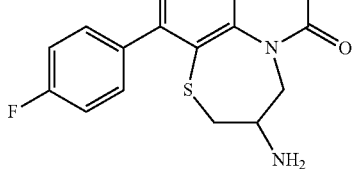

447
-continued
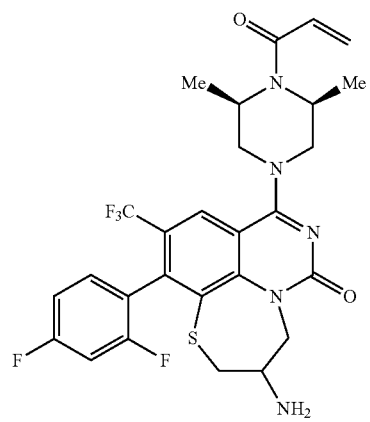
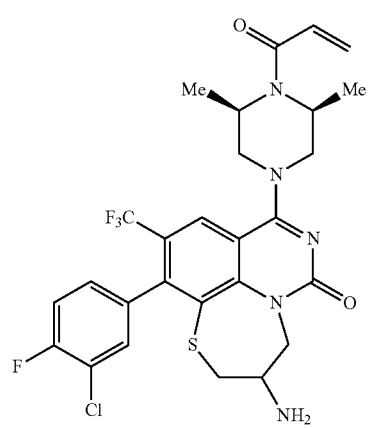
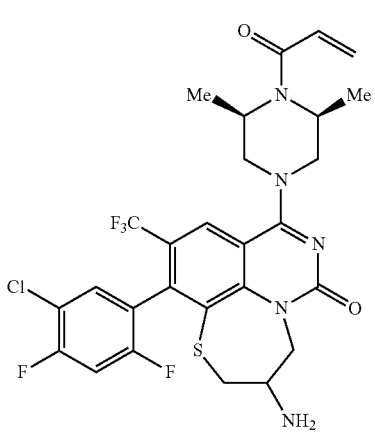
448
-continued
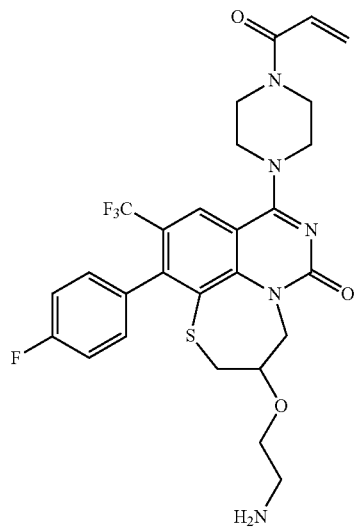
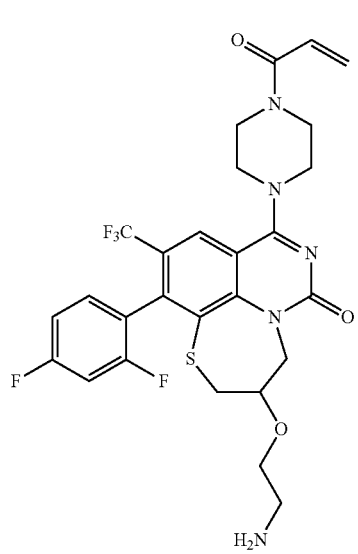
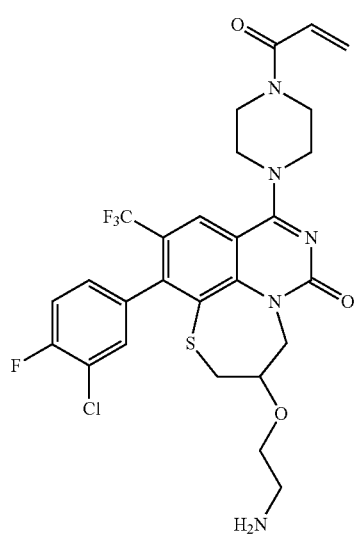

449
-continued
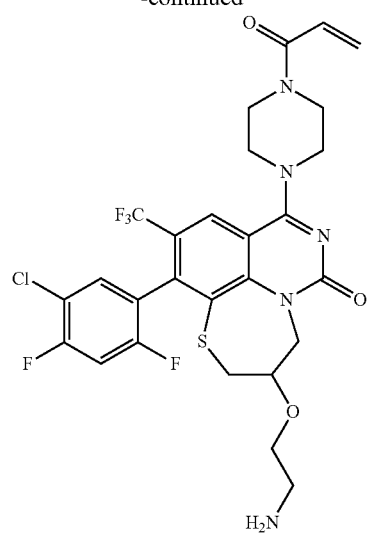
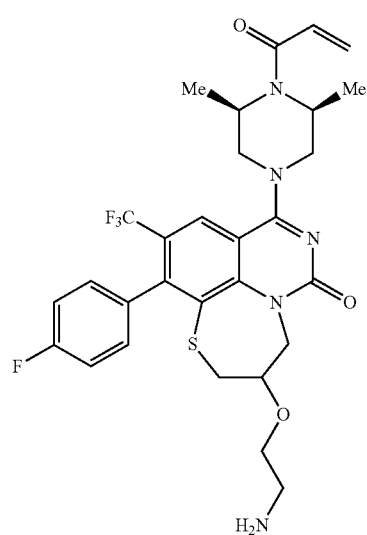
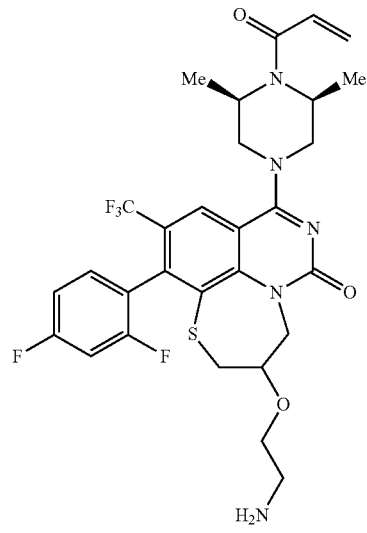
450
-continued
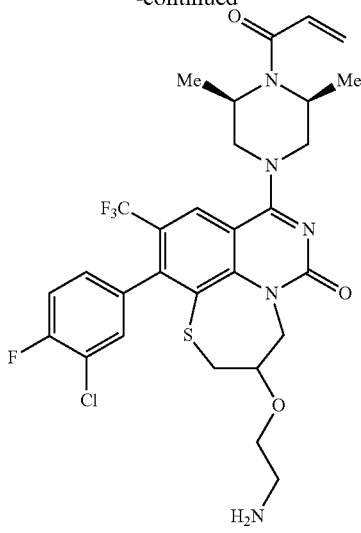
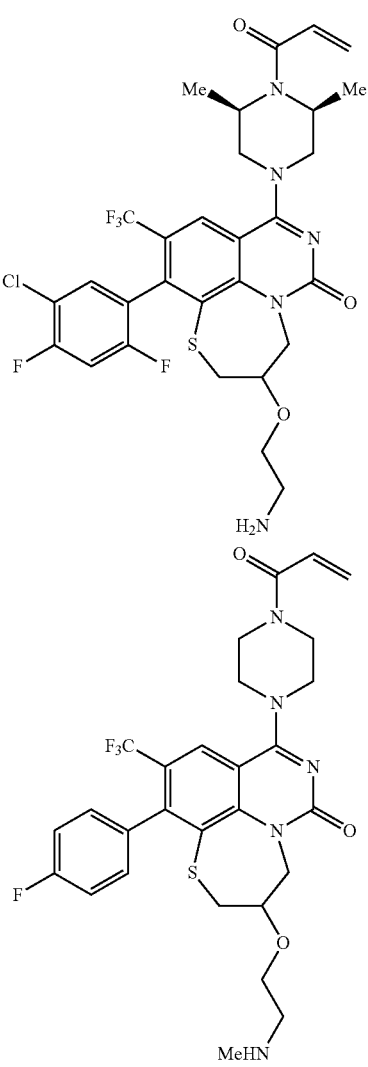

451
-continued
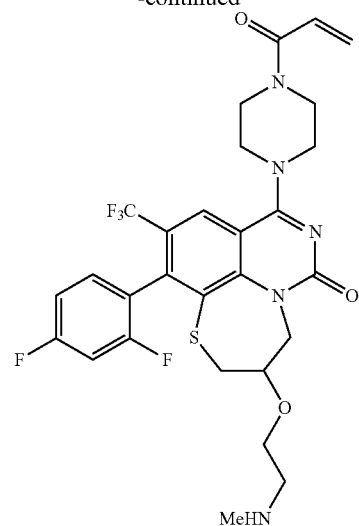
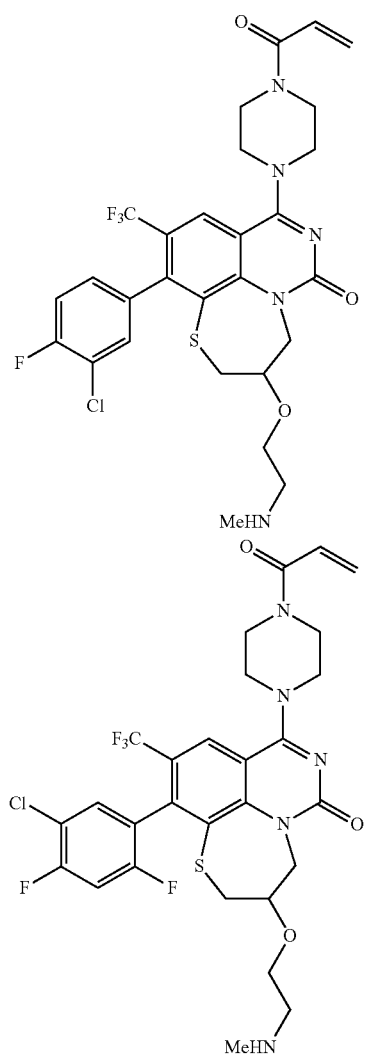
452
-continued
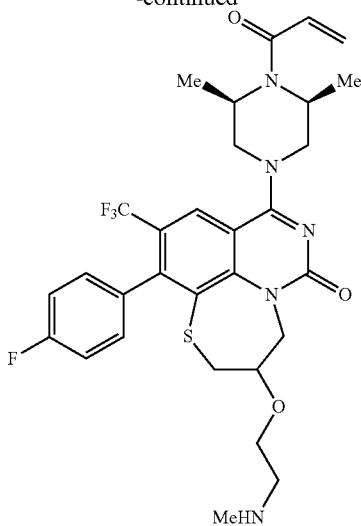
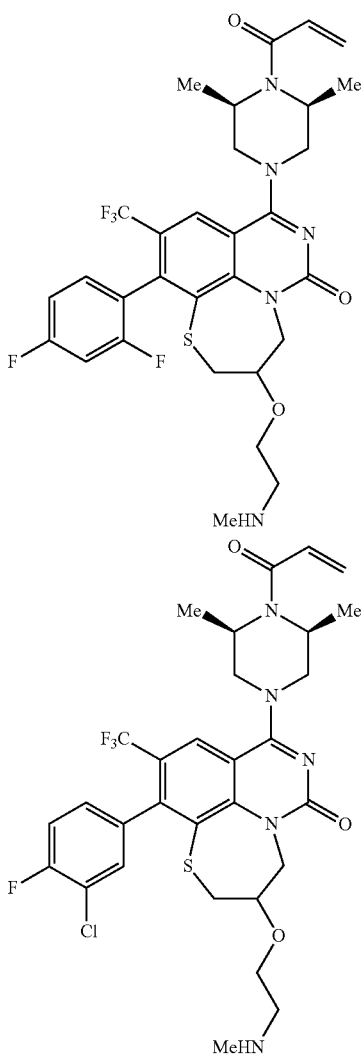

453
-continued
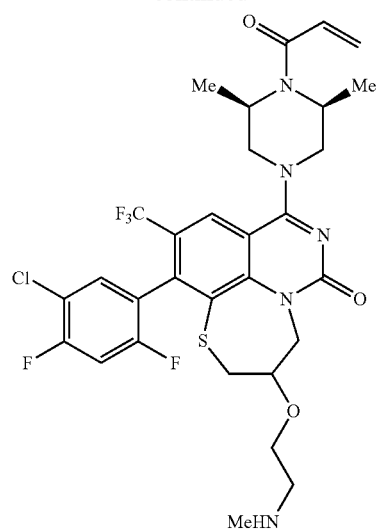
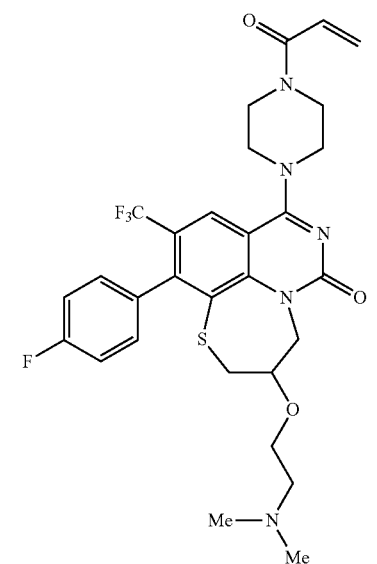
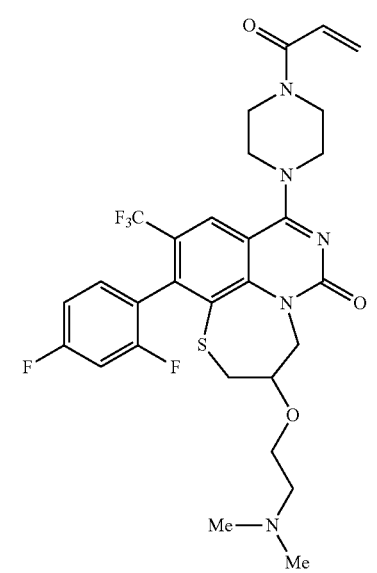
454
-continued
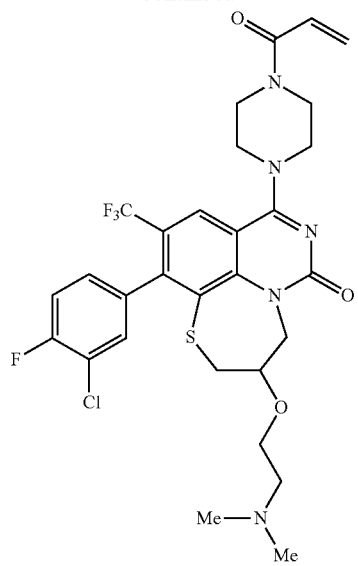
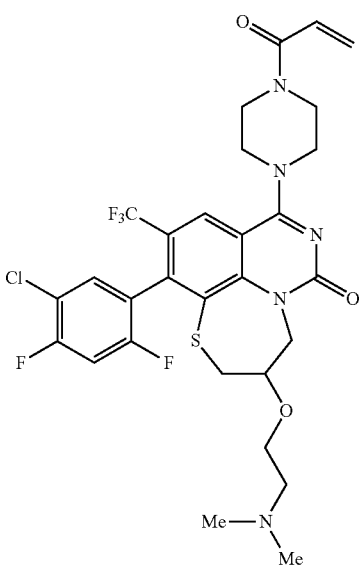
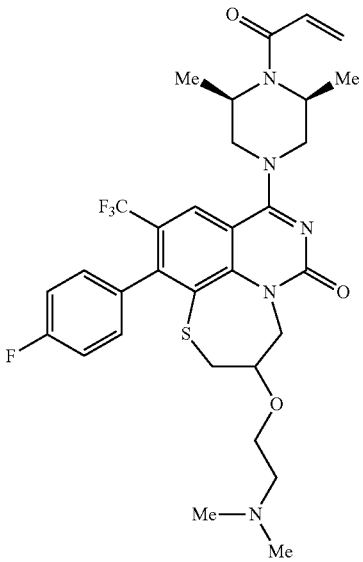

455
-continued
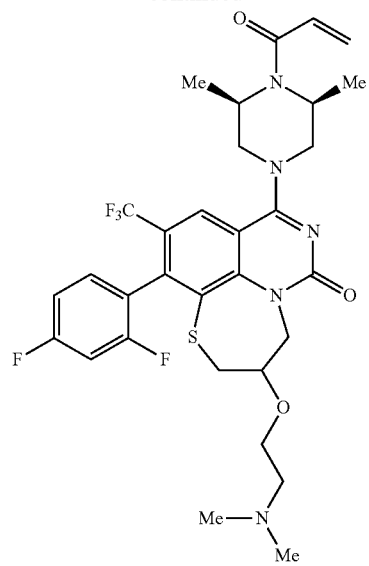

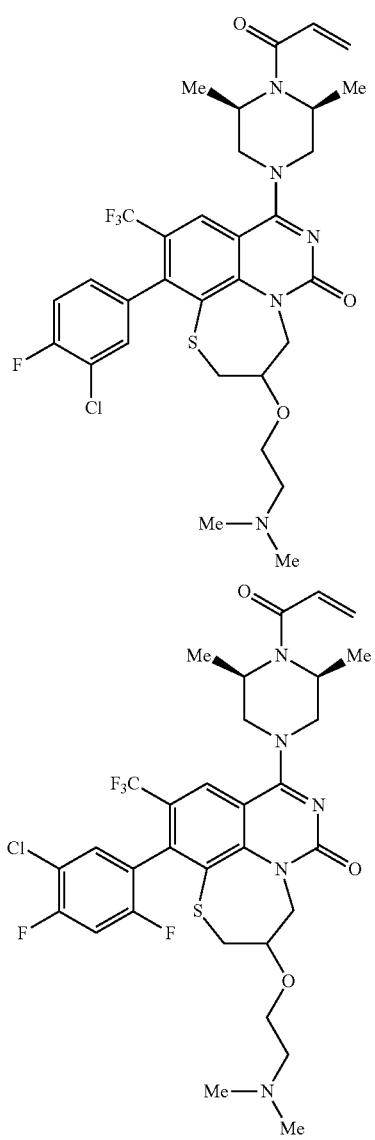
456
-continued
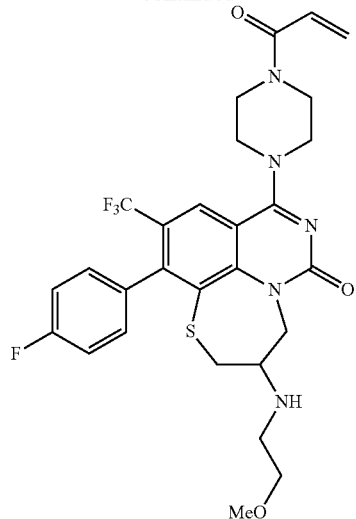
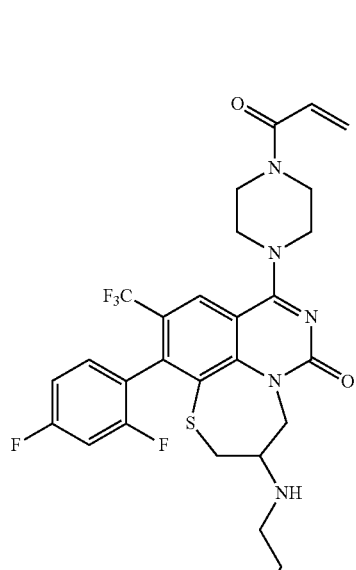
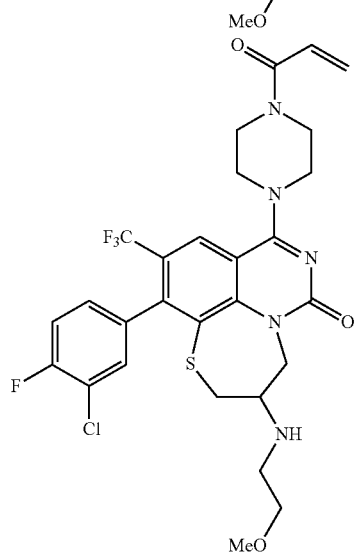

457
-continued

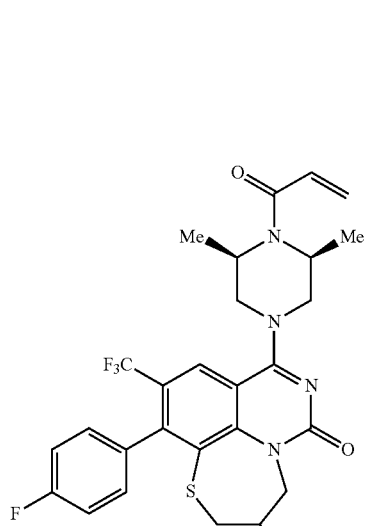

458
-continued
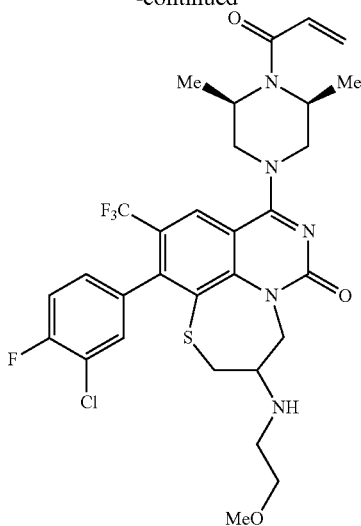
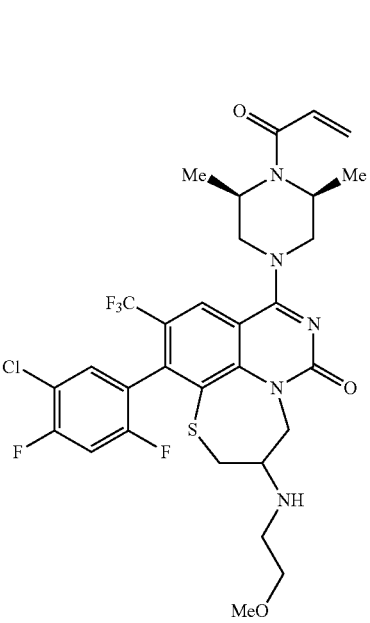
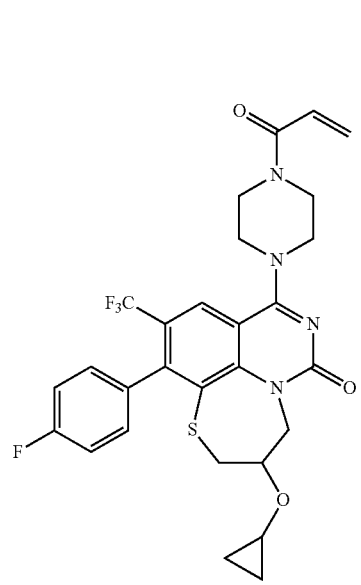

459
-continued
460
-continued
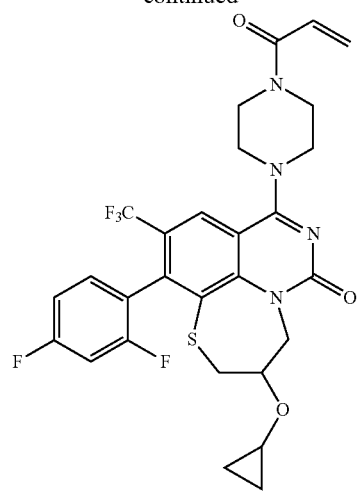
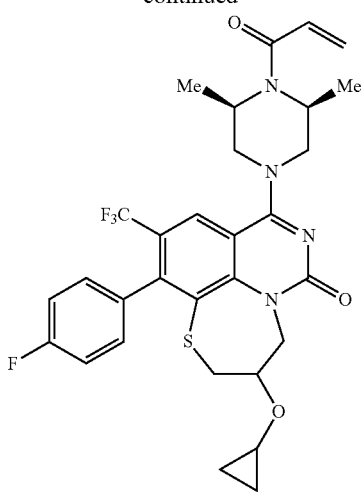

461
-continued

462
-continued
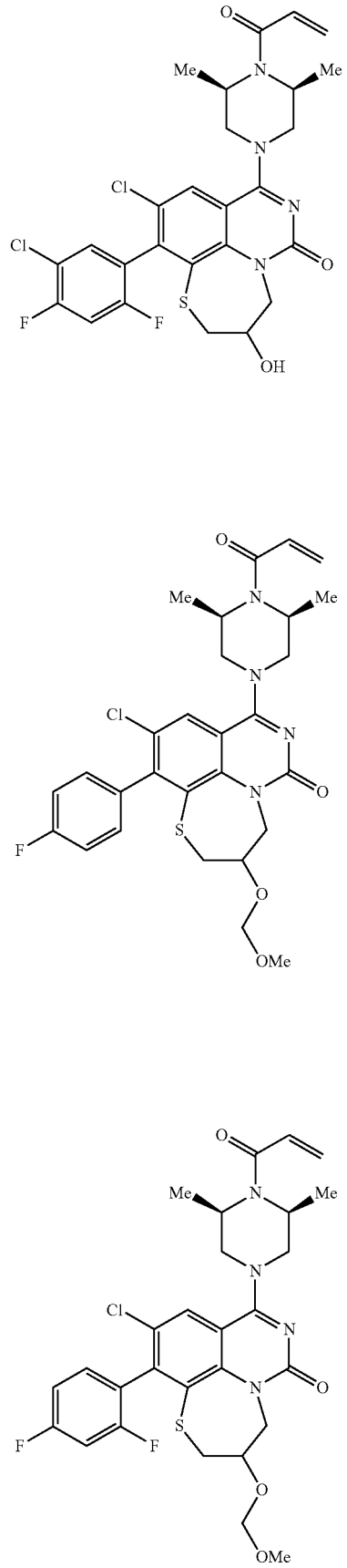

463
-continued
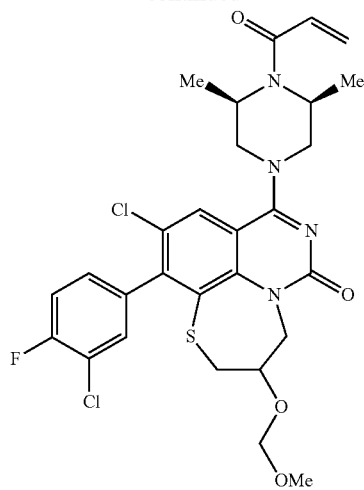
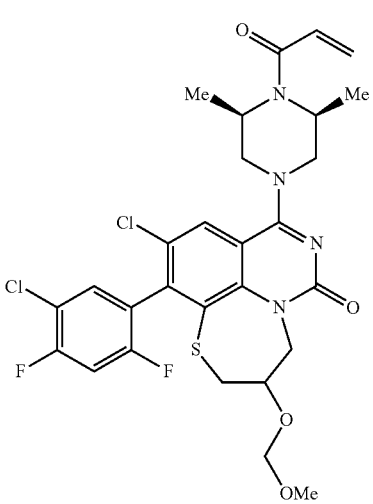
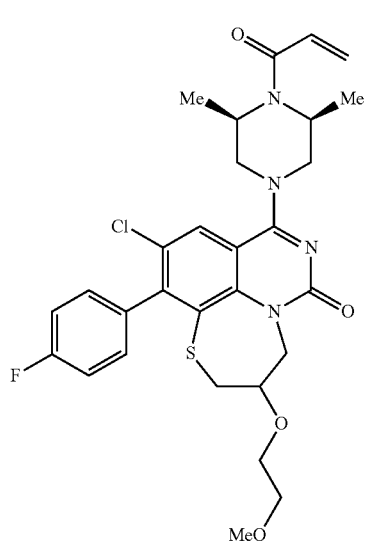
464
-continued
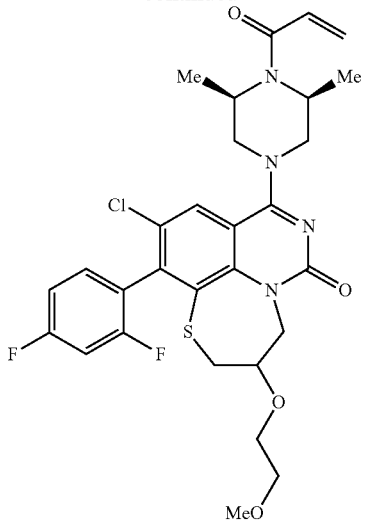
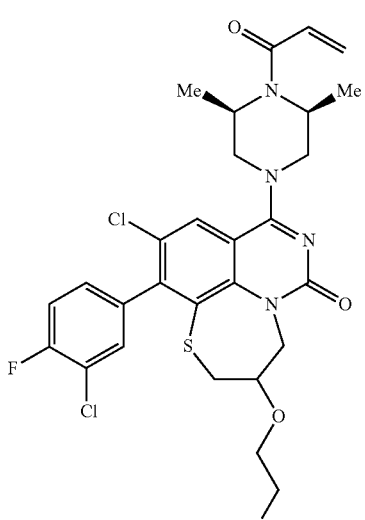
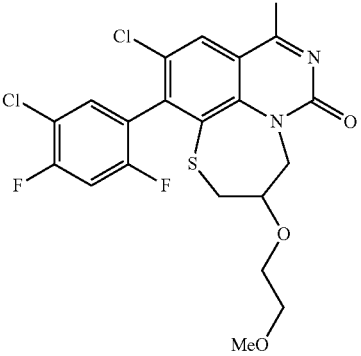

465
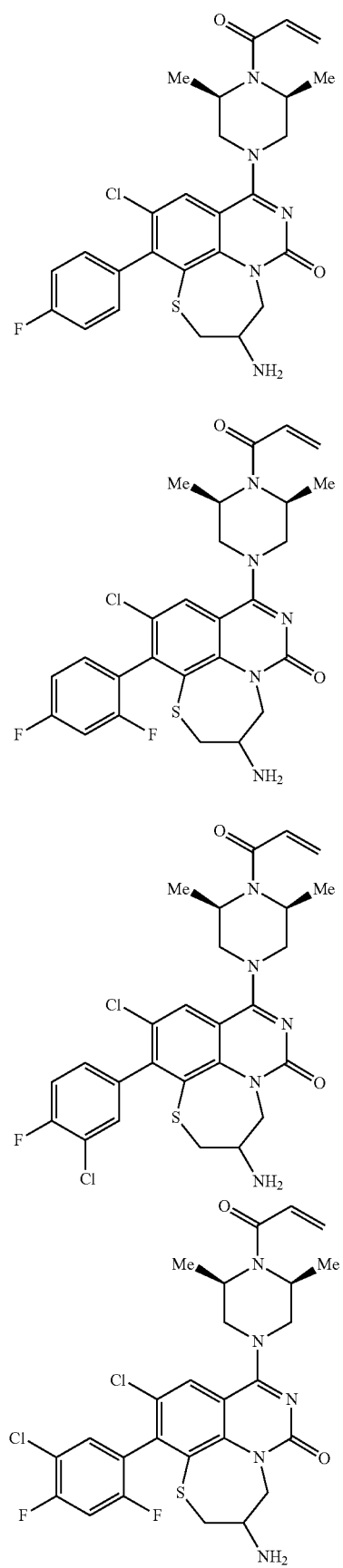
466
-continued
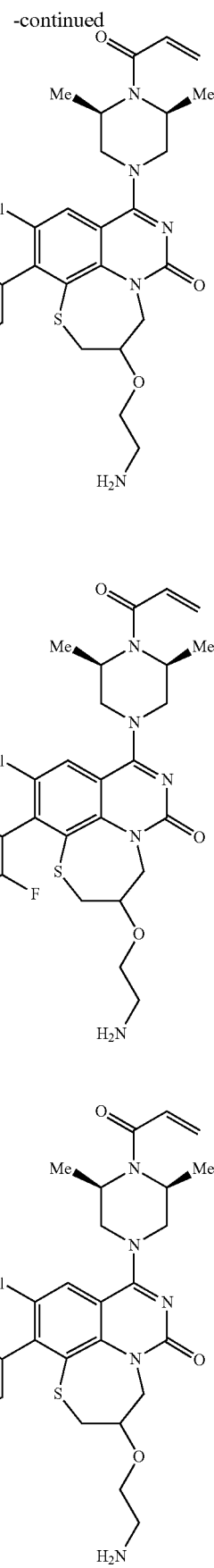

467
-continued
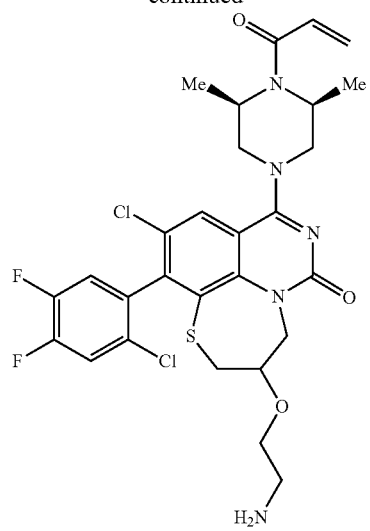
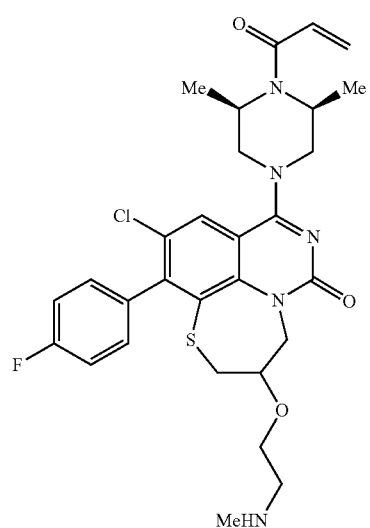
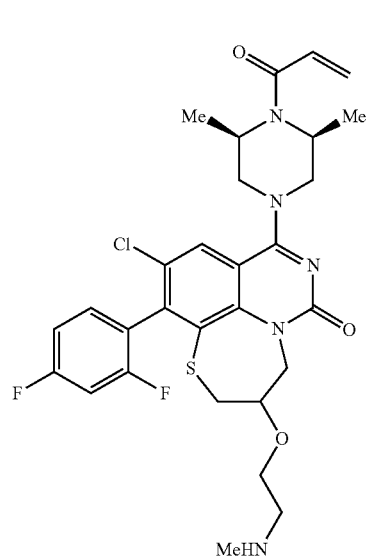
468
-continued
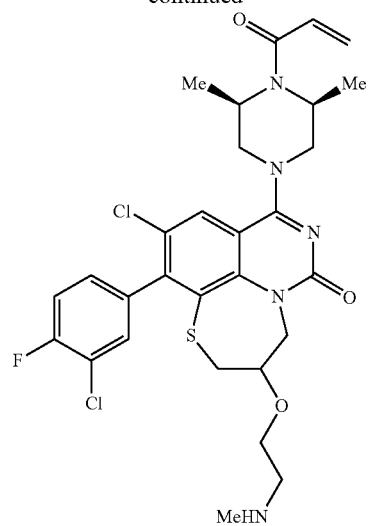
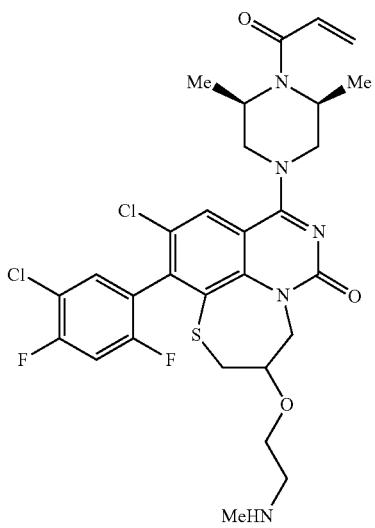
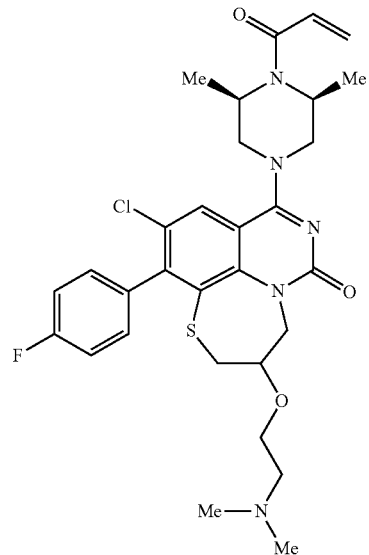

469
-continued
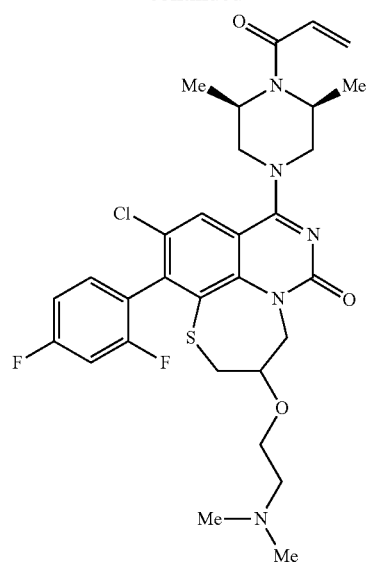
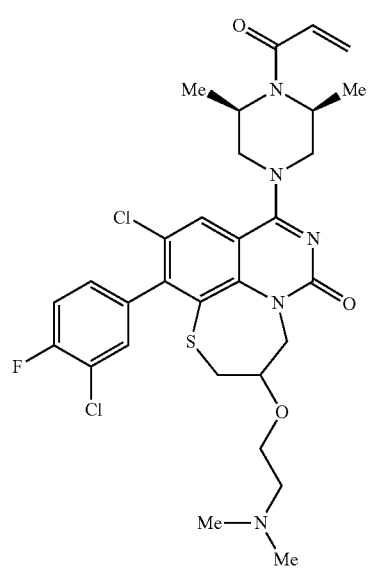
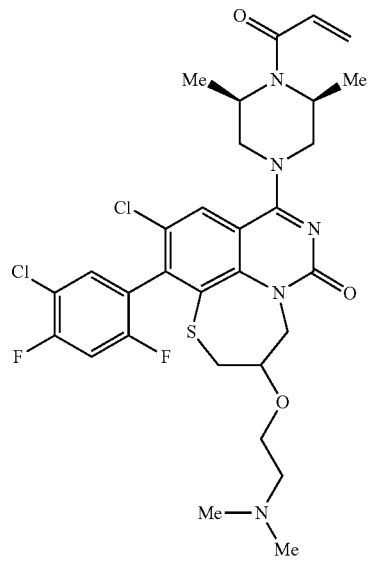
470
-continued
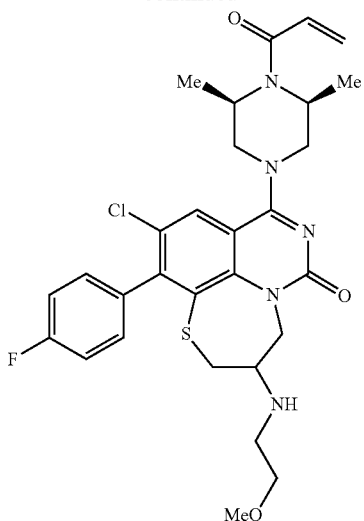
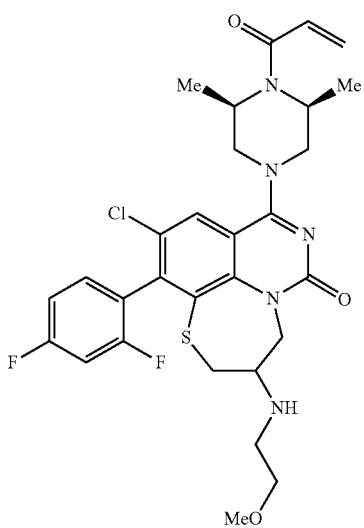
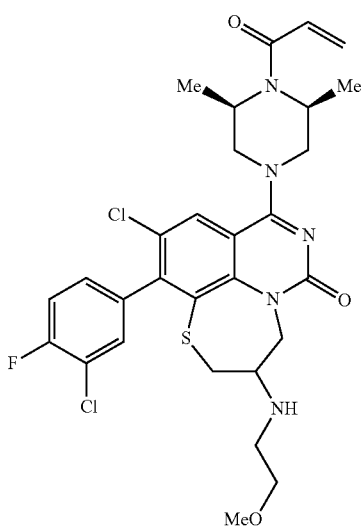

471
-continued
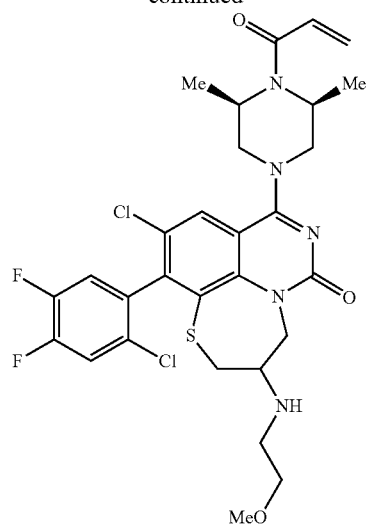
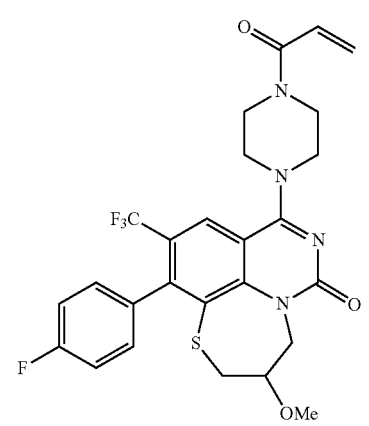
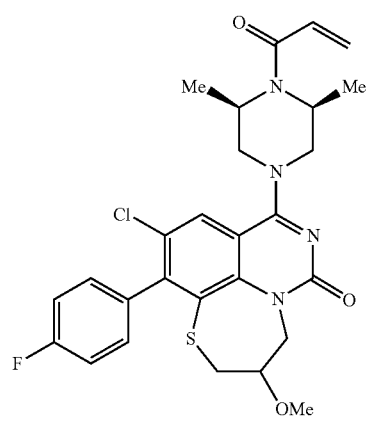
472
-continued
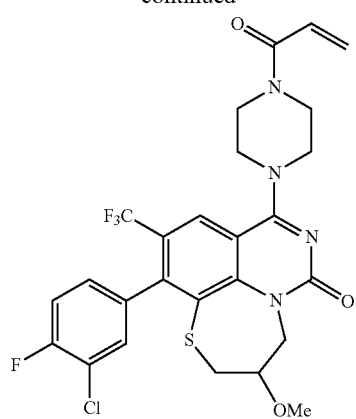
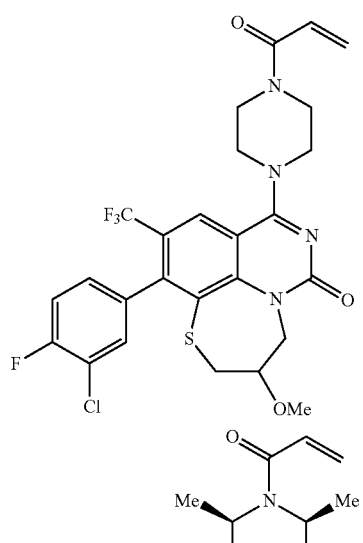
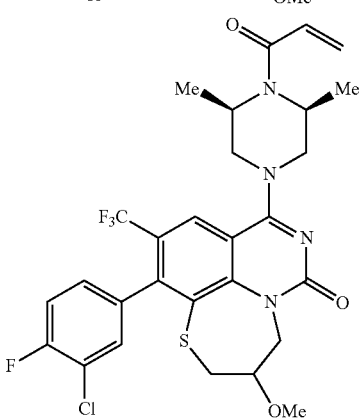
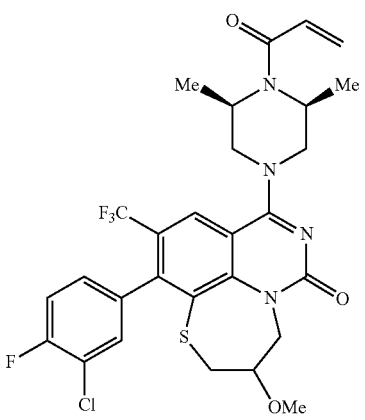

473
-continued
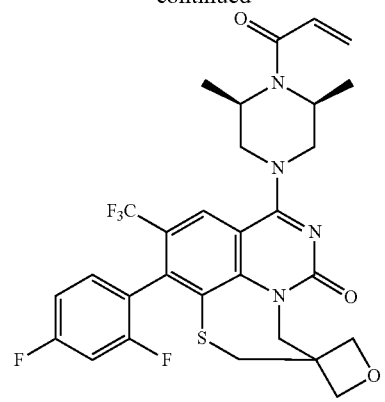
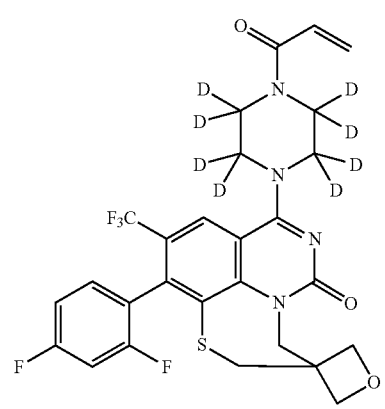
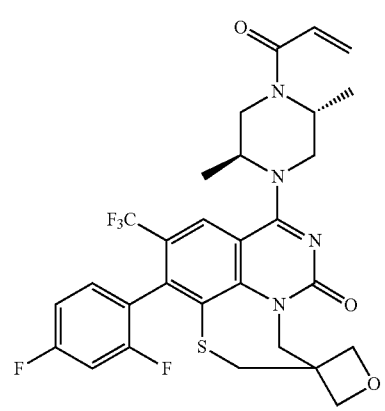
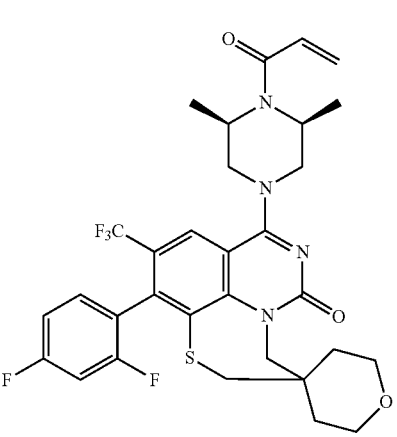
474
-continued
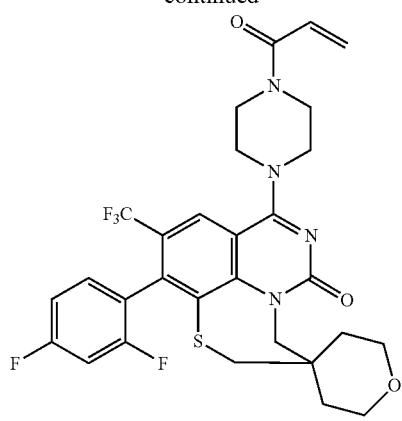
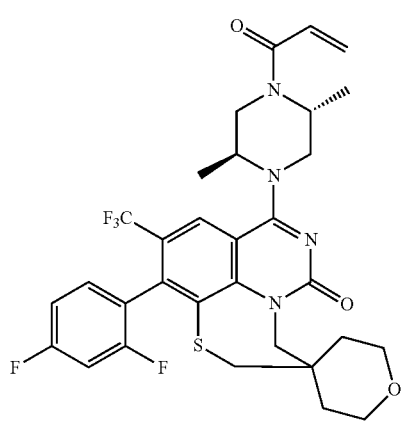
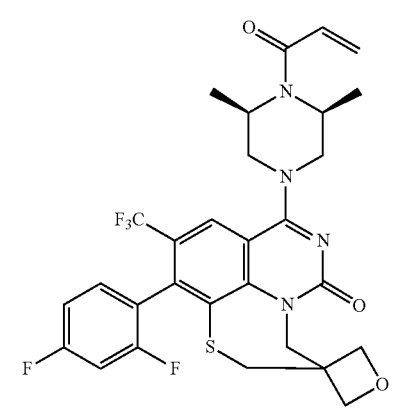
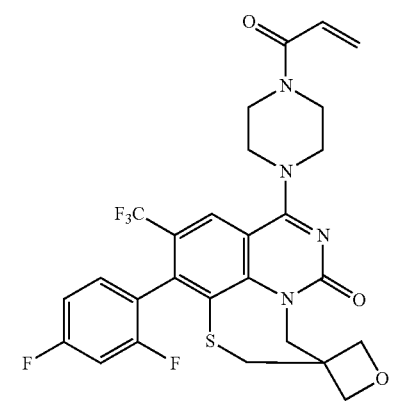

475
-continued
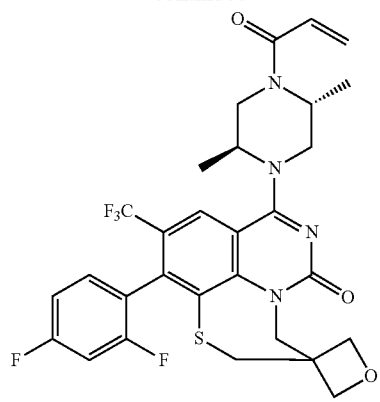
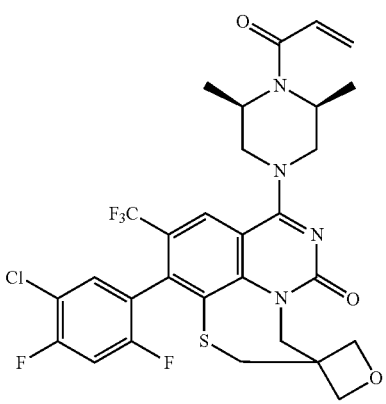

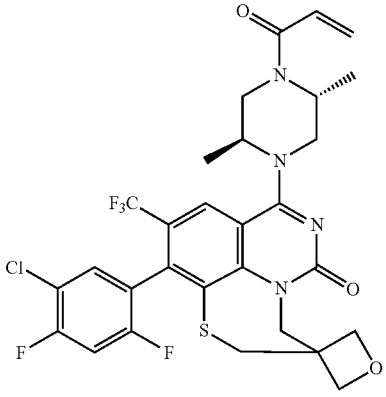
476
-continued
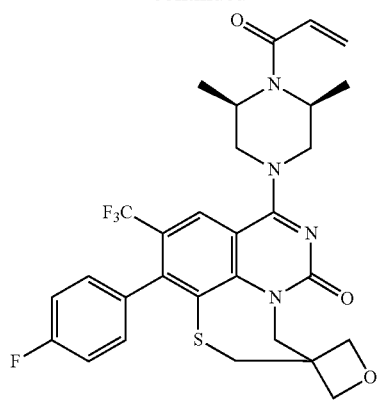
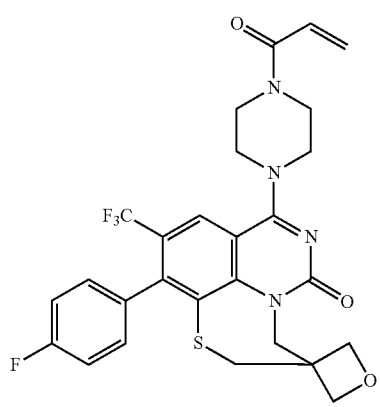
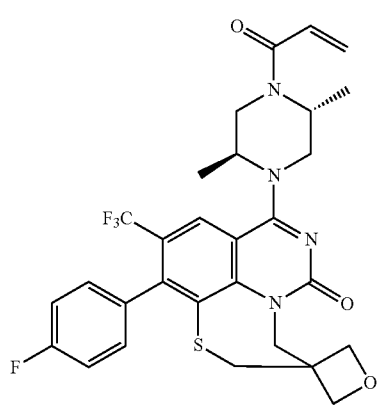
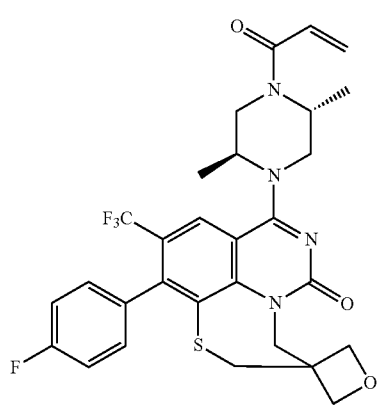
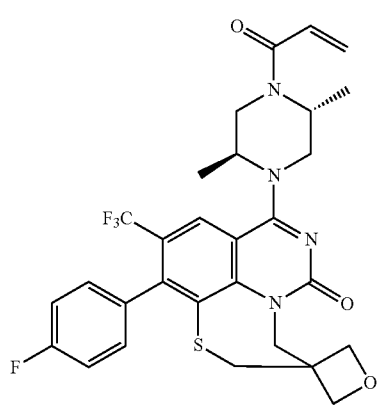

477
-continued
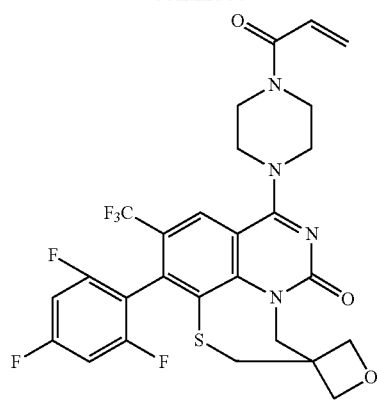
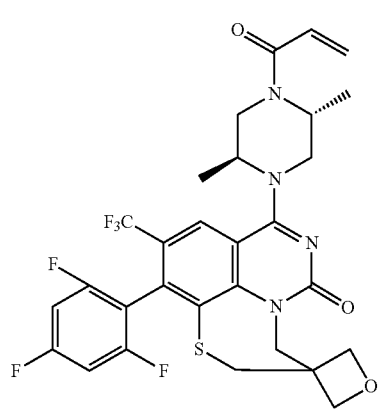
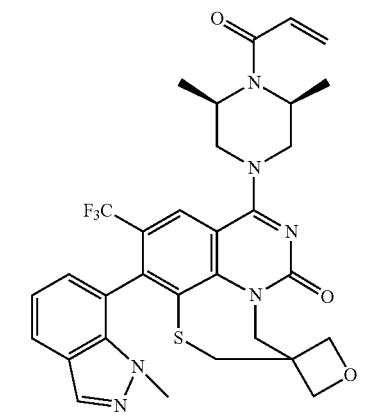
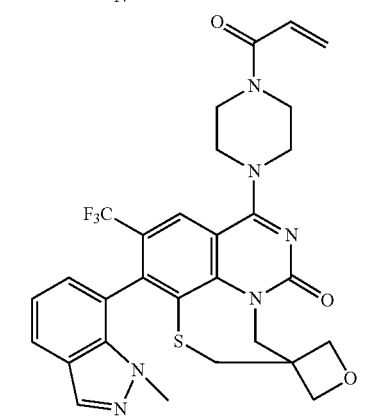
478
-continued
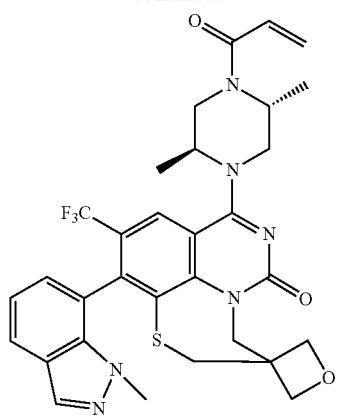
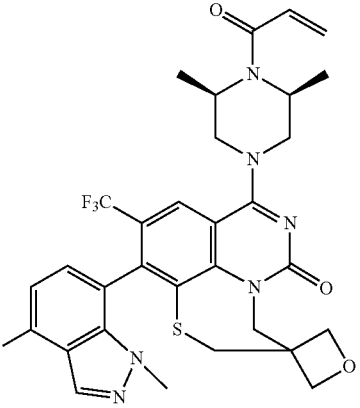
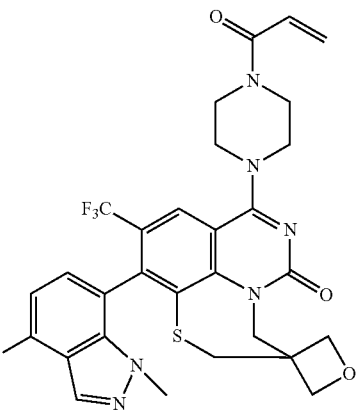
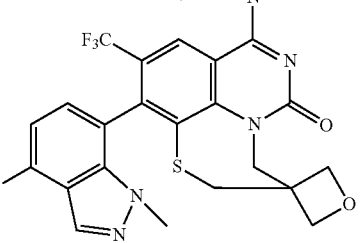

479
-continued
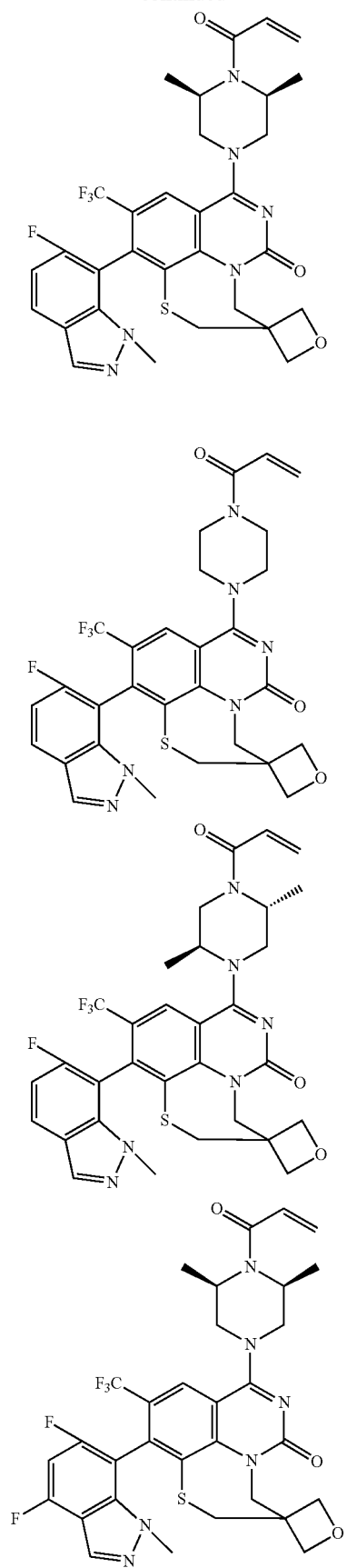
480
-continued
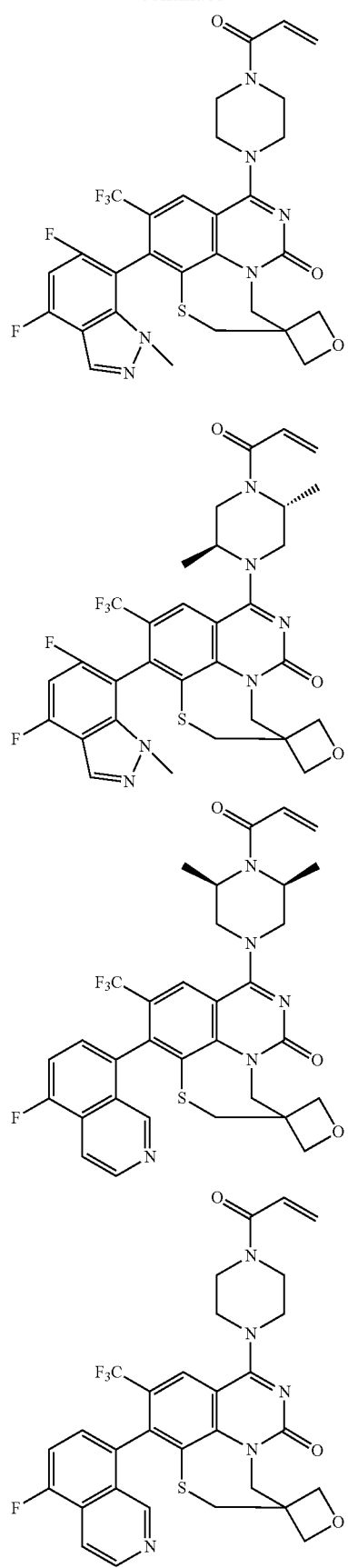

| 481 -continued | 482 -continued |
|---|---|
| 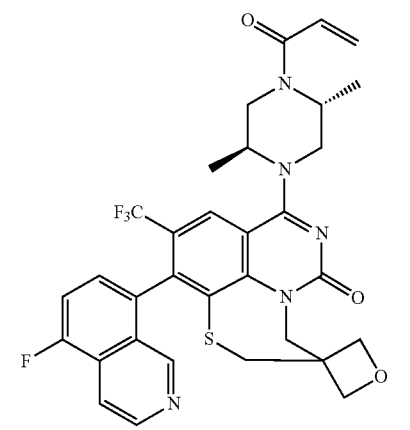 |  |
| 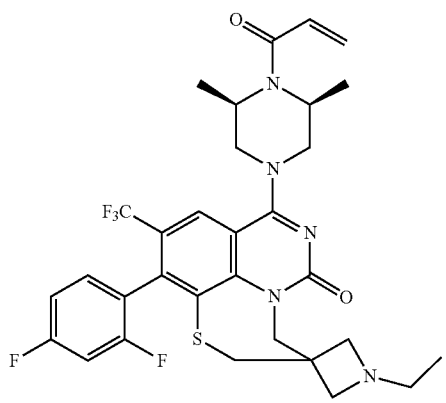 | 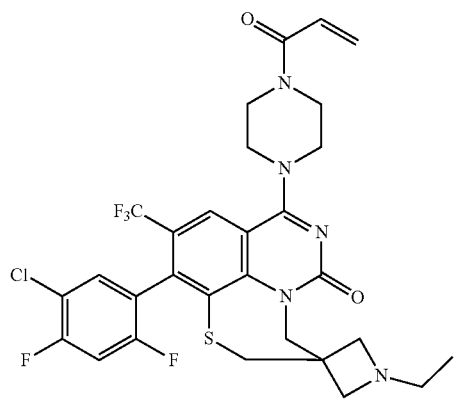 |
| 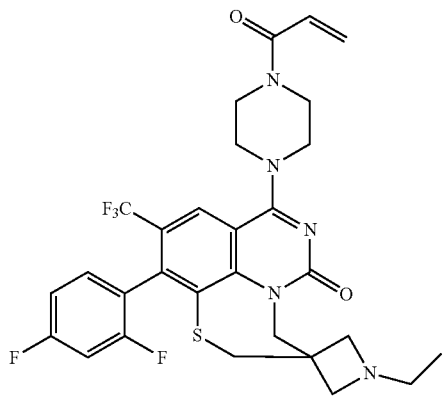 | 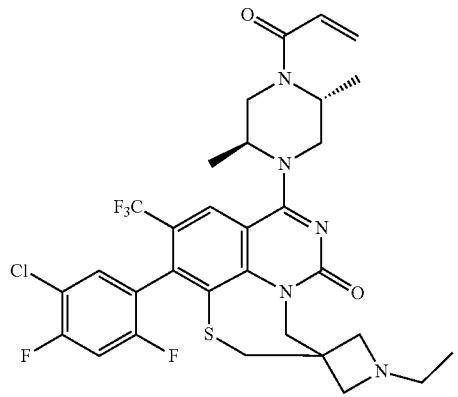 |
| 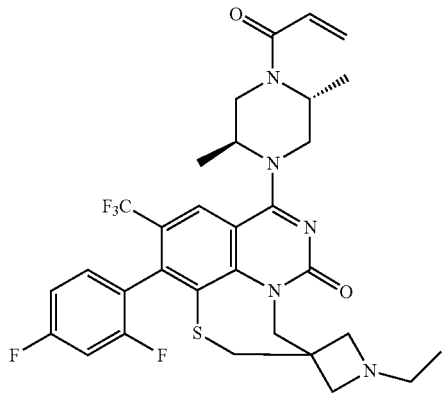 | 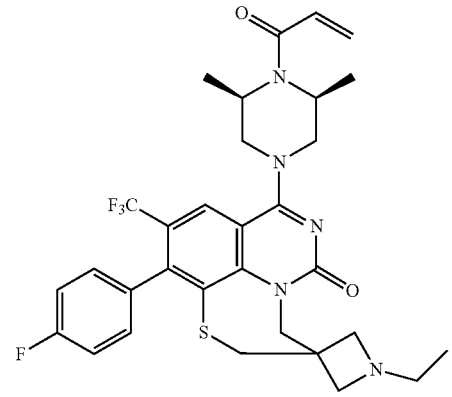 |

483
-continued
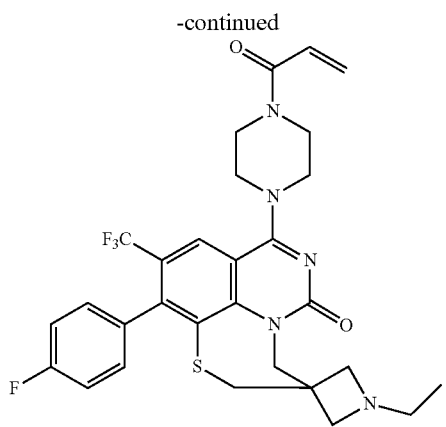
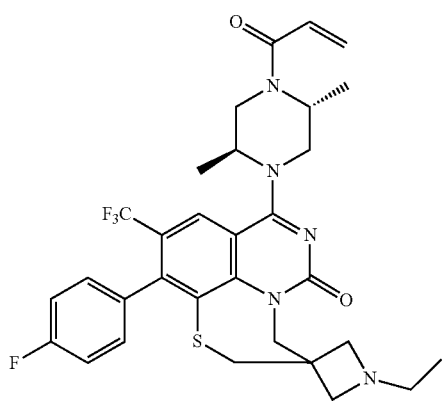
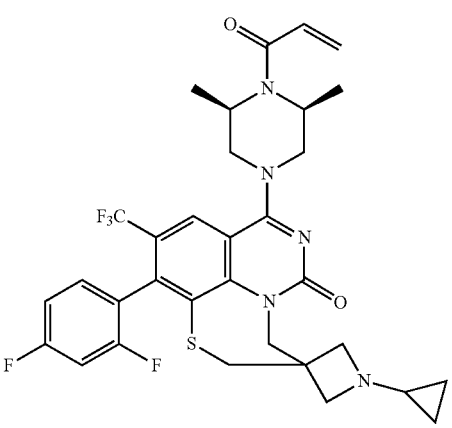
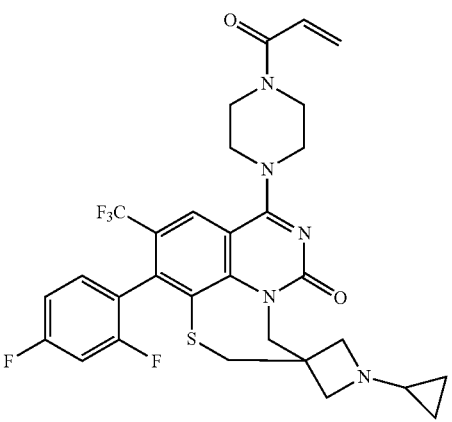
484
-continued
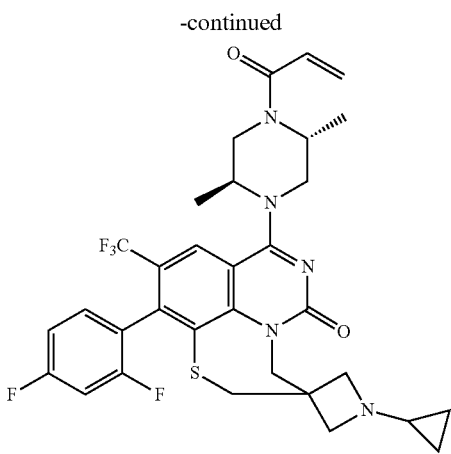
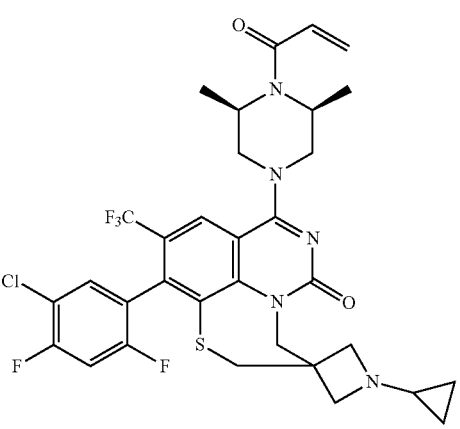
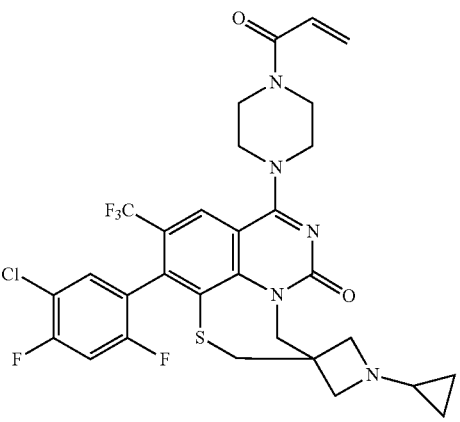
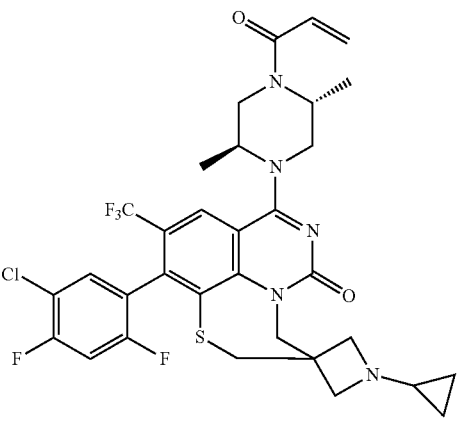

485
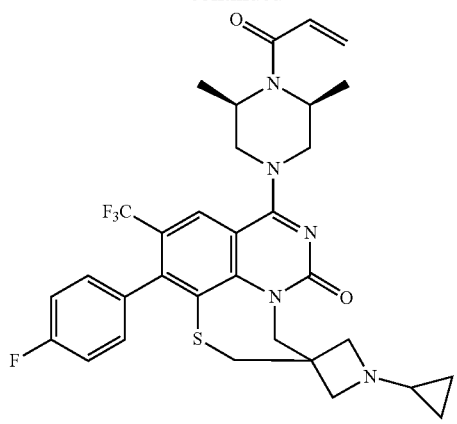
486
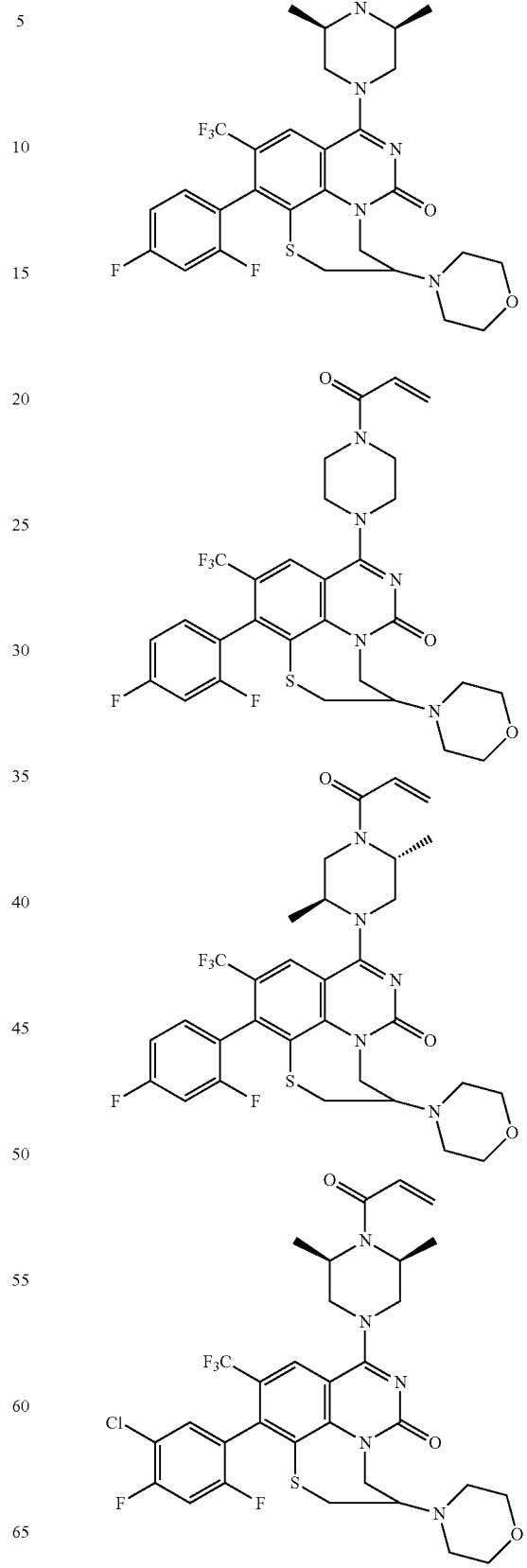

487
-continued
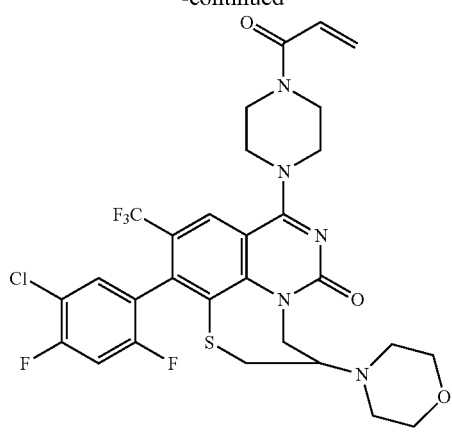
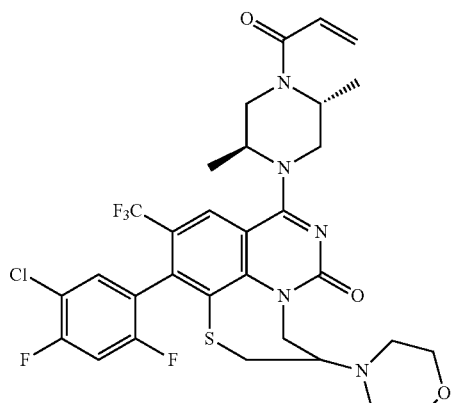
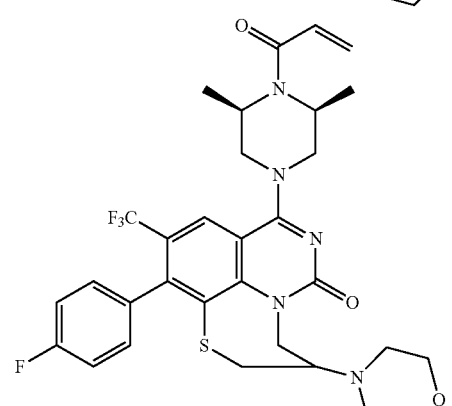
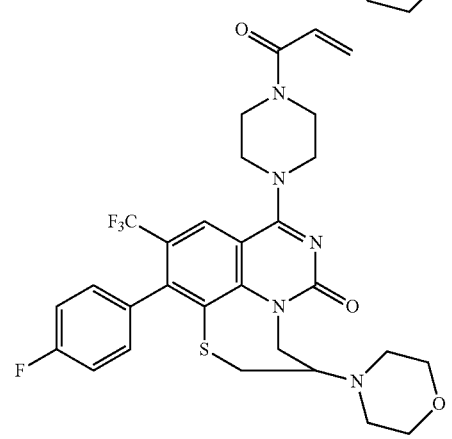
488
-continued
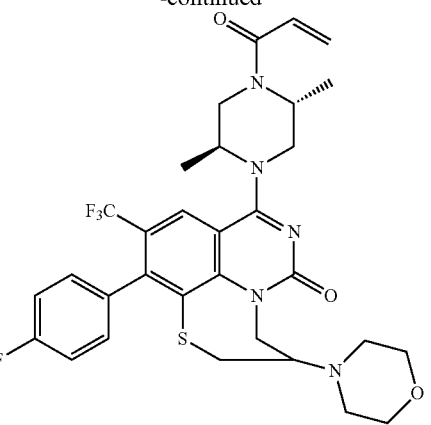
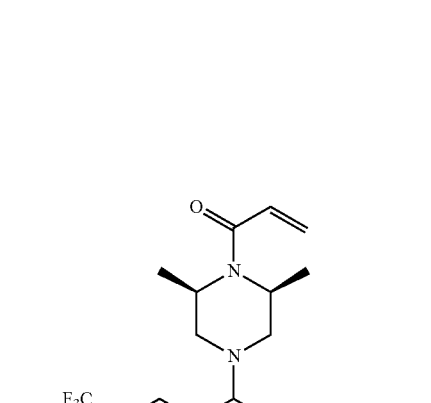
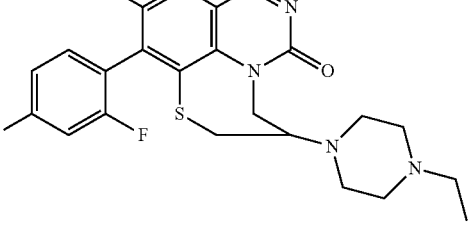
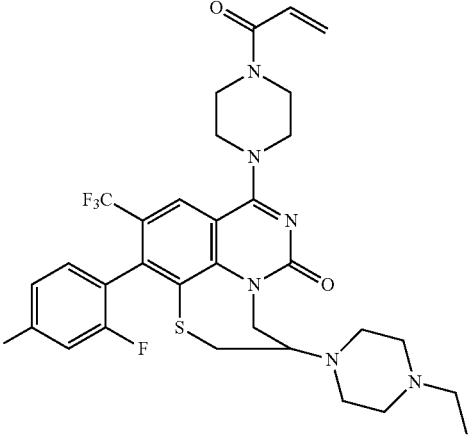

489
-continued
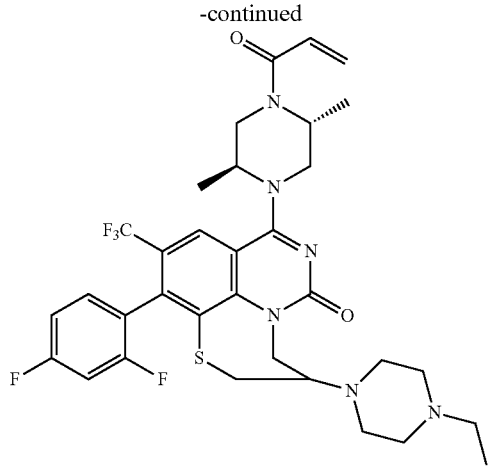
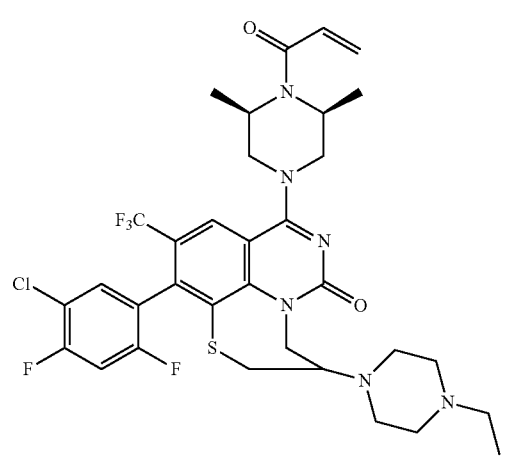
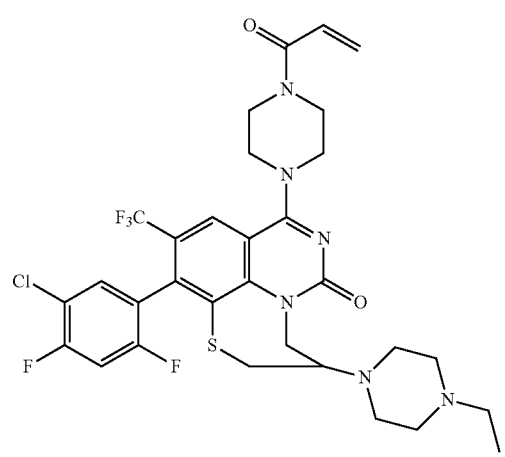
490
-continued
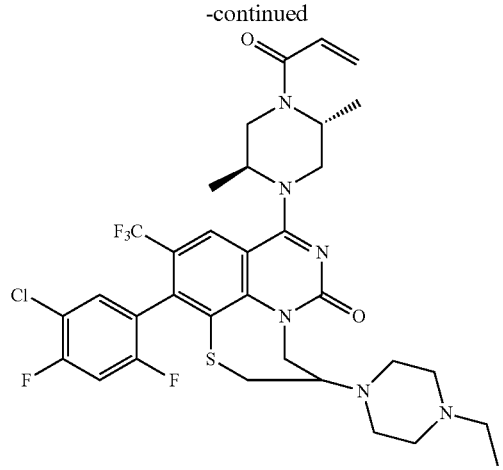
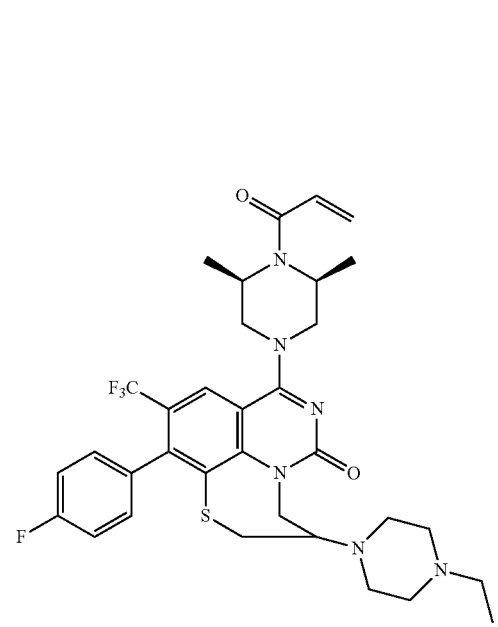
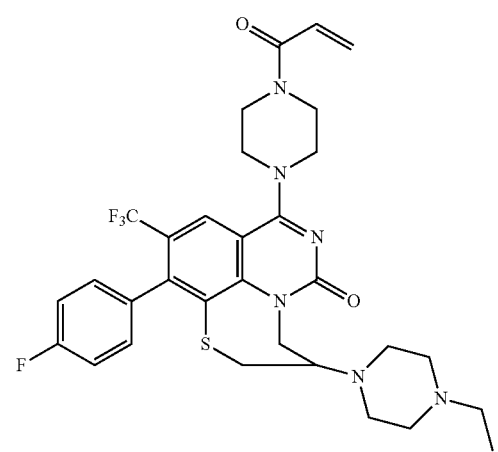

491
-continued
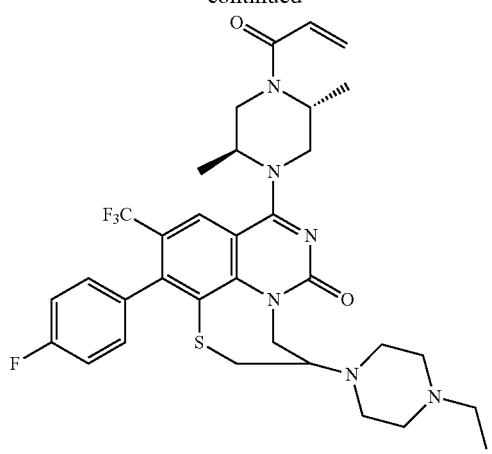
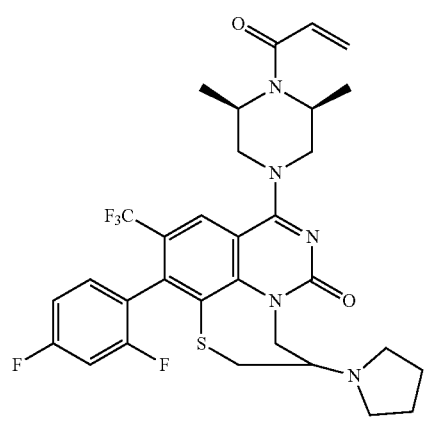
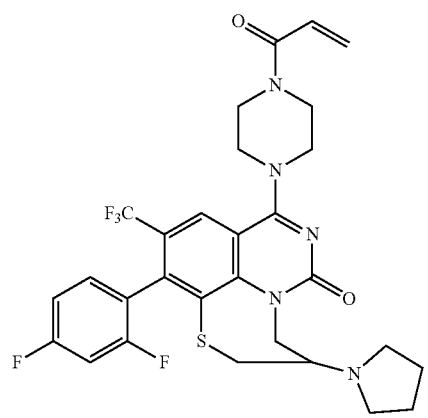

492
-continued
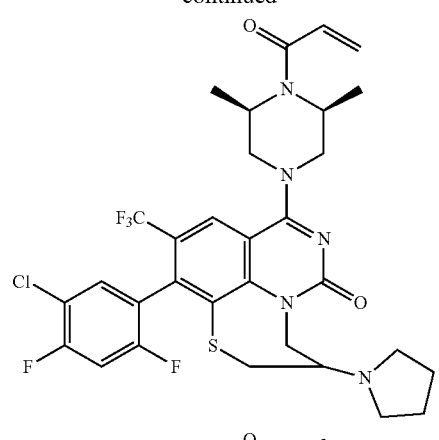
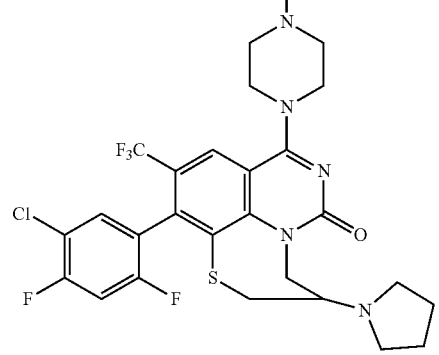
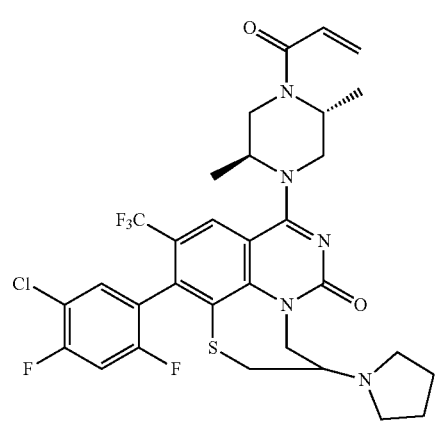
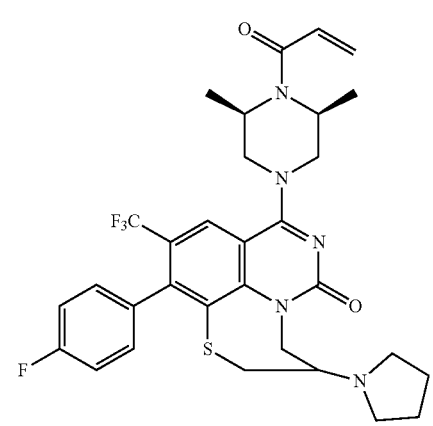

493
-continued
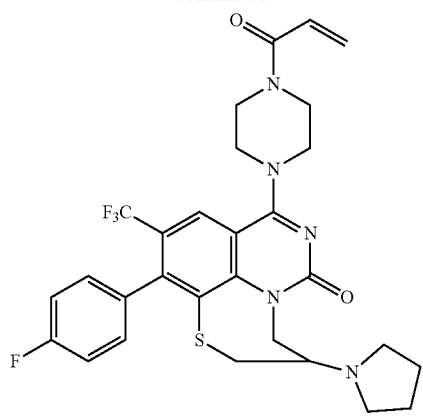
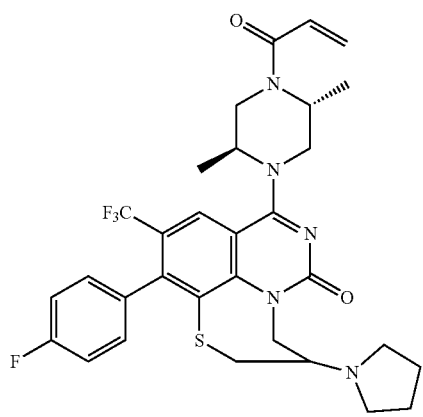

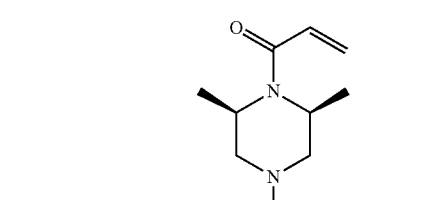
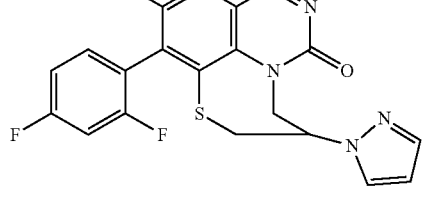
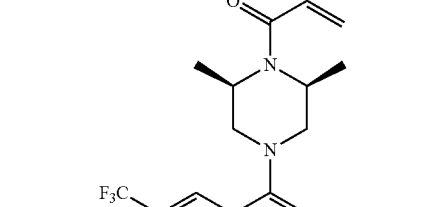
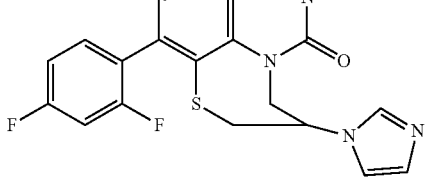
494
-continued
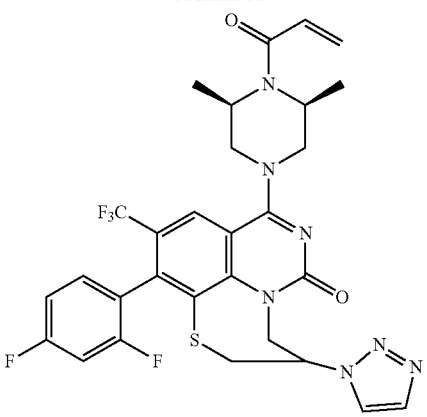
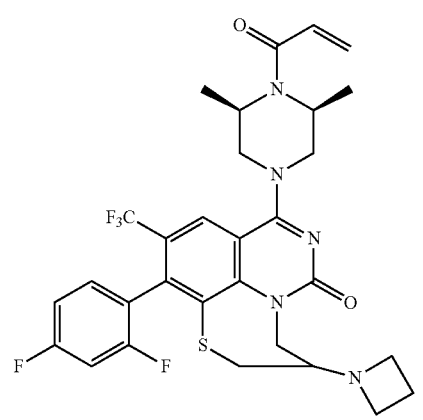
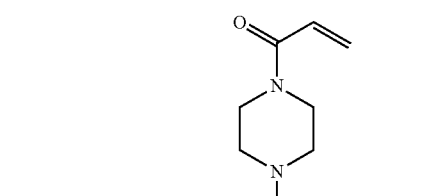
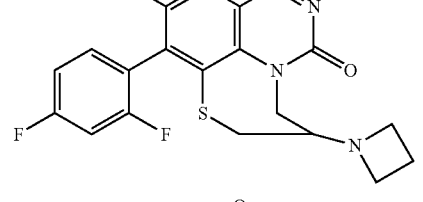
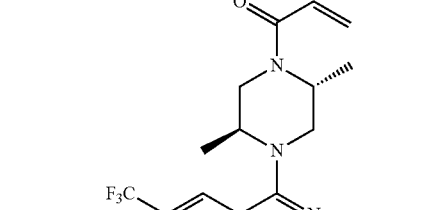
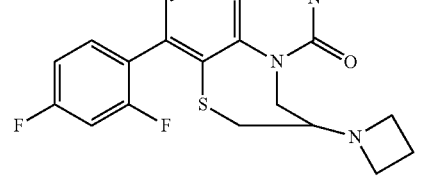

495
-continued
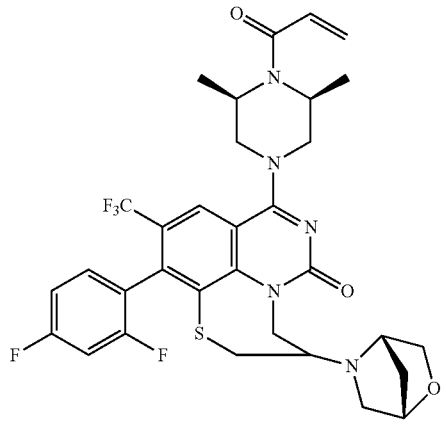
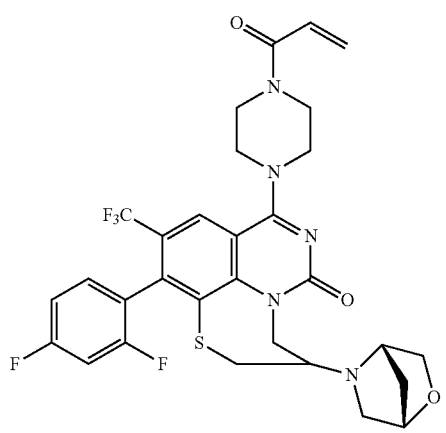

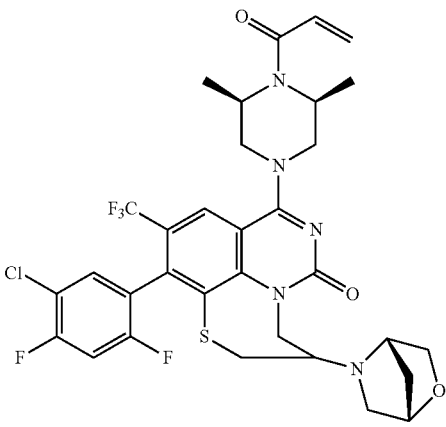
496
-continued
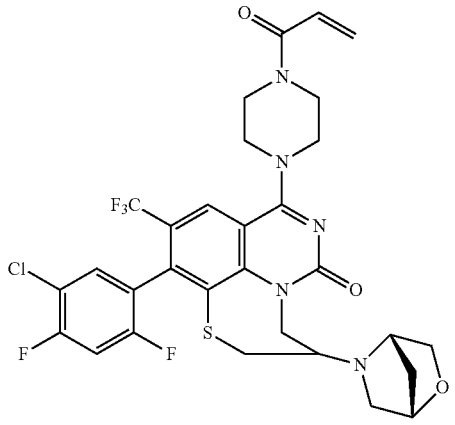
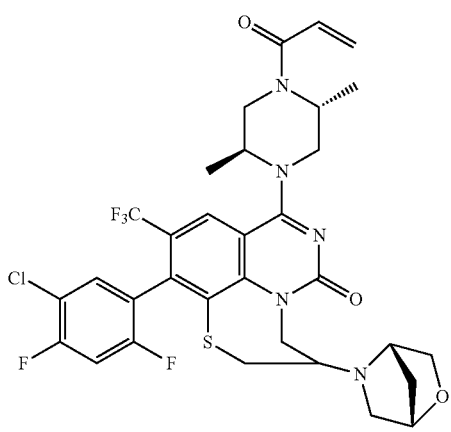
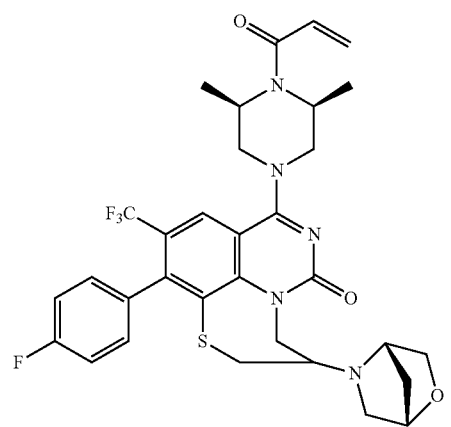
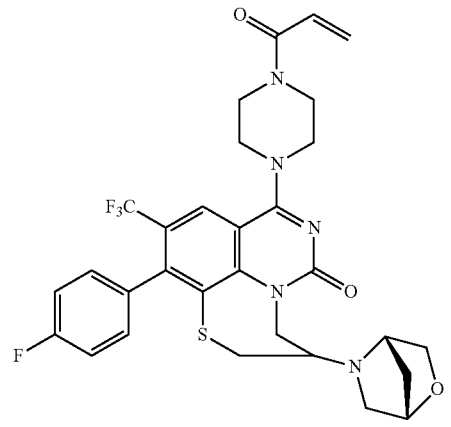

497
-continued
498
-continued
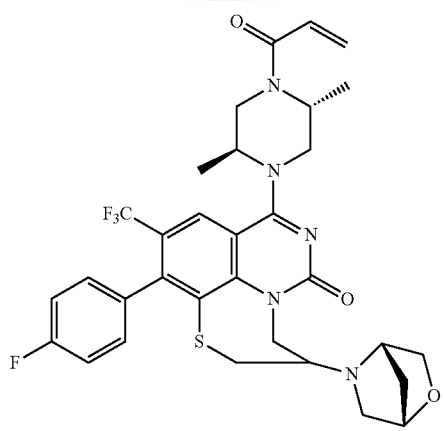
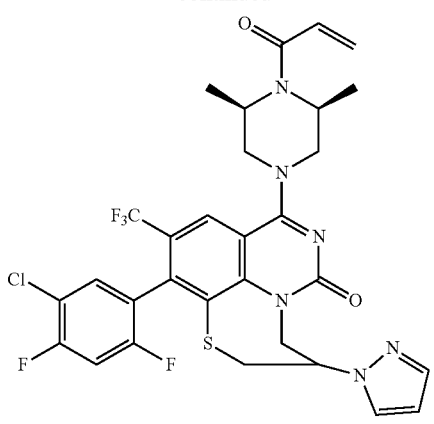

-continued

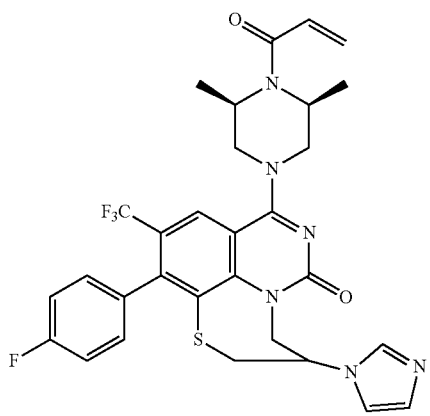

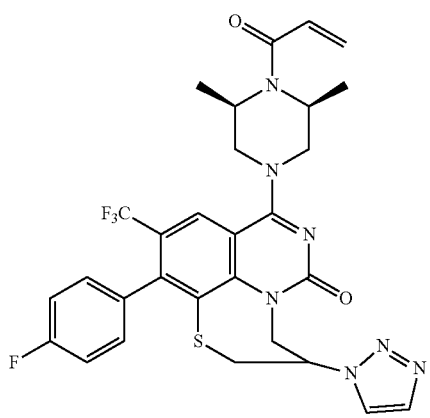

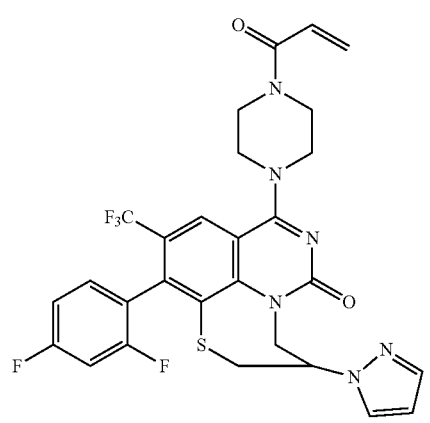

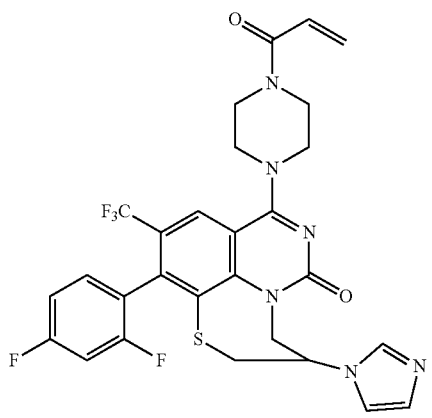

-continued

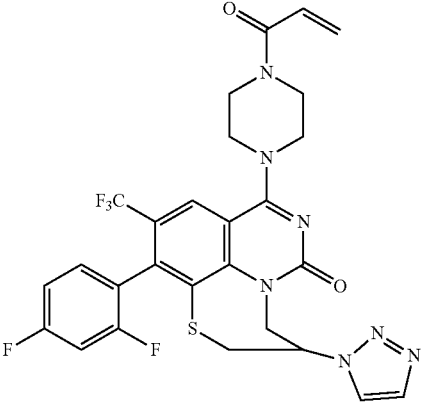

378. A pharmaceutical composition comprising a compound of embodiments 353 to 377.
379. A method of treating a subject with a cancer comprising a K-Ras G12C mutation comprising administering to the subject a compound of any one of embodiments 353 to 377 or pharmaceutical composition thereof.
380. Use of a compound of any one of embodiments 353 to 377 in the manufacture of a medicament for the treatment of a cancer comprising a K-Ras G12C mutation.
381. A pharmaceutically acceptable salt of any one of the compounds of embodiments 1 to 377.

VI. Examples

The following Examples are provided to illustrate exemplary embodiments of the compounds disclosed herein and their preparation.

Various starting materials and other reagents were purchased from commercial suppliers, such as Aldrich Chemical Company, and used without further purification, unless indicated otherwise. Compounds are prepared according to the exemplary procedures provided herein and modifications thereof known to those of skill in the art. The following abbreviations are used throughout the Examples: "Ac" means acetyl, "AcO" or "OAc" means acetoxy, "ACN" means acetonitrile, "aq" means aqueous, "atm" means atmosphere(s), "BOC", "Boc" or "boc" means N-tert-butoxycarbonyl, "Bn" means benzyl, "Bu" means butyl, "nBu" means normal-butyl, "tBu" means tert-butyl, "Cbz" means benzyloxycarbonyl, "DBU" means 1,8-diazabicyclo[5.4.0]undec-7-ene, "DCM" ($CH_2Cl_2$) means methylene chloride/dichloromethane, "de" means diastereomeric excess, "DEA" means diethylamine, "DIPEA" means diisopropylethyl amine, "DMA" means N,N-dimethylacetamide, "DMAP" means 4-dimethylaminopyridine, "DMF" means N,N-dimethyl formamide, "DMSO" means dimethylsulfoxide, "DPPP" means 1,3-bis(diphenylphosphino)propane, "ee" means enantiomeric excess, "Et" means ethyl, "EtOAc" means ethyl acetate, "EtOH" means ethanol, "HATU" means 1-[bis(dimethylamino)methylene]-1H-1,2,3-triazolo[4,5-b]pyridinium 3-oxid hexafluorophosphate, "HOAc" or "AcOH" means acetic acid, "i-Pr" means isopropyl, "IPA" means isopropyl alcohol, "LDA" means lithium diisopropylamide, "LiHMDS" or "LHMDS" means lithium hexamethyldisilazide, "Me" means methyl, "MeOH" means methanol, "$MgSO_4$" means magnesium sulphate, "MS" means mass spectrometry, "MTBE" means methyl tert-butyl ether, $Na_2SO_4$" means sodium sulphate, "NMP" means 1-methyl 2-pyrrolidinone, "Ph" means phenyl, "sat." means saturated, "SFC" means supercritical fluid chromatography, "TBME" or "MTBE" means tert-butyl methyl ether, "TEA" means triethyl amine, "TFA" means trifluoroacetic acid, "THF" means tetrahydrofuran, "TLC" means thin layer chromatography, "Rf" means retention fraction, "about" means approximately, "T" means retention time, "RT" means room temperature, "h" means hours, "min" means minutes, "N" means Normal, "M" means molar, "mL" means milliliter, "mmol" means millimoles, "µmol" means micromoles, "eq." means equivalent, "° C." means degrees Celsius, and "Pa" means pascals. $^1$H-NMR spectra are reported in ppm, and were obtained as $CDCl_3$ solutions (7.25 ppm), DMSO-$D_6$ solutions (2.50 ppm), or $CD_3OD$ solutions (3.4 ppm and 4.8 ppm), any may have used internal tetramethylsilane (0.00 ppm) as an internal standard when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

A. Example 1

7-((S)-4-acryloyl-2-methylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile The title compound was prepared according to the scheme below.

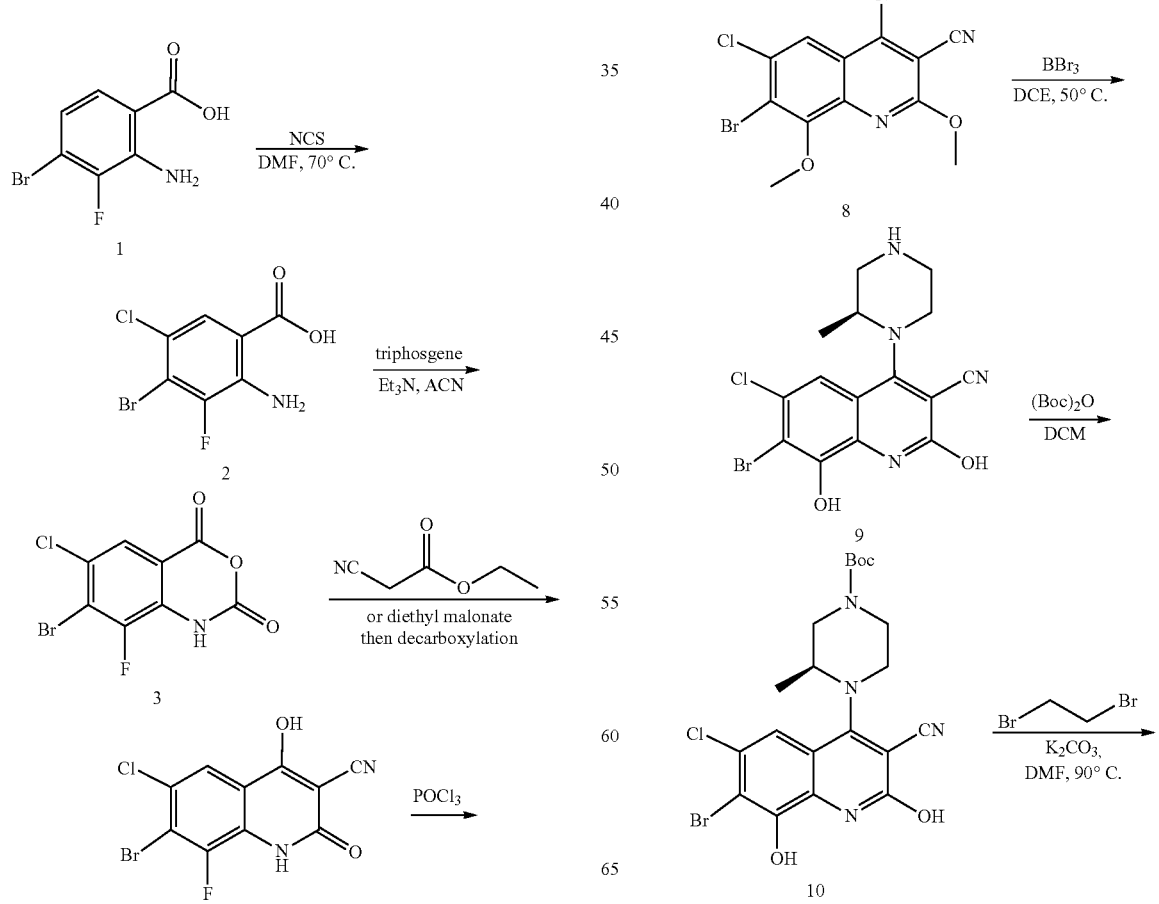

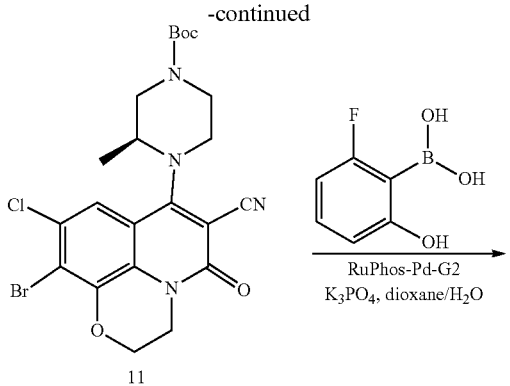

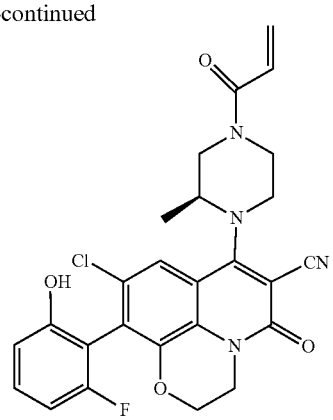

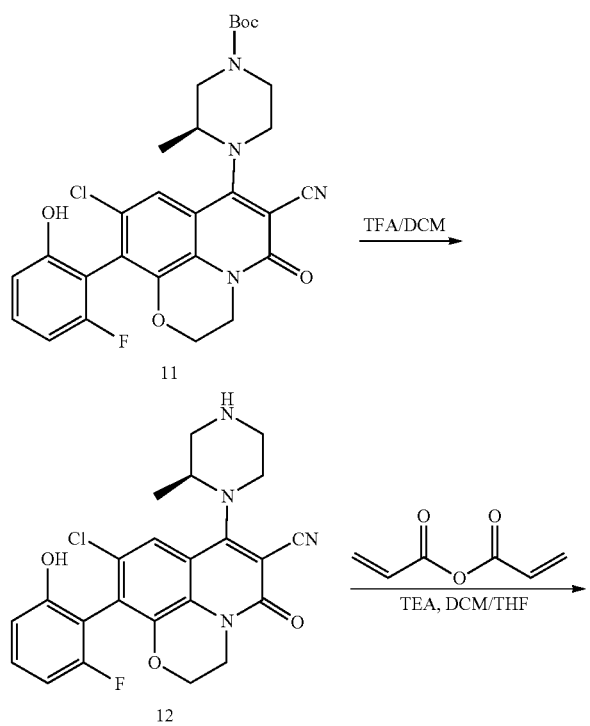

Step 1: 2-amino-4-bromo-5-chloro-3-fluorobenzoic acid

To a solution of 2-amino-4-bromo-3-fluorobenzoic acid (100 g, 0.43 mol) in DMF (800 ml) was added NCS (68 g, 0.51 mol). Then the mixture was heated to 70° C. for 16 hours. After completion, the mixture was quenched with water (1.5 L) and extracted with EA (2 L), dried with $Na_2SO_4$ and concentrated to afford product (139 g, crude) as a gray solid. LC-MS: m/z 268.1 [M−H]−.

Step 2: 7-bromo-6-chloro-8-fluoro-1H-benzo[d][1,3]oxazine-2,4-dione

To a solution of 2-amino-4-bromo-5-chloro-3-fluorobenzoic acid (10.0 g, 37.45 mmol) in acetonitrile (35 mL) was added pyridine (5.92 g, 74.7 mmol) at 50° C., the mixture was stirred at 50° C. for 5 min, then a solution of triphosgene (4.45 g, 15.0 mmol) in DCM (10 mL) was added dropwise. The resulting mixture was stirred for 3 h. After completion, the mixture was cooled to room temperature, filtered and washed with acetonitrile (50 mL) to afford the crude product (8.5 g, 77% yield) as a yellow solid. LC-MS: m/z 293.8 [M−H]+.

Step 3: 7-bromo-6-chloro-8-fluoro-4-hydroxy-2-oxo-1,2-dihydroquinoline-3-carbonitrile A solution of 7-bromo-6-chloro-8-fluoro-1H-benzo[d][1,3]oxazine-2,4-dione (8.5 g, 29.01 mmol) in ethyl 2-cyanoacetate (12 mL), the mixture was stirred at 200° C. for 30 min. After completion, the mixture was cooled to rt, filtered and washed with EA (100 mL) to afford crude product (5.5 g, crude) as brown solid, which was used to next step without further purification. LC-MS: m/z 316.9 [M−H]−.

Step 4: 7-bromo-2,4,6-trichloro-8-fluoroquinoline-3-carbonitrile

A solution of 7-bromo-6-chloro-8-fluoro-4-hydroxy-2-oxo-1,2-dihydroquinoline-3-carbonitrile (5.5 g, 17.32 mmol) in $POCl_3$ (15 mL), the mixture was stirred at 130° C. for 48 h. After completion, the mixture was concentrated under reduced pressure and dissolved with DCM (200 mL), the crude material was poured into water (200 mL), the organic layers were separated concentrated and the crude material was purified by silica gel column using a 4:1 mixture of PE in EA to afford the desired product (2.6 g, 36% yield) as a yellow solid. LC-MS: m/z 336.9 [M–H]⁻.

Step 5: (S)-tert-butyl 4-(7-bromo-2,6-dichloro-3-cyano-8-fluoroquinolin-4-yl)-3-methylpiperazine-1-carboxylate To a solution of 7-bromo-2,4,6-trichloro-8-fluoroquinoline-3-carbonitrile (800 mg, 2.26 mmol) and (S)-tert-butyl 3-methylpiperazine-1-carboxylate (905 mg, 4.52 mmol) in THF (10 mL) was added TEA (685 mg, 6.78 mmol), the mixture was stirred at rt for 16 h. After completion, the mixture was concentrated under reduced pressure and purified by silica gel column using a gradient 8:1 to 4:1 of PE in EA to afford the desired product (450 mg, 39% yield) as orange solid. LC-MS: m/z 519.0 [M+H]+; $^1$H NMR (400 MHz, CDCl$_3$): δ7.87 (d, J=2.0 Hz, 1H), 4.08-4.02 (m, 1H), 3.94-3.91 (m, 1H), 3.86-3.81 (m, 1H), 3.70-3.66 (m, 2H), 3.33-3.28 (m, 1H), 3.24-3.20 (m, 1H), 1.44 (s, 9H), 1.15 (d, J=6.8 Hz, 3H).

Step 6: (S)-tert-butyl 4-(7-bromo-6-chloro-3-cyano-2,8-dimethoxyquinolin-4-yl)-3-methylpiperazine-1-carboxylate To a solution of (S)-tert-butyl 4-(7-bromo-2,6-dichloro-3-cyano-8-fluoroquinolin-4-yl)-3-methylpiperazine-1-carboxylate (450 mg, 0.87 mmol) in THF (5 mL) was added CH$_3$ONa (0.5 mL, 2.62 mmol, 5M in MeOH) at 0° C., the mixture was slowly warmed to rt and stirred for an additional 3 h. After completion, the mixture was dissolved in DCM (150 mL), washed with an aqueous solution of NH$_4$Cl (100 mL×3), the organic layers were dried over Na$_2$SO$_4$ and concentrated under reduced pressure to afford the desired crude product (290 mg, 64% yield) as a yellow solid. LC-MS: m/z 527.0 [M+H]+.

Step 7: (S)-7-bromo-6-chloro-2,8-dihydroxy-4-(2-methylpiperazin-1-yl)quinoline-3-carbonitrile To a solution of (S)-tert-butyl 4-(7-bromo-6-chloro-3-cyano-2,8-dimethoxyquinolin-4-yl)-3-methylpiperazine-1-carboxylate (360 mg, 0.69 mmol) in DCE (5 mL) was added BBr$_3$ (6.8 mL, 6.87 mmol, 1M in DCM) at 0° C. under N$_2$, the mixture was stirred at 50° C. for 16 h. After completion, the mixture was cooled to 0° C., the pH was adjusted to 8~9 with NH$_3$·MeOH and concentrated under reduced pressure to afford the crude product (500 mg) as a yellow solid. LC-MS: m/z 398.9 [M+H]+.

Step 8: (S)-tert-butyl 4-(7-bromo-6-chloro-3-cyano-2,8-dihydroxyquinolin-4-yl)-3-methylpiperazine-1-carboxylate To a solution of (S)-7-bromo-6-chloro-2,8-dihydroxy-4-(2-methylpiperazin-1-yl)quinoline-3-carbonitrile (500 mg, 1.26 mmol) and di-tert-butyl dicarbonate (412 mg, 1.89 mmol) in DCM (8 mL) was added TEA (254 mg, 2.52 mmol). The mixture was stirred at rt for 16 h, concentrated under reduced pressure and purified by silica gel column using a mixture 10:1 of DCM in NH$_3$·MeOH to afford the desired product (300 mg, crude) as a yellow solid.

Step 9: (S)-tert-butyl 4-(10-bromo-9-chloro-6-cyano-5-oxo-3,5-dihydro-2H-[1,4]oxazino[2,3,4-ij]quinolin-7-yl)-3-methylpiperazine-1-carboxylate To a solution of (S)-tert-butyl 4-(7-bromo-6-chloro-3-cyano-2,8-dihydroxyquinolin-4-yl)-3-methylpiperazine-1-carboxylate (300 mg, 0.60 mmol) and 1,2-dibromoethane (341 mg, 1.81 mmol) in DMF (4 mL) was added K$_2$CO$_3$ (250 mg, 1.81 mmol), the mixture was stirred at 90° C. for 3 h, concentrated under reduced pressure and purified by silica gel column using a 50:1 mixture of DCM in MeOH to afford the desired product (165 mg, 53% yield) as a yellow solid. $^1$H NMR (400 MHz, CDCl$_3$): δ 7.57 (s, 1H), 4.63-4.58 (m, 1H), 4.49-4.36 (m, 3H), 4.11-4.03 (m, 2H), 3.98-3.88 (m, 2H), 3.70-3.69 (m, 1H), 3.38-3.32 (m, 1H), 3.22-3.18 (m, 1H), 1.50 (s, 9H), 1.23 (d, J=6.4 Hz, 3H).

Step 10: (3S)-tert-butyl 4-(9-chloro-6-cyano-10-(2-fluoro-6-hydroxyphenyl)-5-oxo-3,5-dihydro-2H-[1,4]oxazino[2,3,4-ij]quinolin-7-yl)-3-methylpiperazine-1-carboxylate To a solution of (S)-tert-butyl 4-(10-bromo-9-chloro-6-cyano-5-oxo-3,5-dihydro-2H-[1,4]oxazino[2,3,4-ij]quinolin-7-yl)-3-methylpiperazine-1-carboxylate (165 mg, 0.32 mmol) and (2-fluoro-6-hydroxyphenyl)boronic acid (247 mg, 1.58 mmol) in dioxane (3 mL) and H$_2$O (0.5 mL) was added RuPhos Pd G2 (23.3 mg, 0.03 mmol) and K$_3$PO$_4$ (204 mg, 0.96 mmol), the mixture was stirred at 100° C. for 5 h. After completion, the mixture was concentrated under reduced pressure and purified by silica gel column using a 60:1 mixture of DCM in MeOH to afford the desired product (98 mg, 56% yield) as a yellow solid.

Step 11: 9-chloro-10-(2-fluoro-6-hydroxyphenyl)-7-((S)-2-methylpiperazin-1-yl)-5-oxo-3,5-dihydro-2H-[1,4]oxazino[2,3,4-ij]quinoline-6-carbonitrile TFA (1 mL) was added to a solution of (3S)-tert-butyl 4-(9-chloro-6-cyano-10-(2-fluoro-6-hydroxyphenyl)-5-oxo-3,5-dihydro-2H-[1,4]oxazino[2,3,4-ij]quinolin-7-yl)-3-methylpiperazine-1-carboxylate (98 mg, 0.18 mmol) in dichloromethane (1 mL) at 0° C., the mixture was stirred at rt for 1 hour. Triethylamine was slowly added to adjust the pH to 8-9. The mixture was concentrated and purified by prep-HPLC with a gradient 5 to 95% of ACN in H$_2$O to give the crude product as a white solid. LC-MS: m/z 455.1 [M+H]+; $^1$H NMR (400 MHz, CD$_3$OD) δ 7.86 (d, J=3.6 Hz, 1H), 7.29 (q, J=8.0 Hz, 1H), 6.76 (d, J=8.4 Hz, 1H), 6.70 (t, J=8.4 Hz, 1H), 4.45-4.42 (m, 1H), 4.38-4.29 (m, 3H), 4.23-4.17 (m, 1H), 3.84-3.82 (m, 1H), 3.68-3.47 (m, 4H), 3.31-3.28 (m, 1H), 1.30 (d, J=6.4 Hz, 3H).

Step 12: 7-((S)-4-acryloyl-2-methylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile Acrylic anhydride (16.6 mg, 0.13 mmol) was added to a mixture of 9-chloro-10-(2-fluoro-6-hydroxyphenyl)-7-((S)-2-methylpiperazin-1-yl)-5-oxo-3,5-dihydro-2H-[1,4]oxazino[2,3,4-ij]quinoline-6-carbonitrile (60 mg, 0.13 mmol) and triethyl amine (39 mg, 0.39 mmol) previously dissolved in a mixture of THF (1 mL) and DCM (1 mL) at −78° C. The resulting mixture was stirred at −78° C. for 0.5 hour and purified by using a C18 column (with a gradient 5% to 95% of ACN in H$_2$O) to afford the desired product (25 mg, 38% yield) as a yellow solid. LC-MS: m/z 509.1 [M+H]+; $^1$H NMR (400 MHz, CDCl$_3$) δ 7.59 (d, J=5.6 Hz, 1H), 7.34-7.28 (m, 1H), 6.84 (d, J=7.6 Hz, 1H), 6.78 (t, J=8.8 Hz, 1H), 6.65-6.56 (m, 1H), 6.42-6.35 (m, 1H), 5.83-5.79 (m, 1H), 4.46-3.90 (m, 8H), 3.72-3.56 (m, 2H), 3.31-3.28 (m, 1H), 1.25 (d, J=6.0 Hz, 3H).

The following compounds were prepared using similar synthetic procedures and their characterization is provided below.

| Ex. | Name | Structure | $^1$H NMR | MS (M + H)$^+$ |
|---|---|---|---|---|
| 38 | 7-((S)-4-acryloyl-2-methylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile | 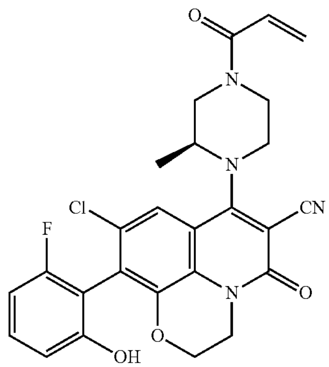 [SMILES: C=CC(=O)N1CCN(c2c(C#N)c(=O)n3c4c(c(-c5c(O)cccc5F)c(Cl)cc24)OCC3)[C@@H](C)C1] | $^1$H NMR (400 MHz, CDCl$_3$) δ 7.59 (d, J = 5.6 Hz, 1H), 7.34-7.28 (m, 1H), 6.84 (d, J = 7.6 Hz, 1H), 6.78 (t, J = 8.8 Hz, 1H), 6.65-6.56 (m, 1H), 6.42-6.35 (m, 1H), 5.83-5.79 (m, 1H), 4.46-3.90 (m, 8H), 3.72-3.56 (m, 2H), 3.31-3.28 (m, 1H),1.25 (d, J = 6.0 Hz, 3H) | 509.1 |
| 39 | (S)-7-((S)-4-acryloyl-2-methylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile | 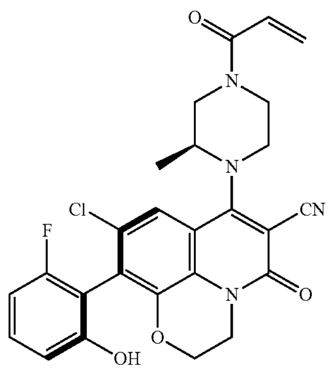 | $^1$H NMR (400 MHz, CDCl$_3$) δ 7.61 (s, 1H), 7.35-7.29 (m, 1H), 6.83-6.77 (m, 2H), 6.62-6.59 (m, 1H), 6.38 (d, J = 16.8 Hz, 1H), 5.80 (d, J = 10.4 Hz, 1H), 4.46-4.40 (m, 2H), 4.27-4.20 (m, 3H), 4.06-3.88 (m, 3H), 3.74-3.55 (m, 2H), 3.33-3.26 (m, 1H), 1.26 (d, J = 5.2 Hz, 3H) | 508.9 |
| 40 | (R)-7-((S)-4-acryloyl-2-methylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile | 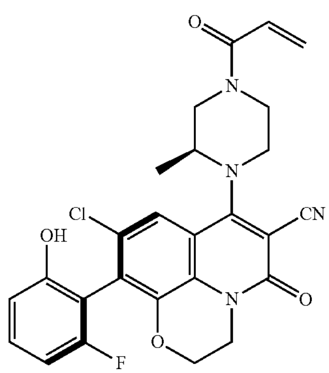 | $^1$H NMR (400 MHz, CDCl$_3$) δ 7.61 (s, 1H), 7.34-7.28 (m, 1H), 6.81-6.76 (m, 2H), 6.64-6.61 (m, 1H), 6.40 (d, J = 16.8 Hz, 1H), 5.82 (d, J = 9.2 Hz, 1H), 4.42-4.26 (m, 3H), 4.21-4.11 (m, 3H), 4.08-3.99 (m, 2H), 3.64-3.56 (m, 2H), 3.33-3.26 (m, 1H), 1.25 (d, J = 5.2 Hz, 3H) | 508.9 |
| 41 | 7-((2S,5R)-4-acryloyl-2,5-dimethylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile | 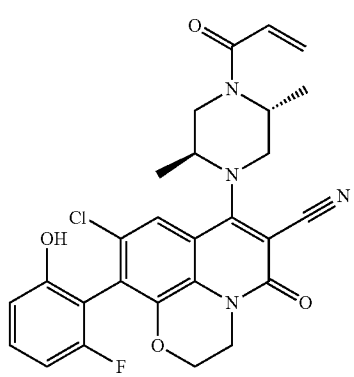 [SMILES: C=CC(=O)N1C[C@H](C)N(c2c(C#N)c(=O)n3c4c(c(-c5c(O)cccc5F)c(Cl)cc24)OCC3)C[C@H]1C] | $^1$H NMR (400 MHz, CDCl$_3$) δ 7.53 (s, 1H), 7.34-7.29 (m, 1H), 6.84-6.77 (m, 2H), 6.58-6.55 (m, 1H), 6.38-6.34 (m, 1H), 5.92-5.77 (m, 2H), 4.50-4.20 (m, 7H), 4.10-3.95 (m, 2H), 3.24-3.14 (m, 1H), 1.43-1.38 (m, 3H), 1.33-1.28 (m, 3H) | 523.2 |

| Ex. | Name | Structure | ¹H NMR | MS (M + H)⁺ |
|---|---|---|---|---|
| 42 | (S)-7-((2S,5R)-4-acryloyl-2,5-dimethylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile | 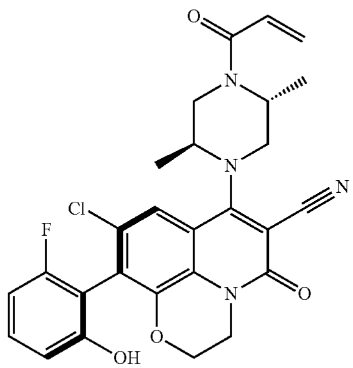 | ¹H NMR (400 MHz, DMSO-d6) δ 9.99 (s, 1H), 7.54 (s, 1H), 7.27 (q, J = 8.4 Hz, 1H), 6.96-6.81 (m, 1H), 6.78 (d, J = 8.0 Hz, 1H), 6.73 (t, J = 8.8 Hz, 1H), 6.18 (dd, J = 16.4 Hz, 2.0 Hz, 1H), 5.74 (dd, J = 10.4 Hz, 2.0 Hz, 1H), 4.90-4.45 (m, 1H), 4.43-4.37 (m, 1H), 4.34-4.26 (m, 1H), 4.25-4.21 (m, 3H), 3.98-3.87 (m, 2H), 3.65-3.50 (m, 0.5H), 3.29-3.26 (m, 1.5H), 1.31-1.23 (m, 3H), 1.19 (d, J = 6.0 Hz, 3H) | 523.2 |
| 43 | (R)-7-((2S,5R)-4-acryloyl-2,5-dimethylpiperazin-1-yl)-9-chloro-10-(2-fluoro-6-hydroxyphenyl)-5-oxo-3,5-dihydro-2H-[1,4]oxazino[2,3,4-ij]quinoline-6-carbonitrile | 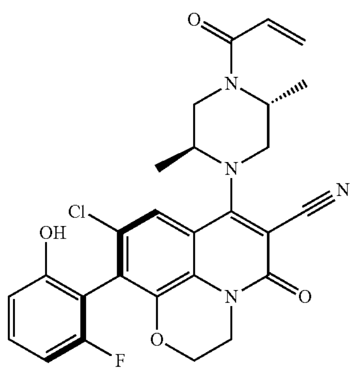 | ¹H NMR (400 MHz, DMSO-d6) δ 10.01 (s, 1H), 7.53 (s, 1H), 7.28 (q, J = 7.2 Hz, 1H), 6.97-6.82 (m, 1H), 6.79 (d, J = 8.4 Hz, 1H), 6.73 (t, J = 8.4 Hz, 1H), 6.18 (dd, J = 16.4 Hz, 2.0 Hz, 1H), 5.74 (dd, J = 10.4 Hz, 2.0 Hz, 1H), 4.92-4.48 (m, 1H), 4.45-4.41 (m, 1H), 4.28-4.17 (m, 4H), 4.03-3.96 (m, 1H), 3.92-3.85 (m, 1H), 3.65-3.51 (m, 0.5H), 3.29-3.22 (m, 1.5H), 1.34-1.23 (m, 3H), 1.19 (d, J = 5.2 Hz, 3H) | 523.2 |
| 44 | 7-((2S,5R)-4-acryloyl-2,5-dimethylpiperazin-1-yl)-9-chloro-10-(2,4-difluorophenyl)-2H-[1,4]oxazino[2,3,4-ij]quinolin-5(3H)-one | 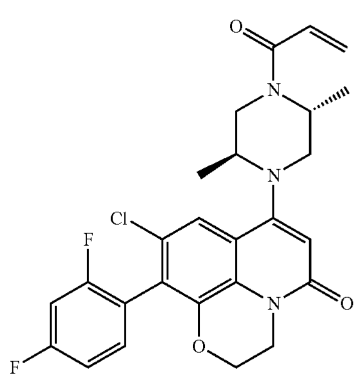 [SMILES: C=CC(=O)N1C[C@H](C)N(c2cc(=O)n3c4c(c(-c5ccc(F)cc5F)c(Cl)cc24)OCC3)C[C@H]1C] | ¹H NMR (400 MHz, CDCl₃) δ 7.51 (d, J = 2.8 Hz, 1H), 7.25-7.29 (m, 1H), 6.92-7.02 (m, 2H), 6.58 (brs, 1H), 6.34-6.36 (m, 1H), 6.11-6.12 (d, 1H), 5.74-5.77 (d, 1H), 5.08 (brs, 0.45 H), 4.18-4.43 (m, 4.5H), 3.95-4.02 (m, 2H), 3.57-3.67 (m, 2H), 2.82-2.86 (m, 1H), 1.45 (d, J = 6.4 Hz, 3H), 1.03 (d, J = 6.4 Hz, 3H). | 500.2 |

B. Example 2

(3R)-7-((2S,5R)-4-acryloyl-2,5-dimethylpiperazin-1-yl)-9-chloro-3-((dimethylamino)methyl)-10-(2-fluoro-6-hydroxyphenyl)-5-oxo-3,5-dihydro-2H-[1,4]oxazino [2,3,4-ij]quinoline-6-carbonitrile The title compound was prepared according to the scheme below.

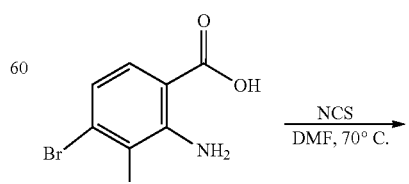

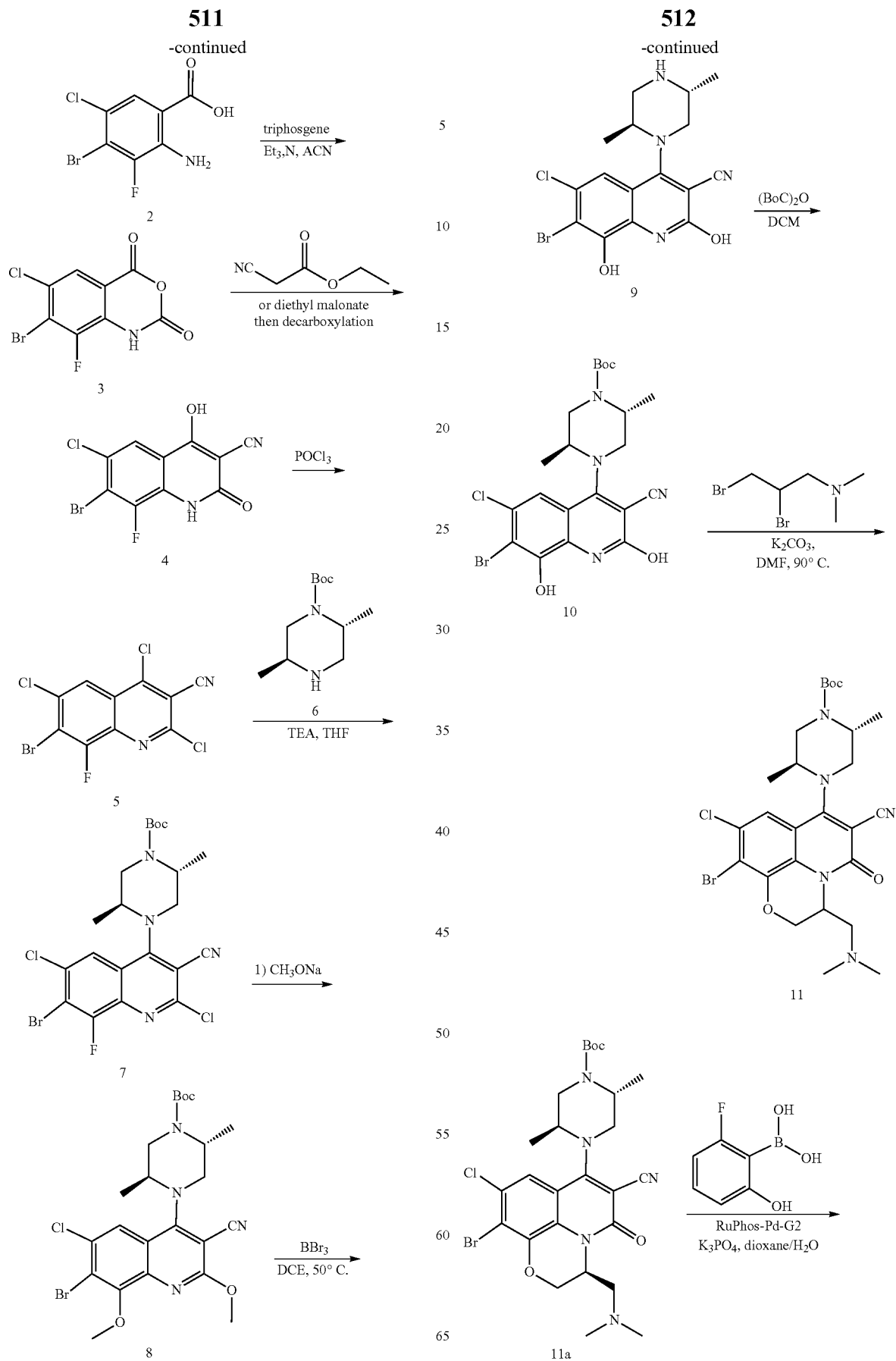

513
-continued
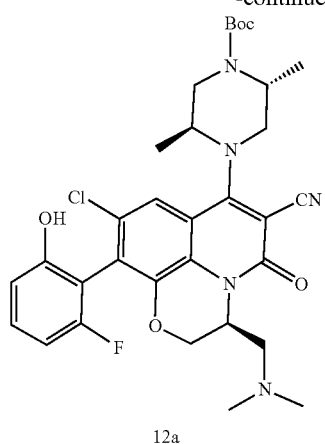
12a
| TFA/DCM →
514
-continued
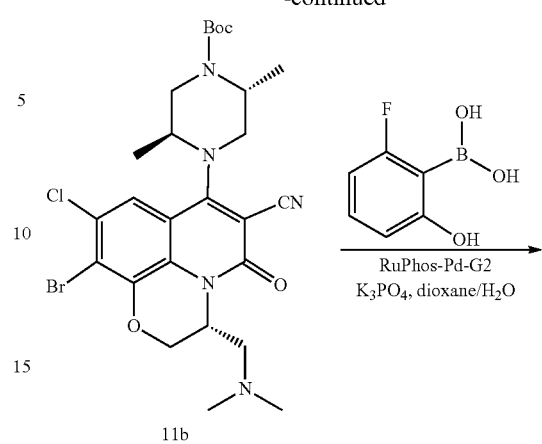
11b
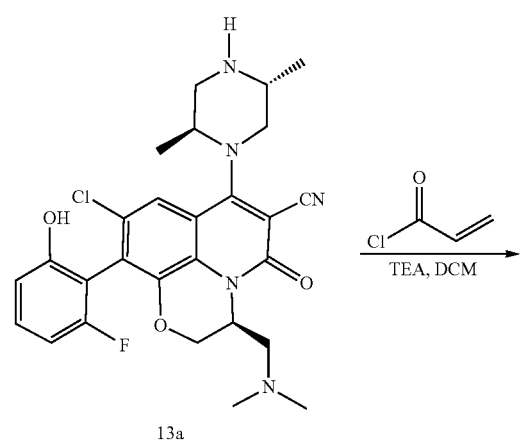
13a
| TEA, DCM →
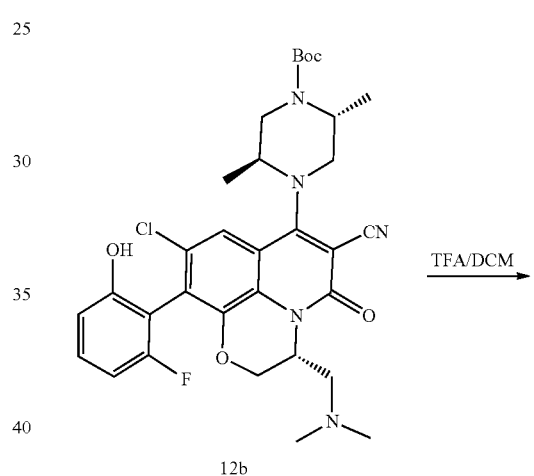
12b
| TFA/DCM →
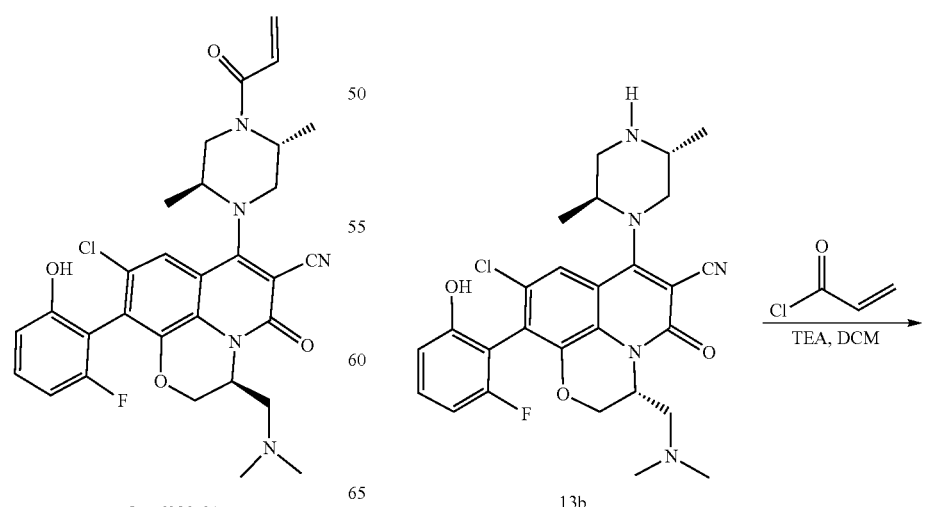
CA-6030-01
13b
| TEA, DCM →

-continued

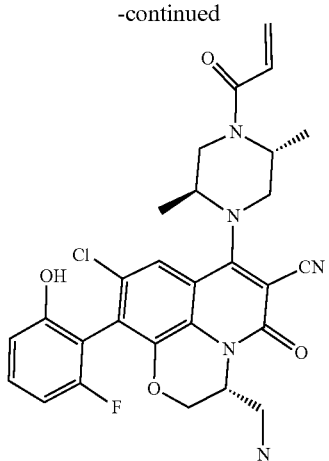

CA-6029-01

Step 1: 2-amino-4-bromo-5-chloro-3-fluorobenzoic acid

To a solution of 2-amino-4-bromo-3-fluorobenzoic acid (100 g, 0.43 mol) in DMF (800 ml) was added NCS (68 g, 0.51 mol) and the reaction mixture was heated to 70° C. for 16 hours. After completion, the reaction was quenched with $H_2O$ (1.5 L), extracted with EA (2 L), dried with $Na_2SO_4$ and concentrated to afford the desired product (139 g, crude) as a grayness solid. LC-MS: m/z 68.1[M−H]⁻.

Step 2: 7-bromo-6-chloro-8-fluoro-1H-benzo[d][1,3]oxazine-2,4-dione

To a solution of 2-amino-4-bromo-5-chloro-3-fluorobenzoic acid (10.0 g, 37.45 mmol) in acetonitrile (35 mL) was added pyridine (5.92 g, 74.7 mmol) at 50° C., the mixture was stirred at 50° C. for 5 min, before adding dropwise a solution of triphosgene (4.45 g, 15.0 mmol) in DCM (10 mL) The resulting mixture was stirred for 3 h, cooled to rt, filtered and washed with acetonitrile (50 mL) to afford the crude product (8.5 g, yield: 77%) as a yellow solid. LC-MS: m/z 293.8 [M−H]⁻.

Step 3: 7-bromo-6-chloro-8-fluoro-4-hydroxy-2-oxo-1,2-dihydroquinoline-3-carbonitrile A solution of 7-bromo-6-chloro-8-fluoro-1H-benzo[d][1,3]oxazine-2,4-dione (8.5 g, 29.01 mmol) in ethyl 2-cyanoacetate (12 mL), the mixture was stirred at 200° C. for 30 min. After completion, the mixture was cooled to rt, filtered and washed with EA (100 mL) to afford the crude product (5.5 g, crude) as a brown solid, which was used to next step without further purification. LC-MS: m/z 316.9 [M−H]⁻.

Step 4: 7-bromo-2,4,6-trichloro-8-fluoroquinoline-3-carbonitrile

A solution of 7-bromo-6-chloro-8-fluoro-4-hydroxy-2-oxo-1,2-dihydroquinoline-3-carbonitrile (5.5 g, 17.32 mmol) in $POCl_3$ (15 mL), the mixture was stirred at 130° C. for 48 h. After completion, the mixture was concentrated under reduced pressure and dissolved with DCM (200 mL), the crude product was poured into water (200 mL), the organic layers were separated, concentrated and the crude material was purified by silica gel column with a 4:1 mixture of PE/EA to afford the desired product (2.6 g, 36% yield) as a yellow solid. LC-MS: m/z 336.9 [M−H]⁻.

Step 5: (2R,5S)-tert-butyl 4-(7-bromo-2,6-dichloro-3-cyano-8-fluoroquinolin-4-yl)-2,5-dimethylpiperazine-1-carboxylate To a solution of 7-bromo-2,4,6-trichloro-8-fluoroquinoline-3-carbonitrile (1.5 g, 4.23 mmol) and (2R,5S)-tert-butyl 2,5-dimethylpiperazine-1-carboxylate (1.8 g, 8.47 mmol) in THF (15 mL) was added TEA (1.28 g, 12.69 mmol). The resulting mixture was stirred at rt for 16 h, concentrated under reduced pressure and purified by silica gel column using a gradient 8:1 to 4:1 of PE in EA to afford the desired product (450 mg, 39% yield) as an orange solid. LC-MS: m/z 533.0 [M+H]⁺; ¹H NMR (400 MHz, $CDCl_3$): δ7.85 (d, J=1.6 Hz, 1H), 4.56-4.52 (m, 1H), 4.37 (dd, J=12.0 Hz, 4.0 Hz, 1H), 4.24-4.19 (m, 1H), 3.95 (d, J=13.2 Hz, 1H), 3.82-3.78 (m, 1H), 3.12 (d, J=8.0 Hz, 1H), 1.56 (s, 9H), 1.33 (d, J=6.4 Hz, 3H), 1.28 (d, J=6.8 Hz, 3H).

Step 6: (2R,5S)-tert-butyl 4-(7-bromo-6-chloro-3-cyano-2,8-dimethoxyquinolin-4-yl)-2,5-dimethylpiperazine-1-carboxylate To a solution of (2R,5S)-tert-butyl 4-(7-bromo-2,6-dichloro-3-cyano-8-fluoroquinolin-4-yl)-2,5-dimethylpiperazine-1-carboxylate (1.35 g, 2.55 mmol) and in THF (12 mL) was added $CH_3ONa$ (1.5 mL, 7.65 mmol, 5M in MeOH) at 0° C., the mixture was slowly warmed to rt (2 hours). After completion, the mixture was dissolved with DCM (150 mL), washed with an aqueous solution of $NH_4Cl$ (100 mL×3), the organic layers were combined, dried over $Na_2SO_4$ and concentrated under reduced pressure to afford the crude product (1.02 g, yield: 74%) as a yellow solid. LC-MS: m/z 541.1 [M+H]⁺.

Step 7: 7-bromo-6-chloro-4-((2S,5R)-2,5-dimethylpiperazin-1-yl)-2,8-dihydroxyquinoline-3-carbonitrile To a solution of (2R,5S)-tert-butyl 4-(7-bromo-6-chloro-3-cyano-2,8-dimethoxyquinolin-4-yl)-2,5-dimethylpiperazine-1-carboxylate (1.02 g, 1.89 mmol) in DCE (6 mL) was added $BBr_3$ (19 mL, 18.89 mmol, 1M in DCM) at 0° C. under $N_2$, the mixture was stirred at 50° C. for 16 hours. After completion, the mixture was cooled to 0° C. and the pH was adjusted to 8~9 with $NH_3$ MeOH, then concentrated under reduced pressure to afford the crude product (1.5 g) as a yellow solid. LC-MS: m/z 413.1 [M+H]⁺.

Step 8: (2R,5S)-tert-butyl 4-(7-bromo-6-chloro-3-cyano-2,8-dihydroxyquinolin-4-yl)-2,5-dimethylpiperazine-1-carboxylate To a solution of 7-bromo-6-chloro-4-((2S,5R)-2,5-dimethylpiperazin-1-yl)-2,8-dihydroxyquinoline-3-carbonitrile (778 mg, 1.89 mmol) and di-tert-butyl dicarbonate (617 mg, 2.83 mmol) in DCM (15 mL) was added TEA (382 mg, 3.78 mmol), the mixture was stirred at rt for 16 h. After completion, the mixture was concentrated under reduced pressure to afford the crude product (1.5 g) as a green solid. LC-MS: m/z 513.1 [M+H]⁺.

Step 9: (2R,5S)-tert-butyl 4-(10-bromo-9-chloro-6-cyano-3-((dimethylamino)methyl)-5-oxo-3,5-dihydro-2H-[1,4]oxazino[2,3,4-ij]quinolin-7-yl)-2,5-dimethylpiperazine-1-carboxylate To a solution of (2R,5S)-tert-butyl 4-(7-bromo-6-chloro-3-cyano-2,8-dihydroxyquinolin-4-yl)-2,5-dimethylpiperazine-1-carboxylate (1.5 g, 2.93 mmol) and 2,3-dibromo-N,N-dimethylpropan-1-amine (5.0 g, 20.51 mmol) in DMF (30 mL) was added $K_2CO_3$ (1.2 g, 8.79 mmol), the mixture was stirred at 90° C. for 16 h. After completion, the mixture was concentrated under reduced pressure and purified by silica gel column with a 50:1 mixture of DCM in MeOH to afford the desired product (175 mg, crude) as a yellow solid. LC-MS: m/z 596.2 [M+H]$^+$. A racemic mixture of Compound 11 (515 mg, 0.87 mmol) was dissolved with MeOH (10 mL) and separated by chiral Prep. HPLC (separation condition: Column: AD-H 5 μm 20*150 mm; Mobile Phase: HEP: IPA (0.1% DEA)=70:30 at 15 mL/min; Temp: 25° C.; Wavelength: 254 nm) to afford the title compounds Compound 11a (80 mg, 16% yield, 100% ee), $^1$H NMR (400 MHz, CDCl$_3$): δ 7.50 (s, 1H), 5.01 (d, J=11.2 Hz, 1H), 4.91 (d, J=10.0 Hz, 1H), 4.52-4.50 (m, 1H), 4.30 (dd, J=12.0 Hz, 3.2 Hz, 1H), 4.18-4.13 (m, 1H), 4.06 (d, J=10.8 Hz, 1H), 3.90 (d, J=13.6 Hz, 1H), 3.74-3.70 (m, 1H), 3.05 (d, J=12.0 Hz, 1H), 2.55 (t, J=11.2 Hz, 1H), 2.38 (s, 6H), 2.31 (dd, J=12.0 Hz, 2.8 Hz, 1H), 1.50 (s, 9H), 1.30 (d, J=6.8 Hz, 3H), 1.28 (d, J=6.8 Hz, 3H); Compound 11b (90 mg, 17% yield, 99.9% ee), $^1$H NMR (400 MHz, CDCl$_3$): δ 7.51 (s, 1H), 5.00-4.95 (m, 2H), 4.54-4.47 (m, 1H), 4.32 (dd, J=12.4 Hz, 4.0 Hz, 1H), 4.12-4.09 (m, 1H), 3.98 (d, J=11.2 Hz, 1H), 3.90 (d, J=13.2 Hz, 1H), 3.73-3.70 (m, 1H), 3.04 (d, J=11.6 Hz, 1H), 2.63 (t, J=11.2 Hz, 1H), 2.38 (s, 6H), 2.33 (dd, J=12.0 Hz, 2.8 Hz, 1H), 1.50 (s, 9H), 1.31 (d, J=6.4 Hz, 3H), 1.28 (d, J=6.8 Hz, 3H). Chiral HPLC Analytical: on AD-H was using 4.6×150 mm column, Mobile Phase: HEP: IPA (0.1% DEA)=70:30 at 0.5 mL/min; Temp: 25° C.; Wavelength: 254 nm).

Compound 11a

Step 10: (2R,5S)-tert-butyl 4-((3S)-9-chloro-6-cyano-3-((dimethylamino)methyl)-10-(2-fluoro-6-hydroxyphenyl)-5-oxo-3,5-dihydro-2H-[1,4]oxazino[2,3,4-ij]quinolin-7-yl)-2,5-dimethylpiperazine-1-carboxylate To a solution of (2R,5S)-tert-butyl 4-((S)-10-bromo-9-chloro-6-cyano-3-((dimethylamino)methyl)-5-oxo-3,5-dihydro-2H-[1,4]oxazino[2,3,4-ij]quinolin-7-yl)-2,5-dimethylpiperazine-1-carboxylate (Compound 11a) (80 mg, 0.13 mmol) and (2-fluoro-6-hydroxyphenyl)boronic acid (105 mg, 0.67 mmol) in dioxane (4 mL) and H$_2$O (1 mL) was added RuPhos Pd G2 (10.5 mg, 0.01 mmol) and K$_3$PO$_4$ (86 mg, 0.40 mmol), the mixture was stirred at 80° C. for 5 h. After completion, the mixture was concentrated under reduced pressure and purified by silica gel column with a 50:1 mixture of DCM in MeOH to afford the desired product Compound 12a (30 mg, yield: 36%) as a yellow solid. LC-MS: m/z 626.3 [M+H]$^+$.

Step 11: (3S)-9-chloro-3-((dimethylamino)methyl)-7-((2S,5R)-2,5-dimethylpiperazin-1-yl)-10-(2-fluoro-6-hydroxyphenyl)-5-oxo-3,5-dihydro-2H-[1,4]oxazino[2,3,4-ij]quinoline-6-carbonitrile TFA (1 mL) was added to a solution of (2R,5S)-tert-butyl 4-((3S)-9-chloro-6-cyano-3-((dimethylamino)methyl)-10-(2-fluoro-6-hydroxyphenyl)-5-oxo-3,5-dihydro-2H-[1,4]oxazino[2,3,4-ij]quinolin-7-yl)-2,5-dimethylpiperazine-1-carboxylate (Compound 12a) (30 mg, 0.05 mmol) in dichloromethane (2 mL) at 0° C., the mixture was stirred at rt for 1 hour. Triethyl amine was slowly added to adjust the pH to 8-9. The mixture was concentrated to give the crude product Compound 13a (35 mg, crude) as a yellow solid. LC-MS: m/z 526.2 [M+H]$^+$.

Step 12: (3S)-7-((2S,5R)-4-acryloyl-2,5-dimethylpiperazin-1-yl)-9-chloro-3-((dimethylamino)methyl)-10-(2-fluoro-6-hydroxyphenyl)-5-oxo-3,5-dihydro-2H-[1,4]oxazino[2,3,4-ij]quinoline-6-carbonitrile Acryloyl chloride (4.5 mg, 0.05 mmol) was added to a mixture of (3S)-9-chloro-3-((dimethylamino)methyl)-7-((2S,5R)-2,5-dimethylpiperazin-1-yl)-10-(2-fluoro-6-hydroxyphenyl)-5-oxo-3,5-dihydro-2H-[1,4]oxazino[2,3,4-ij]quinoline-6-carbonitrile (35 mg, 0.05 mmol) and triethyl amine (10 mg, 0.10 mmol) in DCM (2 mL) at −78° C., the mixture was stirred at −78° C. for 0.5 hour. The mixture was purified by C18 using a gradient 10% to 95% of ACN in H$_2$O to afford the title product (6 mg, 22% yield for 2 steps) as a white solid. LC-MS: m/z 580.1 [M+H]$^+$; $^1$H NMR (400 MHz, CDCl$_3$) δ 7.57-7.39 (m, 1H), 7.25 (q, J=6.8 Hz, 1H), 6.79 (d, J=8.4 Hz, 1H), 6.67 (t, J=8.4 Hz, 1H), 6.32-6.27 (m, 1H), 5.73-5.71 (m, 1H), 5.34-5.29 (m, 1H), 4.45 (d, J=11.6 Hz, 1H), 4.28-4.03 (m, 5H), 3.75-3.55 (m, 1H), 3.25-2.99 (m, 7H), 2.88-2.70 (m, 3H), 1.36-1.26 (m, 6H).

Compound 11b

Step 13: (2R,5S)-tert-butyl 4-((3R)-9-chloro-6-cyano-3-((dimethylamino)methyl)-10-(2-fluoro-6-hydroxyphenyl)-5-oxo-3,5-dihydro-2H-[1,4]oxazino[2,3,4-ij]quinolin-7-yl)-2,5-dimethylpiperazine-1-carboxylate To a solution of (2R,5S)-tert-butyl 4-((R)-10-bromo-9-chloro-6-cyano-3-((dimethylamino)methyl)-5-oxo-3,5-dihydro-2H-[1,4]oxazino[2,3,4-ij]quinolin-7-yl)-2,5-dimethylpiperazine-1-carboxylate (Compound 11b) (55 mg, 0.08 mmol) and (2-fluoro-6-hydroxyphenyl)boronic acid (68 mg, 0.42 mmol) in dioxane (2 mL) and H$_2$O (0.5 mL) was added RuPhos Pd G2 (6.2 mg, 0.008 mmol) and K$_3$PO$_4$ (51 mg, 0.024 mmol), the mixture was stirred at 80° C. for 3 h. After completion, the mixture was concentrated under reduced pressure and purified by silica gel column using a 50:1 mixture of DCM in MeOH to afford the desired product Compound 12b (43 mg, 86% yield) as a yellow solid. LC-MS: m/z 626.3 [M+H]$^+$.

Step 14: (3R)-9-chloro-3-((dimethylamino)methyl)-7-((2S,5R)-2,5-dimethylpiperazin-1-yl)-10-(2-fluoro-6-hydroxyphenyl)-5-oxo-3,5-dihydro-2H-[1,4]oxazino[2,3,4-ij]quinoline-6-carbonitrile TFA (1 mL) was added to a solution of (2R,5S)-tert-butyl 4-((3R)-9-chloro-6-cyano-3-((dimethylamino)methyl)-10-(2-fluoro-6-hydroxyphenyl)-5-oxo-3,5-dihydro-2H-[1,4]oxazino[2,3,4-ij]quinolin-7-yl)-2,5-dimethylpiperazine-1-carboxylate (40 mg, 0.06 mmol) in dichloromethane (2 mL) at 0° C., the mixture was stirred at rt for 1 hour. Triethyl amine was slowly added to adjust the pH to 8-9. The mixture was concentrated to give the crude product Compound 13b (55 mg) as a yellow solid. LC-MS: m/z 526.2 [M+H]⁺.

Step 15: (3R)-7-((2S,5R)-4-acryloyl-2,5-dimethylpiperazin-1-yl)-9-chloro-3-((dimethylamino)methyl)-10-(2-fluoro-6-hydroxyphenyl)-5-oxo-3,5-dihydro-2H-[1,4]oxazino[2,3,4-ij]quinoline-6-carbonitrile Acryloyl chloride (5.8 mg, 0.06 mmol) was added to a mixture of (3R)-9-chloro-3-((dimethylamino)methyl)-7-((2S,5R)-2,5-dimethylpiperazin-1-yl)-10-(2-fluoro-6-hydroxyphenyl)-5-oxo-3,5-dihydro-2H-[1,4]oxazino[2,3,4-ij]quinoline-6-carbonitrile (Compound 13b) (55 mg crude, 0.06 mmol) and triethyl amine (13 mg, 0.13 mmol) in DCM (2 mL) at −78° C., the mixture was stirred at −78° C. for 0.5 hour. The mixture was purified by C18 (with a gradient 5%-95% of ACN in H₂O) to afford the title product (11 mg, 32% yield for 2 steps) as a white solid. LC-MS: m/z 580.3 [M+H]⁺; ¹H NMR (400 MHz, CDCl₃) δ 7.53 (s, 1H), 7.33-7.26 (m, 1H), 6.80-6.75 (m, 2H), 6.66-6.52 (m, 1H), 6.41-6.34 (m, 1H), 5.79 (t, J=8.8 Hz, 1H), 4.94-4.92 (m, 1H), 4.79-4.71 (m, 1H), 4.36-4.30 (m, 3H), 3.92-3.41 (m, 2H), 3.19-3.16 (m, 1H), 2.67 (t, J=22.8 Hz, 1H), 2.45-2.08 (m, 8H), 1.39-1.26 (m, 6H).

The following compounds were prepared using similar synthetic procedures and their characterization is provided below.

Table of examples

| Ex. | Name | Structure | ¹H NMR | MS (M + H)⁺ |
|---|---|---|---|---|
| 49 | (3S)-7-((2S,5R)-4-acryloyl-2,5-dimethylpiperazin-1-yl)-9-chloro-3-((dimethylamino)methyl)-10-(2-fluoro-6-hydroxyphenyl)-5-oxo-3,5-dihydro-2H-[1,4]oxazino[2,3,4-ij]quinoline-6-carbonitrile | 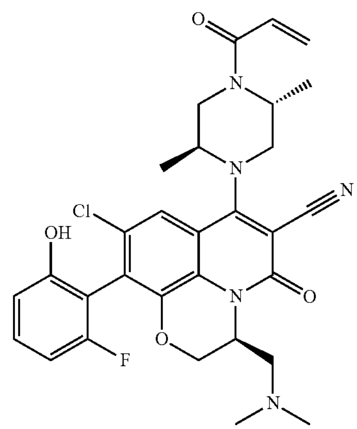 [SMILES: C=CC(=O)N1C[C@H](C)N(c2c(C#N)c(=O)n3c4c(c(-c5c(O)cccc5F)c(Cl)cc24)OC[C@@H]3CN(C)C)C[C@H]1C] | ¹H NMR (400 MHz, CDCl₃) δ 7.53 (s, 1H), 7.33-7.26 (m, 1H), 6.80-6.75 (m, 2H), 6.66-6.52 (m, 1H), 6.41-6.34 (m, 1H), 5.79 (t, J = 8.8 Hz, 1H), 4.94-4.92 (m, 1H), 4.79-4.71 (m, 1H), 4.36-4.30 (m, 3H), 3.92-3.41 (m, 2H), 3.19-3.16 (m, 1H), 2.67 (t, J = 22.8 Hz, 1H), 2.45-2.08 (m, 8H), 1.39-1.26 (m, 6H). | 580.3 |
| 50 | (3R)-7-((2S,5R)-4-acryloyl-2,5-dimethylpiperazin-1-yl)-3-((dimethylamino)methyl)-10-(2-fluoro-6-hydroxyphenyl)-5-oxo-3,5-dihydro-2H-[1,4]oxazino[2,3,4-ij]quinoline-6-carbonitrile | 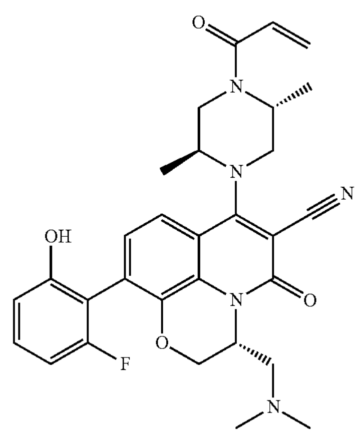 [SMILES: C=CC(=O)N1C[C@H](C)N(c2c(C#N)c(=O)n3c4c(c(-c5c(O)cccc5F)ccc24)OC[C@H]3CN(C)C)C[C@H]1C] | 1H NMR (400 MHz, CDCl₃) δ 7.57-7.39 (m, 1H), 7.25 (q, J = 6.8 Hz, 1H), 6.79 (d, J = 8.4 Hz, 1H), 6.67 (t, J = 8.4 Hz, 1H), 6.32-6.27 (m, 1H), 5.73-5.71 (m, 1H), 5.34-5.29 (m, 1H), 4.45 (d, J = 11.6 Hz, 1H), 4.28-4.03 (m, 5H), 3.75-3.55 (m, 1H), 3.25-2.99 (m, 7H), 2.88-2.70 (m, 3H), 1.36-1.26 (m, 6H). | 580.2 |

-continued

Table of examples

| Ex. | Name | Structure | ¹H NMR | MS (M + H)⁺ |
|---|---|---|---|---|
| 51 | (S)-7-((2S,5R)-4-acryloyl-2,5-dimethylpiperazin-1-yl)-10-(2,4-difluorophenyl)-3-((dimethylamino)methyl)-5-oxo-3,5-dihydro-2H-[1,4]oxazino[2,3,4-ij]quinoline-6-carbonitrile | 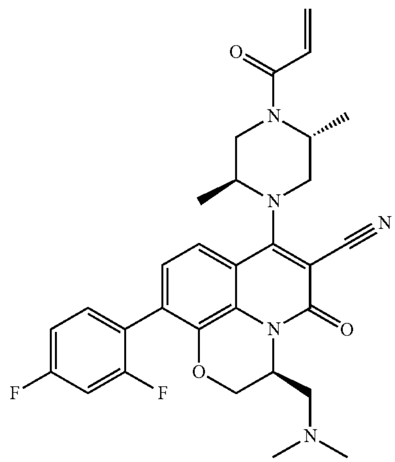 [SMILES: C=CC(=O)N1C[C@H](C)N(c2c(C#N)c(=O)n3c4c(c(-c5ccc(F)cc5F)ccc24)OC[C@@H]3CN(C)C)C[C@H]1C] | ¹H NMR (400 MHz, CDCl₃) δ 7.50-7.32 (m, 2H), 7.19-7.13 (m, 1H), 7.04-6.90 (m, 2H), 6.68-6.50 (m, 1H), 6.36 (dd, J = 1.6 Hz, 16.4 Hz, 1H), 5.81-5.74 (m, 1H), 4.96-4.78 (m, 2H), 4.55-4.10 (m, 4H), 4.05-3.96 (m, 1H), 3.84-3.54 (m, 1H), 3.25-3.14 (m, 1H), 2.68-2.55 (m, 1H), 2.46-2.26 (m, 7H), 1.44-1.23 (m, 6H). | 548.3 |
| 52 | (R)-7-((2S,5R)-4-acryloyl-2,5-dimethylpiperazin-1-yl)-10-(2,4-difluorophenyl)-3-((dimethylamino)methyl)-5-oxo-3,5-dihydro-2H-[1,4]oxazino[2,3,4-ij]quinoline-6-carbonitrile | 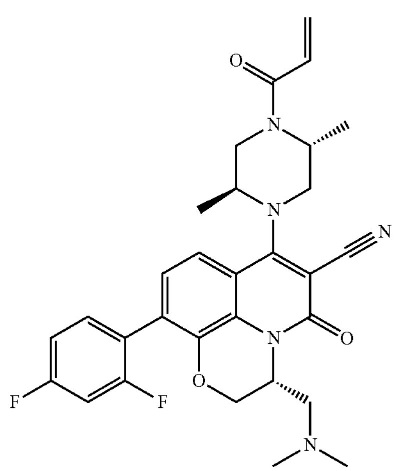 [SMILES: C=CC(=O)N1C[C@H](C)N(c2c(C#N)c(=O)n3c4c(c(-c5ccc(F)cc5F)ccc24)OC[C@H]3CN(C)C)C[C@H]1C] | ¹H NMR (400 MHz, CDCl₃) δ 7.50-7.32 (m, 2H), 7.19-7.13 (m, 1H), 7.04-6.90 (m, 2H), 6.68-6.50 (m, 1H), 6.36 (dd, J = 1.6 Hz, 16.4 Hz, 1H), 5.81-5.74 (m, 1H), 4.96-4.78 (m, 2H), 4.55-4.10 (m, 4H), 4.05-3.96 (m, 1H), 3.84-3.54 (m, 1H), 3.25-3.14 (m, 1H), 2.68-2.55 (m, 1H), 2.46-2.26 (m, 7H), 1.44-1.23 (m, 6H). | 548.2 |

C. Example 3
7-(4-acryloylpiperazin-1-yl)-9-chloro-10-(2-fluoro-6-hydroxyphenyl)-2H-[1,4]oxazino [2,3,4-ij]quinazolin-5(3H)-one
The title compound was prepared according to the scheme below.
(R)-7-(4-acryloylpiperazin-1-yl)-9-chloro-10-(2-fluoro-6-hydroxyphenyl)-2H-[1,4]oxazino[2,3,4-ij]quinazolin-5(3H)-one
(S)-7-(4-acryloylpiperazin-1-yl)-9-chloro-10-(2-fluoro-6-hydroxyphenyl)-2H-[1,4]oxazino[2,3,4-ij]quinazolin-5(3H)-one
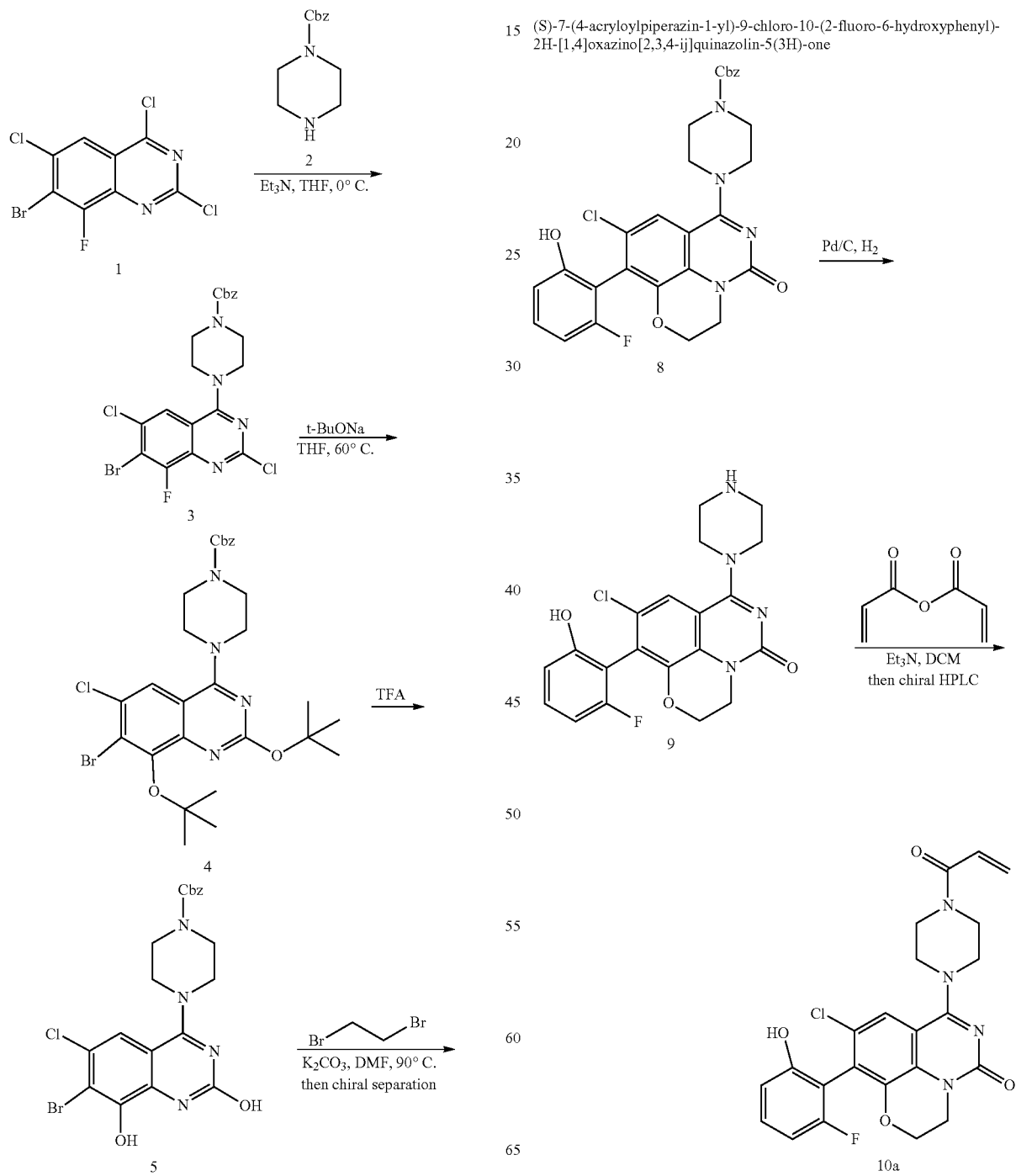

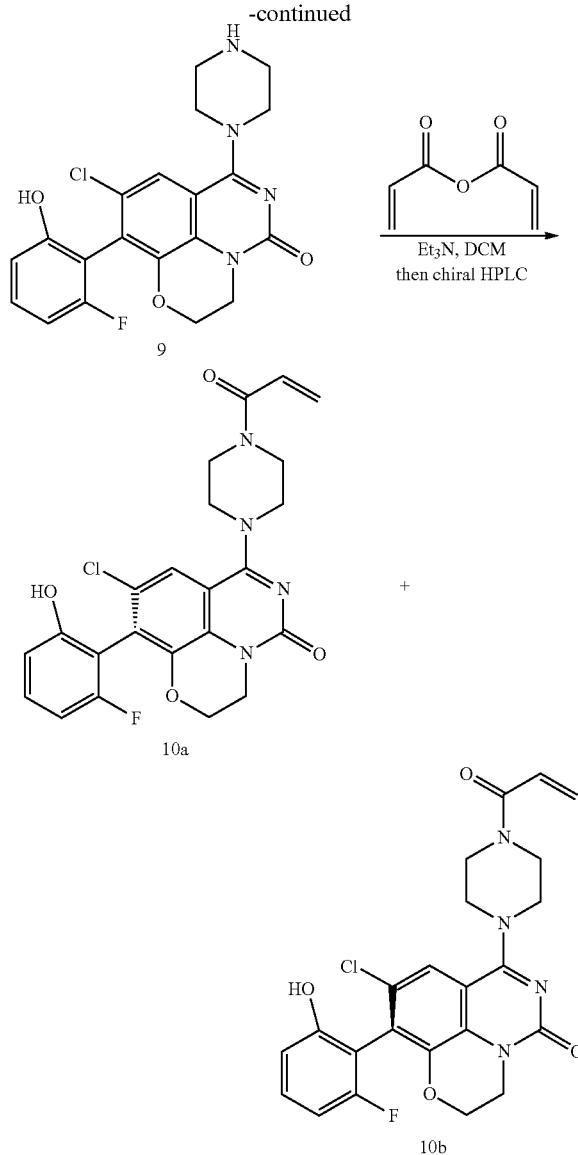

Compound 1 was prepared in three steps:

2-amino-4-bromo-5-chloro-3-fluorobenzoic acid

To a solution of 2-amino-4-bromo-3-fluorobenzoic acid (100 g, 0.43 mol) in DMF (800 ml) was added NCS (68 g, 0.51 mol). Then the mixture was heated to 70° C. for 16 hours. After completion, the mixture was quenched with aqueous H$_2$O (1.5 L) and extracted with EA (2 L), dried with Na$_2$SO$_4$ and concentrated to afford product (139 g, crude) as a grayness solid. LC-MS: m/z 268.1[M–H]$^+$ 7-bromo-6-chloro-8-fluoroquinazoline-2,4-diol To a solution of 2-amino-4-bromo-5-chloro-3-fluorobenzoic acid (139 g, 0.51 mol) and urea (260 g, 4.33 mol) was heated to 180° C., refluxed for 6 h. After completion, the mixture was quenched with water (1.5 L), filtered through a Celite pad, and the filtrate was concentrated to give the crude product (130 g) as a grayness solid. LC-MS m/z=293.1[M–H]$^+$ 7-bromo-2,4,6-trichloro-8-fluoroquinazoline A solution of 7-bromo-6-chloro-8-fluoroquinazoline-2,4-diol (130 g, 0.51 mol) and POCl$_3$ (800 ml) was heated to 120° C., refluxed for 16 h. After completion, the mixture was quenched with aqueous H$_2$O (1.5 L), filtered through a Celite pad, and the filtrate was concentrated and purified by silica column with PE/EA=4:1 to afford product (59 g, 35% yield) as a yellow solid. LC-MS: m/z 311.1[M–H–Cl]$^+$ The remaining synthesis was carried out as follows:

Step 1: benzyl 4-(7-bromo-2,6-dichloro-8-fluoroquinazolin-4-yl)piperazine-1-carboxylate To a cooled mixture of 7-bromo-2,4,6-trichloro-8-fluoroquinazoline (45 g, 0.135 mol) and Et$_3$N (41 g, 0.406 mol) in dioxane was added benzyl piperazine-1-carboxylate (29 g, 0.135 mol) at 0° C. The mixture was stirred at 0° C. for 30 minutes. After completion, the mixture was concentrated and the crude material was purified by column with a gradient 4:1 to 1:1 of PE/EA to afford the desired product (41 g, 60% yield) as a yellow solid. LC-MS: m/z 514 [M+H].

Step 2: benzyl 4-(7-bromo-2,8-di-tert-butoxy-6-chloroquinazolin-4-yl)piperazine-1-carboxylate To a solution of benzyl 4-(7-bromo-2,6-dichloro-8-fluoroquinazolin-4-yl)piperazine-1-carboxylate (41 g, 79.9 mmol) in dry THF (200 ml) was added t-BuONa (100 ml, 199.8 mol, 2 M in THF) solution. Then the mixture was heated to 60° C. for 2 hours. After completion, the mixture was quenched with aqueous NH$_4$Cl and extracted with EA, dried with Na$_2$SO$_4$ and concentrated. The crude material was purified by silica using a mixture 15:1 of PE in EA to afford the desired product (41 g, 85% yield) as a yellow solid. LC-MS: m/z 606.1 [M+H].

Step 3: benzyl 4-(7-bromo-6-chloro-2,8-dihydroxyquinazolin-4-yl)piperazine-1-carboxylate To a solution of benzyl 4-(7-bromo-2,8-di-tert-butoxy-6-chloroquinazolin-4-yl)piperazine-1-carboxylate (6.0 g, 9.9 mmol) in DCM (20 mL) was added TFA (20 mL), the mixture was stirred at 25° C. for 3 hours. After completion, the mixture was concentrated under reduce pressure to afford the crude benzyl 4-(7-bromo-6-chloro-2,8-dihydroxyquinazolin-4-yl)piperazine-1-carboxylate (5 g), which was used in the next step without further purification.

Step 4: benzyl 4-(10-bromo-9-chloro-5-oxo-3,5-dihydro-2H-[1,4]oxazino[2,3,4-ij]quinazolin-7-yl)piperazine-1-carboxylate To a mixture of benzyl 4-(7-bromo-6-chloro-2,8-dihydroxyquinazolin-4-yl)piperazine-1-carboxylate (4 g, crude) and 1,2-dibromoethane (5.2 g, 28 mmol) in DMF (30 mL) was added potassium carbonate (3.86 g, 28 mmol), The reaction was stirred at 0° C. for 3 hours, After completion the reaction, the mixture was concentrated and the residue was purified by silica gel column using a gradient 4:1 to 1:1 of PE in EA to afford the product (3.5 g, 6.73 mmol, 68% yield) as a yellow solid. LC-MS: m/z 521.0 [M+H].

Step 5: benzyl 4-(9-chloro-10-(2-fluoro-6-hydroxyphenyl)-5-oxo-3,5-dihydro-2H-[1,4]oxazino [2,3,4-ij]quinazolin-7-yl)piperazine-1-carboxylate The mixture of benzyl 4-(10-bromo-9-chloro-5-oxo-3,5-dihydro-2H-[1,4]oxazino [2,3,4-ij]quinazolin-7-yl)piperazine-1-carboxylate (3.3 g, 6.34 mmol), (2-fluoro-6-hydroxyphenyl)boronic acid (2.97 g, 190 mmol), RuPhos Pd G2 (466 mg, 0.6 mmol) and tripotassium phosphate (4.03 g, 190 mmol) in dioxane/water (3 mL/0.5 mL) was stirred at 100° C. for 3 hours. After completion, the mixture was concentrated and the residue was purified by silica gel column with a gradient 40:1 to 25:1 of DCM in MeOH to afford the product (2.9 g, 5.26 mmol, 83% yield) as a yellow solid. LC-MS: m/z 550.2 [M+H].

Step 6: 7-(4-acryloylpiperazin-1-yl)-9-chloro-10-(2-fluoro-6-hydroxyphenyl)-2H-[1,4]oxazino[2,3,4-ij]quinazolin-5(3H)-one A solution of benzyl 4-(9-chloro-10-(2-fluoro-6-hydroxyphenyl)-5-oxo-3,5-dihydro-2H-[1,4]oxazino[2,3,4-ij]quinazolin-7-yl)piperazine-1-carboxylate (2.9 g, 5.26 mmol) in DCM (120 mL) was added boron tribromide (1M in DCM, 16 mL, 16 mmol)) at 0° C., the mixture was stirred at 0° C. for 1 hour. After completion, the reaction was quenched with methanol and concentrated to give the crude material 9-chloro-10-(2-fluoro-6-hydroxyphenyl)-7-(piperazin-1-yl)-2H-[1,4]oxazino[2,3,4-ij]quinazolin-5(3H)-one, which was purified by silica gel column with a gradient 15:1 to 10:1 of DCM in MeOH to afford the product (1.5 g, 3.60 mmol, yield: 68%) as a yellow solid. LC-MS: m/z 417.1 [M+H].

Step 7: 7-(4-acryloylpiperazin-1-yl)-9-chloro-10-(2-fluoro-6-hydroxyphenyl)-2H-[1,4]oxazino[2,3,4-ij]quinazolin-5(3H)-one Acrylic anhydride (454 mg, 3.6 mmol) was added to a mixture of 7-(4-acryloylpiperazin-1-yl)-9-chloro-10-(2-fluoro-6-hydroxyphenyl)-2H-[1,4]oxazino[2,3,4-ij]quinazolin-5(3H)-one (1.5 g, 3.60 mmol) and triethyl amine (545 mg, 5.4 mmol) in dichloromethane (12 mL) at −50° C. The mixture was stirred at rt for 1 hour, quenched with water. The aqueous phase was extracted with DCM, washed with brine, dried and concentrated. The residue was purified by prep-HPLC [Column: waters Xbridge C18 5 um 19×150 m; Method: 10%-50% acetonitrile in water (0.1% NH₄HCO₃) at 254 nm; Flowrate: 15 ml/min; GT: 10 min.] to afford the desired product (900 mg, 53% yield) as white solid. LC-MS: m/z 471.2 [M+H]⁺.

The above product (900 mg) was dissolved in MeOH (50 mL), separated by chiral Prep. HPLC (separation condition: Column: Chiralpak IG 5 μm 20×250 mm; Mobile Phase: Hex:EtOH=60:40 at 15 mL/min; Temp: 30° C.; Wavelength: 254 nm) to afford the title compounds (234 mg, 98.8% ee) and (289 mg, 99.8% ee); Chiral HPLC Analytical: on CHIRALPAK® IG was using 5 μm 4.6×250 mm column, Mobile Phase: Hex:EtOH=60:40 at 1 mL/min; Temp: 30° C.; Wavelength: 254 nm). (S)-7-(4-acryloylpiperazin-1-yl)-9-chloro-10-(2-fluoro-6-hydroxyphenyl)-2H-[1,4]oxazino[2,3,4-ij]quinazolin-5(3H)-one: ¹H NMR (400 MHz, DMSO-d6) δ 9.96 (s, 1H), 7.56 (s, 1H), 7.31-7.24 (m, 1H), 6.85-6.70 (m, 3H), 6.19-6.14 (m, 1H), 5.75-5.72 (m, 1H), 4.33-4.30 (m, 2H), 3.92-3.90 (m, 2H), 3.83-3.72 (m, 8H); Peak 1: e.e. =98.8%, Rt=12.65 min. (R)-7-(4-acryloylpiperazin-1-yl)-9-chloro-10-(2-fluoro-6-hydroxyphenyl)-2H-[1,4]oxazino[2,3,4-ij]quinazolin-5(3H)-one: ¹H NMR (400 MHz, DMSO-d6) δ 9.96 (s, 1H), 7.56 (s, 1H), 7.31-7.24 (m, 1H), 6.85-6.70 (m, 3H), 6.19-6.14 (m, 1H), 5.75-5.72 (m, 1H), 4.34-4.30 (m, 2H), 3.92-3.90 (m, 2H), 3.83-3.72 (m, 8H); Peak 2: e.e. =99.8%, Rt=15.94 min.

The following compounds were prepared using similar synthetic procedures and their characterization is provided below.

| Ex. | Name | Structure | ¹H NMR | MS (M + H)⁺ |
|---|---|---|---|---|
| 1 | 7-(4-acryloylpiperazin-1-yl)-9-chloro-10-(2-fluoro-6-hydroxyphenyl)-2H-[1,4]oxazino[2,3,4-ij]quinazolin-5(3H)-one | 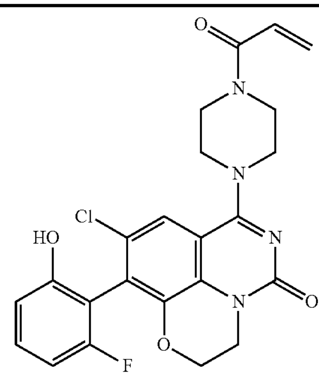 | ¹H NMR (300 MHz, CD₃OD) δ 8.67 (s, 1H), 7.32-7.26 (m, 1H), 6.88-6.68 (m, 3H), 6.30 (d, J = 15 Hz, 4H), 5.83 (d, J = 15 Hz, 1H), 4.40-4.38 (m, 2H), 4.12-4.09 (m, 2H), 4.04-4.01 (m, 4H), 3.92-3.88 (m, 4H) | 471.1 |
| 2 | 7-(2-acryloyl-2,7-diazaspiro[3.5]nonan-7-yl)-9-chloro-10-(2-fluoro-6-hydroxyphenyl)-2H-[1,4]oxazino[2,3,4-ij]quinazolin-5(3H)-one | 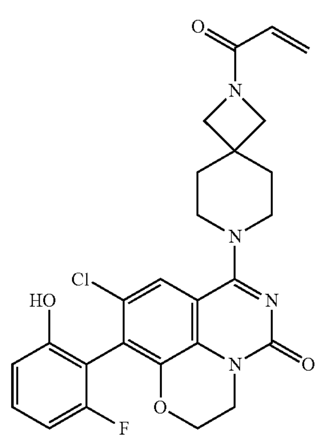 [SMILES: C=CC(=O)N1CC2(CCN(c3nc(=O)n4c5c(c(-c6c(O)cccc6F)c(Cl)cc35)OCC4)CC2)C1] | ¹H NMR (400 MHz, CD₃OD) δ 7.47 (s, 1H), 7.16-7.12 (m, 1H), 6.63-6.54 (m, 2H), 6.32-6.25 (m, 1H), 6.18-6.14 (m, 1H), 5.66-5.66 (m, 1H), 4.29-4.24 (m, 2H), 4.03 (s, 2H), 3.97-3.93 (m, 2H), 3.78-3.76 (m, 6H), 1.94-1.87 (m, 4H). | 511.2 |

-continued

| Ex. | Name | Structure | ¹H NMR | MS (M + H)⁺ |
|---|---|---|---|---|
| 3 | 7-(4-acryloylpiperazin-1-yl)-9-chloro-10-(5-methyl-1H-indazol-4-yl)-2H-[1,4]oxazino[2,3,4-ij]quinazolin-5(3H)-one | 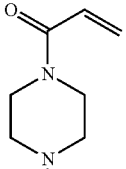 | ¹H NMR (400 MHz, CD₃OD) δ 7.75 (s, 1H), 7.55-7.53 (m, 2H), 7.40-7.38 (m, 1H), 6.87-680 (m, 1H), 6.32-6.27 (m, 1H), 5.84-5.81 (m, 1H), 4.34 (t, J = 4.8 Hz, 2H), 4.10-4.04 (m, 6H), 3.92-3.90 (m, 2H), 2.21 (s, 1H). | 491.2 |
| 4 | (R)-7-(4-acryloylpiperazin-1-yl)-9-chloro-10-(2-fluoro-6-hydroxyphenyl)-2H-[1,4]oxazino[2,3,4-ij]quinazolin-5(3H)-one | 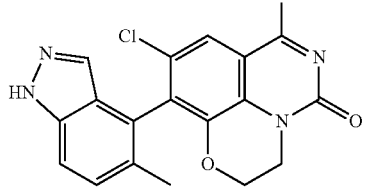 | ¹H NMR (400 MHz, DMSO-d6) δ 9.96 (s, 1H), 7.56 (s, 1H), 7.31-7.24 (m, 1H), 6.85-6.70 (m, 3H), 6.19-6.14 (m, 1H), 5.75-5.72 (m, 1H), 4.33-4.30 (m, 2H), 3.92-3.90 (m, 2H), 3.83-3.72 (m, 8H). | 471.2 |
| 5 | (S)-7-(4-acryloylpiperazin-1-yl)-9-chloro-10-(2-fluoro-6-hydroxyphenyl)-2H-[1,4]oxazino[2,3,4-ij]quinazolin-5(3H)-one | 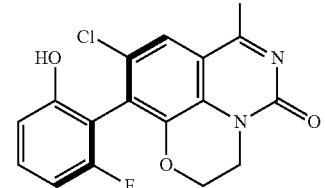 | ¹H NMR (400 MHz, DMSO-d6) δ 9.96 (s, 1H), 7.56 (s, 1H), 7.31-7.24 (m, 1H), 6.85-6.70 (m, 3H), 6.19-6.14 (m, 1H), 5.75-5.72 (m, 1H), 4.34-4.30 (m, 2H), 3.92-3.90 (m, 2H), 3.83-3.72 (m, 8H). | 471.1 |
| 7 | (R)-7-(4-acryloylpiperazin-1-yl)-9-chloro-10-(5-methyl-1H-indazol-4-yl)-2H-[1,4]oxazino[2,3,4-ij]quinazolin-5(3H)-one | 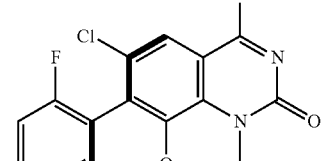 | ¹H NMR (400 MHz, CD₃OD) δ 7.76 (s, 1H), 7.56-7.54 (m, 2H), 7.41-7.39 (m, 1H), 6.88-6.81 (m, 1H), 6.32-6.28 (m, 1H), 5.85-5.82 (m, 1H), 4.34 (t, J = 5.2 Hz, 2H), 4.11-4.04 (m, 6H), 3.92-3.90 (m, 2H), 2.22 (s, 3H). | 490.9 |

| Ex. | Name | Structure | ¹H NMR | MS (M + H)⁺ |
|---|---|---|---|---|
| 8 | (S)-7-(4-acryloylpiperazin-1-yl)-9-chloro-10-(5-methyl-1H-indazol-4-yl)-2H-[1,4]oxazino[2,3,4-ij]quinazolin-5(3H)-one | 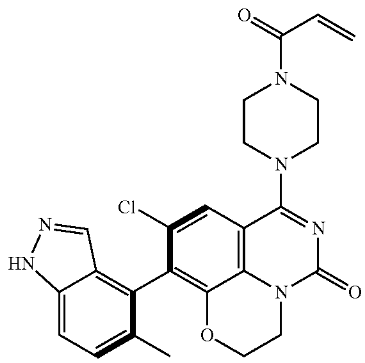 | ¹H NMR (400 MHz, CD₃OD) δ 7.63 (s, 1H), 7.42-7.41 (m, 2H), 7.28-7.26 (m, 1H), 6.75-6.68 (m, 1H), 6.19-6.15 (m, 1H), 5.72-5.69 (m, 1H), 4.21 (t, J = 5.2 Hz, 2H), 3.98-3.91 (m, 6H), 3.80-3.76 (m, 2H), 2.09 (s, 3H). | 490.9 |
| 9 | 7-(4-acryloylpiperazin-1-yl)-9-chloro-10-(3,5-dimethyl-1H-indazol-4-yl)-2H-[1,4]oxazino[2,3,4-ij]quinazolin-5(3H)-one | 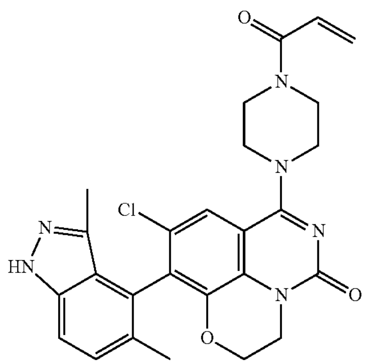 [SMILES: C=CC(=O)N1CCN(c2nc(=O)n3c4c(c(-c5c(C)ccc6[nH]nc(C)c56)c(Cl)cc24)OCC3)CC1] | ¹H NMR (400 MHz, CD₃OD) δ 7.76 (s, 1H), 7.46 (d, J = 8.4 Hz, 1H), 7.36 (d, J = 8.4 Hz, 1H), 6.84 (dd, J = 16.4 Hz, 10.4 Hz, 1H), 6.30 (dd, J = 16.4 Hz, 1.6 Hz, 1H), 5.83 (dd, J = 10.8 Hz, 2.0 Hz, 1H), 4.35 (t, J = 4.8 Hz, 2H), 4.11-4.03 (m, 6H), 3.96-3.89 (m, 4H), 2.16 (s, 3H), 1.97 (s, 3H). | 505.1 |
| 10 | 2-((2S)-4-(9-chloro-10-(2-fluoro-6-hydroxyphenyl)-5-oxo-3,5-dihydro-2H-[1,4]oxazino[2,3,4-ij]quinazolin-7-yl)-1-(2-fluoroacryloyl)piperazin-2-yl)acetonitrile | 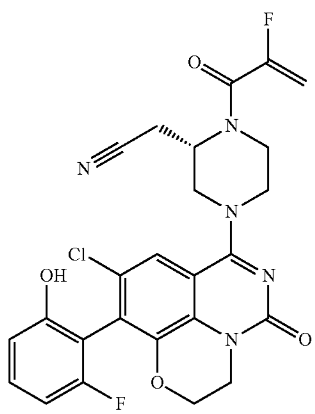 [SMILES: C=C(F)C(=O)N1CCN(c2nc(=O)n3c4c(c(-c5c(O)cccc5F)c(Cl)cc24)OCC3)C[C@@H]1CC#N] | ¹H NMR (400 MHz, CDCl₃) δ 8.11 (s, 1H), 7.51-7.47 (m, 1H), 7.37-7.32 (m, 1H), 6.83-6.79 (m, 1H), 5.55-5.23 (m, 5H), 4.71-4.67 (m, 1H), 4.53-4.30 (m, 3H), 4.26-4.04 (m, 2H), 3.90-3.44 (m, 3H), 3.04-2.76 (m, 1H). | 528.2 |
| 11 | 7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one | 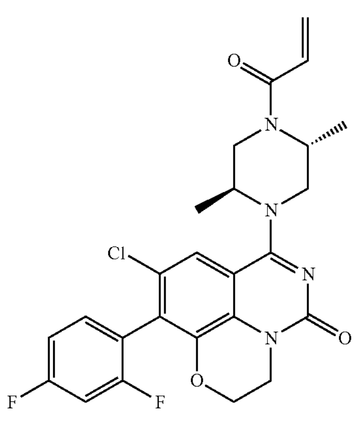 [SMILES: C=CC(=O)N1C[C@H](C)N(c2nc(=O)n3c4c(c(-c5ccc(F)cc5F)c(Cl)cc24)OCC3)C[C@H]1C] | ¹H NMR (400 MHz, CDCl₃) δ 7.41-7.40 (m, 1H), 7.30-7.23 (m, 1H), 7.03-6.93 (m, 2H), 6.65-6.51 (m, 1H), 6.37 (t, J = 14.8 Hz, 1H), 5.77 (t, J = 7.6 Hz, 1H), 5.05-4.84 (m, 1.5H), 4.43-4.22 (m, 4H), 4.18-4.09 (m, 1H), 4.06-3.98 (m, 1H), 3.89-3.80 (m, 1H), 3.75-3.65 (m, 1H), 3.50-3.38 (m, 0.5H), 1.41-1.33 (m, 4H), 1.29-1.24 (m, 2H). | 501.1 |

| Ex. | Name | Structure | ¹H NMR | MS (M + H)⁺ |
|---|---|---|---|---|
| 12 | 7-((2S,5R)-4-acryloyl-2,5-dimethylpiperazin-1-yl)-10-(3-chloro-4-fluorophenyl)-2H-[1,4]oxazino[2,3,4-ij]quinazolin-5(3H)-one | 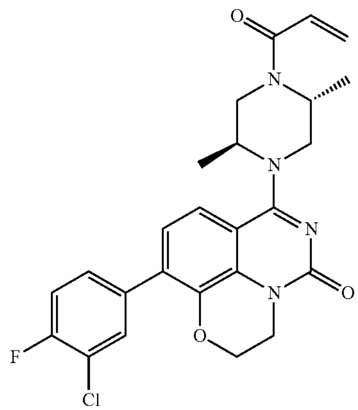 [SMILES: C=CC(=O)N1C[C@H](C)N(c2nc(=O)n3c4c(c(-c5ccc(F)c(Cl)c5)ccc24)OCC3)C[C@H]1C] | ¹H NMR (400 MHz, CDCl₃) δ 7.64 (dd, J = 6.8 Hz, 2.4 Hz, 1H), 7.47-7.43 (m, 1H), 7.35-7.30 (m, 1H), 7.24-7.22 (m, 1H), 7.10-7.06 (m, 1H), 6.68-6.52 (m, 1H), 6.42-6.33 (m, 1H), 5.80-5.75 (m, 1H), 5.09-4.87 (m, 1.5H), 4.48-4.03 (m, 6H), 3.88-3.41 (m, 2.5H), 1.38-1.35 (m, 4H), 1.26-1.23 (m, 2H). | 483.1 |
| 13 | 7-((2S,5R)-4-acryloyl-2,5-dimethylpiperazin-1-yl)-10-(naphthalen-1-yl)-2H-[1,4]oxazino[2,3,4-ij]quinazolin-5(3H)-one | 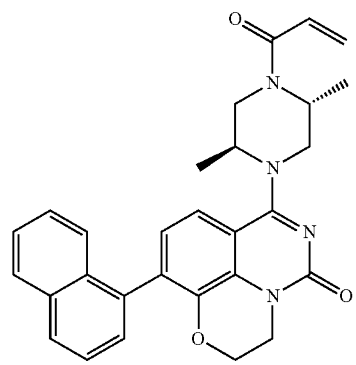 [SMILES: C=CC(=O)N1C[C@H](C)N(c2nc(=O)n3c4c(c(-c5cccc6ccccc56)ccc24)OCC3)C[C@H]1C] | ¹H NMR (400 MHz, CDCl₃) δ 7.94 (d, J = 8.4 Hz, 2H), 7.61-7.50 (m, 3H), 7.47-7.37 (m, 3H), 7.14-7.09 (m, 1H), 6.69-6.53 (m, 1H), 6.42-6.34 (m, 1H), 5.80-5.75 (m, 1H), 5.11-4.98 (m, 1.5H), 4.40-4.04 (m, 6H), 3.93-3.43 (m, 2.5H), 1.42-1.38 (m, 4H), 1.31-1.27 (m, 2H). | 481.2 |
| 14 | 10-(2,4-difluorophenyl)-7-((2S,5R)-2,5-dimethyl-4-propioloylpiperazin-1-yl)-2H-[1,4]oxazino[2,3,4-ij]quinazolin-5(3H)-one | 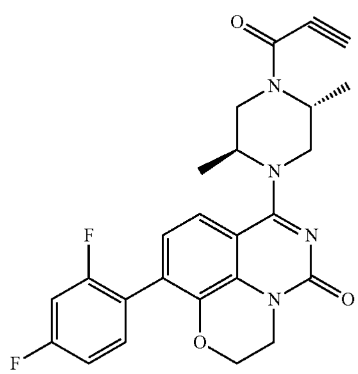 [SMILES: C#CC(=O)N1C[C@H](C)N(c2nc(=O)n3c4c(c(-c5ccc(F)cc5F)ccc24)OCC3)C[C@H]1C] | ¹H NMR (400 MHz, CDCl₃) δ 7.39 (dd, J = 1.6 Hz, J = 4.8 Hz, 1H), 7.30-7.24 (m, 1H), 7.04-6.93 (m, 2H), 5.04-4.70 (m, 2H), 4.45-4.22 (m, 3H), 4.18-4.07 (m, 2H), 4.04-3.96 (m, 1H), 3.91-3.82 (m, 1H), 3.79-3.72 (m, 0.6H), 3.46-3.35 (m, 0.4H), 3.21 (d, J = 1.6 Hz, 0.4H), 3.18 (s, 0.6H), 1.43-1.34 (m, 4H), 1.30-1.22 (m, 2H). | 499.2 |
| 15 | 7-((2S,5R)-4-acryloyl-2,5-dimethylpiperazin-1-yl)-10-(8-chloronaphthalen-1-yl)-2H-[1,4]oxazino[2,3,4-ij]quinazolin-5(3H)-one | 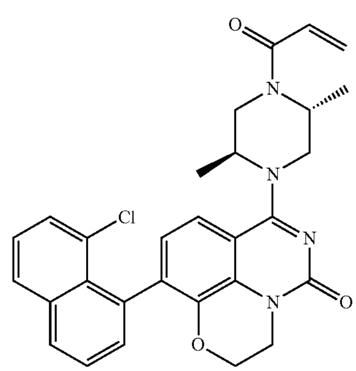 [SMILES: C=CC(=O)N1C[C@H](C)N(c2nc(=O)n3c4c(c(-c5cccc6cccc(Cl)c56)ccc24)OCC3)C[C@H]1C] | ¹H NMR (400 MHz, CDCl₃) δ 7.96-7.94 (m, 1H), 7.88-7.86 (m, 1H), 7.59-7.53 (m, 2H), 7.43-7.31 (m, 3H), 7.10-7.07 (m, 1H), 6.65-6.52 (m, 1H), 6.41-6.34 (m, 1H), 5.79-5.74 (m, 1H), 5.13-4.95 (m, 1.5H), 4.41-4.17 (m, 5H), 4.05-3.64 (m, 3H), 3.52-3.47 (m, 0.5H), 1.41-1.24 (m, 6H). | |

| Ex. | Name | Structure | ¹H NMR | MS (M + H)⁺ |
|---|---|---|---|---|
| 16 | 7-((2S,5R)-4-acryloyl-2,5-dimethylpiperazin-1-yl)-10-(3-chloro-5-fluorophenyl)-2H-[1,4]oxazino[2,3,4-ij]quinazolin-5(3H)-one | 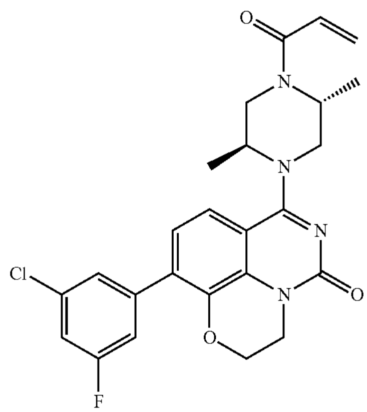 [SMILES: C=CC(=O)N1C[C@H](C)N(c2nc(=O)n3c4c(c(-c5cc(F)cc(Cl)c5)ccc24)OCC3)C[C@H]1C] | ¹H NMR (400 MHz, CDCl₃) δ 7.36-7.33 (m, 2H), 7.22 (d, J = 9.6 Hz, 1H), 7.15-7.07 (m, 2H), 6.64-6.51 (m, 1H), 6.40-6.33 (m, 1H), 5.79-5.75 (m, 1H), 5.07-4.88 (m, 1.6H), 4.48-4.03 (m, 6H), 3.87-3.64 (m, 2H), 3.45-3.42 (m, 0.4H), 1.38-1.23 (m, 6H). | 483.1 |
| 17 | 7-((2S,5R)-4-acryloyl-2,5-dimethylpiperazin-1-yl)-10-(4-chloro-2-fluorophenyl)-2H-[1,4]oxazino[2,3,4-ij]quinazolin-5(3H)-one | 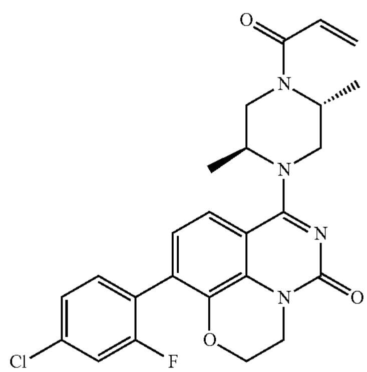 [SMILES: C=CC(=O)N1C[C@H](C)N(c2nc(=O)n3c4c(c(-c5ccc(Cl)cc5F)ccc24)OCC3)C[C@H]1C] | ¹H NMR (400 MHz, CDCl₃) δ 7.34-7.32 (m, 2H), 7.23-7.21 (m, 2H), 7.06-7.03 (m, 1H), 6.67-6.51 (m, 1H), 6.41-6.33 (m, 1H), 5.79-5.75 (m, 1H), 5.07-4.88 (m, 1.6H), 4.40-4.05 (m, 6H), 3.86-3.82 (m, 1H), 3.75-3.634 (m, 1H), 3.46-3.41 (m, 0.4H), 1.37-1.24 (m, 6H). | 483.1 |
| 18 | 7-((2S,5R)-4-(but-2-ynoyl)-2,5-dimethylpiperazin-1-yl)-9-chloro-10-(2,4-difluorophenyl)-2H-[1,4]oxazino[2,3,4-ij]quinazolin-5(3H)-one | 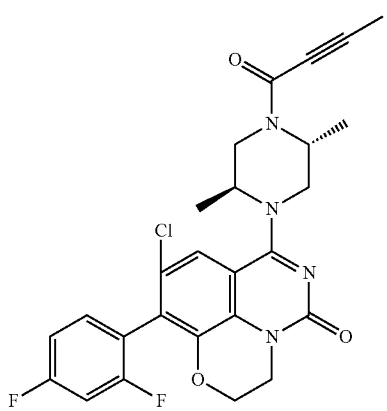 [SMILES: CC#CC(=O)N1C[C@H](C)N(c2nc(=O)n3c4c(c(-c5ccc(F)cc5F)c(Cl)cc24)OCC3)C[C@H]1C] | ¹H NMR (400 MHz, CDCl₃) δ 7.39 (dd, J = 1.6 Hz, J = 5.6 Hz, 1H), 7.30-7.24 (m, 1H), 7.02-6.94 (m, 2H), 5.02-4.70 (m, 2H), 4.45-4.22 (m, 3H), 4.19-3.95 (m, 3H), 3.86-3.70 (m 1.5H), 3.42-3.31 (m, 0.5H), 2.06 (d, J = 1.2 Hz, 1.5H), 2.05 (s, 1.5H), 1.43-1.34 (m, 4H), 1.28-1.23 (m, 2H). | 513.1 |
| 19 | 7-((2S,5R)-4-acryloyl-2,5-dimethylpiperazin-1-yl)-10-(1,6-dimethyl-1H-indazol-7-yl)-2H-[1,4]oxazino[2,3,4-ij]quinazolin-5(3H)-one | 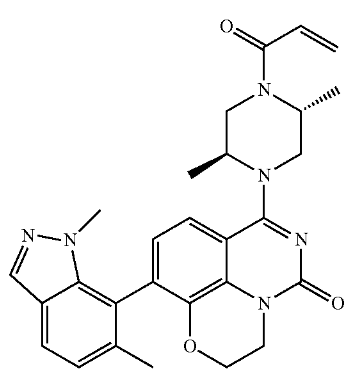 [SMILES: C=CC(=O)N1C[C@H](C)N(c2nc(=O)n3c4c(c(-c5c(C)ccc6cnn(C)c56)ccc24)OCC3)C[C@H]1C] | ¹H NMR (400 MHz, DMSO-d6) δ 8.01 (s, 1H), 7.68 (d, J = 8.4 Hz, 1H), 7.54-7.50 (m, 1H), 7.14-7.06 (m, 2H), 6.84-6.77 (m, 1H), 6.18 (dd, J = 16.4 Hz, J = 2.0 Hz, 1H), 5.76-5.72 (m, 1H), 4.77-4.43 (m, 2H), 4.40-4.24 (m, 2H), 4.16-3.61 (m, 6H), 3.43 (s, 3H), 2.14-2.12 (m, 3H), 1.30-1.18 (m, 6H). | 499.1 |

| Ex. Name | Structure | ¹H NMR | MS (M + H)⁺ |
|---|---|---|---|
| 19a 7-((2S,5R)-4-acryloyl-2,5-dimethylpiperazin-1-yl)-10-(3-fluoropyridin-2-yl)-2H-[1,4]oxazino[2,3,4-ij]quinazolin-5(3H)-one | | ¹H NMR (400 MHz, CDCl₃) δ 8.56 (d, J = 7.2 Hz, 1H), 7.53 (t, J 9.2 Hz, 1H), 7.42-7.35 (m, 2H), 7.29-7.24 (m, 1H), 6.76-6.51 (m, 1H), 6.40-6.32 (m, 1H), 5.78-5.74 (m, 1H), 5.09-4.92 (m, 1.5H), 4.46-3.87 (m, 6H), 3.87-3.63 (m, 2H), 3.49-3.42 (m, 0.5H), 1.38-1.34 (m, 4H), 1.23 (d, J = 6.8 Hz, 2H). | 450.1 |

D. Example 4

(3R)-7-((2S,5R)-4-acryloyl-2,5-dimethylpiperazin-1-yl)-9-chloro-3-((dimethylamino)methyl)-10-(2-fluoro-6-hydroxyphenyl)-5-oxo-3,5-dihydro-2H-[1,4]oxazino[2,3,4-ij]quinoline-6-carbonitrile The title compound was prepared according to the scheme below.

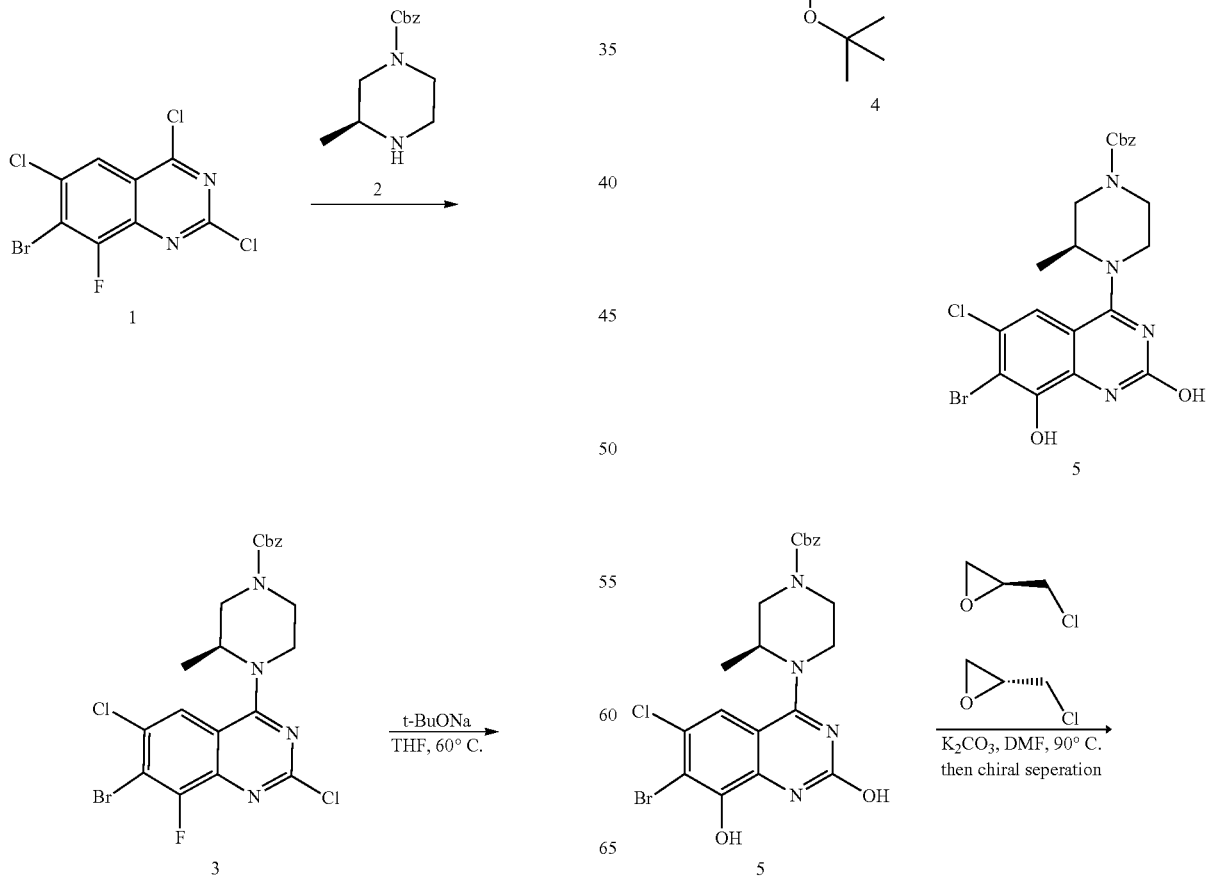

-continued
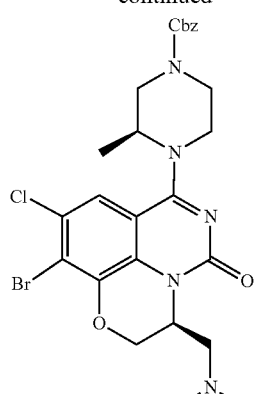
6a
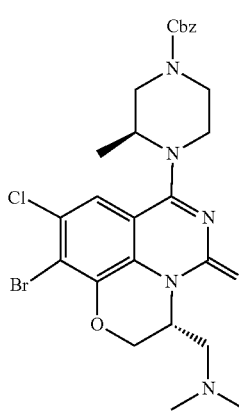
6b
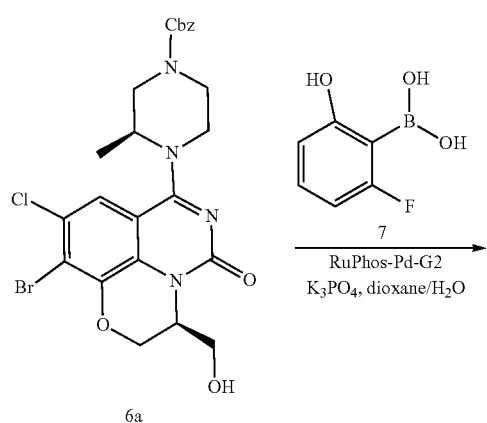
6a
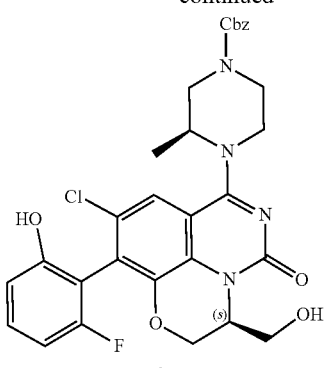
8a
Pd/C, H$_2$ →
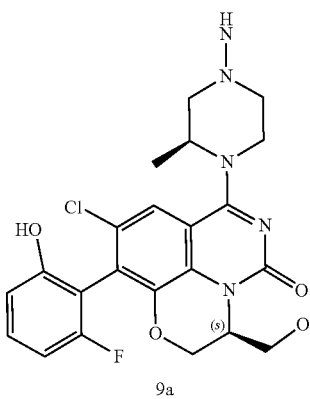
9a
Et$_3$N, DCM
then chiral HPLC →
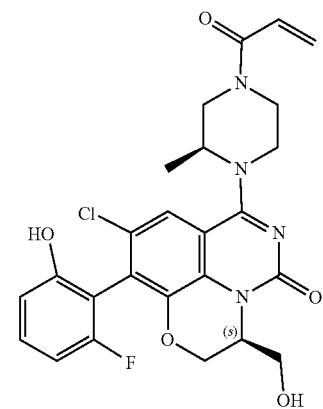
10a
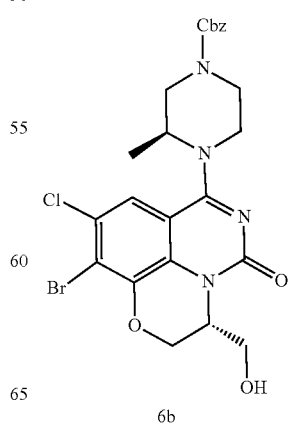
6b

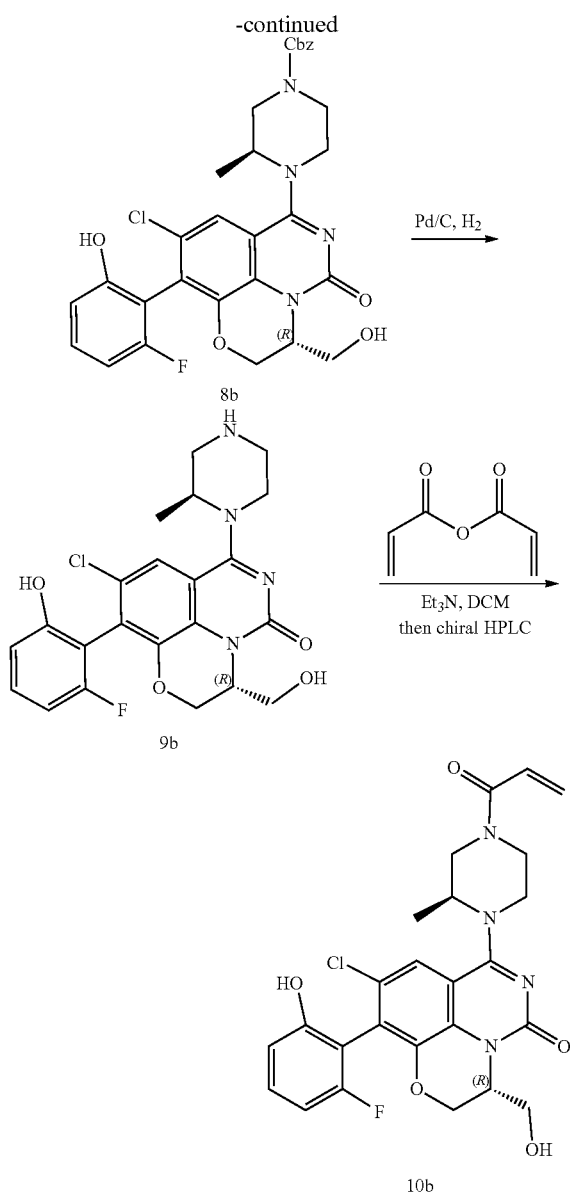

Step 1: S)-benzyl 4-(7-bromo-2,6-dichloro-8-fluoro-quinazolin-4-yl)-3-methylpiperazine-1-carboxylate To a cooled mixture of 7-bromo-2,4,6-trichloro-8-fluoro-quinazoline (8.83 g, 26.75 mmol) and Et₃N (8.10 g, 86.25 mmol) in THF (30 ml) was added (S)-benzyl 3-methylpiperazine-1-carboxylate (5.00 g, 21.4 mmol) at 0° C. The mixture was stirred at 0° C. for 30 minutes. After completion, the mixture was concentrated, the residue was purified by column with a mixture 100:1 of DCM in MeOH (100:1) to afford the desired product (12.50 g, 88% yield) as a yellow solid. LC-MS:m/z 529.1[M+H]⁺.

Step 2: (S)-benzyl 4-(7-bromo-2,8-di-tert-butoxy-6-chloroquinazolin-4-yl)-3-methylpiperazine-1-carboxylate To a solution of (S)-benzyl 4-(7-bromo-2,6-dichloro-8-fluoroquinazolin-4-yl)-3-methylpiperazine-1-carboxylate (12.50 g, 23.67 mmol) in dry THF (40 ml) was added t-BuONa (29 ml, 59.17 mmol, 2 M in THF) solution. Then the mixture was heated to 60° C. for 2 hours. After completion, the mixture was quenched with aqueous NH₄Cl and extracted with EA, dried with Na₂SO₄ and concentrated. The residue was purified by silica with a gradient 20:1 to 4:1 of PE:EA to afford the desired product (13.40 g, 90% yield) as a yellow solid. LC-MS: m/z 621.1[M+H]⁺.

Step 3: (S)-benzyl 4-(7-bromo-6-chloro-2,8-dihydroxyquinazolin-4-yl)-3-methylpiperazine-1-carboxylate To a solution of (S)-benzyl 4-(7-bromo-2,8-di-tert-butoxy-6-chloroquinazolin-4-yl)-3-methylpiperazine-1-carboxylate (13.40 g, 21.57 mmol) in DCM (40 ml) was added TFA (13 ml), the mixture was stirred at 25° C. for 3 hours. After completion, the solvent and excess TFA were removed under reduced pressure and purified by silica column with using a mixture 50:1 of DCM:MeOH to afford the desired product (9.00 g, 82% yield) as a yellow solid. LC-MS: m/z 509.1[M+H]⁺.

Step 4: (S)-benzyl 4-((S)-10-bromo-9-chloro-3-(hydroxymethyl)-5-oxo-3,5-dihydro-2H-[1,4]oxazino[2,3,4-ij]quinazolin-7-yl)-3-methylpiperazine-1-carboxylate and (S)-benzyl 4-((R)-10-bromo-9-chloro-3-(hydroxymethyl)-5-oxo-3,5-dihydro-2H-[1,4]oxazino[2,3,4-ij]quinazolin-7-yl)-3-methylpiperazine-1-carboxylate Half of the crude material obtain in step 3 (4.50 g, 8.86 mmol) was suspended in DMF (15 ml), K₂CO₃ (6.11 g, 44.3 mmol) was added followed by (S)-2-(chloromethyl)oxirane (8.24 g, 88.60 mmol). Then the mixture was heated to 90° C. for 5 hours. After completion, the mixture was concentrated and the residue was purified by column using a mixture 30:1 of DCM in MeOH to afford the desired product (2.21 g, 44% yield) as a yellow solid LC-MS: m/z 565.1 [M+H]⁺.

The second half of crude obtain in step 3 (4.50 g, 8.86 mmol) was suspended in DMF (15 ml), K₂CO₃ (6.11 g, 44.3 mmol) was added followed by (R)-2-(chloromethyl)oxirane (8.24 g, 88.60 mmol). Then the mixture was heated to 90° C. for 5 hours. After completion, the mixture was concentrated, the residue was purified by column chromatography using a mixture of: MeOH (30:1) to afford the desired product (3.66 g, 73% yield) as a yellow solid LC-MS: m/z 565.1 [M+H]⁺. The above diastereomers were mixed (5.87 g, 10.4 mmol) dissolved with MeOH (50 mL) and separated by chiral Prep. HPLC (separation condition: Column: Chiralpak IB 5 μm 20×250 mm; Mobile Phase: Hex:EtOH=55:45 at 25 mL/min; Temp: 30° C.; Wavelength: 254 nm) to afford the title compounds (880 mg, 31% yield, 100% de), and the other diastereomer (1.18 g, 42% yield, 100% de); Chiral HPLC Analytical: on CHIRALPAK® IB was using 5 μm 4.6×250 mm column, Mobile Phase: Hex:EtOH=55:45 at 1 mL/min; Temp: 30° C.; Wavelength: 254 nm).

Step 5: (3S)-benzyl 4-((3S)-9-chloro-10-(2-fluoro-6-hydroxyphenyl)-3-(hydroxymethyl)-5-oxo-3,5-dihydro-2H-[1,4]oxazino[2,3,4-ij]quinazolin-7-yl)-3-methylpiperazine-1-carboxylate A mixture of (S)-benzyl 4-((S)-10-bromo-9-chloro-3-(hydroxymethyl)-5-oxo-3,5-dihydro-2H-[1,4]oxazino[2,3,4-ij]quinazolin-7-yl)-3-methylpiperazine-1-carboxylate (400 mg, 0.71 mmol), (2-fluoro-6-hydroxyphenyl)boronic acid (543 mg, 3.55 mmol), RuPhos Pd G2 (55 mg, 0.071 mmol) and tripotassium phosphate (452 mg, 2.13 mmol) in dioxane (8 mL) and H$_2$O (1 mL) was heated to 100° C. under nitrogen atmosphere for 12 hours. The mixture was concentrated and purified by silica gel column chromatography using a mixture 30:1 of dichloromethane in methanol to give the crude product (330 mg, 78% yield) as yellow solid. LC-MS: m/z 596.1 [M+H]$^+$.

Step 6: (3S)-9-chloro-10-(2-fluoro-6-hydroxyphenyl)-3-(hydroxymethyl)-7-((S)-2-methylpiperazin-1-yl)-2H-[1,4]oxazino[2,3,4-ij]quinazolin-5(3H)-one Pd/C (132 mg) was added to a solution of (3S)-benzyl 4-((3S)-9-chloro-10-(2-fluoro-6-hydroxyphenyl)-3-(hydroxymethyl)-5-oxo-3,5-dihydro-2H-[1,4]oxazino[2,3,4-ij] quinazolin-7-yl)-3-methylpiperazine-1-carboxylate (330 mg, 0.55 mmol) in methanol (3 mL). The mixture was stirred at rt under hydrogen for 1 hours and filtered. The mixture was concentrated and purified by prep-HPLC [Column: waters Xbridge C18 5 um 19*150 m; Method: 10%-50% acetonitrile in water (0.1% NH$_4$HCO$_3$) at 254 nm; Flowrate: 15 ml/min; GT: 10 min.] to give the desired product (220 mg, 86% yield) as light yellow solid. LC-MS: m/z 460.1 [M+H]$^+$. $^1$H NMR (400 MHz, CD$_3$OD) δ 7.56 (s, 1H), 7.30-7.24 (m, 1H), 6.74 (d, J=8.4 Hz, 1H), 6.70-6.65 (m, 1H), 4.85-4.65 (m, 3H), 4.14-4.09 (m, 2H), 3.84-3.80 (m, 1H), 3.69-3.59 (m, 2H), 3.15 (dd, J=13.2 Hz, 4.4 Hz, 1H), 3.05 (d, J=12.8 Hz, 1H), 2.89 (d, J=13.6 Hz, 2H), 1.50 (d, J=6.8 Hz, 3H).

Step 7: (3S)-7-((S)-4-acryloyl-2-methylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one Acrylic anhydride (28 mg, 0.23 mmol) was added to a mixture of (3S)-9-chloro-10-(2-fluoro-6-hydroxyphenyl)-3-(hydroxymethyl)-7-((S)-2-methylpiperazin-1-yl)-2H-[1,4] oxazino[2,3,4-ij]quinazolin-5(3H)-one (110 mg, 0.25 mmol) and triethyl amine (50 mg, 0.50 mmol) in dichloromethane (3 mL) at −50° C. The mixture was stirred at rt for 1 hour and was purified by prep-HPLC [Column: waters Xbridge C18 5 um 19*150 m; Method: 10%-50% acetonitrile in water (0.1% NH$_4$HCO$_3$) at 254 nm; Flowrate: 15 ml/min; GT: 10 min.] to afford the desired product (119 mg, 48% yield) as white solid. LC-MS: m/z 514.5 [M+H]$^+$. The above diastereomer (50 mg) was dissolved in MeOH (50 mL and separated by chiral Prep. HPLC (separation condition: Column: Chiralpak AD-H 5 μm 20×250 mm; Mobile Phase: Hep:EtOH=70:30 at 25 mL/min; Temp: 30° C.; Wavelength: 254 nm) to afford the title compounds (23.1 mg, 31% yield, 100% de), and the undesired diastereoisomer (5.6 mg, 42% yield, 100% de); Chiral HPLC Analytical: on CHIRALPAK® AD-H was using 5 μm 4.6×250 mm column, Mobile Phase: Hep:EtOH=70:30 at 1 mL/min; Temp: 30° C.; Wavelength: 254 nm). $^1$H NMR (400 MHz, CD$_3$OD) δ 7.48 (s, 1H), 7.18-7.12 (m, 1H), 6.78-6.69 (m, 1H), 6.62 (d, J=8.8 Hz, 1H), 6.57 (t, J=9.2 Hz, 1H), 6.18 (dd, J=15.2 Hz, 4.0 Hz, 1H), 5.71 (dd, J=10.8 Hz, 1.6 Hz, 1H), 4.86-4.85 (m, 1H), 4.65-4.60 (m, 1H), 4.58-4.56 (m, 1H), 4.45-4.27 (m, 1H), 4.16-3.91 (m, 3H), 3.71-3.37 (m, 4H), 3.14-2.94 (m, 1H), 1.28 (d, J=6.8 Hz, 3H); Chiral HPLC Analytical: onAD-H was using 4.6×150 mm column, Mobile Phase: HEP:EtOH (0.1% DEA)=70:30 at 0.5 mL/min; Temp: 25° C.; Wavelength: 254 nm), Peak 1: e.e. =98.70%, Rt=4.52 min. $^1$H NMR (400 MHz, CD$_3$OD) δ 7.48 (s, 1H), 7.15 (q, J=6.8 Hz, 1H), 6.77-6.66 (m, 1H), 6.63 (d, J=8.4 Hz, 1H), 6.55 (t, J=8.8 Hz, 1H), 6.18 (dd, J=16.8 Hz, 4.4 Hz, 1H), 5.70 (dd, J=10.8 Hz, 2.0 Hz, 1H), 4.86-4.84 (m, 1H), 4.64-4.60 (m, 1H), 4.60-4.52 (m, 1H), 4.44-4.27 (m, 1H), 4.18-4.09 (m, 1H), 4.06-3.91 (m, 2H), 3.72-3.58 (m, 2.5H), 3.54-3.46 (m, 1H), 3.42-3.25 (m, 0.5H), 3.04-2.88 (m, 1H), 1.27 (d, J=6.4 Hz, 3H); Analytical: onAD-H was using 4.6×150 mm column, Mobile Phase: HEP:EtOH (0.1% DEA)=70:30 at 0.5 mL/min; Temp: 25° C.; Wavelength: 254 nm), Peak 2: e.e. =97.28%, Rt=4.73 min.

The following compounds were prepared using similar synthetic procedures and their characterization is provided below.

| Ex. Name | Structure | $^1$H NMR | MS (M + H)$^+$ |
|---|---|---|---|
| 19b (3R)-7-(4-acryloylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | | $^1$H NMR (400 MHz, CD$_3$OD) δ 7.55 (s, 1H), 7.18-7.13 (m, 1H), 6.74-6.55 (m, 3H), 6.17 (dd, J = 16.8 Hz, 1.6 Hz, 1H), 5.70 (dd, J = 10.8 Hz, 2.0 Hz, 1H), 4.63 (d, J = 11.6 Hz, 1H), 4.57-4.56 (m, 1H), 4.01-3.67 (m, 10H), 3.53 (t, J = 9.2 Hz, 1H). | 501.2 |

-continued

| Ex. | Name | Structure | ¹H NMR | MS (M + H)⁺ |
|---|---|---|---|---|
| 20 | (3R,10R)-7-(4-acryloylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 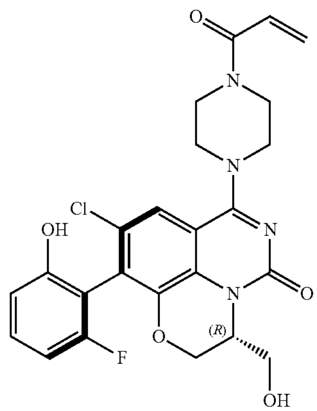 | ¹H NMR (400 MHz, CD₃OD) δ 7.59-7.55 (m, 1H), 7.18-7.12 (m, 1H), 6.73-6.54 (m, 3H), 6.16 (dd, J = 17.2 Hz, 1.6 Hz, 1H), 5.70 (dd, J = 10.4 Hz, 2.0 Hz, 1H), 4.63-4.54 (m, 2H), 4.25-4.22 (m, 1H), 4.00-3.69 (m, 9 H), 3.68-3.47 (m, 1H). | 500.9 |
| 21 | (3S)-7-(4-acryloylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 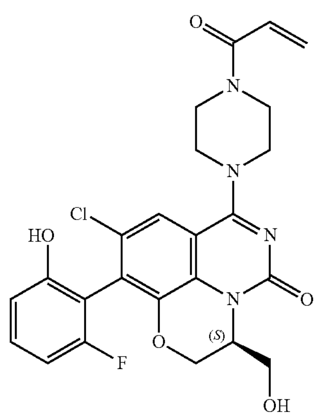 | ¹H NMR (400 MHz, CD₃OD) δ 7.71 (d, J = 1.2 Hz, 0.2H), 7.67 (d, J = 1.2 Hz, 0.8H), 7.30-7.22 (m, 1H), 6.86-6.64 (m, 2H), 6.31-6.24 (dd, J = 2.0, 17.2 Hz, 1H), 5.84-5.78 (dd, J = 1.6, 10.4 Hz, 1H), 4.76-4.64 (m, 1.7H), 4.60-4.51 (m, 0.3H), 4.40-4.30 (m, 0.7H), 4.13-3.77 (m, 9.3H), 3.67-3.58 (m, 1H). | 501.2 |
| 21a | (3R,10R)-7-(4-acryloylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 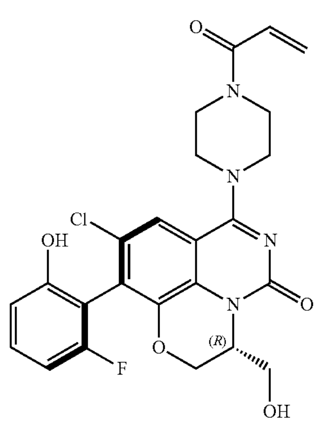 | ¹H NMR (400 MHz, CD₃OD) δ 7.59-7.55 (m, 1H), 7.18-7.12 (m, 1H), 6.73-6.54 (m, 3H), 6.16 (dd, J = 17.2 Hz, 1.6 Hz, 1H), 5.70 (dd, J = 10.4 Hz, 2.0 Hz, 1H), 4.63-4.54 (m, 2H), 4.25-4.22 (m, 1H), 4.00-3.69 (m, 9 H), 3.68-3.47 (m, 1H). | 500.9 |

| Ex. | Name | Structure | ¹H NMR | MS (M + H)⁺ |
|---|---|---|---|---|
| 21b | (3R,10S)-7-(4-acryloylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 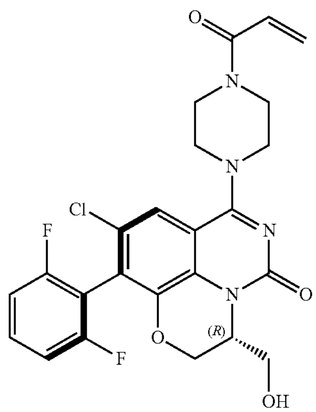 | ¹H NMR (400 MHz, CD₃OD) δ 7.55 (s, 1H), 7.18-7.13 (m, 1H), 6.74-6.55 (m, 3H), 6.17 (d, J = 16.8 Hz, 1H), 5.70 (d, J = 10.8 Hz, 1H), 4.63 (d, J = 11.6 Hz, 1H), 4.57-4.55 (m, 1H), 4.01-3.68 (m, 10H), 3.53 (t, J = 9.2 Hz, 1H). | 500.9 |
| 22 | (3R,10S)-7-((S)-4-acryloyl-2-methylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 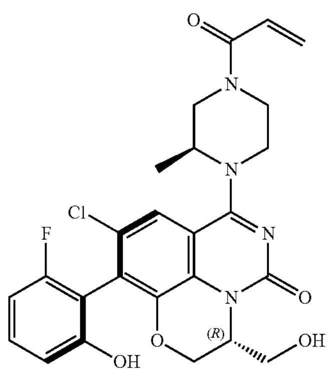 | ¹H NMR (400 MHz, CD₃OD) δ 7.44 (s, 1H), 7.18-7.12 (m, 1H), 6.71-6.55 (m, 3H), 6.18 (dd, J = 4.8 Hz, J = 16.4 Hz, 1H), 5.71 (d, J = 10.8 Hz, 1H), 4.71-4.67 (m, 1H), 4.62 (d, J = 11.2 Hz, 1H), 4.57-4.53 (m, 1H), 4.47-4.26 (m, 2H), 4.06-3.88 (m, 2H), 3.70 (dd, J = 10.8 Hz, J = 4.8 Hz, 1H), 3.55-3.48 (m, 3H), 3.12-3.09 (m, 1H), 1.37 (d, J = 6.4 Hz, 3H) | 515.2 |
| 23 | (3R,10R)-7-((S)-4-acryloyl-2-methylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 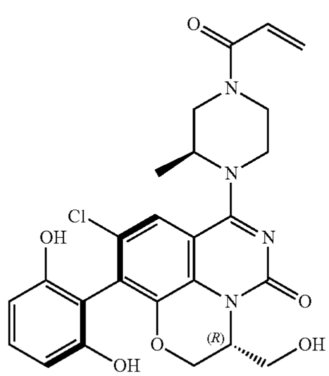 | ¹H NMR (400 MHz, CD₃OD) δ 7.57 (s, 1H), 7.31-7.25 (m, 1H), 6.77-6.67 (m, 3H), 6.30 (dd, J = 5.2 Hz, J = 16 Hz, 1H), 5.83 (d, J = 10.4 Hz, 1H), 4.87-4.83 (m, 1H), 4.75 (d, J = 11.2 Hz, 1H), 4.67-4.65 (m, 1H), 4.58-4.39 (m, 2H), 4.19-4.01 (m, 2H), 3.84 (dd, J = 5.2 Hz, J = 10.8 Hz, 1H), 3.65-3.60 (m, 3H), 3.26-3.20 (m, 1H), 1.50 (d, J = 6.4 Hz, 3H) | 515.2 |
| 24 | (3S,10S)-7-((S)-4-acryloyl-2-methylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 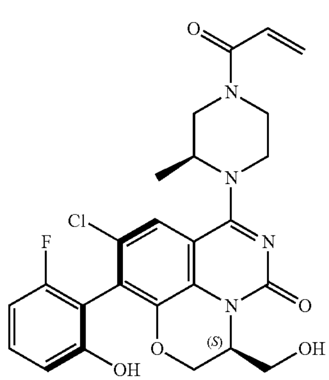 | ¹H NMR (400 MHz, CD₃OD) δ 7.48 (s, 1H), 7.18-7.12 (m, 1H), 6.78-6.69 (m, 1H), 6.62 (d, J = 8.8 Hz, 1H), 6.57 (t, J = 9.2 Hz, 1H), 6.18 (dd, J = 15.2 Hz, 4.0 Hz, 1H), 5.71 (dd, J = 10.8 Hz, 1.6 Hz, 1H), 4.86-4.85 (m, 1H), 4.65-4.60 (m, 1H), 4.58-4.56 (m, 1H), 4.45-4.27 (m, 1H), 4.16-3.91 (m, 3H), 3.71-3.37 (m, 4H), 3.14-2.94 (m, 1H), 1.28 (d, J = 6.8 Hz, 3H) | 515.2 |

-continued

| Ex. | Name | Structure | ¹H NMR | MS (M + H)⁺ |
|---|---|---|---|---|
| 25 | (3S,10R)-7-((S)-4-acryloyl-2-methylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 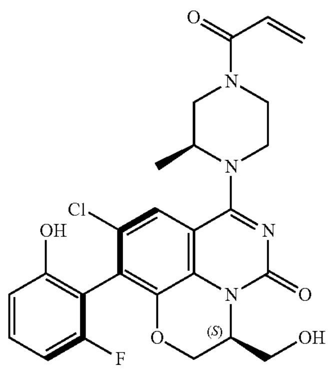 | ¹H NMR (400 MHz, CD₃OD) δ 7.48 (s, 1H), 7.15 (q, J = 6.8 Hz, 1H), 6.77-6.66 (m, 1H), 6.63 (d, J = 8.4 Hz, 1H), 6.55 (t, J = 8.8 Hz, 1H), 6.18 (dd, J = 16.8 Hz, 4.4 Hz, 1H), 5.70 (dd, J = 10.8 Hz, 2.0 Hz, 1H), 4.86-4.84 (m, 1H), 4.64-4.60 (m, 1H), 4.60-4.52 (m, 1H), 4.44-4.27 (m, 1H), 4.18-4.09 (m, 1H), 4.06-3.91 (m, 2H), 3.72-3.58 (m, 2.5H), 3.54-3.46 (m, 1H), 3.42-3.25 (m, 0.5H), 3.04-2.88 (m, 1H), 1.27 (d, J = 6.4 Hz, 3H) | 515.2 |
| 26 | (3S)-7-((2S,5R)-4-acryloyl-2,5-dimethylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 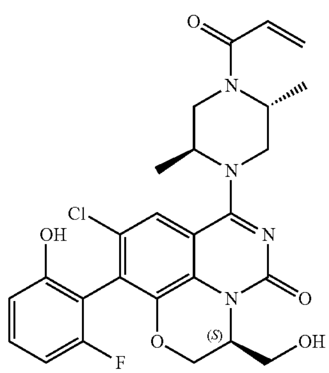 | ¹H NMR (400 MHz, CD₃OD) δ 7.64-7.59 (m, 1H), 7.33-7.24 (m, 1H), 6.93-6.78 (m, 1H), 6.76-6.73 (m, 1H), 6.72-6.67 (m, 1H), 6.33-6.27 (m, 1H), 5.85-5.81 (m, 1H), 4.83-4.68 (m, 2H), 4.53-4.29 (m, 2H), 4.14-4.07 (m, 1H), 3.93-3.78 (m, 3H), 3.70-3.61 (m, 1H), 3.49-3.39 (m, 1H), 3.29-3.09 (m, 1H), 1.50-1.45 (m, 3H), 1.44-1.39 (m, 1.5H), 1.37-1.32 (m, 1.5H) | 529.2 |
| 27 | (3S,10S)-7-((2S,5R)-4-acryloyl-2,5-dimethylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 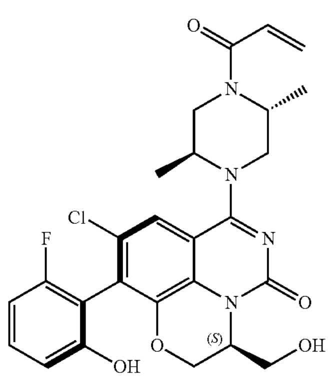 | ¹H NMR (400 MHz, CDCl₃) δ 7.43 (d, J = 8.4 Hz, 1H), 7.24-7.20 (m, 1H), 6.91 (d, J = 7.6 Hz, 1H), 6.71 (t, J = 8.8 Hz, 1H), 6.62-6.42 (m, 1H), 6.39-6.29 (m, 1H), 5.77-5.73 (m, 1H), 5.00-4.91 (m, 0.5H), 4.86-4.78 (m, 1H), 4.75-4.68 (m, 1H), 4.61 (d, J = 11.6 Hz, 1H), 4.46-4.20 (m, 2H), 4.00-3.91 (m, 1H), 3.90-3.79 (m, 2H), 3.59-3.48 (m, 2H), 3.16-3.14 (m, 0.5H), 1.40-1.31 (m, 6H) | 529.2 |
| 28 | (3S,10R)-7-((2S,5R)-4-acryloyl-2,5-dimethylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 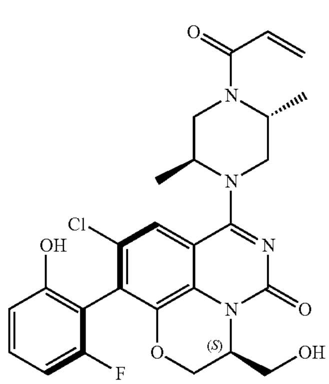 | ¹H NMR (400 MHz, CDCl₃) δ 7.49 (d, J = 11.6 Hz, 1H), 7.35-7.28 (m, 1H), 6.86-6.73 (m, 2H), 6.64-6.40 (m, 0.5H), 6.54-6.49 (m, 0.5H), 6.44-6.33 (m, 1H), 5.82-5.77 (m, 1H), 5.04-4.97 (m, 0.5H), 4.89-4.76 (m, 2H), 4.65-4.51 (m, 1.5H), 4.38-4.29 (m, 1H), 4.24-4.17 (m, 0.5H), 4.11-4.03 (m, 1H), 3.96-3.89 (m, 1H), 3.84-3.77 (m, 1H), 3.72-3.59 (m, 2H), 3.29-3.19 (m, 0.5H), 1.49-1.31 (m, 6H) | 529.2 |

-continued

| Ex. | Name | Structure | ¹H NMR | MS (M + H)⁺ |
|---|---|---|---|---|
| 29 | (3R)-7-((2S,5R)-4-acryloyl-2,5-dimethylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 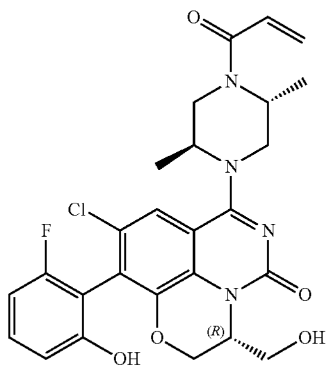 | ¹H NMR (400 MHz, CDCl₃) δ 7.41 (d, J = 8.8 Hz, 1H), 7.33-7.27 (m, 1H), 6.89-6.72 (m, 2H), 6.70-6.30 (m, 2H), 5.83-5.72 (m, 1H), 5.13-4.73 (m, 2.5H), 4.70-4.62 (m, 1H), 4.36-4.21 (m, 1H), 4.18-3.76 (m, 6H), 3.66-3.50 (m, 0.5H), 1.37-1.08 (m, 6H). | 529.3 |
| 31a | (3R,10S)-7-((2S,5R)-4-acryloyl-2,5-dimethylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 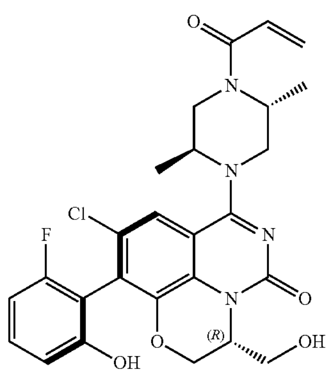 | ¹H NMR (400 MHz, CDCl₃) δ 7.39 (d, J = 13.6 Hz, 1H), 7.24-7.20 (m, 1H), 6.88 (d, J = 8.4 Hz, 1H), 6.73 (t, J = 8.0 Hz, 1H), 6.58-6.38 (m, 1H), 6.31-6.26 (m, 1H), 5.74-5.71 (m, 1H), 4.87 (m, 2.5H), 4.67 (t, J = 5.6 Hz, 1H), 4.22-4.18 (m, 1H), 4.04-3.85 (m, 5H), 3.73-3.62 (m, 0.5H), 3.54-3.42 (m, 1H), 1.24-1.19 (m, 4H), 1.11-1.10 (m, 2H) | 529.2 |
| 32 | (3R,10R)-7-((2S,5R)-4-acryloyl-2,5-dimethylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one | 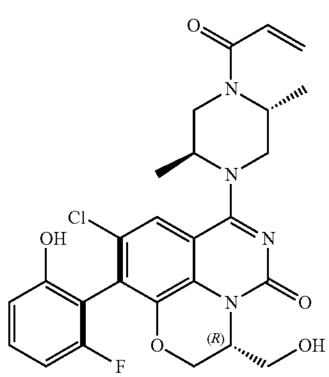 | ¹H NMR (400 MHz, CDCl₃) δ 7.45 (d, J = 12.4 Hz, 1H), 7.31-7.28 (m, 1H), 6.83 (d, J = 8.4 Hz, 1H), 6.75 (t, J = 8.8 Hz, 1H), 6.63-6.51 (m, 1H), 6.42-6.36 (m, 1H), 5.79 (d, J = 10.4 Hz, 1H), 5.09-5.06 (m, 0.5H), 4.89 (d, J = 4.0 Hz, 1H), 4.78 (t, J = 5.6 Hz, 1H), 4.64 (d, J = 11.2 Hz, 1H), 4.31 (d, J = 12.0 Hz, 1H), 4.09 (d, J = 11.2 Hz, 1H), 4.03-3.79 (m, 4.5H), 3.66-3.53 (m, 1H), 1.32-1.17 (m, 4H), 1.15-1.10 (m, 2H); | 529.2 |
| 33 | (3R,10S)-7-((2S,5R)-4-acryloyl-2,5-dimethylpiperazin-1-yl)-9-chloro-1-(2-fluoro-6-hydroxyphenyl)-3-(hydroxymethyl)-2H-[1,4]oxazino[2,3,4-ij]quinazolin-5(3H)-one | 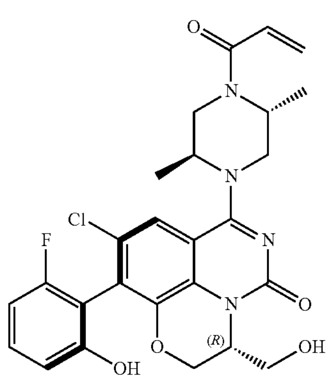 | ¹H NMR (400 MHz, CDCl₃) δ 7.39 (d, J = 13.6 Hz, 1H), 7.24-7.20 (m, 1H), 6.88 (d, J = 8.4 Hz, 1H), 6.73 (t, J = 8.0 Hz, 1H), 6.58-6.38 (m, 1H), 6.31-6.26 (m, 1H), 5.74-5.71 (m, 1H), 4.87 (m, 2.5H), 4.67 (t, J = 5.6 Hz, 1H), 4.22-4.18 (m, 1H), 4.04-3.85 (m, 5H), 3.73-3.62 (m, 0.5H), 3.54-3.42 (m, 1H), 1.24-1.19 (m, 4H), 1.11-1.10 (m, 2H) | 529.2 |

E. Example 5
This Example describes the preparation of an exemplary compound having a pyrimidone-amino-substituted morpholine scaffold and provides data for compounds that are similarly prepared.
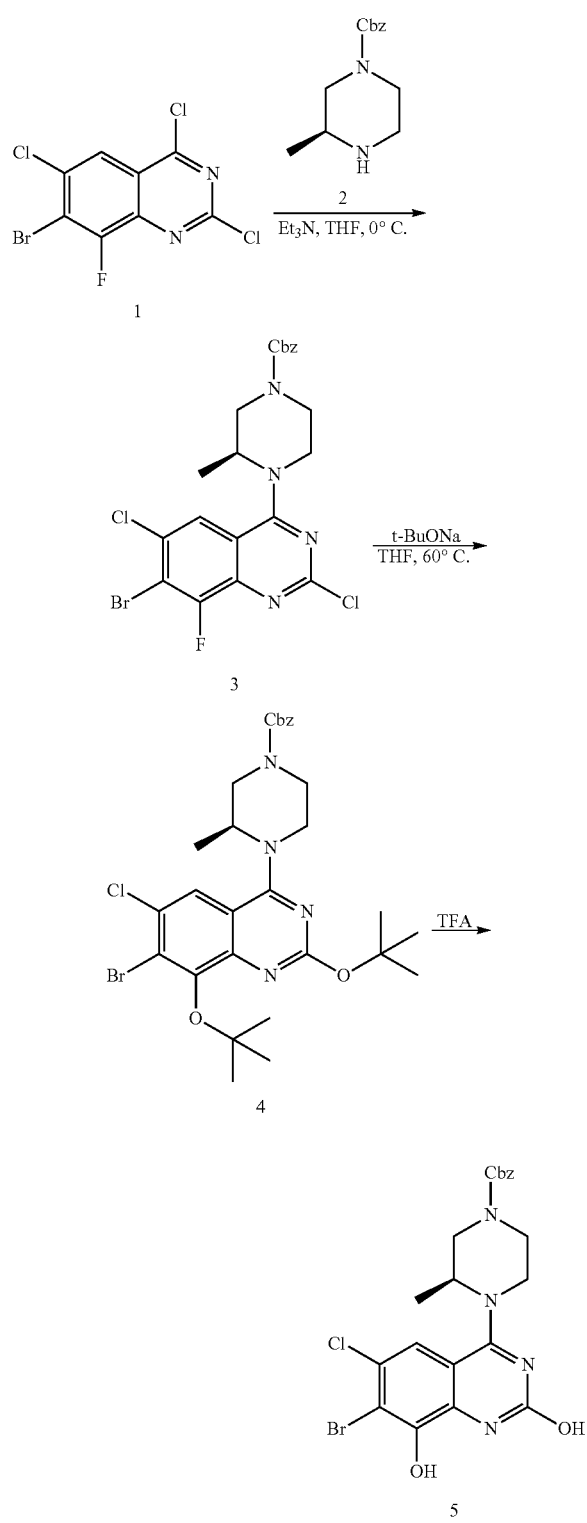

-continued

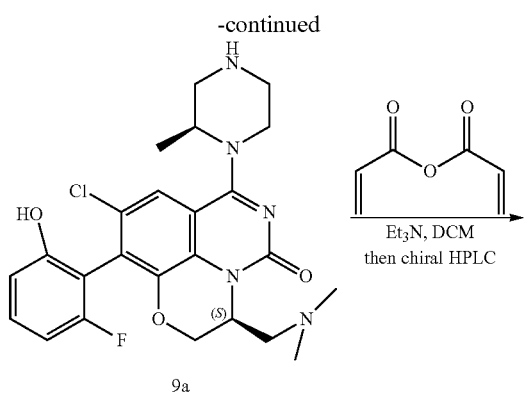
9a

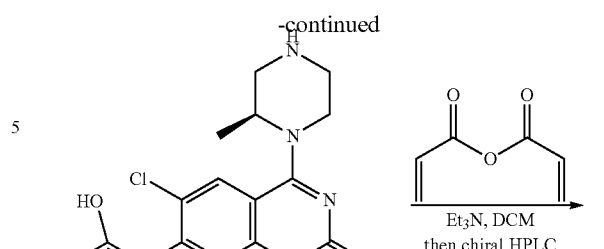

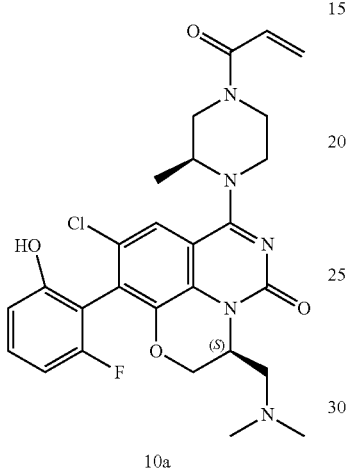
10a

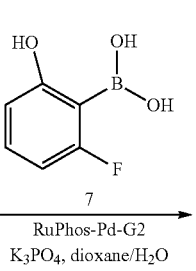
7
RuPhos-Pd-G2
K₃PO₄, dioxane/H₂O

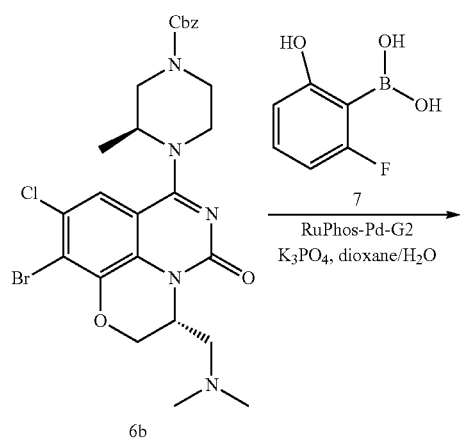
6b

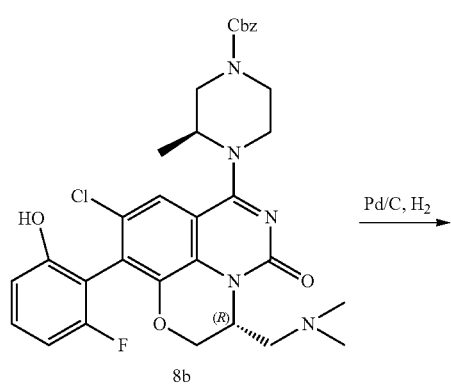
8b

-continued

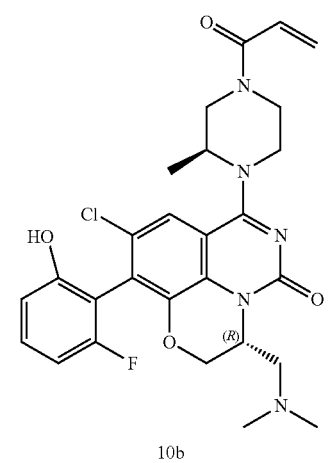
9b, 10b (S)-benzyl 4-(7-bromo-2,6-dichloro-8-fluoroquinazolin-4-yl)-3-methylpiperazine-1-carboxylate To a cooled mixture of 7-bromo-2,4,6-trichloro-8-fluoroquinazoline (8.83 g, 26.75 mmol) and Et₃N (8.10 g, 86.25 mmol) in THF (30 ml) was added (S)-benzyl 3-methylpiperazine-1-carboxylate (5.00 g, 21.4 mmol) at 0° C. The mixture was stirred at 0° C. for 30 minutes. After completion, the mixture was concentrated, the residue was purified by column with a mixture of DCM/MeOH (100:1) to afford the desired product (12.50 g, 88% yield) as a yellow solid. LC-MS: m/z 529.1 [M+H]⁺.

(S)-benzyl 4-(7-bromo-2,8-di-tert-butoxy-6-chloroquinazolin-4-yl)-3-methylpiperazine-1-carboxylate To a solution of (S)-benzyl 4-(7-bromo-2,6-dichloro-8-fluoroquinazolin-4-yl)-3-methylpiperazine-1-carboxylate (12.50 g, 23.67 mmol) in dry THF (40 ml) was added t-BuONa (29 ml, 59.17 mmol, 2 M in THF) solution. Then the mixture was heated to 60° C. for 2 hours. After completion, the mixture was quenched with aqueous NH₄Cl and extracted with EA, dried with Na₂SO₄ and concentrated. The residue was purified by silica with a gradient of PE:EA (20:1 to 4:1) to afford the desired product (13.40 g, 90% yield) as a yellow solid. LC-MS: m/z 621.1[M+H]⁺.

(S)-benzyl 4-(7-bromo-6-chloro-2,8-dihydroxyquinazolin-4-yl)-3-methylpiperazine-1-carboxylate To a solution of (S)-benzyl 4-(7-bromo-2,8-di-tert-butoxy-6-chloroquinazolin-4-yl)-3-methylpiperazine-1-carboxylate (13.40 g, 21.57 mmol) in DCM (40 ml) was added TFA (13 ml), the mixture was stirred at 25° C. for 3 hours. After completion, the solvent and excess TFA were removed under reduced pressure. The crude material was purified by silica column with a mixture of DCM:MeOH (50:1) to afford the desired product (9.00 g, 82% yield) as a yellow solid. LC-MS: m/z 509.1[M+H]$^+$.

(S)-benzyl 4-((S)-10-bromo-9-chloro-3-(hydroxymethyl)-5-oxo-3,5-dihydro-2H-[1,4]oxazino[2,3,4-ij]quinazolin-7-yl)-3-methylpiperazine-1-carboxylate and (S)-benzyl 4-((R)-10-bromo-9-chloro-3-(hydroxymethyl)-5-oxo-3,5-dihydro-2H-[1,4]oxazino[2,3,4-ij]quinazolin-7-yl)-3-methylpiperazine-1-carboxylate The residue (2R,5S)-tert-butyl 4-(7-bromo-6-chloro-2,8-dihydroxyquinazolin-4-yl)-2,5-dimethylpiperazine-1-carboxylate
(1.0 g, 2.04 mmol) was suspended in DMF (10 ml), $K_2CO_3$ (845 mg, 6.12 mmol) was added followed by 2,3-dibromo-N,N-dimethylpropan-1-amine (2.21 g, 4.5 mmol). Then the mixture was heated to 90° C. for 5 hours. After completion, the mixture was concentrated and the residue was purified by column with a mixture of DCM:MeOH (30:1) to afford the title product (390 mg, 33% yield) as a yellow solid LC-MS: m/z 572.1[M+H]$^+$. A racemic mixture of the above (390 mg, 0.68 mmol) was dissolved with MeOH (50 mL) and separated by chiral Prep. HPLC (separation condition: Column: Chiralpak AD-H 5 μm 20×230 mm; Mobile Phase: Hep:EtOH=70:30 at 15 mL/min; Temp: 30° C.; Wavelength: 254 nm) to afford the title compounds Y02376-16007-002P1 Compound 6a (140 mg, 35% yield, 100% ee), Compound 6b (130 g, 33% yield, 100% ee); Chiral HPLC Analytical: on CHIRALPAK® AD-H was using 5 μm 4.6×250 mm column, Mobile Phase: Hep:EtOH=70:30 at 1 mL/min; Temp: 30° C.; Wavelength: 254 nm).

(3S)-benzyl 4-((3S)-9-chloro-10-(2-fluoro-6-hydroxyphenyl)-3-(hydroxymethyl)-5-oxo-3,5-dihydro-2H-[1,4]oxazino[2,3,4-ij]quinazolin-7-yl)-3-methylpiperazine-1-carboxylate A mixture of (S)-benzyl 4-((S)-10-bromo-9-chloro-3-(hydroxymethyl)-5-oxo-3,5-dihydro-2H-[1,4]oxazino[2,3,4-ij]quinazolin-7-yl)-3-methylpiperazine-1-carboxylate (400 mg, 0.71 mmol), (2-fluoro-6-hydroxyphenyl)boronic acid (543 mg, 3.55 mmol), Ruphos Pd G2 (55 mg, 0.071 mmol) and tripotassium phosphate (452 mg, 2.13 mmol) in dioxane (8 mL) and $H_2O$ (1 mL) was heated to 100° C. under nitrogen atmosphere for 12 hours. The mixture was concentrated and was purified by silica gel column chromatography (dichloromethane/methnol=30/1) to give the crude product (330 mg, 78% yield) as yellow solid. LC-MS: m/z 596.1 [M+H]$^+$.

(3S)-9-chloro-10-(2-fluoro-6-hydroxyphenyl)-3-(hydroxymethyl)-7-((S)-2-methylpiperazin-1-yl)-2H-[1,4]oxazino[2,3,4-ij]quinazolin-5(3H)-one Pd/C (132 mg) was added to a solution of (3S)-benzyl 4-((3S)-9-chloro-10-(2-fluoro-6-hydroxyphenyl)-3-(hydroxymethyl)-5-oxo-3,5-dihydro-2H-[1,4]oxazino[2,3,4-ij]quinazolin-7-yl)-3-methylpiperazine-1-carboxylate (330 mg, 0.55 mmol) in methanol (3 mL). The mixture was stirred at rt under hydrogen for 1 hour, filtered, concentrated under reduced pressure and purified by prep-HPLC to give the desired product (220 mg, 86% yield) as light yellow solid. LC-MS: m/z 460.1 [M+H]$^+$. $^1$H NMR (400 MHz, $CD_3OD$) δ 7.56 (s, 1H), 7.30-7.24 (m, 1H), 6.74 (d, J=8.4 Hz, 1H), 6.70-6.65 (m, 1H), 4.85-4.65 (m, 3H), 4.14-4.09 (m, 2H), 3.84-3.80 (m, 1H), 3.69-3.59 (m, 2H), 3.15 (dd, J=13.2 Hz, 4.4 Hz, 1H), 3.05 (d, J=12.8 Hz, 1H), 2.89 (d, J=13.6 Hz, 2H), 1.50 (d, J=6.8 Hz, 3H).

(3S)-7-((S)-4-acryloyl-2-methylpiperazin-1-yl)-9-chloro-10-(2-fluoro-6-hydroxyphenyl)-3-(hydroxymethyl)-2H-[1,4]oxazino[2,3,4-ij]quinazolin-5(3H)-one Acrylic anhydride (28 mg, 0.23 mmol) was added to a mixture of (3S)-9-chloro-10-(2-fluoro-6-hydroxyphenyl)-3-(hydroxymethyl)-7-((S)-2-methylpiperazin-1-yl)-2H-[1,4]oxazino[2,3,4-ij]quinazolin-5(3H)-one (110 mg, 0.25 mmol) and triethyl amine (50 mg, 0.50 mmol) in dichloromethane (3 mL) at −50° C. The mixture was stirred at rt for 1 hour. The mixture was purified by prep-HPLC to afford the product (119 mg, 48% yield) as white solid. LC-MS: m/z 514.5 [M+H]$^+$.

The above diastereomers (50 mg) were dissolved with MeOH (50 mL), separated by chiral Prep. HPLC (separation condition: Column: Chiralpak AD-H 5 μm 20×250 mm; Mobile Phase: Hep:EtOH=70:30 at 25 mL/min; Temp: 30° C.; Wavelength: 254 nm) to afford the title compounds (23.1 mg, 31% yield, 100% de), and (5.6 mg, 42% yield, 100% de); Chiral HPLC Analytical: on CHIRALPAK®k AD-H was using 5 μm 4.6×250 mm column, Mobile Phase: Hep:EtOH=70:30 at 1 mL/min; Temp: 30° C.; Wavelength: 254 nm).

$^1$H NMR (400 MHz, $CD_3OD$) δ 7.48 (s, 1H), 7.18-7.12 (m, 1H), 6.78-6.69 (m, 1H), 6.62 (d, J=8.8 Hz, 1H), 6.57 (t, J=9.2 Hz, 1H), 6.18 (dd, J=15.2 Hz, 4.0 Hz, 1H), 5.71 (dd, J=10.8 Hz, 1.6 Hz, 1H), 4.86-4.85 (m, 1H), 4.65-4.60 (m, 1H), 4.58-4.56 (m, 1H), 4.45-4.27 (m, 1H), 4.16-3.91 (m, 3H), 3.71-3.37 (m, 4H), 3.14-2.94 (m, 1H), 1.28 (d, J=6.8 Hz, 3H); Chiral HPLC Analytical: on AD-H was using 4.6×150 mm column, Mobile Phase: HEP:EtOH (0.1% DEA)=70:30 at 0.5 mL/min; Temp: 25° C.; Wavelength: 254 nm), Peak 1: e.e. =98.70%, Rt=4.52 min.

$^1$H NMR (400 MHz, $CD_3OD$) δ 7.48 (s, TH), 7.15 (q, J=6.8 Hz, TH), 6.77-6.66 (p, 1H), 6.63 (d, J=8.4 Hz, TH), 6.55 (t, J=8.8 Hz, 1H), 6.18 (dd, J=16.8 Hz, 4.4 Hz, 1H), 5.70 (dd, J=10.8 Hz, 2.0 Hz, 1H), 4.86-4.84 (d, 1H), 4.64-4.60 (t, 1H), 4.60-4.52 (m, 1H), 4.44-4.27 (m, 1H), 4.18-4.09 (m, 1H), 4.06-3.91 (i, 2H), 3.72-3.58 (m, 2.5H), 3.54-3.46 (m, 1H), 3.42-3.25 (m, 0.5H), 3.04-2.88 (m, 1H), 1.27 (d, J=6.4 Hz, 3H); Analytical: on AD-H was using 4.6×150 mm column, Mobile Phase: HEP 6-EtOH (01 DEA)=70:30 at 0.5 mL/min; Temp: 25° C.; Wavelength: 254 nm), Peak 2: e.e. =97.28%, Rt=4.73 min.

The following compounds were prepared using similar synthetic procedures and their characterization is provided below.

| Ex. | Name | Structure | ¹H NMR | MS (M + H)⁺ |
|---|---|---|---|---|
| 29 | (3S)-7-((S)-4-acryloyl-2-methylpiperazin-1-yl)-9-chloro-3-((dimethylamino)methyl)-10-(2-fluoro-6-hydroxyphenyl)-2H-[1,4]oxazino[2,3,4-ij]quinazolin-5(3H)-one | 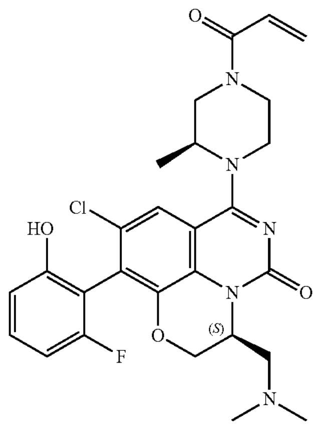 | ¹H NMR (400 MHz, CD₃OD) δ 7.48 (s, 1H), 7.18-7.12 (m, 1H), 6.78-6.69 (m, 1H), 6.62 (d, J = 8.8 Hz, 1H), 6.57 (t, J = 9.2 Hz, 1H), 6.18 (dd, J = 15.2 Hz, 4.0 Hz, 1H), 5.71 (dd, J = 10.8 Hz, 1.6 Hz, 1H), 4.86-4.85 (m, 1H), 4.65-4.60 (m, 1H), 4.58-4.56 (m, 1H), 4.45-4.27 (m, 1H), 4.16-3.91 (m, 3H), 3.71-3.37 (m, 4H), 3.14-2.94 (m, 1H), 1.28 (d, J = 6.8 Hz, 3H) | 556.2 |
| 31 | (3R)-7-((S)-4-acryloyl-2-methylpiperazin-1-yl)-9-chloro-3-((dimethylamino)methyl)-10-(2-fluoro-6-hydroxyphenyl)-2H-[1,4]oxazino[2,3,4-ij]quinazolin-5(3H)-one | 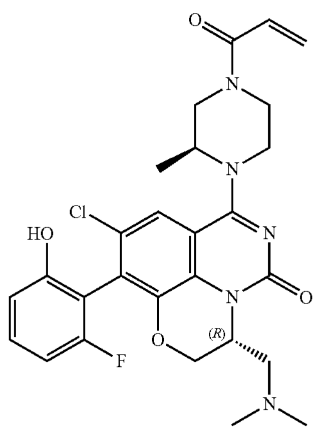 | ¹H NMR (400 MHz, CD₃OD) δ 7.48 (s, 1H), 7.15 (q, J = 6.8 Hz, 1H), 6.77-6.66 (m, 1H), 6.63 (d, J = 8.4 Hz, 1H), 6.55 (t, J = 8.8 Hz, 1H), 6.18 (dd, J = 16.8 Hz, 4.4 Hz, 1H), 5.70 (dd, J = 10.8 Hz, 2.0 Hz, 1H), 4.86-4.84 (m, 1H), 4.64-4.60 (m, 1H), 4.60-4.52 (m, 1H), 4.44-4.27 (m, 1H), 4.18-4.09 (m, 1H), 4.06-3.91 (m, 2H), 3.72-3.58 (m, 2.5H), 3.54-3.46 (m, 1H), 3.42-3.25 (m, 0.5H), 3.04-2.88 (m, 1H), 1.27 (d, J = 6.4 Hz, 3H) | 556.3 |
| 34 | 7-((2S,5R)-4-acryloyl-2,5-dimethylpiperazin-1-yl)-9-chloro-3-((dimethylamino)methyl)-10-(4-fluorophenyl)-2H-[1,4]oxazino[2,3,4-ij]quinazolin-5(3H)-one | 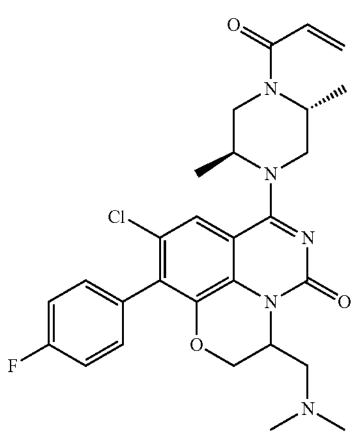 [SMILES: C=CC(=O)N1C[C@H](C)N(c2nc(=O)n3c4c(c(-c5ccc(F)cc5)c(Cl)cc24)OCC3CN(C)C)C[C@H]1C] | 1H NMR (400 MHz, CDCl₃) δ 7.45-7.39 (m, 1H), 7.33-7.29 (m, 2H), 7.18 (t, J = 8.0 Hz, 2H), 6.66-6.51 (m, 1H), 6.37 (t, J = 12.4 Hz, 1H), 5.79-5.75 (m, 1H), 5.01-4.68 (m, 3.5H), 4.40-4.27 (m, 1H), 4.14-3.33 (m, 4.5H), 2.59-2.45 (m, 2H), 2.38 (s, 6H), 1.43-1.21 (m, 6H) | 540.2 |

| Ex. | Name | Structure | ¹H NMR | MS (M + H)⁺ |
|---|---|---|---|---|
| 35 | 7-((2S,5R)-4-acryloyl-2,5-dimethylpiperazin-1-yl)-9-chloro-10-(2,4-difluorophenyl)-3-((dimethylamino)methyl)-2H-[1,4]oxazino[2,3,4-ij]quinazolin-5(3H)-one | 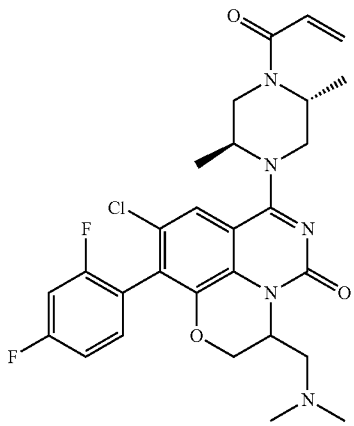 [SMILES: C=CC(=O)N1C[C@H](C)N(c2nc(=O)n3c4c(c(-c5ccc(F)cc5F)c(Cl)cc24)OCC3CN(C)C)C[C@H]1C] | ¹H NMR (400 MHz, CDCl₃) δ 7.43-7.38 (m, 1H), 7.31-7.23 (m, 1H), 7.03-6.93 (m, 2H), 6.66-6.51 (m, 1H), 6.37 (t, J = 16.0 Hz, 1H), 5.71 (t, J = 8.4 Hz, 1H), 5.05-4.69 (m, 3.6H), 4.40-4.30 (m, 1H), 4.11-3.52 (m, 4.5H), 2.61-2.43 (m, 2H), 2.37 (s, 6H), 1.44-1.20 (m, 6H). | 558.2 |
| 36 | (3S)-7-((S)-4-acryloyl-2-methylpiperazin-1-yl)-9-chloro-10-(2,4-difluorophenyl)-3-(morpholinomethyl)-2H-[1,4]oxazino[2,3,4-ij]quinazolin-5(3H)-one | 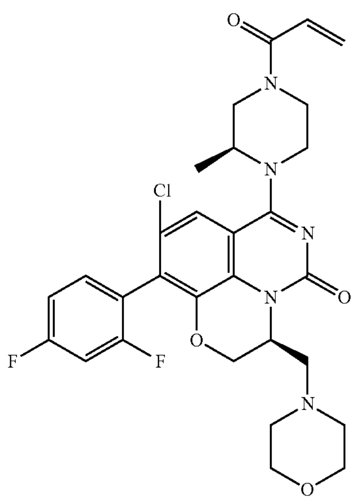 [SMILES: C=CC(=O)N1CCN(c2nc(=O)n3c4c(c(-c5ccc(F)cc5F)c(Cl)cc24)OC[C@@H]3CN2CCOCC2)[C@@H](C)C1] | ¹H NMR (400 MHz, CDCl₃) δ 7.41 (s, 1H), 7.32-7.23 (m, 1H), 7.04-6.93 (m, 2H), 6.59-6.53 (m, 1H), 6.40-6.35 (m, 1H), 5.78 (d, J =10.4 Hz, 1H), 5.00-4.94 (m, 0.5H), 4.79-4.65 (m, 3H), 4.50-4.43 (m, 0.5H), 4.24-4.12 (m, 1H), 4.02-3.97 (m, 1.5H), 3.84-3.80 (m, 0.5H), 3.73-3.49 (m, 6H), 3.25-3.22 (m, 0.5H), 2.98-2.93 (m, 0.5H), 2.72-2.69 (m, 2H), 2.56-2.45 (m, 4H), 1.38 (d, J = 6.4 Hz, 3H) | 586.1 |
| 37 | (3R)-7-((S)-4-acryloyl-2-methylpiperazin-1-yl)-9-chloro-10-(2,4-difluorophenyl)-3-(morpholinomethyl)-2H-[1,4]oxazino[2,3,4-ij]quinazolin-5(3H)-one | 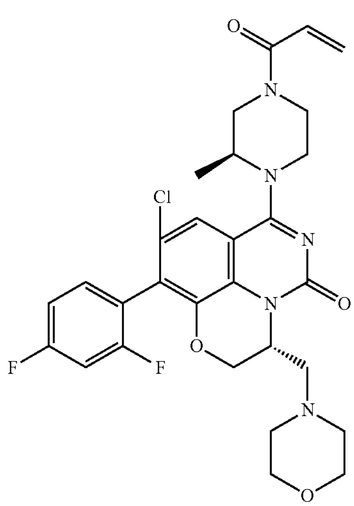 [SMILES: C=CC(=O)N1CCN(c2nc(=O)n3c4c(c(-c5ccc(F)cc5F)c(Cl)cc24)OC[C@H]3CN2CCOCC2)[C@@H](C)C1] | ¹H NMR (400 MHz, CDCl₃) δ 7.39 (d, J = 4.0 Hz, 1H), 7.33-7.23 (m, 1H), 7.04-6.94 (m, 2H), 6.62-6.55 (m, 1H), 6.38 (d, J = 17.2 Hz, 1H), 5.78 (d, J = 10.4 Hz, 1H), 4.81-4.67 (m, 3.5H), 4.45-4.40 (m, 1H), 4.31-4.27 (m, 0.5H), 4.03-3.94 (m, 1.5H), 3.83-3.80 (m, 0.5H), 3.73-3.46 (m, 6H), 3.13-3.05 (m, 1H), 2.74-2.72 (m, 2H) 2.61-2.54 (m, 4H), 1.51-1.45 (m, 3H) | 586.1 |

F. Example 6

This Example describes the preparation of an exemplary compound having a pyridone-piperdine scaffold and provides data for compounds that are similarly prepared.

Reaction Scheme

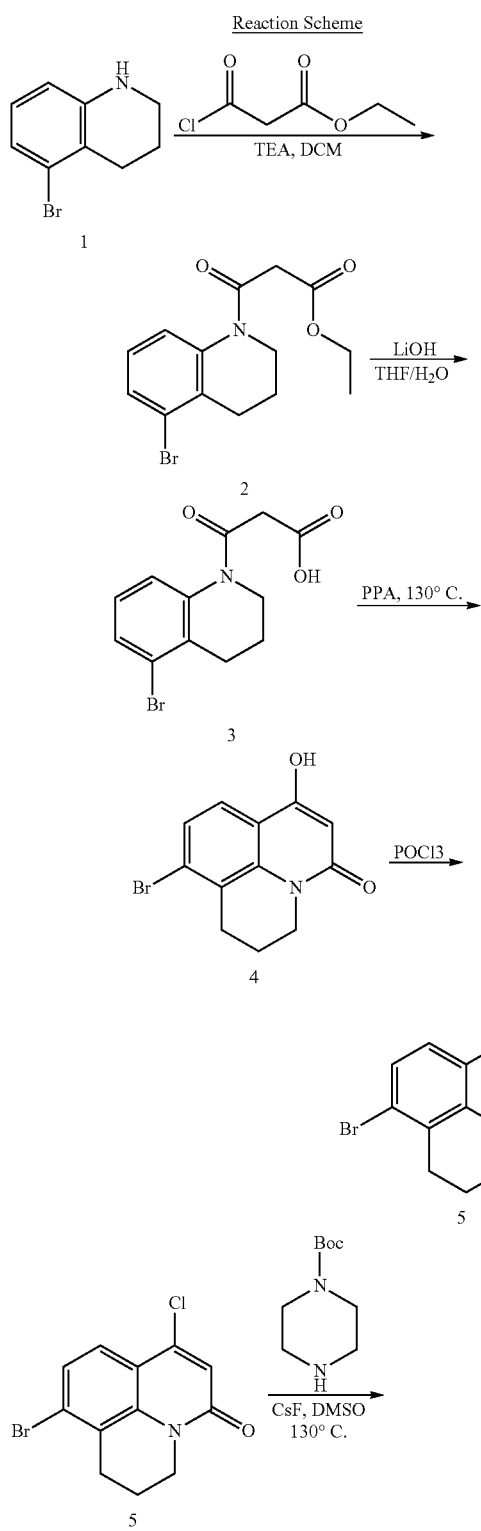

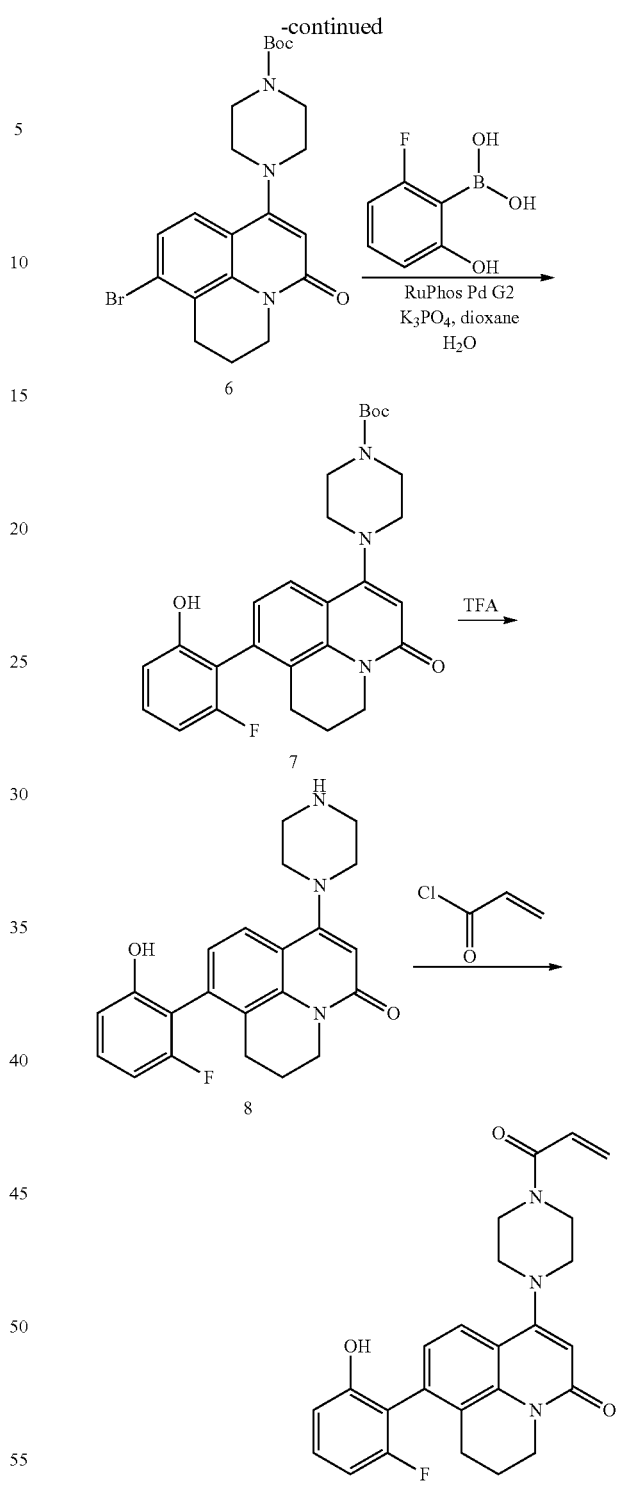

Step 1: ethyl 3-(5-bromo-3,4-dihydroquinolin-1(2H)-yl)-3-oxopropanoate

To a solution of 5-bromo-1,2,3,4-tetrahydroquinoline (10 g, 47.15 mol) and Et$_3$N (14.3 g, 141.45 mmol) in DCM (120 ml) was added ethyl 3-chloro-3-oxopropanoate (7.8 g, 51.86 mmol) at 0° C., the mixture was stirred at rt for 5 hours. After completion, the mixture was concentrated under reduced pressure and purified by silica gel column with PE/EA=6/1 to afford desired product (9.2 g, 60% yield) as pale yellow oil. LC-MS: m/z 326.1/328.1 [M+H]⁺.

Step 2: 3-(5-bromo-3,4-dihydroquinolin-1(2H)-yl)-3-oxopropanoic acid

To a solution of ethyl 3-(5-bromo-3,4-dihydroquinolin-1(2H)-yl)-3-oxopropanoate (9.2 g, 28.3 mmol) in THF (80 mL) and water (20 mL) was added LiOH·H₂O (2.34 g, 56.6 mmol) at 0° C., the mixture was stirred at rt for 5 hours. After completion, THF was removed under reduced pressure and H₂O (100 mL) was added and the pH was adjusted to 3-4 with 3N HCl. The resulting solid was isolated by filtration and washed with H₂O (50 mL) to afford crude product (8.5 g, crude) as pale yellow solid. LC-MS: m/z 297.9/299.9 [M+H]⁺.

Step 3: 8-bromo-1-hydroxy-6,7-dihydropyrido[3,2,1-ij]quinolin-3(5H)-one

A solution of 3-(5-bromo-3,4-dihydroquinolin-1(2H)-yl)-3-oxopropanoic acid (8.5 g, 28.6 mmol) in PPA (25 mL), the mixture was stirred at 130° C. for 16 hours. After completion, the mixture was quenched with H₂O (200 mL), the pH was adjusted to 7-8 with K₂CO₃. The resulting solid was isolated by filtration and washed with H₂O to afford the crude product (7.2 g) as pale yellow solid, which was used to next step without further purification. LC-MS: m/z 280.0/282.0 [M+H]⁺.

Step 4: 8-bromo-1-chloro-6,7-dihydropyrido[3,2,1-ij]quinolin-3(5H)-one

A solution of 8-bromo-1-hydroxy-6,7-dihydropyrido[3,2,1-ij]quinolin-3(5H)-one (7.2 g, 25.8 mmol) in POCl₃ (15 mL), the mixture was stirred at 130° C. for 36 h. After completion, the mixture was concentrated under reduced pressure and dissolved with DCM (200 mL), the crude material was poured into water (200 mL), then extracted with DCM (200 mL×2). The organic layers were combined and concentrated and the crude mixture was purified by silica gel column with a gradient of PE/EA (4/1 to 1/1) to afford desired product (1.8 g, 23% yield) as pale yellow solid. LC-MS: m/z 299.9 [M+H]⁺; ¹H NMR (400 MHz, CDCl₃): δ 7.72 (d, J=8.4 Hz, 1H), 7.47 (d, J=8.8 Hz, 1H), 6.89 (s, 1H), 4.19-4.16 (m, 2H), 3.04 (t, J=6.4 Hz, 2H), 2.15-2.09 (m, 2H).

Step 5: tert-butyl 4-(8-bromo-3-oxo-3,5,6,7-tetrahydropyrido[3,2,1-ij]quinolin-1-yl)piperazine-1-carboxylate To a solution of 8-bromo-1-chloro-6,7-dihydropyrido[3,2,1-ij]quinolin-3(5H)-one (1.8 g, 6.02 mmol) and tert-butyl piperazine-1-carboxylate (1.34 g, 7.22 mmol) in DMSO (6 mL) was added CsF (2.75 g, 18.06 mmol), the mixture was stirred at 130° C. for 30 hours. After completion, the mixture was dissolved in DCM (200 mL), washed with H₂O (200 mL×3), dried over Na₂SO₄ and concentrated under reduced pressure. The crude material was purified by silica gel column with a mixture of PE/EA (1/1) to afford the desired product (1.45 g, 54% yield) as yellow solid. LC-MS: m/z 448.1/450.1 [M+H]⁺.

Step 6: tert-butyl 4-(8-(2-fluoro-6-hydroxyphenyl)-3-oxo-3,5,6,7-tetrahydropyrido[3,2,1-ij]quinolin-1-yl)piperazine-1-carboxylate To a solution of tert-butyl 4-(8-bromo-3-oxo-3,5,6,7-tetrahydropyrido[3,2,1-ij]quinolin-1-yl)piperazine-1-carboxylate (250 mg, 0.56 mmol), RuPhos Pd G2 (46 mg, 0.06 mmol) and K₃PO₄ (356 mg, 1.68 mmol) in a mixture of dioxane (4 mL) and H₂O (0.8 mL) was added (2-fluoro-6-hydroxyphenyl)boronic acid (262 mg, 1.68 mmol). The resulting mixture was stirred at 100° C. under N₂ for 7 hours. After completion, the reaction mixture was concentrated under reduced pressure and purified by silica gel column using a 50/1 mixture of DCM/MeOH to afford the desired product (220 mg, 82% yield) as a yellow solid. LC-MS: m/z 480.2 [M+H]⁺.

Step 7: 8-(2-fluoro-6-hydroxyphenyl)-1-(piperazin-1-yl)-6,7-dihydropyrido [3,2,1-ij]quinolin-3(5H)-one To a solution of tert-butyl 4-(8-(2-fluoro-6-hydroxyphenyl)-3-oxo-3,5,6,7-tetrahydropyrido[3,2,1-ij]quinolin-1-yl)piperazine-1-carboxylate (220 mg, 0.46 mmol) in DCM (3 mL) was added TFA (3 mL) at 0° C., the mixture was stirred at rt for 1 h. After completion, the mixture was concentrated under reduced pressure to afford the crude product (230 mg, crude) as yellow solid, which was used in the next step without further purification. LC-MS: m/z 380.2 [M+H]⁺.

Step 8: 1-(4-acryloylpiperazin-1-yl)-8-(2-fluoro-6-hydroxyphenyl)-6,7-dihydropyrido [3,2,1-ij]quinolin-3(5H)-one To a solution of 8-(2-fluoro-6-hydroxyphenyl)-1-(piperazin-1-yl)-6,7-dihydropyrido[3,2,1-ij]quinolin-3(5H)-one (230 mg, 0.61 mmol) and Et₃N (185 mg, 1.83 mmol) in THF (3 mL) was added acryloyl chloride (54.6 mg, 0.61 mmol) at −78° C., the mixture was stirred at −78° C. for 30 min. After completion, the mixture was quenched with 1 mL of MeOH, concentrated under reduced pressure and purified by C18 with 5-95% ACN in H₂O to afford desired product (90 mg, 34% yield) as a white solid. LC-MS: m/z 434.2 [M+H]⁺; ¹H NMR (400 MHz, CDCl₃) δ 7.74 (d, J=8.0 Hz, 1H), 7.30-7.24 (m, 1H), 7.13 (d, J=8.0 Hz, 1H), 6.86 (d, J=8.8 Hz, 1H), 6.76 (t, J=8.8 Hz, 1H), 6.65-6.58 (m, 1H), 6.35 (dd, J=16.8 Hz, 1.6 Hz, 1H), 6.17 (s, 1H), 5.77 (dd, J=10.4 Hz, 1.6 Hz, 1H), 4.17-4.06 (m, 2H), 3.97-3.91 (m, 4H), 3.12-3.10 (m, 4H), 2.74 (t, J=6.4 Hz, 2H), 2.04-1.97 (m, 2H).

The following compounds were prepared using similar synthetic procedures and their characterization is provided below

| Ex. | Name | Structure | ¹H NMR | MS (M + H)⁺ |
|---|---|---|---|---|
| 45 | 1-(4-acryloylpiperazin-1-yl)-8-(2-fluoro-6-hydroxyphenyl)-6,7-dihydropyrido[3,2,1-ij]quinolin-3(5H)-one | 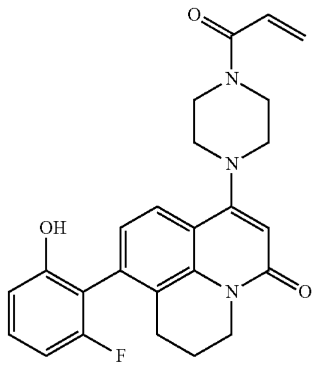 [SMILES: C=CC(=O)N1CCN(c2cc(=O)n3c4c(c(-c5c(O)cccc5F)ccc24)CCC3)CC1] | ¹H NMR (400 MHz, CDCl₃) δ 7.74 (d, J = 8.0 Hz, 1H), 7.30-7.24 (m, 1H), 7.13 (d, J = 8.0 Hz, 1H), 6.86 (d, J = 8.8 Hz, 1H), 6.76 (t, J = 8.8 Hz, 1H), 6.65-6.58 (m, 1H), 6.35 (dd, J = 16.8 Hz, 1.6 Hz, 1H), 6.17 (s, 1H), 5.77 (dd, J = 10.4 Hz, 1.6 Hz, 1H), 4.17-4.06 (m, 2H), 3.97-3.91 (m, 4H), 3.12-3.10 (m, 4H), 2.74 (t, J = 6.4 Hz, 2H), 2.04-1.97 (m, 2H) | 434.2 |
| 46 | 1-(4-acryloylpiperazin-1-yl)-8-(5-methyl-1H-indazol-4-yl)-6,7-dihydropyrido[3,2,1-ij]quinolin-3(5H)-one | 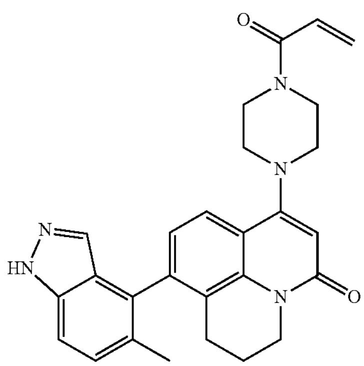 | ¹H NMR (400 MHz, CDCl₃) δ 7.77 (d, J = 8.0 Hz, 1H), 7.54 (s, 1H), 7.46 (d, J = 8.4 Hz, 1H), 7.36 (d, J = 8.8 Hz, 1H), 7.08 (d, J = 8.0 Hz, 1H), 6.64 (dd, J = 16.8 Hz, 10.4 Hz, 1H), 6.36 (dd, J = 16.8 Hz, 2.0 Hz, 1H), 6.26 (s, 1H), 5.78 (dd, J = 10.8 Hz, 2.0 Hz, 1H), 4.16 (t, J = 6.4 Hz, 2H), 3.96-3.81 (m, 4H), 3.20 (s, 4H), 2.52 (t, J = 6.4 Hz, 2H), 2.17 (s, 3H), 1.99-1.95 (m, 2H). | 454.2 |
| 47 | 1-(4-acryloylpiperazin-1-yl)-8-(2,4-difluorophenyl)-6,7-dihydropyrido[3,2,1-ij]quinolin-3(5H)-one | 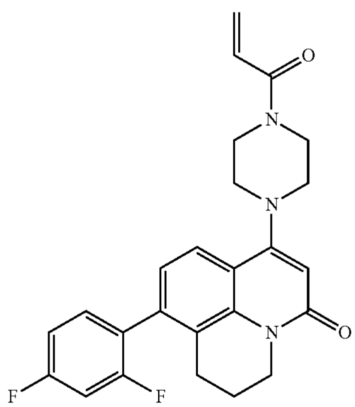 [SMILES: C=CC(=O)N1CCN(c2cc(=O)n3c4c(c(-c5ccc(F)cc5F)ccc24)CCC3)CC1] | ¹H NMR (400 MHz, CDCl₃) δ 7.71 (d, J = 8.4 Hz, 1H), 7.25-7.22 (m, 1H), 7.06 (d, J = 8.4 Hz, 1H), 7.02-6.91 (m, 2H), 6.63 (dd, J = 16.4 Hz, J = 10.4 Hz, 1H), 6.36 (dd, J = 16.4 Hz, J = 1.6 Hz, 1H), 6.22 (s, 1H), 5.77 (dd, J = 10.4 Hz, J = 1.6 Hz, 1H), 4.39-4.23 (m, 1H), 4.15-3.72 (m, 5H), 3.15 (s, 4H), 2.88-2.60 (m, 2H), 2.12-1.88 (m, 2H). | 436.2 |
| 48 | 1-(4-acryloylpiperazin-1-yl)-8-(3,5-dimethyl-1H-indazol-4-yl)-6,7-dihydropyrido[3,2,1-ij]quinolin-3(5H)-one | 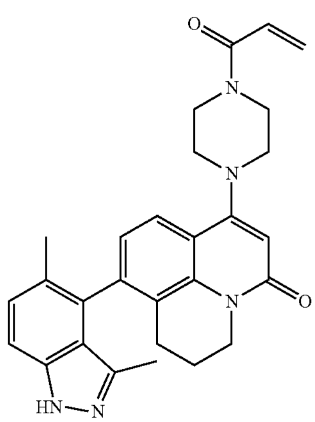 [SMILES: C=CC(=O)N1CCN(c2cc(=O)n3c4c(c(-c5c(C)ccc6[nH]nc(C)c56)ccc24)CCC3)CC1] | ¹H NMR (400 MHz, CDCl₃) δ 7.75 (d, J = 8.4 Hz, 1H), 7.38 (d, J = 8.4 Hz, 1H), 7.32 (d, J = 8.4 Hz, 1H), 7.06 (d, J = 8.4 Hz, 1H), 6.63 (dd, J = 16.8 Hz, 10.8 Hz, 1H), 6.36 (dd, J = 16.8 Hz, 1.6 Hz, 1H), 6.25 (s, 1H), 5.77 (dd, J = 10.4 Hz, 2.0 Hz, 1H), 4.18-4.12 (m, 2H), 4.05-3.77 (m, 4H), 3.26-3.12 (m, 4H), 2.47 (t, J = 6.4 Hz, 2H), 2.11 (s, 3H), 1.99-1.95 (m, 2H), 1.83 (s, 3H). | 468.3 |

Example Pyrimidone-Thiomorpholines-A

1. General Information $^1$H NMR spectra were recorded in either CDCl$_3$ or DMSO-d6 on either a BRUKER AVANCE III 400 MHz or BRUKER FOURIER 300 MHz. The internal standard used was either tetramethylsilane or the residual protonated solvent at 7.26 ppm for CDCl$_3$ or 2.50 ppm for DMSO-d6. Chemical shifts are reported in parts per million (ppm). Abbreviations for NMR data are as follows: s=singlet, d=doublet, t=triplet, m=multiplet, br s=broad singlet, dd=doublet of doublets, dt=doublet of triplets, tt=triplet of triplets, ddd=doublet of doublet of doublets, sextuplet of d=sextuplet of doublets. J indicates the $^1$H NMR coupling constant measured in Hertz.

Mass spectrum was recorded on a Waters ZQ mass spectrometer using alternative-scan positive and negative mode electrospray ionization. Cone voltage: 30V.

Synthetic Scheme 1

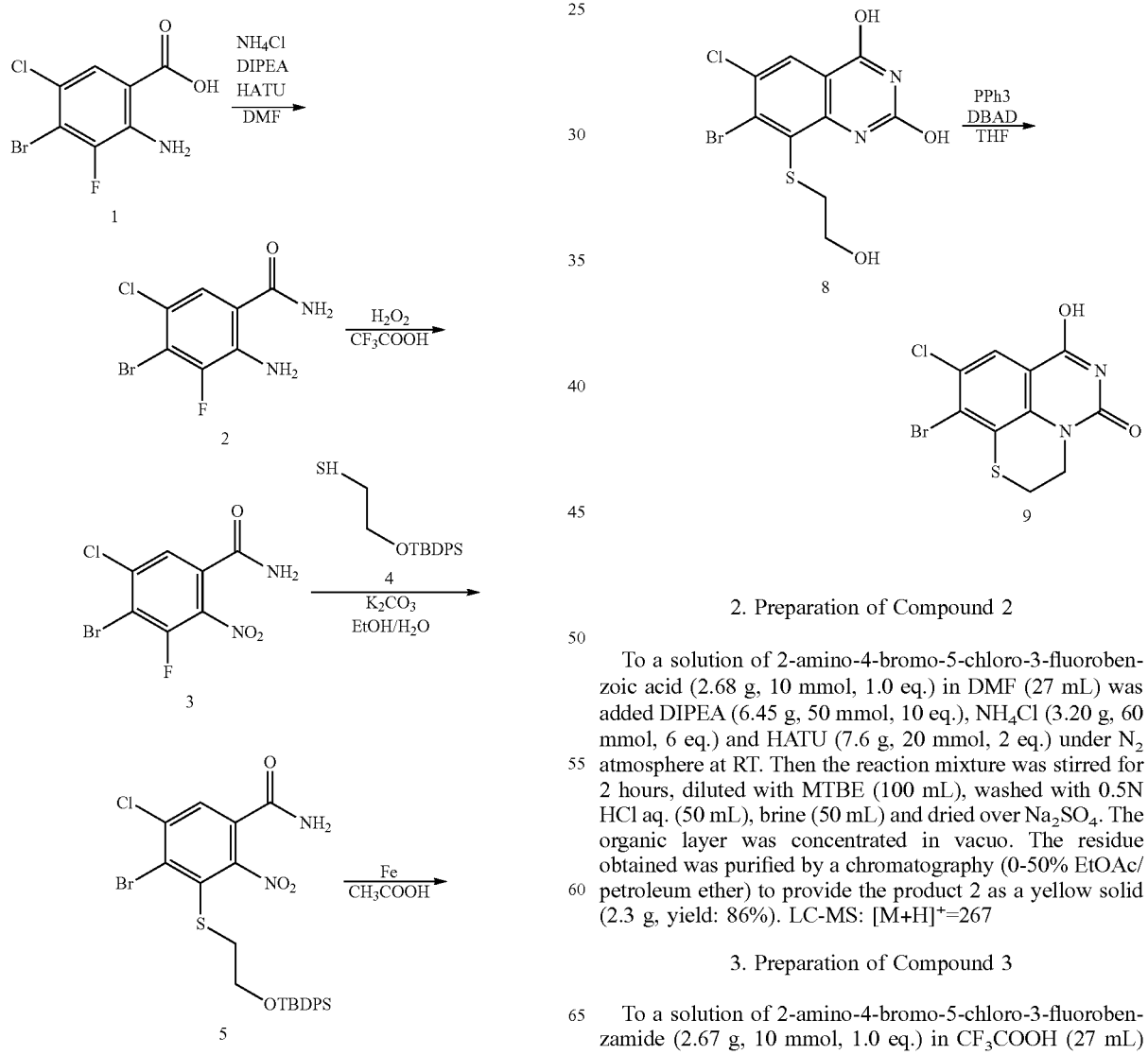

2. Preparation of Compound 2

To a solution of 2-amino-4-bromo-5-chloro-3-fluorobenzoic acid (2.68 g, 10 mmol, 1.0 eq.) in DMF (27 mL) was added DIPEA (6.45 g, 50 mmol, 10 eq.), NH$_4$Cl (3.20 g, 60 mmol, 6 eq.) and HATU (7.6 g, 20 mmol, 2 eq.) under N$_2$ atmosphere at RT. Then the reaction mixture was stirred for 2 hours, diluted with MTBE (100 mL), washed with 0.5N HCl aq. (50 mL), brine (50 mL) and dried over Na$_2$SO$_4$. The organic layer was concentrated in vacuo. The residue obtained was purified by a chromatography (0-50% EtOAc/petroleum ether) to provide the product 2 as a yellow solid (2.3 g, yield: 86%). LC-MS: [M+H]$^+$=267

3. Preparation of Compound 3

To a solution of 2-amino-4-bromo-5-chloro-3-fluorobenzamide (2.67 g, 10 mmol, 1.0 eq.) in CF$_3$COOH (27 mL) was added hydrogen peroxide (5.7 g, 5 0 mmol, 5 eq.).The reaction was stirred at 50° C. for 0.5 hour. Then diluted with MTBE (150 mL), washed with water (100 mL), brine (100 mL), and then dried over Na$_2$SO$_4$. The organic layer was concentrated in vacuo, the residue obtained was purified by a chromatography (0-100% EtOAc/petroleum ether) to provide the product 3 as a yellow solid (1.8 g, yield: 60%). LC-MS: [M+H]$^+$=297

4. Preparation of Compound 5

To a solution of 4-bromo-5-chloro-3-fluoro-2-nitrobenzamide (3.0 g, 10 mmol, 1.0 eq) in EtOH (30 ml) and water (6 mL) was added 2-((tert-butyldiphenylsilyl)oxy)ethane-1-thiol (3.2 g, 10 mmol, 1.0 eq), potassium carbonate (4.2 g, 30 mmol, 3.0 eq). Then the reaction mixture was stirred at 50° C. for 2 hours. The solvent was removed to afford 6.5 g of the crude product which was used in the subsequent step without further purification. LC-MS: [M+H]$^+$=593

5. Preparation of Compound 6

To a solution of compound 5 (6.5 g crude, 10 mmol, 1.0 eq.) in CH$_3$COOH (120 mL) was added Iron powder (2.8 g, 50 mmol, 5 eq.). The reaction mixture was stirred at 50° C. for 2 h. After filtration, the collected solid was washed with EtOAc (500 mL). The organic phase was washed with water 300 mL, brine 300 mL and concentrated in vacuo. The residue obtained was purified by a chromatography (0-100% EtOAc/petroleum ether) to provide the product 6 as a yellow solid (2.8 g, yield: 50%). LC-MS: [M+H]$^+$=563

6. Preparation of Compound 7

To a solution of compound 6 (5.6 g, 10 mmol, 1.0 eq.) in DCM (110 mL) was added DIPEA (2.6 g, 20 mmol, 2 eq.), CDI (4.9 g, 30 mmol, 3.0 eq.) at rt. The reaction mixture was stirred for 16 hours. After filtration, the filter cake was washed with petroleum ether (50 mL) and dried to afford the product 7 as an off-white solid (4.7 g, yield: 80%). LC-MS: [M+H]$^+$=589

7. Preparation of Compound 8

To a solution of compound 7 (5.9 g, 10 mmol, 1.0 eq.) in THF (60 mL) was added tetrabutylammonium fluoride (10 mL, 10 mmol, 1.0 eq.). The reaction mixture was stirred for 3 hours. After diluted with EtOAc (150 mL), washed with H$_2$O (50 mL) and brine (50 mL). The organic layer was dried over Na$_2$SO$_4$ and concentrated in vacuo to give the crude product 8 as an off-white solid (3.16 g, yield: 90%).

8. Preparation of Compound 9

To a solution of 7-bromo-6-chloro-8-((2-hydroxyethyl)thio)quinazoline-2,4-diol (3.5 g, 10 mmol, 1.0 eq.) in THF (100 mL) was added PPh$_3$ (4.5 g, 17 mmol, 1.7 eq.), then DEAD (3.0 g, 17 mmol, 1.7 eq.) at −10~0° C. The reaction mixture was stirred for 1 hour. After diluted with EtOAc (100 mL), washed with water (100 mL), brine (100 mL). The organic layer was dried over Na$_2$SO$_4$ and concentrated in vacuo. The residue obtained was diluted with DCM (100 mL) and stirred for 2 hours. After filtration, the filter cake was washed with DCM (50 mL) and dried to give the product 9 as an off-white solid (1.5 g, yield: 45%). LC-MS: [M+H]$^+$=333

Synthetic Scheme 2

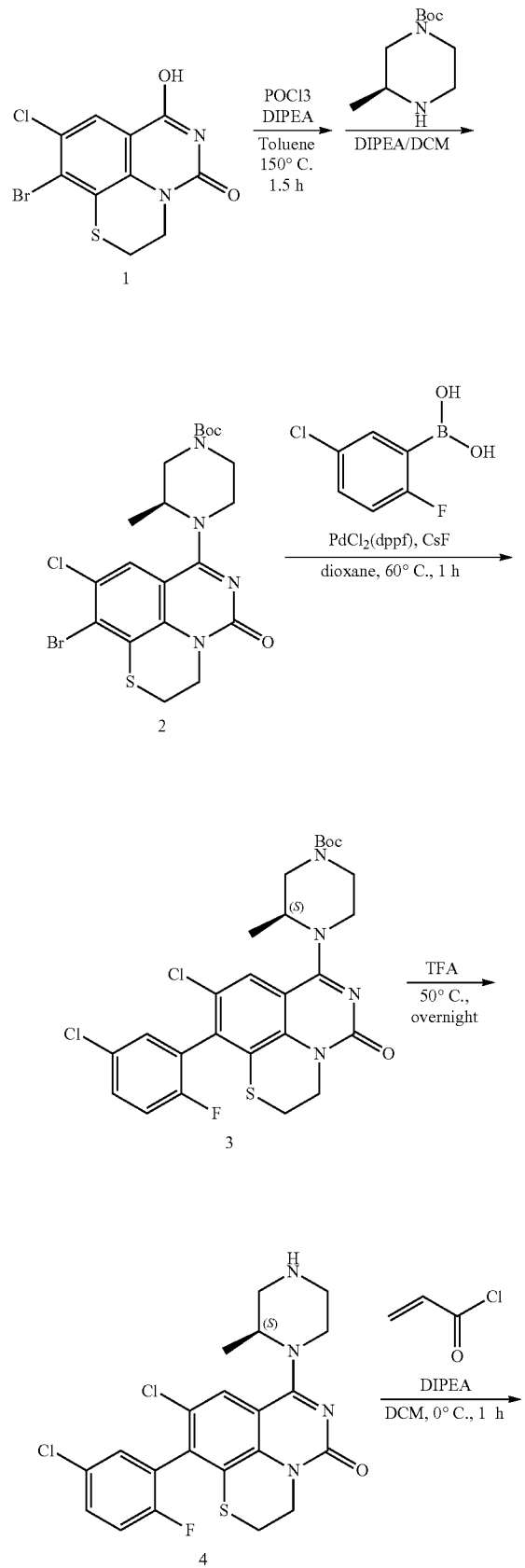

9. Preparation of Compound 2

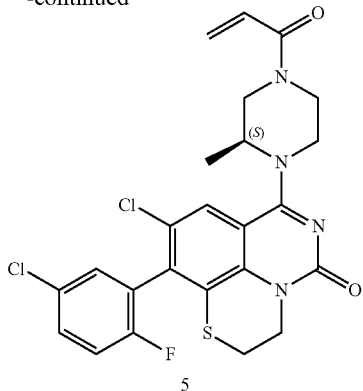

5

To a solution of Compound 1 (1.2 mmol, 400 mg) was in toluene was added POCl$_3$ (3 mL), DIPEA (2.4 mmol, 309 mg) subsequently. The mixture was stirred at 120° C. for 1.5 hrs. The solvent was removed in vacuo. The crude product was used the next step without further purification.

To the solution of above crude product in DCM (10 mL) was added DIPEA (2.4 mmol, 309 mg), followed by addition of tert-butyl (S)-3-methylpiperazine-1-carboxylate (1.2 mmol, 187 mg). Then the reaction solution was stirred at rt for 1 hr. The mixture was diluted with DCM and washed with water. The organic phase was dried over Na$_2$SO$_4$. After filtration, the solvent was removed in vacuo. The residue was purified by a chromatography with (30-50% EtOAc/petroleum ether) to provide compound 2 as a yellow solid (400 mg, 65%). LC-MS: [M+H]$^+$=515.0/517.0, RT=1.735 min. $^1$H NMR (400 MHz, CDCl$_3$) δ 7.44 (s, 1H), 4.64 (s, 1H), 4.40 (s, 2H), 4.07 (s, 1H), 3.89 (s, 1H), 3.52 (s, 1H), 3.26-3.19 (m, 3H), 3.11 (s, 2H), 1.49 (s, 9H), 1.40 (d, J=6.7 Hz, 3H).

10. Preparation of Compound 3

To a solution of Compound 2 (0.28 mmol, 150 mg) in dioxane (5 mL) was added (5-chloro-2-fluorophenyl)boronic acid (0.37 mmol, 63 mg), Pd(dppf)Cl$_2$ (0.056 mmol, 41 mg), and CsF (0.56 mmol, 85 mg) in N$_2$ atmosphere successively. After the reaction was finished, the mixture was filtered, diluted with EtOAc and washed with water. The organic phase was dried over Na$_2$SO$_4$ and concentrated in vacuo. The residue was purified by a chromatography with (30-50% EtOAc/petroleum ether) to afford compound 3 as light-yellow solid (110 mg, 67%). LC-MS: [M+H]$^+$=NO Signal, RT=1.836 min.

11. Preparation of Compound 5

Compound 3 (0.19 mmol, 110 mg) was dissolved in TFA (2 mL), and the mixture was stirred at rt overnight. After the reaction was finished, the mixture was washed with saturated aqueous sodium carbonate, diluted with brine and extracted with DCM. The organic phase was dried over Na$_2$SO$_4$. The solvent was removed in vacuo to give the crude product which was used to the next step without further purification.

To a solution of above product was in DCM (5 mL) was added DIPEA (1.0 mmol, 127 mg), followed by acryloyl chloride (0.24 mmol, 22 mg) at 0° C. Then the mixture was stirred for 1 h. The reaction mixture was washed with saturated aqueous sodium carbonate, brine and extracted with DCM. The organic phase was dried over Na$_2$SO$_4$, and the solvent was removed in vacuo. The residue was purified by pre-HPLC to give compound 5 (yield: 40%). LCMS: [M+H]$^+$=521.0, RT=1.566 min. $^1$H NMR (401 MHz, DMSO) δ 7.64 (d, J=10.8 Hz, 2H), 7.55-7.41 (m, 2H), 6.83 (d, J=10.2 Hz, 1H), 6.30-6.06 (m, 1H), 5.74 (dd, J=10.4, 2.0 Hz, 1H), 4.65 (d, J=31.4 Hz, 1H), 4.47-4.18 (m, 2H), 4.03 (dd, J=27.6, 13.3 Hz, 3H), 3.68-3.41 (m, 2H), 3.27-3.07 (m, 2H), 3.06-2.87 (m, 1H), 1.26 (dd, J=12.9, 6.2 Hz, 3H).

The different-alkyl intermediates were synthesized using corresponding boronic acid for Suzuki reaction and acid (acid chloride or anhydride) for amid formation. The other steps were conducted using the conditions described above.

| Ex. # | Name | Structure | $^1$H NMR | MS | % CAF 10 uM @ 60 min |
|---|---|---|---|---|---|
| 62a | 7-((S)-4-acryloyl-2-methylpiperazin-1-yl)-9-chloro-10-(5-cyclopropyl-2-fluorophenyl)-2,3-dihydro-5H-[1,4]thiazino[2,3,4-ij]quinazolin-5-one | 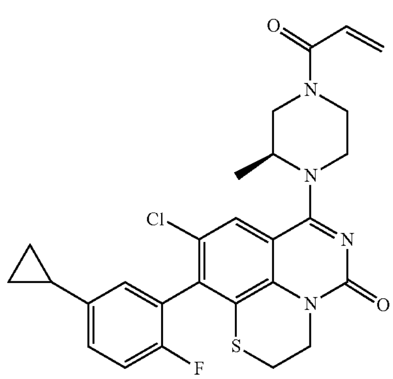 [SMILES: C=CC(=O)N1CCN(c2nc(=O)n3c4c(c(-c5cc(C6CC6)ccc5F)c(Cl)cc24)SCC3)[C@@H](C)C1] | $^1$H NMR (400 MHz, MeOH-d4) δ 7.66 (dd, J = 9.0 Hz, 1H), 7.26-7.18 (m, 1H), 7.11 (t, J = 9.1 Hz, 1H), 6.97-6.90 (m, 1H), 6.89-6.72 (m, 1H), 6.29 (dd, J = 16.8, 8.2 Hz, 1H), 5.81 (dd, J = 10.6, 1.9 Hz, 1H), 4.83-4.70 (m, 1H), 4.60-3.96 (m, 5H), 3.77-3.41 (m, 2H), 3.26-3.03 (m, 3H), 2.00-1.91 (m, 1H), 1.40 (dd, J = 21.1, 6.8 Hz, 3H), 1.03-0.95 (m, 2H), 0.72-0.64 (m, 2H); | 525.04 | 67 |

| Ex. # | Name | Structure | ¹H NMR | MS | % CAF 10 uM @ 60 min |
|---|---|---|---|---|---|
| 63 | (S,E)-9-chloro-10-(3-chloro-5-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one | 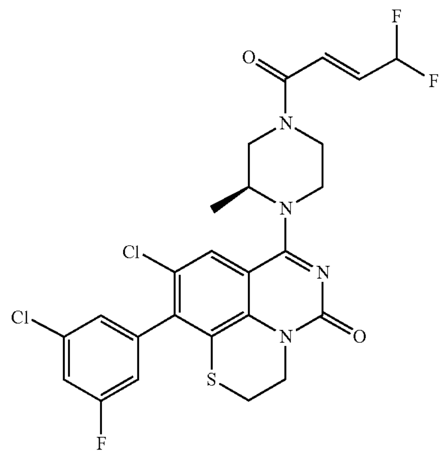 [SMILES: C[C@H]1CN(C(=O)/C=C/C(F)F)CCN1c1nc(=O)n2c3c(c(-c4cc(F)cc(Cl)c4)c(Cl)cc13)SCC2] | 1H NMR (400 MHz, CDCl₃) δ 7.47 (d, J = 6.8 Hz, 1H), 7.23-7.20 (m, 1H), 7.05-7.04 (m, 1H), 6.90-6.88 (m, 1H), 6.83-6.74 (m, 2H), 6.29 (t, J = 54.8 Hz, 1H), 4.87-4.14 (m, 5H), 3.93-3.52 (m, 3H), 3.13-3.01 (m, 3H), 1.45-1.40 (m, 3H). | 569.43 | 75 |
| 64 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one | 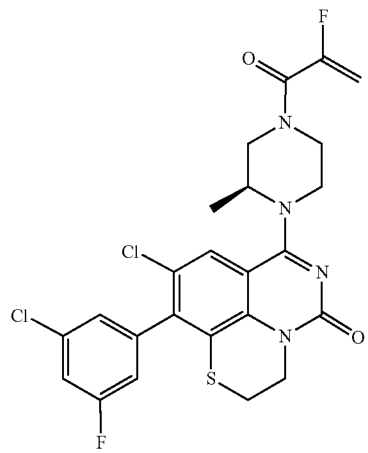 [SMILES: C=C(F)C(=O)N1CCN(c2nc(=O)n3c4c(c(-c5cc(F)cc(Cl)c5)c(Cl)cc24)SCC3)[C@@H](C)C1] | 1H NMR (400 MHz, CDCl₃) δ 7.47 (s, 1H), 7.23-7.20 (m, 1H), 7.05-7.04 (m, 1H), 6.90-6.88 (m, 1H), 5.37 (dd, J = 47.2 Hz, 3.2 Hz, 1H), 5.20 (dd, J = 16.8 Hz, 3.6 Hz, 1H), 4.78-4.74 (m, 1H), 4.50-3.80 (m, 5H), 3.64-3.56 (m, 2H), 3.09 (t, J = 4.8 Hz, 3H), , 1.44 (d, J = 6.8 Hz, 3H). | 537.41 | 3 |
| 65 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one | 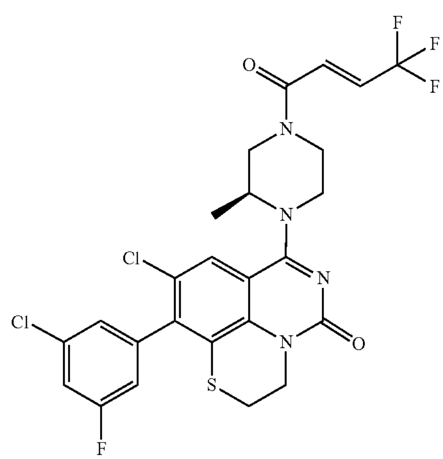 [SMILES: C[C@H]1CN(C(=O)/C=C/C(F)(F)F)CCN1c1nc(=O)n2c3c(c(-c4cc(F)cc(Cl)c4)c(Cl)cc13)SCC2] | 1H NMR (400 MHz, CDCl₃) δ 7.47-7.45 (d, J = 7.2 H, 1H), 7.23-7.20 (m, 1H), 7.05-7.04 (m, 1H), 6.99-6.95 (m, 1H), 6.90-6.88 (m, 1H), 4.87-3.91 (m, 5H), 3.75-3.53 (m, 2H), 3.17-2.99 (m, 3H), 1.45-1.40 (dd, J = 10.8 Hz, 6.4 Hz, 3H). | 587.42 | 70 |

-continued

| Ex. # | Name | Structure | ¹H NMR | MS | % CAF 10 uM @ 60 min |
|---|---|---|---|---|---|
| 66 | (S)-7-(4-acryloyl-2-methylpiperazin-1-yl)-9-chloro-10-(3,5-difluorophenyl)-2,3-dihydro-5H-[1,4]thiazino[2,3,4-ij]quinazolin-5-one | 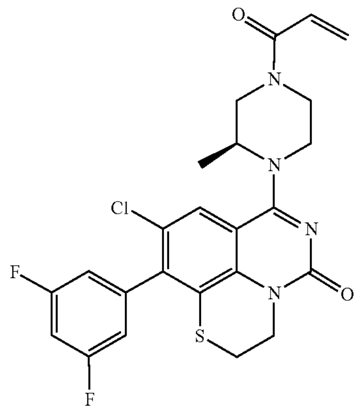 | 1H NMR (400 MHz, CDCl$_3$) δ 7.47 (s, 1H), 6.95-6.90 (m, 1H), 6.80-6.78 (m, 2H), 6.63-6.52 (m, 1H), 6.39-6.35 (m, 1H), 5.80-5.77 (d, J = 10.4 Hz, 1H), 4.88-4.85 (m, 0.5H), 4.70-4.62 (m, 1H), 4.43-4.28 (m, 3H), 4.16-3.96 (m, 1H), 3.84-3.80 (m, 0.5H), 3.66-3.47 (m, 2H), 3.12-2.94 (m, 3H), 1.49-1.41 (m, 3H). | 502.96 | 91 |
| 67 | (S,E)-9-chloro-7-(4-(4,4-difluorobut-2-enoyl)-2-methylpiperazin-1-yl)-10-(3,5-difluorophenyl)-2,3-dihydro-5H-[1,4]thiazino[2,3,4-ij]quinazolin-5-one | 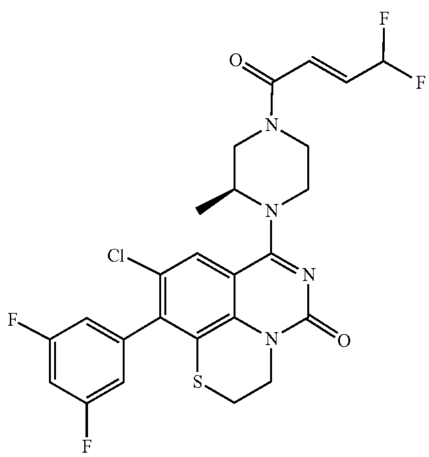 [SMILES: C[C@H]1CN(C(=O)/C=C/C(F)F)CCN1c1nc(=O)n2c3c(c(-c4cc(F)cc(F)c4)c(Cl)cc13)SCC2] | 1H NMR (400 MHz, CDCl$_3$) δ 7.46 (d, J = 6.8 Hz, 1H), 6.95-6.91 (m, 1H), 6.86-6.70 (m, 4H), 6.29 (t, J = 56 Hz, 1H), 4.87-4.86 (m, 0.5H), 4.68-4.65 (m, 1H), 4.47-4.32 (m, 3H), 4.17-3.92 (dd, J = 13.6 Hz, 1H), 3.77-3.74 (m, 0.5H), 3.66-3.51 (m, 2H), 3.16-3.00 (m, 3H), 1.45-1.40 (m, 3H). | 552.97 | 87 |
| 71 | 7-((S)-4-acryloyl-2-methylpiperazin-1-yl)-9-chloro-10-(isoquinolin-8-yl)-2,3-dihydro-5H-[1,4]thiazino[2,3,4-ij]quinazolin-5-one | 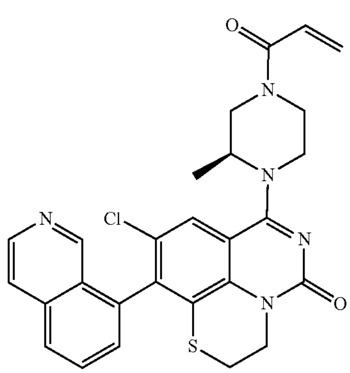 [SMILES: C=CC(=O)N1CCN(c2nc(=O)n3c4c(c(-c5cccc6ccncc56)c(Cl)cc24)SCC3)[C@@H](C)C1] | ¹H NMR (400 MHz, MeOD) δ 8.84-8.14 (m, 2H), 8.00 (d, J = 8.3 Hz, 1H), 7.92-7.74 (m, 2H), 7.67 (d, J = 9.6 Hz, 1H), 7.46 (dt, J = 7.1, 1.4 Hz, 1H), 6.85-6.62 (m, 1H), 6.19 (ddd, J = 17.0, 7.3, 2.0 Hz, 1H), 5.72 (dd, J = 10.6, 1.9 Hz, 1H), 4.85 (d, J = 7.3 Hz, 1H), 4.78-4.68 (m, 1H), 4.52-3.86 (m, 5H), 3.73-3.33 (m, 2H), 3.20-2.92 (m, 3H), 1.35 (d, J = 6.7 Hz, 1H), 1.30 (d, J = 6.7 Hz, 1H) | 518.03 | 87.8 |

-continued

| Ex. # | Name | Structure | ¹H NMR | MS | % CAF 10 uM @ 60 min |
|---|---|---|---|---|---|
| 72 | 7-(7-acetyl-9-acryloyl-3,7,9-triazabicyclo[3.3.1]nonan-3-yl)-9-chloro-10-(2,4-difluorophenyl)-2,3-dihydro-5H-[1,4]oxazino[2,3,4-ij]quinazolin-5-one | 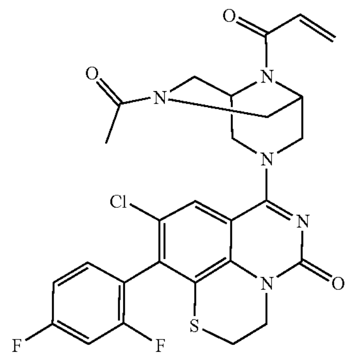 [SMILES: C=CC(=O)N1C2CN(C(C)=O)CC1CN(c1nc(=O)n3c4c(c(-c5ccc(F)cc5F)c(Cl)cc14)SCC3)C2] | ¹H NMR (400 MHz, MeOD) δ 8.45 (s, 1H), 7.62-7.52 (m, 1H), 7.25-7.15 (m, 1H), 7.08-6.90 (m, 2H), 6.76 (td, J = 16.5, 10.6 Hz, 1H), 6.27 (d, J = 10.6, 5.5, 1.9 Hz, 1H), 5.16-5.03 (m, 1H), 4.54-4.27 (m, 4H), 4.08 (dd, J = 13.3, 5.9 Hz, 1H), 4.01-3.79 (m, 2H), 3.43-3.27 (m, 2H), 3.19-2.99 (m, 3H), 2.77 (d, J = 16.1 Hz, 1H), 1.95 (d, J = 11.1 Hz, 2H) | 572.03 | 80.5 |
| 73 | (S)-7-(4-acryloyl-2-methylpiperazin-1-yl)-9-chloro-10-(3-chloro-5-fluorophenyl)-2,3-dihydro-5H-[1,4]thiazino[2,3,4-ij]quinazolin-5-one | 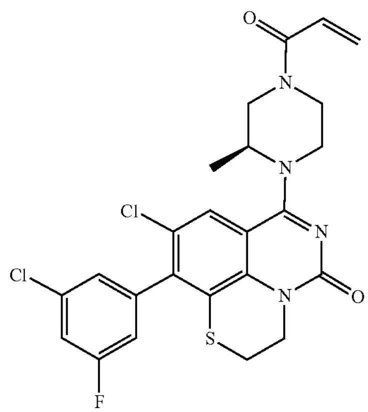 [SMILES: C=CC(=O)N1CCN(c2nc(=O)n3c4c(c(-c5cc(F)cc(Cl)c5)c(Cl)cc24)SCC3)[C@@H](C)C1] | 1H NMR (400 MHz, CDCl₃) δ 7.47 (s, 1H), 7.23-7.20 (m, 1H), 7.07-7.05 (m, 1H), 6.90-6.88 (m, 1H), 6.59 (m, 1H), 6.40-6.35 (dd, 1H), 5.80-5.77 (d, 1H), 4.88-4.67 (m, 2H), 4.46-4.37 (m, 3H), 4.16-3.81 (m, 2H), 3.62-3.50 (m, 2H), 3.13-3.08 (m, 3H), 1.49 (s, 1H). | 519.42 | 73 |
| 74 | 7-((S)-4-acryloyl-2-methylpiperazin-1-yl)-9-chloro-10-(2,3-difluorophenyl)-2,3-dihydro-5H-[1,4]thiazino[2,3,4-ij]quinazolin-5-one | 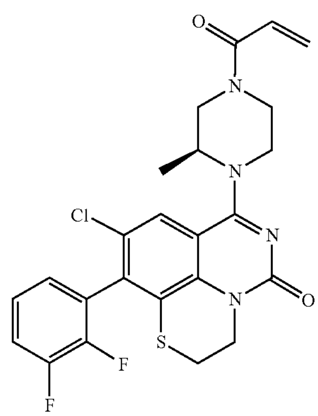 [SMILES: C=CC(=O)N1CCN(c2nc(=O)n3c4c(c(-c5cccc(F)c5F)c(Cl)cc24)SCC3)[C@@H](C)C1] | ¹H NMR (400 MHz, MeOH-d₄) δ 7.69 (d, J = 8.3 Hz, 1H), 7.42 (q, J = 8.2 Hz, 1H), 7.31 (td, J = 8.1, 8.0, 4.6 Hz, 1H), 7.06 (t, J = 6.3 Hz, 1H), 6.91-6.71 (m, 1H), 6.28 (dd, J = 16.8, 6.9 Hz, 1H), 5.80 (dd, J = 10.5, 1.9 Hz, 1H), 4.84-4.74 (m, 1H), 4.60-3.95 (m, 5H), 3.78-3.42 (m, 2H), 3.26-3.00 (m, 3H), 1.40 (dd, J = 20.2, 6.3 Hz, 3H) | 502.96 | 95.6 |
| 75 | 7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one | 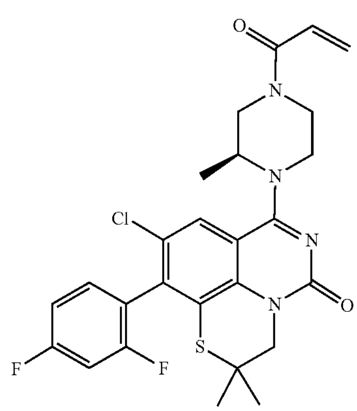 [SMILES: C=CC(=O)N1CCN(c2nc(=O)n3c4c(c(-c5ccc(F)cc5F)c(Cl)cc24)SC(C)(C)C3)[C@@H](C)C1] | | 531.02 | 86.8 |

| Ex. # | Name | Structure | ¹H NMR | MS | % CAF 10 uM @ 60 min |
|---|---|---|---|---|---|
| 77 | (2S)-1-acryloyl-4-(9-chloro-10-(2,4-difluorophenyl)-5-oxo-2,3-dihydro-5H-[1,4]thiazino[2,3,4-ij]quinazolin-7-yl)piperazine-2-carbonitrile | 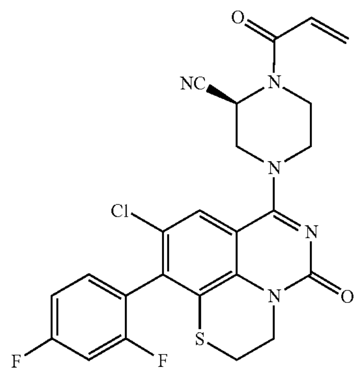 [SMILES: C=CC(=O)N1CCN(c2nc(=O)n3c4c(c(-c5ccc(F)cc5F)c(Cl)cc24)SCC3)C[C@H]1C#N] | 1H NMR (400 MHz, CDCl₃) δ 7.76-7.68 (d, 1H), 7.26-7.17 (brs, 1H), 7.06-6.97 (m, 2H), 6.61-6.45 (m, 2H), 5.93-5.90 (d, 1H), 4.65-4.36 (m, 4H), 4.20-3.84 (m, 3H), 3.47-3.39 (t, 1H), 3.22-3.04 (m, 3H). | 513.95 | 82 |
| 78 | (S)-9-chloro-10-(4-chloro-3-fluorophenyl)-7-(4-(2-fluoroacryloyl)-2-methylpiperazin-1-yl)-2,3-dihydro-5H-[1,4]thiazino[2,3,4-ij]quinazolin-5-one | 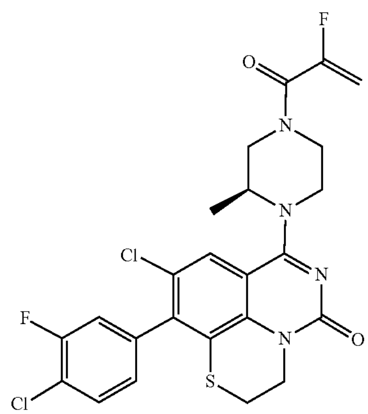 [SMILES: C=C(F)C(=O)N1CCN(c2nc(=O)n3c4c(c(-c5ccc(Cl)c(F)c5)c(Cl)cc24)SCC3)[C@@H](C)C1] | 1H NMR (400 MHz, CDCl₃) δ 7.54 (t, J = 8.0 Hz, 1H), 7.46 (s, 1H), 7.08-7.04 (m, 1H), 7.00-6.97 (m, 1H), 5.42-5.30 (m, 1H), 5.22-5.17 (m, 1H), 4.75 (br, 1H), 4.38-4.23 (m, 4H), 4.00-3.89 (m, 1H), 3.59-3.54 (m, 2H), 3.10-3.07 (m, 3H), 1.45-1.42 (m, 3H). | 537.41 | 6.7 |
| 79 | (S,E)-9-chloro-10-(4-chloro-3-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one | 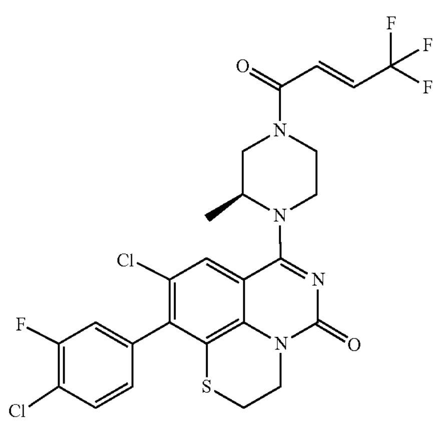 [SMILES: C[C@H]1CN(C(=O)/C=C/C(F)(F)F)CCN1c1nc(=O)n2c3c(c(-c4ccc(Cl)c(F)c4)c(Cl)cc13)SCC2] | 1H NMR (400 MHz, CDCl₃) δ 7.54 (t, J = 8.0 Hz, 1H), 7.47-7.45 (m, 1H), 7.07-7.04 (m, 1H), 6.99-6.90 (m, 2H), 6.84-6.76 (m, 0.5H), 4.88 (br, 0.5H), 4.68-4.64 (m, 1H), 4.48-4.32 (m, 3H), 4.19-3.90 (m, 1H), 3.52-3.74 (m, 2.5H), 3.19-2.97 (m, 3H), 1.45-1.40 (m, 3H). | 587.42 | 92 |

| Ex. # | Name | Structure | ¹H NMR | MS | % CAF 10 uM @ 60 min |
|---|---|---|---|---|---|
| 80 | (S,E)-9-chloro-10-(4-chloro-3-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one | 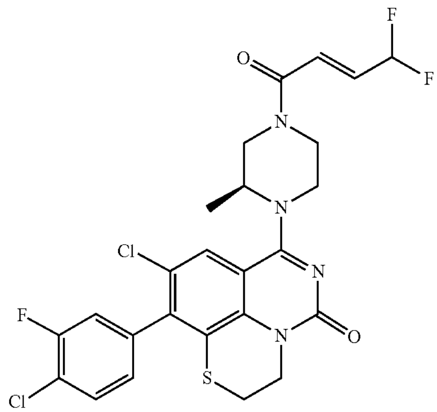 [SMILES: C[C@H]1CN(C(=O)/C=C/C(F)F)CCN1c1nc(=O)n2c3c(c(-c4ccc(Cl)c(F)c4)c(Cl)cc13)SCC2] | 1H NMR (400 MHz, CDCl₃) δ 7.54 (t, J = 7.6 Hz, 1H), 7.47-7.45 (m, 1H), 7.07-7.04 (m, 1H), 6.99-6.97 (m, 1H), 6.82-6.71 (m, 2H), 6.42-6.15 (m, 1H), 4.87 (br, 0.5H), 4.68-4.65 (m, 1H), 4.47-4.29 (m, 3H), 4.18-3.92 (m, 1H), 3.77-3.74 (m, 0.5H), 3.66-3.52 (m, 2H), 3.16-3.00 (m, 3H), 1.45-1.39 (m, 3H). | 569.43 | 93.5 |
| 81 | 2-((2S)-4-(9-chloro-10-(2,4-difluorophenyl)-5-oxo-2,3-dihydro-5H-[1,4]thiazino[2,3,4-ij]quinazolin-7-yl)-1-((E)-4,4,4-trifluorobut-2-enoyl)piperazin-2-yl)acetonitrile | 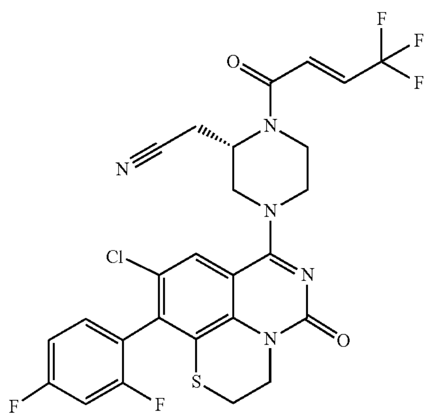 [SMILES: N#CC[C@H]1CN(c2nc(=O)n3c4c(c(-c5ccc(F)cc5F)c(Cl)cc24)SCC3)CCN1C(=O)/C=C/C(F)(F)F] | 1H NMR (400 MHz, CDCl₃) δ 7.59 (s, 1H), 7.28-7.21 (m, 1H), 7.11-7.00 (m, 3H), 6.92-6.80 (m, 1H), 5.14 (s, 0.6H), 4.74-4.63 (m, 1H), 4.45-4.37 (m, 3H), 4.22-3.79 (m, 3H), 3.60-3.49 (m, 1.4H), 3.17-3.14 (t, 2H), 3.00-2.80 (m, 2H). | 595.97 | 89 |
| 82 | 7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 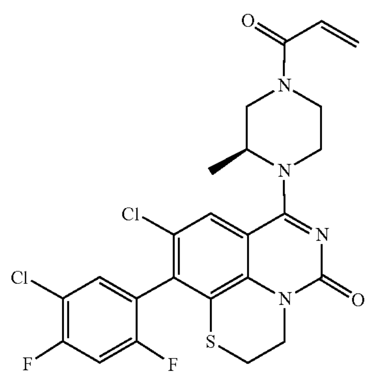 [SMILES: C=CC(=O)N1CCN(c2nc(=O)n3c4c(c(-c5cc(Cl)c(F)cc5F)c(Cl)cc24)SCC3)[C@@H](C)C1] | ¹H NMR (400 MHz, MeOD) δ 8.45 (s, 1H), 7.59 (d, J = 7.3 Hz, 1H), 7.44-7.35 (m, 1H), 7.28 (t, J = 9.2 Hz, 1H), 6.79-6.65 (m, 1H), 6.18 (dd, J = 16.8, 7.0 Hz, 1H), 5.71 (dd, J = 10.6, 1.9 Hz, 1H), 4.69 (s, 1H), 4.51-3.87 (m, 5H), 3.65-3.35 (m, 2H), 3.20-2.83 (m, 4H), 1.30 (dd, J = 17.4, 6.7 Hz, 2H). | 537.41 | 85.8 |
| 83 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluorobenzonitrile | 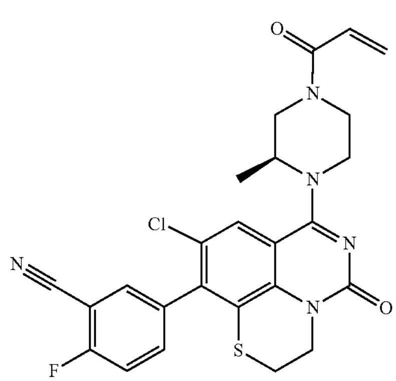 [SMILES: C=CC(=O)N1CCN(c2nc(=O)n3c4c(c(-c5ccc(F)c(C#N)c5)c(Cl)cc24)SCC3)[C@@H](C)C1] | ¹H NMR (400 MHz, MeOD) δ 8.45 (s, 1H), 7.73-7.49 (m, 3H), 7.45 (t, J = 8.9 Hz, 1H), 6.82-6.65 (m, 1H), 6.19 (dd, J = 16.9, 7.1 Hz, 1H), 5.71 (dd, J = 10.5, 1.9 Hz, 1H), 4.73 (s, 1H), 4.46-3.91 (m, 5H), 3.48 (dt, J = 67.1, 13.4 Hz, 2H), 3.20-2.86 (m, 4H), 1.30 (d, J = 6.7 Hz, 2H). | 509.98 | 85.3 |

| Ex. # | Name | Structure | ¹H NMR | MS | % CAF 10 uM @ 60 min |
|---|---|---|---|---|---|
| 84 | | | | | |
| 85 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluoro-N-methylbenzamide | 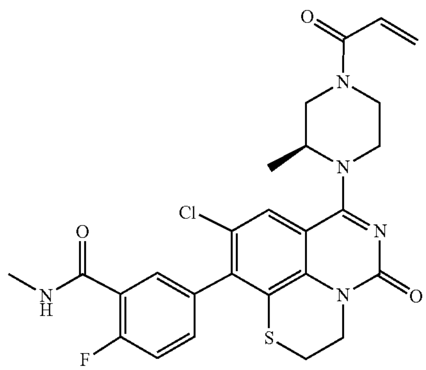 [SMILES: C=CC(=O)N1CCN(c2nc(=O)n3c4c(c(-c5ccc(F)c(C(=O)NC)c5)c(Cl)cc24)SCC3)[C@@H](C)C1] | ¹H NMR (400 MHz, MeOD) δ 7.62-7.51 (m, 2H), 7.37-7.23 (m, 2H), 6.80-6.64 (m, 1H), 6.18 (dd, J = 16.8, 6.9 Hz, 1H), 5.71 (dd, J = 10.6, 2.0 Hz, 1H), 4.73 (s, 1H), 4.49-3.89 (m, 6H), 3.59-3.36 (m, 2H), 3.18-2.89 (m, 4H), 2.85 (s, 3H), 1.30 (dd, J = 6.8, 2.5 Hz, 2H). | 542.02 | 60.3 |
| 86 | 7-((S)-4-acryloyl-2-methylpiperazin-1-yl)-9-chloro-10-(isoquinolin-5-yl)-2,3-dihydro-5H-[1,4]thiazino[2,3,4-ij]quinazolin-5-one | 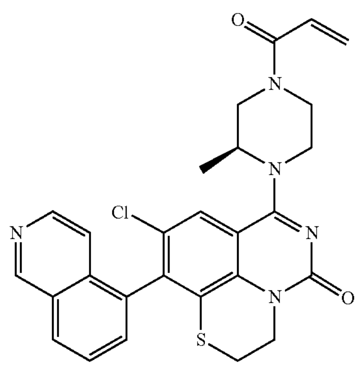 [SMILES: C=CC(=O)N1CCN(c2nc(=O)n3c4c(c(-c5cccc6cnccc56)c(Cl)cc24)SCC3)[C@@H](C)C1] | ¹H NMR (400 MHz, MeOD) δ 9.26 (s, 1H), 8.63-8.24 (m, 2H), 8.17 (d, J = 8.2 Hz, 1H), 7.80-7.47 (m, 3H), 7.23 (d, J = 5.8 Hz, 1H), 6.74 (ddd, J = 21.1, 16.7, 10.6 Hz, 1H), 6.26-6.13 (m, 1H), 5.72 (dd, J = 10.6, 1.9 Hz, 1H), 4.61-3.86 (m, 6H), 3.68-3.39 (m, 2H), 3.17-2.93 (m, 3H), 1.34 (dd, J = 15.2, 6.7 Hz, 2H). | 518.03 | 76.1 |
| 88 | 2-((2S)-1-acryloyl-4-(9-chloro-10-(2,4-difluorophenyl)-5-oxo-2,3-dihydro-5H-[1,4]thiazino[2,3,4-ij]quinazolin-7-yl)piperazin-2-yl)acetonitrile | 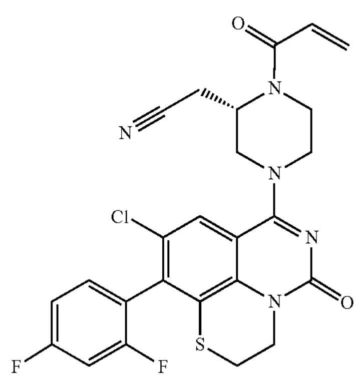 [SMILES: C=CC(=O)N1CCN(c2nc(=O)n3c4c(c(-c5ccc(F)cc5F)c(Cl)cc24)SCC3)C[C@@H]1CC#N] | 1H NMR (400 MHz, CDCl₃) δ 7.55 (m, 1H), 7.26-7.17 (m, 1H), 7.06-6.96 (m, 2H), 6.62-6.55 (m, 1H), 6.42-6.38 (m, 1H), 5.85-5.83 (m, 1H), 5.03-4.97 (m, 1H), 4.67-4.64 (m, 1H), 4.4-4.09 (m, 3H), 4.02-4.01 (m, 1H), 3.76-3.66 (m, 2H), 3.54-3.43 (m, 1H), 3.14-3.09 (m, 2H), 2.94-2.75 (m, 2H). | 527.97 | 90.2 |
| 89 | (S)-7-(4-acryloyl-2-methylpiperazin-1-yl)-9-chloro-10-(4-chloro-3-fluorophenyl)-2,3-dihydro-5H-[1,4]thiazino[2,3,4-ij]quinazolin-5-one | 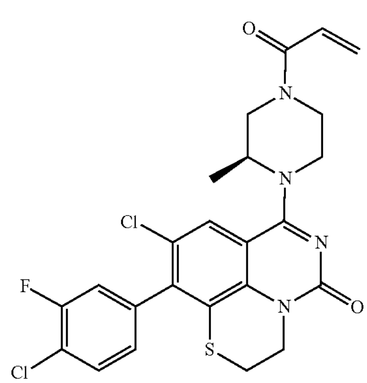 [SMILES: C=CC(=O)N1CCN(c2nc(=O)n3c4c(c(-c5ccc(Cl)c(F)c5)c(Cl)cc24)SCC3)[C@@H](C)C1] | 1H NMR (400 MHz, CDCl₃) δ 7.54 (t, J = 7.6 Hz, 1H), 7.47 (m, 1H), 7.08-7.04 (m, 1H), 6.99-6.97 (m, 1H), 6.66-6.52 (m, 1H), 6.39-6.35 (m, 1H), 5.78 (d, J = 11.2 Hz, 1H), 4.89-4.88 (m, 0.5H), 4.70-4.66 (m, 1H), 4.45-4.32 (m, 3H), 4.17-3.94 (m, 1H), 3.85-3.78 (m, 0.5H), 3.61-3.50 (m, 2H), 3.14-2.90 (m, 3H), 1.41 (s, 3H). | 519.42 | 94.5 |

| Ex. # | Name | Structure | ¹H NMR | MS | % CAF 10 uM @ 60 min |
|---|---|---|---|---|---|
| 90 | (S)-7-(4-acryloyl-2-methylpiperazin-1-yl)-9-chloro-10-(3,4,5-trifluorophenyl)-2,3-dihydro-5H-[1,4]thiazino[2,3,4-ij]quinazolin-5-one | 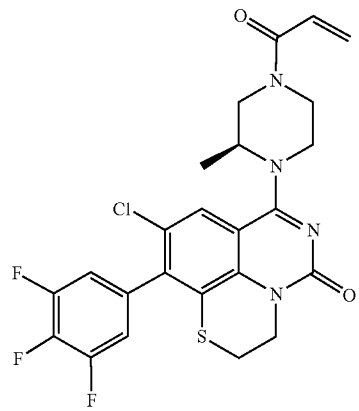 | 1H NMR (400 MHz, CDCl₃) δ 7.46 (s, 1H), 6.89 (s, 2H), 6.67-6.63 (m, 1H), 6.49-6.39 (m, 1H), 5.80-5.77 (m, 1H), 4.89-4.86 (m, 0.5H), 4.72-4.60 (m, 1H), 4.49-4.33 (m, 3H), 4.15-3.97 (m, 1H), 3.84-3.82 (m, 0.5H), 3.65-3.50 (m, 2H), 3.11-2.88 (m, 3H), 1.41 (s, 3H). | 520.95 | 78.8 |
| 93 | (S,E)-9-chloro-10-(3-chloro-4-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one | 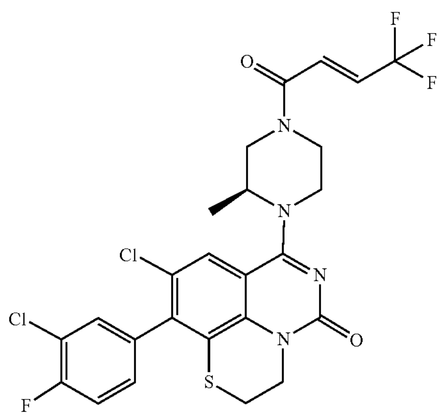 [SMILES: C[C@H]1CN(C(=O)/C=C/C(F)(F)F)CCN1c1nc(=O)n2c3c(c(-c4ccc(F)c(Cl)c4)c(Cl)cc13)SCC2] | 1H NMR (400 MHz, CDCl₃) δ 7.47-7.45 (m, 1H), 7.31-7.29 (m, 2H), 7.14-7.12 (m, 1H), 7.04-6.91 (m, 1H), 6.86-6.76 (m, 1H), 4.87 (s, 0.5H), 4.68-4.64 (m, 1H), 4.48-4.29 (m, 3H), 3.93-3.90 (m, 0.5H), 3.74-3.71 (m, 0.5H), 3.68-3.53 (m, 3H), 3.17-3.15 (m, 0.5H), 3.13-3.02 (m, 2H), 1.50-1.38 (m, 3H). | 587.42 | 95 |
| 95 | 7-(9-acryloyl-7-(methylsulfonyl)-3,7,9-triazabicyclo[3.3.1]nonan-3-yl)-9-chloro-10-(2,4-difluorophenyl)-2,3-dihydro-5H-[1,4]thiazino[2,3,4-ij]quinazolin-5-one | 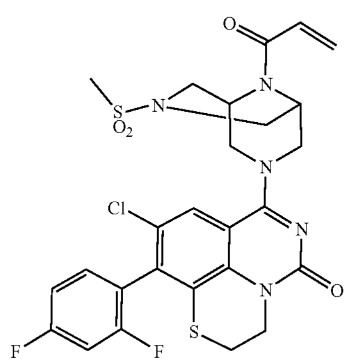 [SMILES: C=CC(=O)N1C2CN(c3nc(=O)n4c5c(c(-c6ccc(F)cc6F)c(Cl)cc35)SCC4)CC1CN(S(C)(=O)=O)C2] | ¹H NMR (400 MHz, MeOD) δ 7.59 (s, 1H), 7.25-7.15 (m, 1H), 7.08-6.97 (m, 2H), 6.79-6.68 (m, 1H), 6.25 (dd, J = 16.7, 1.8 Hz, 1H), 5.77 (dd, J = 10.6, 1.9 Hz, 1H), 4.98-4.84 (m, 1H), 4.76 (s, 1H), 4.48-4.40 (m, 1H), 4.26-3.94 (m, 3H), 3.77-3.55 (m, 4H), 3.04 (h, J = 3.3 Hz, 2H), 2.97-2.79 (m, 2H), 2.55 (s, 3H). | 608.08 | 70.5 |
| 96 | 7-((S)-4-acryloyl-2-methylpiperazin-1-yl)-9-chloro-10-(3-oxoisoindolin-4-yl)-2,3-dihydro-5H-[1,4]thiazino[2,3,4-ij]quinazolin-5-one | 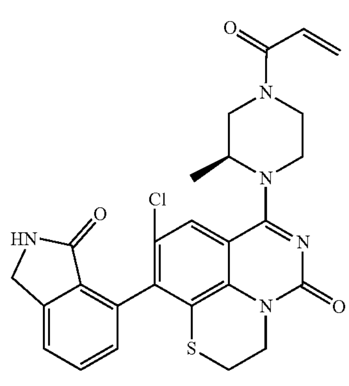 [SMILES: C=CC(=O)N1CCN(c2nc(=O)n3c4c(c(-c5cccc6c5C(=O)NC6)c(Cl)cc24)SCC3)[C@@H](C)C1] | ¹H NMR (400 MHz, MeOH-d₄) δ 7.78-7.67 (m, 2H), 7.63 (d, J = 9.4 Hz, 1H), 7.27 (d, J = 5.3 Hz, 1H), 6.92-6.72 (m, 1H), 6.29 (dd, J = 15.6, 5.2 Hz, 1H), 5.81 (d, J = 10.6 Hz, 1H), 4.86-4.75 (m, 1H), 4.60-3.95 (m, 5H), 4.51 (s, 2H, overlap), 3.78-3.39 (m, 2H), 3.23-2.98 (m, 3H), 1.40 (dd, J = 23.6, 6.7 Hz, 3H) | 522.02 | 54 |

-continued

| Ex. # | Name | Structure | ¹H NMR | MS | % CAF 10 uM @ 60 min |
|---|---|---|---|---|---|
| 98 | (S)-7-(4-acryloyl-2-methylpiperazin-1-yl)-9-chloro-10-(3-chloro-4-fluorophenyl)-2,3-dihydro-5H-[1,4]thiazino[2,3,4-ij]quinazolin-5-one | 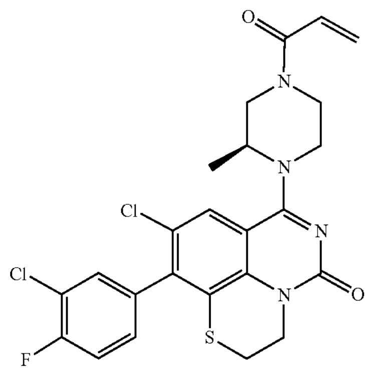 [SMILES: C=CC(=O)N1CCN(c2nc(=O)n3c4c(c(-c5ccc(F)c(Cl)c5)c(Cl)cc24)SCC3)[C@@H](C)C1] | 1H NMR (400 MHz, CDCl$_3$) δ 7.47 (s, 1H), 7.30-7.28 (m, 2H), 6.63-6.52 (m, 1H), 6.40-6.35 (m, 1H), 5.79 (d, J = 11.6 1H), 4.88-4.87 (m, 1H), 4.70-4.63 (m, 1H), 4.45-4.33 (m, 3H), 4.13-4.12 (m, 1H), 3.83-3.79 (m, 0.5H), 3.62-3.51 (m, 2H), 3.11-2.95 (m, 3H), 1.58-1.25 (m, 3H). | 519.42 | 86.4 |
| 99 | (3R)-7-((S)-4-acryloyl-2-methylpiperazin-1-yl)-9-chloro-10-(2,4-difluorophenyl)-3-methyl-2,3-dihydro-5H-[1,4]thiazino[2,3,4-ij]quinazolin-5-one | 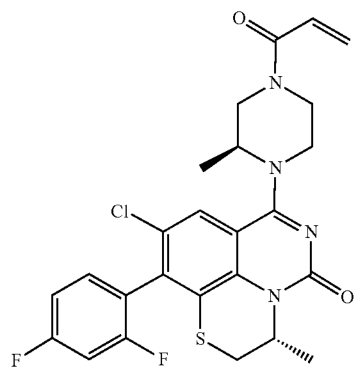 [SMILES: C=CC(=O)N1CCN(c2nc(=O)n3c4c(c(-c5ccc(F)cc5F)c(Cl)cc24)SC[C@H]3C)[C@@H](C)C1] | 1H NMR (400 MHz, CDCl$_3$) δ 7.51 (s, 1H), 7.25-7.19 (m, 1H), 7.07-6.97 (m, 2H), 6.59-6.57 (m, 1H), 6.39-6.36 (d, 1H), 5.79-5.76 (d, 1H), 5.42 (s, 1H), 4.96-4.86 (d, 1H), 4.64-4.62 (d, 1H), 4.02-3.96 (t, 1.5H), 3.83-3.67 (m, 2H), 3.42-3.21 (m, 2H), 2.92-2.87 (m, 1.5H), 1.48-1.45 (t, 3H), 1.33-1.31 (d, 3H). | 516.99 | 87.2 |
| 105 | 7-((S)-4-acryloyl-2-methylpiperazin-1-yl)-9-chloro-10-(2-oxoindolin-4-yl)-2,3-dihydro-5H-[1,4]thiazino[2,3,4-ij]quinazolin-5-one | 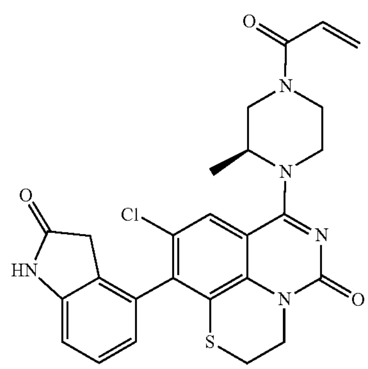 [SMILES: C=CC(=O)N1CCN(c2nc(=O)n3c4c(c(-c5cccc6c5CC(=O)N6)c(Cl)cc24)SCC3)[C@@H](C)C1] | ¹H NMR (400 MHz, MeOH-d$_4$) δ 7.68 (d, J = 4.5 Hz, 1H), 7.36 (t, J = 7.8 Hz, 1H), 7.00 (d, J = 7.8 Hz, 1H), 6.91-6.75 (m, 2H), 6.29 (dd, J = 16.8, 5.7 Hz, 1H), 5.81 (dd, J = 10.6, 1.9 Hz, 1H), 4.85-4.76 (m, 1H), 4.65-3.98 (m, 5H), 3.75-3.43 (m, 2H), 3.31 (s, overlapped with D$_3$COH, 2H), 3.30-3.05 (m, 4H), 1.41 (dd, J = 11.0, 6.7 Hz, 3H) | 522.02 | 18.9 |
| 106 | (S)-7-(4-acryloyl-2-methylpiperazin-1-yl)-9-chloro-10-(4-chloro-2,6-difluorophenyl)-2,3-dihydro-5H-[1,4]thiazino[2,3,4-ij]quinazolin-5-one | 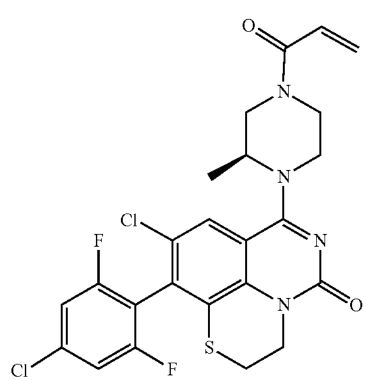 [SMILES: C=CC(=O)N1CCN(c2nc(=O)n3c4c(c(-c5c(F)cc(Cl)cc5F)c(Cl)cc24)SCC3)[C@@H](C)C1] | ¹H NMR (400 MHz, MeOH-d$_4$) δ 8.52 (br s, 1H), 7.71 (s, 1H), 7.31 (d, J = 7.6 Hz, 2H), 6.82 (ddd, J = 21.7, 16.7, 10.6 Hz, 1H), 6.28 (dd, J = 17.1, 6.7 Hz, 1H), 5.81 (dd, J = 10.6, 2.0 Hz, 1H), 4.60-3.96 (m, 5H), 3.74-3.55 (m, 3H), 3.27-3.18 (m, 3H), 1.41 (d, J = 6.8 Hz, 3H) | 537.41 | 45.2 |

| Ex. # | Name | Structure | ¹H NMR | MS | % CAF 10 uM @ 60 min |
|---|---|---|---|---|---|
| 107 | (S)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one | 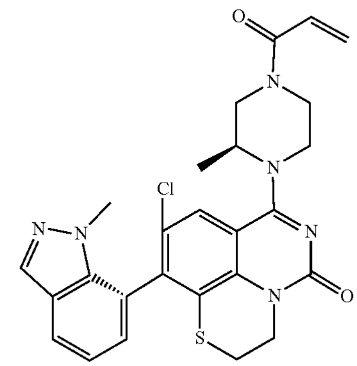 | ¹H NMR (400 MHz, DMSO) δ 8.14 (s, 1H), 7.89 (d, J = 8.0 Hz, 1H), 7.68 (s, 1H), 7.26 (t, J = 7.4 Hz, 1H), 7.17 (s, 1H), 6.85 (dd, J = 27.2, 16.7 Hz, 1H), 6.20 (d, J = 15.8 Hz, 1H), 5.75 (d, J = 10.2 Hz, 1H), 4.70 (s, 1H), 4.45-4.22 (m, 2H), 4.11 (d, J = 39.6 Hz, 3H), 3.56 (s, 5H), 3.15 (s, 2H), 3.01 (s, 1H), 1.28 (s, 3H). | 521.03 | 0 |
| 108 | (R)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one | 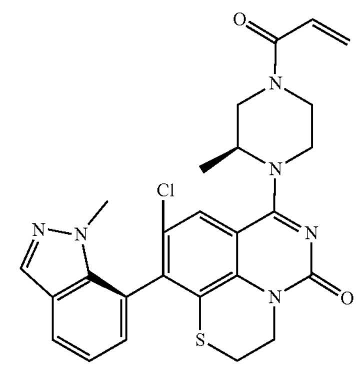 | ¹H NMR (400 MHz, DMSO) δ 8.14 (s, 1H), 7.89 (d, J = 8.0 Hz, 1H), 7.68 (s, 1H), 7.26 (t, J = 7.4 Hz, 1H), 7.17 (s, 1H), 6.85 (dd, J = 27.2, 16.7 Hz, 1H), 6.20 (d, J = 15.8 Hz, 1H), 5.75 (d, J = 10.2 Hz, 1H), 4.70 (s, 1H), 4.45-4.22 (m, 2H), 4.11 (d, J = 39.6 Hz, 3H), 3.56 (s, 5H), 3.15 (s, 2H), 3.01 (s, 1H), 1.28 (s, 3H). | 521.03 | 91.7 |
| 111 | (S,E)-9-chloro-7-(2-methyl-4-(4,4,4-trifluorobut-2-enoyl)piperazin-1-yl)-10-(2,4,6-trifluorophenyl)-2,3-dihydro-5H-[1,4]thiazino[2,3,4-ij]quinazolin-5-one | 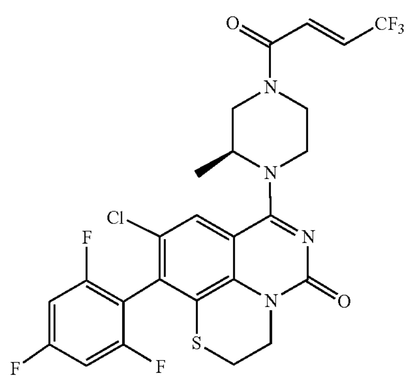 [SMILES: C[C@H]1CN(C(=O)/C=C/C(F)(F)F)CCN1c1nc(=O)n2c3c(c(-c4c(F)cc(F)cc4F)c(Cl)cc13)SCC2] | 1H NMR (400 MHz, CDCl₃) δ 7.49-7.47 (d, 1H), 7.04-6.90 (m, 1H), 6.86-6.76 (m, 3H), 4.87-4.48 (m, 2H), 4.45-4.16 (m, 3H), 3.93-3.50 (m, 3H), 3.18-3.00 (m, 3H), 1.45-1.40 (m, 3H). | 588.95 | 95.2 |
| 112 | 9-chloro-10-(2,4-difluorophenyl)-7-((S)-2-methyl-4-((E)-4,4,4-trifluorobut-2-enoyl)piperazin-1-yl)-2,3-dihydro-5H-[1,4]thiazino[2,3,4-ij]quinazolin-5-one | 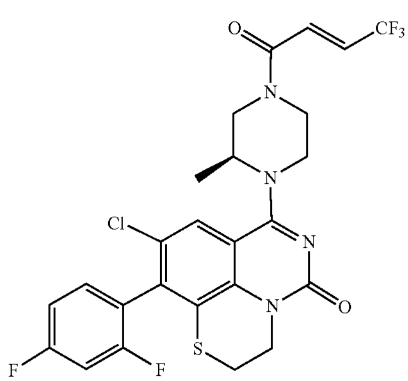 [SMILES: C[C@H]1CN(C(=O)/C=C/C(F)(F)F)CCN1c1nc(=O)n2c3c(c(-c4ccc(F)cc4F)c(Cl)cc13)SCC2] | 1H NMR (400 MHz, CDCl₃) δ 7.48-7.46 (brs, 1H), 7.24-7.17 (brs, 1H), 7.06-6.91 (m, 3H), 6.84-6.76 (m, 1H), 4.93-4.75 (m, 1H), 4.71-4.55 (m, 1H), 4.53-4.42 (m, 1H), 4.39-4.10 (m, 2H), 3.93-3.47 (brs, 3H), 3.21-2.96 (m, 3H), 1.53-1.38 (m, 3H). | 570.96 | 86.2 |

-continued

| Ex. # | Name | Structure | ¹H NMR | MS | % CAF 10 uM @ 60 min |
|---|---|---|---|---|---|
| 113 | 9-chloro-10-(2,4-difluorophenyl)-7-((S)-4-(2-fluoroacryloyl)-2-methylpiperazin-1-yl)-2,3-dihydro-5H-[1,4]thiazino[2,3,4-ij]quinazolin-5-one | 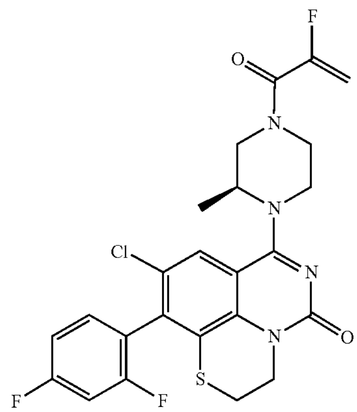 [SMILES: C=C(F)C(=O)N1CCN(c2nc(=O)n3c4c(c(-c5ccc(F)cc5F)c(Cl)cc24)SCC3)[C@@H](C)C1] | 1H NMR (400 MHz, CDCl₃) δ 7.47 (d, 1H), 7.21-7.19 (m, 1H), 7.05-6.97 (m, 2H), 5.42-5.29 (m, 1H), 5.22-5.17 (m, 1H), 4.83-4.72 (brs, 1H), 4.56-4.45 (brs, 1H), 4.45-4.11 (brs, 3H), 4.09-3.88 (brs, 1H), 3.67-3.42 (brs, 2H), 3.11-3.09 (t, 3H), 1.47-1.40 (m, 3H). | 520.95 | 21.7 |
| 119 | 9-chloro-7-((S)-4-((E)-4,4-difluorobut-2-enoyl)-2-methylpiperazin-1-yl)-10-(2,4-difluorophenyl)-2,3-dihydro-5H-[1,4]thiazino[2,3,4-ij]quinazolin-5-one | 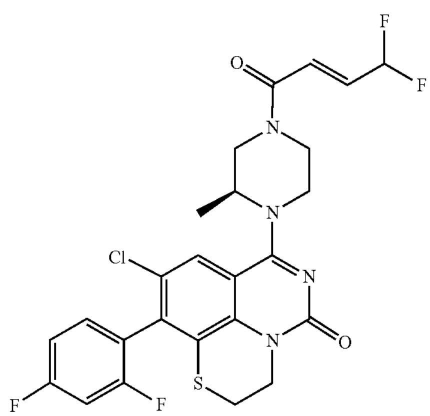 [SMILES: C[C@H]1CN(C(=O)/C=C/C(F)F)CCN1c1nc(=O)n2c3c(c(-c4ccc(F)cc4F)c(Cl)cc13)SCC2] | 1H NMR (400 MHz, CDCl₃) δ 7.47 (brs, 1H), 7.23-7.17 (m, 1H), 7.06-6.96 (m, 2H), 6.83-6.70 (m, 2H), 6.43-6.75 (t, 1H), 4.93-4.57 (m, 2H), 4.53-4.10 (m, 3H), 3.95-3.48 (m, 3H), 3.20-2.97 (m, 3H), 1.59-1.38 (m, 3H). | 552.97 | 97.1 |
| 120 | (S,E)-9-chloro-7-(4-(4,4-difluorobut-2-enoyl)-2-methylpiperazin-1-yl)-10-(2,4,6-trifluorophenyl)-2,3-dihydro-5H-[1,4]thiazino[2,3,4-ij]quinazolin-5-one | 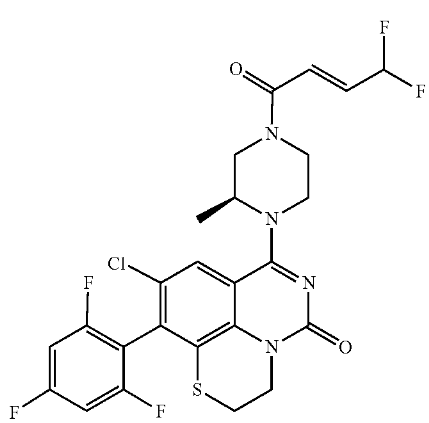 [SMILES: C[C@H]1CN(C(=O)/C=C/C(F)F)CCN1c1nc(=O)n2c3c(c(-c4c(F)cc(F)cc4F)c(Cl)cc13)SCC2] | ¹H NMR (400 MHz, CDCl₃) δ 7.49-7.47 (m, 1H), 6.86-6.69 (m, 4H), 6.28 (t, J = 55.6 Hz, 1H), 4.87-4.65 (m, 1.5H), 4.48-4.32 (m, 3H), 4.19-4.15 (m, 0.5H), 3.95-3.92 (m, 0.5H), 3.77-3.54 (m, 2.5H), 3.15-2.98 (m, 3H), 1.45-1.40 (m, 3H). | 570.96 | 95.9 |

| Ex. # | Name | Structure | ¹H NMR | MS | % CAF 10 uM @ 60 min |
|---|---|---|---|---|---|
| 121 | (2S)-4-(9-chloro-10-(2,4-difluorophenyl)-5-oxo-2,3-dihydro-5H-[1,4]thiazino[2,3,4-ij]quinazolin-7-yl)-1-((E)-4-(dimethylamino)but-2-enoyl)piperazine-2-carbonitrile | 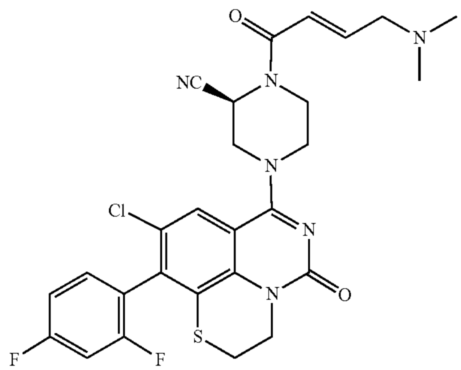 [SMILES: CN(C)C/C=C/C(=O)N1CCN(c2nc(=O)n3c4c(c(-c5ccc(F)cc5F)c(Cl)cc24)SCC3)C[C@H]1C#N] | 1H NMR (400 MHz, DMSO) δ 8.36 (s, 1H), 7.59-7.37 (m, 1H), 7.27 (dd, J = 22.3, 16.0 Hz, 1H), 6.75 (ddd, J = 43.5, 17.4, 10.3 Hz, 1H), 5.32 (p, J = 10.8 Hz, 1H), 4.43 (dd, J = 31.3, 19.2 Hz, 1H), 4.31-4.14 (m, 1H), 4.14-3.94 (m, 1H), 3.71 (s, 1H), 3.60 (s, 2H), 3.09 (d, J = 5.8 Hz, 2H), 2.21 (d, J = 27.5 Hz, 2H), 2.09-1.91 (m, 2H), 1.44 (dd, J = 17.1, 7.1 Hz, 2H), 1.24 (s, 6H). | 571.04 | 3.6 |
| 123 | (R)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one | 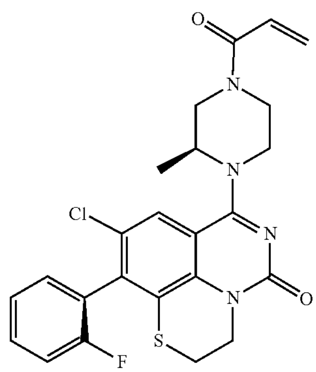 | ¹H NMR (400 MHz, DMSO-d₆) δ 7.64 (s, 1H), 7.47-7.61 (m, 1H), 7.23-7.44 (m, 3H), 6.68-6.94 (m, 1H), 6.18 (dd, J = 7.07, 16.45 Hz, 1H), 5.74 (dd, J = 2.31, 10.44 Hz, 1H), 4.69 (br. s., 1H), 4.40 (d, J = 11.63 Hz, 1H), 4.27 (d, J = 12.51 Hz, 2H), 4.12 (d, J = 12.38 Hz, 1H), 4.00 (d, J = 12.88 Hz, 3H), 3.57 (br. s., 1H), 3.05-3.24 (m, 2H), 1.25 (d, J = 6.50 Hz, 3H) | 484.97 | 91.3 |
| 124 | (S)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one | 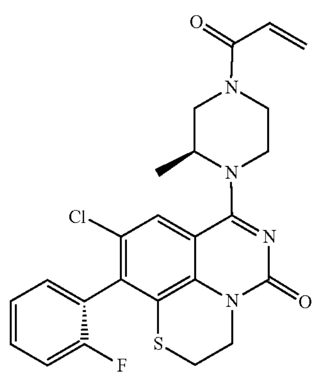 | ¹H NMR (400 MHz, DMSO-d₆) δ 7.50-7.74 (m, 2H), 7.20-7.44 (m, 3H), 6.72-7.01 (m, 1H), 6.18 (dd, J = 6.00, 16.51 Hz, 1H), 5.66-5.80 (m, 1H), 4.63 (br. s., 1H), 4.41 (d, J = 12.63 Hz, 1H), 4.17-4.34 (m, 1H), 3.89-4.13 (m, 3H), 3.54 (d, J = 9.51 Hz, 1H), 3.10-3.21 (m, 3H), 3.07-2.88 (m, 1H), 1.22-1.35 (m, 3H) | 484.97 | 96 |
| 125 | (2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl)piperazine-2-carbonitrile | 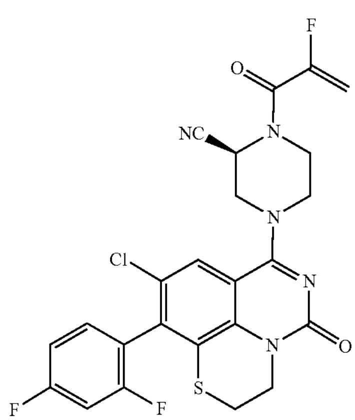 [SMILES: C=C(F)C(=O)N1CCN(c2nc(=O)n3c4c(c(-c5ccc(F)cc5F)c(Cl)cc24)SCC3)C[C@H]1C#N] | 1H NMR (400 MHz, ) δ 7.78 (d, J = 11.2 Hz, 1H), 7.49 (td, J = 9.7, 2.4 Hz, 1H), 7.45-7.37 (m, 1H), 7.28 (td, J = 8.5, 2.4 Hz, 1H), 5.59 (d, J = 10.9 Hz, 1H), 5.54 (q, J = 4.4 Hz, 1H), 5.46 (dd, J = 37.9, 4.3 Hz, 1H), 4.54-4.42 (m, 1H), 4.37 (ddd, J = 13.7, 5.8, 2.5 Hz, 0.5H), 4.30-4.04 (m, 3H), 3.98 (ddd, J = 13.9, 8.9, 2.6 Hz, 0.5H), 3.68 (dd, J = 14.1, 3.5 Hz, 1H), 3.60 (dd, J = 14.2, 3.6 Hz, 1H), 3.28-3.06 (m, 3H). | 531.94 | 94.5 |

-continued

| Ex. # | Name | Structure | ¹H NMR | MS | % CAF 10 uM @ 60 min |
|---|---|---|---|---|---|
| 127 | 7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one | 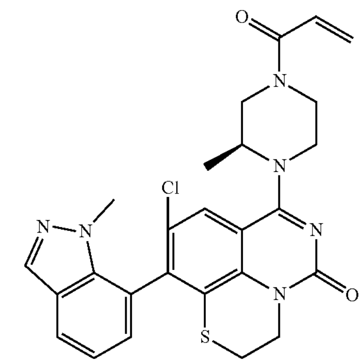 [SMILES: C=CC(=O)N1CCN(c2nc(=O)n3c4c(c(-c5cccc6cnn(C)c56)c(Cl)cc24)SCC3)[C@@H](C)C1] | ¹H NMR (400 MHz, DMSO) δ 8.14 (s, 1H), 7.89 (d, J = 8.0 Hz, 1H), 7.68 (s, 1H), 7.26 (t, J = 7.4 Hz, 1H), 7.17 (s, 1H), 6.85 (dd, J = 27.2, 16.7 Hz, 1H), 6.20 (d, J = 15.8 Hz, 1H), 5.75 (d, J = 10.2 Hz, 1H), 4.70 (s, 1H), 4.45-4.22 (m, 2H), 4.11 (d, J = 39.6 Hz, 3H), 3.56 (s, 5H), 3.15 (s, 2H), 3.01 (s, 1H), 1.28 (s, 3H). | 521.03 | 60 |
| 130 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one | 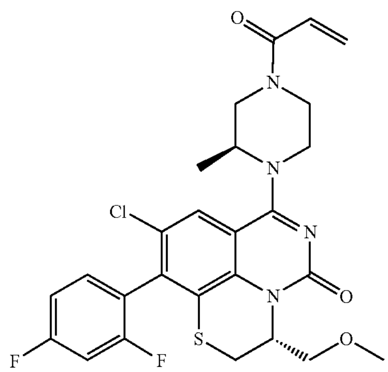 [SMILES: C=CC(=O)N1CCN(c2nc(=O)n3c4c(c(-c5ccc(F)cc5F)c(Cl)cc24)SC[C@H]3COC)[C@@H](C)C1] | | 547.02 | 94.5 |
| 134 | 7-(4-acryloylhexahydrofuro[3,4-b]pyrazin-1(2H)-yl)-9-chloro-10-(2,4-difluorophenyl)-2,3-dihydro-5H-[1,4]thiazino[2,3,4-ij]quinazolin-5-one | 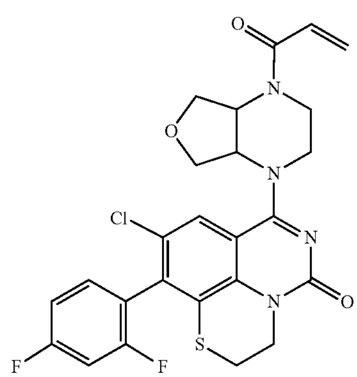 [SMILES: C=CC(=O)N1CCN(c2nc(=O)n3c4c(c(-c5ccc(F)cc5F)c(Cl)cc24)SCC3)C2COCC21] | ¹H NMR (400 MHz, MeOD) δ 7.64 (d, J = 13.5 Hz, 1H), 7.26-7.15 (m, 1H), 7.10-6.97 (m, 2H), 6.78-6.61 (m, 1H), 6.17 (dd, J = 16.7, 1.9 Hz, 1H), 5.70 (dd, J = 10.5, 2.0 Hz, 1H), 4.97-4.82 (m, 2H), 4.40-4.18 (m, 2H), 4.14-3.41 (m, 8H), 3.16-3.01 (m, 2H) | 530.97 | 85 |
| 135 | 7-(3-acryloyl-3,6-diazabicyclo[3.1.1]heptan-6-yl)-9-chloro-10-(2,4-difluorophenyl)-2,3-dihydro-5H-[1,4]thiazino[2,3,4-ij]quinazolin-5-one | 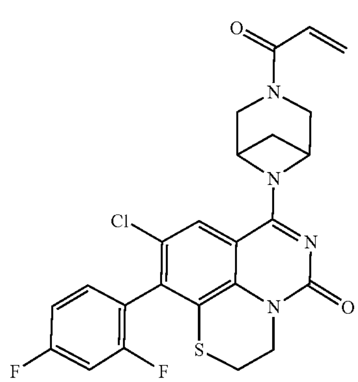 [SMILES: C=CC(=O)N1CC2CC(C1)N2c1nc(=O)n2c3c(c(-c4ccc(F)cc4F)c(Cl)cc13)SCC2] | ¹H NMR (400 MHz, MeOD) δ 7.98 (d, J = 22.3 Hz, 1H), 7.19 (tdd, J = 8.7, 6.3, 1.9 Hz, 1H), 7.09-6.94 (m, 2H), 6.79-6.60 (m, 1H), 6.17-6.02 (m, 1H), 5.75-5.54 (m, 1H), 4.78-4.26 (m, 4H), 4.19-4.03 (m, 2H), 3.70-3.35 (m, 2H), 3.11-2.96 (m, 2H), 2.45-2.16 (m, 2H) | 500.95 | 0 |

-continued

| Ex. # | Name | Structure | ¹H NMR | MS | % CAF 10 uM @ 60 min |
|---|---|---|---|---|---|
| 136 | 7-((S)-4-acryloyl-2-methylpiperazin-1-yl)-9-chloro-10-(2-oxopyridin-1(2H)-yl)-2,3-dihydro-5H-[1,4]thiazino[2,3,4-ij]quinazolin-5-one | 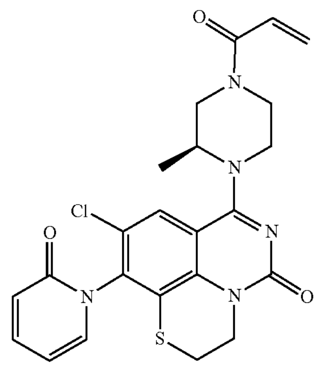 [SMILES: C=CC(=O)N1CCN(c2nc(=O)n3c4c(c(-n5ccccc5=O)c(Cl)cc24)SCC3)[C@@H](C)C1] | 1H NMR (400 MHz, DMSO) δ 8.09 (d, J = 4.7 Hz, 1H), 7.93 (t, J = 7.7 Hz, 1H), 7.62 (s, 1H), 7.27-7.13 (m, 2H), 7.01-6.65 (m, 1H), 6.18 (dd, J = 15.8, 7.0 Hz, 1H), 5.74 (d, J = 10.4 Hz, 1H), 4.63 (s, 1H), 4.33 (dd, J = 56.3, 12.7 Hz, 1H), 4.23-4.07 (m, 2H), 4.01 (d, J = 12.4 Hz, 2H), 3.55 (d, J = 12.7 Hz, 2H), 3.15 (d, J = 24.1 Hz, 2H), 2.98 (d, J = 12.5 Hz, 1H), 1.26 (d, J = 5.7 Hz, 3H). | 483.97 | 89.4 |
| 137 | (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one | 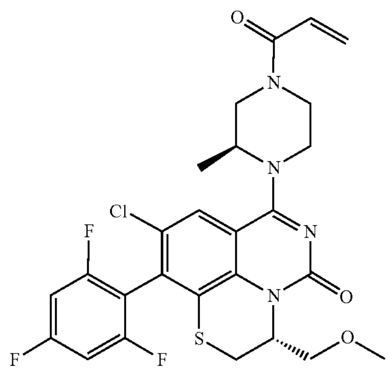 [SMILES: C=CC(=O)N1CCN(c2nc(=O)n3c4c(c(-c5c(F)cc(F)cc5F)c(Cl)cc24)SC[C@H]3COC)[C@@H](C)C1] | | 565.01 | 86.8 |
| 145 | 7-(5-acryloyl-2,5-diazabicyclo[4.2.0]octan-2-yl)-9-chloro-10-(2,4-difluorophenyl)-2,3-dihydro-5H-[1,4]thiazino[2,3,4-ij]quinazolin-5-one | 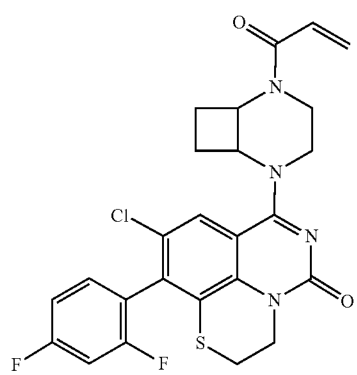 [SMILES: C=CC(=O)N1CCN(c2nc(=O)n3c4c(c(-c5ccc(F)cc5F)c(Cl)cc24)SCC3)C2CCC21] | ¹H NMR (400 MHz, MeOD) δ 7.67 (d, J = 1.8 Hz, 1H), 7.28-7.13 (m, 1H), 7.09-6.91 (m, 2H), 6.34 (dd, J = 16.8, 10.3 Hz, 1H), 6.19 (dd, J = 16.8, 2.1 Hz, 1H), 5.67 (dd, J = 10.2, 2.1 Hz, 1H), 4.69-4.45 (m, 1H), 4.36-4.26 (m, 1H), 4.24-4.07 (m, 2H), 4.04-3.90 (m, 2H), 3.85-3.71 (m, 1H), 3.71-3.57 (m, 1H), 3.16-2.94 (m, 2H), 2.48-2.22 (m, 2H), 2.01-1.83 (m, 1H), 1.68-1.52 (m, 1H) | 514.97 | 58 |
| 146 | (S)-7-(4-acryloyl-2-methylpiperazin-1-yl)-9-chloro-10-(2,4,6-trifluorophenyl)-2,3-dihydro-5H-[1,4]thiazino[2,3,4-ij]quinazolin-5-one | 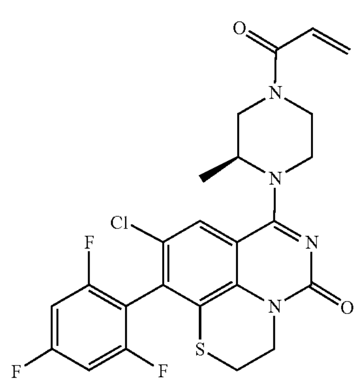 [SMILES: C=CC(=O)N1CCN(c2nc(=O)n3c4c(c(-c5c(F)cc(F)cc5F)c(Cl)cc24)SCC3)[C@@H](C)C1] | ¹H NMR (400 MHz, DMSO) δ 7.67 (s, 1H), 7.47 (t, J = 8.8 Hz, 2H), 6.94-6.70 (m, 1H), 6.18 (dd, J = 16.7, 6.4 Hz, 1H), 5.74 (dd, J = 10.4, 2.0 Hz, 1H), 4.66 (s, 1H), 4.33 (dd, J = 54.2, 13.2 Hz, 1H), 4.22-3.91 (m, 4H), 3.55 (d, J = 13.7 Hz, 2H), 3.22 (t, J = 4.9 Hz, 2H), 3.17-2.92 (m, 1H), 1.26 (d, J = 6.4 Hz, 3H). | 520.95 | 90.7 |

-continued

| Ex. # | Name | Structure | ¹H NMR | MS | % CAF 10 uM @ 60 min |
|---|---|---|---|---|---|
| 148 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide | 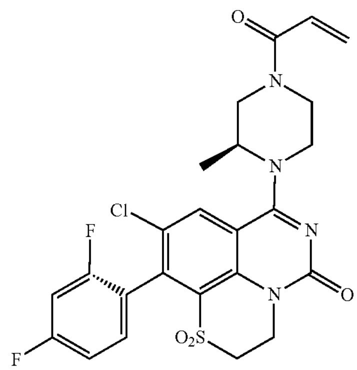 | 1H NMR (400 MHz, CDCl₃) δ 7.86 (s, 1H), 7.38-7.33 (m, 1H), 7.06-6.93 (m, 2H), 6.60-6.53 (m, 1H), 6.41-6.37, (m, 1H), 5.81-5.79 m, 1H), 5.05-5.01 2m, 1H), 4.78-4.71 (m, 1H), 4.59-4.35 (m, 3H), 4.01-3.85 (m, 1H), 3.62-3.44 (m, 4H), 3.04 (m, 1H), 1.45 (d, 3H). | 534.96 | 95.9 |
| 149 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide | 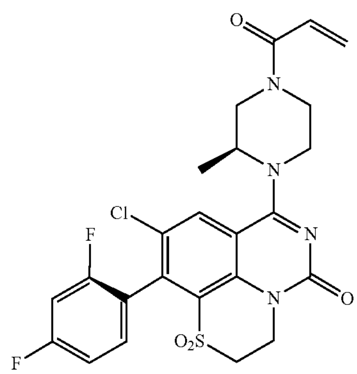 | ¹H NMR (400 MHz, CDCl₃) δ 7.87 (s, 1H), 7.37-7.31 (m, 1H), 7.06-6.93 (m, 2H), 6.41-6.37 (m, 1H), 6.35-6.31, (m, 1H), 5.81-5.79 m, 1H), 5.06-5.01 (m, 1.5H), 4.78-4.71 (m, 1H), 4.51-4.07 (m, 3H), 3.98-3.44 (m, 4.5H), 3.21-2.91 (m, 1H), 1.41 (s, 3H). | 534.96 | 52.8 |
| 150 | 7-((R)-4-acryloyl-2-(hydroxymethyl)piperazin-1-yl)-9-chloro-10-(2,4-difluorophenyl)-2,3-dihydro-5H-[1,4]thiazino[2,3,4-ij]quinazolin-5-one | 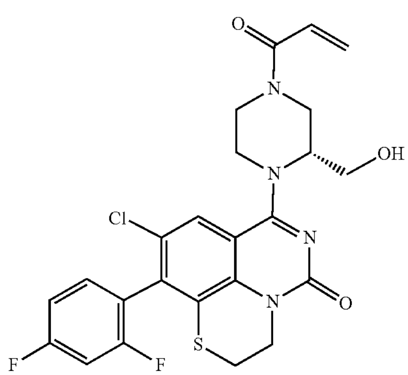 [SMILES: C=CC(=O)N1CCN(c2nc(=O)n3c4c(c(-c5ccc(F)cc5F)c(Cl)cc24)SCC3)[C@@H](CO)C1] | 1H NMR (400 MHz, DMSO) δ 7.90 (dd, J = 40.4, 14.2 Hz, 1H), 7.48 (td, J = 9.7, 2.5 Hz, 1H), 7.44-7.36 (m, 1H), 7.27 (td, J = 8.5, 2.4 Hz, 1H), 6.82 (ddd, J = 16.7, 10.5, 2.2 Hz, 1H), 6.16 (dd, J = 16.6, 2.1 Hz, 1H), 5.72 (dd, J = 10.4, 2.2 Hz, 1H), 5.11 (dd, J = 11.5, 5.8 Hz, 1H), 4.53 (s, 1H), 4.36-3.87 (m, 6H), 3.70-3.38 (m, 4H), 3.23-3.01 (m, 2H). | 518.96 | 59.9 |
| 151 | (S)-7-(4-acryloyl-2-methylpiperazin-1-yl)-9-chloro-10-(4-fluorophenyl)-2,3-dihydro-5H-[1,4]thiazino[2,3,4-ij]quinazolin-5-one | 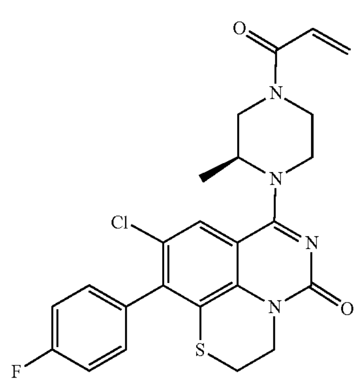 [SMILES: C=CC(=O)N1CCN(c2nc(=O)n3c4c(c(-c5ccc(F)cc5)c(Cl)cc24)SCC3)[C@@H](C)C1] | 1H NMR (400 MHz, DMSO) δ 7.61 (s, 1H), 7.45-7.21 (m, 4H), 6.93-6.75 (m, 1H), 6.18 (dd, J = 16.4, 7.3 Hz, 1H), 5.74 (dd, J = 10.4, 2.2 Hz, 1H), 4.65 (s, 1H), 4.34 (dd, J = 55.7, 12.7 Hz, 1H), 4.04 (dd, J = 40.6, 26.7 Hz, 4H), 3.54 (d, J = 14.0 Hz, 2H), 3.14 (t, J = 4.9 Hz, 2H), 2.96 (t, J = 11.7 Hz, 1H), 1.26 (d, J = 6.3 Hz, 3H). | 484.97 | 94.1 |

| Ex. # | Name | Structure | ¹H NMR | MS | % CAF 10 uM @ 60 min |
|---|---|---|---|---|---|
| 152 | 7-((S)-4-acryloyl-2-methylpiperazin-1-yl)-9-chloro-10-(2-fluoro-5-hydroxyphenyl)-2,3-dihydro-5H-[1,4]thiazino[2,3,4-ij]quinazolin-5-one | 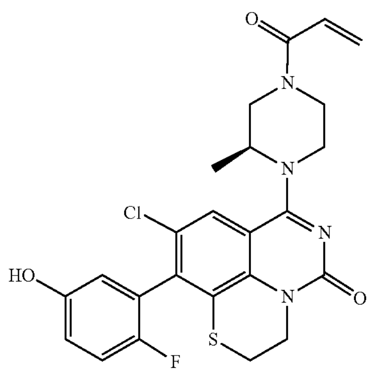 | 1H NMR (400 MHz, DMSO) δ 9.65 (s, 1H), 7.60 (d, J = 9.4 Hz, 1H), 7.17 (t, J = 9.1 Hz, 1H), 6.92-6.74 (m, 2H), 6.59 (dt, J = 5.3, 2.5 Hz, 1H), 6.18 (dd, J = 16.4, 6.0 Hz, 1H), 5.74 (dd, J = 10.4, 2.2 Hz, 1H), 4.65 (d, J = 25.8 Hz, 1H), 4.47-4.17 (m, 2H), 4.16-3.92 (m, 3H), 3.66-3.43 (m, 1H), 3.24-3.06 (m, 3H), 2.96 (d, J = 12.7 Hz, 1H), 1.26 (dd, J = 14.7, 6.1 Hz, 3H). | 500.97 | 55.3 |
| 153 | 7-((S)-4-acryloyl-2-methylpiperazin-1-yl)-9-chloro-10-(2-chloro-5-hydroxyphenyl)-2,3-dihydro-5H-[1,4]thiazino[2,3,4-ij]quinazolin-5-one | 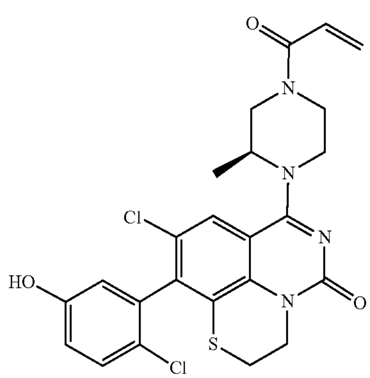 [SMILES: C=CC(=O)N1CCN(c2nc(=O)n3c4c(c(-c5cc(O)ccc5F)c(Cl)cc24)SCC3)[C@@H](C)C1] | 1H NMR (400 MHz, DMSO) δ 9.94 (s, 1H), 7.60 (s, 1H), 7.40 (d, J = 8.7 Hz, 1H), 6.89 (dd, J = 8.7, 2.9 Hz, 1H), 6.81 (dd, J = 17.7, 10.0 Hz, 1H), 6.62 (t, J = 2.6 Hz, 1H), 6.18 (dd, J = 16.4, 5.9 Hz, 1H), 5.74 (dd, J = 10.4, 2.3 Hz, 1H), 4.65 (s, 1H), 4.46-3.94 (m, 5H), 3.67-3.47 (m, 1H), 3.23-3.08 (m, 33H), 2.99 (d, J = 12.7 Hz, 1H), 1.25 (d, J = 6.7 Hz, 3H). | 517.43 | 55.7 |
| 154 | (R)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one | 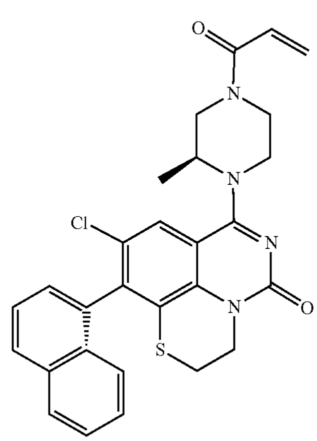 | ¹H NMR (400 MHz, DMSO) δ 8.05 (t, J = 8.5 Hz, 2H), 7.66 (dd, J = 15.7, 8.5 Hz, 2H), 7.57 (t, J = 7.5 Hz, 1H), 7.47 (t, J = 7.6 Hz, 1H), 7.39 (dd, J = 6.1, 3.3 Hz, 1H), 7.35 (dd, J = 8.3, 3.6 Hz, 1H), 6.95-6.75 (m, 1H), 6.26-6.11 (m, 1H), 5.75 (dd, J = 10.4, 2.3 Hz, 1H), 4.84-4.60 (m, 1H), 4.49-4.19 (m, 2H), 4.19-3.94 (m, 3H), 3.70-3.39 (m, 2H), 3.23-2.90 (m, 3H), 1.37-1.24 (m, 3H). | 517.04 | 24 |

-continued

| Ex. # | Name | Structure | ¹H NMR | MS | % CAF 10 uM @ 60 min |
|---|---|---|---|---|---|
| 155 | (S)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one | 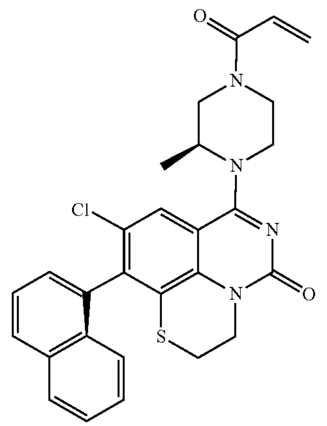 | ¹H NMR (400 MHz, DMSO) δ 8.05 (t, J = 8.5 Hz, 2H), 7.66 (dd, J = 15.7, 8.5 Hz, 2H), 7.57 (t, J = 7.5 Hz, 1H), 7.47 (t, J = 7.6 Hz, 1H), 7.39 (dd, J = 6.1, 3.3 Hz, 1H), 7.35 (dd, J = 8.3, 3.6 Hz, 1H), 6.95-6.75 (m, 1H), 6.26-6.11 (m, 1H), 5.75 (dd, J = 10.4, 2.3 Hz, 1H), 4.84-4.60 (m, 1H), 4.49-4.19 (m, 2H), 4.19-3.94 (m, 3H), 3.70-3.39 (m, 2H), 3.23-2.90 (m, 3H), 1.37-1.24 (m, 3H). | 517.04 | 92.2 |
| 159 | 7-((S)-4-acryloyl-2-methylpiperazin-1-yl)-9-chloro-10-(5-methyl-1H-indazol-4-yl)-2,3-dihydro-5H-[1,4]thiazino[2,3,4-ij]quinazolin-5-one | 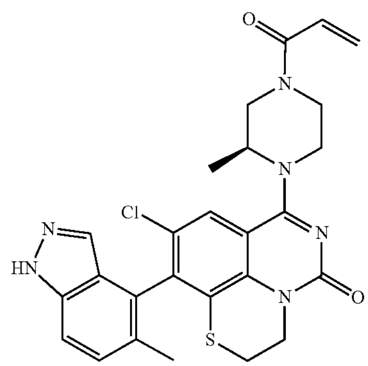 [SMILES: C=CC(=O)N1CCN(c2nc(=O)n3c4c(c(-c5c(C)ccc6[nH]ncc56)c(Cl)cc24)SCC3)[C@@H](C)C1] | 1H NMR (400 MHz, DMSO) δ 13.11 (s, 1H), 7.66 (s, 1H), 7.57-7.47 (m, 2H), 7.35 (d, J = 8.6 Hz, 1H), 6.93-6.75 (m, 1H), 6.19 (dd, J = 17.7, 6.2 Hz, 1H), 5.75 (dd, J = 10.4, 2.3 Hz, 1H), 4.70 (s, 1H), 4.50-4.21 (m, 1H), 4.21-3.92 (m, 4H), 3.58 (s, 1H), 3.23-2.86 (m, 4H), 2.12 (s, 3H), 1.29 (d, J = 5.8 Hz, 3H). | 521.03 | 37.2 |
| 160 | 7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one | 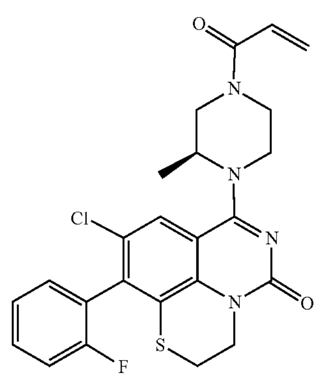 [SMILES: C=CC(=O)N1CCN(c2nc(=O)n3c4c(c(-c5ccccc5F)c(Cl)cc24)SCC3)[C@@H](C)C1] | 1H NMR (400 MHz, DMSO) δ 7.68-7.52 (m, 2H), 7.47-7.26 (m, 3H), 6.82 (s, 1H), 6.18 (dd, J = 16.9, 7.0 Hz, 1H), 5.74 (dd, J = 10.4, 2.3 Hz, 1H), 4.76-4.56 (m, 1H), 4.47-4.18 (m, 2H), 4.18-3.92 (m, 3H), 3.66-3.42 (m, 1H), 3.24-3.07 (m, 3H), 3.07-2.88 (m, 1H), 1.26 (dd, J = 13.3, 6.8 Hz, 3H). | 484.97 | 72.7 |
| 161 | (2R,5R)-4-acryloyl-1-(9-chloro-10-(2,4-difluorophenyl)-5-oxo-2,3-dihydro-5H-[1,4]thiazino[2,3,4-ij]quinazolin-7-yl)-5-methylpiperazine-2-carbonitrile | 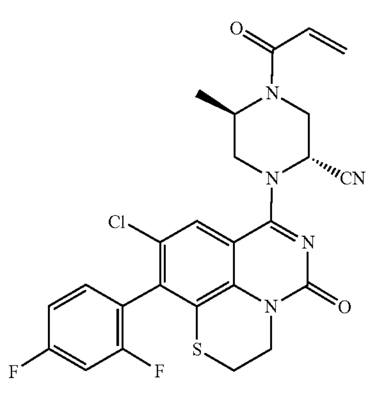 [SMILES: C=CC(=O)N1C[C@H](C#N)N(c2nc(=O)n3c4c(c(-c5ccc(F)cc5F)c(Cl)cc24)SCC3)C[C@H]1C] | ¹H NMR (400 MHz, DMSO) δ 8.35 (s, 1H), 7.53 (td, J = 9.6, 2.2 Hz, 1H), 7.41 (td, J = 14.5, 8.0 Hz, 1H), 7.36-7.28 (m, 1H), 6.92 (s, 1H), 6.39-6.13 (m, 1H), 5.87 (d, J = 10.9 Hz, 1H), 5.19 (d, J = 16.6 Hz, 1H), 4.88 (dd, J = 22.7, 14.2 Hz, 1H), 4.61 (d, J = 10.7 Hz, 1H), 4.52-4.39 (m, 1H), 4.38-4.27 (m, 1H), 4.24-4.07 (m, 1H), 3.24-2.95 (m, 4H), 1.21 (s, 3H). | 527.97 | 1 |

| Ex. # | Name | Structure | ¹H NMR | MS | % CAF 10 uM @ 60 min |
|---|---|---|---|---|---|
| 162 | 7-((S)-4-acryloyl-2-methylpiperazin-1-yl)-9-chloro-10-(5-(difluoromethyl)-2-fluorophenyl)-2,3-dihydro-5H-[1,4]thiazino[2,3,4-ij]quinazolin-5-one | 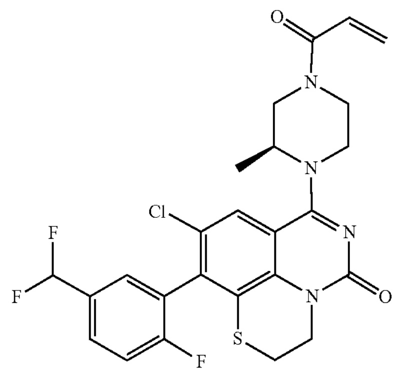 [SMILES: C=CC(=O)N1CCN(c2nc(=O)n3c4c(c(-c5cc(C(F)F)ccc5F)c(Cl)cc24)SCC3)[C@@H](C)C1] | ¹H NMR (400 MHz, DMSO) δ 7.89-7.71 (m, 1H), 7.65 (d, J = 10.2 Hz, 1H), 7.62-7.53 (m, 2H), 7.12 (t, J = 55.6 Hz, 1H), 6.92-6.71 (m, 1H), 6.18 (dd, J = 16.4, 6.3 Hz, 1H), 5.74 (dd, J = 10.4, 2.3 Hz, 1H), 4.78-4.54 (m, 1H), 4.47-4.18 (m, 2H), 4.18-3.88 (m, 3H), 3.56 (d, J = 11.6 Hz, 2H), 3.27-3.08 (m, 2H), 3.05-2.89 (m, 1H), 1.26 (dd, J = 13.8, 6.5 Hz, 3H). | 534.98 | 39 |
| 163 | 7-((S)-4-acryloyl-2-methylpiperazin-1-yl)-9-chloro-10-(5-(difluoromethoxy)-2-fluorophenyl)-2,3-dihydro-5H-[1,4]thiazino[2,3,4-ij]quinazolin-5-one | 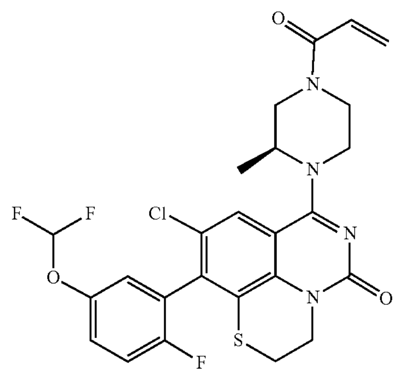 [SMILES: C=CC(=O)N1CCN(c2nc(=O)n3c4c(c(-c5cc(OC(F)F)ccc5F)c(Cl)cc24)SCC3)[C@@H](C)C1] | 1H NMR (400 MHz, DMSO) δ 7.64 (d, J = 8.1 Hz, 1H), 7.50 (t, J = 8.9 Hz, 1H), 7.42-7.36 (m, 1H), 7.27 (t, J = 73.6 Hz, 1H), 7.20 (td, J = 5.5, 3.0 Hz, 1H), 6.91-6.72 (m, 1H), 6.18 (dd, J = 15.9, 6.3 Hz, 1H), 5.74 (dd, J = 10.4, 2.3 Hz, 1H), 4.75-4.54 (m, 1H), 4.46-4.18 (m, 2H), 4.17-3.90 (m, 3H), 3.67-3.43 (m, 2H), 3.25-3.07 (m, 2H), 3.05-2.87 (m, 1H), 1.26 (dd, J = 10.3, 6.8 Hz, 3H). | 550.98 | 41.4 |
| 165 | 7-(6-acryloyl-3,6-diazabicyclo[3.1.1]heptan-3-yl)-9-chloro-10-(2,4-diflurorophenyl)-2,3-dihydro-5H-[1,4]thiazino[2,3,4-ij]quinazolin-5-one | 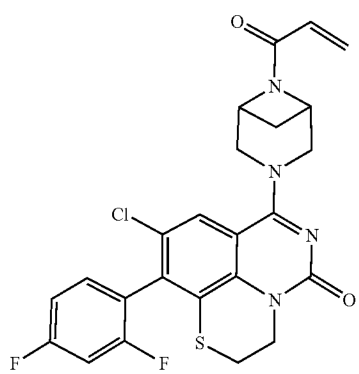 [SMILES: C=CC(=O)N1C2CC1CN(c1nc(=O)n3c4c(c(-c5ccc(F)cc5F)c(Cl)cc14)SCC3)C2] | ¹H NMR (400 MHz, MeOD) δ 7.93 (d, J = 1.1 Hz, 1H), 7.25-7.15 (m, 1H), 7.09-6.93 (m, 2H), 6.39 (dd, J = 16.9, 10.3 Hz, 1H), 6.20 (dt, J = 16.9, 1.7 Hz, 1H), 5.69 (dd, J = 10.3, 1.8 Hz, 1H), 4.51-4.04 (m, 7H), 3.07 (dd, 2H), 2.69 (q, J = 6.6 Hz, 1H), 1.61 (d, J = 9.1 Hz, 1H) | 500.95 | 16.9 |
| 167 | 7-((S)-4-acryloyl-2-methylpiperazin-1-yl)-9-chloro-10-(2-(trifluoromethyl)phenyl)-2,3-dihydro-5H-[1,4]thiazino[2,3,4-ij]quinazolin-5-one | 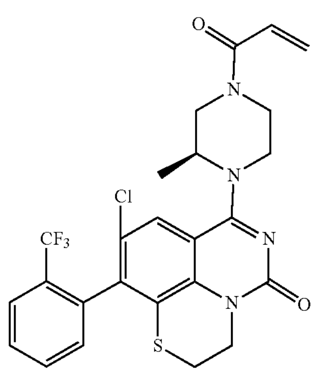 [SMILES: C=CC(=O)N1CCN(c2nc(=O)n3c4c(c(-c5ccccc5C(F)(F)F)c(Cl)cc24)SCC3)[C@@H](C)C1] | 1H NMR (400 MHz, DMSO) δ 7.92 (d, J = 8.0 Hz, 1H), 7.84 (t, J = 7.5 Hz, 1H), 7.73 (t, J = 7.6 Hz, 1H), 7.63 (s, 1H), 7.41-7.26 (m, 1H), 6.95-6.75 (m, 1H), 6.25-6.13 (m, 1H), 5.74 (dd, J = 10.4, 2.3 Hz, 1H), 4.77-4.57 (m, 1H), 4.47-4.22 (m, 1H), 4.21-3.95 (m, 4H), 3.66-3.37 (m, 2H), 3.20-3.08 (m, 2H), 3.05-2.91 (m, 1H), 1.26 (d, J = 6.8 Hz, 3H). | 534.98 | 69.8 |

| Ex. # | Name | Structure | ¹H NMR | MS | % CAF 10 uM @ 60 min |
|---|---|---|---|---|---|
| 168 | 7-((S)-4-acryloyl-2-methylpiperazin-1-yl)-9-chloro-10-(2-fluoro-6-hydroxyphenyl)-2,3-dihydro-5H-[1,4]thiazino[2,3,4-ij]quinazolin-5-one | 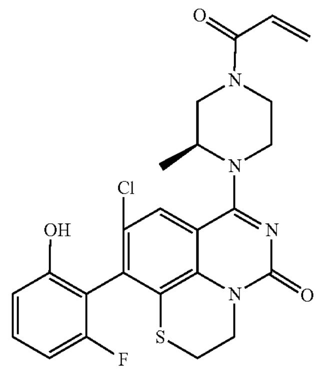 [SMILES: C=CC(=O)N1CCN(c2nc(=O)n3c4c(c(-c5c(O)cccc5F)c(Cl)cc24)SCC3)[C@@H](C)C1] | ¹H NMR (400 MHz, DMSO) δ 10.08-10.05 (m, 1H), 7.59 (s, 1H), 7.31 (dd, J = 15.4, 8.3 Hz, 1H), 6.88-6.69 (m, 3H), 6.23-6.11 (m, 1H), 5.74 (dd, J = 10.4, 2.3 Hz, 1H), 4.71-4.56 (m, 1H), 4.45-4.23 (m, 1H), 4.21-3.91 (m, 4H), 3.60-3.45 (m, 2H), 3.16-3.11 (m, 2H), 3.03-2.90 (m, 1H), 1.26 (d, J = 6.0 Hz, 3H). | 500.97 | 30.6 |
| 169 | 7-((S)-4-acryloyl-2-(azetidin-1-ylmethyl)piperazin-1-yl)-9-chloro-10-(2,4-difluorophenyl)-2,3-dihydro-5H-[1,4]thiazino[2,3,4-ij]quinazolin-5-one | 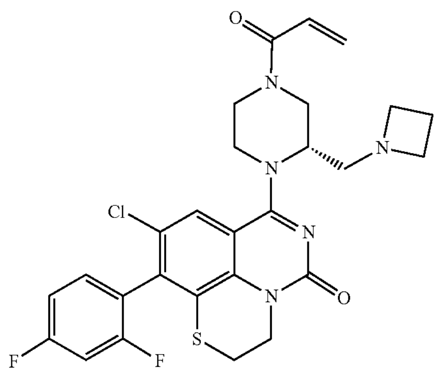 [SMILES: C=CC(=O)N1CCN(c2nc(=O)n3c4c(c(-c5ccc(F)cc5F)c(Cl)cc24)SCC3)[C@@H](CN2CCC2)C1] | ¹H NMR (400 MHz, DMSO) δ 8.01 (d, J = 57.6 Hz, 1H), 7.56-7.44 (m, 1H), 7.40 (dd, J = 14.6, 7.8 Hz, 1H), 7.28 (td, J = 8.5, 2.5 Hz, 1H), 6.82 (d, J = 9.7 Hz, 1H), 6.17 (d, J = 16.8 Hz, 1H), 5.74 (s, 1H), 4.47-4.24 (m, 3H), 4.16-4.01 (m, 3H), 3.40 (dd, J = 12.4, 5.9 Hz, 1H), 3.35 (s, 1H), 3.30 (s, 1H), 3.15 (dd, J = 42.2, 31.1 Hz, 7H), 2.88 (dd, J = 21.5, 10.7 Hz, 1H), 1.93 (s, 2H). | 558.04 | 23.3 |
| 170 | (S)-7-(4-acryloyl-2-methylpiperazin-1-yl)-9-chloro-10-(2,6-difluorophenyl)-2,3-dihydro-5H-[1,4]thiazino[2,3,4-ij]quinazolin-5-one | 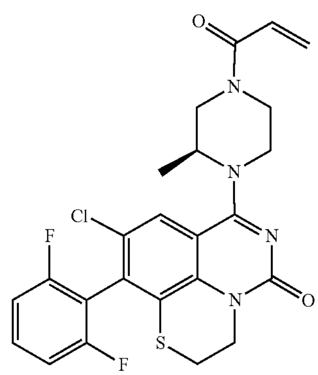 [SMILES: C=CC(=O)N1CCN(c2nc(=O)n3c4c(c(-c5c(F)cccc5F)c(Cl)cc24)SCC3)[C@@H](C)C1] | ¹H NMR (400 MHz, DMSO) δ 7.71-7.61 (m, 2H), 7.32 (t, J = 8.4 Hz, 2H), 6.90-6.75 (m, 1H), 6.23-6.12 (m, 1H), 5.74 (dd, J = 10.4, 2.3 Hz, 1H), 4.74-4.60 (m, 1H), 4.45-3.95 (m, 5H), 3.64-3.48 (m, 2H), 3.21 (t, J = 5.1 Hz, 2H), 3.17-2.92 (m, 1H), 1.27 (d, J = 6.5 Hz, 3H). | 502.96 | 75.9 |
| 171 | 7-((S)-4-acryloyl-2-methylpiperazin-1-yl)-9-chloro-10-(2,5-dichlorophenyl)-2,3-dihydro-5H-[1,4]thiazino[2,3,4-ij]quinazolin-5-one | 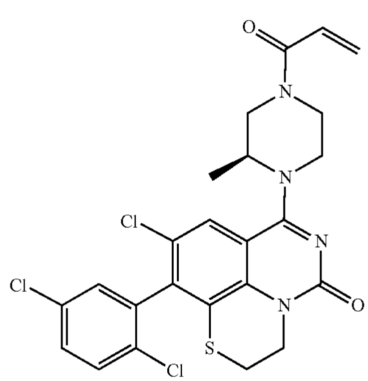 [SMILES: C=CC(=O)N1CCN(c2nc(=O)n3c4c(c(-c5cc(Cl)ccc5Cl)c(Cl)cc24)SCC3)[C@@H](C)C1] | ¹H NMR (400 MHz, DMSO) δ 7.71 (d, J = 8.7 Hz, 1H), 7.65 (d, J = 4.1 Hz, 1H), 7.61 (dd, J = 8.7, 2.6 Hz, 1H), 7.48 (dd, J = 6.3, 2.5 Hz, 1H), 6.90-6.77 (m, 1H), 6.18 (dd, J = 17.3, 7.9 Hz, 1H), 5.74 (dd, J = 10.4, 2.3 Hz, 1H), 4.67 (s, 1H), 4.45-3.95 (m, 5H), 3.64-3.48 (m, 2H), 3.25-3.11 (m, 2H), 3.07-2.91 (m, 1H), 1.26 (d, J = 6.3 Hz, 3H). | 535.87 | 48.9 |

-continued

| Ex. # | Name | Structure | ¹H NMR | MS | % CAF 10 uM @ 60 min |
|---|---|---|---|---|---|
| 172 | 7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one | 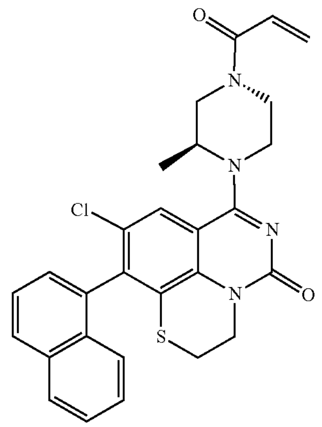 | ¹H NMR (400 MHz, DMSO) δ 8.05 (t, J = 8.5 Hz, 2H), 7.66 (dd, J = 15.7, 8.5 Hz, 2H), 7.57 (t, J = 7.5 Hz, 1H), 7.47 (t, J = 7.6 Hz, 1H), 7.39 (dd, J = 6.1, 3.3 Hz, 1H), 7.35 (dd, J = 8.3, 3.6 Hz, 1H), 6.95-6.75 (m, 1H), 6.26-6.11 (m, 1H), 5.75 (dd, J = 10.4, 2.3 Hz, 1H), 4.84-4.60 (m, 1H), 4.49-4.19 (m, 2H), 4.19-3.94 (m, 3H), 3.70-3.39 (m, 2H), 3.23-2.90 (m, 3H), 1.37-1.24 (m, 3H). | 517.04 | 51.9 |
| 173 | (2R)-4-acryloyl-1-(9-chloro-10-(2,4-difluorophenyl)-5-oxo-2,3-dihydro-5H-[1,4]thiazino[2,3,4-ij]quinazolin-7-yl)piperazine-2-carbonitrile | 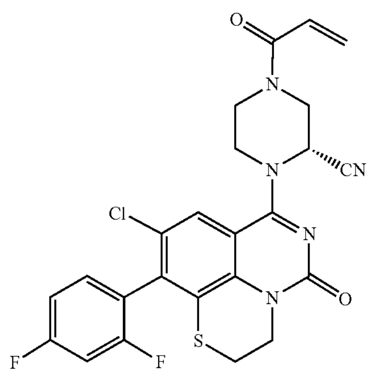 [SMILES: C=CC(=O)N1CCN(c2nc(=O)n3c4c(c(-c5ccc(F)cc5F)c(Cl)cc24)SCC3)[C@@H](C#N)C1] | ¹H NMR (400 MHz, DMSO) δ 8.24 (s, 1H), 7.53 (td, J = 9.6, 2.3 Hz, 1H), 7.44-7.37 (m, 1H), 7.36-7.26 (m, 1H), 6.91 (s, 1H), 6.27 (d, J = 16.0 Hz, 1H), 5.86 (d, J = 11.0 Hz, 1H), 4.83 (d, J = 8.6 Hz, 2H), 4.61-4.48 (m, 1H), 4.35-4.00 (m, 3H), 3.03-2.78 (m, 5H). | 513.95 | 2.2 |
| 174 | 7-((S)-4-acryloyl-2-methylpiperazin-1-yl)-9-chloro-10-(3-chloro-2-fluorophenyl)-2,3-dihydro-5H-[1,4]thiazino[2,3,4-ij]quinazolin-5-one | 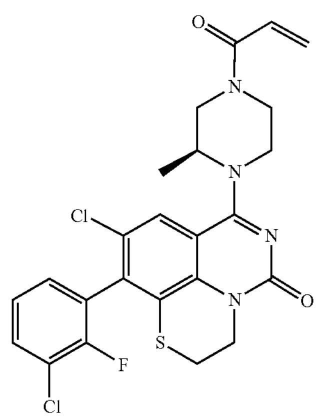 [SMILES: C=CC(=O)N1CCN(c2nc(=O)n3c4c(c(-c5cccc(Cl)c5F)c(Cl)cc24)SCC3)[C@@H](C)C1] | 1H NMR (401 MHz, DMSO) δ 7.79-7.73 (m, 1H), 7.65 (d, J = 8.4 Hz, 1H), 7.42 (t, J = 7.9 Hz, 1H), 7.33 (dddd, J = 7.8, 6.3, 4.6, 1.7 Hz, 1H), 6.94-6.75 (m, 1H), 6.18 (dd, J = 16.8, 6.3 Hz, 1H), 5.74 (dd, J = 10.4, 2.3 Hz, 1H), 4.66 (d, J = 25.0 Hz, 1H), 4.45-4.19 (m, 2H), 4.18-3.91 (m, 3H), 3.51 (dd, J = 43.2, 15.1 Hz, 2H), 3.26-3.09 (m, 2H), 2.97 (dd, J = 24.1, 11.9 Hz, 1H), 1.26 (dd, J = 12.0, 6.6 Hz, 3H). | 519.42 | 93.8 |
| 175 | 7-((S)-4-acryloyl-2-methylpiperazin-1-yl)-9-chloro-10-(5-chloro-2-fluorophenyl)-2,3-dihydro-5H-[1,4]thiazino[2,3,4-ij]quinazolin-5-one | 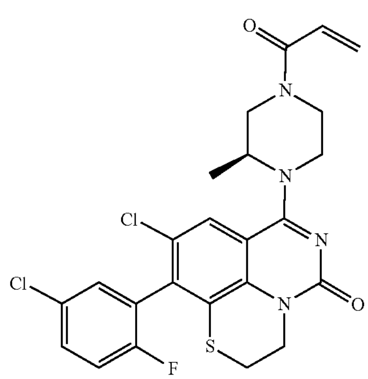 | 1H NMR (401 MHz, DMSO) δ 7.64 (d, J = 10.8 Hz, 2H), 7.55-7.41 (m, 2H), 6.83 (d, J = 10.2 Hz, 1H), 6.30-6.06 (m, 1H), 5.74 (dd, J = 10.4, 2.0 Hz, 1H), 4.65 (d, J = 31.4 Hz, 1H), 4.47-4.18 (m, 2H), 4.03 (dd, J = 27.6, 13.3 Hz, 3H), 3.68-3.41 (m, 2H), 3.27-3.07 (m, 2H), 3.06-2.87 (m, 1H), 1.26 (dd, J = 12.9, 6.2 Hz, 3H). | 519.42 | 79.8 |

-continued

| Ex. # | Name | Structure | ¹H NMR | MS | % CAF 10 uM @ 60 min |
|---|---|---|---|---|---|
| 176 | 2-((2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl)piperazin-2-yl)acetonitrile | 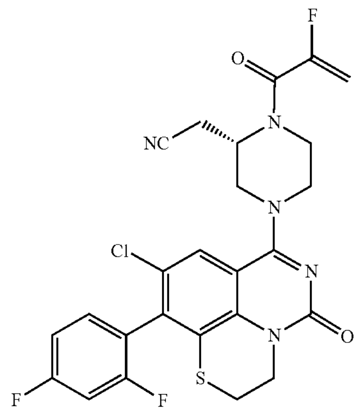 [SMILES: C=C(F)C(=O)N1CCN(c2nc(=O)n3c4c(c(-c5ccc(F)cc5F)c(Cl)cc24)SCC3)C[C@@H]1CC#N] | ¹H NMR (400 MHz, DMSO) δ 7.85 (d, J = 15.6 Hz, 1H), 7.54-7.36 (m, 2H), 7.29 (td, J = 8.5, 2.4 Hz, 1H), 5.42 (dd, J = 17.9, 4.0 Hz, 1H), 5.31 (d, J = 50.2 Hz, 1H), 4.88 (s, 1H), 4.45-4.35 (m, 1H), 4.26 (d, J = 13.8 Hz, 1H), 4.19 (d, J = 10.7 Hz, 2H), 3.93 (dd, J = 12.0, 8.8 Hz, 1H), 3.35-3.08 (m, 6H), 3.02 (dd, J = 17.1, 5.7 Hz, 1H). | 545.96 | 40.5 |
| 177 | (S)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide | 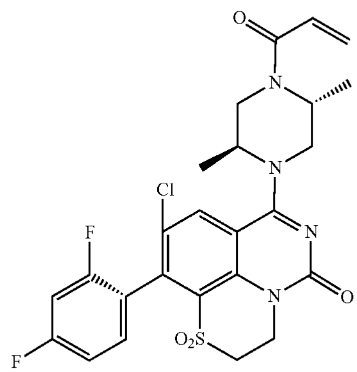 | ¹H NMR (400 MHz, DMSO) δ 8.21-8.03 (m, 1H), 7.49-7.34 (m, 2H), 7.24 (td, J = 8.5, 2.3 Hz, 1H), 6.89-6.71 (m, 1H), 6.17 (dd, J = 16.7, 2.2 Hz, 1H), 5.74 (ddd, J = 10.4, 5.0, 2.2 Hz, 1H), 4.82-4.34 (m, 3H), 4.27-3.97 (m, 2H), 3.96-3.48 (m, 5H), 1.41-1.03 (m, 6H). | 548.99 | 93.5 |
| 178 | (R)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide | 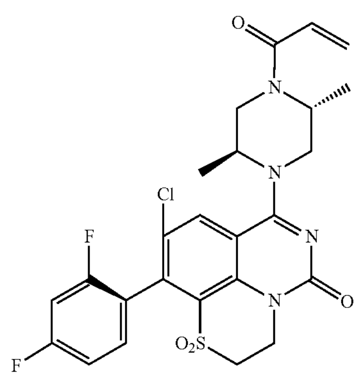 | ¹H NMR (400 MHz, DMSO) δ 8.21-8.03 (m, 1H), 7.49-7.34 (m, 2H), 7.24 (td, J = 8.5, 2.3 Hz, 1H), 6.89-6.71 (m, 1H), 6.17 (dd, J = 16.7, 2.2 Hz, 1H), 5.74 (ddd, J = 10.4, 5.0, 2.2 Hz, 1H), 4.82-4.34 (m, 3H), 4.27-3.97 (m, 2H), 3.96-3.48 (m, 5H), 1.41-1.03 (m, 6H). | 548.99 | 58.3 |
| 179 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 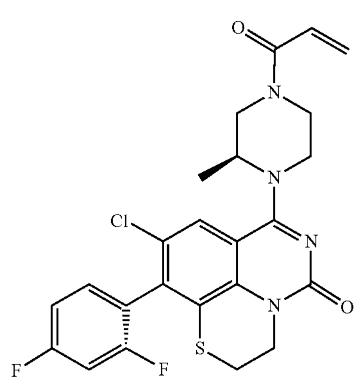 | 1H NMR (400 MHz, CDCl₃) δ 7.48 (s, 1H), 7.24-7.18 (m, 1H), 7.06-6.96 (m, 2H), 6.66-6.52 (m, 1H), 6.38 (dd, J = 16.8 Hz, 1.6 Hz, 1H), 5.78 (d, J = 10.8 Hz, 1H), 4.83-4.48 (m, 3H), 4.41-4.20 (m, 2H), 4.00-3.48 (m, 3H), 3.12-2.97 (m, 3H), 1.48-1.46 (m, 3H). | 502.96 | 96 |

| Ex. # | Name | Structure | ¹H NMR | MS | % CAF 10 uM @ 60 min |
|---|---|---|---|---|---|
| 180 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 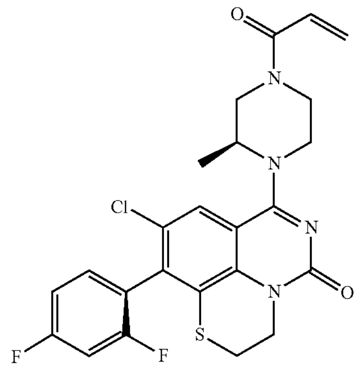 | 1H NMR (400 MHz, CDCl3) δ 7.48 (s, 1H), 7.23-7.17 (m, 1H), 7.06-6.96 (m, 2H), 6.66-6.51 (m, 1H), 6.38 (dd, J = 16.8 Hz, 1.6 Hz, 1H), 5.78 (d, J = 12.0 Hz, 1H), 4.95-4.45 (m, 3H), 4.34-3.98 (m, 3H), 3.80-3.47 (m, 2H), 3.17-2.91 (m, 3H), 1.39-1.38 (m, 3H). | 502.96 | 94.7 |
| 181 | 7-(5-acryloyl-2,5-diazabicyclo[2.2.2]octan-2-yl)-9-chloro-10-(2,4-difluorophenyl)-2,3-dihydro-5H-[1,4]thiazino[2,3,4-ij]quinazolin-5-one | 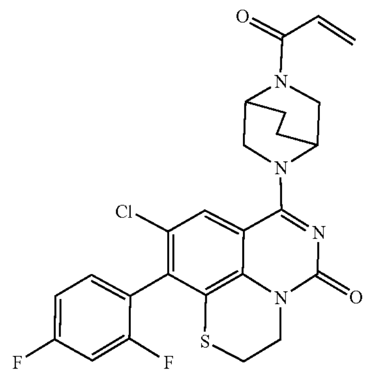 [SMILES: C=CC(=O)N1CC2CCC1CN2c1nc(=O)n2c3c(c(-c4ccc(F)cc4F)c(Cl)cc13)SCC2] | ¹H NMR (400 MHz, MeOD) δ 7.84-7.69 (m, 1H), 7.20 (dtd, J = 10.5, 8.5, 6.3 Hz, 1H), 7.04 (qd, J = 6.8, 2.6 Hz, 2H), 6.60 (dddd, J = 44.5, 16.8, 10.5, 3.6 Hz, 1H), 6.27-6.13 (m, 1H), 5.77-5.62 (m, 1H), 4.93 (s, 1H), 4.70 (t, J = 2.9 Hz, 1H), 4.43 (ddt, J = 14.4, 6.1, 3.1 Hz, 1H), 4.23-3.63 (m, 5H), 3.14-2.98 (m, 2H), 2.37-2.21 (m, 1H), 2.04-1.77 (m, 3H) | 514.97 | 28.7 |
| 182 | 7-(9-acryloyl-3-oxa-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one | 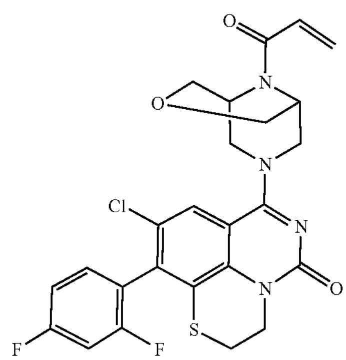 [SMILES: C=CC(=O)N1C2COCC1CN(c1nc(=O)n3c4c(c(-c5ccc(F)cc5F)c(Cl)cc14)SCC3)C2] | ¹H NMR (400 MHz, MeOD) δ 7.65 (s, 1H), 7.20 (td, J = 8.5, 6.3 Hz, 1H), 7.09-6.98 (m, 2H), 6.72 (m, 1H), 6.25 (dd, J = 16.8, 1.9 Hz, 1H), 5.76 (dd, J = 10.5, 1.9 Hz, 1H), 4.92-4.80 (m, 1H), 4.71 (ddt, J = 16.8, 13.3, 1.9 Hz, 1H), 4.55-4.48 (m, 1H), 4.37-4.26 (m, 1H), 4.21 (s, 1H), 4.12-3.89 (m, 3H), 3.78-3.70 (m, 1H), 3.63 (m, 3H), 3.15-3.00 (m, 2H) | 530.97 | 94.4 |
| 183 | 7-((2S,5R)-4-acryloyl-2,5-dimethylpiperazin-1-yl)-9-chloro-10-(naphthalen-1-yl)-2,3-dihydro-5H-[1,4]thiazino[2,3,4-ij]quinazolin-5-one | 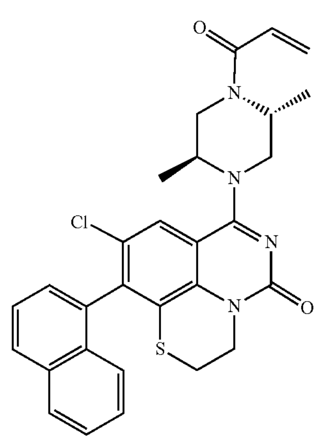 | ¹H NMR (400 MHz, DMSO) δ 8.05 (t, J = 8.5 Hz, 2H), 7.72 (d, J = 4.5 Hz, 1H), 7.68-7.62 (m, 1H), 7.62-7.53 (m, 1H), 7.53-7.43 (m, 1H), 7.43-7.31 (m, 2H), 6.89-6.75 (m, 1H), 6.18 (dd, J = 16.6, 2.3 Hz, 1H), 5.80-5.69 (m, 1H), 4.82-4.40 (m, 2H), 4.40-4.08 (m, 2H), 4.08-3.38 (m, 4H), 3.21-2.94 (m, 2H), 1.37-1.12 (m, 6H). | 531.07 | 45.3 |

| Ex. # | Name | Structure | ¹H NMR | MS | % CAF 10 uM @ 60 min |
|---|---|---|---|---|---|
| 184 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide | 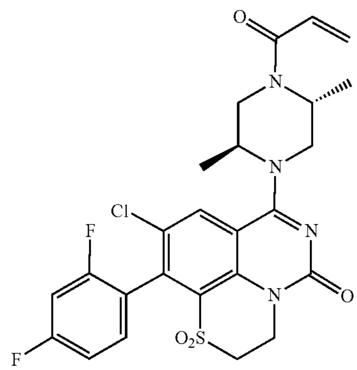 [SMILES: C=CC(=O)N1C[C@H](C)N(c2nc(=O)n3c4c(c(-c5ccc(F)cc5F)c(Cl)cc24)S(=O)(=O)CC3)C[C@H]1C] | ¹H NMR (400 MHz, DMSO) δ 8.21-8.03 (m, 1H), 7.49-7.34 (m, 2H), 7.24 (td, J = 8.5, 2.3 Hz, 1H), 6.89-6.71 (m, 1H), 6.17 (dd, J = 16.7, 2.2 Hz, 1H), 5.74 (ddd, J = 16.7, 2.2 Hz, 1H), 5.74 (ddd, J = 10.4, 5.0, 2.2 Hz, 1H), 4.82-4.34 (m, 3H), 4.27-3.97 (m, 2H), 3.96-3.48 (m, 5H), 1.41-1.03 (m, 6H). | 548.99 | 91.4 |
| 189 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one | 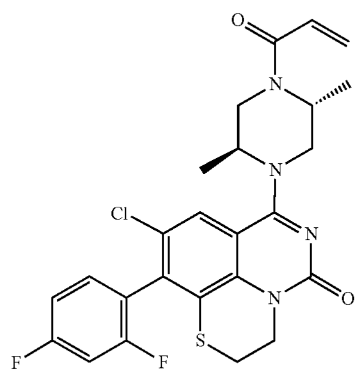 [SMILES: C=CC(=O)N1C[C@H](C)N(c2nc(=O)n3c4c(c(-c5ccc(F)cc5F)c(Cl)cc24)SCC3)C[C@H]1C] | ¹H NMR (400 MHz, CDCl₃) δ 7.57-7.45 (m, 1H), 7.24-7.15 (m, 1H), 7.09-6.92 (m, 2H), 6.69-6.48 (m, 1H), 6.45-6.28 (m, 1H), 5.82-5.72 (m, 1H), 5.12-4.91 (m, 1H), 4.90-4.55 (m, 1H), 4.52-4.19 (m, 2H), 4.20-3.96 (m, 1H), 3.94-3.33 (m, 3H), 3.20-3.01 (m, 2H), 1.53-1.18 (m, 6H). | 516.99 | 93.8 |
| 190 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide | 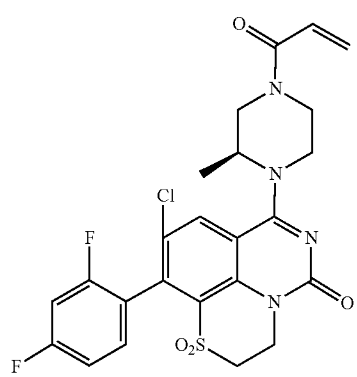 [SMILES: C=CC(=O)N1CCN(c2nc(=O)n3c4c(c(-c5ccc(F)cc5F)c(Cl)cc24)S(=O)(=O)CC3)[C@@H](C)C1] | ¹H NMR (401 MHz, DMSO) δ: 7.88 (s, 1H), 7.30-7.40 (m, 1H), 6.94-7.08 (m, 2H), 6.49-6.19 (m, 1H), 6.39 (d, J = 16.8 Hz, 1H), 5.80 (d, J = 10.4 Hz, 1H), 4.49-5.10 (m, 1H), 4.10-4.48 (m, 4H), 2.80-4.10 (m, 6H), 1.39-1.50 (m, 3H). | 534.96 | 88.8 |
| 191 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide | 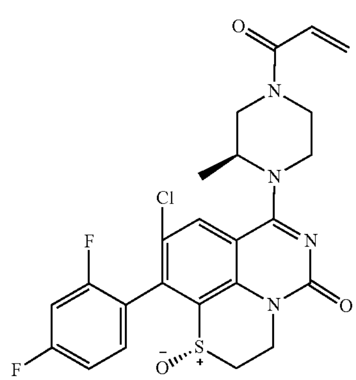 [SMILES: C=CC(=O)N1CCN(c2nc(=O)n3c4c(c(-c5ccc(F)cc5F)c(Cl)cc24)[S@@+]([O-])CC3)[C@@H](C)C1] | ¹H NMR (401 MHz, DMSO) δ: 7.89 (s, 1H), 7.11-7.20 (m, 1H), 7.03-7.10 (m, 2H), 6.49-6.19 (m, 1H), 6.39 (d, J = 16.4 Hz, 1H), 5.80 (d, J = 10.4 Hz, 1H), 4.38-5.20 (m, 3H), 3.30-4.30 (m, 6H), 2.78-3.35 (m, 2H), 1.39-1.42 (m, 3H). | 518.96 | 26.6 |

| Ex. # | Name | Structure | ¹H NMR | MS | % CAF 10 uM @ 60 min |
|---|---|---|---|---|---|
| 192 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide | 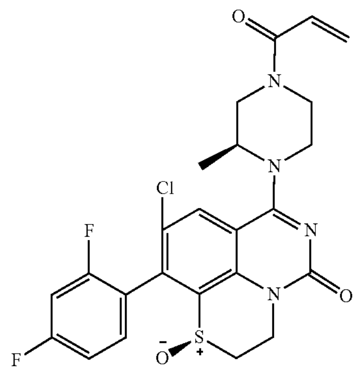 [SMILES: C=CC(=O)N1CCN(c2nc(=O)n3c4c(c(-c5ccc(F)cc5F)c(Cl)cc24)[S@+]([O-])CC3)[C@@H](C)C1] | ¹H NMR (401 MHz, DMSO) δ: 7.90 (s, 1H), 7.47-7.55 (m, 1H), 6.98-7.18 (m, 2H), 6.49-6.19 (m, 1H), 6.39 (d, J = 16.4 Hz, 1H), 5.80 (d, J = 8.8 Hz, 1H), 4.40-5.20 (m, 3H), 3.35-4.35 (m, 6H), 2.78-3.33 (m, 2H), 1.39-1.41 (m, 3H). | 518.96 | 62.4 |
| 193 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 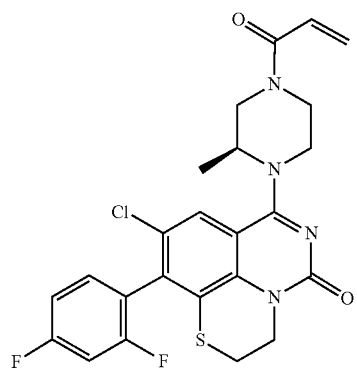 [SMILES: C=CC(=O)N1CCN(c2nc(=O)n3c4c(c(-c5ccc(F)cc5F)c(Cl)cc24)SCC3)[C@@H](C)C1] | ¹H NMR (401 MHz, DMSO) δ: 7.48 (s, 1H), 7.16-7.23 (m, 1H), 6.95-7.08 (m, 2H), 6.48-6.69 (m, 1H), 6.38 (d, J = 19.6 Hz, 1H), 5.78 (d, J = 10.0 Hz, 1H), 4.95-4.45 (m, 3H), 4.34-3.98 (m, 3H), 3.80-3.47 (m, 2H), 3.17-2.91 (m, 3H), 1.39-1.38 (m, 3H). | 502.96 | 97 |

Example 84: 7-(9-acryloyl-3,3-dioxido-3-thia-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one

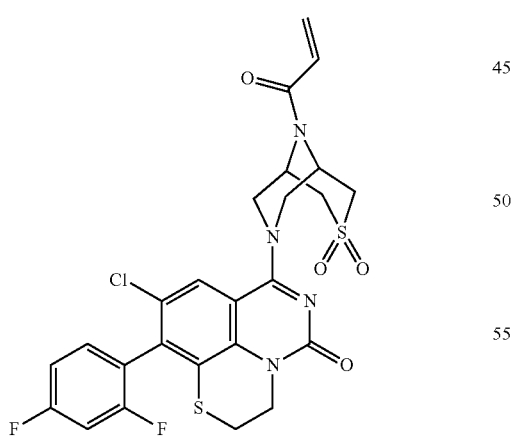

Over a solution of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one (50 mg, 0.095 mmol) in dichloromethane (1 mL), triethylamine (54 mg, 0.57 mmol) and acryloyl chloride (17 mg, 0.19 mmol) were added at 0° C. The reaction mixture was stirred at room temperature for two hours. The solvent was removed in vacuo to obtain a residue that was purified by preparative HPLC to afford the desired product (9.2 mg, 15%) as an off-white solid.

m/z (ESI, +ve)=579.0 (M+H)⁺.

¹H NMR (400 MHz, DMSO) δ 7.95 (s, 1H), 7.52-7.44 (m, 1H), 7.41-7.38 (m, 1H), 7.29-7.25 (m, 1H), 6.45-6.41 (m, 1H), 6.29-6.25 (m, 1H), 6.03 (d, J=12 Hz, 1H), 4.60-4.53 (m, 2H), 4.245-4.23 (m, 1H), 4.03-3.88 (m, 3H), 3.65-3.55 (m, 2H), 3.52-3.47 (m, 1H), 3.23-3.05 (m, 3H), 2.73 (s, 2H)

Step 1: N,N-dibromobenzenesulfonamide

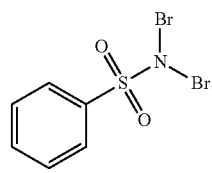 [SMILES: O=S(=O)(c1ccccc1)N(Br)Br]

A solution of benzenesulfonamide (100 g, 0.6362 mol) and KOH (103 g, 1.8357 mol) in water (700 mL) was stirred at room temperature for 30 min. Bromine (91 mL, 1.7766 mol) was added dropwise and the mixture stirred for 16 hours. The reaction was filtered and the solid was washed with water and dried under reduced pressure to afford N,N-dibromobenzenesulfonamide (240 g) as a yellow solid.

Step 2: diethyl 3,3'-((phenylsulfonyl)azanediyl)bis(2-bromopropanoate)

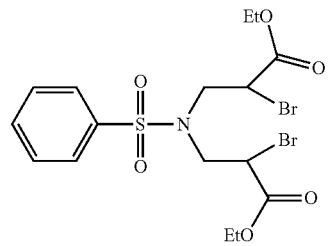 [SMILES: CCOC(=O)C(Br)CN(CC(Br)C(=O)OCC)S(=O)(=O)c1ccccc1]

Ethyl prop-2-enoate (119.2 g, 1.19 mol) was added to a solution of N,N-dibromobenzenesulfonamide (75 g, 0.24 mol) in dichloromethane (500 mL) at room temperature. The mixture was stirred at 45° C. under light for 4 hours. Volatiles were removed under reduced pressure and the crude material purified by silica gel column chromatography (ethyl acetate/hexanes=0-12%) to afford diethyl 3,3'-((phenylsulfonyl)azanediyl)bis(2-bromopropanoate) as a white solid.

m/z (ESI, +ve)=515.9/517.9 (M+H)$^+$.

Step 3: diethyl-1-benzyl-4-(phenylsulfonyl)piperazine-cis-2,6-dicarboxylate

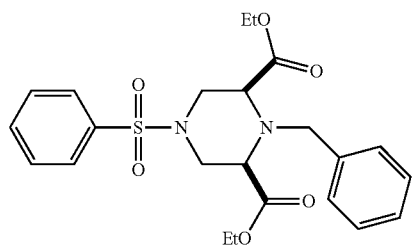 [SMILES: CCOC(=O)[C@H]1CN(S(=O)(=O)c2ccccc2)C[C@@H](C(=O)OCC)N1Cc1ccccc1]

To a solution of diethyl 3,3'-((phenylsulfonyl)azanediyl)bis(2-bromopropanoate) (50 g, 0.0970 mol) in toluene (150 mL) was added phenylmethanamine (52 g, 0.4853 mol). After stirring at 90° C. for 5 h, the mixture was cooled to room temperature and filtered. The filtrate was concentrated to afford a residue that was purified by silica gel chromatography (ethyl acetate/hexanes, 0-20%) to afford the desired product (26 g) as a white solid.

$^1$H NMR (400 MHz, CDCl$_3$) δ 7.78-7.74 (m, 2H), 7.65-7.60 (m, 1H), 7.56-7.52 (m, 2H), 7.30-7.20 (m, 5H), 4.03 (q, J=7.2 Hz, 4H), 3.93 (s, 2H), 3.42-3.38 (m, 2H), 3.36-3.31 (m, 2H), 3.18-3.13 (m, 2H), 1.23 (t, J=7.2 Hz, 6H).

Step 4: Cis-(1-benzyl-4-(phenylsulfonyl)piperazine-2,6-diyl)dimethanol

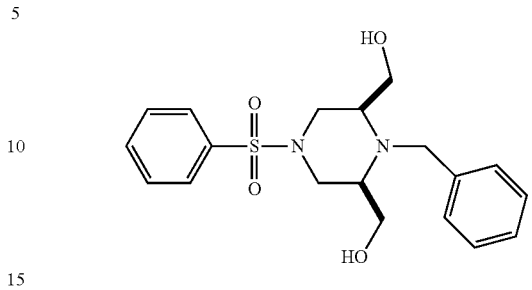

To a solution of diethyl-1-benzyl-4-(phenylsulfonyl)piperazine-cis-2,6-dicarboxylate (20 g, 0.0434 mol) in THF (150 mL) was slowly added lithium aluminum hydride (5.8 g, 0.1528 mol) at 0° C. under nitrogen atmosphere. After stirring at 25° C. for 4 h, the mixture was quenched with water (6 mL) and diluted with Na$_2$CO$_3$ (1 L). The mixture was extracted with ethyl acetate (500 mL×4). The combined organic layer was washed with brine (500 mL), dried over Na$_2$SO$_4$ and concentrated under reduced pressure. The residue was dried by evaporation under reduced pressure to afford 4-(benzenesulfonyl)-1-benzyl-cis-[2,6-(hydroxymethyl)piperazin-2-yl]methanol (32.8 g) as a white solid.

$^1$H NMR (400 MHz, CDCl$_3$) δ 7.78-7.75 (m, 2H), 7.66-7.61 (m, 1H), 7.58-7.54 (m, 2H), 7.35-7.22 (m, 5H), 3.85 (s, 2H), 3.73-3.66 (m, 2H), 3.61-3.55 (m, 2H), 3.28-3.22 (m, 2H), 2.95-2.90 (m, 4H), 2.03 (m, 2H).

Step 5: 1-benzyl-cis-(2,6-bis(chloromethyl))-4-(phenylsulfonyl)piperazine

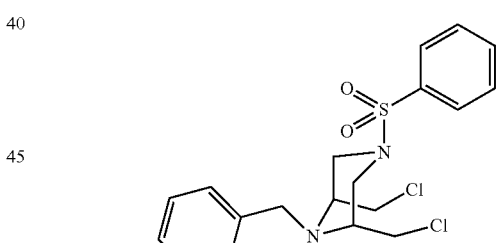

To a solution of Cis-(1-benzyl-4-(phenylsulfonyl)piperazine-2,6-diyl)dimethanol (32.8 g, 0.0871 mol) in DMF (150 mL) was added thionyl chloride (32 mL, 0.4411) dropwise at 0° C. under nitrogen atmosphere. After stirring at room temperature for 4 hours, saturated aqueous sodium carbonate (900 mL) was added at 0° C. The mixture was extracted with ethyl acetate (500 mL×5) and the combined organic layers washed with water (500 mL×5), brine (500 mL), dried over Na$_2$SO$_4$ and concentrated under reduced pressure to afford the desired final product as a white solid.

$^1$H NMR (400 MHz, CDCl$_3$) δ 7.81-7.78 (m, 2H), 7.65-7.62 (m, 1H), 7.59-7.54 (m, 2H), 7.35-7.20 (m, 5H), 3.89 (s, 2H), 3.74-3.70 (m, 2H), 3.58-3.54 (m, 2H), 3.49-3.43 (m, 2H), 3.05-3.01 (m, 2H), 2.67-2.62 (m, 2H).

Step 6: 9-benzyl-7-(phenylsulfonyl)-3-thia-7,9-diazabicyclo[3.3.1]nonane

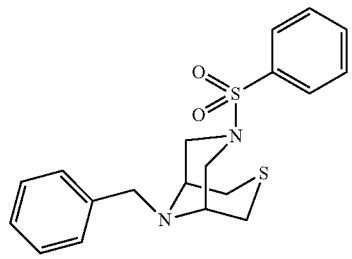 [SMILES: O=S(=O)(c1ccccc1)N1CC2CSCC(C1)N2Cc1ccccc1]

A mixture of 1-benzyl-cis-(2,6-bis(chloromethyl))-4-(phenylsulfonyl)piperazine 0.01 mol) and Na$_2$S (4.7 g, 0.06 mol) in EtOH (30 mL) was stirred at 80° C. for 16 hours. The mixture was cooled to room temperature, concentrated and the resulting residue was taken up in water (100 mL) and extracted with ethyl acetate (50 mL×4). The combined organic layers were washed with brine (50 mL), dried over Na$_2$SO$_4$ and concentrated under reduced pressure. The crude material was purified by silica gel column (ethyl acetate:hexanes=0-20%) to afford 7-(benzenesulfonyl)-9-benzyl-3-thia-7,9-diazabicyclo[3.3.1]nonane (2.1 g) as a yellow solid.

$^1$H NMR (400 MHz, CDCl$_3$) δ7.82-7.79 (m, 2H), 7.62-7.53 (m, 3H), 7.29-7.23 (m, 5H), 3.89 (s, 2H), 3.77-3.72 (m, 2H), 3.44-3.39 (m, 2H), 3.03-2.98 (m, 4H), 2.30-2.26 (m, 2H).

Step 7: tert-butyl-9-benzyl-3-thia-7,9-diazabicyclo[3.3.1]nonane-7-carboxylate

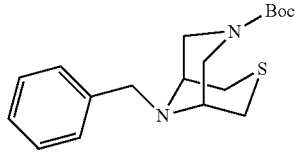 [SMILES: CC(C)(C)OC(=O)N1CC2CSCC(C1)N2Cc1ccccc1]

To a solution of 9-benzyl-7-(phenylsulfonyl)-3-thia-7,9-diazabicyclo[3.3.1]nonane (500 mg, 1.3 mmol) in THF (10 mL) was added KPPh$_2$ (0.5 M, 6.6 mL, 3.3 mmol) dropwise at −78° C. under nitrogen atmosphere. The solution was stirred at −78° C. for 3 hours and quenched with HCl (2 M, 5.2 mL, 10.4 mmol) followed by NaOH (2 M, 10.5 mL, 21 mmol). Boc anhydride (728 mg, 3.34 mmol) was added and the mixture was stirred at room temperature for 16 hours. The reaction was quenched with water (50 mL) and extracted with ethyl acetate (30 mL×3). The combined organic layers were washed with brine (30 mL) and concentrated to get a residue which was purified with preparative thin layer chromatography (ethyl acetate:hexanes=1:4, Rf=0.5) to afford tert-butyl 9-benzyl-3-thia-7,9-diazabicyclo[3.3.1]nonane-7-carboxylate (270 mg) as yellow solid.

$^1$H NMR (400 MHz, CDCl$_3$) δ 7.38-7.25 (m, 5H), 4.23-1.18 (m, 1H), 4.10-4.05 (m, 1H), 3.95 (s, 21), 3.48-3.32 (m, 4H), 2.88-2.83 (m, 2H), 2.31-2.26 (m, 1H), 2.19-2.13 (m, 1H), 1.49 (s, 9H).

Step 8: tert-butyl-9-benzyl-3-thia-7,9-diazabicyclo[3.3.1]nonane-7-carboxylate 3,3-dioxide

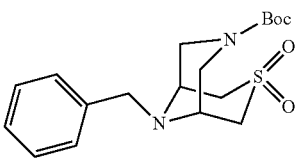 [SMILES: CC(C)(C)OC(=O)N1CC2CS(=O)(=O)CC(C1)N2Cc1ccccc1]

To a solution of tert-butyl-9-benzyl-3-thia-7,9-diazabicyclo[3.3.1]nonane-7-carboxylate (1 g, 3.0 mmol) in dichloromethane (20 ml) was added 3-chloroperoxybenzoic acid (1.29 g, 7.5 mmol) at 0° C. The reaction mixture was stirred at room temperature for 30 minutes and quenched with saturated Na$_2$S$_2$O$_3$ (50 mL) and extracted with dichloromethane (30 mL×3). The organic layers were combined, washed with brine (20 mL), dried over sodium sulphate and concentrated. The resulting residue was purified by silica gel chromatography to afford tert-butyl-9-benzyl-3-thia-7,9-diazabicyclo[3.3.1]nonane-7-carboxylate 3,3-dioxide (0.9 g, 90%) as a light yellow solid.

m/z (ESI, +ve)=367.1 (M+H)$^+$.

Step 9: tert-butyl-3-thia-7,9-diazabicyclo[3.3.1]nonane-7-carboxylate 3,3-dioxide

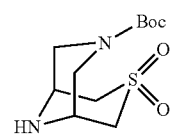

A solution tert-butyl-9-benzyl-3-thia-7,9-diazabicyclo[3.3.1]nonane-7-carboxylate 3,3-dioxide (2.5 g, 0.27 mmol) Pd/Ba$_2$SO$_4$ (7.78 g) and HCl (5 drops) in methanol (30 mL) was hydrogenated at room temperature for 2 hours. The mixture was filtered and concentrated to afford tert-butyl-3-thia-7,9-diazabicyclo[3.3.1]nonane-7-carboxylate 3,3-dioxide (1.3 g, 72%) as a white solid after purification by flash chromatography.

m/z (ESI, +ve)=277.1 (M+H)$^+$.

Step 10: 3-thia-7,9-diazabicyclo[3.3.1]nonane 3,3-dioxide

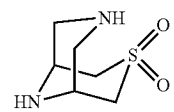

A solution of tert-butyl-3-thia-7,9-diazabicyclo[3.3.1]nonane-7-carboxylate 3,3-dioxide (1.2 g) in dichloromethane/trifluoroacetic acid (5/1, 20 mL) was stirred at room temperature for 4 hours. The solution was concentrated and the resulting residue purified by reversed phase chromatography to afford 3-thia-7,9-diazabicyclo[3.3.1]nonane 3,3-dioxide (620 mg) as a white solid.

m/z (ESI, +ve)=177.1 (M+H)⁺.

Step 11: methyl 2-amino-4-bromobenzoate

A solution of 2-amino-4-bromobenzoic acid (100 g, 0.4628 mol) in thionyl chloride (400 mL) was stirred at 80° C. for 2 hours. The mixture was cooled to room temperature and concentrated under reduced pressure. The residue was dissolved in dichloromethane (500 mL) and cooled down to 0° C. Methanol (200 ml) was added and the mixture stirred at 0° C. for 1 hour. After that time, the reaction was quenched with saturated aqueous NaHCO₃ (400 mL) and extracted with dichloromethane (300 mL×3). The combined organic layers were washed with brine (300 mL), dried over sodium sulphate and concentrated to afford methyl 2-amino-4-bromobenzoate (100 g, 80%) as a yellowish green solid.

m/z (ESI, +ve)=230.0 (M+H)⁺.

Step 12: methyl 2-acetamido-4-bromobenzoate

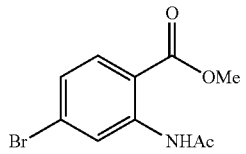

To a solution of methyl 2-amino-4-bromobenzoate (60 g, 0.26 mol) in acetic acid (300 mL) at room temperature, was added acetic anhydride (26.6 g, 0.2608 mol). The mixture was stirred at 100° C. for 2 hours and cooled down to room temperature. Water was added (400 mL) and the resulting suspension was filtered to afford methyl 2-acetamido-4-bromobenzoate (58 g) as a yellow solid.

m/z (ESI, +ve)=272.0 (M+H)⁺.

¹H NMR (400 MHz, DMSO) δ 10.63 (s, 1H), 8.53 (s, 1H), 7.83 (d, J=8.0 Hz, 1H), 7.39 (dd, J=8.0, 2.0, 1H), 3.86 (s, 3H), 2.15 (s, 3H).

Step 13: methyl 2-acetamido-4-bromo-5-chlorobenzoate

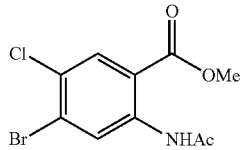

To a solution of methyl 2-acetamido-4-bromobenzoate (58 g, 0.21 mol) in DMF (250 mL), was added N-chlorosuccinimide (28.48 g, 0.21 mol) at room temperature. The mixture was stirred at 85° C. for 16 hours, diluted with water (250 mL) and extracted with ethyl acetate (250 mL×3). The combined organic layers were washed with brine (200 mL×4), dried over Na₂SO₄, filtered and concentrated to give a yellow oil which was purified by flash chromatography with ethyl acetate in hexanes (50-100%). The resulting material was dissolved in DMF (250 mL) and N-chlorosuccinimide (14.2 g, 0.1067 mol) was added. The mixture was stirred at 85° C. for 3 hours and quenched with water (250 mL). The solution was extracted with ethyl acetate (250 mL×3) and the combined organic layers were washed with brine (200 mL×4), dried over Na₂SO₄, filtered and concentrated to afford a residue that was purified by silica gel chromatography (ethyl acetate:hexanes=0-55%) to afford methyl 2-acetamido-4-bromo-5-chlorobenzoate (47 g, 72%) as a yellow solid.

m/z (ESI, +ve)=305.9 (M+H)⁺.

Step 14: methyl 2-amino-4-bromo-5-chlorobenzoate

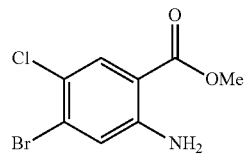

Methyl 4-bromo-5-chloro-2-acetamidobenzoate (47 g, 0.15 mol) was dissolved in a methanolic solution of HCl (5M, 500 mL) and the mixture stirred at 80° C. for 2 hours. The reaction was diluted with water (500 mL) and filtered to afford methyl 2-amino-4-bromo-5-chlorobenzoate (crude, 39 g, 90%) as a white solid.

m/z (ESI, +ve)=263.9 (M+H)⁺.

Step 15: methyl 5-amino-2-chloro-2',4'-difluoro-[1,1'-biphenyl]-4-carboxylate

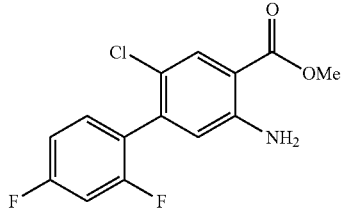

To a mixture of methyl 2-amino-4-bromo-5-chlorobenzoate (39 g, 0.15 mol) in dioxane/H₂O (240 mL) were added (2,4-difluorophenyl)boronic acid (23.69 g, 0.15 mol), 1,1'-bis(diphenylphosphino)ferrocene palladium dichloride (21.95 g, 0.03 mol) and Cs₂CO₃ (146.62 g, 0.45 mol). The mixture was stirred at 100° C. for 10 hours, quenched with H₂O (200 mL) and extracted with ethyl acetate (100 mL×3). The combined organic layers were washed with brine (200 mL), dried over sodium sulphate and concentrated to afford a crude material that was purified by silica gel chromatography to afford methyl 5-amino-2-chloro-2',4'-difluoro-[1,1'-biphenyl]-4-carboxylate (27.1 g, 61%) as a yellow solid.

m/z (ESI, +ve)=298.1 (M+H)⁺.

¹H NMR (400 MHz, DMSO) δ 7.78 (s, 1H), 7.47-7.36 (m, 2H), 7.23-7.18 (m, 1H), 6.85 (s, 2H), 6.82 (s, 1H), 3.83 (s, 3H).

Step 16: methyl 3-amino-6-chloro-2',4'-difluoro-2-iodo-[1,1'-biphenyl]-4-carboxylate


To a solution of methyl 5-amino-2-chloro-2',4'-difluoro-[1,1'-biphenyl]-4-carboxylate (27.1 g, 90.9 mmol) in AcOH (240 mL) was added N-iodosuccinamide (22.4 g, 99.5 mmol). The mixture was stirred at room temperature for 2 hours. The volatiles were removed under reduced pressure and the resulting residue was dissolved in ethyl acetate (30 mL) and washed with saturated aqueous $Na_2S_2O_3$ (20 mL×3), brine (20 mL×3), dried with $Na_2SO_4$ and filtered. The filtrate was concentrated and the crude material triturated in ethyl acetate (15 mL). The solid was collected by filtration and dried to afford methyl 3-amino-6-chloro-2',4'-difluoro-2-iodo-[1,1'-biphenyl]-4-carboxylate (22.1 g, 57%) as an off-white solid.

$^1$H NMR (400 MHz, DMSO) δ 7.92 (s, 1H), 7.46-7.40 (m, 1H), 7.34-7.22 (m, 2H), 6.92 (s, 2H), 3.87 (s, 3H).

Step 17: 3-amino-6-chloro-2',4'-difluoro-2-iodo-[1,1'-biphenyl]-4-carboxylic acid

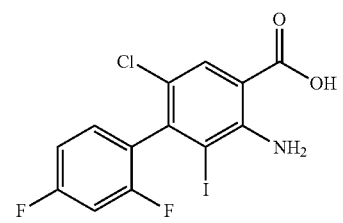 [SMILES: Nc1c(C(=O)O)cc(Cl)c(-c2ccc(F)cc2F)c1I]

To a solution of methyl 3-amino-6-chloro-2',4'-difluoro-2-iodo-[1,1'-biphenyl]-4-carboxylate (22.1 g, 52.1 mmol) in THF/methanol/water (75/75/35 mL) was added NaOH (21 g, 0.525 mol). The mixture was stirred at room temperature for 16 hours. The organic solvents were removed and the residue was acidified to pH=4-5 by addition of 5 M HCl and extracted with ethyl acetate (300 mL×3). The combined organic layers were washed with brine (200 mL), dried over $Na_2SO_4$ and concentrated to afford 3-amino-6-chloro-2',4'-difluoro-2-iodo-[1,1'-biphenyl]-4-carboxylic acid (20 g, 99%) as a yellow solid.

$^1$H NMR (400 MHz, DMSO) δ 7.92 (s, 1H), 7.43-7.19 (m, 5H).

Step 18: 6-chloro-7-(2,4-difluorophenyl)-8-iodoquinazoline-2,4(1H,3H)-dione

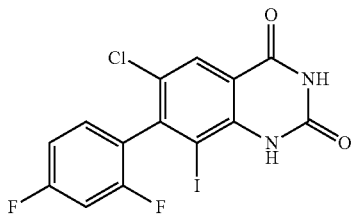 [SMILES: O=c1[nH]c(=O)c2cc(Cl)c(-c3ccc(F)cc3F)c(I)c2[nH]1]

A mixture of 3-amino-6-chloro-2',4'-difluoro-2-iodo-[1,1'-biphenyl]-4-carboxylic acid (20 g, 48.8 mmol) and urea (350 g, 5.8 mol) was stirred at 200° C. for 2 hours. The solid was taken up in ethyl acetate (4×500 mL) and washed with water (500 mL) and brine (300 mL). The organic layer was dried over $Na_2SO_4$, concentrated and the residue purified by silica gel chromatography (dichloromethane:methanol=9:1) to afford 6-chloro-7-(2,4-difluorophenyl)-8-iodoquinazoline-2,4(1H,3H)-dione (14 g, 66%) as a white solid.

$^1$H NMR (400 MHz, DMSO) δ 11.77 (s, 1H), 9.60 (s, 1H), 8.04 (s, 1H), 7.51-7.45 (m, 1H), 7.32-7.22 (m, 2H), 6.79 (s, 2H).

Step 19: 6-chloro-7-(2,4-difluorophenyl)-8-((2-hydroxyethyl)thio)quinazoline-2,4(1H,3H)-dione

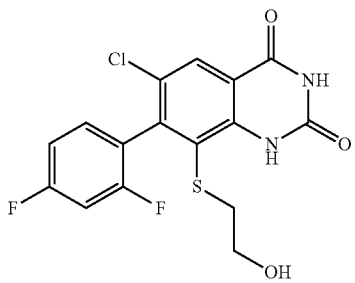

To a mixture of 6-chloro-7-(2,4-difluorophenyl)-8-iodoquinazoline-2,4(1H,3H)-dione (5 g, 11.5 mmol), CuI (437 mg, 2.3 mmol) and $K_2CO_3$ (4.8 g, 34.8 mmol) in isopropyl alcohol:ethylene glycol (100 mL:50 mL) was added 2-mercaptoethan-1-ol (3 mL, 38.5 mmol) at room temperature. The mixture was stirred at 90° C. for 16 hours. The reaction mixture was concentrated and the residue purified by reversed phase chromatography to afford 6-chloro-7-(2,4-difluorophenyl)-8-((2-hydroxyethyl)thio)quinazoline-2,4 (1H,3H)-dione (3.2 g, 72%) as a white solid.

$^1$H NMR (400 MHz, DMSO) δ 11.73 (s, 1H), 10.33 (s, 1H), 8.06 (s, 1H), 7.45-7.38 (m, 2H), 7.28-7.22 (m, 1H), 5.37 (t, J=4.8 Hz, 1H), 3.38-3.36 (m, 2H), 2.65-2.61 (m, 2H).

Step 20: 9-chloro-10-(2,4-difluorophenyl)-2,3-dihydro-5H-[1,4]thiazino[2,3,4-ij]quinazoline-5,7(6H)-dione

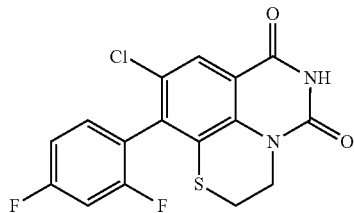 [SMILES: O=c1[nH]c(=O)n2c3c(c(-c4ccc(F)cc4F)c(Cl)cc13)SCC2]

To a solution of triphenylphosphine (4.6 g, 17.7 mmol) in THF (50 mL) was added DIAD (3.6 g, 17.7 mmol) at 0° C. under nitrogen atmosphere and the mixture stirred at 0° C. for 20 minutes. 6-chloro-7-(2,4-difluorophenyl)-8-((2-hydroxyethyl)thio)quinazoline-2,4(1H,3H)-dione (3.4 g, 8.83 mmol) was added and the reaction mixture was stirred at room temperature for 16 hours. The mixture was concentrated and the crude material purified by reversed phase chromatography to afford 9-chloro-10-(2,4-difluorophenyl)-2,3-dihydro-5H-[1,4]thiazino[2,3,4-ij]quinazoline-5,7(6H)-dione (1.6 g, 49%) as a white solid.

m/z (ESI, +ve)=367.0 (M+H)$^+$.

$^1$H NMR (400 MHz, DMSO-d$_6$) δ 11.90 (s, 1H), 7.86 (s, 1H), 7.51-7.46 (m, 1H), 7.41-7.35 (m, 1H), 7.30-7.25 (m, 1H), 4.39-4.33 (m, 1H), 4.10-4.03 (m, 1H), 3.20-3.10 (m, 2H).

Step 21: 9-chloro-10-(2,4-difluorophenyl)-7-(3,3-dioxido-3-thia-7,9-diazabicyclo [3.3.1]nonan-7-yl)-2,3-dihydro-5H-[1,4]thiazino[2,3,4-ij]quinazolin-5-one

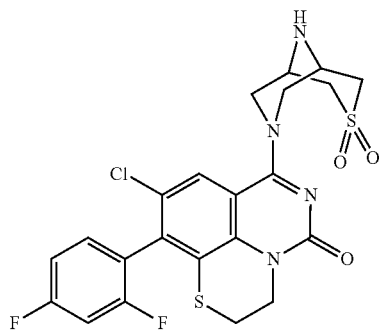 [SMILES: O=c1nc(N2CC3CS(=O)(=O)CC(C2)N3)c2cc(Cl)c(-c3ccc(F)cc3F)c3c2n1CCS3]

To a solution of 9-chloro-10-(2,4-difluorophenyl)-2,3-dihydro-5H-[1,4]thiazino[2,3,4-ij]quinazoline-5,7(6H)-dione (300 mg, 0.82 mmol) in toluene (5 mL) were added N,N-diisopropylethylamine (634 mg, 4.9 mmol) and POCl$_3$ (5 mL). The reaction mixture was stirred at 120° C. for 1.5 hours. The reaction mixture was concentrated and the residue redissolved in dichloroethane (5 mL) and added slowly over a solution of 3-thia-7,9-diazabicyclo[3.3.1]nonane 3,3-dioxide (577 mg, 3.27 mmol) and N,N-diisopropylethylamine (634 mg, 4.9 mmol) in dichloroethane (5 mL) at 0° C. The reaction mixture was stirred at room temperature for 1 hour, concentrated and the crude residue purified by preparative thin layer chromatography to afford 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one (150 mg, 34%) as a yellow solid.

m/z (ESI, +ve)=525.0 (M+H)$^+$.

$^1$H NMR (400 MHz, DMSO) δ 8.76-8.71 (m, 1H), 7.94-7.89 (m, 1H), 7.50-7.45 (m, 1H), 7.41-7.38 (m, 1H), 7.29-7.25 (m, 1H), 4.53-4.40 (m, 1H), 4.26-4.21 (m, 1H), 4.18-4.05 (m, 1H), 4.00-3.90 (m, 2H), 3.62-3.48 (m, 5H), 3.24-3.08 (m, 4H), 3.00-2.85 (m, 1H).

Example 100: 7-(4-acryloyl-6,6-dioxidohexahydrothieno[3,4-b]pyrazin-1(2H)-yl)-10-(2,4-difluorophenyl)-9-(trifluoromethyl)-2,3-dihydro-5H-[1,4]thiazino[2,3,4-ij]quinazolin-5-one

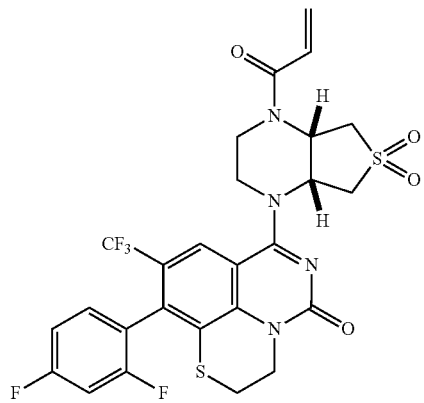

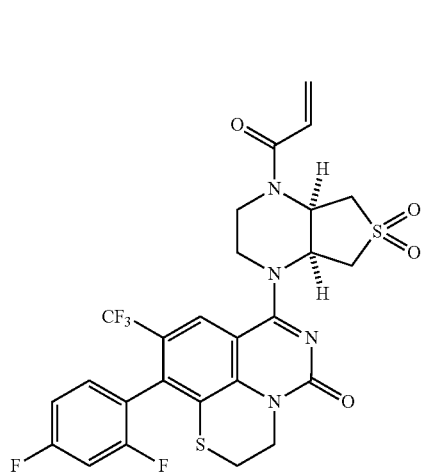

The title compound was prepared analogously to Example 84 where 10-(2,4-difluorophenyl)-7-(6,6-dioxidohexahydrothieno[3,4-b]pyrazin-1(2H)-yl)-9-(trifluoromethyl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one.

m/z (ESI, +ve)=613.0 (M+H)$^+$.

Step 1: methyl 3-amino-2',4'-difluoro-[1,1'-biphenyl]-4-carboxylate

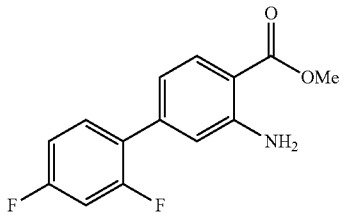 [SMILES: COC(=O)c1ccc(-c2ccc(F)cc2F)cc1N]

A solution of methyl 2-amino-4-bromobenzoate (11 g, 0.0478 mol) (2,4-difluorophenyl)boronic acid (8.3 g, 0.052 mol),1,1'-bis(diphenylphosphino)ferrocene palladium dichloride (7.0 g, 0.0095 mol) and $Cs_2CO_3$ (46.7 g, 0.1434 mol) in dioxane:$H_2O$ (4:1, 220 mL) was stirred at 100° C. for 16 hours. The reaction was cooled to room temperature, diluted with water (100 mL) and extracted with ethyl acetate (3×100 mL). The organic layers were combined and washed with brine (200 mL), dried over $Na_2SO_4$ and concentrated. The residue was purified by silica gel chromatography to afford methyl 3-amino-2',4'-difluoro-[1,1'-biphenyl]-4-carboxylate (11 g, 86%) as alight yellow solid.

m/z (ESI, +ve)=264.1 (M+H)+.

Step 2: methyl 5-amino-2',4'-difluoro-2-iodo-[1,1'-biphenyl]-4-carboxylate

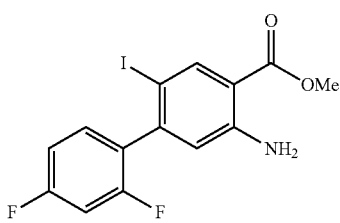

A solution of methyl 3-amino-2',4'-difluoro-[1,1'-biphenyl]-4-carboxylate (11.7 g, 0.044 mol) and N-iodosuccinimide (10 g, 0.044 mmol) in DMF (100 mL) was stirred at room temperature for 16 hours. The solution was diluted with water (500 mL) and extracted with ethyl acetate (3×100 mL). The organic layer was washed with brine (300 mL), dried over $Na_2SO_4$ and concentrated to yield a residue that was purified by silica gel chromatography affording methyl 5-amino-2',4'-difluoro-2-iodo-[1,1'-biphenyl]-4-carboxylate (15.4 g, 89%) as a yellow solid.

m/z (ESI, +ve)=390.0 (M+H)+.

Step 3: methyl 5-acetamido-2',4'-difluoro-2-iodo-[1,1'-biphenyl]-4-carboxylate

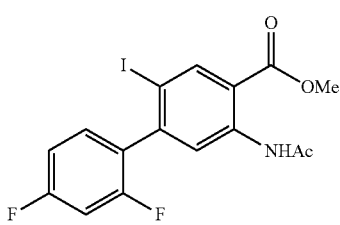 [SMILES: COC(=O)c1cc(I)c(-c2ccc(F)cc2F)cc1NC(C)=O]

To a solution of methyl 2-amino-4-(2,4-difluorophenyl)-5-iodobenzoate (22 g, 0.0565 mol) in AcOH (40 mL) was added acetic anhydride (5.77 g, 0.0565 mol), the mixture was stirred at 100° C. for 2 h. The mixture was quenched with water (1000 mL) and filtered, the filter cake was collected and dried under reduced pressure to afford methyl 5-acetamido-2',4'-difluoro-2-iodo-[1,1'-biphenyl]-4-carboxylate (5.26 g, 70%) as a white solid.

$^1$H NMR (400 MHz, DMSO-d6) δ10.54 (s, 1H), 8.36 (s, 1H), 8.19 (s, 1H), 7.46-7.41 (m, 2H), 7.25-7.20 (m, 1H), 3.93 (s, 3H), 2.18 (s, 3H).

Step 4: methyl 5-acetamido-2',4'-difluoro-2-(trifluoromethyl)-[1,1'-biphenyl]-4-carboxylate

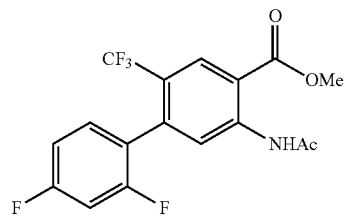 [SMILES: COC(=O)c1cc(C(F)(F)F)c(-c2ccc(F)cc2F)cc1NC(C)=O]

A solution of methyl 4-(2,4-difluorophenyl)-2-acetamido-5-iodobenzoate (8.7 mg, 20.2 mmol), copper(I) iodide (5.4 g, 28.4 mmol) and tetrabutylammonium iodide (3.7 g, 10.0 mmol) in HMPA (60 mL) was stirred at 90° C. for 20 minutes. Methyl 2,2-difluoro-2-(fluorosulfonyl)acetate (29 g, 151.0 mmol) was added and the resulting mixture stirred at 90° C. for 16 hours. The solution was cooled to room temperature, diluted with water (150 mL), extracted with ethyl acetate (3×150 mL) and the organic layers washed with brine (100 mL), dried over $Na_2SO_4$ and concentrated to afford a residue which was purified by silica gel chromatography (ethyl acetate:hexanes=0-25%). 5-acetamido-2',4'-difluoro-2-(trifluoromethyl)-[1,1'-biphenyl]-4-carboxylate was isolated as a yellow solid in 70% yield.

$^1$H NMR (400 MHz, DMSO-d6) δ10.81 (s, 1H), 8.33 (s, 1H), 8.26 (s, 1H), 7.46-7.41 (m, 2H), 7.25-7.20 (m, 1H), 3.93 (s, 3H), 2.18 (s, 3H).

Step 5: methyl 5-amino-2',4'-difluoro-2-(trifluoromethyl)-[1,1'-biphenyl]-4-carboxylate

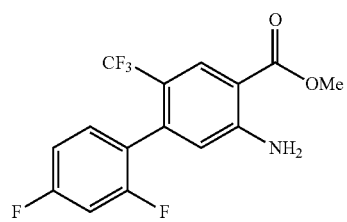 [SMILES: COC(=O)c1cc(C(F)(F)F)c(-c2ccc(F)cc2F)cc1N]

A solution of methyl 5-acetamido-2',4'-difluoro-2-(trifluoromethyl)-[1,1'-biphenyl]-4-carboxylate (5.26 g, 14.1 mmol) in a methanolic solution of HCl (100 mL) was stirred at 80° C. for 2 hours and concentrated to afford a residue that was dissolved in ethyl acetate (500 mL) and washed with water (2×100 mL). The organic layer was washed with brine (150 mL), dried over $Na_2SO_4$ and concentrated to afford methyl 5-amino-2',4'-difluoro-2-(trifluoromethyl)-[1,1'-biphenyl]-4-carboxylate (5.2 g) as brown oil.

m/z (ESI, +ve)=332.0 (M+H)$^+$.

Step 6: methyl 3-amino-2',4'-difluoro-2-iodo-6-(trifluoromethyl)-[1,1'-biphenyl]-4-carboxylate

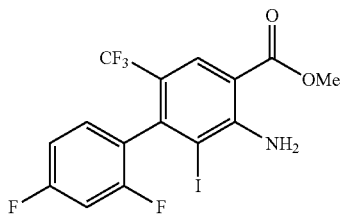

To a solution of methyl 5-amino-2',4'-difluoro-2-(trifluoromethyl)-[1,1'-biphenyl]-4-carboxylate (5.3 g, 16 mmol) in AcOH (35 mL) was added N-iodosuccinamide (3.4 g, 15 mmol) and stirred at 25° C. for 16 h. The solution was concentrated, the residue dissolved in ethyl acetate (400 mL) and washed with Na$_2$S$_2$O$_3$/NaHCO$_3$ (3×100 mL), brine (100 mL), dried over Na$_2$SO$_4$ and concentrated to afford methyl 3-amino-2',4'-difluoro-2-iodo-6-(trifluoromethyl)-[1,1'-biphenyl]-4-carboxylate (5 g) as a yellow solid.

m/z (ESI, +ve)=457.9 (M+H)$^+$.

Step 7: 3-amino-2',4'-difluoro-2-iodo-6-(trifluoromethyl)-[1,1'-biphenyl]-4-carboxylic acid

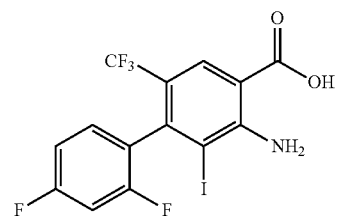

To a mixture of methyl 3-amino-2',4'-difluoro-2-iodo-6-(trifluoromethyl)-[1,1'-biphenyl]-4-carboxylate (10 g, 21.8 mmol) in THF (24 mL), methanol (16 mL) and water (16 mL) was added NaOH (8.72 g, 218 mmol). The reaction mixture was stirred at room temperature for 2 hours. The mixture was concentrated under reduced pressure to afford a residue. 1 M HCl was added over this crude material and the pH adjusted to 5-6, extracted with EtOAc (20 mL×3). The organic phases were combined, washed with brine (10 mL), dried over Na$_2$SO$_4$ and filtered. The filtrate was concentrated under reduced pressure to afford the 3-amino-2',4'-difluoro-2-iodo-6-(trifluoromethyl)-[1,1'-biphenyl]-4-carboxylic acid (9 g, 89%) as a pink solid.

m/z (ESI, +ve)=442.94 (M+H)$^+$.

Step 8: 7-(2,4-difluorophenyl)-8-iodo-6-(trifluoromethyl)quinazoline-2,4(1H,3H)-dione

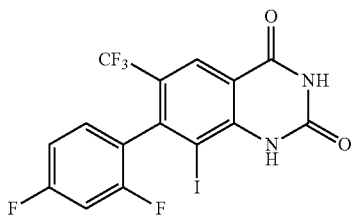 [SMILES: O=c1[nH]c(=O)c2cc(C(F)(F)F)c(-c3ccc(F)cc3F)c(I)c2[nH]1]

3-amino-2',4'-difluoro-2-iodo-6-(trifluoromethyl)-[1,1'-biphenyl]-4-carboxylic acid (13 g, 29.34 mmol) was added to urea (105.64 g, 1760.4 mmol). The reaction mixture was stirred at 100° C. for 2 h. The mixture was cooled to 100° C., water (500 mL) was added and stirred for 30 min, filtered and the filter cake was washed with EtOAc (1400 mL). The filtrate was collected and concentrated under reduced pressure to afford a solid that was washed with methanol (100 mL) to afford 7-(2,4-difluorophenyl)-8-iodo-6-(trifluoromethyl)quinazoline-2,4(1H,3H)-dione (5.8 g, 42%) as a yellow solid.

m/z (ESI, +ve)=467.94 (M+H)$^+$.

Step 9: 7-(2,4-difluorophenyl)-8-((2-hydroxyethyl)thio)-6-(trifluoromethyl)quinazoline-2,4(1H,3H)-dione

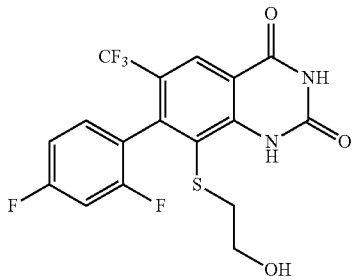 [SMILES: O=c1[nH]c(=O)c2cc(C(F)(F)F)c(-c3ccc(F)cc3F)c(SCCO)c2[nH]1]

To a solution of 7-(2,4-difluorophenyl)-8-iodo-6-(trifluoromethyl)quinazoline-2,4(1H,3H)-dione (5.8 g, 0.0124 mol), Cuprous iodide (470 mg, 0.0024 mol) and Potassium carbonate (5.14 g, 00.0372 mol) in isopropyl alcohol (30 ml) and ethylene glycol (60 ml) was added 2-mercaptoethan-1-ol (2.91 g, 0.0372 mol). The reaction mixture was stirred at 85° C. for 36 hours. The mixture was concentrated under reduced pressure and the crude material purified by reverse column chromatography (phase A: water (0.1% TFA), phase B: CAN, 0~41%) to afford 7-(2,4-difluorophenyl)-8-((2-hydroxyethyl)thio)-6-(trifluoromethyl)quinazoline-2,4(1H,3H)-dione (2.1 g, 39%) as a white solid.

m/z (ESI, +ve)=418.04 (M+H)$^+$.

Step 10: 10-(2,4-difluorophenyl)-9-(trifluoromethyl)-2,3-dihydro-5H-[1,4]thiazino[2,3,4-ij]quinazoline-5,7(6H)-dione

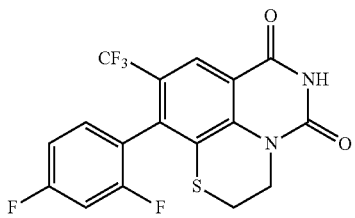

To a solution of Triphenylphosphine (1.69 g, 6.4 mmol) in THF (10 ml) cooled to 0° C. was added N,N-Diisopropylethylamine (1.30 g, 6.4 mmol) and stirred for 30 minutes. 7-(2,4-difluorophenyl)-8-((2-hydroxyethyl)thio)-6-(trifluoromethyl)quinazoline-2,4(1H,3H)-dione (1.8 g, 6.4 mmol) was added and stirred at 0° C. for 1 hour. The mixture was concentrated under reduced pressure and the residue purified by reverse column chromatography (phase A: water (0.1% TFA), phase B: ACN; 0~50%) to afford 10-(2,4-difluorophenyl)-9-(trifluoromethyl)-2,3-dihydro-5H-[1,4]thiazino[2,3,4-ij]quinazoline-5,7(6H)-dione (1.4 g, 77%) as a white solid.

m/z (ESI, +ve)=400.03 (M+H)$^+$.

$^1$H NMR (400 MHz, DMSO-d6) δ12.03 (s, 1H), 8.10 (s, 1H), 7.52-7.45 (m, 1H), 7.38-7.32 (m, 1H), 7.29-7.18 (m, 1H), 4.34-4.32 (m, 1H), 4.16-4.07 (m, 1H), 3.23-3.10 (m, 2H).

Step 11: diethyl pyrazine-2,3-dicarboxylate

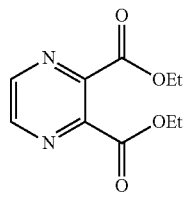 [SMILES: CCOC(=O)c1nccnc1C(=O)OCC]

To a solution of pyrazine-2,3-dicarboxylic acid (15 g, 0.03 mol) in EtOH (100 mL) was added thionyl chloride (10 mL) at 0° C. The mixture was stirred at 80° C. for 2 h. The solvent was removed to afford a residue that was purified by silica gel chromatography to afford diethyl pyrazine-2,3-dicarboxylate (18.5 g, 92%) as a light-yellow oil.

m/z (ESI, +ve)=225.1 (M+H)$^+$.

$^1$H NMR (400 MHz, DMSO) δ 8.96 (s, 2H), 4.40 (d, J=8.0 Hz, 4H), 1.33 (t, J=8.0 Hz, 6H).

Step 12: syn-(diethyl-piperazine-2,3-dicarboxylate)

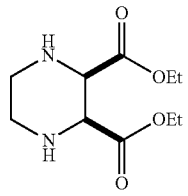 [SMILES: CCOC(=O)[C@H]1NCCN[C@H]1C(=O)OCC]

A mixture of diethyl pyrazine-2,3-dicarboxylate (13.8 g, 0.062 mol) and 10% palladium on carbon (2.4 g) in EtOH (50 ml) was stirred under hydrogen at 50 psi for 20 h. The suspension was filtered through a pad of celite and the filter cake was washed with EtOH. The filtrate was concentrated under reduced pressure to afford diethyl (2S,3R)-piperazine-2,3-dicarboxylate (13.8 g, 97%) as a brown oil.

m/z (ESI, +ve)=231.2 (M+H)$^+$.

Step 13: diethyl-1,4-dibenzylpiperazine-cis-2,3-dicarboxylate

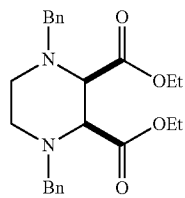 [SMILES: CCOC(=O)[C@@H]1[C@H](C(=O)OCC)N(Cc2ccccc2)CCN1Cc1ccccc1]

To a solution of cis-(diethyl-piperazine-2,3-dicarboxylate) (13.8 g, 0.06 mol) in ACN (60 mL) were added (bromomethyl)benzene (20.5 g, 0.12 mol) and potassium carbonate (24.9 g, 0.18 mol). The mixture was stirred at room temperature for 16 h. The solvent was removed, the residue was suspended in H$_2$O (100 mL) and extracted with ethyl acetate (50 mL×3). The combined organic layers were washed with brine (50 mL), dried over sodium sulphate and concentrated in vacuo to afford a residue that was purified by silica gel chromatography to afford the desired product (14.8 g, 56%) as a light yellow oil.

m/z (ESI, +ve)=411.2 (M+H)$^+$.

$^1$H NMR (400 MHz, DMSO) δ 7.34-7.23 (m, 10H), 4.21-4.00 (m, 4H), 3.83-3.78 (m, 2H), 3.49 (s, 2H), 3.44-3.41 (m, 2H), 3.00-2.98 (m, 2H), 2.27-2.23 (m, 2H), 1.19 (t, J=8.0 Hz, 6H).

Step 14: (1,4-dibenzylpiperazine-cis-2,3-diyl)dimethanol

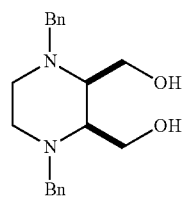 [SMILES: OC[C@@H]1[C@H](CO)N(Cc2ccccc2)CCN1Cc1ccccc1]

To a solution of diethyl-1,4-dibenzylpiperazine-cis-2,3-dicarboxylate (14.8 g, 0.036 mol) in THF (100 mL) was added LiAlH$_4$ (2.73 g, 0.072 mmol) at 0° C. The mixture was stirred at room temperature for 5 h and then quenched with 10% NaOH and extracted with ethyl acetate (30 mL×3). The combined organic layers were washed with brine (50 mL), dried over sodium sulphate and concentrated under reduced pressure to afford (1,4-dibenzylpiperazine-cis-2,3-diyl)dimethanol (11.5 g, 97%) as a yellow solid.

m/z (ESI, +ve)=327.2 (M+H)$^+$.

$^1$H NMR (400 MHz, DMSO) δ 7.32-7.26 (m, 8H), 7.31-7.19 (m, 2H), 4.69 (t, J=4.0 Hz, 2H), 3.96-3.92 (m,

2H), 3.81-3.76 (m, 2H), 3.66-3.63 (m, 2H), 3.44-3.41 (m, 2H), 2.74-2.73 (m, 2H), 2.55-2.51 (m, 2H), 2.23-2.18 (m, 2H).

Step 15: 1,4-dibenzylpiperazine-cis-2,3-diyl-bis(methylene) dimethanesulfonate

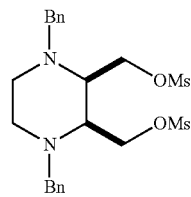 [SMILES: CS(=O)(=O)OC[C@@H]1[C@H](COS(C)(=O)=O)N(Cc2ccccc2)CCN1Cc1ccccc1]

To a solution of (1,4-dibenzylpiperazine-cis-2,3-diyl)dimethanol (3.26 g, 10 mmol) in dichloromethane (30 mL) at 0° C. was added Et$_3$N (3.03 g, 30 mmol), followed by MsCl (2.85 g, 25 mmol). The reaction mixture was stirred at 0° C. for 2 hours. Upon completion, the mixture was washed with brine (20 mL) three times. The organic layers were dried over anhydrous Na$_2$SO$_4$ and concentrated under reduced pressure to afford 1,4-dibenzylpiperazine-cis-2,3-diyl-bis(methylene) dimethanesulfonate (3.6 g, 75%) which was used directly in the next step.

Step 16: 1,4-dibenzyl-cis-octahydrothieno[3,4-b]pyrazine

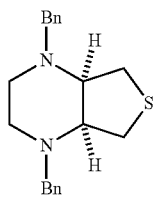 [SMILES: c1ccc(CN2CCN(Cc3ccccc3)[C@H]3CSC[C@H]32)cc1]

To a solution of 1,4-dibenzylpiperazine-cis-2,3-diyl-bis(methylene) dimethanesulfonate (3.6 g, 7.5 mmol) in EtOH (30 mL) was added Na$_2$S (2.9 g, 37.5 mmol). The mixture was stirred at 80° C. for 16 hours, cooled down to room temperature and concentrated. The residue was diluted with water (30 mL) and extracted with EtOAc (30 mL×3). The combined organic layers were dried over anhydrous Na$_2$SO$_4$ and concentrated to afford a residue that was purified by column chromatrography yielding the desired product as light yellow oil (1.8 g, 75%).

m/z (ESI, +ve)=325.0 (M+H)$^+$.

Step 17: cis-octahydrothieno[3,4-b]pyrazine

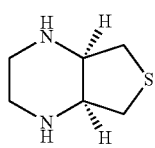

To a solution of 1,4-dibenzyl-cis-octahydrothieno[3,4-b]pyrazine (1 g, 3.1 mmol) in dichloroethane (10 mL) was added 1-chloroethyl chloroformate (4.43 g, 31 mmol). The reaction mixture was stirred at 80° C. for 16 hours, cooled down to room temperature and concentrated. The residue was dissolved in methanol (10 ml) and stirred at 80° C. for 4 hours. The resulting suspension was filtered and the filter cake was washed with methanol and dried to afford the desired product (0.44 g, 92%) as a white solid.

m/z (ESI, +ve)=145.2 (M+H)$^+$.

Step 18: dibenzyl-cis-hexahydrothieno[3,4-b]pyrazine-1,4-dicarboxylate

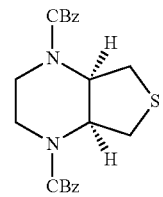

To a solution of cis-octahydrothieno[3,4-b]pyrazine (440 mg, 3.05 mmol) in dioxane/water (20 mL) at 0° C., benzyl chloroformate (1.1 g, 6.71 mmol) and NaHCO$_3$ (366 mg, 9.15 mmol) were added. The reaction mixture was stirred at room temperature for 16 hours. The solvent was removed, H$_2$O (20 mL) was added and the mixture extracted with ethyl acetate (20 mL×3). The organic layers were combined, washed with brine (50 mL), dried over sodium sulphate and concentrated in vacuo to afford a residue that was purified by silica gel chromatography to afford dibenzyl-cis-hexahydrothieno[3,4-b]pyrazine-1,4-dicarboxylate (870 mg, 69%) as colorless oil.

m/z (ESI, +ve)=413.2 (M+H)$^+$.

Step 19: dibenzyl-cis-hexahydrothieno[3,4-b]pyrazine-1,4-dicarboxylate 6,6-dioxide

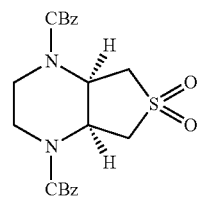

To a solution of dibenzyl-cis-hexahydrothieno[3,4-b]pyrazine-1,4-dicarboxylate (840 mg, 2.04 mmol) in dichloromethane (10 mL) at 0° C., was added 3-chloroperoxybenzoic acid (880 mg, 5.1 mmol).and the reaction mixture was stirred at room temperature for 4 hours. The reaction was quenched with H$_2$O (20 mL) and extracted with dichloromethane (10 mL×3). The combined organic layers were washed with brine (20 mL), dried over sodium sulphate and concentrated to afford a residue that was purified by silica gel chromatography to afford dibenzyl-cis-hexahydrothieno[3,4-b]pyrazine-1,4-dicarboxylate 6,6-dioxide (920 mg, 91%) as a white solid.

m/z (ESI, +ve)=467.1 (M+Na)$^+$.

639

Step 20: cis-octahydrothieno[3,4-b]pyrazine 6,6-dioxide

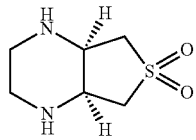

To a solution of dibenzyl-cis-hexahydrothieno[3,4-b]pyrazine-1,4-dicarboxylate 6,6-dioxide (760 mg, 1.71 mmol) in acetic acid (20 ml) was added bromhidric acid (6 ml). The reaction mixture was stirred at 50° C. for 20 hours. The suspension was filtered, the solid washed with ethyl acetate and dried to afford cis-octahydrothieno[3,4-b]pyrazine 6,6-dioxide (340 mg, 74%) as a white solid.

m/z (ESI, +ve)=177.1 (M+H)⁺.
$^1$H NMR (400 MHz, D$_2$O) δ 4.43 (d, J=5.0 Hz, 2H), 3.70-3.66 (m, 4H), 3.38-3.28 (m, 4H).

Step 21: 10-(2,4-difluorophenyl)-7-(6,6-dioxido-hexahydrothieno[3,4-b]pyrazin-1(2H)-yl)-9-(trifluoromethyl)-2,3-dihydro-5H-[1,4]thiazino[2,3,4-ij]quinazolin-5-one

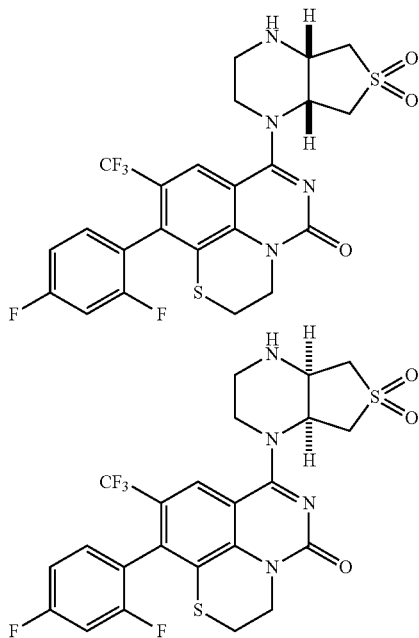

To a solution of 10-(2,4-difluorophenyl)-9-(trifluoromethyl)-2,3-dihydro-5H-[1,4]thiazino[2,3,4-ij]quinazoline-5,7(6H)-dione (70 mg, 0.05 mmol) in toluene (1 mL) were added N,N-diisopropylethylamine (135 mg, 1.0 mmol) and POCl$_3$ (1 mL). The reaction mixture was stirred at 120° C. for 1.5 hours, cooled down to room temperature and concentrated to afford a residue that was dissolved in dichloroethane (1 mL) and added to a solution of octahydrothieno[3,4-b]pyrazine 6,6-dioxide (118 mg, 0.35 mmol) and N,N-diisopropylethylamine (135 mg, 1.0 mmol) in dichloroethane (1 mL). The reaction mixture was stirred at room temperature for 1 hour, concentrated and the resulting solid purified by silica gel chromatography to afford 10-(2,4-difluorophenyl)-7-(6,6-dioxidohexahydrothieno[3,4-b]pyrazin-1(2H)-yl)-9-(trifluoromethyl)-2,3-dihydro-5H-[1,4]thiazino[2,3,4-ij]quinazolin-5-one (50 mg, 51%) as a yellow solid.

m/z (ESI, +ve)=559.1 (M+H)⁺.

Example 101: 7-(9-acryloyl-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one

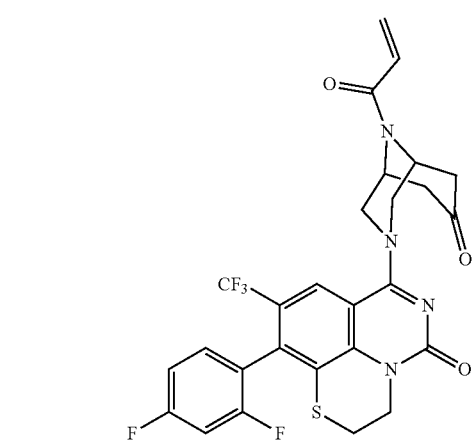 [SMILES: C=CC(=O)N1C2CC(=O)CC1CN(c1nc(=O)n3c4c(c(-c5ccc(F)cc5F)c(C(F)(F)F)cc14)SCC3)C2]

The title compound was prepared analogously to Example 84 where 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 23% yield as a yellow solid.

m/z (ESI, +ve)=577.0 (M+H)⁺.
$^1$H NMR (400 MHz, methanol-d4) δ 7.91 (s, 1H), 7.31-7.26 (m, 1H), 7.14-7.09 (m, 2H), 6.96-6.89 (m, 1H), 6.37 (d, J=20.0 Hz, 1H), 5.88 (d, J=12.0 Hz, 1H), 5.28 (m, 1H), 4.95 (m, 1H), 4.52-4.28 (m, 3H), 4.22-4.20 (m, 1H), 3.48-3.36 (m, 2H), 3.20-3.18 (m, 2H), 2.85-2.78 (m, 2H), 2.63-2.52 (m, 2H).

Step 1: diethyl 4,4'-((4-methoxybenzyl)azanediyl)(2E,2'E)-bis(but-2-enoate)

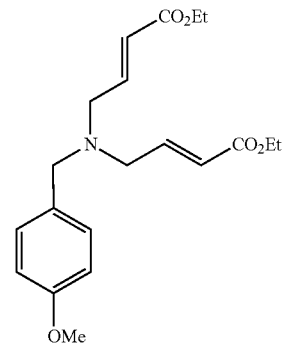 [SMILES: CCOC(=O)/C=C/CN(C/C=C/C(=O)OCC)Cc1ccc(OC)cc1]

To a solution of (4-methoxyphenyl)methanamine (25 g, 182.2 mmol, 1.0 eq) in ethanol (400 mL) at room temperature, was added dropwise DIPEA (70.6 g, 546.6 mmol, 3.0 eq) and ethyl 4-bromocrotonate (86.6 g, 401.1 mmol, 2.2 eq). The resulting mixture was heated at 40° C. for 16 hours and ethanol was removed under reduced pressure. Water (400 ml) was added and the mixture extracted with ethyl acetate (200 ml×3). The organic layers were combined, washed with brine (400 ml) dried over with $Na_2SO_4$ and filtered. The filtrate was concentrated to afford a residue that was purified by flash chromatography with hexanes/ethyl acetate=10/1 to give diethyl 4,4'-((4-methoxybenzyl)azanediyl)(2E,2'E)-bis(but-2-enoate) (56.8 g, 86%) as a yellow oil.

m/z (ESI, +ve)=362.2.

Step 2: cis-diethyl 2,2'-(4-(4-methoxybenzyl)piperazine-2,6-diyl)diacetate

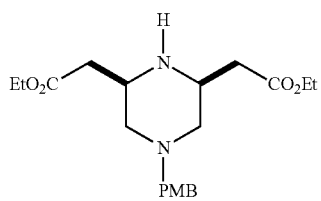

To a solution of diethyl 4,4'-((4-methoxybenzyl)azanediyl)(2E,2'E)-bis(but-2-enoate) (15 g, 41.53 mmol, 1.0 eq) in ethanol (55 mL) was added aqueous ammonia (25 ml). The resulting mixture was stirred at 80° C. for 7 hours in a sealed flask. Volatiles were removed under reduced pressure, water (30 ml) was added and the mixture extracted with EtOAc (30 ml×3). The organic layers were combined, washed with brine (40 ml) dried over with $Na_2SO_4$ and filtered. The filtrate was concentrated and the resulting residue purified by silica gel chromatography (hexanes/ethyl acetate=1/1) to afford the desired compound (10.9 g. 69%) as a colorless oil.

m/z (ESI, +ve)=379.2

Step 3: cis-diethyl 2,2'-(piperazine-2,6-diyl)diacetate

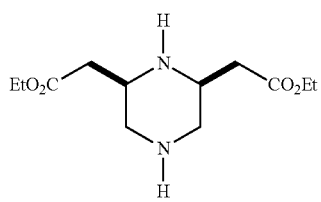 [SMILES: CCOC(=O)C[C@H]1CNC[C@@H](CC(=O)OCC)N1]

To a solution of cis-diethyl 2,2'-(4-(4-methoxybenzyl)piperazine-2,6-diyl)diacetate (10 g, 26.44 mmol, 1.0 eq) in TFA (50 mL) was added anisole (3 ml). The resulting mixture was stirred at 90° C. for 24 hours and concentrated. The residue was purified by flash chromatography with methanol/dichloromethane (1/20) to afford cis-diethyl 2,2'-(piperazine-2,6-diyl)diacetate (5.4 g) as a gray solid.

m/z (ESI, +ve)=259.2

Step 4: di-tert-butyl-cis-(2,6-bis(2-ethoxy-2-oxoethyl))piperazine-1,4-dicarboxylate

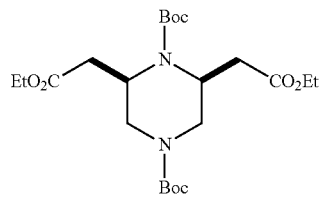 [SMILES: CCOC(=O)C[C@@H]1CN(C(=O)OC(C)(C)C)C[C@H](CC(=O)OCC)N1C(=O)OC(C)(C)C]

To a solution of cis-diethyl 2,2'-(piperazine-2,6-diyl)diacetate (10 g, 39.1 mmol, 1.0 eq) in dichloromethane (80 mL), was added $Et_3N$ (23.7 g, 234.7 mmol, 6.0 eq) and Boc anhydride (25.6 g, 117.3 mmol, 3.0 eq). After 4 hours, water (100 ml) was added and the mixture extracted with dichloromethane (50 ml×3). The organic layer was washed with brine (50 ml), dried over $Na_2SO_4$ and filtered. The filtrate was concentrated to afford a residue that was purified by flash chromatography (hexanes/ethyl acetate=5/1~1/1) to afford di-tert-butyl-cis-(2,6-bis(2-ethoxy-2-oxoethyl))piperazine-1,4-dicarboxylate (9.86 g, 55%) as a white solid.

Step 5: 3,9-di-tert-butyl 6-ethyl-7-oxo-3,9-diazabicyclo[3.3.1]nonane-3,6,9-tricarboxylate

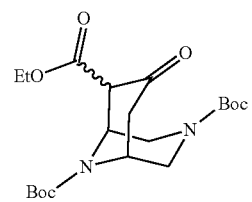 [SMILES: CCOC(=O)C1C(=O)CC2CN(C(=O)OC(C)(C)C)CC1N2C(=O)OC(C)(C)C]

To a solution of di-tert-butyl-cis-(2,6-bis(2-ethoxy-2-oxoethyl))piperazine-1,4-dicarboxylate (4.7 g, 10.26 mmol, 1.0 eq) in THF (20 mL) was added potassium tert-butoxide (4.03 g, 35.89 mmol, 3.5 eq) and the resulting mixture was stirred at 40° C. for 3 hours. The reaction mixture was concentrated and water (30 ml) was added followed by extraction with ethyl acetate (10 ml×3). The organic layers were combined, washed with brine (20 ml) dried over with $Na_2SO_4$ and filtered. The filtrate was concentrated to afford a crude material that was purified by flash chromatography (hexanes/ethyl acetate=10/1) to afford 3,9-di-tert-butyl 6-ethyl-7-oxo-3,9-diazabicyclo[3.3.1]nonane-3,6,9-tricarboxylate (2.24 g, 53%) as a white solid.

m/z (ESI, +ve)=257.2

Step 6: 3,9-diazabicyclo[3.3.1]nonan-7-one

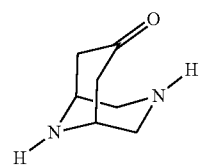

A solution of 3,9-di-tert-butyl 6-ethyl-7-oxo-3,9-diazabicyclo[3.3.1]nonane-3,6,9-tricarboxylate (2.0 g, 4.85 mmol, 1.0 eq) in concentrated HCl (15 ml) was stirred at 100° C. for 48 hours. The pH was adjusted to 8 and the volatiles removed under reduced pressure. The resulting crude material (550 mg, 81%) was used in the next step without further purification.

m/z (ESI, +ve)=141.2

Step 7: 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one

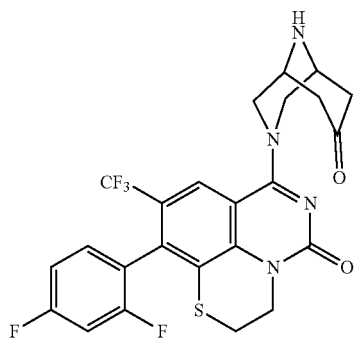 [SMILES: O=C1CC2CN(c3nc(=O)n4c5c(c(-c6ccc(F)cc6F)c(C(F)(F)F)cc35)SCC4)CC(C1)N2]

To a solution of 10-(2,4-difluorophenyl)-9-(trifluoromethyl)-2,3-dihydro-5H-[1,4]thiazino[2,3,4-ij]quinazoline-5,7(6H)-dione (100 mg, 0.25 mmol) in toluene (1 mL) were added N,N-diisopropylethylamine (386 mg, 3 mmol) and POCl$_3$ (1 mL). The reaction mixture was stirred at 120° C. for 1.5 hours and concentrated. The residue was dissolved in dichloroethane (1 mL) and added to a mixture of 3,9-diazabicyclo[3.3.1]nonan-7-one (210 mg, 1.5 mmol) and NaHCO$_3$ (837 mg, 9.97 mmol) in DMF (1 mL) at 0° C. The resulting reaction mixture was stirred at room temperature for 1 hour and concentrated to afford a residue that was purified by silica gel chromatography to afford 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (50 mg, 34%) as a brown solid.

m/z (ESI, +ve)=523.1 (M+H)$^+$.

Example 102: 8-((S)-4-acryloyl-2-methylpiperazin-1-yl)-10-chloro-11-(2,4-difluorophenyl)-3,4-dihydro-2H,6H-[1,4]thiazepino[2,3,4-ij]quinazolin-6-one

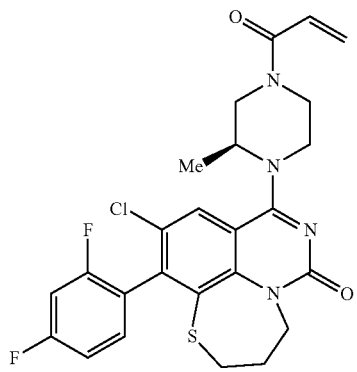 [SMILES: C=CC(=O)N1CCN(c2nc(=O)n3c4c(c(-c5ccc(F)cc5F)c(Cl)cc24)SCCC3)[C@@H](C)C1]

The title compound was prepared analogously to Example 84 where 10-chloro-11-(2,4-difluorophenyl)-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 21% yield as a yellow solid m/z (ESI, +ve)=517.1 (M+H)$^+$.

$^1$H NMR (400 MHz, DMSO) δ 7.64 (d, J=12.0 Hz, 1H), 7.51-7.39 (m, 2H), 7.28-7.24 (m, 1H), 6.85-6.81 (m, 1H), 6.20-6.16 (m, 1H), 5.74 (d, J=12.0 Hz, 1H), 4.71-4.32 (m, 4H), 4.26-3.89 (m, 3H), 3.57 (s, 1H), 3.25-2.86 (m, 3H), 2.05-2.01 (m, 2H), 1.27-1.23 (m, 3H).

Step 1: 6-chloro-7-(2,4-difluorophenyl)-8-((3-hydroxypropyl)thio)quinazoline-2,4(1H,3H)-dione

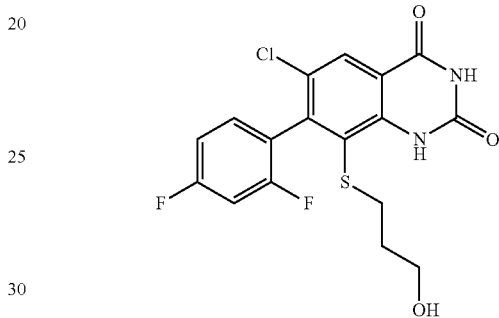

To a mixture of 6-chloro-7-(2,4-difluorophenyl)-8-iodo-1,3-dihydroquinazoline-2,4-dione (1 g, 2.3 mmol), potassium carbonate (0.95 g, 6.9 mmol), copper(I) iodide (0.09 g, 0.4 mmol) in isopropyl alcohol:ethylene glycol=2:1 (18 mL), was added 3-sulfanylpropan-1-ol (0.64 g, 6.9 mmol). The mixture was stirred at 90° C. for 2 hours and concentrated to afford a residue that was taken up in water (10 mL) and extracted with ethyl acetate (15 mL×3). The combined organic layers were washed with brine (10 mL), dried over Na$_2$SO$_4$ and filtered. The crude product was purified by column chromatography on silica gel eluted with ethyl acetate in hexanes (0-100%) to afford a yellow solid that was subjected to chromatography on C18 column using acetonitrile:water (0-100%) as mobile phase. 6-chloro-7-(2,4-difluorophenyl)-8-[(3-hydroxypropyl)sulfanyl]-1,3-dihydroquinazoline-2,4-dione (800 mg, 65%) was isolated as a white solid.

m/z (ESI, +ve)=399.0 (M+H)$^+$.

Step 2: 10-chloro-11-(2,4-difluorophenyl)-3,4-dihydro-2H,6H-[1,4]thiazepino[2,3,4-ij]quinazoline-6,8(7H)-dione

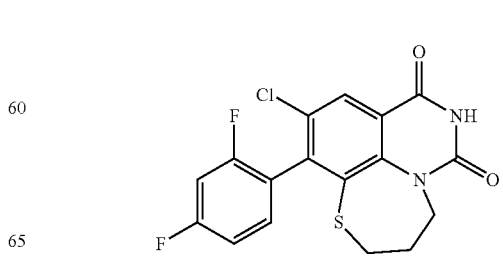

To a solution of PPh₃ (740 mg, 2.82 mmol) in THF (10 mL) at 0° C. was added a solution of DIAD (570.4 mg, 2.82 mmol) in THF (3 mL). The mixture was stirred at 0° C. for 20 minutes and 6-chloro-7-(2,4-difluorophenyl)-8-[(3-hydroxypropyl) sulfanyl]-1,3-dihydroquinazoline-2,4-dione (750 mg, 1.88 mmol) in THF (17 mL) at 0° C. was added. The reaction was allowed to reach room temperature over 3 hours. Volatiles were removed under reduced pressure and the resulting crude material was purified by column chromatography on C18 column with acetonitrile:water (0-100%) as mobile phase to afford 10-chloro-11-(2,4-difluorophenyl)-3,4-dihydro-2H,6H-[1,4]thiazepino[2,3,4-ij]quinazoline-6,8(7H)-dione (250 mg, 35%) as a yellow-green solid.

m/z (ESI, +ve)=381.0 (M+H)⁺.

Step 3: tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate

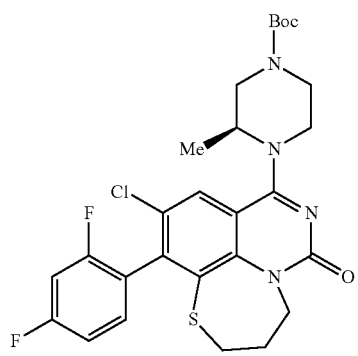 [SMILES: C[C@H]1CN(C(=O)OC(C)(C)C)CCN1c1nc(=O)n2c3c(c(-c4ccc(F)cc4F)c(Cl)cc13)SCCC2]

To a mixture of 10-chloro-11-(2,4-difluorophenyl)-3,4-dihydro-2H,6H-[1,4]thiazepino[2,3,4-ij]quinazoline-6,8 (7H)-dione (250 mg, 0.65 mmol) in toluene (8 mL) at room temperature, DIPEA (850 mg, 6.57 mmol) and phosphoryl trichloride (8 mL) were added. The mixture was stirred at 120° C. for 1.5 hours and concentrated. The residue was dissolved in dichloroethane (4 mL) and the solution added to a mixture of tert-butyl (3S)-3-methylpiperazin-1-yl formate (397 mg, 1.97 mmol) and N, N-diisopropylethylamine (850 mg, 6.57 mmol) in dichloroethane (7 mL) at 0° C. The mixture was allowed to reach room temperature over 2 hours and then concentrated under reduced pressure. The crude product was purified by column chromatography on silica gel (ethyl acetate/dichloromethane=0-30%) to afford tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate (175 mg, 35%) as yellow oil.

m/z (ESI, +ve)=563.2 (M+H)⁺.

Step 4: 10-chloro-11-(2,4-difluorophenyl)-8-((S)-2-methylpiperazin-1-yl)-3,4-dihydro-2H,6H-[1,4]thiazepino[2,3,4-ij]quinazolin-6-one

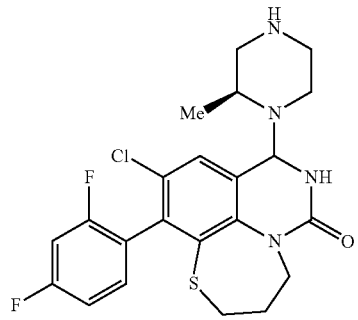 [SMILES: C[C@H]1CNCCN1C1NC(=O)N2CCCSc3c(-c4ccc(F)cc4F)c(Cl)cc1c32]

A mixture of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate (175 ng, 0.31 mmol) and TFA (2 mL) in dichloromethane (8 mL) was stirred at room temperature for 2 hours. The mixture was concentrated to afford a product that was used in the next step without further purification.

m/z (ESI, +ve)=463.1 (M+H)⁺.

Example 103: 7-((S)-4-acryloyl-2-methylpiperazin-1-yl)-10-(2,4-difluorophenyl)-9-methoxy-2,3-dihydro-5H-[1,4]thiazino[2,3,4-ij]quinazolin-5-one

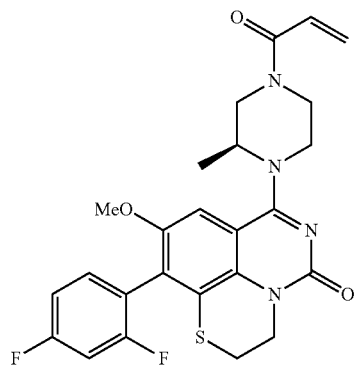 [SMILES: C=CC(=O)N1CCN(c2nc(=O)n3c4c(c(-c5ccc(F)cc5F)c(OC)cc24)SCC3)[C@@H](C)C1]

The title compound was prepared analogously to Example 84 where 10-(2,4-difluorophenyl)-9-methoxy-7-((S)-2-methylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 34% yield as a yellow solid m/z (ESI, +ve)=499.1 (M+H)⁺.

1H NMR (400 MHz, DMSO-d6) δ 7.60-7.30 (m, 2H), 7.22-7.18 (m, 1H), 7.06-6.99 (m, 1H), 6.88-6.77 (m, 1H), 6.20-6.16 (m, 1H), 5.76-5.72 (m, 1H), 4.68-4.62 (m, 1H), 4.50-4.06 (m, 4H), 4.02-3.90 (m, 1H), 3.76 (s, 3H), 3.57-3.42 (m, 2H), 3.17-2.96 (m, 3H), 1.33-1.27 (m, 3H).

Step 1: tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate

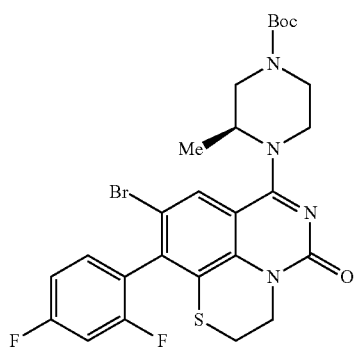 [SMILES: C[C@H]1CN(C(=O)OC(C)(C)C)CCN1c1nc(=O)n2c3c(c(-c4ccc(F)cc4F)c(Br)cc13)SCC2]

To a solution of 9-bromo-10-(2,4-difluorophenyl)-2,3-dihydro-5H-[1,4]thiazino[2,3,4-ij]quinazoline-5,7(6H)-dione (2 g, 0.0048 mol) and DIPEA (7.4 g, 57.6 mmol) in toluene (10 mL), POCl$_3$ (10 mL) was added and the mixture stirred at 120° C. for 1.5 hours. The reaction mixture was concentrated, the residue was dissolved in dichloroethane (20 mL) and added to a solution of tert-butyl (S)-3-methylpiperazine-1-carboxylate (2.9 g, 14.4 mmol) and DIPEA (7.4 g, 57.6 mmol) in dichloroethane (10 mL) previously cooled down to 0° C. The cooling bath was removed and the reaction mixture stirred at room temperature for one additional hour. Elimination of volatiles at reduced pressure afforded a residue that was purified by flash chromatography to afford tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (2.5 g, 83%) as a yellow solid.

m/z (ESI, +ve)=593.0 (M+H)$^+$.

Step 2: tert-butyl (3S)-4-(10-(2,4-difluorophenyl)-9-methoxy-5-oxo-2,3-dihydro-5H-[1,4]thiazino[2,3,4-ij]quinazolin-7-yl)-3-methylpiperazine-1-carboxylate

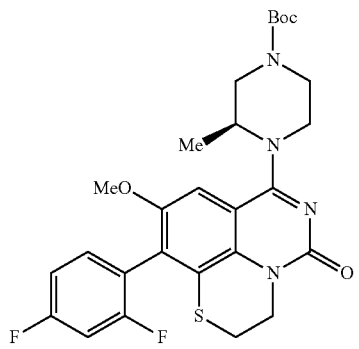 [SMILES: COc1cc2c(N3CCN(C(=O)OC(C)(C)C)C[C@@H]3C)nc(=O)n3c2c(c1-c1ccc(F)cc1F)SCC3]

A mixture of (tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (900 mg, 1.5 mmol), palladium diacetate (34 mg, 0.15 mmol), t-BuXphos (128 mg, 0.3 mmol) and Cs$_2$CO$_3$ (733 mg, 2.25 mmol) in toluene (15 mL) and methanol (15 mL) was stirred at 80° C. for 16 hours. The mixture was cooled down to room temperature and the solids filtered out. The filtrate was concentrated under reduced pressure to afford a residue that was purified by preparative TLC to afford tert-butyl (3S)-4-(10-(2,4-difluorophenyl)-9-methoxy-5-oxo-2,3-dihydro-5H-[1,4]thiazino[2,3,4-ij]quinazolin-7-yl)-3-methylpiperazine-1-carboxylate (180 mg, 18%) as a yellow solid.

m/z (ESI, +ve)=545.2 (M+H)$^+$.

Step 3: 10-(2,4-difluorophenyl)-9-methoxy-7-((S)-2-methylpiperazin-1-yl)-2,3-dihydro-5H-[1,4]thiazino[2,3,4-ij]quinazolin-5-one

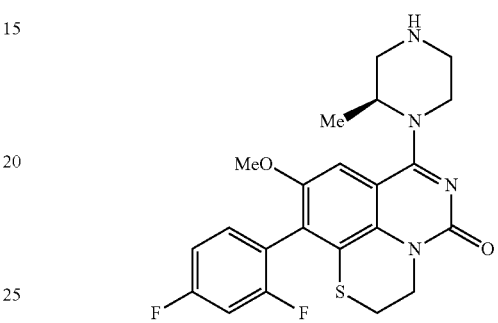

To a solution of tert-butyl (3S)-4-(10-(2,4-difluorophenyl)-9-methoxy-5-oxo-2,3-dihydro-5H-[1,4]thiazino[2,3,4-ij]quinazolin-7-yl)-3-methylpiperazine-1-carboxylate (200 mg, 0.37 mmol) in dichloromethane (10 mL) was added ZnBr$_2$ (825 mg, 3.67 mmol). The reaction mixture was stirred at 25° C. for 1 hour, quenched with water (10 mL) and extracted with dichloromethane (10 mL×3). The organic layers were combined, washed with water (10 mL), dried over sodium sulfate and filtered. The filtrate was concentrated under reduced pressure to afford 10-(2,4-difluorophenyl)-9-methoxy-7-((S)-2-methylpiperazin-1-yl)-2,3-dihydro-5H-[1,4]thiazino[2,3,4-ij]quinazolin-5-one (160 mg, 73%) as a yellow solid.

m/z (ESI, +ve)=445 (M+H)$^+$.

Example 104: 2-((2S)-4-acryloyl-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile

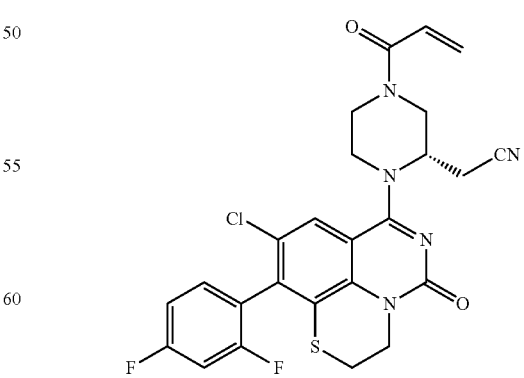

The title compound was prepared analogously to Example 84 where 2-((2S)-1-(9-chloro-10-(2,4-difluorophenyl)-5-oxo-2,3-dihydro-5H-[1,4]thiazino[2,3,4-ij]quinazolin-7-yl)

piperazin-2-yl)acetonitrile was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 45% yield as a yellow solid m/z (ESI, +ve)=528.0 (M+H)$^+$.

1H NMR (400 MHz, methanol-d4) δ 7.77-7.76 (m, 1H), 7.35-7.27 (m, 1H), 7.14-7.11 (m, 2H), 6.84-6.76 (m, 1H), 6.29 (d, J=16.0 Hz, 1H), 5.82 (d, J=12.0 Hz, 1H), 5.20-5.10 (m, 1H), 4.61-4.14 (m, 5H), 3.89-3.73 (m, 1H), 3.50-3.40 (m, 2H), 3.25-2.89 (m, 4H).

tert-butyl (3S)-4-(9-chloro-10-(2,4-difluorophenyl)-5-oxo-2,3-dihydro-5H-[1,4]thiazino[2,3,4-ij]quinazolin-7-yl)-3-(cyanomethyl)piperazine-1-carboxylate

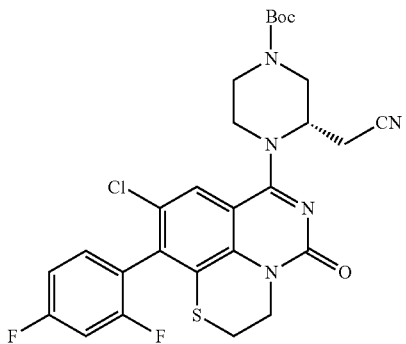

To a mixture of 9-chloro-10-(2,4-difluorophenyl)-2,3-dihydro-5H-[1,4]thiazino[2,3,4-ij]quinazoline-5,7(6H)-dione (700 mg, 1.9 mmol) and DIPEA (2.94 g, 22.8 mmol) in toluene (10 mL), was added POCl$_3$ (10 mL). The reaction mixture was stirred at 120° C. for 1.5 h. The solvent was removed under reduced pressure to afford a residue that was taken up in dichloroethane (20 mL) and added to a mixture of tert-butyl (3S)-3-(cyanomethyl)piperazin-1-yl formate (1293 mg, 5.72 mmol) and DIEA (2941 mg, 22.8 mmol) in DCE (20 mL). The resulting reaction mixture was stirred at 60° C. for 16 hours and concentrated under reduced pressure. Purification by preparative TLC (ethyl acetate/hexanes=1/1) afforded tert-butyl (3S)-4-(9-chloro-10-(2,4-difluorophenyl)-5-oxo-2,3-dihydro-5H-[1,4]thiazino[2,3,4-ij]quinazolin-7-yl)-3-(cyanomethyl)piperazine-1-carboxylate (380 mg, 30%) as a yellow solid.

m/z (ESI, +ve)=574.1 (M+H)$^+$.

Step 2: 2-((2S)-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile

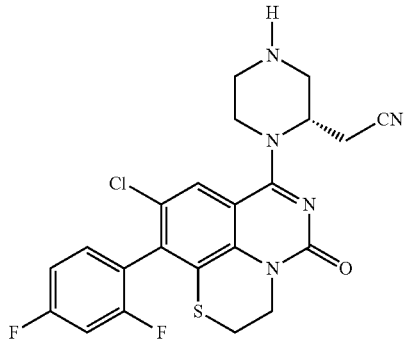 [SMILES: N#CC[C@H]1CNCCN1c1nc(=O)n2c3c(c(-c4ccc(F)cc4F)c(Cl)cc13)SCC2]

To a mixture of tert-butyl (3S)-4-(9-chloro-10-(2,4-difluorophenyl)-5-oxo-2,3-dihydro-5H-[1,4]thiazino[2,3,4-ij]quinazolin-7-yl)-3-(cyanomethyl)piperazine-1-carboxylate (350 mg, 0.61 mmol) in dichloromethane (4 mL) was added ZnBr$_2$ (1369 mg, 6.1 mmol). The reaction mixture was stirred at 25° C. for 1 hour, quenched with water (10 mL) and extracted with dichloromethane (10 mL×3). The organic layers were combined, washed with water (10 mL), dried over sodium sulfate and filtered. The filtrate was concentrated under reduced pressure to afford 2-((2S)-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile (250 mg, 78%) as a yellow solid.

m/z (ESI, +ve)=474.1 (M+H)$^+$.

Example 114: 7-((S)-4-acryloyl-2-methylpiperazin-1-yl)-10-(2,4-difluorophenyl)-9-ethyl-2,3-dihydro-5H-[1,4]thiazino[2,3,4-ij]quinazolin-5-one

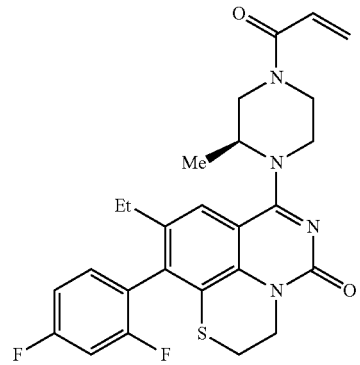 [SMILES: C=CC(=O)N1CCN(c2nc(=O)n3c4c(c(-c5ccc(F)cc5F)c(CC)cc24)SCC3)[C@@H](C)C1]

The title compound was prepared analogously to Example 84 where 10-(2,4-difluorophenyl)-9-ethyl-7-((S)-2-methylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 30% yield as a yellow solid m/z (ESI, +ve)=497.2 (M+H)$^+$.

$^1$H NMR (400 MHz, methanol-d4) δ 7.49 (d, J=4.0 Hz, 1H), 7.26-7.21 (m, 1H), 7.14-7.09 (m, 2H), 6.88-6.76 (m, 1H), 6.28 (dd, J=16.0 Hz, 8.0 Hz, 1H), 5.80 (d, J=12.0 Hz, 1H), 4.79-4.54 (m, 1H), 4.41-4.38 (m, 2H), 4.23-4.15 (m, 2H), 4.04-3.99 (m, 1H), 3.70-3.45 (m, 2H), 3.18-3.08 (m, 3H), 2.46-2.34 (m, 2H), 1.42 (dd, J=16.0 Hz, 8.0 Hz, 3H), 1.12-1.04 (m, 3H).

Step 1: tert-butyl (3S)-4-(10-(2,4-difluorophenyl)-9-ethyl-5-oxo-2,3-dihydro-5H-[1,4]thiazino[2,3,4-ij]quinazolin-7-yl)-3-methylpiperazine-1-carboxylate

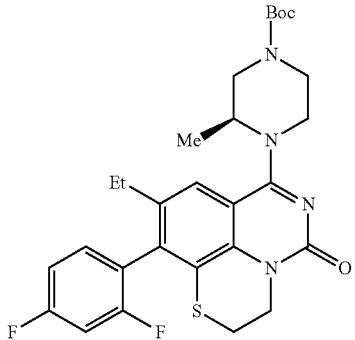

To a solution of tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (500 mg, 0.84 mmol), Pd(dppf)Cl₂ (123 mg, 0.17 mmol) and diethylzinc (1M, 8.4 mL) in THF (10 mL) at −78° C. The reaction mixture was stirred at 80° C. for 4 hours, quenched with water (20 mL) and extracted with ethyl acetate (20 mL×3). The organic layers were combined, washed with brine (50 mL), dried over sodium sulphate and concentrated. Purification by silica gel chromatography afforded tert-butyl (3S)-4-(10-(2,4-difluorophenyl)-9-ethyl-5-oxo-2,3-dihydro-5H-[1,4]thiazino[2,3,4-ij]quinazolin-7-yl)-3-methylpiperazine-1-carboxylate (400 mg, 87%) as a yellow solid.
m/z (ESI, +ve)=543.2 (M+H)⁺.

Step 2: 10-(2,4-difluorophenyl)-9-ethyl-7-((S)-2-methylpiperazin-1-yl)-2,3-dihydro-5H-[1,4]thiazino[2,3,4-ij]quinazolin-5-one

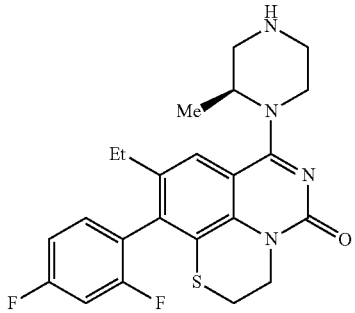 [SMILES: CCc1cc2c(N3CCNC[C@@H]3C)nc(=O)n3c2c(c1-c1ccc(F)cc1F)SCC3]

To a solution of tert-butyl (3S)-4-(10-(2,4-difluorophenyl)-9-ethyl-5-oxo-2,3-dihydro-5H-[1,4]thiazino[2,3,4-ij]quinazolin-7-yl)-3-methylpiperazine-1-carboxylate (400 mg, 0.74 mmol) in dichloromethane (6 mL) at 0° C., was added trifluoroacetic acid (2 mL). The reaction mixture was stirred at room temperature for 2 hours and concentrated in vacuo to afford 10-(2,4-difluorophenyl)-9-ethyl-7-((S)-2-methylpiperazin-1-yl)-2,3-dihydro-5H-[1,4]thiazino[2,3,4-ij]quinazolin-5-one (300 mg, 91%) as a yellow solid.
m/z (ESI, +ve)=443.1 (M+H)⁺.

Example 115: 7-((S)-4-acryloyl-2-methylpiperazin-1-yl)-10-(2,4-difluorophenyl)-9-methyl-2,3-dihydro-5H-[1,4]thiazino[2,3,4-ij]quinazolin-5-one

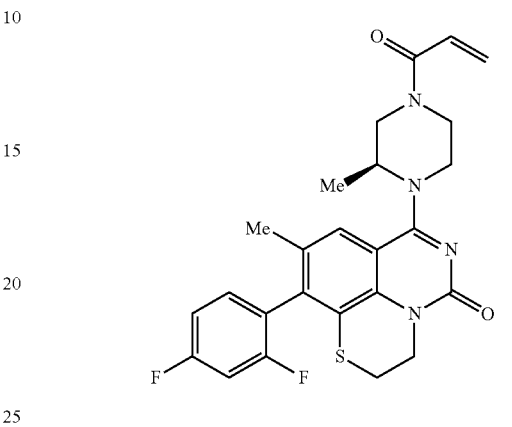

The title compound was prepared analogously to Example 84 where tert-butyl (3S)-4-(10-(2,4-difluorophenyl)-9-methyl-5-oxo-2,3-dihydro-5H-[1,4]thiazino[2,3,4-ij]quinazolin-7-yl)-3-methylpiperazine-1-carboxylate was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 25% yield as a yellow solid
m/z (ESI, +ve)=483.1 (M+H)⁺.

Step 1: tert-butyl (3S)-4-(10-(2,4-difluorophenyl)-9-methyl-5-oxo-2,3-dihydro-5H-[1,4]thiazino[2,3,4-ij]quinazolin-7-yl)-3-methylpiperazine-1-carboxylate

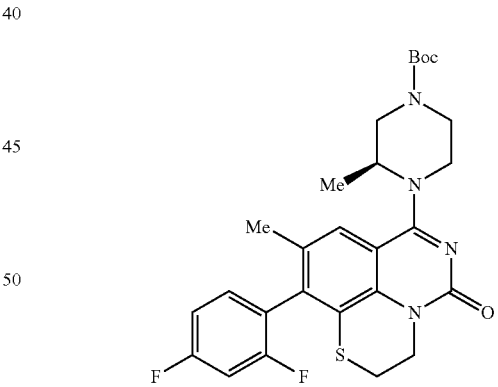

2,4,6-trimethyl-1,3,5,2,4,6-trioxatriborinane (175 mg, 1.39 mmol) was added to a mixture of tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (550 mg, 0.93 mmol), [1,1'-bis(diphenylphosphino)ferrocene]dichloropalladium(II) (136 mg, 0.19 mmol) and cesium carbonate (910 mg, 2.8 mmol) in dioxane/H₂O (5/1, 60 mL). After the reaction was completed by LCMS, volatiles were removed under reduced pressure to afford a residue that was purified by flash chromatography to afford tert-butyl (3S)-4-(10-(2,4-difluorophenyl)-9-methyl-5-oxo-2,3-dihydro-5H-[1,4]thiazino[2, 3,4-ij]quinazolin-7-yl)-3-methylpiperazine-1-carboxylate (390 mg, 75%) as a yellow solid.

m/z (ESI, +ve)=529.2 (M+H)+.

Step 2: 10-(2,4-difluorophenyl)-9-methyl-7-((S)-2-methylpiperazin-1-yl)-2,3-dihydro-5H-[1,4]thiazino[2,3,4-ij]quinazolin-5-one

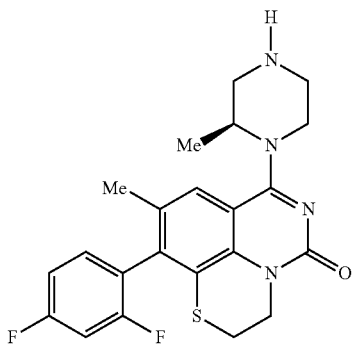 [SMILES: Cc1cc2c(N3CCNC[C@@H]3C)nc(=O)n3c2c(c1-c1ccc(F)cc1F)SCC3]

To a solution of tert-butyl (3S)-4-(10-(2,4-difluorophenyl)-9-methyl-5-oxo-2,3-dihydro-5H-[1,4]thiazino[2,3,4-ij]quinazolin-7-yl)-3-methylpiperazine-1-carboxylate (390 mg, 0.73 mmol) in dichloromethane (5 mL) at 0° C., was added trifluoroacetic acid (2 mL). The reaction mixture was stirred at room temperature for 2 hours and concentrated to afford 10-(2,4-difluorophenyl)-9-methyl-7-((S)-2-methylpiperazin-1-yl)-2,3-dihydro-5H-[1,4]thiazino[2,3,4-ij]quinazolin-5-one (300 mg, 95%) as a yellow solid.

m/z (ESI, +ve)=429.1 (M+H)+.

Example 116: 7-(6-acryloyl-1-oxo-2,6,9-triazaspiro[4.5]decan-9-yl)-9-chloro-10-(2,4-difluorophenyl)-2,3-dihydro-5H-[1,4]thiazino[2,3,4-ij]quinazolin-5-one

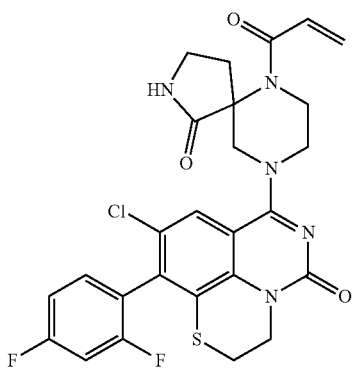 [SMILES: C=CC(=O)N1CCN(c2nc(=O)n3c4c(c(-c5ccc(F)cc5F)c(Cl)cc24)SCC3)CC12CCNC2=O]

The title compound was prepared analogously to Example 84 where 9-chloro-10-(2,4-difluorophenyl)-7-(1-oxo-2,6,9-triazaspiro[4.5]decan-9-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 50% yield as a white solid m/z (ESI, +ve)=558.0 (M+H)+.

1H NMR (400 MHz, DMSO) δ 7.84 (d, J=4.0 Hz, 1H), 7.77 (s, 1H), 7.51-7.37 (m, 2H), 7.31-7.24 (m, 1H), 6.76-6.70 (m, 1H), 6.13 (d, J=16.0 Hz, 1H), 5.74 (d, J=12.0 Hz, 1H), 4.46 (m, 0.5H), 4.26 (m, 0.5H), 4.07-3.81 (m, 7H), 3.34-3.30 (m, 1H), 3.28-3.19 (m, 2H), 3.15-3.05 (m, 1H), 2.35-2.33 (m, 1H), 2.20 (m, 1H).

Step 1: 4-(tert-butoxycarbonyl)piperazine-2-carboxylic acid

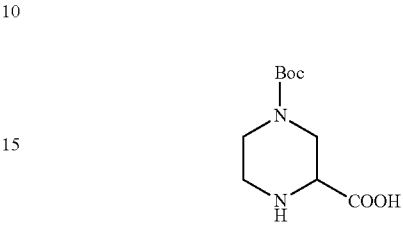

To a solution of piperazine-2-carboxylic acid (20 g, 153.7 mmol) in dioxane/water (1/1, 400 mL) at 0° C., was added NaHCO3 (19.37 g, 230.5 mmol), followed by Boc-anhydride (42.3 mL, 184.47 mmol). The reaction mixture was warmed to room temperature and stirred for 16 hours. The mixture was concentrated under reduced pressure and the crude was used directly in next step.

m/z (ESI, +ve)=175.1 (M+H)+.

Step 2: 1-((benzyloxy)carbonyl)-4-(tert-butoxycarbonyl)piperazine-2-carboxylic acid

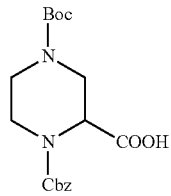 [SMILES: CC(C)(C)OC(=O)N1CCN(C(=O)OCc2ccccc2)C(C(=O)O)C1]

To a solution of 4-(tert-butoxycarbonyl)piperazine-2-carboxylic acid (35 g, 0.152 mol) in dioxane:water (1:1, 500 mL) at 0° C., was added NaHCO3 (25.56 g, 0.304 mol) followed by Cbz-Cl (31 g, 0.182 mol). The mixture was warmed to room temperature and stirred for 16 hours. The reaction mixture was diluted with water (100 mL), acidified with 1N HCl and extracted with EtOAc (100 mL×3). The combined organic layers were washed with brine and dried over anhydrous Na2SO4, filtered and concentrated under reduced pressure to afford 1-((benzyloxy)carbonyl)-4-(tert-butoxycarbonyl)piperazine-2-carboxylic acid as thick syrup.

m/z (ESI, +ve)=265.1 (M+H)+.

Step 3: 1-benzyl 4-(tert-butyl) 2-methyl piperazine-1,2,4-tricarboxylate

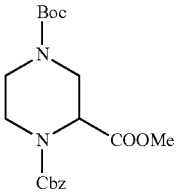 [SMILES: COC(=O)C1CN(C(=O)OC(C)(C)C)CCN1C(=O)OCc1ccccc1]

To a solution of 1-((benzyloxy)carbonyl)-4-(tert-butoxycarbonyl)piperazine-2-carboxylic acid (46 g, 0.126 mol) in DMF (460 mL) were added K$_2$CO$_3$ (21 g, 0.151 mmol) and MeI (12 mL, 0.189 mol). The reaction mixture was stirred at room temperature for 16 hours. The mixture was diluted with water and extracted with Et$_2$O (300 mL×2). The combined organic layers were washed with water (100 mL) and brine (100 mL), dried over anhydrous Na$_2$SO$_4$ and concentrated under reduced pressure. The residue was purified by silica gel column chromatography (hexanes/EtOAc=10/1) to afford 1-benzyl 4-(tert-butyl) 2-methyl piperazine-1,2,4-tricarboxylate (25 g, 52%) as white solid.

m/z (ESI, +ve)=279.1 (M-100).

Step 4: 1-benzyl 4-(tert-butyl) 2-methyl 2-(cyanomethyl)piperazine-1,2,4-tricarboxylate

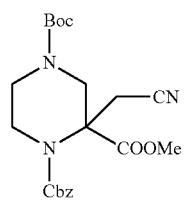 [SMILES: COC(=O)C1(CC#N)CN(C(=O)OC(C)(C)C)CCN1C(=O)OCc1ccccc1]

To a solution of 1-benzyl 4-(tert-butyl) 2-methyl piperazine-1,2,4-tricarboxylate (5 g, 13.22 mmol) in THF (50 mL) at −78° C., was added LiHMDS (1M in THF) (15 mL, 0.151 mmol). The mixture was stirred at room temperature for 1 hour and bromo acetonitrile (1.4 mL, 19.84 mol) was added and stirring continued for another 16 hours. The reaction mixture was quenched with saturated aqueous NH$_4$Cl and extracted with EtOAc (200 mL×2). The combined organic layers were washed with brine (100 mL), dried over anhydrous Na$_2$SO$_4$ and concentrated under reduced pressure. The residue was purified by silica gel column column chromatography (hexanes/ethyl acetate=5/1) to afford 1-benzyl 4-(tert-butyl) 2-methyl 2-(cyanomethyl)piperazine-1,2,4-tricarboxylate (1.5 g, 27%) as thick syrup.

m/z (ESI, +ve)=362.1 (M-55).

Step 5: 6-benzyl 9-(tert-butyl) 1-oxo-2,6,9-triazaspiro[4.5]decane-6,9-dicarboxylate

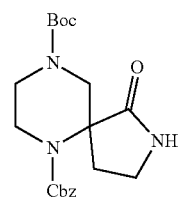

A solution of 1-benzyl 4-(tert-butyl) 2-methyl 2-(cyanomethyl)piperazine-1,2,4-tricarboxylate (1.5 g, 3.59 mmol) and Raney-nickel in methanol (20 mL) was hydrogenated for 16 hours. After consumption of the starting material, the reaction mixture was filtered, the filtrate was concentrated under reduced pressure and the residue was purified by column chromatography (hexanes/ethyl acetate=20/1) to afford tert-butyl 1-oxo-2,6,9-triazaspiro[4.5]decane-9-carboxylate (0.6 g, 67%) as white solid.

$^1$H NMR (400 MHz, CDCl$_3$) δ 7.00-6.77 (m, 1H), 3.90-3.74 (m, 2H), 3.39-3.33 (m, 2H), 2.97-2.79 (m, 4H), 2.36-2.25 (m, 2H), 2.06-2.01 (m, 1H), 1.44 (s, 9H).

Step 6: benzyl 1-oxo-2,6,9-triazaspiro[4.5]decane-6-carboxylate

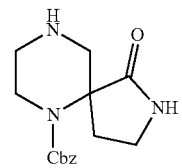 [SMILES: O=C(OCc1ccccc1)N1CCNCC12CCNC2=O]

To a solution of tert-butyl 1-oxo-2,6,9-triazaspiro[4.5]decane-9-carboxylate (0.6 g, 2.4 mmol) in dichloromethane (15 mL), HCl in dioxane (4 M) (2.4 mL, 9.6 mmol) was added and the reaction mixture was stirred at room temperature for 6 hours. After consumption of the starting material, the reaction mixture was concentrated under reduced pressure to afford 2,6,9-triazaspiro[4.5]decan-1-one (370 mg, 98%) as white solid.

m/z (ESI, +ve)=156.1 (M+H)$^+$.

Step 7: 9-chloro-10-(2,4-difluorophenyl)-7-(1-oxo-2,6,9-triazaspiro[4.5]decan-9-yl)-2,3-dihydro-5H-[1,4]thiazino[2,3,4-ij]quinazolin-5-one

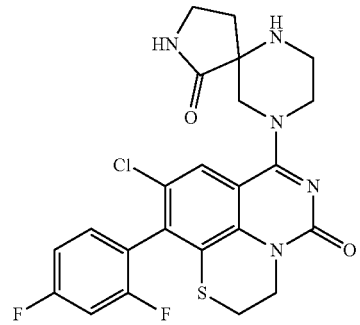 [SMILES: O=C1NCCC12CN(c1nc(=O)n3c4c(c(-c5ccc(F)cc5F)c(Cl)cc14)SCC3)CCN2]

A solution of 9-chloro-10-(2,4-difluorophenyl)-2,3-dihydro-5H-[1,4]thiazino[2,3,4-ij]quinazoline-5,7(6H)-dione (250 mg, 0.68 mmol), potassium carbonate (281 mg, 2.0 mmol) and tosyl chloride (266 mg, 1.4 mmol) in acetonitrile (15 mL) was stirred for 16 hours at room temperature. A second batch of K$_2$CO$_3$ (281 mg, 1.4 mmol) was added, followed by 2,6,9-triazaspiro[4.5]decan-1-one (217 mg, 1.4 mmol). The reaction mixture was stirred at room temperature for 6 hours. After consumption of starting material, the reaction mixture was concentrated under reduced pressure to afford a residue that was purified by reversed phase column chromatography (0.5% TFA in water/acetonitrile=3/1) to afford 9-chloro-10-(2,4-difluorophenyl)-7-(1-oxo-2,6,9-triazaspiro[4.5]decan-9-yl)-2,3-dihydro-5H-[1,4]thiazino[2,3,4-ij]quinazolin-5-one as white solid (150 mg, 44%).

m/z (ESI, +ve)=504.0 (M+H)$^+$.

Example 117: 2-((2R)-4-acryloyl-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile

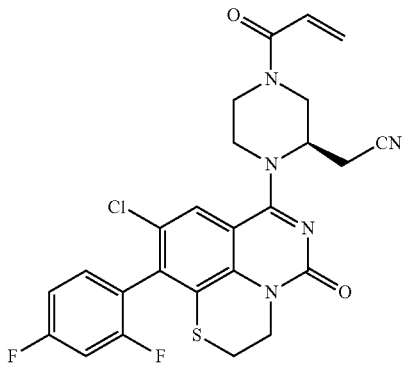 [SMILES: C=CC(=O)N1CCN(c2nc(=O)n3c4c(c(-c5ccc(F)cc5F)c(Cl)cc24)SCC3)[C@H](CC#N)C1]

The title compound was prepared analogously to Example 84 where 2-((2R)-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 13% yield as a white solid.

m/z (ESI, +ve)=528.0 (M+H)$^+$.

1H NMR (400 MHz, DMSO) δ 7.69 (d, J=8.0 Hz, 1H), 7.55-7.35 (m, 2H), 7.33-7.24 (m, 1H), 6.88-6.72 (m, 1H), 6.18 (d, J=16.0 Hz, 1H), 5.76 (d, J=8.0 Hz, 1H), 5.16-4.97 (m, 1H), 4.53-3.51 (m, 7H), 3.19-2.77 (m, 5H).

Step 1: 1-benzyl 4-(tert-butyl) (S)-2-(hydroxymethyl)piperazine-1,4-dicarboxylate

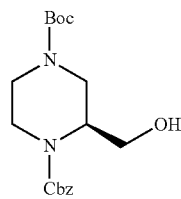

To a solution of tert-butyl (3S)-3-(hydroxymethyl)piperazin-1-yl formate (5 g, 23 mmol) in ethyl acetate (90 mL) was added NaHCO$_3$ (5.8 g, 69 mmol), H$_2$O (45 mL) and CbzCl (5.1 g, 30 mmol). The reaction mixture was stirred at 25° C. for 2 h. The organic layer was washed with H$_2$O (30 mL×2), dried over Na$_2$SO$_4$ and concentrated. The residue was purified by silica gel column chromatography (hexanes: ethyl acetate=2:1) to give tert-butyl (3S)-4-{3-[(formyloxy)methyl]phenyl}-3-(hydroxymethyl)piperazin-1-yl formate (6 g, 70%) as yellow oil.

m/z (ESI, +ve)=373.1 (M+Na)$^+$.

Step 2: 1-benzyl 4-(tert-butyl) (S)-2-(((methylsulfonyl)oxy)methyl)piperazine-1,4-dicarboxylate

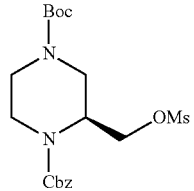

To a solution of 1-benzyl 4-(tert-butyl) (S)-2-(hydroxymethyl)piperazine-1,4-dicarboxylate (11.6 g, 33 mmol) in 2-methyltetrahydrofuran (140 mL) was added triethylamine (10.0 g, 99 mmol) and methanesulfonyl chloride (4.43 g, 38.9 mmol). The reaction mixture was stirred at room temperature for 1 hour. Ethyl acetate was added and the mixture washed with H$_2$O (80 mL×2), dried over Na$_2$SO$_4$ and concentrated under vacuum to afford 1-benzyl 4-(tert-butyl) (S)-2-(((methylsulfonyl)oxy)methyl)piperazine-1,4-dicarboxylate (14.5 g, 97%) as yellow oil.

m/z (ESI, +ve)=451.1 (M+Na)$^+$.

Step 3: 1-benzyl 4-(tert-butyl) (R)-2-(cyanomethyl)piperazine-1,4-dicarboxylate

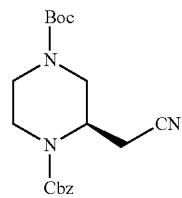 [SMILES: CC(C)(C)OC(=O)N1CCN(C(=O)OCc2ccccc2)[C@H](CC#N)C1]

To a solution of 1-benzyl 4-(tert-butyl) (S)-2-(((methylsulfonyl)oxy)methyl)piperazine-1,4-dicarboxylate (14.6 g, 34 mmol) in dimethylacetamide (80 mL) was added sodium cyanide (6.7 g, 136 mmol) and the reaction mixture was stirred at 60° C. for 15 hours. The mixture was diluted with water (100 mL) and extracted with ethyl acetate (100 mL×2). The combined organic layers were washed with H$_2$O (100 mL×2), dried over Na$_2$SO$_4$ and concentrated under vacuum. The residue was purified by silica gel column chromatography (hexanes:ethyl acetate=2:1) to give 1-benzyl 4-(tert-butyl) (R)-2-(cyanomethyl)piperazine-1,4-dicarboxylate (9 g, 73%) as yellow oil.

m/z (ESI, +ve)=382.1 (M+Na)$^+$.

Step 4: tert-butyl (R)-3-(cyanomethyl)piperazine-1-carboxylate

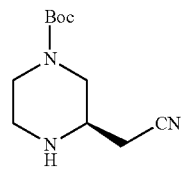 [SMILES: CC(C)(C)OC(=O)N1CCN[C@H](CC#N)C1]

A solution of 1-benzyl 4-(tert-butyl) (R)-2-(cyanomethyl)piperazine-1,4-dicarboxylate (4.5 g, 12.5 mmol), aqueous ammonia (6 mL) and 10% Palladium on carbon (500 mg) in methanol (60 mL) was hydrogenated at room temperature for 1 hour. The reaction was filtered through celite and concentrated to afford tert-butyl (R)-3-(cyanomethyl)piperazine-1-carboxylate (2.8 g, 94%) as white solid.

m/z (ESI, +ve)=451.3 (2M+H)$^+$.

Step 5: tert-butyl (3R)-4-(9-chloro-10-(2,4-difluorophenyl)-5-oxo-2,3-dihydro-5H-[1,4]thiazino[2,3,4-ij]quinazolin-7-yl)-3-(cyanomethyl)piperazine-1-carboxylate

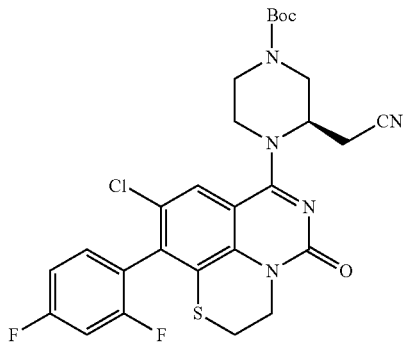 [SMILES: CC(C)(C)OC(=O)N1CCN(c2nc(=O)n3c4c(c(-c5ccc(F)cc5F)c(Cl)cc24)SCC3)[C@H](CC#N)C1]

To a solution of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one (400 mg, 1.09 mmol), tert-butyl (3R)-3-(cyanomethyl)piperazin-1-yl formate (370.0 mg, 1.63 mmol) and benzotriazol-1-yloxytripyrrolidinophosphonium hexafluorophosphate (609.7 mg, 1.30 mmol) in acetonitrile (12 mL) was added DBU (248.9 mg, 1.63 mmol). The reaction mixture was stirred at room temperature for 16 hours. The mixture was concentrated and the crude product was purified by silica gel column chromatography (hexanes:ethyl acetate=1:4) to afford tert-butyl (3R)-4-(9-chloro-10-(2,4-difluorophenyl)-5-oxo-2,3-dihydro-5H-[1,4]thiazino[2,3,4-ij]quinazolin-7-yl)-3-(cyanomethyl)piperazine-1-carboxylate (300 mg, 43%) as yellow solid.

m/z (ESI, +ve)=574.1 (M+H)$^+$.

Step 6: 2-((2R)-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile

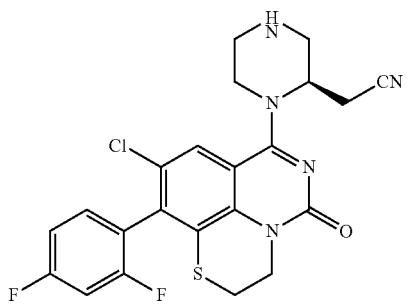 [SMILES: N#CC[C@@H]1CNCCN1c1nc(=O)n2c3c(c(-c4ccc(F)cc4F)c(Cl)cc13)SCC2]

A solution of tert-butyl (3R)-4-(9-chloro-10-(2,4-difluorophenyl)-5-oxo-2,3-dihydro-5H-[1,4]thiazino[2,3,4-ij]quinazolin-7-yl)-3-(cyanomethyl)piperazine-1-carboxylate (150 mg, 0.26 mmol) in HCl-dioxane (4 M) was stirred at 0° C. for 30 minutes. The resulting mixture was concentrated to afford 2-((2R)-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile (150 mg, 72.8%) as a yellow solid.

m/z (ESI, +ve)=474.1 (M+H)$^+$.

Example 118: 7-(4-acryloyl-6-(methylsulfonyl)octahydro-1H-pyrrolo[3,4-b]pyrazin-1-yl)-9-chloro-10-(2,4-difluorophenyl)-2,3-dihydro-5H-[1,4]thiazino[2,3,4-ij]quinazolin-5-one

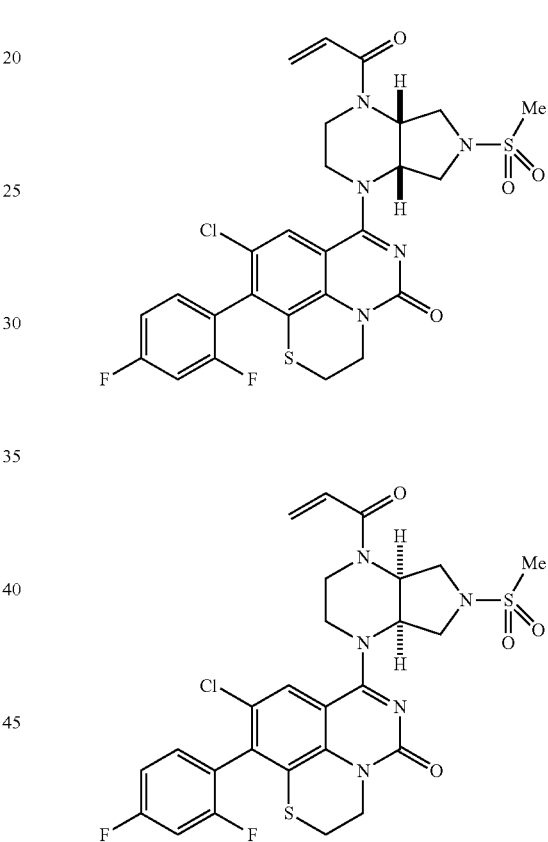

The title compound was prepared analogously to Example 84 where 9-chloro-10-(2,4-difluorophenyl)-7-(6-(methylsulfonyl)octahydro-1H-pyrrolo[3,4-b]pyrazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 11% yield as a pale yellow solid m/z (ESI, +ve)=608.1 (M+H)$^+$.

1H NMR (400 MHz, methanol-d4) δ 7.84-7.82 (m, 1H), 7.34-7.26 (m, 1H), 7.19-7.08 (m, 2H), 6.86-6.73 (m, 1H), 6.31 (d, J=16 Hz, 1H), 5.83 (d, J=12 Hz, 1H), 5.15-5.04 (m, 1H), 4.65-4.59 (m, 1H), 4.42-4.35 (m, 1H), 4.23-4.03 (m, 2H), 3.96-3.92 (m, 1H), 3.85-3.77 (m, 3H), 3.75-3.60 (m, 2H), 3.24-3.11 (m, 3H), 2.96-2.91 (m, 3H).

Step 1: 1,4-dibenzyl-6-(2,4-dimethoxybenzyl)-cis-octahydro-1H-pyrrolo[3,4-b]pyrazine

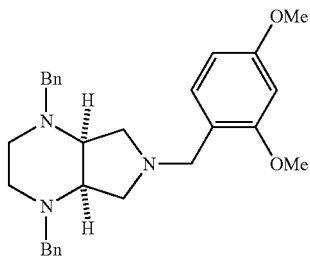 [SMILES: COc1ccc(CN2C[C@@H]3[C@H](C2)N(Cc2ccccc2)CCN3Cc2ccccc2)c(OC)c1]

To a solution of 4-(4-(3-chloro-5-((triisopropylsilyl)oxy)phenyl)-5-iodo-3-(trifluoromethyl)-1H-pyrazol-1-yl)benzonitrile (3 g, 6.1 mmol) in toluene (20 mL) was added (2,4-dimethoxyphenyl)methanamine (3.1 g, 18.4 mmol). The mixture was stirred at reflux for 16 hours. The reaction mixture was quenched with water and then extracted with dichloromethane (10 mL×3). The combined organic layers were dried with $Na_2SO_4$, filtered and concentrated in vacuo. The crude product was purified on a C18 column to afford 1,4-dibenzyl-6-(2,4-dimethoxybenzyl)-cis-octahydro-1H-pyrrolo[3,4-b]pyrazine (800 mg, 25%) as a white solid.

m/z (ESI, +ve)=458.2 $(M+H)^+$.

Step 2: 1,4-dibenzyl-cis-octahydro-1H-pyrrolo[3,4-b]pyrazine

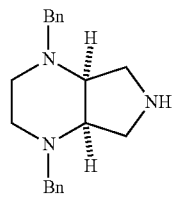 [SMILES: c1ccc(CN2CCN(Cc3ccccc3)[C@H]3CNC[C@H]32)cc1]

A solution of 1,4-dibenzyl-6-(2,4-dimethoxybenzyl)-cis-octahydro-1H-pyrrolo[3,4-b]pyrazine (800 mg, 1.8 mmol) in trifluoroacetic acid (10 mL) was stirred at 50° C. for 2 hours. The reaction mixture was concentrated under reduced pressure to afford 1,4-dibenzyl-cis-octahydro-1H-pyrrolo[3,4-b]pyrazine (500 mg, 90%) as a yellow solid.

m/z (ESI, +ve)=308.2 $(M+H)^+$.

Step 3: 1,4-dibenzyl-6-(methylsulfonyl)octahydro-1H-pyrrolo[3,4-b]pyrazine

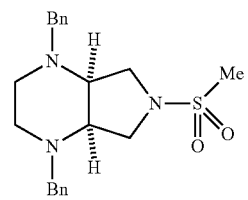 [SMILES: CS(=O)(=O)N1C[C@@H]2[C@H](C1)N(Cc1ccccc1)CCN2Cc1ccccc1]

To a solution of 1,4-dibenzyl-cis-octahydro-1H-pyrrolo[3,4-b]pyrazine (500 mg, 1.6 mmol) and triethylamine (822 mg, 8.1 mmol) in dichloromethane (20 mL) at 0° C., mesyl chloride (916 mg, 8 mmol) was added. The mixture was stirred at 0° C. for 1 h and washed with $H_2O$ (50 mL×3), dried with $Na_2SO_4$, filtered and concentrated in vacuo. The crude product was purified by C18 column to give 1,4-dibenzyl-6-(methylsulfonyl)octahydro-1H-pyrrolo[3,4-b]pyrazine (350 mg, 50%) as a white solid.

m/z (ESI, +ve)=386.2 $(M+H)^+$

Step 4: 6-(methylsulfonyl)-cis-octahydro-1H-pyrrolo[3,4-b]pyrazine

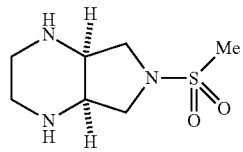

A solution of 1,4-dibenzyl-6-(methylsulfonyl)octahydro-1H-pyrrolo[3,4-b]pyrazine (350 mg, 0.907 mmol), aqueous ammonia (0.1 mL) and 10% palladium on carbon (180 mg) in methanol (5 mL), was hydrogenated at room temperature for 16 hours. The mixture was filtered and concentrated to afford 6-(methylsulfonyl)-cis-octahydro-1H-pyrrolo[3,4-b]pyrazine (250 mg) as colorless oil.

$^1$H NMR (400 MHz, DMSO) δ 4.11-4.09 (m, 1H), 3.66-3.03 (m, 1H), 3.59-3.53 (m, 1H), 3.11-3.03 (m, 4H), 3.01-2.96 (m, 4H), 2.78-2.75 (m, 2H).

Step 5: 9-chloro-10-(2,4-difluorophenyl)-7-(6-(methylsulfonyl)-cis-octahydro-1H-pyrrolo[3,4-b]pyrazin-1-yl)-2,3-dihydro-5H-[1,4]thiazino[2,3,4-ij]quinazolin-5-one

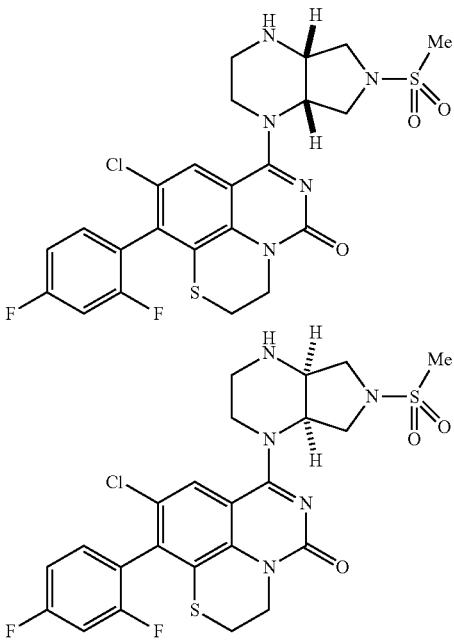

Benzotriazol-1-yl-oxytripyrrolidinophosphonium hexafluorophosphate (459 mg, 1.64 mmol) and DBU (187 mg, 1.23 mmol) were added to a solution of 9-chloro-10-

(2,4-difluorophenyl)-2,3-dihydro-5H-[1,4]thiazino[2,3,4-ij]quinazoline-5,7(6H)-dione (300 mg, 0.82 mmol) in acetonitrile (5 mL) at room temperature. After 20 minutes, 6-(methylsulfonyl)octahydro-1H-pyrrolo[3,4-b]pyrazine (337 mg, 1.64 mmol) was added and the reaction mixture was stirred at room temperature for another 16 hours. The reaction mixture was concentrated under reduced pressure to afford a residue that was purified by silica gel chromatography to afford 9-chloro-10-(2,4-difluorophenyl)-7-(6-(methylsulfonyl)-cis-octahydro-1H-pyrrolo[3,4-b]pyrazin-1-yl)-2,3-dihydro-5H-[1,4]thiazino[2,3,4-ij]quinazolin-5-one (55 mg, 9%) as a yellow solid.

m/z (ESI, +ve)=554.1 (M+H)$^+$.

Example 128: 7-(5-acryloyl-1-oxo-2,5,8-triazaspiro[3.5]nonan-8-yl)-9-chloro-10-(2,4-difluorophenyl)-2,3-dihydro-5H-[1,4]thiazino[2,3,4-ij]quinazolin-5-one

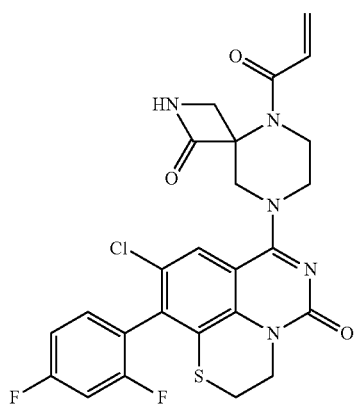 [SMILES: C=CC(=O)N1CCN(c2nc(=O)n3c4c(c(-c5ccc(F)cc5F)c(Cl)cc24)SCC3)CC12CNC2=O]

The title compound was prepared analogously to Example 84 where 9-chloro-10-(2,4-difluorophenyl)-7-(1-oxo-2,5,8-triazaspiro[3.5]nonan-8-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 17% yield as a white solid m/z (ESI, +ve)=544

1H NMR (400 MHz, DMSO) δ 8.11 (s, 1H), 7.83 (s, 1H), 7.51-7.37 (m, 2H), 7.29-7.26 (m, 1H), 6.77-6.70 (m, 1H), 6.19 (d, J=16 Hz), 5.80 (d, J=12 Hz), 4.47-4.01 (m, 7H), 3.55-3.52 (m, 1H), 3.29-3.04 (m, 4H)

Step 1: ethyl 1,4-dibenzylpiperazine-2-carboxylate

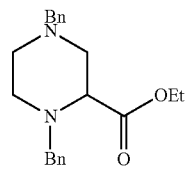 [SMILES: CCOC(=O)C1CN(Cc2ccccc2)CCN1Cc1ccccc1]

A solution of ethyl 2,3-dibromopropionate (25.7 g, 0.1 mol) in toluene (120 mL) was added to a solution of N,N'-dibenzylethylenediamine (24.0 g, 0.1 mol) and triethylamine (22.3 uL, 0.22 mol) in toluene (120 mL) previously warmed up to 80 deg. The reaction mixture was stirred at 80° C. for three hours and washed with water and brine, dried over Na$_2$SO$_4$, filtered and concentrated under reduced pressure. Ethyl 1,4-dibenzylpiperazine-2-carboxylate was isolated as a light-yellow oil in 89% yield Step 2: 5,8-dibenzyl-2,5,8-triazaspiro[3.5]nonan-1-one

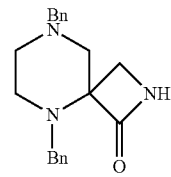 [SMILES: O=C1NCC12CN(Cc1ccccc1)CCN2Cc1ccccc1]

To a solution of ethyl 1,4-dibenzylpiperazine-2-carboxylate (3.4 g, 10 mmol) in THF (34 mL) was added paraformaldehyde (300 mg, 10 mmol) and LiHMDS (1M in THF) (40 mL, 40 mmol) at −10° C. The reaction mixture was brought to room temperature and stirred for 4 hours. The reaction mixture was diluted with water (200 mL) and extracted with ethyl acetate (3×100 mL). The combined organic layers were dried over Na$_2$SO$_4$ and concentrated to afford 5,8-dibenzyl-2,5,8-triazaspiro[3.5]nonan-1-one as white solid in 80% yield H NMR (400 MHz, CDCl$_3$) δ 7.41-7.19 (m, 10H), 5.81 (s, 1H), 3.98 (d, J=13.0 Hz, 1H), 3.63 (dd, J=25.3, 9.3 Hz, 2H), 3.42 (dd, J=33.4, 13.1 Hz, 2H), 3.18 (d, J=5.7 Hz, 1H), 2.84 (d, J=10.9 Hz, 1H), 2.72-2.53 (m, 3H), 2.38-2.21 (m, 2H).

Step 3: 2,5,8-triazaspiro[3.5]nonan-1-one

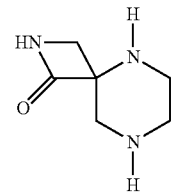

A solution of 5,8-dibenzyl-2,5,8-triazaspiro[3.5]nonan-1-one (3.2 g, 10 mmol) and Pd(OH)2 (140 mg, 1 mmol) in methanol (32 ml) was hydrogenated at room temperature for 6 hours. The reaction was filtered and concentrated to afford the desired product as a light-yellow oil in 93% yield Step 4: 9-chloro-10-(2,4-difluorophenyl)-7-(1-oxo-2,5,8-triazaspiro[3.5]nonan-8-yl)-2,3-dihydro-5H-[1,4]thiazino[2,3,4-ij]quinazolin-5-one

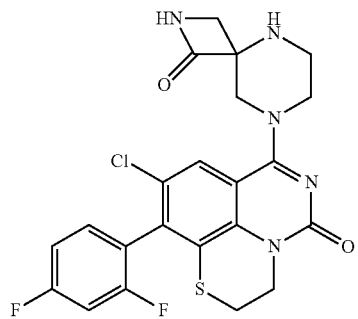 [SMILES: O=C1NCC12CN(c1nc(=O)n3c4c(c(-c5ccc(F)cc5F)c(Cl)cc14)SCC3)CCN2]

A mixture of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one (120 mg, 0.66 mmol), POCl3 (1 ml) and DIPEA (130 mg, 1 mmol) was stirred at 120° C. for 2 hours. The reaction mixture was then allowed to cool to room temperature and volatiles removed under reduced pressure to afford a brown oil that was immediately dissolved in dichloromethane (10 ml). DIPEA (426 mg, 3.3 mmol) and 2,5,8-triazaspiro[3.5]nonan-1-one (185 mg, 1.3 mmol) were added and the resulting mixture stirred at room temperature for 2 hours. The reaction mixture was diluted with dichloromethane (100 ml), washed with water (50 ml), brine (50 ml) dried over Na2SO4, filtered and concentrated in vacuo to afford 9-chloro-10-(2,4-difluorophenyl)-7-(1-oxo-2,5,8-triazaspiro[3.5]nonan-8-yl)-2,3-dihydro-5H-[1,4]thiazino[2,3,4-ij]quinazolin-5-one as a yellow solid in 49% yield.

m/z (ESI, +ve)=490

Example 129: 7-(9-acryloyl-3-thia-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one

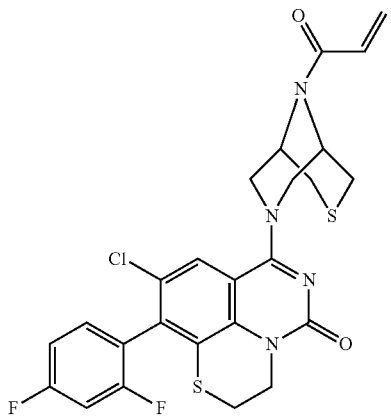 [SMILES: C=CC(=O)N1C2CSCC1CN(c1nc(=O)n3c4c(c(-c5ccc(F)cc5F)c(Cl)cc14)SCC3)C2]

The title compound was prepared analogously to Example 84 where 7-(3-thia-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 4% yield as a white solid.

m/z (ESI, +ve)=547.0 (M+H)+.

1H NMR (400 MHz, methanol-d4) δ 7.81 (s, 1H), 7.34-7.28 (m, 1H), 7.16-7.10 (m, 2H), 6.81 (dd, J=8.0 Hz, 16.0 Hz, 1H), 6.30 (d, J=16.0 Hz, 1H), 5.83 (d, J=8.0 Hz, 1H), 5.02-4.95 (m, 1H), 4.81-4.76 (m, 1H), 4.70-4.60 (m, 1H), 4.43-4.38 (m, 1H), 4.20-4.17 (m, 1H), 3.91-3.86 (m, 1H), 3.81-3.76 (m, 1H), 3.19-3.13 (m, 4H), 2.77-2.65 (m, 3H).

Step 1: tert-butyl-3-thia-7,9-diazabicyclo[3.3.1]nonane-7-carboxylate

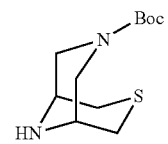

A mixture of tert-butyl-9-benzyl-3-thia-7,9-diazabicyclo[3.3.1]nonane-7-carboxylate (1 g, 3.0 mmol), NH4OH (0.2 mL) and Pd(OH)2/C (20%, 5 g) in methanol (10 mL) was hydrogenated for 16 hours at room temperature. The mixture was filtered and concentrated to afford tert-butyl-3-thia-7,9-diazabicyclo[3.3.1]nonane-7-carboxylate (400 mg, 93%) as a yellow solid.

1H NMR (400 MHz, DMSO) δ 4.07-3.97 (m, 2H), 3.26-3.22 (m, 2H), 3.10-3.01 (m, 4H), 2.51 (m, 1H), 2.40-2.36 (m, 1H), 1.41 (s, 9H).

Step 2: 3-thia-7,9-diazabicyclo[3.3.1]nonane

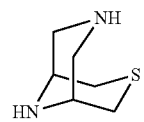

A solution of tert-butyl-3-thia-7,9-diazabicyclo[3.3.1]nonane-7-carboxylate (400 mg) in dichloromethane/trifluoroacetic acid (5/1, 6 mL) was stirred at room temperature for 4 hours. The solution was concentrated to afford a residue that was purified by reversed phase chromatography to afford the desired product (263 mg) as a white solid.

Step 3: 7-(3-thia-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one

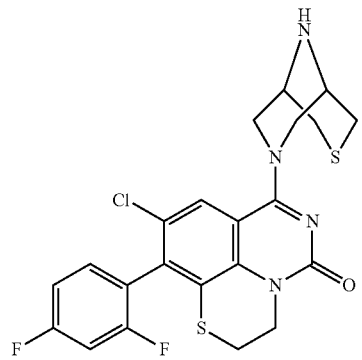 [SMILES: O=c1nc(N2CC3CSCC(C2)N3)c2cc(Cl)c(-c3ccc(F)cc3F)c3c2n1CCS3]

The title compound was prepared analogously to Example 84 where 3-thia-7,9-diazabicyclo[3.3.1]nonane was substituted in place of 3-thia-7,9-diazabicyclo[3.3.1]nonane 3,3-dioxide in 4% yield as a white solid.

m/z (ESI, +ve)=493.0 (M+H)⁺.

Example 131: 7-((4-acryloyl-6,6-dioxidohexahydrothieno[3,4-b]pyrazin-1(2H)-yl)-9-chloro-10-(2,4-difluorophenyl)-2,3-dihydro-5H-[1,4]thiazino[2,3,4-ij]quinazolin-5-one

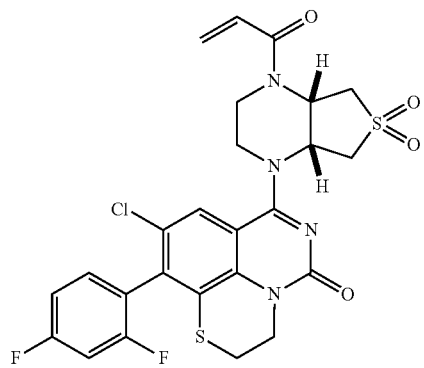

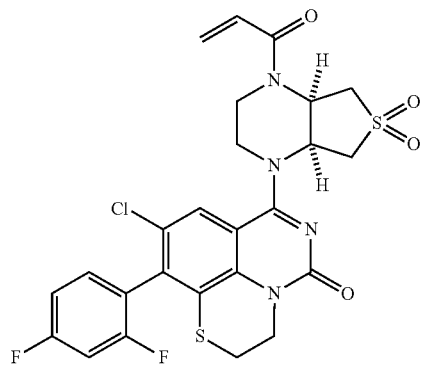

The title compound was prepared analogously to Example 84 where 9-chloro-10-(2,4-difluorophenyl)-7-(6,6-dioxidohexahydrothieno[3,4-b]pyrazin-1(2H)-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 27% yield as a yellow solid.

m/z (ESI, +ve)=579.0 (M+H)⁺.

$^1$H NMR (400 MHz, methanol-d4) δ 7.87 (d, J=2.0 Hz, 1H), 7.35-7.22 (m, 1H), 7.12 (t, J=9.6 Hz, 2H), 6.84-6.68 (m, 1H), 6.30 (d, J=16.8 Hz, 1H), 5.83 (d, J=10.8 Hz, 1H), 5.42-5.38 (m, 1H), 4.74-4.65 (m, 1H), 4.57 (s, 1H), 4.30-4.08 (m, 2H), 4.08-3.82 (m, 3H), 3.78-3.61 (m, 5H), 3.29-3.12 (m, 2H).

Step 1: 9-chloro-10-(2,4-difluorophenyl)-7-(6,6-dioxidohexahydrothieno[3,4-b]pyrazin-1(2H)-yl)-2,3-dihydro-5H-[1,4]thiazino[2,3,4-ij]quinazolin-5-one

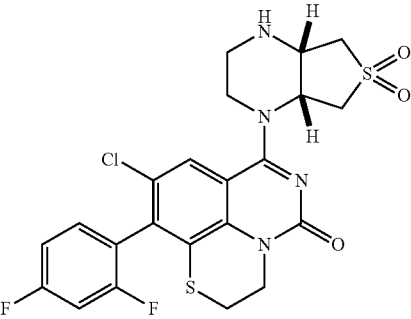

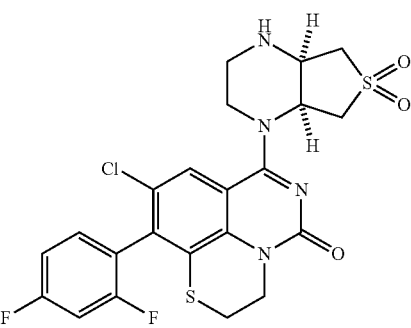

A mixture of 9-chloro-10-(2,4-difluorophenyl)-2,3-dihydro-5H-[1,4]thiazino[2,3,4-ij]quinazoline-5,7(6H)-dione (250 mg, 0.68 mmol), tosyl chloride (634 mg, 1.36 mmol) and potassium carbonate (321 mg, 2.04 mmol) in acetonitrile (10 ml) was stirred at room temperature for 16 hours. cis-octahydrothieno[3,4-b]pyrazine 6,6-dioxide (240 mg, 1.36 mmol) and potassium carbonate (321 mg, 2.04 mmol) were added and the reaction mixture was stirred at room temperature for 1 h. The solvent was removed in vacuo to afford a residue that was purified by silica gel chromatography to afford 9-chloro-10-(2,4-difluorophenyl)-7-((4aR,7aS)-6,6-dioxidohexahydrothieno[3,4-b]pyrazin-1(2H)-yl)-2,3-dihydro-5H-[1,4]thiazino[2,3,4-ij]quinazolin-5-one (135 mg, 34%) as a yellow solid.

m/z (ESI, +ve)=525.0 (M+H)⁺.

Example 132: 7-((S)-4-acryloyl-2-methylpiperazin-1-yl)-10-(2,4-difluorophenyl)-5-oxo-2,3-dihydro-5H-[1,4]thiazino[2,3,4-ij]quinazoline-9-carbonitrile

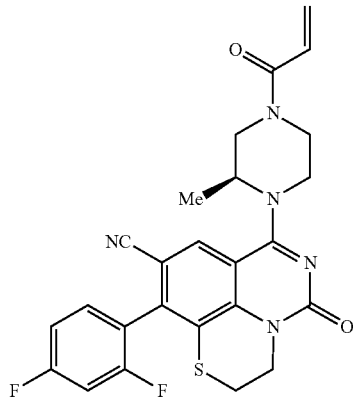 [SMILES: C=CC(=O)N1CCN(c2nc(=O)n3c4c(c(-c5ccc(F)cc5F)c(C#N)cc24)SCC3)[C@@H](C)C1]

The title compound was prepared analogously to Example 84 where 9-bromo-10-(2,4-difluorophenyl)-7-((S)-2-methylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 27% yield as a yellow solid.

m/z (ESI, +ve)=494.1 (M+H)$^+$.

$^1$H NMR (400 MHz, methanol-d4) δ 8.00 (d, J=10.4 Hz, 1H), 7.46-7.43 (m, 1H), 7.23-7.15 (m, 2H), 6.87-6.76 (m, 1H), 6.29 (dd, J=6.0 Hz, 16.8 Hz, 1H), 5.81 (dd, J=1.6 Hz, 10.4 Hz, 1H), 4.89-4.65 (m, 1H), 4.55-4.40 (m, 2H), 4.30-4.02 (m, 3H), 3.80-3.60 (m, 2H), 3.55-3.42 (m, 1H), 3.23-3.19 (m, 2H), 1.40 (dd, J=6.8 Hz, 16.4 Hz, 3H).

Step 1: 9-bromo-10-(2,4-difluorophenyl)-7-((S)-2-methylpiperazin-1-yl)-2,3-dihydro-5H-[1,4]thiazino[2,3,4-ij]quinazolin-5-one

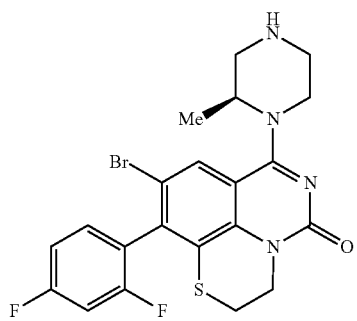 [SMILES: C[C@H]1CNCCN1c1nc(=O)n2c3c(c(-c4ccc(F)cc4F)c(Br)cc13)SCC2]

To a solution of tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (900 mg, 1.52 mmol) in dichloromethane (20 mL) was added trifluoroacetic acid (5 mL). The reaction mixture was stirred at 25° C. for 1 hour. The mixture was concentrated under reduced pressure to afford a residue that was redissolved in dichloromethane (20 mL), washed with saturated NaHCO$_3$, dried over anhydrous Na$_2$SO$_4$ and filtered. Evaporation of volatiles under reduced pressure afforded 9-bromo-10-(2,4-difluorophenyl)-7-((S)-2-methylpiperazin-1-yl)-2,3-dihydro-5H-[1,4]thiazino[2,3,4-ij]quinazolin-5-one (700 mg, 84%) as a yellow solid.

m/z (ESI, +ve)=493.0 (M+H)$^+$.

Step 2: 10-(2,4-difluorophenyl)-7-((S)-2-methylpiperazin-1-yl)-5-oxo-2,3-dihydro-5H-[1,4]thiazino[2,3,4-ij]quinazoline-9-carbonitrile

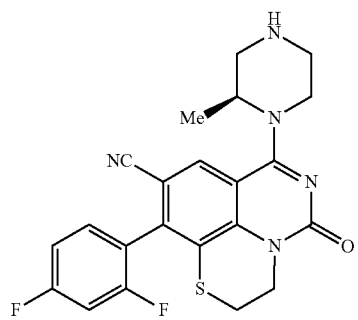 [SMILES: C[C@H]1CNCCN1c1nc(=O)n2c3c(c(-c4ccc(F)cc4F)c(C#N)cc13)SCC2]

To a mixture of 9-bromo-10-(2,4-difluorophenyl)-7-((S)-2-methylpiperazin-1-yl)-2,3-dihydro-5H-[1,4]thiazino[2,3,4-ij]quinazolin-5-one (700 mg, 1.42 mmol), zinc cyanide (333 mg, 2.84 mmol), 1,1'-bis(diphenylphosphino)ferrocene palladium dichloride (208 mg, 0.284 mmol) and Xantphos (328 mg, 0.568 mmol) in dimethylacetamide (10 mL) was added DIPEA (366 mg, 2.84 mmol). The reaction mixture was stirred at 140° C. for 16 hours and the insoluble materials were filtered out. The solution was concentrated under reduced pressure to afford a residue that was purified by reverse phase chromatography to afford 10-(2,4-difluorophenyl)-7-((S)-2-methylpiperazin-1-yl)-5-oxo-2,3-dihydro-5H-[1,4]thiazino[2,3,4-ij]quinazoline-9-carbonitrile (200 mg, 28%) as yellow oil.

m/z (ESI, +ve)=440.1 (M+H)$^+$.

Example 133: 7-(5-acryloyl-2-methyl-1-oxo-2,5,8-triazaspiro[3.5]nonan-8-yl)-9-chloro-10-(2,4-difluorophenyl)-2,3-dihydro-5H-[1,4]thiazino[2,3,4-ij]quinazolin-5-one

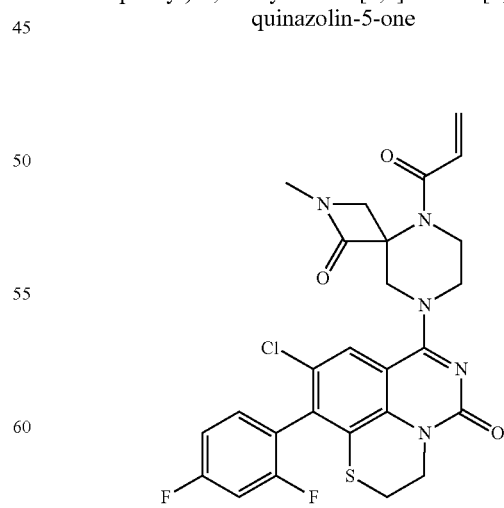

The title compound was prepared analogously to Example 84 where 9-chloro-10-(2,4-difluorophenyl)-7-(2-methyl-1-oxo-2,5,8-triazaspiro[3.5]nonan-8-yl)-2,3-dihydro-5H-[1,4]

thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 22% yield as a white solid.

m/z (ESI, +ve)=558

1H NMR (400 MHz, DMSO) δ 7.83 (d, J=2.7 Hz, 1H), 7.48 (td, J=9.8, 2.5 Hz, 1H), 7.44-7.34 (m, 1H), 7.27 (t, J=8.5 Hz, 1H), 6.73 (ddd, J=16.6, 10.4, 2.4 Hz, 1H), 6.24-6.14 (m, 1H), 5.80 (dd, J=11.4, 1.1 Hz, 1H), 4.52-4.22 (m, 1H), 4.19-4.01 (m, 2H), 4.00-3.78 (m, 4H), 3.54 (dd, J=11.5, 5.1 Hz, 1H), 3.36 (dd, J=11.6, 5.9 Hz, 2H), 3.25-3.02 (m, 2H), 2.76 (s, 3H).

Step 1: 5,8-dibenzyl-2-methyl-2,5,8-triazaspiro[3.5]nonan-1-one

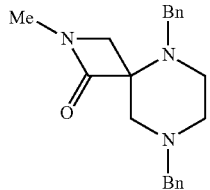 [SMILES: CN1CC2(CN(Cc3ccccc3)CCN2Cc2ccccc2)C1=O]

NaH (600 mg, 15 mmol, 1.5 equiv) was added over a solution of 5,8-dibenzyl-2,5,8-triazaspiro[3.5]nonan-1-one (3.2 g, 10 mmol, 1.0 equiv) in DMF (32 ml) at room temperature. After 30 minutes, methyl iodide (2.9 g, 20 mmol, 2 eq) was added and the reaction stirred for 2 hours. The reaction was quenched with aqueous NH4Cl, extractered with methyl tertbutyl ether and washed with brine. The volatiles were removed in vacuo to afford 5,8-dibenzyl-2-methyl-2,5,8-triazaspiro[3.5]nonan-1-one as a light-yellow solid in 90% yield.

Step 2: 2-methyl-2,5,8-triazaspiro[3.5]nonan-1-one

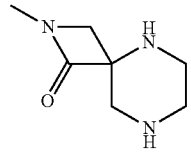

A solution of 5,8-dibenzyl-2-methyl-2,5,8-triazaspiro[3.5]nonan-1-one (3.4 g, 10 mmol, 1.0 equiv) and Pd(OH)2 (0.1 equiv) in methanol (34 ml) was hydrogenated at room temperature for 6 hours. The reaction was filtered through celite and concentrated in vacuo, to afford the desired product in 90% yield.

m/z (ESI, +ve)=156.

Step 3: 9-chloro-10-(2,4-difluorophenyl)-7-(2-methyl-1-oxo-2,5,8-triazaspiro[3.5]nonan-8-yl)-2,3-dihydro-5H-[1,4]thiazino[2,3,4-ij]quinazolin-5-one

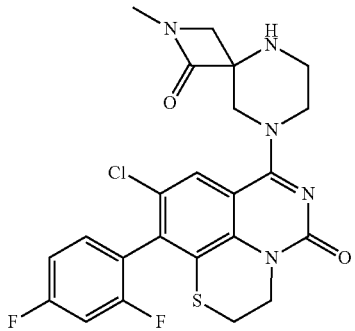 [SMILES: CN1CC2(CN(c3nc(=O)n4c5c(c(-c6ccc(F)cc6F)c(Cl)cc35)SCC4)CCN2)C1=O]

A mixture of 2-methyl-2,5,8-triazaspiro[3.5]nonan-1-one (120 mg, 0.33 mmol), POCl3 (1 ml) and DIPEA (130 mg, 1 mmol) was stirred at 120° C. for 2 hours. The reaction mixture was allowed to cool to room temperature and concentrated under reduced pressure at 60° C. to afford the crude product as a brown oil. This residue was taken up in dichloromethane (10 ml) and DIPEA (426 mg, 3.3 mmol, 10 equiv) and 2-methyl-2,5,8-triazaspiro[3.5]nonan-1-one (200 mg, 1.3 mmol, 4 equiv) were added. The resulting reaction mixture was stirred for 2 hours at room temperature and diluted with dichloromethane (100 ml), washed with water (50 ml), brine (50 mL), dried over Na2SO4, filtered and concentrated to afford the crude product as a yellow solid in 60% yield.

m/z (ESI, +ve)=504

Example 138: 7-(9-acryloyl-7-oxo-3,9-diazabicyclo[3.3.1]nonan-3-yl)-9-chloro-10-(2,4-difluorophenyl)-2,3-dihydro-5H-[1,4]thiazino[2,3,4-ij]quinazolin-5-one

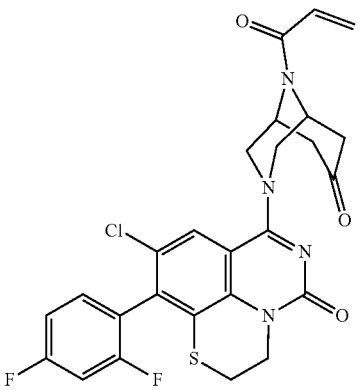 [SMILES: C=CC(=O)N1C2CC(=O)CC1CN(c1nc(=O)n3c4c(c(-c5ccc(F)cc5F)c(Cl)cc14)SCC3)C2]

The title compound was prepared analogously to Example 84 where 9-chloro-10-(2,4-difluorophenyl)-7-(7-oxo-3,9-diazabicyclo[3.3.1]nonan-3-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 11% yield as a white solid.

m/z (ESI, +ve)=543

1H NMR (400 MHz) δ 8.42 (s, 1H), 7.52 (s, 1H), 7.47 (d, J=7.8 Hz, 1H), 7.40 (dd, J=15.1, 7.7 Hz, 1H), 7.28 (t, J=7.5 Hz, 1H), δ 7.01-6.85 (m, 1H), 6.26 (d, J=16.8 Hz, 1H), 5.83 (d, J=10.7 Hz, 1H), 5.14 (s, 1H), 4.91 (s, 1H), 4.34-4.20 (m, 1H), 4.18-3.97 (m, 4H), 3.30-3.11 (m, 4H), 2.84-2.65 (m, 2H).

Step 1: 9-chloro-10-(2,4-difluorophenyl)-7-(7-oxo-3,9-diazabicyclo[3.3.1]nonan-3-yl)-2,3-dihydro-5H-[1,4]thiazino[2,3,4-ij]quinazolin-5-one

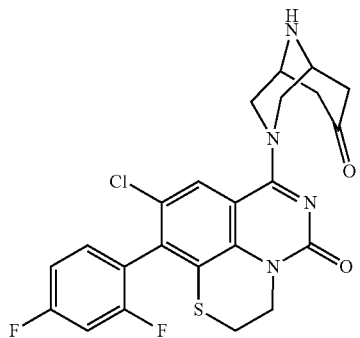 [SMILES: O=C1CC2CN(c3nc(=O)n4c5c(c(-c6ccc(F)cc6F)c(Cl)cc35)SCC4)CC(C1)N2]

A mixture of 9-chloro-10-(2,4-difluorophenyl)-2,3-dihydro-5H-[1,4]thiazino[2,3,4-ij]quinazoline-5,7(6H)-dione (120 mg, 0.33 mmol), POCl3 (1 ml) and DIPEA (130 mg, 1 mmol) was stirred at 120° C. for 2 hours. The reaction mixture was then allowed to cool down to room temperature followed by elimination of the volatiles under reduced pressure at 60° C. The remaining brown oil was taken up in DMF (10 ml) and potassium carbonate (415 mg, 2 mmol, 9 equiv) and 3,9-diazabicyclo[3.3.1]nonan-7-one (280 mg, 2 mmol, 6 equiv) were added and the mixture stirred at room temperature for 2 hours. The reaction was diluted with ethyl acetate (100 ml), washed with water (50 ml) and brine (50 ml), dried over Na2SO4, filtered and concentrated in vacuo to afford the desired product as a yellow solid (80 mg) in 50% yield.

m/z (ESI, +ve)=489.

Example 139: 7-((R)-4-acryloyl-3-methylpiperazin-1-yl)-9-chloro-10-(2,4-difluorophenyl)-2,3-dihydro-5H-[1,4]thiazino[2,3,4-ij]quinazolin-5-one

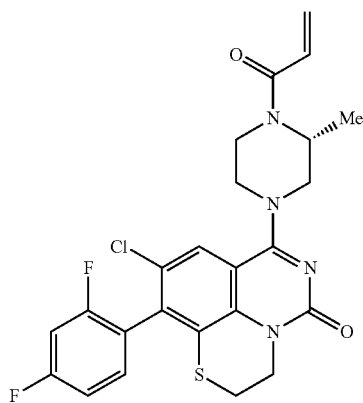 [SMILES: C=CC(=O)N1CCN(c2nc(=O)n3c4c(c(-c5ccc(F)cc5F)c(Cl)cc24)SCC3)C[C@H]1C]

The title compound was prepared analogously to Example 84 where -chloro-10-(2,4-difluorophenyl)-7-((R)-3-methylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 39% yield as a yellow solid.

m/z (ESI, +ve)=504.1 (M+H)+.

1H NMR (400 MHz, methanol-d4) δ 7.78 (s, 1H), 7.34-7.22 (m, 1H), 7.15-7.11 (m, 2H), 6.81-6.75 (m, 1H), 6.25 (d, J=16.4, Hz 1H), 5.78 (d, J=10.8 Hz, 1H), 4.57-4.52 (m, 1H), 4.40-4.24 (m, 3H), 4.20-4.16 (m, 1H), 4.10-4.04 (m, 1H), 3.79 (dd, J=13.6 Hz, 4.0 Hz, 1H), 3.70 (dd, J=13.6 Hz, 4.0 Hz, 1H), 3.51-3.46 (m, 1H), 3.24-3.11 (m, 2H), 1.33-1.29 (m, 3H).

Step 1: tert-butyl (2R)-4-(9-chloro-10-(2,4-difluorophenyl)-5-oxo-2,3-dihydro-5H-[1,4]thiazino[2,3,4-ij]quinazolin-7-yl)-2-methylpiperazine-1-carboxylate

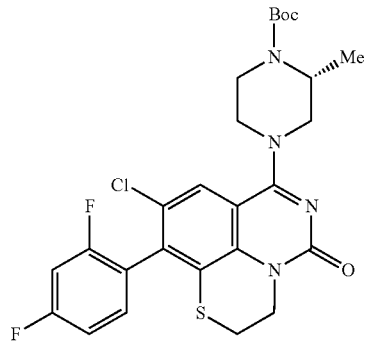 [SMILES: C[C@@H]1CN(c2nc(=O)n3c4c(c(-c5ccc(F)cc5F)c(Cl)cc24)SCC3)CCN1C(=O)OC(C)(C)C]

To a solution of 9-chloro-10-(2,4-difluorophenyl)-2,3-dihydro-5H-[1,4]thiazino[2,3,4-ij]quinazoline-5,7(6H)-dione (400 mg, 1.09 mmol) in ACN (5 mL) were added benzotriazol-1-yl-oxytripyrrolidinophosphonium hexafluorophosphate (610 mg, 1.3 mmol) and DBU (249 mg, 1.635 mmol). The reaction mixture was stirred at room temperature for 20 minutes. tert-butyl (R)-2-methylpiperazine-1-carboxylate (439 mg, 2.18 mmol) was added and the reaction mixture was stirred at room temperature for another 16 hours. The mixture was concentrated under reduced pressure to afford a residue that was purified by silica gel chromatography to yield tert-butyl (2R)-4-(9-chloro-10-(2,4-difluorophenyl)-5-oxo-2,3-dihydro-5H-[1,4]thiazino[2,3,4-ij]quinazolin-7-yl)-2-methylpiperazine-1-carboxylate (320 mg, 53%) as a yellow solid.

m/z (ESI, +ve)=549.2 (M+H)+.

1H NMR (400 MHz, DMSO) δ 7.72 (d, J=3.2 Hz, 1H), 7.50 (dd, J=9.6 Hz, 2.4 Hz, 1H), 7.47-7.37 (m, 1H), 7.28 (td, J=8.4 Hz, 2.4 Hz, 1H), 4.36-4.32 (m, 2H), 4.19-3.89 (m, 4H), 3.81-3.76 (m, 1H), 3.54-3.48 (m, 1H), 3.23-3.09 (m, 3H), 1.43 (s, 9H), 1.27-1.08 (m, 4H).

Step 2: 9-chloro-10-(2,4-difluorophenyl)-7-((R)-3-methylpiperazin-1-yl)-2,3-dihydro-5H-[1,4]thiazino[2,3,4-ij]quinazolin-5-one

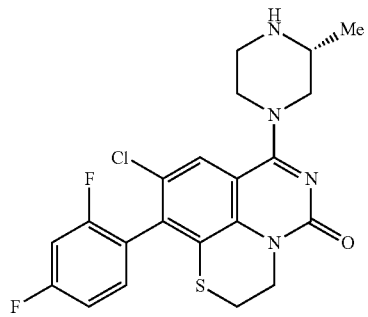 [SMILES: C[C@@H]1CN(c2nc(=O)n3c4c(c(-c5ccc(F)cc5F)c(Cl)cc24)SCC3)CCN1]

To a solution of tert-butyl (2R)-4-(9-chloro-10-(2,4-difluorophenyl)-5-oxo-2,3-dihydro-5H-[1,4]thiazino[2,3,4-ij]quinazolin-7-yl)-2-methylpiperazine-1-carboxylate (320 mg, 0.58 mmol) in dichloromethane (6 mL) was added trifluoroacetic acid (2 mL). The reaction mixture was stirred at room temperature for 1 hour. The solution was concentrated under reduced pressure to afford 9-chloro-10-(2,4-difluorophenyl)-7-((R)-3-methylpiperazin-1-yl)-2,3-dihydro-5H-[1,4]thiazino[2,3,4-ij]quinazolin-5-one (300 mg) as a light yellow solid.

m/z (ESI, +ve)=449.1 (M+H)+.

Example 140: 7-((S)-4-acryloyl-3-methylpiperazin-1-yl)-9-chloro-10-(2,4-difluorophenyl)-2,3-dihydro-5H-[1,4]thiazino[2,3,4-ij]quinazolin-5-one

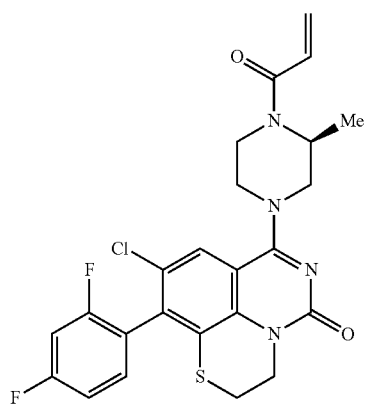 [SMILES: C=CC(=O)N1CCN(c2nc(=O)n3c4c(c(-c5ccc(F)cc5F)c(Cl)cc24)SCC3)C[C@@H]1C]

The title compound was prepared analogously to Example 84 where 9-chloro-10-(2,4-difluorophenyl)-7-((S)-3-methylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 22% yield as a yellow solid.

m/z (ESI, +ve)=504.1 (M+H)+.

$^1$H NMR (400 MHz, methanol-d4) δ 7.78 (s, 1H), 7.41-7.26 (m, 1H), 7.17-7.07 (m, 2H), 6.78 (dd, J=16.8 Hz, 10.8 Hz, 1H), 6.27 (s, 1H), 5.78 (d, J=10.8 Hz, 1H), 4.57-4.52 (m, 1H), 4.32-4.24 (m, 3H), 4.12-4.01 (m, 1H), 3.82-3.68 (m, 2H), 3.51-3.46 (m, 1H), 3.23-3.12 (m, 2H), 1.30 (d, J=7.2 Hz, 3H).

Step 1: tert-butyl (2S)-4-(9-chloro-10-(2,4-difluorophenyl)-5-oxo-2,3-dihydro-5H-[1,4]thiazino[2,3,4-ij]quinazolin-7-yl)-2-methylpiperazine-1-carboxylate

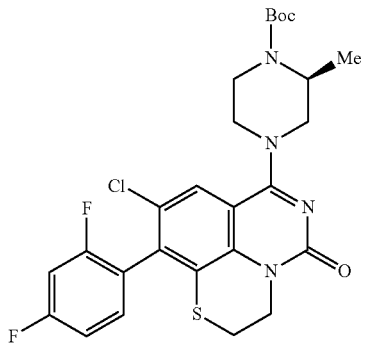 [SMILES: C[C@H]1CN(c2nc(=O)n3c4c(c(-c5ccc(F)cc5F)c(Cl)cc24)SCC3)CCN1C(=O)OC(C)(C)C]

To a solution of 9-chloro-10-(2,4-difluorophenyl)-2,3-dihydro-5H-[1,4]thiazino[2,3,4-ij]quinazoline-5,7(6H)-dione (400 mg, 1.09 mmol) in ACN (5 mL) were added benzotriazol-1-yl-oxytripyrrolidinophosphonium hexafluorophosphate (610 mg, 1.3 mmol) and DBU (249 mg, 1.635 mmol). The reaction mixture was stirred at room temperature for 20 minutes. Then tert-butyl (S)-2-methylpiperazine-1-carboxylate (439 mg, 2.18 mmol) was added. After stirring at room temperature for 16 hours the mixture was concentrated to afford a residue that was purified by silica gel chromatography affording tert-butyl (2S)-4-(9-chloro-10-(2,4-difluorophenyl)-5-oxo-2,3-dihydro-5H-[1,4]thiazino[2,3,4-ij]quinazolin-7-yl)-2-methylpiperazine-1-carboxylate (300 mg, 49%) as a yellow solid.

m/z (ESI, +ve)=549.2 (M+H)+.

Step 2: 9-chloro-10-(2,4-difluorophenyl)-7-((S)-3-methylpiperazin-1-yl)-2,3-dihydro-5H-[1,4]thiazino[2,3,4-ij]quinazolin-5-one

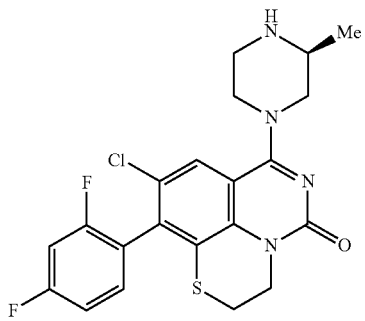 [SMILES: C[C@H]1CN(c2nc(=O)n3c4c(c(-c5ccc(F)cc5F)c(Cl)cc24)SCC3)CCN1]

To a solution of tert-butyl (2S)-4-(9-chloro-10-(2,4-difluorophenyl)-5-oxo-2,3-dihydro-5H-[1,4]thiazino[2,3,4-ij]quinazolin-7-yl)-2-methylpiperazine-1-carboxylate (290 mg, 0.54 mmol) in dichloromethane (6 mL) was added trifluoroacetic acid (2 mL) at 0° C. The reaction mixture was stirred at room temperature for 1 hour. The mixture was concentrated to afford 9-chloro-10-(2,4-difluorophenyl)-7-((S)-3-methylpiperazin-1-yl)-2,3-dihydro-5H-[1,4]thiazino[2,3,4-ij]quinazolin-5-one (290 mg) as a light yellow solid.

m/z (ESI, +ve)=449.1 (M+H)+.

Example 141: 7-((S)-4-acryloyl-2-methylpiperazin-1-yl)-10-(2,4-difluorophenyl)-9-(trifluoromethyl)-2,3-dihydro-5H-[1,4]thiazino[2,3,4-ij]quinazolin-5-one

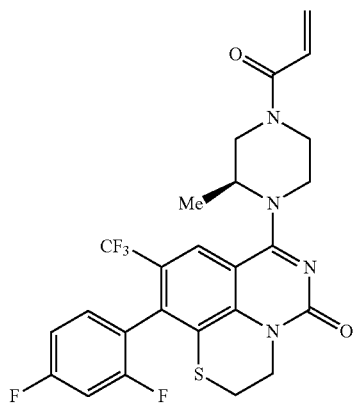 [SMILES: C=CC(=O)N1CCN(c2nc(=O)n3c4c(c(-c5ccc(F)cc5F)c(C(F)(F)F)cc24)SCC3)[C@@H](C)C1]

The title compound was prepared analogously to Example 84 where 10-(2,4-difluorophenyl)-7-((S)-2-methylpiperazin-1-yl)-9-(trifluoromethyl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 14% yield as a white solid.

m/z (ESI, +ve)=537.13 (M+H)$^+$.

$^1$H NMR (400 MHz, DMSO-d6) δ 7.80 (d, J=4.2 Hz, 1H), 7.52-7.44 (m, 1H), 7.42-7.33 (m, 1H), 7.31-7.23 (m, 1H), 6.93-6.75 (m, 1H), 6.25-6.12 (m, 1H), 5.74 (dd, J=10.4, 2.4 Hz, 1H), 4.78-4.57 (m, 1H), 4.45-3.96 (m, 5H), 3.71-3.43 (m, 2H), 3.24-2.94 (m, 3H), 1.37-1.27 (m, 3H).

Step 1: tert-butyl (3S)-4-(10-(2,4-difluorophenyl)-5-oxo-9-(trifluoromethyl)-2,3-dihydro-5H-[1,4]thiazino[2,3,4-ij]quinazolin-7-yl)-3-methylpiperazine-1-carboxylate

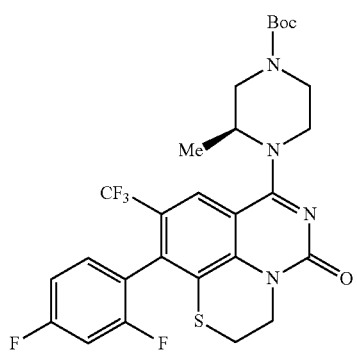 [SMILES: C[C@H]1CN(C(=O)OC(C)(C)C)CCN1c1nc(=O)n2c3c(c(-c4ccc(F)cc4F)c(C(F)(F)F)cc13)SCC2]

To a solution of 10-(2,4-difluorophenyl)-9-(trifluoromethyl)-2,3-dihydro-5H-[1,4]thiazino[2,3,4-ij]quinazoline-5,7(6H)-dione (500 mg, 1.25 mmol) in toluene (5 mL) were added N,N-diisopropylethylamine (970 mg, 7.5 mmol) and POCl$_3$ (5 mL) and the mixture was stirred at 100° C. for 1.5 hours. The mixture was concentrated and redissolved in dichloroethane (8 mL) and over this solution, a second solution of tert-butyl (S)-3-methylpiperazine-1-carboxylate (750 mg, 3.75 mmol) and N,N-diisopropylethylamine (1580 mg, 12.25 mmol) in DCE 8 (mL) was added. The resulting mixture was stirred at room temperature for 1 hour and quenched by addition of water (10 mL). The mixture was extracted with ethyl acetate (15 mL×3), the combined organic layers were washed with brine (20 mL), dried over Na$_2$SO$_4$ and concentrated to afford a residue that was purified by reverse phase column chromatography (phase A: water (0.1% TFA), phase B: ACN; 0-65%) to afford tert-butyl (3S)-4-(10-(2,4-difluorophenyl)-5-oxo-9-(trifluoromethyl)-2,3-dihydro-5H-[1,4]thiazino[2,3,4-ij]quinazolin-7-yl)-3-methylpiperazine-1-carboxylate (700 mg, 96%) as a yellow solid.

m/z (ESI, +ve)=583.17 (M+H)$^+$.

Step 2: 10-(2,4-difluorophenyl)-7-((S)-2-methylpiperazin-1-yl)-9-(trifluoromethyl)-2,3-dihydro-5H-[1,4]thiazino[2,3,4-ij]quinazolin-5-one

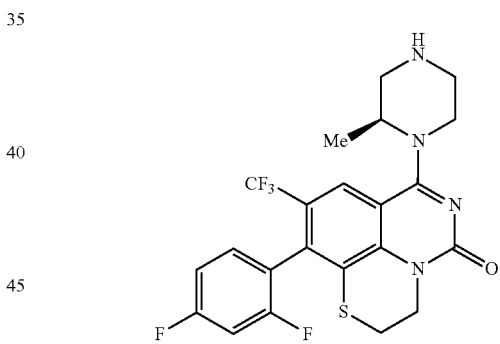

To a solution of tert-butyl (3S)-4-(10-(2,4-difluorophenyl)-5-oxo-9-(trifluoromethyl)-2,3-dihydro-5H-[1,4]thiazino[2,3,4-ij]quinazolin-7-yl)-3-methylpiperazine-1-carboxylate (400 mg, 0.68 mmol) in dichloromethane (9 mL) cooled to 0° C. was added trifluoroacetic acid (3 mL) and the reaction mixture was stirred at room temperature for 1 hour. The mixture was concentrated to afford 10-(2,4-difluorophenyl)-7-((S)-2-methylpiperazin-1-yl)-9-(trifluoromethyl)-2,3-dihydro-5H-[1,4]thiazino[2,3,4-ij]quinazolin-5-one (300 mg, 90%) as a yellow solid and used in the next step without further purification.

m/z (ESI, +ve)=483.12 (M+H)$^+$.

Example 142: 7-((S)-4-acryloyl-2-methylpiperazin-1-yl)-9-bromo-10-(2,4-difluorophenyl)-2,3-dihydro-5H-[1,4]thiazino[2,3,4-ij]quinazolin-5-one

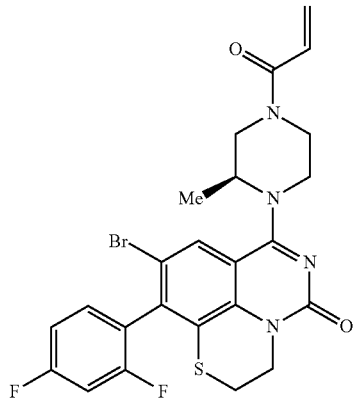 [SMILES: C=CC(=O)N1CCN(c2nc(=O)n3c4c(c(-c5ccc(F)cc5F)c(Br)cc24)SCC3)[C@@H](C)C1]

The title compound was prepared analogously to Example 84 where 9-bromo-10-(2,4-difluorophenyl)-7-((S)-2-methylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 40% yield as a yellow solid.

m/z (ESI, +ve)=547.0 (M+H)$^+$.

1H NMR (400 MHz, methanol-d$_4$) δ 7.84 (d, J=5.6 Hz, 1H), 7.30-7.24 (m, 1H), 7.15-7.10 (m, 2H), 6.88-6.74 (m, 1H), 6.29 (dd, J=6.4 Hz, 16.4 Hz, 1H), 5.80 (dd, J=1.6 Hz, 10.4 Hz, 1H), 4.80-4.51 (m, 1H), 4.41-4.23 (m, 2H), 4.18-3.75 (m, 2H), 3.74-3.45 (m, 3H), 3.23-3.09 (m, 3H), 1.41 (dd, J=6.8 Hz, 10 Hz, 3H).

Step 1: tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate

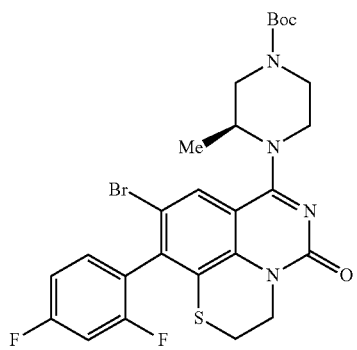 [SMILES: C[C@H]1CN(C(=O)OC(C)(C)C)CCN1c1nc(=O)n2c3c(c(-c4ccc(F)cc4F)c(Br)cc13)SCC2]

To a mixture of 9-bromo-10-(4-fluorophenyl)-2,3-dihydro-5H-[1,4]thiazino[2,3,4-ij]quinazoline-5,7(6H)-dione (90 mg, 0.22 mmol) and K$_2$CO$_3$ (91 mg, 0.66 mmol) in acetonitrile (4 mL) was added tosyl chloride (84 mg, 0.44 mmol). The reaction mixture was stirred at room temperature for 16 hours. tert-butyl (S)-3-methylpiperazine-1-carboxylate (133 mg, 0.66 mmol) and K$_2$CO$_3$ (91 mg, 0.66 mmol) were added and the reaction mixture was stirred at room temperature for another hour. The reaction mixture was quenched with water (5 mL), extracted with ethyl acetate (10 mL×3) and the organic layers were combined, washed with brine (10 mL), dried over Na$_2$SO$_4$ and filtered. The filtrate was concentrated under reduced pressure to afford a residue that was purified by reversed phase chromatography (80% A in B; A=CH$_3$CN, B=0.1% TFA in water) to afford tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (90 mg, 61%) as yellow oil.

m/z (ESI, +ve)=593.1 (M+H)$^+$.

Step 2: 9-bromo-10-(2,4-difluorophenyl)-7-((S)-2-methylpiperazin-1-yl)-2,3-dihydro-5H-[1,4]thiazino[2,3,4-ij]quinazolin-5-one

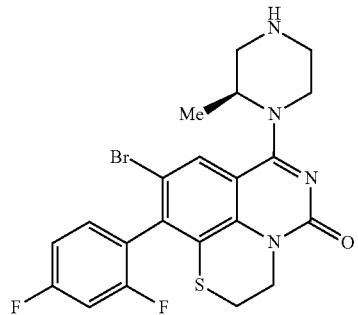 [SMILES: C[C@H]1CNCCN1c1nc(=O)n2c3c(c(-c4ccc(F)cc4F)c(Br)cc13)SCC2]

To a mixture of tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (90 mg, 0.15 mmol) in dichloromethane (5 mL) was added TFA (2 mL). This solution was stirred at room temperature for 1 hour and the mixture was concentrated under reduced pressure to afford 9-bromo-10-(2,4-difluorophenyl)-7-((S)-2-methylpiperazin-1-yl)-2,3-dihydro-5H-[1,4]thiazino[2,3,4-ij]quinazolin-5-one (85 mg) as yellow oil.

m/z (ESI, +ve)=493.0 (M+H)$^+$.

Example 143: 7-((S)-4-acryloyl-2-methylpiperazin-1-yl)-9-cyclopropyl-10-(2,4-difluorophenyl)-2,3-dihydro-5H-[1,4]thiazino[2,3,4-ij]quinazolin-5-one

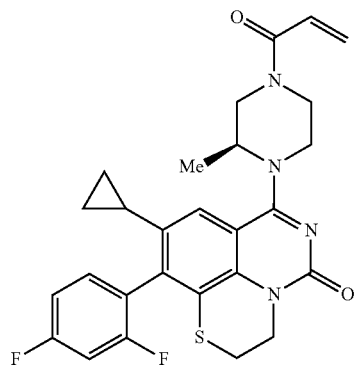 [SMILES: C=CC(=O)N1CCN(c2nc(=O)n3c4c(c(-c5ccc(F)cc5F)c(C5CC5)cc24)SCC3)[C@@H](C)C1]

The title compound was prepared analogously to Example 84 where 9-cyclopropyl-10-(2,4-difluorophenyl)-7-((S)-2-methylpiperazin-1-yl)-2,3-dihydro-5H-[1,4]thiazino[2,3,4-ij]quinazolin-5-one was substituted in place of 9-chloro-10-

(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 65% yield as a yellow solid.

m/z (ESI, +ve)=509.1 (M+H)$^+$.

$^1$H NMR (400 MHz, methanol-d4) δ 7.32-7.25 (m, 1H), 7.18 (d, J=2.0 Hz, 1H), 7.12 (t, J=8.8 Hz, 2H), 6.88-6.74 (m, 1H), 6.27 (dd, J=16.4 Hz, 7.2 Hz, 1H), 5.80 (dd, J=10.4 Hz, 2.0 Hz, 1H), 4.79-4.71 (m, 1H), 4.60-4.45 (m, 1H), 4.36-4.30 (m, 1H), 4.23-4.17 (m, 1H), 4.11-3.98 (m, 2H), 3.67-3.44 (m, 2H), 3.16-3.04 (m, 3H), 1.56-1.50 (m, 1H), 1.46-1.38 (m, 3H), 0.78-0.71 (m, 2H), 0.67-0.58 (m, 2H).

Step 1: tert-butyl (3S)-4-(9-cyclopropyl-10-(2,4-difluorophenyl)-5-oxo-2,3-dihydro-5H-[1,4]thiazino[2,3,4-ij]quinazolin-7-yl)-3-methylpiperazine-1-carboxylate

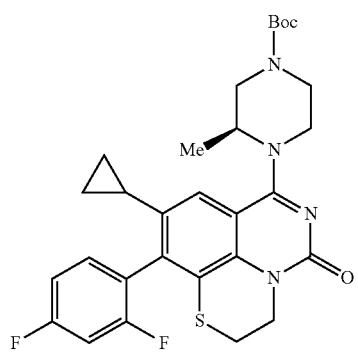 [SMILES: C[C@H]1CN(C(=O)OC(C)(C)C)CCN1c1nc(=O)n2c3c(c(-c4ccc(F)cc4F)c(C4CC4)cc13)SCC2]

A mixture of tert-butyl (3S)-4-(9-bromo-10-(2,4-difluorophenyl)-5-oxo-2,3-dihydro-5H-[1,4]thiazino[2,3,4-ij]quinazolin-7-yl)-3-methylpiperazine-1-carboxylate (200 mg, 0.34 mmol), cyclopropyl boronic acid (35 mg, 0.41 mmol), potassium carbonate (141 mg, 1.02 mmol) and 1,1'-Bis(diphenylphosphino)ferrocene palladium dichloride (50 mg, 0.068 mmol) in dioxane (10 mL) and water (2 mL) was stirred at 100° C. for 16 hours. The reaction was quenched by the addition of water (20 mL) and extracted with ethyl acetate (10 mL×3). The organic layers were combined, washed with brine (20 mL), dried over sodium sulphate and concentrated under reduced pressure to afford a residue that was purified by silica gel chromatography to afford tert-butyl (3S)-4-(9-cyclopropyl-10-(2,4-difluorophenyl)-5-oxo-2,3-dihydro-5H-[1,4]thiazino[2,3,4-ij]quinazolin-7-yl)-3-methylpiperazine-1-carboxylate (130 mg, 65%) as a white solid.

m/z (ESI, +ve)=555.2 (M+H)$^+$.

Step 2: 9-cyclopropyl-10-(2,4-difluorophenyl)-7-((S)-2-methylpiperazin-1-yl)-2,3-dihydro-5H-[1,4]thiazino[2,3,4-ij]quinazolin-5-one

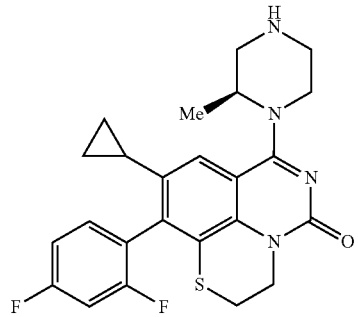 [SMILES: C[C@H]1CNCCN1c1nc(=O)n2c3c(c(-c4ccc(F)cc4F)c(C4CC4)cc13)SCC2]

To a solution of tert-butyl (3S)-4-(9-cyclopropyl-10-(2,4-difluorophenyl)-5-oxo-2,3-dihydro-5H-[1,4]thiazino[2,3,4-ij]quinazolin-7-yl)-3-methylpiperazine-1-carboxylate (130 mg, 0.02 mmol) in dichloromethane (3 mL) was added trifluoroacetic acid (1 ml). After stirring at room temperature for 1 hour, the reaction mixture was concentrated in vacuo to afford a yellow solid (100 mg, 86%) that was used directly in the next step without further purification.

m/z (ESI, +ve)=455.1 (M+H)$^+$.

Example 144: 7-(4-acryloylhexahydrothieno[3,4-b]pyrazin-1(2H)-yl)-9-chloro-10-(2,4-difluorophenyl)-2,3-dihydro-5H-[1,4]thiazino[2,3,4-ij]quinazolin-5-one

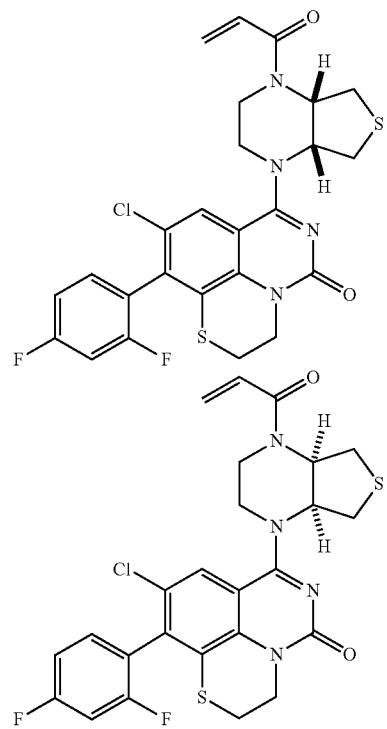

The title compound was prepared analogously to Example 84 where 9-chloro-10-(2,4-difluorophenyl)-7-(hexahydrothieno[3,4-b]pyrazin-1(2H)-yl)-2,3-dihydro-5H-[1,4]thiazino [2,3,4-ij]quinazolin-5-one (mixture of four stereoisomers) was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 10% yield as a yellow solid.

m/z (ESI, +ve)=548.0 (M+H)$^+$.

$^1$H NMR (400 MHz, methanol-d4) δ 7.82 (m, 1H), 7.29-7.16 (m, 1H), 7.14-7.11 (m, 2H), 6.82-6.75 (m, 1H), 6.31-6.26 (m, 1H), 5.81 (dd, J=10.4 Hz, 2.0 Hz, 1H), 5.06-4.99 (m, 2H), 4.65-4.60 (m, 1H), 4.40-4.37 (m, 1H), 4.31-4.10 (m, 2H), 4.03-3.94 (m, 2H), 3.88-3.83 (m, 1H), 3.48-3.36 (m, 2H), 3.25-3.13 (m, 3H).

Step 1: cis-octahydrothieno[3,4-b]pyrazine

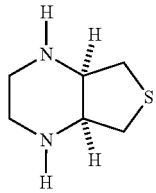

To a solution of 1,4-dibenzyl-cis-octahydrothieno[3,4-b]pyrazine (1 g, 3.1 mmol) in dichloroethane (10 mL) was added 1-chloroethyl chloroformate (4.43 g, 31 mmol). The reaction mixture was stirred at 80° C. for 16 hours, cooled down to room temperature and concentrated. The residue was dissolved in methanol (10 ml) and stirred at 80° C. for another 4 hours. The suspension was filtered and the filter cake was washed with methanol and dried to afford cis-octahydrothieno[3,4-b]pyrazine (0.44 g, 92%) as a white solid.

m/z (ESI, +ve)=145.2 (M+H)+

Step 2: 9-chloro-10-(2,4-difluorophenyl)-7-(hexahydrothieno[3,4-b]pyrazin-1(2H)-yl)-2,3-dihydro-5H-[1,4]thiazino[2,3,4-ij]quinazolin-5-one

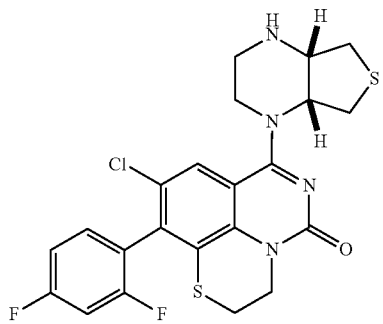

-continued

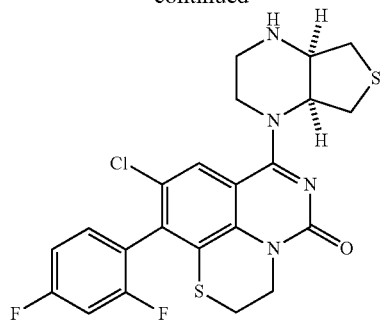

To a solution of 9-chloro-10-(2,4-difluorophenyl)-2,3-dihydro-5H-[1,4]thiazino[2,3,4-ij]quinazoline-5,7(6H)-dione (300 mg, 0.82 mmol) in acetonitrile (10 mL), benzotriazol-1-yl-oxytripyrrolidinophosphonium hexafluorophosphate (459 mg, 0.984 mmol) and DBU (344 mg, 2.25 mmol) were added. The mixture was stirred for 20 minutes and cis-octahydrothieno[3,4-b]pyrazine (237 mg, 1.64 mmol) and DBU (344 mg, 2.25 mmol) were added. The reaction mixture was stirred at room temperature for 16 hours and concentrated to afford a residue that was purified by preparative HPLC to afford 9-chloro-10-(2,4-difluorophenyl)-7-(hexahydrothieno[3,4-b]pyrazin-1(2H)-yl)-2,3-dihydro-5H-[1,4]thiazino[2,3,4-ij]quinazolin-5-one (98 mg, 22%) as a light yellow solid.

m/z (ESI, +ve)=493.1 (M+H)$^+$.

$^1$H NMR (400 MHz, methanol-d4) δ 7.75 (d, J=8.8 Hz, 1H), 7.31-7.27 (m, 1H), 7.17-7.11 (m, 2H), 5.29-5.16 (m, 1H), 4.51-4.18 (m, 3H), 4.16-4.12 (m, 1H), 3.85-3.71 (m, 1H), 3.55-3.38 (m, 3H), 3.23-3.12 (m, 3H), 2.91 (dd, J=13.2 Hz, 4.0 Hz, 1H), 1.87-1.83 (m, 2H).

Example 156: 7-((3S,5S)-4-acryloyl-3,5-dimethylpiperazin-1-yl)-9-chloro-10-(2,4-difluorophenyl)-2,3-dihydro-5H-[1,4]thiazino[2,3,4-ij]quinazolin-5-one

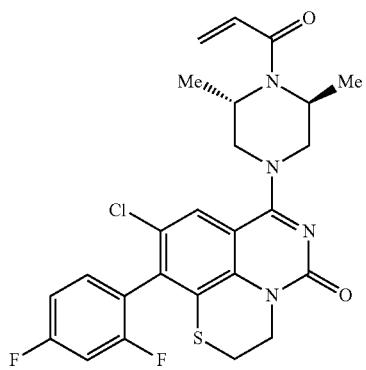 [SMILES: C=CC(=O)N1[C@@H](C)CN(c2nc(=O)n3c4c(c(-c5ccc(F)cc5F)c(Cl)cc24)SCC3)C[C@@H]1C]

The title compound was prepared analogously to Example 84 where 9-chloro-10-(2,4-difluorophenyl)-7-((3S,5S)-3,5-dimethylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 49% yield as a yellow solid.

m/z (ESI, +ve)=517.3 (M+H)$^+$.

¹H NMR (400 MHz, DMSO) δ 7.97 (d, J=5.8 Hz, 1H), 7.48 (td, J=9.6, 2.2 Hz, 1H), 7.45-7.34 (m, 1H), 7.28 (ddd, J=11.4, 8.4, 3.3 Hz, 1H), 6.75 (ddd, J=16.5, 10.4, 1.7 Hz, 1H), 6.23 (dd, J=16.6, 2.4 Hz, 1H), 5.75 (dd, J=10.3, 2.4 Hz, 1H), 4.59 (dd, J=11.0, 3.5 Hz, 1H), 4.50-4.44 (m, 2H), 4.25 (d, J=11.6 Hz, 2H), 3.91-3.82 (m, 1H), 3.79 (d, J=13.4 Hz, 2H), 3.30-3.21 (m, 1H), 3.16-3.04 (m, 1H), 1.28 (dd, J=17.7, 10.5 Hz, 6H).

Step 1: 9-chloro-10-(2,4-difluorophenyl)-7-((3S,5S)-3,5-dimethylpiperazin-1-yl)-2,3-dihydro-5H-[1,4]thiazino[2,3,4-ij]quinazolin-5-one

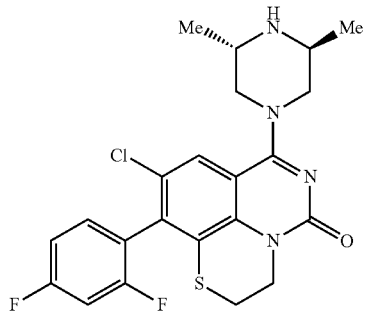 [SMILES: C[C@H]1CN(c2nc(=O)n3c4c(c(-c5ccc(F)cc5F)c(Cl)cc24)SCC3)C[C@H](C)N1]

9-chloro-10-(2, 4-difluoropenyl)-7-hydroxy-2, 3-dihydro-5H-[1, 4]thiazino[2, 3, 4-ij]quinazolin-5-one (0.4 mmol, 150 mg) was dissolved in toluene and POCl₃ (1 mL) and DIPEA (0.8 mmol, 103 mg) were added. The mixture was stirred at 120° C. for 1.5 hours and the solvent removed under reduced pressure. The residue was dissolved in dichloromethane (2 mL) and DIPEA (0.8 mmol, 103 mg) and (2S,6S)-2,6-dimethylpiperazine dihydrochloride (0.8 mmol, 150 mg) were added. This solution was stirred for 30 minutes at room temperature and diluted with dichloromethane and water. The organic layer was separated, dried with Na₂SO₄, filtered and concentrated under reduced pressure. The residue was purified by a chromatography (hexanes:ethyl acetate=30-40%) to afford 9-chloro-10-(2,4-difluorophenyl)-7-((3S, 5S)-3,5-dimethylpiperazin-1-yl)-2,3-dihydro-5H-[1,4]thiazino[2,3,4-ij]quinazolin-5-one as a yellow solid (160 mg, 86%).

m/z (ESI, +ve)=463.2 (M+H)⁺.

¹H NMR (400 MHz, DMSO) δ 9.54 (s, 1H), 7.75 (d, J=10.4 Hz, 1H), 7.52-7.45 (m, 1H), 7.44-7.34 (m, 1H), 7.28 (td, J=8.5, 2.2 Hz, 1H), 4.43-4.21 (m, 2H), 4.05 (dd, J=9.1, 4.3 Hz, 2H), 4.02 (d, J=4.6 Hz, 1H), 3.96 (s, 1H), 3.26-3.18 (m, 2H), 3.18-3.09 (m, 2H), 1.33 (d, J=6.2 Hz, 6H).

Example 157: 7-((3R,5S)-4-acryloyl-3,5-dimethylpiperazin-1-yl)-9-chloro-10-(2,4-difluorophenyl)-2,3-dihydro-5H-[1,4]thiazino[2,3,4-ij]quinazolin-5-one

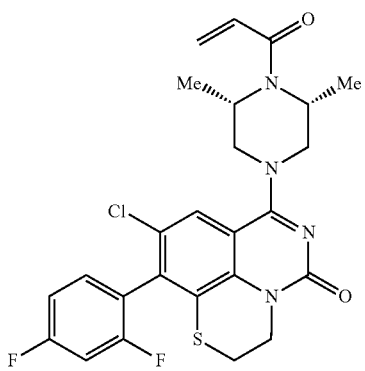 [SMILES: C=CC(=O)N1[C@H](C)CN(c2nc(=O)n3c4c(c(-c5ccc(F)cc5F)c(Cl)cc24)SCC3)C[C@@H]1C]

The title compound was prepared analogously to Example 84 where 9-chloro-10-(2,4-difluorophenyl)-7-((3R,5S)-3,5-dimethylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 27% yield as a yellow solid.

m/z (ESI, +ve)=517.3 (M+H)⁺.

¹H NMR (400 MHz, DMSO) δ 7.79 (s, 1H), 7.49 (td, J=9.7, 2.5 Hz, 1H), 7.41 (td, J=8.5, 6.6 Hz, 1H), 7.28 (td, J=8.5, 2.2 Hz, 1H), 6.80 (dd, J=16.6, 10.5 Hz, 1H), 6.18 (dd, J=16.6, 2.4 Hz, 1H), 5.74 (dd, J=10.4, 2.4 Hz, 1H), 4.56 (s, 2H), 4.27 (ddd, J=13.8, 6.1, 3.1 Hz, 1H), 4.10 (t, J=12.5 Hz, 2H), 4.07-4.00 (m, 1H), 3.35 (dt, J=10.7, 5.1 Hz, 2H), 3.26-3.12 (m, 2H), 1.43-1.28 (m, 6H).

Step 1: tert-butyl (2R,6S)-4-(9-chloro-10-(2,4-difluorophenyl)-5-oxo-2,3-dihydro-5H-[1,4]thiazino[2,3,4-ij]quinazolin-7-yl)-2,6-dimethylpiperazine-1-carboxylate

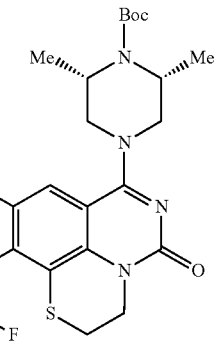

The title compound was prepared analogously to Example 156, Step 1 where (2R,6S)-2,6-dimethylpiperazine dihydrochloride was substituted in place of (2S,6S)-2,6-dimethylpiperazine dihydrochloride in 71% yield as a yellow solid.

m/z (ESI, +ve)=563.1 (M+H)⁺.

¹H NMR (400 MHz, DMSO) δ 7.77 (s, 1H), 7.48 (td, J=9.7, 2.4 Hz, 1H), 7.40 (td, J=8.4, 6.6 Hz, 1H), 7.28 (td,

J=8.5, 2.4 Hz, 1H), 4.32-4.25 (m, 1H), 4.25-4.17 (m, 2H), 4.06 (dd, J=10.0, 7.9 Hz, 2H), 4.02 (dd, J=7.5, 4.1 Hz, 1H), 3.31-3.24 (m, 2H), 3.23-3.14 (m, 2H), 1.44 (s, 9H), 1.32 (dd, J=13.9, 6.8 Hz, 6H).

Step 2: 9-chloro-10-(2,4-difluorophenyl)-7-((3R, 5S)-3,5-dimethylpiperazin-1-yl)-2,3-dihydro-5H-[1,4]thiazino[2,3,4-ij]quinazolin-5-one

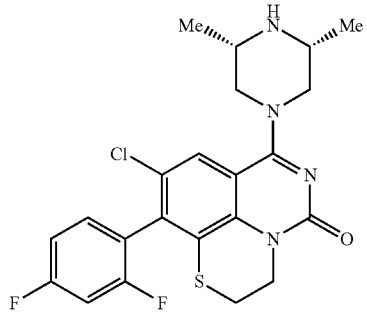 [SMILES: C[C@@H]1CN(c2nc(=O)n3c4c(c(-c5ccc(F)cc5F)c(Cl)cc24)SCC3)C[C@H](C)N1]

(tert-butyl (2R, 6S)-4-(9-chloro-10-(2, 4-difluorophenyl)-5-oxo-2, 3-dihydro-5H-[1, 4]thiazino[2, 3, 4-ij]quinazolin-7-yl)-2, 6-dimethylpiperazine-1-carboxylate) (0.21 mmol, 120 mg) was dissolved in dichloromethane (2 mL), and trimethylsilyl trifluoromethanesulfonate (0.42 mmol, 93 mg) was added. The mixture was stirred for 30 minutes at room temperature. The solvent was removed under reduced pressure to afford a solid (160 mg) that was directly used in the next steps without further purification.

m/z (ESI, +ve)=464.1 (M+H)⁺.

Example 158: 7-((R)-4-acryloyl-2-methylpiperazin-1-yl)-9-chloro-10-(2,4-difluorophenyl)-2,3-dihydro-5H-[1,4]thiazino[2,3,4-ij]quinazolin-5-one

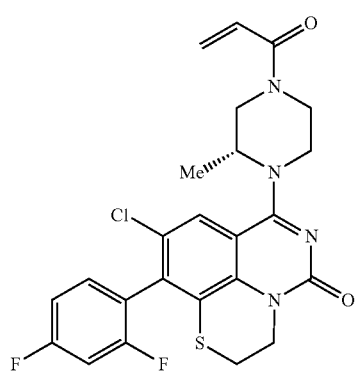 [SMILES: C=CC(=O)N1CCN(c2nc(=O)n3c4c(c(-c5ccc(F)cc5F)c(Cl)cc24)SCC3)[C@H](C)C1]

The title compound was prepared analogously to Example 84 where 9-chloro-10-(2,4-difluorophenyl)-7-((R)-2-methylpiperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 22% yield as a yellow solid.

m/z (ESI, +ve)=503.2 (M+H)⁺.

¹H NMR (400 MHz, DMSO) δ 7.63 (d, J=9.1 Hz, 1H), 7.48 (td, J=9.6, 2.3 Hz, 1H), 7.41 (tdd, J=8.4, 6.6, 4.9 Hz, 1H), 7.28 (td, J=8.5, 2.4 Hz, 1H), 6.83 (dd, J=27.5, 17.2 Hz, 1H), 6.18 (dd, J=16.6, 6.5 Hz, 1H), 5.74 (dd, J=10.4, 2.3 Hz, 1H), 4.66 (d, J=27.0 Hz, 1H), 4.46-4.21 (m, 2H), 4.11 (d, J=21.3 Hz, 1H), 4.07-3.95 (m, 2H), 3.68-3.44 (m, 2H), 3.23-3.13 (m, 2H), 3.13-2.90 (m, 1H), 1.26 (dd, J=13.0, 6.6 Hz, 3H).

Step 1: tert-butyl (R)-4-(10-bromo-9-chloro-5-oxo-2,3-dihydro-5H-[1,4]thiazino[2,3,4-ij]quinazolin-7-yl)-3-methylpiperazine-1-carboxylate

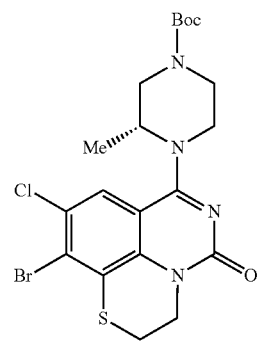 [SMILES: C[C@@H]1CN(C(=O)OC(C)(C)C)CCN1c1nc(=O)n2c3c(c(Br)c(Cl)cc13)SCC2]

Over a solution of 10-bromo-9-chloro-2, 3-dihydro-5H-[1, 4]thiazino[2, 3, 4-ij]quinazoline-5, 7(6H)-dione) (0.6 mmol, 200 mg in toluene, POCl₃ (1.5 mL) and DIPEA (1.2 mmol, 155 mg) were added. The mixture was stirred at 120° C. for 1.5 hours and the volatiles removed under reduced pressure. The resulting crude material was dissolved in dichloromethane (2 mL) followed by addition of DIPEA (1.2 mmol, 155 mg) and benzyl tert-butyl (R)-3-methylpiperazine-1-carboxylate (1.2 mmol, 240 mg). The reaction was stirred at room temperature for one hour and quenched with dichloromethane and water. The organic layer was dried with Na₂SO₄, filtered and concentrated under reduced pressure to afford a residue that was purified by chromatography (hexanes:ethyl acetate=30-40%) to afford compound 2 as a yellow solid (260 mg, 84%).

m/z (ESI, +ve)=515.0 (M+H)⁺.

¹H NMR (400 MHz, CDCl₃) δ 7.44 (s, 1H), 4.66 (s, 1H), 4.39 (s, 2H), 4.12 (q, J=7.1 Hz, 2H), 3.90 (s, 2H), 3.51 (d, J=13.0 Hz, 2H), 3.24-3.20 (m, 2H), 1.49 (s, 9H), 1.40 (d, J=6.7 Hz, 3H).

Step 2: tert-butyl (3R)-4-(9-chloro-10-(2,4-difluorophenyl)-5-oxo-2,3-dihydro-5H-[1,4]thiazino[2,3,4-ij]quinazolin-7-yl)-3-methylpiperazine-1-carboxylate

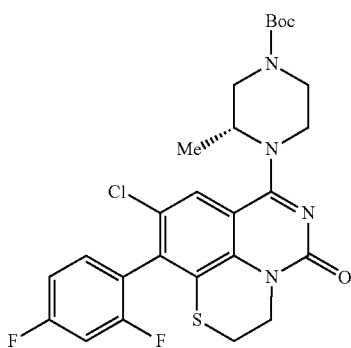 [SMILES: C[C@@H]1CN(C(=O)OC(C)(C)C)CCN1c1nc(=O)n2c3c(c(-c4ccc(F)cc4F)c(Cl)cc13)SCC2]

A mixture of tert-butyl (R)-4-(10-bromo-9-chloro-5-oxo-2,3-dihydro-5H-[1,4]thiazino[2,3,4-ij]quinazolin-7-yl)-3-methylpiperazine-1-carboxylate (0.5 mmol, 258 mg), (2,4-difluorophenyl) boronic acid (0.7 mmol, 110 mg), Pd(dppf)Cl$_2$ (0.1 mmol, 73 mg) and CsF (1.0 mmol, 152 mg) was dissolved in dioxane (6 mL) and refluxed overnight. The mixture was filtered, diluted with ethyl acetate and water and the organic layer dried with Na$_2$SO$_4$. After elimination of volatiles under reduced pressure, the resulting residue was purified by a silica gel chromatography (hexanes:ethyl acetate=40-50%) to afford tert-butyl (3R)-4-(9-chloro-10-(2,4-difluorophenyl)-5-oxo-2,3-dihydro-5H-[1,4]thiazino[2,3,4-ij]quinazolin-7-yl)-3-methylpiperazine-1-carboxylate as light yellow solid (120 mg, 47%).

m/z (ESI, +ve)=549.1 (M+H)$^+$.

$^1$H NMR (400 MHz, CDCl$_3$) δ 7.49 (s, 1H), 7.24-7.16 (m, 1H), 7.07-7.01 (m, 1H), 7.01-6.96 (m, 1H), 5.00 (d, J=187.3 Hz, 1H), 4.65 (s, 2H), 4.18 (d, J=23.2 Hz, 2H), 4.14-4.04 (m, 2H), 3.91 (s, 1H), 3.53 (s, 1H), 3.11 (s, 2H), 1.49 (s, 9H), 1.26 (t, J=7.1 Hz, 3H).

Step 3: 9-chloro-10-(2,4-difluorophenyl)-7-((R)-2-methylpiperazin-1-yl)-2,3-dihydro-5H-[1,4]thiazino[2,3,4-ij]quinazolin-5-one

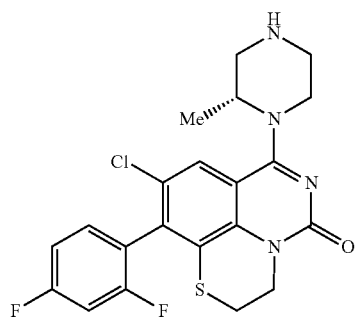 [SMILES: C[C@@H]1CNCCN1c1nc(=O)n2c3c(c(-c4ccc(F)cc4F)c(Cl)cc13)SCC2]

tert-butyl (3R)-4-(9-chloro-10-(2, 4-difluorophenyl)-5-oxo-2,-dihydro-5H-[1,4]thiazino[2, 3, 4-ij]quinazolin-7-yl)-3-methylpiperazine-1-carboxylate) (0.22 mmol, 120 mg) was dissolved in dichloromethane (2 mL), and trimethylsilyl trifluoromethanesulfonate (0.44 mmol, 96 mg) was added. The mixture was stirred for 30 minutes at room temperature and the solvent removed under reduced pressure to afford the desired product and used in the next step without further purification.

m/z (ESI, +ve)=449.0 (M+H)$^+$.

Example 164: 7-(4-acryloylpiperazin-1-yl)-9-chloro-10-(2,4-difluorophenyl)-2,3-dihydro-5H-[1,4]thiazino[2,3,4-ij]quinazolin-5-one

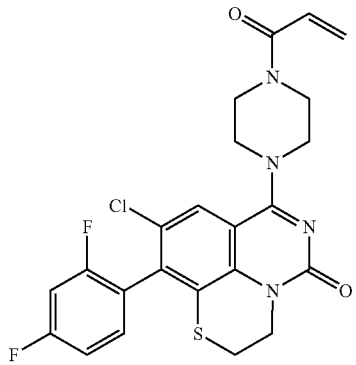 [SMILES: C=CC(=O)N1CCN(c2nc(=O)n3c4c(c(-c5ccc(F)cc5F)c(Cl)cc24)SCC3)CC1]

The title compound was prepared analogously to Example 84 where 9-chloro-10-(2,4-difluorophenyl)-7-(piperazin-1-yl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 60% yield as a white solid.

m/z (ESI, +ve)=489.1 (M+H)$^+$.

$^1$H NMR (400 MHz, DMSO) δ 7.72 (s, 1H), 7.56-7.35 (m, 2H), 7.28 (td, J=8.5, 2.3 Hz, 1H), 6.82 (dd, J=16.7, 10.4 Hz, 1H), 6.17 (dd, J=16.7, 2.3 Hz, 1H), 5.74 (dd, J=10.4, 2.3 Hz, 1H), 4.27 (ddd, J=13.8, 6.2, 2.8 Hz, 1H), 4.02 (ddd, J=13.8, 8.0, 2.9 Hz, 1H), 3.78 (dt, J=25.9, 13.0 Hz, 8H), 3.22-3.11 (m, 2H).

Step 1: tert-butyl 4-(9-chloro-10-(2,4-difluorophenyl)-5-oxo-2,3-dihydro-5H-[1,4]thiazino[2,3,4-ij]quinazolin-7-yl)piperazine-1-carboxylate

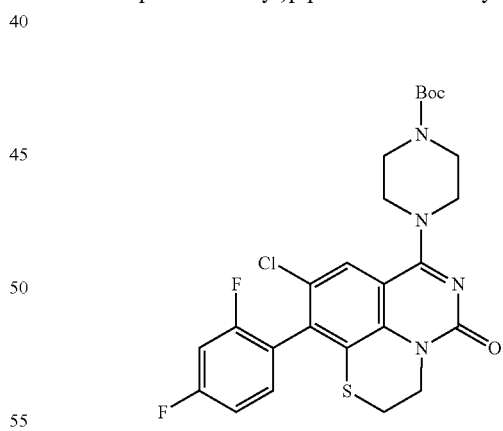

A mixture of 9-chloro-10-(2,4-difluorophenyl)-2,3-dihydro-5H-[1,4]thiazino[2,3,4-ij]quinazoline-5,7(6H)-dione (120 mg, 0.33 mmol), POCl3 (1 ml) and DIPEA (130 mg, 1 mmol) was stirred at 120° C. for 2 hours. The reaction mixture was then allowed to cool to room temperature and concentrated to afford a residue that was taken up in in dichloromethane (10 ml). DIPEA (320 mg, 2.5 mmol, 10 equiv) and tert-butyl piperazine-1-carboxylate (186 mg, 1 mmol, 4 equiv) were sequentially added and the mixture stirred at room temperature for 2 hours. The reaction was diluted with dichloromethane (100 ml), washed with 0.1 N HCl aq (100 ml), brine (50 mL), dried over Na₂SO₄, filtered and concentrated in vacuo to afford a residue that was purified by chromatography (ethyl acetate:hexanes=50-100%) to afford tert-butyl 4-(9-chloro-10-(2,4-difluorophenyl)-5-oxo-2,3-dihydro-5H-[1,4]thiazino[2,3,4-ij]quinazolin-7-yl)piperazine-1-carboxylate as a yellow solid (120 mg, 90%).

LC-m/z (ESI, +ve)=535.1 (M+H)⁺.

¹H NMR (400 MHz, CDCl₃) δ 7.52 (s, 1H), 7.20 (td, J=8.3, 6.4 Hz, 1H), 7.07-6.94 (m, 2H), 4.55 (dt, J=9.2, 4.4 Hz, 1H), 4.24 (dt, J=11.5, 5.4 Hz, 1H), 3.88-3.73 (m, 4H), 3.68-3.56 (m, 4H), 3.10 (t, J=5.2 Hz, 2H), 1.49 (s, 9H).

Step 2: 9-chloro-10-(2,4-difluorophenyl)-7-(piperazin-1-yl)-2,3-dihydro-5H-[1,4]thiazino[2,3,4-ij]quinazolin-5-one

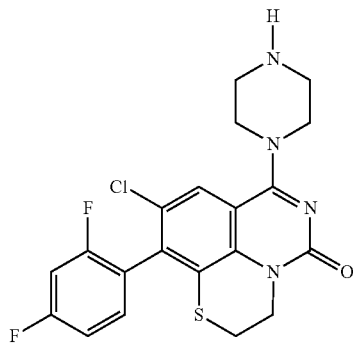 [SMILES: O=c1nc(N2CCNCC2)c2cc(Cl)c(-c3ccc(F)cc3F)c3c2n1CCS3]

A solution of tert-butyl 4-(9-chloro-10-(2,4-difluorophenyl)-5-oxo-2,3-dihydro-5H-[1,4]thiazino[2,3,4-ij]quinazolin-7-yl)piperazine-1-carboxylate (120 mg, 0.22 mmol, 1.0 equiv) in dichloromethane (2 mL) and trifluoroacetic acid (0.5 ml) was stirred at room temperature for 2 hours. The reaction mixture was diluted with dichloromethane (100 mL), washed with 5% sodium carbonate and brine (50 ml). The organic layer was separated and dried with Na₂SO₄, the solvent was removed under reduced pressure to afford 9-chloro-10-(2,4-difluorophenyl)-7-(piperazin-1-yl)-2,3-dihydro-5H-[1,4]thiazino[2,3,4-ij]quinazolin-5-one as a yellow solid in 89% yield.

m/z (ESI, +ve)=435.1 (M+H)⁺.

Example 166: 7-(4-acryloyl-3-oxopiperazin-1-yl)-9-chloro-10-(2,4-difluorophenyl)-2,3-dihydro-5H-[1,4]thiazino[2,3,4-ij]quinazolin-5-one

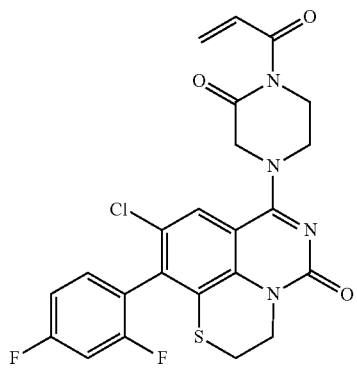 [SMILES: C=CC(=O)N1CCN(c2nc(=O)n3c4c(c(-c5ccc(F)cc5F)c(Cl)cc24)SCC3)CC1=O]

(9-chloro-10-(2,4-difluorophenyl)-7-(3-oxopiperazin-1-yl)-2,3-dihydro-5H-[1,4]thiazino[2,3,4-ij]quinazolin-5-one) (0.11 mmol, 50 mg) was dissolved in dioxane (4 mL), and L-lutidine (0.22 mmol, 23 mg), acrylic anhydride (0.22 mmol, 28 mg) were added. The mixture was stirred at 80° C. overnight, diluted with dichloromethane, washed with hydrochloric acid (1M) and brine. The organic layer was separated and dried with Na₂SO₄, the solvent was removed under reduced pressure and the crude residue purified by preparative HPLC to afford 7-(4-acryloyl-3-oxopiperazin-1-yl)-9-chloro-10-(2,4-difluorophenyl)-2,3-dihydro-5H-[1,4]thiazino[2,3,4-ij]quinazolin-5-one (6 mg, 10%).

m/z (ESI, +ve)=503.2 (M+H)⁺.

¹H NMR (400 MHz, DMSO) δ 7.81 (s, 1H), 7.48 (td, J=9.7, 2.5 Hz, 1H), 7.41 (td, J=8.4, 6.6 Hz, 1H), 7.28 (td, J=8.5, 2.4 Hz, 1H), 7.09 (dd, J=17.0, 10.4 Hz, 1H), 6.26 (dd, J=17.0, 1.8 Hz, 1H), 5.84 (dd, J=10.4, 1.8 Hz, 1H), 4.57 (q, J=17.3 Hz, 2H), 4.34-4.25 (m, 1H), 4.16-4.07 (m, 1H), 4.01 (td, J=12.1, 7.0 Hz, 2H), 3.92 (dd, J=8.9, 4.8 Hz, 2H), 3.24-3.16 (m, 2H), 3.15-3.07 (m, 2H).

Step 1: 10-bromo-9-chloro-7-(3-oxopiperazin-1-yl)-2,3-dihydro-5H-[1,4]thiazino[2,3,4-ij]quinazolin-5-one

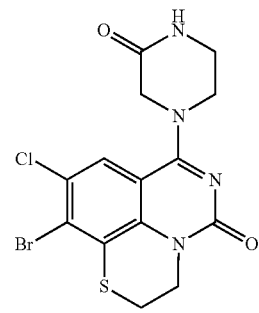 [SMILES: O=C1CN(c2nc(=O)n3c4c(c(Br)c(Cl)cc24)SCC3)CCN1]

10-bromo-9-chloro-2,3-dihydro-5H-[1,4]thiazino[2,3,4-ij]quinazoline-5,7(6H)-dione (0.45 mmol, 150 mg) was dissolved in toluene and POCl3 (1 mL) and DIPEA (0.9 mmol, 116 mg) were added. The mixture was stirred at 120° C. for 1.5 hours and the volatiles removed to afford a residue that was dissolved in dichloromethane (5 mL) and the resulting solution treated with DIPEA (0.9 mmol, 116 mg) and piperazin-2-one (0.9 mmol, 90 mg). The reaction was stirred for 1 hour at room temperature and diluted with dichloromethane and water. The organic layer was dried with Na₂SO₄, filtered, and concentrated under reduced pressure. The residue was purified by chromatography with dichloromethane/MeOH=30/1-20/1 to afford 10-bromo-9-chloro-7-(3-oxopiperazin-1-yl)-2,3-dihydro-5H-[1,4]thiazino[2,3,4-ij]quinazolin-5-one as a yellow solid (100 mg, 53%).

m/z (ESI, +ve)=415.0 (M+H)⁺.

Step 2: 9-chloro-10-(2,4-difluorophenyl)-7-(3-oxopiperazin-1-yl)-2,3-dihydro-5H-[1,4]thiazino[2,3,4-ij]quinazolin-5-one

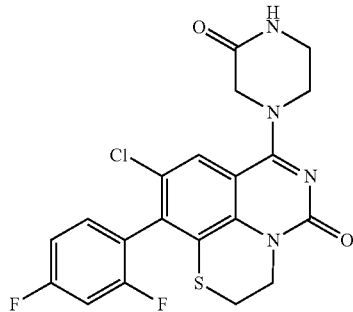 [SMILES: O=C1CN(c2nc(=O)n3c4c(c(-c5ccc(F)cc5F)c(Cl)cc24)SCC3)CCN1]

10-bromo-9-chloro-7-(3-oxopiperazin-1-yl)-2,3-dihydro-5H-[1,4]thiazino[2,3,4-ij]quinazolin-5-one (0.24 mmol, 100 mg), 2,4-difluorophenyl) boronic acid (0.36 mmol, 57 mg), Pd(dppf)Cl2 (0.072 mmol, 59 mg) and CsF (0.5 mmol, 76 mg) were dissolved in dioxane (4 mL) and the mixture stirred at 90° C. for 2 hours. The mixture was diluted with dichloromethane and water and the organic layer separated, dried with Na₂SO₄, and concentrated under reduced pressure. The residue was purified by a chromatography with dichloromethane:MeOH=60:1-40:1 to afford 9-chloro-10-(2,4-difluorophenyl)-7-(3-oxopiperazin-1-yl)-2,3-dihydro-5H-[1,4]thiazino[2,3,4-ij]quinazolin-5-one as a light yellow solid (62 mg, 58%).

m/z (ESI, +ve)=449.0 (M+H)⁺.

Example 185: 7-((R)-4-acryloyl-2-((methylsulfonyl)methyl)piperazin-1-yl)-9-chloro-10-(2,4-difluorophenyl)-2,3-dihydro-5H-[1,4]thiazino[2,3,4-ij]quinazolin-5-one

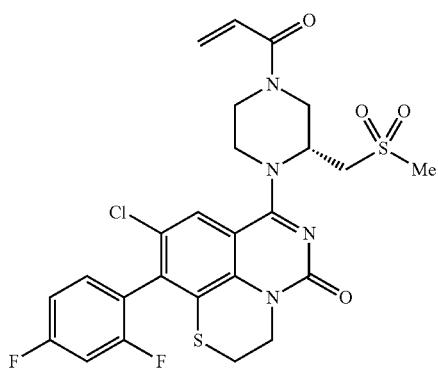 [SMILES: C=CC(=O)N1CCN(c2nc(=O)n3c4c(c(-c5ccc(F)cc5F)c(Cl)cc24)SCC3)[C@@H](CS(C)(=O)=O)C1]

Over a solution of 9-chloro-10-(2,4-difluorophenyl)-7-((R)-2-((methylsulfonyl)methyl)piperazin-1-yl)-2,3-dihydro-5H-[1,4]thiazino[2,3,4-ij]quinazolin-5-one in dichloromethane (2 mL) at 0° C., DIPEA (0.3 mmol, 39 mg) was added followed by acryloyl chloride (0.18 mmol, 17 mg) and stirred for 1 hour. The reaction mixture was diluted with dichloromethane and washed with saturated aqueous sodium carbonate, and brine. The separated organic layer was dried with Na₂SO₄, and the solvent removed under reduced pressure to afford a crude residue that was purified by preparative HPLC to yield 7-((R)-4-acryloyl-2-((methylsulfonyl)methyl)piperazin-1-yl)-9-chloro-10-(2,4-difluorophenyl)-2,3-dihydro-5H-[1,4]thiazino[2,3,4-ij]quinazolin-5-one (25 mg, 29%).

m/z (ESI, +ve)=581.3 (M+H)⁺.

1H NMR (400 MHz, DMSO) δ 7.85 (d, J=16.7 Hz, 1H), 7.48 (dd, J=10.7, 8.5 Hz, 1H), 7.44-7.37 (m, 1H), 7.28 (t, J=8.5 Hz, 1H), 6.81 (dd, J=44.3, 27.8 Hz, 1H), 6.19 (d, J=16.7 Hz, 1H), 5.77 (d, J=10.6 Hz, 1H), 5.20 (s, 1H), 4.91 (s, 1H), 4.45-4.25 (m, 2H), 4.16 (s, 2H), 4.05-3.83 (m, 2H), 3.60 (s, 2H), 3.39 (s, 2H), 3.24-3.12 (m, 2H), 3.07 (t, J=19.0 Hz, 4H).

Step 1: tert-butyl (R)-4-(10-bromo-9-chloro-5-oxo-2,3-dihydro-5H-[1,4]thiazino[2,3,4-ij]quinazolin-7-yl)-3-((methylsulfonyl)methyl)piperazine-1-carboxylate

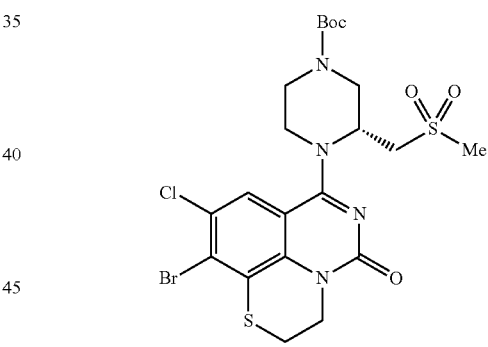

10-bromo-9-chloro-2,3-dihydro-5H-[1,4]thiazino[2,3,4-ij]quinazoline-5,7(6H)-dione (0.9 mmol, 300 mg) was dissolved in toluene and POCl₃ (2.5 mL) and DIPEA (1.8 mmol, 232 mg) were added. The mixture was stirred at 120° C. for 1.5 hours and concentrated.

The crude material was dissolved in 1,2-dichloroethane (10 mL), and DIPEA (1.8 mmol, 232 mg) and tert-butyl (R)-2-((methylsulfonyl)methyl)piperazine-1-carboxylate (1.8 mmol, 500 mg) were added. The reaction solution was stirred overnight at 50° C. and quenched with dichloromethane and water. The organic layer was dried with Na₂SO₄, filtered and concentrated under reduced pressure. The residue was purified by chromatography with dichloromethane/methanol=30/1-20/1 to afford tert-butyl (R)-4-(10-bromo-9-chloro-5-oxo-2,3-dihydro-5H-[1,4]thiazino[2,3,4-ij]quinazolin-7-yl)-3-((methylsulfonyl)methyl)piperazine-1-carboxylate as a yellow solid (200 mg, 37%).

m/z (ESI, +ve)=593.3 (M+H)⁺.

Step 2: tert-butyl (3R)-4-(9-chloro-10-(2,4-difluorophenyl)-5-oxo-2,3-dihydro-5H-[1,4]thiazino[2,3,4-ij]quinazolin-7-yl)-3-((methylsulfonyl)methyl)piperazine-1-carboxylate

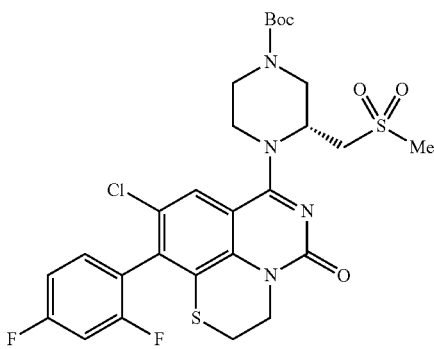 [SMILES: CC(C)(C)OC(=O)N1CCN(c2nc(=O)n3c4c(c(-c5ccc(F)cc5F)c(Cl)cc24)SCC3)[C@@H](CS(C)(=O)=O)C1]

tert-butyl (R)-4-(10-bromo-9-chloro-5-oxo-2, 3-dihydro-5H-[1,4]thiazino[2, 3, 4-ij]quinazolin-7-yl)-3-((methylsulfonyl)methyl)piperazine-1-carboxylate (0.27 mmol, 160 mg), (2, 4-difluorophenyl) boronic acid (0.30 mmol, 47 mg), (dppf)PdCl$_2$ (0.054 mmol, 44 mg) and CsF (0.54 mmol, 82 mg) were dissolved in dioxane (5 mL) and refluxed overnight. The mixture was filtered and diluted with dichloromethane and water. The organic layer was dried with Na$_2$SO$_4$ and concentrated under reduced pressure. The residue was purified by a chromatography with dichloromethane/methanol=60/1-40/1 to afford tert-butyl (3R)-4-(9-chloro-10-(2,4-difluorophenyl)-5-oxo-2,3-dihydro-5H-[1,4]thiazino[2,3,4-ij]quinazolin-7-yl)-3-((methylsulfonyl)methyl)piperazine-1-carboxylate as a light yellow solid (140 mg, 74%).

m/z (ESI, +ve)=627.0 (M+H)$^+$.

Step 3: 9-chloro-10-(2,4-difluorophenyl)-7-((R)-2-((methylsulfonyl)methyl)piperazin-1-yl)-2,3-dihydro-5H-[1,4]thiazino[2,3,4-ij]quinazolin-5-one

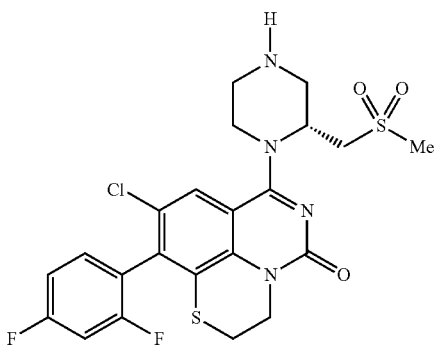 [SMILES: CS(=O)(=O)C[C@H]1CNCCN1c1nc(=O)n2c3c(c(-c4ccc(F)cc4F)c(Cl)cc13)SCC2]

tert-butyl (3R)-4-(9-chloro-10-(2, 4-difluorophenyl)-5-oxo-2, 3-dihydro-5H-[1,4]thiazino[2, 3, 4-ij]quinazolin-7-yl)-3-((methylsulfonyl)methyl) piperazine-1-carboxylate) (0.16 mmol, 100 mg) was dissolved in dichloromethane (2 mL), and trimethylsilyl trifluoromethanesulfonate (0.32 mmol, 71 mg) was added. The mixture was stirred for 30 minutes at room temperature and the solvent removed under reduced pressure to afford a crude residue which was directly used in the next step Example 186: 7-((R)-4-acryloyl-3-((methylsulfonyl)methyl)piperazin-1-yl)-9-chloro-10-(2,4-difluorophenyl)-2,3-dihydro-5H-[1,4]thiazino[2,3,4-ij]quinazolin-5-one

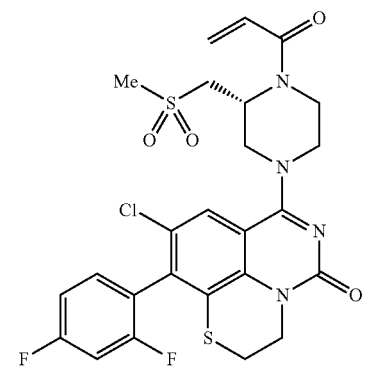 [SMILES: C=CC(=O)N1CCN(c2nc(=O)n3c4c(c(-c5ccc(F)cc5F)c(Cl)cc24)SCC3)C[C@@H]1CS(C)(=O)=O]

benzyl (2R)-4-(9-chloro-10-(2, 4-difluorophenyl)-5-oxo-2, 3-dihydro-5H-[1, 4]thiazino[2, 3, 4-ij]quinazolin-7-yl)-2-((methylsulfonyl)methyl)piperazine-1-carboxylate) (0.15 mmol, 100 mg) was dissolved in TFA (2 mL) and the mixture was stirred at 55° C. overnight. The mixture was washed with saturated aqueous sodium carbonate, diluted with brine and dichloromethane. The organic phase was dried with Na$_2$SO$_4$, and the solvent was removed under reduced pressure to afford a residue that was dissolved in dichloromethane (2 mL) and cooled down to 0° C. DIPEA (0.3 mmol, 39 mg) and acryloyl chloride (0.18 mmol, 17 mg) were added and the mixture stirred for 1 hour. The reaction mixture was washed with saturated aqueous sodium carbonate, diluted with brine and dichloromethane. The organic layer was separated and dried with Na$_2$SO$_4$, and the solvent was removed under reduced pressure to afford a crude material that was purified by preparative HPLC yielding 7-((R)-4-acryloyl-3-((methylsulfonyl)methyl)piperazin-1-yl)-9-chloro-10-(2,4-difluorophenyl)-2,3-dihydro-5H-[1, 4]thiazino[2,3,4-ij]quinazolin-5-one in 29% yield m/z (ESI, +ve)=581.3 (M+H)$^+$.

1H NMR (400 MHz, DMSO) δ 7.85 (d, J=16.7 Hz, 1H), 7.48 (dd, J=10.7, 8.5 Hz, 1H), 7.44-7.37 (m, 1H), 7.28 (t, J=8.5 Hz, 1H), 6.81 (dd, J=44.3, 27.8 Hz, 1H), 6.19 (d, J=16.7 Hz, 1H), 5.77 (d, J=10.6 Hz, 1H), 5.20 (s, 1H), 4.91 (s, 1H), 4.45-4.25 (m, 2H), 4.16 (s, 2H), 4.05-3.83 (m, 2H), 3.60 (s, 2H), 3.39 (s, 2H), 3.24-3.12 (m, 2H), 3.07 (t, J=19.0 Hz, 4H).

Step 1: benzyl (R)-4-(10-bromo-9-chloro-5-oxo-2,3-dihydro-5H-[1,4]thiazino[2,3,4-ij]quinazolin-7-yl)-2-((methylsulfonyl)methyl)piperazine-1-carboxylate

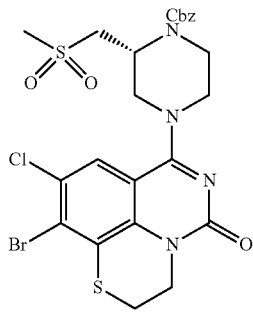 [SMILES: CS(=O)(=O)C[C@H]1CN(c2nc(=O)n3c4c(c(Br)c(Cl)cc24)SCC3)CCN1C(=O)OCc1ccccc1]

The title compound was prepared analogously to Example 164, step 1 where 10-bromo-9-chloro-2, 3-dihydro-5H-[1, 4]thiazino[2, 3, 4-ij]quinazoline-5, 7(6H)-dione was substituted in place of 9-chloro-10-(2,4-difluorophenyl)-2,3-dihydro-5H-[1,4]thiazino[2,3,4-ij]quinazoline-5,7(6H)-dione in 54% yield.

m/z (ESI, +ve)=628.2 (M+H)⁺.

Step 2: Benzyl (2R)-4-(9-chloro-10-(2,4-difluorophenyl)-5-oxo-2,3-dihydro-5H-[1,4]thiazino[2,3,4-ij]quinazolin-7-yl)-2-((methylsulfonyl)methyl)piperazine-1-carboxylate

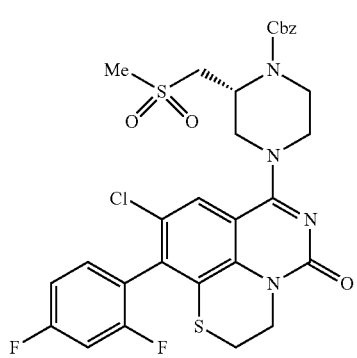 [SMILES: CS(=O)(=O)C[C@H]1CN(c2nc(=O)n3c4c(c(-c5ccc(F)cc5F)c(Cl)cc24)SCC3)CCN1C(=O)OCc1ccccc1]

Benzyl (R)-4-(10-bromo-9-chloro-5-oxo-2, 3-dihydro-5H-[1, 4]thiazino[2, 3, 4-ij]quinazolin-7-yl)-2-((methylsulfonyl)methyl)piperazine-1-carboxylate) (0.4 mmol, 250 mg), (2,4-difluorophenyl) boronic acid (0.44 mmol, 69 mg), XPhos-Pd-G2 (0.04 mmol, 31 mg), XPhos (0.04 mmol, 19 mg) and Cs₂CO₃ (0.8 mmol, 174 mg) were dissolved in dioxane (4.5 mL) and water (1.5 mL). The reaction was refluxed overnight and the insoluble materials filtered. The solution was diluted with dichloromethane and water and the organic layer was dried with Na₂SO₄ and concentrated under reduced pressure. The residue was purified by chromatography (dichloromethane/methanol=60:1-40:1) to afford benzyl (2R)-4-(9-chloro-10-(2,4-difluorophenyl)-5-oxo-2,3-dihydro-5H-[1,4]thiazino[2,3,4-ij]quinazolin-7-yl)-2-((methylsulfonyl)methyl)piperazine-1-carboxylate as light yellow solid (120 mg, 45%).

m/z (ESI, +ve)=661.44 (M+H)⁺.

Example 187: 7-((S)-4-acryloyl-3-((methylsulfonyl)methyl)piperazin-1-yl)-9-chloro-10-(2,4-difluorophenyl)-2,3-dihydro-5H-[1,4]thiazino[2,3,4-ij]quinazolin-5-one

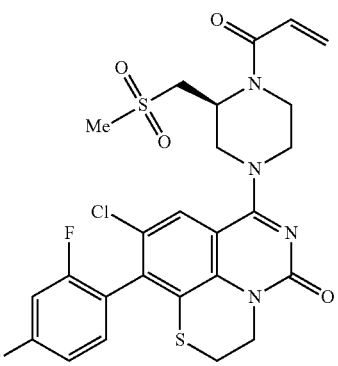

The title compound was prepared analogously to Example 186, where benzyl (S)-4-(10-bromo-9-chloro-5-oxo-2,3-dihydro-5H-[1,4]thiazino[2,3,4-ij]quinazolin-7-yl)-2-((methylsulfonyl)methyl)piperazine-1-carboxylate was substituted in place of benzyl (2R)-4-(9-chloro-10-(2, 4-difluorophenyl)-5-oxo-2, 3-dihydro-5H-[1, 4]thiazino[2, 3, 4-ij]quinazolin-7-yl)-2-((methylsulfonyl)methyl)piperazine-1-carboxylate) in 45% yield.

m/z (ESI, +ve)=581.3 (M+H)⁺.

1H NMR (400 MHz, DMSO) δ 7.94-7.80 (m, 1H), 7.60-7.38 (m, 2H), 7.28 (td, J=8.5, 2.3 Hz, 1H), 6.85 (ddd, J=61.0, 16.4, 10.5 Hz, 1H), 6.19 (dd, J=16.7, 1.5 Hz, 1H), 5.77 (d, J=10.3 Hz, 1H), 5.07 (d, J=118.9 Hz, 1H), 4.45-4.25 (m, 2H), 4.17 (d, J=5.0 Hz, 2H), 4.07-3.72 (m, 2H), 3.73-3.60 (m, 2H), 3.51-3.42 (m, 2H), 3.27-3.12 (m, 2H), 3.06 (d, J=22.7 Hz, 3H).

Step 1: benzyl (S)-4-(10-bromo-9-chloro-5-oxo-2,3-dihydro-5H-[1,4]thiazino[2,3,4-ij]quinazolin-7-yl)-2-((methylsulfonyl)methyl)piperazine-1-carboxylate

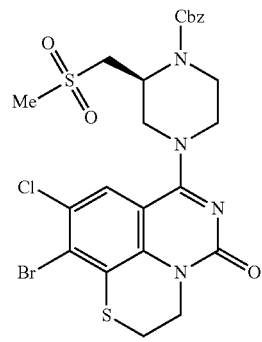 [SMILES: CS(=O)(=O)C[C@@H]1CN(c2nc(=O)n3c4c(c(Br)c(Cl)cc24)SCC3)CCN1C(=O)OCc1ccccc1]

The title compound was prepared analogously to Example 186, step 1 where 7-((S)-4-acryloyl-3-((methylsulfonyl)methyl)piperazin-1-yl)-9-chloro-10-(2,4-difluorophenyl)-2, 3-dihydro-5H-[1,4]thiazino[2,3,4-ij]quinazolin-5-one was substituted in place of 10-bromo-9-chloro-2, 3-dihydro-5H-[1, 4]thiazino[2, 3, 4-ij]quinazoline-5, 7(6H)-dione in 48% yield.

m/z (ESI, +ve)=627.1 (M+H)⁺.

1H NMR (400 MHz, CDCl₃) δ 7.48 (s, 1H), 7.38 (s, 5H), 5.20 (dd, J=24.6, 12.0 Hz, 2H), 4.86 (s, 1H), 4.48 (d, J=13.5 Hz, 2H), 4.35~4.25 (m, 1H), 4.21~4.18 (m, 2H), 3.62 (d, J=11.5 Hz, 1H), 3.39 (s, 3H), 3.23 (s, 3H), 3.11~2.95 (m, 2H), 2.75~2.65 (m, 1H).

Step 2: Benzyl (2S)-4-(9-chloro-10-(2,4-difluorophenyl)-5-oxo-2,3-dihydro-5H-[1,4]thiazino[2,3,4-ij]quinazolin-7-yl)-2-((methylsulfonyl)methyl)piperazine-1-carboxylate

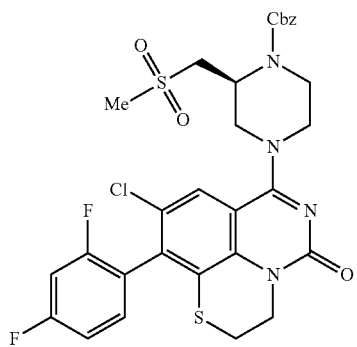 [SMILES: CS(=O)(=O)C[C@@H]1CN(c2nc(=O)n3c4c(c(-c5ccc(F)cc5F)c(Cl)cc24)SCC3)CCN1C(=O)OCc1ccccc1]

Benzyl (S)-4-(10-bromo-9-chloro-5-oxo-2,3-dihydro-5H-[1,4]thiazino[2,3,4-ij]quinazolin-7-yl)-2-((methylsulfonyl)methyl)piperazine-1-carboxylate (150 mg, 0.24 mmol, 1.0 equiv), (2,4-difluorophenyl)boronic acid (76 mg, 0.48 mmol, 2.0 equiv), CsF (146 mg, 0.96 mmol, 4 equiv) and Pd(dppf)Cl2 (35 mg, 0.048 mmol, 0.2 equiv) were dissolved in 1,4-dioxane (1.5 ml) and the reaction stirred for 2 hours at 70° C. The reaction was stopped by addition of water and dichlormethane and the separated organic layer was dried over Na₂SO4, filtered and concentrated to afford a residue that was purified by chromatography (ethyl acetate:hexanes=50-100%) to afford benzyl (2S)-4-(9-chloro-10-(2,4-difluorophenyl)-5-oxo-2,3-dihydro-5H-[1,4]thiazino[2,3,4-ij]quinazolin-7-yl)-2-((methylsulfonyl)methyl)piperazine-1-carboxylate as a yellow solid (140 mg, 88%).

m/z (ESI, +ve)=661.2 (M+H)⁺.

Example 188

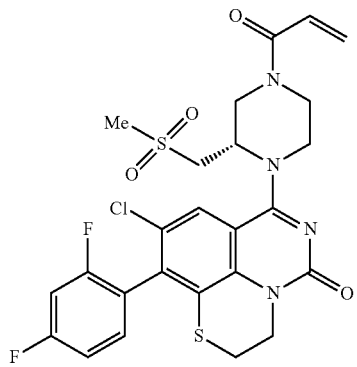 [SMILES: C=CC(=O)N1CCN(c2nc(=O)n3c4c(c(-c5ccc(F)cc5F)c(Cl)cc24)SCC3)[C@H](CS(C)(=O)=O)C1]

The title compound was prepared analogously to Example 185 where 9-chloro-10-(2,4-difluorophenyl)-7-((S)-2-((methylsulfonyl)methyl)piperazin-1-yl)-2,3-dihydro-5H-[1,4]thiazino[2,3,4-ij]quinazolin-5-one was substituted in place of 9-chloro-10-(2,4-difluorophenyl)-7-((R)-2-((methylsulfonyl)methyl)piperazin-1-yl)-2,3-dihydro-5H-[1,4]thiazino[2,3,4-ij]quinazolin-5-one in 51% yield as a white solid.

m/z (ESI, +ve)=581.3 (M+H)⁺.

1H NMR (400 MHz, DMSO) δ 7.65 (d, J=6.8 Hz, 1H), 7.49 (td, J=9.7, 2.5 Hz, 1H), 7.44-7.34 (m, 1H), 7.28 (t, J=8.4 Hz, 1H), 6.81 (dd, J=16.6, 10.5 Hz, 1H), 6.19 (d, J=16.5 Hz, 1H), 5.77 (d, J=8.9 Hz, 1H), 5.34 (t, J=32.0 Hz, 1H), 4.55-4.45 (m, 1H), 4.40-4.07 (m, 2H), 4.05-3.75 (m, 4H), 3.60-3.45 (m, 1H), 3.23-3.13 (m, 3H), 3.13 (d, J=15.2 Hz, 3H), 2.95-2.80 (m, 1H).

Step 1: tert-butyl (S)-4-(10-bromo-9-chloro-5-oxo-2,3-dihydro-5H-[1,4]thiazino[2,3,4-ij]quinazolin-7-yl)-3-((methylsulfonyl)methyl)piperazine-1-carboxylate

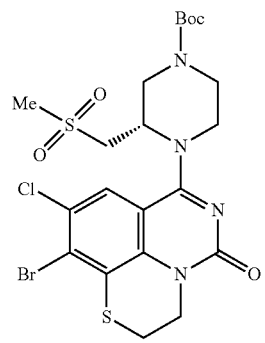 [SMILES: CC(C)(C)OC(=O)N1CCN(c2nc(=O)n3c4c(c(Br)c(Cl)cc24)SCC3)[C@H](CS(C)(=O)=O)C1]

The title compound was prepared analogously to Example 185, step 1 where tert-butyl (S)-3-((methylsulfonyl)methyl)piperazine-1-carboxylate was substituted in place of tert-butyl (R)-3-((methylsulfonyl)methyl)piperazine-1-carboxylate in 47% yield as a white solid.

m/z (ESI, +ve)=593.1 (M+H)⁺

Step 2: tert-butyl (3S)-4-(9-chloro-10-(2,4-difluorophenyl)-5-oxo-2,3-dihydro-5H-[1,4]thiazino[2,3,4-ij]quinazolin-7-yl)-3-((methylsulfonyl)methyl)piperazine-1-carboxylate

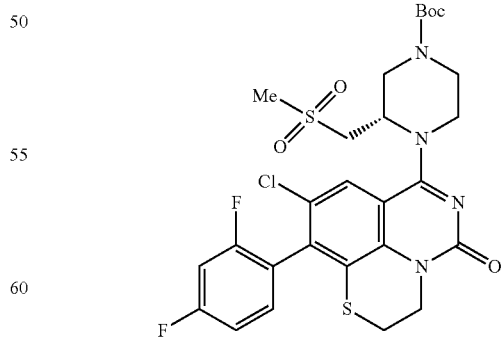

The title compound was prepared analogously to Example 185, step 2 where tert-butyl (S)-4-(10-bromo-9-chloro-5-oxo-2, 3-dihydro-5H-[1,4]thiazino[2, 3, 4-ij]quinazolin-7-yl)-3-((methylsulfonyl)methyl)piperazine-1-carboxylate was substituted in place of tert-butyl (R)-4-(10-bromo-9-chloro-5-oxo-2, 3-dihydro-5H-[1,4]thiazino[2, 3, 4-ij]quinazolin-7-yl)-3-((methylsulfonyl)methyl)piperazine-1-carboxylate in 80% yield as a yellow solid.

m/z (ESI, +ve)=627.2 (M+H)⁺

Step 3: 9-chloro-10-(2,4-difluorophenyl)-7-((S)-2-((methylsulfonyl)methyl)piperazin-1-yl)-2,3-dihydro-5H-[1,4]thiazino[2,3,4-ij]quinazolin-5-one

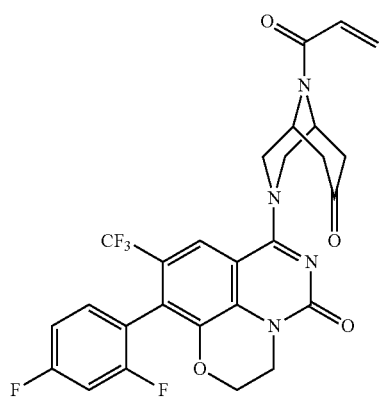 [SMILES: C=CC(=O)N1C2CC(=O)CC1CN(c1nc(=O)n3c4c(c(-c5ccc(F)cc5F)c(C(F)(F)F)cc14)OCC3)C2]

Trifluoroacetic acid (0.5 mL) was added over a solution of tert-butyl (3S)-4-(9-chloro-10-(2,4-difluorophenyl)-5-oxo-2,3-dihydro-5H-[1,4]thiazino[2,3,4-ij]quinazolin-7-yl)-3-((methylsulfonyl)methyl)piperazine-1-carboxylate (120 mg, 0.19 mmol, 1.0 equiv) in dichloromethane (1.5 ml). The reaction was stirred for 2 hours at room temperature, diluted with dichloromethane (100 ml) and washed with 5% sodium carbonate and brine (50 ml). The organic layer was dried with Na₂SO₄ and concentrated to afford the desired product which was used in the next step without further purification.

m/z (ESI, +ve)=527.1 (M+H)⁺

Example 337: 7-(9-acryloyl-7-oxo-3,9-diazabicyclo[3.3.1]nonan-3-yl)-10-(2,4-difluorophenyl)-9-(trifluoromethyl)-2,3-dihydro-5H-[1,4]oxazino[2,3,4-ij]quinazolin-5-one

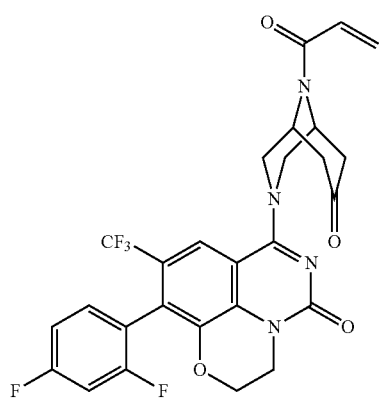 [SMILES: C=CC(=O)N1C2CC(=O)CC1CN(c1nc(=O)n3c4c(c(-c5ccc(F)cc5F)c(C(F)(F)F)cc14)OCC3)C2]

To a solution of 10-(2,4-difluorophenyl)-7-(7-oxo-3,9-diazabicyclo[3.3.1]nonan-3-yl)-9-(trifluoromethyl)-2,3-dihydro-5H-[1,4]oxazino[2,3,4-ij]quinazolin-5-one (90 mg, 0.18 mmol) in dichloromethane (5 mL) at 0° C., triethylamine (108 mg, 1.06 mmol) and acryloyl chloride (32 mg, 0.35 mmol) were added. The reaction mixture was stirred at room temperature for 1 hour and concentrated to afford a residue that was purified by preparative HPLC to afford 7-(9-acryloyl-7-oxo-3,9-diazabicyclo[3.3.1]nonan-3-yl)-10-(2,4-difluorophenyl)-9-(trifluoromethyl)-2,3-dihydro-5H-[1,4]oxazino[2,3,4-ij]quinazolin-5-one (29.1 mg, 27%) as a white solid.

m/z (ESI, +ve)=561.1 (M+H)⁺.

¹H NMR (400 MHz, DMSO) δ 7.67 (s, 1H), 7.41-7.35 (m, 2H), 7.23-7.20 (m, 1H), 7.00-6.90 (m, 1H), 6.27 (d, J=16.0 Hz, 1H), 5.84 (d, J=12.0 Hz, 1H), 5.18 (s, 1H), 4.94 (s, 1H), 4.36-4.29 (m, 2H), 4.24-4.06 (m, 2H), 4.01-3.95 (m, 2H), 3.26-3.14 (m, 2H), 2.89-2.72 (m, 2H), 2.46-2.43 (m, 2H).

Step 1: 10-(2,4-difluorophenyl)-7-(7-oxo-3,9-diazabicyclo[3.3.1]nonan-3-yl)-9-(trifluoromethyl)-2,3-dihydro-5H-[1,4]oxazino[2,3,4-ij]quinazolin-5-one

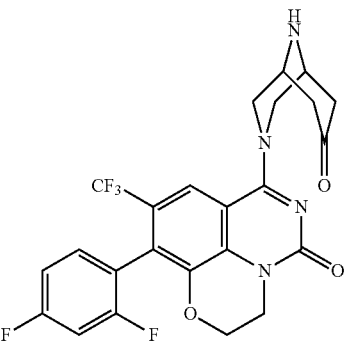 [SMILES: O=C1CC2CN(c3nc(=O)n4c5c(c(-c6ccc(F)cc6F)c(C(F)(F)F)cc35)OCC4)CC(C1)N2]

To a solution of 10-(2,4-difluorophenyl)-9-(trifluoromethyl)-2,3-dihydro-5H-[1,4]oxazino[2,3,4-ij]quinazoline-5,7(6H)-dione (180 mg, 0.47 mmol) in toluene (3 mL), N,N-diisopropylethylamine (725 mg, 5.6 mmol) and POCl₃ (3 mL) were added. The reaction mixture was stirred at 120° C. for 1.5 hours and the volatiles removed under reduced pressure. The resulting residue was dissolved in dichloroethane (2 mL) and added to a solution of 3,9-diazabicyclo[3.3.1]nonan-7-one (398 mg, 1.87 mmol) and NaHCO₃ (785 mg, 9.3 mmol) in DMF (5 mL) at 0° C. The cooling bath was removed and the reaction mixture stirred at room temperature for 1 hour. The solvent was removed and the crude material was purified by silica gel chromatography to afford 10-(2,4-difluorophenyl)-7-(7-oxo-3,9-diazabicyclo[3.3.1]nonan-3-yl)-9-(trifluoromethyl)-2,3-dihydro-5H-[1,4]oxazino[2,3,4-ij]quinazolin-5-one (90 mg, 36%) as a light yellow solid.

m/z (ESI, +ve)=507.1 (M+H)⁺.

Example 338: 8-(9-acryloyl-7-oxo-3,9-diazabicyclo[3.3.1]nonan-3-yl)-11-(2,4-difluorophenyl)-10-(trifluoromethyl)-3,4-dihydro-2H,6H-[1,4]oxazepino[2,3,4-ij]quinazolin-6-one

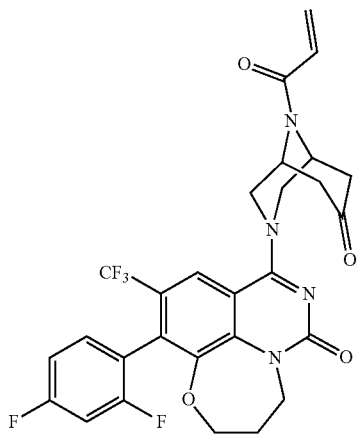 [SMILES: C=CC(=O)N1C2CC(=O)CC1CN(c1nc(=O)n3c4c(c(-c5ccc(F)cc5F)c(C(F)(F)F)cc14)OCCC3)C2]

The title compound was prepared analogously to Example 337, where 11-(2,4-difluorophenyl)-8-(7-oxo-3,9-diazabicyclo[3.3.1]nonan-3-yl)-10-(trifluoromethyl)-3,4-dihydro-2H,6H-[1,4]oxazepino[2,3,4-ij]quinazolin-6-one was substituted in place of 10-(2,4-difluorophenyl)-7-(7-oxo-3,9-diazabicyclo[3.3.1]nonan-3-yl)-9-(trifluoromethyl)-2,3-dihydro-5H-[1,4]oxazino[2,3,4-ij]quinazolin-5-one in 24% yield.

m/z (ESI, +ve)=575.1 (M+H)$^+$.

$^1$H NMR (400 MHz, DMSO) δ 7.71 (s, 1H), 7.42-7.38 (m, 2H), 7.24-7.19 (m, 1H), 7.02-6.98 (m, 1H), 6.27 (d, J=16.0 Hz, 1H), 5.84 (d, J=12.0 Hz, 1H), 5.17 (s, 1H), 4.93 (s, 1H), 4.39-4.24 (m, 2H), 4.21-3.98 (m, 4H), 3.21-3.09 (m, 2H), 2.82-2.73 (m, 2H), 2.46-2.43 (m, 2H), 2.23-2.11 (m, 2H).

Step 1: 7-(2,4-difluorophenyl)-8-(3-hydroxypropoxy)-6-(trifluoromethyl)quinazoline-2,4(1H,3H)-dione

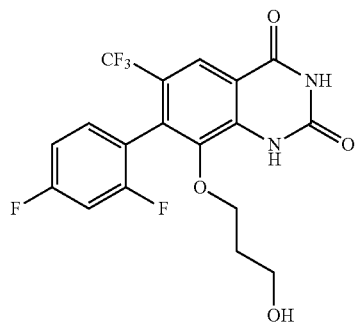 [SMILES: O=c1[nH]c(=O)c2cc(C(F)(F)F)c(-c3ccc(F)cc3F)c(OCCCO)c2[nH]1]

A mixture of 7-(2,4-difluorophenyl)-8-iodo-6-(trifluoromethyl)quinazoline-2,4(1H,3H)-dione (1.5 g, 3.2 mmol), potassium carbonate (1.33 g, 9.6 mmol) and cupric chloride (0.09 g, 0.6 mmol) in propane-1,3-diol (20 mL) was stirred at 140° C. for 16 hours. The reaction was quenched with water (20 mL), extracted with ethyl acetate (20 mL×3) and the combined organic layers washed with brine (20 mL), dried over Na$_2$SO$_4$ and filtered. Chromatography in silica gel afforded 7-(2,4-difluorophenyl)-8-(3-hydroxypropoxy)-6-(trifluoromethyl)quinazoline-2,4(1H,3H)-dione (340 mg, 23%) as a yellow solid.

m/z (ESI, +ve)=417.1 (M+H)$^+$.

Step 2: 11-(2,4-difluorophenyl)-10-(trifluoromethyl)-3,4-dihydro-2H,6H-[1,4]oxazepino[2,3,4-ij]quinazoline-6,8(7H)-dione

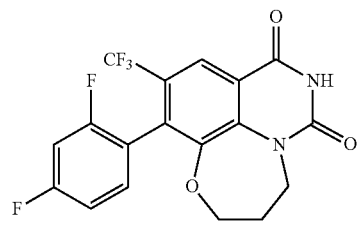 [SMILES: O=c1[nH]c(=O)n2c3c(c(-c4ccc(F)cc4F)c(C(F)(F)F)cc13)OCCC2]

To a mixture of PPh3 (320 mg, 1.22 mmol) in THF (3 mL) was added DIAD (247 mg, 1.22 mmol) in THF (3 mL) at 0° C. The solution was stirred at that temperature for 20 minutes and 7-(2,4-difluorophenyl)-8-(3-hydroxypropoxy)-6-(trifluoromethyl)quinazoline-2,4(1H,3H)-dione (340 mg, 0.81 mmol) was added as a solution in THF (4 mL). The mixture was allowed to reach room temperature over 2 hours and the volatiles were removed under reduced pressure. Purification of the residue by column chromatography afforded 11-(2,4-difluorophenyl)-10-(trifluoromethyl)-3,4-dihydro-2H,6H-[1,4]oxazepino[2,3,4-ij]quinazoline-6,8(7H)-dione (187 mg, 51%) as a yellow-green solid.

m/z (ESI, +ve)=399.1 (M+H)$^+$.

Step 3: 11-(2,4-difluorophenyl)-8-(7-oxo-3,9-diazabicyclo[3.3.1]nonan-3-yl)-10-(trifluoromethyl)-3,4-dihydro-2H,6H-[1,4]oxazepino[2,3,4-ij]quinazolin-6-one

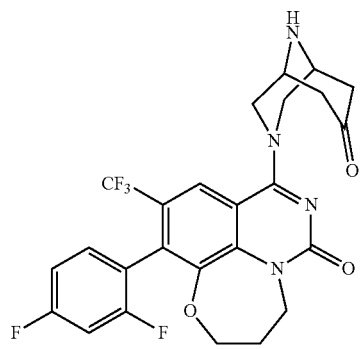 [SMILES: O=C1CC2CN(c3nc(=O)n4c5c(c(-c6ccc(F)cc6F)c(C(F)(F)F)cc35)OCCC4)CC(C1)N2]

To a solution of 11-(2,4-difluorophenyl)-10-(trifluoromethyl)-3,4-dihydro-2H,6H-[1,4]oxazepino[2,3,4-ij]quinazoline-6,8(7H)-dione (180 mg, 0.45 mmol) in toluene (3 mL), N,N-diisopropylethylamine (699 mg, 5.4 mmol) and POCl$_3$ (3 mL) were added. The reaction mixture was stirred at 120° C. for 1.5 hours and concentrated. The resulting residue was dissolved in dichloroethane (2 mL) and added over a mixture of 3,9-diazabicyclo[3.3.1]nonan-7-one (384 mg, 1.8 mmol) and NaHCO$_3$ (757 mg, 9.0 mmol) in DMF (5 mL) at 0° C. This new reaction mixture was stirred at room temperature for 1 hour and after evaporation of the volatiles and purification of the crude material by chromatography, 11-(2,4-difluorophenyl)-8-(7-oxo-3,9-diazabicyclo[3.3.1]nonan-3-yl)-10-(trifluoromethyl)-3,4-dihydro-2H,6H-[1,4]oxazepino[2,3,4-ij]quinazolin-6-one (50 mg, 20%) was isolated as a light yellow solid.

m/z (ESI, +ve)=521.1 (M+H)$^+$.

Example Pyrimidone-Thiomorpholines-B

12. General Information

1H NMR spectra were recorded in either CDCl$_3$ or DMSO-d6 on either a BRUKER AVANCE III 400 MHz or BRUKER FOURIER 300 MHz. The internal standard used was either tetramethylsilane or the residual protonated solvent at 7.26 ppm for CDCl$_3$ or 2.50 ppm for DMSO-d6. Chemical shifts are reported in parts per million (ppm). Abbreviations for NMR data are as follows: s=singlet, d=doublet, t=triplet, m=multiplet, br s=broad singlet, dd=doublet of doublets, dt=doublet of triplets, tt=triplet of triplets, ddd=doublet of doublet of doublets, sextuplet of d=sextuplet of doublets. J indicates the 1H NMR coupling constant measured in Hertz.

Mass spectrum was recorded on a Waters ZQ mass spectrometer using alternative-scan positive and negative mode electrospray ionisation. Cone voltage: 30V.

13. Syntheses of Intermediates for Substituted Tricyclic Thiomorpholine Compounds 6-chloro-7-(2,4-difluorophenyl)-8-iodoquinazoline-2,4(1H,3H)-dione Reaction Scheme 1

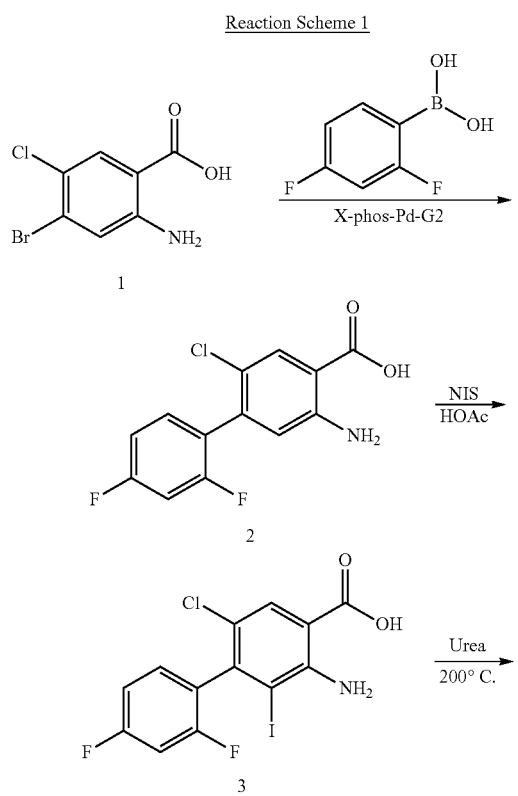

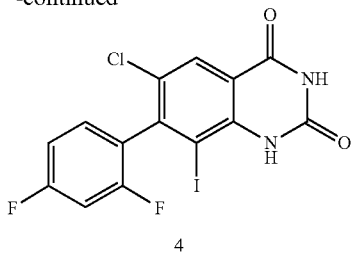

5-amino-2-chloro-2',4'-difluoro-[1,1'-biphenyl]-4-carboxylic acid (2)

To a mixture of 2-amino-4-bromo-5-chlorobenzoic acid (20 g, 79.7 mmol), (2,4-difluorophenyl)boronic acid (37.8 g, 239.1 mmol) and K$_2$CO$_3$ (33 g, 239.1 mmol) in dioxane/H$_2$O (200 mL/40 mL) was added Xphos-Pd-G2 (4.7 g, 5.6 mmol). The reaction mixture was stirred at 80° C. under nitrogen atmosphere for 6 hours. The mixture was filtrated and diluted with H$_2$O. The pH was adjusted to 2 with 2N HCl, then extracted with EtOAc. The organic layer was washed with brine and then concentrated in vacuo. The solid obtained was washed with ACN to give 5-amino-2-chloro-2',4'-difluoro-[1,1'-biphenyl]-4-carboxylic acid (7.6 g+17 g crude) as an off white solid.

LC-MS: m/z 284.2 [M+H]$^+$ 3-amino-6-chloro-2',4'-difluoro-2-iodo-[1,1'-biphenyl]-4-carboxylic acid (3)

To a mixture of 5-amino-2-chloro-2',4'-difluoro-[1,1'-biphenyl]-4-carboxylic acid (21.6 g, 76.3 mmol) in AcOH (250 mL) was added NIS (25.7 g, 114.4 mmol) at 0° C. The reaction mixture was stirred at rt overnight. The reaction mixture was concentrated in vacuum and diluted with H$_2$O. The reaction was quenched by Na$_2$S$_2$O$_3$ (aq), then extracted with EtOAc (200 mL). The organic phase was washed with brine (150 mL), concentrated in vacuum to give the crude product 3-amino-6-chloro-2',4'-difluoro-2-iodo-[1,1'-biphenyl]-4-carboxylic acid (26 g crude) as brown solid.

LC-MS: m/z 409.9[M+H]$^+$.

6-chloro-7-(2,4-difluorophenyl)-8-iodoquinazoline-2,4(1H,3H)-dione (4)

To a 250 mL glass pressure vessel equipped with stirring bar was charged 3-amino-6-chloro-2',4'-difluoro-2-iodo-[1,1'-biphenyl]-4-carboxylic acid (26 g, 63.56 mmol) and urea (38 g, 635.6 mol). The vessel was placed on a preheated block at 200° C. and the reaction was stirred for 4 h. The mixture reaction mixture was cooled to 80° C. and diluted with water. After filtration, the filter cake was washed with Petroleum Ether/EtOAc (30 mL/10 mL) to give 6-chloro-7-(2,4-difluorophenyl)-8-iodoquinazoline-2,4(1H,3H)-dione (7.6 g, yield: 27%) as a white solid.

LC-MS: m/z 433.1[M−H]$^+$.

5-((tert-butyldiphenylsilyl)oxy)-1-mercaptopentan-2-ol

Reaction Scheme 2

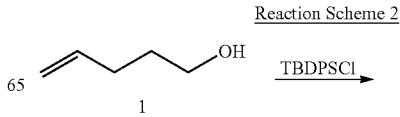

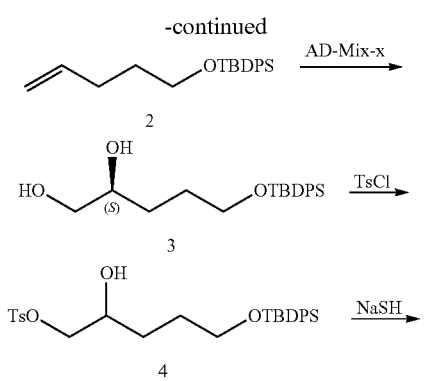

tert-butyl(pent-4-en-1-yloxy)diphenylsilane (2)

To a solution of pent-4-en-1-ol (25 g, 290 mmol) and imidazole (29 g, 435 mmol) in DMF (400 mL) was added TBDPSCl (95 g, 348 mmol) at 0° C. The mixture was stirred at rt for 16 hours. The mixture was concentrated to remove most of DMF followed by the addition of $H_2O$ (500 mL. The resulting mixture was extracted with EtOAc (500 mL×3). The organic layers were combined and concentrated under reduced pressure. The residue was purified by silica gel column with 1% EA in PE to afford the product (74 g, 79%) as light yellow oil. MS (ESI) m/z 325.2 $[M+H]^+$.

5-((tert-butyldiphenylsilyl)oxy)pentane-1,2-diol (3)

To a solution of tert-butyl(pent-4-en-1-yloxy)diphenylsilane (58 g, 179 mmol) in t-BuOH (300 mL) and $H_2O$ (300 mL) was added AD-mix-α (232 g) at 0° C. The mixture was stirred at rt for 16 hours. The reaction was quenched with $NaS_2O_3$ aqueous solution and stirred at rt for 2 h. Then the mixture was extracted with EtOAc (500 mL×3). The organic layer was concentrated, and the residue was purified by silica gel column with 5% MeOH in DCM to afford the product (55 g, 85%) as light yellow oil. MS (ESI) m/z 359.2 $[M+H]^+$.

5-((tert-butyldiphenylsilyl)oxy)-2-hydroxypentyl 4-methylbenzenesulfonate (4)

To a solution of 5-((tert-butyldiphenylsilyl)oxy)pentane-1,2-diol (54 g, 152 mmol) and TEA (43 mL, 304 mmol) in DCM (500 mL) was added TsCl (32 g, 167 mmol) at 0° C. The mixture was stirred at rt for 16 hours. 500 mL of $H_2O$ was added and extracted with DCM (500 mL×3). The organic layer was concentrated, and the residue was purified by silica gel column with 10% EtOAc in PE to afford the product (50 g, 64%) as light yellow oil. MS (ESI) m/z 513.2 $[M+H]^+$.

5-((tert-butyldiphenylsilyl)oxy)-1-mercaptopentan-2-ol (5)

To a solution of 5-((tert-butyldiphenylsilyl)oxy)-2-hydroxypentyl 4-methylbenzenesulfonate (44 g, 87 mmol) in the dry DMF (120 mL) was added NaSH (14 g, 260 mmol). The mixture was stirred at rt for 1 h. 500 mL $H_2O$ was added and extracted with EtOAc (400 mL×3). The organic layer was concentrated, and the residue was purified by silica gel column with 8% EtOAc in Petroleum Ether to afford the product (22 g, 67%) as light yellow oil. MS (ESI) m/z 375.1 $[M+H]^+$.

7-(2,4-difluorophenyl)-8-iodo-6-(trifluoromethyl)quinazoline-2,4(1H,3H)-dione

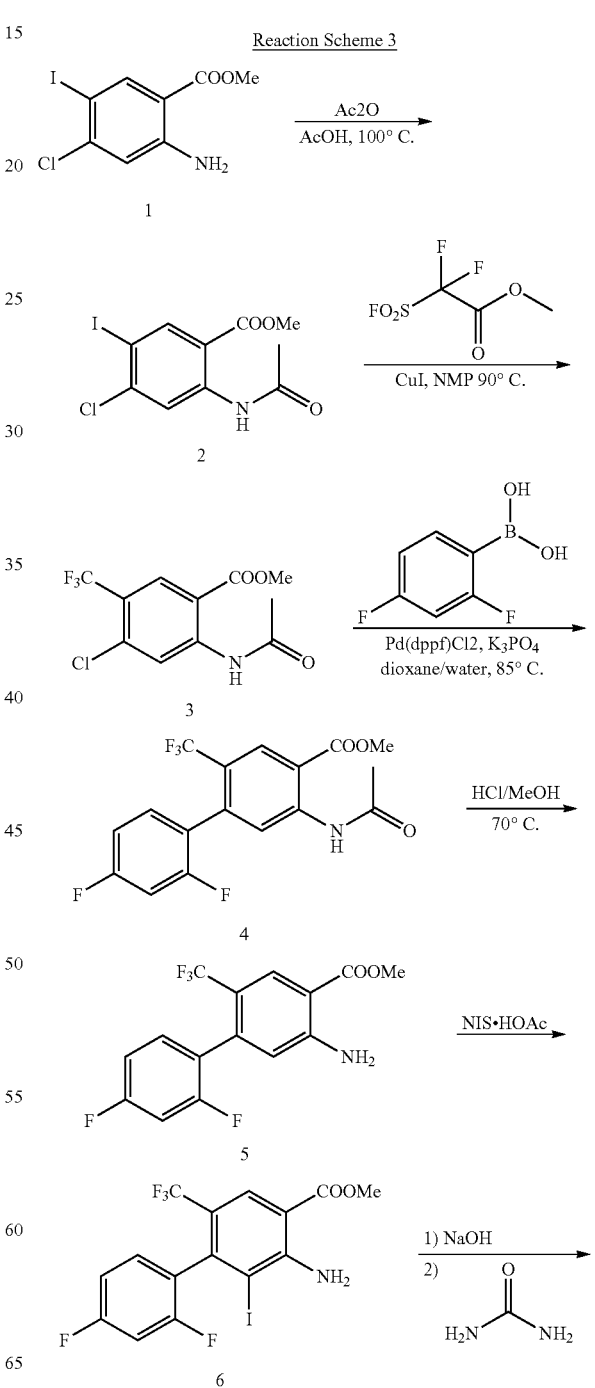

Reaction Scheme 3

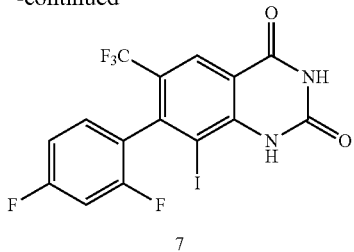

7 methyl 2-acetamido-4-chloro-5-iodobenzoate (2)

To a mixture of methyl 2-amino-4-chloro-5-iodobenzoate (50.00 g, 160.51 mmol) in AcOH (500 mL) was added Ac₂O (19.66 g, 192.61 mmol). The mixture was stirred at 100° C. for 16 hours. After completion, the mixture was cooled to rt, filtered and washed with Petroleum Ether (200 mL) to afford crude product (35 g, yield: 62%) as white solid. MS (ESI) m/z 353.9 [M+H]⁺.

methyl 2-acetamido-4-chloro-5-(trifluoromethyl)benzoate (3)

To a mixture of methyl 2-acetamido-4-chloro-5-iodobenzoate (35.00 g, 98.98 mmol) in DMF (350 mL) was added methyl 2,2-difluoro-2-(fluorosulfonyl)acetate (70.09 g, 395.99 mmol), HMPA (70.98 g, 395.99 mmol) and CuI (15.05 g, 79.19 mmol). The mixture was stirred at 90° C. under N₂ for 16 hours. After completion, the mixture was poured into water (300 mL), extracted with EtOAc (200 mL×3). The combined organic phases were washed with brine (500 mL) and dried over Na₂SO₄, After filtration and concentration, the residue was purified by silica gel column with Petroleum Ether/EtOAc=100/1 to 20/1 to afford desired product (25.00 g, yield: 84%) as white solid. MS (ESI) m z 296.0 [M+H]⁺.

Methyl 5-acetamido-2',4'-difluoro-2-(trifluoromethyl)-[1,1'-biphenyl]-4-carboxylate (4)

To a mixture of methyl 2-acetamido-4-chloro-5-(trifluoromethyl)benzoate (20.00 g, 98.98 mmol) in dioxane (200 mL) and water (20 mL) was added (2,4-difluorophenyl)boronic acid (35.02 g, 202.95 mmol), Pd(dppf)Cl₂ (7.42 g, 10.14 mmol) and K₃PO₄ (43.08 g, 202.95 mmol). The mixture was stirred at 85° C. under N₂ for 2 h. (2,4-difluorophenyl)boronic acid (35.02 g, 202.95 mmol) was added to above solution, then the mixture was stirred at 85° C. under N₂ for 16 hours. After completion, the mixture was poured into water (200 mL), extracted with EtOAc (150 mL×3). The combined organic phases were washed with brine (300 mL) and dried over Na₂SO₄, After filtration and concentration, the residue was purified by silica gel column using a gradient of Petroleum Ether/EtOAc (50/1 to 15/1) to afford the desired product (16.60 g, yield: 62%) as white solid. MS (ESI) m/z 374.0 [M+H]⁺

Methyl 5-amino-2',4'-difluoro-2-(trifluoromethyl)-[1,1'-biphenyl]-4-carboxylate (5)

A mixture of methyl 5-acetamido-2',4'-difluoro-2-(trifluoromethyl)-[1,1'-biphenyl]-4-carboxylate (26.00 g, 69.65 mmol) in HCl/MeOH (300 mL) was stirred at 70° C. for 2 h. The mixture was concentrated and a saturated aqueous solution of NaHCO₃ (100 mL) was added. The resulting mixture was extracted with EtOAc (50 mL×3). The combined organic phases were combined, washed with brine (100 mL) and dried over Na₂SO₄. The solvent was removed in vacuo to afford the crude product (23.00 g) as a yellow solid. MS (ESI) m/z 332.0 [M+H]⁺

Methyl 3-amino-2',4'-difluoro-2-iodo-6-(trifluoromethyl)-[1,1'-biphenyl]-4-carboxylate (6)

To a mixture of methyl 5-amino-2',4'-difluoro-2-(trifluoromethyl)-[1,1'-biphenyl]-4-carboxylate (23.00 g, 69.44 mmol) in AcOH (200 mL) was added NIS (18.75 g, 83.32 mmol). The mixture was stirred at 50° C. for 2 h. After completion, the mixture was poured into water (200 mL), extracted with EtOAc (150 mL×3). The combined organic phases were washed with brine (300 mL) and dried over Na₂SO₄. After filtration and concentration, the residue was purified by silica gel column with Petroleum Ether/EtOAc=200/1 to 20/1 to afford the desired product (26.00 g, 62% yield) as white solid. MS (ESI) m/z 457.9 [M+H]⁺

7-(2,4-difluorophenyl)-8-iodo-6-(trifluoromethyl)quinazoline-2,4(1H,3H)-dione (7)

To a solution of methyl 3-amino-2',4'-difluoro-2-iodo-6-(trifluoromethyl)-[1,1'-biphenyl]-4-carboxylate (25.00 g, 54.69 mmol) in dioxane (200 mL) and water (200 mL) was added NaOH (4.37 g, 109.38 mmol). The mixture was stirred at 90° C. for 3 h. After completion, the mixture was poured into water (200 mL). Adjusted pH=4~5 and extracted with EtOAc (150 mL×3). The combined organic phases were washed with brine (300 mL) and dried over Na₂SO₄. The solvent was removed in vacuo to give 3-amino-2',4'-difluoro-2-iodo-6-(trifluoromethyl)-[1,1'-biphenyl]-4-carboxylic acid (24 g, crude) as yellow solid.

A mixture of 3-amino-2',4'-difluoro-2-iodo-6-(trifluoromethyl)-[1,1'-biphenyl]-4-carboxylic acid (5.00 g, 11.28 mmol) and urea (13.55 g, 225.68 mmol) was stirred at 198° C. for 6 hours. After completion, the mixture was cooled to 80° C., water (200 mL) was added to the solution and stirred for 1 h. The mixture was filtrated to afford the desired product (3.00 g, 56% yield) as a white solid. MS (ESI) m/z 467.9 [M+H]⁺

(R)-benzyl 4-(2-hydroxy-3-mercaptopropyl)piperidine-1-carboxylate

Reaction Scheme 4

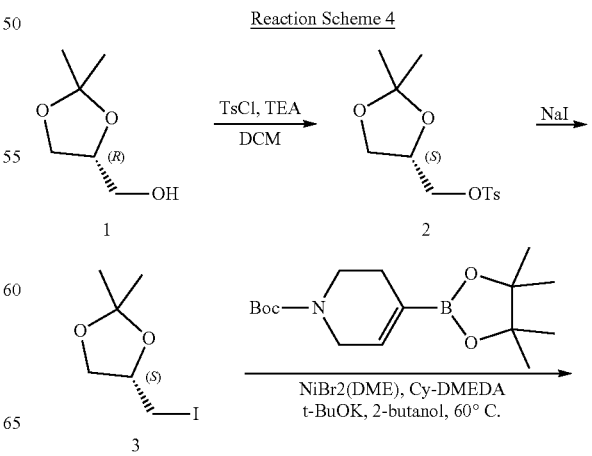

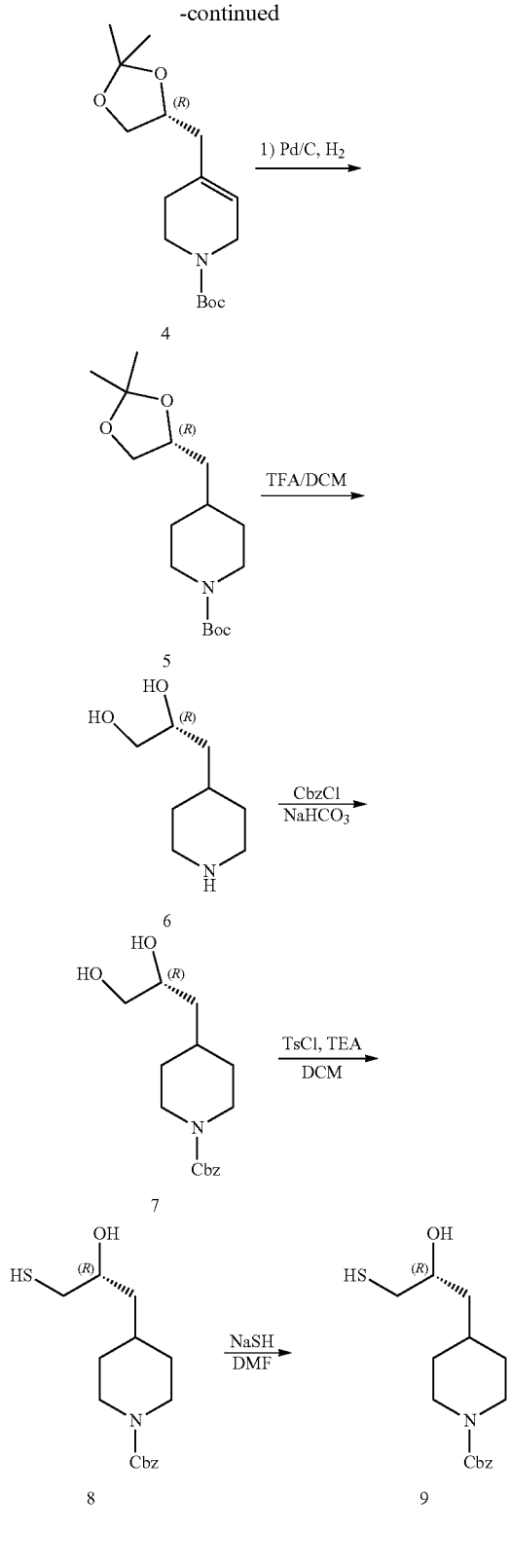

(S)-(2,2-dimethyl-1,3-dioxolan-4-yl)methyl 4-methylbenzenesulfonate (2)

To a mixture of (R)-(2,2-dimethyl-1,3-dioxolan-4-yl) methanol (50 g, 378 mmol), DMAP (6.0 g, 49 mmol) and TEA (105 mL, 755 mmol) in DCM (500 mL) was added TsCl (108.2 g, 567.5 mmol) at 0° C. The mixture was stirred at rt overnight. The reaction solution was poured into NaHCO$_3$ (aq) (1.2 L) and stirred for 1 h. The mixture was extracted with DCM (200 mL). The organic layer was washed with water (1 L), dried over Na$_2$SO$_4$, filtered and concentrated under reduced pressure to afford the title compound (119.3 g, crude) as a colorless oil, which was used to next step without further purification. MS (ESI) m/z 287.1 [M+H]$^+$.

(S)-4-(iodomethyl)-2,2-dimethyl-1,3-dioxolane (3)

To a mixture of (S)-(2,2-dimethyl-1,3-dioxolan-4-yl) methyl 4-methylbenzenesulfonate (119.3 g, 378.3 mmol) in acetone (900 mL) was added NaI (1.12 kg, 7.57 mol). The mixture was stirred at 75° C. overnight. The reaction solution was filtered and the solvent was removed in vacuo. The residue was redissolved with EtOAc (1 L) and the resulting solution was washed with water (1.5 L), Na$_2$SO$_3$ (aq, 500 mL) and brine (500 mL). The water phase was extracted with EtOAc (1 L). The combined organic phases were dried over Na$_2$SO$_4$, filtered and concentrated under reduced pressure. The residue was purified by silica gel chromatography (10% ethyl acetate in petroleum ether) to afford the title compound (81.4 g, 1.08 mmol, 83% yield) as yellow liquid. $^1$H NMR (400 MHz, CDCl$_3$) δ 4.31-4.25 (m, 1H), 4.17-4.13 (m, 1H), 3.80-3.77 (m, 1H), 3.27-3.24 (m, 1H), 3.14 (t, J=8.8 Hz, 1H), 1.46 (s, 3H), 1.35 (s, 3H).

(R)-tert-butyl 4-((2,2-dimethyl-1,3-dioxolan-4-yl)methyl)-5,6-dihydropyridine-1(2H)-carboxylate (4)

To a mixture of tert-butyl 4-(4,4,5,5-tetramethyl-1,3,2-dioxaborolan-2-yl)-5,6-dihydropyridine-1(2H)-carboxylate (54 g, 174.8 mmol) in dioxane (550 ml) was added Ni(dme)Br$_2$ (5.4 g, 17.5 mmol), Cy-DMEDA (2.48 g, 17.5 mmol) and t-BuOK (39.2 g, 349.6 mmol) at 0° C. under N$_2$. The mixture was heated to 60° C. for 18 hours and was diluted with H$_2$O and extracted with EtOAc. The organic layer was washed with water and brine. The solvent was removed in vacuo, and the residue was purified by column with a mixture of Petroleum Ether/EtOAc (10:1) to afford (R)-tert-butyl 4-((2,2-dimethyl-1,3-dioxolan-4-yl)methyl)-5,6-dihydropyridine-1(2H)-carboxylate (29.5 g, 57% yield) as a yellow oil; LC-MS:m/z 198.1.[M+H-Boc]$^+$.

(R)-tert-butyl 4-((2,2-dimethyl-1,3-dioxolan-4-yl)methyl)piperidine-1-carboxylate (5)

To a mixture of (R)-tert-butyl 4-((2,2-dimethyl-1,3-dioxolan-4-yl)methyl)-5,6-dihydropyridine-1(2H)-carboxylate (29.5 g, 99.3 mol) in MeOH (300 mL) was added Pd/C (7 g). The mixture was stirred at rt under H$_2$ for 4 h. The reaction was determined to be completed by LCMS and the mixture was filtered. The filtrate was concentrated under reduced pressure to afford (R)-tert-butyl 4-((2,2-dimethyl-1,3-dioxolan-4-yl)methyl)piperidine-1-carboxylate (22 g, crude) as yellow oil; LC-MS: m/z 200.2 [M+H-Boc]$^+$.

(R)-3-(piperidin-4-yl)propane-1,2-diol (6)

To a mixture of (R)-tert-butyl 4-((2,2-dimethyl-1,3-dioxolan-4-yl)methyl)piperidine-1-carboxylate (22 g, 73.6 mmol) in DCM (40 ml) at rt was added TFA (40 mL). Then the mixture was stirred at rt for 2 h. After completion, the pH was adjusted to 7~8 with NH$_3$·H$_2$O. The mixture was concentrated to afford crude compound 6 (R)-3-(piperidin-4-yl)propane-1,2-diol (13 g, crude) as pale yellow oil; LC-MS: m/z 160.1. [M+H]$^+$.

(R)-benzyl 4-(2,3-dihydroxypropyl)piperidine-1-carboxylate (7)

To a mixture of (R)-3-(piperidin-4-yl)propane-1,2-diol (12 g, 75.5 mol) and Na$_2$CO$_3$ (24 g, 226.5 mmol) in THF (90 mL) and H$_2$O (90 mL) was added CbzCl (19.3 g, 113.2 mol) slowly at 0° C. Then the mixture was stirred at 0° C. for 3 h. The mixture was extracted with EA (500 mL), the organic phase was washed with brine (300 mL). The solvent was removed in vacuo, and the residue was purified by silica gel column with a mixture of DCM/MeOH (30/1) to afford the title (R)-benzyl 4-(2,3-dihydroxypropyl)piperidine-1-carboxylate (15 g, 68% yield) as colorless oil. LC-MS: m/z 294.1[M+H]$^+$.

(R)-benzyl 4-(2-hydroxy-3-mercaptopropyl)piperidine-1-carboxylate (8)

To a solution of (R)-benzyl 4-(2,3-dihydroxypropyl)piperidine-1-carboxylate (15 g, 51.13 mmol) and TEA (10.3 g, 102.26 mmol) in DCM (150 mL) was added TsCl (8.77 g, 46.02 mmol) at 0° C. The mixture was stirred at rt for 4 hours and H$_2$O (500 mL) was added. The reaction mixture was extracted with DCM (500 mL×3). The solvent was removed in vacuo, and the residue was purified by silica gel column with a mixture of DCM/MeOH (20/1) to afford the title product (13.6 g, 59%) as light yellow oil. MS (ESI) m/z 448.1 [M+H]$^+$.

(R)-benzyl 4-(2-hydroxy-3-mercaptopropyl)piperidine-1-carboxylate (9)

To a solution of (R)-benzyl 4-(2-hydroxy-3-mercaptopropyl)piperidine-1-carboxylate (13.6 g, 30.42 mmol) in the dry DMF (50 mL) was added NaSH (5.1 g, 91.28 mmol), the mixture was stirred at rt under N$_2$ for 1 hour. H$_2$O (200 mL) was added and the resulting mixture was extracted with EA (200 mL×3). The solvent was removed in vacuo, and the residue was purified by silica gel column using a mixture of PE/EA (2/1) to afford the desired product (5.3 g, 56%) as light yellow oil. MS (ESI) m/z 310.1 [M+H]$^+$.

(R)-benzyl 4-(3-hydroxy-2-mercaptopropyl)piperazine-1-carboxylate

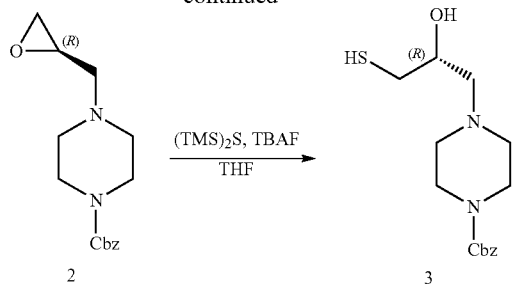

(R)-benzyl 4-(oxiran-2-ylmethyl)piperazine-1-carboxylate (2)

To a solution of (S)-oxiran-2-ylmethyl 3-nitrobenzenesulfonate (25 g, 96.52 mmol) in ACN (150 mL) was added benzyl piperazine-1-carboxylate (19.3 g, 75.75 mmol) and K$_2$CO$_3$ (24 g, 175.5 mmol) at 0° C. under nitrogen atmosphere. The mixture was stirred at room temperature for 22 hours. After completion, the solvent was removed in vacuo, and the residue was purified by silica gel column with a mixture of DCM/MeOH (50:1) to afford the desired crude product (24.5 g) as a light yellow oil. LC-MS: m/z 277.4 [M+H]$^+$.

(R)-benzyl 4-(3-hydroxy-2-mercaptopropyl)piperazine-1-carboxylate (3)

To a mixture of (R)-benzyl 4-(oxiran-2-ylmethyl)piperazine-1-carboxylate (24.5 g, 88.7 mmol) and triphenylphosphine (17.4 g, 97.5 mmol) in THF (250 mL) was slowly added TBAF (26.7 mL, 26.7 mmol, 1M in THF) at 0° C. under nitrogen atmosphere. The mixture was stirred at room temperature for 1 h. After completion, the solvent was removed in vacuo, and the residue was purified by silica gel column with a gradient of DCM/MeOH=100:1-80:1 to afford the title product (20.8 g, 67 mmol, yield: 76%) as a colorless oil. $^1$H NMR (400 MHz, CDCl$_3$) δ 7.36-7.31 (m, 5H), 5.13 (s, 2H), 3.80-3.78 (m, 1H), 3.54-3.50 (m, 4H), 3.39 (s, 1H), 2.66-2.57 (m, 4H), 2.46-2.40 (m, 4H), 1.57-1.52 (m, 1H); LC-MS: m/z 311.5 [M+H]$^+$.

6-chloro-7-(2,4,6-trifluorophenyl)-8-iodoquinazoline-2,4(1H,3H)-dione

Reaction Scheme 5

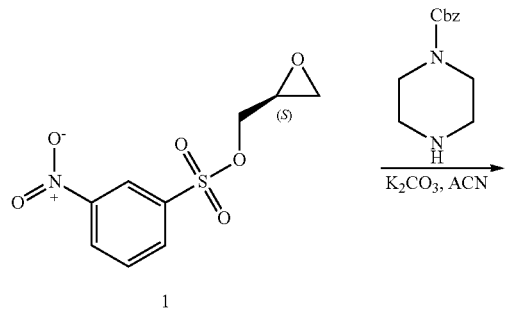

Reaction Scheme 6

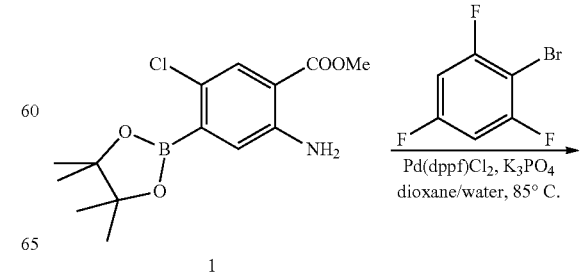

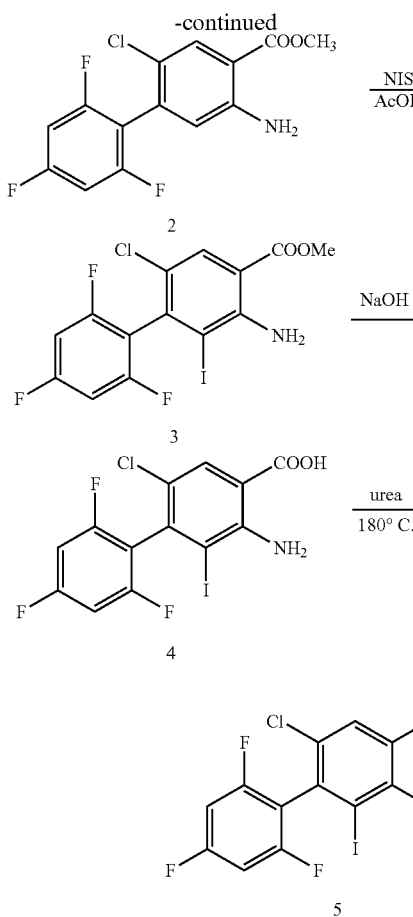

methyl 5-amino-2-chloro-2',4',6'-trifluoro-[1,1'-biphenyl]-4-carboxylate (2)

To a mixture of methyl 2-amino-5-chloro-4-(4,4,5,5-tetramethyl-1,3,2-dioxaborolan-2-yl)benzoate (11.00 g, 35.4 mmol) in THF (50 mL) and water (10 mL) was added 2-bromo-1,3,5-trifluorobenzene (22.39 g, 106.1 mmol), Xphos-Pd-G2 (2.78 mg, 3.54 mmol) and K₃PO₄ (22.49 g, 106.1 mmol). The reaction mixture was stirred at 55° C. under N₂ for 15 h, After completion, the solvent was removed in vacuo, and the residue was purified by silica gel column with a gradient of Petroleum Ether/EtOAc (20/1 to 2/1) to afford the desired product (10.8 g, 95% yield) as yellow solid. MS (ESI) m/z 316.0 [M+H]⁺ methyl 3-amino-6-chloro-2',4',6'-trifluoro-2-iodo-[1,1'-biphenyl]-4-carboxylate (3)

To a mixture of methyl 5-amino-2-chloro-2',4',6'-trifluoro-[1,1'-biphenyl]-4-carboxylate (10.8 g, 34.18 mmol) in acetic acid (50 mL) was added NIS (11.54 g, 51.27 mmol). The mixture was stirred at 30° C. for 12 h. After completion, the mixture was concentrated and the residue was poured into sat·NaHCO₃ (100 mL), extracted with EtOAc (50 mL×3). The combined organic phases were washed with brine (100 mL), dried over Na₂SO₄, and concentrated to give the crude product (7.36 g, crude) as yellow solid.

3-amino-6-chloro-2',4',6'-trifluoro-2-iodo-[1,1'-biphenyl]-4-carboxylic acid (4)

To a mixture of methyl 3-amino-6-chloro-2',4',6'-trifluoro-2-iodo-[1,1'-biphenyl]-4-carboxylate (7.36 g, 16.70 mmol) in methanol (100 mL) and water (10 mL) was added NaOH (2.67 g, 66.76 mmol). The mixture was stirred at 70° C. for 3 h. After completion, the mixture was poured into water (200 mL), the pH was adjusted to 4~5 and the mixture was extracted with EtOAc (50 mL×3). The combined organic phases was washed with brine (50 mL), dried over Na₂SO₄, and concentrated to give the product (4.56 g, 46% yield) as yellow solid. MS (ESI) m/z 427.9 [M+H]⁺

6-chloro-8-iodo-7-(2,4,6-trifluorophenyl)quinazoline-2,4(1H,3H)-dione (5)

A mixture of 3-amino-6-chloro-2',4',6'-trifluoro-2-iodo-[1,1'-biphenyl]-4-carboxylic acid (4.56 g, 10.67 mmol) and urea (12.81 g, 213.58 mmol) was stirred at 180° C. for 6 h. After completion, the mixture was cooled to 80° C. Water (200 mL) was added to the mixture and stirred for 1 hour. The mixture was filtrated to give desired product (2.4 g, yield: 51%) as pale yellow solid. MS (ESI) m/z 452.9 [M+H]⁺

Syntheses of Substituted Tricyclic Thiomorpholine Compounds

G. Example 99

(3R)-7-((S)-4-acryloyl-2-methylpiperazin-1-yl)-9-chloro-10-(2,4-difluorophenyl)-3-methyl-2H-[1,4]thiazino[2,3,4-ij]quinazolin-5(3H)-one

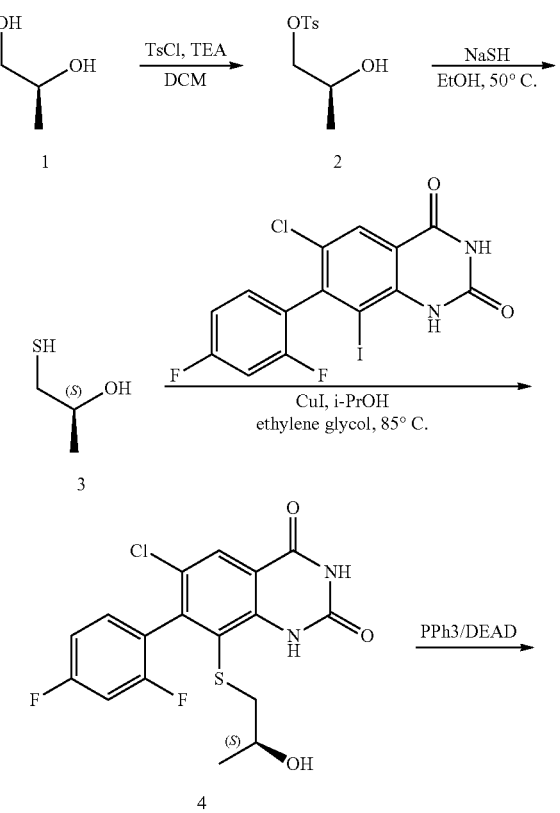

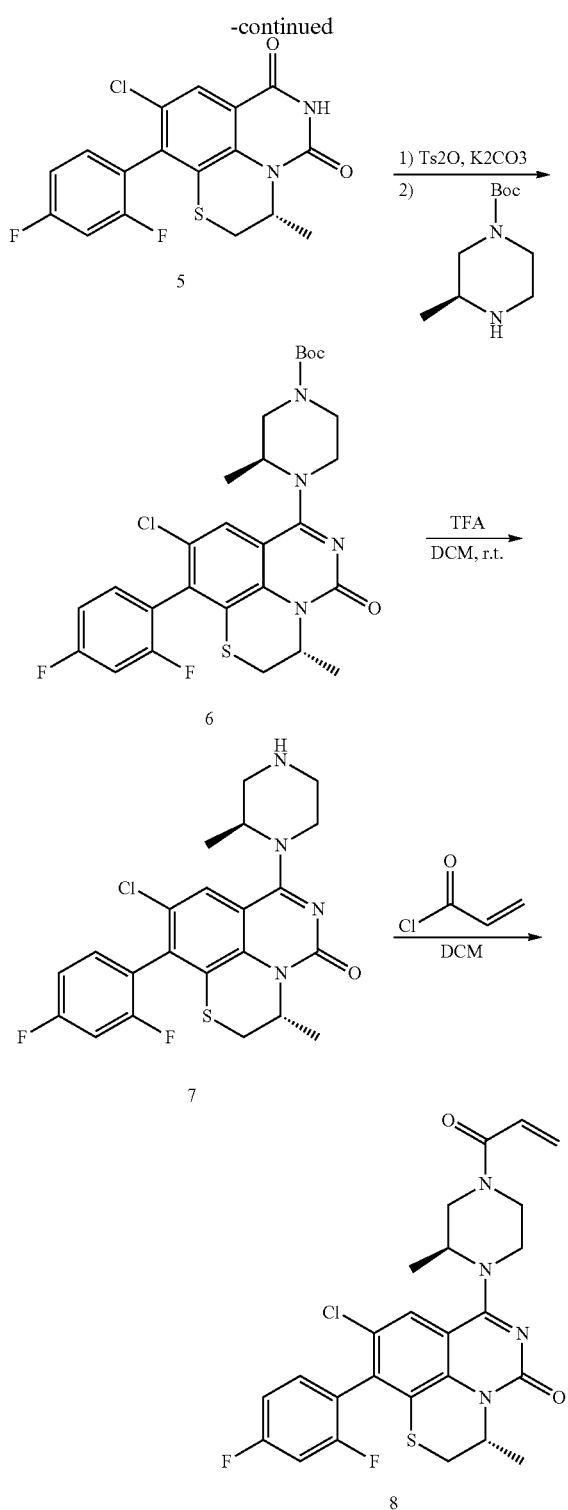

(S)-2-hydroxypropyl 4-methylbenzenesulfonate (2)

To a mixture of (S)-propane-1,2-diol (3.5 g, 46 mmol) and TEA (7.7 mL, 55.2 mmol) in DCM (30 mL) was added TsCl (8.78 g, 46 mmol) at 0° C. The mixture was stirred at rt for 2 hours. The solvent was evaporated and the residue was purified by silica gel chromatography (50% ethyl acetate in petroleum ether) to afford the title compound (3.0 g, 13 mmol, 28% yield) as colorless oil. MS (ESI) m/z 230.28 [M+H]$^+$.

(S)-1-mercaptopropan-2-ol (3)

To a mixture of (S)-2-hydroxypropyl 4-methylbenzenesulfonate (1.5 g, 6.5 mmol) in EtOH (10 mL) was added NaHS (1.1 g, 19.5 mmol). The mixture was stirred at 50° C. for 0.5 h. The solvent was removed in vacuo, and the residue was diluted with DCM. The filtrate was concentrated under reduce pressure to give the title compound (599 mg, 6.5 mmol, crude) as colorless oil.

6-chloro-7-(2,4-difluorophenyl)-8-(((S)-2-hydroxypropyl)thio)quinazoline-2,4(1H,3H)-dione (4)

The mixture of 6-chloro-7-(2,4-difluorophenyl)-8-iodo-quinazoline-2,4(1H,3H)-dione (1.5 g, 3.45 mmol), CuI (262 mg, 1.38 mmol), (S)-1-mercaptopropan-2-ol (599 mg, 3.45 mmol) and K$_2$CO$_3$ (1.43 g, 10.3 mmol) in iso-Propyl alcohol and ethylene glycol (15 mL, v/v=2:1) was stirred under nitrogen atmosphere at 85° C. for 5 hours. After completion, the mixture was concentrated and the residue was purified by silica gel column with a gradient of DCM/MeOH (50:1-30:1) to afford the desired product (311 mg, 0.78 mmol, 22% yield) as a light yellow solid. LC-MS: m/z 398.9 [M−H]$^+$.

(3R)-9-chloro-10-(2,4-difluorophenyl)-3-methyl-2H-[1,4]thiazino[2,3,4-ij]quinazoline-5,7(3H,6H)-dione (5)

To a mixture of 6-chloro-7-(2,4-difluorophenyl)-8-(((S)-2-hydroxypropyl)thio)quinazoline-2,4(1H,3H)-dione (321 mg, 0.8 mmol) and triphenylphosphine (1.26 g, 4.83 mmol) in THF (50 mL) was slowly added DEAD (842 mg, 4.83 mmol) at 0° C. under nitrogen atmosphere. The mixture was stirred at room temperature for 1 hour. DCM (50 mL) was added. The organic phase was washed with water (50 mL×2) and dried over Na$_2$SO$_4$. The solvent was removed in vacuo, and the residue was purified by silica gel column with a mixture of Petroleum Ether/EtOAc (0-50%) to afford the title product (100 mg, 0.26 mmol, 32% yield) as a yellow solid. LC-MS: m/z 380.9 [M−H]$^+$.

(3S)-tert-butyl 4-((3R)-9-chloro-10-(2,4-difluorophenyl)-3-methyl-5-oxo-3,5-dihydro-2H-[1,4]thiazino[2,3,4-ij]quinazolin-7-yl)-3-methylpiperazine-1-carboxylate (6)

To a solution of (3R)-9-chloro-10-(2,4-difluorophenyl)-3-methyl-2H-[1,4]thiazino[2,3,4-ij] quinazoline-5,7(3H,6H)-dione (100 mg, 0.26 mmol) and K$_2$CO$_3$ (181 mg, 1.31 mmol), DMAP (4 mg, 0.02 mmol) in ACN (2 mL) was added Ts$_2$O (128 mg, 0.39 mmol). The mixture was stirred at rt for 5 hours. Then (S)-tert-butyl 3-methylpiperazine-1-carboxylate (117 mg, 0.41 mmol) and TEA (0.1 mL, 0.78 mmol) was added to above mixture and stirred at rt for 2 h. After completion, the mixture was concentrated under reduced pressure, and the residue was purified by silica gel column with a gradient of PE/EA (20%-80%) to afford desired product (72 mg, yield: 49%) as yellow solid. LC-MS: m/z 563.0 [M+H]$^+$;

(3R)-9-chloro-10-(2,4-difluorophenyl)-3-methyl-7-((S)-2-methylpiperazin-1-yl)-2H-[1,4]thiazino[2,3,4-ij]quinazolin-5(3H)-one (7)

To a solution of (3S)-tert-butyl 4-((3R)-9-chloro-10-(2,4-difluorophenyl)-3-methyl-5-oxo-3,5-dihydro-2H-[1,4]thiazino[2,3,4-ij]quinazolin-7-yl)-3-methylpiperazine-1-carboxylate (72 mg, 0.12 mmol) in dichloromethane (2 mL) was added TFA (0.7 mL) at 0° C. The mixture was stirred at rt for 1 hour and concentrated to give the crude product (72 mg, crude) as yellow solid. LC-MS: m/z 463.0 [M+H]$^+$;

(3R)-7-((S)-4-acryloyl-2-methylpiperazin-1-yl)-9-chloro-10-(2,4-difluorophenyl)-3-methyl-2H-[1,4]thiazino[2,3,4-ij]quinazolin-5(3H)-one (8)

To a mixture of (3R)-9-chloro-10-(2,4-difluorophenyl)-3-methyl-7-((S)-2-methylpiperazin-1-yl)-2H-[1,4]thiazino[2,3,4-ij]quinazolin-5(3H)-one (72 mg, 0.12 mmol) and triethyl amine (65 mg, 0.64 mmol) in dichloromethane (3 mL) was added acrylic anhydride (32 mg, 0.25 mmol) at 0° C. The mixture was stirred at rt for 1 hour. The solvent was removed in vacuo, and the residue was purified by prep-HPLC to afford the desired product (25 mg, 38% yield) as yellow solid. LC-MS: m/z 517.1 [M+H]$^+$.

H. Example 341

(3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one

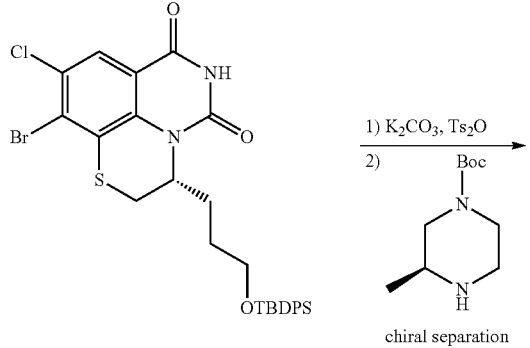

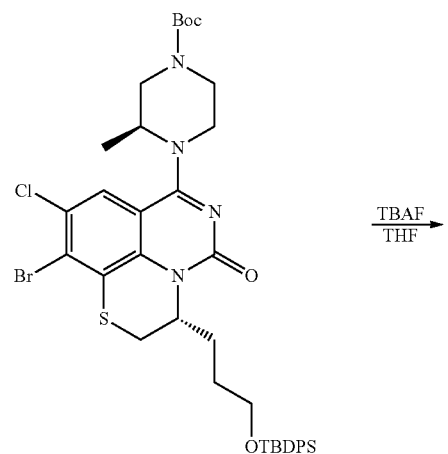

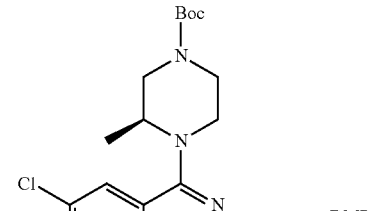

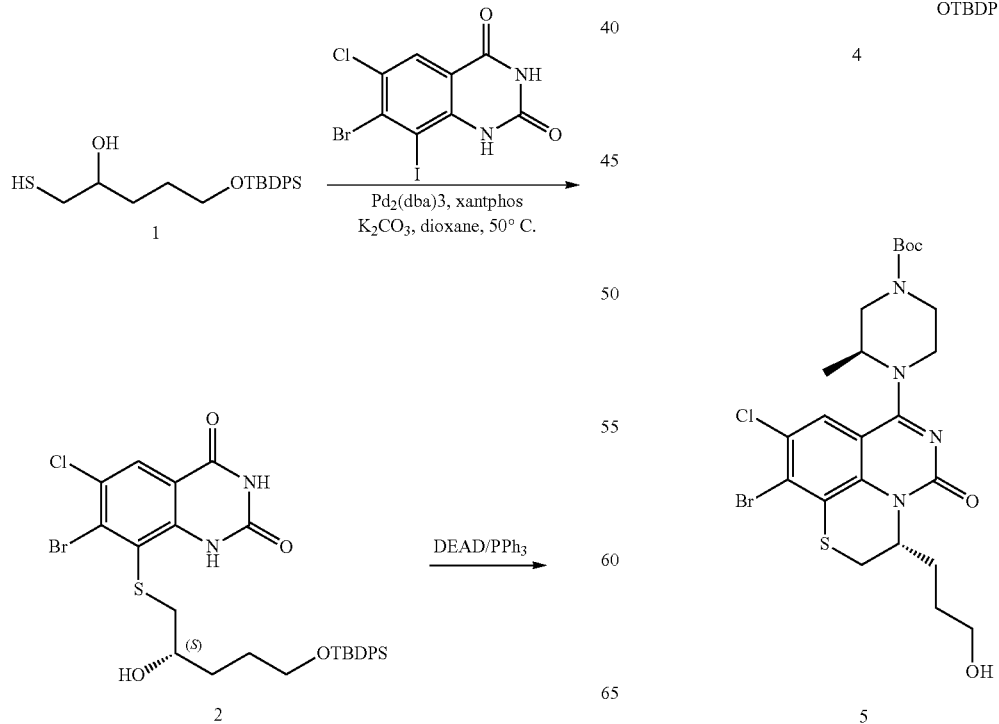

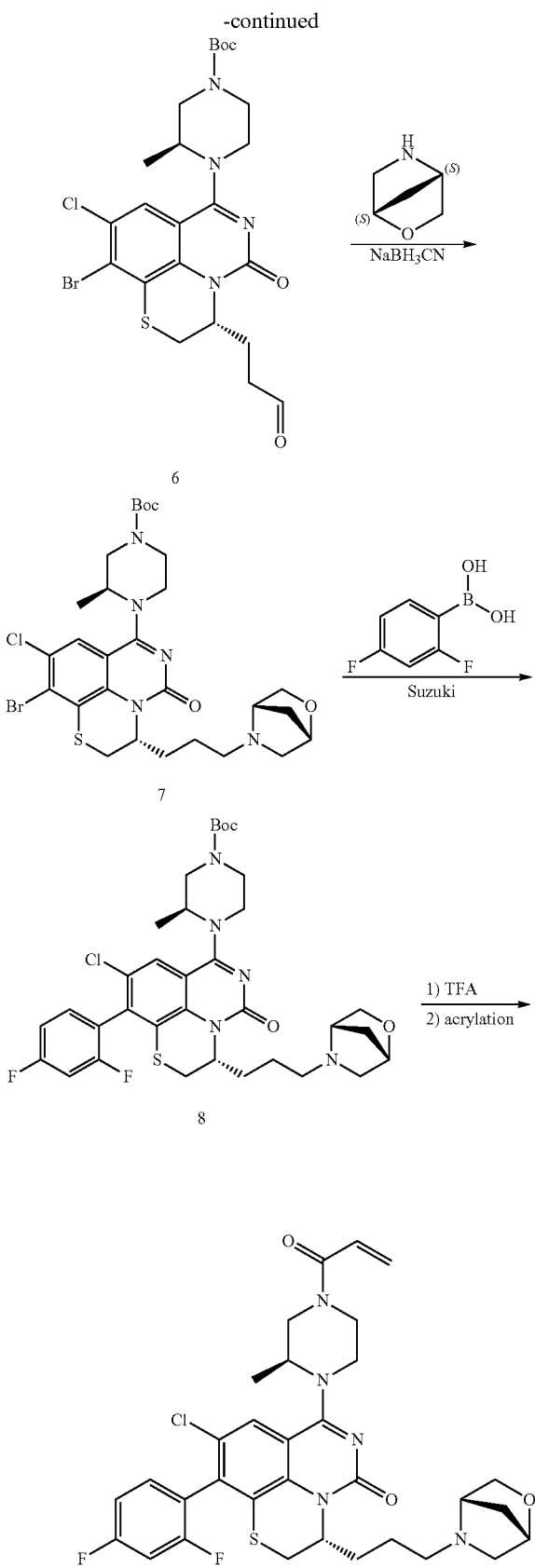

(S)-7-bromo-8-((5-((tert-butyldiphenylsilyl)oxy)-2-hydroxypentyl)thio)-6-chloroquinazoline-2,4(1H,3H)-dione (2)

To a mixture of 7-bromo-6-chloro-8-iodoquinazoline-2,4 (1H,3H)-dione (572 mg, 1.42 mmol), Xantphos (123 mg, 0.21 mmol), $K_2CO_3$ (392 mg, 2.84 mmol) in dioxane (10 mL) was added 5-((tert-butyldiphenylsilyl)oxy)-1-mercaptopentan-2-ol (800 mg, 2.14 mmol) and $Pd_2(dba)_3$ (128 mg, 0.14 mmol) at rt. The reaction mixture was stirred at 50° C. under nitrogen atmosphere for 22 hours. After removing the solvent, the residue was purified by silica gel column chromatography (dichloromethane/methnol=100/1 to 50/1) to afford compound (2) (S)-7-bromo-8-((5-((tert-butyldiphenylsilyl)oxy)-2-hydroxypentyl)thio)-6-chloroquinazoline-2,4(1H,3H)-dione (510 mg, yield: 550%) as a light yellow solid.

LC-MS: m/z 647.6 [M–H]$^+$ (R)-10-bromo-3-(3-((tert-butyldiphenylsilyl)oxy)propyl)-9-chloro-2H-[1,4]thiazino[2,3,4-ij]quinazoline-5,7(3H,6H)-dione (3)

To a mixture of (S)-7-bromo-8-((5-((tert-butyldiphenylsilyl)oxy)-2-hydroxypentyl)thio)-6-chloroquinazoline-2,4 (1H,3H)-dione (1.0 g, 1.51 mmol) and triphenylphosphine (587.1 mg, 2.25 mmol) in THF (10 mL) was added DEAD (411.7 mg, 2.25 mmol) slowly at 0° C. under nitrogen atmosphere. The mixture was stirred at room temperature for 1 hour. The organic phase was washed with water (50 mL×2), dried over $Na_2SO_4(S)$ and concentrated. The residue was purified by silica gel column with a gradient of PE/EA=0-50% to afford the product (788.1 mg, 1.25 mmol, yield: 83%) as a yellow solid. LC-MS: m/z=630.1 [M–H]$^+$.

(S)-tert-butyl 4-((R)-10-bromo-3-(3-((tert-butyldiphenylsilyl)oxy)propyl)-9-chloro-5-oxo-3,5-dihydro-2H-[1,4]thiazino[2,3,4-ij]quinazolin-7-yl)-3-methylpiperazine-1-carboxylate(4)

To a solution of (R)-10-bromo-3-(3-((tert-butyldiphenylsilyl)oxy)propyl)-9-chloro-2H-[1,4]thiazino[2,3,4-ij]quinazoline-5,7(3H,6H)-dione (1.68 mg, 2.67 mmol) and $K_2CO_3$ (1.84 g, 13.35 mmol) in ACN (20 mL) was added TPSCl (1.2 g, 4.05 mmol), the mixture was stirred at rt for 5 h. After the reaction was completed, (S)-tert-butyl 3-methylpiperazine-1-carboxylate (1.60 g, 8.01 mmol) was added. The resulting mixture was stirred at rt for 2 hours. After completion, the mixture was concentrated under reduced pressure and the residue was purified by silica gel column with a gradient of DCM/MeOH (30:1-20:1) to afford desired product (610 mg, 28% yield) as yellow solid. MS (ESI) m z 813.2 [M+H]$^+$.

(S)-tert-butyl 4-((R)-10-bromo-9-chloro-3-(3-hydroxypropyl)-5-oxo-3,5-dihydro-2H-[1,4]thiazino[2,3,4-ij]quinazolin-7-yl)-3-methylpiperazine-1-carboxylate (5)

To a solution of (S)-tert-butyl 4-((R)-10-bromo-3-(3-((tert-butyldiphenylsilyl) oxy)propyl)-9-chloro-5-oxo-3,5-dihydro-2H-[1,4]thiazino[2,3,4-ij]quinazolin-7-yl)-3-methylpiperazine-1-carboxylate (610 mg, 0.75 mmol) in THF (5 mL) was added TBAF (1 mL, 1M in THF). The mixture was stirred at 20° C. for 2 hours. The reaction mixture was poured into water (50 mL) and extracted with EtOAc (20 mL×3). The combined organic phases were washed with brine (10 mL), dried over Na$_2$SO$_4$, and concentrated. The residue was purificatied by silica gel column with as gradient of DCM/MeOH (30:1-20:1) to give the product (320 mg, 0.56 mmol) as yellow solid. LC-MS: m/z 575.1 [M+H]$^+$ (S)-tert-butyl 4-((R)-10-bromo-9-chloro-5-oxo-3-(3-oxopropyl)-3,5-dihydro-2H-[1,4]thiazino[2,3,4-ij]quinazolin-7-yl)-3-methylpiperazine-1-carboxylate (6)

To a solution of 4-((R)-10-bromo-9-chloro-3-(3-hydroxypropyl)-5-oxo-3,5-dihydro-2H-[1,4]thiazino[2,3,4-ij]quinazolin-7-yl)-3-methylpiperazine-1-carboxylate(5) (290 mg, 0.5 mmol) in DCM (5 mL) was added Dess-martin reagent (318 mg, 0.75 mmol). The mixture was stirred at 20° C. under nitrogen atmosphere for 2 hours. After removing the solvent, the residue was purified by silica gel column chromatography (dichloromethane/methanol=30/1) to give the product (275 mg, 96% yield) as yellow solid. LC-MS: m/z 573.1 [M+H]$^+$ (S)-tert-butyl 4-((R)-3-(3-((1S,4S)-2-oxa-5-azabicyclo[2.2.1]heptan-5-yl)propyl)-10-bromo-9-chloro-5-oxo-3,5-dihydro-2H-[1,4]thiazino[2,3,4-ij]quinazolin-7-yl)-3-methylpiperazine-1-carboxylate (7)

To a solution of (S)-tert-butyl 4-((R)-10-bromo-9-chloro-5-oxo-3-(3-oxopropyl)-3,5-dihydro-2H-[1,4]thiazino[2,3,4-ij]quinazolin-7-yl)-3-methylpiperazine-1-carboxylate (275 mg, 0.50 mmol) and (1S,4S)-2-oxa-5-azabicyclo[2.2.1]heptane (150 mg, 1.5 mmol) in DCM was added sodium cyanoborohydride (150 mg, 0.75 mmol). The mixture was stirred at 20° C. for 2 hours. After removing the solvent, the residue was purified by silica gel column chromatography (dichloromethane/methanol=20/1) to give the desired product (300 mg, 90% yield) as yellow solid. LC-MS: m/z 656.2 [M+H]$^+$ (3S)-tert-butyl 4-((3R)-3-(3-((1S,4S)-2-oxa-5-azabicyclo[2.2.1]heptan-5-yl)propyl)-9-chloro-10-(2,4-difluorophenyl)-5-oxo-3,5-dihydro-2H-[1,4]thiazino[2,3,4-ij]quinazolin-7-yl)-3-methylpiperazine-1-carboxylate (8)

A mixture of (S)-tert-butyl 4-((R)-3-(3-((1S,4S)-2-oxa-5-azabicyclo[2.2.1]heptan-5-yl)propyl)-10-bromo-9-chloro-5-oxo-3,5-dihydro-2H-[1,4]thiazino[2,3,4-ij]quinazolin-7-yl)-3-methylpiperazine-1-carboxylate (140 mg, 0.21 mmol), (2,4-difluorophenyl)boronic acid (160 mg, 1.05 mmol), Pd(dppf)Cl$_2$ (15 mg, 0.02 mmol) and K$_3$PO$_4$ (125 mg, 0.63 mmol) in dioxane (5 mL) and H$_2$O (0.8 mL) was heated to 85° C. under nitrogen atmosphere for 3 hours. The mixture was concentrated, and the residue was purified by silica gel column chromatography (dichloromethane/methanol=30/1) to give the crude product (130 mg, crude) as brown solid. LC-MS: m/z 688.2 [M+H]$^+$ (3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one (9)

The mixture of (3S)-tert-butyl 4-((3R)-3-(3-((1S,4S)-2-oxa-5-azabicyclo[2.2.1]heptan-5-yl)propyl)-9-chloro-10-(2,4-difluorophenyl)-5-oxo-3,5-dihydro-2H-[1,4]thiazino[2,3,4-ij]quinazolin-7-yl)-3-methylpiperazine-1-carboxylate (130 mg, 0.19 mmol) in DCM/TFA (3 mL/1 mL) was stirred at 20° C. for 1 hour. Removing solvent in vacuo gave the crude product as the TFA salt (160 mg, crude).

To the mixture of above product (160 mg, crude) and triethyl amine (57 mg, 0.57 mmol) in dichloromethane (3 mL) was added acrylic anhydride (47.8 mg, 0.38 mmol) slowly at 0° C. The mixture was stirred for 1 hour. After removing solvent in vacuo, the residue was purified by prep-HPLC to afford the desired product (60 mg, 50% yield) as white solid. LC-MS: m/z 642.2 [M+H]$^+$.

I. Example 76

7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one

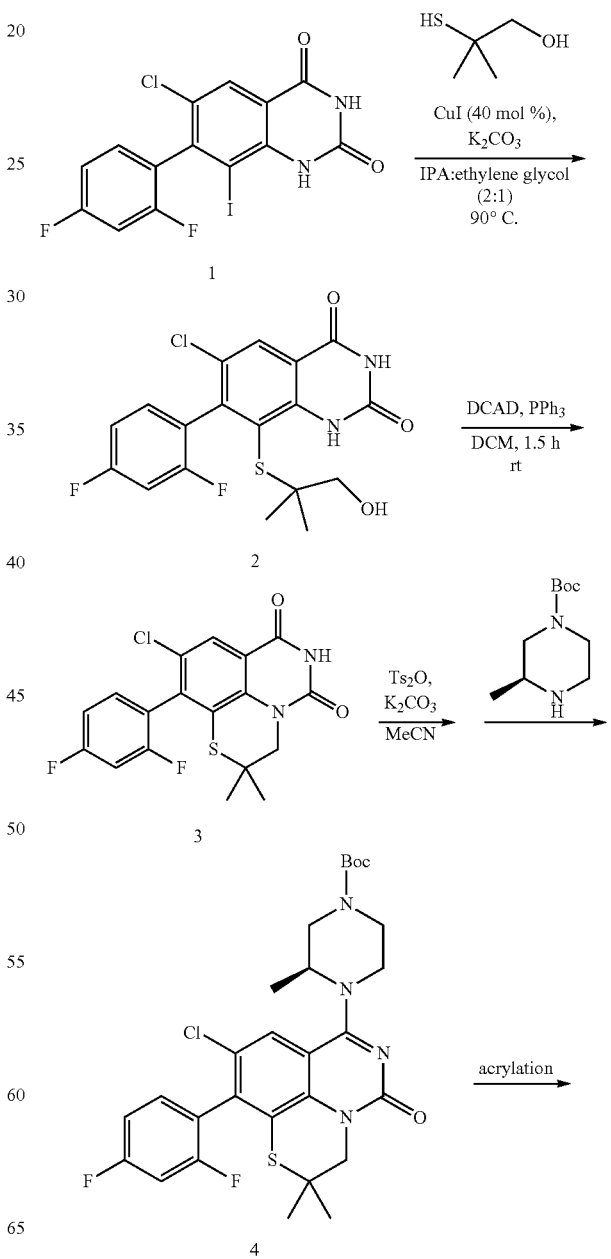

-continued

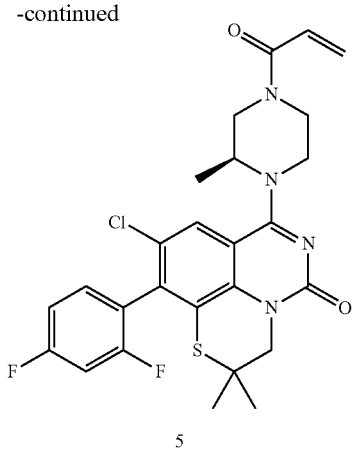

5

6-chloro-7-(2,4-difluorophenyl)-8-((1-hydroxy-2-methylpropan-2-yl)thio)quinazoline-2,4(1H,3H)-dione (2)

Compound 1 (50 mg, 0.123 mmol, 1 equiv) and 2-mercapto-2-methylpropan-1-ol (26 mg, 0.246 mmol, 2 equiv) was added to a 5 mL microwave vial and dissolved in 2-isopropyl alcohol (0.5 mL) and ethylene glycol (0.25 mL). Next, the solution was degassed with $N_2$ for 30 min and CuI (9.4 mg, 0.049 mmol, 0.4 equiv) and $K_2CO_3$ (53 mg, 0.381 mmol, 3 equiv) were added followed by additional degassing with $N_2$ for 20 min. The microwave vial was fitted with a crimp-top cap and placed on a heated block at 90° C. The resulting reaction mixture was heterogenous and light tan in color. After 33 hours, the vial was removed from the heating block, allowed to cool, and the solvent was removed under reduced pressure. This was performed in two separate batches (50 mg, each) and combined. The combined crude material was suspended in $CH_2Cl_2$ and filtered. The filtrate was collected, and the solvent was removed by rotary evaporation. The crude material was purified by flash column chromatography using an Isolera One Biotage instrument (0-4% MeOH/$CH_2Cl_2$, 10 g column, 0% (5 CV), 0-4% (20 CV), 4% (5 CV)) to provide a brown oil (45 mg) containing unknown impurities, but used in the subsequent step: TLC (3% MeOH/$CH_2Cl_2$) $R_f$=0.17; $^1$H NMR (400 MHz, CDCl$_3$) δ 8.27 (dd, J=8.8 Hz, 1H), 7.14-6.91 (m, 3H), 4.01-3.82 (m, 2H), 3.51-3.30 (m, 2H), 1.34 (s, 3H), 1.30 (s, 3H); LRMS-ESI (m/z) [M+H]$^+$ calculated for $C_{18}H_{16}ClF_2N_2O_3S$ 413.05, found 413.1.

9-chloro-10-(2,4-difluorophenyl)-2,2-dimethyl-2,3-dihydro-5H-[1,4]thiazino[2,3,4-ij]quinazoline-5,7(6H)-dione (3)

Compound 2 (20 mg, 0.048 mmol, 1 equiv) and PPh$_3$ (19 mg, 0.073 mmol, 1.5 equiv) was added to a 10 mL round-bottom flask under a $N_2$ atmosphere and dissolved in $CH_2Cl_2$ (1 mL, 0.05 M). A solution of DCAD (27 mg, 0.073 mmol, 1.5 equiv) in $CH_2Cl_2$ (0.73 mL, 0.5 M) was added dropwise to the reaction mixture at room temperature. After 1 h, the reaction reached 31% conversion determined by LC-MS. Additional DCAD (27 mg, 0.073 mmol, 1.5 equiv) and PPh$_3$ (19 mg, 0.073 mmol, 1.5 equiv) was added to the reaction mixture and after 15 min the reaction reached full conversion by LC-MS. The reaction mixture was diluted with $CH_2Cl_2$ (ca. 50 mL) and the precipitate filtered. The filtrate was collected, and the solvent was removed by rotary evaporation. The crude material was purified by preparative thin-layer chromatography (Silica Gel 60 F$_{254}$, 0.5 mm) using 3% MeOH/$CH_2Cl_2$ to provide compound 3 (13 mg, 68%) as a white solid: TLC (3% MeOH/$CH_2Cl_2$) $R_f$=0.51; $^1$H NMR (400 MHz, MeOH-d$_4$) δ 7.98 (s, 1H), 7.18-7.04 (m, 3H), 4.24 (d, J=13.4 Hz, 1H), 3.98 (d, J=13.4 Hz, 1H), 1.40 (s, 3H), 1.37 (s, 3H); LRMS-ESI (m/z) [M−H]$^−$ calculated for $C_{18}H_{12}ClF_2N_2O_2S$ 393.03, found 393.0.

tert-Butyl (3S)-4-(9-chloro-10-(2,4-difluorophenyl)-2,2-dimethyl-5-oxo-2,3-dihydro-5H-[1,4]thiazino[2,3,4-ij]quinazolin-7-yl)-3-methylpiperazine-1-carboxylate (4)

Compound 3 (13 mg, 0.033 mmol, 1 equiv) was dissolved in MeCN (0.4 mL, 0.1 M) under a $N_2$ atmosphere in a 1 dr vial. $K_2CO_3$ (13.7 mg, 0.099 mmol, 3 equiv) was added to the reaction mixture and the reaction mixture was briefly sonicated. p-Toluenesulfonic anhydride (22 mg, 0.066 mmol, 2 equiv) was added to the reaction mixture at room temperature. The reaction mixture was stirred for 14 h and reached near full conversion determined by LC-MS. Next, tert-butyl (S)-3-methylpiperazine-1-carboxylate (13.2 mg, 0.066 mmol, 2 equiv) and $K_2CO_3$ (13.2 mg, 0.066 mmol, 2 equiv) was added to the vial and stirred for 15 min at room temperature. The intermediate was determined to be fully consumed by LC-MS and the solvent was removed by under reduced pressure. The mixture was transferred with $CH_2Cl_2$ to a separatory funnel, washed with aqueous saturated NH$_4$Cl (10 mL) and H$_2$O (10 mL), extracted with $CH_2Cl_2$ (2×50 mL), dried over Na$_2$SO$_4$, and filtered. The solvent was removed by rotary evaporation to afford compound 4 (26 mg) as a yellow oil which contained starting material (~47%; determined by LC-MS) in addition to other minor unknown impurities. This material was used as is in the subsequent step: TLC (3% MeOH/$CH_2Cl_2$) $R_f$=0.32; LRMS-ESI (m/z) [M+H]$^+$ calculated for $C_{28}H_{32}ClF_2N_4O_3S$ 577.19, found 577.2.

7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one (5)

Compound 4 (26 mg crude, 0.045 mmol, 1 equiv) was dissolved in anhydrous $CH_2Cl_2$ (3 mL) in a 20 dr vial followed by the addition of CF$_3$COOH (1 mL) at room temperature and capped. After 15 min, the reaction was determined to be complete by LC-MS and the solvent was removed by rotary evaporation. The reaction mixture was dissolved in MeOH, loaded onto a HyperSep SCX plug, and flushed with MeOH (ca. 20 mL). Next, the desired intermediate was eluted with 1N NH$_3$ in MeOH (ca. 20 mL) and collected. The solvent was removed by rotary evaporation and the crude material was dissolved in anhydrous $CH_2Cl_2$ (3 mL) in a 20 dr vial and capped. Next, DIPEA (8 μL, 0.045 mmol, 1 equiv) was added by syringe to the reaction at room temperature followed by acryloyl chloride (3.6 μL, 0.045 mmol, 1 equiv) and capped. After 15 min, the reaction was determined to be complete by LC-MS and the solvent was removed by rotary evaporation. The crude material was dissolved in MeOH, filtered with a 0.45 m PTFE plug, and purified by preparative RP-HPLC (Luna 5 μM C18(2) 100 Å, 100×30 mm, 5-95% MeCN+0.1% (v/v) HCOOH and H$_2$O+0.1% (v/v) HCOOH). The product fractions were collected, and the solvent was removed by rotary evaporation, followed by lyophilization (−91 to −71° C.; <0.01 mbar) in deionized water to afford compound 5 (1.46 mg) as a white solid: $^1$H NMR (400 MHz, MeOH-$d_4$) δ 7.71 (d, J=4.5 Hz, 1H), 7.33-7.22 (m, 1H), 7.18-7.09 (m, 2H), 6.91-6.73 (m, 1H), 6.29 (dd, J=16.2. 7.2 Hz, 1H), 5.81 (dd, J=10.6. 1.9 Hz, 1H), 4.68-3.93 (m, 5H), 3.80-3.45 (m, 2H), 1.42 (s, 3H), 1.38 (s, 3H); LRMS-ESI (m/z) [M+H]+ calculated for $C_{26}H_{26}ClF_2N_4O_2S$ 531.14, found 531.2.
J. Example 350
(3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one
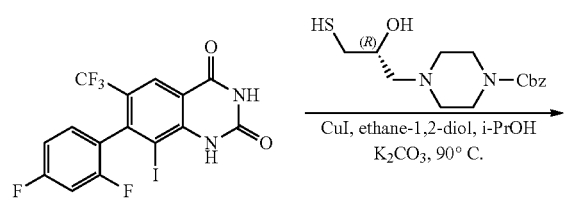
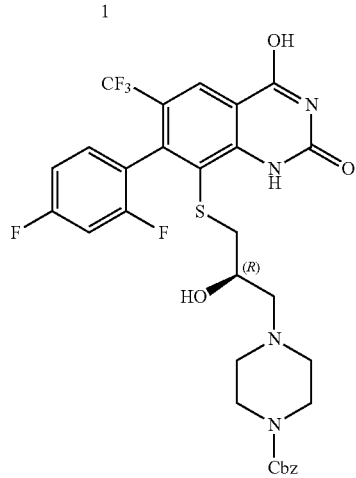
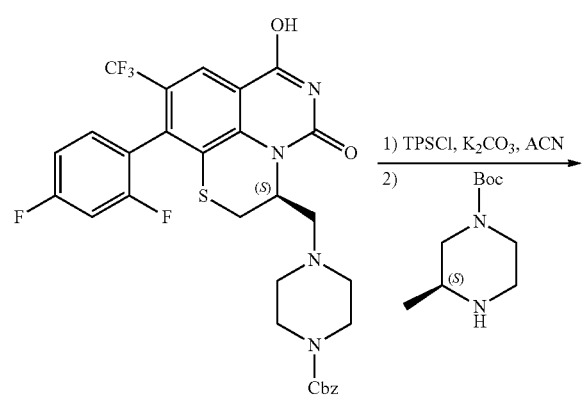
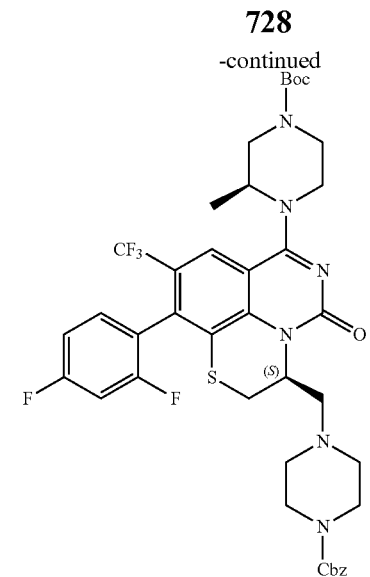
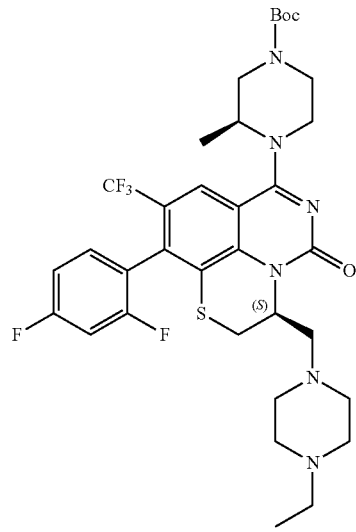

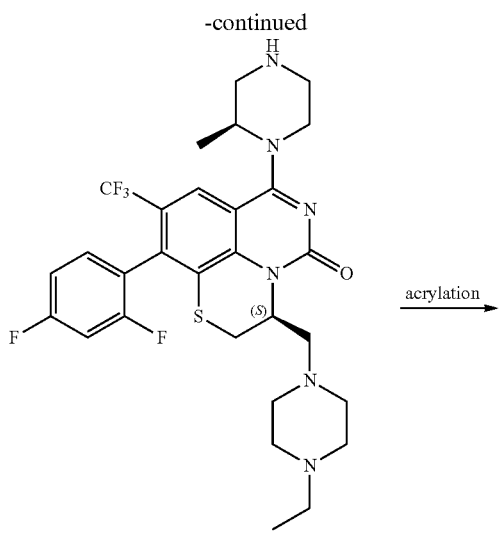

7 acrylation

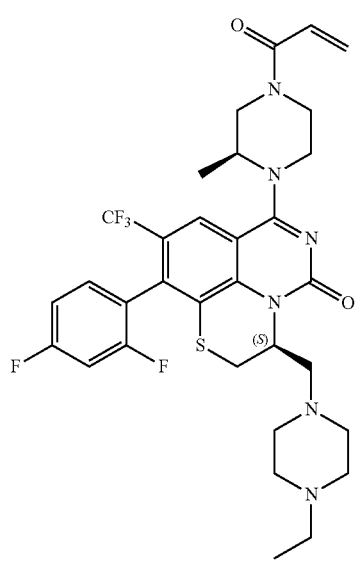

8 benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)piperazine-1-carboxylate (2)

The mixture of 7-(2,4-difluorophenyl)-8-iodo-6-(trifluoromethyl)quinazoline-2,4(1H,3H)-dione (2.3 g, 4.91 mmol), (R)-benzyl 4-(2-hydroxy-3-mercaptopropyl)piperazine-1-carboxylate (2.28 g, 7.38 mmol), CuI (750 mg, 3.93 mmol) and $K_2CO_3$ (2.03 g, 14.73 mmol) in ethane-1,2-diol (30 mL) and i-PrOH (30 mL) was stirred under nitrogen atmosphere at 85° C. for 22 hours. After removing solvent in vacuo, the residue was purified by silica gel column using DCM/MeOH=50:1 as eluent to afford the title product (1.2 g, 1.84 mmol, 37% yield) as a light yellow solid. MS (ESI) m/z 651.5 [M+H]$^+$.

benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)piperazine-1-carboxylate (3)

To a mixture of benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)piperazine-1-carboxylate (1.2 g, 1.84 mmol) and triphenylphosphine (964 mmol, 3.68 mmol) in THF (30 mL) was added DEAD (640 mg, 3.68 mmol) slowly at 0° C. under nitrogen atmosphere. The mixture was stirred at room temperature for 1 h. DCM (50 mL) was added. The organic phase was washed with water (50 mL×2), dried over $Na_2SO_4$, filtered and concentrated. The residue was purified by silica gel column with a gradient of PE/EA (10:1-5:1 to afford the desired product (710 mg, 1.12 mmol, 61% yield) as a light yellow solid. MS (ESI) m/z 633.6 [M+H]$^+$.

(3S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (4)

To a mixture of benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)piperazine-1-carboxylate (710 mg, 1.20 mmol) and $K_2CO_3$ (497 mg, 3.61 mmol) in ACN (20 mL) was added TPSCl (543 mg, 1.8 mmol). The mixture was stirred at rt for 5 h. After the reaction was completed, (S)-tert-butyl 3-methylpiperazine-1-carboxylate (720 mg, 3.6 mmol) and TEA (370 mg, 3.6 mmol) was added. The resulting mixture was stirred at rt for 2 hours. The reaction mixture was concentrated under reduced pressure and the residue was purified by silica gel column with a gradient of PE/EA (20%-80%) to afford desired product (720 mg, yield: 68%) as yellow solid. MS (ESI) m/z 815.3 [M+H]$^+$.

(3S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-3-methylpiperazine-1-carboxylate (5)

The mixture of benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)piperazine-1-carboxylate (640 mg, 0.78 mmol) and Pd/C (500 mg) in methanol was stirred under hydrogen atmosphere for 3 hours. After filtration, the solvent was removed in vacuo. The residue was purification by silica gel column with a gradient of DCM/MeOH (5%-10%) to afford desired product (410 mg, 77% yield) as yellow solid. MS (ESI) m/z 680.2 [M+H]$^+$.

(3S)-tert-butyl 4-((3S)-10-(2,4-difluorophenyl)-3-((4-ethylpiperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (6)

To a mixture of (3S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-3-methylpiperazine-1-carboxylate (150 mg, 0.22 mmol) and acetaldehyde (0.5 mL, 40% in water) in EtOH was added sodium triacetoxyborohydride (88 mg, 0.44 mmol).

The mixture was stirred at 20° C. for 2 hours. After removing solvent in vacuo, the residue was purified by silica gel column chromatography (dichloromethane/methanol=30/1) to give the product (118 mg, 75% yield) as yellow solid. MS (ESI) m/z 709.2 [M+H]+

(3S)-10-(2,4-difluorophenyl)-3-((4-ethylpiperazin-1-yl)methyl)-7-((S)-2-methylpiperazin-1-yl)-9-(trifluoromethyl)-2H-[1,4]thiazino[2,3,4-ij]quinazolin-5(3H)-one (7)

To a solution of (3S)-tert-butyl 4-((3S)-10-(2,4-difluorophenyl)-3-((4-ethylpiperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (110 mg, 0.16 mmol) in DCM (3 mL) was added TFA (0.8 mL). The mixture was stirred at 20° C. for 2 hours. The mixture was concentrated to give the crude product as the TFA salt which was used in next step without further purification.

(3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one (8)

To a mixture of (3S)-10-(2,4-difluorophenyl)-3-((4-ethylpiperazin-1-yl)methyl)-7-((S)-2-methylpiperazin-1-yl)-9-(trifluoromethyl)-2H-[1,4]thiazino[2,3,4-ij]quinazolin-5(3H)-one (80 mg, 0.13 mmol) and triethyl amine (41 mg, 0.40 mmol) in DCM (3 mL) was added acrylic anhydride (124.5 mg, 0.187 mmol) at 0° C. The mixture was stirred at 0° C. for 1 hour. After concentration, the residue was purified by prep-HPLC (5%-95% ACN in H$_2$O) to afford the product (25 mg, 29% yield) as white powder. $^1$H NMR (400 MHz, CDCl$_3$) δ 7.75 (s, 1H), 7.20-7.15 (m, 1H), 7.04-6.93 (m, 2H), 6.62-6.53 (m, 1H), 6.39-6.52 (m, 1H), 5.75 (d, J=9.2 Hz, 1H), 5.37-5.28 (m, 1H), 4.72-4.68 (m, 1H), 4.51-4.26 (m, 2H), 3.99-3.38 (m, 5H), 3.11-2.97 (m, 2H), 2.82-2.76 (m, 3H), 2.59-2.37 (m, 8H), 1.26-1.22 (m, 3H), 1.09 (t, J=7.2 Hz, 3H). MS (ESI) m/z 663.3 [M+H]+

K. Example 352

(3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one

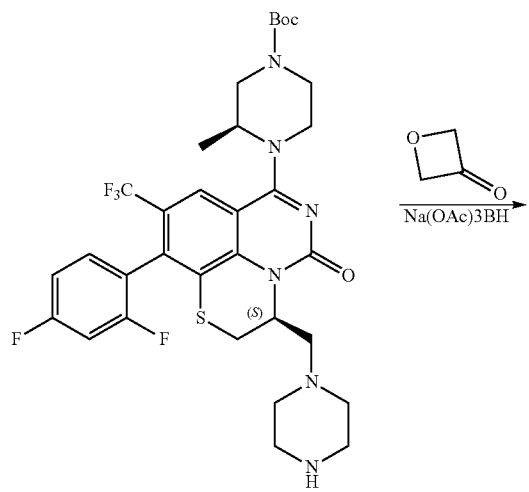

1

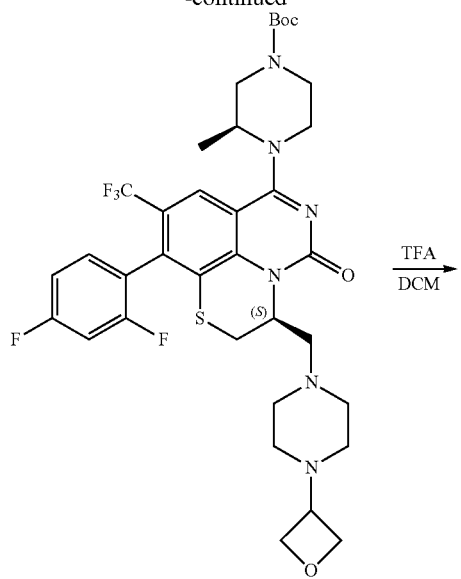

2

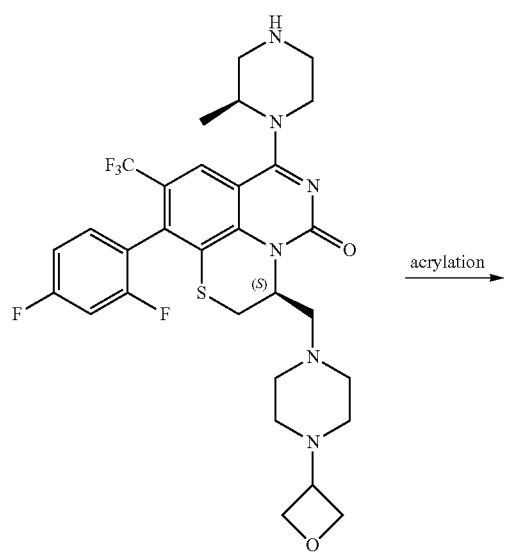

3

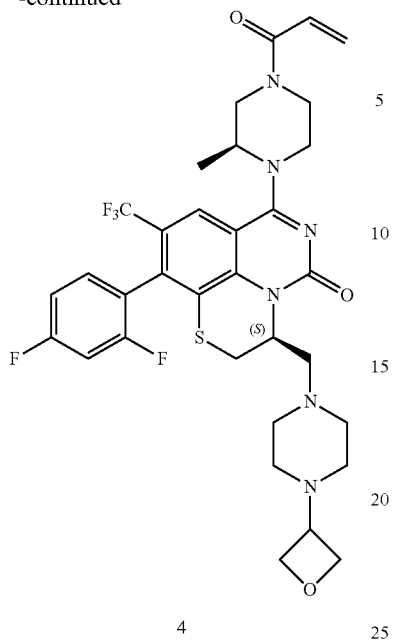

4

(3S)-tert-butyl4-((3S)-10-(2,4-difluorophenyl)-3-((4-(oxetan-3-yl)piperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (2)

To a solution of (3S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-3-methylpiperazine-1-carboxylate (150 mg, 0.22 mmol) and oxetan-3-one (158 mg, 2.2 mmol) in DCM was added sodium triacetoxyborohydride (27 mg, 0.44 mmol). The mixture was stirred at 20° C. for 2 hours. After removing solvent in vacuo, the residue was purified by silica gel column chromatography (dichloromethane/methanol=30/1) to give the product (150 mg, crude) as yellow solid. MS (ESI) m/z 737.2 [M+H]+

(3S)-10-(2,4-difluorophenyl)-7-((S)-2-methylpiperazin-1-yl)-3-((4-(oxetan-3-yl)piperazin-1-yl)methyl)-9-(trifluoromethyl)-2H-[1,4]thiazino[2,3,4-ij]quinazolin-5(3H)-one(3)

To a solution of (3S)-tert-butyl4-((3S)-10-(2,4-difluorophenyl)-3-((4-(oxetan-3-yl)piperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (150 mg, crude) in DCM (3 mL) was added TFA (0.8 mL). The mixture was stirred at 20° C. for 1 hours. The mixture was concentrated to give the crude product as the TFA salt (160 mg, crude) which was used in next step without further purification.

(3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one(4)

To a solution of (3S)-10-(2,4-difluorophenyl)-7-((S)-2-methylpiperazin-1-yl)-3-((4-(oxetan-3-yl)piperazin-1-yl) methyl)-9-(trifluoromethyl)-2H-[1,4]thiazino[2,3,4-ij]quinazolin-5(3H)-one (130 mg, 0.18 mmol) and triethyl amine (61 mg, 0.60 mmol) in DCM (3 mL) was added acrylic anhydride (51.0 mg, 0.41 mmol) at 0° C. The mixture was stirred at 0° C. for 1 hour. After removing solvent in vacuo, the residue was purified by prep-HPLC (5%-95% ACN in H2O) to afford the product (24 mg, 0.04 mmol) as white powder. 1H NMR (400 MHz, CDCl3) δ 7.77 (s, 1H), 7.21-7.15 (m, 1H), 7.04-6.93 (m, 2H), 6.65-6.35 (m, 2H), 5.78 (d, J=8.4 Hz, 1H), 5.33-5.30 (m, 1H), 4.69-4.42 (m, 7H), 3.80-3.40 (m, 6H), 3.08-2.99 (m, 2H), 2.88-2.74 (m, 3H), 2.58-2.53 (m, 3H), 2.31-2.17 (m, 3H), 1.49-1.48 (m, 3H). MS (ESI) m/z 691.2 [M+H]+

L. Example 353

(3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one

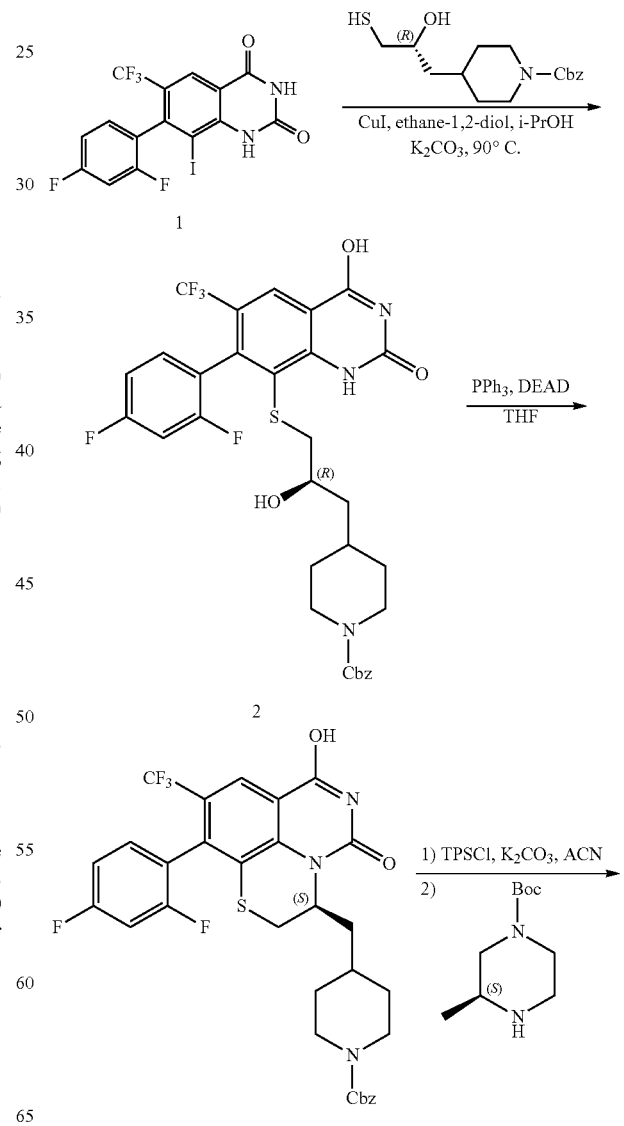

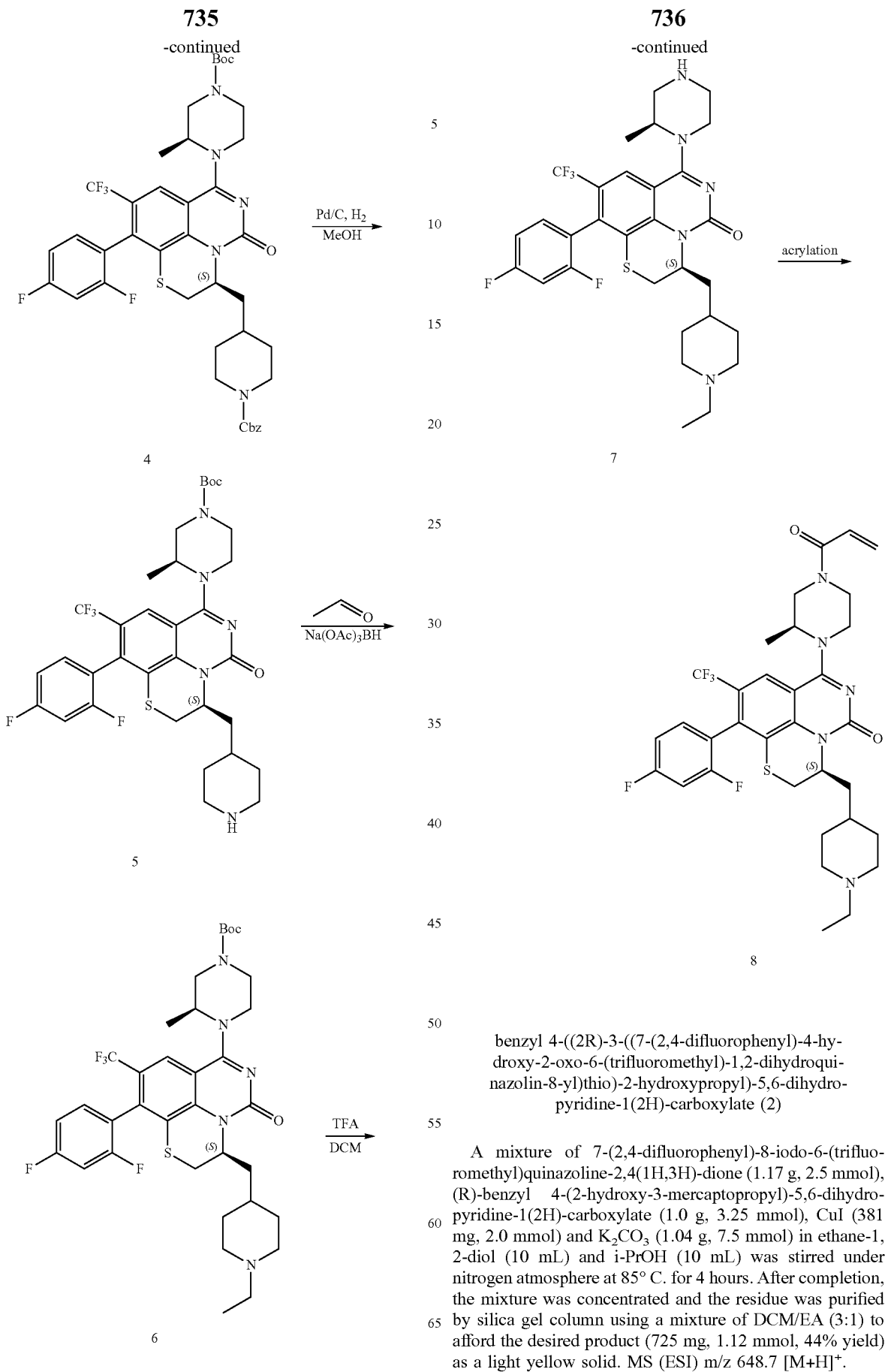

benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)-5,6-dihydropyridine-1(2H)-carboxylate (2)

A mixture of 7-(2,4-difluorophenyl)-8-iodo-6-(trifluoromethyl)quinazoline-2,4(1H,3H)-dione (1.17 g, 2.5 mmol), (R)-benzyl 4-(2-hydroxy-3-mercaptopropyl)-5,6-dihydropyridine-1(2H)-carboxylate (1.0 g, 3.25 mmol), CuI (381 mg, 2.0 mmol) and K$_2$CO$_3$ (1.04 g, 7.5 mmol) in ethane-1,2-diol (10 mL) and i-PrOH (10 mL) was stirred under nitrogen atmosphere at 85° C. for 4 hours. After completion, the mixture was concentrated and the residue was purified by silica gel column using a mixture of DCM/EA (3:1) to afford the desired product (725 mg, 1.12 mmol, 44% yield) as a light yellow solid. MS (ESI) m/z 648.7 [M+H]$^+$.

benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)-5,6-dihydropyridine-1(2H)-carboxylate (3)

To a solution of benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)-5,6-dihydropyridine-1(2H)-carboxylate (525 mg, 0.81 mmol) and triphenylphosphine (850 mmol, 3.25 mmol) in THF (150 mL) was added DEAD (566 mg, 3.25 mmol) slowly at 0° C. under nitrogen atmosphere. The mixture was stirred at room temperature for 1 h. EtOAc (150 mL) was added. The organic phase was washed with water (100 mL×2), dried over Na$_2$SO$_4$, filtered and concentrated. The residue was purified by C18 with 30-95% ACN in H$_2$O to afford the desired product (390 mg, 0.62 mmol, yield: 77%) as a light yellow solid. MS (ESI) m/z 630.7 [M+H]$^+$.

(3S)-tert-butyl 4-((3S)-3-((1-((benzyloxy)carbonyl)-1,2,3,6-tetrahydropyridin-4-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (4)

To a solution of benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)-5,6-dihydropyridine-1(2H)-carboxylate (390 mg, 0.62 mmol) and K$_2$CO$_3$ (856 mg, 6.2 mmol) in ACN (8 mL) was added Ts$_2$O (304 mg, 0.93 mmol). The mixture was stirred at rt for 5 h. After the reaction was completed, (S)-tert-butyl 3-methylpiperazine-1-carboxylate (372 mg, 1.86 mmol) was added. The resulting mixture was stirred at rt for 20 min. After removing solvent in vacuo, the residue was purified by C18 with 30-95% ACN in H$_2$O to afford desired product (280 mg, yield: 56%) as yellow solid. MS (ESI) m/z 812.2 [M+H]$^+$.

(3S)-tert-butyl 4-((3S)-10-(2,4-difluorophenyl)-5-oxo-3-(piperidin-4-ylmethyl)-9-(trifluoromethyl)-3,5-dihydro-2H-[1,4]thiazino[2,3,4-ij]quinazolin-7-yl)-3-methylpiperazine-1-carboxylate (5)

The mixture of (3S)-tert-butyl 4-((3S)-3-((1-((benzyloxy)carbonyl)-1,2,3,6-tetrahydropyridin-4-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (240 mg, 0.296 mmol) and Pd/C (500 mg) in EtOH was stirred under hydrogen atmosphere (50 psi) for 18 hours. After filtration, the filtrate was concentrated to afford crude product (200 mg, crude) as yellow solid. MS (ESI) m/z 680.1 [M+H]$^+$.

(3S)-tert-butyl 4-((3S)-10-(2,4-difluorophenyl)-3-((1-ethylpiperidin-4-yl)methyl)-5-oxo-9-(trifluoromethyl)-3,5-dihydro-2H-[1,4]thiazino[2,3,4-ij]quinazolin-7-yl)-3-methylpiperazine-1-carboxylate (6)

To a mixture of (3S)-tert-butyl 4-((3S)-10-(2,4-difluorophenyl)-5-oxo-3-(piperidin-4-ylmethyl)-9-(trifluoromethyl)-3,5-dihydro-2H-[1,4]thiazino[2,3,4-ij]quinazolin-7-yl)-3-methylpiperazine-1-carboxylate (200 mg, 0.296 mmol) and acetaldehyde (0.5 mL, 40% in water) in EtOH was added sodium triacetoxyborohydride (125 mg, 0.59 mmol). The mixture was stirred at 20° C. for 2 hours. After removing solvent in vacuo, the residue was purified by silica gel column chromatography (dichloromethane/methanol=30/1) to give the product (124 mg, 59% yield) as yellow solid. MS (ESI) m/z 708.2 [M+H]$^+$ (3S)-10-(2,4-difluorophenyl)-3-((1-ethylpiperidin-4-yl)methyl)-7-((S)-2-methylpiperazin-1-yl)-9-(trifluoromethyl)-2H-[1,4]thiazino[2,3,4-ij]quinazolin-5(3H)-one (7)

To the mixture of (3S)-tert-butyl 4-((3S)-10-(2,4-difluorophenyl)-3-((1-ethylpiperidin-4-yl)methyl)-5-oxo-9-(trifluoromethyl)-3,5-dihydro-2H-[1,4]thiazino[2,3,4-ij]quinazolin-7-yl)-3-methylpiperazine-1-carboxylate (124 mg, 0.17 mmol) in DCM (2 mL) was added TFA (2 mL). The mixture was stirred at 20° C. for 2 hours. The mixture was concentrated to give the crude product as the TFA salt which was used in next step without further purification.

(3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one (8)

To a mixture of (3S)-10-(2,4-difluorophenyl)-3-((1-ethylpiperidin-4-yl)methyl)-7-((S)-2-methylpiperazin-1-yl)-9-(trifluoromethyl)-2H-[1,4]thiazino[2,3,4-ij]quinazolin-5(3H)-one (100 mg, 0.165 mmol) and triethyl amine (33 mg, 0.33 mmol) in DCM (2 mL) was added acrylic anhydride (21 mg, 0.165 mmol) at 0° C. The mixture was stirred at 0° C. for 1 hour. After removing solvent in vacuo, the residue was purified by silica gel column with DCM/MeOH (containing 5% NH$_3$)=30/1 to afford the product (40 mg, 37% yield) as white powder. $^1$H NMR (400 MHz, CDCl$_3$) δ 7.79 (s, 1H), 7.29-7.15 (m, 1H), 7.06-6.95 (m, 2H), 6.61-6.53 (m, 1H), 6.37 (d, J=15.6 Hz, 1H), 5.78 (d, J=6.0 Hz, 1H), 5.43-5.38 (m, 1H), 4.71-4.69 (m, 1H), 4.52-4.27 (m, 2H), 3.98-3.95 (m, 0.5H), 3.83-3.80 (m, 0.5H), 3.61-3.43 (m, 2H), 3.13-2.92 (m, 5H), 2.42 (q, J=7.2 Hz, 2H), 2.01-1.90 (m, 3H), 1.78-1.72 (m, 3H), 1.52-1.32 (m, 6H), 1.09 (t, J=7.2 Hz, 3H). MS (ESI) m/z 662.2 [M+H]$^+$.

M. Example 354

(3S)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one

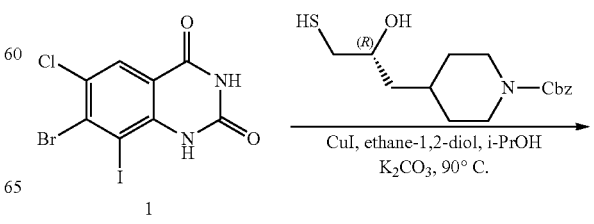

739
-continued
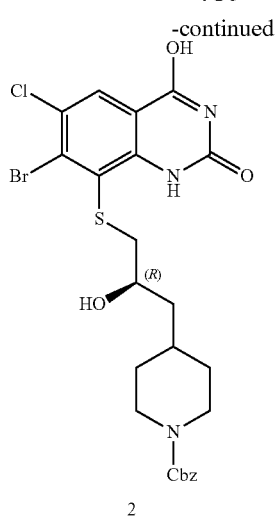
2
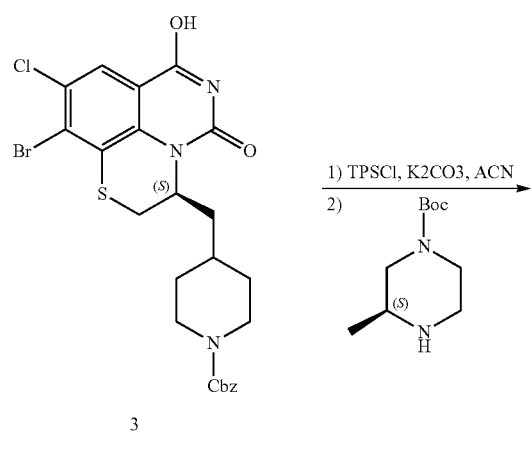
3
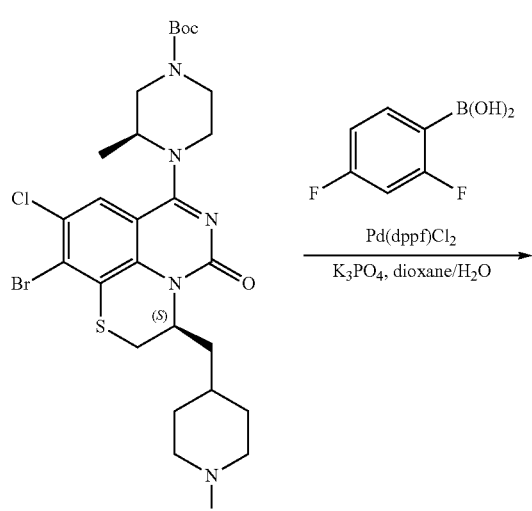
4
740
-continued
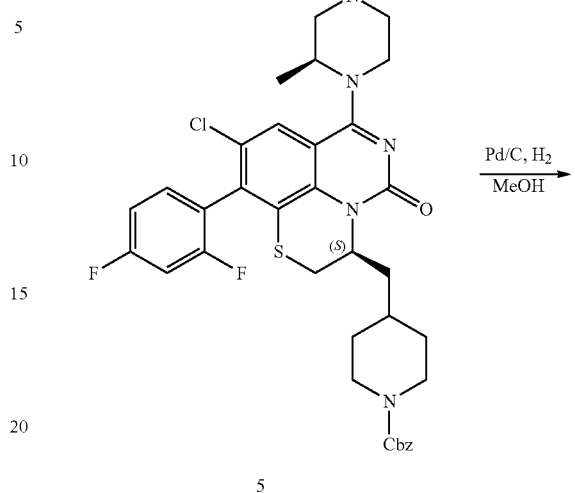
5
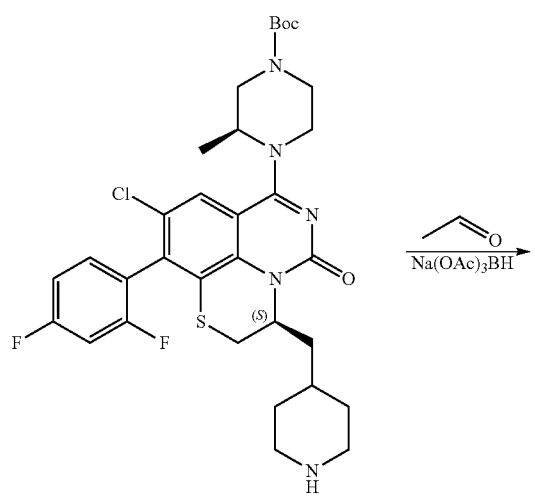
6
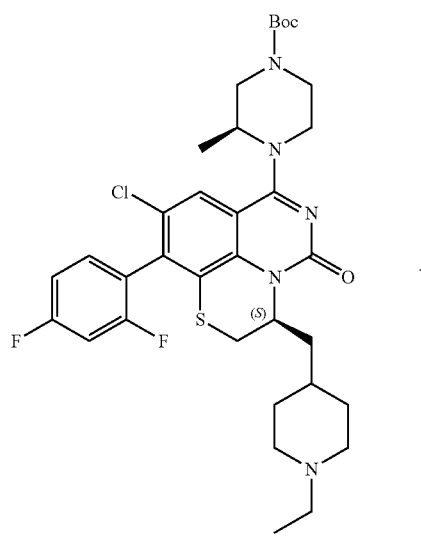
7

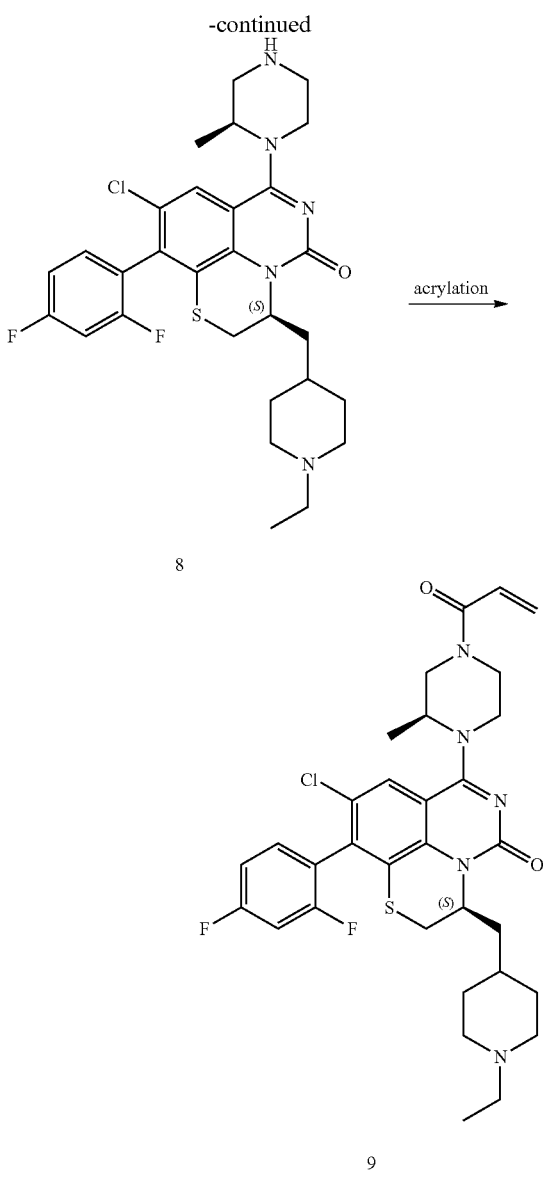

8

9

(R)-benzyl 4-(3-((7-bromo-6-chloro-4-hydroxy-2-oxo-1,2-dihydroquinazolin-8-yl)thio)-2-hydroxypropyl)piperidine-1-carboxylate (2)

The mixture of 7-bromo-6-chloro-8-iodoquinazoline-2,4 (1H,3H)-dione (4.9 g, 12.25 mmol), (R)-benzyl 4-(2-hydroxy-3-mercaptopropyl)piperidine-1-carboxylate (5.3 g, 17.15 mmol), $Pd_2(dba)_3$ (1.13 g, 1.23 mmol), XantPhos (1.06 g, 1.84 mmol) and $K_2CO_3$ (3.38 g, 24.5 mmol) in dioxane (60 mL) was stirred under nitrogen atmosphere at 50° C. for 18 hours. After removing solvent in vacuo, the residue was purified by silica gel column with a mixture of DCM/EA (3/1) to afford the product (3.8 g, yield: 54%) as a light yellow solid. MS (ESI) m/z 584.5 [M+H]$^+$.

(S)-benzyl 4-((10-bromo-9-chloro-7-hydroxy-5-oxo-3,5-dihydro-2H-[1,4]thiazino[2,3,4-ij]quinazolin-3-yl)methyl)piperidine-1-carboxylate (3)

To a mixture of (R)-benzyl 4-(3-((7-bromo-6-chloro-4-hydroxy-2-oxo-1,2-dihydroquinazolin-8-yl)thio)-2-hydroxypropyl)piperidine-1-carboxylate (3.38 g, 5.8 mmol) and triphenylphosphine (6.08 g, 23.2 mmol) in THF (1000 mL) was added DEAD (4.04 g, 23.2 mmol) slowly at 0° C. under nitrogen atmosphere. The mixture was stirred at room temperature for 1 h. The reaction mixture was concentrated and the residue was purified by C18 with 30-95% ACN in $H_2O$ to afford the product (2.4 g, 73% yield) as a light yellow solid. MS (ESI) m/z 566.5 [M+H]$^+$.

(S)-tert-butyl 4-((S)-3-((1-((benzyloxy)carbonyl) piperidin-4-yl)methyl)-10-bromo-9-chloro-5-oxo-3, 5-dihydro-2H-[1,4]thiazino[2,3,4-ij]quinazolin-7-yl)-3-methylpiperazine-1-carboxylate (4)

To a solution of (S)-benzyl 4-((10-bromo-9-chloro-7-hydroxy-5-oxo-3,5-dihydro-2H-[1,4]thiazino[2,3,4-ij]quinazolin-3-yl)methyl)piperidine-1-carboxylate (1.2 g, 2.12 mmol) and $K_2CO_3$ (2.9 g, 21.2 mmol) in ACN (50 mL) was added $Ts_2O$ (1.38 g, 4.24 mmol). The mixture was stirred at rt for 5 h. After the reaction was completed, (S)-tert-butyl 3-methylpiperazine-1-carboxylate (1.2 g, 6.36 mmol) was added. The resulting mixture was stirred at rt for 20 min. After removing the solvent in vacuo, the residue was purified by C18 with 30-95% ACN in $H_2O$ to afford desired product (1.2 g, 80% yield) as yellow solid. MS (ESI) m/z 746.0 [M+H]$^+$.

(3S)-tert-butyl 4-((3S)-3-((1-((benzyloxy)carbonyl) piperidin-4-yl)methyl)-9-chloro-10-(2,4-difluorophenyl)-5-oxo-3,5-dihydro-2H-[1,4]thiazino[2,3,4-ij] quinazolin-7-yl)-3-methylpiperazine-1-carboxylate (5)

To a mixture of (S)-tert-butyl 4-((S)-3-((1-((benzyloxy) carbonyl)piperidin-4-yl)methyl)-10-bromo-9-chloro-5-oxo-3,5-dihydro-2H-[1,4]thiazino[2,3,4-ij]quinazolin-7-yl)-3-methylpiperazine-1-carboxylate (1.15 g, 1.5 mmol) and (2,4-difluorophenyl)boronic acid (1.2 g, 7.5 mmol) in dioxane (20 mL) and $H_2O$ (4 mL) was added Pd(dppf)$Cl_2$ (219 mg, 0.3 mmol) and $K_3PO_4$ (954 mg, 4.5 mmol). The mixture was stirred at 80° C. under $N_2$ for 12 hours. After filtration, the filtrate was concentrated to afford crude product (1.3 g, crude) as yellow solid. MS (ESI) m/z 780.1 [M+H]$^+$.

(3S)-tert-butyl 4-((3S)-9-chloro-10-(2,4-difluorophenyl)-5-oxo-3-(piperidin-4-ylmethyl)-3,5-dihydro-2H-[1,4]thiazino[2,3,4-ij]quinazolin-7-yl)-3-methylpiperazine-1-carboxylate (6)

The mixture of (3S)-tert-butyl 4-((3S)-3-((1-((benzyloxy) carbonyl)piperidin-4-yl)methyl)-9-chloro-10-(2,4-difluorophenyl)-5-oxo-3,5-dihydro-2H-[1,4]thiazino[2,3,4-ij]quinazolin-7-yl)-3-methylpiperazine-1-carboxylate (1.3 g, 1.6 mmol) and Pd/C (1.3 g) in EtOH was stirred under hydrogen atmosphere for 4 hours. After filtration, the filtrate was concentrated to afford crude product (850 mg, crude) as yellow solid. MS (ESI) m z 646.8 [M+H]$^+$.

(3S)-tert-butyl 4-((3S)-9-chloro-10-(2,4-difluorophenyl)-3-((1-ethylpiperidin-4-yl)methyl)-5-oxo-3,5-dihydro-2H-[1,4]thiazino[2,3,4-ij]quinazolin-7-yl)-3-methylpiperazine-1-carboxylate (7)

To a mixture of (3S)-tert-butyl 4-((3S)-9-chloro-10-(2,4-difluorophenyl)-5-oxo-3-(piperidin-4-ylmethyl)-3,5-dihydro-2H-[1,4]thiazino[2,3,4-ij]quinazolin-7-yl)-3-methylpiperazine-1-carboxylate (200 mg, 0.3 mmol) and acetaldehyde (0.5 mL, 40% in water) in EtOH was added sodium triacetoxyborohydride (98 mg, 0.46 mmol). The mixture was stirred at 20° C. for 2 hours. After removing the solvent in vacuo, and the residue was purified by silica gel column chromatography (dichloromethane/methanol=10/1) to give the desired product (180 mg, 89% yield) as yellow solid. MS (ESI) m/z 674.2 [M+H]$^+$.

(3S)-9-chloro-10-(2,4-difluorophenyl)-3-((1-ethylpiperidin-4-yl)methyl)-7-((S)-2-methylpiperazin-1-yl)-2H-[1,4]thiazino[2,3,4-ij]quinazolin-5(3H)-one (8)

To the mixture of (3S)-tert-butyl 4-((3S)-9-chloro-10-(2,4-difluorophenyl)-3-((1-ethylpiperidin-4-yl)methyl)-5-oxo-3,5-dihydro-2H-[1,4]thiazino[2,3,4-ij]quinazolin-7-yl)-3-methylpiperazine-1-carboxylate (180 mg, 0.27 mmol) in DCM (2 mL) was added TFA (2 mL). The mixture was stirred at 20° C. for 2 hours. The reaction mixture was concentrated to give the crude product as the TFA salt, which was used in next step without further purification.

(3S)-7-((S)-4-acryloyl-2-methylpiperazin-1-yl)-9-chloro-10-(2,4-difluorophenyl)-3-((1-ethylpiperidin-4-yl)methyl)-2H-[1,4]thiazino[2,3,4-ij]quinazolin-5(3H)-one (9)

To a mixture of (3S)-10-(2,4-difluorophenyl)-3-((1-ethylpiperidin-4-yl)methyl)-7-((S)-2-methylpiperazin-1-yl)-9-(trifluoromethyl)-2H-[1,4]thiazino[2,3,4-ij]quinazolin-5(3H)-one (100 mg, 0.17 mmol) and triethyl amine (34 mg, 0.34 mmol) in DCM (2 mL) was added acrylic anhydride (22 mg, 0.17 mmol) at 0° C. The mixture was stirred at 0° C. for 1 hour. After removing solvent in vacuo, the residue was purified by prep-HPLC with a mixture of 5-95% ACN in H$_2$O to afford the desired product (30 mg, 28% yield) as white powder. $^1$H NMR (400 MHz, CDCl$_3$) δ 7.48 (s, 1H), 7.24-7.18 (m, 1H), 7.07-6.95 (m, 2H), 6.67-6.52 (m, 1H), 6.36 (d, J=16.8 Hz, 1H), 5.75 (d, J=10.4 Hz, 1H), 5.41-5.28 (m, 1H), 4.74-4.66 (m, 1H), 4.56-4.54 (m, 0.5H), 4.48-4.35 (m, 1H), 4.22-4.16 (m, 0.5H), 3.99-3.77 (m, 1H), 3.59-3.39 (m, 3H), 3.09-3.00 (m, 2H), 2.84-2.76 (m, 3H), 2.55-2.35 (m, 9H), 1.48-1.43 (m, 3H), 1.08-1.04 (m, 3H). MS (ESI) m/z 629.3 [M+H]$^+$.

N. Example 355

(3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one

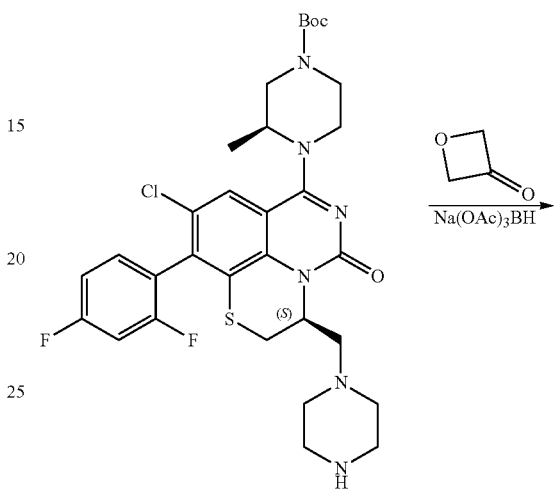

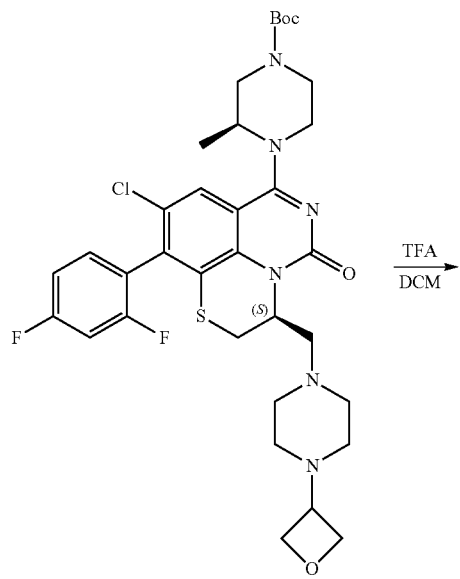

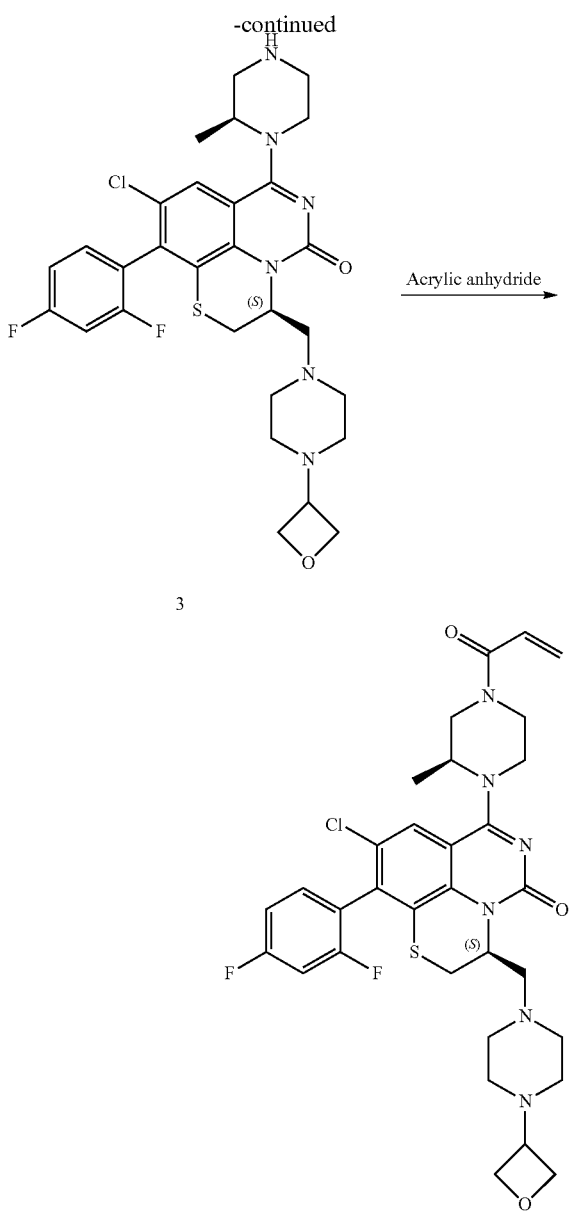

3

Acrylic anhydride →

4

(3S)-tert-butyl 4-((3S)-9-chloro-10-(2,4-difluorophenyl)-3-((4-(oxetan-3-yl) piperazin-1-yl)methyl)-5-oxo-3,5-dihydro-2H-[1,4]thiazino[2,3,4-ij]quinazolin-7-yl)-3-methylpiperazine-1-carboxylate (2)

To a solution of (3S)-tert-butyl 4-((3S)-9-chloro-10-(2,4-difluorophenyl)-5-oxo-3-(piperazin-1-ylmethyl)-3,5-dihydro-2H-[1,4]thiazino[2,3,4-ij]quinazolin-7-yl)-3-methylpiperazine-1-carboxylate (200 mg, 0.31 mmol) and oxetan-3-one (1.5 mL) in DCM (1.5 mL) was added sodium triacetoxyborohydride (88 mg, 0.44 mmol). The mixture was stirred at 20° C. for 2 hours. After removing the solvent in vacuo, the residue was purified by silica gel column chromatography (dichloromethane/methanol=30/1) to give the desired product (120 mg, 55% yield) as yellow solid. MS (ESI) m/z 703.2 [M+H]+

(3S)-9-chloro-10-(2,4-difluorophenyl)-7-((S)-2-methylpiperazin-1-yl)-3-((4-(oxetan-3-yl)piperazin-1-yl)methyl)-2H-[1,4]thiazino[2,3,4-ij]quinazolin-5(3H)-one (3)

To a solution of (3S)-tert-butyl 4-((3S)-9-chloro-10-(2,4-difluorophenyl)-3-((4-(oxetan-3-yl)piperazin-1-yl)methyl)-5-oxo-3,5-dihydro-2H-[1,4]thiazino[2,3,4-ij]quinazolin-7-yl)-3-methylpiperazine-1-carboxylate (120 mg, 0.17 mmol) in dichloromethane (3 mL) was added TFA (1 mL) at 0° C. After removing the solvent in vacuo, the residue was purified by silica gel column chromatography (dichloromethane/methanol=20/1) to give the desired product (100 mg, crude) as yellow solid. LC-MS: m/z 603.1 [M+H]+;

(3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one (4)

To a mixture of (3S)-9-chloro-10-(2,4-difluorophenyl)-7-((S)-2-methylpiperazin-1-yl)-3-((4-(oxetan-3-yl)piperazin-1-yl)methyl)-2H-[1,4]thiazino[2,3,4-ij]quinazolin-5(3H)-one (80 mg, 0.13 mmol) and triethyl amine (26 mg, 0.26 mmol) in dichloromethane (3 mL) was added acrylic anhydride (25 mg, 0.19 mmol) at 0° C. The mixture was stirred at rt for 1 hour. After removing the solvent in vacuo, the residue was purified by prep-HPLC to afford the desired product (35 mg, 41% yield) as yellow solid. LC-MS: m/z 657.1 [M+H]+.
$^1$H NMR (400 MHz, CDCl$_3$) δ 7.48 (s, 1H), 7.24-7.18 (m, 1H), 7.07-6.95 (m, 2H), 6.66-6.51 (m, 1H), 6.37 (d, J=16.4 Hz, 1H), 5.77 (d, J=10.8 Hz, 1H), 5.40-5.27 (m, 1H), 4.71-4.58 (m, 5.5H), 4.52-4.36 (m, 1H), 4.20 (s, 0.5H), 3.99-3.77 (m, 1H), 3.57-3.37 (m, 4H), 3.09-3.01 (m, 2H), 2.85-2.87 (m, 3H), 2.57-2.55 (m, 3H), 2.35-2.31 (m, 4H), 1.48-1.43 (m, 3H).

O. Example 356

(3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one

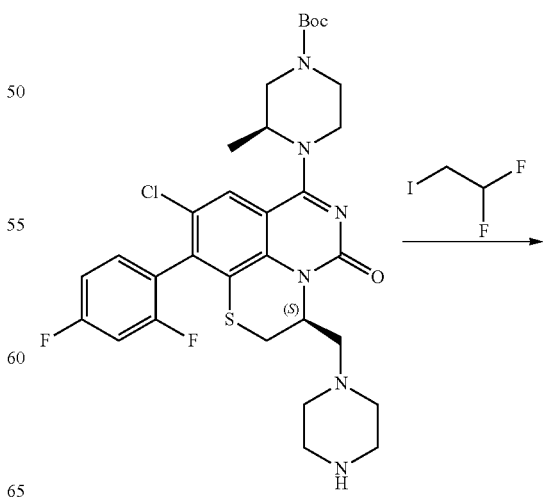

1

747
-continued

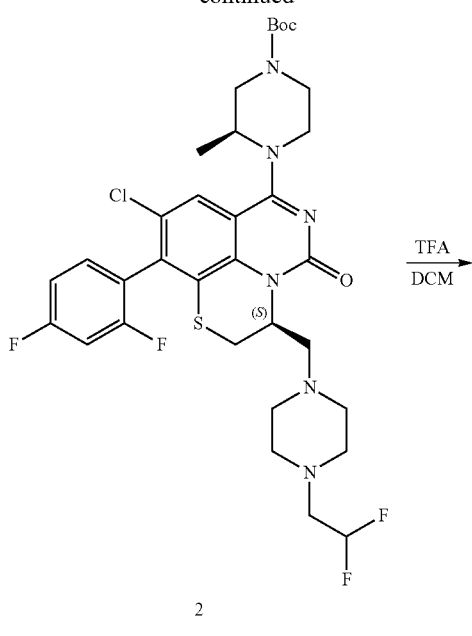

2

TFA
DCM
→

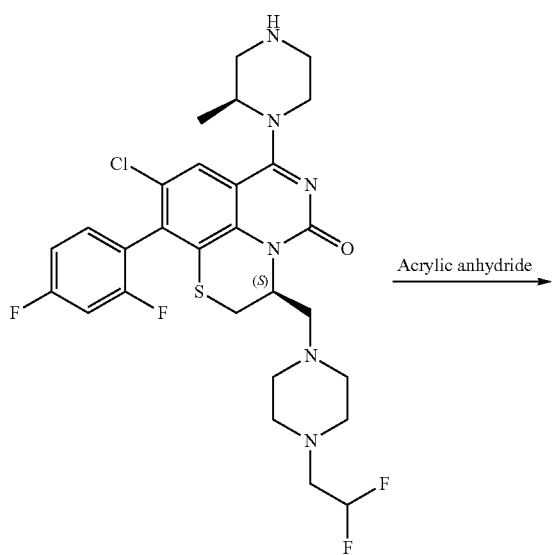

3

748
-continued

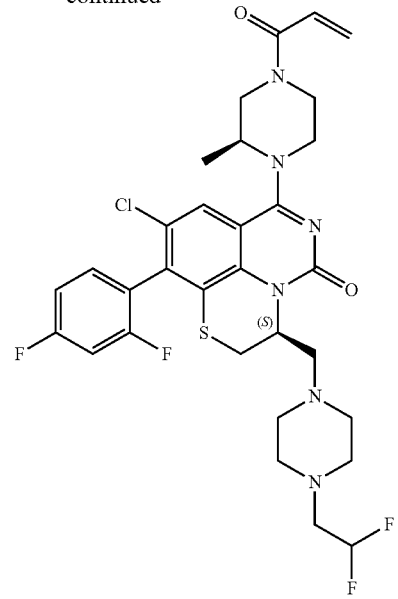

4

(3S)-tert-butyl 4-((3S)-9-chloro-3-((4-(2,2-difluoro-ethyl)piperazin-1-yl)methyl)-10-(2,4-difluorophenyl)-5-oxo-3,5-dihydro-2H-[1,4]thiazino[2,3,4-ij]quinazolin-7-yl)-3-methylpiperazine-1-carboxylate (2)

To a solution of (3S)-tert-butyl 4-((3S)-9-chloro-10-(2,4-difluorophenyl)-5-oxo-3-(piperidin-4-ylmethyl)-3,5-dihydro-2H-[1,4]thiazino[2,3,4-ij]quinazolin-7-yl)-3-methylpiperazine-1-carboxylate (210 mg, 0.32 mmol) and 1,1-difluoro-2-iodoethane (311 mg, 1.62 mmol) in ACN (10 mL) was added $K_2CO_3$ (224 mg, 1.62 mmol). The mixture stirred was at 85° C. for 16 hours. After removing solvent in vacuo, the residue was purified by silica gel column chromatography (dichloromethane/methanol=40/1) to give the desired product (130 mg, 56% yield) as yellow solid. MS (ESI) m/z 711.8 [M+H]$^+$ (3S)-9-chloro-3-((4-(2,2-difluoroethyl)piperazin-1-yl)methyl)-10-(2,4-difluorophenyl)-7-((S)-2-methylpiperazin-1-yl)-2H-[1,4]thiazino[2,3,4-ij]quinazolin-5(3H)-one (3)

To a solution of (3S)-tert-butyl 4-((3S)-9-chloro-3-((4-(2,2-difluoroethyl)piperazin-1-yl)methyl)-10-(2,4-difluorophenyl)-5-oxo-3,5-dihydro-2H-[1,4]thiazino[2,3,4-ij]quinazolin-7-yl)-3-methylpiperazine-1-carboxylate (130 mg, 0.18 mmol) in dichloromethane (3 mL) was added TFA (1 mL) at 0° C. After removing solvent in vacuo, the residue was purified by silica gel column chromatography (dichloromethane/methanol=20/1) to give the product (92 mg, 84% yield) as yellow solid. LC-MS: m/z 611.7[M+H]$^+$;

(3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one (4)

To a solution of (3S)-9-chloro-3-((4-(2,2-difluoroethyl)piperazin-1-yl)methyl)-10-(2,4-difluorophenyl)-7-((S)-2-

Acrylic anhydride
→ methylpiperazin-1-yl)-2H-[1,4]thiazino[2,3,4-ij]quinazolin-5(3H)-one (70 mg, 0.11 mmol) and triethyl amine (22 mg, 0.22 mmol) in dichloromethane (3 mL) was added acrylic anhydride (25 mg, 0.19 mmol) at 0° C. The mixture was stirred at rt for 1 hour. After removing solvent in vacuo, the residue was purified by prep-HPLC to afford the product (41 mg, 42% yield) as yellow solid. LC-MS: m/z 665.8 [M+H]$^+$.

$^1$H NMR (400 MHz, CDCl$_3$) δ 7.48 (s, 1H), 7.24-7.18 (m, 1H), 7.07-6.95 (m, 2H), 6.66-6.51 (m, 1H), 6.36 (d, J=16.8 Hz, 1H), 6.00-5.70 (m, 2H), 5.40-5.32 (m, 1H), 4.71-4.65 (m, 1H), 4.56-4.35 (m, 1.5H), 4.23-4.17 (m, 0.5H), 3.99-3.78 (m, 1H), 3.64-3.37 (m, 3H), 3.08-3.00 (m, 2H), 2.84-2.67 (m, 5H), 2.58-2.52 (m, 7H), 1.48-1.43 (m, 3H).

P. Example 19

(3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one

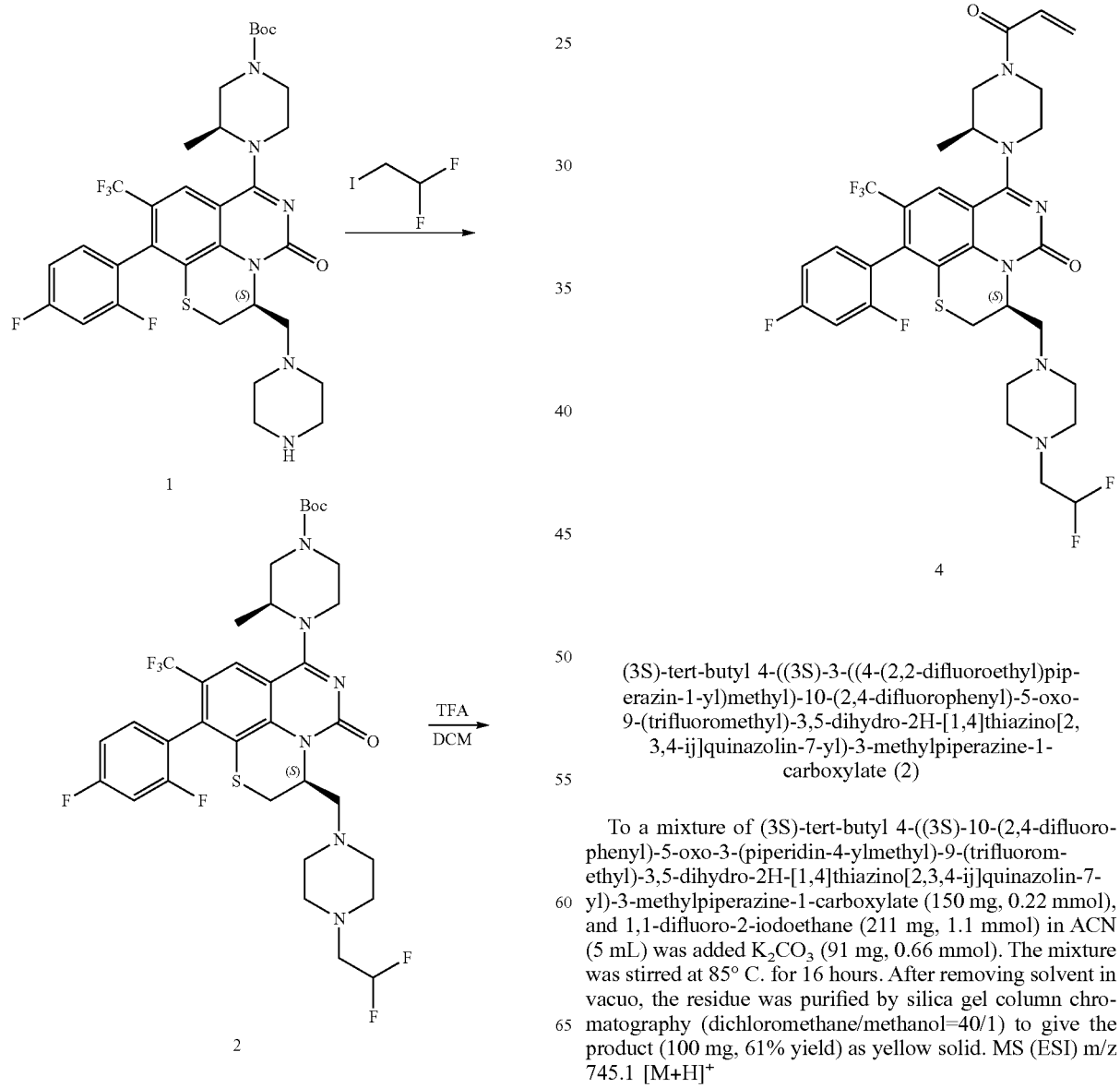

(3S)-tert-butyl 4-((3S)-3-((4-(2,2-difluoroethyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (2)

To a mixture of (3S)-tert-butyl 4-((3S)-10-(2,4-difluorophenyl)-5-oxo-3-(piperidin-4-ylmethyl)-9-(trifluoromethyl)-3,5-dihydro-2H-[1,4]thiazino[2,3,4-ij]quinazolin-7-yl)-3-methylpiperazine-1-carboxylate (150 mg, 0.22 mmol), and 1,1-difluoro-2-iodoethane (211 mg, 1.1 mmol) in ACN (5 mL) was added K$_2$CO$_3$ (91 mg, 0.66 mmol). The mixture was stirred at 85° C. for 16 hours. After removing solvent in vacuo, the residue was purified by silica gel column chromatography (dichloromethane/methanol=40/1) to give the product (100 mg, 61% yield) as yellow solid. MS (ESI) m/z 745.1 [M+H]$^+$

751

(3S)-3-((4-(2,2-difluoroethyl)piperazin-1-yl)methyl)-10-(2,4-difluorophenyl)-7-((S)-2-methylpiperazin-1-yl)-9-(trifluoromethyl)-2H-[1,4]thiazino[2,3,4-ij]quinazolin-5(3H)-one (3)

To a solution of (3S)-tert-butyl 4-((3S)-3-((4-(2,2-difluoroethyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (100 mg, 0.13 mmol) in dichloromethane (3 mL) was added TFA (1 mL) at 0° C. for 1 hour. After removing solvent in vacuo, the residue was purified by silica gel column chromatography (dichloromethane/methanol=20/1) to give the desired product (150 mg, crude) as yellow solid. LC-MS: m/z 645.1[M+H]$^+$;

752

(3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one (4)

To a mixture of (3S)-3-((4-(2,2-difluoroethyl)piperazin-1-yl)methyl)-10-(2,4-difluorophenyl)-7-((S)-2-methylpiperazin-1-yl)-9-(trifluoromethyl)-2H-[1,4]thiazino[2,3,4-ij]quinazolin-5(3H)-one (100 mg, 0.15 mmol) and triethyl amine (38 mg, 0.3 mmol) in dichloromethane (3 mL) was added acrylic anhydride (25 mg, 0.19 mmol) at 0° C. The mixture was stirred at rt for 1 hour. After removing the solvent in vacuo, the residue was purified by prep-HPLC to afford the product (30 mg, 28% yield) as yellow solid. LC-MS: m/z 699.1 [M+H]$^+$; $^1$H NMR (400 MHz, CDCl$_3$) δ 7.77 (s, 1H), 7.20-7.16 (m, 1H), 7.07-6.94 (m, 2H), 6.71-6.51 (m, 1H), 6.41-6.35 (m, 1H), 6.00-5.69 (m, 2H), 5.38-5.32 (m, 1H), 4.75-4.61 (m, 1H), 4.52-4.23 (m, 2H), 4.04-3.77 (m, 1H), 3.67-3.39 (in 3H), 3.16-2.80 (in 2H), 2.79-2.66 (m, 5H), 2.61-2.52 (m, 7H), 1.54-1.43 (in 3H).

Summary Table

| Ex. # | Name | Structure | $^1$H NMR | MS (M + H)$^+$ |
|---|---|---|---|---|
| 137 | (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one | 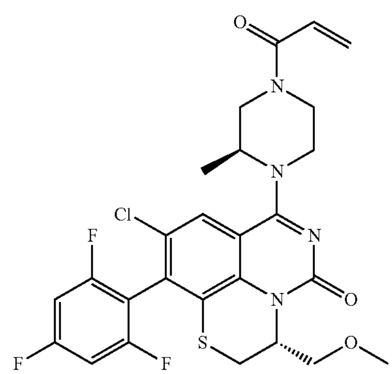 [SMILES: C=CC(=O)N1CCN(c2nc(=O)n3c4c(c(-c5c(F)cc(F)cc5F)c(Cl)cc24)SC[C@H]3COC)[C@@H](C)C1] | $^1$H NMR (400 MHz, CDCl$_3$) δ 7.52-7.49 (brs, 1H), 6.86-6.82 (m, 1H), 6.60-6.56 (m, 1H), 6.39-6.35 (m, 1H), 5.78 (d, J = 2.4 Hz, 1H), 5.44 (brs, 1H), 5.01-4.47 (m, 2H), 4.09-3.99 (m, 1.5H), 3.83-3.62 (m, 4H), 3.49-3.32 (m, 5H), 3.05-3.01 (m, 1H), 2.90-2.85 (m, 0.5H), 2.64-2.45 (m, 3H), 1.88-1.80 (m, 4H), 1.53-1.46 (m, 2H), 1.34 (d, J = 6.4 Hz, 3H). | 565.1 |
| 130 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one | 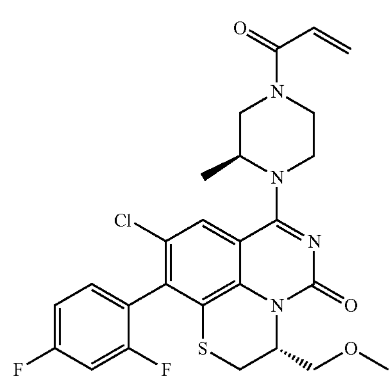 [SMILES: C=CC(=O)N1CCN(c2nc(=O)n3c4c(c(-c5ccc(F)cc5F)c(Cl)cc24)SC[C@H]3COC)[C@@H](C)C1] | $^1$H NMR (400 MHz, CDCl$_3$) δ 7.52-7.49 (brs, 1H), 7.24-7.19 (m, 1H), 7.07-6.95 (m, 2H), 6.59-6.57 (m, 1H), 6.39-6.32 (m, 1H), 5.78 (d, J = 2.4 Hz, 1H), 5.43-5.39 (m, 1H), 5.01-4.47 (m, 2H), 4.09-3.99 (m, 1.5H), 3.83-3.62 (m, 4H), 3.49-3.32 (m, 5H), 3.06-3.01 (m, 1H), 2.90-2.85 (m, 0.5H), 2.64-2.45 (m, 3H), 1.88-1.80 (m, 4H), 1.53-1.46 (m, 2H), 1.34 (d, J = 6.4 Hz, 3H). | 547.1 |

-continued

Summary Table

| Ex. # | Name | Structure | ¹H NMR | MS (M + H)⁺ |
|---|---|---|---|---|
| 99 | (3R)-7-((S)-4-acryloyl-2-methylpiperazin-1-yl)-9-chloro-10-(2,4-difluorophenyl)-3-methyl-2H-[1,4]thiazino[2,3,4-ij]quinazolin-5(3H)-one | 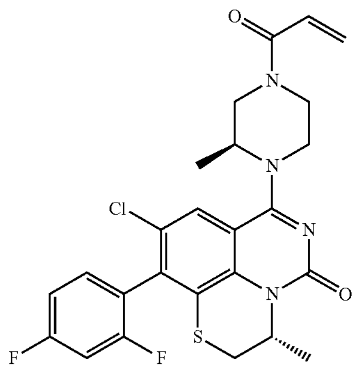 [SMILES: C=CC(=O)N1CCN(c2nc(=O)n3c4c(c(-c5ccc(F)cc5F)c(Cl)cc24)SC[C@H]3C)[C@@H](C)C1] | 1H NMR (400 MHz, CDCl₃) δ 7.51 (s, 1H), 7.25-7.19 (m, 1H), 7.07-6.97 (m, 2H), 6.59-6.57 (m, 1H), 6.39-6.36 (d, 1H), 5.79-5.76 (d, 1H), 5.42 (s, 1H), 4.96-4.86 (d, 1H), 4.64-4.62 (d, 1H), 4.02-3.96 (t, 1.5H), 3.83-3.67 (m, 2H), 3.42-3.21 (m, 2H), 2.92-2.87 (m, 1.5H), 1.48-1.45 (t, 3H), 1.33-1.31 (d, 3H). | 517.1 |
| 339 | (R)-3-(3-((1S,4S)-2-oxa-5-aza-bicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 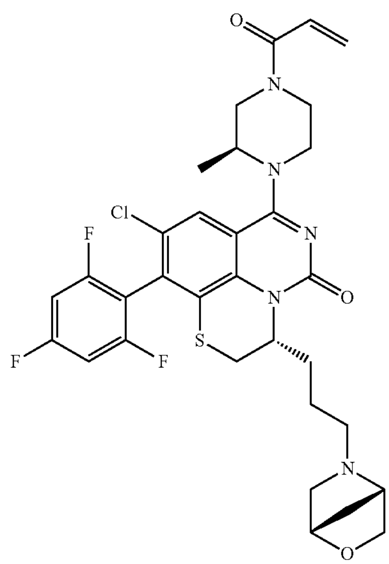 [SMILES: C=CC(=O)N1CCN(c2nc(=O)n3c4c(c(-c5c(F)cc(F)cc5F)c(Cl)cc24)SC[C@H]3CCCN2C[C@@H]3C[C@H]2CO3)[C@@H](C)C1] | ¹H NMR (400 MHz, CDCl₃) δ 7.51 (brs, 1H), 6.84 (t, J = 8.0 Hz, 1H), 6.63-6.53 (m, 1H), 6.39-6.35 (m, 1H), 5.78 (d, J = 11.2 Hz, 1H), 5.32 (brs, 1H), 4.94-4.75 (m, 1H), 4.67-4.55 (m, 1H), 4.38 (s, 1H), 4.09-4.00 (m, 2H), 3.83-3.44 (m, 5H), 3.24-3.05 (m, 2H), 2.71-2.51 (m, 3H), 1.95-1.88 (m, 4H), 1.58-1.53 (m, 2H), 1.36 (d, J = 7.2 Hz, 3H). | 660.2 |
| 340 | (S)-3-(3-((1S,4S)-2-oxa-5-aza-bicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 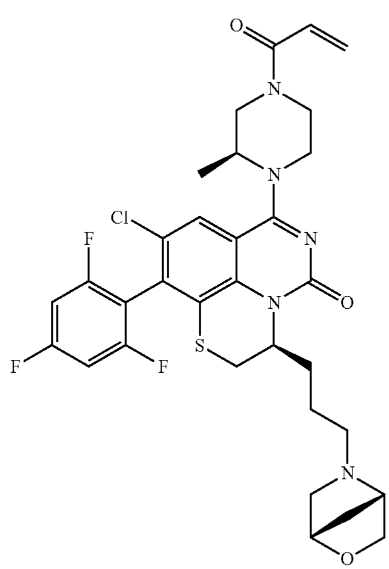 [SMILES: C=CC(=O)N1CCN(c2nc(=O)n3c4c(c(-c5c(F)cc(F)cc5F)c(Cl)cc24)SC[C@@H]3CCCN2C[C@@H]3C[C@H]2CO3)[C@@H](C)C1] | ¹H NMR (400 MHz, CDCl₃) δ 7.50 (s, 1H), 6.84 (t, J = 8.0 Hz, 1H), 6.63-6.53 (m, 1H), 6.39-6.35 (m, 1H), 5.78 (d, J = 11.2 Hz, 1H), 5.32 (brs, 1H), 4.70-4.25 (m, 4H), 4.09-3.96 (m, 2H), 3.61-3.41 (m, 4H), 3.26-2.93 (m, 4H), 2.71-2.51 (m, 3H), 1.95-1.84 (m, 4H), 1.52-1.45 (m, 3H). | 660.2 |

-continued

Summary Table

| Ex. # | Name | Structure | ¹H NMR | MS (M + H)⁺ |
|---|---|---|---|---|
| 341 | (3R)-3-(3-((1S,4S)-2-oxa-5-aza-bicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 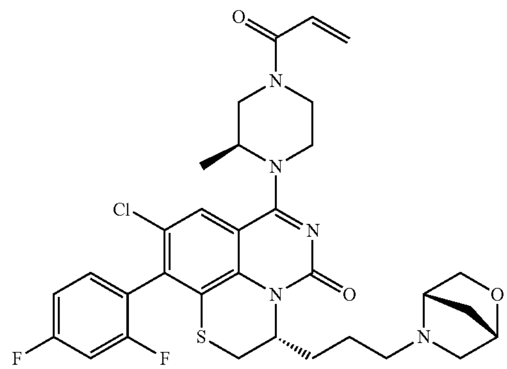 [SMILES: C=CC(=O)N1CCN(c2nc(=O)n3c4c(c(-c5ccc(F)cc5F)c(Cl)cc24)SC[C@H]3CCCN2C[C@@H]3C[C@H]2CO3)[C@@H](C)C1] | ¹H NMR (400 MHz, CDCl₃) δ 7.50 (brs, 1H), 7.24-7.19 (m, 1H), 7.07-6.96 (m, 2H), 6.59-6.52 (m, 1H), 6.39-6.32 (m, 1H), 5.78 (d, J = 2.4 Hz, 1H), 5.32 (brs, 1H), 4.93-4.63 (m, 4H), 4.37-4.36 (m, 2H), 4.09-3.98 (m, 2.5H), 3.83-3.57 (m, 3H), 3.45-3.25 (m, 2H), 3.14-3.04 (m, 2.5H), 2.90-2.87 (m, 1H), 2.64-2.45 (m, 3H), 1.88-1.80 (m, 4H), 1.53-1.46 (m, 2H), 1.34 (d, J = 6.8 Hz, 3H). | 642.3 |
| 342 | (3S)-3-(3-((1S,4S)-2-oxa-5-aza-bicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 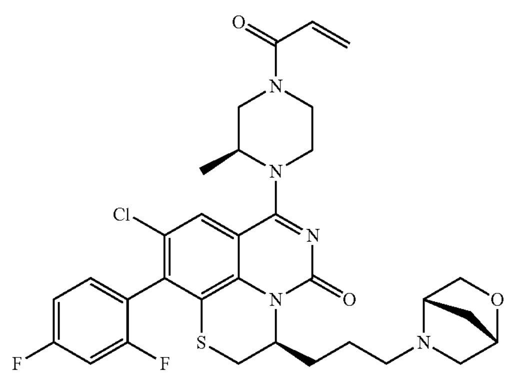 [SMILES: C=CC(=O)N1CCN(c2nc(=O)n3c4c(c(-c5ccc(F)cc5F)c(Cl)cc24)SC[C@@H]3CCCN2C[C@@H]3C[C@H]2CO3)[C@@H](C)C1] | 1H NMR (400 MHz, CDCl₃) δ 7.49 (s, 1H), 7.26-7.18 (m, 1H), 7.07-6.95 (m, 2H), 6.62-6.53 (m, 1H), 6.39-6.36 (d, 1H), 5.79-5.78 (d, 1H), 5.34-5.28 (m, 1H), 4.74-4.70 (m, 1H), 4.54-4.23 (m, 3H), 3.99-3.96 (dd, 1.5H), 3.81-3.45 (m, 4.5H), 3.09-2.86 (m, 4H), 2.7-2.46 (m, 3H), 1.92-1.75 (m, 4H), 1.66-1.36 (m, 5H). | 642.2 |
| 343 | (S)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 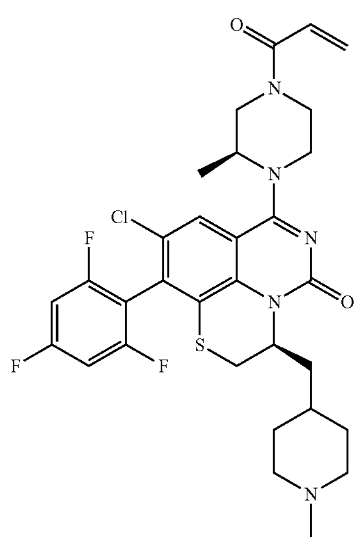 [SMILES: C=CC(=O)N1CCN(c2nc(=O)n3c4c(c(-c5c(F)cc(F)cc5F)c(Cl)cc24)SC[C@@H]3CC2CCN(C)CC2)[C@@H](C)C1] | 1H NMR (400 MHz, CDCl₃) δ 7.51 (s, 1H), 6.85 (t, J = 8.0 Hz, 2H), 6.63-6.54 (m, 1H), 6.40-6.36 (m, 1H), 5.78 (d, J = 9.6 Hz, 1H), 5.47-5.46 (m, 1H), 4.75-4.66 (m, 1H), 4.57-4.43 (m, 1H), 4.38-4.18 (m, 1H), 3.97-3.79 (m, 1H), 3.61-3.46 (m, 2H), 3.19-3.16 (m, 1H), 3.09-2.98 (m, 2H), 2.89-2.84 (m, 2H), 2.27 (s, 3H), 2.02-1.91 (m, 2.5H), 1.81-1.76 (m, 2.5H), 1.48-1.31 (m, 7H). | 632.2 |

-continued

Summary Table

| Ex. # | Name | Structure | ¹H NMR | MS (M + H)⁺ |
|---|---|---|---|---|
| 344 | (R)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 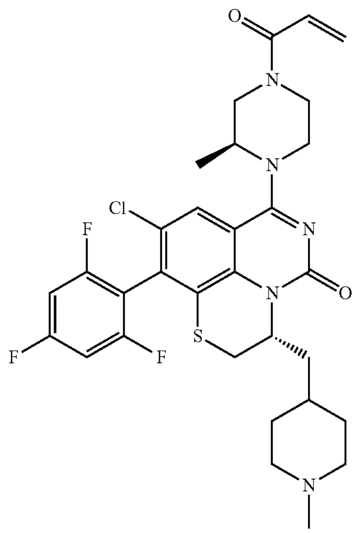 [SMILES: C=CC(=O)N1CCN(c2nc(=O)n3c4c(c(-c5c(F)cc(F)cc5F)c(Cl)cc24)SC[C@H]3CC2CCN(C)CC2)[C@@H](C)C1] | 1H NMR (400 MHz, CDCl$_3$) δ 7.52-7.51 (m, 1H), 6.85 (t, J = 8.0 Hz, 2H), 6.63-6.53 (m, 1H), 6.38 (dd, J = 16.8 Hz, 1.6 Hz, 1H), 5.78 (d, J = 10.8 Hz, 1H), 5.48-5.46 (m, 1H), 4.91-4.89 (m, 0.5H), 4.74-4.64 (m, 1H), 4.50-4.47 (m, 0.5H), 4.17-3.97 (m, 1.5H), 3.84-3.46 (m, 3H), 3.20-3.16 (m, 1.5H), 3.02-2.92 (m, 1.5H), 2.87-2.81 (m, 2H), 2.25 (s, 3H), 1.99-1.84 (m, 2.5H), 1.64-1.58 (m, 2H), 1.44-1.32 (m, 7H). | 632.2 |
| 345 | (3R)-7-((S)-4-acryloyl-2-methylpiperazin-1-yl)-9-chloro-10-(2,4-difluorophenyl)-3-((1-methylpiperidin-4-yl)methyl)-2H-[1,4]thiazino[2,3,4-ij]quinazolin-5(3H)-one | 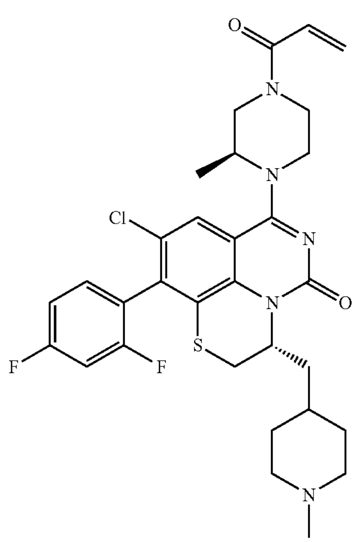 [SMILES: C=CC(=O)N1CCN(c2nc(=O)n3c4c(c(-c5ccc(F)cc5F)c(Cl)cc24)SC[C@H]3CC2CCN(C)CC2)[C@@H](C)C1] | 1H NMR (400 MHz, CDCl$_3$) δ 7.51 (s, 1H), 7.24-7.20 (m, 1H), 7.07-6.96 (m, 2H), 6.59-6.57 (m, 1H), 6.37 (d, J = 15.6 Hz, 1H), 5.78 (d, J = 10.8 Hz, 1H), 5.48-5.42 (m, 1H), 4.91-4.89 (m, 0.5H), 4.71-4.63 (m, 1H), 4.48-4.47 (m, 0.5H), 4.12-3.98 (m, 1.5H), 3.83-3.49 (m, 3H), 3.22-3.11 (m, 1.5H), 2.99-2.86 (m, 3.5H), 2.30 (s, 3H), 1.98-1.91 (m, 1.5H), 1.51-1.33 (m, 10H). | 614.2 |

-continued

Summary Table

| Ex. # | Name | Structure | ¹H NMR | MS (M + H)⁺ |
|---|---|---|---|---|
| 346 | (3R)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 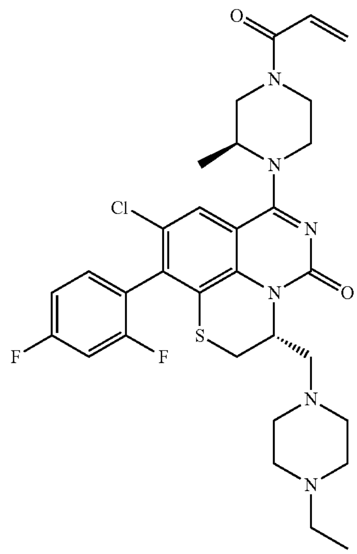 [SMILES: C=CC(=O)N1CCN(c2nc(=O)n3c4c(c(-c5ccc(F)cc5F)c(Cl)cc24)SC[C@H]3CN2CCN(CC)CC2)[C@@H](C)C1] | ¹H NMR (400 MHz, CDCl₃) δ 7.51-7.49 (m, 1H), 7.24-7.18 (m, 1H), 7.07-6.95 (m, 2H), 6.61-6.53 (m, 1H), 5.78 (d, J = 11.2 Hz, 1H), 5.38-5.31 (m, 1H), 4.990-4.46 (m, 2H), 4.19-4.00 (m, 1.5H), 3.83-3.40 (m, 3.5H), 3.14-2.98 (m, 2H), 2.84-2.65 (m, 3H), 2.54-2.30 (m, 9H), 1.36 (d, J = 6.4 Hz, 2H), 1.08-1.02 (m, 3H). | 629.3 |
| 76 | 7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one | 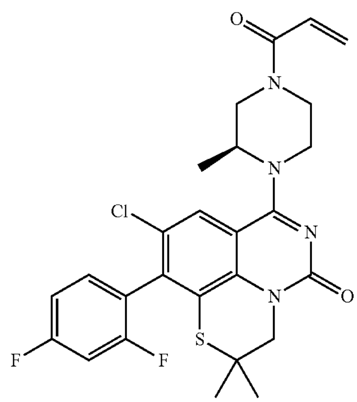 [SMILES: C=CC(=O)N1CCN(c2nc(=O)n3c4c(c(-c5ccc(F)cc5F)c(Cl)cc24)SC(C)(C)C3)[C@@H](C)C1] | ¹H NMR (400 MHz, MeOH-d₄) δ 7.71 (d, J = 4.5 Hz, 1H), 7.33-7.22 (m, 1H), 7.18-7.09 (m, 2H), 6.91-6.73 (m, 1H), 6.29 (dd, J = 16.2, 7.2 Hz, 1H), 5.81 (dd, J = 10.6, 1.9 Hz, 1H), 4.68-3.93 (m, 5H), 3.80-3.45 (m, 2H), 1.42 (s, 3H), 1.38 (s, 3H) | 531.2 |
| 347 | (3R)-7-((S)-4-acryloyl-2-methylpiperazin-1-yl)-9-chloro-3-((4-(2,2-difluoro-ethyl)piperazin-1-yl)methyl)-10-(2,4-difluorophenyl)-2H-[1,4]thiazino[2,3,4-ij]quinazolin-5(3H)-one | 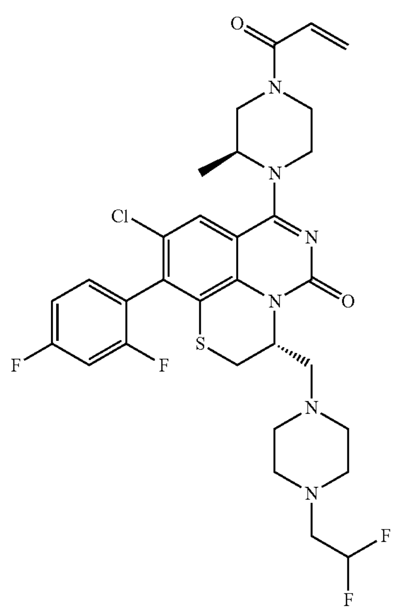 | 1H NMR (400 MHz, CDCl₃) δ 7.49 (brs, 1H), 7.23-7.17 (m, 1H), 7.07-6.95 (m, 2H), 6.62-6.55 (m, 1H), 6.39-6.34 (m, 1H), 6.01-5.70 (m, 2H), 5.38-5.30 (m, 1H), 4.92-4.54 (m, 2H), 4.11-3.99 (m, 1.5H), 3.82-3.21 (m, 4.5H), 3.02-2.83 (m, 2H), 2.74-2.67 (m, 5H), 2.60-2.52 (m, 7H), 1.45 (d, J = 6.8 Hz, 3H). | 665.2 |

-continued

Summary Table

| Ex. # | Name | Structure | ¹H NMR | MS (M + H)⁺ |
|---|---|---|---|---|
| 348 | (3R)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 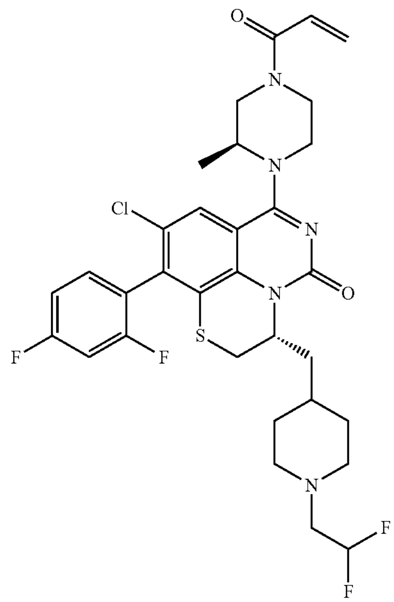 [SMILES: C=CC(=O)N1CCN(c2nc(=O)n3c4c(c(-c5ccc(F)cc5F)c(Cl)cc24)SC[C@H]3CC2CCN(CC(F)F)CC2)[C@@H](C)C1] | 1H NMR (400 MHz, CDCl₃) δ 7.51 (s, 1H), 7.24-7.20 (m, 1H), 7.07-6.96 (m, 2H), 6.62-6.53 (m, 1H), 6.37 (dd, J = 16.4 Hz, 1.2 Hz, 1H), 6.00-5.71 (m, 2H), 5.44-5.43 (m, 1H), 4.91-4.88 (m, 0.5 H), 4.72-4.63 (m, 1H), 4.48-4.45 (m, 0.5H), 4.13-3.96 (m, 1.5H), 3.83-3.62 (m, 1.5H), 3.59-3.45 (m, 1H), 3.23-3.20 (m, 0.5H), 3.18-3.10 (m, 1H), 2.99-2.87 (m, 3.5H), 2.74-2.65 (m, 2H), 2.24-2.14 (m, 2H), 1.75-1.73 (m, 3H), 1.45-1.35 (m, 7H). | 664.3 |
| 349 | (R)-7-((S)-4-acryloyl-2-methylpiperazin-1-yl)-9-chloro-3-((1-(2,2-difluoroethyl)piperidin-4-yl)methyl)-10-(4-fluorophenyl)-2H-[1,4]thiazino[2,3,4-ij]quinazolin-5(3H)-one | 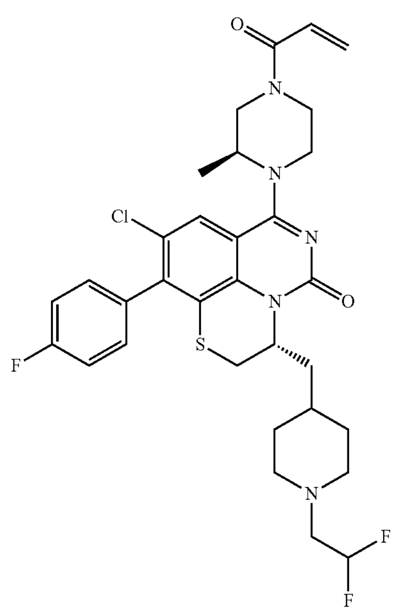 [SMILES: C=CC(=O)N1CCN(c2nc(=O)n3c4c(c(-c5ccc(F)cc5)c(Cl)cc24)SC[C@H]3CC2CCN(CC(F)F)CC2)[C@@H](C)C1] | 1H NMR (400 MHz, CDCl₃) δ 7.51 (s, 1H), 7.25-7.19 (m, 4H), 6.63-6.52 (m, 1H), 6.37 (dd, J = 16.8 Hz, 1.6 Hz, 1H), 6.01-5.71 (m, 2H), 5.43-5.41 (m, 1H), 4.91-4.88 (m, 0.5 H), 4.71-4.63 (m, 1H), 4.49-4.46 (m, 0.5H), 4.15-4.00 (m, 1.5H), 3.83-3.64 (m, 1.5H), 3.61-3.47 (m, 1H), 3.23-3.21 (m, 0.5H), 3.10-3.06 (m, 1H), 2.96-2.89 (m, 3.5H), 2.75-2.66 (m, 2H), 2.23-2.13 (m, 2H), 1.87-1.74 (m, 4H), 1.47-1.33 (m, 6H). | 646.2 |

-continued

Summary Table

| Ex. # | Name | Structure | ¹H NMR | MS (M + H)⁺ |
|---|---|---|---|---|
| 350 | (3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one | 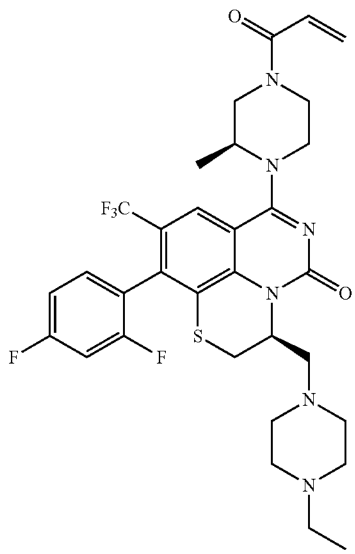 [SMILES: C=CC(=O)N1CCN(c2nc(=O)n3c4c(c(-c5ccc(F)cc5F)c(C(F)(F)F)cc24)SC[C@@H]3CN2CCN(CC)CC2)[C@@H](C)C1] | 1H NMR (400 MHz, CDCl₃) δ 7.75 (s, 1H), 7.20-7.15 (m, 1H), 7.04-6.93 (m, 2H), 6.62-6.53 (m, 1H), 6.39-6.52 (m, 1H), 5.75 (d, J = 9.2 Hz, 1H), 5.37-5.28 (m, 1H), 4.72-4.68 (m, 1H), 4.51-4.26 (m, 2H), 3.99-3.38 (m, 5H), 3.11-2.97 (m, 2H), 2.82-2.76 (m, 3H), 2.59-2.37 (m, 8H), 1.26-1.22 (m, 3H), 1.09 (t, J = 7.2 Hz, 3H). | 663.3 |
| 351 | (S)-7-((S)-4-acryloyl-2-methylpiperazin-1-yl)-9-chloro-3-((4-ethylpiperazin-1-yl)methyl)-10-(2,4,6-trifluorophenyl)-2H-[1,4]thiazino[2,3,4-ij]quinazolin-5(3H)-one | 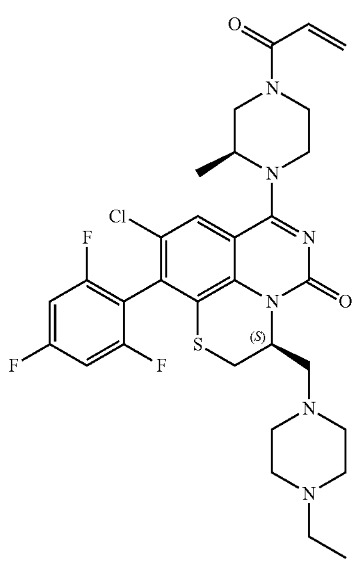 | 1H NMR (400 MHz, CDCl₃) δ 7.49 (s, 1H), 6.86-6.82 (m, 2H), 6.70-6.48 (m, 1H), 6.39-6.34 (m, 1H), 5.79-5.76 (m, 1H), 5.45-5.33 (m, 1H), 4.76-4.64 (m, 1H), 4.61-4.24 (m, 1.5H), 4.14-4.01 (m, 0.5H), 4.01-3.74 (m, 1H), 3.62-3.41 (m, 3H), 3.08-3.05 (m, 2H), 2.82-2.78 (m, 3H), 2.55-2.36 (m, 9H), 1.48-1.43 (m, 3H), 1.09-1.05 (m, 3H) | 647.2 |

-continued

Summary Table

| Ex. # | Name | Structure | ¹H NMR | MS (M + H)+ |
|---|---|---|---|---|
| 352 | (3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one | 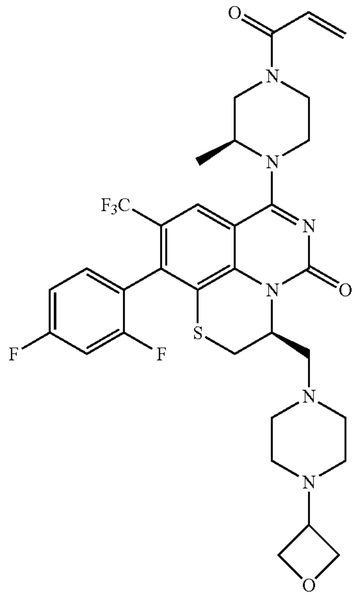 [SMILES: C=CC(=O)N1CCN(c2nc(=O)n3c4c(c(-c5ccc(F)cc5F)c(C(F)(F)F)cc24)SC[C@@H]3CN2CCN(C3COC3)CC2)[C@@H](C)C1] | 1H NMR (400 MHz, CDCl$_3$) δ 7.77 (s, 1H), 7.21-7.15 (m, 1H), 7.04-6.93 (m, 2H), 6.65-6.35 (m, 2H), 5.78 (d, J = 8.4 Hz, 1H), 5.33-5.30 (m, 1H), 4.69-4.42 (m, 7H), 3.80-3.40 (m, 6H), 3.08-2.99 (m, 2H), 2.88-2.74 (m, 3H), 2.58-2.53 (m, 3H), 2.31-2.17 (m, 3H), 1.49-1.48 (m, 3H). | 691.2 |
| 353 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one | 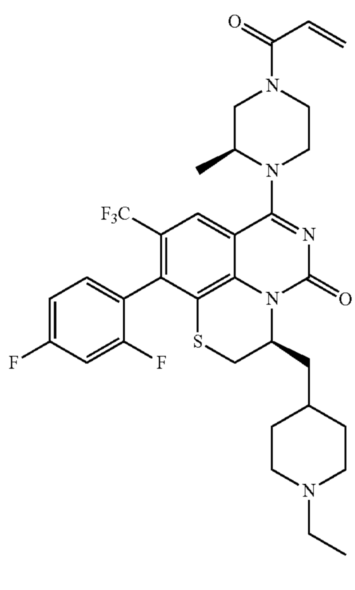 [SMILES: C=CC(=O)N1CCN(c2nc(=O)n3c4c(c(-c5ccc(F)cc5F)c(C(F)(F)F)cc24)SC[C@@H]3CC2CCN(CC)CC2)[C@@H](C)C1] | ¹H NMR (400 MHz, CDCl$_3$) δ 7.79 (s, 1H), 7.29-7.15 (m, 1H), 7.06-6.95 (m, 2H), 6.61-6.53 (m, 1H), 6.37 (d, J = 15.6 Hz, 1H), 5.78 (d, J = 6.0 Hz, 1H), 5.43-5.38 (m, 1H), 4.71-4.69 (m, 1H), 4.52-4.27 (m, 2H), 3.98-3.95 (m, 0.5H), 3.83-3.80 (m, 0.5H), 3.61-3.43 (m, 2H), 3.13-2.92 (m, 5H), 2.42 (q, J = 7.2 Hz, 2H), 2.01-1.90 (m, 3H), 1.78-1.72 (m, 3H), 1.52-1.32 (m, 6H), 1.09 (t, J = 7.2 Hz, 3H). | 662.2 |

Summary Table

| Ex. # | Name | Structure | ¹H NMR | MS (M + H)⁺ |
|---|---|---|---|---|
| 354 | (3S)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 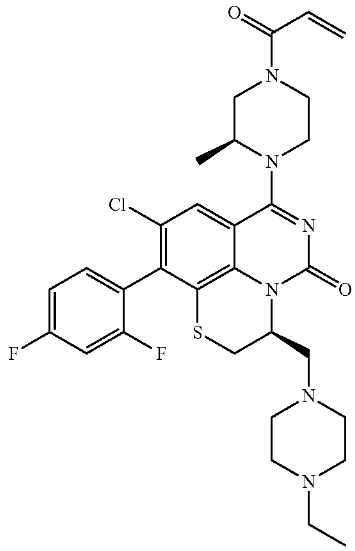 [SMILES: C=CC(=O)N1CCN(c2nc(=O)n3c4c(c(-c5ccc(F)cc5F)c(Cl)cc24)SC[C@@H]3CN2CCN(CC)CC2)[C@@H](C)C1] | ¹H NMR (400 MHz, CDCl₃) δ 7.48 (s, 1H), 7.24-7.18 (m, 1H), 7.07-6.95 (m, 2H), 6.67-6.52 (m, 1H), 6.36 (d, J = 16.8 Hz, 1H), 5.75 (d, J = 10.4 Hz, 1H), 5.41-5.28 (m, 1H), 4.74-4.66 (m, 1H), 4.56-4.54 (m, 0.5H), 4.48-4.35 (m, 1H), 4.22-4.16 (m, 0.5H), 3.99-3.77 (m, 1H), 3.59-3.39 (m, 3H), 3.09-3.00 (m, 2H), 2.84-2.76 (m, 3H), 2.55-2.35 (m, 9H), 1.48-1.43 (m, 3H), 1.08-1.04 (m, 3H). | 629.3 |
| 355 | (3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one | 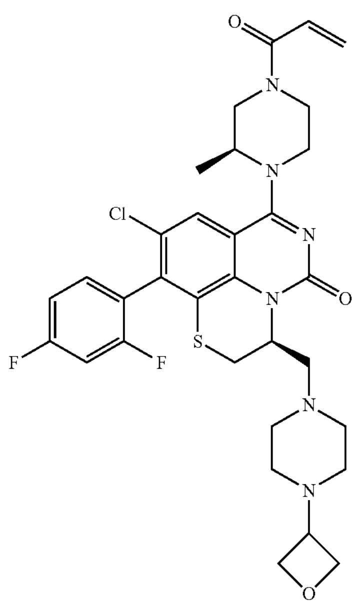 [SMILES: C=CC(=O)N1CCN(c2nc(=O)n3c4c(c(-c5ccc(F)cc5F)c(Cl)cc24)SC[C@@H]3CN2CCN(C3COC3)CC2)[C@@H](C)C1] | ¹H NMR (400 MHz, CDCl₃) δ 7.48 (s, 1H), 7.24-7.18 (m, 1H), 7.07-6.95 (m, 2H), 6.66-6.51 (m, 1H), 6.37 (d, J = 16.4 Hz, 1H), 5.77 (d, J = 10.8 Hz, 1H), 5.40-5.27 (m, 1H), 4.71-4.58 (m, 5.5H), 4.52-4.36 (m, 1H), 4.20 (s, 0.5H), 3.99-3.77 (m, 1H), 3.57-3.37 (m, 4H), 3.09-3.01 (m, 2H), 2.85-2.87 (m, 3H), 2.57-2.55 (m, 3H), 2.35-2.31 (m, 4H), 1.48-1.43 (m, 3H). | 657.3 |

Summary Table

| Ex. # | Name | Structure | ¹H NMR | MS (M + H)⁺ |
|---|---|---|---|---|
| 356 | (3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 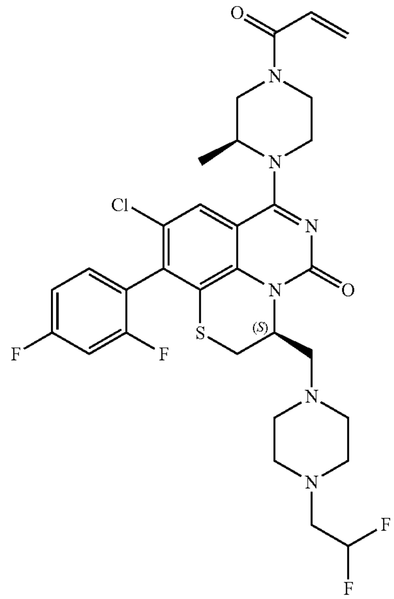 | ¹H NMR (400 MHz, CDCl₃) δ 7.48 (s, 1H), 7.24-7.18 (m, 1H), 7.07-6.95 (m, 2H), 6.66-6.51 (m, 1H), 6.36 (d, J = 16.8 Hz, 1H), 6.00-5.70 (m, 2H), 5.40-5.32 (m, 1H), 4.71-4.65 (m, 1H), 4.56-4.35 (m, 1.5H), 4.23-4.17 (m, 0.5H), 3.99-3.78 (m, 1H), 3.64-3.37 (m, 3H), 3.08-3.00 (m, 2H), 2.84-2.67 (m, 5H), 2.58-2.52 (m, 7H), 1.48-1.43 (m, 3H). | 665.3 |
| 19 | (3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one | 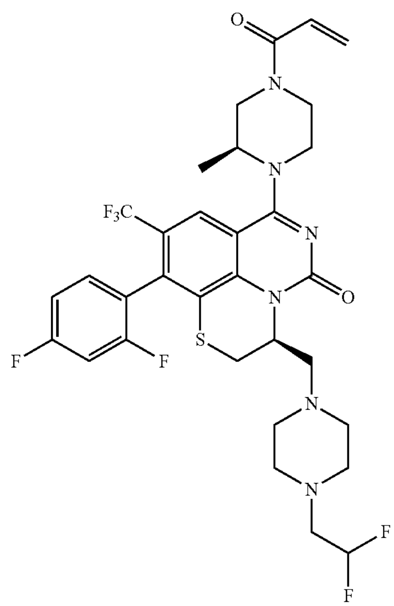 [SMILES: C=CC(=O)N1CCN(c2nc(=O)n3c4c(c(-c5ccc(F)cc5F)c(C(F)(F)F)cc24)SC[C@@H]3CN2CCN(CC(F)F)CC2)[C@@H](C)C1] | ¹H NMR (400 MHz, CDCl₃) δ 7.77 (s, 1H), 7.20-7.16 (m, 1H), 7.07-6.94 (m, 2H), 6.71-6.51 (m, 1H), 6.51-6.35 (m, 1H), 6.00-5.69 (m, 2H), 5.38-5.32 (m, 1H), 4.75-4.61 (m, 1H), 4.52-4.23 (m, 2H), 4.04-3.77 (m, 1H), 3.67-3.39 (m, 3H), 3.16-2.80 (m, 2H), 2.79-2.66 (m, 5H), 2.61-2.52 (m, 7H), 1.54-1.43 (m, 3H). | 699.6 |

Further Tricyclic Morpholine Examples

Q. General Information

¹H NMR spectra were recorded in either CDCl₃ or DMSO-d6 on either a BRUKER AVANCE III 400 MHz or BRUKER FOURIER 300 MHz. The internal standard used was either tetramethylsilane or the residual protonated solvent at 7.26 ppm for CDCl₃ or 2.50 ppm for DMSO-d6. Chemical shifts are reported in parts per million (ppm).

Abbreviations for NMR data are as follows: s=singlet, d=doublet, t=triplet, m=multiplet, br s=broad singlet, dd=doublet of doublets, dt=doublet of triplets, tt=triplet of triplets, ddd=doublet of doublet of doublets, sextuplet of d=sextuplet of doublets. J indicates the ¹H NMR coupling constant measured in Hertz.

Mass spectrum was recorded on a Waters ZQ mass spectrometer using alternative-scan positive and negative mode electrospray ionization. Cone voltage: 30V.

Syntheses of Intermediates

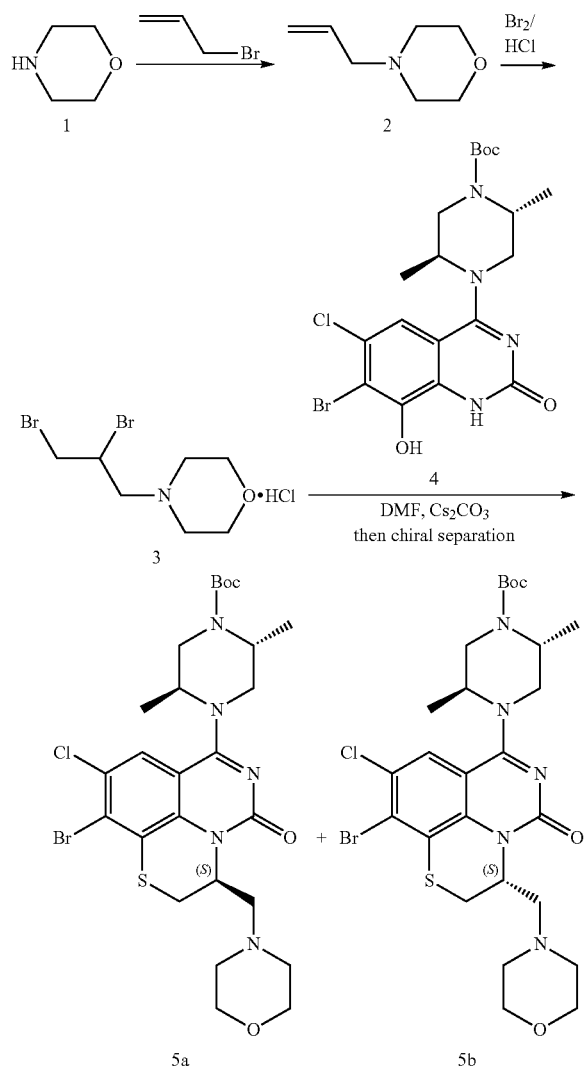

4-allylmorpholine (2)

To a solution of morpholine (72 g, 0.82 mol) in DCM (400 mL) was added 3-bromoprop-1-ene (20 g, 10.16 mol) dropwise at 0° C. The mixture was stirred at 0° C. for 10 min. The mixture was diluted with 1M NaOH, extracted with DCM. The combine organic layer was dried over $Na_2SO_4$, concentrated in vacuo at 35° C. The residue was purified by column chromatography on silica-gel (Petroleum Ether:EtOAc=5:1) to afford the title compound (12g, 94.35 mmol, 59% yield) as colorless oil. $^1$H NMR (400 MHz, $CDCl_3$) δ 5.90-5.80 (m, 1H), 5.22-5.15 (m, 2H), 3.73-3.71 (m, 4H), 3.0-2.98 (m, 2H), 2.45-2.44 (m, 4H).

4-(2,3-dibromopropyl)morpholine hydrochloride (3)

To a solution of 4-allylmorpholine (12 g, 94.35 mmol) in $H_2O$ (10 mL) was added 36% HCl (8.9 ml, 103 mmol). The reaction mixture was heated to 50° C. Then $Br_2$ (4.8 ml, 94.35 mmol) was added at such a rate that the temperature did not exceed 60° C. When the addition was completed, water was evaporated to dryness. Toluene was added, the mixture was concentrated to afford the title compound (14 g, 94.35 mmol, 100% yield) as orange oil. MS (ESI) m/z 288.1 $[M+H]^+$.

(2R,5S)-tert-butyl 4-((S)-10-bromo-9-chloro-3-(morpholinomethyl)-5-oxo-3,5-dihydro-2H-[1,4]oxazino[2,3,4-ij]quinazolin-7-yl)-2,5-dimethylpiperazine-1-carboxylate (5a) and (2R,5S)-tert-butyl 4-((R)-10-bromo-9-chloro-3-(morpholinomethyl)-5-oxo-3,5-dihydro-2H-[1,4]oxazino[2,3,4-ij]quinazolin-7-yl)-2,5-dimethylpiperazine-1-carboxylate (5b)

A mixture of (2R,5S)-tert-butyl 4-(7-bromo-6-chloro-2,8-dihydroxyquinazolin-4-yl)-2,5-dimethylpiperazine-1-carboxylate (2.5 g, 5.12 mmol), 4-(2,3-dibromopropyl)morpholine hydrochloride (11.6 g, 35.9 mmol) and $K_2CO_3$ (7.07 g, 51.2 mmol) in DMF (6 mL) was stirred at 90° C. overnight. The solvent was evaporated, and the residue was purified by silica gel chromatography (1% MeOH in DCM) to afford a racemic mixture. The separation was conducted with chiral Prep. HPLC (separation condition: Column: AD-H 5 μm 20×150 mm; Mobile Phase: HEP:IPA (0.1% DEA)=70:30 at 15 mL/min; Temp: 25° C.; Wavelength: 254 nm) to afford the title compounds: 5a (850 mg) and 5b (850 mg). MS (ESI) m/z 612.1 $[M+H]^+$.

Reaction Scheme

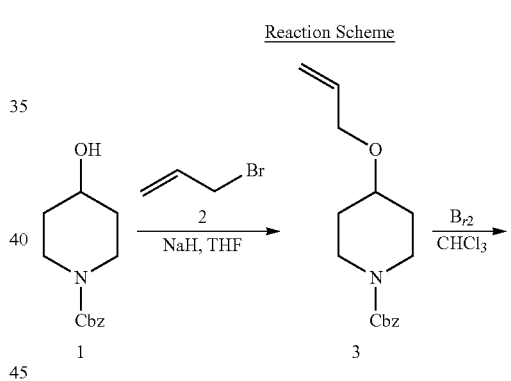

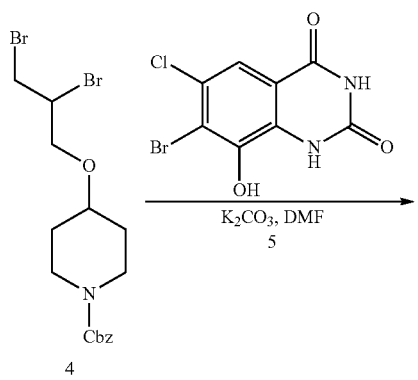

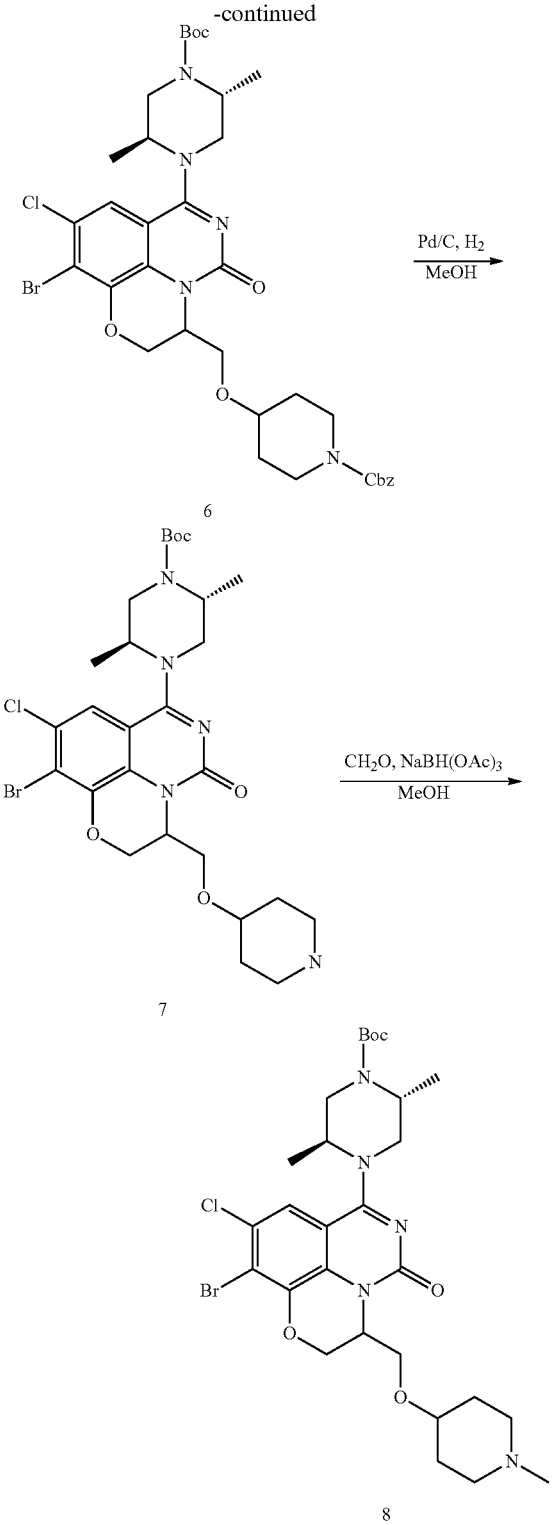

mixture was stirred at rt overnight. The mixture was quenched with NH₄Cl (aq) and extracted with EtOAc (500 mL). The organic phase was washed with brine (300 mL), concentrated to afford Compound (3) benzyl 4-(allyloxy) piperidine-1-carboxylate (30 g crude) as yellow oil.

LC-MS:m/z 276.2[M+H]⁺.

benzyl 4-(2,3-dibromopropoxy)piperidine-1-carboxylate (4)

To a mixture of benzyl 4-(allyloxy)piperidine-1-carboxylate (29.5 g, 01. mol) in CHCl₃ (200 mL) was added Br₂ (12.4 mL, 0.11 mol) slowly at 0° C. The mixture was stirred at 0° C. for 2 h. The reaction was quenched with Na₂S2O3 (aq), then extracted with DCM (300 mL). The organic phase was washed with brine (300 mL), dried and concentrated. The residue was purified by silica gel column (Petroleum Ether:EtOAc=10:1) to give the compound (4) (37.1 g, yield: 85%) as colorless oil.

LC-MS:m/z 433.9[M+H]⁺.

(2R,5S)-tert-butyl 4-(3-(((1-((benzyloxy)carbonyl)piperidin-4-yl)oxy)methyl)-10-bromo-9-chloro-5-oxo-3,5-dihydro-2H-[1,4]oxazino[2,3,4-ij]quinazolin-7-yl)-2,5-dimethylpiperazine-1-carboxylate (6)

To a mixture of compound (5) 7-bromo-6-chloro-8-hydroxyquinazoline-2,4(1H,3H)-dione (6 g, 12.3 mmol) and compound (4) (13.3 g, 30.7 mmol) in DMF (50 ml) at rt was added K₂CO₃ (6.8 g, 49.2 mmol). Then the mixture was heated at 90° C. for 24 h. After completion, the mixture was diluted with H₂O extracted with EtOAc, washed with water, brine and concentrated under reduced pressure. The residue was purified by column with using a mixture of DCM:MeOH (50:1) as eluent to afford the desired compound 6 (8.2 g, 84% yield) as a yellow oil.

LC-MS:m/z 760.1.[M+H]⁺.

(2R,5S)-tert-butyl 4-(10-bromo-9-chloro-5-oxo-3-((piperidin-4-yloxy)methyl)-3,5-dihydro-2H-[1,4]oxazino[2,3,4-ij]quinazolin-7-yl)-2,5-dimethylpiperazine-1-carboxylate (7)

To a mixture of compound (6) (2R,5S)-tert-butyl4-(3-(((1-((benzyloxy)carbonyl)piperidin-4-yl)oxy)methyl)-10-bromo-9-chloro-5-oxo-3,5-dihydro-2H-[1,4]oxazino[2,3,4-ij]quinazolin-7-yl)-2,5-dimethylpiperazine-1-carboxylate (530 mg, 0.668 mmol) in MeOH (7 ml) at rt was added Pd/C (160 mg). Then the mixture was stirred at rt for 3 h under H₂ atmosphere. After completion, the mixture was filtrated and purified by column with using a mixture of DCM:MeOH (40:1) as eluent to afford compound 7 (2R,5S)-tert-butyl 4-(10-bromo-9-chloro-5-oxo-3-((piperidin-4-yloxy)methyl)-3,5-dihydro-2H-[1,4]oxazino[2,3,4-ij]quinazolin-7-yl)-2,5-dimethylpiperazine-1-carboxylate (337 mg, yield: 77%) as a pale brown solid.

LC-MS: m/z 626.1[M+H]⁺.

(2R,5S)-tert-butyl 4-(10-bromo-9-chloro-3-(((1-methylpiperidin-4-yl)oxy)methyl)-5-oxo-3,5-dihydro-2H-[1,4]oxazino[2,3,4-ij]quinazolin-7-yl)-2,5-dimethylpiperazine-1-carboxylate (8)

To a mixture of compound (7) (2R,5S)-tert-butyl 4-(10-bromo-9-chloro-5-oxo-3-((piperidin-4-yloxy)methyl)-3,5-dihydro-2H-[1,4]oxazino[2,3,4-ij]quinazolin-7-yl)-2,5-dimethylpiperazine-1-carboxylate (337 mg, 0.511 mmol) and benzyl 4-(allyloxy)piperidine-1-carboxylate (3)

To a mixture of benzyl 4-hydroxypiperidine-1-carboxylate (23.5 g, 0.10 mol) in THF (200 mL) was added NaH (6.0 g, 0.15 mol) slowly at 0° C. The resulting mixture was stirred at 0° C. for 30 min, warmed to rt and stirred for 1 h. Then 3-bromoprop-1-ene (13.3 g, 0.11 mol) was added. The CH₂O (31 mg, 1.022 mmol) in MeOH (5 ml) was added NaBH(OAc)₃ (217 mg, 1.022 mmol) at rt. Then the mixture was stirred at rt for 1 h. After completion, the mixture was concentrated, and the residue was purified by column chromatography using a mixture of DCM:MeOH 30:1 (containing 5‰NH₃) to afford compound 8 (2R,5S)-tert-butyl 4-(10-bromo-9-chloro-3-(((1-methylpiperidin-4-yl)oxy)methyl)-5-oxo-3,5-dihydro-2H-[1,4]oxazino[2,3,4-ij]quinazolin-7-yl)-2,5-dimethylpiperazine-1-carboxylate (316 mg, yield: 92%) as a pale yellow solid. LC-MS:m/z 640.2 [M+H]⁺.

R. Example 245 and 246

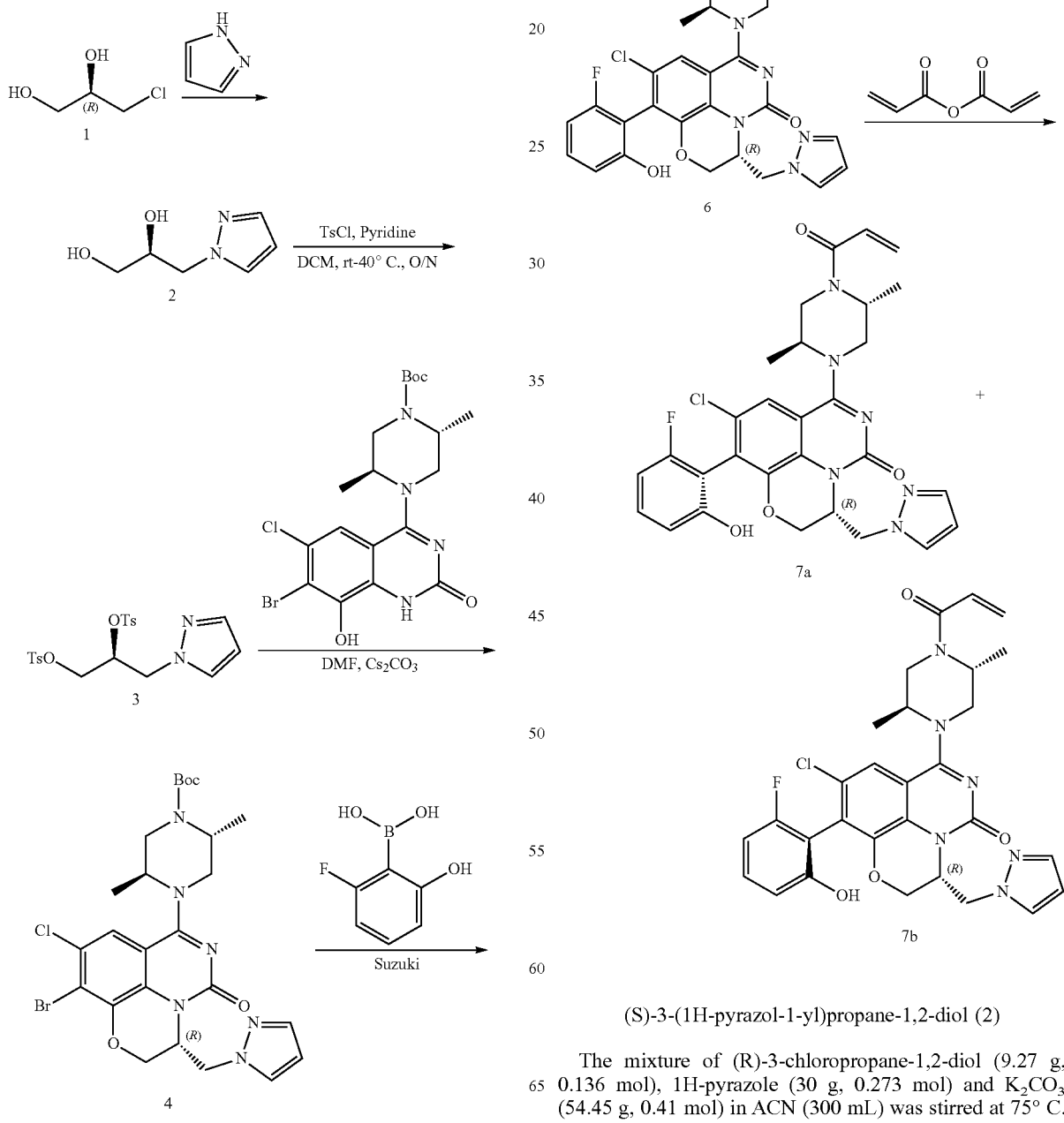

(S)-3-(1H-pyrazol-1-yl)propane-1,2-diol (2)

The mixture of (R)-3-chloropropane-1,2-diol (9.27 g, 0.136 mol), 1H-pyrazole (30 g, 0.273 mol) and K₂CO₃ (54.45 g, 0.41 mol) in ACN (300 mL) was stirred at 75° C. overnight. After filtration, the solvent was removed in vacuo. The residue was purified by silica gel column chromatography using a mixture of DCM:MeOH (30:1) to afford the title compound (7.85 g, 55.28 mmol, 40% yield) as white solid. 1H NMR (400 MHz, CDCl$_3$) δ 7.50 (s, 1H), 7.44 (s, 1H), 6.26-6.25 (m, 1H), 4.25-4.22 (m, 2H), 4.09-4.05 (m, 2H), 3.59-3.54 (m, 2H), 3.36 (s, 1H).

(S)-3-(1H-pyrazol-1-yl)propane-1,2-diyl bis(4-methylbenzenesulfonate) (3)

To a solution of (S)-3-(1H-pyrazol-1-yl)propane-1,2-diol (7.85 g, 55.28 mmol) in DCM (40 mL) was added pyridine (40 mL) and TsCl (31.5 g, 165 mmol) at 0° C. The mixture was stirred at rt overnight. The mixture was diluted with water, extracted with DCM, the combine organic layer was washed with brine, dried over Na$_2$SO$_4$ and concentrated in vacuo. The residue was purified by column chromatography on silica-gel (Petroleum Ether:EtOAc=2:1) to afford the title compound (20 g, 44.44 mmol, 80% yield) as colorless oil. $^1$H NMR (400 MHz, CDCl$_3$) δ 7.22-7.70 (m, 2H), 7.61-7.59 (m, 2H), 7.35-7.32 (m, 4H), 7.27-7.25 (m, 2H), 6.13-6.12 (m, 1H), 4.93-4.91 (m, 1H), 4.39-4.31 (m, 2H), 4.21-4.17 (m, 1H), 4.00-3.96 (m, 1H), 2.46-2.43 (m, 6H).

(2R,5S)-tert-butyl 4-((R)-3-((1H-pyrazol-1-yl)methyl)-10-bromo-9-chloro-5-oxo-3,5-dihydro-2H-[1,4]oxazino[2,3,4-ij]quinazolin-7-yl)-2,5-dimethylpiperazine-1-carboxylate (4)

A mixture of (2R,5S)-tert-butyl 4-(7-bromo-6-chloro-8-hydroxy-2-oxo-1,2-dihydroquinazolin-4-yl)-2,5-dimethylpiperazine-1-carboxylate (3 g, 6.69 mmol), 6(S)-3-(1H-pyrazol-1-yl)propane-1,2-diyl bis(4-methylbenzenesulfonate) (9 g, 20.8 mmol) and K$_2$CO$_3$ (2.77 g, 20.18 mmol) in DMF (30 mL) was stirred at 90° C. overnight. The mixture was diluted with water, extracted with EtOAc. The combine organic layer was washed with brine, dried over Na$_2$SO$_4$ and concentrated in vacuo. The residue was purified by silica-gel column chromatography (DCM:MeOH=50:1) to afford 1.5 g crude solid, which was further purified by column chromatography (DCM:MeOH=100:1) to afford the title compound (520 mg, 0.875 mmol, 12% yield) as yellow solid, MS (ESI) m/z 595.4 [M+H]$^+$.

(2R,5S)-tert-butyl 4-((3R)-3-((1H-pyrazol-1-yl)methyl)-9-chloro-10-(2-fluoro-6-hydroxyphenyl)-5-oxo-3,5-dihydro-2H-[1,4]oxazino[2,3,4-ij]quinazolin-7-yl)-2,5-dimethylpiperazine-1-carboxylate (5)

A mixture of (2R,5S)-tert-butyl 4-((R)-3-((1H-pyrazol-1-yl)methyl)-10-bromo-9-chloro-5-oxo-3,5-dihydro-2H-[1,4]oxazino[2,3,4-ij]quinazolin-7-yl)-2,5-dimethylpiperazine-1-carboxylate (300 mg, 0.5 mmol), (2-fluoro-6-hydroxyphenyl)boronic acid (236 mg, 1.5 mmol), Ruphos G2 (39 mg, 0.05 mmol) and K$_2$CO$_3$ (209 mg, 1.5 mmol) in dioxane/H$_2$O (5/1) (5 mL) was stirred at 90° C. under N$_2$ overnight. The mixture was concentrated in vacuo. The residue was purified by silica-gel column chromatography (DCM:MeOH=50:1) to afford a yellow solid, which was further purified by column chromatography on silica-gel (DCM:MeOH=80:1) to afford the title compound (250 mg, 0.4 mmol, 59% yield) as yellow solid. LC-MS: m/z 625.5 [M+H]$^+$.

(3R)-3-((1H-pyrazol-1-yl)methyl)-9-chloro-7-((2S,5R)-2,5-dimethylpiperazin-1-yl)-10-(2-fluoro-6-hydroxyphenyl)-2H-[1,4]oxazino[2,3,4-ij]quinazolin-5(3H)-one (6)

To a solution of (2R,5S)-tert-butyl 4-((3R)-3-((1H-pyrazol-1-yl)methyl)-9-chloro-10-(2-fluoro-6-hydroxyphenyl)-5-oxo-3,5-dihydro-2H-[1,4]oxazino[2,3,4-ij]quinazolin-7-yl)-2,5-dimethylpiperazine-1-carboxylate (250 mg, 0.4 mmol) in DCM (3 ml) was added TFA (1 ml). The mixture was stirred at rt for 2 hours. The mixture was concentrated in vacuo, adjust to pH=7-8 with NH$_3$·MeOH by NH$_3$·MeOH. The purification by silica-gel column chromatography (DCM:NH$_3$·MeOH=30:1) afforded the title compound (160 mg, 0.3 mmol, 76% yield) as yellow solid. LC-MS: m/z 525.2[M+H]$^+$.

(3R)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2H-[1,4]oxazino[2,3,4-ij]quinazolin-5(3H)-one (7)

To a solution of (3R)-3-((1H-pyrazol-1-yl)methyl)-9-chloro-7-((2S,5R)-2,5-dimethylpiperazin-1-yl)-10-(2-fluoro-6-hydroxyphenyl)-2H-[1,4]oxazino[2,3,4-ij]quinazolin-5(3H)-one (160 mg, 0.30 mmol) and Et$_3$N in dichloromethane (2 mL) was added acrylic anhydride (57.6 mg, 0.457 mmol). The mixture was stirred at rt for 2 hours. The mixture was concentrated in vacuo, and the residue was purified by silica-gel column chromatography (DCM:MeOH=30:1) to afford a yellow solid. The solid was purified by prep-Chiral to afford the product 7a (42.6 mg, 35.5% yield) as yellow solid. LC-MS: m/z 579.3 [M+H]$^+$. $^1$H NMR (400 MHz, CDCl$_3$) δ 7.42-7.41 (m, 1H), 7.36-7.29 (m, 2H), 7.18 (d, J=6 Hz, 1H), 6.89 (d, J=8 Hz, 1H), 6.76 (t, J=8.8 Hz, 1H), 6.65-6.48 (m, 1H), 6.37 (t, J=14.6 Hz, 1H), 6.06-6.05 (m, 1H), 5.77 (t, J=9.8 Hz, 1H), 5.02-5.00 (m, 1.5H), 4.79-4.73 (m, 2H), 4.56-4.38 (m, 3H), 4.33-4.30 (m, 1H, 4.19 (t, J=9.8 Hz, 1H), 3.65 (s, 1H), 3.67-3.51 (m, 1H), 3.18-3.14 (m, 0.5H), 1.50 (d, J=6.8 Hz, 2H), 1.42 (t, J=7.4 Hz, 4H).

and the product 7b (20 mg, 16% yield) as yellow solid. LC-MS: m/z 579.3 [M+H]$^+$. $^1$H NMR (400 MHz, CDCl$_3$) δ 7.52-7.51 (m, 1H), 7.49-7.48 (m, 2H), 7.32-7.28 (m, 1H), 6.81-6.75 (m, 2H), 6.63-6.51 (m, 1H), 6.38 (t, J=16.2 Hz, 1H), 6.25 (s, 1H), 5.79 (t, J=9.4 Hz, 1H), 5.00-4.81 (m, 3H), 4.53-4.31 (m, 4H), 4.19 (d, J=14 Hz, 0.5H), 4.02-3.97 (m, 1H), 3.75-3.66 (m, 2H), 3.31-3.27 (m, 0.5H), 1.47-1.36 (m, 6H).

S. Example 256

(3R)-7-((2S,5R)-4-acryloyl-2,5-dimethylpiperazin-1-yl)-9-chloro-10-(2,4-difluorophenyl)-3-((4-methylpiperazin-1-yl)methyl)-2H-[1,4]oxazino[2,3,4-ij]quinazolin-5(3H)-one Reaction Scheme

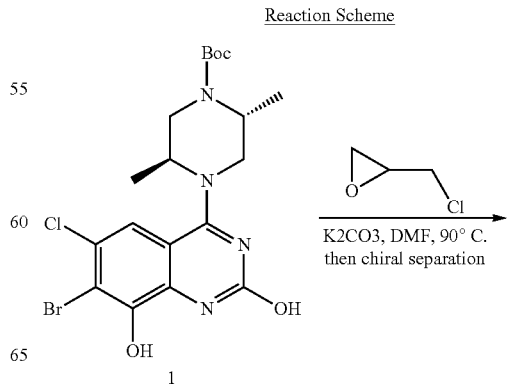

779
-continued
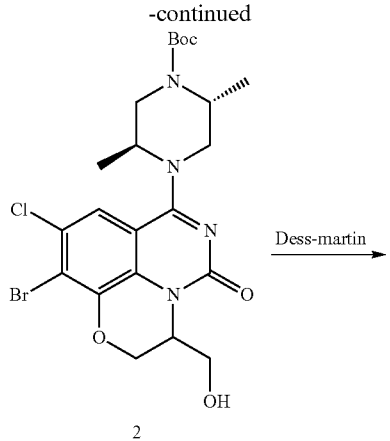
2
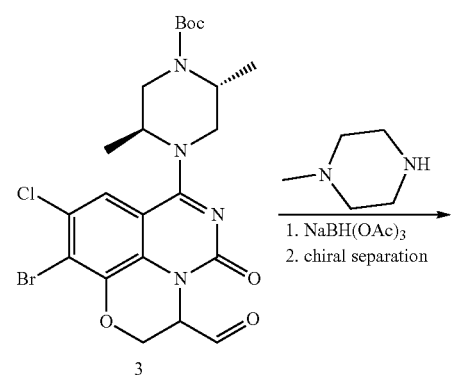
3
780
-continued
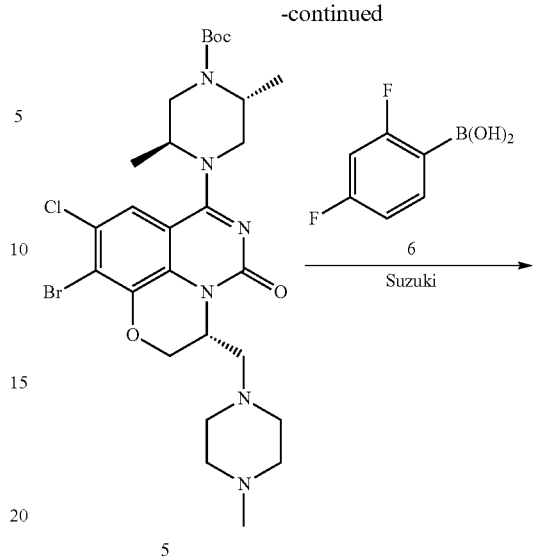
5
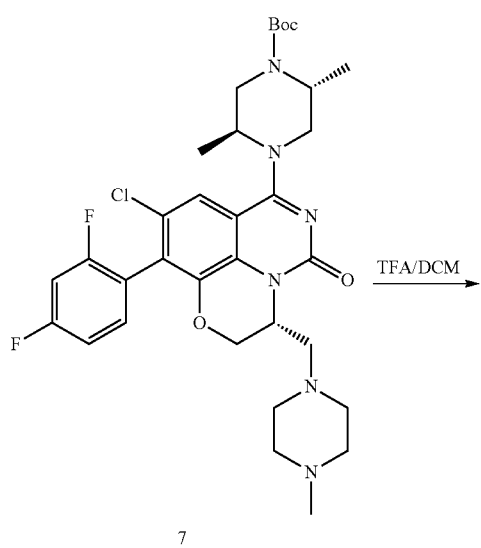
7
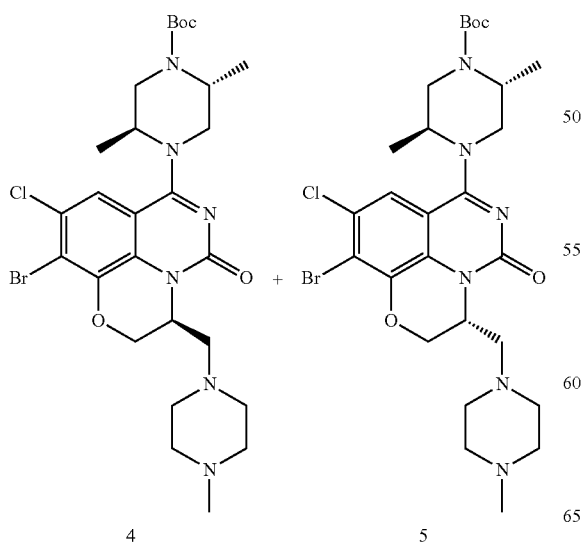
4     5
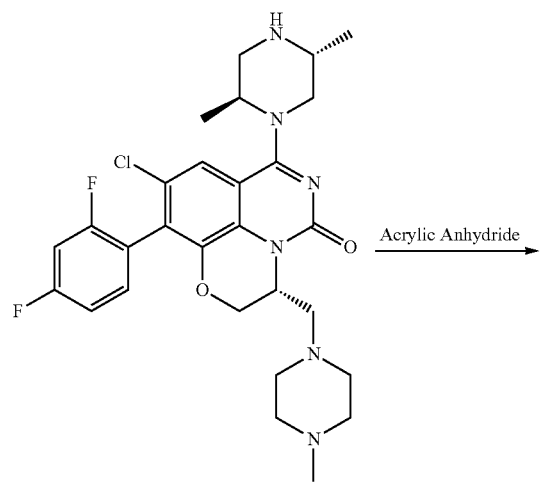
8

-continued

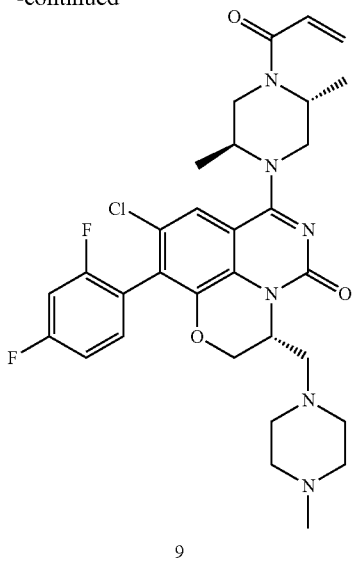

9

(2R,5S)-tert-butyl 4-(10-bromo-9-chloro-3-(hydroxymethyl)-5-oxo-3,5-dihydro-2H-[1,4]oxazino[2,3,4-ij]quinazolin-7-yl)-2,5-dimethylpiperazine-1-carboxylate (2)

A mixture of (2R,5S)-tert-butyl-4-(7-bromo-6-chloro-2,8-dihydroxyquinazolin-4-yl)-2,5-dimethylpiperazine-1-carboxylate (2 g, 4.09 mmol), 2-(chloromethyl)oxirane (3.8 g, 40.8 mmol) and K$_2$CO$_3$ (1.69 g, 12.29 mmol) in DMF (15 mL) was stirred at 90° C. overnight. The mixture was diluted with water and extracted with EtOAc (20 mL×2). The combined organic layer was washed with brine, dried over Na$_2$SO$_4$, and concentrated. The residue was purified by column chromatography on silica-gel (DCM:MeOH=100:1) to afford the title compound (1.5 g, 2.75 mmol, 67% yield) as yellow solid, MS (ESI) m z 545.4 [M+H]

(2R,5S)-tert-butyl4-(10-bromo-9-chloro-3-formyl-5-oxo-3,5-dihydro-2H-[1,4]oxazino[2,3,4-ij]quinazolin-7-yl)-2,5-dimethylpiperazine-1-carboxylate (3)

To a solution of (2R,5S)-tert-butyl 4-(10-bromo-9-chloro-3-(hydroxymethyl)-5-oxo-3,5-dihydro-2H-[1,4]oxazino[2,3,4-ij]quinazolin-7-yl)-2,5-dimethylpiperazine-1-carboxylate (2.8 g, 5.15 mmol) and 4A molecular sieve (5 g) in DCM (10 mL) was added Dess-Martin (2.62 g, 6.18 mmol). The mixture was stirred at rt for 1h. After filtration, the filtrate was concentrated. The residue was purified by silica column (DCM:EA=5:1) to afford the title compound (3.18 g, crude) as yellow solid. LC-MS: m/z 543.0 [M+H]$^+$.

(2R,5S)-tert-butyl 4-(10-bromo-9-chloro-3-((4-methylpiperazin-1-yl)methyl)-5-oxo-3,5-dihydro-2H-[1,4]oxazino[2,3,4-ij]quinazolin-7-yl)-2,5-dimethylpiperazine-1-carboxylate (5)

To a solution of (2R,5S)-tert-butyl 4-(10-bromo-9-chloro-3-formyl-5-oxo-3,5-dihydro-2H-[1,4]oxazino[2,3,4-ij]quinazolin-7-yl)-2,5-dimethylpiperazine-1-carboxylate (1.06 g, 1.95 mmol) and 1-methylpiperazine (390.6 mg, 3.9 mmol) in DCM (10 mL) was added NaBH(OAc)$_3$ (826.6 mg, 3.9 mmol). The mixture was stirred at rt under N$_2$ for 1h. Then the mixture was concentrated, and the residue was purified by silica column (DCM:NH$_3$-MeOH=40:1) to afford (2R, 5S)-tert-butyl 4-(10-bromo-9-chloro-3-((4-methylpiperazin-1-yl)methyl)-5-oxo-3,5-dihydro-2H-[1,4]oxazino[2,3,4-ij] quinazolin-7-yl)-2,5-dimethylpiperazine-1-carboxylate (850 mg, 1.36 mmol) as brown solid.

The racemic product of (2R,5S)-tert-butyl 4-(10-bromo-9-chloro-3-((4-methylpiperazin-1-yl)methyl)-5-oxo-3,5-dihydro-2H-[1,4]oxazino[2,3,4-ij]quinazolin-7-yl)-2,5-dimethylpiperazine-1-carboxylate (850 mg, 1.36 mmol) was separated by chiral Prep. HPLC (separation condition: Column: AD-H 5 µm 20×150 mm; Mobile Phase: HEP:IPA (0.1% DEA)=60:40 at 15 mL/min; Temp: 25° C.; Wavelength: 254 nm) to afford the title compound (2R,5S)-tert-butyl 4-((R)-10-bromo-9-chloro-3-((4-methylpiperazin-1-yl)methyl)-5-oxo-3,5-dihydro-2H-[1,4]oxazino[2,3,4-ij] quinazolin-7-yl)-2,5-dimethylpiperazine-1-carboxylate (440 mg, 52% yield, 100% ee), and (2R,5S)-tert-butyl 4-((S)-10-bromo-9-chloro-3-((4-methylpiperazin-1-yl)methyl)-5-oxo-3,5-dihydro-2H-[1,4]oxazino[2,3,4-ij]quinazolin-7-yl)-2,5-dimethylpiperazine-1-carboxylate (310 mg, 36% yield, 99% ee); Chiral HPLC Analytical: on AD-H was using 4.6×150 mm column, Mobile Phase: HEP:IPA (0.1% DEA)=60:40 at 0.5 mL/min; Temp: 25° C.; Wavelength: 254 nm).

(2R,5S)-tert-butyl-((3R)-9-chloro-10-(2,4-difluorophenyl)-3-((4-methylpiperazin-1-yl)methyl)-5-oxo-3,5-dihydro-2H-[1,4]oxazino[2,3,4-ij]quinazolin-7-yl)-2,5-dimethylpiperazine-1-carboxylate (7)

A mixture of (2R,5S)-tert-butyl 4-((R)-10-bromo-9-chloro-3-((4-methylpiperazin-1-yl)methyl)-5-oxo-3,5-dihydro-2H-[1,4]oxazino[2,3,4-ij]quinazolin-7-yl)-2,5-dimethylpiperazine-1-carboxylate (100 mg, 0.16 mmol), (2,4-difluorophenyl)boronic acid (60 mg, 0.38 mmol), K$_3$PO$_4$ (102 mg, 0.48 mmol), Pd(dppf)Cl$_2$ (13 mg, 0.016 mmol) and dioxane/H$_2$O (4 mL/0.5 mL) was stirred at 80° C. under N$_2$ overnight. The mixture was concentrated under reduced pressure and the residue was purified by silica column (DCM:MeOH=40:1) to afford the title compound (64 mg, 61% yield) as brown solid. LC-MS: m/z 659.2 [M+H]$^+$.

(3R)-9-chloro-10-(2,4-difluorophenyl)-7-((2S,5R)-2,5-dimethylpiperazin-1-yl)-3-((4-methylpiperazin-1-yl)methyl)-2H-[1,4]oxazino[2,3,4-ij]quinazolin-5(3H)-one (8)

To a solution of (2R,5S)-tert-butyl 4-((3R)-9-chloro-10-(2,4-difluorophenyl)-3-((4-methylpiperazin-1-yl)methyl)-5-oxo-3,5-dihydro-2H-[1,4]oxazino[2,3,4-ij]quinazolin-7-yl)-2,5-dimethylpiperazine-1-carboxylate (64 mg, 0.097 mmol) in DCM (2 mL) was added TFA (1 mL). The mixture was stirred at rt for 2 h. The mixture was concentrated under reduced pressure and adjusted to pH=7-8 with NH$_3$·MeOH. The solvent was removed in vacuo, and the residue was purified by silica column (DCM:MeOH=20:1) to afford the title compound (55 mg, crude) as brown solid. LC-MS: m/z 559.5 [M+H]$^+$.

(3R)-7-((2S,5R)-4-acryloyl-2,5-dimethylpiperazin-1-yl)-9-chloro-10-(2,4-difluorophenyl)-3-((4-methylpiperazin-1-yl)methyl)-2H-[1,4]oxazino[2,3,4-ij]quinazolin-5(3H)-one (9)

To a solution of (3R)-9-chloro-10-(2,4-difluorophenyl)-7-((2S,5R)-2,5-dimethylpiperazin-1-yl)-3-((4-methylpiperazin-1-yl)methyl)-2H-[1,4]oxazino[2,3,4-ij]quinazolin-5

(3H)-one (55 mg, 0.10 mmol) and TEA (20 mg, 0.20 mmol) in DCM (4 mL) was added acrylic anhydride (19 mg, 0.15 mmol) at 0° C. The mixture was stirred at rt for 1 h. After concentration, the residue was purified by prep-HPLC with 30-95% ACN in $H_2O$ to afford the title compound (28 mg, 47% yield) as white solid. LC-MS: m/z 613.2 [M+H]$^+$. $^1$H NMR (400 MHz, CDCl$_3$) δ 7.42-7.38 (m, 1H), 7.30-7.28 (m, 1H), 7.04-6.93 (m, 2H), 6.66-6.51 (m, 1H), 6.37 (t, J=15.6 Hz, 1H), 5.77 (t, J=7.2 Hz, 1H), 5.05-4.84 (m, 1H), 4.79-4.67 (m, 2H), 4.41-4.25 (m, 1H), 4.09-3.80 (m, 4H), 3.68-3.65 (m, 0.6H), 3.55-3.51 (m, 0.4H), 2.85-2.66 (m, 2H), 2.62-2.40 (m, 8H), 2.26 (d, J=2.4 Hz, 3H), 1.35-1.21 (m, 6H).

The following compounds were prepared using similar synthetic procedures and their characterization is provided below in the Summary Table below.

Summary Table

| Ex. | Name | Structure | $^1$H NMR | MS (M + H)$^+$ |
|---|---|---|---|---|
| 202 | (3S-7-((2S,5R)-4-acryloyl-2,5-dimethylpiperazin-1-yl)-9-chloro-10-(2,4-difluorophenyl)-3-((3,3-difluoropyrrolidin-1-yl)methyl)-2H-[1,4]oxazino[2,3,4-ij]quinazolin-5(3H)-one | 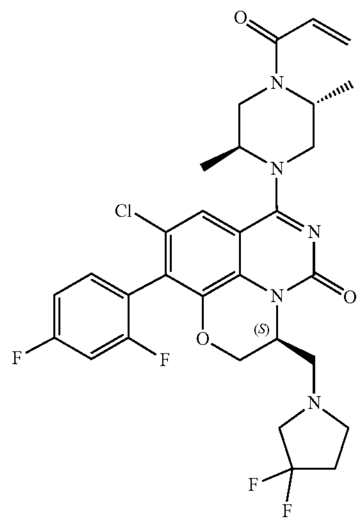 | $^1$H NMR (400 MHz, CDCl$_3$) δ 7.46-44 (m, 1H), 7.24-7.22 (m, 1H), 7.01-6.95 (m, 2H), 6.67-6.50 (m, 1H), 6.41-6.33 (m, 1H), 5.59-5.55 (m, 1H), 4.97 (s, 1H), 4.83-4.78 (m, 1H), 4.58-4.01 (m, 5H), 3.92-3.77 (m, 2H), 3.68-3.49 (m, 1H), 3.26-3.15 (m, 1H), 3.11-2.96 (m, 3H), 2.86-2.73 (m, 1H), 2.31-2.19 (m, 2H),, 1.34-1.32 (m, 3H), 1.24-1.22(m, 3H). | 620.2 |
| 203 | (3S)-7-((2S,5R)-4-acryloyl-2,5-dimethylpiperazin-1-yl)-9-chloro-10-(2,4-difluorophenyl)-3-(morpholinomethyl)-2H-[1,4]oxazino[2,3,4-ij]quinazolin-5(3H)-one | 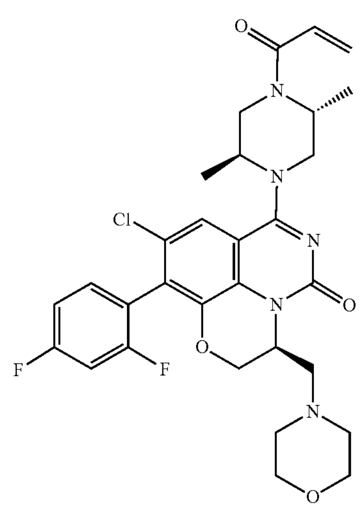 [SMILES: C=CC(=O)N1C[C@H](C)N(c2nc(=O)n3c4c(c(-c5ccc(F)cc5F)c(Cl)cc24)OC[C@@H]3CN2CCOCC2)C[C@H]1C] | $^1$H NMR (400 MHz, CDCl$_3$) δ 7.42-7.39 (m, 1H), 7.30-7.26 (m, 1H), 7.04-6.93 (m, 2H), 6.65-6.51 (m, 1H), 6.37 (t, J = 16.0 Hz, 1H), 5.77 (d, J = 8.0 Hz, 1H), 5.03-4.95 (m, 1.5H), 4.80-4.71 (m, 2H), 4.39-4.26 (m, 1H), 4.05-4.00 (m, 1.5H), 3.93-3.84 (m, 2H), 3.70-3.52 (m, 5H), 2.76-2.67 (m, 2H), 2.60-2.45 (m, 4H), 1.35-1.20 (m, 6H). | 600.2 |

Summary Table

| Ex. | Name | Structure | ¹H NMR | MS (M + H)⁺ |
|---|---|---|---|---|
| 204 | (3R)-7-((2S,5R)-4-acryloyl-2,5-dimethylpiperazin-1-yl)-9-chloro-10-(2,4-difluorophenyl)-3-(morpholinomethyl)-2H-[1,4]oxazino[2,3,4-ij]quinazolin-5(3H)-one | 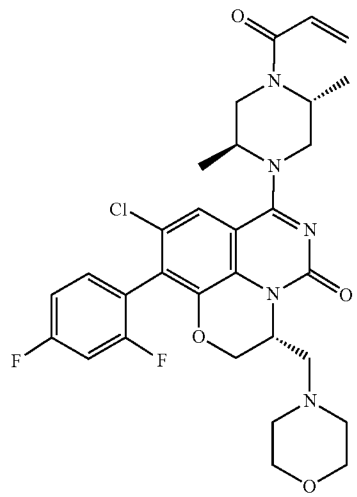 [SMILES: C=CC(=O)N1C[C@H](C)N(c2nc(=O)n3c4c(c(-c5ccc(F)cc5F)c(Cl)cc24)OC[C@H]3CN2CCOCC2)C[C@H]1C] | ¹H NMR (400 MHz, CDCl₃) δ 7.44 (s, 1H), 7.33-7.22 (m, 1H), 7.04-6.94 (m, 2H), 6.66-6.51 (m, 1H), 6.37 (t, J = 16.0 Hz, 1H), 5.77 (d, J = 8.0 Hz, 1H), 4.94-4.90 (m, 1H), 4.81-4.70 (m, 2.5 H), 4.40-4.27 (m, 1.4 H), 4.10-3.95 (m, 1.6H), 3.83-3.65 (m, 6.5H), 2.67-2.66 (m, 2H), 2.55-2.50 (m, 4H), 1.44-1.28 (m, 6H). | 600.2 |
| 205 | (3S)-7-((2S,5R)-4-acryloyl-2,5-dimethylpiperazin-1-yl)-9-chloro-10-(5-chloro-2-fluorophenyl)-3-((3,3-difluoropyrrolidin-1-yl)methyl)-2H-[1,4]oxazino[2,3,4-ij]quinazolin-5(3H)-one | 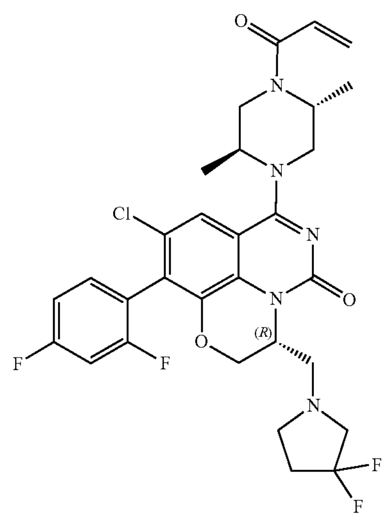 | ¹H NMR (400 MHz, CDCl₃) δ 7.46-7.38 (m, 2H), 7.25-7.22 (m, 1H), 7.16-7.12 (m, 1H), 6.65-6.49 (m, 1H), 6.37 (t, J = 15.2 Hz, 1H), 5.79-5.74 (m, 1H), 4.97-4.96 (m, 1H), 4.84-4.77 (m, 1H), 4.57-4.44 (m, 1H), 4.37-4.21 (m, 3H), 4.14-3.99 (m, 1H), 3.89-3.77 (m, 2H), 3.68-3.47 (m, 1H), 3.27-3.16 (m, 1H), 3.12-2.99 (m, 3H), 2.86-2.74 (m, 1H), 2.30-2.19 (m, 2H), 1.34-1.23 (m, 6H). | 636.2 |
| 207 | (3R)-7-((2S,5R)-4-acryloyl-2,5-dimethylpiperazin-1-yl)-9-chloro-10-(2,4-difluorophenyl)-3-((3,3-difluoropyrrolidin-1-yl)methyl)-2H-[1,4]oxazino[2,3,4-ij]quinazolin-5(3H)-one | 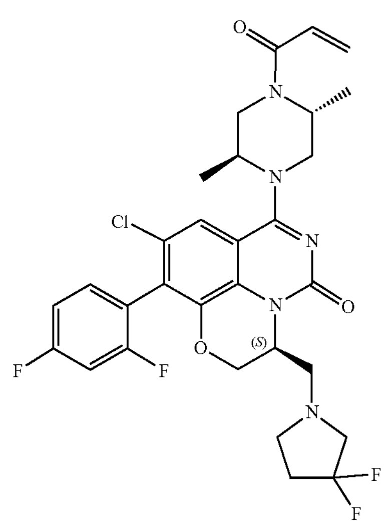 | ¹H NMR (400 MHz, CDCl₃) δ 7.50-7.49 (m, 1H), 7.25-7.22 (m, 1H), 7.03-6.93 (m, 2H), 6.69-6.51 (m, 1H), 6.41-6.34 (m, 1H), 5.80-5.75 (m, 1H), 5.00-4.62 (m, 3H), 4.38-3.96 (m, 5H), 3.81-3.66 (m, 2H), 3.23-2.96 (m, 4H), 2.86-2.75 (m, 1H), 2.31-2.22 (m, 2H), 1.43-1.33 (m, 6H). | 620.2 |

-continued

Summary Table

| Ex. | Name | Structure | ¹H NMR | MS (M + H)⁺ |
|---|---|---|---|---|
| 208 | (3R,10R)-7-((2S,5R)-4-acryloyl-2,5-dimethylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one | 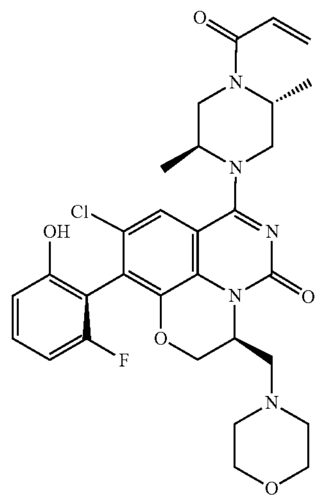 | ¹H NMR (400 MHz, CDCl₃) δ 7.44-7.43 (m, 1H), 7.34-7.26 (m, 1H), 6.83-6.77 (m, 2H), 6.65-6.50 (m, 1H), 6.37 (t, J = 16.0 Hz, 1H), 6.11-6.05 (m, 1H), 5.77 (d, J = 8.0 Hz, 1H), 4.99-4.73 (m, 3.5H), 4.31-4.28 (m, 1H), 4.13-3.95 (m, 2H), 3.88-3.49 (m, 6.5H), 2.67-2.66 (m, 2H), 2.59-2.47 (m, 4H), 1.33-1.23 (m, 6H). | 598.3 |
| 209 | (3R,10S)-7-((2S,5R)-4-acryloyl-2,5-dimethylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one | 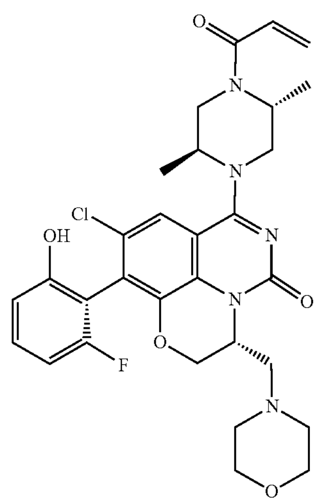 | ¹H NMR (400 MHz, CDCl₃) δ 7.46 (s, 1H), 7.34-7.26 (m, 1H), 6.85-6.77 (m, 2H), 6.64-6.51 (m, 1H), 6.39 (t, J = 16.0 Hz, 1H), 6.11-6.05 (m, 1H), 5.80-5.77 (m, 1H), 5.02-4.96 (m, 1H), 4.81-4.73 (m, 2.5H), 4.36-4.27 (m, 1H), 4.11-4.00 (m, 1.5H), 3.82-3.36 (m, 7H), 2.66-2.65 (m, 2H), 2.59-2.50 (m, 4H), 1.39-1.25 (m, 6H). | 598.3 |
| 210 | (3R,10R)-7-((2S,5R)-4-acryloyl-2,5-dimethylpiperazin-1-yl)-9-chloro-10-(2-fluoro-6-hydroxyphenyl)-3-(morpholinomethyl)-2,3-dihydro-5H-[1,4]oxazino[2,3,4-ij]quinazolin-5-one | 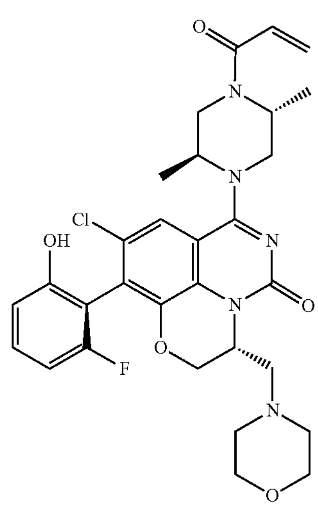 | ¹H NMR (400 MHz, CDCl₃) δ 7.46 (s, 1H), 7.34-7.26 (m, 1H), 6.85-6.77 (m, 2H), 6.64-6.51 (m, 1H), 6.39 (t, J = 16.0 Hz, 1H), 6.11-6.05 (m, 1H), 5.80-5.77 (m, 1H), 5.02-4.96 (m, 1H), 4.81-4.73 (m, 2.5H), 4.36-4.27 (m, 1H), 4.11-4.00 (m, 1.5H), 3.82-3.36 (m, 7H), 2.66-2.65 (m, 2H), 2.59-2.50 (m, 4H), 1.39-1.25 (m, 6H). | |

-continued

Summary Table

| Ex. | Name | Structure | ¹H NMR | MS (M + H)⁺ |
|---|---|---|---|---|
| 212 | (3R)-7-((2S,5R)-4-acryloyl-2,5-dimethylpiperazin-1-yl)-9-chloro-10-(5-chloro-2-fluorophenyl)-3-(morpholinomethyl)-2H-[1,4]oxazino[2,3,4-ij]quinazolin-5(3H)-one | 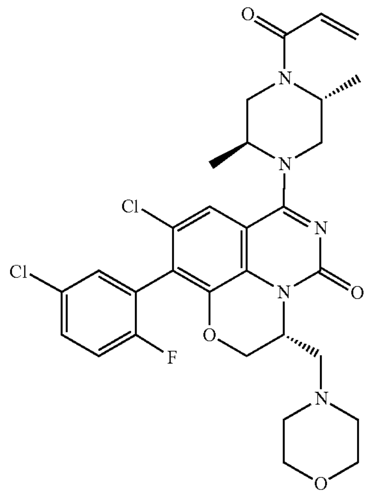 [SMILES: C=CC(=O)N1C[C@H](C)N(c2nc(=O)n3c4c(c(-c5cc(Cl)ccc5F)c(Cl)cc24)OC[C@H]3CN2CCOCC2)C[C@H]1C] | ¹H NMR (400 MHz, CDCl₃) δ 7.43-7.40 (m, 2H), 7.32-7.30 (m, 1H), 7.17-7.13 (m, 1H), 6.63-6.51 (m, 1H), 6.37 (t, J = 16.0 Hz, 1H), 5.78 (t, J = 16.0 Hz, 1H). 5.00-4.70 (m, 3.5H), 4.40-4.31 (m, 1.5H), 4.10-3.98 (m, 1.5H), 3.83-3.61 (m, 6H), 3.37-3.36 (m, 0.5 H), 2.67-2.66 (m, 2H), 2.55-2.53 (m, 4H), 1.44-1.25 (m, 6H). | 616.2 |
| 213 | (3R)-7-((2S,5R)-4-acryloyl-2,5-dimethylpiperazin-1-yl)-9-chloro-10-(2,4-difluorophenyl)-3-(2-morpholinoethyl)-2H-[1,4]oxazino[2,3,4-ij]quinazolin-5(3H)-one | 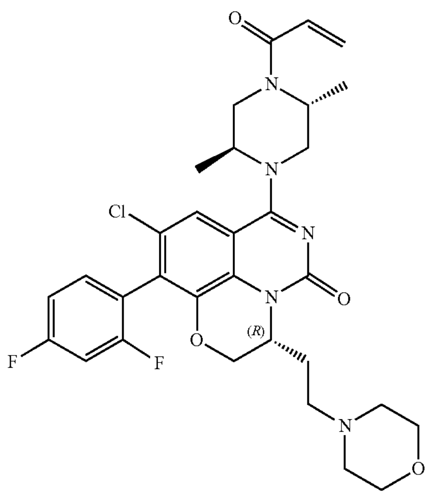 | ¹H NMR (400 MHz, CDCl₃) δ 7.45 (s, 1H), 7.31-7.23 (m, 1H), 7.03-6.93 (m, 2H), 6.67-6.52 (m, 1H), 6.37 (t, J = 15.2 Hz, 1H), 5.77 (t, J = 8.0 Hz, 1H), 5.02 (s, 0.5H), 4.89-4.78 (m, 2H), 4.60-4.49 (m, 1H), 4.41-4.32 (m, 1H), 4.15-4.03 (m, 1.5H), 3.79-3.65 (m, 6.5H), 3.34-3.30 (m, 0.5H), 2.50-2.35 (m, 6H), 2.04-1.81 (m, 2H), 1.45-1.33 (m, 6H). | 614.2 |
| 227 | (3R,10R)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one | 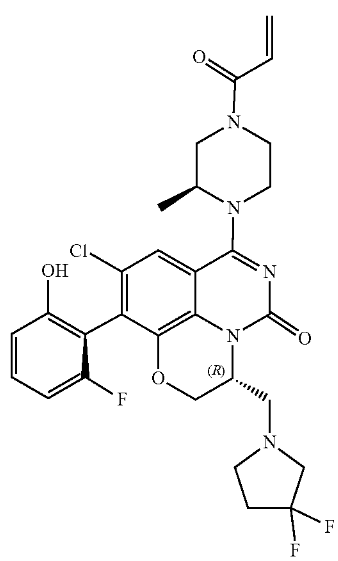 | ¹H NMR (400 MHz, CDCl₃) δ 7.42 (s, 1H), 7.29-7.23 (m, 1H), 6.89-6.84 (m, 1H), 6.74 (t, J = 8.4 Hz, 1H), 6.65-6.49 (m, 1H), 6.42-6.34 (m, 1H), 5.83-5.71 (m, 1H), 4.75-4.18 (m, 7.5H), 3.93-3.76 (m, 1H), 3.57-3.38 (m, 1H), 3.15-2.92 (m, 5.5H), 2.73 (s, 1H), 2.19 (s, 2H), 1.44-1.39 (m, 3H). | 604.2 |

-continued

Summary Table

| Ex. | Name | Structure | ¹H NMR | MS (M + H)⁺ |
|---|---|---|---|---|
| 228 | (3S,10S)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one | 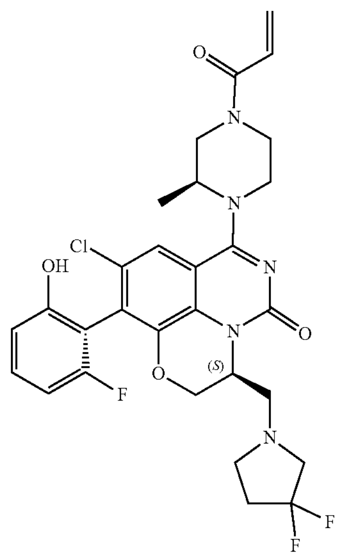 | ¹H NMR (400 MHz, CDCl₃) δ 7.39 (s, 1H), 7.30-7.23 (m, 1H), 6.86 (d, J = 8.4 Hz, 1H), 6.74 (t, J = 8.4 Hz, 1H), 6.64-6.49 (m, 1H), 6.38-6.31 (m, 1H), 5.78 (d, J = 10.4 Hz, 1H), 4.71-4.56 (m, 2.5H), 4.40-4.09 (m, 4.5H), 3.94-3.73 (m, 1H), 3.54-3.38 (m, 2H), 3.13-2.90 (m, 5H), 2.77-2.72 (m, 1H), 2.27-2.17 (m, 2H), 1.45-1.41 (m, 3H). | 604.2 |
| 229 | (3S,10R)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one | 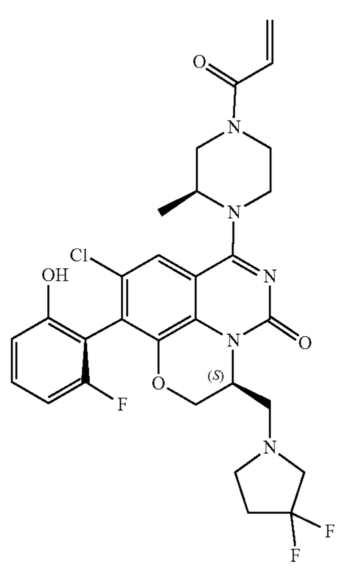 | ¹H NMR (400 MHz, CDCl₃) δ 7.42 (s, 1H), 7.30-7.24 (m, 1H), 6.84 (d, J = 8.0 Hz, 1H), 6.75 (t, J = 8.4 Hz, 1H), 6.63-6.53 (m, 1H), 6.39-6.35 (m, 1H), 5.78 (d, J = 10.4 Hz, 1H), 4.95 (s, 0.5H), 4.73-4.60 (m, 2H), 4.45-3.91 (m, 5H), 3.78-3.36 (m, 3H), 3.14-2.92 (m, 5H), 2.77-2.75 (m, 1H), 2.26-2.19 (m, 2H), 1.34-133 (m, 3H). | 604.2 |

-continued

Summary Table

| Ex. | Name | Structure | $^1$H NMR | MS (M + H)$^+$ |
|---|---|---|---|---|
| 230 | (3R,10S)-7-((S)-4-acryloyl-2-methylpiperazin-1-yl)-9-chloro-3-((3,3-difluoropyrrolidin-1-yl)methyl)-10-(2-fluoro-6-hydroxyphenyl)-2,3-dihydro-5H-[1,4]oxazino[2,3,4-ij]quinazolin-5-one | 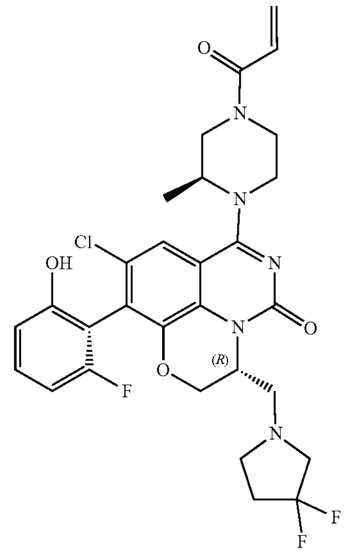 | $^1$H NMR (400 MHz, CDCl$_3$) δ 7.43 (s, 1H), 7.29-7.23 (m, 1H), 6.83 (d, J = 8.4 Hz, 1H), 6.74 (t, J = 8.4 Hz, 1H), 6.64-6.52 (m ,1H), 6.43-6.34 (m, 1H), 5.82-5.76 (m, 1H), 4.95 (s, 0.5H), 4.71 (s, 0.5H), 4.58-4.43 (m, 3H), 4.28-4.17 (m, 2.5H), 4.11-3.93 (m, 1H), 3.78-3.60 (m, 2H), 3.51-3.37 (m, 1H), 3.18-2.91 (m, 5H), 2.77-2.75 (m, 1H), 2.25-2.18 (m, 2H), 1.34-1.33 (m, 3H). | 604.2 |
| 232 | (3S)-7-((2S,5R)-4-acryloyl-2,5-dimethylpiperazin-1-yl)-3-(azetidin-1-ylmethyl)-9-chloro-10-(2,4-difluorophenyl)-2H-[1,4]oxazino[2,3,4-ij]quinazolin-5(3H)-one | 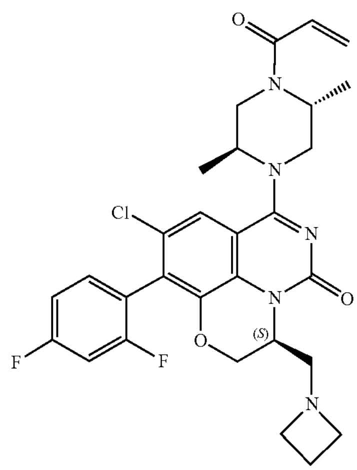 | $^1$H NMR (400 MHz, CDCl$_3$) δ 7.43 (s, 1H), 7.33-7.20 (m, 1H), 7.03-6.93 (m, 2H), 6.67-6.51 (m, 1H), 6.37 (t, J = 16 Hz, 1H), 5.78 (t, J = 8.4 Hz, 1H), 5.02-4.91 (m, 1H), 4.81-4.78 (m, 0.5H), 4.68-4.54 (m, 2H), 4.41-4.30 (m, 1H), 4.13-4.09 (m, 0.5H), 3.96-3.91 (m, 1H), 3.82-3.66 (m, 2H), 3.33-3.28 (m, 3H), 2.66-2.65 (m, 2H), 2.10-2.05 (m, 2H), 1.43-1.31 (m, 6H). | 570.2 |
| 233 | (3R)-7-((2S,5R)-4-acryloyl-2,5-dimethylpiperazin-1-yl)-3-(azetidin-1-ylmethyl)-9-chloro-10-(2,4-difluorophenyl)-2H-[1,4]oxazino[2,3,4-ij]quinazolin-5(3H)-one | 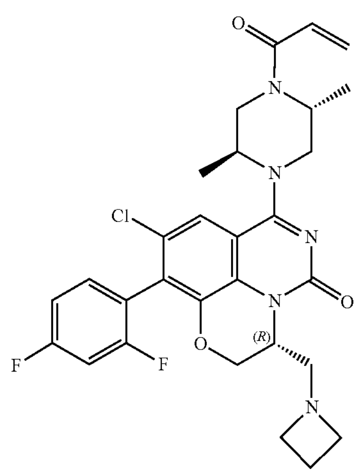 | $^1$H NMR (400 MHz, CDCl$_3$) δ 7.41-7.38 (m, 1H), 7.33-7.21 (m, 1H), 7.02-6.92 (m, 2H), 6.63-6.51 (m, 1H), 6.37 (t, J = 16.4 Hz, 1H), 5.77 (t, J = 6.4 Hz, 1H), 5.02-4.89 (m, 1.5H), 4.72-4.69 (m, 1H), 4.54-4.53 (m, 1H), 4.32-4.30 (m, 1H), 4.03-3.81 (m, 3.5H), 3.70-3.65 (m, 0.5H), 3.57-3.54 (m, 0.5H), 3.37-3.30 (m, 4H), 2.73-2.62 (m, 2H), 2.10-2.07 (m, 2H), 1.34-1.20 (m, 6H). | 570.2 |

-continued

Summary Table

| Ex. | Name | Structure | ¹H NMR | MS (M + H)⁺ |
|---|---|---|---|---|
| 234 | (3R)-3-((1H-pyrazol-1-yl)methyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one | 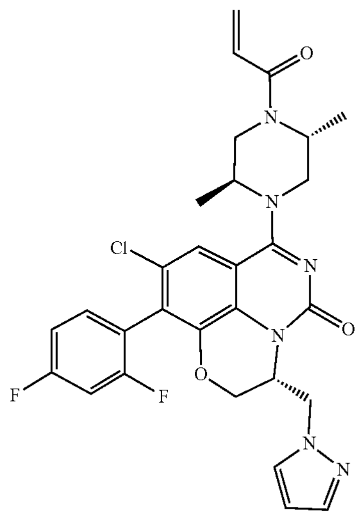 [SMILES: C=CC(=O)N1C[C@H](C)N(c2nc(=O)n3c4c(c(-c5ccc(F)cc5F)c(Cl)cc24)OC[C@H]3Cn2cccn2)C[C@H]1C] | ¹H NMR (400 MHz, CDCl$_3$) δ 7.52 (s, 1H), 7.48-7.44 (m, 2H), 7.34-7.28 (m, 0.5H), 7.23-7.20 (m, 0.5H), 7.05-6.91 (m, 2H), 6.67-6.51 (m, 1H), 6.37 (t, J = 15.2 Hz, 1H), 6.25 (s, 1H), 5.78 (t, J = 8.8 Hz, 1H), 5.03-4.82 (m, 3H), 4.55-4.35 (m, 4H), 4.20-4.15 (m, 0.5H), 4.01 (t, J = 13.8 Hz, 1H), 3.77-3.66 (m, 2H), 3.34-3.30 (m, 0.5H), 1.47-1.35 (m, 6H). | 581.2 |
| 235 | (3R)-7-((2S,5R)-4-acryloyl-2,5-dimethylpiperazin-1-yl)-9-chloro-10-(2,4-difluorophenyl)-3-((methyl(2,2,2-trifluoroethyl)amino)methyl)-2H-[1,4]oxazino[2,3,4-ij]quinazolin-5(3H)-one | 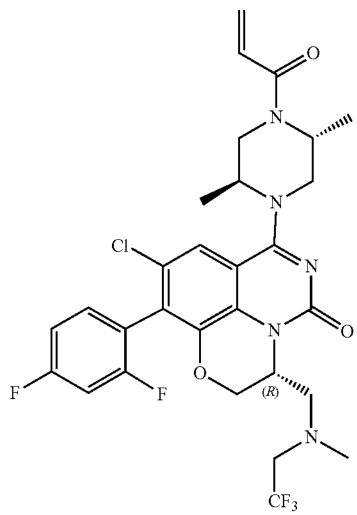 | ¹H NMR (400 MHz, CDCl$_3$) δ 7.45 (s, 1H), 7.25-7.18 (m, 1H), 7.04-6.92 (m, 2H), 6.65-6.50 (m, 1H), 6.37 (t, J = 15.6 Hz, 1H), 5.79-5.75 (m, 1H), 4.98-4.97 (m, 1H), 4.82-4.67 (m, 1H), 4.52-4.81 (m, 1H), 4.34-4.08 (m, 4H), 3.92-3.78 (m, 2H), 3.53-3.48 (m, 2H), 3.30-3.08 (m, 2H), 2.59 (d, J = 6.4 Hz, 3H), 1.36 (d, J = 6.8 Hz, 4H), 1.24-1.22 (m, 2H). | 626.3 |
| 236 | (3S)-3-((1H-pyrazol-1-yl)methyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one | 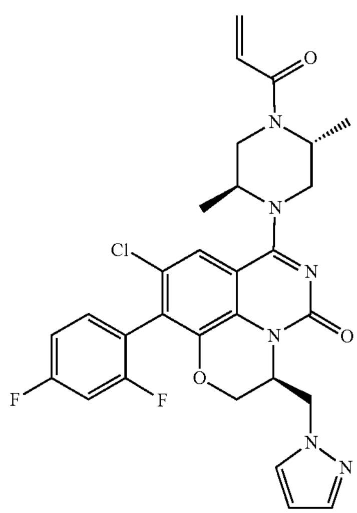 [SMILES: C=CC(=O)N1C[C@H](C)N(c2nc(=O)n3c4c(c(-c5ccc(F)cc5F)c(Cl)cc24)OC[C@@H]3Cn2cccn2)C[C@H]1C] | ¹H NMR (400 MHz, CDCl$_3$) δ 7.55-7.42 (m, 3H), 7.34-7.28 (m, 1H), 7.05-6.91 (m, 2H), 6.65-6.51 (m, 1H), 6.38 (t, J = 16 Hz, 1H), 6.28-6.26 (m, 1H), 5.80-5.76 (m, 1H), 5.11-5.10 (m, 0.5H), 5.01-4.88 (m, 2H), 4.57-4.54 (d, J = 12 Hz, 1.5H), 4.44-4.30 (m, 2H), 4.09-3.54 (m, 5H), 1.36-1.19 (m, 6H). | 581.2 |

-continued

Summary Table

| Ex. | Name | Structure | ¹H NMR | MS (M + H)⁺ |
|---|---|---|---|---|
| 237 | (3S)-7-((2S,5R)-4-acryloyl-2,5-dimethylpiperazin-1-yl)-9-chloro-10-(2,4-difluorophenyl)-3-((methyl(2,2,2-trifluoroethyl)amino)methyl)-2H-[1,4]oxazino[2,3,4-ij]quinazolin-5(3H)-one | 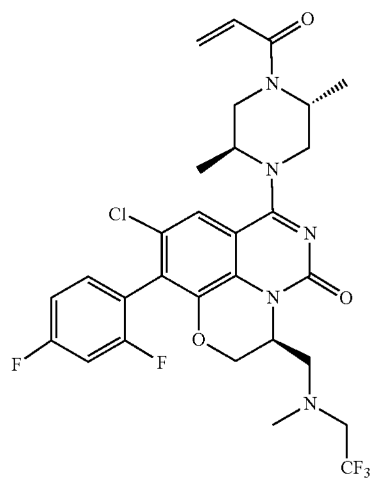 [SMILES: C=CC(=O)N1C[C@H](C)N(c2nc(=O)n3c4c(c(-c5ccc(F)cc5F)c(Cl)cc24)OC[C@@H]3CN(C)CC(F)(F)F)C[C@H]1C] | ¹H NMR (400 MHz, CDCl₃) δ 7.48 (s, 1H), 7.25-7.21 (m, 1H), 7.03-6.94 (m, 2H), 6.62-6.51 (m, 1H), 6.41-6.33 (m, 1H), 5.80-5.75 (m, 1H), 4.99-4.92 (m, 1H), 4.81-4.64 (m, 1.5H), 4.37-4.25 (m, 3H), 4.19-3.94 (m, 2H), 3.83-3.65 (m, 2H), 3.51-3.39 (m, 1.5H), 3.28-3.13 (m, 2H), 2.60 (d, J = 10.4 Hz, 3H), 1.38-1.28 (m, 6H). | 626.3 |
| 238 | (3S)-3-((1H-imidazol-1-yl)methyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one | 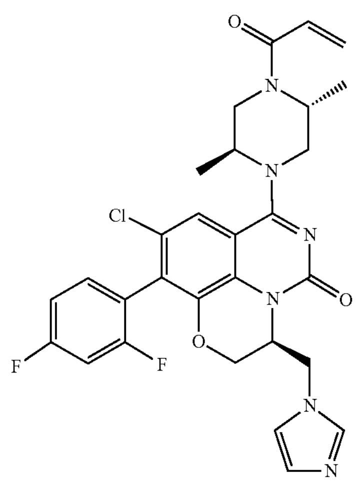 [SMILES: C=CC(=O)N1C[C@H](C)N(c2nc(=O)n3c4c(c(-c5ccc(F)cc5F)c(Cl)cc24)OC[C@@H]3Cn2ccnc2)C[C@H]1C] | ¹H NMR (400 MHz, CDCl₃) δ 7.55-7.43 (m, 2H), 7.34-7.23 (m, 1H), 7.08-7.00 (m, 3H), 6.97-6.92 (m, 1H), 6.67-6.51 (m, 1H), 6.38 (t, J = 14.4 Hz, 1H), 5.78 (t, J = 9.6 Hz, 1H), 5.06-4.80 (m, 2.5H), 4.57-3.93 (m, 6H), 43.78-3.63 (m, 2H), 3.32-3.25 (m, 0.5H), 1.52-1.25 (m, 6H). | 581.2 |
| 239 | (3S,10R)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2H-[1,4]oxazino[2,3,4-ij]quinazolin-5(3H)-one | 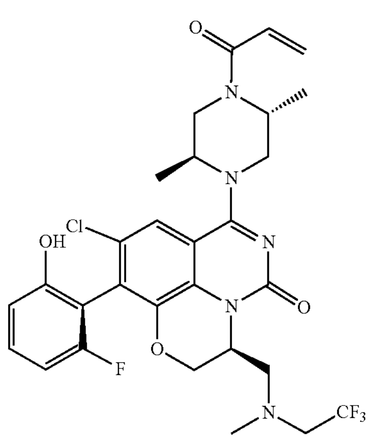 | ¹H NMR (400 MHz, CDCl₃) δ 7.48 (s, 1H), 7.28 (m, 1H), 6.85-6.74 (m, 3H), 6.53 (m, 1H), 6.42-6.39 (m, 1H), 5.79-5.77 (m, 1H), 4.94-4.62 (m, 2.5H), 4.37-4.32 (m, 3H), 4.21-4.17 (m, 1H), 4.01-3.98 (m, 0.5H), 3.80-3.76 (m, 1H), 3.66 (m, 1H), 3.48-3.36 (m, 1H), 3.26-3.16 (m, 2H), 2.57 (s, 3H), 1.35-1.24 (m, 6H). | 624.2 |

| Ex. | Name | Structure | ¹H NMR | MS (M + H)⁺ |
|---|---|---|---|---|
| 240 | (3S,10S)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2H-[1,4]oxazino[2,3,4-ij]quinazolin-5(3H)-one | 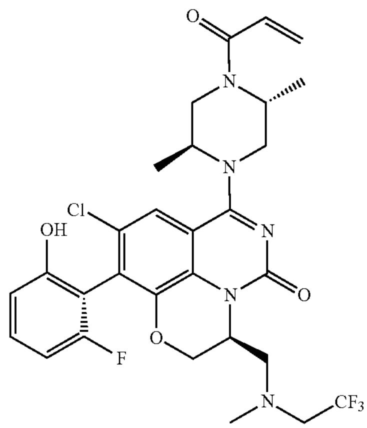 | ¹H NMR (400 MHz, CDCl₃) δ 7.49 (s, 1H), 7.29-7.28 (m, 1H), 6.86-6.75 (m, 3H), 6.64-6.53 (m, 1H), 6.42-6.34 (m, 1H), 5.79-5.76 (m, 1H), 4.97-4.80 (m, 2.5H), 4.32-4.22 (m, 4H), 4.00-3.96 (m, 0.5H), 3.77-3.67 (m, 2.5H), 3.49 (s, 1H), 3.38-3.35 (m, 0.5H), 3.22-3.13 (m, 2H), 2.56 (s, 3H), 1.36-1.24 (m, 6H). | 624.2 |
| 241 | (3R,10R)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2H-[1,4]oxazino[2,3,4-ij]quinazolin-5(3H)-one | 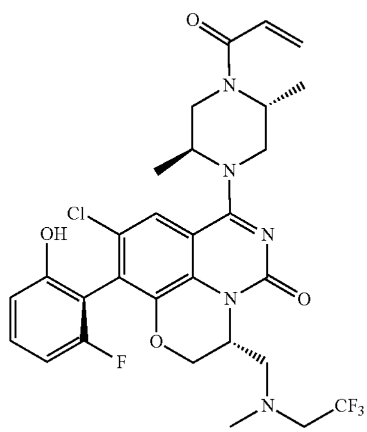 | ¹H NMR (400 MHz, CDCl₃) δ 7.49-7.47 (m, 1H), 7.33-7.28 (m, 1H), 6.82-6.76 (m, 2H), 6.65-6.50 (m, 1H), 6.41-6.34 (m, 1H), 5.79-5.74 (m, 2H), 4.99-4.94 (m, 1H), 4.81-4.78 (m, 0.5H), 4.67-4.64 (m, 1H), 4.36-4.26 (m, 4H), 4.12-4.08 (m, 0.5H), 3.96-3.63 (m, 3H), 3.53-3.47 (m, 1H), 3.29-3.07 (m, 2H), 2.57 (s, 3H), 1.34 (d, J = 6.8 Hz, 4H), 1.23 (d, J = 6.8 Hz, 2H). | 624.3 |
| 242 | (3R,10S)-7-((2S,5R)-4-acryloyl-2,5-dimethylpiperazin-1-yl)-9-chloro-10-(2-fluoro-6-hydroxyphenyl)-3-((methyl(2,2,2-trifluoroethyl)amino)methyl)-2H-[1,4]oxazino[2,3,4-ij]quinazolin-5(3H)-one | 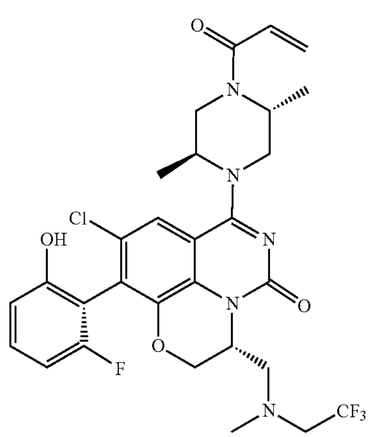 | ¹H NMR (400 MHz, CDCl₃) δ 7.48-7.47 (m, 1H), 7.33-7.29 (m, 1H), 6.80 (t, J = 8.2 Hz, 2H), 6.61-6.50 (m, 1H), 6.37 (t, J = 16 Hz, 1H), 5.77 (t, J = 8 Hz, 1H), 4.97-4.93 (m, 1H), 4.86-4.82 (m, 0.5H), 4.60-4.57 (m, 1H), 4.44-4.40 (m, 1H), 4.33-4.27 (m, 2H), 4.22-4.18 (m, 1H), 4.13-4.10 (m, 0.5H), 3.64-3.63 (m, 3H), 3.53-3.44 (m, 1H), 3.29-3.13 (m, 2H), 2.57 (s, 3H), 1.34 (d, J = 6.4 Hz, 4H), 1.24 (d, J = 6.8 Hz, 2H). | 624.3 |

-continued

Summary Table

| Ex. | Name | Structure | ¹H NMR | MS (M + H)⁺ |
|---|---|---|---|---|
| 243 | (3S,10S)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2H-[1,4]oxazino[2,3,4-ij]quinazolin-5(3H)-one | 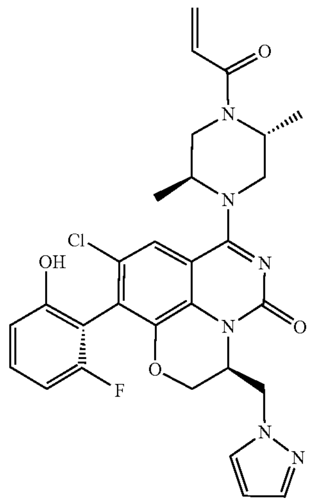 | ¹H NMR (400 MHz, CDCl₃) δ 8.31-8.24 (m, 1H), 7.47-7.46 (m, 1H), 7.32-7.29 (t, J = 6.2 Hz, 2H), 7.20 (m, 1H), 6.88-6.86 (d, J = 8 Hz, 1H), 6.79-6.75 (t, J = 8 Hz, 1H), 6.63-6.50 (m, 1H), 6.41-6.33 (t, J = 8 Hz, 1H), 6.09-6.08 (m, 1H), 5.78-5.74 (m, 1H), 5.09-4.91 (m, 2.5H), 4.71-4.65 (m, 1H), 4.57-4.52 (m, 1H), 4.44-4.42 (d, J = 8 Hz, 1H), 4.28-4.18 (m, 2H), 3.99-3.84 (m, 2.5H), 3.66-3.56 (m, 1H), 1.31-1.25 (m, 4H), 1.15-1.14 (d, J = 6.8 Hz, 2H). | 579.2 |
| 244 | (3S,10R)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2H-[1,4]oxazino[2,3,4-ij]quinazolin-5(3H)-one | 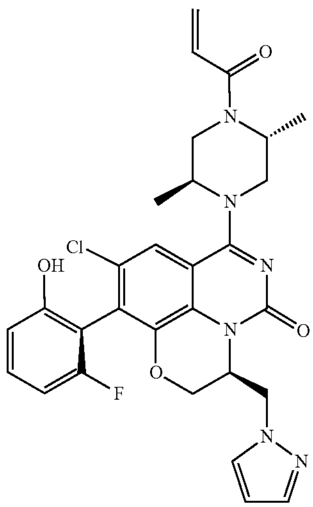 | ¹H NMR (400 MHz, CDCl₃) δ 7.54-7.44 (m, 3H), 7.31-7.28 (m, 1H), 6.83-6.76 (m, 2H), 6.62-6.52 (m, 1H), 6.43-6.36 (m, 1H), 6.26-6.25 (s, 1H), 5.81-5.78 (d, J = 12 Hz, 1H), 5.09-4.90 (m, 2.5H), 4.56-4.53 (d, J = 12 Hz, 1H), 4.42-4.27 (m, 3H), 4.08-3.95 (m, 2.5H), 3.88-3.83 (m, 1H), 3.66-3.52 (dd, J = 12 Hz, J = 12 Hz, 1H), 1.33-1.28 (m, 4H), 1.18-1.16 (d, J = 6.8 Hz, 2H). | 579.2 |
| 245 | (3R,10R)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2H-[1,4]oxazino[2,3,4-ij]quinazolin-5(3H)-one | 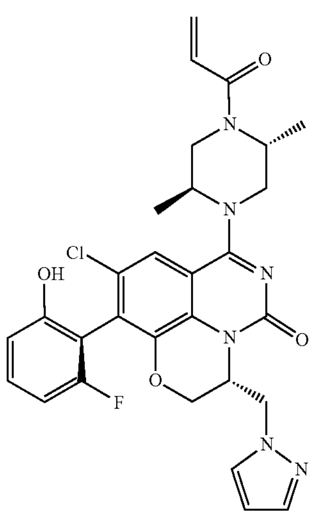 | ¹H NMR (400 MHz, CDCl₃) δ 7.52-7.51 (m, 1H), 7.49-7.48 (m, 2H), 7.32-7.28 (m, 1H), 6.81-6.75 (m, 2H), 6.63-6.51 (m, 1H), 6.38 (t, J = 16.2 Hz, 1H), 6.25 (s, 1H), 5.79 (t, J = 9.4 Hz, 1H), 5.00-4.81 (m, 3H), 4.53-4.31 (m, 4H), 4.19 (d, J = 14 Hz, 0.5H), 4.02-3.97 (m, 1H), 3.75-3.66 (m, 2H), 3.31-3.27 (m, 0.5H), 1.47-1.36 (m, 6H). | 579.2 |

-continued

Summary Table

| Ex. | Name | Structure | ¹H NMR | MS (M + H)⁺ |
|---|---|---|---|---|
| 246 | (3R,10S)-3-((1H-pyrazol-1-yl)methyl)-7-((2S,5R)-4-acryloyl-2,5-dimethylpiperazin-1-yl)-9-chloro-10-(2-fluoro-6-hydroxyphenyl)-2H-[1,4]oxazino[2,3,4-ij]quinazolin-5(3H)-one | 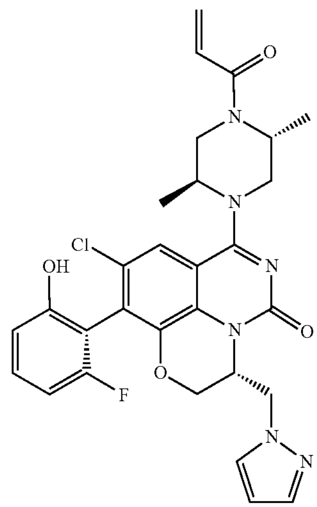 | ¹H NMR (400 MHz, CDCl$_3$) δ 7.42-7.41 (m, 1H), 7.36-7.29 (m, 2H), 7.18 (d, J = 6 Hz, 1H), 6.89 (d, J = 8 Hz, 1H), 6.76 (t, J = 8.8 Hz, 1H), 6.65-6.48 (m, 1H), 6.37 (t, J = 14.6 Hz, 1H), 6.06-6.05 (m, 1H), 5.77 (t, J = 9.8 Hz, 1H), 5.02-5.00 (m, 1.5H), 4.79-4.73 (m, 2H), 4.56-4.38 (m, 3H), 4.33-4.30 (m, 1H), 4.19 (t, J = 9.8 Hz, 1H), 3.65 (s, 1H), 3.67-3.51 (m, 1H), 3.18-3.14 (m, 0.5H), 1.50 (d, J = 6.8 Hz, 2H), 1.42 (t, J = 7.4 Hz, 4H). | 579.2 |
| 248 | (3S)-3-((1H-imidazol-1-yl)methyl)-7-((2S,5R)-4-acryloyl-2,5-dimethylpiperazin-1-yl)-9-chloro-10-(2-fluoro-6-hydroxyphenyl)-2H-[1,4]oxazino[2,3,4-ij]quinazolin-5(3H)-one | 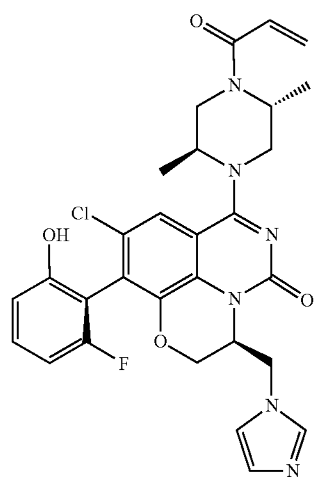 | ¹H NMR (400 MHz, CDCl$_3$) δ 7.58 (s, 1H), 7.52 (d, J = 10.0 Hz, 1H), 7.32-7.27 (m, 1H), 7.12 (s, 1H), 7.05 (s, 1H), 6.86 (d, J = 7.6 Hz, 1H), 6.78 (t, J = 8.4 Hz, 1H), 6.72-6.50 (m, 1H), 6.38 (t, J = 16.8 Hz, 1H), 5.79 (t, J = 10.0 Hz, 1H), 5.02-4.83 (m, 2.5H), 4.56-3.24 (m, 3H), 4.11-3.92 (m, 3H), 3.76-3.63 (m, 2H), 3.29-3.25 (m, 0.5H), 1.57-1.17 (m, 6H). | 579.2 |
| 256 | (3R)-7-((2S,5R)-4-acryloyl-2,5-dimethylpiperazin-1-yl)-9-chloro-10-(2,4-difluorophenyl)-3-((4-methylpiperazin-1-yl)methyl)-2H-[1,4]oxazino[2,3,4-ij]quinazolin-5(3H)-one | 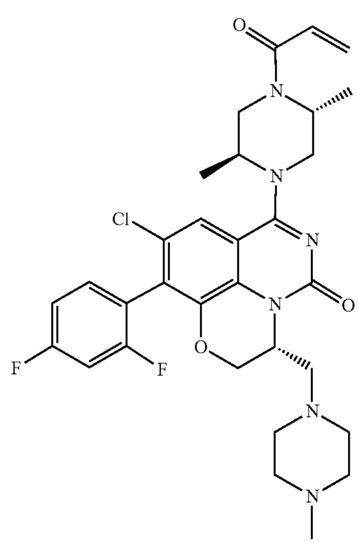 [SMILES: C=CC(=O)N1C[C@H](C)N(c2nc(=O)n3c4c(c(-c5ccc(F)cc5F)c(Cl)cc24)OC[C@H]3CN2CCN(C)CC2)C[C@H]1C] | ¹H NMR (400 MHz, CDCl$_3$) δ 7.42-7.38 (m, 1H), 7.30-7.28 (m, 1H), 7.04-6.93 (m, 2H), 6.66-6.51 (m, 1H), 6.37 (t, J = 15.6 Hz, 1H), 5.77 (t, J = 7.2 Hz, 1H), 5.05-4.84 (m, 1H), 4.79-4.67 (m, 2H), 4.41-4.25 (m, 1H), 4.09-3.80 (m, 4H), 3.68-3.65 (m, 0.6H), 3.55-3.51 (m, 0.4H), 2.85-2.66 (m, 2H), 2.62-2.40 (m, 8H), 2.26 (d, J = 2.4 Hz, 3H), 1.35-1.21 (m, 6H). | 613.2 |

| Ex. | Name | Structure | ¹H NMR | MS (M + H)⁺ |
|---|---|---|---|---|
| 257 | (3S)-7-((2S,5R)-4-acryloyl-2,5-dimethylpiperazin-1-yl)-9-chloro-10-(2,4-difluorophenyl)-3-((4-methylpiperazin-1-yl)methyl)-2H-[1,4]oxazino[2,3,4-ij]quinazolin-5(3H)-one | 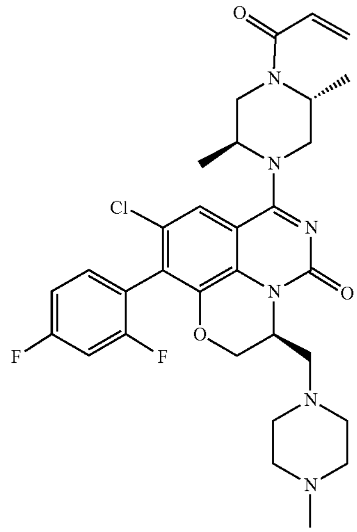 [SMILES: C=CC(=O)N1C[C@H](C)N(c2nc(=O)n3c4c(c(-c5ccc(F)cc5F)c(Cl)cc24)OC[C@@H]3CN2CCN(C)CC2)C[C@H]1C] | ¹H NMR (400 MHz, CDCl₃) δ 7.43 (s, 1H), 7.33-7.22 (m, 1H), 7.04-6.94 (m, 2H), 6.66-6.51 (m, 1H), 6.37 (t, J = 14.4 Hz, 1H), 5.77 (t, J = 8 Hz, 1H), 4.99-4.69 (m, 3.7H), 4.39-4.26 (m, 1.3H), 4.09-3.94 (m, 1.6H), 3.83-3.65 (m, 2H), 3.41-3.35 (m, 0.4H), 2.79-2.66 (m, 2H), 2.57-2.54 (m, 4.4H), 2.48-2.31 (m, 3.6H), 2.26 (s, 3H), 1.43-1.28 (m, 6H). | 613.2 |
| 267 | (3R)-3-((1H-imidazol-1-yl)methyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one | 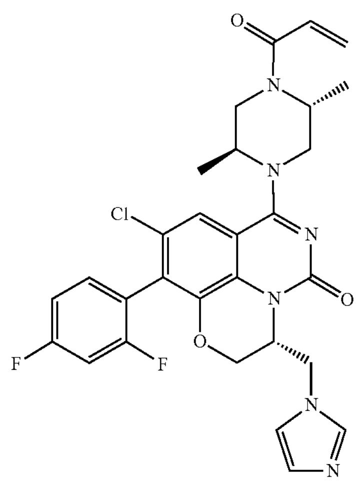 [SMILES: C=CC(=O)N1C[C@H](C)N(c2nc(=O)n3c4c(c(-c5ccc(F)cc5F)c(Cl)cc24)OC[C@H]3Cn2ccnc2)C[C@H]1C] | ¹H NMR (400 MHz, CDCl₃) δ 7.61-7.40 (m, 2H), 7.35-7.25 (m, 1H), 7.13-6.95 (m, 4H), 6.66-6.51 (m, 1H), 6.38 (t, J = 15.6 Hz, 1H), 5.82-5.74 (m, 1H), 5.40-5.06 (m, 1H), 5.01-4.83 (m, 2H), 4.52-4.41 (m, 1H), 4.40-3.88 (m, 6H), 3.74-3.53 (m, 1H), 1.40-1.25 (m, 6H). | 581.2 |
| 268 | (3R)-7-((2S,5R)-4-acryloyl-2,5-dimethylpiperazin-1-yl)-9-chloro-10-(2,4-difluorophenyl)-3-((1,1-dioxidothiomorpholino)methyl)-2H-[1,4]oxazino[2,3,4-ij]quinazolin-5(3H)-one | 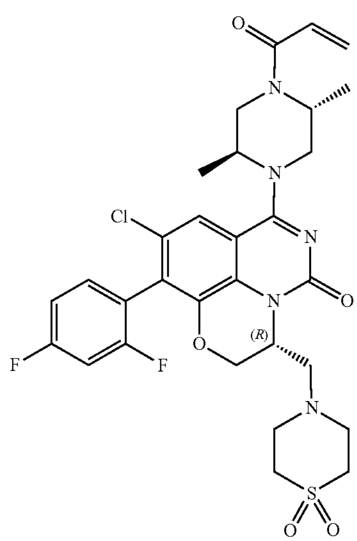 | ¹H NMR (400 MHz, CDCl₃) δ 7.47-7.45 (m, 1H), 7.24-7.20 (m, 1H), 7.04-6.94 (m, 2H), 6.53-6.49 (m, 1H), 6.38 (t, J = 14.8 Hz, 1H), 5.78 (t, J = 8.8 Hz, 1H), 5.00-4.98 (m, 1H), 4.83-4.63 (m, 1.5H), 4.38-4.08 (m, 4.5H), 3.96-3.78 (m, 2H), 3.68-3.43 (m, 2H), 3.21-3.19 (m, 4H), 3.05-3.04 (m, 4H), 1.36-1.34 (m, 4H), 1.25-1.21 (m, 2H). | 648.2 |

-continued

Summary Table

| Ex. | Name | Structure | ¹H NMR | MS (M + H)⁺ |
|---|---|---|---|---|
| 269 | (3S)-7-((2S,5R)-4-acryloyl-2,5-dimethylpiperazin-1-yl)-9-chloro-10-(2,4-difluorophenyl)-3-((1,1-dioxidothiomorpholino)methyl)-2H-[1,4]oxazino[2,3,4-ij]quinazolin-5(3H)-one | 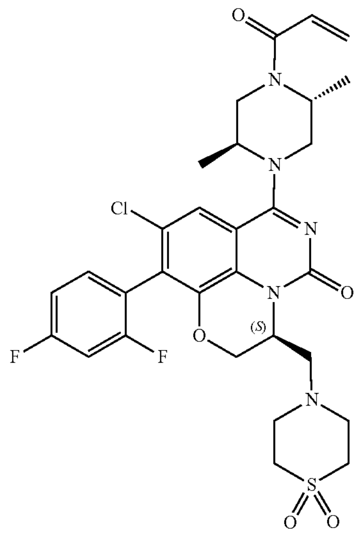 | ¹H NMR (400 MHz, CDCl₃) δ 7.50 (s, 1H), 7.26-7.20 (m, 1H), 7.04-6.93 (m, 2H), 6.66-6.51 (m, 1H), 6.38 (t, J = 16.8 Hz, 1H), 5.78 (t, J = 8.8 Hz, 1H), 4.99-4.96 (m, 0.5H), 4.92-4.85 (m, 1H), 4.77-4.72 (m, 1H), 4.41-4.18 (m, 4H), 4.09-3.97 (m, 1H), 3.83-3.66 (m, 2H), 3.57-3.51 (m, 1H), 3.41-3.36 (m, 0.5H), 3.23-3.17 (m, 4H), 3.07-3.03 (m, 4H), 1.39-1.37 (m, 4H), 1.32-1.28 (m, 2H). | 648.2 |
| 274 | (3S)-7-((2S,5R)-4-acryloyl-2,5-dimethylpiperazin-1-yl)-9-chloro-10-(2,4-difluorophenyl)-3-((4-methyl-2-oxopiperazin-1-yl)methyl)-2,3-dihydro-5H-[1,4]oxazino[2,3,4-ij]quinazolin-5-one | 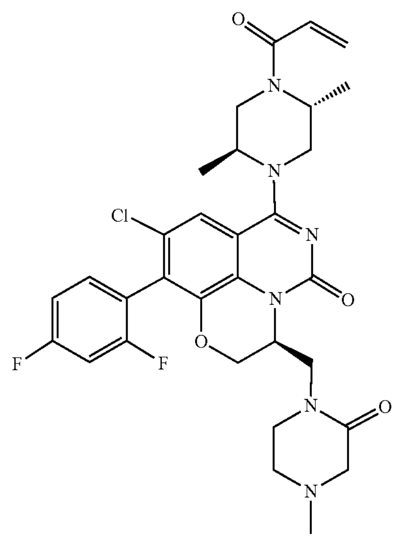 [SMILES: C=CC(=O)N1C[C@H](C)N(c2nc(=O)n3c4c(c(-c5ccc(F)cc5F)c(Cl)cc24)OC[C@@H]3CN2CCN(C)CC2=O)C[C@H]1C] | ¹H NMR (400 MHz, CDCl₃) δ 7.42-7.36 (m, 1.5H), 7.23-7.20 (m, 0.5H), 7.04-6.90 (m, 2H), 6.63-6.51 (m, 1H), 6.38 (t, J = 16.0 Hz, 1H), 5.78 (t, J = 6.4 Hz, 1H), 5.05-4.89 (m, 2.5H), 4.52-4.44 (m, 1H), 4.31-4.28 (m, 1H), 4.24-4.16 (m, 0.5H), 4.11-4.02 (m, 2H), 3.88-3.79 (m, 2H), 3.69-3.55 (m, 1.5H), 3.48-3.45 (m, 2H), 3.36-3.31 (m, 0.5H), 3.09-3.05 (m, 1H), 2.92-2.62 (m, 3H), 2.30 (s, 3H), 1.40-1.37 (m, 4H), 1.30-1.23 (m, 2H). | 627.2 |
| 276 | (3S)-7-((2S,5R)-4-acryloyl-2,5-dimethylpiperazin-1-yl)-9-chloro-10-(2,4-difluorophenyl)-3-(((1-methylpiperidin-4-yl)oxy)methyl)-2H-[1,4]oxazino[2,3,4-ij]quinazolin-5(3H)-one | 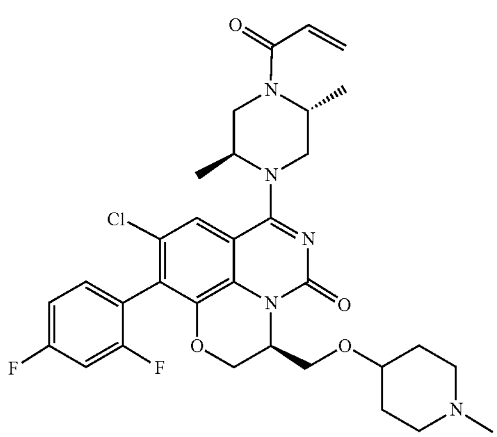 [SMILES: C=CC(=O)N1C[C@H](C)N(c2nc(=O)n3c4c(c(-c5ccc(F)cc5F)c(Cl)cc24)OC[C@@H]3COC2CCN(C)CC2)C[C@H]1C] | ¹H NMR (400 MHz, CDCl₃) δ 7.44 (s, 1H), 7.31-7.29 (m, 1H), 7.03-6.93 (m, 2H), 6.63-6.51 (m, 1H), 6.38 (t, J = 15.2 Hz, 1H), 5.78 (t, J = 8.4 Hz, 1H), 5.02-4.81 (m, 3H), 4.72 (d, J = 10.8 Hz, 1H), 4.40-4.31 (m, 1.5H), 4.16-3.97 (m, 1.5H), 3.80-3.66 (m, 3H), 3.58-3.52 (m, 1H), 3.38-3.31 (m, 1H), 2.59-2.57 (m, 2H), 2.23-2.20 (m, 3H), 2.11-2.06 (m, 2H), 1.84-1.78 (m, 2H), 1.55-1.49 (m, 2H), 1.44-1.41 (m, 4H), 1.34 (t, J = 10 Hz, 2H). | 628.3 |

| Ex. | Name | Structure | ¹H NMR | MS (M + H)⁺ |
|---|---|---|---|---|
| 277 | (3S)-7-((2S,5R)-4-acryloyl-2,5-dimethylpiperazin-1-yl)-9-chloro-10-(2,4-difluorophenyl)-3-((((R)-1-methylpyrrolidin-2-yl)methoxy)methyl)-2H-[1,4]oxazino[2,3,4-ij]quinazolin-5(3H)-one | 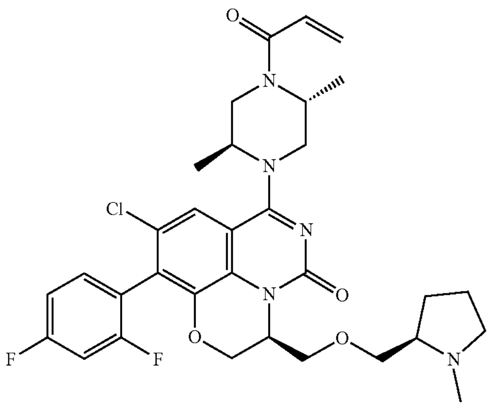 [SMILES: C=CC(=O)N1C[C@H](C)N(c2nc(=O)n3c4c(c(-c5ccc(F)cc5F)c(Cl)cc24)OC[C@@H]3COC[C@H]2CCCN2C)C[C@H]1C] | ¹H NMR (400 MHz, CDCl₃) δ 7.44 (s, 1H), 7.35-7.30 (m, 0.5H), 7.24-7.20 (m, 0.5H), 7.05-6.92 (m, 2H), 6.64-6.50 (m, 1H), 6.37 (t, J = 15.2 Hz, 1H), 5.78 (t, J = 8 Hz, 1H), 5.02-4.81 (m, 3H), 4.69 (d, J = 10.8 Hz, 1H), 4.40-4.34 (m, 1.5H), 4.17-4.09 (m, 0.5H), 4.00 (t, J = 11.2 Hz, 1H), 3.80-3.55 (m, 6.5H), 3.35 (d, J = 12 Hz, 0.5H), 3.19-3.17 (m, 1H), 2.62 (s, 3H), 2.39-2.27 (m, 1H), 1.97-1.87 (m, 1H), 1.80-1.72 (m, 3H), 1.48-1.16 (m, 6H). | 628.3 |
| 280 | (3R)-7-((2S,5R)-4-acryloyl-2,5-dimethylpiperazin-1-yl)-9-chloro-10-(2,4-difluorophenyl)-3-((4-methyl-2-oxopiperazin-1-yl)methyl)-2H-[1,4]oxazino[2,3,4-ij]quinazolin-5(3H)-one | 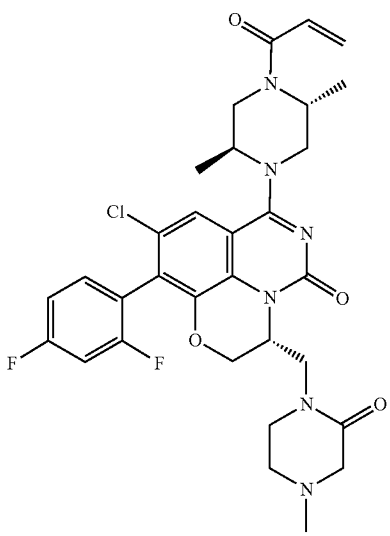 [SMILES: C=CC(=O)N1C[C@H](C)N(c2nc(=O)n3c4c(c(-c5ccc(F)cc5F)c(Cl)cc24)OC[C@H]3CN2CCN(C)CC2=O)C[C@H]1C] | ¹H NMR (400 MHz, CDCl₃) δ 7.42-7.35 (m, 1.5H), 7.24-7.21 (m, 0.5H), 7.04-6.91 (m, 2H), 6.61-6.51 (m, 1H), 6.37 (t, J = 16.0 Hz, 1H), 5.77 (t, J = 8.4 Hz, 1H), 4.97-4.90 (m, 2.5H), 4.48-4.50 (m, 1H), 4.35-4.31 (m, 1H), 4.22-4.18 (m, 0.5H), 4.11-4.05 (m, 1.5H), 3.86-3.46 (m, 6.5H), 3.10-3.06 (m, 1H), 3.00-2.91 (m, 1H), 2.69-2.61 (m, 2H), 2.30 (s, 3H), 1.38 (d, J = 6.4 Hz, 4H), 1.28-1.23 (m, 2H). | 627.3 |
| 285 | (3R)-7-((2S,5R)-4-acryloyl-2,5-dimethylpiperazin-1-yl)-9-chloro-10-(2,4-difluorophenyl)-3-((((1R,5S)-8-methyl-3,8-diazabicyclo[3.2.1]octan-3-yl)methyl)-2H-[1,4]oxazino[2,3,4-ij]quinazolin-5(3H)-one | 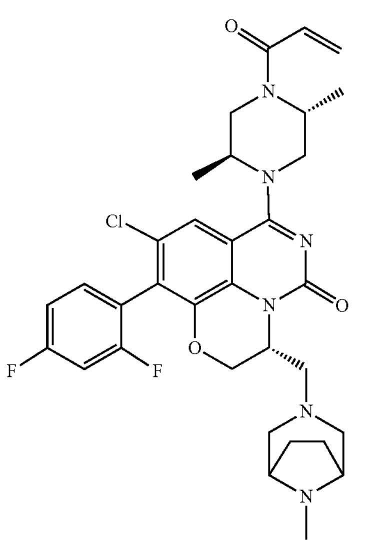 [SMILES: C=CC(=O)N1C[C@H](C)N(c2nc(=O)n3c4c(c(-c5ccc(F)cc5F)c(Cl)cc24)OC[C@H]3CN2CC3CCC(C2)N3C)C[C@H]1C] | ¹H NMR (400 MHz, CDCl₃) δ 7.40-7.37 (m, 1H), 7.31-7.28 (m, 1H), 7.04-6.93 (m, 2H), 6.61-6.51 (m, 1H), 6.37 (t, J = 15.6 Hz, 1H), 5.78-5.74 (m, 1H), 5.02-4.88 (m, 2H), 4.59-4.53 (m, 1H), 4.34-4.30 (m, 1H), 4.03-3.98 (m, 1H), 3.91-3.84 (m, 2H), 3.67-3.54 (m, 1H), 3.38-3.37 (m, 1H), 3.04-2.97 (m, 1H), 2.67-2.52 (m, 3H), 2.35-2.11 (m, 6H), 1.91-1.70 (m, 5H), 1.33-1.19 (m, 6H). | 639.3 |

Summary Table

| Ex. | Name | Structure | ¹H NMR | MS (M + H)⁺ |
|---|---|---|---|---|
| 286 | (3S)-7-((2S,5R)-4-acryloyl-2,5-dimethylpiperazin-1-yl)-9-chloro-10-(2,4-difluorophenyl)-3-(((1R,5S)-8-methyl-3,8-diazabicyclo[3.2.1]octan-3-yl)methyl)-2H-[1,4]oxazino[2,3,4-ij]quinazolin-5(3H)-one | 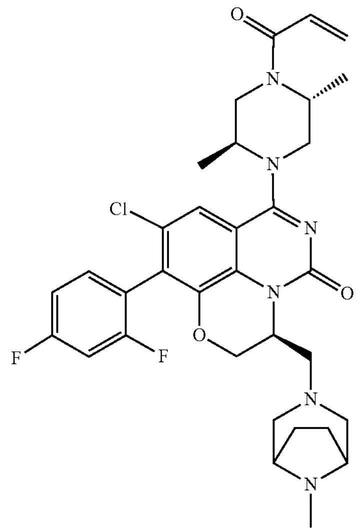 [SMILES: C=CC(=O)N1C[C@H](C)N(c2nc(=O)n3c4c(c(-c5ccc(F)cc5F)c(Cl)cc24)OC[C@@H]3CN2CC3CCC(C2)N3C)C[C@H]1C] | ¹H NMR (400 MHz, CDCl₃) δ 7.43 (s, 1H), 7.33-7.28 (m, 1H), 7.04-6.94 (m, 2H), 6.66-6.51 (m, 1H), 6.37 (t, J = 15.6 Hz, 1H), 5.79-5.74 (m, 1H), 5.02-4.84 (m, 2H), 4.63-4.57 (m, 1H), 4.40-3.96 (m, 3H), 3.81-3.65 (m, 2H), 3.66-3.65 (m, 1H), 3.04-3.00 (m, 1H), 2.61-2.51 (m, 3H), 2.41-2.35 (m, 1H), 2.22-2.10 (m, 5H), 1.93-1.74 (m, 5H), 1.44-1.31 (m, 6H). | 639.3 |
| 287 | (3R)-7-((2S,5R)-4-acryloyl-2,5-dimethylpiperazin-1-yl)-9-chloro-10-(2,4-difluorophenyl)-3-((((R)-1-methylpyrrolidin-2-yl)methoxy)methyl)-2H-[1,4]oxazino[2,3,4-ij]quinazolin-5(3H)-one | 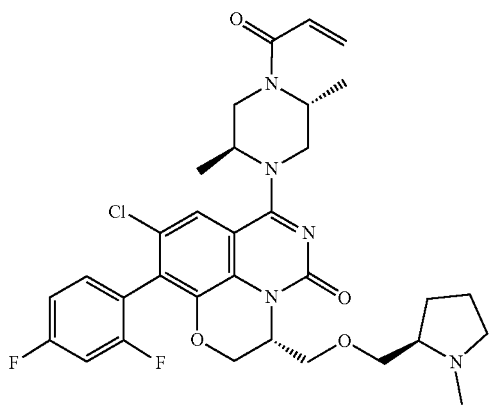 [SMILES: C=CC(=O)N1C[C@H](C)N(c2nc(=O)n3c4c(c(-c5ccc(F)cc5F)c(Cl)cc24)OC[C@H]3COC[C@H]2CCCN2C)C[C@H]1C] | ¹H NMR (400 MHz, CDCl₃) δ 7.44 (s, 1H), 7.35-7.30 (m, 0.5H), 7.24-7.20 (m, 0.5H), 7.05-6.92 (m, 2H), 6.64-6.50 (m, 1H), 6.37 (t, J = 15.2 Hz, 1H), 5.78 (t, J = 8 Hz, 1H), 5.02-4.81 (m, 3H), 4.69 (d, J = 10.8 Hz, 1H), 4.40-4.34 (m, 1.5H), 4.17-4.09 (m, 0.5H), 4.00 (t, J = 11.2 Hz, 1H), 3.80-3.55 (m, 6.5H), 3.35 (d, J = 12 Hz, 0.5H), 3.19-3.17 (m, 1H), 2.62 (s, 3H), 2.39-2.27 (m, 1H), 1.97-1.87 (m, 1H), 1.80-1.72 (m, 3H), 1.48-1.16 (m, 6H). | 628.3 |
| 290 | (3S)-7-((2S,5R)-4-acryloyl-2,5-dimethylpiperazin-1-yl)-9-chloro-10-(2,4-difluorophenyl)-3-(((1R,5S)-8-(oxetan-3-yl)-3,8-diazabicyclo[3.2.1]octan-3-yl)methyl)-2H-[1,4]oxazino[2,3,4-ij]quinazolin-5(3H)-one | 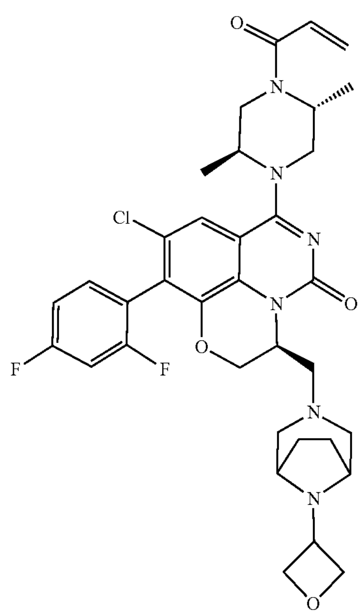 [SMILES: C=CC(=O)N1C[C@H](C)N(c2nc(=O)n3c4c(c(-c5ccc(F)cc5F)c(Cl)cc24)OC[C@@H]3CN2CC3CCC(C2)N3C2COC2)C[C@H]1C] | ¹H NMR (400 MHz, CDCl₃) δ 7.42 (s, 1H), 7.32-7.30 (m, 1H), 7.04-6.93 (m, 2H), 6.64-6.51 (m, 1H), 6.38 (t, J = 15.2 Hz, 1H), 5.79-5.74 (m, 1H), 4.98-4.83 (m, 2.5H), 4.66-4.63 (m, 3H), 4.53-4.51 (m, 2H), 4.39-4.21 (m, 1.5H), 4.06-3.40 (m, 5H), 2.98-2.97 (m, 2H), 2.75-2.48 (m, 6H), 1.84-1.65 (m, 4H), 1.40-1.25 (m, 6H). | 681.3 |

-continued

Summary Table

| Ex. | Name | Structure | ¹H NMR | MS (M + H)⁺ |
|---|---|---|---|---|
| 291 | (3R)-7-((2S,5R)-4-acryloyl-2,5-dimethylpiperazin-1-yl)-9-chloro-10-(2,4-difluorophenyl)-3-(((1R,5S)-8-(oxetan-3-yl)-3,8-diazabicyclo[3.2.1]octan-3-yl)methyl)-2H-[1,4]oxazino[2,3,4-ij]quinazolin-5(3H)-one | 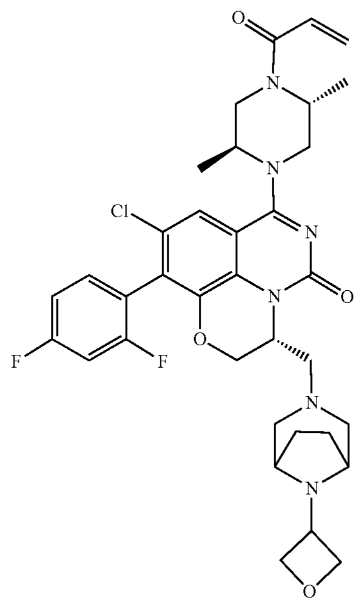 [SMILES: C=CC(=O)N1C[C@H](C)N(c2nc(=O)n3c4c(c(-c5ccc(F)cc5F)c(Cl)cc24)OC[C@H]3CN2CC3CCC(C2)N3C2COC2)C[C@H]1C] | ¹H NMR (400 MHz, CDCl₃) δ 7.41-7.39 (m, 1H), 7.30-7.27 (m, 1H), 7.03-6.93 (m, 2H), 6.63-6.51 (m, 1H), 6.41-6.33 (m, 1H), 5.78-5.74 (m, 1H), 4.96-4.85 (m, 1.5H), 4.75-4.63 (m, 4H), 4.53-4.49 (m, 2H), 4.37-4.31 (m, 1H), 4.13-3.96 (m, 2H), 3.88-3.76 (m, 1.5H), 3.67-3.46 (m, 2H), 2.99-2.98 (m, 2H), 2.82-2.41 (m, 6H), 1.81-1.62 (m, 4H), 1.35-1.22 (m, 6H). | 681.3 |
| 292 | (3R,10S)-3-((1H-pyrazol-1-yl)methyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one | 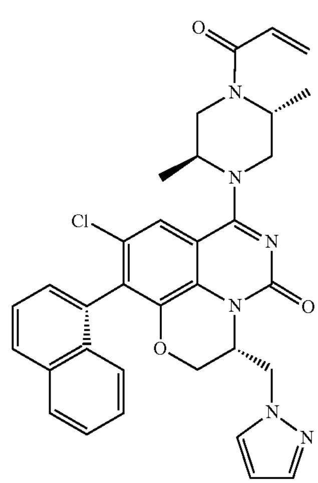 | ¹H NMR (400 MHz, CDCl₃) δ 7.97 (t, J = 7.2 Hz, 2H), 7.61-7.49 (m, 3H), 7.47-7.43 (m, 1H), 7.41-7.35 (m, 4H), 6.63-6.532 (m, 1H), 6.42-6.34 (m, 1H), 6.16-6.15 (m, 1H), 5.80-5.74 (m, 1H), 5.73 (s, 0.5H), 4.98-4.96 (m, 2H), 4.61-4.57 (m, 1H), 4.39-4.20 (m, 3H), 4.16-4.12 (m, 0.5H), 4.05-3.98 (m, 2H), 3.94-3.87 (m, 1H), 3.71-3.59 (m, 1H), 1.39-1.36 (m, 4H), 1.25-1.23 (m, 2H). | 595.3 |

-continued

Summary Table

| Ex. | Name | Structure | ¹H NMR | MS (M + H)⁺ |
|---|---|---|---|---|
| 293 | (3R)-7-((2S,5R)-4-acryloyl-2,5-dimethylpiperazin-1-yl)-9-chloro-10-(2,4-difluorophenyl)-3-((4-hydroxy-1-methylpiperidin-4-yl)methyl)-2H-[1,4]oxazino[2,3,4-ij]quinazolin-5(3H)-one | 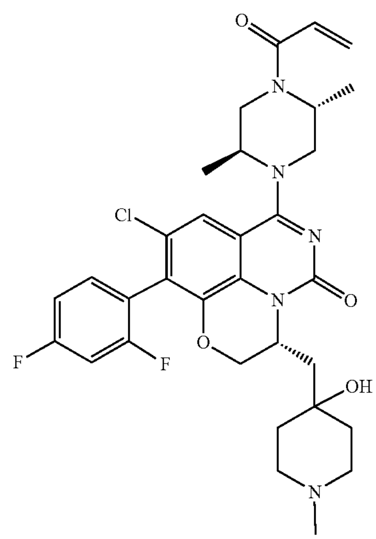 [SMILES: C=CC(=O)N1C[C@H](C)N(c2nc(=O)n3c4c(c(-c5ccc(F)cc5F)c(Cl)cc24)OC[C@H]3CC2(O)CCN(C)CC2)C[C@H]1C] | ¹H NMR (400 MHz, CDCl₃) δ 7.46-7.40 (m, 1H), 7.36-7.28 (m, 0.5H), 7.07-6.91 (m, 2.5H), 6.65-5.49 (m, 1H), 6.37 (t, J = 15.2 Hz, 1H), 5.80-5.73 (m, 1H), 5.36-5.32 (m, 0.5H), 5.13-4.88 (m, 2.5H), 4.48-4.25 (m, 2H), 4.18-3.83 (m, 4H), 3.70-3.63 (m, 1H), 3.57-3.39 (m, 1H), 2.69-2.42 (m, 4H), 2.32 (d, J = 4.0 Hz, 3H), 2.04-1.91 (m, 2H), 1.72-1.52 (m, 2H), 1.37-1.28 (m, 4H), 1.22-1.15 (m, 2H). | 628.3 |
| 294 | (3R,10R)-7-((2S,5R)-4-acryloyl-2,5-dimethylpiperazin-1-yl)-9-chloro-3-((4-methylpiperazin-1-yl)methyl)-10-(naphthalen-1-yl)-2H-[1,4]oxazino[2,3,4-ij]quinazolin-5(3H)-one | 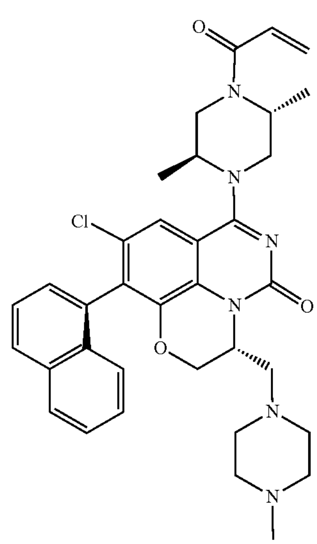 | ¹H NMR (400 MHz, CDCl₃) δ 7.97 (t, J = 9.2 Hz, 2H), 7.61 (t, J = 7.6 Hz, 1H), 7.55-7.49 (m, 2H), 7.44 (t, J = 7.2 Hz, 1H), 7.38-7.26 (m, 2H), 6.68-6.53 (m, 1H), 6.38 (t, J = 17.2 Hz, 1H), 5.78 (t, J = 8.8 Hz, 1H), 5.05-4.98 (m, 1H), 4.69-4.68 (m, 1H), 4.59 (d, J = 14.8 Hz, 1H), 4.36 (d, J = 14.8 Hz, 1H), 3.91 (d, J = 12.4 Hz, 2H), 3.71-3.53 (m, 2H), 2.61-2.17 (m, 14H), 1.38-1.31 (m, 6H). | 627.3 |

-continued

Summary Table

| Ex. | Name | Structure | ¹H NMR | MS (M + H)⁺ |
|---|---|---|---|---|
| 295 | (3R,10R)-7-((2S,5R)-4-acryloyl-2,5-dimethylpiperazin-1-yl)-9-chloro-3-((4-methylpiperazin-1-yl)methyl)-10-(naphthalen-1-yl)-2H-[1,4]oxazino[2,3,4-ij]quinazolin-5(3H)-one | 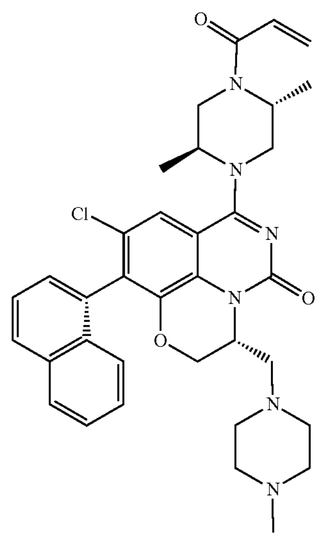 | ¹H NMR (400 MHz, CDCl₃) δ 7.96 (t, J = 10.8 Hz, 2H), 7.61 (t, J = 8.4 Hz, 1H), 7.53-7.46 (m, 2H), 7.42-7.36 (m, 3H), 6.67-6.53 (m, 1H), 6.38 (t, J = 16 Hz, 1H), 5.78 (t, J = 8.8 Hz, 1H), 5.07 (d, J = 5.2 Hz, 1H), 4.96-4.95 (m, 2H), 4.37-4.32 (m, 1H), 4.10-4.84 (m, 4H), 3.70-3.84 (m, 1H), 2.71-2.31 (m, 10H), 2.22 (s, 3H), 1.37-1.24 (m, 6H). | 627.3 |
| 296 | (3S)-7-((2S,5R)-4-acryloyl-2,5-dimethylpiperazin-1-yl)-9-chloro-10-(2,4-difluorophenyl)-3-((((S)-1-methylpyrrolidin-2-yl)methoxy)methyl)-2,3-dihydro-5H-[1,4]oxazino[2,3,4-ij]quinazolin-5-one | 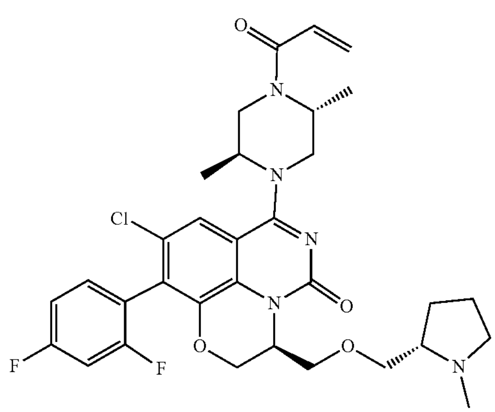 [SMILES: C=CC(=O)N1C[C@H](C)N(c2nc(=O)n3c4c(c(-c5ccc(F)cc5F)c(Cl)cc24)OC[C@@H]3COC[C@@H]2CCCN2C)C[C@H]1C] | ¹H NMR (400 MHz, CDCl₃) δ 7.44 (s, 1H), 7.32-7.20 (m, 1H), 7.03-6.93 (m, 2H), 6.67-6.51 (m, 1H), 6.37 (t, J = 15.2 Hz, 1H), 5.77 (t, J = 8.8 Hz, 1H), 5.05-5.02 (m, 0.5H), 4.97-4.77 (m, 2H), 4.69 (d, J = 11.2 Hz, 1H), 4.41-4.28 (m, 1.5H), 4.14-4.09 (m, 0.5H), 4.03-3.97 (m, 1H), 3.81-3.55 (m, 5.5H), 3.41-3.33 (m, 1.5H), 3.07-2.99 (m, 1H), 2.35 (d, J = 7.2 Hz, 3H), 2.25-2.15 (m, 1H), 1.91-1.81 (m, 1H), 1.75-1.66 (m, 2H), 1.56-1.49 (m, 1.5H), 1.43-1.32 (m, 6H). | 628.3 |
| 297 | (3R)-7-((2S,5R)-4-acryloyl-2,5-dimethylpiperazin-1-yl)-9-chloro-10-(2,4-difluorophenyl)-3-(((1-methylpiperidin-4-yl)oxy)methyl)-2H-[1,4]oxazino[2,3,4-ij]quinazolin-5(3H)-one | 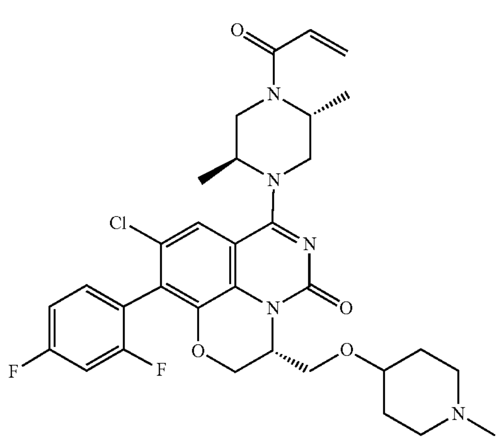 [SMILES: C=CC(=O)N1C[C@H](C)N(c2nc(=O)n3c4c(c(-c5ccc(F)cc5F)c(Cl)cc24)OC[C@H]3COC2CCN(C)CC2)C[C@H]1C] | ¹H NMR (400 MHz, CDCl₃) δ 7.41-7.38 (m, 1H), 7.29-7.24 (m, 1H), 7.03-6.93 (m, 2H), 6.65-6.51 (m, 1H), 6.37 (t, J = 16.0 Hz, 1H), 5.79-5.75 (m, 1H), 5.05-4.73 (m, 4H), 4.36-4.27 (m, 1H), 4.09-3.50 (m, 7H), 3.44-3.34 (m, 1H), 2.64-2.47 (m, 2H), 2.22 (d, J = 6.0 Hz, 3H), 2.17-2.05 (m, 2H), 1.88-1.69 (m, 3H), 1.34-1.19 (m, 6H). | 628.3 |

-continued

Summary Table

| Ex. | Name | Structure | ¹H NMR | MS (M + H)⁺ |
|---|---|---|---|---|
| 300 | (3R,10R)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one | 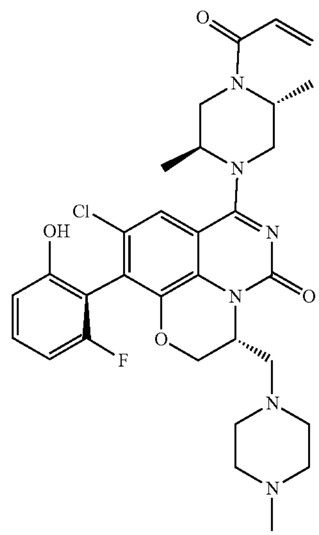 | ¹H NMR (400 MHz, CDCl₃) δ 7.43-7.42 (m, 1H), 7.28-7.23 (m, 1H), 6.74-6.68 (m, 2H), 6.65-6.50 (m, 1H), 6.38 (t, J = 8.4 Hz, 1H), 5.76 (t, J = 8.8 Hz, 1H), 4.99-4.87 (m, 1.5H), 4.65-4.62 (m, 2H), 4.31-4.25 (m, 1H), 4.05-3.98 (m, 1.5H), 3.94-3.82 (m, 2H), 3.67-3.63 (m, 0.5H), 3.55-3.52 (m, 0.5H), 2.70-2.66 (m, 2H), 2.56-2.46 (m, 8H), 2.38 (s, 3H), 1.33-1.31 (m, 4H), 1.23-1.21 (m, 2H). | 611.2 |
| 301 | (3R,10S)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one | 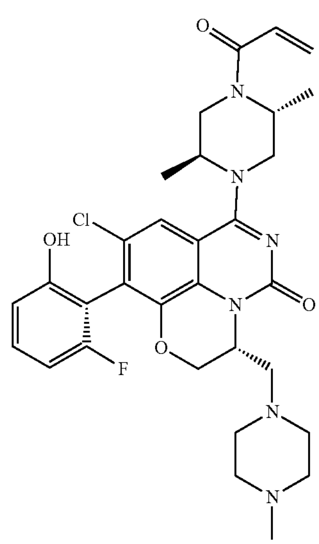 | ¹H NMR (400 MHz, CDCl₃) δ 7.44-7.41 (m, 1H), 7.33-7.27 (m, 1H), 6.82-6.75 (m, 2H), 6.62-6.51 (m, 1H), 6.38 (t, J = 12.0 Hz, 1H), 5.77 (t, J = 6.8 Hz, 1H), 5.00-4.95 (m, 0.5H), 4.92-4.83 (m, 1H), 4.75-4.72 (m, 2H), 4.34-4.30 (m, 1H), 4.06-4.02 (m, 1.5H), 3.97-3.76 (m, 2H), 3.67-3.64 (m, 0.5H), 3.53-3.50 (m, 0.5H), 2.82-2.78 (m, 2H), 2.72-2.52 (m, 7.5H), 2.35 (s, 3H), 1.35-1.29 (m, 4H), 1.25-1.20 (m, 2H). | 611.2 |

-continued

Summary Table

| Ex. | Name | Structure | ¹H NMR | MS (M + H)⁺ |
|---|---|---|---|---|
| 305 | (3S,10R)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one | 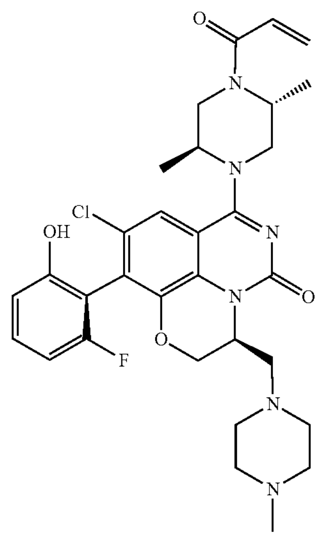 | ¹H NMR (400 MHz, CDCl₃) δ 7.46 (s, 1H), 7.34-7.26 (m, 1H), 6.81-6.77 (m, 2H), 6.67-6.51 (m, 1H), 6.38 (t, J = 15.2, 1H), 5.78 (t, J = 10.4, 1H), 4.99-4.65 (m, 4H), 4.36-4.33 (m, 1.5H), 4.11-3.99 (m, 1.5H), 3.81-3.65 (m, 2.5H), 3.71-3.55 (m, 0.5H), 2.84-2.55 (m, 10H), 2.39 (s, 3H), 1.38-1.26 (m, 6H). | 611.2 |
| 306 | (3R,10R)-3-((1H-pyrazol-1-yl)methyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one | 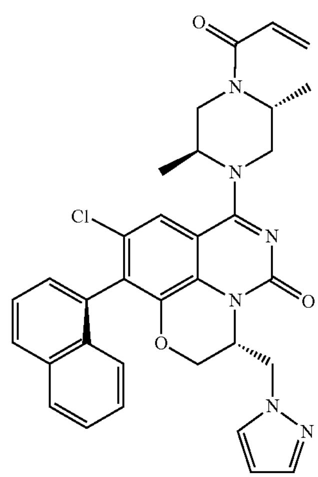 | ¹H NMR (400 MHz, CDCl₃) δ 7.98-7.93 (m, 2H), 7.61 (t, J = 7.6 Hz, 1H), 7.52-7.49 (m, 3H), 7.43-7.39 (m, 3H), 7.35-7.32 (m, 1H), 6.60-6.53 (m, 1H), 6.39 (t, J = 15.6 Hz, 1H), 6.24-6.23 (m, 1H), 5.80-5.76 (m, 1H), 5.12-4.91 (m, 2.5H), 4.57-4.54 (m, 1H), 4.42-4.33 (m, 3H), 4.17-4.14 (m, 0.5H), 4.07-3.90 (m, 3H), 3.72-3.56 (m, 1H), 1.39-1.38 (m, 4H), 1.28-1.25 (m, 2H). | 595.2 |
| 307 | (2S)-N-(((3R)-7-((2S,5R)-4-acryloyl-2,5-dimethylpiperazin-1-yl)-9-chloro-10-(2,4-difluorophenyl)-5-oxo-3,5-dihydro-2H-[1,4]oxazino[2,3,4-ij]quinazolin-3-yl)methyl)-N-cyclopropyl-1-methylpyrrolidine-2-carboxamide | 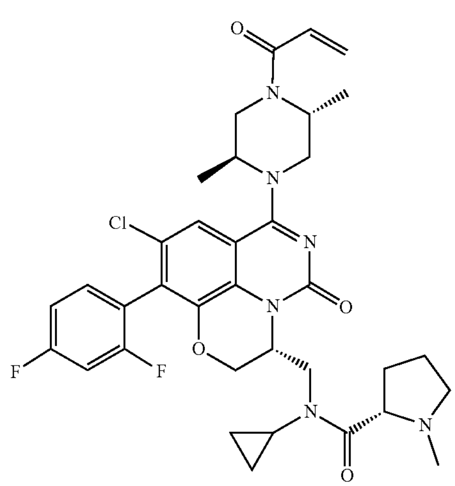 [SMILES: C=CC(=O)N1C[C@H](C)N(c2nc(=O)n3c4c(c(-c5ccc(F)cc5F)c(Cl)cc24)OC[C@H]3CN(C(=O)[C@@H]2CCCN2C)C2CC2)C[C@H]1C] | ¹H NMR (400 MHz, CDCl₃) δ 7.45-7.44 (m, 1H), 7.26-7.22 (m, 1H), 7.02-6.93 (m, 2H), 6.63-6.51 (m, 1H), 6.37 (t, J = 15.6 Hz, 1H), 5.77 (t, J = 7.6 Hz, 1H), 5.35-5.34 (m, 1H), 5.15-4.86 (m, 1.5H), 4.55-4.46 (m, 1H), 4.37-4.33 (m, 1H), 4.12-3.98 (m, 2H), 3.88-3.85 (m, 2H), 3.71-3.60 (m, 1.5H), 3.50-3.46 (m, 1H), 3.24-3.21 (m, 1H), 2.93-2.80 (m, 1H), 2.47-2.36 (m, 3H), 2.24-2.14 (m, 1H), 2.04-1.75 (m, 3H), 1.36-1.24 (m, 8H), 0.88-0.72 (m, 4H). | 681.2 |

-continued

Summary Table

| Ex. | Name | Structure | ¹H NMR | MS (M + H)⁺ |
|---|---|---|---|---|
| 308 | (3S,10S)-7-((2S,5R)-4-acryloyl-2,5-dimethylpiperazin-1-yl)-9-chloro-3-((4-methylpiperazin-1-yl)methyl)-10-(naphthalen-1-yl)-2,3-dihydro-5H-[1,4]oxazino[2,3,4-ij]quinazolin-5-one | 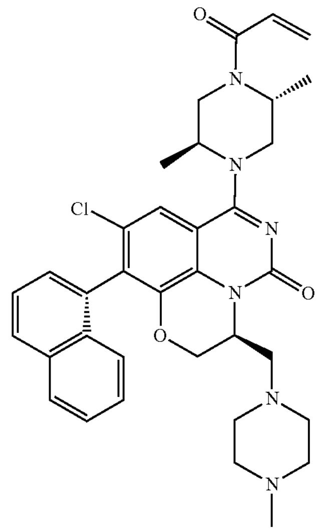 | ¹H NMR (400 MHz, CDCl₃) δ 7.96 (t, J = 8.8 Hz, 2H), 7.61 (t, J = 7.2 Hz, 1H), 7.54-7.50 (m, 2H), 7.44-7.40 (m, 2H), 7.32 (t, J = 9.2 Hz, 1H), 6.68-6.52 (m, 1H), 6.38 (t, J = 15.6 Hz, 1H), 5.78 (t, J = 7.2 Hz, 1H), 5.04-4.96 (m, 1H), 4.92-4.83 (m, 0.5H), 4.80-4.70 (m, 1H), 4.56-4.52 (m, 1H), 4.42-4.31 (m, 1.5H), 4.14-4.11 (m, 0.5H), 3.90-3.84 (m, 2H), 3.77-3.67 (m, 1H), 3.45-3.42 (m, 0.5H), 2.79-2.63 (m, 2H), 2.60-2.42 (m, 5H), 2.40-2.29 (m, 3H), 2.22 (s, 3H), 1.44-1.40 (m, 4H), 1.37-1.26 (m, 2H). | 627.3 |
| 309 | (3S,10R)-7-((2S,5R)-4-acryloyl-2,5-dimethylpiperazin-1-yl)-9-chloro-3-((4-methylpiperazin-1-yl)methyl)-10-(naphthalen-1-yl)-2,3-dihydro-5H-[1,4]oxazino[2,3,4-ij]quinazolin-5-one | 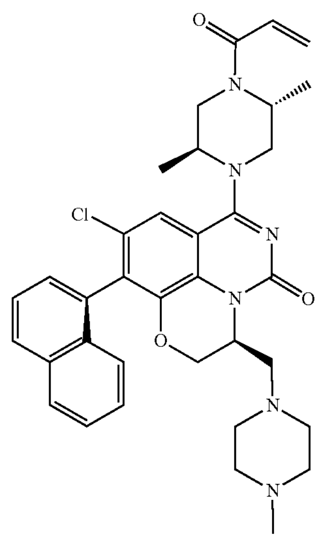 | ¹H NMR (400 MHz, CDCl₃) δ 7.96 (t, J = 9.2 Hz, 2H), 7.61 (t, J = 7.6 Hz, 1H), 7.54-7.50 (m, 2H), 7.44-7.39 (m, 2H), 7.36 (d, J = 6.8 Hz, 1H), 6.68-6.52 (m, 1H), 6.38 (t, J = 15.2 Hz, 1H), 5.78 (t, J = 8.8 Hz, 1H), 5.04-4.72 (m, 3H), 4.57 (d, J = 11.6 Hz, 1H), 4.42-4.35 (m, 1H), 4.19-4.16 (m, 0.5H), 3.95-3.92 (m, 1H), 3.84-3.78 (m, 1H), 3.71-3.68 (m, 1H), 3.39-3.36 (m, 0.5H), 2.74-2.62 (m, 2H), 2.59-2.48 (m, 5H), 2.38-2.29 (m, 3H), 2.23 (s, 3H), 1.47-1.37 (m, 6H). | 627.3 |
| 310 | (2S)-N-(((3S)-7-((2S,5R)-4-acryloyl-2,5-dimethylpiperazin-1-yl)-9-chloro-10-(2,4-difluorophenyl)-5-oxo-2,3-dihydro-5H-[1,4]oxazino[2,3,4-ij]quinazolin-3-yl)methyl)-N-cyclopropyl-1-methylpyrrolidine-2-carboxamide | 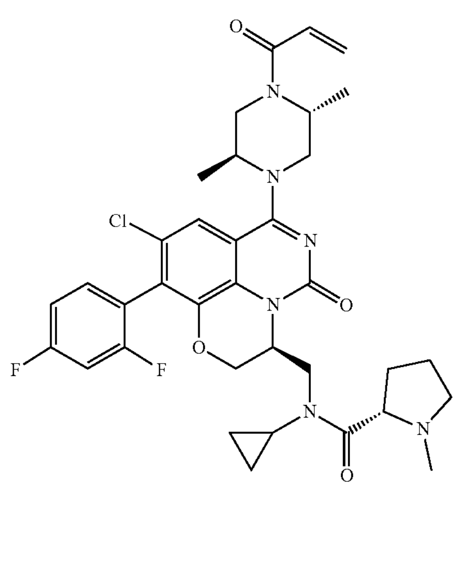 [SMILES: C=CC(=O)N1C[C@H](C)N(c2nc(=O)n3c4c(c(-c5ccc(F)cc5F)c(Cl)cc24)OC[C@@H]3CN(C(=O)[C@@H]2CCCN2C)C2CC2)C[C@H]1C] | ¹H NMR (400 MHz, CDCl₃) δ 7.46 (s, 1H), 7.39-7.19 (m, 1H), 7.04-6.91 (m, 2H), 6.67-6.51 (m, 1H), 6.37 (t, J = 15.6 Hz, 1H), 5.78 (t, J = 7.6 Hz, 1H), 5.09-4.85 (m, 2H), 4.53-4.29 (m, 2H), 4.09-4.00 (m, 1H), 3.84-3.55 (m, 4H), 3.21-3.13 (m, 1H), 2.84-2.78 (m, 1H), 2.38-2.29 (m, 3H), 2.24-2.18 (m, 1H), 2.02-1.91 (m, 2H), 1.86-1.76 (m, 2H), 1.43-1.26 (m, 9H), 0.93-0.78 (m, 4H). | 681.2 |

-continued

Summary Table

| Ex. | Name | Structure | ¹H NMR | MS (M + H)⁺ |
|---|---|---|---|---|
| 314 | (3S,10S)-7-((2S,5R)-4-acryloyl-2,5-dimethylpiperazin-1-yl)-9-chloro-10-(2-fluoro-6-hydroxyphenyl)-3-((4-methylpiperazin-1-yl)methyl)-2,3-dihydro-5H-[1,4]oxazino[2,3,4-ij]quinazolin-5-one | 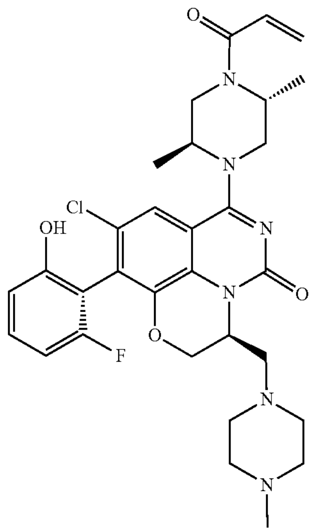 | ¹H NMR (400 MHz, CDCl₃) δ 7.28 (d, J = 4.4 Hz, 1H), 7.15 (t, J = 8.0 Hz, 1H), 6.92 (d, J = 8.4 Hz, 1H), 6.63 (t, J = 8.8 Hz, 1H), 6.59-6.43 (m, 1H), 6.29 (t, J = 15.6 Hz, 1H), 5.23 (s, 1H), 4.75-4.62 (m, 2H), 4.49 (d, J = 11.2 Hz, 1H), 3.68-3.54 (m, 2H), 3.23-3.16 2(m, 1H), 2.91-2.63 (m, 10H), 2.59 (s, 3H), 1.31-1.31 (m, 6H). | 611.2 |
| 317 | (3R,10R)-3-((1H-imidazol-1-yl)methyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one | 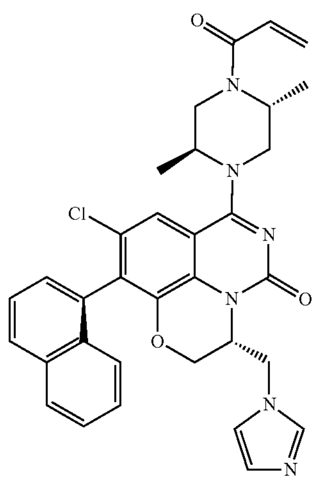 | ¹H NMR (400 MHz, CDCl₃) δ 7.98-7.93 (m, 2H), 7.74 (br, 1H), 7.64 (t, J = 7.6 Hz, 1H), 7.55-7.49 (m, 2H), 7.42-7.37 (m, 2H), 7.30-7.28 (m, 1H), 7.07 (br, 1H), 7.02-7.00 (m, 1H), 6.59-6.52 (m, 1H), 6.39 (t, J = 14.8 Hz, 1H), 5.79 (t, J = 6.0 Hz, 1H), 5.14 (br, 0.5H), 5.00 (br, 1H), 4.84 (br, 1H), 4.43-3.91 (m, 7.5H), 3.72-3.64 (m, 1H), 1.42-1.37 (m, 4H), 1.33-1.28 (m, 2H). | 595.2 |
| 318 | (3R,10S)-3-((1H-imidazol-1-yl)methyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one | 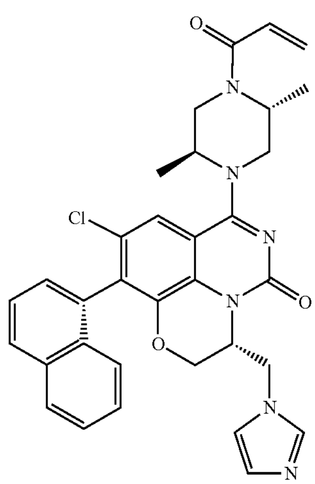 | ¹H NMR (400 MHz, CDCl₃) δ 7.98 (t, J = 8.0 Hz, 2H), 7.62-7.45 (m, 5H), 7.37-7.35 (m, 2H), 7.03 (s, 1H), 6.94 (s, 1H), 6.62-6.52 (m, 1H), 6.39 (t, J = 14.4 Hz, 1H), 5.78 (t, J = 5.6 Hz, 1H), 5.16 (br, 0.5H), 4.99-4.86 (m, 2H), 4.46-4.35 (m, 2H), 4.11-3.91 (m, 5.5H), 3.72-3.61 (m, 1H), 1.48-1.33 (m, 4H), 1.28-1.22 (m, 2H). | 595.2 |

| Ex. | Name | Structure | ¹H NMR | MS (M + H)⁺ |
|---|---|---|---|---|
| 319 | (3R,10S)-3-((1H-pyrazol-1-yl)methyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one | 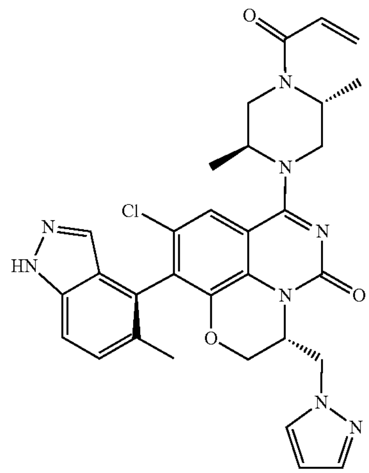 | ¹H NMR (400 MHz, CDCl₃) δ 10.09 (m, 1H), 7.59 (s, 1H), 7.53-7.50 (m, 2H), 7.44-7.36 (m, 2H), 7.26 (m, 1H), 6.67-6.52 (m, 1H), 6.42-6.34 (m, 1H), 6.20-6.19 (m, 1H), 5.80-5.76 (m, 1H), 5.11-4.98 (m, 2.5H), 4.58-4.55 (m, 1H), 4.44-4.14 (m, 3H), 4.06-3.84 (m, 4H), 3.71-3.54 (m, 1.5H), 2.20 (s, 3H), 1.40-1.39 (m, 4H), 1.27-1.25 (d, J = 9.2 Hz, 2H). | 599.3 |
| 320 | (3R,10R)-3-((1H-pyrazol-1-yl)methyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one | 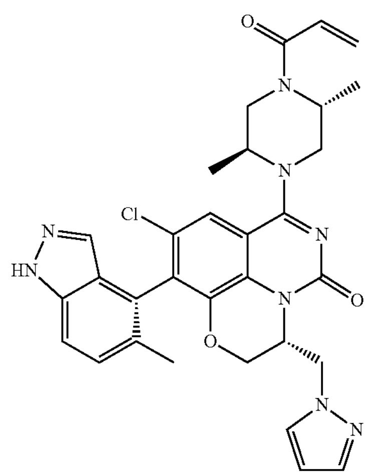 | ¹H NMR (400 MHz, CDCl₃) δ 10.07 (m, 1H), 7.57 (m, 2H), 7.52-7.50 (m, 2H), 7.46 (s, 1H), 7.41-7.39 (d, J = 8.4 Hz, 1H), 6.63-6.53 (m, 1H), 6.43-6.35 (m, 1H), 6.27-6.26 (m, 1H), 5.80-5.76 (m, 1H), 5.10-4.92 (m, 2.5H), 4.58-4.55 (m, 1H), 4.43-4.27 (m, 3H), 4.16-3.91 (m, 4H), 3.72-3.56 (m, 1.5H), 2.28 (s, 3H), 1.39-1.37 (d, J = 6.8 Hz, 4H), 1.28-1.27 (d, J = 6.4 Hz, 2H). | 599.3 |
| 335 | (3R)-7-((2S,5R)-4-acryloyl-2,5-dimethylpiperazin-1-yl)-9-chloro-10-(2,4-difluorophenyl)-3-((((S)-1-methylpyrrolidin-3-yl)oxy)methyl)-2H-[1,4]oxazino[2,3,4-ij]quinazolin-5(3H)-one | 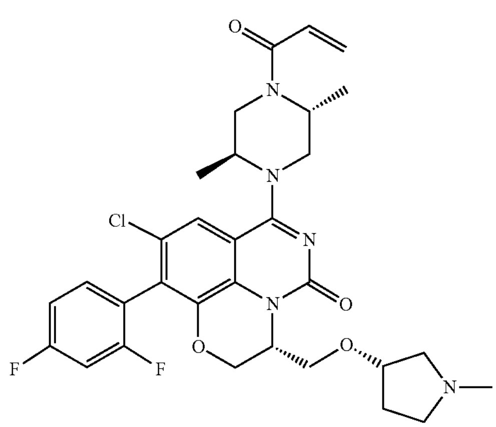 | ¹H NMR (400 MHz, CDCl₃) δ 7.7.38 (m, 1H), 7.28-7.26 (m, 1H), 7.01-6.95 (m, 2H), 6.57-6.51 (m, 1H), 6.41-6.33 (m, 1H), 5.78-5.75 (m, 1H), 5.05-4.78 (m, 2H), 4.75-4.72 (m, 2H), 4.31-4.28 (m, 1H), 4.10-4.07 (m, 3H), 3.99-3.86 (m, 2H), 3.72-3.59 (m, 3H), 3.45-3.40 (m, 1H), 2.67-2.64 (m, 2.5H), 2.35 (s, 3H), 2.07-2.03 (m, 1.5H), 1.32-1.21 (m, 6H). | 614.2 |

Summary Table
| Ex. | Name | Structure | ¹H NMR | MS (M + H)⁺ |
|---|---|---|---|---|
| 336 | (3S)-7-((2S,5R)-4-acryloyl-2,5-dimethylpiperazin-1-yl)-9-chloro-10-(2,4-difluorophenyl)-3-((((S)-1-methylpyrrolidin-3-yl)oxy)methyl)-2H-[1,4]oxazino[2,3,4-ij]quinazolin-5(3H)-one | 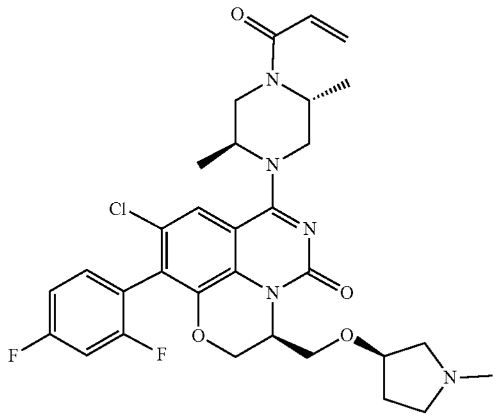 [SMILES: C=CC(=O)N1C[C@H](C)N(c2nc(=O)n3c4c(c(-c5ccc(F)cc5F)c(Cl)cc24)OC[C@@H]3CO[C@@H]2CCN(C)C2)C[C@H]1C] | ¹H NMR (400 MHz, CDCl₃) δ 7.43-7.41 (m, 1H), 7.31-7.28 (m, 0.4H), 7.22-7.20 (m, 0.6H), 7.03-6.91 (m, 2H), 6.66-6.50 (m, 1H), 6.37 (t, J = 15.6 Hz, 1H), 5.77 (t, J = 9.2 Hz, 1H), 5.01-4.82 (m, 2.5H), 4.76-4.68 (m, 1H), 4.40-4.29 (m, 1H), 4.15-3.94 (m, 2.5H), 3.79-3.60 (m, 3H), 3.48-3.29 (m, 2H), 2.68-2.61 (m, 3H), 2.37-2.29 (m, 4H), 2.07-1.99 (m, 1H), 1.79-1.62 (m, 1H), 1.44-1.32 (m, 6H). | 614.2 |
Syntheses of Intermediates
Reaction Scheme
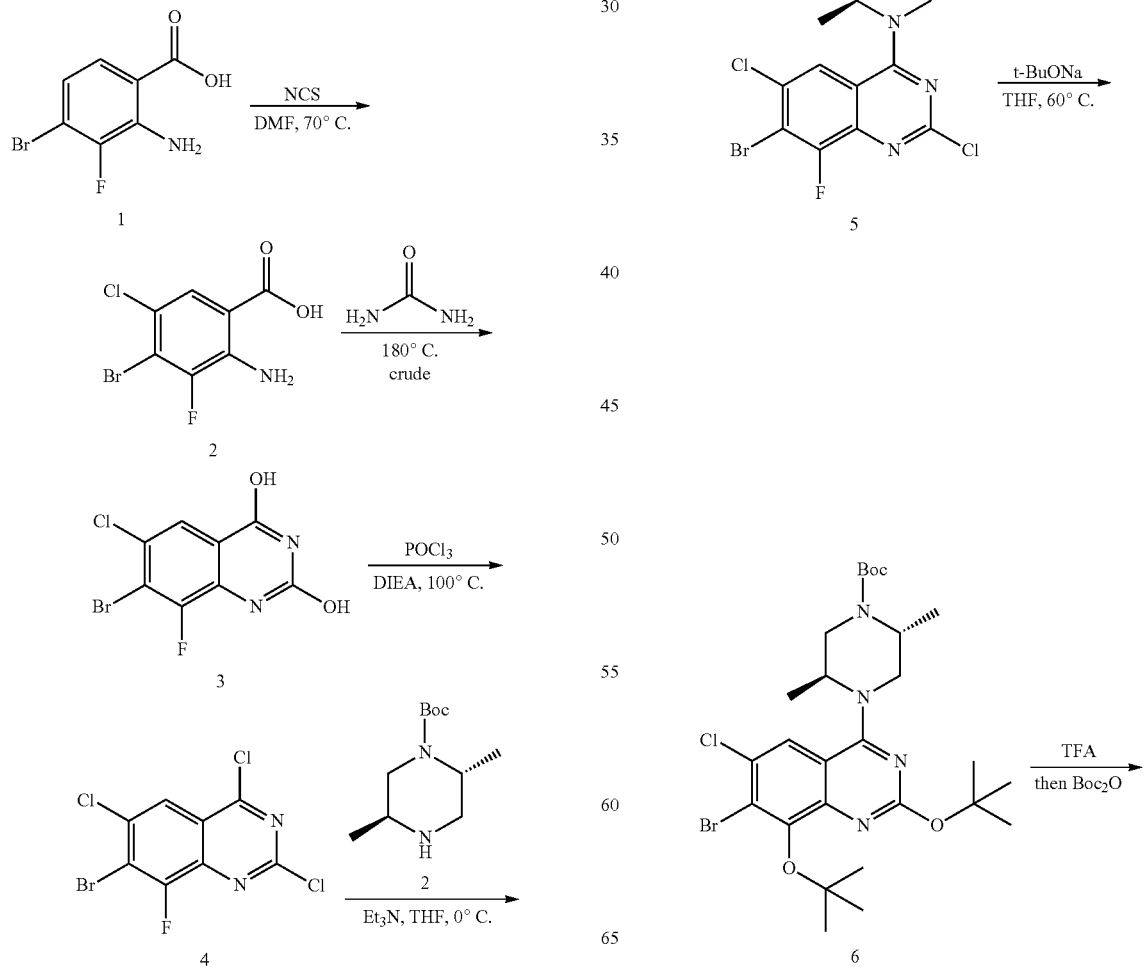

-continued

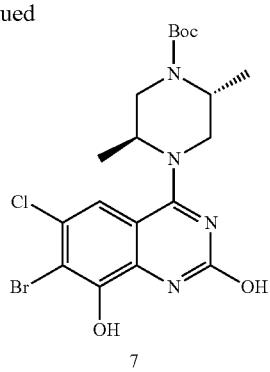

7

2-amino-4-bromo-5-chloro-3-fluorobenzoic acid (2)

To a solution of 2-amino-4-bromo-3-fluorobenzoic acid (100 g, 0.43 mol) in DMF (800 mL) was added NCS (68 g, 0.51 mol). Then the mixture was heated to 70° C. for 16 hours. After completion, the mixture was quenched with aqueous $H_2O$ (1.5 L) and extracted with EA (2 L), dried with $Na_2SO_4$ and concentrated to afford product (139 g, crude) as a grayness solid. LC-MS: m/z 268.1[M–H]$^+$

7-bromo-6-chloro-8-fluoroquinazoline-2,4-diol (3)

The mixture of 2-amino-4-bromo-5-chloro-3-fluorobenzoic acid (139 g, 0.51 mol) and urea (260 g, 4.33 mol) was heated to 180° C. for 6 h. After completion, the mixture was quenched with aqueous $H_2O$ (1.5 L), filtered through a Celite pad, and the filtrate was concentrated to give the crude product (130 g, crude) as a grayness solid. LC-MS: m/z 293.1[M–H]$^+$

7-bromo-2,4,6-trichloro-8-fluoroquinazoline (4)

The mixture of 7-bromo-6-chloro-8-fluoroquinazoline-2,4-diol (130 g, 0.51 mol) and $POCl_3$ (800 mL) was heated to 120° C. for 16 hours. After completion, the mixture was quenched with aqueous $H_2O$ (1.5 L), filtered through a Celite pad, and the filtrate was concentrated and purified by silica column with PE/EA=4:1 to afford product (59 g, 35% yield:) as a yellow solid. LC-MS: m/z 311.1 [M–H–Cl]$^+$

(2R,5S)-tert-butyl-4-(7-bromo-2,6-dichloro-8-fluoroquinazolin-4-yl)-2,5-dimethylpiperazine-1-carboxylate (5)

To a cooled mixture of 7-bromo-2,4,6-trichloro-8-fluoroquinazoline (25 g, 75.76 mmol) and $Et_3N$ (15.3 g, 151.5 mmol) in THF (200 mL) was added (2R,5S)-tert-butyl 2,5-dimethylpiperazine-1-carboxylate (16.2 g, 75.76 mmol) at 0° C. The mixture was stirred at room temperature for 4 hours. After completion, the mixture was dissolved with EtOAc (500 mL), washed with water (300 mL×3), dried over $Na_2SO_4$, filtered and concentrated to afford desired product (35.78 g, yield: 93%) as yellow solid, which was used to next step without further purification. LC-MS: m/z 509.3[M+H].

(2R,5S)-tert-butyl-4-(7-bromo-2,6-di-tert-butoxy-6-chloroquinazolin-4-yl)-2,5-dimethyl-piperazine-1-carboxylate (6)

To a solution of (2R,5S)-tert-butyl 4-(7-bromo-2,6-dichloro-8-fluoroquinazolin-4-yl)-2,5-dimethyl piperazine-1-carboxylate (35.78 g, 70.4 mmol) in dry THF (180 mL) was added t-BuONa (16.9 g, 176.08 mmol). Then the mixture was heated to 60° C. for 4 hours. After completion, the mixture was quenched with aqueous $NH_4Cl$ and extracted with EtOAc, dried with $Na_2SO_4$ and concentrated. The residue was purified by silica using a mixture of PE:EA (15:1) as eluent to afford product (33 g, 78% yield) as a yellow solid. LC-MS: m/z 601.5[M+H].

(2R,5S)-tert-butyl-4-(7-bromo-6-chloro-2,8-dihydroxyquinazolin-4-yl)-2,5-dimethyl piperazine-1-carboxylate (7)

To a solution of (2R,5S)-tert-butyl-4-(7-bromo-2,8-di-tert-butoxy-6-chloroquinazolin-4-yl)-2,5-dimethylpiperazine-1-carboxylate (33 g, 55.0 mmol) in DCM (70 mL) was added TFA (70 mL), the mixture was stirred at 25° C. for 3 hours. After completion, the mixture was concentrated under reduce pressure to afford the crude 7-bromo-6-chloro-4-((2S,5R)-2,5-dimethylpiperazin-1-yl) quinazoline-2,8-diol (30 g), which was used in the next step without further purification. To a solution of 7-bromo-6-chloro-4-((2S,5R)-2,5-dimethylpiperazin-1-yl)quinazoline-2,8-diol (33 g, 85.05 mmol) in DCM (150 mL) was added $(Boc)_2O$ (18.54 g, 85.05 mmol), the mixture was stirred at rt for 16 hours. After completion, the mixture was concentrated. The residue was purified by silica with a mixture of DCM/MeOH (5% $NH_3$) (40:1) to afford the desired product (24 g, 58% yield) as light green solid. LC-MS: m/z 489.3[M+H].

Reaction Scheme

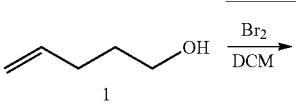

1

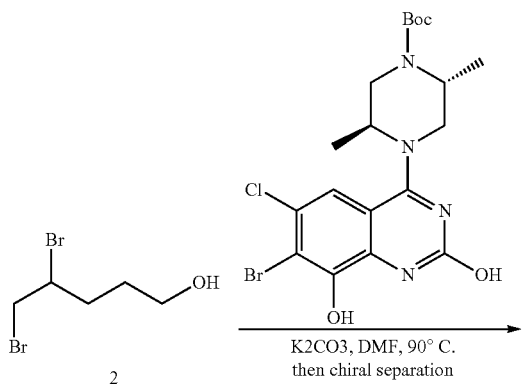

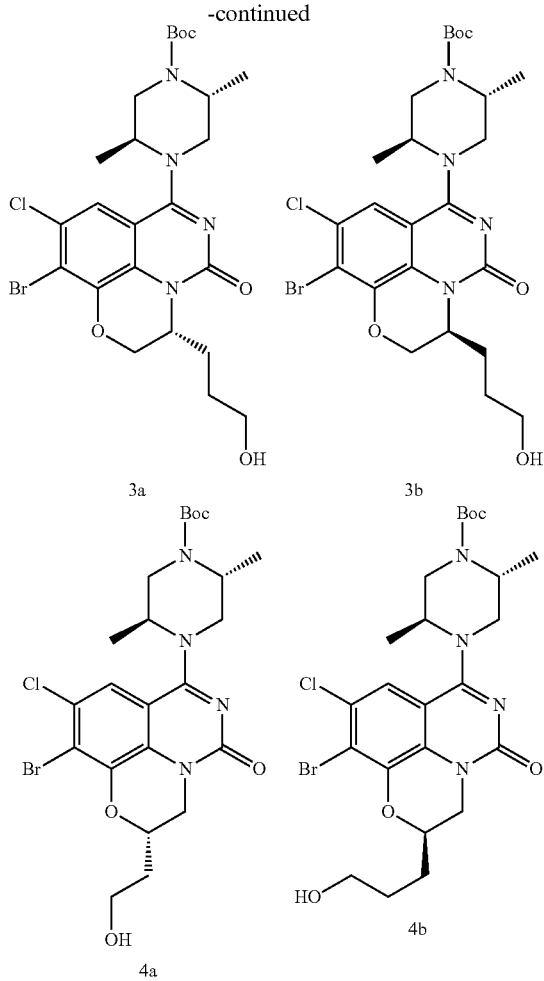

3a

3b

4a

4b

4,5-dibromopentan-1-ol (2)

To a cooled mixture of pent-4-en-1-ol (25 g, 0.29 mol) in DCM (180 mL) was added $Br_2$ (50.5 g, 0.32 mol) at 0° C. The mixture was stirred at 0° C. for 20 minutes. After completion, the mixture was quenched by $Na_2S_2O_3$ (aq.), then extracted with DCM, concentrated and the residue was purified by column with using PE/EA (10:1) as eluent to afford the desired product (44 g, 63% yield) as a colorless oil.

(2R,5S)-tert-butyl 4-((R)-10-bromo-9-chloro-3-(3-hydroxypropyl)-5-oxo-3,5-dihydro-2H-[1,4] oxazino[2,3,4-ij]quinazolin-7-yl)-2,5-dimethylpiperazine-1-carboxylate (3a)

The residue ((2R,5S)-tert-butyl-4-(7-bromo-6-chloro-2,8-dihydroxyquinazolin-4-yl)-2,5-dimethyl piperazine-1-carboxylate (15 g, 30.73 mmol) was dissolved in DMF (180 ml), $K_2CO_3$ (16.9 g, 122.92 mmol) was added followed by 4,5-dibromopentan-1-ol (22.5 g, 92.21 mmol). Then the mixture was heated to 90° C. overnight. After completion, the mixture was diluted with $H_2O$, then extracted with EA, washed with water and brine, concentrated and purified by column using a mixture of DCM/MeOH (30:1) as eluent to afford product (12.98 g, 31% yield) as a yellow solid. LC-MS: m/z 571.0[M+H]⁺.

Above racemic mixture was dissolved with MeOH (15 mL) and separated by chiral Prep. HPLC (separation condition: Column: AD-H 5 μm 20×250 mm; Mobile Phase: HEP:IPA (0.1% DEA)=70:30 at 15 mL/min; Temp: 25° C.; Wavelength: 254 nm) to afford the title compounds (3.26 g, 25% yield, 100% ee); Chiral HPLC Analytical: on; AD-H was using 5 μm 4.6×250 mm column, Mobile Phase: HEP IPA (0.1% DEA)=70:30 at 1 mL/min; Temp: 25° C.; Wavelength: 254 nm).

T. Example 270

(3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one Synthetic Scheme

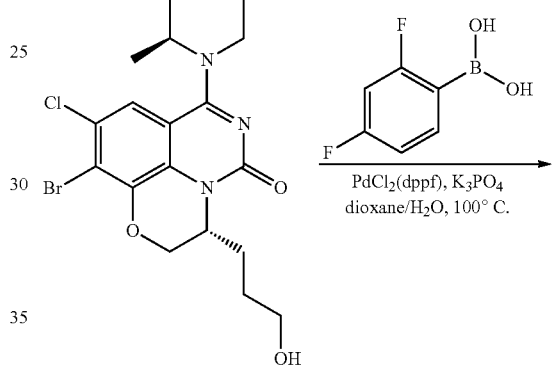

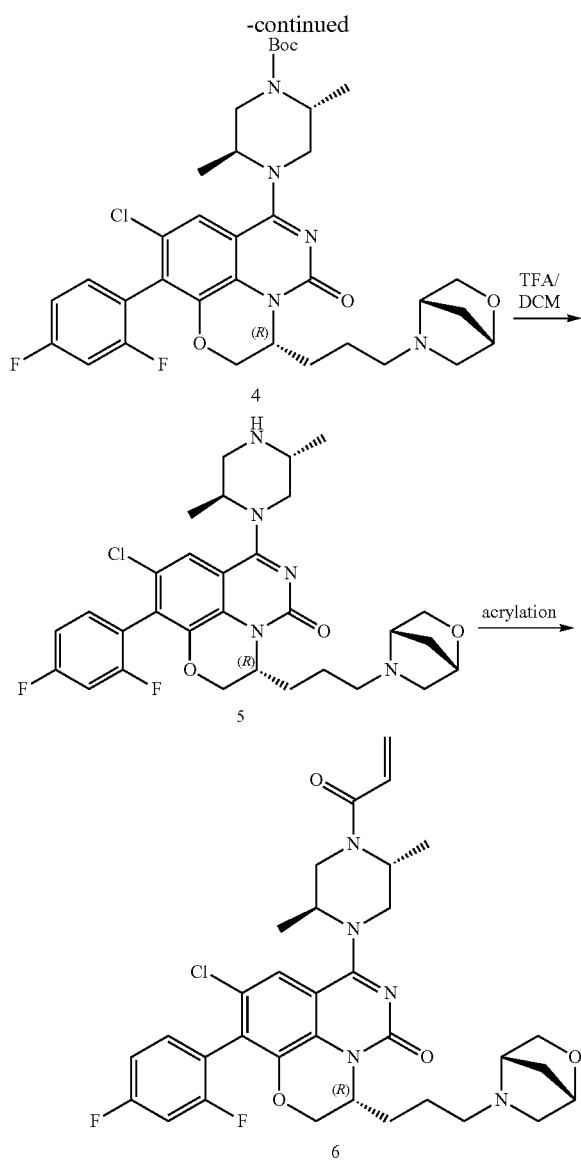

(2R,5S)-tert-butyl4-((3R)-9-chloro-10-(2,4-difluorophenyl)-3-(3-hydroxypropyl)-5-oxo-3,5-dihydro-2H-[1,4]oxazino[2,3,4-ij]quinazolin-7-yl)-2,5-dimethylpiperazine-1-carboxylate (2)

The mixture of (S)-benzyl (2R,5S)-tert-butyl 4-((R)-10-bromo-9-chloro-3-(3-hydroxypropyl)-5-oxo-3,5-dihydro-2H-[1,4]oxazino[2,3,4-ij]quinazolin-7-yl)-2,5-dimethylpiperazine-1-carboxylate (1.2 g, 2.10 mmol), (2,4-difluorophenyl)boronic acid (992 mg, 6.31 mmol), Pd(dppf)Cl$_2$ (307 mg, 0.42 mmol) and K$_3$PO$_4$ (2.2 g, 10.50 mmol) in a mixture of dioxane (20 mL) and H$_2$O (4 mL) was heated at 85° C. under nitrogen atmosphere for 3 hours. The reaction mixture was concentrated, and the residue was purified by silica gel column chromatography (dichloromethane/methanol=30/1) to give the crude product (1.15 g, 90% yield) as brown solid. LC-MS: m/z 605.2 [M+H]$^+$ (2R,5S)-tert-butyl 4-((3R)-9-chloro-10-(2,4-difluorophenyl)-5-oxo-3-(3-oxopropyl)-3,5-dihydro-2H-[1,4]oxazino[2,3,4-ij]quinazolin-7-yl)-2,5-dimethylpiperazine-1-carboxylate (3)

To a mixture of (2R,5S)-tert-butyl4-((3R)-9-chloro-10-(2,4-difluorophenyl)-3-(3-hydroxypropyl)-5-oxo-3,5-dihydro-2H-[1,4]oxazino[2,3,4-ij]quinazolin-7-yl)-2,5-dimethylpiperazine-1-carboxylate (1.15 g, 1.9 mmol) in DCM (20 mL) was added Dess-martin reagent (1.61 g, 3.8 mmol), the mixture was stirred at 20° C. under nitrogen atmosphere for 3 hours, concentrated, and the residue was purified by silica gel column chromatography (dichloromethane/methanol=30/1) to give the desired product (1.1 g, 96% yield) as yellow solid. LC-MS: m/z 603.2 [M+H]$^+$ (2R,5S)-tert-butyl-4-((3R)-3-(3-((1S,4S)-2-oxa-5-azabicyclo[2.2.1]heptan-5-yl)propyl)-9-chloro-10-(2,4-difluorophenyl)-5-oxo-3,5-dihydro-2H-[1,4]oxazino[2,3,4-ij]quinazolin-7-yl)-2,5-dimethylpiperazine-1-carboxylate (4)

To a mixture of (2R,5S)-tert-butyl-4-((3R)-9-chloro-10-(2,4-difluorophenyl)-5-oxo-3-(3-oxopropyl)-3,5-dihydro-2H-[1,4]oxazino[2,3,4-ij]quinazolin-7-yl)-2,5-dimethylpiperazine-1-carboxylate (210 mg, 0.34 mmol) and (1S,4S)-2-oxa-5-azabicyclo[2.2.1]heptane (70 mg, 0.68 mmol) in DCM was added sodium cyanoborohydride (43 mg, 0.68 mmol). The mixture was stirred at 20° C. for 2 hours and concentrated. The residue was purified by silica gel column chromatography (dichloromethane/methanol=30/1) to give the product (330 mg, 78% yield) as yellow solid. LC-MS: m/z 686.2 [M+H]$^+$ (3R)-3-(3-((1S,4S)-2-oxa-5-azabicyclo[2.2.1]heptan-5-yl)propyl)-9-chloro-10-(2,4-difluorophenyl)-7-((2S,5R)-2,5-dimethylpiperazin-1-yl)-2H-[1,4]oxazino[2,3,4-ij]quinazolin-5(3H)-one (5)

The solution of (2R,5S)-tert-butyl-4-((3R)-3-(3-((1S,4S)-2-oxa-5-azabicyclo[2.2.1] heptan-5-yl)propyl)-9-chloro-10-(2,4-difluorophenyl)-5-oxo-3,5-dihydro-2H-[1,4]oxazino[2,3,4-ij]quinazolin-7-yl)-2,5-dimethylpiperazine-1-carboxylate (142 mg, 0.21 mmol) in DCM/TFA (3 mL/1 mL) was stirred at 20° C. for 1 hour, concentrated and concentrated reduced pressure to give the crude product as a TFA salt.

(3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one (6)

To a mixture of (3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one (110 mg, 0.25 mmol) and triethyl amine (50 mg, 0.50 mmol) in dichloromethane (3 mL) was added acrylic anhydride (28 mg, 0.23 mmol) at 0° C. The mixture was stirred for 1 hour and then concentrated. The residue was purified by prep-HPLC to afford the product (119 mg, 48% yield) as white solid. LC-MS: m/z 640.2 [M+H]$^+$.

Table of examples

| Ex. # | Name | Structure | $^1$H NMR | MS (M + H)$^+$ |
|---|---|---|---|---|
| 215 | (3S)-7-((2S,5R)-4-acryloyl-2,5-dimethylpiperazin-1-yl)-9-chloro-10-(2,4-difluorophenyl)-3-(3-morpholinopropyl)-2,3-dihydro-5H-[1,4]oxazino[2,3,4-ij]quinazolin-5-one | 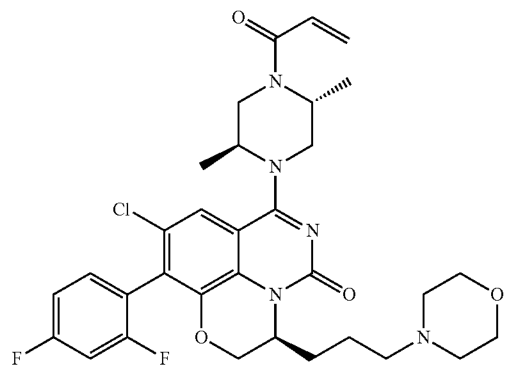 [SMILES: C=CC(=O)N1C[C@H](C)N(c2nc(=O)n3c4c(c(-c5ccc(F)cc5F)c(Cl)cc24)OC[C@@H]3CCCN2CCOCC2)C[C@H]1C] | $^1$H NMR (400 MHz, CDCl$_3$) δ 7.44-7.40 (m, 1H), 7.28-7.24 (m, 1H), 7.04-6.92 (m, 2H), 6.48-6.51 (m, 1H), 6.37 (t, J = 15.2 Hz, 1H), 5.79-5.75 (m, 1H), 5.03-4.89 (m, 1.5H), 4.70-4.69 (m, 1H), 4.49-4.46 (m, 1H), 4.31-4.29 (m, 1H), 4.10-4.05 (m, 1.5H), 3.92-3.86 (m, 2H), 3.73-3.54 (m, 5H), 2.45-2.35 (m, 4H), 1.84-1.71 (m, 2H), 1.65-1.60 (m, 4H), 1.43-1.20 (m, 6H). | 628.3 |
| 216 | (3R)-7-((2S,5R)-4-acryloyl-2,5-dimethylpiperazin-1-yl)-9-chloro-10-(5-chloro-2-fluorophenyl)-3-(3-morpholinopropyl)-2,3-dihydro-5H-[1,4]oxazino[2,3,4-ij]quinazolin-5-one | 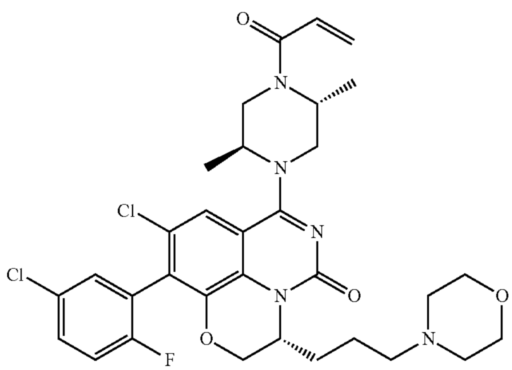 [SMILES: C=CC(=O)N1C[C@H](C)N(c2nc(=O)n3c4c(c(-c5cc(Cl)ccc5F)c(Cl)cc24)OC[C@H]3CCCN2CCOCC2)C[C@H]1C] | $^1$H NMR (400 MHz, CDCl$_3$) δ 7.48-7.38 (m, 2H), 7.32-7.22 (m, 1H), 7.14 (t, J = 9.2 Hz, 1H), 6.68-6.50 (m, 1H), 6.44-6.31 (m, 1H), 5.84-5.73 (m, 1H), 5.07-4.97 (m, 0.5H), 4.95-4.86 (m, 0.5H), 4.84-4.71 (m, 1.5H), 4.49-4.28 (m, 2H), 4.14-3.97 (m, 1.5H), 3.85-3.62 (m, 6.5H), 3.41-3.31 (m, 0.5H), 2.49-2.30 (m, 6H), 1.86-1.53 (m, 4H), 1.47-1.28 (m, 6H). | 644.3 |
| 218 | (3R)-7-((2S,5R)-4-acryloyl-2,5-dimethylpiperazin-1-yl)-9-chloro-10-(2,4-difluorophenyl)-3-(3-morpholinopropyl)-2,3-dihydro-5H-[1,4]oxazino[2,3,4-ij]quinazolin-5-one | 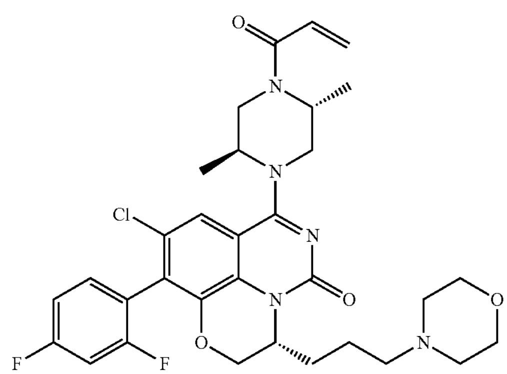 [SMILES: C=CC(=O)N1C[C@H](C)N(c2nc(=O)n3c4c(c(-c5ccc(F)cc5F)c(Cl)cc24)OC[C@H]3CCCN2CCOCC2)C[C@H]1C] | $^1$H NMR (400 MHz, CDCl$_3$) δ 7.45 (s, 1H), 7.31-7.27 (m, 1H), 7.03-6.92 (m, 2H), 6.63-6.51 (m, 1H, 6.41-6.33 (m, 1H), 5.79-5.75 (m, 1H), 5.01-4.91 (m, 1H), 4.80-4.75 (m, 1.5H), 4.45-4.30 (m, 2.5H), 4.08-3.98 (m, 1.5H), 3.83-3.67 (m, 6H), 3.38-3.35 (m, 0.5H), 2.40-2.34 (m, 6H), 1.79-1.71 (m, 3H), 1.41-1.25 (m, 6H). | 628.3 |
| 225 | (3S,10R)-7-((2S,5R)-4-acryloyl-2,5-dimethylpiperazin-1-yl)-9-chloro-10-(2-fluoro-6-hydroxyphenyl)-3-(3-morpholinopropyl)-2,3-dihydro-5H-[1,4]oxazino[2,3,4-ij]quinazolin-5-one | 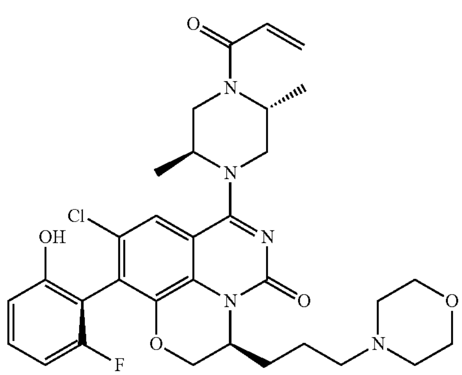 | $^1$H NMR (400 MHz, CDCl$_3$) δ 7.45-7.42 (m, 1H), 7.32-7.29 (m, 1H), 6.82 (d, J = 8.4 Hz, 1H), 6.75 (t, J = 8.8 Hz, 1H), 6.64-6.52 (m, 1H), 6.43-6.36 (m, 1H), 5.79 (d, J = 10.4 Hz, 1H), 5.03-5.01 (m, 0.5H), 4.91-4.84 (m, 1H), 4.71-4.68 (m, 1H), 4.48-4.45 (m, 1H), 4.34-4.31 (m, 1H), 4.09-4.06 (m, 1H), 4.02-3.99 (m, 0.5H), 3.93-3.87 (m, 1.5H), 3.81-3.77 (m, 0.5H), 3.71-3.63 (m, 4.5H), 3.56-3.52 (m, 0.5H), 2.45-2.39 (m, 6H), 1.80-1.74 (m, 4H), 1.34-1.19 (m, 6H). | 626.3 |

-continued

Table of examples

| Ex. # | Name | Structure | ¹H NMR | MS (M + H)⁺ |
|---|---|---|---|---|
| 226 | (3S,10S)-7-((2S,5R)-4-acryloyl-2,5-dimethylpiperazin-1-yl)-9-chloro-10-(2-fluoro-6-hydroxyphenyl)-3-(3-morpholinopropyl)-2,3-dihydro-5H-[1,4]oxazino[2,3,4-ij]quinazolin-5-one | 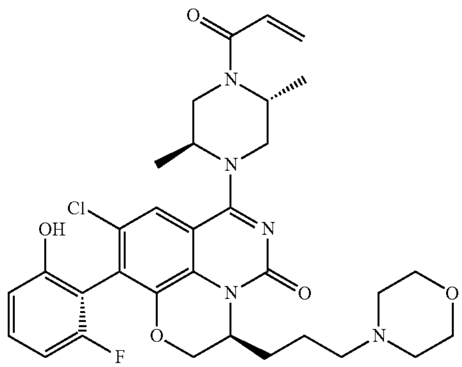 | ¹H NMR (400 MHz, CDCl$_3$) δ 7.42 (d, J = 9.6 Hz, 1H), 7.30-7.24 (m, 1H), 6.76-6.68 (m, 2H), 6.66-6.51 (m, 1H), 6.38 (t, J = 15.6 Hz, 1H), 5.78 (t, J = 8.8 Hz, 1H), 5.07-5.03 (m, 0.5H), 4.96-4.88 (m, 1H), 4.60-4.59 (m, 1H), 4.33-4.30 (m, 2H), 4.02-3.86 (m, 3.5H), 3.71-3.69 (m, 4H), 3.65-3.56 (m, 1H), 2.62-2.56 (m, 1H), 2.48-2.45 (m, 4H), 2.34-2.22 (m, 1H), 1.82-1.70 (m, 2H), 1.62-1.58 (m, 2H), 1.32-1.29 (m, 4H), 1.22-1.21 (m, 2H). | 626.3 |
| 247 | (2S)-7-((2S,5R)-4-acryloyl-2,5-dimethylpiperazin-1-yl)-9-chloro-10-(2,4-difluorophenyl)-2-(3-hydroxypropyl)-2,3-dihydro-5H-[1,4]oxazino[2,3,4-ij]quinazolin-5-one | 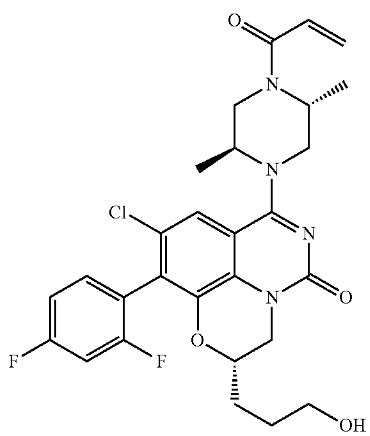 [SMILES: C=CC(=O)N1C[C@H](C)N(c2nc(=O)n3c4c(c(-c5ccc(F)cc5F)c(Cl)cc24)O[C@@H](CCCO)C3)C[C@H]1C] | 1H NMR (400 MHz, CDCl$_3$) δ 7.46-7.41 (m, 1H), 7.35-7.19 (m, 1H), 7.06-6.92 (m, 2H), 6.68-6.50 (m, 1H), 6.38 (t, J = 15.2 Hz, 1H), 5.78 (t, J = 11.2 Hz, 1H), 5.06-4.76 (m, 1.6H), 4.54-4.30 (m, 2.4H), 4.24-4.10 (m, 1.6H), 3.82-3.55 (m, 4.4H), 3.52-3.44 (m, 0.6H), 3.38-3.27 (m, 0.4H), 1.84-1.72 (m, 2H), 1.68-1.53 (m, 2H), 1.49-1.34 (m, 6H). | |
| 249 | (2R)-7-((2S,5R)-4-acryloyl-2,5-dimethylpiperazin-1-yl)-9-chloro-10-(2,4-difluorophenyl)-2-(3-hydroxypropyl)-2,3-dihydro-5H-[1,4]oxazino[2,3,4-ij]quinazolin-5-one | 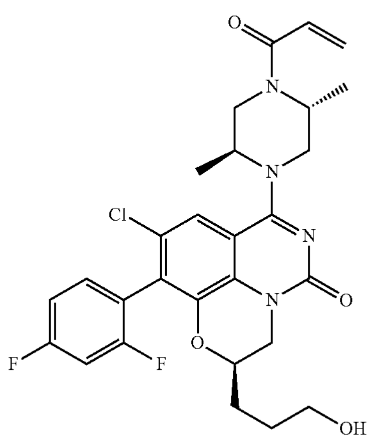 [SMILES: C=CC(=O)N1C[C@H](C)N(c2nc(=O)n3c4c(c(-c5ccc(F)cc5F)c(Cl)cc24)O[C@H](CCCO)C3)C[C@H]1C] | 1H NMR (400 MHz, CDCl$_3$) δ 7.39 (d, J = 11.2 Hz, 1H), 7.33-7.23 (m, 1H), 7.03-6.93 (m, 2H), 6.61-6.51 (m, 1H), 6.37 (t, J = 16.8 Hz, 1H), 5.78 (t, J = 5.2 Hz, 1H), 5.10-5.09 (m, 0.6H), 4.96-4.94 (m, 1H), 4.47-4.19 (m, 3H), 4.06-3.85 (m, 2.4H), 3.67-3.44 (m, 4H), 1.81-1.75 (m, 2H), 1.67-1.59 (m, 2H), 1.36-1.32 (m, 4H), 1.19 (d, J = 7.2 Hz, 2H). | |

-continued

Table of examples

| Ex. # | Name | Structure | ¹H NMR | MS (M + H)⁺ |
|---|---|---|---|---|
| 250 | (3S)-7-((2S,5R)-4-acryloyl-2,5-dimethylpiperazin-1-yl)-9-chloro-10-(2,4-difluorophenyl)-3-(3-hydroxypropyl)-2,3-dihydro-5H-[1,4]oxazino[2,3,4-ij]quinazolin-5-one | 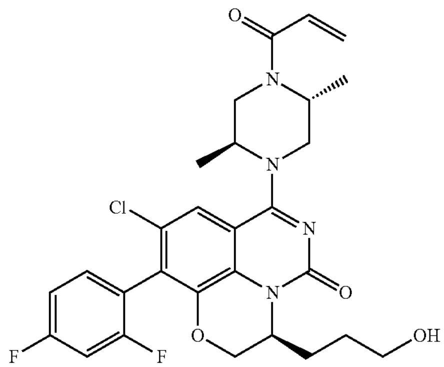 [SMILES: C=CC(=O)N1C[C@H](C)N(c2nc(=O)n3c4c(c(-c5ccc(F)cc5F)c(Cl)cc24)OC[C@@H]3CCCO)C[C@H]1C] | 1H NMR (400 MHz, CDCl₃) δ 7.52 (s, 1H), 7.34-7.21 (m, 1H), 7.04-6.93 (m, 2H), 6.67-6.51 (m, 1H), 6.37 (t, J = 14.4 Hz, 1H), 5.77 (t, J = 8.8 Hz, 1H), 5.03-5.02 (m, 0.6H), 4.90-4.81 (m, 2H), 4.43-4.30 (m, 2.4H), 4.18-4.12 (m, 0.6H), 4.07-4.01 (m, 1H), 3.80-3.66 (m, 4H), 3.32 (d, J = 14.0 Hz, 0.4H), 2.82-2.71 (m, 1H), 1.91-1.83 (m, 2H), 1.76-1.64 (m, 1H), 1.46-1.31 (m, 6H). | |
| 251 | (3R)-7-((2S,5R)-4-acryloyl-2,5-dimethylpiperazin-1-yl)-9-chloro-10-(2,4-difluorophenyl)-3-(3-hydroxypropyl)-2,3-dihydro-5H-[1,4]oxazino[2,3,4-ij]quinazolin-5-one | 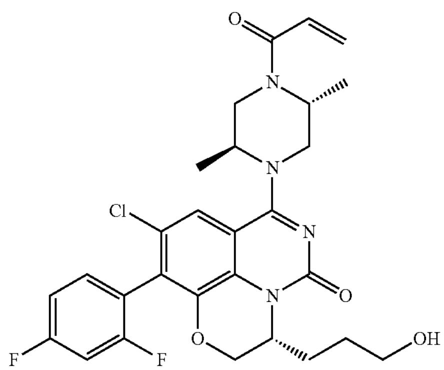 [SMILES: C=CC(=O)N1C[C@H](C)N(c2nc(=O)n3c4c(c(-c5ccc(F)cc5F)c(Cl)cc24)OC[C@H]3CCCO)C[C@H]1C] | ¹H NMR (400 MHz, CDCl₃) δ 7.44 (d, J = 9.6 Hz, 1H), 7.33-7.25 (m, 1H), 7.03-6.97 (m, 2H), 6.62-6.52 (m, 1H), 6.38 (t, J = 16.4 Hz, 1H), 5.78-5.76 (m, 1H), 5.07-4.77 (m, 2.7H), 4.47-3.76 (m, 7H), 3.69-3.66 (m, 2H), 3.59-3.56 (m, 0.3H), 1.74-1.63 (m, 4H), 1.34-1.14 (m, 6H). | |
| 252 | (3S)-3-(3-((1R,5S)-3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2H-[1,4]oxazino[2,3,4-ij]quinazolin-5(3H)-one | 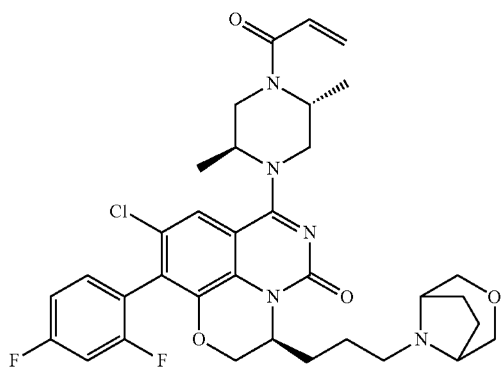 [SMILES: C=CC(=O)N1C[C@H](C)N(c2nc(=O)n3c4c(c(-c5ccc(F)cc5F)c(Cl)cc24)OC[C@@H]3CCCN2C3CCC2COC3)C[C@H]1C] | ¹H NMR (400 MHz, CDCl₃) δ 7.94 (brs, 1H), 7.49-7.47 (m, 1H), 7.34-7.20 (m, 1H), 7.05-6.92 (m, 2H), 6.64-6.50 (m, 1H), 6.38 (t, J = 14.8 Hz, 1H), 5.79 (t, J = 9.2 Hz, 1H), 5.04-5.03 (m, 0.5 H), 4.88-4.72 (m, 2H), 4.38 (t, J = 11.2 Hz, 2H), 4.22-4.09 (m, 2H), 4.05-3.78 (m, 4H), 3.74-3.67 (m, 4H), 3.37-3.26 (m, 1H), 3.12-3.08 (m, 1.5H), 2.25 (d, J = 7.6 Hz, 4H), 1.91-1.76 (m, 4H), 1.49-1.33 (m, 6H). | 654.2 |
| 253 | (3R)-7-((2S,5R)-4-acryloyl-2,5-dimethylpiperazin-1-yl)-9-chloro-10-(2,4-difluorophenyl)-3-(3-(1,1-dioxidothiomorpholino)propyl)-2,3-dihydro-5H-[1,4]oxazino[2,3,4-ij]quinazolin-5-one | 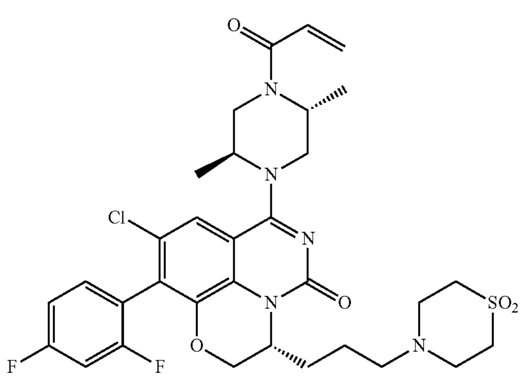 [SMILES: C=CC(=O)N1C[C@H](C)N(c2nc(=O)n3c4c(c(-c5ccc(F)cc5F)c(Cl)cc24)OC[C@H]3CCCN2CCS(=O)(=O)CC2)C[C@H]1C] | ¹H NMR (400 MHz, CDCl₃) δ 7.44-7.41 (m, 1H), 7.31-7.27 (m, 1H), 7.04-6.94 (m, 2H), 6.61-6.51 (m, 1H), 6.37 (t, J = 16 Hz, 1H), 5.79-5.75 (m, 1H), 5.05-4.90 (m, 1.5 H), 4.69-4.66 (m, 1H), 4.45 (d, J = 11.6 Hz, 1H), 4.33-4.31 (m, 1H), 4.11-3.82 (m, 3.5H), 3.68-3.53 (m, 1H), 3.02-2.94 (m, 8H), 2.56-2.52 (m, 2H), 1.88-1.60 (m, 4H), 1.34-1.29 (m, 4H), 1.23-1.19 (m, 2H). | |

-continued

Table of examples

| Ex. # | Name | Structure | ¹H NMR | MS (M + H)⁺ |
|---|---|---|---|---|
| 254 | (3R)-3-(3-(3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 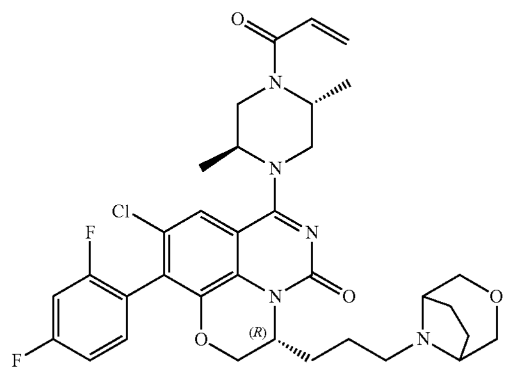 | ¹H NMR (400 MHz, CDCl₃) δ 7.43-7.40 (m, 1H), 7.29-7.26 (m, 1H), 7.03-6.92 (m, 2H), 6.66-6.51 (m, 1H), 6.37 (t, J = 16 Hz, 1H), 5.79-5.74 (m, 1H), 5.02-4.93 (m, 1.5 H), 4.72-4.66 (m, 1H), 4.49 (d, J = 11.6 Hz, 1H), 4.09-3.88 (m, 3.5H), 3.64-3.46 (m, 5H), 3.02-2.99 (m, 2H), 2.31-2.26 (m, 2H), 1.85-1.84 (m, 5H), 1.82-1.69 (m, 3H), 1.34-1.33 (m, 4H), 1.26-1.19 (m, 2H). | 654.2 |
| 255 | (3S)-7-((2S,5R)-4-acryloyl-2,5-dimethylpiperazin-1-yl)-9-chloro-10-(2,4-difluorophenyl)-3-(3-(1,1-dioxidothiomorpholino)propyl)-2,3-dihydro-5H-[1,4]oxazino[2,3,4-ij]quinazolin-5-one | 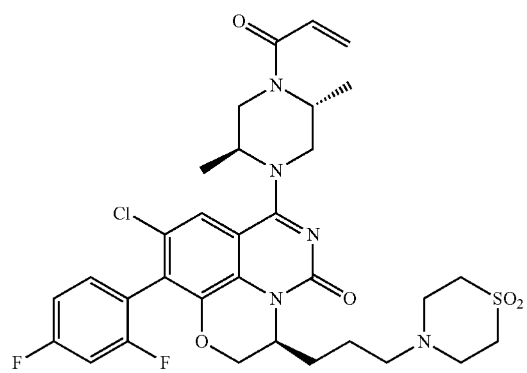 [SMILES: C=CC(=O)N1C[C@H](C)N(c2nc(=O)n3c4c(c(-c5ccc(F)cc5F)c(Cl)cc24)OC[C@@H]3CCCN2CCS(=O)(=O)CC2)C[C@H]1C] | ¹H NMR (400 MHz, CDCl₃) δ 7.47 (s, 1H), 7.33-7.22 (m, 1H), 7.05-6.94 (m, 2H), 6.63-6.51 (m, 1H), 6.38 (t, J = 11.2 Hz, 1H), 5.78 (t, J = 8.4 Hz, 1H), 5.03-5.01 (m, 0.5H), 4.94-4.89 (m, 0.5H), 4.78-4.76 (m, 1.5H), 4.43-4.32 (m, 2.5H), 4.13-4.00 (m, 1.5H), 3.79-3.67 (m, 2H), 3.39-3.32 (m, 0.5H), 3.02-2.96 (m, 8H), 2.57-2.53 (m, 2H), 1.81-1.76 (m, 2H), 1.70-1.60 (m, 2H), 1.45-1.31 (m, 6H). | 676.3 |
| 258 | (2S)-7-((2S,5R)-4-acryloyl-2,5-dimethylpiperazin-1-yl)-9-chloro-10-(2,4-difluorophenyl)-2-(3-morpholinopropyl)-2,3-dihydro-5H-[1,4]oxazino[2,3,4-ij]quinazolin-5-one | 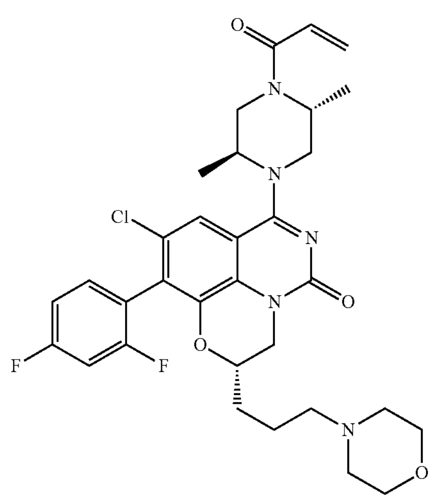 [SMILES: C=CC(=O)N1C[C@H](C)N(c2nc(=O)n3c4c(c(-c5ccc(F)cc5F)c(Cl)cc24)O[C@@H](CCCN2CCOCC2)C3)C[C@H]1C] | 1H NMR (400 MHz, CDCl₃) δ 7.46-7.41 (m, 1H), 7.34-7.18 (m, 1H), 7.03-6.89 (m, 2H), 6.68-6.50 (m, 1H), 6.37 (t, J = 15.2 Hz, 1H), 5.78 (t, J = 8.8 Hz, 1H), 5.06-4.77 (m, 1.5H), 4.53-4.29 (m, 2.5H), 4.22-4.08 (m, 1.5H), 3.82-3.54 (m, 6.5H), 3.50-3.42 (m, 0.6H), 3.38-3.27 (m, 0.4H), 2.38-2.22 (m, 6H), 1.77-1.64 (m, 2H), 1.60-1.33 (m, 8H). | |

-continued

Table of examples

| Ex. # | Name | Structure | ¹H NMR | MS (M + H)⁺ |
|---|---|---|---|---|
| 259 | (3S)-7-((2S,5R)-4-acryloyl-2,5-dimethylpiperazin-1-yl)-9-chloro-10-(2,4-difluorophenyl)-3-(3-(4-methylpiperazin-1-yl)propyl)-2,3-dihydro-5H-[1,4]oxazino[2,3,4-ij]quinazolin-5-one | 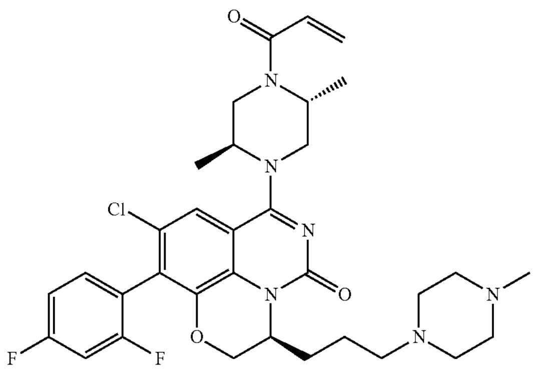 [SMILES: C=CC(=O)N1C[C@H](C)N(c2nc(=O)n3c4c(c(-c5ccc(F)cc5F)c(Cl)cc24)OC[C@@H]3CCCN2CCN(C)CC2)C[C@H]1C] | ¹H NMR (400 MHz, CDCl₃) δ 7.44 (s, 1H), 7.32-7.21 (m, 1H), 7.04-6.93 (m, 2H), 6.64-6.51 (m, 1H), 6.37 (t, J = 14.8 Hz, 1H), 5.77 (t, J = 8.0 Hz, 1H), 5.06-4.90 (m, 1H), 4.79-4.77 (m, 1.5H), 4.44 (d, J = 11.6 Hz, 1H), 4.33-4.30 (m, 1.5H), 4.11-3.98 (m, 1.5H), 3.83-3.65 (m, 2H), 3.39-3.35 (m, 0.5H), 2.43-2.35 (m, 9H), 2.27 (s, 3H), 1.82-1.74 (m, 2H), 1.64-1.59 (m, 3H), 1.41-1.31 (m, 6H). | 641.3 |
| 260 | (2R)-7-((2S,5R)-4-acryloyl-2,5-dimethylpiperazin-1-yl)-9-chloro-10-(2,4-difluorophenyl)-2-(3-(4-methylpiperazin-1-yl)propyl)-2,3-dihydro-5H-[1,4]oxazino[2,3,4-ij]quinazolin-5-one | 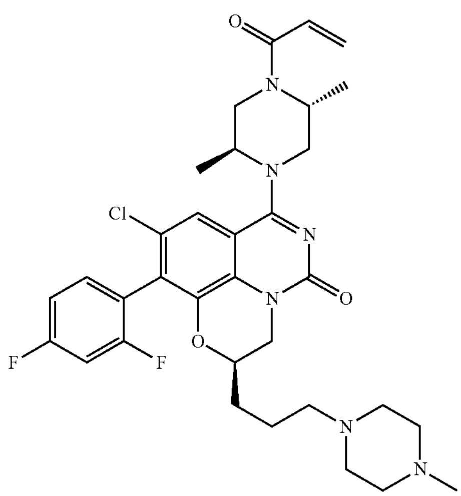 [SMILES: C=CC(=O)N1C[C@H](C)N(c2nc(=O)n3c4c(c(-c5ccc(F)cc5F)c(Cl)cc24)O[C@H](CCCN2CCN(C)CC2)C3)C[C@H]1C] | 1H NMR (400 MHz, CDCl₃) δ 7.40-7.37 (m, 1H), 7.33-7.27 (m, 0.6H), 7.24-7.20 (m, 0.4H), 7.02-6.91 (m, 2H), 6.62-6.51 (m, 1H), 6.37 (t, J = 15.6 Hz, 1H), 5.78-5.75 (m, 1H), 5.09-5.08 (m, 0.5H), 4.95-4.93 (m, 1H), 4.46-4.29 (m, 2H), 4.15-3.85 (m, 3.5H), 3.67-3.41 (m, 2H), 2.56-2.21 (m, 13H), 1.74-1.66 (m, 2H), 1.62-1.46 (m, 2H), 1.35-1.33 (m, 4H), 1.19 (d, J = 6.8 Hz, 2H). | |
| 261 | (2R)-2-(3-(3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 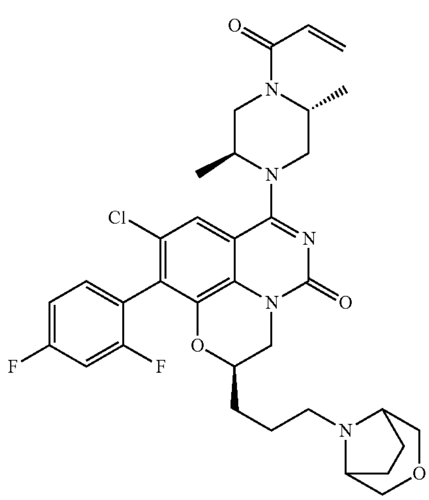 [SMILES: C=CC(=O)N1C[C@H](C)N(c2nc(=O)n3c4c(c(-c5ccc(F)cc5F)c(Cl)cc24)O[C@H](CCCN2C4CCC2COC4)C3)C[C@H]1C] | 1H NMR (400 MHz, CDCl₃) δ 7.40-7.37 (m, 1H), 7.34-7.28 (m, 0.6H), 7.23-7.21 (m, 0.4H), 7.02-6.90 (m, 2H), 6.62-6.51 (m, 1H), 6.37 (t, J = 15.6 Hz, 1H), 5.79-5.75 (m, 1H), 5.09-5.07 (m, 0.5H), 4.95-4.93 (m, 1H), 4.48-3.85 (m, 5.5H), 3.67-3.43 (m, 6H), 2.89-2.87 (m, 2H), 2.23-2.18 (m, 2H), 1.82-1.70 (m, 6H), 1.59-1.47 (m, 2H), 1.33-1.30 (m, 4H), 1.20 (d, J = 6.4 Hz, 2H). | |

| Ex. # | Name | Structure | ¹H NMR | MS (M + H)⁺ |
|---|---|---|---|---|
| 262 | (2S)-2-(3-(3-oxa-8-azabicyclo[3.2.1]octan-8-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 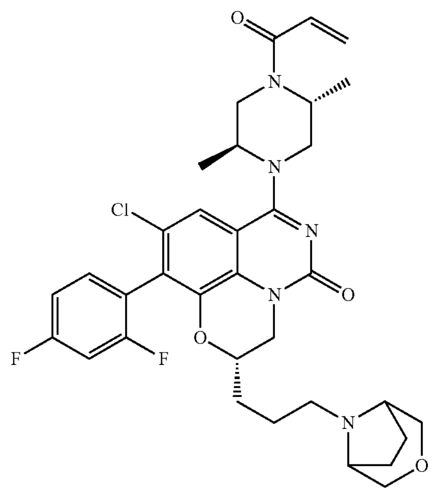 [SMILES: C=CC(=O)N1C[C@H](C)N(c2nc(=O)n3c4c(c(-c5ccc(F)cc5F)c(Cl)cc24)O[C@@H](CCCN2C4CCC2COC4)C3)C[C@H]1C] | 1H NMR (400 MHz, CDCl₃) δ 7.46-7.41 (m, 1H), 7.35-7.19 (m, 1H), 7.04-6.90 (m, 2H), 6.68-6.50 (m, 1H), 6.37 (t, J = 15.6 Hz, 1H), 5.78 (m, J = 8.4 Hz, 1H), 5.06-4.77 (m, 1.6H), 4.54-4.27 (m, 2.4H), 4.22-4.10 (m, 1.6H), 3.82-3.55 (m, 4.4H), 3.52-3.44 (m, 2.5H), 3.38-3.27 (m, 0.5H), 2.96-2.84 (m, 2H), 2.28-2.16 (m, 2H), 1.89-1.68 (m, 6H), 1.55-1.32 (m, 8H). | |
| 263 | (2S)-7-((2S,5R)-4-acryloyl-2,5-dimethylpiperazin-1-yl)-9-chloro-10-(2,4-difluorophenyl)-2-(3-(4-methylpiperazin-1-yl)propyl)-2,3-dihydro-5H-[1,4]oxazino[2,3,4-ij]quinazolin-5-one | 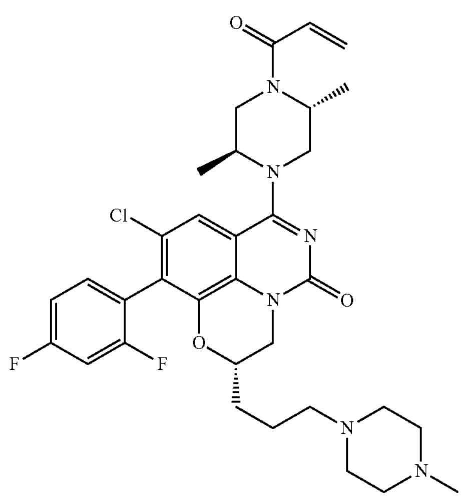 [SMILES: C=CC(=O)N1C[C@H](C)N(c2nc(=O)n3c4c(c(-c5ccc(F)cc5F)c(Cl)cc24)O[C@@H](CCCN2CCN(C)CC2)C3)C[C@H]1C] | 1H NMR (400 MHz, CDCl₃) δ 7.45-7.41 (m, 1H), 7.34-7.18 (m, 1H), 7.03-6.90 (m, 2H), 6.67-6.49 (m, 1H), 6.37 (t, J = 15.2 Hz, 1H), 5.77 (m, J = 9.2 Hz, 1H), 5.06-4.77 (m, 1.6H), 4.52-4.28 (m, 2.4H), 4.22-4.07 (m, 1.6H), 3.82-3.62 (m, 2H), 3.59-3.52 (m, 0.4H), 3.49-3.42 (m, 0.6H), 3.38-3.28 (m, 0.4H), 2.57-2.20 (m, 13H), 1.76-1.69 (m, 2H), 1.59-1.33 (m, 8H). | |
| 264 | (3R)-7-((2S,5R)-4-acryloyl-2,5-dimethylpiperazin-1-yl)-9-chloro-10-(2,4-difluorophenyl)-3-(3-(4-methylpiperazin-1-yl)propyl)-2,3-dihydro-5H-[1,4]oxazino[2,3,4-ij]quinazolin-5-one | 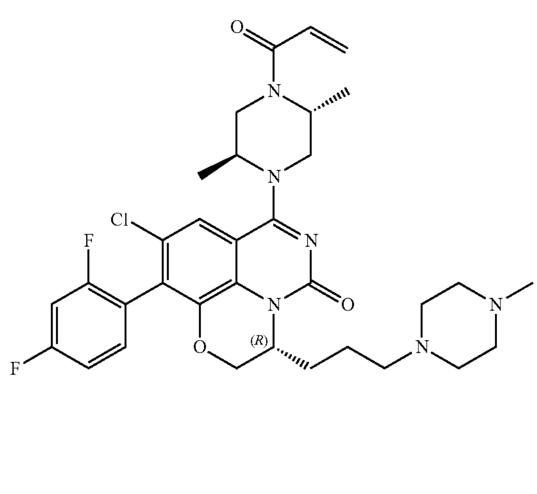 | ¹H NMR (400 MHz, CDCl₃) δ 7.43-7.40 (m, 1H), 7.30-7.23 (m, 1H), 7.04-6.92 (m, 2H), 6.66-6.51 (m, 1H), 6.37 (t, J = 16 Hz, 1H), 5.79-5.75 (m, 1H), 5.02-4.90 (m, 1.5H), 4.69-4.67 (m, 1H), 4.48-4.45 (m, 1H), 4.33-4.28 (m, 1H), 4.09-3.81 (m, 3.5H), 3.68-3.54 (m, 1H), 2.38-2.34 (m, 2H), 2.27 (s, 3H), 1.65-1.60 (m, 12H), 1.34-1.20 (m, 6H). | 641.4 |

-continued

Table of examples

| Ex. # | Name | Structure | ¹H NMR | MS (M + H)⁺ |
|---|---|---|---|---|
| 265 | (3S,10S)-7-((2S,5R)-4-acryloyl-2,5-dimethylpiperazin-1-yl)-9-chloro-10-(2-fluoro-6-hydroxyphenyl)-3-(3-morpholinopropyl)-2,3-dihydro-5H-[1,4]oxazino[2,3,4-ij]quinazolin-5-one | 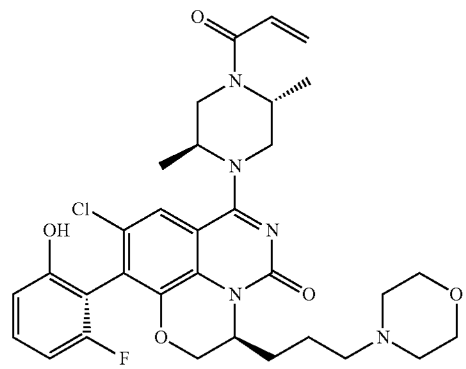 | ¹H NMR (400 MHz, CDCl₃) δ 12.57 (brs, 1H), 7.50 (d, J = 4.8 Hz, 1H), 7.30-7.27 (m, 1H), 6.88 (d, J = 8.8 Hz, 1H), 6.72 (d, J = 8.8 Hz, 1H), 6.65-6.51 (m, 1H), 6.38 (t, J = 14.8 Hz, 1H), 5.80-5.75 (m, 1H), 5.07-4.79 (m, 2H), 4.58-4.34 (m, 2.5H), 4.16-4.13 (m, 1H), 3.98-3.80 (m, 3.5H), 3.63-3.47 (m, 2.5H), 3.28-3.23 (m, 1H), 3.01-2.94 (m, 1H), 2.82-2.61 (m, 2.5H), 2.23-1.98 (m, 2H), 1.88-1.72 (m, 3H), 1.67-1.62 (m, 2H), 1.50-1.39 (m, 6H). | 626.3 |
| 266 | (3S)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 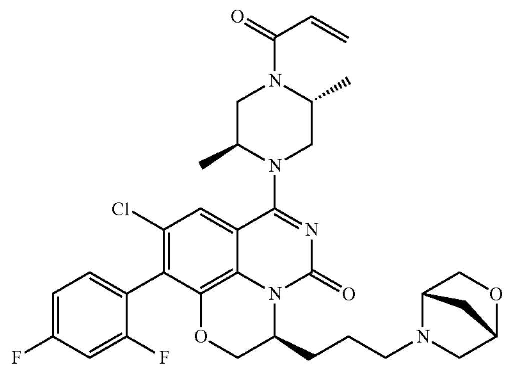 [SMILES: C=CC(=O)N1C[C@H](C)N(c2nc(=O)n3c4c(c(-c5ccc(F)cc5F)c(Cl)cc24)OC[C@@H]3CCCN2C[C@@H]3C[C@H]2CO3)C[C@H]1C] | 1H NMR (400 MHz, CDCl₃) δ 7.48 (s, 1H), 7.33-7.31 (m, 0.5H), 7.24-7.20 (m, 0.5H), 7.05-6.92 (m, 2H), 6.63-6.50 (m, 1H), 6.38 (t, J = 14.4 Hz, 1H), 5.78 (t, J = 8.8 Hz, 1H), 5.04-5.02 (m, 0.5H), 4.89-4.88 (m, 0.5H), 4.84-4.81 (m, 1.5H), 4.60-4.50 (m, 1H), 4.47-4.35 (m, 3H), 4.26-4.14 (m, 1.5H), 4.07-4.01 (m, 1H), 3.82-3.67 (m, 4H), 3.42-3.31 (m, 2.5H), 3.13-3.12 (m, 0.5H), 2.89-2.84 (m, 0.5H), 2.55-2.51 (m, 0.5H), 2.24-2.23 (m, 0.5H), 2.17-2.14 (m, 1.5H), 1.88-1.75 (m, 4H), 1.48-1.33 (m, 6H). | |
| 271 | (3R)-7-((2S,5R)-4-acryloyl-2,5-dimethylpiperazin-1-yl)-9-chloro-10-(2,4-difluorophenyl)-3-(3-(3,3-difluoropyrrolidin-1-yl)propyl)-2,3-dihydro-5H-[1,4]oxazino[2,3,4-ij]quinazolin-5-one | 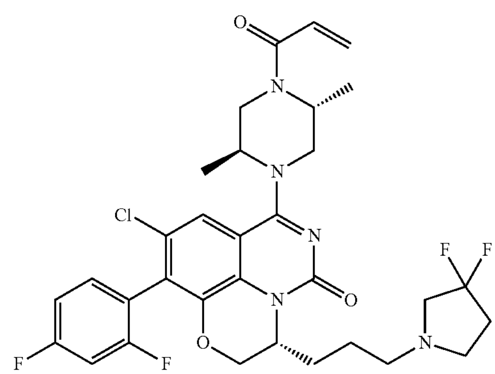 [SMILES: C=CC(=O)N1C[C@H](C)N(c2nc(=O)n3c4c(c(-c5ccc(F)cc5F)c(Cl)cc24)OC[C@H]3CCCN2CCC(F)(F)C2)C[C@H]1C] | 1H NMR (400 MHz, CDCl₃) δ 7.43-7.40 (m, 1H), 7.30-7.28 (m, 1H), 7.03-6.93 (m, 2H), 6.61-6.51 (m, 1H), 6.37 (t, J = 16.8 Hz, 1H), 5.77 (t, J = 8.0 Hz, 1H), 5.04-4.88 (m, 1.5H), 4.71-4.68 (m, 1H), 4.46 (d, J = 11.6 Hz, 1H), 4.33-4.28 (m, 1H), 4.09-4.01 (m, 1.4H), 3.92-3.83 (m, 2H), 3.68-3.65 (m, 0.6H), 3.57-3.53 (m, 0.5H), 2.89-2.80 (m, 2H), 2.76-2.66 (m, 2H), 2.49-2.47 (m, 2H), 2.29-2.17 (m, 2H), 1.85-1.61 (m, 4H), 1.50-1.30 (m, 4H), 1.27-1.20 (m, 2H). | |
| 272 | (3R)-3-(3-(1H-imidazol-1-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 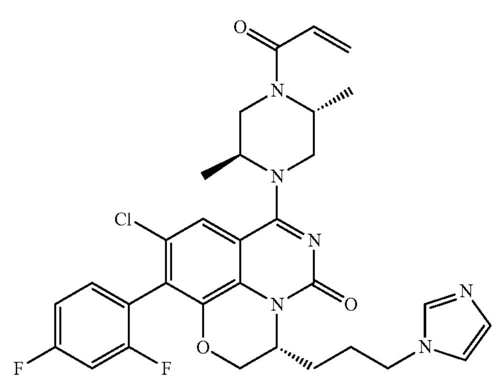 [SMILES: C=CC(=O)N1C[C@H](C)N(c2nc(=O)n3c4c(c(-c5ccc(F)cc5F)c(Cl)cc24)OC[C@H]3CCCn2ccnc2)C[C@H]1C] | ¹H NMR (400 MHz, CDCl₃) δ 7.46-7.42 (m, 2H), 7.25-7.21 (m, 1H), 7.05-6.90 (m, 4H), 6.58-6.51 (m, 1H), 6.37 (t, J = 16 Hz, 1H), 5.79-5.75 (m, 1H), 5.03-4.90 (m, 1.5H), 4.72 (m, 1H), 4.40-4.38 (m, 2H), 4.09-3.81 (m, 5.5H), 3.65-3.55 (m, 1H), 1.91-1.78 (m, 3H), 1.61-1.59 (m, 1H), 1.37-1.20 (m, 6H). | 609.3 |

-continued

Table of examples

| Ex. # | Name | Structure | ¹H NMR | MS (M + H)⁺ |
|---|---|---|---|---|
| 273 | 1-(3-((3R)-7-((2S,5R)-4-acryloyl-2,5-dimethylpiperazin-1-yl)-9-chloro-10-(2,4-difluorophenyl)-5-oxo-2,3-dihydro-5H-[1,4]oxazino[2,3,4-ij]quinazolin-3-yl)propyl)-N-cyclopropylazetidine-3-carboxamide | 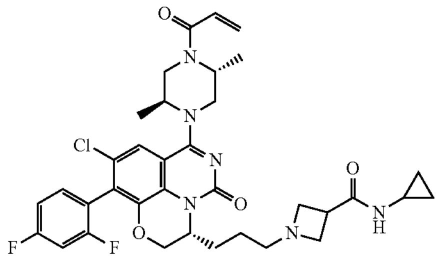 [SMILES: C=CC(=O)N1C[C@H](C)N(c2nc(=O)n3c4c(c(-c5ccc(F)cc5F)c(Cl)cc24)OC[C@H]3CCCN2CC(C(=O)NC3CC3)C2)C[C@H]1C] | ¹H NMR (400 MHz, CDCl₃) δ 7.43-7.39 (m, 1H), 7.31-7.29 (m, 1H), 7.04-6.93 (m, 2H), 6.58-6.51 (m, 1H), 6.41-6.25 (m, 2H), 5.77 (t, J = 7.2 Hz, 1H), 4.96-4.94 (m, 2H), 4.67-4.64 (m, 1H), 4.44 (d, J = 11.6 Hz, 1H), 4.31-4.29 (m, 1H), 4.08-4.01 (m, 1.5H), 3.92-3.85 (m, 2.5H), 3.68-3.56 (m, 2H), 3.36-3.33 (m, 1.5H), 3.25-3.22 (m, 1.5H), 2.98 (t, J = 6.8 Hz, 1H), 2.73-2.68 (m, 1H), 2.46-2.42 (m, 2H), 1.82-1.79 (m, 1H), 1.49-1.40 (m, 2H), 1.34-1.25 (m, 4H), 1.22-1.20 (m, 2H), 0.78-0.73 (m, 2H), 0.50-0.46 (m, 2H). | 681.3 |
| 278 | (3R)-7-((2S,5R)-4-acryloyl-2,5-dimethylpiperazin-1-yl)-9-chloro-10-(2,4-difluorophenyl)-3-(3-(4-(prop-1-en-2-yl)piperidin-1-yl)propyl)-2,3-dihydro-5H-[1,4]oxazino[2,3,4-ij]quinazolin-5-one | 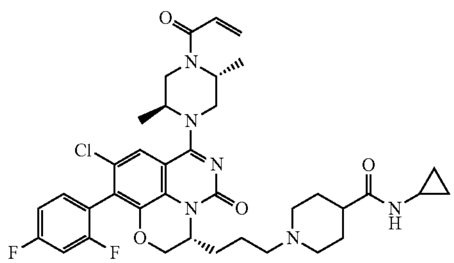 [SMILES: C=CC(=O)N1C[C@H](C)N(c2nc(=O)n3c4c(c(-c5ccc(F)cc5F)c(Cl)cc24)OC[C@H]3CCCN2CCC(C(=O)NC3CC3)CC2)C[C@H]1C] | ¹H NMR (400 MHz, CDCl₃) δ 7.43-7.40 (m, 1H), 7.32-7.28 (m, 0.7H), 7.25-7.23 (m, 0.3H), 7.05-6.93 (m, 2H), 6.65-6.51 (m, 1H), 6.37 (t, J = 16.0 Hz, 1H), 5.96 (br, 1H), 5.77 (t, J = 8.0 Hz, 1H), 4.95-4.90 (m, 1.5H), 4.71-4.69 (m, 1H), 4.51-4.47 (m, 1H), 4.35-4.30 (m, 1H), 4.09-4.00 (m, 1.5H), 3.96-3.82 (m, 2H), 3.68-3.53 (m, 1H), 3.10-3.04 (m, 2H), 2.72-2.66 (m, 1H), 2.54 (br, 2H), 2.30-2.17 (m, 3H), 2.03-1.92 (m, 2H), 1.81-1.71 (m, 6H), 1.37-1.30 (m, 4H), 1.24-1.20 (m, 2H), 0.78-0.70 (m, 2H), 0.49-0.45 (m, 2H). | 709.4 |
| 279 | (3R)-7-((2S,5R)-4-acryloyl-2,5-dimethylpiperazin-1-yl)-9-chloro-10-(2,4-difluorophenyl)-3-(3-(3-fluoroazetidin-1-yl)propyl)-2,3-dihydro-5H-[1,4]oxazino[2,3,4-ij]quinazolin-5-one | 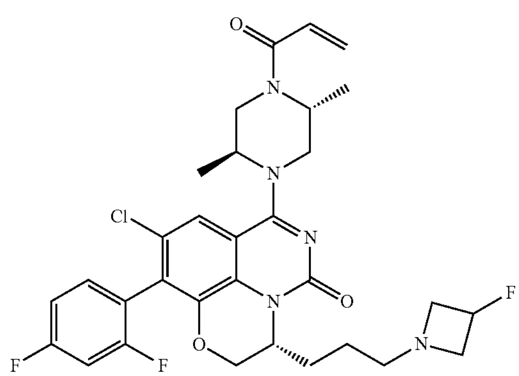 [SMILES: C=CC(=O)N1C[C@H](C)N(c2nc(=O)n3c4c(c(-c5ccc(F)cc5F)c(Cl)cc24)OC[C@H]3CCCN2CC(F)C2)C[C@H]1C] | ¹H NMR (400 MHz, CDCl₃) δ 7.42-7.39 (m, 1H), 7.30-7.28 (m, 0.6H), 7.25-7.23 (m, 0.4H), 7.03-6.93 (m, 2H), 6.63-6.51 (m, 1H), 6.37 (t, J = 15.6 Hz, 1H), 5.77 (t, J = 6.4 Hz, 1H), 5.15-5.13 (m, 0.5H), 5.01-4.88 (m, 2H), 4.69-4.67 (m, 1H), 4.44 (d, J = 11.6 Hz, 1H), 4.36-4.31 (m, 1H), 4.08-4.01 (m, 1.5H), 3.92-3.81 (m, 2H), 3.68-3.53 (m, 3H), 3.12-3.03 (m, 2H), 2.50 (t, J = 6.8 Hz, 2H), 1.81-1.77 (m, 2H), 1.48-1.46 (m, 2H), 1.34-1.20 (m, 4H), 1.16-1.14 (m, 2H). | 616.3 |
| 281 | (3S,10S)-3-(3-(3-oxa-8-azabicyclo[3.2.1]octan-8-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one | 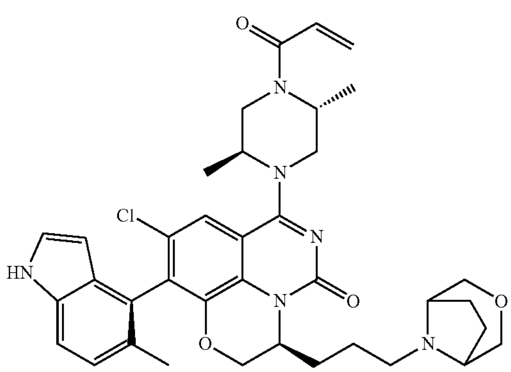 | ¹H NMR (400 MHz, CDCl₃) δ 10.24 (brs, 1H), 7.57-7.48 (m, 3H), 7.39 (d, J = 8.4 Hz 1H), 6.69-6.51 (m, 1H), 6.38 (t, J = 15.6 Hz, 1H), 5.78 (t, J = 8.8 Hz, 1H), 5.08-5.01 (m, 0.5 H), 4.96-4.73 (m, 2H), 4.46-4.33 (m, 2.3H), 4.22-4.16 (m, 0.5H), 3.99-3.91 (m, 1H), 3.85-3.57 (m, 4H), 3.50-3.35 (m, 2.7H), 3.05-2.93 (m, 2H), 2.37-2.20 (m, 5H), 1.91-1.78 (m, 5H), 1.76-1.67 (m, 2H), 1.56-1.51 (m, 1H), 1.48-1.35 (m, 6H). | 672.3 |

| Ex. # | Name | Structure | ¹H NMR | MS (M + H)⁺ |
|---|---|---|---|---|
| 282 | (3S,10R)-3-(3-(3-oxa-8-azabicyclo[3.2.1]octan-8-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one | 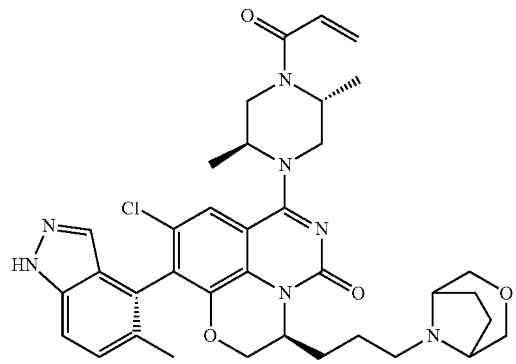 | ¹H NMR (400 MHz, CDCl₃) δ 10.70 (brs, 1H), 7.57-7.48 (m, 3H), 7.37 (d, J = 8.4 Hz 1H), 6.68-6.50 (m, 1H), 6.38 (t, J = 15.2 Hz, 1H), 5.78 (t, J = 9.6 Hz, 1H), 5.08-4.99 (m, 0.5 H), 4.94-4.80 (m, 1H), 4.75-4.68 (m, 1H), 4.42-4.25 (m, 2.5H), 4.20-4.03 (m, 2.3H), 3.99-3.92 (m, 1H), 3.84-3.52 (m, 6H), 3.42-3.34 (m, 0.7H), 3.02-2.78 (m, 2H), 2.22-2.04 (m, 7H), 1.90-1.77 (m, 2H), 1.69-1.55 (m, 2H), 1.45-1.33 (m, 6H). | 672.3 |
| 283 | (3R)-7-((2S,5R)-4-acryloyl-2,5-dimethylpiperazin-1-yl)-9-chloro-10-(2,4-difluorophenyl)-3-(3-(4-methyl-3-oxopiperazin-1-yl)propyl)-2,3-dihydro-5H-[1,4]oxazino[2,3,4-ij]quinazolin-5-one | 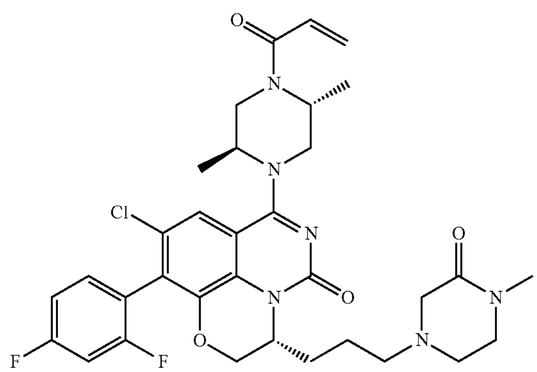 [SMILES: C=CC(=O)N1C[C@H](C)N(c2nc(=O)n3c4c(c(-c5ccc(F)cc5F)c(Cl)cc24)OC[C@H]3CCCN2CCN(C)C(=O)C2)C[C@H]1C] | ¹H NMR (400 MHz, CDCl₃) δ 7.43-7.40 (m, 1H), 7.31-7.29 (m, 1H), 7.05-6.93 (m, 2H), 6.63-6.51 (m, 1H), 6.37 (t, J = 15.6 Hz, 1H), 5.79-5.74 (m, 1H), 5.04-4.87 (m, 1.5H), 4.69-4.67 (m, 1H), 4.45 (d, J = 11.2 Hz, 1H), 4.36-4.30 (m, 1H), 4.09-4.00 (m, 1.5H), 3.92-3.81 (m, 2H), 3.68-3.54 (m, 1H), 3.32-3.24 (m, 2H), 3.14-3.02 (m, 2H), 2.93 (d, J = 2.0 Hz, 3H), 2.69-2.62 (m, 2H), 2.42 (t, J = 7.2 Hz, 2H), 1.87-1.74 (m, 2H), 1.72-1.61 (m, 2H), 1.34-1.30 (m, 4H), 1.27-1.18 (m, 2H). | 655.3 |
| 284 | (3R)-7-((2S,5R)-4-acryloyl-2,5-dimethylpiperazin-1-yl)-9-chloro-10-(2,4-difluorophenyl)-3-(3-(methyl(2,2,2-trifluoroethyl)amino)propyl)-2,3-dihydro-5H-[1,4]oxazino[2,3,4-ij]quinazolin-5-one | 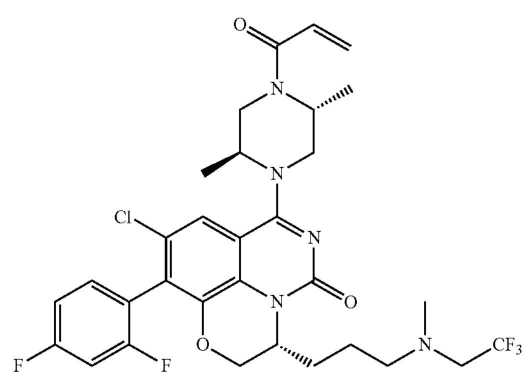 [SMILES: C=CC(=O)N1C[C@H](C)N(c2nc(=O)n3c4c(c(-c5ccc(F)cc5F)c(Cl)cc24)OC[C@H]3CCCN(C)CC(F)(F)F)C[C@H]1C] | ¹H NMR (400 MHz, CDCl₃) δ 7.43-7.40 (m, 1H), 7.31-7.27 (m, 0.7H), 7.26-7.23 (m, 0.3H), 7.03-6.92 (m, 2H), 6.61-6.51 (m, 1H), 6.37 (t, J = 15.2 Hz, 1H), 5.77 (t, J = 6.8 Hz, 1H), 5.02-4.89 (m, 1.5H), 4.71-4.67 (m, 1H), 4.46 (d, J = 12.0 Hz, 1H), 4.34-4.28 (m, 1H), 4.09-3.83 (m, 3.5H), 3.68-3.52 (m, 1H), 3.00-2.90 (m, 2H), 2.60-2.52 (m, 2H), 2.40 (t, J = 4.4 Hz, 3H), 1.81-1.76 (m, 1H), 1.73-1.66 (m, 1H), 1.60-1.57 (m, 2H), 1.34-1.30 (m, 4H), 1.25-1.20 (m, 2H). | 654.2 |
| 298 | (3R)-7-((2S,5R)-4-acryloyl-2,5-dimethylpiperazin-1-yl)-9-chloro-3-(3-(3,3-difluoroazetidin-1-yl)propyl)-10-(2,4-difluorophenyl)-2,3-dihydro-5H-[1,4]oxazino[2,3,4-ij]quinazolin-5-one | 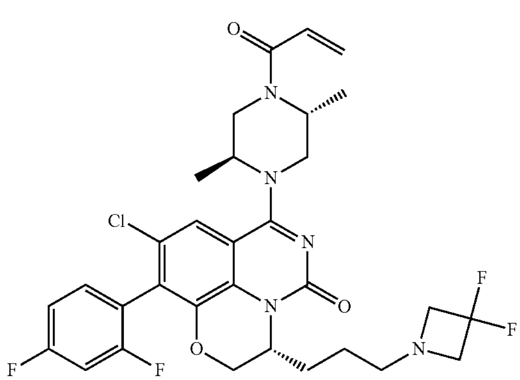 [SMILES: C=CC(=O)N1C[C@H](C)N(c2nc(=O)n3c4c(c(-c5ccc(F)cc5F)c(Cl)cc24)OC[C@H]3CCCN2CC(F)(F)C2)C[C@H]1C] | ¹H NMR (400 MHz, CDCl₃) δ 7.41 (t, J = 8 Hz, 1H), 7.31-7.27 (m, 1H), 7.04-6.94 (m, 2H), 6.63-6.51 (m, 1H), 6.41-6.33 (m, 1H), 5.79-5.75 (m, 1H), 5.03-4.89 (m, 1.5H), 4.71-4.67 (m, 1H), 4.44 (d, J = 11.6 Hz, 1H), 4.35-4.28 (m, 1H), 4.09-4.01 (m, 1.5H), 3.87-3.81 (m, 2H), 3.67 (d, J = 12.8 Hz, 0.5H), 3.57-3.50 (m, 4.5H), 2.59 (t, J = 7.2 Hz, 2H), 1.81-1.79 (m, 1H), 1.76-1.67 (m, 1H), 1.54-1.43 (m, 2H), 1.35-1.30 (m, 3H), 1.27-1.20 (m, 3H). | 634.2 |

-continued

Table of examples

| Ex. # | Name | Structure | ¹H NMR | MS (M + H)⁺ |
|---|---|---|---|---|
| 299 | (3R)-3-(3-(2-oxa-6-azaspiro[3.3]heptan-6-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 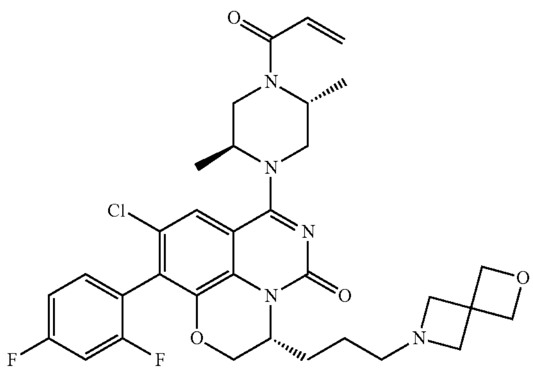 [SMILES: C=CC(=O)N1C[C@H](C)N(c2nc(=O)n3c4c(c(-c5ccc(F)cc5F)c(Cl)cc24)OC[C@H]3CCCN2CC3(COC3)C2)C[C@H]1C] | ¹H NMR (400 MHz, CDCl₃) δ 7.43-7.40 (m, 1H), 7.30-7.23 (m, 1H), 7.04-6.94 (m, 2H), 6.61-6.51 (m, 1H), 6.37 (t, J = 15.6 Hz, 1H), 5.79-5.75 (m, 1H), 5.02-4.88 (m, 1.5H), 4.71 (d, J = 3.2 Hz, 4H), 4.69-4.66 (m, 1H), 4.44 (d, J = 11.6 Hz, 1H), 4.32-4.31 (m, 1H), 4.08-4.03 (m, 1.5H), 3.92-3.81 (m, 2H), 3.68-3.53 (m, 1H), 3.30 (s, 3H), 2.38 (t, J = 6.8 Hz, 2H), 1.83-1.75 (m, 2H), 1.48-1.20 (m, 9H). | 640.2 |
| 311 | (3R)-7-((2S,5R)-4-acryloyl-2,5-dimethylpiperazin-1-yl)-9-chloro-10-(2,4-difluorophenyl)-3-(3-(3-methyl-3,8-diazabicyclo[3.2.1]octan-8-yl)propyl)-2,3-dihydro-5H-[1,4]oxazino[2,3,4-ij]quinazolin-5-one | 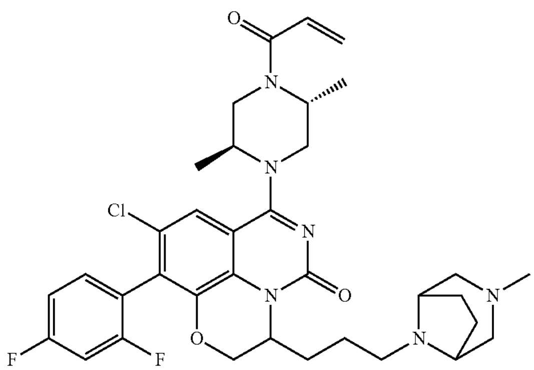 [SMILES: C=CC(=O)N1C[C@H](C)N(c2nc(=O)n3c4c(c(-c5ccc(F)cc5F)c(Cl)cc24)OCC3CCCN2C3CCC2CN(C)C3)C[C@H]1C] | ¹H NMR (400 MHz, CDCl₃) δ 7.42-7.40 (m, 1H), 7.29-7.23 (m, 1H), 7.03-6.92 (m, 2H), 6.58-6.51 (m, 1H), 6.37 (t, J = 16.0 Hz, 1H), 5.77 (t, J = 7.6 Hz, 1H), 5.02-4.89 (m, 1.5H), 4.72-4.70 (m, 1H), 4.49 (d, J = 11.6 Hz, 1H), 4.33-4.30 (m, 1H), 4.08-4.00 (m, 1.5H), 3.92-3.85 (m, 2H), 3.68-3.64 (m, 0.5H), 3.57-3.56 (m, 0.5H), 3.14-3.11 (m, 2H), 2.58-2.56 (m, 2H), 2.39-2.35 (m, 2H), 2.26-2.24 (m, 2H), 2.20 (s, 3H), 1.82-1.69 (m, 6H), 1.63-1.55 (m, 2H), 1.34-1.30 (m, 4H), 1.25-1.20 (m, 2H). | 6673 |
| 312 | (3R)-3-(3-(8-oxa-3-azabicyclo[3.2.1]octan-3-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 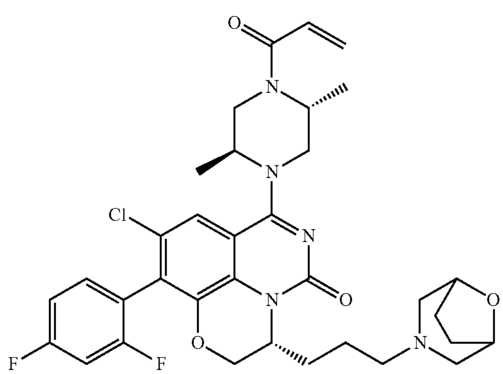 [SMILES: C=CC(=O)N1C[C@H](C)N(c2nc(=O)n3c4c(c(-c5ccc(F)cc5F)c(Cl)cc24)OC[C@H]3CCCN2CC3CCC(C2)O3)C[C@H]1C] | ¹H NMR (400 MHz, CDCl₃) δ 7.43-7.40 (m, 1H), 7.30-7.23 (m, 1H), 7.03-6.92 (m, 2H), 6.63-6.51 (m, 1H), 6.37 (t, J = 15.6 Hz, 1H), 5.77 (t, J = 6.8 Hz, 1H), 5.03-4.89 (m, 1.5H), 4.68 (br, 1H), 4.46 (d, J = 11.2 Hz, 1H), 4.37-4.31 (m, 1H), 4.24 (s, 2H), 4.09-4.00 (m, 1.5H), 3.92-3.81 (m, 2H), 3.68-3.53 (m, 1H), 2.53-2.51 (m, 2H), 2.30-2.22 (m, 4H), 1.83-1.80 (m, 5H), 1.56-1.50 (m, 2H), 1.34-1.20 (m, 7H). | 654.3 |
| 315 | (3R)-3-(3-((1R,4R)-2-oxa-5-azabicyclo[2.2.1]heptan-5-yl)propyl)-7-((2S,5R)-4-acryloyl-2,5-dimethylpiperazin-1-yl)-9-chloro-10-(2,4-difluorophenyl)-2,3-dihydro-5H-[1,4]oxazino[2,3,4-ij]quinazolin-5-one | 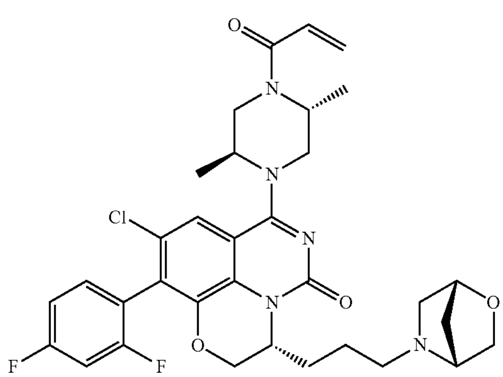 [SMILES: C=CC(=O)N1C[C@H](C)N(c2nc(=O)n3c4c(c(-c5ccc(F)cc5F)c(Cl)cc24)OC[C@H]3CCCN2C[C@H]3C[C@@H]2CO3)C[C@H]1C] | ¹H NMR (400 MHz, CDCl₃) δ 7.43-7.40 (m, 1H), 7.30-7.24 (m, 1H), 7.03-6.92 (m, 2H), 6.62-6.51 (m, 1H), 6.37 (t, J = 16 Hz, 1H), 5.77 (t, J = 7.2 Hz, 1H), 5.02-4.90 (m, 1.5H), 4.71-4.69 (m, 1H), 4.49-4.46 (m, 1H), 4.40-4.31 (m, 1H), 4.09-4.04 (m, 2.5H), 3.99-3.82 (m, 2H), 3.68-3.51 (m, 3H), 2.95-2.52 (m, 4H), 1.93-1.76 (m, 5.5H), 1.35-1.28 (m, 5H), 1.25-1.21 (m, 2.5H). | 640.2 |

-continued

Table of examples

| Ex. # | Name | Structure | ¹H NMR | MS (M + H)⁺ |
|---|---|---|---|---|
| 321 | (3R)-7-((2S,5R)-4-acryloyl-2,5-dimethylpiperazin-1-yl)-9-chloro-10-(2,4-difluorophenyl)-3-(3-(3-methyl-3,8-diazabicyclo[3.2.1]octan-8-yl)propyl)-2,3-dihydro-5H-[1,4]oxazino[2,3,4-ij]quinazolin-5-one | 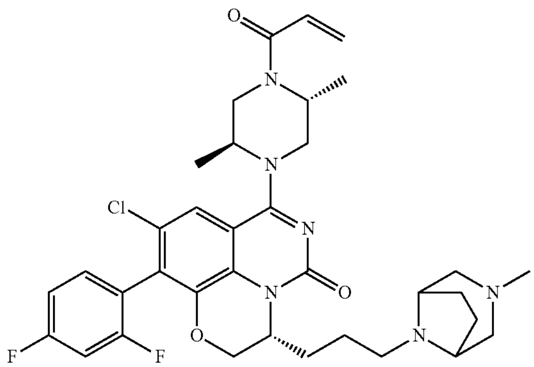 [SMILES: C=CC(=O)N1C[C@H](C)N(c2nc(=O)n3c4c(c(-c5ccc(F)cc5F)c(Cl)cc24)OC[C@H]3CCCN2C3CCC2CN(C)C3)C[C@H]1C] | ¹H NMR (400 MHz, CDCl₃) δ 7.42-7.39 (m, 1H), 7.30-7.28 (m, 1H), 7.003-6.93 (m, 2H), 6.61-6.50 (m, 1H), 6.40-6.32 (m, 1H), 5.78-5.74 (m, 1H), 5.02-4.88 (m, 1.5H), 4.68 (brs, 1H), 4.47-4.30 (m, 2H), 4.08-4.01 (m, 1.5H), 3.91-3.83 (m, 2H), 3.67-3.53 (m, 1H), 3.05 (s, 2H), 2.57-2.53 (m, 2H), 2.33-2.26 (m, 7H), 1.86-1.79 (m, 4H), 1.56-1.50 (m, 4H), 1.34-1.19 (m, 6H). | 571.2 |
| 322 | (3R,10S)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(naphthalen-1-yl)-2,3-dihydro-5H-[1,4]oxazino[2,3,4-ij]quinazolin-5-one | 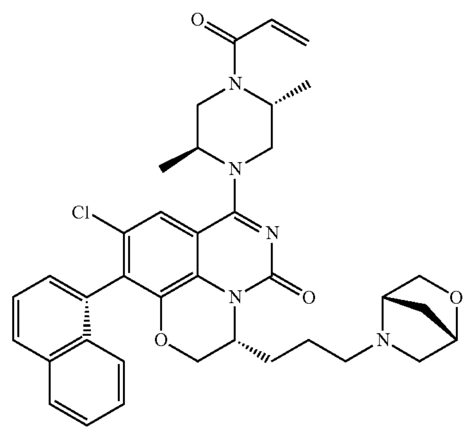 | ¹H NMR (400 MHz, CDCl₃) δ 7.98-7.94 (m, 2H), 7.61 (t, J = 7.2 Hz, 1H), 7.54-7.46 (m, 2H), 7.43-7.34 (m, 3H), 6.64-6.53 (m, 1H), 6.42-6.34 (m, 1H), 5.78 (t, J = 7.6 Hz, 1H), 5.10-4.91 (m, 1.5H), 4.69 (s, 1H), 4.38-4.30 (m, 3H), 4.12-3.83 (m, 5H), 3.72-3.47 (m, 2.5H), 2.95-2.81 (m, 1H), 2.68-2.41 (m, 2H), 1.89-1.75 (m, 5H), 1.43-1.34 (m, 4H), 1.30-1.18 (m, 4H). | 654.4 |
| 323 | (3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-cyclopropyl-10-(2,4-difluorophenyl)-2,3-dihydro-5H-[1,4]oxazino[2,3,4-ij]quinazolin-5-one | 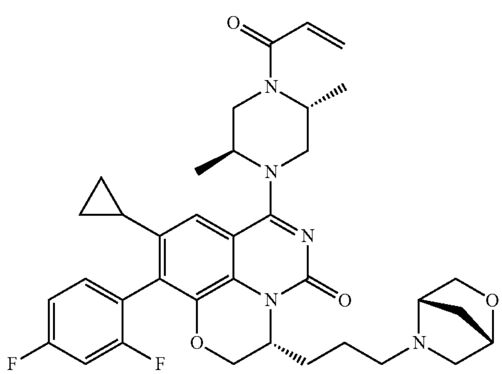 [SMILES: C=CC(=O)N1C[C@H](C)N(c2nc(=O)n3c4c(c(-c5ccc(F)cc5F)c(C5CC5)cc24)OC[C@H]3CCCN2C[C@@H]3C[C@H]2CO3)C[C@H]1C] | ¹H NMR (400 MHz, CDCl₃) δ 7.30-7.22 (m, 1H), 7.00-6.93 (m, 3H), 6.67-6.52 (m, 1H), 6.37 (t, J = 15.2 Hz, 1H), 5.77 (t, J = 8.4 Hz, 1H), 5.02-4.82 (m, 1.5H), 4.71-4.66 (m, 1H), 4.44-4.29 (m, 3H), 4.04-3.85 (m, 4H), 3.76-3.64 (m, 1H), 3.59-3.49 (m, 1.5H), 3.43-3.42 (m, 1H), 2.89-2.85 (m, 1H), 2.62-2.51 (m, 2H), 2.46 (d, J = 10.4 Hz, 1H), 1.84-1.78 (m, 2H), 1.74-1.63 (m, 3H), 1.57-1.51 (m, 2H), 1.34-1.20 (m, 6H), 0.79-0.71 (m, 2H), 0.58-0.48 (m, 2H). | 646.4 |
| 325 | (3R,10S)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one | 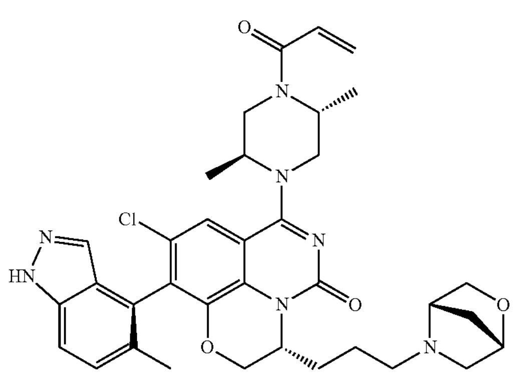 | ¹H NMR (400 MHz, CDCl₃) δ 7.55-7.49 (m, 3H), 7.39 (d, J = 9.2 Hz, 1H), 6.61-6.52 (m, 1H), 6.38 (t, J = 16 Hz, 1H), 5.78 (t, J = 9.2 Hz, 1H), 5.06-4.91 (m, 2H), 4.71 (s, 1H), 4.44-4.36 (m, 3H), 4.11-3.82 (m, 5H), 3.69 (d, J = 12.8 Hz, 1H), 3.64-3.55 (m, 2H), 2.76-2.60 (m, 3H), 2.23 (s, 3H), 1.94-1.76 (m, 6H), 1.39-1.37 (m, 3H), 1.28-1.26 (m, 3H). | 658.4 |

-continued

Table of examples

| Ex. # | Name | Structure | ¹H NMR | MS (M + H)⁺ |
|---|---|---|---|---|
| 326 | (3R,10R)-3-(3-((1S,4S)-2-oxa-5-azabicyclo[2.2.1]heptan-5-yl)propyl)-7-((2S,5R)-4-acryloyl-2,5-dimethylpiperazin-1-yl)-9-chloro-10-(5-methyl-1H-indazol-4-yl)-2,3-dihydro-5H-[1,4]oxazino[2,3,4-ij]quinazolin-5-one | 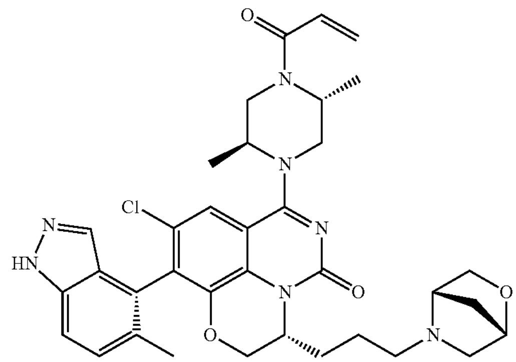 | ¹H NMR (400 MHz, CDCl₃) δ 7.55-7.49 (m, 3H), 7.39 (d, J = 9.2 Hz, 1H), 6.67-6.52 (m, 1H), 6.38 (t, J = 16.4 Hz, 1H), 5.79 (t, J = 10.4 Hz, 1H), 5.02-4.95 (m, 1.5H), 4.73 (s, 1H), 4.39 (s, 1H), 4.34 (d, J = 11.6 Hz, 3H), 4.16-3.87 (m, 5H), 3.77-3.69 (m, 2H), 3.57 (d, J = 14.4 Hz, 0.5H), 3.28-3.03 (m, 2H), 2.21 (m, 3H), 2.07-2.04 (m, 2H), 1.90-1.73 (m, 5H), 1.39 (d, J = 6.4 Hz, 4H), 1.30 (d, J = 6.8 Hz, 2H). | 658.4 |
| 327 | (3R)-7-((2S,5R)-4-acryloyl-2,5-dimethylpiperazin-1-yl)-9-chloro-10-(2,4-difluorophenyl)-3-(3-(methyl(oxetan-3-yl)amino)propyl)-2,3-dihydro-5H-[1,4]oxazino[2,3,4-ij]quinazolin-5-one | 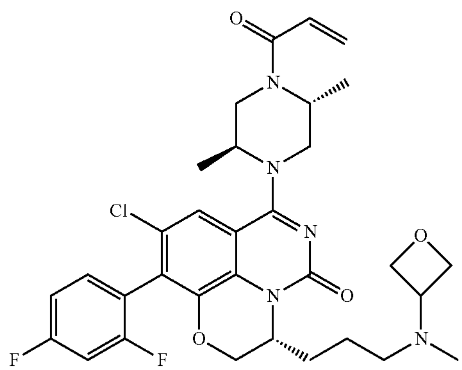 [SMILES: C=CC(=O)N1C[C@H](C)N(c2nc(=O)n3c4c(c(-c5ccc(F)cc5F)c(Cl)cc24)OC[C@H]3CCCN(C)C2COC2)C[C@H]1C] | ¹H NMR (400 MHz, CDCl₃) δ 7.42 (t, J = 5.6 Hz, 1H), 7.32-7.28 (m, 0.6H), 7.26-7.24 (m, 0.4H), 7.03-6.93 (m, 2H), 6.66-6.51 (m, 1H), 6.73 (t, J = 16.0 Hz, 1H), 5.77 (t, J = 8.8 Hz, 1H), 5.02-4.89 (m, 1.5H), 4.71 (s, 1H), 4.63-3.53 (m, 4H), 4.48-4.45 (m, 1H), 4.37-4.28 (m, 1H), 4.10-3.81 (m, 2H), 3.69-3.51 (m, 2H), 2.24-2.08 (m, 2H), 2.04 (s, 3H), 1.86-1.65 (m, 4H), 1.35-1.21 (m, 6H). | 628.3 |
| 330 | (3R)-7-((2S,5R)-4-acryloyl-2,5-dimethylpiperazin-1-yl)-9-chloro-10-(2,4-difluorophenyl)-3-(3-((S)-3-fluoropyrrolidin-1-yl)propyl)-2,3-dihydro-5H-[1,4]oxazino[2,3,4-ij]quinazolin-5-one | 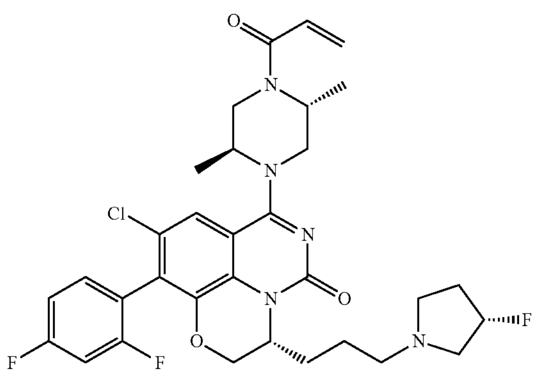 [SMILES: C=CC(=O)N1C[C@H](C)N(c2nc(=O)n3c4c(c(-c5ccc(F)cc5F)c(Cl)cc24)OC[C@H]3CCCN2CC[C@H](F)C2)C[C@H]1C] | ¹H NMR (400 MHz, CDCl₃) δ 7.42-7.40 (m, 1H), 7.31-7.23 (m, 1H), 7.03-6.93 (m, 2H), 6.63-6.51 (m, 1H), 6.37 (t, J = 15.6 Hz, 1H), 5.77 (t, J = 7.2 Hz, 1H), 5.22-5.19 (m, 0.5H), 5.08-4.88 (m, 2H), 4.70-4.69 (m, 1H), 4.47 (d, J = 11.6 Hz, 1H), 4.33-4.30 (m, 1H), 4.09-4.01 (m, 1.5H), 3.91-3.81 (m, 2H), 3.68-3.53 (m, 1H), 2.92-2.77 (m, 2H), 2.65-2.32 (m, 4H), 2.22-1.98 (m, 2.5H), 1.88-1.80 (m, 1.5H), 1.71-1.63 (m, 2H), 1.34-1.30 (m, 4H), 1.28-1.18 (m, 2H). | 630.3 |
| 331 | (3R)-7-((2S,5R)-4-acryloyl-2,5-dimethylpiperazin-1-yl)-9-chloro-10-(2,4-difluorophenyl)-3-(3-(oxetan-3-yl(2,2,2-trifluoroethyl)amino)propyl)-2,3-dihydro-5H-[1,4]oxazino[2,3,4-ij]quinazolin-5-one | 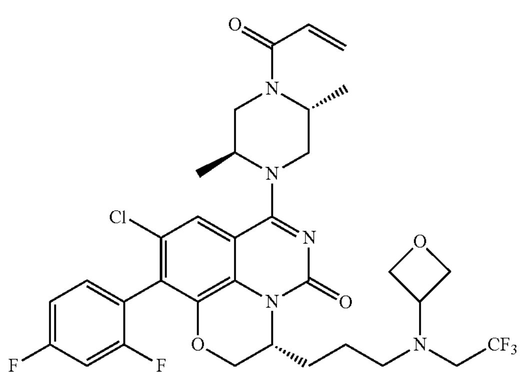 [SMILES: C=CC(=O)N1C[C@H](C)N(c2nc(=O)n3c4c(c(-c5ccc(F)cc5F)c(Cl)cc24)OC[C@H]3CCCN(CC(F)(F)F)C2COC2)C[C@H]1C] | ¹H NMR (400 MHz, CDCl₃) δ 7.44-7.41 (m, 1H), 7.30-7.24 (m, 1H), 7.04-6.93 (m, 2H), 6.64-6.51 (m, 1H), 6.37 (t, J = 15.2 Hz, 1H), 5.79-5.75 (m, 1H), 5.02-4.88 (m, 1.5H), 4.73-4.64 (m, 3H), 4.57-4.52 (m, 2H), 4.46-4.30 (m, 2H), 4.10-4.01 (m, 2.5H), 3.93-3.82 (m, 2H), 3.68-3.53 (m, 1H), 3.20-3.11 (m, 2H), 2.73-2.69 (m, 2H), 1.84-1.76 (m, 1H), 1.72-1.64 (m, 1H), 1.57-1.50 (m, 2H), 1.34-1.20 (m, 6H). | 696.3 |

Table of examples

| Ex. # | Name | Structure | ¹H NMR | MS (M + H)⁺ |
|---|---|---|---|---|
| 332 | (3R)-3-(3-((1S,4S)-2-oxa-5-azabicyclo[2.2.1]heptan-5-yl)propyl)-7-((2S,5R)-4-acryloyl-2,5-dimethylpiperazin-1-yl)-10-(2,4-difluorophenyl)-5-oxo-2,3-dihydro-5H-[1,4]oxazino[2,3,4-ij]quinazoline-9-carbonitrile | 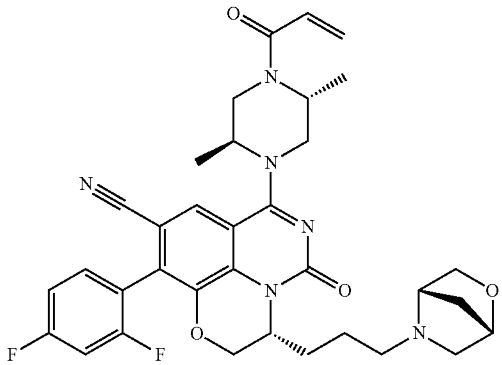 [SMILES: C=CC(=O)N1C[C@H](C)N(c2nc(=O)n3c4c(c(-c5ccc(F)cc5F)c(C#N)cc24)OC[C@H]3CCCN2C[C@@H]3C[C@H]2CO3)C[C@H]1C] | ¹H NMR (400 MHz, CDCl₃) δ 7.70-7.68 (m, 1H), 7.45-7.35 (m, 1H), 7.10-6.98 (m, 2H), 6.58-6.51 (m, 1H), 6.43-6.28 (m, 1H), 5.79 (t, J = 8 Hz, 1H), 5.03-4.89 (m, 1.5H), 4.76-4.72 (m, 1H), 4.58-4.54 (m, 1H), 4.46 (s, 1H), 4.13-4.00 (m, 2.5H), 3.93-3.87 (m, 2H), 3.73-3.54 (m, 3H), 3.09-3.04 (m, 1H), 2.85-2.69 (m, 3H), 2.06-1.84 (m, 5H), 1.37-1.20 (m, 8H). | 799.5 |
| 334 | (3R)-7-((2S,5R)-4-acryloyl-2,5-dimethylpiperazin-1-yl)-9-chloro-10-(2,4-difluorophenyl)-3-(3-((S)-3-methoxypyrrolidin-1-yl)propyl)-2,3-dihydro-5H-[1,4]oxazino[2,3,4-ij]quinazolin-5-one | 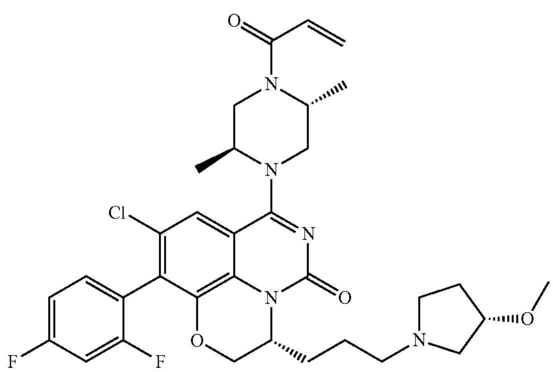 [SMILES: C=CC(=O)N1C[C@H](C)N(c2nc(=O)n3c4c(c(-c5ccc(F)cc5F)c(Cl)cc24)OC[C@H]3CCCN2CC[C@H](OC)C2)C[C@H]1C] | ¹H NMR (400 MHz, CDCl₃) δ 7.42-7.40 (m, 1H), 7.32-7.28 (m, 0.72H), 7.26-7.23 (m, 0.21H), 7.03-6.93 (m, 2H), 6.66-6.51 (m, 1H), 6.37 (t, J = 16.4 Hz, 1H), 5.79-5.75 (m, 1H), 5.02-4.89 (m, 1H), 4.69 (s, 1H), 4.47 (d, J = 11.6 Hz, 1H), 4.34-4.31 (m, 1H), 4.08-3.88 (m, 4H), 3.68-3.54 (m, 1H), 3.26 (d, J = 2.0 Hz, 3H), 2.69-2.46 (m, 6H), 2.06-1.98 (m, 1H), 1.86-1.64 (m, 6H), 1.35-1.21 (m, 6H). | 642.2 |

The different tertial amine intermediates were synthesized using aldehyde intermediate 3 and corresponding amine through reductive amination reaction. The rest steps were conducted under the conditions described above.

Syntheses of Intermediates

Reaction Scheme

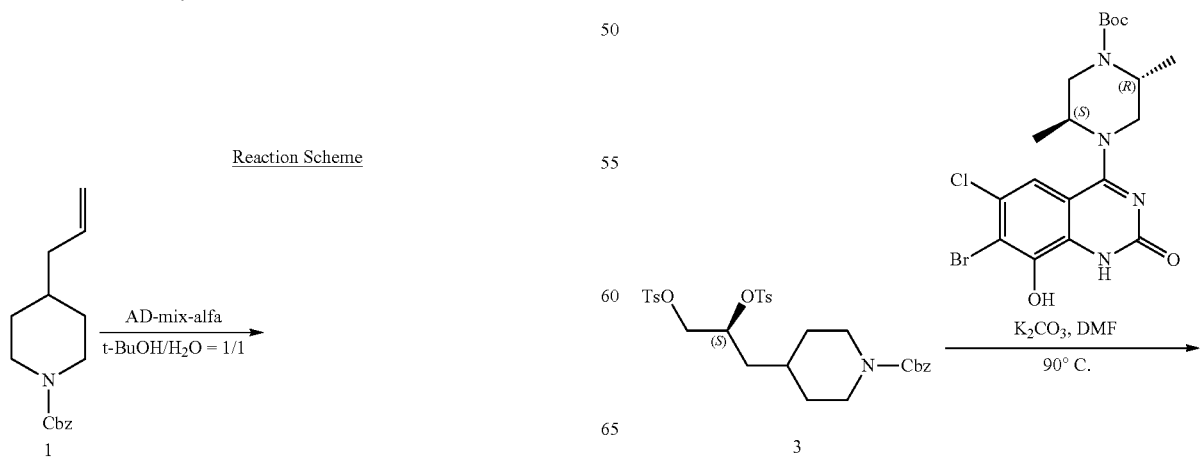

(S)-benzyl 4-(2,3-dihydroxypropyl)piperidine-1-carboxylate (2)

To a mixture of benzyl 4-allylpiperidine-1-carboxylate (500 mg, 1.93 mmol) in t-butanol (9 mL) and H₂O (9 mL) was added AD-mix-alfa (2 g) at 0° C. The mixture was stirred at rt overnight. LCMS showed completed, EA (50 mL) was added followed by Na₂SO₃ (30 mL) in portions. The reaction was stirred for 10 min at 0° C. and 30 min at rt. The organic phase was separated, and the aqueous layer was extracted with EtOAc. The combined organic phase was dried over Na₂SO₄, concentrated. The residue was purified by silica gel chromatography (5% MeOH in DCM) to afford the title compound (446 mg, 1.52 mmol, 79% yield) as pale-yellow oil. MS (ESI) m/z 294.1[M+H].

(S)-benzyl 4-(2,3-bis(tosyloxy)propyl)piperidine-1-carboxylate (3)

To a mixture of (S)-benzyl 4-(2,3-dihydroxypropyl)piperidine-1-carboxylate (446 mg, 1.52 mmol) in DCM (6 mL) and TEA (461 mg, 4.57 mmol) was added TsCl (1.16 g, 6.08 mmol) at 0° C. The mixture was stirred at rt overnight. The solvent was evaporated, and the residue was purified by silica gel chromatography (20% ethyl acetate in petroleum ether) to afford the title compound (650 mg, 1.08 mmol, 71% yield) as colorless oil. MS (ESI) m/z 602.1 [M+H]⁺.

(2R,5S)-tert-butyl-4-((R)-3-((1-((benzyloxy)carbonyl)piperidin-4-yl)methyl)-10-bromo-9-chloro-5-oxo-3,5-dihydro-2H-[1,4]oxazino[2,3,4-ij]quinazolin-7-yl)-2,5-dimethylpiperazine-1-carboxylate (4)

To a mixture of (2R,5S)-tert-butyl 4-(7-bromo-6-chloro-2,8-dihydroxyquinazolin-4-yl)-2,5-dimethylpiperazine-1-carboxylate (74 mg, 0.15 mmol) and (S)-benzyl 4-(2,3-bis(tosyloxy) propyl)piperidine-1-carboxylate (272 mg, 0.15 mmol) in DCM (6 mL) was added K₂CO₃ (62 mg, 0.45 mmol), the mixture was stirred at 90° C. overnight. The solvent was evaporated and the residue was purified by silica gel chromatography (2% MeOH in DCM) to afford the title compound (85 mg, 0.11 mmol, 76% yield) as white solid, e.e. =58%, contained 25% region-isomer. MS (ESI) m/z 746.0 [M+H]⁺.

Example 288

(3R)-7-((2S,5R)-4-acryloyl-2,5-dimethylpiperazin-1-yl)-9-chloro-10-(2,4-difluorophenyl)-3-((1-methylpiperidin-4-yl)methyl)-2H-[1,4]oxazino[2,3,4-ij]quinazolin-5(3H)-one Reaction Scheme

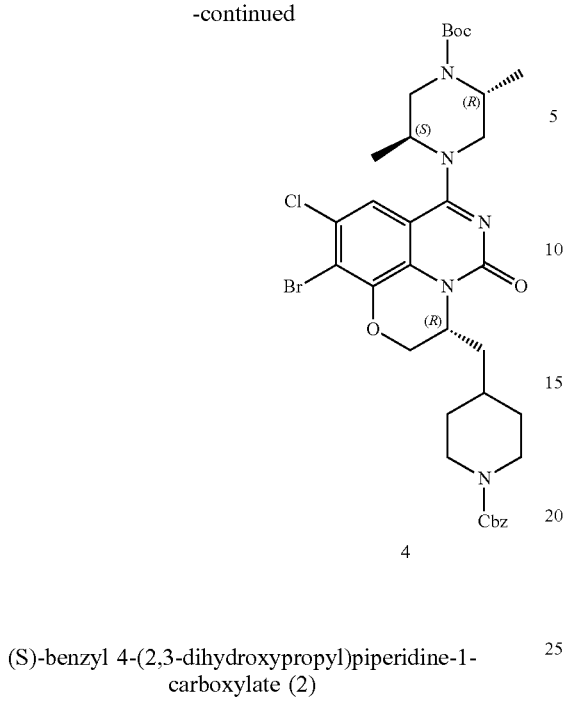

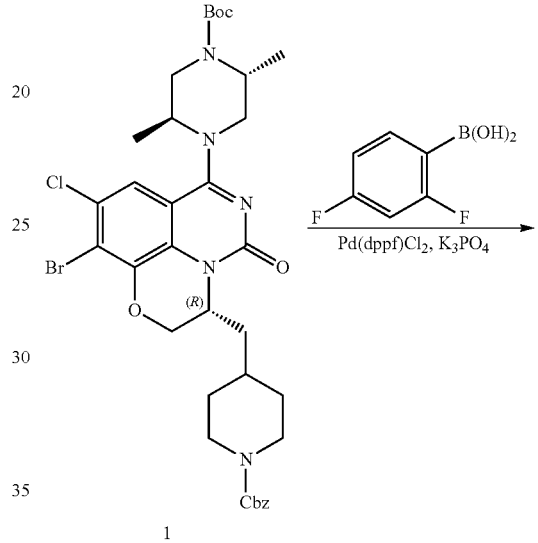

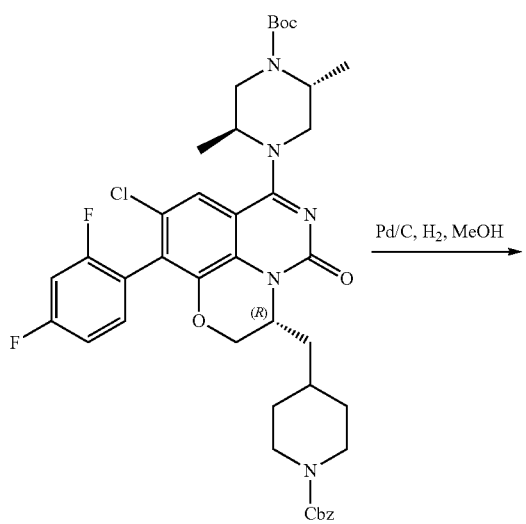

-continued

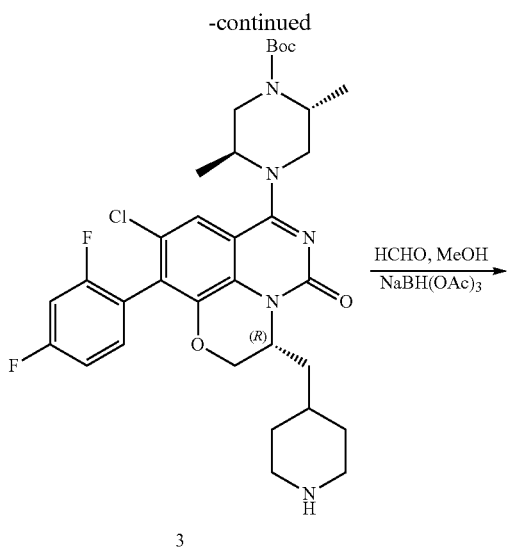

3

HCHO, MeOH
―――――――→
NaBH(OAc)₃

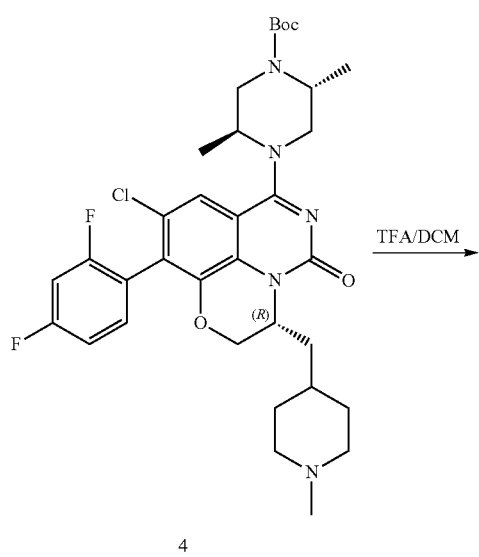

4

TFA/DCM
―――――→

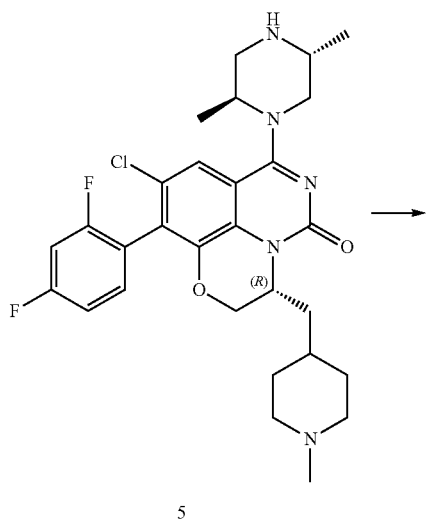

5

→

-continued

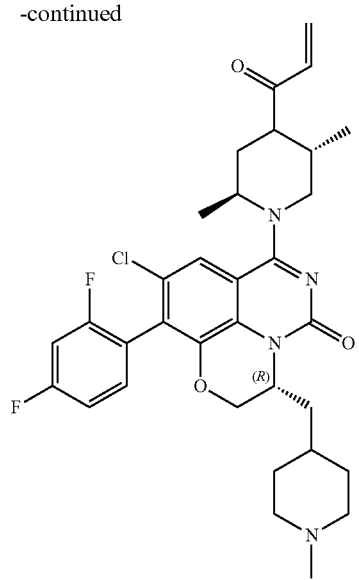

6

(2R,5S)-tert-butyl-4-((3R)-3-((1-((benzyloxy)carbo-
nyl)piperidin-4-yl)methyl)-9-chloro-10-(2,4-difluo-
rophenyl)-5-oxo-3,5-dihydro-2H-[1,4]oxazino[2,3,4-
ij]quinazolin-7-yl)-2,5-dimethylpiperazine-1-
carboxylate (2)

The mixture of (2R,5S)-tert-butyl 4-((R)-3-((1-((benzy-
loxy)carbonyl)piperidin-4-yl)methyl)-10-bromo-9-chloro-
5-oxo-3,5-dihydro-2H-[1,4]oxazino[2,3,4-ij]quinazolin-7-
yl)-2,5-dimethylpiperazine-1-carboxylate (250 mg, 0.34
mmol), (2,4-difluorophenyl)boronic acid (212 mg, 1.34
mmol), Pd(dppf)Cl₂ (25 mg, 0.034 mmol) and (214 mg,
1.008 mmol) in a mixture of dioxane (3 mL) and H₂O (0.5
mL) was heated at 80° C. under nitrogen atmosphere for 8
hours. The mixture was concentrated, and the residue was
purified by silica gel column chromatography (dichlo-
romethane/methanol=50/1) to give the crude product (245
mg, 93% yield) as pale-yellow solid. LC-MS: m/z 778.1
[M+H]⁺.

(2R,5S)-tert-butyl-4-((3R)-9-chloro-10-(2,4-difluo-
rophenyl)-5-oxo-3-(piperidin-4-ylmethyl)-3,5-di-
hydro-2H-[1,4]oxazino[2,3,4-ij]quinazolin-7-yl)-2,5-
dimethylpiperazine-1-carboxylate (3)

To a solution of (2R,5S)-tert-butyl-4-((3R)-3-((1-((benzy-
loxy)carbonyl)piperidin-4-yl) methyl)-9-chloro-10-(2,4-dif-
luorophenyl)-5-oxo-3,5-dihydro-2H-[1,4]oxazino[2,3,4-ij]
quinazolin-7-yl)-2,5-dimethylpiperazine-1-carboxylate (245
mg, 0.32 mmol) in MeOH (3 mL) was added Pd/C (80 mg).
The mixture was stirred at rt under H₂ for 1 hour. After
completion, the mixture was filtered and concentrated under
reduced pressure to afford the desired product (188 mg, 91% yield) as a yellow solid, which was used to next step without further purification. LC-MS: m/z 644.2[M+H]⁺.

(2R,5S)-tert-butyl 4-((3R)-9-chloro-10-(2,4-difluorophenyl)-3-((1-methylpiperidin-4-yl)methyl)-5-oxo-3,5-dihydro-2H-[1,4]oxazino[2,3,4-ij]quinazolin-7-yl)-2,5-dimethylpiperazine-1-carboxylate (4)

To a solution of (2R,5S)-tert-butyl-4-((3R)-9-chloro-10-(2,4-difluorophenyl)-5-oxo-3-(piperidin-4-ylmethyl)-3,5-dihydro-2H-[1,4]oxazino[2,3,4-ij]quinazolin-7-yl)-2,5-dimethylpiperazine-1-carboxylate (188 mg, 0.29 mmol) and HCHO (50 mg, 0.58 mmol, 35% in H$_2$O) in MeOH (3 mL) was added NaB(OAc)$_3$H (123 mg, 0.58 mmol). The mixture was stirred at rt for 2 hours. After completion, the solvent was removed in vacuo. The residue was purified by silica column with using a mixture of DCM:MeOH (20:1) to afford the desired product (173 mg, yield: 91%) as pale yellow solid. LC-MS: m/z 658.2[M+H]⁺.

(3R)-9-chloro-10-(2,4-difluorophenyl)-7-((2S,5R)-2,5-dimethylpiperazin-1-yl)-3-((1-methylpiperidin-4-yl)methyl)-2H-[1,4]oxazino[2,3,4-ij]quinazolin-5(3H)-one (5)

To a solution of (2R,5S)-tert-butyl 4-((3R)-9-chloro-10-(2,4-difluorophenyl)-3-((1-methylpiperidin-4-yl)methyl)-5-oxo-3,5-dihydro-2H-[1,4]oxazino[2,3,4-ij]quinazolin-7-yl)-2,5-dimethylpiperazine-1-carboxylate (173 mg, 0.26 mmol) in DCM (1 ml) was added TFA (1 ml). The mixture was stirred at rt for 2 hours. After completion, the solvent and the excess of TFA were removed to afford the crude product (120 mg) as a yellow solid, which was used to next step without further purification. LC-MS: m/z 558.1[M+H]⁺.

(3R)-7-((2S,5R)-4-acryloyl-2,5-dimethylpiperazin-1-yl)-9-chloro-10-(2,4-difluorophenyl)-3-((1-methylpiperidin-4-yl)methyl)-2H-[1,4]oxazino[2,3,4-ij]quinazolin-5(3H)-one (6)

To a mixture of (3R)-9-chloro-10-(2,4-difluorophenyl)-7-((2S,5R)-2,5-dimethylpiperazin-1-yl)-3-((1-methylpiperidin-4-yl)methyl)-2H-[1,4]oxazino[2,3,4-ij]quinazolin-5 (3H)-one (120 mg, 0.21 mmol) and triethyl amine (42 mg, 0.42 mmol) in dichloromethane (2 mL) was added acrylic anhydride (27 mg, 0.21 mmol) at 0° C. The mixture was stirred at 0° C. for 1 hour. After completion, the solvent was removed in vacuo. The residue was purified by prep-HPLC to afford the product (17 mg, 13% yield) as a white solid. LC-MS: m/z 612.3 [M+H]⁺. ¹H NMR (400 MHz, CD$_3$OD) δ 7.43-7.41 (m, 1H), 7.33-7.26 (m, 1H), 7.04-6.94 (m, 2H), 6.66-6.51 (m, 1H), 6.37 (t, J=15.6 Hz, 1H), 5.79-5.75 (m, 1H), 5.03-4.97 (m, 1H), 4.88-4.82 (m, 1.5H), 4.43-4.29 (m, 2H), 4.09-4.05 (m, 1.5H), 3.97-3.79 (m, 2H), 3.68-3.51 (m, 1H), 2.92-2.86 (m, 2H), 2.30 (s, 3H), 2.07-1.92 (m, 2H), 1.88-1.64 (m, 5H), 1.62-1.48 (m, 2H), 1.35-1.33 (m, 3H), 1.26-1.21 (m, 3H).

The different-alkyl intermediates were synthesized using corresponding aldehyde. ketone through reductive amination reaction or alkylation with alkyl halide. The additional steps were conducted under the conditions described above.

| Ex. # | Name | Structure | ¹H NMR | MS (M + H)⁺ |
|---|---|---|---|---|
| 288 | (3R)-7-((2S,5R)-4-acryloyl-2,5-dimethylpiperazin-1-yl)-9-chloro-10-(2,4-difluorophenyl)-3-((1-methylpiperidin-4-yl)methyl)-2H-[1,4]oxazino[2,3,4-ij]quinazolin-5(3H)-one | 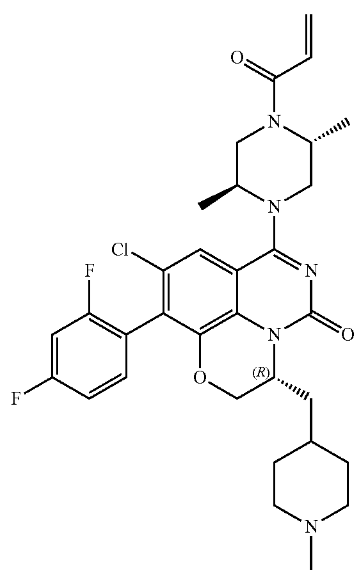 | 1H NMR (400 MHz, CD$_3$OD) δ 7.43-7.41 (m, 1H), 7.33-7.26 (m, 1H), 7.04-6.94 (m, 2H), 6.66-6.51 (m, 1H), 6.37 (t, J = 15.6 Hz, 1H), 5.79-5.75 (m, 1H), 5.03-4.97 (m, 1H), 4.88-4.82 (m, 1.5H), 4.43-4.29 (m, 2H), 4.09-4.05 (m, 1.5H), 3.97-3.79 (m, 2H), 3.68-3.51 (m, 1H), 2.92-2.86 (m, 2H), 2.30 (s, 3H), 2.07-1.92 (m, 2H), 1.88-1.64 (m, 5H), 1.62-1.48 (m, 2H), 1.35-1.33 (m, 3H), 1.26-1.21 (m, 3H). | 612.3 |

| Ex. # | Name | Structure | ¹H NMR | MS (M + H)⁺ |
|---|---|---|---|---|
| 316 | (3R)-7-((2S,5R)-4-acryloyl-2,5-dimethylpiperazin-1-yl)-9-chloro-10-(2,4-difluorophenyl)-3-((1-(oxetan-3-yl)piperidin-4-yl)methyl)-2H-[1,4]oxazino[2,3,4-ij]quinazolin-5(3H)-one | 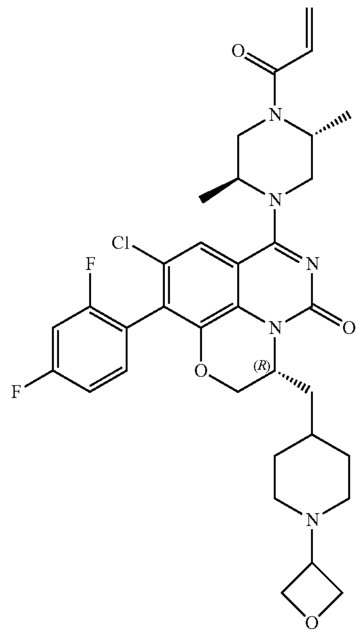 | 1H NMR (400 MHz, CDCl₃) δ 7.43-7.40 (m, 1H), 7.32-7.24 (m, 1H), 7.04-6.94 (m, 2H), 6.63-6.51 (m, 1H), 6.37 (t, J = 15.2 Hz, 1H), 5.79-5.75 (m, 1H), 5.02-4.96 (m, 1H), 4.88-4.81 (m, 1.5H), 4.65-4.61 (m, 4H), 4.02 (d, J = 11.6 Hz, 1H), 4.37-4.28 (m, 1H), 4.10-4.04 (m, 1.5H), 3.96-3.80 (m, 2H), 3.68-3.65 (m, 0.5H), 3.54-3.42 (m, 1.5H), 2.74-2.69 (m, 2H), 1.83-1.80 (m, 4H), 1.75-1.67 (m, 1H), 1.44-1.39 (m, 2H), 1.35-1.33 (m, 6H), 1.26-1.19 (m, 2H). | 654.2 |
| 324 | (3S)-7-((2S,5R)-4-acryloyl-2,5-dimethylpiperazin-1-yl)-9-chloro-10-(2,4-difluorophenyl)-3-((1-methylpiperidin-4-yl)methyl)-2H-[1,4]oxazino[2,3,4-ij]quinazolin-5(3H)-one | 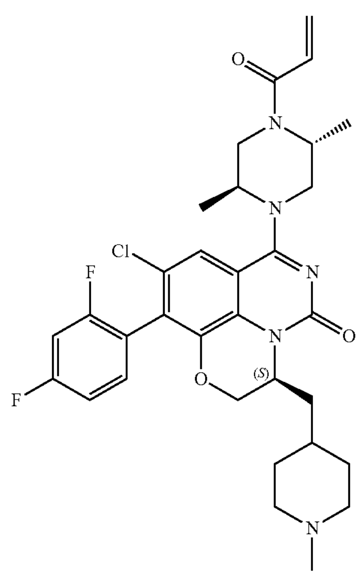 | 1H NMR (400 MHz, CDCl₃) δ 7.43 (s, 1H), 7.34-7.22 (m, 1H), 7.04-6.93 (m, 2H), 6.64-6.51 (m, 1H), 6.37 (t, J = 15.6 Hz, 1H), 5.77 (t, J = 6.0 Hz, 1H), 4.99-4.82 (m, 3H), 4.40-4.26 (m, 2.5H), 4.08-3.99 (m, 1.5H), 3.84-3.65 (m, 2.5H), 3.42-3.38 (m, 0.5H), 2.83 (d, J = 9.6 Hz, 2H), 2.26 (s, 3H), 2.02-1.88 (m, 4H), 1.39-1.27 (m, 10H). | 612.4 |

| Ex. # | Name | Structure | ¹H NMR | MS (M + H)⁺ |
|---|---|---|---|---|
| 328 | (3R)-7-((2S,5R)-4-acryloyl-2,5-dimethylpiperazin-1-yl)-9-chloro-3-((1-(2,2-difluoroethyl)piperidin-4-yl)methyl)-10-(2,4-difluorophenyl)-2H-[1,4]oxazino[2,3,4-ij]quinazolin-5(3H)-one | 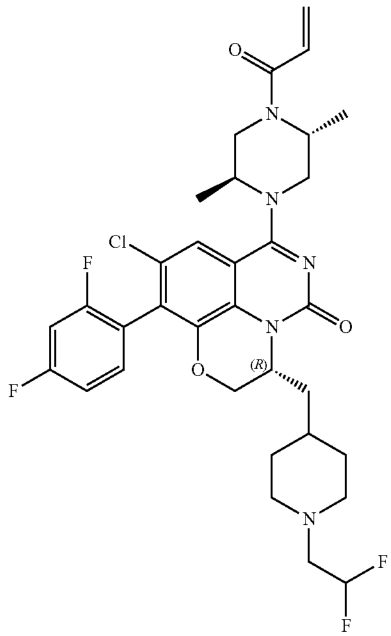 | 1H NMR (400 MHz, CDCl₃) δ 7.43-7.40 (m, 1H), 7.32-7.24 (m, 1H), 7.05-6.94 (m, 2H), 6.66-6.54 (m, 1H), 6.37 (t, J = 15.2 Hz, 1H), 6.01-5.71 (m, 2H), 5.01-4.96 (m, 1H), 4.92-4.81 (m, 1.5H), 4.42 (d, J = 11.6 Hz, 1H), 4.37-4.30 (m, 1H), 4.07 (t, J = 10.4 Hz, 1.5H), 3.96-3.78 (m, 2H), 3.68-3.65 (m, 0.5H), 3.55-3.51 (m, 0.5H), 2.92 (t, J = 12.0 Hz, 2H), 2.71 (td, J = 15.2 Hz, 3.2 Hz, 2H), 2.24-2.14 (m, 2H), 1.78-1.71 (m, 2H), 1.69-1.64 (m, 1H), 1.46-1.41 (m, 2H), 1.35-1.33 (m, 6H), 1.27-1.21 (m, 2H). | 662.4 |
| 329 | (3R)-7-((2S,5R)-4-acryloyl-2,5-dimethylpiperazin-1-yl)-9-chloro-3-((1-cyclopropylpiperidin-4-yl)methyl)-10-(2,4-difluorophenyl)-2H-[1,4]oxazino[2,3,4-ij]quinazolin-5(3H)-one | 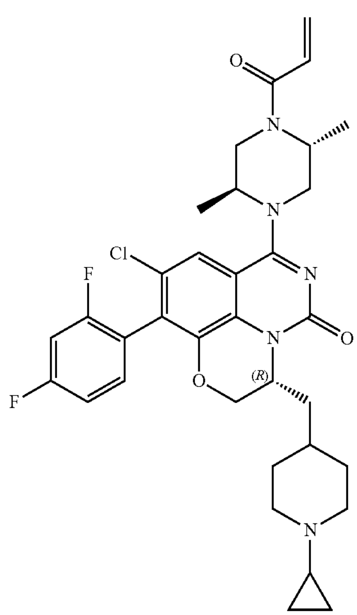 | 1H NMR (400 MHz, CDCl₃) δ 7.43-7.40 (m, 1H), 7.32-7.24 (m, 1H), 7.04-6.94 (m, 2H), 6.63-6.51 (m, 1H), 6.37 (t, J = 15.6 Hz, 1H), 5.77 (t, J = 7.6 Hz, 1H), 5.01-4.93 (m, 1H), 4.88-4.81 (m, 1.5H), 4.43 (d, J = 11.6 Hz, 1H), 4.38-4.28 (m, 1H), 4.09-4.04 (m, 1.5H), 3.93-3.79 (m, 2H), 3.68-3.64 (m, 0.5H), 3.54-3.50 (m, 0.5H), 3.01 (t, J = 10.8 Hz, 2H), 2.20-2.10 (m, 2H), 1.75-1.69 (m, 2H), 1.61-1.54 (m, 2H), 1.42-1.39 (m, 1H), 1.35-1.33 (m, 6H), 1.27-1.21 (m, 3H), 0.43-0.41 (m, 4H). | 638.4 |

| Ex. # | Name | Structure | ¹H NMR | MS (M + H)⁺ |
|---|---|---|---|---|
| 333 | (3R)-7-((2S,5R)-4-acryloyl-2,5-dimethylpiperazin-1-yl)-9-chloro-10-(2,4-difluorophenyl)-3-((1-ethylpiperidin-4-yl)methyl)-2H-[1,4]oxazino[2,3,4-ij]quinazolin-5(3H)-one | 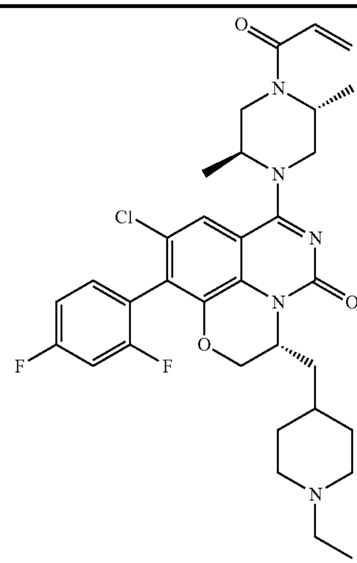 | ¹H NMR (400 MHz, CDCl₃) δ 7.45-7.43 (m, 1H), 7.32-7.23 (m, 1H), 7.05-6.94 (m, 2H), 6.65-6.51 (m, 1H), 6.37 (t, J = 15.2 Hz, 1H), 5.77 (t, J = 6.8 Hz, 1H), 4.98-4.91 (m, 2.5H), 4.38-4.31 (m, 2H), 4.10-3.87 (m, 4H), 3.69-3.65 (m, 0.5H), 3.55-3.52 (m, 0.5H), 3.79-3.75 (m, 2H), 2.94-2.89 (m, 2H), 2.65-2.57 (m, 2.5H), 2.43-2.19 (m, 2H), 2.02-1.60 (m, 8H), 1.39-1.34 (m, 4H), 1.26-1.21 (m, 2H). | 626.3 |

Table of homomorpholine tricyclic compounds

| Ex. # | Name | Structure | ¹H NMR | MS (M + H)⁺ |
|---|---|---|---|---|
| 402 | 8-((2S,5R)-4-acryloyl-2,5-dimethylpiperazin-1-yl)-10-chloro-11-(2,4-difluorophenyl)-3,4-dihydro-[1,4]oxazepino[2,3,4-ij]quinazolin-6(2H)-one | 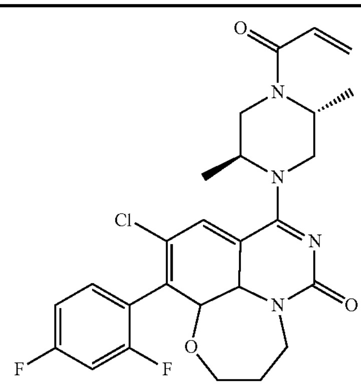 | ¹H NMR (400 MHz, CDCl₃) δ 7.45 (s, 1H), 7.24-7.19 (m, 1H), 7.02-6.93 (m, 2H), 6.63-6.51 (m, 1H), 6.37 (t, J = 15.2 Hz, 1H), 5.77 (t, J = 6.8 Hz, 1H), 4.95-4.93 (m, 1H), 4.80-4.79 (m, 0.5H), 4.66-4.56 (m, 1H), 4.43-4.17 (m, 4H), 4.10-4.06 (m, 0.5H), 3.96-3.73 (m, 2H), 3.66 (d, J = 13.6 Hz, 0.5H), 3.48-3.45 (m, 0.5H), 2.34-2.28 (m, 2H), 1.36-1.34 (m, 4H), 1.26 (d, J = 6.8 Hz, 2H). | 515.1 |
| 403 | 8-((2S,5R)-4-acryloyl-2,5-dimethylpiperazin-1-yl)-10-chloro-11-(2,4-difluorophenyl)-2H-spiro[[1,4]oxazepino[2,3,4-ij]quinazoline-3,3'-oxetan]-6(4H)-one | 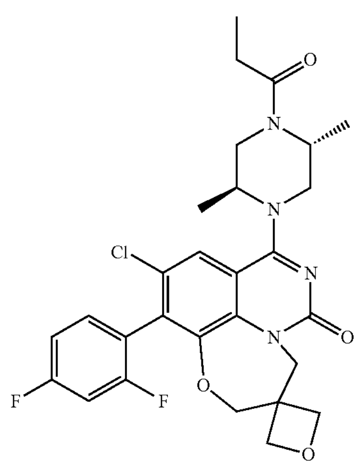 [SMILES: CCC(=O)N1C[C@H](C)N(c2nc(=O)n3c4c(c(-c5ccc(F)cc5F)c(Cl)cc24)OCC2(COC2)C3)C[C@H]1C] | ¹H NMR (400 MHz, CDCl₃) δ 7.47 (s, 1H), 7.26-7.19 (m, 1H), 7.04-6.94 (m, 2H), 6.66-6.50 (m, 1H), 6.41-6.33 (m, 1H), 5.80-5.75 (m, 1H), 5.00-4.89 (m, 3H), 4.81-4.69 (m, 2H), 4.54-4.50 (m, 2H), 4.48-4.44 (m, 1H), 4.43-4.42 (m, 1H), 4.39-4.28 (m, 2H), 4.16-4.10 (m, 1H), 3.96-3.65 (m, 2H), 1.36 (d, J = 6.4 Hz, 4H), 1.28-1.26 (d, J = 6.8 Hz, 2H). | 557.3 |

-continued

Table of homomorpholine tricyclic compounds

| Ex. # | Name | Structure | ¹H NMR | MS (M + H)⁺ |
|---|---|---|---|---|
| 405 | 8-((2S,5R)-4-acryloyl-2,5-dimethylpiperazin-1-yl)-10-chloro-11-(5-chloro-2,4-difluorophenyl)-1'-methyl-2H-spiro[[1,4]oxazepino[2,3,4-ij]quinazoline-3,4'-piperidin]-6(4H)-one | 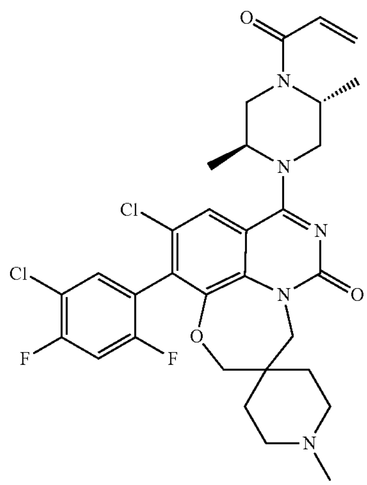 [SMILES: C=CC(=O)N1C[C@H](C)N(c2nc(=O)n3c4c(c(-c5cc(Cl)c(F)cc5F)c(Cl)cc24)OCC2(CCN(C)CC2)C3)C[C@H]1C] | ¹H NMR (400 MHz, CDCl₃) δ 7.45 (s, 1H), 7.32-7.29 (m, 1H), 7.05 (t, J = 8.4 Hz, 1H), 6.65-6.51 (m, 1H), 6.37 (t, J = 14.8 Hz, 1H), 5.78-5.75 (m, 1H), 4.95 (d, J = 26 Hz, 1H), 4.77-4.57 (m, 1H), 4.38-4.24 (m, 2H), 4.11-3.88 (m, 5H), 3.67 (m, 0.5H), 3.42 (m, 0.5H), 2.68-2.60 (m, 4H), 2.40 (s, 3H), 1.82-1.77 (m, 4H), 1.37-1.26 (m, 6H). | 632.2 |
| 406 | (3S)-8-((2S,5R)-4-acryloyl-2,5-dimethylpiperazin-1-yl)-10-chloro-11-(5-chloro-2,4-difluorophenyl)-3-morpholino-3,4-dihydro-[1,4]oxazepino[2,3,4-ij]quinazolin-6(2H)-one | 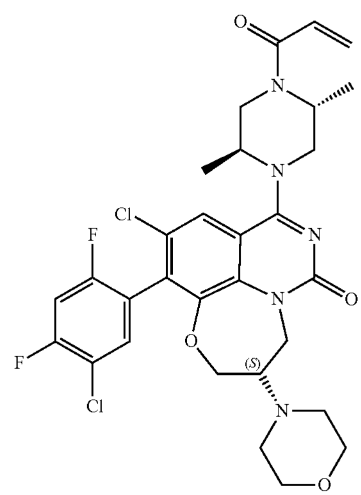 | ¹H NMR (400 MHz, CDCl₃) δ 7.44 (s, 1H), 7.39-7.29 (m, 1H), 7.06 (t, J = 8.8 Hz, 1H), 6.66-6.54 (m, 1H), 6.37 (t, J = 14.8 Hz, 1H), 5.78 (t, J = 8.4 Hz, 1H), 5.34-4.73 (m, 3H), 4.41-3.99 (m, 6H), 3.76-3.66 (m, 5H), 3.34-2.95 (m, 2H), 2.68-2.50 (m, 3H), 1.40-1.38 (m, 3H), 1.26-1.24 (m, 3H). | 634.2 |
| 407 | (3R)-8-((2S,5R)-4-acryloyl-2,5-dimethylpiperazin-1-yl)-10-chloro-11-(5-chloro-2,4-difluorophenyl)-3-morpholino-3,4-dihydro-[1,4]oxazepino[2,3,4-ij]quinazolin-6(2H)-one | 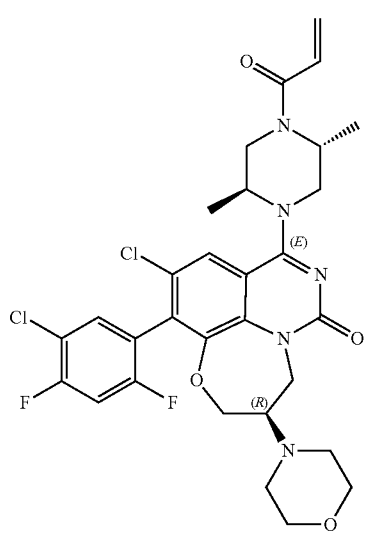 | ¹H NMR (400 MHz, CDCl₃) δ 7.41-7.33 (m, 2H), 7.08-7.03 (m, 1H), 6.62-6.50 (m, 1H), 6.41-6.32 (m, 1H), 5.79-5.73 (m, 1H), 5.53-5.43 (m, 1H), 5.02-4.88 (m, 3H), 4.36-4.31 (m, 1H), 4.09-3.84 (m, 4H), 3.60-3.82 (m, 4H), 2.71-2.49 (m, 5H), 1.34-1.26 (m, 3H), 1.25-1.19 (m, 3H). | 634.2 |

The compounds in the table above are prepared in a manner similar to that illustrated in the examples below Syntheses of Intermediates

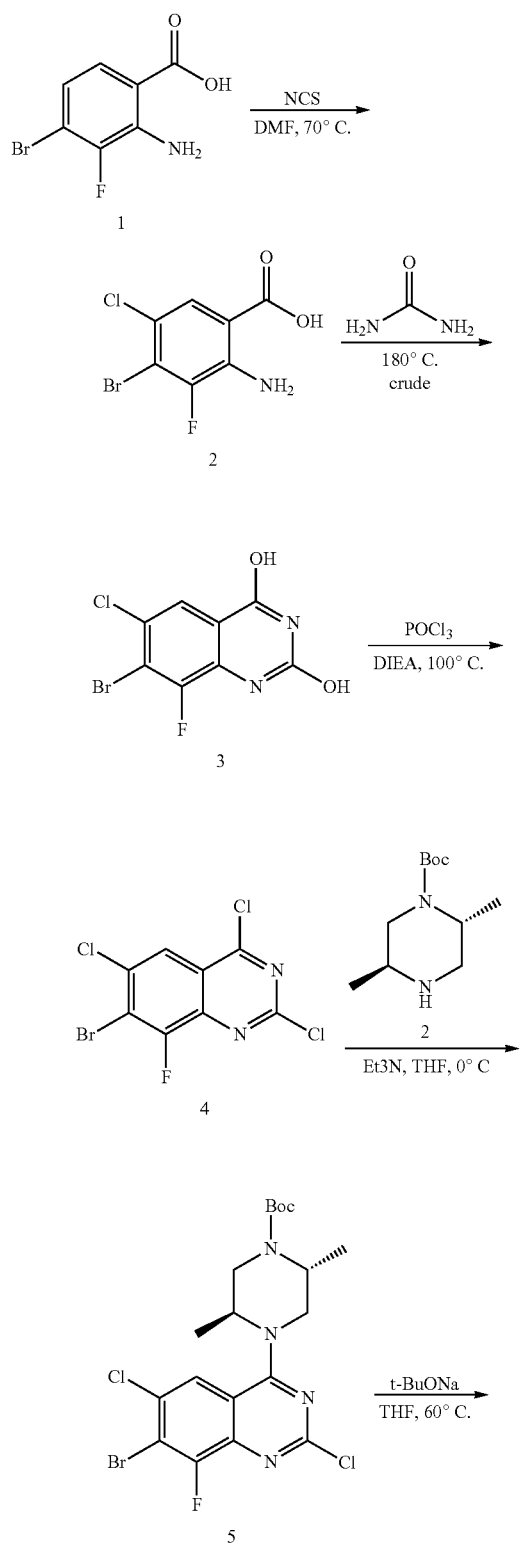

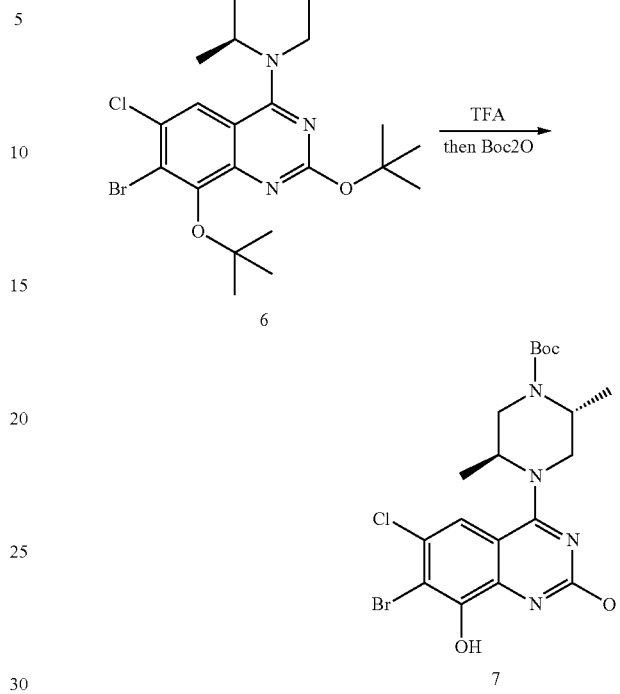

2-amino-4-bromo-5-chloro-3-fluorobenzoic acid (2)

To a solution of 2-amino-4-bromo-3-fluorobenzoic acid (100 g, 0.43 mol) in DMF (800 mL) was added NCS (68 g, 0.51 mol). Then the mixture was heated to 70° C. for 16 hours. After completion, the mixture was quenched with aqueous $H_2O$ (1.5 L) and extracted with EtOAc (2 L), dried with $Na_2SO_4$ and concentrated to afford product (139 g, crude) as a grayness solid. LC-MS m/z: 268.1[M–H]$^+$ 7-bromo-6-chloro-8-fluoroquinazoline-2,4-diol (3)

The mixture of 2-amino-4-bromo-5-chloro-3-fluorobenzoic acid (139 g, 0.51 mol) and urea (260 g, 4.33 mol) was heated to 180° C. for 6 hours. After completion, the mixture was quenched with aqueous $H_2O$ (1.5 L), filtered through a Celite pad. The filtrate was concentrated to give the crude product (130 g, crude) as a grayness solid. LC-MS m/z: 293.1[M–H]$^+$ 7-bromo-2,4,6-trichloro-8-fluoroquinazoline (4)

The mixture of 7-bromo-6-chloro-8-fluoroquinazoline-2,4-diol (130 g, 0.51 mol) and $POCl_3$ (800 mL) was heated to 120° C. for 16 hours. After completion, the mixture was quenched with aqueous $H_2O$ (1.5 L), filtered through a Celite pad. The filtrate was concentrated and purified by silica column using a mixture of Petroleum Ether/ EtOAc=4:1 to afford product (59 g, 35% yield) as a yellow solid. LC-M m/z: 311.1[M–H–Cl]$^+$ (2R,5S)-tert-butyl-4-(7-bromo-2,6-dichloro-8-fluoroquinazolin-4-yl)-2,5-dimethylpiperazine-1-carboxylate (5)

To a mixture of 7-bromo-2,4,6-trichloro-8-fluoroquinazoline (25 g, 75.76 mmol) and $Et_3N$ (15.3 g, 151.5 mmol) in THF (200 mL) was added (2R,5S)-tert-butyl 2,5-dimethylpiperazine-1-carboxylate (16.2 g, 75.76 mmol) at 0° C. The mixture was stirred at room temperature for 4 hours. After completion, the mixture was diluted with EtOAc (500 mL), washed with water (300 mL×3), dried over $Na_2SO_4$, filtered and concentrated to afford desired product (35.78 g, 93% yield) as yellow solid, which was used to next step without further purification. LC-MS m/z: 509.3[M+H].

(2R,5S)-tert-butyl-4-(7-bromo-2,8-di-tert-butoxy-6-chloroquinazolin-4-yl)-2,5-dimethyl-piperazine-1-carboxylate (6)

To a solution of (2R,5S)-tert-butyl 4-(7-bromo-2,6-dichloro-8-fluoroquinazolin-4-yl)-2,5-dimethyl piperazine-1-carboxylate (35.78 g, 70.4 mmol) in dry THF (180 mL) was added t-BuONa (16.9 g, 176.08 mmol). Then the mixture was heated to 60° C. for 4 hours. After completion, the mixture was quenched with aqueous $NH_4Cl$ and extracted with EtOAc and dried with $Na_2SO_4$. The organic layer was concentrated, and the residue was purified by silica a mixture of Petroleum Ether/EtOAc=15:1 to afford product (33 g, 78% yield) as a yellow solid. LC-MS: m/z=601.5[M+H].

(2R,5S)-tert-butyl-4-(7-bromo-6-chloro-2,8-dihydroxyquinazolin-4-yl)-2,5-dimethyl piperazine-1-carboxylate (7)

To a solution of (2R,5S)-tert-butyl-4-(7-bromo-2,8-di-tert-butoxy-6-chloroquinazolin-4-yl)-2,5-dimethylpiperazine-1-carboxylate (33 g, 55.0 mmol) in DCM (70 mL) was added TFA (70 mL). The mixture was stirred at 25° C. for 3 hours. After completion, the mixture was concentrated under reduce pressure to afford the crude 7-bromo-6-chloro-4-((2S,5R)-2,5-dimethylpiperazin-1-yl) quinazoline-2,8-diol (30 g, crude), which was used in the next step without further purification.
To a solution of 7-bromo-6-chloro-4-((2S,5R)-2,5-dimethylpiperazin-1-yl)quinazoline-2,8-diol (33 g, 85.05 mmol) in DCM (150 mL) was added $(Boc)_2O$ (18.54 g, 85.05 mmol). The mixture was stirred at room temperature for 16 hours. After completion, the mixture was concentrated. The residue was purified by silica using a mixture of DCM/MeOH (containing 0.5% ammonium hydroxide)=40:1 to afford product (24 g, 58% yield) as light green solid. LC-MS m/z: 489.3[M+H].

Example 402: 8-((2S,5R)-4-acryloyl-2,5-dimethylpiperazin-1-yl)-10-chloro-11-(2,4-difluorophenyl)-3,4-dihydro-[1,4]oxazepino[2,3,4-ij]quinazolin-6 (2H)-one

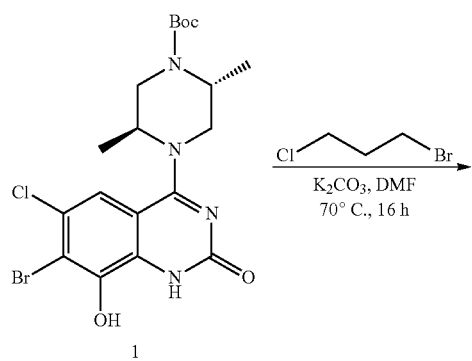

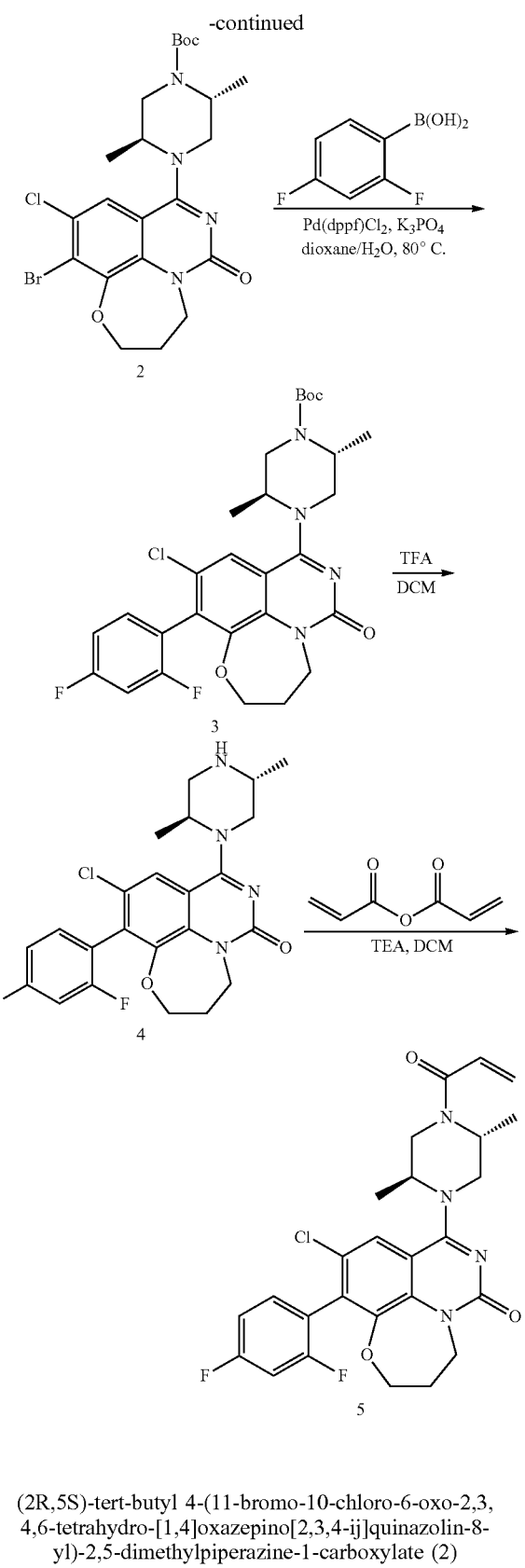

(2R,5S)-tert-butyl 4-(11-bromo-10-chloro-6-oxo-2,3,4,6-tetrahydro-[1,4]oxazepino[2,3,4-ij]quinazolin-8-yl)-2,5-dimethylpiperazine-1-carboxylate (2)

To mixture of (2R,5S)-tert-butyl 4-(7-bromo-6-chloro-8-hydroxy-2-oxo-1,2-dihydroquinazolin-4-yl)-2,5-dimethylpiperazine-1-carboxylate (4.8 g, 10 mmol) and 1-bromo- 3-chloropropane (3.0 g, 20 mmol) in N,N-Dimethylformamide was added potassium carbonate (4.0 g, 30 mmol). The mixture was stirred at 80° C. for 16 hours. After completion, the mixture was concentrated and the residue was purified by silica gel column chromatography using a mixture of methanol (1-2%) in dichloromethane to afford the product (2.9 g, 5.5 mmol, 56% yield). MS (ESI) m/z: 529.2 [M+H]$^+$.

(2R,5S)-tert-butyl 4-(10-chloro-11-(2,4-difluorophenyl)-6-oxo-2,3,4,6-tetrahydro-[1,4]oxazepino[2,3,4-ij]quinazolin-8-yl)-2,5-dimethylpiperazine-1-carboxylate (3)

To a solution of (2R,5S)-tert-butyl 4-(11-bromo-10-chloro-6-oxo-2,3,4,6-tetrahydro-[1,4]oxazepino[2,3,4-ij]quinazolin-8-yl)-2,5-dimethylpiperazine-1-carboxylate (1 g, 1.894 mmol) in 1,4-dioxane (20 mL) and water (3 mL) was added tripotassium phosphate (1.513 g, 5,682 mmol), (2,4-difluorophenyl)boronic acid (1.495 mg, 9.470 mmol) and [1,1'-bis(diphenylphosphino)ferrocene]dichloropalladium (II)1,1'-bis(diphenylphosphino)ferrocene-palladium(II)dichloride (139 mg, 0.189 mmol). The resulting mixture was stirred at 85° C. under nitrogen atmosphere for 4 hours. After completion, the mixture was concentrated and the residue was purified by silica gel column chromatography using a gradient of dichloromethane/methanol (100/1 to 30/1) to afford the desired product (2R,5S)-tert-butyl 4-(10-chloro-11-(2,4-difluorophenyl)-6-oxo-2,3,4,6-tetrahydro-[1,4]oxazepino[2,3,4-ij]quinazolin-8-yl)-2,5-dimethylpiperazine-1-carboxylate (876 mg, 83% yield) as a yellow solid. MS (ESI) m/z: 561.7 [M+H]$^+$.

10-chloro-11-(2,4-difluorophenyl)-8-((2S,5R)-2,5-dimethylpiperazin-1-yl)-3,4-dihydro-[1,4]oxazepino[2,3,4-ij]quinazolin-6(2H)-one (4)

To a mixture of (2R,5S)-tert-butyl 4-(10-chloro-11-(2,4-difluorophenyl)-6-oxo-2,3,4,6-tetrahydro-[1,4]oxazepino[2,3,4-ij]quinazolin-8-yl)-2,5-dimethylpiperazine-1-carboxylate (300 mg, 0.545 mmol) in dichloromethane (5 mL) was added trifluoroacetic acid (1 mL) at 0° C. The reaction solution was stirred at room temperature for 1 hour. After completion, the mixture was concentrated and the residue was purified by silica gel column chromatography using a mixture of dichloromethane/methanol (15/1) to afford 10-chloro-11-(2,4-difluorophenyl)-8-((2S,5R)-2,5-dimethylpiperazin-1-yl)-3,4-dihydro-[1,4]oxazepino[2,3,4-ij]quinazolin-6(2H)-one (170 mg, 69% yield) as a yellow solid. MS (ESI) m/z: 461.2[M+H]$^+$.

8-((2S,5R)-4-acryloyl-2,5-dimethylpiperazin-1-yl)-10-chloro-11-(2,4-difluorophenyl)-3,4-dihydro-[1,4]oxazepino[2,3,4-ij]quinazolin-6(2H)-one (5)

To a mixture of 10-chloro-11-(2,4-difluorophenyl)-8-((2S,5R)-2,5-dimethylpiperazin-1-yl)-3,4-dihydro-[1,4]oxazepino[2,3,4-ij]quinazolin-6(2H)-one (150 mg, 0.318 mmol) and triethyl amine (48 mg, 0.478 mmol) in dichloromethane (5 mL) was added acrylic anhydride (48 mg, 0.382 mmol) at 0° C. The mixture was stirred at 0° C. for 1 hour. After completion, the mixture was poured into ice-water (50 mL) and extracted with ethyl acetate (3×20 mL). The organic layer was concentrated and the residue was purified by preparative high performance liquid chromatography (20% to 95% acetonitrile in water) to afford 8-((2S,5R)-4-acryloyl-2,5-dimethylpiperazin-1-yl)-10-chloro-11-(2,4-difluorophenyl)-3,4-dihydro-[1,4]oxazepino[2,3,4-ij]quinazolin-6(2H)-one (110 mg, 66% yield) as a white solid. $^1$H NMR (400 MHz, CDCl$_3$) δ 7.45 (s, 1H), 7.24-7.19 (m, 1H), 7.02-6.93 (m, 2H), 6.63-6.51 (m, 1H), 6.37 (t, J=15.2 Hz, 1H), 5.77 (t, J=6.8 Hz, 1H, 4.95-4.93 (m, 1H), 4.80-4.79 (m, 0.5H), 4.66-4.56 (m, 1H), 4.43-4.17 (m, 4H), 4.10-4.06 (m, 0.5H), 3.96-3.73 (m, 2H), 3.66 (d, J=13.6 Hz, 0.5H), 3.48-3.45 (m, 0.5H), 2.34-2.28 (m, 2H), 1.36-1.34 (m, 4H), 1.26 (d, J=6.8 Hz, 2H). MS (ESI) m/z: 515.1 [M+H]$^+$.

U. Example 403

8-((2S,5R)-4-acryloyl-2,5-dimethylpiperazin-1-yl)-10-chloro-11-(2,4-difluorophenyl)-2H-spiro[[1,4]oxazepino[2,3,4-ij]quinazoline-3,3'-oxetan]-6(4H)-one

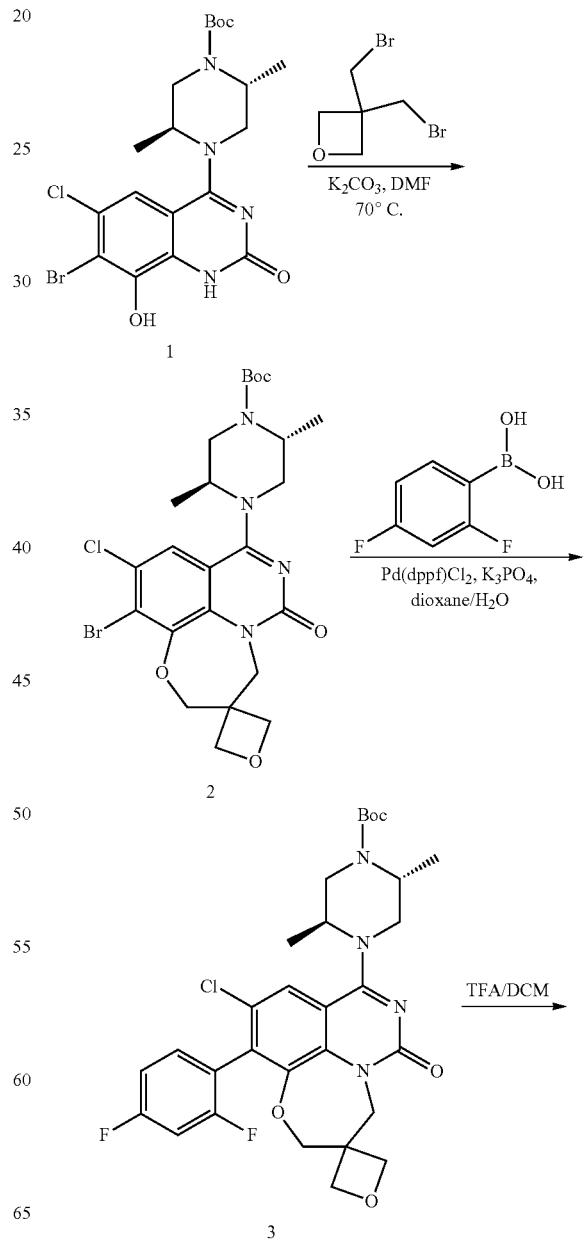

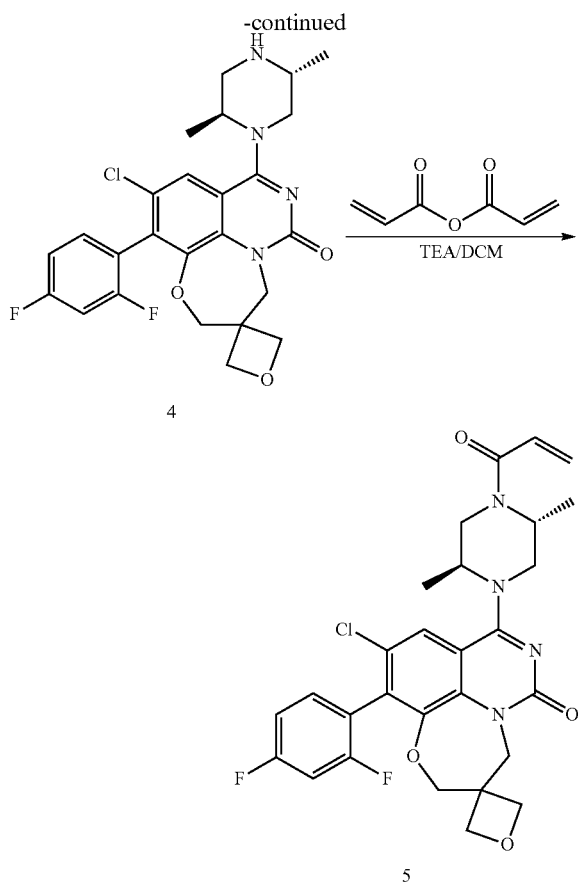

(2R,5S)-tert-butyl 4-(11-bromo-10-chloro-6-oxo-4, 6-dihydro-2H-spiro [[1,4]oxazepino[2,3,4-ij]quinazoline-3,3'-oxetan]-8-yl)-2,5-dimethylpiperazine-1-carboxylate (2)

To a mixture of (2R,5S)-tert-butyl 4-(7-bromo-6-chloro-8-hydroxy-2-oxo-1,2-dihydroquinazolin-4-yl)-2,5-dimethylpiperazine-1-carboxylate (2.4 g, 5 mmol) and 3,3-bis(bromomethyl)oxetane (2.5 g, 10 mmol) in N,N-Dimethylformamide (20 mL) was added potassium carbonate (6.7 g, 50 mmol). The mixture was stirred at 80° C. for 16 hours. After completion, the mixture was concentrated. The residue was purified by silica gel column chromatography (1-2% methanol in dichloromethane) to afford the desired product (1.56 g, 2.7 mmol, 54% yield). MS (ESI) m/z: 571.1 [M+H]$^+$.

(2R,5S)-tert-butyl 4-(10-chloro-11-(2,4-difluorophenyl)-6-oxo-4,6-dihydro-2H-spiro[[1,4]oxazepino[2, 3,4-ij]quinazoline-3,3'-oxetan]-8-yl)-2,5-dimethylpiperazine-1-carboxylate (3)

To a solution of (2R,5S)-tert-butyl 4-(11-bromo-10-chloro-6-oxo-4,6-dihydro-2H-spiro[[1,4]oxazepino[2,3,4-ij]quinazoline-3,3'-oxetan]-8-yl)-2,5-dimethylpiperazine-1-carboxylate (300 mg, 0.53 mmol), 2,4-difluorophenylboronic acid (417 mg, 2.64 mmol) and tripotassium phosphate (421 mg, 1.58 mmol) in 1,4-dioxane (10 mL) and water (2 mL) was added 1,1'-bis(diphenylphosphino)ferrocene]dichloropalladium(II) (76 mg, 0.11 mmol) at room temperature under nitrogen atmosphere. The mixture was stirred at 80° C. under nitrogen atmosphere for 3 hours. After completion, the mixture was diluted with water and extracted with ethyl acetate (3×100 mL), washed with brine (100 mL), dried over anhydrous sodium sulfate. The organic layer was concentrated, the residue was purified by silica gel column using a mixture of dichloromethane/methanol (200/1) to afford the (2R,5S)-tert-butyl 4-(10-chloro-11-(2,4-difluorophenyl)-6-oxo-4,6-dihydro-2H-spiro[[1,4]oxazepino[2,3,4-ij]quinazoline-3,3'-oxetan]-8-yl)-2,5-dimethylpiperazine-1-carboxylate (260 mg, 81% yield) as yellow solid. MS (ESI) m/z: 603.7 [M+H]$^+$.

10-chloro-11-(2,4-difluorophenyl)-8-((2S,5R)-2,5-dimethylpiperazin-1-yl)-2H-spiro[[1,4]oxazepino[2,3,4-ij]quinazoline-3,3'-oxetan]-6(4H)-one (4)

To a mixture of (2R,5S)-tert-butyl 4-(10-chloro-11-(2,4-difluorophenyl)-6-oxo-4,6-dihydro-2H-spiro[[1,4]oxazepino[2,3,4-ij]quinazoline-3,3'-oxetan]-8-yl)-2,5-dimethylpiperazine-1-carboxylate (260 mg, 0.43 mmol) in dichloromethane (5 mL) was added trifluoroacetic acid (2 mL). The mixture was stirred at room temperature for 1 hour. After completion, the mixture was concentrated and purified by silica gel column using a mixture of Dichloromethane/MeOH (containing 0.5% ammonium hydroxide) (30/1) to afford 10-chloro-11-(2,4-difluorophenyl)-8-((2S,5R)-2,5-dimethylpiperazin-1-yl)-2H-spiro[[1,4]oxazepino[2,3,4-ij]quinazoline-3,3'-oxetan]-6(4H)-one (168 mg, crude) as yellow solid. MS (ESI) m/z: 503.2 [M+H]$^+$.

8-((2S,5R)-4-acryloyl-2,5-dimethylpiperazin-1-yl)-10-chloro-11-(2,4-difluorophenyl)-2H-spiro[[1,4]oxazepino[2,3,4-ij]quinazoline-3,3'-oxetan]-6(4H)-one (5)

To a mixture of 10-chloro-11-(2,4-difluorophenyl)-8-((2S,5R)-2,5-dimethylpiperazin-1-yl)-2H-spiro[[1,4]oxazepino[2,3,4-ij]quinazoline-3,3'-oxetan]-6(4H)-one (140 mg, 0.28 mmol) and triethylamine (84 mg, 0.83 mmol) in dichloromethane (5 mL) was added acrylic anhydride (105 mg, 0.83 mmol) at 0° C. The mixture was stirred at 0° C. under nitrogen for 1 hour. After completion, the mixture was poured into water (10 mL), extracted with ethyl acetate (5 mL×3). The combined organic phase was washed with brine (10 mL), dried over anhydrous sodium sulfate and concentrated. The residue was purified by preparative High Performance Liquid Chromatography (5-95% acetonitrile in water) to afford 8-((2S,5R)-4-acryloyl-2,5-dimethylpiperazin-1-yl)-10-chloro-11-(2,4-difluorophenyl)-2H-spiro[[1,4]oxazepino [2,3,4-ij]quinazoline-3,3'-oxetan]-6(4H)-one (50 mg, 34% yield) as a white solid. $^1$H NMR (400 MHz, CDCl3) δ 7.47 (s, 1H), 7.26-7.19 (m, 1H), 7.04-6.94 (m, 2H), 6.66-6.50 (m, 1H), 6.41-6.33 (m, 1H), 5.80-5.75 (m, 1H), 5.00-4.89 (m, 3H), 4.81-4.69 (m, 2H), 4.54-4.50 (m, 2H), 4.48-4.44 (m, 1H), 4.43-4.42 (m, 1H), 4.39-4.28 (m, 2H), 4.16-4.10 (m, 1H), 3.96-3.65 (m, 2H), 1.36 (d, J=6.4 Hz, 4H), 1.28-1.26 (d, J=6.8 Hz, 2H). MS (ESI) m/z: 557.3 [M+H]$^+$.

V. Example 405
8-((2S,5R)-4-acryloyl-2,5-dimethylpiperazin-1-yl)-10-chloro-11-(5-chloro-2,4-difluorophenyl)-1'-methyl-2H-spiro[[1,4]oxazepino [2,3,4-ij]quinazoline-3,4'-piperidin]-6(4H)-one
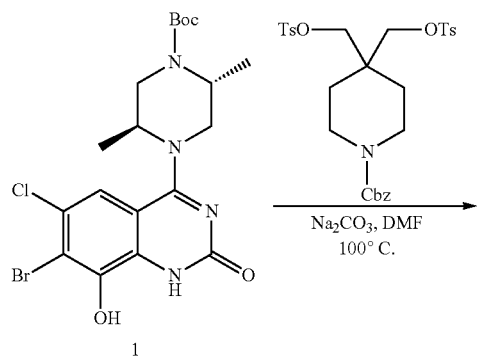
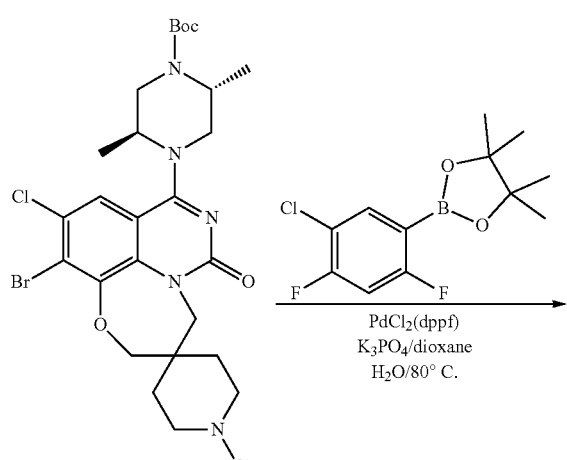
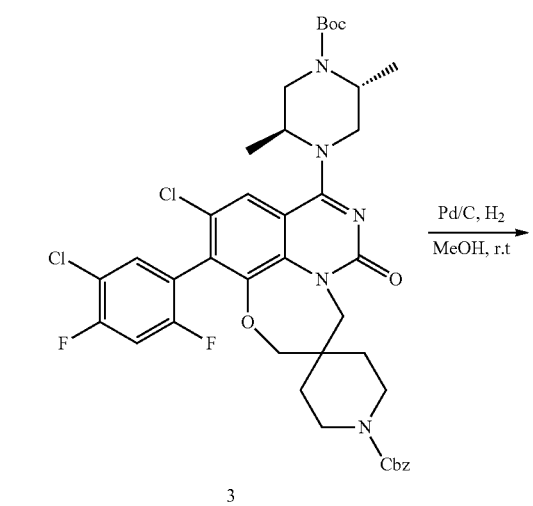
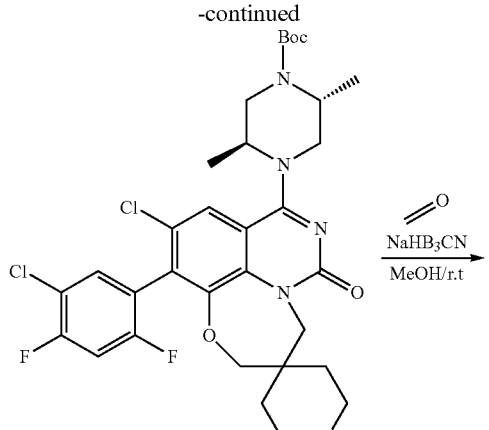
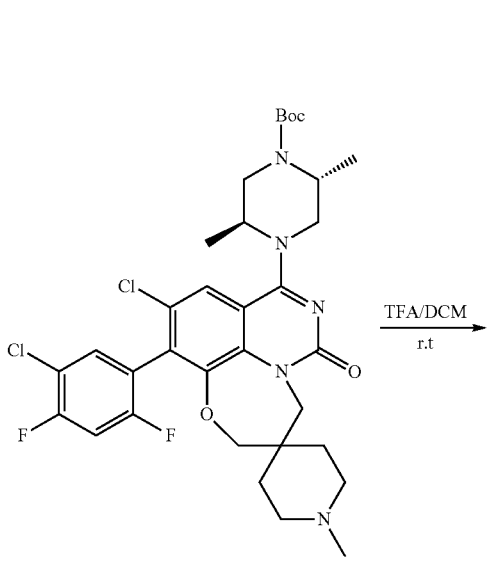
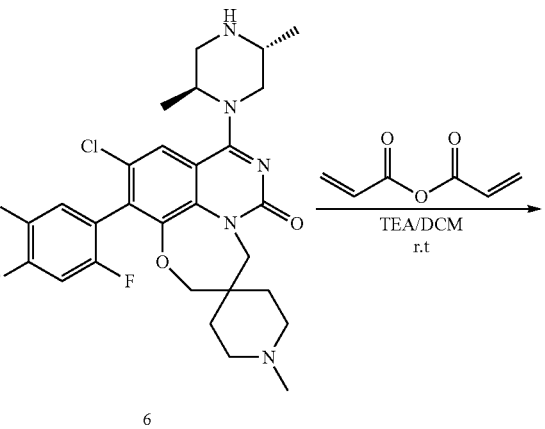

-continued

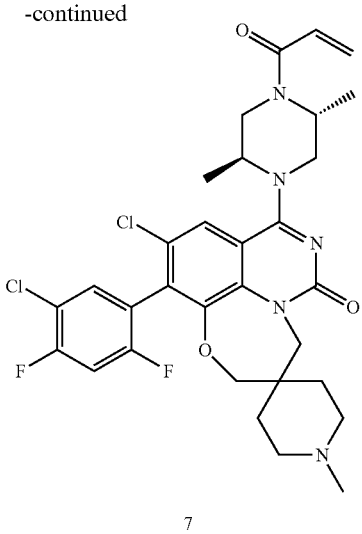

7

Benzyl 11-bromo-8-((2S,5R)-4-(tert-butoxycarbonyl)-2,5-dimethylpiperazin-1-yl)-10-chloro-6-oxo-4,6-dihydro-2H-spiro[[1,4]oxazepino [2,3,4-ij]quinazoline-3,4'-piperidine]-1'-carboxylate (2)

A mixture of (2R,5S)-tert-butyl 4-(7-bromo-6-chloro-8-hydroxy-2-oxo-1,2-dihydroquinazolin-4-yl)-2,5-dimethylpiperazine-1-carboxylate (500 ng, 1.02 mmol), sodium carbonate (326 mg, 3.07 mmol) and benzyl 4,4-bis((tosyloxy)methyl)piperidine-1-carboxylate (950 mg, 1.61 mmol) in N,N-dimethylformamide (3 mL) was heated in microwave at 100° C. for 2 hours. After completion, the mixture was concentrated. The residue was purified by silica column using a mixture of dichloromethane/methanol=40:1 to afford benzyl 11-bromo-8-((2S,5R)-4-(tert-butoxycarbonyl)-2,5-dimethylpiperazin-1-yl)-10-chloro-6-oxo-4,6-dihydro-2H-spiro[[1,4]oxazepino[2,3,4-ij]quinazoline-3,4'-piperidine]-1'-carboxylate (160 mg, 21% yield) as yellow solid. MS (ESI) m/z: 732.3 [M+H]$^+$.

Benzyl 8-((2S,5R)-4-(tert-butoxycarbonyl)-2,5-dimethylpiperazin-1-yl)-10-chloro-11-(5-chloro-2,4-difluorophenyl)-6-oxo-4,6-dihydro-2H-spiro[[1,4]oxazepino[2,3,4-ij]quinazoline-3,4'-piperidine]-1'-carboxylate (3)

To a solution of benzyl 11-bromo-8-((2S,5R)-4-(tert-butoxycarbonyl)-2,5-dimethylpiperazin-1-yl)-10-chloro-6-oxo-4,6-dihydro-2H-spiro[[1,4]oxazepino[2,3,4-ij]quinazoline-3,4'-piperidine]-1'-carboxylate (230 mg, 0.31 mmol) in 1,4-dioxane (8 mL) and water (1 mL) were added tripotassium phosphate (328 mg, 1.55 mmol), 2-(5-chloro-2,4-difluorophenyl)-4,4,5,5-tetramethyl-1,3,2-dioxaborolane (863 mg, 3.15 mmol), and [1,1'-bis(diphenylphosphino)ferrocene]dichloropalladium(II) (II) (45 mg, 0.06 mmol). The mixture was stirred at 80° C. under nitrogen atmosphere for 10 hours. After completion, the mixture was diluted with tetrahydrofuran (100 mL) and filtered. After concentration, the residue was purified by silica gel column chromatography using a gradient of dichloromethane/methanol (100/1 to 30/1) to afford benzyl 8-((2S,5R)-4-(tert-butoxycarbonyl)-2,5-dimethylpiperazin-1-yl)-10-chloro-11-(5-chloro-2,4-difluorophenyl)-6-oxo-4,6-dihydro-2H-spiro[[1,4]oxazepino[2,3,4-ij]quinazoline-3,4'-piperidine]-1'-carboxylate (230 mg, crude) as a yellow solid. MS (ESI) m/z: 798.3 [M+H]$^+$.

(2R,5S)-tert-butyl 4-(10-chloro-11-(5-chloro-2,4-difluorophenyl)-6-oxo-4,6-dihydro-2H-spiro[[1,4]oxazepino[2,3,4-ij]quinazoline-3,4'-piperidin]-8-yl)-2,5-dimethylpiperazine-1-carboxylate (4)

To solution of benzyl 8-((2S,5R)-4-(tert-butoxycarbonyl)-2,5-dimethylpiperazin-1-yl)-10-chloro-11-(5-chloro-2,4-difluorophenyl)-6-oxo-4,6-dihydro-2H-spiro[[1,4]oxazepino[2,3,4-ij]quinazoline-3,4'-piperidine]-1'-carboxylate (230 mg, 0.31 mmol) in methanol (8 mL) was added 10% palladium on charcoal (150 mg) at room temperature. The mixture was stirred at room temperature under hydrogen atmosphere for 3 hours. After completion, the mixture was filtered and concentrated to afford (2R,5S)-tert-butyl 4-(10-chloro-11-(5-chloro-2,4-difluorophenyl)-6-oxo-4,6-dihydro-2H-spiro[[1,4]oxazepino[2,3,4-ij]quinazoline-3,4'-piperidin]-8-yl)-2,5-dimethylpiperazine-1-carboxylate (100 mg, crude) as yellow solid. MS (ESI) m/z: 664.1 [M+H]$^+$.

(2R,5S)-tert-butyl 4-(10-chloro-11-(5-chloro-2,4-difluorophenyl)-1'-methyl-6-oxo-4,6-dihydro-2H-spiro[[1,4]oxazepino[2,3,4-ij]quinazoline-3,4'-piperidin]-8-yl)-2,5-dimethylpiperazine-1-carboxylate (5)

To solution of (2R,5S)-tert-butyl 4-(10-chloro-11-(5-chloro-2,4-difluorophenyl)-6-oxo-4,6-dihydro-2H-spiro[[1,4]oxazepino[2,3,4-ij]quinazoline-3,4'-piperidin]-8-yl)-2,5-dimethylpiperazine-1-carboxylate (100 mg, 0.31 mmol) and formaldehyde (0.5 mL, 0.44 mmol, 35% in water) in methanol (4 mL) was added sodium cyanoborohydride (29 mg, 0.46 mmol) at room temperature under nitrogen atmosphere. The mixture was stirred at room temperature for 3 hours. After completion, the mixture was concentrated. The residue was purified by silica gel column using a gradient of dichloromethane/methanol (50/1 to 20/1) to afford the (2R,5S)-tert-butyl 4-(10-chloro-11-(5-chloro-2,4-difluorophenyl)-1'-methyl-6-oxo-4,6-dihydro-2H-spiro[[1,4]oxazepino[2,3,4-ij]quinazoline-3,4'-piperidin]-8-yl)-2,5-dimethylpiperazine-1-carboxylate (44 mg, crude) as yellow solid. MS (ESI) m/z: 678.9 [M+H]$^+$ 10-chloro-11-(5-chloro-2,4-difluorophenyl)-8-((2S,5R)-2,5-dimethylpiperazin-1-yl)-1'-methyl-2H-spiro[[1,4]oxazepino[2,3,4-ij]quinazoline-3,4'-piperidin]-6(4H)-one (6)

To a mixture of (2R,5S)-tert-butyl 4-(10-chloro-11-(5-chloro-2,4-difluorophenyl)-1'-methyl-6-oxo-4,6-dihydro-2H-spiro[[1,4]oxazepino[2,3,4-ij]quinazoline-3,4'-piperidin]-8-yl)-2,5-dimethylpiperazine-1-carboxylate (44 mg, 0.06 mmol) in dichloromethane (2 ml) was added trifluoroacetic acid (0.7 mL) at 0° C. The reaction solution was stirred at room temperature for 1 h. After completion, the mixture was concentrated and the residue was purified by silica gel column using a mixture of 5% methanol in dichloromethane to afford 10-chloro-11-(5-chloro-2,4-difluorophenyl)-8-((2S,5R)-2,5-dimethylpiperazin-1-yl)-1'-methyl-2H-spiro[[1,4]oxazepino[2,3,4-ij]quinazoline-3,4'- piperidin]-6(4H)-one (30 mg, crude) as a yellow-brown solid. MS (ESI) m/z: 578.4[M+H]+.

8-((2S,5R)-4-acryloyl-2,5-dimethylpiperazin-1-yl)-10-chloro-11-(5-chloro-2,4-difluorophenyl)-1'-methyl-2H-spiro[[1,4]oxazepino[2,3,4-ij]quinazoline-3,4'-piperidin]-6(4H)-one (7)

To a mixture of 10-chloro-11-(5-chloro-2,4-difluorophenyl)-8-((2S,5R)-2,5-dimethylpiperazin-1-yl)-1'-methyl-2H-spiro[[1,4]oxazepino[2,3,4-ij]quinazoline-3,4'-piperidin]-6(4H)-one (30 mg, 0.05 mmol) and triethyl amine (15 mg, 0.15 mmol) in dichloromethane (2 ml) was added acrylic anhydride (10 mg, 0.08 mmol) at 0° C. The mixture was stirred at 0° C. for 1 h. After completion, the mixture was poured into ice-water (10 mL) and extracted with ethyl acetate (3×20 mL). After concentration, the residue was purified by preparative High Performance Liquid Chromatography (20% to 95% acetonitrile in water) to afford 8-((2S,5R)-4-acryloyl-2,5-dimethylpiperazin-1-yl)-10-chloro-11-(5-chloro-2,4-difluorophenyl)-1'-methyl-2H-spiro[[1,4]oxazepino[2,3,4-ij]quinazoline-3,4'-piperidin]-6(4H)-one (3 mg, 10% yield) as a white solid. $^1$H NMR (400 MHz, CDCl$_3$) δ 7.45 (s, 1H), 7.32-7.29 (m, 1H), 7.05 (t, J=8.4 Hz, 1H), 6.65-6.51 (m, 1H), 6.37 (t, J=14.8 Hz, 1H), 5.78-5.75 (m, 1H), 4.95 (d, J=26 Hz, 1H), 4.77-4.57 (m, 1H), 4.38-4.24 (m, 2H), 4.11-3.88 (m, 5H), 3.67 (m, 0.5H), 3.42 (m, 0.5H), 2.68-2.60 (m, 4H), 2.40 (s, 3H), 1.82-1.77 (m, 4H), 1.37-1.26 (m, 6H). MS (ESI) m/z: 632.1 [M+H]+.

W. Example 406 and 407

(3S)-8-((2S,5R)-4-acryloyl-2,5-dimethylpiperazin-1-yl)-10-chloro-11-(5-chloro-2,4-difluorophenyl)-3-morpholino-3,4-dihydro-2H,6H-[1,4]oxazepino[2,3,4-ij]quinazolin-6-one and (3R)-8-((2S,5R)-4-acryloyl-2,5-dimethylpiperazin-1-yl)-10-chloro-11-(5-chloro-2,4-difluorophenyl)-3-morpholino-3,4-dihydro-2H,6H-[1,4]oxazepino[2,3,4-ij]quinazolin-6-one

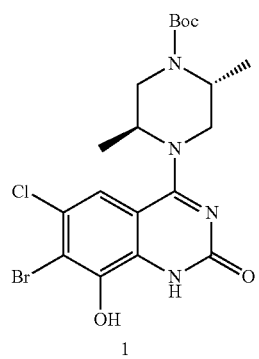

1

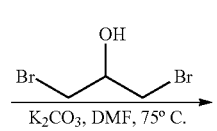

K$_2$CO$_3$, DMF, 75° C.

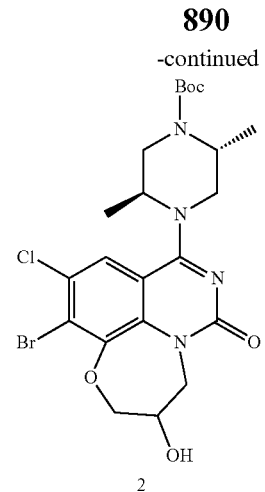

2

TEA, MsCl
————————
DCM, 0° C.

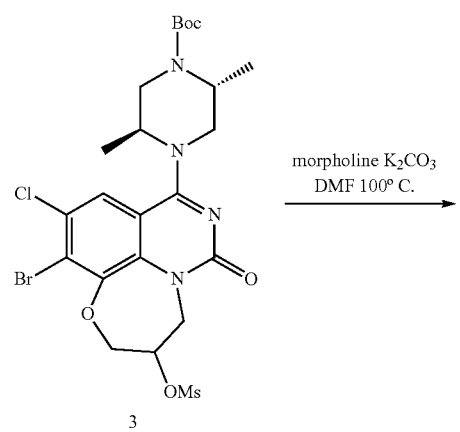

3 morpholine K$_2$CO$_3$
————————
DMF 100° C.

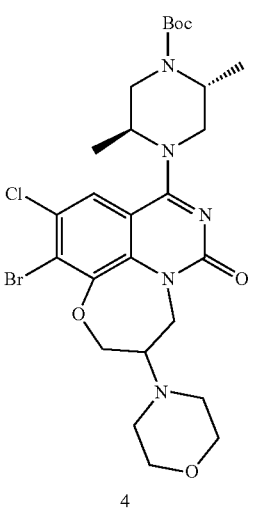

4 chiral seperation
————————

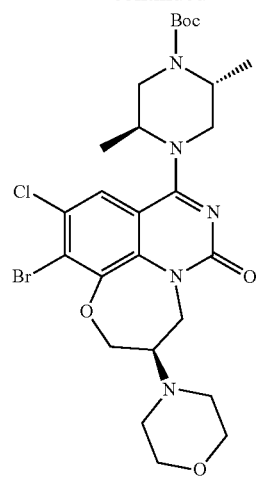
4a
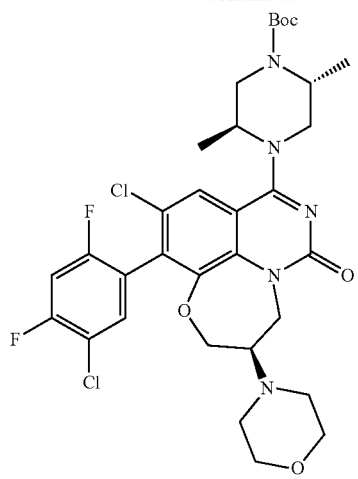
5a
TFA/DCM
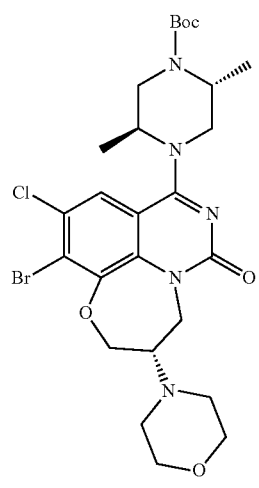
4b
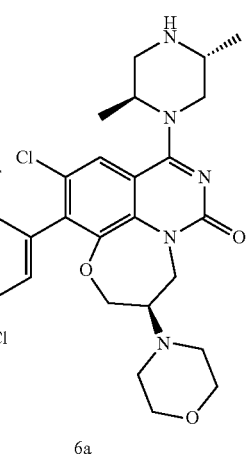
6a
acrylic anhydride, TEA, DCM
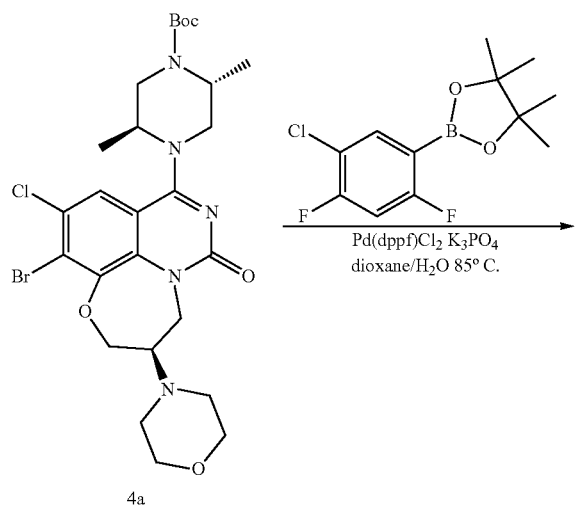
4a
Pd(dppf)Cl$_2$ K$_3$PO$_4$
dioxane/H$_2$O 85° C.
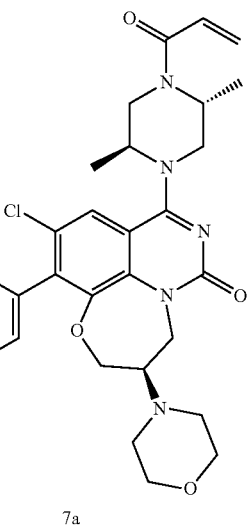
7a

893

-continued

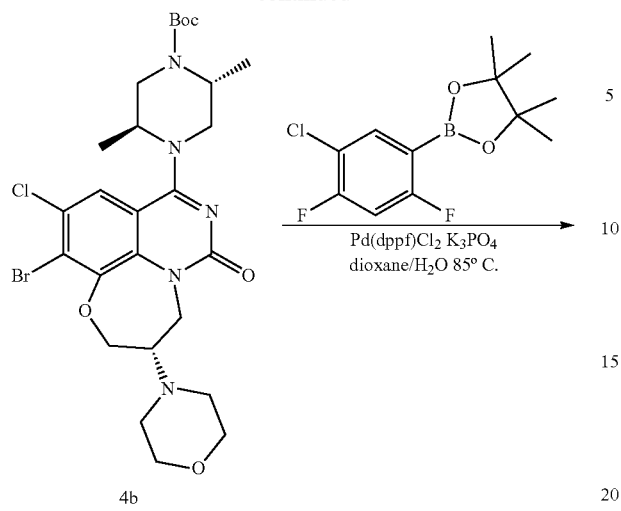

4b

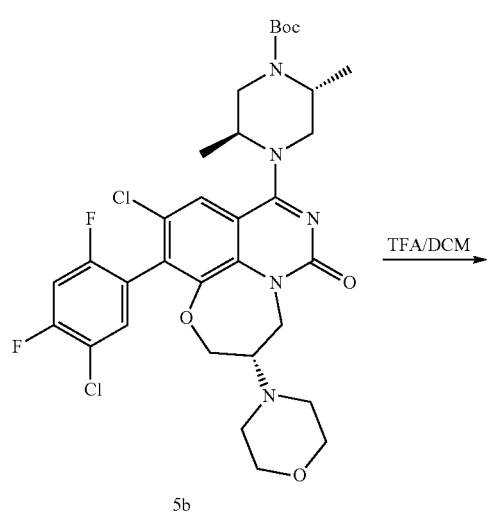

5b

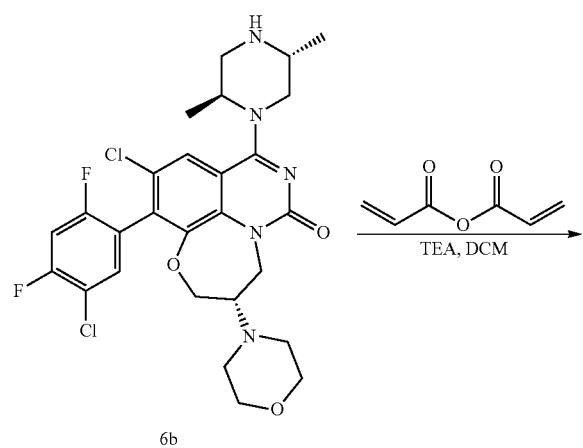

6b

894

-continued

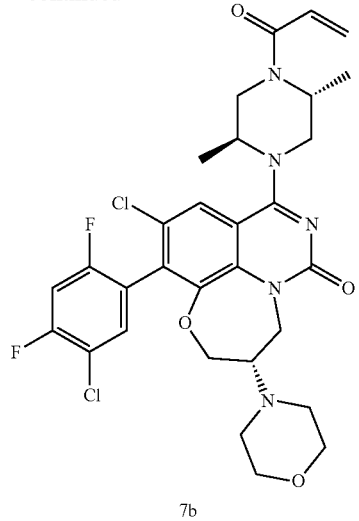 [SMILES: C=CC(=O)N1C[C@H](C)N(c2nc(=O)n3c4c(c(-c5cc(Cl)c(F)cc5F)c(Cl)cc24)OC[C@@H](N2CCOCC2)C3)C[C@H]1C]

7b (2R,5S)-tert-butyl 4-(11-bromo-10-chloro-3-hydroxy-6-oxo-2,3,4,6-tetrahydro-[1,4]oxazepino[2,3,4-ij]quinazolin-8-yl)-2,5-dimethylpiperazine-1-carboxylate (2)

To a mixture of (2R,5S)-tert-butyl 4-(7-bromo-6-chloro-8-hydroxy-2-oxo-1,2-dihydroquinazolin-4-yl)-2,5-dimethylpiperazine-1-carboxylate (2.0 g, 4.1 mmol) and 1,3-dibromopropan-2-ol (1.35 g, 6.2 mmol) in N,N-Dimethylformamide (10 mL) was added Potassium carbonate (1.69 g, 12.3 mmol). The mixture was stirred at 75° C. for 16 hours. After completion, the mixture was concentrated and the residue was purified by silica gel column chromatography (1-2% methanol in dichloromethane) to afford the product (1.6 g, 2.9 mmol, 72% yield). MS (ESI) m/z: 545.2 [M+H]$^+$.

(2R,5S)-tert-butyl 4-(11-bromo-10-chloro-3-((methylsulfonyl)oxy)-6-oxo-2,3,4,6-tetrahydro-[1,4]oxazepino[2,3,4-ij]quinazolin-8-yl)-2,5-dimethylpiperazine-1-carboxylate (3)

To a mixture of (2R,5S)-tert-butyl 4-(11-bromo-10-chloro-3-hydroxy-6-oxo-2,3,4,6-tetrahydro-[1,4]oxazepino[2,3,4-ij]quinazolin-8-yl)-2,5-dimethylpiperazine-1-carboxylate (1.0 g, 1.60 mmol) and triethylamine (1.01 g, 7.50 mmol) in dichloromethane (30 mL) was added methanesulfonyl chloride (863 mg, 7.50 mmol) at 0° C. The mixture was stirred at room temperature for 2 hours. After completion, the mixture was concentrated. The residue was purified by silica gel column using a mixture of dichloromethane/methanol (50:1) to afford the crude product (3.1 g, crude) as a yellow solid. MS (ESI) m/z: 623.6 [M+H]$^+$.

(2R,5S)-tert-butyl 4-(11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (4)

To a mixture of (2R,5S)-tert-butyl 4-(11-bromo-10-chloro-3-((methylsulfonyl)oxy)-6-oxo-2,3,4,6-tetrahydro-[1,4]oxazepino[2,3,4-ij]quinazolin-8-yl)-2,5-dimethylpiperazine-1-carboxylate (3.1 g, 4.98 mmol) and morpholine (5 mL) in N,N-dimethylformamide (5 mL) was added potassium carbonate (2.06 g, 14.94 mmol) and potassium iodide (83 mg, 0.49 mmol) in the sealed vial under nitrogen atmosphere. The mixture was stirred in the microwave reactor at 100° C. for 3 hours. After completion, the mixture was concentrated. The residue was purified by silica gel column using a mixture of dichloromethane/methanol (50:1) to afford the (2R,5S)-tert-butyl 4-(11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (390 mg, 0.71 mmol) as a white solid. MS (ESI) m/z: 614.2 [M+H]$^+$.

(2R,5S)-tert-butyl 4-((R)-11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (4a) & (2R,5S)-tert-butyl 4-((S)-11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (4b)

The racemic mixture of (2R,5S)-tert-butyl 4-(11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (390 mg, 0.68 mmol) was separated by chiral Prep. HPLC (separation condition: Column: Chiralpak AD-H 5 μm 20×230 mm; Mobile Phase: Hep/EtOH=70/30 at 15 mL/min; Temp: 30° C.; Wavelength: 254 nm) to afford (2R,5S)-tert-butyl 4-((R)-11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (60 mg, 0.1 mmol) and (2R,5S)-tert-butyl 4-((S)-11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (81 mg, 0.1 mmol)

(2R,5S)-tert-butyl 4-((3R)-10-chloro-11-(5-chloro-2,4-difluorophenyl)-3-morpholino-6-oxo-2,3,4,6-tetrahydro-[1,4]oxazepino[2,3,4-ij]quinazolin-8-yl)-2,5-dimethylpiperazine-1-carboxylate (5a)

To a mixture of (2R,5S)-tert-butyl 4-((R)-11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (60 mg, 0.10 mmol), [1,1'-bis(diphenylphosphino)ferrocene]dichloropalladium(II) (14 mg, 0.02 mmol) and potassium orthophosphate (62 m g, 0.30 mmol) in dioxane (3 mL) and water (0.5 mL) was added 2-(5-chloro-2,4-difluorophenyl)-4,4,5,5-tetramethyl-1,3,2-dioxaborolane (274 mg, 1.0 mmol). The mixture was stirred at 85° C. under N$_2$ for 4 hours. After completion, the mixture was concentrated. The residue was purified by silica gel column using a mixture of dichloromethane/methanol (50:1) to afford the product (61 mg, 0.088 mmol) as a yellow solid. MS (ESI) m/z: 680.2 [M+H]$^+$.

(3R)-10-chloro-11-(5-chloro-2,4-difluorophenyl)-8-((2S,5R)-2,5-dimethylpiperazin-1-yl)-3-morpholino-3,4-dihydro-[1,4]oxazepino[2,3,4-ij]quinazolin-6(2H)-one (6a)

To a solution of (2R,5S)-tert-butyl 4-((3R)-10-chloro-11-(5-chloro-2,4-difluorophenyl)-3-morpholino-6-oxo-2,3,4,6-tetrahydro-[1,4]oxazepino[2,3,4-ij]quinazolin-8-yl)-2,5-dimethylpiperazine-1-carboxylate (61 mg, 0.088 mmol) in DCM (3 mL) was added TFA (1 mL) at 20° C. The mixture was stirred at room temperature for 1 h. After completion, the mixture was concentrated under reduced pressure to afford the crude product as the TFA salt (58 mg, crude) as yellow solid. MS (ESI) m/z: 580.2 [M+H]$^+$.

(3R)-8-((2S,5R)-4-acryloyl-2,5-dimethylpiperazin-1-yl)-10-chloro-11-(5-chloro-2,4-difluorophenyl)-3-morpholino-3,4-dihydro-[1,4]oxazepino[2,3,4-ij]quinazolin-6(2H)-one (7a)

To a solution of (3R)-10-chloro-11-(5-chloro-2,4-difluorophenyl)-8-((2S,5R)-2,5-dimethylpiperazin-1-yl)-3-morpholino-3,4-dihydro-[1,4]oxazepino[2,3,4-ij]quinazolin-6(2H)-one (58 mg, crude) and TEA (40 mg, 0.4 mmol) in Dichloromethane (3 mL) was added acrylic anhydride (17 mg, 0.14 mmol) at 0° C. The mixture was stirred at 0° C. for 1 hour. After completion, the mixture was concentrated under reduced pressure and the residue was purified by preparative High Performance Liquid Chromatography (10% to 95% acetonitrile in water) afford desired product (21 mg, 0.03 mmol) as a white powder. $^1$H NMR (400 MHz, CDCl$_3$) δ 7.41-7.33 (m, 2H), 7.08-7.03 (m, 1H), 6.62-6.50 (m, 1H), 6.41-6.32 (m, 1H), 5.79-5.73 (m, 1H), 5.53-5.43 (m, 1H), 5.02-4.88 (m, 3H), 4.36-4.31 (m, 1H), 4.09-3.84 (m, 4H), 3.60-3.82 (m, 4H), 2.71-2.49 (m, 5H), 1.34-1.26 (m, 3H), 1.25-1.19 (m, 3H). MS (ESI) m/z: 634.2 [M+H]$^+$.

(2R,5S)-tert-butyl 4-((3S)-10-chloro-11-(5-chloro-2,4-difluorophenyl)-3-morpholino-6-oxo-2,3,4,6-tetrahydro-[1,4]oxazepino[2,3,4-ij]quinazolin-8-yl)-2,5-dimethylpiperazine-1-carboxylate (5b)

To a mixture of (2R,5S)-tert-butyl 4-((S)-11-bromo-10-chloro-3-morpholino-6-oxo-2,3,4,6-tetrahydro-[1,4]oxazepino[2,3,4-ij]quinazolin-8-yl)-2,5-dimethylpiperazine-1-carboxylate (81 mg, 0.13 mmol), Pd(dppf)Cl$_2$ (36 mg, 1.3 mmol) and K$_3$PO$_4$ (54 m g, 0.39 mmol) in dioxane (2.5 mL) and water (0.5 mL) was added 2-(5-chloro-2,4-difluorophenyl)-4,4,5,5-tetramethyl-1,3,2-dioxaborolane (274 mg, 1.0 mmol). The mixture was stirred at 85° C. under N$_2$ for 4 hours. After completion, the mixture was concentrated. The residue was purified by silica gel column using a mixture of dichloromethane/methanol (50:1) to afford the product (150 mg, crude) as a yellow solid. MS (ESI) m/z: 680.7 [M+H]$^+$.

(3S)-10-chloro-11-(5-chloro-2,4-difluorophenyl)-8-((2S,5R)-2,5-dimethylpiperazin-1-yl)-3-morpholino-3,4-dihydro-[1,4]oxazepino[2,3,4-ij]quinazolin-6(2H)-one (6b)

To a solution of (2R,5S)-tert-butyl 4-((3S)-10-chloro-11-(5-chloro-2,4-difluorophenyl)-3-morpholino-6-oxo-2,3,4,6-tetrahydro-[1,4]oxazepino[2,3,4-ij]quinazolin-8-yl)-2,5-dimethylpiperazine-1-carboxylate (150 mg, 0.17 mmol) in DCM (3 mL) was added TFA (1 mL) at 0° C. The mixture was stirred at room temperature for 1 hour. After completion, the mixture was concentrated under reduced pressure to afford the crude product as the TFA salt (50 mg, crude) as yellow solid. MS (ESI) m/z: 580.6 [M+H]$^+$.

(3S)-8-((2S,5R)-4-acryloyl-2,5-dimethylpiperazin-1-yl)-10-chloro-11-(5-chloro-2,4-difluorophenyl)-3-morpholino-3,4-dihydro-[1,4]oxazepino [2,3,4-ij]quinazolin-6(2H)-one (7b)

To a solution of (3S)-10-chloro-11-(5-chloro-2,4-difluorophenyl)-8-((2S,5R)-2,5-dimethylpiperazin-1-yl)-3-morpholino-3,4-dihydro-[1,4]oxazepino[2,3,4-ij]quinazolin-6(2H)-one (50 mg, crude) and TEA (40 mg, 0.4 mmol) in dichloromethane (3 mL) was added acrylic anhydride (20 mg, 0.16 mmol) at 0° C. The mixture was stirred at 0° C. for 1 hour. After completion, the mixture was concentrated under reduced pressure and the residue was purified by preparative High Performance Liquid Chromatography (10% to 95% acetonitrile in water) afford desired product (20 mg, 0.03 mmol) as a pale-yellow powder. $^1$H NMR (400 MHz, CDCl$_3$) δ 7.44 (s, 1H), 7.39-7.29 (m, 1H), 7.06 (t, J=8.8 Hz, 1H), 6.66-6.54 (m, 1H), 6.37 (t, J=14.8 Hz, 1H), 5.78 (t, J=8.4 Hz, 1H), 5.34-4.73 (m, 3H), 4.41-3.99 (m, 6H), 3.76-3.66 (m, 5H), 3.34-2.95 (m, 2H), 2.68-2.50 (m, 3H), 1.40-1.38 (m, 3H), 1.26-1.24 (m, 3H). MS (ESI) m/z: 634.2 [M+H]$^+$.

TABLE 8

Table of Thiomorpholines

| Ex. # | Name | Structure | $^1$H NMR | MS (M + H)$^+$ |
|---|---|---|---|---|
| 408 | 7-((S)-4-acryloyl-2-methylpiperazin-1-yl)-9-chloro-10-(5-fluoro-1H-indazol-4-yl)-2,3-dihydro-5H-[1,4]thiazino[2,3,4-ij]quinazolin-5-one | 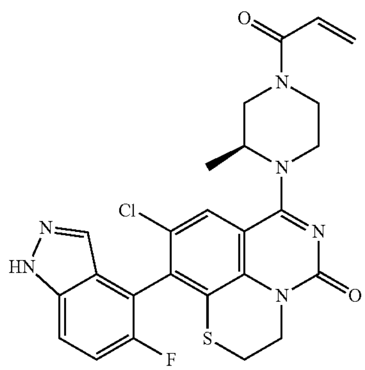 [SMILES: C=CC(=O)N1CCN(c2nc(=O)n3c4c(c(-c5c(F)ccc6[nH]ncc56)c(Cl)cc24)SCC3)[C@@H](C)C1] | $^1$H NMR (400 MHz, MeOH-d$_4$) δ 7.75 (br s, 1H), 7.72 (d, J = 7.4 Hz, 1H), 7.25 (dd, J = 10.9, 7.8 Hz, 1H), 7.00 (ddd, J = 7.9, 4.0, 1.8 Hz, 1H), 6.83 (ddd, J = 21.7, 16.7, 10.5 Hz, 1H), 6.29 (dd, J = 16.5, 6.6 Hz, 1H), 5.82 (dd, J = 10.6, 1.9 Hz, 1H), 4.85-4.78 (m, 1H), 4.63-3.99 (m, 5H), 3.78-3.44 (m, 2H), 3.25-3.02 (m, 2H), 1.44 (d, J = 6.7 Hz, 1.5H), 1.40 (d, J = 6.8 Hz, 1.5H). | 525.2 |
| 408a | 7-((S)-4-acryloyl-2-methylpiperazin-1-yl)-9-chloro-10-(3,5-difluoropyridin-2-yl)-2H-[1,4]thiazino[2,3,4-ij]quinazolin-5(3H)-one | 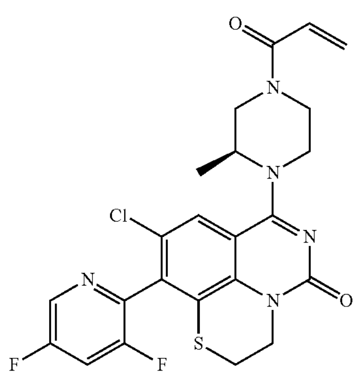 [SMILES: C=CC(=O)N1CCN(c2nc(=O)n3c4c(c(-c5ncc(F)cc5F)c(Cl)cc24)SCC3)[C@@H](C)C1] | $^1$H NMR (400 MHz, CDCl$_3$) δ 8.53 (d, J = 2 Hz, 1H), 7.49 (s, 1H), 7.42-7.38 (m, 1H), 6.61-6.52 (m, 1H), 6.40-6.36 (m, 1H), 5.78 (d, J = 10 Hz, 1H), 4.69 (s, 0.5H), 4.66-4.50 (m, 3H), 4.29-4.15 (m, 2H), 3.99-3.96 (m, 0.5H), 3.83-3.79 (m, 0.5H), 3,64-3.47 (m, 2H), 3.14-3.04 (m, 2.5H), 1.47-1.37 (m, 3H). | 504.1 |
| 409 | 7-((S)-4-acryloyl-2-methylpiperazin-1-yl)-9-chloro-10-(2,4,5-trifluorophenyl)-2,3-dihydro-5H-[1,4]thiazino[2,3,4-ij]quinazolin-5-one | 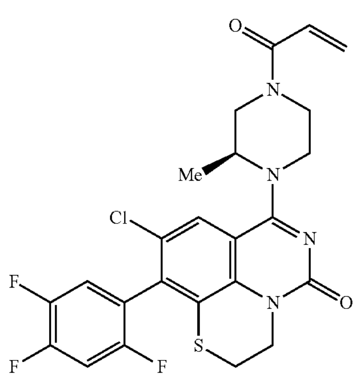 [SMILES: C=CC(=O)N1CCN(c2nc(=O)n3c4c(c(-c5cc(F)c(F)cc5F)c(Cl)cc24)SCC3)[C@@H](C)C1] | 1H NMR (400 MHz, MeOD) δ 7.59 (d, J = 6.9 Hz, 1H), 7.42-7.04 (m, 2H), 6.85-6.60 (m, 1H), 6.27-6.10 (m, 1H), 5.71 (dd, J = 10.6, 1.9 Hz, 1H), 4.68 (s, 1H), 4.53-4.25 (m, 2H), 4.23-3.84 (m, 3H), 3.68-3.31 (m, 2H), 3.18-2.85 (m, 3H), 1.30 (dd, J = 16.5, 6.7 Hz, 3H). | 521.1 |

TABLE 8-continued

Table of Thiomorpholines

| Ex. # | Name | Structure | ¹H NMR | MS (M + H)⁺ |
|---|---|---|---|---|
| 419 | 7-((S)-4-acryloyl-2-methylpiperazin-1-yl)-9-chloro-10-(7-fluoro-1H-indazol-4-yl)-2,3-dihydro-5H-[1,4]thiazino[2,3,4-ij]quinazolin-5-one | 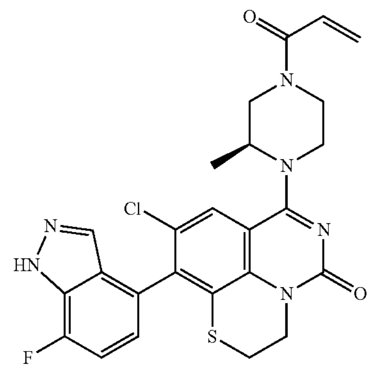 [SMILES: C=CC(=O)N1CCN(c2nc(=O)n3c4c(c(-c5ccc(F)c6[nH]ncc56)c(Cl)cc24)SCC3)[C@@H](C)C1] | ¹H NMR (400 MHz, MeOH-d₄) δ 7.74 (d, J = 2.7 Hz, 1H), 7.72-7.65 (m, 3H), 7.35 (t, J = 9.3 Hz, 1H), 6.92-6.75 (m, 1H), 6.29 (dd, J = 16.7, 6.2 Hz, 1H), 5.82 (dd, J = 10.6, 1.9 Hz, 1H), 4.62-3.98 (m, 6H), 3.77-3.42 (m, 2H), 3.15 (t, J = 5.3 Hz, 3H), 1.43 (t, J = 6.8 Hz, 3H). | 525.2 |
| 419a | (2S)-4-(9-chloro-10-(2,4-difluorophenyl)-5-oxo-3,5-dihydro-2H-[1,4]thiazino[2,3,4-ij]quinazolin-7-yl)-1-(2-fluoroacryloyl)piperazine-2-carbonitrile | 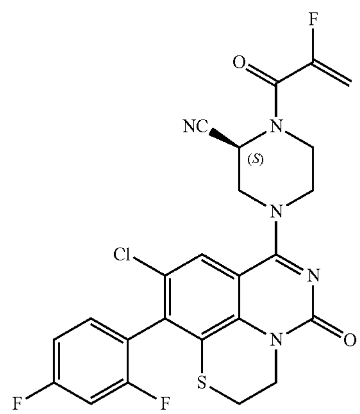 | ¹H NMR (400 MHz, CDCl₃) δ 7.70 (d, J = 30.4, 1H), 7.23-7.18 (m, 1H), 7.06-6.97 (m, 2H), 5.82-5.47 (m, 2H), 5.36-5.31 (m, 1H), 4.70-4.45 (m, 2H), 4.42-4.19 (m, 3H), 3.87-3.69 (m, 1H), 3.52-3.43 (m, 1H), 3.27-3.19 (m, 1H), 3.13-3.08 (m, 2H). | 532.1 |
| 427 | 7-((S)-4-acryloyl-2-methylpiperazin-1-yl)-9-chloro-10-(2-chloro-4-fluorophenyl)-2,3-dihydro-5H-[1,4]thiazino[2,3,4-ij]quinazolin-5-one | 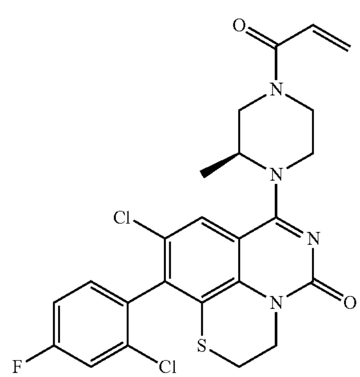 [SMILES: C=CC(=O)N1CCN(c2nc(=O)n3c4c(c(-c5ccc(F)cc5Cl)c(Cl)cc24)SCC3)[C@@H](C)C1] | ¹H NMR (400 MHz, MeOH-d₄) δ 7.68 (d, J = 5.5 Hz, 1H), 7.43 (dd, J = 8.7, 2.4 Hz, 1H), 7.34-7.18 (m, 2H), 6.82 (dddd, J = 21.7, 16.5, 10.7, 2.5 Hz, 1H), 6.28 (dd, J = 16.8, 5.4 Hz, 1H), 5.81 (dd, J = 10.6, 1.9 Hz, 1H), 4.79 (br s, 1H), 4.60-3.97 (m, 6H), 3.76-3.41 (m, 2H), 3.26-3.03 (m, 3H), 1.43 (d, J = 6.7 Hz, 1.5H), 1.39 (d, J = 6.7 Hz, 1.5H). | 519.1 |
| 427a | 7-((S)-4-acryloyl-2-methylpiperazin-1-yl)-9-chloro-10-(5-chloro-2,4-difluorophenyl)-2H-[1,4]thiazino[2,3,4-ij]quinazolin-5(3H)-one | 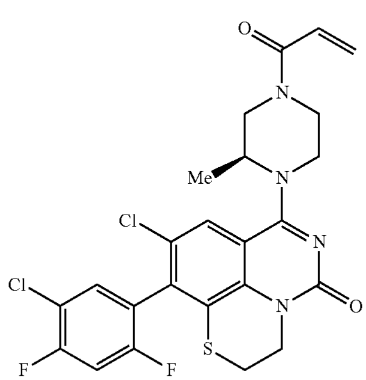 [SMILES: C=CC(=O)N1CCN(c2nc(=O)n3c4c(c(-c5cc(Cl)c(F)cc5F)c(Cl)cc24)SCC3)[C@@H](C)C1] | ¹H NMR (400 MHz, CD₃OD) δ 6.78 (d, J = 6.8 Hz, 1H), 6.57 (t, J = 6.8 Hz, 1H), 6.48-6.44 (t, J = 9.6 Hz, 1H), 5.92-5.87 (m, 1H), 5.40-5.34 (m, 1H), 4.90 (d, J = 10.4 Hz, 1H), 3.88-3.87 (m, 1H), 3.67-3.09 (m, 5H), 2.83-2.58 (m, 2H), 2.31-2.28 (m, 3H), 0.52-0.46 (m, 3H) | 537.1 |

TABLE 8-continued

Table of Thiomorpholines

| Ex. # | Name | Structure | ¹H NMR | MS (M + H)⁺ |
|---|---|---|---|---|
| 441 | 7-((S)-4-acryloyl-2-methylpiperazin-1-yl)-9-chloro-10-(5-fluoroquinolin-8-yl)-2,3-dihydro-5H-[1,4]thiazino[2,3,4-ij]quinazolin-5-one | 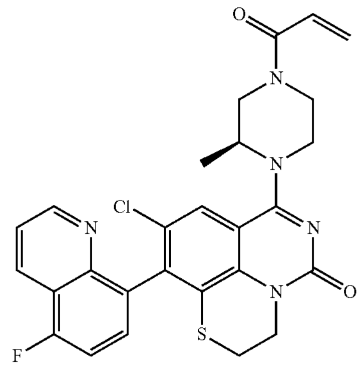 [SMILES: C=CC(=O)N1CCN(c2nc(=O)n3c4c(c(-c5ccc(F)c6cccnc56)c(Cl)cc24)SCC3)[C@@H](C)C1] | ¹H NMR (400 MHz, MeOH-d₄) δ 8.83 (dd, J = 4.3, 1.7 Hz, 1H), 8.65 (dd, J = 8.6, 1.7 Hz, 1H), 7.77-7.60 (m, 3H), 7.49 (t, J = 9.6 Hz, 1H), 6.84 (ddd, J = 22.8, 16.8, 10.5 Hz, 1H), 6.29 (dd, J = 16.8, 6.7 Hz, 1H), 5.82 (dd, J = 10.5, 1.9 Hz, 1H), 4.82 (br s, 1H), 4.63-3.99 (m, 5H), 3.79-3.41 (m, 2H), 3.24-2.95 (m, 3H), 1.46 (d, J = 6.8 Hz, 1.5H), 1.38 (d, J = 6.7 Hz, 1.5H) | 536.2 |
| 410 | (S)-7-((S)-4-acryloyl-2-methylpiperazin-1-yl)-9-chloro-3-((4-ethylpiperazin-1-yl)methyl)-10-(4-fluorophenyl)-2H-[1,4]thiazino[2,3,4-ij]quinazolin-5(3H)-one | 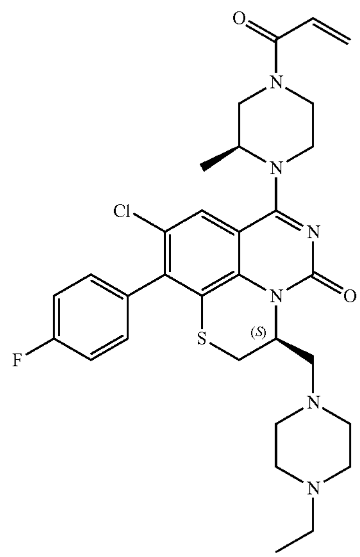 | ¹H NMR (400 MHz, CDCl₃) δ 7.47 (s, 1H), 7.23-7.20 (m, 4H), 6.65-6.50 (m, 1H), 6.36 (d, J = 16.8 Hz, 1H), 5.77 (d, J = 10.8 Hz, 1H), 5.39-5.30 (m, 1H), 4.74-4.64 (m, 1H), 4.57-4.16 (m, 2H), 3.98-3.78 (m, 1H), 3.64-3.36 (m, 3H), 3.09-2.95 (m, 2H), 2.84-2.73 (m, 3H), 2.55-2.35 (m, 9H), 1.47-1.43 (m, 3H), 1.08-1.04 (m, 3H),. | 611.2 |
| 411 | (3S)-7-((S)-4-acryloyl-2-methylpiperazin-1-yl)-9-chloro-10-(2,4-difluorophenyl)-3-((4-methylpiperazin-1-yl)methyl)-2H-[1,4]thiazino[2,3,4-ij]quinazolin-5(3H)-one | 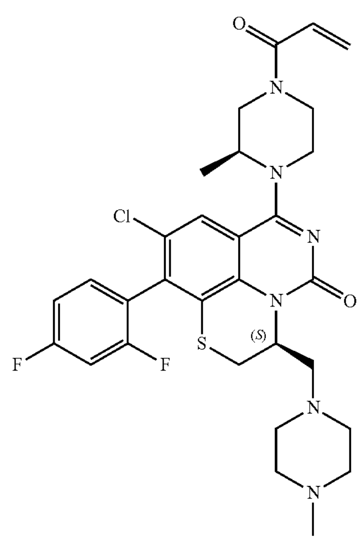 | ¹H NMR (400 MHz, CDCl₃) δ 7.48 (s, 1H), 7.24-7.18 (m, 1H), 7.06-6.95 (m, 2H), 6.66-6.50 (m, 1H), 6.36 (d, J = 16.8 Hz, 1H), 5.77 (d, J = 10.4 Hz, 1H), 5.41-5.28 (m, 1H), 4.73-4.19 (m, 3H), 3.98-3.78 (m, 1H), 3.60-3.39 (m, 3H), 3.08-3.00 (m, 2H), 2.84-2.76 (m, 3H), 2.55-2.39 (m, 7H), 2.55 (m, 3H), 1.48-1.43 (m, 3H). | 615.2 |

TABLE 8-continued

Table of Thiomorpholines

| Ex. # | Name | Structure | ¹H NMR | MS (M + H)⁺ |
|---|---|---|---|---|
| 412 | (3S)-7-((S)-4-acryloyl-2-methylpiperazin-1-yl)-9-chloro-10-(5-chloro-2,4-difluorophenyl)-3-((4-ethylpiperazin-1-yl)methyl)-2H-[1,4]thiazino[2,3,4-ij]quinazolin-5(3H)-one | 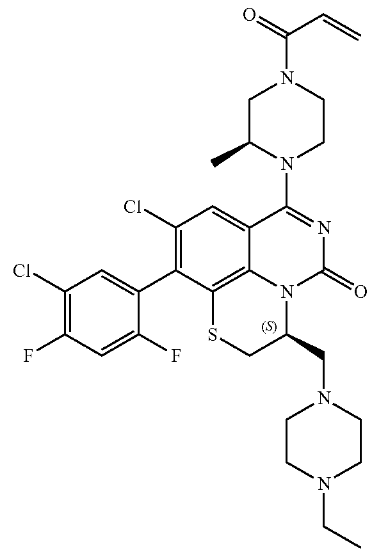 | ¹H NMR (400 MHz, CDCl₃) δ 7.48 (s, 1H), 7.30 (t, J = 7.6 Hz, 1H), 7.12-7.07 (m, 1H), 6.66-6.52 (m, 1H), 6.39-6.35 (m, 1H), 5.78 (d, J = 10.8 Hz, 1H), 5.40-5.34 (m, 1H), 4.71-4.64 (m, 1H), 4.54-4.32 (m, 1.5H), 4.20-4.17 (m, 0.5H), 3.98-3.96 (m, 0.5H), 3.82-3.79 (m, 0.5H), 3.59-3.57 (m, 1.5H), 3.45-3.42 (m, 1.5H), 3.05-3.02 (m, 2H), 2.84-2.74 (m, 3H), 2.57-2.36 (m, 9H), 1.48-1.44 (m, 3H), 1.09-1.05 (m, 3H). | 663.2 |
| 413 | (3S)-7-((S)-4-acryloyl-2-methylpiperazin-1-yl)-9-chloro-10-(2,4-difluorophenyl)-3-((1-ethylpiperidin-4-yl)methyl)-2H-[1,4]thiazino[2,3,4-ij]quinazolin-5(3H)-one | 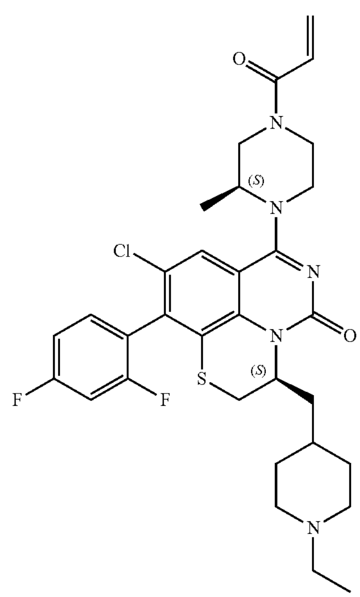 | ¹H NMR (400 MHz, CDCl₃) δ 7.49 (s, 1H), 7.24-7.18 (m, 1H), 7.07-6.96 (m, 2H), 6.61-6.52 (m, 1H), 5.79-5.76 (d, J = 11.2 Hz, 1H), 5.46 (s, 1H), 4.75-4.15 (m, 4H), 3.58-3.46 (m, 1H), 3.13-3.07 (m, 2H), 3.02-2.89 (m, 3H), 2.39-2.37 (dd, J = 2.0 Hz, 2H), 1.93-1.88 (m, 2H), 1.79-1.66 (m, 3H), 1.46-1.42 (d, J = 14.4 Hz, 2H), 1.36-1.32 (m, 2H), 1.09-1.05 (m, 3H). | 628.3 |

TABLE 8-continued

Table of Thiomorpholines

| Ex. # | Name | Structure | ¹H NMR | MS (M + H)⁺ |
|---|---|---|---|---|
| 414 | (3S)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 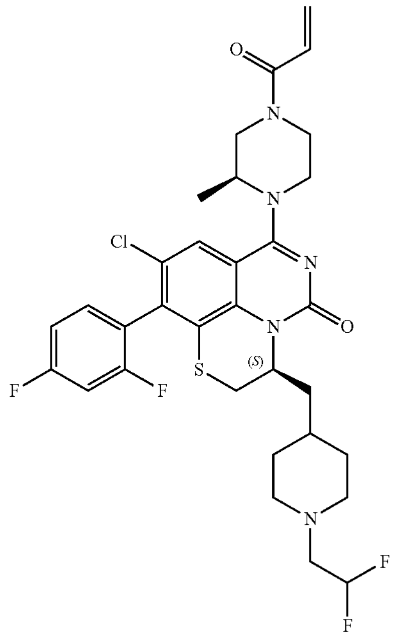 | ¹H NMR (400 MHz, CDCl₃) δ 7.50 (s, 1H), 7.26-7.24 (m, 1H), 7.07-6.97 (m, 2H), 6.67-6.51 (m, 1H), 6.35 (d, J = 23.6 Hz, 1H), 6.01-5.70 (m, 2H), 5.51-5.37 (m, 1H), 4.78-4.64 (m, 1H), 4.59-4.16 (m, 2H), 4.03-3.76 (m, 1H), 3.64-3.42 (m, 2H), 3.15-3.03 (m, 2H), 2.98-2.87 (m, 3H), 2.74-2.63 (m, 2H), 2.22-2.08 (m, 2H), 1.77-1.71 (m, 4H), 1.48-1.28 (m, 6H). | 664.3 |
| 415 | (3S)-7-((S)-4-acryloyl-2-methylpiperazin-1-yl)-9-chloro-10-(2,4-difluorophenyl)-3-((1-(oxetan-3-yl)piperidin-4-yl)methyl)-2H-[1,4]thiazino[2,3,4-ij]quinazolin-5(3H)-one | 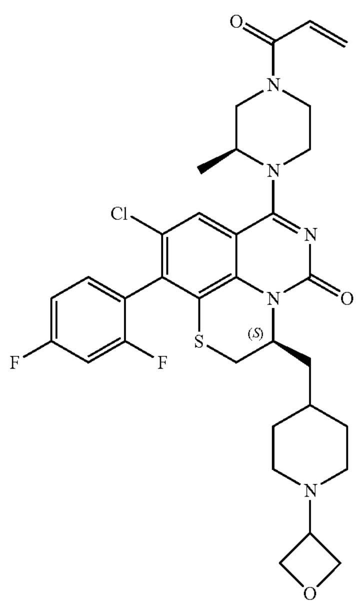 | ¹H NMR (400 MHz, CDCl₃) δ 7.50 (s, 1H), 7.24-7.20 (m, 1H), 7.07-6.97 (m, 2H), 6.61-6.51 (m, 1H), 6.35 (d, J = 27.2 Hz, 1H), 5.79 (d, J = 18.4 Hz, 1H), 5.49-5.36 (m, 1H), 4.74-4.60 (m, 5H), 4.56-4.15 (m, 2H), 4.01-3.77 (m, 1H), 3.63-3.40 (m, 3H), 3.17-(m, 4H), 1.55-1.21 (m, 8H). | 656.3 |

TABLE 8-continued

Table of Thiomorpholines

| Ex. # | Name | Structure | ¹H NMR | MS (M + H)⁺ |
|---|---|---|---|---|
| 416 | (3S)-7-((S)-4-acryloyl-2-methylpiperazin-1-yl)-9-chloro-3-((4-ethylpiperazin-1-yl)methyl)-10-(2,4,5-trifluorophenyl)-2H-[1,4]thiazino[2,3,4-ij]quinazolin-5(3H)-one | 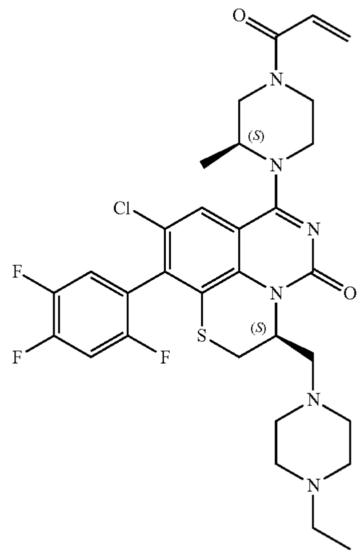 | ¹H NMR (400 MHz, CDCl₃) δ 7.48 (s, 1H), 7.12-7.07 (m, 2H), 6.66-6.51 (m, 1H), 6.37 (d, J = 16.8 Hz, 1H), 5.78 (d, J = 10.8 Hz, 1H), 5.40-5.34 (m, 1H), 4.72-4.66 (m, 1H), 4.54-4.53 (m, 0.5H), 4.44-4.34 (m, 1H), 4.20-4.16 (m, 0.5H), 3.98-3.95 (m, 0.5H), 3.82-3.78 (m, 0.5H), 3.58-3.56 (m, 1.5H), 3.44-3.41 (m, 1.5H), 3.05-3.01 (m, 2H), 2.81-2.75 (m, 3H), 2.57-2.40 (m, 8H), 1.45 (d, J = 19.6 Hz, 4H), 1.25 (s, 3H), 1.10-1.06 (m, 3H). | 647.3 |
| 421 | (3S)-7-((S)-4-acryloyl-2-methylpiperazin-1-yl)-9-chloro-3-((1-(oxetan-3-yl)piperidin-4-yl)methyl)-10-(2,4,5-trifluorophenyl)-2H-[1,4]thiazino[2,3,4-ij]quinazolin-5(3H)-one | 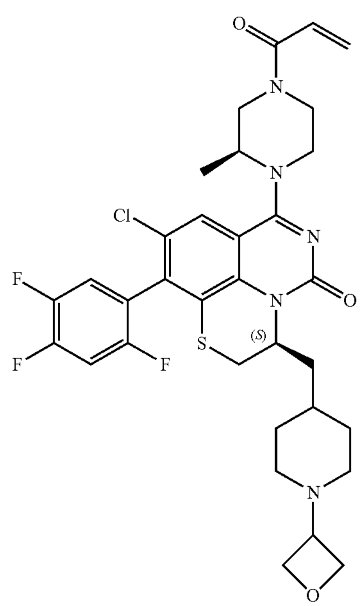 | ¹H NMR (400 MHz, CDCl₃) δ 7.50 (s, 1H), 7.15-7.05 (m, 2H), 6.62-6.52 (m, 1H), 6.37 (d, J = 16.8 Hz, 1H), 5.78 (d, J = 10.8 Hz, 1H), 5.48-5.41 (m, 1H), 4.75-4.55 (m, 5.5H), 4.44-4.35 (m, 1H), 4.20-4.17 (m, 0.5H), 3.98-3.94 (m, 0.5H), 3.82-3.79 (m, 0.5H), 3.59-3.40 (m, 3H), 3.15-2.97 (m, 3H), 2.71-2.68 (m, 2H), 1.84-1.68 (m, 6H), 1.47-1.27 (m, 6H). | 674.3 |

TABLE 8-continued

Table of Thiomorpholines

| Ex. # | Name | Structure | ¹H NMR | MS (M + H)⁺ |
|---|---|---|---|---|
| 422 | (3S)-7-((S)-4-acryloyl-2-methylpiperazin-1-yl)-9-chloro-3-((4-cyclopropylpiperazin-1-yl)methyl)-10-(2,4-difluorophenyl)-2H-[1,4]thiazino[2,3,4-ij]quinazolin-5(3H)-one | 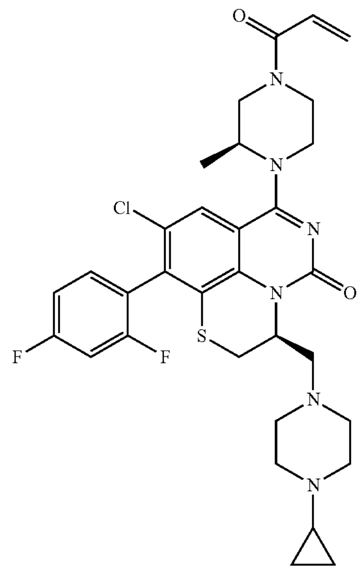 [SMILES: C=CC(=O)N1CCN(c2nc(=O)n3c4c(c(-c5ccc(F)cc5F)c(Cl)cc24)SC[C@@H]3CN2CCN(C3CC3)CC2)[C@@H](C)C1] | ¹H NMR (400 MHz, CDCl₃) δ 7.48 (s, 1H), 7.24-7.18 (m, 1H), 7.06-6.95 (m, 2H), 6.66-6.50 (m, 1H), 6.36 (d, J = 16.4 Hz, 1H), 5.77 (d, J = 10.8 Hz, 1H), 5.40-5.31 (m, 1H), 4.73-4.68 (m, 1H), 4.55-4.15 (m, 2H), 3.99-3.77 (m, 1H), 3.59-3.41 (m, 3H), 3.08-3.00 (m, 2H), 2.83-2.48 (m, 10H), 1.48-1.43 (m, 3H), 1.26 (m, 1H), 0.42-0.39 (m, 4H). | 641.3 |
| 423 | (3S)-7-((S)-4-acryloyl-2-methylpiperazin-1-yl)-9-chloro-10-(2,4-difluorophenyl)-3-((1-methylpiperidin-4-yl)methyl)-2H-[1,4]thiazino[2,3,4-ij]quinazolin-5(3H)-one | 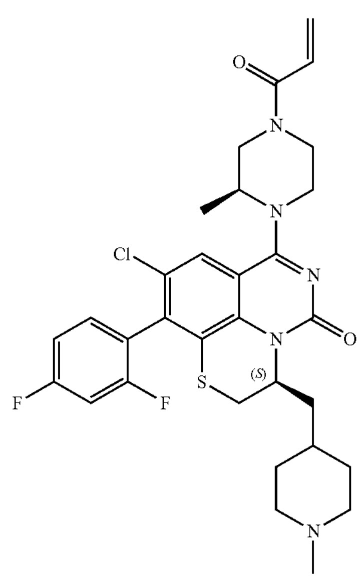 | ¹H NMR (400 MHz, CDCl₃) δ 7.50 (s, 1H), 7.24-7.18 (m, 1H), 7.08-6.97 (m, 2H), 6.68-6.32 (m, 2H), 5.80-5.36 (m, 2H), 4.78-4.66 (m, 1H), 4.62-4.15 (m, 2H), 4.00-3.76 (m, 1H), 3.62-3.42 (m, 2H), 3.16-2.83 (m, 6H), 2.29 (s, 3H), 1.92-1.64 (m, 9H), 1.41-1.24 (m, 3H). | 614.3 |

TABLE 8-continued

Table of Thiomorpholines

| Ex. # | Name | Structure | ¹H NMR | MS (M + H)⁺ |
|---|---|---|---|---|
| 424 | (R)-7-((S)-4-acryloyl-2-methylpiperazin-1-yl)-9-chloro-3-((4-ethylpiperazin-1-yl)methyl)-10-(2,4,6-trifluorophenyl)-2H-[1,4]thiazino[2,3,4-ij]quinazolin-5(3H)-one | 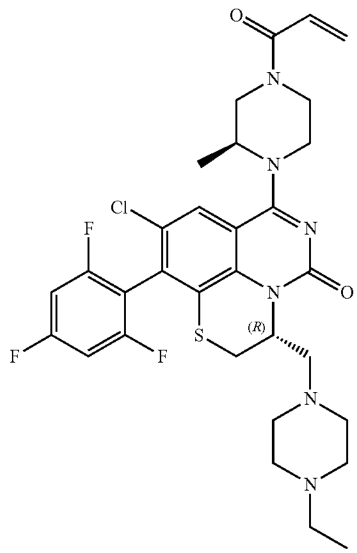 | ¹H NMR (400 MHz, CDCl₃) δ 7.50 (s, 1H), 6.84 (t, J = 7.2 Hz, 2H), 6.59-6.55 (m, 1H), 6.39-6.35 (m, 1H), 6.79-6.77 (d, J = 10.2 Hz, 1H), 5.41-5.40 (m, 1H), 4.90-4.63 (m, 2H), 4.04-4.01 (m, 2H), 3.7-3.65 (m, 2H), 3.46-3.43 (d, J = 12.8 Hz, 2H), 3.27-3.06 (m, 2H), 2.94-2.82 (m, 3H), 2.55-2.52 (m, 2H), 2.46-2.45 (m, 2H), 2.43-2.41 (m, 2H), 2.40-2.38 (m, 3H), 1.37-1.36 (d, J = 6.8 Hz, 3H), 1.10-1.06 (m, 3H). | 647.3 |
| 425 | (S)-7-((S)-4-acryloyl-2-methylpiperazin-1-yl)-10-(4-fluorophenyl)-3-((1-(oxetan-3-yl)piperidin-4-yl)methyl)-9-(trifluoromethyl)-2H-[1,4]thiazino[2,3,4-ij]quinazolin-5(3H)-one | 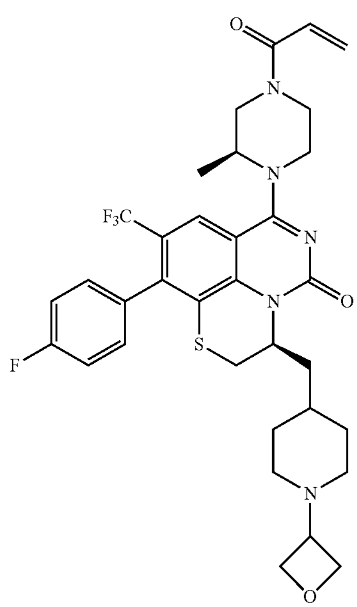 [SMILES: C=CC(=O)N1CCN(c2nc(=O)n3c4c(c(-c5ccc(F)cc5)c(C(F)(F)F)cc24)SC[C@@H]3CC2CCN(C3COC3)CC2)[C@@H](C)C1] | ¹H NMR (400 MHz, CDCl₃) δ 7.78 (s, 1H), 7.25-7.16 (m, 4H), 6.62-6.53 (m, 1H), 6.39-6.35 (m, 1H), 5.79 (d, J = 10.4 Hz, 1H), 5.40-5.39 (m, 1H), 4.68-4.58 (m, 5H), 4.48-4.25 (m, 2H), 3.98-3.80 (m, 1H), 3.63-3.38 (m, 3H), 3.07-3.04 (m, 2H), 2.98-2.94 (m, 1H), 2.70 (t, J = 12.4 Hz, 2H), 1.84-1.69 (m, 6H), 1.52-1.40 (m, 4H), 1.39-1.26 (m, 2H). | 672.3 |

TABLE 8-continued

Table of Thiomorpholines

| Ex. # | Name | Structure | ¹H NMR | MS (M + H)⁺ |
|---|---|---|---|---|
| 426 | (3S)-7-((S)-4-acryloyl-2-methylpiperazin-1-yl)-9-chloro-10-(5-chloro-2,4-difluorophenyl)-3-((1-(oxetan-3-yl)piperidin-4-yl)methyl)-2H-[1,4]thiazino[2,3,4-ij]quinazolin-5(3H)-one | 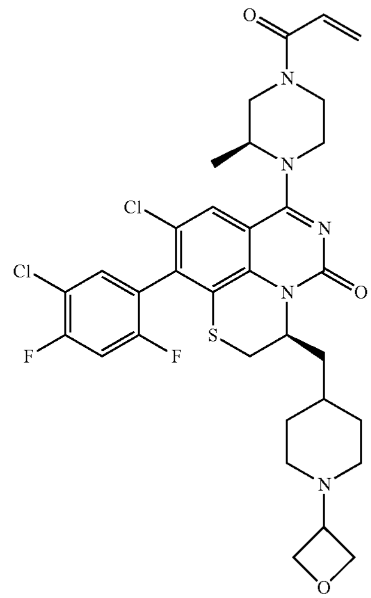 [SMILES: C=CC(=O)N1CCN(c2nc(=O)n3c4c(c(-c5cc(Cl)c(F)cc5F)c(Cl)cc24)SC[C@@H]3CC2CCN(C3COC3)CC2)[C@@H](C)C1] | ¹H NMR (400 MHz, CDCl₃) δ 7.50 (s, 1H), 7.34-7.28 (m, 1H), 7.13-7.07 (m, 1H), 6.62-6.52 (m, 1H), 6.37 (d, J = 17.2 Hz, 1H), 5.78 (d, J = 10.8 Hz, 1H), 5.49-5.43 (m, 1H), 4.73-4.54 (m, 5.5H), 4.47-4.33 (m, 1H), 4.21-4.17 (m, 0.5H), 3.99-3.96 (m, 0.5H), 3.83-3.80 (m, 0.5H), 3.58-3.49 (m, 1.5H), 3.49-3.39 (m, 1.5H), 3.16-2.97 (m, 3H), 2.74-2.70 (m, 2H), 1.84-1.74 (m, 5H), 1.46-1.32 (m, 7H). | 690.3 |
| 428 | (S)-7-((S)-4-acryloyl-2-methylpiperazin-1-yl)-3-((1-(2,2-difluoroethyl)piperidin-4-yl)methyl)-10-(4-fluorophenyl)-9-(trifluoromethyl)-2H-[1,4]thiazino[2,3,4-ij]quinazolin-5(3H)-one | 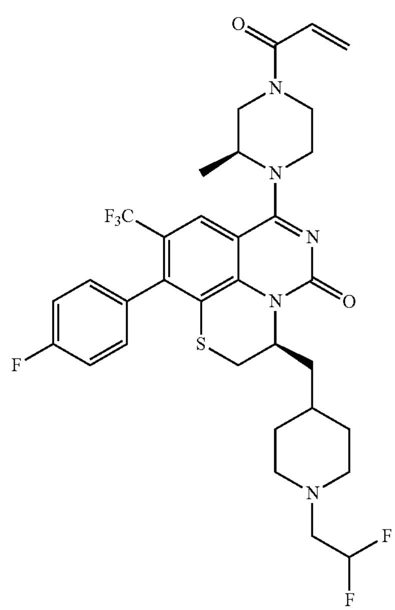 [SMILES: C=CC(=O)N1CCN(c2nc(=O)n3c4c(c(-c5ccc(F)cc5)c(C(F)(F)F)cc24)SC[C@@H]3CC2CCN(CC(F)F)CC2)[C@@H](C)C1] | ¹H NMR (400 MHz, CDCl₃) δ 7.78 (s, 1H), 7.21-7.16 (m, 4H), 6.62-6.54 (m, 1H), 6.39 (d, J = 16.4 Hz, 1H), 6.00-5.70 (m, 2H), 5.39-5.37 (m, 1H), 4.68-4.66 (m, 1H), 4.48-4.39 (m, 1.5H), 4.29-4.25 (m, 0.5H), 3.98-3.95 (m, 0.5H), 3.83-3.80 (m, 0.5H), 3.63-3.44 (m, 2H), 3.07 (d, J = 13.2 Hz, 2H), 2.97-2.87 (m, 3H), 2.74-2.65 (m, 2H), 2.21-2.11 (m, 2H), 1.74-1.67 (m, 4H), 1.52-1.40 (m, 4H), 1.31-1.27 (m, 2H). | 680.3 |

TABLE 8-continued

Table of Thiomorpholines

| Ex. # | Name | Structure | ¹H NMR | MS (M + H)⁺ |
|---|---|---|---|---|
| 429 | (3S)-7-((S)-4-acryloyl-2-methylpiperazin-1-yl)-3-((1-(2,2-difluoroethyl)piperidin-4-yl)methyl)-10-(2,4-difluorophenyl)-9-(trifluoromethyl)-2H-[1,4]thiazino[2,3,4-ij]quinazolin-5(3H)-one 1,1-dioxide | 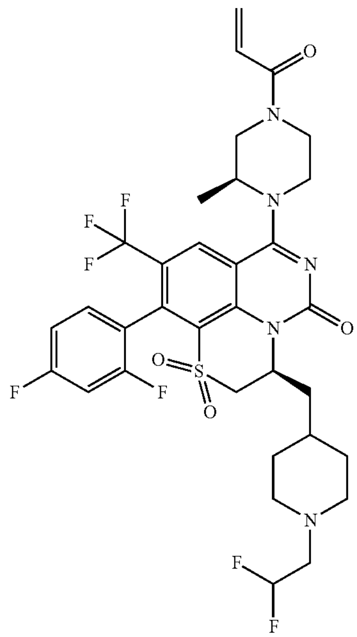 [SMILES: C=CC(=O)N1CCN(c2nc(=O)n3c4c(c(-c5ccc(F)cc5F)c(C(F)(F)F)cc24)S(=O)(=O)C[C@@H]3CC2CCN(CC(F)F)CC2)[C@@H](C)C1] | ¹H NMR (400 MHz, CDCl₃) δ 8.15 (s, 1H), 7.43-7.26 (m, 1H), 7.02-6.89 (m, 2H), 6.56 (dd, J = 14.6 Hz, 1.6 Hz, 1H), 6.34 (d, J = 16.4 Hz, 1H), 6.00-5.70 (m, 2H), 5.08-5.04 (m, 1H), 5.04-4.30 (m, 3H), 4.14-3.77 (m, 2H), 3.72-3.43 (m, 3H), 3.33-3.07 (m, 1H), 2.96-2.89 (m, 2H), 2.74-2.65 (m, 2H), 2.22-2.07 (m, 3H), 1.78-1.62 (m, 4H), 1.45-1.25 (m, 5H) | 730.3 |
| 430 | (S)-7-((S)-4-acryloyl-2-methylpiperazin-fluorophenyl)-9-(trifluoromethyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 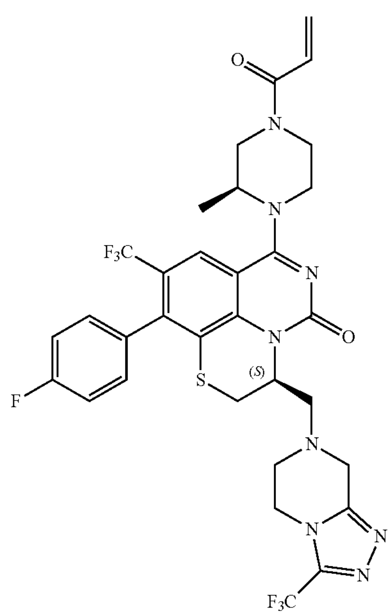 | ¹H NMR (400 MHz, CDCl₃) δ 7.80 (s, 1H), 7.21-7.20 (m, 4H), 6.61-6.52 (m, 1H), 6.39-6.35 (m, 1H), 5.79 (d, J = 10.4 Hz, 1H), 5.35-5.31 (brs, 1H), 4.76-4.73 (m, 1H), 4.65-4.56 (m, 1H), 4.43-4.33 (m, 2H), 4.17-3.96 (m, 3H), 3.93-3.80 (m, 1H), 3.60-3.42 (m, 4H), 3.20-3.06 (m, 4H), 2.97-2.94 (m, 1H), 1.55-1.50 (m, 3H). | 723.3 |

TABLE 8-continued

Table of Thiomorpholines

| Ex. # | Name | Structure | ¹H NMR | MS (M + H)⁺ |
|---|---|---|---|---|
| 432 | (3R)-7-((S)-4-acryloyl-2-methylpiperazin-1-yl)-9-chloro-10-(2,4-difluorophenyl)-3-(((1-ethylazetidin-3-yl)oxy)methyl)-2,3-dihydro-5H-[1,4]thiazino[2,3,4-ij]quinazolin-5-one | 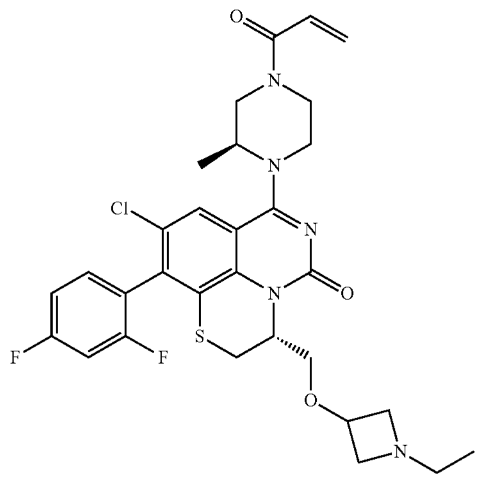 [SMILES: C=CC(=O)N1CCN(c2nc(=O)n3c4c(c(-c5ccc(F)cc5F)c(Cl)cc24)SC[C@H]3COC2CN(CC)C2)[C@@H](C)C1] | ¹H NMR (400 MHz, MeOH-d₄) δ 7.76 (s, 1H), 7.39-7.26 (m, 1H), 7.23-7.07 (m, 2H), 6.91-6.74 (m, 1H), 6.29 (dd, J = 16.6, 4.6 Hz, 1H), 5.81 (d, J = 10.6 Hz, 1H), 5.40-5.25 (m, 1H), 5.03-4.93 (m, 1H), 4.65-4.35 (m, 2H), 4.33-4.00 (m, 3H), 3.98-3.57 (m, 6H), 3.51-3.34 (m, 3H), 3.27-2.94 (m, 3H), 1.40-1.26 (m, 3H), 1.25-1.11 (m, 3H) | 616.2 |
| 433 | 7'-((S)-4-acryloyl-2-methylpiperazin-1-yl)-9'-chloro-10'-(2,4-difluorophenyl)-3'H,5'H-spiro[cyclopropane-1,2'-[1,4]thiazino[2,3,4-ij]quinazolin]-5'-one | 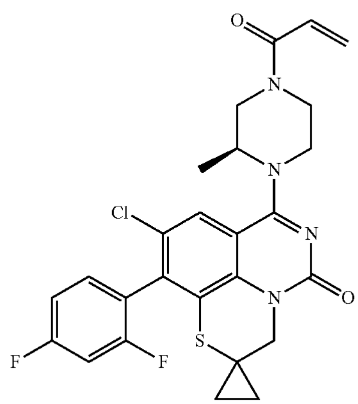 [SMILES: C=CC(=O)N1CCN(c2nc(=O)n3c4c(c(-c5ccc(F)cc5F)c(Cl)cc24)SC2(CC2)C3)[C@@H](C)C1] | ¹H NMR (400 MHz, MeOH-d₄) δ 7.61 (d, J = 6.6 Hz, 1H), 7.18 (tdd, J = 8.7, 6.3, 2.3 Hz, 1H), 7.09-6.96 (m, 2H), 6.72 (dddd, J = 20.7, 16.7, 10.5, 3.3 Hz, 1H), 6.19 (dd, J = 16.9, 6.2 Hz, 1H), 5.71 (dd, J = 10.6, 2.0 Hz, 1H), 5.04 (d, J = 8.6 Hz, 1H), 4.58-4.40 (m, 1H), 4.36-3.87 (m, 4H), 3.72-3.35 (m, 4H), 1.34 (d, J = 6.8 Hz, 1.5H), 1.29 (d, J = 6.7 Hz, 1.5H), 1.08-0.99 (m, 2H), 0.93-0.76 (m, 2H) | 529.2 |
| 434 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one 1,1-dioxide | 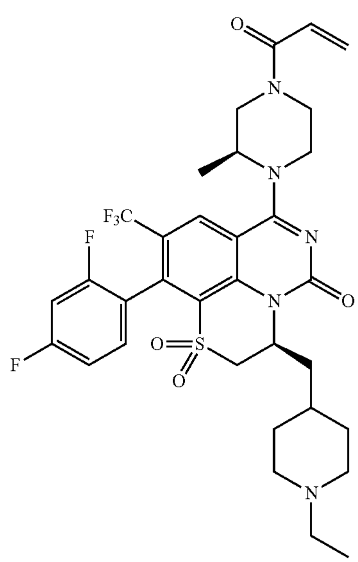 [SMILES: C=CC(=O)N1CCN(c2nc(=O)n3c4c(c(-c5ccc(F)cc5F)c(C(F)(F)F)cc24)S(=O)(=O)C[C@@H]3CC2CCN(CC)CC2)[C@@H](C)C1] | ¹H NMR (400 MHz, CDCl₃) δ 8.15 (s, 1H), 7.43-7.31 (m, 1H), 7.03-6.89 (m, 2H), 6.60-6.53 (m, 1H), 6.39 (dd, J = 1.2 Hz, 16.8 Hz, 1H), 5.81 (d, J = 10.4 Hz, 1H), 5.58-5.57 (m, 1H), 4.75-4.33 (m, 3H), 4.03-3.82 (m, 1H), 3.69-3.45 (m, 4H), 3.13-3.05 (m, 3H), 2.58-2.52 (m, 2H), 2.24-2.09 (m, 3H), 1.92-1.86 (m, 2H), 1.58-1.52 (m, 7H), 1.18 (t, J = 6.8 Hz, 3H). | 694.2 |

TABLE 8-continued

Table of Thiomorpholines

| Ex. # | Name | Structure | ¹H NMR | MS (M + H)⁺ |
|---|---|---|---|---|
| 435 | (3S)-7-((S)-4-acryloyl-2-methylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 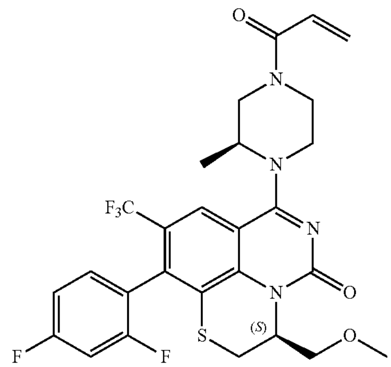 | ¹H NMR (400 MHz, CDCl₃) δ 7.77 (s, 1H), 7.21-7.16 (m, 1H), 7.04-6.94 (m, 2H), 6.66-6.51 (m, 1H), 6.37 (d, J = 16.8 Hz, 1H), 5.78 (d, J = 10.4 Hz, 1H), 5.40-5.38 (m, 1H), 4.74-4.29 (m, 3H), 3.99-3.80 (m, 1H), 3.67-3.34 (m, 8H), 3.11-2.99 (m, 2H), 1.55-1.50 (m, 3H). | 581.1 |
| 436 | (3S)-7-((S)-4-acryloyl-2-methylpiperazin-1-yl)-10-(2,4-difluorophenyl)-3-(methoxymethyl)-9-(trifluoromethyl)-2H-[1,4]thiazino[2,3,4-ij]quinazolin-5(3H)-one 1,1-dioxide | 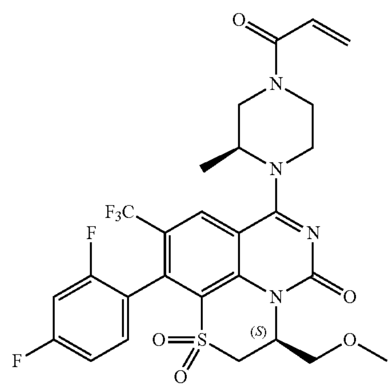 | ¹H NMR (400 MHz, CDCl₃) δ 8.13 (s, 1H), 7.42-7.30 (m, 1H), 7.03-6.88 (m, 2H), 6.66-6.50 (m, 1H), 6.39 (dd, J = 1.6 Hz, 16.8 Hz, 1H), 5.80 (d, J = 10.4 Hz, 1H), 5.54-5.50 (m, 1H), 4.78-4.35 (m, 3H), 4.06-3.73 (m, 4H), 3.61-3.48 (m, 3H), 3.39 (d, J = 8.0 Hz, 3H), 3.10-3.03 (m, 1H), 1.58-1.46 (m, 3H). | 613.2 |
| 437 | (3S)-7-((S)-4-acryloyl-2-methylpiperazin-1-yl)-10-(2,4-difluorophenyl)-3-((tetrahydro-2H-pyran-4-yl)methyl)-9-(trifluoromethyl)-2H-[1,4]thiazino[2,3,4-ij]quinazolin-5(3H)-one | 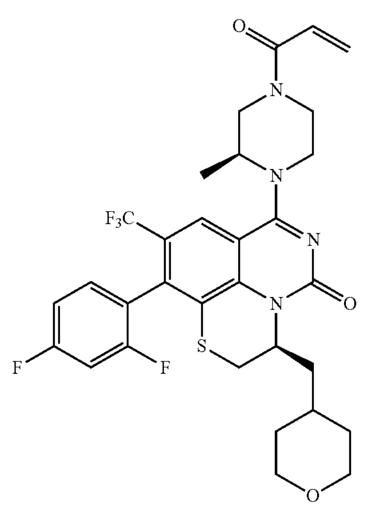 [SMILES: C=CC(=O)N1CCN(c2nc(=O)n3c4c(c(-c5ccc(F)cc5F)c(C(F)(F)F)cc24)SC[C@@H]3CC2CCOCC2)[C@@H](C)C1] | ¹H NMR (400 MHz, CDCl₃) δ 7.79 (s, 1H), 7.23-7.15 (m, 1H), 7.05-6.95 (m, 2H), 6.62-6.55 (m, 1H), 6.39-6.35 (m, 1H), 5.79 (d, J = 10.4 Hz, 1H), 5.45-5.42 (m, 1H), 4.70-4.69 (m, 1H), 4.48-4.39 (m, 1.5H), 4.31-4.28 (m, 0.5H), 3.94 (t, J = 11.6 Hz, 2.5H), 3.83-3.81 (m, 0.5H), 3.61-3.45 (m, 2H), 3.42-3.32 (m, 2H), 3.14-3.97 (m, 3H), 1.80-1.72 (m, 4H), 1.53-1.35 (m, 5H), 1.32-1.26 (m, 1H). | 635.2 |

TABLE 8-continued

Table of Thiomorpholines

| Ex. # | Name | Structure | ¹H NMR | MS (M + H)⁺ |
|---|---|---|---|---|
| 438 | (3S)-7-((S)-4-acryloyl-2-methylpiperazin-1-yl)-9-chloro-10-(2,4-difluorophenyl)-3-((tetrahydro-2H-pyran-4-yl)methyl)-2H-[1,4]thiazino[2,3,4-ij]quinazolin-5(3H)-one | 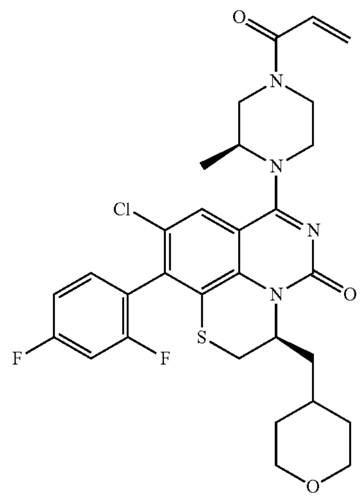 [SMILES: C=CC(=O)N1CCN(c2nc(=O)n3c4c(c(-c5ccc(F)cc5F)c(Cl)cc24)SC[C@@H]3CC2CCOCC2)[C@@H](C)C1] | ¹H NMR (400 MHz, CDCl$_3$) δ 7.50 (s, 1H), 7.24-7.19 (m, 1H), 7.08-6.96 (m, 2H), 6.62-6.54 (m, 1H), 6.39 (d, J = 16 Hz, 1H), 5.79 (d, J = 10.8 Hz, 1H), 5.46 (s, 1H), 4.74-4.66 (m, 1H), 4.56 (s, 0.5H), 4.44-4.35 (m, 1H), 4.20 (s, 0.5H), 3.96-3.91 (m, 2.5H), 3.91-3.79 (m, 0.5H), 3.58 (s, 1.5H), 3.48-3.46 (m, 0.5H), 3.42-3.31 (m, 2H), 3.15-3.06 (m, 2H), 2.99 (d, J = 13.6 Hz, 1H), 1.77-1.62 (m, 5H), 1.47 (d, J = 12.8 Hz, 4H), 1.39-1.30 (m, 1H). | 601.2 |
| 443 | (3S)-7-((2S,5R)-4-acryloyl-2,5-dimethylpiperazin-1-yl)-3-((4-(2,2-difluoroethyl)piperazin-1-yl)methyl)-9-(trifluoromethyl)-10-(2,4,5-trifluorophenyl)-2H-[1,4]thiazino[2,3,4-ij]quinazolin-5(3H)-one | 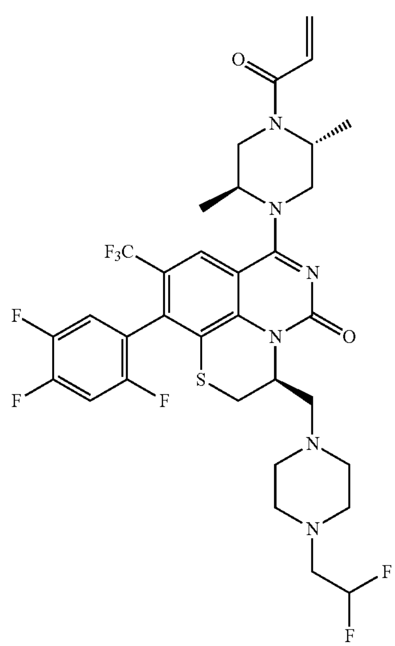 [SMILES: C=CC(=O)N1C[C@H](C)N(c2nc(=O)n3c4c(c(-c5cc(F)c(F)cc5F)c(C(F)(F)F)cc24)SC[C@@H]3CN2CCN(CC(F)F)CC2)C[C@H]1C] | ¹H NMR (400 MHz, CDCl$_3$) δ 7.83 (s, 1H), 7.09-7.04 (m, 2H), 6.65-6.50 (m, 1H), 6.37 (t, J = 14.0 Hz, 1H), 6.01-5.70 (m, 2H), 5.37 (br, 1H), 5.04 (br, 0.5H), 4.08-4.65 (m, 1H), 4.44-4.33 (m, 1.5H), 4.08-4.02 (m, 0.5H), 3.77-3.63 (m, 2H), 3.42-3.01 (m, 3H), 2.75-2.56 (m, 11.5H), 1.48-1.37 (m, 6H). | 731.3 |

TABLE 8-continued

Table of Thiomorpholines

| Ex. # | Name | Structure | ¹H NMR | MS (M + H)⁺ |
|---|---|---|---|---|
| 444 | (S)-7-((S)-4-acryloyl-2-methylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 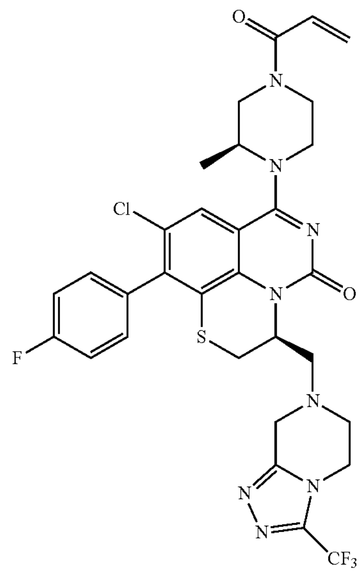 [SMILES: C=CC(=O)N1CCN(c2nc(=O)n3c4c(c(-c5ccc(F)cc5)c(Cl)cc24)SC[C@@H]3CN2CCn3c(nnc3C(F)(F)F)C2)[C@@H](C)C1] | ¹H NMR (400 MHz, CDCl₃) δ 7.51 (s, 1H), 7.23 (d, J = 7.2 Hz, 4H), 6.64-6.49 (m, 1H), 6.39-6.35 (m, 1H), 5.79-5.76 (m, 1H), 5.33-5.29 (m, 1H), 4.73-4.24 (m, 4H), 4.16-3.79 (m, 4H), 3.60-3.40 (m, 3H), 3.33-3.29 (m, 1H), 3.17-3.05 (m, 3H), 2.94-2.90 (m, 1H), 1.47 (d, J = 14.0 Hz, 3H). | 689.2 |
| 445 | (S)-7-((2S,5R)-4-acryloyl-2,5-dimethylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 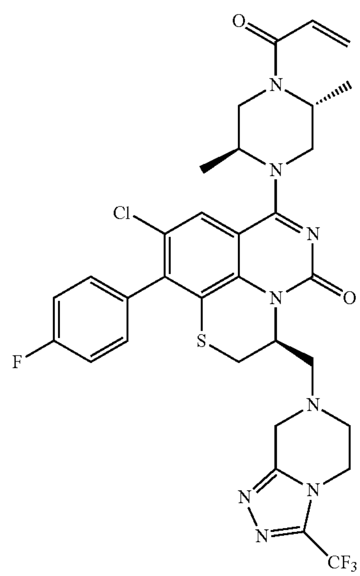 [SMILES: C=CC(=O)N1C[C@H](C)N(c2nc(=O)n3c4c(c(-c5ccc(F)cc5)c(Cl)cc24)SC[C@@H]3CN2CCn3c(nnc3C(F)(F)F)C2)C[C@H]1C] | ¹H NMR (400 MHz, CDCl₃) δ 7.56 (d, J = 9.6 Hz, 1H), 7.23 (d, J = 6.8 Hz, 4H), 6.64-6.49 (m, 1H), 6.36 (t, J = 15.6 Hz, 1H), 5.77 (t, J = 7.6 Hz, 1H), 5.42-5.40 (m, 1H), 5.00-4.99 (m, 1H), 4.82-4.72 (m, 1H), 4.38-3.99 (m, 6H), 3.79-3.66 (m, 2H), 3.35-3.19 (m, 3H), 3.10-3.07 (d, J = 11.6 Hz, 2H), 2.93 (d, J = 12.4 Hz, 1H), 1.45-1.38 (m, 3H), 1.31-1.28 (m, 3H). | 703.3 |
| 446 | (3S)-7-((S)-4-acryloyl-2-methylpiperazin-1-yl)-9-chloro-10-(5-chloro-2,4-difluorophenyl)-3-((methoxymethoxy)methyl)-2H-[1,4]thiazino[2,3,4-ij]quinazolin-5(3H)-one | 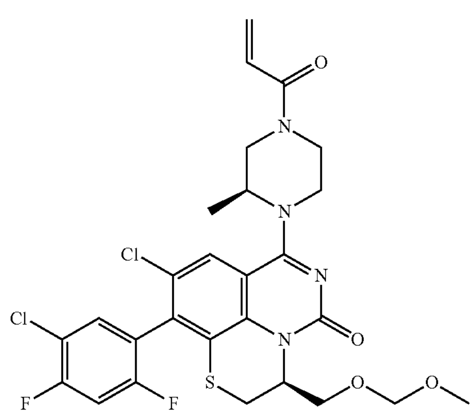 [SMILES: C=CC(=O)N1CCN(c2nc(=O)n3c4c(c(-c5cc(Cl)c(F)cc5F)c(Cl)cc24)SC[C@@H]3COCOC)[C@@H](C)C1] | ¹H NMR (400 MHz, CDCl₃) δ 7.49 (s, 1H), 7.32-7.28 (m, 1H), 7.12-7.06 (m 1H), 6.72-6.45 (m, 1H), 6.39-6.35 (m, 1H), 5.78 (d, J = 10.4 Hz, 1H), 5.44 (brs, 1H), 4.98-4.97 (m, 1H), 4.69-4.62 (m, 2H), 4.15-3.95 (m, 1H), 3.82-3.76 (m, 3H), 3.40-3.35 (m, 4H), 3.35-2.78 (m, 2H), 1.65-1.63 (m, 3H), 1.35 (d, J = 6.8 Hz, 3H). | 611.1 |

| Ex. # | Name | Structure | ¹H NMR | MS (M + H)⁺ |
|---|---|---|---|---|
| 447 | (3S)-7-((S)-4-acryloyl-2-methylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 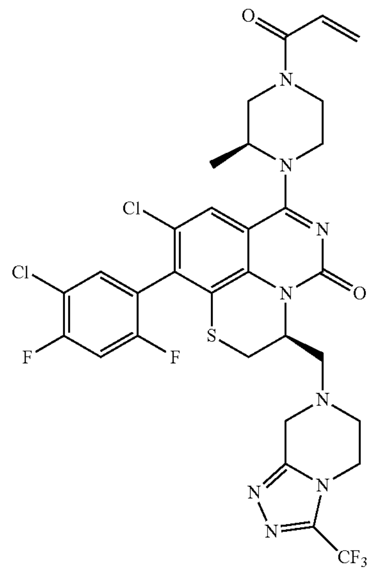 [SMILES: C=CC(=O)N1CCN(c2nc(=O)n3c4c(c(-c5cc(Cl)c(F)cc5F)c(Cl)cc24)SC[C@@H]3CN2CCn3c(nnc3C(F)(F)F)C2)[C@@H](C)C1] | ¹H NMR (400 MHz, CDCl₃) δ 7.51 (s, 1H), 7.32-7.29 (m, 1H), 7.13-7.09 (m, 1H), 6.61-6.52 (m, 1H), 6.39-6.35 (m, 1H), 5.79 (d, J = 10.4 Hz, 1H), 5.37-5.36 (m, 1H), 4.69-4.67 (m, 1H), 4.57-4.31 (m, 3H), 4.27-3.95 (m, 4H), 3.60-3.35 (m, 4H), 3.19-2.90 (m, 5H), 1.47-1.41 (m, 3H). | 741.2 |
| 448 | (3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 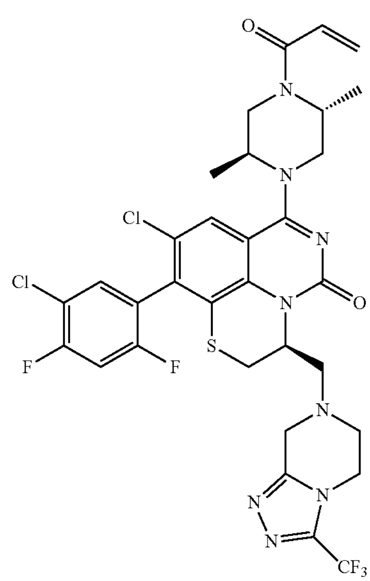 [SMILES: C=CC(=O)N1C[C@H](C)N(c2nc(=O)n3c4c(c(-c5cc(Cl)c(F)cc5F)c(Cl)cc24)SC[C@@H]3CN2CCn3c(nnc3C(F)(F)F)C2)C[C@H]1C] | ¹H NMR (400 MHz, CDCl₃) δ 7.59-7.53 (m, 1H), 7.33-7.28 (m, 1H), 7.13-7.08 (m, 1H), 6.61-6.48 (m, 1H), 6.40-6.32 (m, 1H), 5.79-5.75 (m, 1H), 5.54-5.38 (m, 1H), 5.03-4.96 (m, 0.5 H), 4.80-4.70 (m, 1H), 4.38-4.09 (m, 2.5H), 4.07-3.96 (m, 3.5H), 3.71-3.65 (m, 2H), 3.30-3.08 (m, 5.5H), 2.96-2.91 (m, 1H), 1.46-1.38 (m, 3H), 1.32-1.25 (m, 3H). | 755.2 |

TABLE 8-continued

Table of Thiomorpholines

| Ex. # | Name | Structure | ¹H NMR | MS (M + H)⁺ |
|---|---|---|---|---|
| 449 | (3S)-3-(2-oxa-7-azaspiro[3.5]nonan-7-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one | 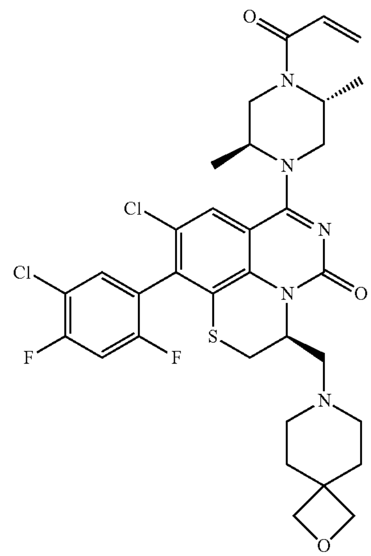 [SMILES: C=CC(=O)N1C[C@H](C)N(c2nc(=O)n3c4c(c(-c5cc(Cl)c(F)cc5F)c(Cl)cc24)SC[C@@H]3CN2CCC3(CC2)COC3)C[C@H]1C] | ¹H NMR (400 MHz, CDCl₃) δ 7.52 (s, 1H), 7.29-7.27 (m, 1H), 7.12-7.06 (m, 1H), 6.65-6.50 (m, 1H), 6.37 (t, J = 14.8 Hz, 1H), 5.79-5.75 (m, 1H), 5.42 (s, 1H), 5.00-4.68 (m, 2H), 4.38-3.97 (m, 6H), 3.78-3.65 (m, 2H), 3.36-3.35 (m, 1H), 3.05-3.00 (m, 1H), 2.71-2.37 (m, 6H), 1.81 (br, 4H), 1.39-1.25 (m, 6H). | 690.2 |
| 455 | (S)-8-(4-acryloyl-2-methylpiperazin-1-yl)-10-(trifluoromethyl)-11-(2,4,6-trifluorophenyl)-3,4-dihydro-2H,6H-[1,4]thiazepino[2,3,4-ij]quinazolin-6-one | 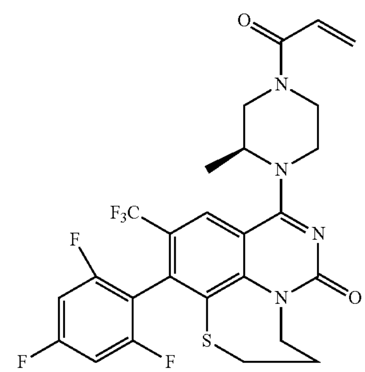 [SMILES: C=CC(=O)N1CCN(c2nc(=O)n3c4c(c(-c5c(F)cc(F)cc5F)c(C(F)(F)F)cc24)SCCC3)[C@@H](C)C1] | ¹H NMR (400 MHz, MeOH-d₄) δ 7.64 (s, 1H), 6.96 (t, J = 8.5 Hz, 2H), 6.72 (ddd, J = 21.6, 16.6, 10.6 Hz, 1H), 6.18 (dd, J = 16.8, 6.3 Hz, 1H), 5.71 (dd, J = 10.6, 2.0 Hz, 1H), 5.13-4.99 (m, 2H), 4.60-4.48 (m, 4H), 4.33-3.84 (m, 2H), 3.63-3.45 (m, 3H), 2.18-2.03 (m, 2H), 1.31 (d, J = 6.8 Hz, 3H) | 535.2 |
| 456 | (3S)-3-(2-oxa-7-azaspiro[3.5]nonan-7-ylmethyl)-7-((S)-4-acryloyl-2-methylpiperazin-1-yl)-9-chloro-10-(5-chloro-2,4-difluorophenyl)-2H-[1,4]thiazino[2,3,4-ij]quinazolin-5(3H)-one | 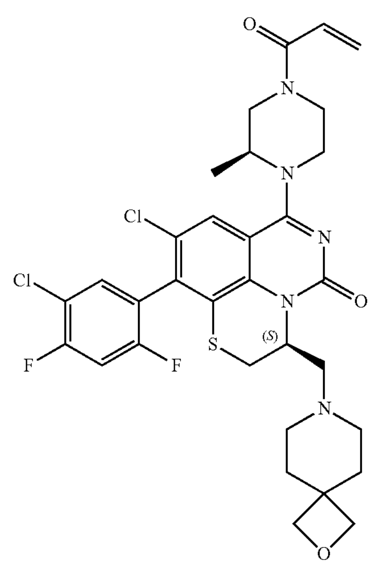 | ¹H NMR (400 MHz, CDCl₃) δ 7.47 (s, 1H), 7.29 (t, J = 8.0 Hz, 1H), 7.12-7.06 (m, 1H), 6.65-6.50 (m, 1H), 6.39-6.34 (m, 1H), 5.77 (d, J = 11.2 Hz, 1H), 5.36-5.26 (m, 1H), 4.72-4.64 (m, 1H), 4.57-4.49 (m, 0.5H), 4.44-4.38 (m, 5H), 4.23-4.18 (m, 0.5H), 3.99-3.78 (m, 1H), 3.75-3.41 (m, 3H), 3.06-2.99 (m, 2H), 2.79-2.59 (m, 3H), 2.48-2.36 (m, 3H), 1.86-1.80 (m, 4H), 1.48-1.44 (m, 3H). | 676.3 |

TABLE 8-continued

Table of Thiomorpholines

| Ex. # | Name | Structure | ¹H NMR | MS (M + H)⁺ |
|---|---|---|---|---|
| 457 | (3S)-7-((S)-4-acryloyl-2-methylpiperazin-1-yl)-9-chloro-10-(5-chloro-2,4-difluorophenyl)-3-((4-(2,2-difluoroethyl)piperazin-1-yl)methyl)-2H-[1,4]thiazino[2,3,4-ij]quinazolin-5(3H)-one | 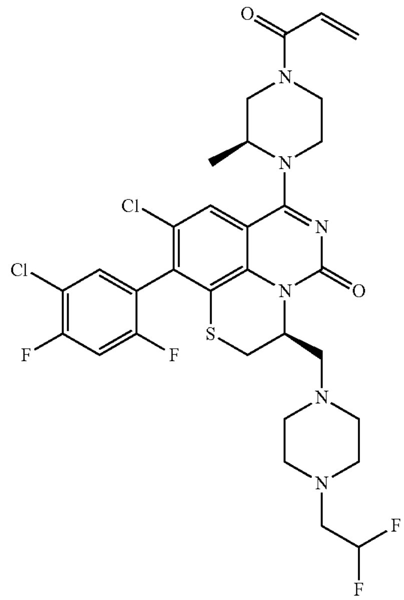 [SMILES: C=CC(=O)N1CCN(c2nc(=O)n3c4c(c(-c5cc(Cl)c(F)cc5F)c(Cl)cc24)SC[C@@H]3CN2CCN(CC(F)F)CC2)[C@@H](C)C1] | ¹H NMR (400 MHz, CDCl₃) δ 7.48 (s, 1H), 7.31-7.28 (m, 1H), 7.10 (q, J = 8.4 Hz, 1H), 6.62-6.51 (m, 1H), 6.37 (d, J = 16.8 Hz, 1H), 6.00-5.72 (m, 2H), 5.40-5.29 (m, 1H), 4.80-4.70 (m, 1H), 4.64-4.61 (m, 0.5H), 4.51-4.29 (m, 1H), 4.23-3.16 (m, 0.5H), 4.04-3.37 (m, 5H), 3.18-2.92 (m, 3H), 2.76-2.44 (m, 10H), 1.49-1.44 (m, 3H). | 699.2 |
| 458 | (3S)-7-((S)-4-acryloyl-2-methylpiperazin-1-yl)-9-chloro-10-(5-chloro-2,4-difluorophenyl)-3-((4-cyclopropylpiperazin-1-yl)methyl)-2H-[1,4]thiazino[2,3,4-ij]quinazolin-5(3H)-one | 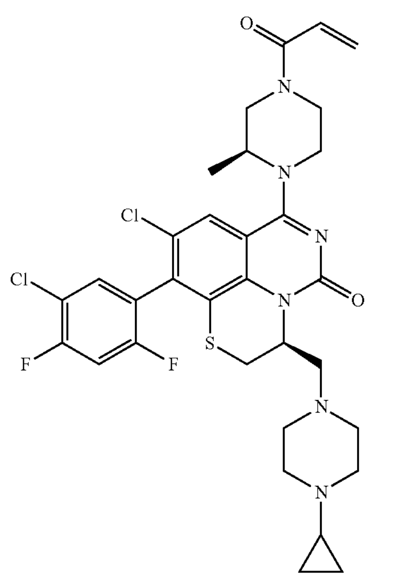 [SMILES: C=CC(=O)N1CCN(c2nc(=O)n3c4c(c(-c5cc(Cl)c(F)cc5F)c(Cl)cc24)SC[C@@H]3CN2CCN(C3CC3)CC2)[C@@H](C)C1] | ¹H NMR (400 MHz, CDCl₃) δ 7.48 (s, 1H), 7.33-7.28 (m, 1H), 7.13-7.06 (m, 1H), 6.67-6.48 (m, 1H), 6.37 (d, J = 20.4 Hz, 1H), 5.77 (d, J = 17.6 Hz, 1H), 5.43-5.29 (m, 1H), 4.75-4.67 (m, 1H), 4.57-3.94 (m, 3H), 3.82-3.40 (m, 4H), 3.10-3.01 (m, 2H), 2.84-2.49 (m, 9H), 1.50-1.42 (m, 3H), 1.27-1.26 (m, 1H), 0.46-0.44 (m, 4H). | 675.2 |

TABLE 8-continued

Table of Thiomorpholines

| Ex. # | Name | Structure | ¹H NMR | MS (M + H)⁺ |
|---|---|---|---|---|
| 459 | (3S)-7-((2S,5R)-4-acryloyl-2,5-dimethylpiperazin-1-yl)-9-chloro-3-((3-(trifluoromethyl)-5,6-dihydro-[1,2,4]triazolo[4,3-a]pyrazin-7(8H)-yl)methyl)-10-(2,4,5-trifluorophenyl)-2H-[1,4]thiazino[2,3,4-ij]quinazolin-5(3H)-one | 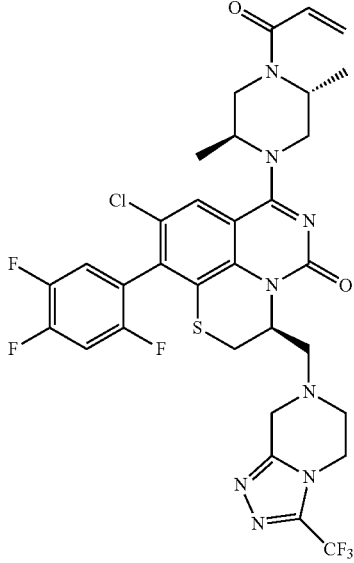 [SMILES: C=CC(=O)N1C[C@H](C)N(c2nc(=O)n3c4c(c(-c5cc(F)c(F)cc5F)c(Cl)cc24)SC[C@@H]3CN2CCn3c(nnc3C(F)(F)F)C2)C[C@H]1C] | ¹H NMR (400 MHz, CDCl₃) δ 7.59-7.53 (m, 1H), 7.16-7.03 (m, 2H), 6.61-6.48 (m, 1H), 6.40-6.32 (m, 1H), 5.79-5.75 (m, 1H), 5.53-5.43 (brs, 1H), 5.04-4.96 (brs, 0.5 H), 4.83-4.71 (m, 1H), 4.36-4.03 (m, 6H), 3.75-3.66 (m, 2H), 3.33-3.03 (m, 5.5H), 2.94-2.88 (m, 1H), 1.46-1.36 (m, 3H), 1.32-1.26 (m, 3H) | 739.2 |
| 460 | 3S)-3-(2-oxa-7-azaspiro[3.5]nonan-7-ylmethyl)-7-((2S,5R)-4-acryloyl-2,5-dimethylpiperazin-1-yl)-9-chloro-10-(2,4,5-trifluorophenyl)-2H-[1,4]thiazino[2,3,4-ij]quinazolin-5(3H)-one | 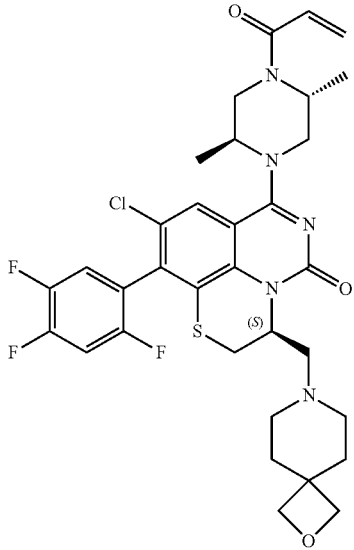 | ¹H NMR (400 MHz, CDCl₃) δ 7.53 (s, 1H), 7.14-7.04 (m, 2H), 6.66-6.50 (m, 1H), 6.37 (t, J = 14.4 Hz, 1H), 5.77 (t, J = 7.6 Hz, 1H), 5.42-5.37 (m, 1H), 5.00-4.82 (m, 1H), 5.70-5.68 (m, 0.5H), 4.38-4.31 (m, 5H), 4.21-3.96 (m, 1H), 3.81-3.65 (m, 2.5H), 3.37-3.30 (m, 1H), 3.04-3.01 (m, 1H), 2.73-2.35 (m, 6H), 1.84-1.79 (m, 4H), 1.39-1.30 (m, 6H). | 674.3 |

TABLE 8-continued

Table of Thiomorpholines

| Ex. # | Name | Structure | ¹H NMR | MS (M + H)⁺ |
|---|---|---|---|---|
| 461 | (3S)-7-((2S,5R)-4-acryloyl-2,5-dimethylpiperazin-1-yl)-9-chloro-10-(5-chloro-2,4-difluorophenyl)-3-((1-(2,2-difluoroethyl)piperidin-4-yl)methyl)-2H-[1,4]thiazino[2,3,4-ij]quinazolin-5(3H)-one | 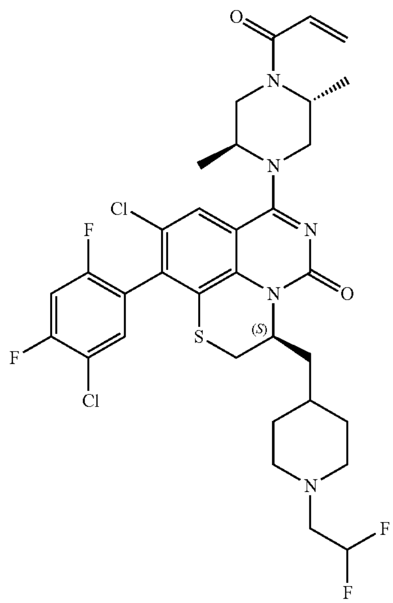 | ¹H NMR (400 MHz, CDCl₃) δ 7.52-7.51 (m, 1H), 7.34-7.30 (m, 1H), 7.12-7.07 (m, 1H), 6.61-6.51 (m, 1H), 6.37 (t, J = 13.6 Hz, 1H), 5.99-5.70 (m, 1H), 5.78-5.75 (m, 1H), 5.53-5.50 (m, 1H), 4.97-4.90 (m, 1.5H), 4.75-4.73 (m, 0.5H), 4.38-4.29 (m, 1H), 4.20-4.17 (m, 0.5H), 3.98-3.81 (m, 2H), 3.74-3.65 (m, 1H), 3.40-3.38 (m, 0.5H), 3.18-3.12 (m, 1H), 2.97-2.88 (m, 3H), 2.72-2.63 (m, 2H), 2.18-2.08 (m, 2H), 1.85-1.83 (m, 1H), 1.71-1.65 (m, 2H), 1.40-1.38 (m, 5H), 1.30-1.25 (m, 4H). | 714.2 |
| 462 | (S)-3-(2-oxa-7-azaspiro[3.5]nonan-7-ylmethyl)-7-((S)-4-acryloyl-2-methylpiperazin-1-yl)-9-chloro-10-(4-fluorophenyl)-2H-[1,4]thiazino[2,3,4-ij]quinazolin-5(3H)-one | 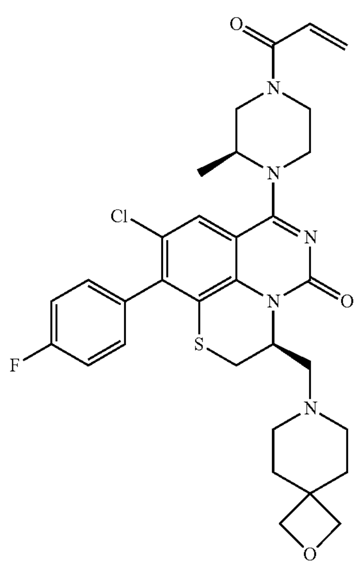 [SMILES: C=CC(=O)N1CCN(c2nc(=O)n3c4c(c(-c5ccc(F)cc5)c(Cl)cc24)SC[C@@H]3CN2CCC3(CC2)COC3)[C@@H](C)C1] | ¹H NMR (400 MHz, CDCl₃) δ 7.48 (s, 1H), 7.23-7.18 (m, 4H), 6.62-6.52 (m, 1H), 6.36 (d, J = 18.0 Hz, 1H), 5.77 (d, J = 10.8 Hz, 1H), 5.29-5.27 (m, 1H), 4.74-4.70 (m, 1H), 4.64 (m, 0.5H), 4.54-4.38 (m, 5H), 4.21-4.19 (m, 0.5H), 3.96-3.95 (m, 0.5H), 3.81-3.77 (m, 0.5H), 3.62-3.49 (m, 2H), 3.37-3.36 (m, 1H), 3.12-3.07 (m, 1H), 3.00-2.94 (m, 1H), 2.79-2.73 (m, 1H), 2.65-2.55 (m, 2H), 2.49-2.47 (m, 1H), 2.43-2.35 (m, 2H), 1.88-1.75 (m, 4H), 1.48-1.44 (m, 3H). | 624.3 |

TABLE 8-continued

Table of Thiomorpholines

| Ex. # | Name | Structure | ¹H NMR | MS (M + H)⁺ |
|---|---|---|---|---|
| 463 | (3S)-7-((S)-4-acryloyl-2-methylpiperazin-1-yl)-9-chloro-3-((3-(trifluoromethyl)-5,6-dihydro-[1,2,4]triazolo[4,3-a]pyrazin-7(8H)-yl)methyl)-10-(2,4,5-trifluorophenyl)-2H-[1,4]thiazino[2,3,4-ij]quinazolin-5(3H)-one | 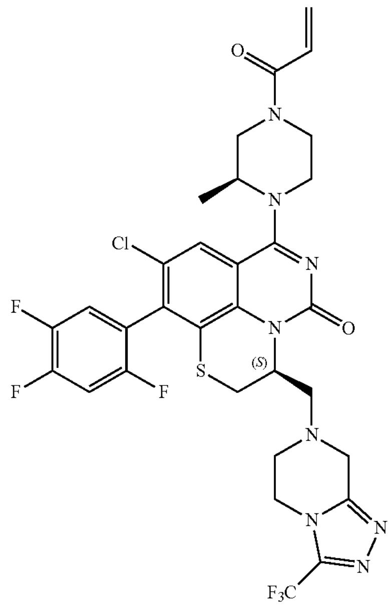 | ¹H NMR (400 MHz, CDCl₃) δ 7.51 (s, 1H), 7.15-7.04 (m, 2H), 6.63-6.50 (m, 1H), 6.39-6.35 (m, 1H), 5.78 (d, J = 10.8 Hz, 1H), 5.37-5.35 (m, 1H), 4.70-4.68 (m, 1H), 4.55-4.27 (m, 3H), 4.18-3.78 (m, 4H), 3.51-3.77 (m, 4H), 3.18-2.90 (m, 5H), 1.52-1.44 (m, 3H). | 725.2 |
| 466 | (3R)-7-((S)-4-acryloyl-2-methylpiperazin-1-yl)-9-chloro-3-((methoxymethoxy)methyl)-10-(2,4,5-trifluorophenyl)-2H-[1,4]thiazino[2,3,4-ij]quinazolin-5(3H)-one | 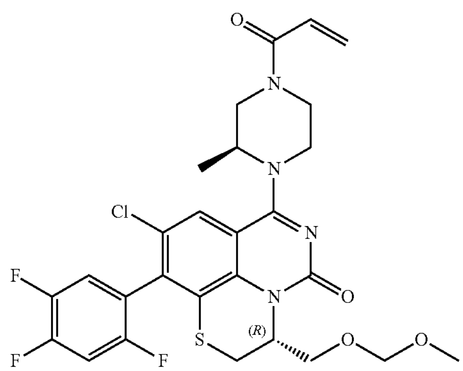 | ¹H NMR (400 MHz, CDCl₃) δ 7.52-7.50 (m, 1H), 7.15-7.06 (m, 2H), 6.59-6.53 (m, 1H), 6.38 (d, J = 16.4 Hz, 1H), 5.78 (d, J = 10.0 Hz, 1H), 5.49-5.45 (m, 1H), 4.97-4.94 (m, 0.5H), 4.65 (dt, J = 16.0 Hz, 8.0 Hz, 3H), 4.52-4.46 (m, 0.5H), 4.10-3.96 (m, 1.5H), 3.82-3.60 (m, 4.5H), 3.45-3.35 (m, 4H), 3.26-3.19 (m, 0.5H), 3.19-3.10 (m, 1H), 2.92-2.87 (m, 0.5H), 1.35 (d, J = 6.4 Hz, 3H). | 595.1 |
| 467 | (3S)-7-((2S,5R)-4-acryloyl-2,5-dimethylpiperazin-1-yl)-9-chloro-10-(5-chloro-2,4-difluorophenyl)-3-((1-cyclopropylpiperidin-4-yl)methyl)-2H-[1,4]thiazino[2,3,4-ij]quinazolin-5(3H)-one | 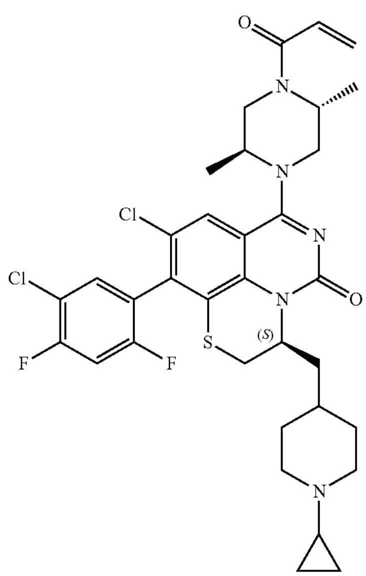 | ¹H NMR (400 MHz, CDCl₃) δ 7.51-7.50 (m, 1H), 7.34-7.28 (m, 1H), 7.12-7.07 (m, 1H), 6.66-6.51 (m, 1H), 6.37 (t, J = 14.4 Hz, 1H), 5.78 (d, J = 10.0 Hz, 1H), 5.51-5.49 (m, 1H), 4.96-4.92 (m, 1H), 4.76-4.75 (m, 0.5H), 4.37-4.30 (m, 0.7H), 4.22-4.13 (m, 0.5H), 3.98-3.65 (m, 3H), 3.42-3.37 (m, 0.3H), 3.16-3.12 (m, 1H), 2.98-2.96 (m, 3H), 2.14-2.04 (m, 2H), 1.84-1.82 (m, 1H), 1.51-1.49 (m, 2H), 1.39 (d, J = 6.4 Hz, 6H), 1.29-1.25 (m, 5H), 0.41-0.37 (m, 4H). | 688.2 |

TABLE 8-continued

Table of Thiomorpholines

| Ex. # | Name | Structure | ¹H NMR | MS (M + H)⁺ |
|---|---|---|---|---|
| 468 | (3S)-7-((2S,5R)-4-acryloyl-2,5-dimethylpiperazin-1-yl)-9-chloro-10-(2,4-difluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 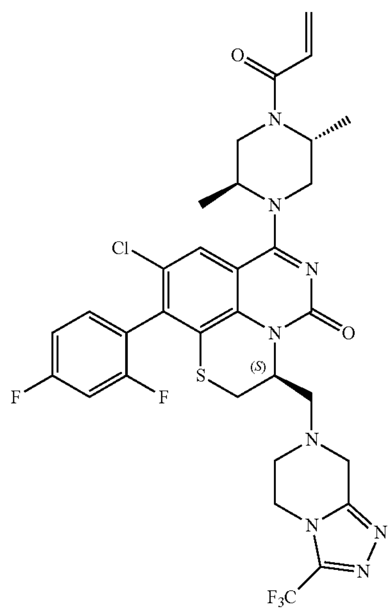 | ¹H NMR (400 MHz, CDCl₃) δ 7.59-7.56 (m, 1H), 7.26-7.18 (m, 1H), 7.08-6.98 (m, 2H), 6.64-6.49 (m, 1H), 6.40-6.33 (m, 1H), 5.79-5.75 (m, 1H), 5.44-5.42 (m, 1H), 5.02-5.00 (m, 0.5H), 4.80-4.72 (m, 1H), 4.39-3.96 (m, 6.5H), 3.75-3.65 (m, 2H), 3.30-3.26 (m, 2H), 3.18-3.11 (m, 2H), 3.08-3.02 (m, 1H), 2.92-2.89 (m, 1H), 1.46-1.43 (m, 3H), 1.33-1.27 (m, 3H). | 721.3 |
| 469 | (3S)-3-(2-oxa-7-azaspiro[3.5]nonan-7-ylmethyl)-7-((S)-4-acryloyl-2-methylpiperazin-1-yl)-9-chloro-10-(2,4,5-trifluorophenyl)-2H-[1,4]thiazino[2,3,4-ij]quinazolin-5(3H)-one | 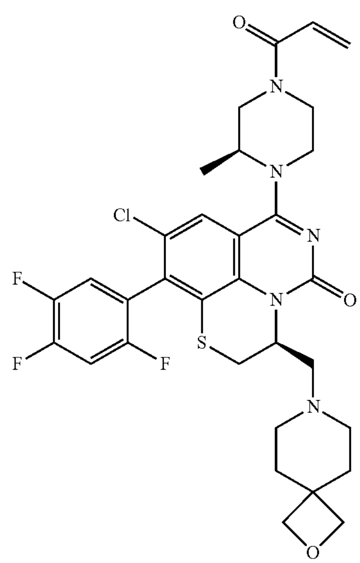 [SMILES: C=CC(=O)N1CCN(c2nc(=O)n3c4c(c(-c5cc(F)c(F)cc5F)c(Cl)cc24)SC[C@@H]3CN2CCC3(CC2)COC3)[C@@H](C)C1] | ¹H NMR (400 MHz, CDCl₃) δ 7.47 (s, 1H), 7.14-7.04 (m, 2H), 6.61-6.51 (m, 1H), 6.39-6.34 (m, 1H), 5.77 (d, J = 11.6 Hz, 1H), 5.37-5.26 (m, 1H), 4.96-4.94 (m, 1H), 4.56-4.34 (m, 5.5H), 4.21-4.19 (m, 0.5H), 3.97-3.93 (m, 0.5H), 3.81-3.78 (m, 0.5H), 3.62-3.41 (m, 3H), 3.05-2.99 (m, 2H), 2.78-2.70 (m, 1H), 2.60-2.59 (m, 2H), 2.48-2.35 (m, 3H), 1.86-1.80 (m, 4H), 1.48-1.44 (m, 3H). | 660.2 |
| 470 | (3R)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 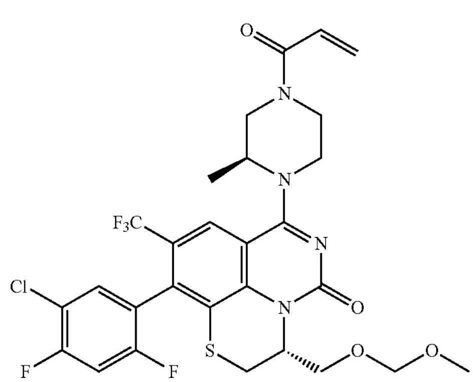 [SMILES: C=CC(=O)N1CCN(c2nc(=O)n3c4c(c(-c5cc(Cl)c(F)cc5F)c(C(F)(F)F)cc24)SC[C@H]3COCOC)[C@@H](C)C1] | ¹H NMR (400 MHz, CDCl₃) δ 7.78-7.75 (m, 1H), 7.29-7.26 (m, 1H), 7.10 9-7.04 (m, 1H), 6.59-6.53 (m, 1H), 6.40-6.36 (m, 1H), 5.79 (dd, J = 10.0 Hz, 1.2 Hz, 1H), 5.52-5.44 (m, 1H), 5.05-4.95 (m, 0.5H), 4.99-4.62 (m, 3H), 4.11-4.00 (m, 1H), 3.85-3.68 (m, 3H), 3.67-3.45 (m, 1H), 3.41-3.05 (m, 5H), 3.10-3.05 (m, 1H), 2.90-2.86 (m, 0.5H), 1.38 (d, J = 6.8 Hz, 3H). | 645.1 |

TABLE 8-continued

Table of Thiomorpholines

| Ex. # | Name | Structure | ¹H NMR | MS (M + H)⁺ |
|---|---|---|---|---|
| 471 | (3R)-7-((S)-4-acryloyl-2-methylpiperazin-1-yl)-3-((methoxymethoxy)methyl)-9-(trifluoromethyl)-10-(2,4,5-trifluorophenyl)-2H-[1,4]thiazino[2,3,4-ij]quinazolin-5(3H)-one | 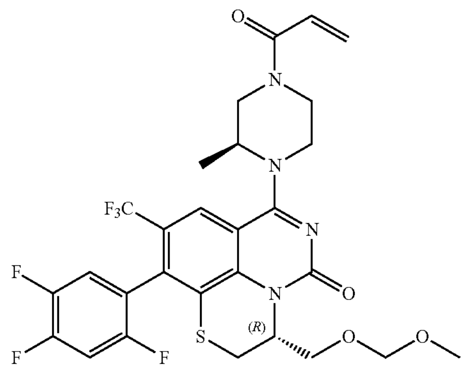 | ¹H NMR (400 MHz, CDCl₃) δ 7.76 (s, 1H), 7.12-7.03 (m, 2H), 6.59-6.53 (m, 1H), 6.38 (dd, J = 16.8, 1.6 Hz, 1H), 5.79 (dd, J = 10.4, 1.2 Hz, 1H), 5.79 (brs, 1H), 5.00 (brs, 0.5H), 4.81-4.62 (m, 3H), 4.50-4.47 (m, 0.5H), 4.14-4.00 (m, 1.5H), 3.89-3.64 (m, 4.5H), 3.42-3.35 (m, 4.5H), 3.10-3.04 (m, 1H), 2.92-2.86 (m, 0.5H), 1.38 (d, J = 6.8 Hz, 3H). | 629.2 |
| 472 | (3S)-3-(2-oxa-7-azaspiro[3.5]nonan-7-ylmethyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 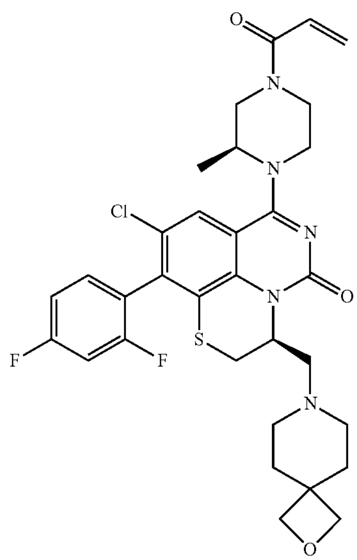 [SMILES: C=CC(=O)N1CCN(c2nc(=O)n3c4c(c(-c5ccc(F)cc5F)c(Cl)cc24)SC[C@@H]3CN2CCC3(CC2)COC3)[C@@H](C)C1] | ¹H NMR (400 MHz, CDCl₃) δ 7.48 (s, 1H), 7.21 (q, J = 27.6 Hz, 1H), 7.07-6.95 (m, 2H), 6.66-6.50 (m, 1H), 6.37 (d, J = 18.4 Hz, 1H), 5.77 (d, J = 10.0 Hz, 1H), 5.38-5.26 (m, 1H), 4.73-4.69 (m, 1H), 4.62-4.59 (m, 0.5H), 4.38-4.35 (m, 5H), 4.21-4.17 (m, 0.5H), 3.98-3.78 (m, 1H), 3.65-3.54 (m, 2H), 3.50-3.03 (m, 4H), 2.81-2.67 (m, 1H), 2.59-2.50 (m, 2H), 2.48-2.30 (m, 2H), 2.00-1.71 (m, 4H), 1.49-1.39 (m, 3H). | 642.2 |
| 473 | (S)-3-(2-oxa-7-azaspiro[3.5]nonan-7-ylmethyl)-7-((2S,5R)-4-acryloyl-2,5-dimethylpiperazin-1-yl)-9-chloro-10-(4-fluorophenyl)-2H-[1,4]thiazino[2,3,4-ij]quinazolin-5(3H)-one | 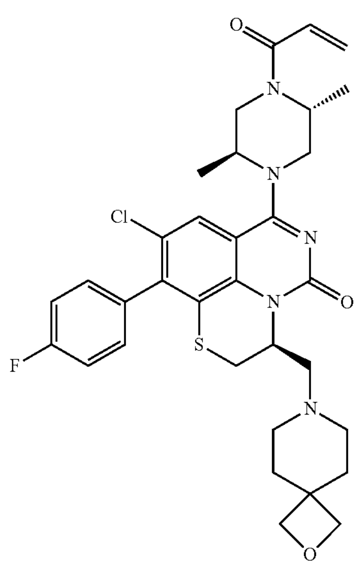 [SMILES: C=CC(=O)N1C[C@H](C)N(c2nc(=O)n3c4c(c(-c5ccc(F)cc5)c(Cl)cc24)SC[C@@H]3CN2CCC3(CC2)COC3)C[C@H]1C] | ¹H NMR (400 MHz, CDCl₃) δ 7.53 (s, 1H), 7.23-7.19 (m, 4H), 6.66-6.50 (m, 1H), 6.37 (t, J = 14.4, 1H), 5.77 (t, J = 8.4 Hz, 1H), 5.44-5.29 (m, 1H), 4.98-4.66 (m, 2H), 4.55-4.46 (m, 1H), 4.38 (s, 4H), 4.32-4.19 (m, 1H), 3.99 (d, J = 13.6 Hz, 1H), 3.81-3.60 (m, 2H), 3.38-3.25 (m, 1H), 2.96 (d, J = 12.4 Hz, 1H), 2.76-2.37 (m, 6H), 1.84-1.80 (m, 3H), 1.39-1.26 (m, 6H). | 638.3 |

TABLE 8-continued

Table of Thiomorpholines

| Ex. # | Name | Structure | ¹H NMR | MS (M + H)⁺ |
|---|---|---|---|---|
| 474 | (3S)-7-((S)-4-acryloyl-2-methylpiperazin-1-yl)-9-chloro-10-(5-fluoroquinolin-8-yl)-3-(methoxymethyl)-2,3-dihydro-5H-[1,4]thiazino[2,3,4-ij]quinazolin-5-one | 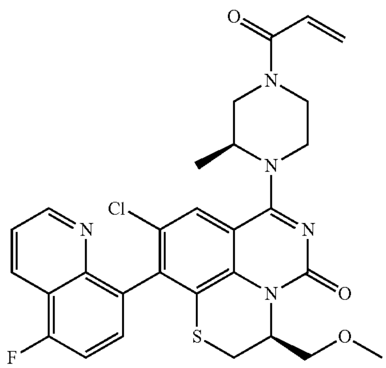 [SMILES: C=CC(=O)N1CCN(c2nc(=O)n3c4c(c(-c5ccc(F)c6cccnc56)c(Cl)cc24)SC[C@@H]3COC)[C@@H](C)C1] | ¹H NMR (400 MHz, MeOH-d₄) δ 8.83 (dd, J = 4.3, 1.7 Hz, 1H), 8.66 (dd, J = 8.5, 1.8 Hz, 1H), 7.72 (d, J = 2.9 Hz, 1H), 7.66 (td, J = 8.6, 5.1 Hz, 2H), 7.56-7.47 (m, 1H), 6.83 (ddd, J = 27.5, 16.7, 10.5 Hz, 1H), 6.29 (dd, J = 16.8, 7.5 Hz, 1H), 5.82 (d, J = 9.8 Hz, 1H), 5.41-5.25 (m, 1H), 4.86-4.69 (m, 2H), 4.64-4.32 (m, 2H), 4.24-3.97 (m, 1H), 3.76-3.46 (m, 4H), 3.33 (s, 3H), 3.27-3.06 (m, 3H), 1.48 (dd, J = 7.0, 3.3 Hz, 3H) | 580.2 |
| 475 | (3S)-7-((2S,5R)-4-acryloyl-2,5-dimethylpiperazin-1-yl)-9-chloro-3-((1-cyclopropylpiperidin-4-yl)methyl)-10-(2,4,5-trifluorophenyl)-2H-[1,4]thiazino[2,3,4-ij]quinazolin-5(3H)-one | 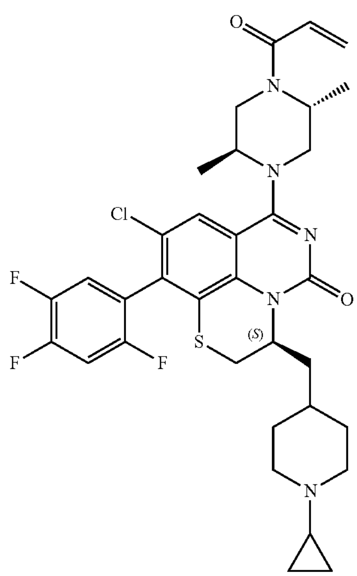 | ¹H NMR (400 MHz, CDCl₃) δ 7.51-7.50 (m, 1H), 7.14-7.07 (m, 2H), 6.65-6.51 (m, 1H), 6.37 (t, J = 15.6 Hz, 1H), 5.78-5.75 (m, 1H), 5.54-5.50 (m, 1H), 4.96-4.90 (m, 1H), 4.76-4.74 (m, 0.5H), 4.38-4.30 (m, 1H), 4.20 (d, J = 10.4 Hz, 0.5H), 3.98-3.94 (m, 0.6H), 3.85-3.81 (m, 1H), 3.75-3.64 (m, 1H), 3.43-3.38 (m, 0.4H), 3.17-3.12 (m, 1H), 2.97-2.95 (m, 3H), 2.14-2.05 (m, 2H), 2.05-1.82 (m, 1H), 1.51-1.50 (m, 1H), 1.39-1.37 (m, 5H), 1.29-1.25 (m, 7H), 0.42-0.37 (m, 4H). | 672.3 |

TABLE 8-continued

Table of Thiomorpholines

| Ex. # | Name | Structure | ¹H NMR | MS (M + H)⁺ |
|---|---|---|---|---|
| 476 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4,5-trifluorophenyl)-2H-[1,4]thiazino[2,3,4-ij]quinazolin-5(3H)-one | 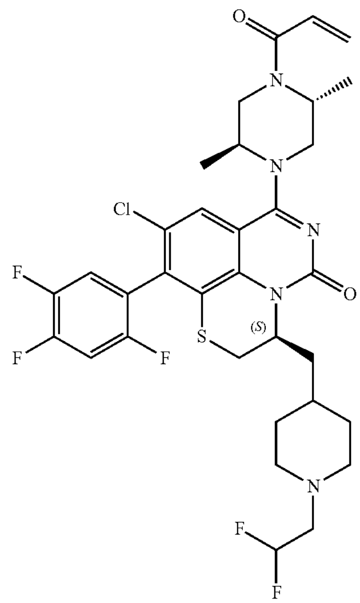 | ¹H NMR (400 MHz, CDCl₃) δ 7.52 (s, 1H), 7.14-7.06 (m, 2H), 6.65-6.51 (m, 1H), 6.37 (t, J = 15.2 Hz, 1H), 5.98-5.70 (m, 2H), 5.53-5.51 (m, 1H), 4.98-4.89 (m, 1H), 4.75-4.73 (s, 0.5H), 4.37-4.29 (m, 1H), 4.22-4.19 (m, 0.5H), 3.99-3.95 (m, 0.5H), 3.84 (d, J = 13.2 Hz, 1H), 3.73-3.68 (m, 1H), 3.40-3.36 (m, 0.5H), 3.17-3.12 (m, 1H), 2.97-2.88 (m, 3H), 2.72-2.64 (m, 2H), 2.18-2.08 (m, 2H), 1.85-1.81 (m, 1H), 1.68-1.62 (m, 2H), 1.39 (d, J = 5.6 Hz, 6H), 1.27 (t, J = 7.6 Hz, 4H). | 696.2 |
| 477 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 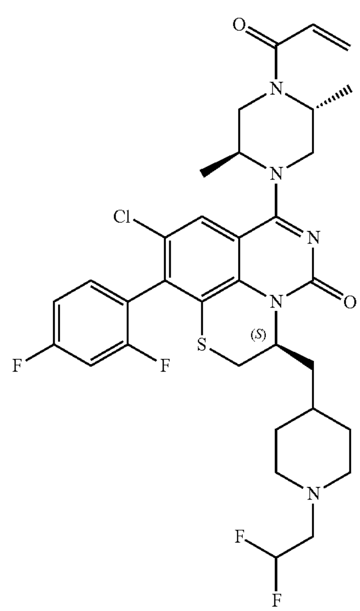 | ¹H NMR (400 MHz, CDCl₃) δ 7.52 (s, 1H), 7.24-7.20 (m, 1H), 7.05-6.96 (m, 2H), 6.65-6.51 (m, 1H), 6.37 (t, J = 13.6 Hz, 1H), 5.99-5.69 (m, 2H), 5.52-5.50 (m, 1H), 4.98-4.91 (m, 1H), 4.76-4.74 (m, 0.5H), 4.38-4.30 (m, 1H), 4.23-4.19 (m, 0.5H), 4.00-3.97 (m, 0.5H), 3.82-3.64 (m, 2H), 3.41-3.37 (m, 0.5H), 3.15-3.11 (m, 1H), 2.94-2.87 (m, 3H), 2.68 (t, J = 14.8 Hz, 2H), 2.18-2.08 (m, 2H), 1.86-1.83 (m, 1H), 1.70-1.66 (m, 2H), 1.38-1.36 (m, 6H), 1.28 (t, J = 7.6 Hz, 4H). | 678.2 |

TABLE 8-continued

Table of Thiomorpholines

| Ex. # | Name | Structure | ¹H NMR | MS (M + H)⁺ |
|---|---|---|---|---|
| 478 | (3S)-7-((2S,5R)-4-acryloyl-2,5-dimethylpiperazin-1-yl)-9-chloro-3-((1-cyclopropylpiperidin-4-yl)methyl)-10-(2,4-difluorophenyl)-2H-[1,4]thiazino[2,3,4-ij]quinazolin-5(3H)-one | 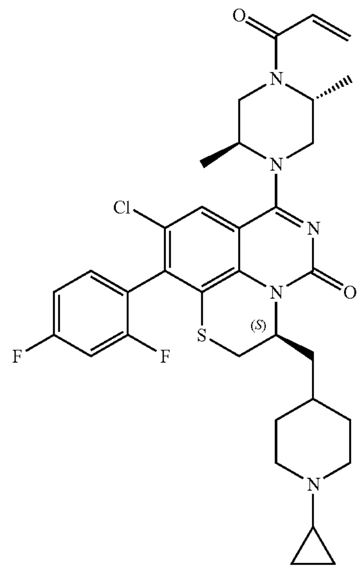 | ¹H NMR (400 MHz, CDCl₃) δ 7.51 (s, 1H), 7.26-7.20 (m, 1H), 7.04-6.96 (m, 2H), 6.65-6.51 (m, 1H), 6.36 (t, J = 15.2 Hz, 1H), 5.77 (d, J = 10.4 Hz, 1H), 5.53-5.50 (m, 1H), 4.96-4.92 (m, 1H), 4.76-4.74 (m, 0.5H), 4.38-4.30 (m, 1H), 4.21-4.18 (m, 0.5H), 3.99-3.96 (m, 0.6H), 3.83-3.63 (m, 2H), 3.42-3.38 (m, 0.4H), 3.16-3.11 (m, 1H), 2.99-2.92 (m, 3H), 2.12-2.04 (m, 2H), 1.84-1.82 (m, 1H), 1.50-1.48 (m, 2H), 1.37-1.35 (m, 5H), 1.29-1.26 (m, 6H), 0.41-0.37 (m, 4H). | 654.2 |
| 479 | (3R)-7-((S)-4-acryloyl-2-methylpiperazin-1-yl)-9-chloro-10-(2,4-difluorophenyl)-3-((methoxymethoxy)methyl)-2H-[1,4]thiazino[2,3,4-ij]quinazolin-5(3H)-one | 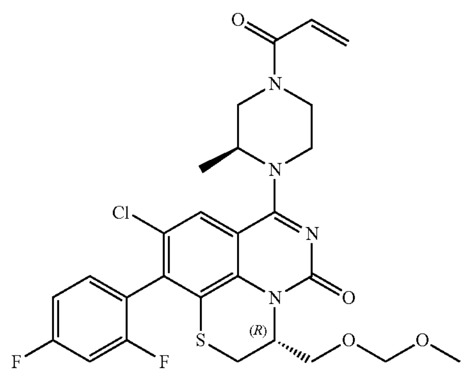 | ¹H NMR (400 MHz, CDCl₃) δ 7.52-7.50 (m, 1H), 7.22 (m, 1H), 7.07-6.95 (m, 2H), 6.60-6.53 (m, 1H), 6.37 (dd, J = 16.8, 1.2 Hz, 1H), 5.77 (d, J = 10.4 Hz, 1H), 5.50-5.40 (m, 1H), 5.10-4.85 (m, 0.5H), 4.82-4.62 (m, 3H), 4.52-4.46 (m, 0.5H), 4.10-3.99 (m, 1.5H), 3.83-3.57 (m, 4H), 3.49-3.35 (m, 4.5H), 3.30-3.20 (m, 0.4H), 3.07 (d, J = 13.6 Hz, 1H), 2.95-2.85 (m, 0.6H), 1.34 (d, J = 6.4 Hz, 3H). | 577.2 |
| 480 | (3S)-7-((S)-4-acryloyl-2-methylpiperazin-1-yl)-9-chloro-3-((4-(2,2-difluoroethyl)piperazin-1-yl)methyl)-10-(2,4,5-trifluorophenyl)-2H-[1,4]thiazino[2,3,4-ij]quinazolin-5(3H)-one | 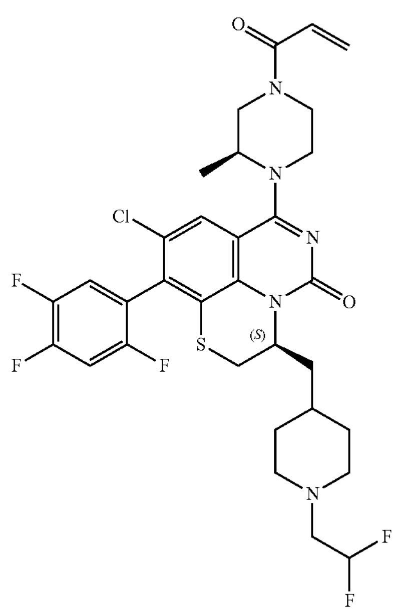 | ¹H NMR (400 MHz, CDCl₃) δ 7.48 (s, 1H), 7.14-7.04 (m, 2H), 6.62-6.51 (m, 1H), 6.37 (d, J = 16.8 Hz, 1H), 6.00-5.72 (m, 2H), 5.34-5.33 (m, 1H), 4.74-4.65 (m, 1H), 4.53-4.36 (m, 1.5H), 4.21-4.16 (m, 0.5H), 3.97-3.95 (m, 0.5H), 3.81-3.77 (m, 0.5H), 3.57-3.50 (m, 1.5H), 3.42 (d, J = 13.2 Hz ,1.5H), 3.04-3.01 (m, 2H), 2.87-2.67 (m, 5H), 2.55-2.53 (m, 7H), 1.48-1.44 (m, 3H). | 683.2 |

TABLE 8-continued

Table of Thiomorpholines

| Ex. # | Name | Structure | ¹H NMR | MS (M + H)⁺ |
|---|---|---|---|---|
| 481 | (S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2H-[1,4]thiazino[2,3,4-ij]quinazolin-5(3H)-one | 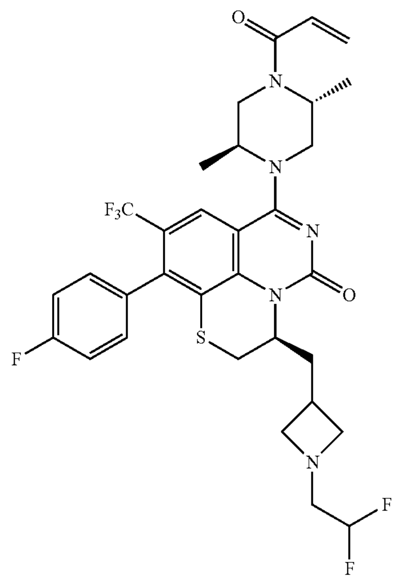 [SMILES: C=CC(=O)N1C[C@H](C)N(c2nc(=O)n3c4c(c(-c5ccc(F)cc5)c(C(F)(F)F)cc24)SC[C@@H]3CC2CN(CC(F)F)C2)C[C@H]1C] | ¹H NMR (400 MHz, CDCl₃) δ 7.84 (s, 1H), 7.26-7.25 (m, 1H), 7.21-7.17 (m, 3H), 6.67-6.51 (m, 1H), 6.38 (t, J = 15.6 Hz, 1H), 5.84-5.54 (m, 2H), 5.27-5.26 (m, 1H), 5.06-5.01 (m, 0.5H), 4.84-4.83 (m, 0.5H), 4.71-4.70 (m, 0.5H), 4.42-4.32 (m, 1.5H), 4.06-4.03 (m, 0.5H), 3.80-3.67 (m, 2H), 3.59-3.52 (m, 2H), 3.33-3.29 (m, 0.5H), 3.06-2.97 (m, 3H), 2.88-2.84 (m, 1H), 2.79-2.70 (m, 2H), 2.61-2.53 (m, 1H), 2.06 (t, J = 6.8 Hz, 1H), 1.47-1.38 (m, 6H). | 666.3 |
| 482 | (3S,10S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 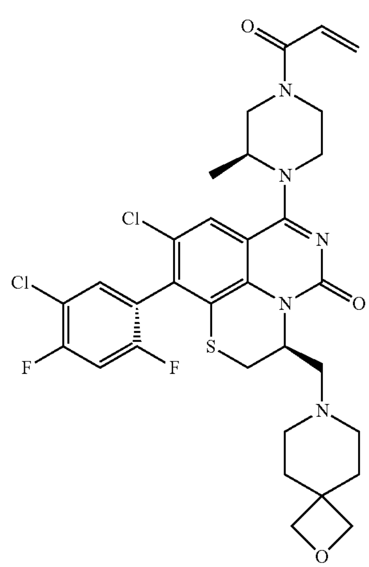 | ¹H NMR (400 MHz, CDCl₃) δ 7.48 (s, 1H), 7.29 (t, J = 3.2 Hz, 1H), 7.10 (t, J = 8.8 Hz, 1H), 6.66-6.51 (m, 1H), 6.37 (d, J = 18 Hz, 1H), 5.77 (d, J = 10.8 Hz, 1H), 5.36-5.27 (m, 1H), 4.70-4.66 (m, 1H), 4.54-4.19 (m, 6H), 3.99-3.78 (m, 1H), 3.62-3.38 (m, 3H), 3.08-2.99 (m, 2H), 2.78-2.34 (m, 6H), 1.93-1.78 (m, 4H), 1.48-1.45 (m, 3H). | 676.3 |

TABLE 8-continued

Table of Thiomorpholines

| Ex. # | Name | Structure | ¹H NMR | MS (M + H)⁺ |
|---|---|---|---|---|
| 483 | (3S,10R)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 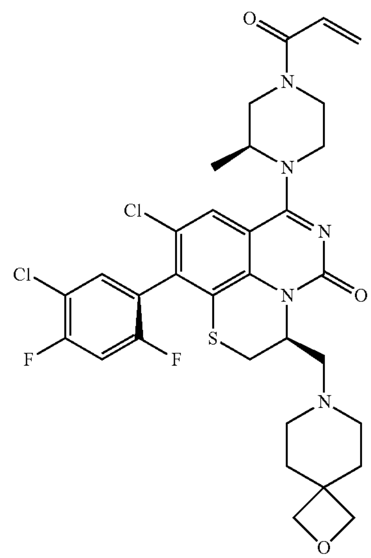 | ¹H NMR (400 MHz, CDCl₃) δ 7.48 (s, 1H), 7.29 (t, J = 8.4 Hz, 1H), 7.09 (t, J = 8.4 Hz, 1H), 6.66-6.50 (m, 1H), 6.37 (d, J = 16.4 Hz, 1H), 5.77 (d, J = 10.4 Hz, 1H), 5.40-5.29 (m, 1H), 4.73-4.66 (m, 1H), 4.56-4.52 (m, 0.5H), 4.46-4.38 (m, 5H), 4.23-4.18 (m, 0.5H), 3.98-3.78 (m, 1H), 3.63-3.42 (m, 3H), 3.05-3.02 (m, 2H), 2.74-2.35 (m, 6H), 1.92-1.83 (m, 4H), 1.50-1.42 (m, 3H). | 676.3 |
| 484 | (3S,10S)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 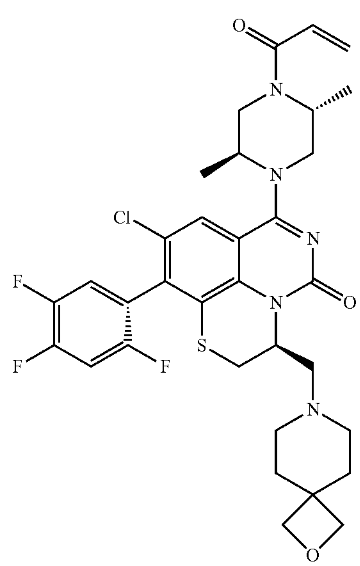 | ¹H NMR (400 MHz, CDCl₃) δ 7.52 (s, 1H), 7.14-7.05 (m, 2H), 6.66-6.50 (m, 1H), 6.37 (t, J = 14.4 Hz, 1H), 5.77 (t, J = 8.0 Hz, 1H), 5.42-5.34 (m, 1H), 5.00-4.83 (m, 1H), 4.73-4.68 (m, 0.5H), 4.38-4.23 (m, 5H), 4.01-3.98 (m, 0.5H), 3.81-3.65 (m, 2H), 3.38-3.31 (m, 1.5H), 3.16-3.00 (m, 1.5H), 2.74-2.38 (m, 6H), 1.85-1.80 (m, 4H), 1.41-1.38 (m, 6H). | 674.3 |

TABLE 8-continued

Table of Thiomorpholines

| Ex. # | Name | Structure | ¹H NMR | MS (M + H)⁺ |
|---|---|---|---|---|
| 485 | (3S,10R)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 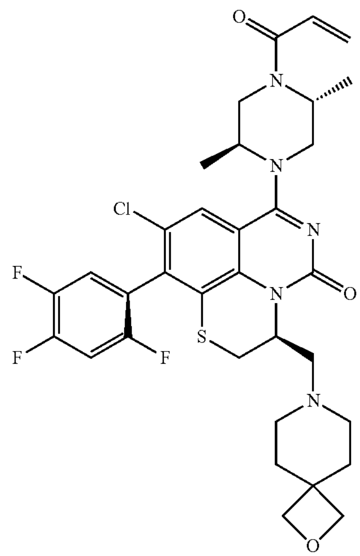 | ¹H NMR (400 MHz, CDCl₃) δ 7.53 (s, 1H), 7.13-7.04 (m, 2H), 6.66-6.50 (m, 1H), 6.37 (t, J = 14.0 Hz, 1H), 5.77 (t, J = 6.8 Hz, 1H), 5.42-5.36 (m, 1H), 4.99-4.84 (m, 1H), 4.75-4.70 (m, 0.5H), 4.37-4.23 (m, 5H), 4.01-3.98 (m, 0.5H), 3.81-3.65 (m, 2H), 3.39-3.31 (m, 1.5H), 3.16-3.01 (m, 1.5H), 2.72-2.35 (m, 6H), 1.85-1.81 (m, 4H), 1.41-1.32 (m, 6H). | 674.3 |
| 491 | (3S)-7-((2S,5R)-4-acryloyl-2,5-dimethylpiperazin-1-yl)-3-(methoxymethyl)-9-(trifluoromethyl)-10-(2,4,5-trifluorophenyl)-2H-[1,4]thiazino[2,3,4-ij]quinazolin-5(3H)-one | 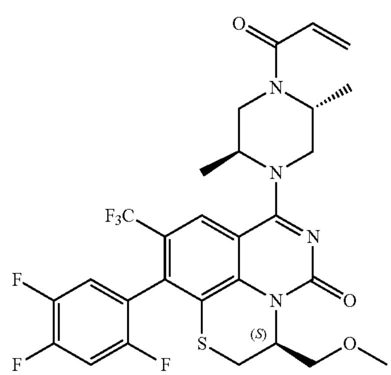 | ¹H NMR (400 MHz, CDCl₃) δ 7.86-7.83 (m, 1H), 7.11-7.02 (m, 2H), 6.66-6.50 (m, 1H), 6.37 (t, J = 14.4 Hz, 1H), 5.78 (t, J = 8.4 Hz, 1H), 5.43-5.39 (m, 1H), 5.07-5.04 (m, 0.6H), 4.80-4.66 (m, 1H), 4.43-4.33 (m, 1.4H), 4.13-4.07 (m, 0.5H), 3.75-3.62 (m, 4H), 3.40-3.34 (m, 4H), 3.26-3.21 (m, 0.5H), 3.05-3.02 (m, 1H), 1.49-1.41 (m, 6H). | 613.2 |
| 492 | (3S)-7-((2S,5R)-4-acryloyl-2,5-dimethylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one | 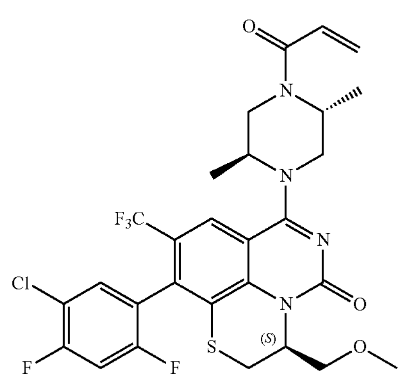 | ¹H NMR (400 MHz, CDCl₃) δ 7.86-7.83 (m, 1H), 7.30-7.28 (m, 1H), 7.07 (t, J = 8.8 Hz, 1H), 6.66-6.50 (m, 1H), 6.37 (t, J = 14.4 Hz, 1H), 5.78 (t, J = 8.8 Hz, 1H), 5.45-5.41 (m, 1H), 5.08-5.04 (m, 0.6H), 4.79-4.67 (m, 1H), 4.44-4.33 (m, 1.4H), 4.12-4.06 (m, 0.5H), 3.72-3.62 (m, 4H), 3.41-3.34 (m, 4H), 3.27-3.20 (m, 0.5H), 3.05-3.02 (m, 1H), 1.49-1.40 (m, 6H). | 629.2 |

TABLE 8-continued

Table of Thiomorpholines

| Ex. # | Name | Structure | ¹H NMR | MS (M + H)⁺ |
|---|---|---|---|---|
| 493 | (3S)-7-((2S,5R)-4-acryloyl-2,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 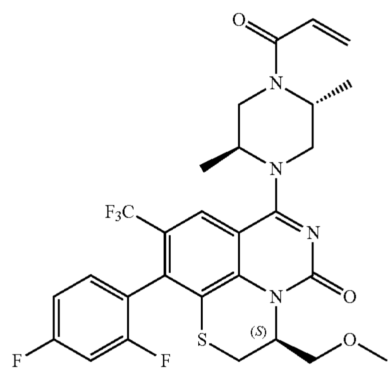 | ¹H NMR (400 MHz, CDCl₃) δ 7.86-7.83 (m, 1H), 7.22-7.13 (m, 1H), 7.05-6.94 (m, 2H), 6.67-6.50 (m, 1H), 6.37 (t, J = 14.8 Hz, 1H), 5.77 (t, J = 8.8 Hz , 1H), 5.45-5.39 (m, 1H), 5.07-5.05 (m, 0.6H), 4.81-4.68 (m, 1H), 4.44-4.34 (m, 1.4H), 4.15-4.07 (m, 0.5H), 3.76-3.60 (m, 4H), 3.42-3.26 (m, 4.5H), 3.05-3.00 (m, 1H), 1.49-1.41 (m, 6H). | 595.2 |
| 494 | (3S)-7-((2S,5R)-4-acryloyl-2,5-dimethylpiperazin-1-yl)-9-chloro-10-(2,4-difluorophenyl)-3-(methoxymethyl)-2H-[1,4]thiazino[2,3,4-ij]quinazolin-5(3H)-one | 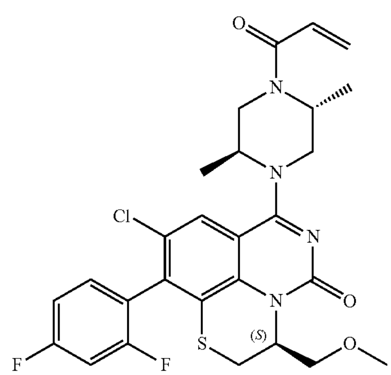 | ¹H NMR (400 MHz, CDCl₃) δ 7.56 (s, 1H), 7.24-7.17 (m, 1H), 7.07-6.98 (m, 2H), 6.67-6.52 (m, 1H), 6.37 (t, J = 14.4 Hz, 1H), 5.79-5.75 (m, 1H), 5.52-5.46 (m, 1H), 5.10-5.02 (m, 0.6H), 4.84-4.71 (m, 1H), 4.40-4.32 (m, 1.4H), 4.08-4.02 (m, 0.6H), 3.79-3.55 (m, 4H), 3.49 (d, J = 6.4 Hz, 3H), 3.32-3.29 (m, 1.4H), 3.05-3.02 (m, 1H), 1.44-1.34 (m, 6H). | 561.2 |
| 495 | (3S)-7-((2S,5R)-4-acryloyl-2,5-dimethylpiperazin-1-yl)-9-chloro-10-(5-chloro-2,4-difluorophenyl)-3-((4-(2,2-difluoroethyl)piperazin-1-yl)methyl)-2H-[1,4]thiazino[2,3,4-ij]quinazolin-5(3H)-one | 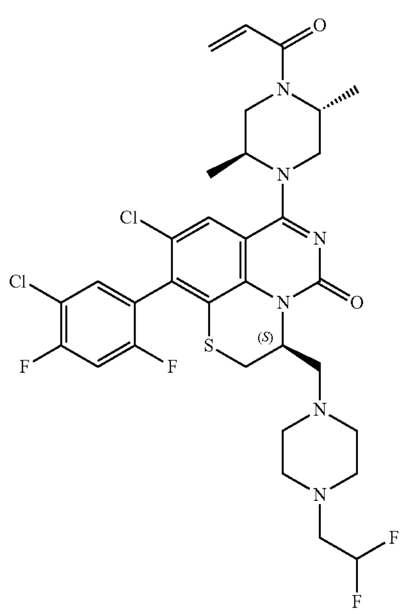 | ¹H NMR (400 MHz, CDCl₃) δ 7.52 (s, 1H), 7.31-7.28 (m, 1H), 7.12-7.06 (m, 1H), 6.66-6.50 (m, 1H), 6.37 (t, J = 16 Hz, 1H), 6.00-5.70 (m, 2H), 5.43-5.36 (m, 1H), 4.99-4.69 (m, 1.5H), 4.40-4.21 (m, 1.5H), 3.98 (d, J = 14 Hz, 0.5H), 3.82-3.65 (m, 2H), 3.35-5.33 (m, 1.5H), 3.05-3.02 (m, 1H), 2.74-2.67 (m, 5H), 2.57-2.54 (m, 7H), 1.39-1.37 (m, 3H), 1.35-1.26 (m, 3H). | 713.2 |

TABLE 8-continued

Table of Thiomorpholines

| Ex. # | Name | Structure | ¹H NMR | MS (M + H)⁺ |
|---|---|---|---|---|
| 496 | (3S)-7-((2S,5R)-4-acryloyl-2,5-dimethylpiperazin-1-yl)-9-chloro-10-(5-chloro-2,4-difluorophenyl)-3-(methoxymethyl)-2H-[1,4]thiazino[2,3,4-ij]quinazolin-5(3H)-one | 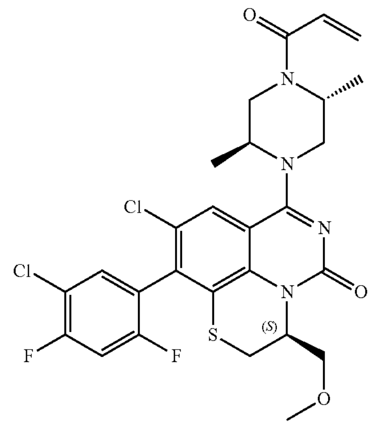 | ¹H NMR (400 MHz, CDCl₃) δ 7.57-7.52 (m, 1H), 7.33-7.29 (m, 1H), 7.12-7.07 (m, 1H), 6.64-6.50 (m, 1H), 6.41-6.33 (m, 1H), 5.80-5.75 (m, 1H), 5.47 (s, 1H), 5.01 (s, 0.5H), 4.84 (s, 0.5H), 4.70 (s, 0.5H), 4.38-4.30 (m, 1H), 4.06-4.03 (m, 0.5H), 3.80-3.57 (m, 4H), 3.41-3.37 (d, J = 16.0 Hz, 3H), 3.34-3.31 (m, 1H), 3.06-3.03 (m, 1H), 1.43-1.34 (m, 6H). 1.25 (s, 1H) | 595.1 |
| 497 | (S)-7-((2S,5R)-4-acryloyl-2,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one | 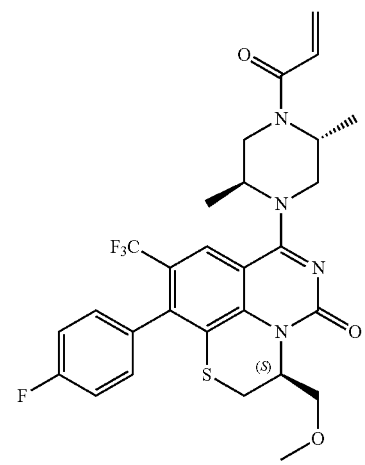 | ¹H NMR (400 MHz, CDCl₃) δ 7.85-7.83 (d, J = 8.0 Hz, 1H), 7.24-7.15 (m, 4H), 6.67-6.51 (m, 1H), 6.41-6.34 (m, 1H), 5.80-5.76 (m, 1H), 5.41-5.40 (m, 1H), 5.06 (s, 0.5H), 4.81-4.79 (m, 0.5H), 4.46-4.34 (m, 1H), 4.13-4.09 (d, J = 16.0 Hz, 0.5H), 3.72-3.62 (m, 4H), 3.40 (s, 3H), 3.32-3.21 (m, 2H), 2.99-2.97 (d, J = 8.0 Hz, 0.5H), 1.50-1.42 (m, 6H), 1.25 (m, 1H). | 577.2 |
| 498 | (3S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2H-[1,4]thiazino[2,3,4-ij]quinazolin-5(3H)-one | 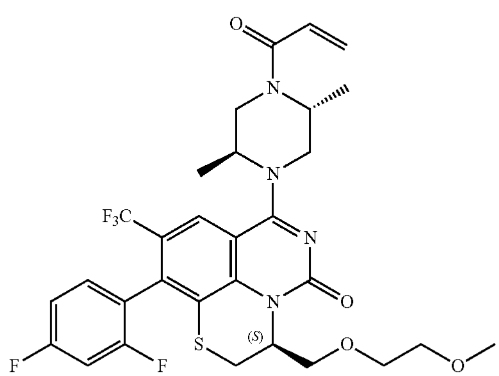 | ¹H NMR (400 MHz, CDCl₃) δ 7.87-7.83 (m, 1H), 7.19-7.15 (m, 1H), 7.03-6.95 (m, 2H), 6.67-6.51 (m, 1H), 6.37 (t, J = 14.4 Hz, 1H), 5.78 (t, J = 9.2 Hz, 1H), 5.50-5.36 (m, 1H), 5.14-5.00 (m, 0.6H), 4.78-4.66 (m, 1H), 4.45-4.41 (m, 1H), 4.41-4.34 (m, 0.4H), 4.16-4.08 (m, 0.6H), 3.78-3.63 (m, 6H), 3.52 (t, J = 4.8 Hz, 2H), 3.41-3.38 (m, 1H), 3.35 (s, 3H), 3.26-3.22 (m, 0.4H), 3.05-2.95 (m, 1H), 1.50-1.44 (m, 6H). | 639.3 |

TABLE 8-continued

Table of Thiomorpholines

| Ex. # | Name | Structure | ¹H NMR | MS (M + H)⁺ |
|---|---|---|---|---|
| 499 | (3S)-7-((2S,5R)-4-acryloyl-2,5-dimethylpiperazin-1-yl)-9-chloro-10-(5-chloro-2,4-difluorophenyl)-3-((4-cyclopropylpiperazin-1-yl)methyl)-2H-[1,4]thiazino[2,3,4-ij]quinazolin-5(3H)-one | 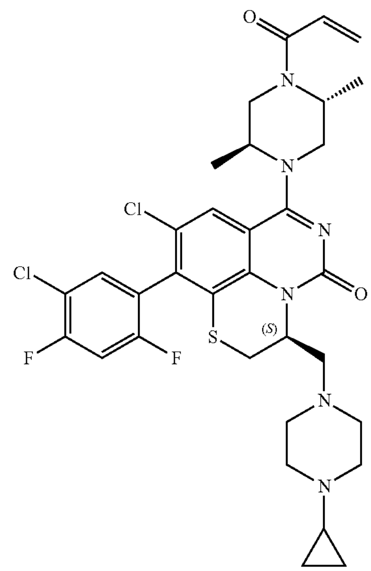 | ¹H NMR (400 MHz, CDCl₃) δ 7.52 (s, 1H), 7.32-7.30 (m, 1H), 7.13-7.05 (m, 1H), 6.67-6.489 (m, 1H), 6.37 (t, J = 13.6 Hz, 1H), 5.79-5.75 (m, 1H), 5.48-5.37 (m, 1H), 5.01-4.67 (m, 2H), 4.42-3.95 (m, 2H), 3.84-3.66 (m, 2H), 3.40-3.31 (m, 1H), 3.10-3.08 (m, 1H), 2.82-2.48 (m, 10H), 1.46-1.24 (m, 7H), 0.57-0.40 (m, 4H). | 689.3 |
| 500 | (3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one | 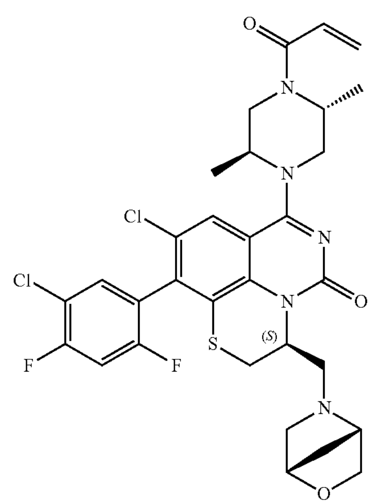 | ¹H NMR (400 MHz, CDCl₃) δ 7.54-7.52 (m, 1H), 7.32-7.25 (m, 1H), 7.12-7.06 (m, 1H), 6.66-6.50 (m, 1H), 6.41-6.33 (m, 1H), 5.79-5.75 (m, 1H), 5.28-5.24 (m, 1H), 5.01-4.70 (m, 2H), 4.40-4.26 (m, 2H), 4.02-3.90 (m, 2H), 3.69-3.55 (m, 4H), 3.46-3.29 (m, 1H), 3.03-2.86 (m, 5H), 1.77-1.65 (m, 2H), 1.52-1.33 (m, 6H). | 662.3 |

TABLE 8-continued

Table of Thiomorpholines

| Ex. # | Name | Structure | $^1$H NMR | MS (M + H)$^+$ |
|---|---|---|---|---|
| 501 | (3S)-7-((2S,5R)-4-acryloyl-2,5-dimethylpiperazin-1-yl)-9-chloro-10-(2,4-difluorophenyl)-3-((2-methoxyethoxy)methyl)-2H-[1,4]thiazino[2,3,4-ij]quinazolin-5(3H)-one | 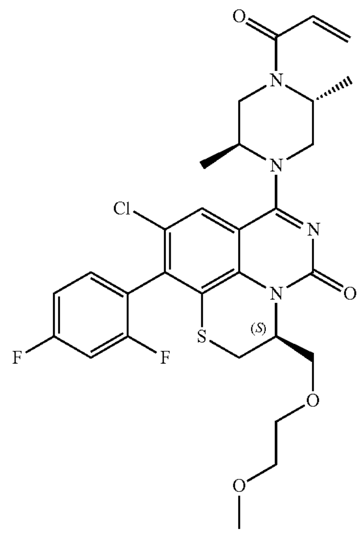 | $^1$H NMR (400 MHz, CDCl$_3$) δ 7.75-7.54 (m, 1H), 7.27-7.18 (m, 1H), 7.08-6.95 (m, 2H), 6.67-6.50 (m, 1H), 6.37 (t, J = 16.0 Hz, 1H), 5.80-5.75 (m, 1H), 5.50-5.47 (m, 1H), 5.03-5.00 (m, 0.5H), 4.83-4.69 (m, 1H), 4.41-4.32 (m, 1.5H), 4.10-4.03 (m, 0.5H), 3.82-3.62 (m, 6.5H), 3.54-3.50 (m, 2H), 3.38-3.35 (m, 4H), 3.05-3.02 (m, 1H), 1.45-1.36 (m, 6H). | 605.2 |
| 502 | (3S)-7-((2S,5R)-4-acryloyl-2,5-dimethylpiperazin-1-yl)-9-chloro-10-(5-chloro-2,4-difluorophenyl)-3-((2-methoxyethoxy)methyl)-2H-[1,4]thiazino[2,3,4-ij]quinazolin-5(3H)-one | 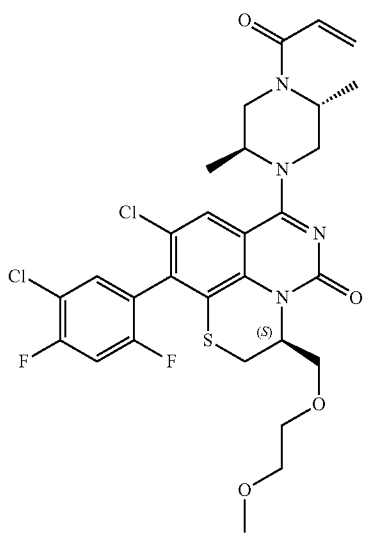 | $^1$H NMR (400 MHz, CDCl$_3$) δ 7.56-7.53 (m, 1H), 7.32-7.28 (m, 1H), 7.12-7.06 (m, 1H), 6.67-6.50 (m, 1H), 6.37 (t, J = 14.4 Hz, 1H), 5.80-5.75 (m, 1H), 5.49-5.47 (m, 1H), 5.03-5.00 (m, 0.5H), 4.82-4.68 (m, 1H), 4.42-4.31 (m, 1.5H), 4.08-4.02 (m, 0.5H), 3.83-3.62 (m, 6.5H), 3.55-3.50 (m, 2H), 3.37-3.30 (m, 4H), 3.06-3.02 (m, 1H), 1.43-1.35 (m, 6H). | 639.2 |
| 506 | (3S)-7-((3S,5R)-4-acryloyl-3,5-dimethylpiperazin-1-yl)-9-chloro-3-(methoxymethyl)-10-(2,4,5-trifluorophenyl)-2,3-dihydro-5H-[1,4]thiazino[2,3,4-ij]quinazolin-5-one | 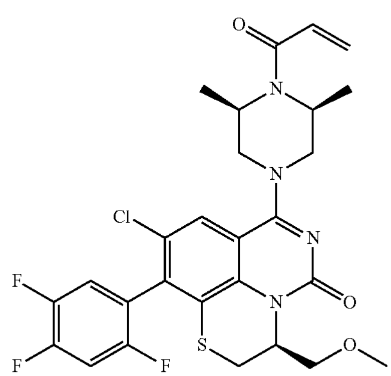 [SMILES: C=CC(=O)N1[C@H](C)CN(c2nc(=O)n3c4c(c(-c5cc(F)c(F)cc5F)c(Cl)cc24)SC[C@@H]3COC)C[C@@H]1C] | $^1$H NMR (400 MHz, MeOH-d$_4$) δ 7.90 (s, 1H), 7.46-7.27 (m, 2H), 6.83 (dd, J = 16.7, 10.6 Hz, 1H), 6.28 (dd, J = 16.7, 2.0 Hz, 1H), 5.80 (dd, J = 10.6, 2.0 Hz, 1H), 5.40-5.31 (m, 1H), 1.57-1.50 (m, 3H), 1.43-1.36 (m, 3H) | 579.2 |

TABLE 8-continued

Table of Thiomorpholines

| Ex. # | Name | Structure | ¹H NMR | MS (M + H)⁺ |
|---|---|---|---|---|
| 508 | (3S,10S)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 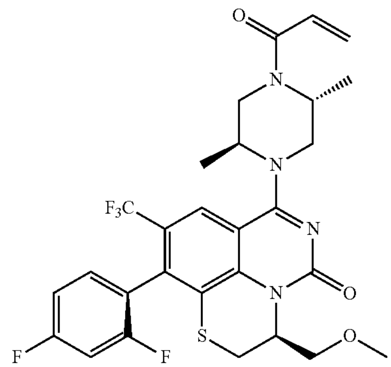 | ¹H NMR (400 MHz, CDCl₃) δ 7.84 (d, J = 12 Hz, 1H), 7.16 (q, J = 7.6 Hz, 1H), 7.05-6.94 (m, 2H), 6.66-6.50 (m, 1H), 6.37 (t, J = 14.8 Hz, 1H), 5.78 (t, J = 8.4 Hz, 1H), 5.45-5.43 (m, 1H), 5.08-5.04 (m, 0.6H), 4.82-4.65 (m, 1H), 4.43-4.33 (m, 1.4H), 4.11-4.17 (m, 0.5H), 3.73-3.61 (m, 4H), 3.42-3.31 (m, 4H), 3.26-3.21 (m, 0.5H), 3.01 (d, J = 13.6 Hz, 1H), 1.50-1.41 (m, 6H). | 595.2 |
| 509 | (3S,10R)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 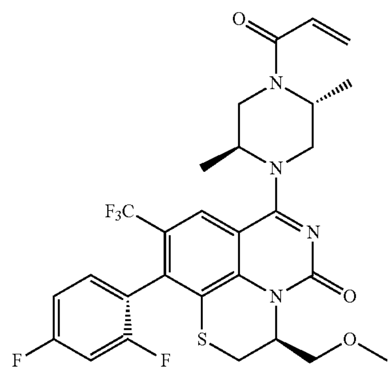 | ¹H NMR (400 MHz, CDCl₃) δ 7.84 (d, J = 6.4 Hz, 1H), 7.19 (q, J = 8.0 Hz, 1H), 7.04-6.94 (m, 2H), 6.66-6.50 (m, 1H), 6.37 (t, J = 14.8 Hz, 1H), 5.77 (t, J = 9.2 Hz, 1H), 5.41-5.39 (m, 1H), 5.07-5.04 (m, 0.6H), 4.80-4.66 (m, 1H), 4.44-4.35 (m, 1.4H), 4.15-4.12 (m, 0.5H), 3.72-3.64 (m, 4H), 3.39-3.32 (m, 4H), 3.26-3.22 (m, 0.5H), 3.02 (d, J = 13.2 Hz, 1H), 1.49-1.43 (m, 6H). | 595.2 |
| 510 | (3S,10S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 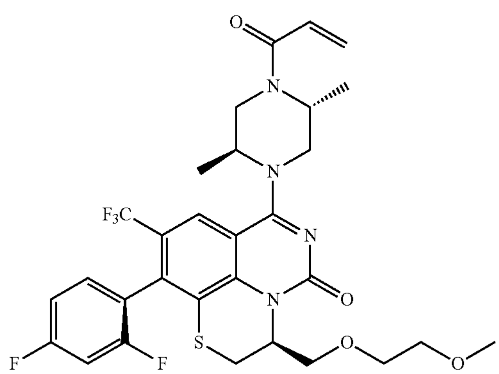 | ¹H NMR (400 MHz, CDCl₃) δ 7.86-7.83 (m, 1H), 7.16 (q, J = 7.6 Hz, 1H), 7.05-7.01 (m, 1H), 6.98-6.93 (m, 1H), 6.67-6.51 (m, 1H), 6.37 (t, J = 14.8 Hz, 1H), 5.78 (t, J = 8.4 Hz, 1H), 5.48-5.41 (m, 1H), 5.11-5.03 (m, 0.5H), 4.79-4.67 (m, 1H), 4.41-4.35 (m, 1.5H), 4.11-4.08 (m, 0.5H), 3.79-3.63 (m, 6H), 3.52 (t, J = 4.8 Hz, 2H), 3.42-3.38 (m, 1H), 3.35 (s, 3H), 3.25-3.22 (m, 0.5H), 3.03-2.99 (m, 1H), 1.50-1.42 (m, 6H). | 639.3 |
| 511 | (3S,10R)-7-((2S,5R)-4-acryloyl-2,5-dimethylpiperazin-1-yl)-10-2,4-difluorophenyl)-3-((2-methoxyethoxy)methyl)-9-(trifluoromethyl)-2,3-dihydro-5H-[1,4]thiazino[2,3,4-ij]quinazolin-5-one | 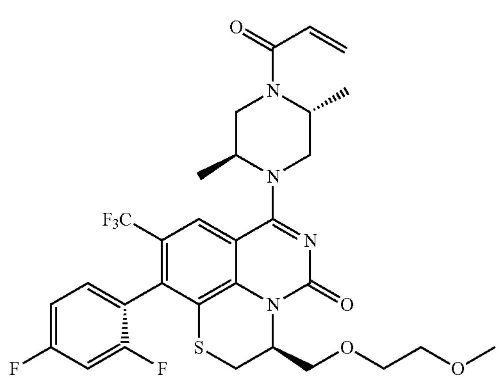 | ¹H NMR (400 MHz, CDCl₃) δ 7.86-7.83 (m, 1H), 7.18 (q, J = 8.0 Hz, 1H), 7.04-6.94 (m, 2H), 6.67-6.50 (m, 1H), 6.37 (t, J = 15.6 Hz, 1H), 5.80-5.75 (m, 1H), 5.46-5.36 (m, 1H), 5.11-5.01 (m, 0.5H), 4.78-4.67 (m, 1H), 4.45-4.31 (m, 1.5H), 4.16-4.12 (m, 0.5H), 3.78-3.60 (m, 6H), 3.52 (t, J = 4.8 Hz, 2H), 3.41-3.38 (m, 1H), 3.35 (s, 3H), 3.26-3.22 (m, 0.5H), 3.03 (d, J = 13.2 Hz, 1H), 1.49-1.43 (m, 6H). | 639.2 |

TABLE 8-continued

Table of Thiomorpholines

| Ex. # | Name | Structure | ¹H NMR | MS (M + H)⁺ |
|---|---|---|---|---|
| 512 | (S)-7-((2S,5R)-4-acryloyl-2,5-dimethylpiperazin-1-yl)-10-(4-fluorophenyl)-3-((2-methoxyethoxy)methyl)-9-(trifluoromethyl)-2H-[1,4]thiazino[2,3,4-ij]quinazolin-5(3H)-one | 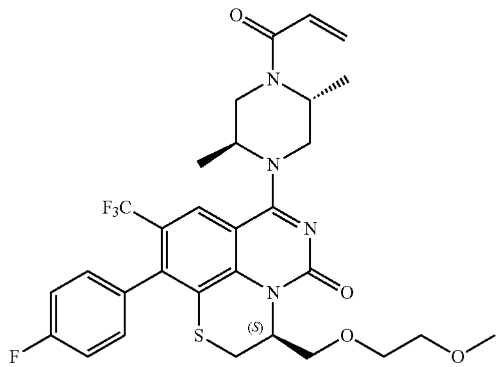 | ¹H NMR (400 MHz, CDCl₃) δ 7.84 (d, J = 10.0 Hz, 1H), 7.26-7.12 (m, 4H), 6.70-6.48 (m, 1H), 6.37 (t, J = 15.0 Hz, 1H), 5.78 (t, J = 8.8 Hz, 1H), 5.46-5.36 (m, 1H), 5.12-5.04 (m, 0.5H), 4.78-4.67 (m, 1H), 4.42 (d, J = 13.6 Hz, 1H), 4.38-4.30 (m, 0.5H), 4.11 (m, 0.5H), 3.82-3.58 (m, 6H), 3.52 (t, J = 4,6 Hz, 2H), 3.40-3.32 (m, 4H), 3.28-3.20 (m, 0.5H), 3.02-2.92 (m, 1H), 1.52-1.40 (m, 6H). | 621.3 |
| 513 | (3S)-7-((3S,5R)-4-acryloyl-3,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 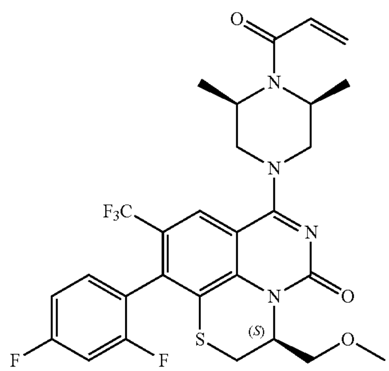 | ¹H NMR (400 MHz, CDCl₃) δ 8.07 (s, 1H), 7.17 (q, J = 8.0 Hz, 1H), 7.06-6.93 (m, 2H), 6.62 (dd, J = 10.4 Hz, 16.8 Hz, 1H), 6.40 (dd, J = 2.0 Hz, 16.8 Hz, 1H), 5.77 (dd, J = 2.0 Hz, 10.4 Hz, 1H), 5.48-5.41 (m, 1H), 4.79-4.53 (m, 2H), 4.21-4.16 (m, 2H), 3.69-3.59 (m, 2H), 3.37-3.30 (m, 6H), 3.05-2.99 (m, 1H), 1.62 (d, J = 6.8 Hz, 3H), 1.47 (d, J = 6.8 Hz, 3H). | 595.2 |
| 514 | (3S)-7-(4-acryloylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 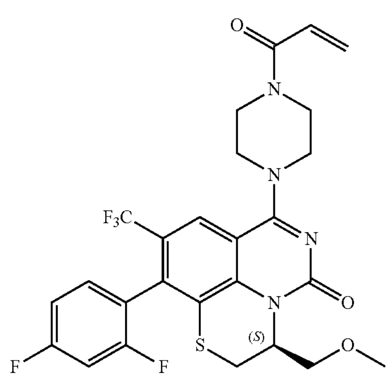 | ¹H NMR (400 MHz, CDCl₃) δ 7.81 (s, 1H), 7.18 (q, J = 6.4 Hz, 1H), 7.05-6.93 (m, 2H), 6.59 (dd, J = 10.4 Hz, 16.8 Hz, 1H), 6.37 (dd, J = 2.0 Hz, 16.8 Hz, 1H), 5.78 (dd, J = 2.0 Hz, 10.4 Hz, 1H), 5.47-5.39 (m, 1H), 4.00-3.92 (m, 3H), 3.81-3.78 (m, 5H), 3.69-3.60 (m, 2H), 3.39 (s, 3H), 3.37-3.33 (m, 1H), 3.04-2.98 (m, 1H). | 567.2 |

TABLE 8-continued

Table of Thiomorpholines

| Ex. # | Name | Structure | ¹H NMR | MS (M + H)⁺ |
|---|---|---|---|---|
| 515 | (S)-7-((2S,5R)-4-acryloyl-2,5-dimethylpiperazin-1-yl)-9-chloro-3-((4-(2,2-difluoroethyl)piperazin-1-yl)methyl)-10-(4-fluorophenyl)-2H-[1,4]thiazino[2,3,4-ij]quinazolin-5(3H)-one | 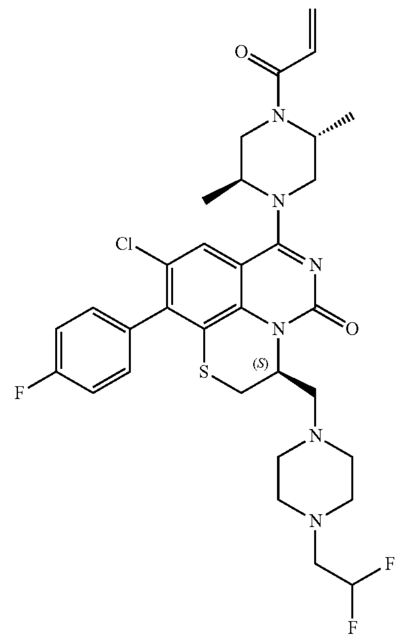 | ¹H NMR (400 MHz, CDCl₃) δ 7.52 (s, 1H), 7.26-7.16 (m, 4H), 6.66-6.51 (m, 1H), 6.40-6.33 (m, 1H), 5.99-5.70 (m, 2H), 5.41-5.36 (m, 1H), 4.98-4.72 (m, 1.5H), 4.39-4.22 (m, 1H), 4.00-3.97 (m, 0.5H), 3.83-3.65 (m, 2H), 3.36-3.27 (m, 1.5H), 3.00-2.96 (m, 1H), 2.80-2.61 (m, 5.5H), 2.61-2.50 (m, 7H), 1.39-1.30 (m, 6H). | 661.3 |
| 516 | (S)-7-((S)-4-acryloyl-2-methylpiperazin-1-yl)-10-(4-fluorophenyl)-3-((methoxymethoxy)methyl)-9-(trifluoromethyl)-2H-[1,4]thiazino[2,3,4-ij]quinazolin-5(3H)-one | 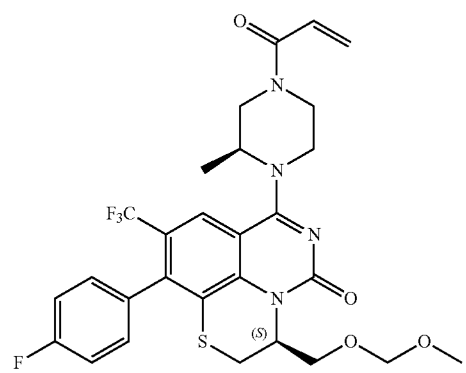 | ¹H NMR (400 MHz, CDCl₃) δ 7.77 (s, 1H), 7.21-7.14 (m, 4H), 6.66-6.51 (m, 1H), 6.39 (d, J = 16.8 Hz, 1H), 5.79 (d, J = 8 Hz, 1H), 5.41 (s, 1H), 4.68-4.62 (m, 3H), 4.53-4.30 (m, 2H), 3.99-3.94 (m, 1H), 3.83-3.79 (m, 2H), 3.65-3.43 (m, 2.5H), 3.37 (s, 3H), 3.35-3.33 (m, 0.5H), 3.09-2.98 (m, 2H), 1.55-1.49 (m, 3H). | 593.3 |
| 517 | (S)-7-((2S,5R)-4-acryloyl-2,5-dimethylpiperazin-1-yl)-9-chloro-3-((4-cyclopropylpiperazin-1-yl)methyl)-10-(4-fluorophenyl)-2H-[1,4]thiazino[2,3,4-ij]quinazolin-5(3H)-one | 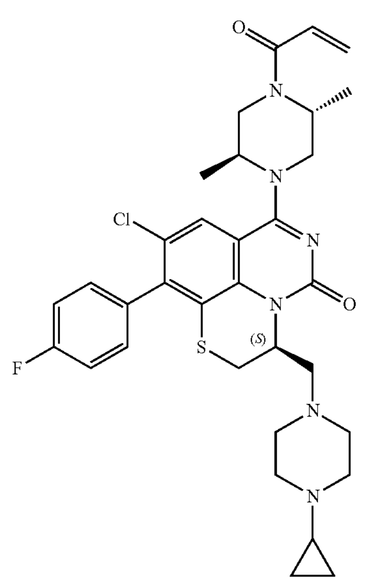 | ¹H NMR (400 MHz, CDCl₃) δ 7.52 (s, 1H), 7.24-7.19 (m, 4H), 6.67-6.49 (m, 1H), 6.36 (t, J = 14.4 Hz, 1H), 5.79-5.73 (m, 1H), 5.47-5.37 (m, 1H), 5.02-4.69 (m, 2H), 4.42-3.97 (m, 2H), 3.86-3.61 (m, 2H), 3.40-3.29 (m, 1H), 3.05-2.94 (m, 1H), 2.83-2.48 (m, 10H), 1.39-1.24 (m, 7H), 0.57-0.36 (m, 4H). | 637.3 |

TABLE 8-continued

Table of Thiomorpholines

| Ex. # | Name | Structure | ¹H NMR | MS (M + H)⁺ |
|---|---|---|---|---|
| 518 | (3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 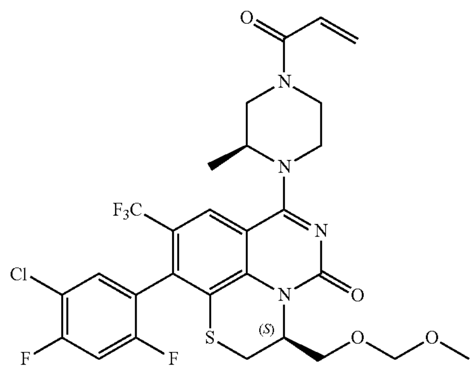 | ¹H NMR (400 MHz, CDCl₃) δ 7.78 (s, 1H), 7.31-7.24 (m, 1H), 7.10- (m, 1H), 6.67-6.50 (m, 1H), 6.38 (dd, J = 16.8 Hz, 2.0 Hz, 1H), 5.79 (d, J = 10.4 Hz, 1H), 5.50-5.38 (m, 1H), 4.80-4.62 (m, 3H), 4.59-4.26 (m, 2H), 4.06-3.92 (m, 0.5H), 3.90-3.74 (m, 2.5H), 3.67-3.47 (m, 1.5H), 3.46-3.33 (m, 4.5H), 3.17-2.96 (m, 2H), 1.61-1.44 (m, 3H). | 645.2 |
| 519 | (3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(2,4-difluorophenyl)-2H-[1,4]thiazino[2,3,4-ij]quinazolin-5(3H)-one | 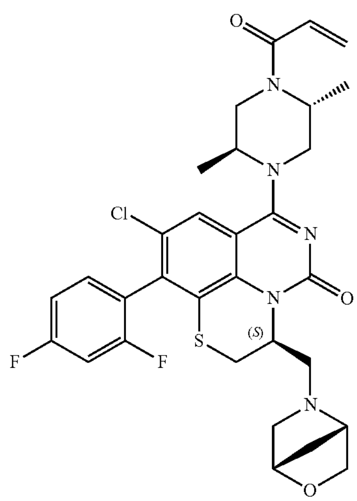 | ¹H NMR (400 MHz, CDCl₃) δ 7.55-7.52 (m, 1H), 7.25-7.18 (m, 1H), 7.07-6.96 (m, 2H), 6.66-6.50 (m, 1H), 6.41-6.33 (m, 1H), 5.79-5.75 (m, 1H), 5.28-5.26 (m, 1H), 5.01-4.70 (m, 2H), 4.40-4.32 (m, 2H), 4.04-3.30 (m, 9H), 3.03-2.84 (m, 5H), 1.42-1.33 (m, 6H). | 628.2 |
| 520 | (3S)-7-((S)-4-acryloyl-2-methylpiperazin-1-yl)-9-chloro-3-((4-cyclopropylpiperazin-1-yl)methyl)-10-(2,4,5-trifluorophenyl)-2H-[1,4]thiazino[2,3,4-ij]quinazolin-5(3H)-one | 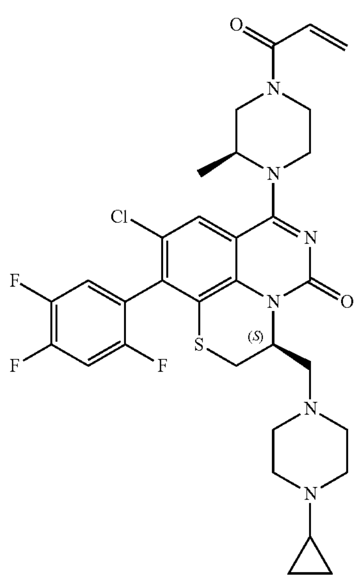 | ¹H NMR (400 MHz, CDCl₃) δ 7.49 (s, 1H), 7.14-7.04 (m, 2H), 6.66-6.50 (m, 1H), 6.37 (dd, J = 2.0 Hz, J = 1.2 Hz, 1H), 5.78 (d, J = 11.6 Hz, 1H), 5.41-5.31 (m, 1H), 4.76-3.79 (m, 5H), 3.56-3.39 (m, 4H), 3.09-3.04 (m, 3H), 2.95-2.52 (m, 8H), 1.50-1.43 (m, 4H), 0.87-0.35 (m, 3H). | 659.3 |

TABLE 8-continued

Table of Thiomorpholines

| Ex. # | Name | Structure | ¹H NMR | MS (M + H)⁺ |
|---|---|---|---|---|
| 521 | (3S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2H-[1,4]thiazino[2,3,4-ij]quinazolin-5(3H)-one | 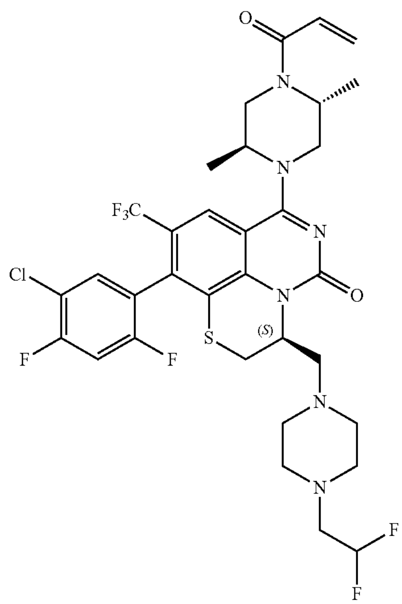 | ¹H NMR (400 MHz, CDCl₃) δ 7.83 (s, 1H), 7.09-7.04 (m, 1H), 6.66-6.50 (m, 1H), 6.37 (t, J = 14.0 Hz, 1H), 6.00-5.72 (m, 2H), 5.42-5.31 (m, 1H), 5.08-4.64 (m, 2H), 4.43-4.33 (m, 1H), 4.12-4.01 (m, 1H), 3.72-3.64 (m, 3H), 3.41-3.01 (m, 4H), 2.79-2.53 (m, 10H), 1.47-1.37 (m, 6H). | 747.3 |
| 522 | (3S)-7-((S)-4-acryloyl-2-methylpiperazin-1-yl)-3-((methoxymethoxy)methyl)-9-(trifluoromethyl)-10-(2,4,5-trifluorophenyl)-2H-[1,4]thiazino[2,3,4-ij]quinazolin-5(3H)-one | 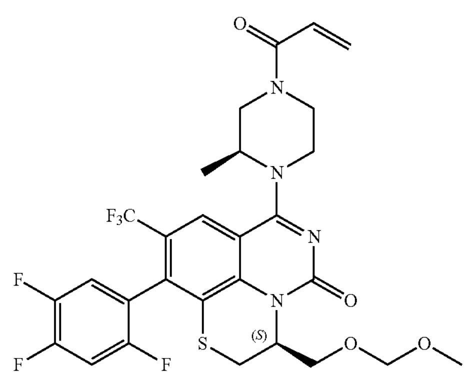 | ¹H NMR (400 MHz, CDCl₃) δ 7.78 (s, 1H), 7.13-7.00 (m, 2H), 6.70-6.48 (m, 1H), 6.38 (dd, J = 16.8 Hz, 1.6 Hz, 1H), 5.79 (d, J = 10.4 Hz, 1H), 5.52-5.37 (m, 1H), 4.78-4.60 (m, 3H), 4.58-4.26 (m, 2H), 4.06-3.92 (m, 0.5H), 3.89-3.74 (m, 2.5H), 3.69-3.42 (m, 1.5H), 3.42-3.27 (m, 4.5H), 3.98-3.16 (m, 2H), 1.62-1.42 (m, 3H). | 629.2 |
| 523 | (3S)-7-(9-acryloyl-7,7-difluoro-3,9-diazabicyclo[3.3.1]nonan-3-yl)-10-(2,4-difluorophenyl)-3-(methoxymethyl)-9-(trifluoromethyl)-2H-[1,4]thiazino[2,3,4-ij]quinazolin-5(3H)-one | 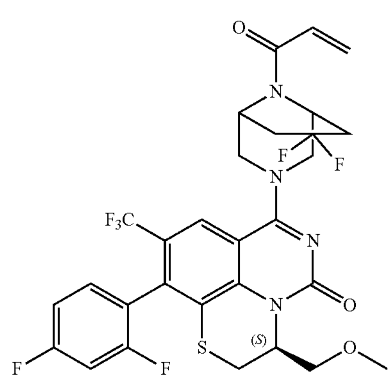 | ¹H NMR (400 MHz, CDCl₃) δ 8.01-7.94 (m, 1H), 7.21-7.15 (m, 1H), 7.05-6.94 (m, 2H), 6.63-6.56 (m, 1H), 6.43 (dd, J = 1.6 Hz, 16.8 Hz, 1H), 5.86 (d, J = 10 Hz, 1H), 5.44-5.33 (m, 1H), 5.16-5.15 (m, 1H), 4.77-4.69 (m, 1H), 4.55-4.51 (m, 1H), 4.38-4.28 (m, 1H), 3.66-3.50 (m, 3H), 3.39-3.32 (m, 4H), 3.04-2.98 (m, 1H), 2.60-2.32 (m, 4H), 2.04-1.98 (m, 1H). | 643.2 |

TABLE 8-continued

Table of Thiomorpholines

| Ex. # | Name | Structure | ¹H NMR | MS (M + H)⁺ |
|---|---|---|---|---|
| 544 | (3S,10S)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 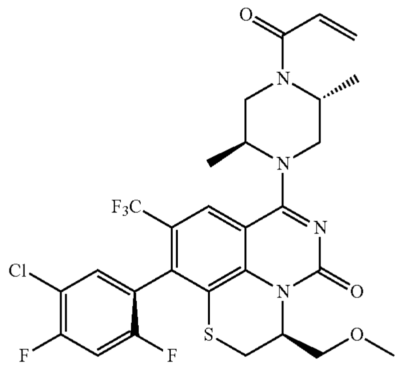 | ¹H NMR (400 MHz, CDCl$_3$) δ 7.84 (d, J = 10.8 Hz, 1H), 7.26-7.23 (m, 1H), 7.07 (t, J = 8.8 Hz, 1H), 6.67-6.50 (m, 1H), 6.37 (t, J = 14.0 Hz, 1H), 5.78 (t, J = 8.8 Hz, 1H), 5.46-5.41 (m, 1H), 5.09-5.03 (m, 0.6H), 4.80-4.65 (m, 1H), 4.44-4.33 (m, 1.4H), 4.10-4.07 (m, 0.5H), 3.72-3.63 (m, 4H), 3.39-3.34 (m, 4H), 3.25-3.21 (m, 0.5H), 3.05-3.01 (m, 1H), 1.50-1.44 (m, 6H). | 629.2 |
| 545 | (3S,10R)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 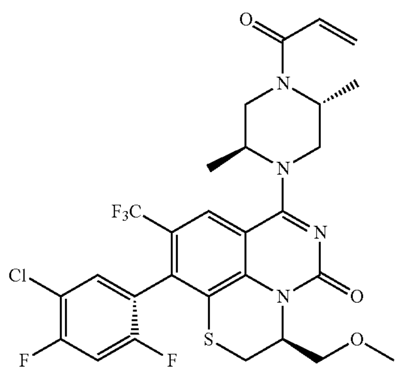 | ¹H NMR (400 MHz, CDCl3) δ 7.84-7.84 (m, 1H), 7.30-7.28 (m, 1H), 7.07 (t, J = 8.4 Hz, 1H), 6.66-6.50 (m, 1H), 6.37 (t, J = 14.0 Hz, 1H), 5.80-5.75 (m, 1H), 5.44-5.40 (m, 1H), 5.08-5.03 (m, 0.6H), 4.80-4.66 (m, 1H), 4.44-4.34 (m, 1.4H), 4.13-4.09 (m, 0.5H), 3.75-3.65 (m, 4H), 3.41-3.35 (m, 4H), 3.26-3.23 (m, 0.5H), 3.05-3.02 (m, 1H), 1.49-1.42 (m, 6H). | 629.2 |
| 546 | (3S,10S)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 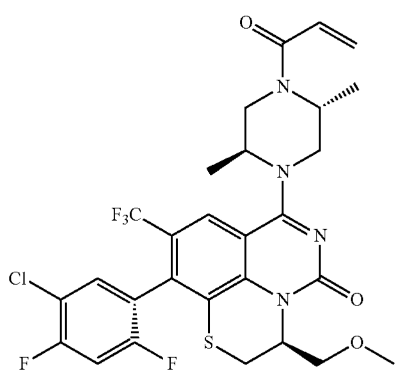 | ¹H NMR (400 MHz, CDCl3) δ 8.07 (s, 1H), 7.18 (q, J = 8.0 Hz, 1H), 7.05-6.93 (m, 2H), 6.62 (dd, J = 6.0 Hz, 16.4 Hz, 1H), 6.40 (dd, J = 1.6 Hz, 16.4 Hz, 1H), 5.77 (dd, J = 1.6 Hz, 10.4 Hz, 1H), 5.48-5.45 (m, 1H), 4.70-4.60 (m, 1H), 4.22-4.17 (m, 2H), 3.74-3.60 (m, 3H), 3.39-3.31 (m, 6H), 3.03-2.99 (m, 1H), 1.63-1.61 (m, 3H), 1.47 (d, J = 7.2 Hz, 3H). | 595.2 |
| 547 | (3S,10R)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 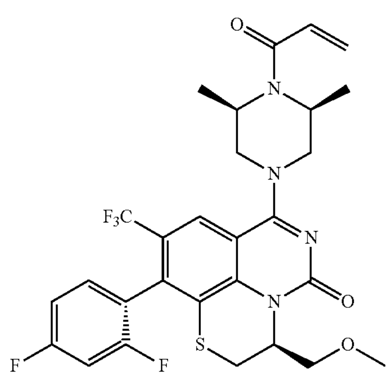 | ¹H NMR (400 MHz, CDCl$_3$) δ 8.07 (s, 1H), 7.18 (q, J = 7.6 Hz, 1H), 7.04-6.94 (m, 2H), 6.62 (dd, J = 10.0 Hz, 16.8 Hz, 1H), 6.40 (dd, J = 2.0 Hz, 16.8 Hz, 1H), 5.77 (dd, J = 2.0 Hz, 10.8 Hz, 1H), 5.46-5.42 (m, 1H), 4.73-4.61 (m, 1H), 4.21-4.16 (m, 2H), 3.74-3.64 (m, 3H), 3.40-3.30 (m, 6H), 3.03 (dd, J = 2.4 Hz, 13.2 Hz, 1H), 1.63-1.61 (m, 3H), 1.47 (d, J = 7.2 Hz, 3H). | 595.2 |

TABLE 8-continued

Table of Thiomorpholines

| Ex. # | Name | Structure | ¹H NMR | MS (M + H)⁺ |
|---|---|---|---|---|
| 548 | (3S,10R)-7-((S)-4-acryloyl-2-methylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one | 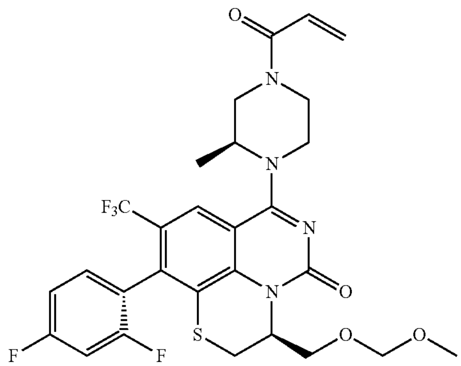 | 1H NMR (400 MHz, CDCl$_3$) δ 7.77 (s, 1H), 7.18 (q, J = 8.0 Hz, 1H), 7.04-6.95 (m, 2H), 6.66-6.51 (m, 1H), 6.40 (d, J = 16.8 Hz, 1H), 5.79 (d, J = 10.4 Hz, 1H), 5.427-5.425 (m, 1H), 4.71-4.62 (m, 3H), 4.54-4.34 (m, 2H), 4.02-3.96 (m, 1H), 3.81-3.79 (m, 2H), 3.63-3.60 (m, 1H), 3.52-3.39 (m, 2H), 3.35 (s, 3H), 3.09-3.01 (m, 2H), 1.58-1.51 (m, 3H). | 611.3 |
| 549 | (3S,10S)-7-((S)-4-acryloyl-2-methylpiperazin-1-yl)-10-(2,4-difluorophenyl)-3-((methoxymethoxy)methyl)-9-(trifluoromethyl)-2H-[1,4]thiazino[2,3,4-ij]quinazolin-5(3H)-one | 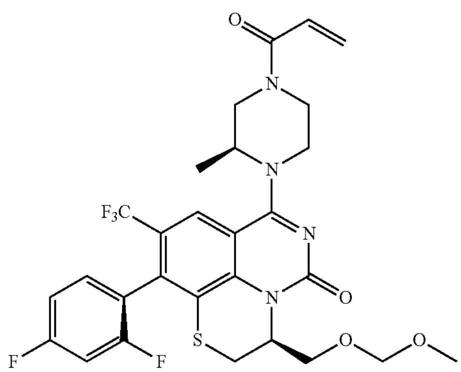 | 1H NMR (400 MHz, CDCl$_3$) δ 7.78 (s, 1H), 7.20-7.15 (m, 1H), 7.03 (t, J = 7.6 Hz, 1H), 6.98-6.93 (m, 1H), 6.64-6.51 (m, 1H), 6.39 (d, J = 16.4 Hz, 1H), 5.79 (d, J = 9.6 Hz, 1H), 5.46-5.45 (m, 1H), 4.72-4.62 (m, 3H), 4.51-4.28 (m, 2H), 3.97-3.94 (m, 1H), 3.82-3.78 (m, 2H), 3.64-3.53 (m, 1H), 3.49-3.38 (m, 2H), 3.38 (s, 3H), 3.07-3.05 (m, 2H), 1.56-1.50 (m, 3H). | 611.2 |
| 550 | (3S)-7-((2S,5R)-4-acryloyl-2,5-dimethylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 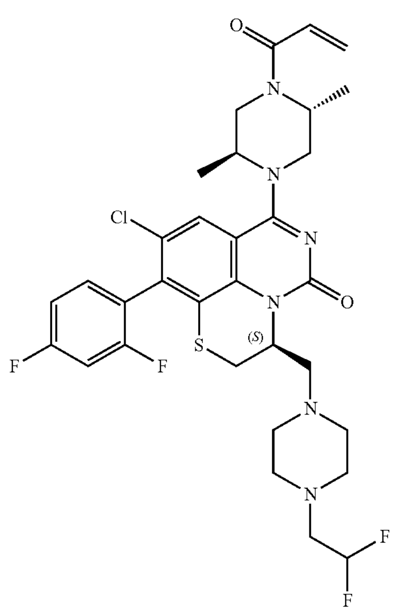 | ¹H NMR (400 MHz, CDCl$_3$) δ 7.54 (s, 1H), 7.21 (q, J = 8.4 Hz, 1H), 7.07-6.95 (m, 2H), 6.66-6.50 (m, 1H), 6.37 (t, J = 14.8 Hz, 1H), 5.99-5.71 (m, 2H), 5.48-5.38 (m, 1H), 5.01-4.70 (m, 1.5H), 4.39-4.24 (m, 1.5H), 4.07-3.97 (m, 0.5H), 3.80-3.65 (m, 2.5H), 3.40-3.26 (m, 1.5H), 3.09-2.99 (m, 1.5H), 2.84-2.64 (m, 5.5H), 2.64-2.45 (m, 5.5H), 1.45-1.25 (m, 6H). | 679.2 |

TABLE 8-continued

Table of Thiomorpholines

| Ex. # | Name | Structure | ¹H NMR | MS (M + H)⁺ |
|---|---|---|---|---|
| 551 | (3S)-7-((2S,5R)-4-acryloyl-2,5-dimethylpiperazin-1-yl)-9-chloro-3-((4-cyclopropylpiperazin-1-yl)methyl)-10-(2,4-difluorophenyl)-2H-[1,4]thiazino[2,3,4-ij]quinazolin-5(3H)-one | 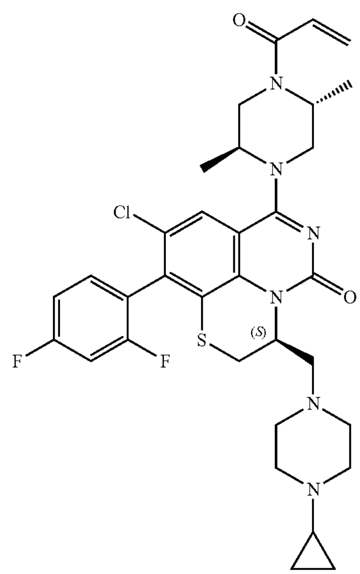 | ¹H NMR (400 MHz, CDCl₃) δ 7.53 (s, 1H), 7.22 (q, J = 8.0 Hz, 1H), 7.07-6.95 (m, 2H), 6.66-6.50 (m, 1H), 6.37 (t, J = 16.8 Hz, 1H), 5.79-5.75 (m, 1H), 5.49-5.38 (m, 1H), 4.99-4.72 (m, 1.5H), 4.40-4.22 (m, 1.5H), 4.01-3.99 (m, 0.5H), 3.82-3.65 (m, 2.5H), 3.37-3.28 (m, 1H), 3.06-3.03 (m, 1H), 2.95-2.45 (m, 10H), 1.47-1.30 (m, 7H), 0.84-0.15 (m, 4H). | 655.3 |
| 552 | (3S,10R)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 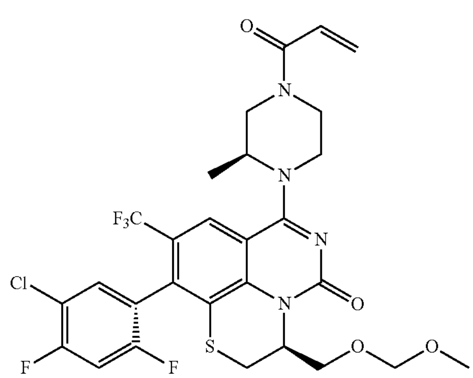 | ¹H NMR (400 MHz, CDCl₃) δ 7.78 (m, 1H), 7.31-7.24 (m, 1H), 7.08 (t, J = 8.8 Hz, 1H), 6.67-6.50 (m, 1H), 6.38 (dd, J = 16.8 Hz, 2.0 Hz, 1H), 5.79 (d, J = 10.0 Hz, 1H), 5.50-5.38 (m, 1H), 4.80-4.62 (m, 3H), 4.59-4.29 (m, 2H), 4.06-3.92 (m, 0.5H), 3.89-3.75 (m, 2.5H), 3.67-3.47 (m, 1.5H), 3.46-3.32 (m, 4.5H), 3.15-2.97 (m, 2H), 1.58-1.46 (m, 3H). | 645.2 |
| 553 | (3S,10S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 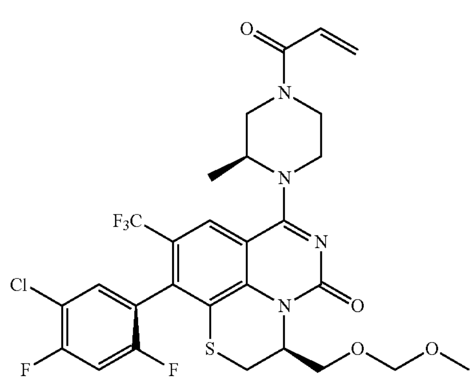 | ¹H NMR (400 MHz, CDCl₃) δ 7.78 (m, 1H), 7.30-7.24 (m, 1H), 7.07 (td, J = 8.8 Hz, 2 Hz, 1H), 6.67-6.50 (m, 1H), 6.38 (d, J = 16.8 Hz, 1H), 5.79 (d, J = 10.4 Hz, 1H), 5.51-5.40 (m, 1H), 4.78-4.60 (m, 3H), 4.59-4.26 (m, 2H), 4.04-3.92 (m, 0.5H), 3.88-3.74 (m, 2.5H), 3.67-3.47 (m, 1.5H), 3.46-3.32 (m, 4.5H), 3.15-2.97 (m, 2H), 1.58-1.45 (m, 3H). | 645.2 |

TABLE 8-continued

Table of Thiomorpholines

| Ex. # | Name | Structure | ¹H NMR | MS (M + H)⁺ |
|---|---|---|---|---|
| 554 | (3S,10S)-7-((2S,5R)-4-acryloyl-2,5-dimethylpiperazin-1-yl)-10-(5-chloro-2,4-difluorophenyl)-3-((2-methoxyethoxy)methyl)-9-(trifluoromethyl)-2H-[1,4]thiazino[2,3,4-ij]quinazolin-5(3H)-one | 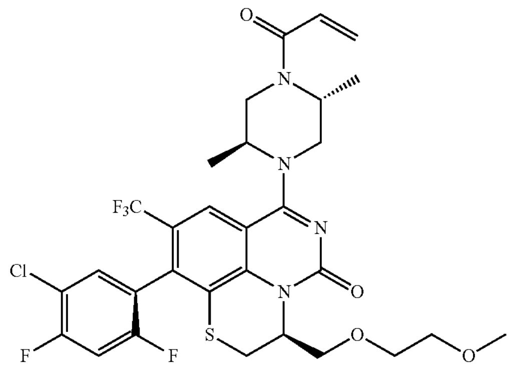 | ¹H NMR (400 MHz, CDCl₃) δ 7.86-7.83 (m, 1H), 7.23-7.21 (m, 1H), 7.06 (t, J = 4.8 Hz, 1H), 6.67-6.51 (m, 1H), 6.38 (t, J = 14.4 Hz, 1H), 5.78 (t, J = 8.8 Hz, 1H), 5.48-5.40 (m, 1H), 5.10-5.02 (m, 0.5H), 4.77-4.65 (m, 1H), 4.44-4.34 (m, 1.5H), 4.11-4.07 (m, 0.5H), 3.76-3.70 (m, 4H), 3.68-3.61 (m, 2H), 3.52 (t, J = 4.8 Hz, 2H), 3.42 (d, J = 12.8 Hz, 1H), 3.36 (s, 3H), 3.24-3.21 (m, 0.5H), 3.04-3.00 (m, 1H), 1.50-1.42 (m, 6H). | 673.2 |
| 555 | (3S,10R)-7-((2S,5R)-4-acryloyl-2,5-dimethylpiperazin-1-yl)-10-(5-chloro-2,4-difluorophenyl)-3-((2-methoxyethoxy)methyl)-9-(trifluoromethyl)-2,3-dihydro-5H-[1,4]thiazino[2,3,4-ij]quinazolin-5-one | 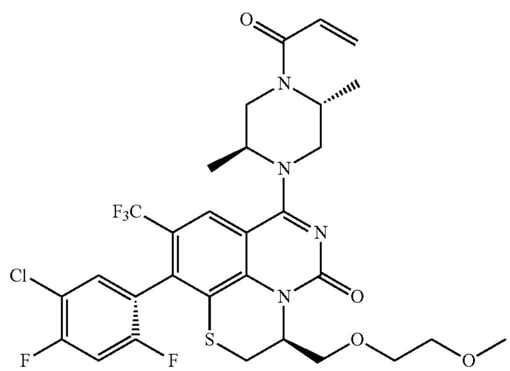 | ¹H NMR (400 MHz, CDCl₃) δ 7.844 (d, J = 8.4 Hz, 1H), 7.293-7.27 (m, 1H), 7.07 (t, J = 4.8 Hz, 1H), 6.67-6.50 (m, 1H), 6.37 (m, 1H), 5.78 (t, J = 8.8 Hz, 1H), 5.48-5.40 (m, 1H), 5.11-5.00 (m, 0.5H), 4.81-4.77 (m, 1H), 4.44-4.31 (m, 1.5H), 4.13-4.09 (m, 0.5H), 3.78-3.61 (m, 4H), 3.68-3.61 (m, 2H), 3.53 (t, J = 4.8 Hz, 2H), 3.43 (d, J = 13.6 Hz, 1H), 3.36 (s, 3H), 3.26-3.21 (m, 0.5H), 3.05-3.01 (m, 1H), 1.50-1.42 (m, 6H). | 673.2 |
| 556 | (3S,10R)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2H-[1,4]thiazino[2,3,4-ij]quinazolin-5(3H)-one | 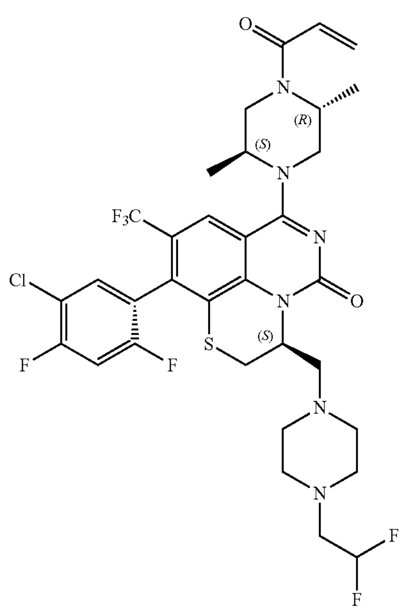 | ¹H NMR (400 MHz, CDCl₃) δ 7.87(s, 1H), 7.10 (t, J = 11.6 Hz, 1H), 6.71-6.53 (m, 1H), 6.46-6.37 (m, 1H), 6.10-5.69 (m, 1H), 5.85-5.79 (m, 1H), 5.49-5.39 (m, 1H), 5.14-4.69 (m, 2H), 4.48-4.37 (m, 1H), 4.17-4.08 (m, 1H), 3.80-3.65 (m, 3H), 3.46-3.26 (m, 2H), 3.11-3.00 (m, 2H), 2.80-2.56 (m, 10H), 1.51-1.40 (m, 6H). | 747.3 |

TABLE 8-continued

Table of Thiomorpholines

| Ex. # | Name | Structure | ¹H NMR | MS (M + H)⁺ |
|---|---|---|---|---|
| 557 | (3S,10S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2H-[1,4]thiazino[2,3,4-ij]quinazolin-5(3H)-one | 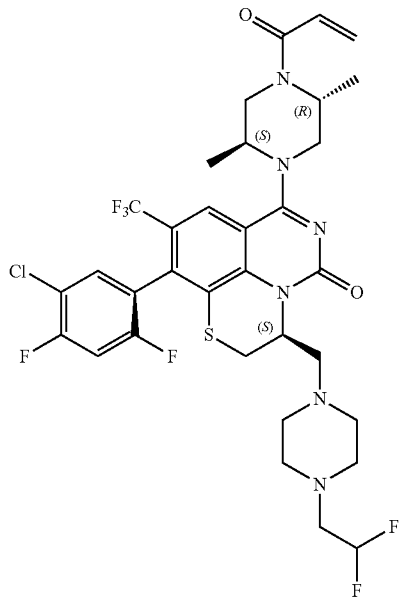 | ¹H NMR (400 MHz, CDCl₃) δ 7.90 (s, 1H), 7.14 (t, J = 12.0 Hz, 1H), 6.68-6.49 (m, 1H), 6.42-6.33 (m, 1H), 6.07-5.65 (m, 1H), 5.81-5.76 (m, 1H), 5.42-5.32 (m, 1H), 5.09-4.64 (m, 2H), 4.45-4.40 (m, 1H), 4.11-4.01 (m, 1H), 3.78-3.63 (m, 3H), 3.43-3.24 (m, 2H), 3.11-2.99 (m, 2H), 2.78-2.54 (m, 10H), 1.51-1.45 (m, 6H). | 747.3 |
| 558 | (S)-7-((2S,5R)-4-acryloyl-2,5-dimethylpiperazin-1-yl)-9-chloro-10-(4-fluorophenyl)-3-((2-methoxyethoxy)methyl)-2H-[1,4]thiazino[2,3,4-ij]quinazolin-5(3H)-one | 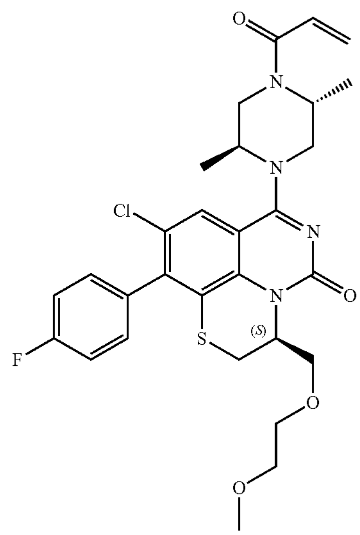 | ¹H NMR (400 MHz, CDCl₃) δ 7.56-7.53 (m, 1H), 7.24-7.17 (m, 4H), 6.67-6.50 (m, 1H), 6.41-6.33 (m, 1H), 5.80-5.75 (m, 1H), 5.50-5.45 (m, 1H), 5.04-4.98 (m, 0.5H), 4.86-4.68 (m, 1H), 4.41-4.33 (m, 1.5H), 4.08-4.03 (m, 0.5H), 3.83-3.64 (m, 6.5H), 3.54-3.51 (m, 2H), 3.36-3.19 (m, 4H), 3.01-2.97 (m, 1H), 1.44-1.36 (m, 6H). | 587.2 |
| 559 | (3S)-7-((3S,5R)-4-acryloyl-3,5-dimethylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one | 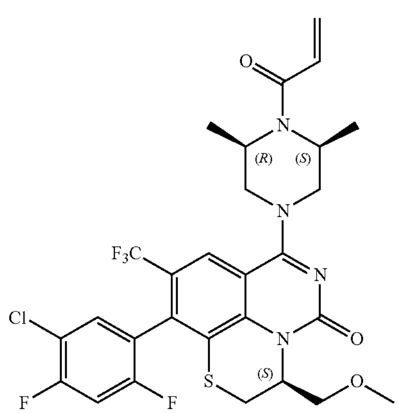 | ¹H NMR (400 MHz, CDCl₃) δ 8.06 (s, 1H), 7.28-7.24 (m, 1H), 7.09-7.04 (m, 1H), 6.65-6.59 (m, 1H), 6.40 (dd, J = 1.6 Hz, 16.8 Hz, 1H), 5.77 (dd, J = 1.6 Hz, 10.8 Hz, 1H), 5.50-5.43 (m, 1H), 4.75-4.59 (m, 2H), 4.21-4.15 (m, 2H), 3.67-3.62 (m, 2H), 3.41-3.30 (m, 6H), 3.05-3.01 (m, 1H), 1.62-1.61 (m, 3H), 1.49 (d, J = 7.2 Hz, 3H). | 629.1 |

TABLE 8-continued

Table of Thiomorpholines

| Ex. # | Name | Structure | ¹H NMR | MS (M + H)⁺ |
|---|---|---|---|---|
| 560 | (3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one | 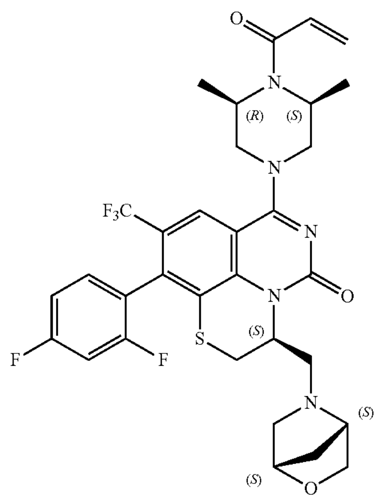 | ¹H NMR (400 MHz, CDCl₃) δ 8.07 (s, 1H), 7.21-7.14 (m, 1H), 7.06-6.93 (m, 2H), 6.66-6.59 (m, 1H), 6.43-6.38 (m, 1H), 5.77 (d, J = 12.0 Hz, 1H), 5.28-5.24 (m, 1H), 4.74-4.60 (m, 2H), 4.43-4.37 (m, 1H), 4.19 (d, J = 13.6 Hz, 2H), 3.91-3.84 (m, 1H), 3.69-3.31 (m, 5.5H), 2.99-2.85 (m, 4.5H), 1.75-1.66 (m, 2H), 1.60-1.58 (m, 3H), 1.49-1.41 (m, 3H). | 662.3 |
| 561 | 2-(4-(((3S)-7-((2S,5R)-4-acryloyl-2,5-dimethylpiperazin-1-yl)-10-(2,4-difluorophenyl)-5-oxo-9-(trifluoromethyl)-3,5-dihydro-2H-[1,4]thiazino[2,3,4-ij]quinazolin-3-yl)methyl)piperazin-1-yl)acetonitrile | 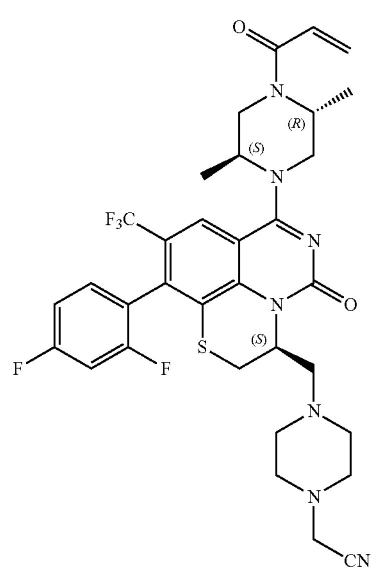 | ¹H NMR (400 MHz, CDCl₃) δ 7.51 (d, J = 2.0 Hz, 1H), 7.24-7.18 (m, 1H), 7.06-6.96 (m, 2H), 5.50-5.43 (m, 1H), 4.63-4.54 (m, 1H), 4.18-4.12 (m, 1H), 3.59-3.47 (m, 1H), 3.14-2.84 (m, 8H), 2.40-2.34 (m, 2H), 1.95-1.69 (m, 7H), 1.52 (dd, J = 1.6 Hz, 1.6 Hz, 3H), 1.44-1.31 (m, 3H), 1.08-1.04 (m, 3H). | 688.3 |

TABLE 8-continued

Table of Thiomorpholines

| Ex. # | Name | Structure | ¹H NMR | MS (M + H)⁺ |
|---|---|---|---|---|
| 562 | (3S)-7-((2S,5R)-4-acryloyl-2,5-dimethylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one | 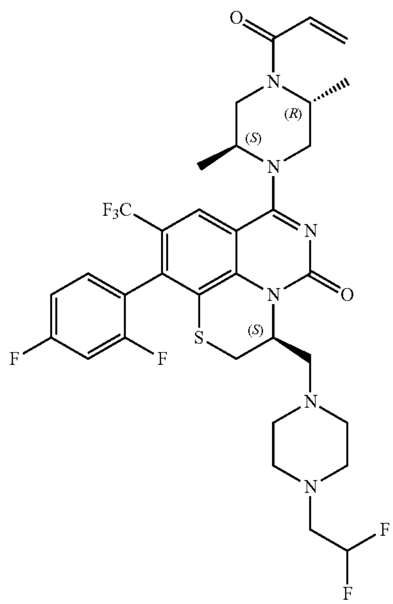 | ¹H NMR (400 MHz, CDCl₃) δ 7.87 (s, 1H), 7.26-7.17 (m, 1H), 7.10-6.98 (m, 2H), 6.76-6.54 (m, 1H), 6.46-6.38 (m, 1H), 6.11-5.70 (m, 1H), 5.85-5.79 (m, 1H), 5.47-5.35 (m, 1H), 5.13-5.07 (m, 0.5H), 4.85-4.70 (m, 1H), 4.48-4.37 (m, 1.5H), 4.19-4.05 (m, 1H), 3.79-3.64 (m, 2H), 3.44-5.28 (m, 2H), 3.11-3.02 (m, 1H), 2.79-2.53 (m, 11H), 1.51-1.42 (m, 6H). | 713.3 |
| 563 | (3S,10R)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 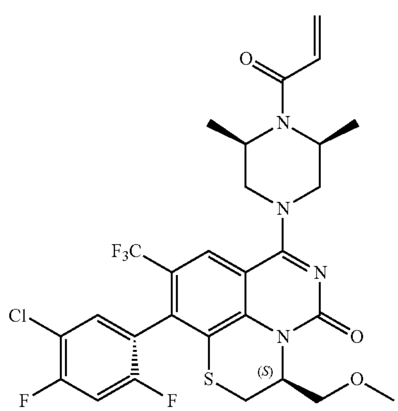 | ¹H NMR (400 MHz, CDCl₃) δ 8.06 (s, 1H), 7.28-7.24 (m, 1H), 7.07 (t, J = 8.8 Hz, 1H), 6.65-6.59 (m, 1H), 6.40 (dd, J = 1.6 Hz, 16.8 Hz, 1H), 5.77 (dd, J = 1.2 Hz, 10.0 Hz, 1H), 5.45-5.44 (m, 1H), 4.73-4.58 (m, 2H), 4.21-4.15 (m, 2H), 3.67-3.64 (m, 2H), 3.41-3.31 (m, 6H), 3.05-3.01 (m, 1H), 1.61 (m, J = 6.8 Hz, 3H), 1.47 (d, J = 6.8 Hz, 3H). | 629.2 |
| 564 | (3S,10S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 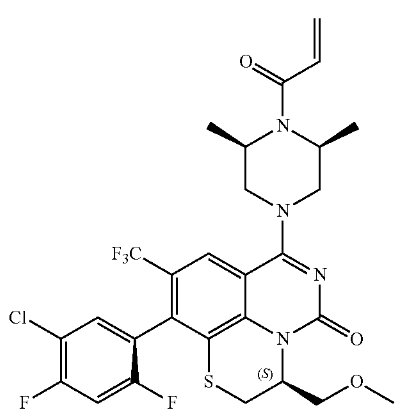 | ¹H NMR (400 MHz, CDCl₃) δ 8.07 (s, 1H), 7.28-7.25 (m, 1H), 7.07 (t, J = 8.8 Hz, 1H), 6.65-6.59 (m, 1H), 6.40 (dd, J = 1.6 Hz, 16.4 Hz, 1H), 5.77 (dd, J = 1.6 Hz, 10.4 Hz, 1H), 5.48-5.45 (m, 1H), 4.76-4.59 (m, 2H), 4.21-4.16 (m, 2H), 3.68-3.59 (m, 2H), 3.39-3.30 (m, 6H), 3.04-3.00 (m, 1H), 1.61-1.59 (m, 3H), 1.46 (d, J = 6.4 Hz, 3H). | 629.2 |

TABLE 8-continued

Table of Thiomorpholines

| Ex. # | Name | Structure | ¹H NMR | MS (M + H)⁺ |
|---|---|---|---|---|
| 565 | (3S,10S)-3-((2-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one | 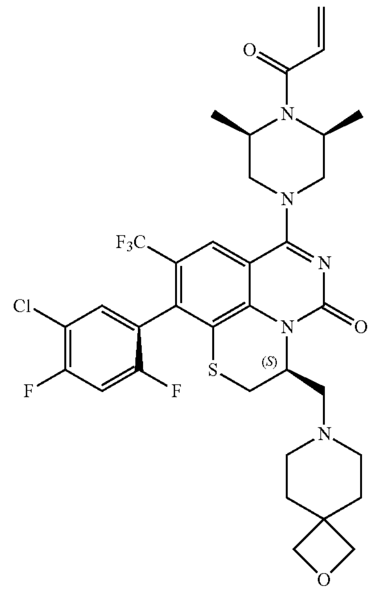 | ¹H NMR (400 MHz, CDCl₃) δ 8.06 (s, 1H), 7.28-7.27 (m, 1H), 7.07 (t, J = 8.4 Hz, 1H), 6.65-6.58 (m, 1H), 6.43-6.38 (dd, J = 1.6 Hz, 16.8 Hz, 1H), 5.79-5.76 (dd, J = 1.6 Hz, 10.4 Hz, 1H), 5.34-5.29 (m, 1H), 4.67-4.65 (m, 2H), 4.39-4.37 (m, 4H), 4.20-4.15 (m, 2H), 3.47-3.06 (m, 3H), 3.01-2.97 (m, 1H), 2.74-2.58 (m, 3H), 2.54-2.29 (m, 3H), 1.83-1.81 (m, 4H), 1.61-1.59 (m, 3H), 1.48-1.46 (m, 3H). | 724.2 |
| 566 | (3S,10R)-3-((2-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one | 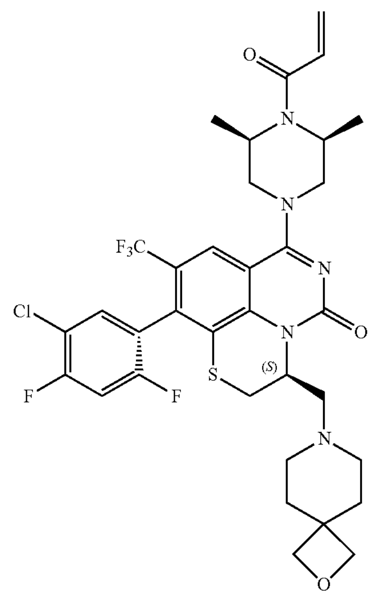 | ¹H NMR (400 MHz, CDCl₃) δ 8.06 (s, 1H), 7.28-7.27 (m, 1H), 7.07 (t, J = 8.8 Hz, 1H), 6.65-6.58 (m, 1H), 6.43-6.38 (dd, J = 1.6 Hz, 16.4 Hz, 1H), 5.78-5.76 (dd, J = 1.6 Hz, 10.4 Hz, 1H), 5.33-5.32 (m, 1H), 4.67-4.60 (m, 2H), 4.39-4.37 (m, 4H), 4.19-4.16 (m, 2H), 3.46-3.30 (m, 3H), 3.01-2.98 (m, 1H), 2.77-2.60 (m, 3H), 2.46-2.35 (m, 3H), 1.84-1.82 (m, 4H), 1.61-1.59 (m, 3H), 1.49-1.48 (m, 3H). | 724.2 |
| 567 | (3S)-7-((3S,5R)-4-acryloyl-3,5-dimethylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 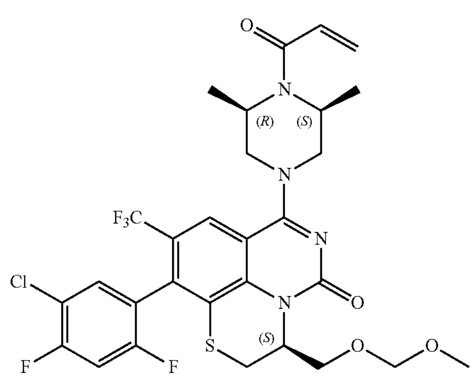 | ¹H NMR (400 MHz, CDCl₃) δ 8.06 (s, 1H), 7.29-7.27 (m, 1H), 7.10-7.04 (m, 1H), 6.65-6.59 (m, 1H), 6.42 (dd, J = 1.6 Hz, 16.4 Hz, 1H), 5.78 (dd, J = 1.6 Hz, 10.4 Hz, 1H), 5.50-5.46 (m, 1H), 4.68-4.62 (m, 4H), 4.21-4.17 (m, 2H), 3.80-3.76 (m, 2H), 3.42-3.32 (m, 6H), 3.09-3.04 (m, 1H), 1.59 (d, J = 2.8 Hz, 3H), 1.49-1.46 (m, 3H). | 659.3 |

TABLE 8-continued

Table of Thiomorpholines

| Ex. # | Name | Structure | ¹H NMR | MS (M + H)⁺ |
|---|---|---|---|---|
| 568 | (3S)-7-((3S,5R)-4-acryloyl-3,5-dimethylpiperazin-1-yl)-10-(5-chloro-2,4-difluorophenyl)-3-(hydroxymethyl)-9-(trifluoromethyl)-2H-[1,4]thiazino[2,3,4-ij]quinazolin-5(3H)-one | 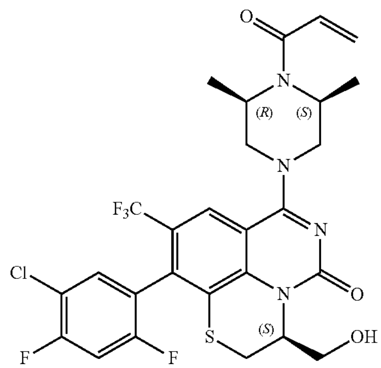 | ¹H NMR (400 MHz, CDCl₃) δ 8.08 (s, 1H), 7.26-7.23 (m, 1H), 7.10-7.04 (m, 1H), 6.65-6.58 (m, 1H), 6.43 (dd, J = 1.2 Hz, 16.8 Hz, 1H), 5.79-5.76 (m, 1H), 5.37-5.34 (m, 1H), 4.73-4.61 (m, 2H), 4.23-4.20 (m, 2H), 4.00-3.87 (m, 2H), 3.45-3.31 (m, 3H), 3.09-3.05 (m, 1H), 1.80-1.73 (m, 1H), 1.63 (d, J = 7.2 Hz, 3H), 1.46-1.43 (m, 3H). | 615.3 |
| 569 | (3S,10R)-7-((2S,5R)-4-acryloyl-2,5-dimethylpiperazin-1-yl)-9-chloro-3-((4-(2,2-difluoroethyl)piperazin-1-yl)methyl)-10-(1-methyl-1H-indazol-7-yl)-2,3-dihydro-5H-[1,4]thiazino[2,3,4-ij]quinazolin-5-one | 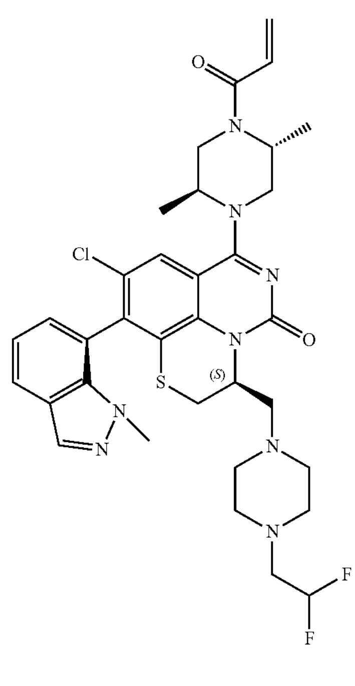 | ¹H NMR (400 MHz, CDCl₃) δ 8.06 (s, 1H), 7.86 (d, J = 8.0 Hz, 1H), 7.62 (d, J = 12.8 Hz, 1H), 7.30-7.28 (m, 1H), 7.15 (d, J = 6.8 Hz, 1H), 6.75-6.51 (m, 1H), 6.38 (t, J = 14.0 Hz, 1H), 5.99-5.69 (m, 2H), 5.37-5.33 (m, 1H), 5.07 (m, 0.5H), 4.82-4.70 (m, 1H), 4.45-4.35 (m, 1.5H), 4.15 (m, 0.5H), 3.78-3.61 (m, 5.5H), 3.33-3.24 (m, 2H), 3.07-3.05 (m, 1H), 2.73-2.51 (m, 11H), 1.50-1.43 (m, 6H). | 697.3 |

TABLE 8-continued

Table of Thiomorpholines

| Ex. # | Name | Structure | ¹H NMR | MS (M + H)⁺ |
|---|---|---|---|---|
| 570 | (3S,10S)-7-((2S,5R)-4-acryloyl-2,5-dimethylpiperazin-1-yl)-9-chloro-3-((4-(2,2-difluoroethyl)piperazin-1-yl)methyl)-10-(1-methyl-1H-indazol-7-yl)-2,3-dihydro-5H-[1,4]thiazino[2,3,4-ij]quinazolin-5-one | 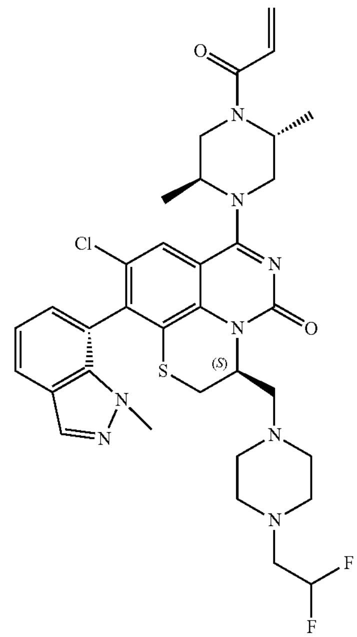 | ¹H NMR (400 MHz, CDCl₃) δ 8.06 (s, 1H), 7.86 (d, J = 8.0 Hz, 1H), 7.59 (m, 1H), 7.24-7.22 (m, 1H), 7.12 (d, J = 6.8 Hz, 1H), 6.67-6.51 (m, 1H), 6.38 (t, J = 15.6 Hz, 1H), 5.99-5.71 (m, 2H), 5.51-5.45 (m, 1H), 5.01-4.77 (m, 1.5H), 4.42-4.35 (m, 1H), 3.84-3.62 (m, 6H), 3.42-3.23 (m, 2.5H), 3.01 (m, 2H), 2.73-2.56 (m, 10H), 1.42-1.32 (m, 6H). | 697.3 |
| 571 | (3S)-7-(9-acryloyl-7-oxo-3,9-diazabicyclo[3.3.1]nonan-3-yl)-10-(2,4-difluorophenyl)-3-(methoxymethyl)-9-(trifluoromethyl)-2H-[1,4]thiazino[2,3,4-ij]quinazolin-5(3H)-one | 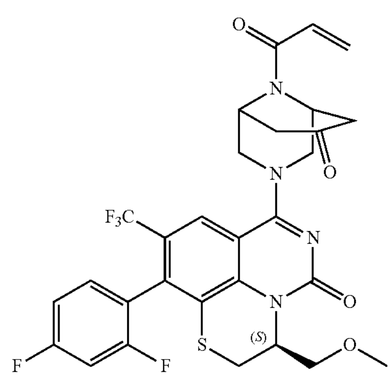 | ¹H NMR (400 MHz, CDCl₃) δ 7.85 (s, 1H), 7.19-7.13 (m, 1H), 7.05-6.94 (m, 2H), 6.72-6.64 (m, 1H), 6.49-6.45 (m, 1H), 5.90 (d, J = 10.4 Hz, 1H), 5.50-5.36 (m, 2H), 4.78-4.73 (m, 1H), 4.26-4.14 (m, 2H), 3.67-3.57 (m, 2H), 3.36-3.22 (m, 6H), 3.04-2.98 (m, 1H), 2.90-2.75 (m, 3H), 2.67-2.57 (m, 1H). | 621.2 |
| 572 | (3S)-7-(4-acryloylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one | 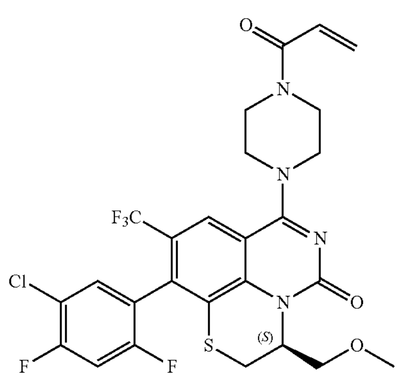 | ¹H NMR (400 MHz, CDCl₃) δ 7.80 (s, 1H), 7.29-7.27 (m, 1H), 7.09-7.05 (m, 1H), 6.62-6.55 (m, 1H), 6.37 (dd, J = 1.6 Hz, 16.8 Hz, 1H), 5.90 (dd, J = 1.2 Hz, 10.4 Hz, 1H), 5.46-5.41 (m, 1H), 3.99-3.91 (m, 3H), 3.80-3.79 (m, 5H), 3.67-3.63 (m, 2H), 3.41-3.36 (m, 4H), 3.04-3.00 (m, 1H). | 601.1 |

TABLE 8-continued

Table of Thiomorpholines

| Ex. # | Name | Structure | ¹H NMR | MS (M + H)⁺ |
|---|---|---|---|---|
| 573 | (S)-7-((2S,5R)-4-acryloyl-2,5-dimethylpiperazin-1-yl)-9-chloro-10-(4-fluorophenyl)-3-(methoxymethyl)-2H-[1,4]thiazino[2,3,4-ij]quinazolin-5(3H)-one | 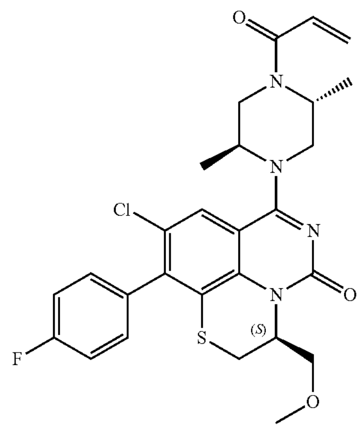 | ¹H NMR (400 MHz, CDCl₃) δ 7.60 (s, 1H), 7.29-7.22 (m, 4H), 6.67-6.58 (m, 1H), 6.45-6.43 (m, 1H), 5.85-5.80 (m, 1H), 5.52-5.50 (m, 1H), 5.07-5.06 (m, 0.5H), 4.91-4.87 (m, 0.5H), 4.78-4.75 (m, 0.5H), 4.41-4.36 (m, 1H), 4.15-4.07 (m, 1H), 3.84-3.77 (m, 2H), 3.74-3.67 (m, 2H), 3.44 (s, 3H), 3.35-3.31 (m, 1.5H), 3.05-3.01 (m, 1H), 1.50-1.40 (m, 6H). | 543.2 |
| 574 | (S)-7-((2S,5R)-4-acryloyl-2,5-dimethylpiperazin-1-yl)-3-((4-(2,2-difluoroethyl)piperazin-1-yl)methyl)-10-(4-fluorophenyl)-9-(trifluoromethyl)-2H-[1,4]thiazino[2,3,4-ij]quinazolin-5(3H)-one | 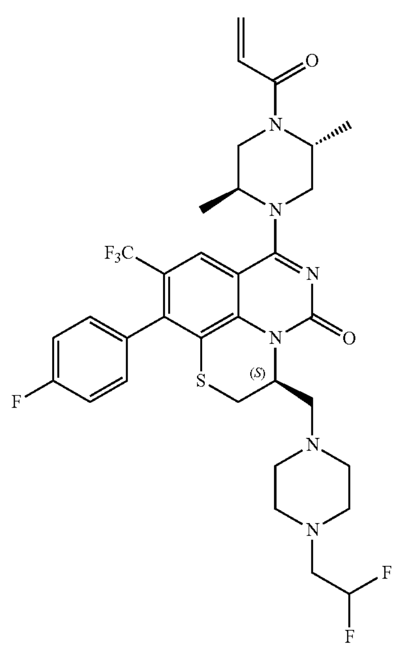 | ¹H NMR (400 MHz, CDCl₃) δ 7.90 (s, 1H), 7.28-7.21 (m, 4H), 6.70-6.40 (m, 2H), 6.12-5.82 (m, 2H), 5.42-5.38 (m, 1H), 5.13-5.10 (m, 0.5H), 4.86-4.73 (m, 1H), 4.50-4.38 (m, 1.5H), 3.77-3.73 (m, 2H), 3.41-3.30 (m, 2H), 3.06-2.97 (m, 1H), 2.91-2.80 (m, 4H), 2.72-2.64 (m, 4H), 1.66-1.65 (m, 3H), 1.56-1.49 (m, 4H), 1.25-1.23 (m, 3H). | 659.3 |

TABLE 8-continued

Table of Thiomorpholines

| Ex. # | Name | Structure | ¹H NMR | MS (M + H)+ |
|---|---|---|---|---|
| 575 | 2-(4-(((3S)-7-((2S,5R)-4-acryloyl-2,5-dimethylpiperazin-1-yl)-10-(2,4-difluorophenyl)-5-oxo-9-(trifluoromethyl)-3,5-dihydro-2H-[1,4]thiazino[2,3,4-ij]quinazolin-3-yl)methyl)piperazin-1-yl)acetamide | 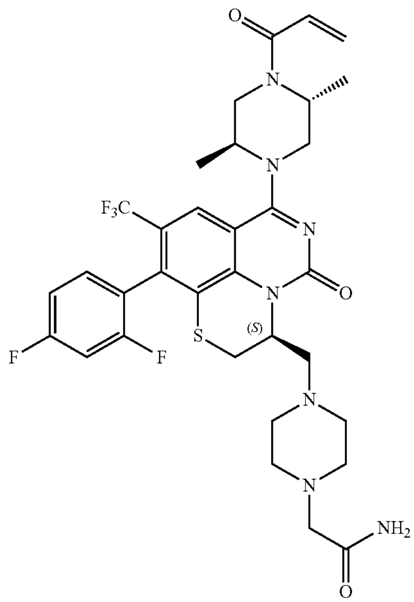 | ¹H NMR (400 MHz, CDCl₃) δ 7.84 (s, 1H), 7.21-7.14 (m, 1H), 7.05-6.94 (m, 2H), 6.66-6.50 (m, 1H), 6.37 (t, J = 14.8 Hz, 1H), 5.78 (t, J = 8.4 Hz, 1H), 5.45-5.27 (m, 2H), 5.05-5.02 (m, 0.5H), 4.78-4.67 (m, 1H), 4.41-4.35 (m, 1.5H), 4.10-4.05 (m, 0.5H), 3.75-3.50 (m, 3H), 3.36-2.95 (m, 5.5H), 2.93-2.50 (m, 9H), 1.49-1.39 (m, 6H). | 706.3 |
| 576 | (3S,10S)-3-(2-oxa-7-azaspiro[3.5]nonan-7-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one | 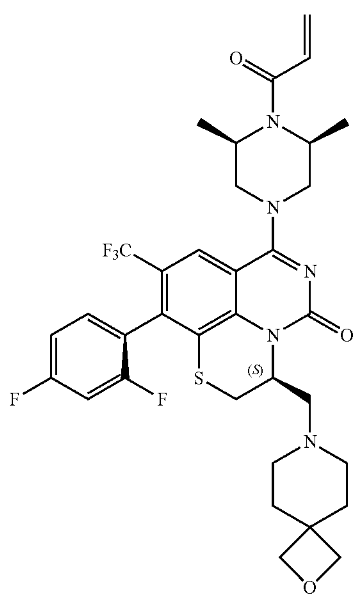 | ¹H NMR (400 MHz, CDCl₃) δ 8.06 (s, 1H), 7.18 (q, J = 8.4 Hz, 1H), 7.06-6.94 (m, 2H), 6.65-6.59 (m, 1H), 6.40 (dd, J = 16.8 Hz, 2.0 Hz, 1H), 5.77 (dd, J = 10.4 Hz, 1.6 Hz, 1H), 5.37-5.35 (m, 1H), 4.72-4.65 (m, 2H), 4.46-4.32 (m, 4H), 4.20-4.17 (m, 2H), 3.48-3.30 (m, 3H), 3.00-2.96 (m, 1H), 2.76-2.66 (m, 1H), 2.65-2.51 (m, 2H), 2.47-2.28 (m, 3H), 1.82-1.81 (m, 4H), 1.61-1.60 (m, 3H), 1.48 (d, J = 6.4 Hz, 3H). | 690.2 |

TABLE 8-continued

Table of Thiomorpholines

| Ex. # | Name | Structure | ¹H NMR | MS (M + H)⁺ |
|---|---|---|---|---|
| 577 | (3S)-3-(2-oxa-7-azaspiro[3.5]nonan-7-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one | 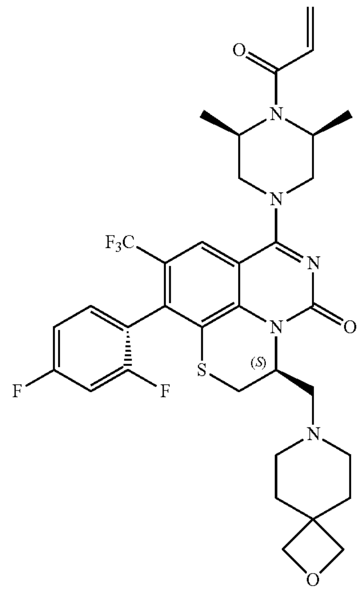 | ¹H NMR (400 MHz, CDCl₃) δ 8.06 (s, 1H), 7.17 (q, J = 8.0 Hz, 1H), 7.04-6.95 (m, 2H), 6.65-6.59 (m, 1H), 6.42-6.38 (m, 1H), 5.78-5.76 (dd, J = 10.4 Hz, 1.6 Hz, 1H), 5.32-5.31 (m, 1H), 4.66-4.57 (m, 2H), 4.44-4.32 (m, 4H), 4.20-4.16 (m, 2H), 3.44-3.30 (m, 3H), 3.07-2.98 (m, 1H), 2.76-2.71 (m, 1H), 2.68-2.52 (m, 2H), 2.49-2.27 (m, 3H), 1.80-1.71 (m, 4H), 1.62-1.60 (m, 3H), 1.49-1.42 (m, 3H). | 690.3 |
| 578 | (3S,10R)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 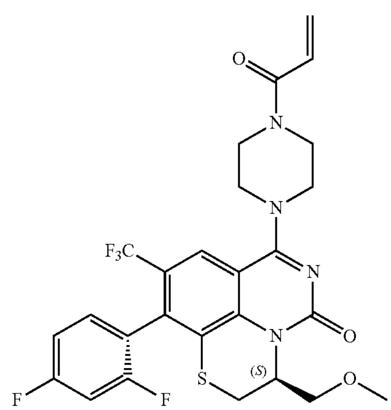 | ¹H NMR (400 MHz, CDCl₃) δ 7.80 (s, 1H), 7.18 (q, J = 8.0 Hz, 1H), 7.04-6.95 (m, 2H), 6.59 (dd, J = 10.8 Hz, 16.8 Hz, 1H), 6.37 (d, J = 15.6 Hz, 1H), 5.78 (dd, J = 1.2 Hz, 10.0 Hz, 1H), 5.44-5.39 (m, 1H), 4.01-3.91 (m, 3H), 3.80-3.78 (m, 5H), 3.66-3.64 (m, 2H), 3.39-3.33 (m, 4H), 3.04-3.00 (m, 1H). | 567.2 |
| 579 | (3S,10S)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 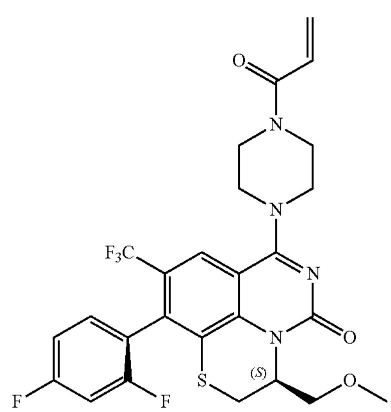 | ¹H NMR (400 MHz, CDCl₃) δ 7.81 (s, 1H), 7.18 (q, J = 6.4 Hz, 1H), 7.05-6.93 (m, 2H), 6.59 (dd, J = 10.4 Hz, 16.8 Hz, 1H), 6.37 (dd, J = 2.0 Hz, 16.8 Hz, 1H), 5.78 (dd, J = 2.0 Hz, 10.4 Hz, 1H), 5.47-5.39 (m, 1H), 4.00-3.92 (m, 3H), 3.81-3.78 (m, 5H), 3.69-3.60 (m, 2H), 3.39 (s, 3H), 3.37-3.33 (m, 1H), 3.04-2.98 (m, 1H). | 567.2 |

TABLE 8-continued

Table of Thiomorpholines

| Ex. # | Name | Structure | ¹H NMR | MS (M + H)⁺ |
|---|---|---|---|---|
| 580 | (3S,10S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 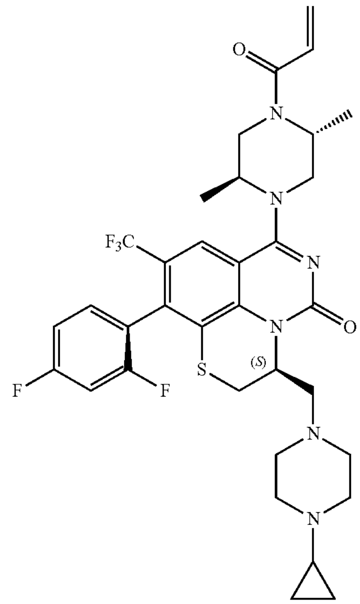 | ¹H NMR (400 MHz, CDCl₃) δ 7.87 (d, J = 6.0, 1H), 7.31-7.27 (m, 1H), 7.16-7.10 (m, 2H), 6.73-6.55 (m, 1H), 6.46-6.37 (m, 1H), 5.84-5.79 (m, 1H), 5.44-5.42 (m, 1H), 5.13-4.70 (m, 1.5H), 4.47-4.36 (m, 1H), 4.11-3.70 (m, 3H), 3.52-3.32 (m, 1.5H), 3.11-3.03 (m, 1H), 2.84-2.55 (m, 10H), 1.52-1.43 (m, 7H), 0.57-0.42 (m, 4H). | 689.3 |
| 581 | (3S,10R)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 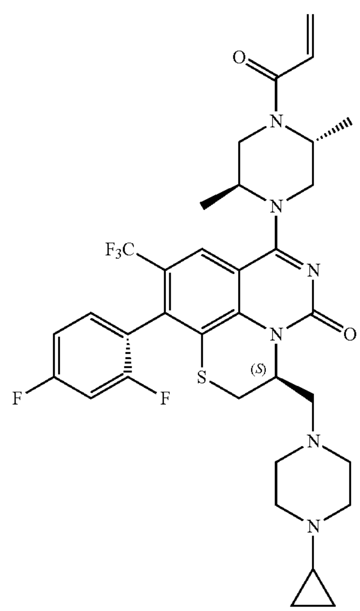 | ¹H NMR (400 MHz, CDCl₃) δ 7.87 (s, 1H), 7.28-7.19 (m, 1H), 7.09-6.98 (m, 2H), 6.72-6.54 (m, 1H), 6.46-6.37 (m, 1H), 5.86-5.79 (m, 1H), 5.42-5.35 (m, 1H), 5.12-4.68 (m, 1.5H), 4.52-4.33 (m, 1H), 4.19-3.67 (m, 3H), 3.51-3.27 (m, 1.5H), 3.10-3.05 (m, 1H), 2.87-2.51 (m, 10H), 1.52-1.29 (m, 7H), 0.59-0.44 (m, 4H). | 689.3 |

TABLE 8-continued

Table of Thiomorpholines

| Ex. # | Name | Structure | ¹H NMR | MS (M + H)⁺ |
|---|---|---|---|---|
| 587 | (3S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2H-[1,4]thiazino[2,3,4-ij]quinazolin-5(3H)-one | 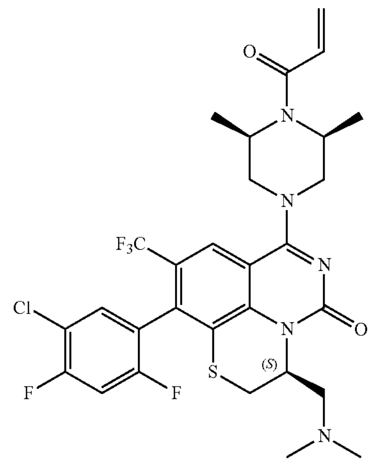 | ¹H NMR (400 MHz, CDCl$_3$) δ 8.07 (s, 1H), 7.29-7.28 (m, 1H), 7.10-7.04 (m, 1H), 6.66-6.59 (m, 1H), 6.44-6.38 (m, 1H), 5.77 (dd, J = 10.4 Hz, 1.2 Hz, 1H), 5.42-5.36 (m, 1H), 4.68-4.64 (m, 2H), 4.18 (d, J = 13.2 Hz, 2H), 3.55-3.50 (m, 1H), 3.41-3.31 (m, 2H), 3.07-3.00 (m, 1H), 2.91-2.82 (m, 1H), 2.45-2.32 (m, 7H), 1.62-1.59 (m, 3H), 1.50-1.46 (m, 3H). | 642.2 |
| 588 | 8'-((2S,5R)-4-Acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 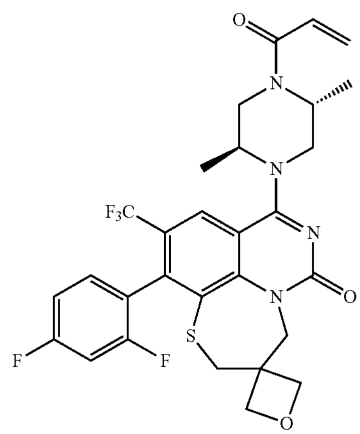 [SMILES: C=CC(=O)N1C[C@H](C)N(c2nc(=O)n3c4c(c(-c5ccc(F)cc5F)c(C(F)(F)F)cc24)SCC2(COC2)C3)C[C@H]1C] | ¹H NMR (400 MHz, MeOH-d$_4$) δ 7.97 (d, J = 2.7 Hz, 1H), 7.30 (dq, J = 13.7, 7.6 Hz, 1H), 7.11 (t, J = 8.3 Hz, 2H), 6.90-6.72 (m, 1H), 6.28 (ddd, J = 16.7, 5.6, 2.0 Hz, 1H), 5.80 (ddd, J = 9.7, 7.2, 2.0 Hz, 1H), 4.87-4.60 (m, 3H), 4.55-4.36 (m, 3H), 4.34-3.69 (m, 4H), 3.62-3.40 (m, 3H), 1.49-1.25 (m, 6H) | 607.2 |
| 489 | 8'-(4-Acryloylpiperazin-1-yl-2,2,3,3,5,5,6,6-d$_8$)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 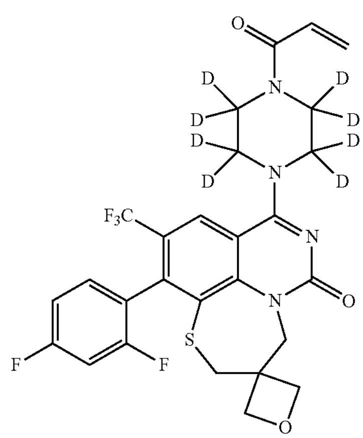 [SMILES: [2H]C1([2H])N(C(=O)C=C)C([2H])([2H])C([2H])([2H])N(c2nc(=O)n3c4c(c(-c5ccc(F)cc5F)c(C(F)(F)F)cc24)SCC2(COC2)C3)C1([2H])[2H]] | ¹H NMR (400 MHz, MeOH-d$_4$) δ 8.00 (s, 1H), 7.30 (q, J = 7.7 Hz, 1H), 7.11 (t, J = 8.7 Hz, 2H), 6.80 (dd, J = 16.7, 10.6 Hz, 1H), 6.27 (dd, J = 16.7, 1.9 Hz, 1H), 5.80 (dd, J = 10.6, 2.0 Hz, 1H), 4.82-4.54 (m, 2H), 4.43 (d, J = 5.5 Hz, 2H), 3.61-3.46 (m, 2H), 3.23-3.11 (m, 2H) | 587.2 |

Syntheses of Intermediates

7-chloro-8-iodo-6-(trifluoromethyl)quinazoline-2,4 (1H,3H)-dione

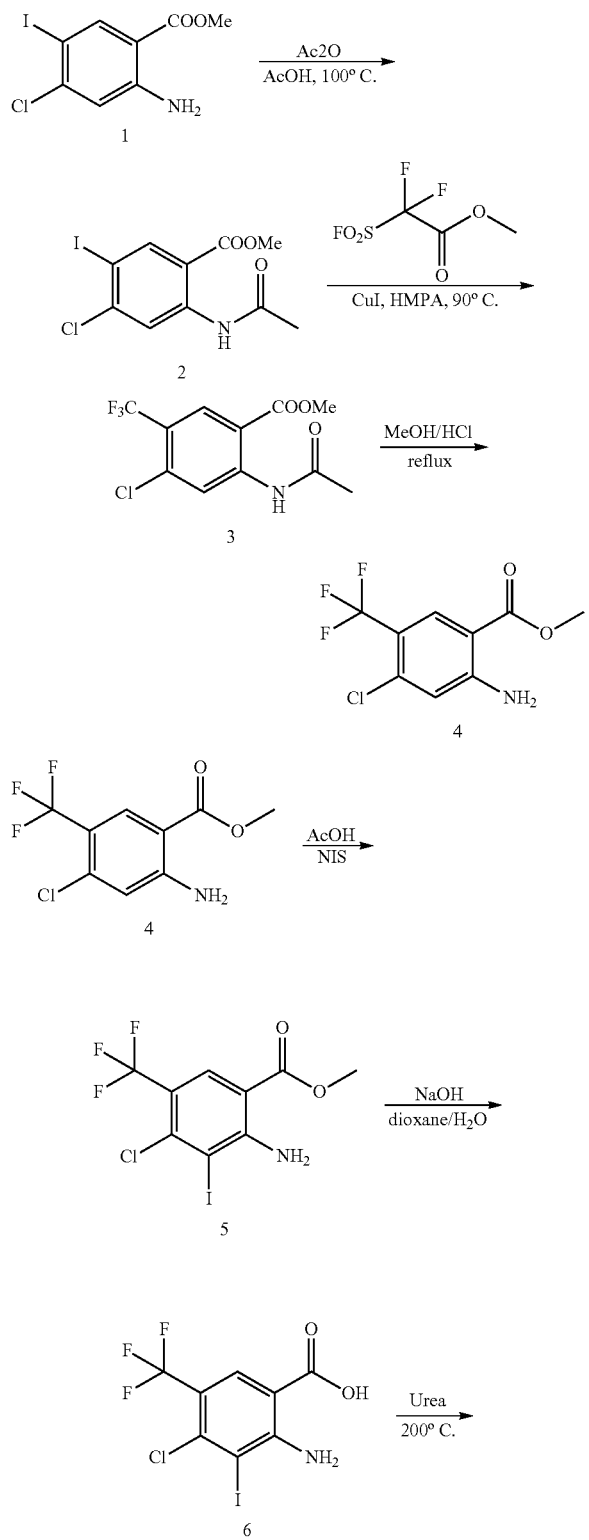

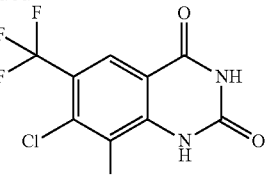

Methyl 2-acetamido-4-chloro-5-iodobenzoate (2)

To a mixture of methyl 2-amino-4-chloro-5-iodobenzoate (50.00 g, 160.51 mmol) in AcOH (500 mL) was added Ac$_2$O (19.66 g, 192.61 mmol). The mixture was stirred at 100° C. for 16 hours. After completion, the mixture was cooled to room temperature, filtered and washed with Petroleum Ether (200 mL) to afford crude product (35 g, 62% yield) as white solid. MS (ESI) m/z: 353.9 [M+H]$^+$.

Methyl 2-acetamido-4-chloro-5-(trifluoromethyl)benzoate (3)

To a mixture of methyl 2-acetamido-4-chloro-5-iodobenzoate (35.00 g, 98.98 mmol) in DMF (350 mL) was added methyl 2,2-difluoro-2-(fluorosulfonyl)acetate (70.09 g, 395.99 mmol), HMPA (70.98 g, 395.99 mmol) and CuI (15.05 g, 79.19 mmol). The mixture was stirred at 90° C. under N$_2$ for 16 hours. After completion, the mixture was poured into water (300 mL), extracted with EtOAc (3×200 mL). The combined organic phase was washed with brine (500 mL) and dried over Na$_2$SO$_4$. After filtration and concentration, the residue was purified by silica gel column using a gradient of Petrolum Ether/EtOAc (100/1 to 20/1) to afford desired product (25.00 g, 84% yield) as white solid. MS (ESI) m/z: 296.0 [M+H]$^+$.

Methyl 2-amino-4-chloro-5-(trifluoromethyl)benzoate (4)

A mixture of methyl 2-acetamido-4-chloro-5-(trifluoromethyl)benzoate (20.00 g, 67.79 mmol) in HCl/MeOH (200 mL) was stirred at 70° C. for 2 hours. The mixture was concentrated and a saturated aqueous solution of NaHCO$_3$ (100 mL) was added. The resulting mixture was extracted with EtOAc (3×50 mL). The combined organic phase was washed with brine (100 mL) and dried over Na$_2$SO$_4$. The solvent was removed in vacuo to afford the crude product (18.00 g, crude) as a yellow solid. MS (ESI) m/z: 254.0 [M+H]$^+$

Methyl 2-amino-4-chloro-3-iodo-5-(trifluoromethyl) benzoate (5)

To a mixture of methyl 2-amino-4-chloro-5-(trifluoromethyl)benzoate (28.00 g, 110.23 mmol) in AcOH (280 mL) was added N-Iodosuccinimide (35.00 g, 143.29 mmol). The mixture was stirred at 50° C. for 16 hours. After completion, the mixture was poured into water (400 mL), extracted with EtOAc (3×250 mL). The combined organic phases were washed with brine (400 mL) and dried over Na$_2$SO$_4$. After filtration and concentration, the residue was washed with PE (200 mL) to afford the crude product (38.00 g, crude) as white solid. MS (ESI) m/z: 379.9 [M+H]+

2-amino-4-chloro-3-iodo-5-(trifluoromethyl)benzoic acid (6)

To a solution of methyl 2-amino-4-chloro-3-iodo-5-(trifluoromethyl)benzoate (25.00 g, 65.96 mmol) in dioxane (200 mL) and water (200 mL) was added NaOH (5.28 g, 131.92 mmol). The mixture was stirred at 90° C. for 3 hours. After completion, the mixture was poured into water (200 mL). The pH was adjusted to 4~5 and extracted with EtOAc (3×150 mL). The combined organic phase was washed with brine (300 mL) and dried over Na$_2$SO$_4$. The solvent was removed in vacuum to give 2-amino-4-chloro-3-iodo-5-(trifluoromethyl)benzoic acid (23 g, crude) as yellow solid. MS (ESI) m/z: 365.9 [M+H]+

7-chloro-8-iodo-6-(trifluoromethyl)quinazoline-2,4 (1H,3H)-dione (7)

A mixture of 2-amino-4-chloro-3-iodo-5-(trifluoromethyl)benzoic acid (5 g, 13.71 mmol) and urea (16.45 g, 274.2 mmol) was stirred at 200° C. for 5 hours. After completion, the mixture was cooled to 80° C., water (100 mL) was added to the solution and stirred for 1 hour. The mixture was extracted with EtOAc (3×100 mL). The combined organic phase was washed with brine (100 mL) and dried over Na$_2$SO$_4$. After filtration and concentration, the residue was purified by silica gel column using a mixture of Petrolum Ether/EtOAc (4/1) to afford the desired product (1.76 g, 33% yield) as a white solid. MS (ESI) m/z: 388.8 [M−H]−

11'-Chloro-10'-(trifluoromethyl)-2'H,4'H,6'H-spiro[oxetane-3,3'-[1,4]thiazepino[2,3,4-ij]quinazoline]-6',8'(7'H)-dione

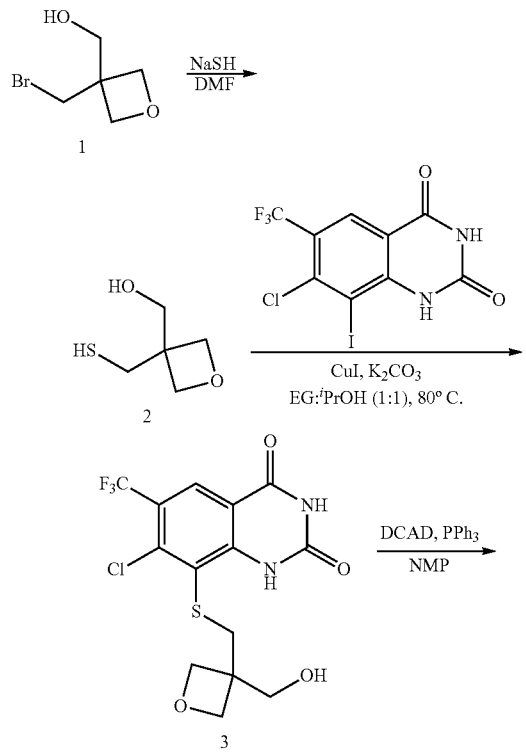

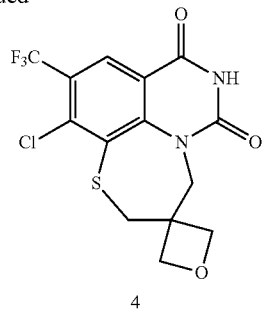

[3-(Sulfanylmethyl)oxetan-3-yl]methanol (2)

Sodium hydrosulfide hydrate (0.209 g, 2.82 mmol, 1.1 equiv) was suspended in anhydrous DMF (18 mL) and purged with argon. (3-(bromomethyl)oxetan-3-yl)methanol (0.3 mL, 2.57 mmol, 1.0 equiv) was dissolved in anhydrous DMF (1 mL) in a separated vial and purged with argon. After 15 min, the solution of (3-(bromomethyl)oxetan-3-yl)methanol was added to the sodium hydrosulfide suspension and the sealed vial was stirred at 45° C. for 2 hours under argon. After, the reaction mixture was used in the next step without characterization, work-up and purification (transferred to the vessel via syringe under argon atmosphere).

7-Chloro-8-({[3-(hydroxymethyl)oxetan-3-yl]methyl}sulfanyl)-6-(trifluoromethyl)-1,2,3,4-tetrahydroquinazoline-2,4-dione (3)

To the vial containing 7-chloro-8-iodo-6-(trifluoromethyl)-1,2,3,4-tetrahydroquinazoline-2,4-dione (1.0 g, 2.56 mmol, 1.0 equiv), K$_2$CO$_3$ (0.708 g, 5.12 mmol, 2.0 equiv) and copper(I) iodide (0.488 g, 2.56 mmol, 1.0 equiv) was added. Solvents, isopropanol (40 mL) and ethylene glycol (40 mL) were added, and the vial was purged with argon for 20 min. Next, crude [3-(sulfanylmethyl)oxetan-3-yl]methanol (0.344 g, 2.56 mmol, 1.0 equiv) was added to the reaction mixture via syringe under argon. The sealed vial was stirred at 80° C. overnight. According to UPLC, 15% of aryl iodide remained. Next, additional freshly prepared [3-(sulfanylmethyl)oxetan-3-yl]methanol (0.138 g, 1.02 mmol, 0.4 equiv) was added. The reaction vial was purged with argon, sealed, and stirred overnight at 80° C. According to UPLC, 6% of aryl iodide remained. Next, the reaction mixture was concentrated, and the obtained oil was suspended in a saturated aqueous NH$_4$Cl solution then stirred vigorously for 20 min. The NH$_4$Cl solution was washed with EtOAc (3×100 mL), then the combined organic layers were washed with saturated aqueous NH$_4$Cl (1×100 mL) and dried over MgSO$_4$. The combined organic layers were concentrated by rotary evaporation. Purification by flash chromatography (Interchim puriFlash® F0120 silica gel column, MeOH/EtOAc=10:90, 60 min) afforded the title compound in poor purity. Re-purification by chromatography (Interchim, puriFlash® F0120 silica gel column) with EtOAc/acetone (1:1, 30 min) afforded the title compound as a white solid (0.535 g, 53% yield): $^1$H NMR (300 MHz, DMSO-d$_6$) δ 11.86 (s, 1H), 10.58 (s, 1H), 8.20 (s, 1H), 5.12 (t, J=5.4 Hz, 1H), 4.31 (s, 4H), 3.71 (d, J=5.1 Hz, 2H), 3.21 (s, 2H); LRMS-ESI (m/z) [M−H]− calculated for C$_{14}$H$_{11}$ClF$_3$N$_2$O$_4$S 395.01, found 395.3.

1005

11'-Chloro-10'-(trifluoromethyl)-2'H,4'H,6'H-spiro[oxetane-3,3'-[1,4]thiazepino[2,3,4-ij]quinazoline]-6',8'(7'H)-dione (4)

7-Chloro-8-({[3-(hydroxymethyl)oxetan-3-yl]methyl}sulfanyl)-6-(trifluoromethyl)-1,2,3,4-tetrahydroquinazoline-2,4-dione (0.485 g, 1.222 mmol, 1.0 eq) and triphenylphosphine (1.28 g, 4.89 mmol, 4.0 equiv) were dissolved in CH$_2$Cl$_2$ (anhydrous, 19.4 mL) and cooled to 0° C. under argon over 15 minutes before dropwise addition of di-p-chlorobenzyl azodicarboxylate (Di-(4-chlorobenzyl) azodicarboxylate, 1.80 g, 4.89 mmol, 4.0 equiv) in anhydrous CH$_2$Cl$_2$ over 1 min. The reaction was allowed to stir at 0° C. under argon for 60 min. UPLC after 60 min indicated no remaining starting material. The precipitated solid was isolated by filtration under vacuum and washed with CH$_2$Cl$_2$. The filtrate was washed with saturated aqueous NH$_4$Cl. The layers were separated, and aqueous layer was washed with CH$_2$Cl$_2$ (2×25 mL). The combined organic layers were dried on a rotary evaporator. Purification by column chromatography (Interchim puriFlash© F0080 silica gel column), eluting with EtOAc/hexanes (3:2, 60 min) afforded the title compound. Fractions with the desired product were evaporated to dryness by rotary evaporation and the obtained material was suspended in mixture of hexanes/EtOAc (5:3) and vigorously stirred. The solid was filtered off and dried under vacuum. The title compound was obtained as a white solid (340 mg, 67% yield): $^1$H NMR (300 MHz, DMSO-d$_6$) δ 12.01 (s, 1H), 8.04 (s, 1H), 7.46-7.40 (m, 2H), 5.08 (s, 2H), 4.39 (d, J=5.7 Hz, 2H), 3.72 (br s, 2H); $^{13}$C NMR (75 MHz, DMOS-d$_6$) δ 160.7, 156.3, 151.6, 145.1, 135.6, 129.7, 128.6, 128.4, 123.0, 116.3, 77.5, 65.1, 51.4, 41.4, 37.6; LRMS-ESI (m/z) [M–H]$^-$ calculated for C$_{14}$H$_9$ClF$_3$N$_2$O$_3$S 377.00, found 376.84.

X. Example 448

(3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one

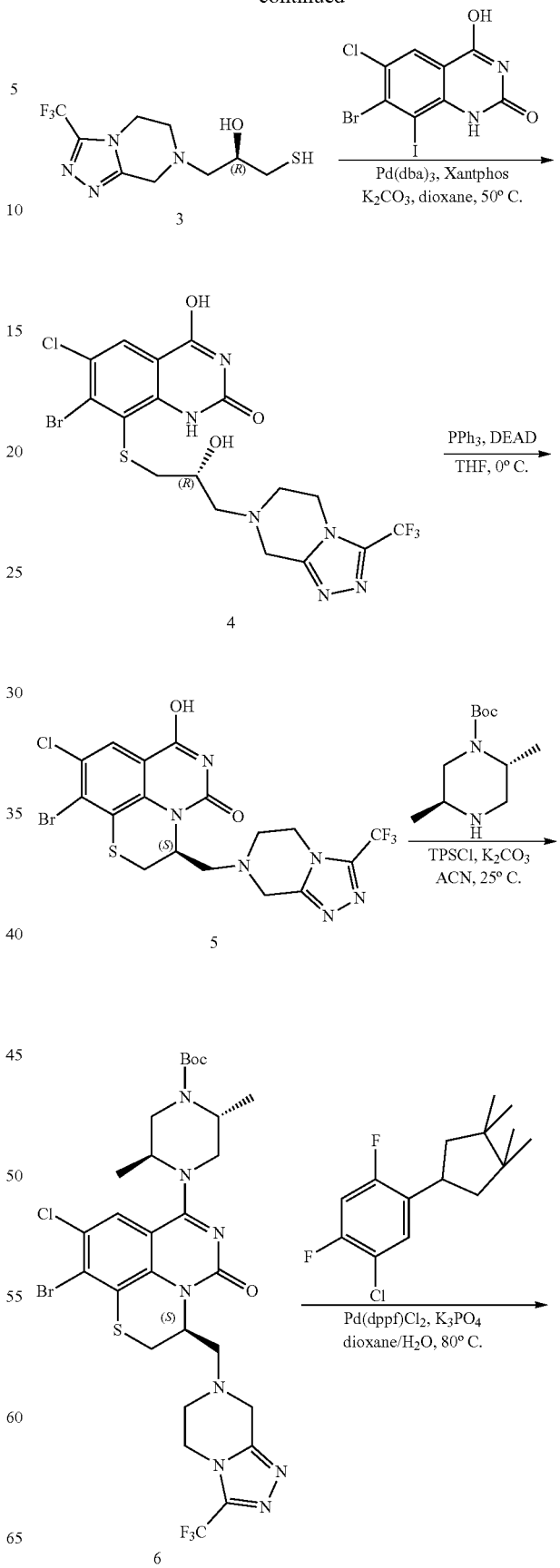

1007
-continued

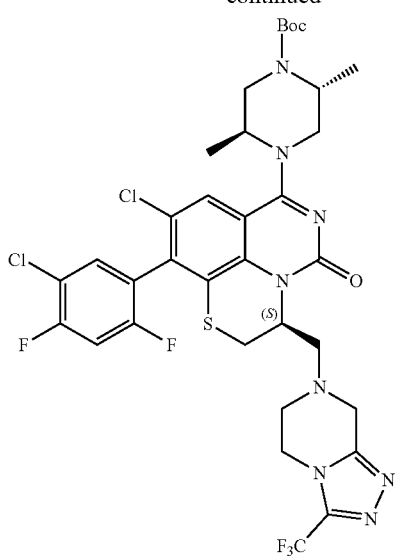

7

→ TFA/DCM

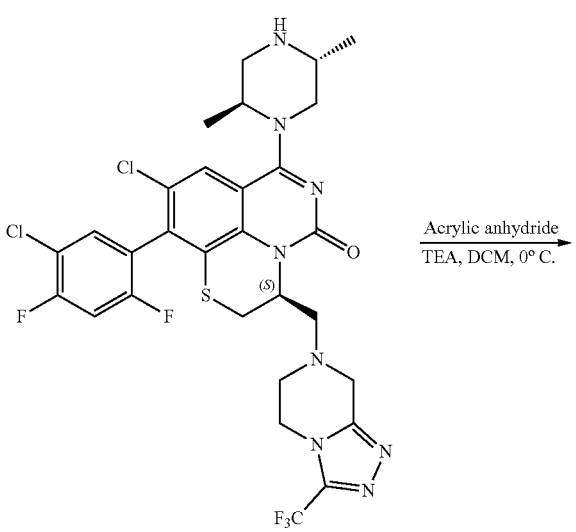

8

1008
-continued

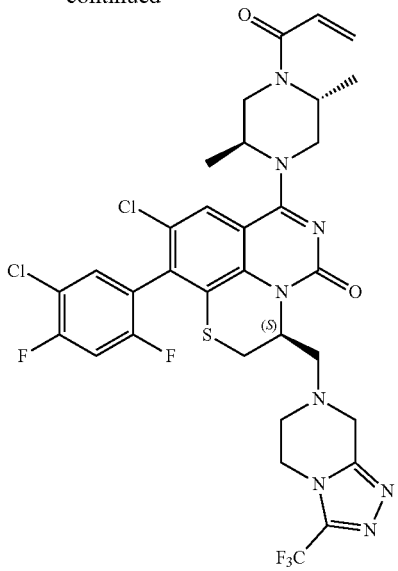

9

(R)-7-(oxiran-2-ylmethyl)-3-(trifluoromethyl)-5,6,7,8-tetrahydro-[1,2,4]triazolo[4,3-a]pyrazine (2)

To a mixture of (S)-oxiran-2-ylmethyl 3-nitrobenzenesulfonate (7.9, 30.7 mmol), 3-(trifluoromethyl)-5,6,7,8-tetrahydro-[1,2,4]triazolo[4,3-a]pyrazine (7.0 g, 30.7 mmol) in acetonitrile (50 mL) was added potassium carbonate (12.7 g, 92.1 mmol) at 20° C. under nitrogen atmosphere. The mixture was stirred under nitrogen atmosphere at room temperature for 20 hours. After completion, the mixture was concentrated. The residue was purified by silica gel column eluting with 2% methanol in dichloromethane to afford the product (6.2 g, 24.7 mmol) as a pale yellow oil. MS (ESI) m/z: 249.1 [M+H]$^+$.

(R)-1-mercapto-3-(3-(trifluoromethyl)-5,6-dihydro-[1,2,4]triazolo[4,3-a]pyrazin-7(8H)-yl)propan-2-ol (3)

To a mixture of (R)-7-(oxiran-2-ylmethyl)-3-(trifluoromethyl)-5,6,7,8-tetrahydro-[1,2,4]triazolo[14,3-a]pyrazine (6.1 g, 24.6 mmol) and tetrabutylammonium fluoride (30.7 mL, 30.7 mmol, 1.0 M in tetrahydrofuran) in tetrahydrofuran (50 mL) was added 1,1,1,3,3,3-hexamethyldisilathiane (5.4 g, 30.7 mmol) at 0° C. The mixture was stirred at room temperature for 2 hrs. After completion, the mixture was poured into water (200 mL), extracted with ethyl acetate (3×200 mL). The combined organic phase was washed with brine (300 mL) and dried over anhydrous sodium sulfate. The mixture was concentrated and the residue was purified by silica gel column eluting with dichloromethane/methanol (50/1) to afford (R)-1-mercapto-3-(3-(trifluoromethyl)-5,6-dihydro-[1,2,4]triazolo[4,3-a]pyrazin-7(8H)-yl)propan-2-ol (4.8 g, 17.0 mmol, 70% yield) as a pale yellow oil. MS (ESI) m/z: 283.1 [M+H]$^+$.

(R)-7-bromo-6-chloro-4-hydroxy-8-((2-hydroxy-3-(3-(trifluoromethyl)-5,6-dihydro-[1,2,4]triazolo[4,3-a]pyrazin-7(8H)-yl)propyl)thio)quinazolin-2(1H)-one (4)

To a mixture of 7-bromo-6-chloro-4-hydroxy-8-iodoquinazolin-2(1H)-one (3.9 g, 10.0 mmol), potassium carbonate Acrylic anhydride
TEA, DCM, 0° C.

(4.14 g, 30.0 mmol), (R)-1-mercapto-3-(3-(trifluoromethyl)-5,6-dihydro-[1,2,4]triazolo[4,3-a]pyrazin-7(8H)-yl)propan-2-ol (3.1 g, 11.0 mmol) and 4,5-bis(diphenyl-phosphino)-9,9-dimethylxanthene (1.16 g, 2.0 mmol) in dioxane (128 mL) was added tris(dibenzylideneacetone) dipalladium (0.92 g, 1.0 mmol). The mixture was stirred at 55° C. under nitrogen atmosphere for 8 hrs. After completion, the mixture was filtered. The filtrate was concentrated and the residue was purified by silica gel column chromatography (1-5% methanol in dichloromethane) to afford (R)-7-bromo-6-chloro-4-hydroxy-8-((2-hydroxy-3-(3-(trifluoromethyl)-5,6-dihydro-[1,2,4]triazolo[4,3-a]pyrazin-7(8H)-yl)propyl)thio)quinazolin-2(1H)-one (3.5 g, 63% yield) as a yellow solid. MS (ESI) m/z: 557.0 [M+H]⁺.

(S)-10-bromo-9-chloro-7-hydroxy-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (5)

To a mixture of (R)-7-bromo-6-chloro-4-hydroxy-8-((2-hydroxy-3-(3-(trifluoromethyl)-5,6-dihydro-[1,2,4]triazolo[4,3-a]pyrazin-7(8H)-yl)propyl)thio)quinazolin-2(1H)-one (3.5 g, 6.3 mmol) and triphenylphosphine (2.0 g, 7.5 mmol) in tetrahydrofuran (25 mL) was added diethyl azodicarboxylate (1.6 g, 7.5 mmol) at 0° C. The mixture was stirred at 0° C. for 20 min. After completion, the mixture was concentrated. The residue was purified by flash chromatography column (C18, 5-95% acetonitrile in water) to afford (S)-10-bromo-9-chloro-7-hydroxy-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one as a pale yellow solid. MS (ESI): m/z: 539.0 [M+H]⁺.

(2R,5S)-tert-butyl 4-((S)-10-bromo-9-chloro-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (6)

To a mixture of (S)-10-bromo-9-chloro-7-hydroxy-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (1.05 g, 2.0 mmol) and K₂CO₃ (828 mg, 6.0 mmol) in acetonitrile (10 mL) was added 2,4,6-triisopropylbenzene-1-sulfonyl chloride (906 mg, 3.0 mmol). The mixture was stirred at 20° C. for 5 hours. To the mixture was added (2R,5S)-tert-butyl 2,5-dimethylpiperazine-1-carboxylate (1.28 g, 6.0 mmol) and stirred at 20° C. for another 3 hours. After completion, the mixture was concentrated under reduced pressure. The residue was purified by silica gel column with 1-5% methanol in dichloromethane as gradient to afford desired product (580 mg, 0.80 mmol, 40% yield) as yellow solid. LC-MS m/z: 735.1 [M+H]⁺;

(2R,5S)-tert-butyl 4-((3S)-9-chloro-10-(5-chloro-2,4-difluorophenyl)-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (7)

To a mixture of (2R,5S)-tert-butyl 4-((S)-10-bromo-9-chloro-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (210 mg, 0.28 mmol) and tripotassium orthophosphate (178 mg, 0.84 mmol) in 1,4-dioxane (5 mL) and water (1 mL) were added [1,1'-bis(diphenylphosphino)ferrocene]dichloropalladium(II) (40.2 mg, 0.05 mmol) and 2-(5-chloro-2,4-difluorophenyl)-4,4,5,5-tetramethyl-1,3,2-dioxaborolane (391 mg, 1.4 mmol). The mixture was stirred at 90° C. for 3 hours. After completion, the mixture was concentrated and the residue was purified by silica gel column with 1-5% methanol in dichloromethane as gradient to afford (2R,5S)-tert-butyl 4-((3S)-9-chloro-10-(5-chloro-2,4-difluorophenyl)-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (203 mg, 0.25 mmol) as yellow solid. MS (ESI) m/z: 801.2 [M+H]⁺.

(3S)-9-chloro-10-(5-chloro-2,4-difluorophenyl)-7-((2S,5R)-2,5-dimethylpiperazin-1-yl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (8)

To a cooled mixture of (2R,5S)-tert-butyl 4-((3S)-9-chloro-10-(5-chloro-2,4-difluorophenyl)-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (203 mg, 0.25 mmol) in dichloromethane (3 ml) was added trifluoroacetic acid (1 mL) at 20° C. The reaction solution was stirred at room temperature for 1 hour. After completion, the mixture was concentrated. The residue was purified by silica gel column with 1-5% methanol in dichloromethane as gradient to afford (3S)-9-chloro-10-(5-chloro-2,4-difluorophenyl)-7-((2S,5R)-2,5-dimethylpiperazin-1-yl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (116 mg, 0.165 mmol) as a yellow solid. MS (ESI) m/z: 701.2[M+H]⁺.

(3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (9)

To a mixture of (3S)-9-chloro-10-(5-chloro-2,4-difluorophenyl)-7-((2S,5R)-2,5-dimethylpiperazin-1-yl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (116 mg, 0.165 mmol) and triethyl amine (100 mg, 1.0 mmol) in dichloromethane (5 mL) was added acrylic anhydride (31 mg, 0.25 mmol) at 0° C. The mixture was stirred at 0° C. for 1 h. After completion, the mixture was poured into ice-water (50 mL) and extracted with ethyl acetate (3×20 mL). The organic layer was dried over Na₂SO₄ and concentrated. The residue was purified by preparative High Performance Liquid Chromatography (10% to 95% acetonitrile in water) to afford the product as a white solid (43 mg, 0.06 mmol). ¹H NMR (400 MHz, CDCl₃) δ 7.59-7.53 (m, 1H), 7.33-7.28 (m, 1H), 7.13-7.08 (m, 1H), 6.61-6.48 (m, 1H), 6.40-6.32 (m, 1H), 5.79-5.75 (m, 1H), 5.54-5.38 (brs, 1H), 5.03-4.96 (brs, 0.5 H), 4.80-4.70 (m, 1H), 4.38-4.09 (m, 2.5H), 4.07-3.96 (m, 3.5H), 3.71-3.65 (m, 2H), 3.30-3.08 (m, 5.5H), 2.96-2.91 (m, 1H), 2.90-2.83 (m, 2H), 1.46-1.38 (m, 3H), 1.32-1.25 (m, 3H). MS (ESI) m/z: 755.1 [M+H]⁺.

1011
Y. Example 462
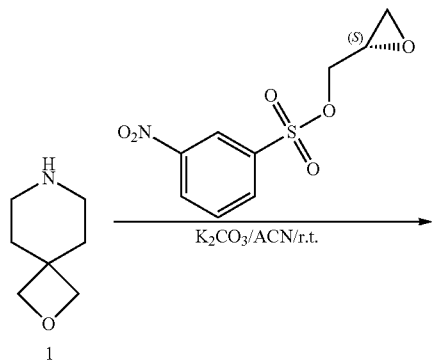
1
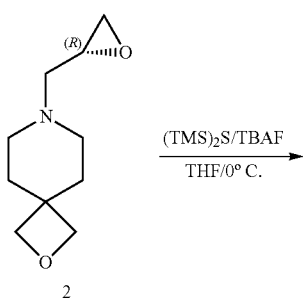
2
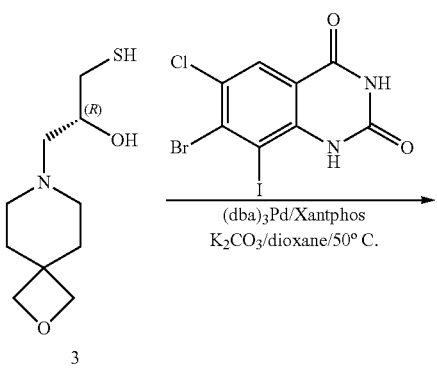
3
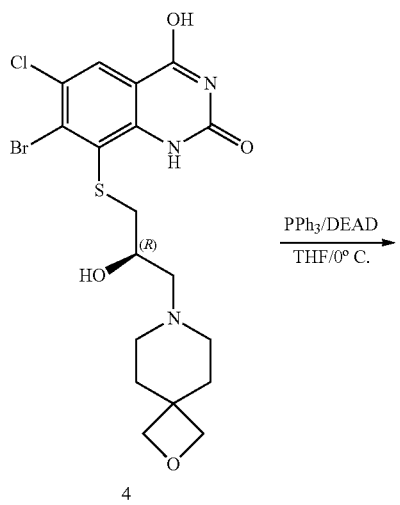
4
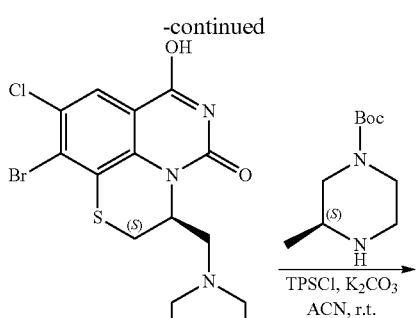
5
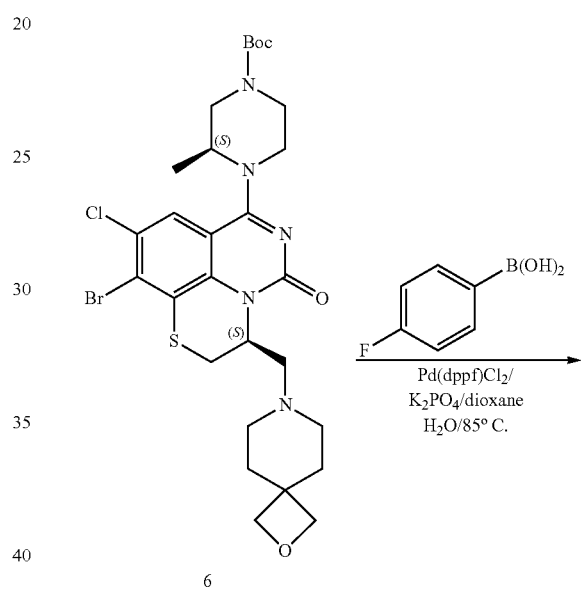
6
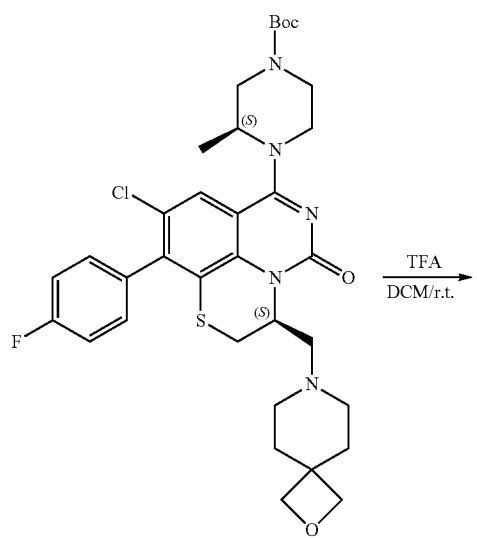
7

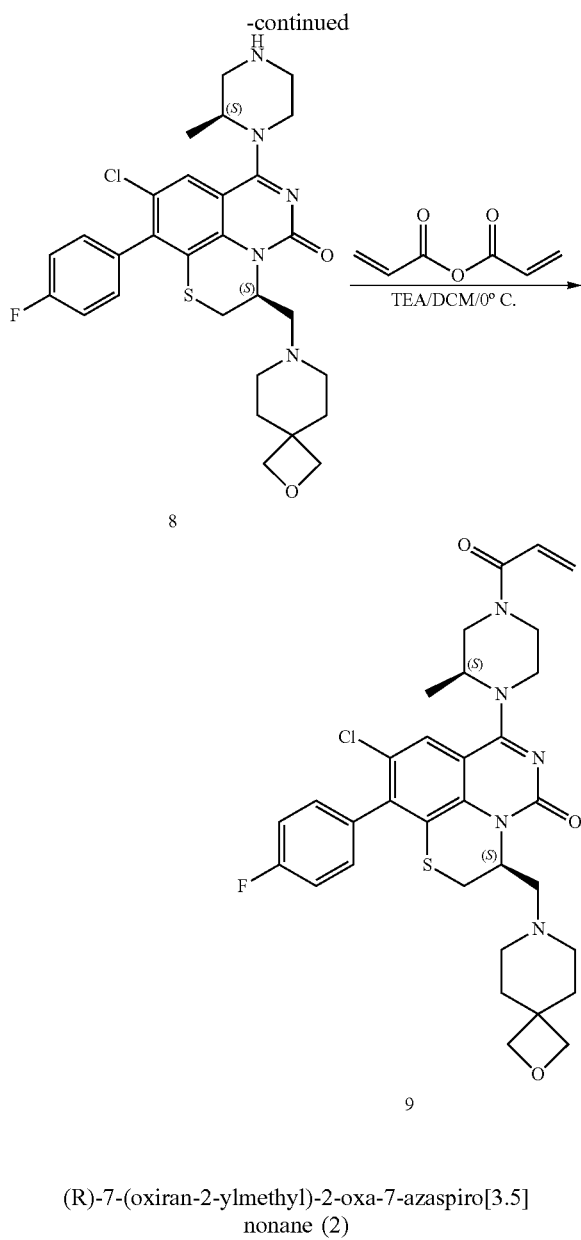

(R)-7-(oxiran-2-ylmethyl)-2-oxa-7-azaspiro[3.5]nonane (2)

To a mixture of (S)-oxiran-2-ylmethyl 3-nitrobenzenesulfonate (5.9 g, 22.8 mmol), 2-oxa-7-azaspiro[3.5]nonane oxalate (4.5 g, 20.7 mmol) in acetonitrile (60 mL) was added potassium carbonate (14.3 g, 103.6 mmol) at 0° C. under nitrogen atmosphere. The mixture was stirred at room temperature for 16 hours. After completion, the mixture was concentrated and the residue was purified by silica gel column eluting a mixture of dichloromethane/methanol (20/1) to afford (R)-7-(oxiran-2-ylmethyl)-2-oxa-7-azaspiro[3.5]nonane (3.45 g, 91% yield) as a brown oil. MS (ESI) m/z: 180.1 [M+H]$^+$.

(R)-1-mercapto-3-(2-oxa-7-azaspiro[3.5]nonan-7-yl)propan-2-ol (3)

To a mixture of (R)-7-(oxiran-2-ylmethyl)-2-oxa-7-azaspiro[3.5]nonane (3.74 g, 20.4 mmol) in tetrahydrofuran (70 mL) was added 1,1,1,3,3,3-hexamethyldisilathiane (5.45 g, 30.6 mmol) and tetrabutylammonium fluoride (1.0 M in tetrahydrofuran, 6.1 mL, 6.1 mmol) at 0° C. The resulting mixture was stirred at room temperature for 6 hours. After completion, the mixture was concentrated and the residue was purified by silica gel column eluting with dichloromethane/methanol (20/1) to afford (R)-1-mercapto-3-(2-oxa-7-azaspiro[3.5]nonan-7-yl)propan-2-ol (3.47 g, 78% yield) as a brown oil. MS (ESI) m/z: 218.2 [M+H]$^+$.

(R)-7-bromo-6-chloro-4-hydroxy-8-((2-hydroxy-3-(2-oxa-7-azaspiro[3.5]nonan-7-yl)propyl)thio)quinazolin-2(1H)-one (4)

To a solution of 7-bromo-6-chloro-8-iodoquinazoline-2,4(1H,3H)-dione (4.93 g, 12.3 mmol) in dioxane (50 mL) were added potassium carbonate (5.09 g, 36.8 mmol), (R)-1-mercapto-3-(2-oxa-7-azaspiro[3.5]nonan-7-yl)propan-2-ol (3.47 g, 16.0 mmol), 4,5-bis(diphenyl-phosphino)-9,9-dimethylxanthene (1.42 g, 2.45 mmol) and tris(dibenzylideneacetone) dipalladium (1.12 g, 1.23 mmol). The mixture was stirred at 50° C. under nitrogen atmosphere for 16 hours. After completion, the mixture was concentrated and the residue was purified by silica gel column eluting with dichloromethane/methanol (20/1) to afford (R)-7-bromo-6-chloro-4-hydroxy-8-((2-hydroxy-3-(2-oxa-7-azaspiro[3.5]nonan-7-yl)propyl)thio)quinazolin-2(1H)-one (4.47 g, 74% yield) as an orange solid. MS (ESI) m/z: 492.4 [M+H]$^+$.

(S)-3-(2-oxa-7-azaspiro[3.5]nonan-7-ylmethyl)-10-bromo-9-chloro-7-hydroxy-2H-[1,4]thiazino[2,3,4-ij]quinazolin-5(3H)-one (5)

To a mixture of (R)-7-bromo-6-chloro-4-hydroxy-8-((2-hydroxy-3-(2-oxa-7-azaspiro[3.5]nonan-7-yl)propyl)thio)quinazolin-2(1H)-one (3.9 g, 7.95 mmol) and triphenylphosphoranylidene (4.16 g, 15.9 mmol) in tetrahydrofuran (70 mL) was added diethyl azodicarboxylate (2.77 g, 15.9 mmol). The mixture was stirred at room temperature for 2 hours. After completion, the mixture was poured into ice-water (100 mL) and extracted with ethyl acetate (3×100 mL). The mixture was concentrated and the residue was purified by silica gel column eluting with dichloromethane/methanol (50/1) to afford (S)-3-(2-oxa-7-azaspiro[3.5]nonan-7-ylmethyl)-10-bromo-9-chloro-7-hydroxy-2H-[1,4]thiazino[2,3,4-ij]quinazolin-5(3H)-one (2.66 g, 71% yield) as a light yellow solid. MS (ESI) m/z: 474.4 [M+H]$^+$.

(S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-3-methylpiperazine-1-carboxylate (6)

To a mixture of (S)-3-(2-oxa-7-azaspiro[3.5]nonan-7-ylmethyl)-10-bromo-9-chloro-7-hydroxy-2H-[1,4]thiazino[2,3,4-ij]quinazolin-5(3H)-one (1.20 g, 2.54 mmol) and potassium carbonate (1.63 g, 25.40 mmol) in acetonitrile (100 mL) was added 2,4,6-triisopropylbenzenesulfonyl chloride (2.30 g, 7.63 mmol) at 0° C. The mixture was stirred at 0° C. for 30 min and at 30° C. for 1 hour. After completion, (2R,5S)-tert-butyl 2,5-dimethylpiperazine-1-carboxylate (1.53 g, 7.63 mmol) was added into the reaction solution. The reaction mixture was stirred at 0° C. for another 1 hour. After completion, the mixture was poured into ice-water (300 mL) and extracted with ethyl acetate (3×200 mL). The mixture was concentrated and the residue was purified by flash chromatography column (C18, acetonitrile/water=20% to 95%) to afford (S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-3-methylpiperazine-1-carboxylate (860 mg, 51% yield) as a pale-white solid. MS (ESI) m/z: 655.3[M+H]⁺.

(S)-tert-butyl 4-((S)-3-(2-oxa-7-azaspiro[3.5]nonan-7-ylmethyl)-9-chloro-10-(4-fluorophenyl)-5-oxo-3,5-dihydro-2H-[1,4]thiazino [2,3,4-ij]quinazolin-7-yl)-3-methylpiperazine-1-carboxylate (7)

To a mixture of (S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-3-methylpiperazine-1-carboxylate (200 mg, 0.30 mmol) and tripotassium orthophosphate (325 mg, 1.53 mmol) in 1,4-dioxane (8 mL) and water (1 mL) was added [1,1'-bis(diphenylphosphino)ferrocene]dichloropalladium(II) (45 mg, 0.06 mmol) and (4-fluorophenyl)boronic acid (214 mg, 1.52 mmol). The mixture was stirred at 85° C. for 2 hours. After completion, the mixture was diluted with tetrahydrofuran (50 mL) and insoluble solid was filtered out. The mixture was concentrated and the residue was purified by silica gel column eluting with dichloromethane/methanol (50/1) to afford (S)-tert-butyl 4-((S)-3-(2-oxa-7-azaspiro[3.5]nonan-7-ylmethyl)-9-chloro-10-(4-fluorophenyl)-5-oxo-3,5-dihydro-2H-[1,4]thiazino [2,3,4-ij]quinazolin-7-yl)-3-methylpiperazine-1-carboxylate (214 mg, crude) as a light yellow oil. MS (ESI) m/z: 670.2 [M+H]⁺.

(S)-3-(2-oxa-7-azaspiro[3.5]nonan-7-ylmethyl)-9-chloro-10-(4-fluorophenyl)-7-((S)-2-methylpiperazin-1-yl)-2H-[1,4]thiazino[2,3,4-ij]quinazolin-5(3H)-one (8)

To a mixture of (S)-tert-butyl 4-((S)-3-(2-oxa-7-azaspiro[3.5]nonan-7-ylmethyl)-9-chloro-10-(4-fluorophenyl)-5-oxo-3,5-dihydro-2H-[1,4]thiazino[2,3,4-ij]quinazolin-7-yl)-3-methylpiperazine-1-carboxylate (214 mg, 0.32 mmol) in dichloromethane (3 mL) was added trifluoroacetic acid (1 mL). The mixture was stirred at room temperature for 30 min. After completion, the mixture was purified by silica gel column eluting with dichloromethane/methanol (50/1) to afford (S)-3-(2-oxa-7-azaspiro[3.5]nonan-7-ylmethyl)-9-chloro-10-(4-fluorophenyl)-7-((S)-2-methylpiperazin-1-yl)-2H-[1,4]thiazino[2,3,4-ij]quinazolin-5(3H)-one (130 mg, 71% yield) as a yellow solid. MS (ESI) m/z: 570.1 [M+H]⁺.

(S)-3-(2-oxa-7-azaspiro[3.5]nonan-7-ylmethyl)-7-((S)-4-acryloyl-2-methylpiperazin-1-yl)-9-chloro-10-(4-fluorophenyl)-2H-[1,4]thiazino[2,3,4-ij]quinazolin-5(3H)-one (9)

To a mixture of (S)-3-(2-oxa-7-azaspiro[3.5]nonan-7-ylmethyl)-9-chloro-10-(4-fluorophenyl)-7-((S)-2-methylpiperazin-1-yl)-2H-[1,4]thiazino[2,3,4-ij]quinazolin-5(3H)-one (100 mg, 0.17 mmol) and triethylamine (54 mg, 0.51 mmol) in dichloromethane (3 mL) was added acrylic anhydride (43 mg, 0.34 mmol) at 0° C. The mixture was stirred at 0° C. for 1 hour. After completion, the mixture was poured into ice-water (15 mL) and extracted with ethyl acetate (3×15 mL). After concentration, the residue was purified by preparative high performance liquid chromatography (20% to 95% acetonitrile in water as gradient) to afford the product (50 mg, 46% yield) as a light-yellow solid.
¹H NMR (400 MHz, CDCl₃) δ 7.48 (s, 1H), 7.23-7.18 (m, 4H), 6.62-6.52 (m, 1H), 6.36 (d, J=18.0 Hz, 1H), 5.77 (d, J=10.8 Hz, 1H), 5.29-5.27 (m, 1H), 4.74-4.70 (m, 1H), 4.64 (m, 0.5H), 4.54-4.38 (m, 5H), 4.21-4.19 (m, 0.5H), 3.96-3.95 (m, 0.5H), 3.81-3.77 (m, 0.5H), 3.62-3.49 (m, 2H), 3.37-3.36 (m, 1H), 3.12-3.07 (m, 1H), 3.00-2.94 (m, 1H), 2.79-2.73 (m, 1H), 2.65-2.55 (m, 2H), 2.49-2.47 (m, 1H), 2.43-2.35 (m, 2H), 1.88-1.75 (m, 4H), 1.48-1.44 (m, 3H). MS (ESI) m/z: 624.1 [M+H]⁺.

Z. Example 481

(S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2,3-dihydro-5H-[1,4]thiazino[2,3,4-ij]quinazolin-5-one

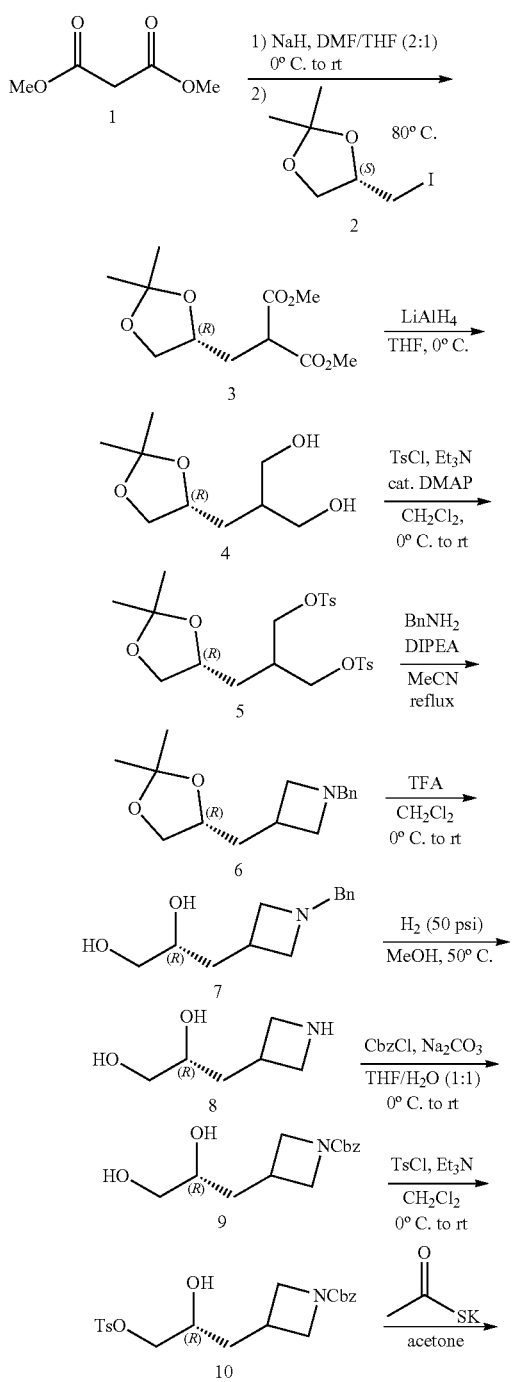

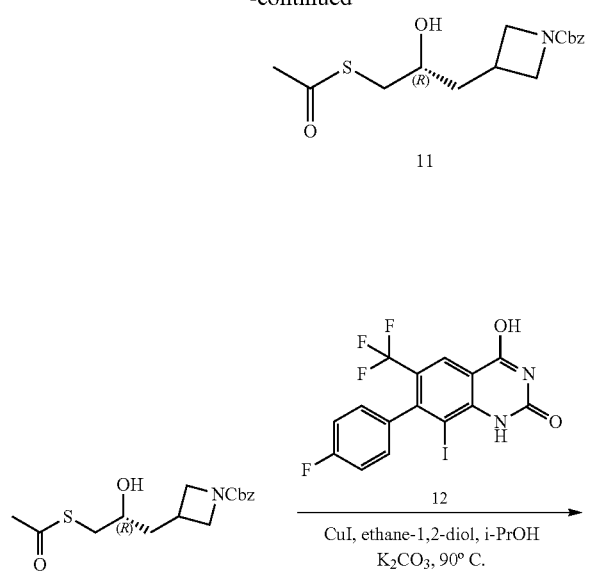
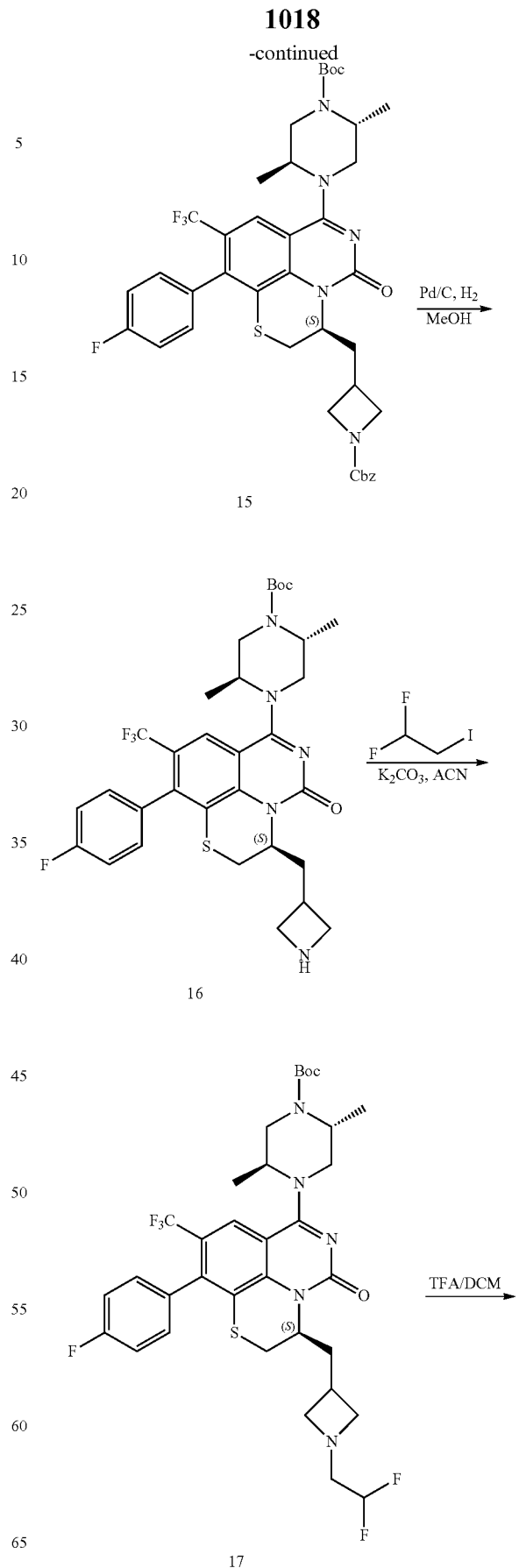

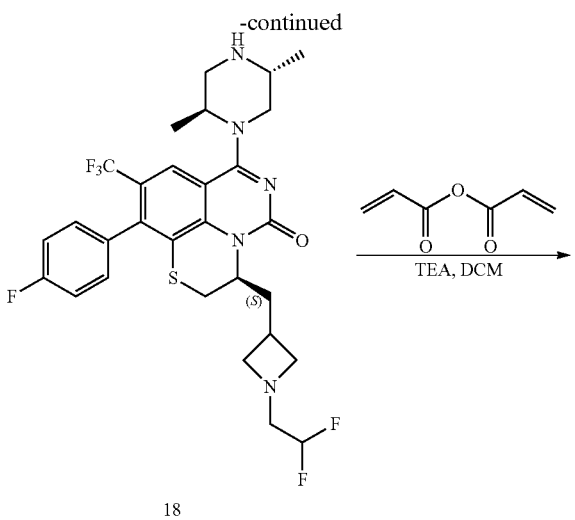

(R)-dimethyl 2-((2,2-dimethyl-1,3-dioxolan-4-yl)methyl)malonate (3)

To a mixture of sodium hydride (4.58 g, 190.87 mmol) in dimethylformide (208 mL) and tetrahydrofuran (104 mL) was added dimethyl malonate (21.6 g, 163.6 mmol) dropwise at 0° C. under nitrogen atmosphere. The mixture was allowed to warm up to room temperature for 1 hour, then (S)-4-(iodomethyl)-2,2-dimethyl-1,3-dioxolane (26.4 g, 109.07 mmol) was added dropwise. The mixture was heated to 80° C. and stirred overnight. After completion, the mixture was quenched with saturated aqueous ammonium chloride solution, the aqueous layer was extracted with ethyl acetate (2×500 mL). The organic layer was dried over anhydrous sodium sulfate, filtered and concentrated. The residue was purified by silica gel column eluting with petroleum ether/ethyl acetate (50/1) to afford (R)-dimethyl 2-((2,2-dimethyl-1,3-dioxolan-4-yl)methyl)malonate (18 g, 67% yield) as pale yellow liquid. $^1$H NMR (400 MHz, CDCl$_3$) δ 4.16-4.10 (m, 1H), 4.08-4.04 (m, 1H), 3.76 (s, 3H), 3.74 (s, 3H), 3.63-3.56 (m, 2H), 2.24-2.18 (m, 1H), 2.13-2.06 (m, 1H), 1.39 (s, 3H), 1.32 (s, 3H).

(R)-2-((2,2-dimethyl-1,3-dioxolan-4-yl)methyl)propane-1,3-diol (4)

To a mixture of lithium aluminum hydride (4.07 g, 107.2 mmol) in tetrahydrofuran (150 mL) was added dropwise (R)-dimethyl 2-((2,2-dimethyl-1,3-dioxolan-4-yl)methyl)malonate (8.8 g, 35.74 mmol) at 0° C. under nitrogen atmosphere. The mixture was stirred at 0° C. to room temperature for 2 hours. After completion, the mixture was diluted with ether (100 mL) and cooled to 0° C., quenched with 4 mL water, then 4 mL 15% sodium hydroxide solution and 12 mL water. The organic layer was separated, dried over anhydrous sodium sulfate, filtered and concentrated to afford (R)-2-((2,2-dimethyl-1,3-dioxolan-4-yl)methyl)propane-1,3-diol (5.32 g, 78% yield) as colorless oil, which was used to next step without further purification. $^1$H NMR (400 MHz, CDCl$_3$) δ 4.25-4.18 (m, 1H), 4.09 (t, J=6.8 Hz, 1H), 3.77-3.68 (m, 4H), 3.53 (t, J=7.6 Hz, 1H), 1.93-1.87 (m, 1H), 1.75-1.68 (m, 1H), 1.63-1.54 (m, 1H), 1.42 (s, 3H), 1.36 (s, 3H).

(R)-2-((2,2-dimethyl-1,3-dioxolan-4-yl)methyl)propane-1,3-diyl bis(4-methylbenzenesulfonate) (5)

To a solution of (R)-2-((2,2-dimethyl-1,3-dioxolan-4-yl)methyl)propane-1,3-diol (5.32 g, 27.96 mmol), 4-dimethylaminopyridine (444 mg, 3.63 mmol) and triethyl amine (11.3 g, 111.84 mmol) in dichloromethane (50 mL) was added 4-toluene sulfonyl chloride (18.98 g, 99.54 mmol) at 0° C. The mixture was stirred at room temperature overnight. 200 mL water was added and extracted with dichloromethane (3×200 mL). The organic phase was concentrated and the residue was purified by silica gel column eluting with petroleum ether/ethyl acetate=10/1 to afford (R)-2-((2,2-dimethyl-1,3-dioxolan-4-yl)methyl)propane-1,3-diyl bis(4-methylbenzenesulfonate) (10.16 g, 73% yield) as white solid. MS (ESI) m/z: 499.1 [M+H]$^+$.

(R)-1-benzyl-3-((2,2-dimethyl-1,3-dioxolan-4-yl)methyl)azetidine (6)

To a solution of (R)-2-((2,2-dimethyl-1,3-dioxolan-4-yl)methyl)propane-1,3-diyl bis(4-methylbenzenesulfonate) (9.9 g, 19.8 mmol), phenylmethanamine (7.6 mL, 69.44 mmol) in acetonitrile (90 mL) was added N,N-diisopropylethylamine (7.6 mL, 43.69 mmol) at room temperature. The mixture was heated to reflux overnight. After completion, 200 mL water was added and extracted with dichloromethane (3×200 mL). The organic phase was concentrated and the residue was purified by silica gel column eluting with petroleum ether/ethyl acetate=1/1 to afford (R)-1-benzyl-3-((2,2-dimethyl-1,3-dioxolan-4-yl)methyl)azetidine (2.84 g, 55% yield) as brown liquid. MS (ESI) m/z: 262.2 [M+H]$^+$.

(R)-3-(1-benzylazetidin-3-yl)propane-1,2-diol (7)

To a mixture of (R)-1-benzyl-3-((2,2-dimethyl-1,3-dioxolan-4-yl)methyl)azetidine (2.84 g, 10.88 mmol) in dichloromethane (28 mL) was added trifluoroacetic acid (14 mL) at room temperature. Then the mixture was stirred at room temperature for 2 hours. After completion, the mixture was concentrated and adjusted pH to 7-8 with ammonia solution, then concentrated to afford (R)-3-(1-benzylazetidin-3-yl)propane-1,2-diol (9.4 g, crude) as yellow solid, which was used to next step without further purification. MS (ESI) m/z: 222.1[M+H]$^+$.

(R)-3-(azetidin-3-yl)propane-1,2-diol (8)

To a solution of (R)-3-(1-benzylazetidin-3-yl)propane-1,2-diol (4.577 g, 20.7 mmol) in methanol (30 mL) was added palladium on charcoal (10%) (400 mg) at room temperature. The mixture was stirred under hydrogen protection at 50° C. overnight. After completion, the mixture was filtered and concentrated to afford (R)-3-(azetidin-3-yl)propane-1,2-diol (4.2 g, crude) as yellow oil, which was used to next step without further purification. MS (ESI) m/z: 132.1 [M+H]$^+$.

(R)-benzyl 3-(2,3-dihydroxypropyl)azetidine-1-carboxylate (9)

To a mixture of (R)-3-(azetidin-3-yl)propane-1,2-diol (1.43 g, 10.88 mol) and sodium carbonate (3.46 g, 32.64 mmol) in tetrahydrofuran (28 mL) and water (28 mL) was added benzyl carbonochloridate (2.23 g, 13.06 mol) slowly at 0° C. The mixture was stirred at 0° C. overnight. After completion, the mixture was extracted with ethyl acetate (100 mL), the organic phase was washed with brine (100 mL×2), dried over anhydrous sodium sulfate, filtered and concentrated. The residue was purified by silica gel column eluting with dichloromethane/methanol=50/1 to afford (R)-benzyl 3-(2,3-dihydroxypropyl)azetidine-1-carboxylate (1.6 g, 55% yield for 2 steps) as colorless oil; MS (ESI) m/z: 266.1[M+H]$^+$.

(R)-benzyl 3-(2-hydroxy-3-(tosyloxy)propyl)azetidine-1-carboxylate (10)

To a solution of (R)-benzyl 3-(2,3-dihydroxypropyl)azetidine-1-carboxylate (1.6 g, 6.03 mmol) and triethyl amine (1.22 g, 12.06 mmol) in dichloromethane (30 mL) was added 4-toluene sulfochloride (1.03 g, 5.43 mmol) at 0° C. The mixture was stirred at room temperature for 4 hours. After completion, the mixture was concentrated and the residue was purified by silica gel column eluting with dichloromethane/methanol (50/1) to afford the (R)-benzyl 3-(2-hydroxy-3-(tosyloxy)propyl)azetidine-1-carboxylate (1.7 g, 67% yield) as pale yellow oil. MS (ESI) m/z: 420.1 [M+H]$^+$.

(R)-benzyl 3-(3-(acetylthio)-2-hydroxypropyl)azetidine-1-carboxylate (11)

To a mixture of (R)-benzyl 3-(2-hydroxy-3-(tosyloxy)propyl)azetidine-1-carboxylate (1.4 g, 3.34 mmol) in acetone (20 mL) was added potassium ethanethioate (1.14 g, 10.02 mmol). The mixture was stirred at 50° C. under nitrogen atmosphere for 1 hour. After completion, the mixture was filtered, and the filtrate was concentrated. The residue was purified by silica gel column eluting with dichloromethane/methanol (60/1) to afford (R)-benzyl 3-(3-(acetylthio)-2-hydroxypropyl)azetidine-1-carboxylate (800 mg, 74% yield) as colorless oil. MS (ESI) m/z: 324.1 [M+H]$^+$.

(R)-benzyl 3-(3-((7-(4-fluorophenyl)-4-hydroxy-2-oxo-6-(trifluoromethyl)-1,2-dihydroquinazolin-8-yl)thio)-2-hydroxypropyl)azetidine-1-carboxylate (13)

The mixture of 7-(4-fluorophenyl)-4-hydroxy-8-iodo-6-(trifluoromethyl)quinazolin-2(1H)-one (927 mg, 2.06 mmol), (R)-benzyl 3-(3-(acetylthio)-2-hydroxypropyl)azetidine-1-carboxylate (800 mg, 2.48 mmol), copper (I) iodide (197 mg, 1.03 mmol) and potassium carbonate (853 mg, 6.18 mmol) in ethane-1,2-diol (12 mL) and i-PrOH (12 mL) was stirred under nitrogen atmosphere at 85° C. for 18 hours. After completion, ethyl acetate (200 mL) was added, the organic phase was washed with water (2×150 mL), dried over anhydrous sodium sulfate, filtered and concentrated. The residue was purified by silica gel column with dichloromethane/ethyl acetate (3/1) to afford (R)-benzyl 3-(3-((7-(4-fluorophenyl)-4-hydroxy-2-oxo-6-(trifluoromethyl)-1,2-dihydroquinazolin-8-yl)thio)-2-hydroxypropyl)azetidine-1-carboxylate (320 mg, crude) as yellow solid. MS (ESI) m/z: 604.0 [M+H]$^+$.

Benzyl 3-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)azetidine-1-carboxylate (14)

To a mixture of (R)-benzyl 3-(3-((7-(4-fluorophenyl)-4-hydroxy-2-oxo-6-(trifluoromethyl)-1,2-dihydroquinazolin-8-yl)thio)-2-hydroxypropyl)azetidine-1-carboxylate (258 mg, 0.43 mmol) and triphenylphosphoranylidene (448 mg, 1.71 mmol) in tetrahydrofuran (80 mL) was added 1,2-bis[(4-chlorophenyl)methyl] ester (627 mg, 1.71 mmol) at 0° C. The mixture was stirred at 0° C. for 45 min. After completion, the mixture was poured into ice-water (100 mL) and extracted with ethyl acetate (3×50 mL). The mixture was concentrated and the residue was purified by C18 column with 30-95% acetonitrile in water as gradient to afford benzyl 3-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)azetidine-1-carboxylate (117 mg, 47% yield) as white solid. MS (ESI) m/z: 586.0 [M+H]$^+$.

(2R,5S)-tert-butyl 4-((S)-3-((1-((benzyloxy)carbonyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (15)

To a solution of benzyl 3-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)azetidine-1-carboxylate (75 mg, 0.128 mmol) and potassium carbonate (177 mg, 1.282 mmol) in acetonitrile (6 mL) was added 4-methylbenzenesulfonic anhydride (104 mg, 0.320 mmol) in portions at room temperature. The mixture was stirred at room temperature under nitrogen atmosphere for 5 hours. After completion, (2R,5S)-tert-butyl 2,5-dimethylpiperazine-1-carboxylate (110 mg, 0.512 mmol) was added into the reaction solution. The mixture was stirred at room temperature for anther 0.5 hour. After completion, the mixture was poured into ice-water (50 mL) and extracted with ethyl acetate (3×50 mL), dried over Na$_2$SO$_4$ and concentrated. The residue was purified by Flash chromatography column (C18, acetonitrile/water=30% to 95%) to afford (2R,5S)-tert-butyl 4-((S)-3-((1-((benzyloxy)carbonyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (60 mg, 60% yield) as a pale yellow solid. MS (ESI) m/z: 782.9 [M+H]$^+$.

(2R,5S)-tert-butyl 4-((S)-3-(azetidin-3-ylmethyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (16)

To solution of (2R,5S)-tert-butyl 4-((S)-3-((1-((benzyloxy)carbonyl)azetidin-3-yl)methyl)-10-(4-fluorophenyl)-5- oxo-9-(trifluoromethyl)-3,5-dihydro-2H-[1,4]thiazino[2,3,4-ij]quinazolin-7-yl)-2,5-dimethylpiperazine-1-carboxylate (60 mg, 0.077 mmol) in methanol (2 mL) was added palladium on charcoal (10%) (50 mg) at room temperature. The mixture was stirred under hydrogen at room temperature for 3 hours. After completion, the mixture was filtered and concentrated to afford (2R,5S)-tert-butyl 4-((S)-3-(azetidin-3-ylmethyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (47 mg, 94% yield) as pale yellow solid. MS (ESI) m/z: 648.8 [M+H]$^+$.

(2R,5S)-tert-butyl 4-((S)-3-((1-(2,2-difluoroethyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (17)

To solution of (2R,5S)-tert-butyl 4-((S)-3-(azetidin-3-ylmethyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (47 mg, 0.07 mmol) and 1,1-difluoro-2-iodoethane (42 mg, 0.22 mmol) in acetonitrile (1 mL) was added potassium carbonate (30 mg, 0.22 mmol). The mixture was stirred at 90° C. under nitrogen protection overnight. After completed, the mixture was concentrated and purified by silica gel column eluting with dichloromethane/ammonia-methanol (40/1) to afford the (2R,5S)-tert-butyl 4-((S)-3-((1-(2,2-difluoroethyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (40 mg, 78% yield) as pale yellow solid. MS (ESI) m/z: 712.8 [M+H]$^+$.

(S)-3-((1-(2,2-difluoroethyl)azetidin-3-yl)methyl)-7-((2S,5R)-2,5-dimethylpiperazin-1-yl)-10-(4-fluorophenyl)-9-(trifluoromethyl)-2H-[1,4]thiazino[2,3,4-ij]quinazolin-5(3H)-one (18)

To a solution of (2R,5S)-tert-butyl 4-((S)-3-((i-(2,2-difluoroethyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (40 mg, 0.056 mmol) in dichloromethane (1 mL) was added trifluoroacetic acid (1 mL) at 0° C. The reaction solution was stirred at room temperature for 1 hour. After completion, the mixture was concentrated and adjusted pH to 8-9 by ammonia in methanol. The mixture was concentrated and purified by silica gel column eluting with dichloromethane/methanol (containing 0.5% ammonia) (20/1) to afford the (S)-3-((1-(2,2-difluoroethyl)azetidin-3-yl)methyl)-7-((2S,5R)-2,5-dimethylpiperazin-1-yl)-10-(4-fluorophenyl)-9-(trifluoromethyl)-2H-[1,4]thiazino[2,3,4-ij]quinazolin-5(3H)-one (33 mg, 96% yield) as pale yellow solid. MS (ESI) m/z: 612.7 [M+H]$^+$.

(S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2H-[1,4]thiazino[2,3,4-ij]quinazolin-5(3H)-one (19)

To a mixture of (S)-3-((1-(2,2-difluoroethyl)azetidin-3-yl)methyl)-7-((2S,5R)-2,5-dimethylpiperazin-1-yl)-10-(4-fluorophenyl)-9-(trifluoromethyl)-2H-[1,4]thiazino[2,3,4-ij]quinazolin-5(3H)-one (33 mg, 0.054 mmol) and triethyl amine (11 mg, 0.108 mmol) in dichloromethane (1 mL) was added acrylic anhydride (7 mg, 0.054 mmol) at 0° C. The mixture was stirred at 0° C. for 1 hour. After completion, the mixture was poured into ice-water (20 mL) and extracted with dichloromethane (3×15 mL), dried over Ns$_2$SO$_4$, and concentrated. The residue was purified by preparative high Performance liquid chromatography (20% to 95% acetonitrile in water as gradient) to afford (S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2H-[1,4]thiazino[2,3,4-ij]quinazolin-5(3H)-one (14 mg, 39% yield) as a white solid. MS (ESI) m/z: 666.3 [M+H]$^+$.

$^1$H NMR (400 MHz, CDCl$_3$) δ 7.84 (s, 1H), 7.26-7.25 (m, 1H), 7.21-7.17 (m, 3H), 6.67-6.51 (m, 1H), 6.38 (t, J=15.6 Hz, 1H), 5.84-5.54 (m, 2H), 5.27-5.26 (m, 1H), 5.06-5.01 (m, 0.5H), 4.84-4.83 (m, 0.5H), 4.71-4.70 (m, 0.5H), 4.42-4.32 (m, 1.5H), 4.06-4.03 (m, 0.5H), 3.80-3.67 (m, 2H), 3.59-3.52 (m, 2H), 3.33-3.29 (m, 0.5H), 3.06-2.97 (m, 3H), 2.88-2.84 (m, 1H), 2.79-2.70 (m, 2H), 2.61-2.53 (m, 1H), 2.06 (t, J=6.8 Hz, 1H), 1.47-1.38 (m, 6H).

AA. Example 496

(3S)-7-((2S,5R)-4-acryloyl-2,5-dimethylpiperazin-1-yl)-9-chloro-10-(5-chloro-2,4-difluorophenyl)-3-(methoxymethyl)-2H-[1,4]thiazino[2,3,4-ij]quinazolin-5(3H)-one (8)

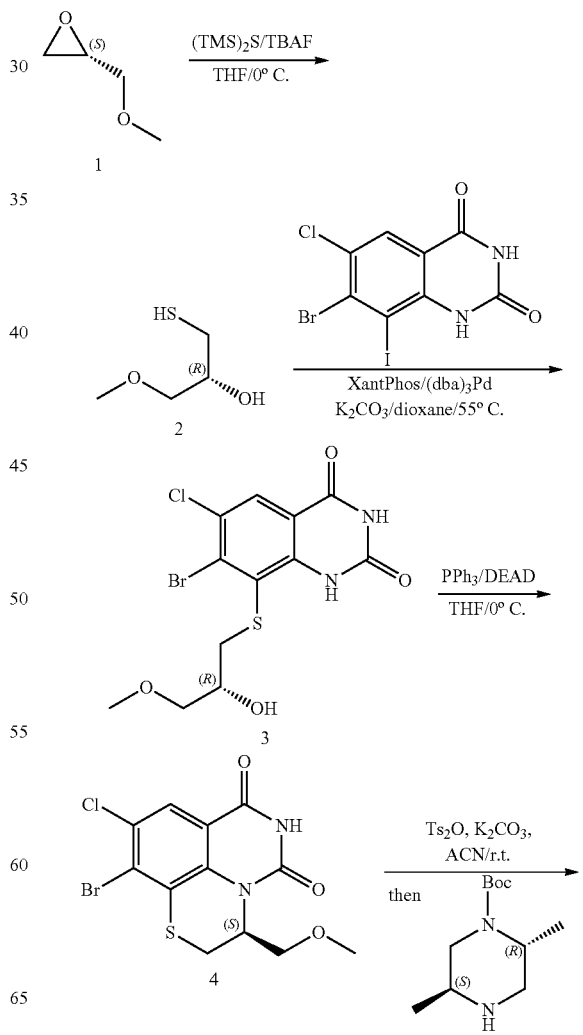

-continued

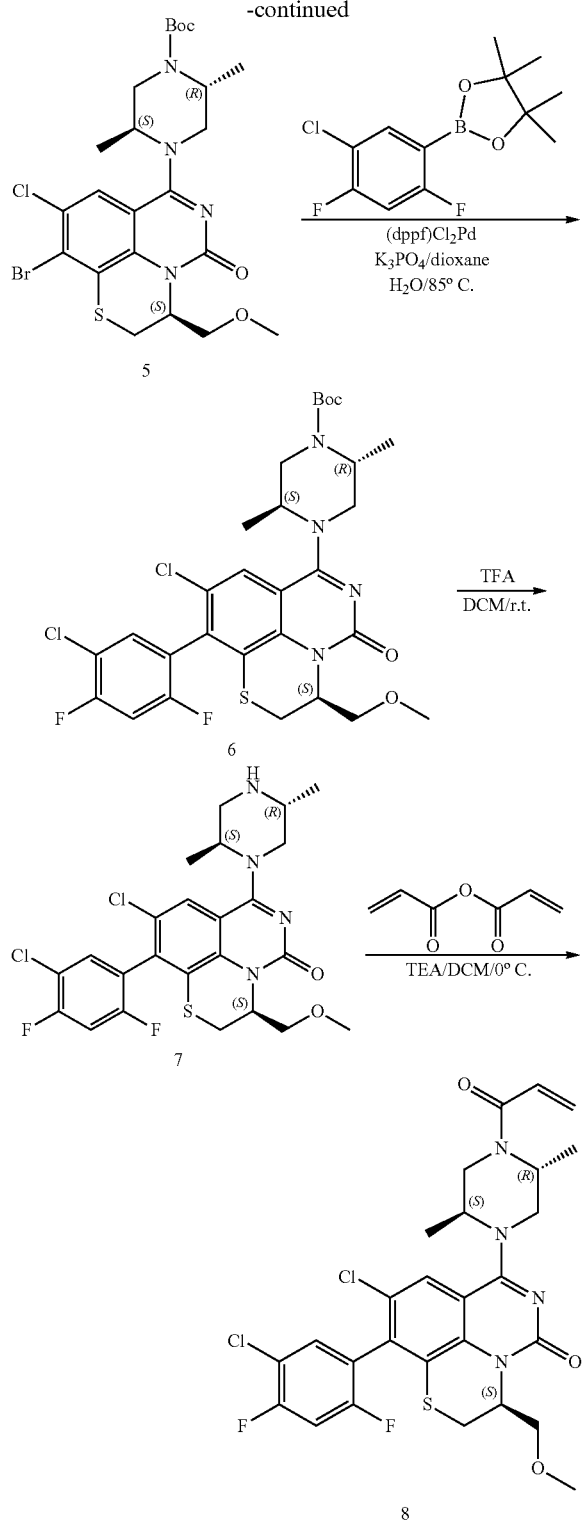

(R)-1-mercapto-3-methoxypropan-2-ol (2)

To a mixture of (S)-2-(methoxymethyl)oxirane (10.00 g, 113.6 mmol) in tetrahydrofuran (150 mL) was added 1,1,1,3,3,3-hexamethyldisilathiane (30.33 g, 170.4 mmol) and tetrabutylammonium fluoride (1.0 M in tetrahydrofuran, 34.1 mL, 34.1 mmol) at 0° C. The mixture was stirred at room temperature for 2 hrs. After completion, the mixture was poured into water (300 mL), extracted with ethyl acetate (3×200 mL). The combined organic phase was washed with brine (300 mL) and dried over anhydrous sodium sulfate. After filtration and concentration, the residue was purified by silica gel column eluting with petroleum ether/ethyl acetate (3/1) to afford (R)-1-mercapto-3-methoxypropan-2-ol (17.0 g, crude) as a colorless oil.

$^1$H NMR (300 MHz, CDCl$_3$) δ 3.86-3.82 (m, 1H), 3.49-3.46 (m, 1H), 3.41-3.37 (m, 4H), 2.71-2.64 (m, 1H), 1.55-1.50 (m, 1H).

(R)-7-bromo-6-chloro-8-((2-hydroxy-3-methoxypropyl)thio)quinazoline-2,4(1H,3H)-dione (3)

To a solution of 7-bromo-6-chloro-8-iodoquinazoline-2,4(1H,3H)-dione (4.00 g, 9.97 mmol) in dioxane (100 mL) were added potassium carbonate (4.13 g, 29.91 mmol), (R)-1-mercapto-3-methoxypropan-2-ol (2.43 g, 19.94 mmol), 4,5-bis(diphenyl-phosphino)-9,9-dimethylxanthene (1.15 g, 1.99 mmol) and tris(dibenzylideneacetone) dipalladium (915 mg, 1.0 mmol). The mixture was stirred at 55° C. under nitrogen atmosphere for 18 hrs. After completion, the mixture was diluted with tetrahydrofuran (300 mL) and filtered. After concentration, the residue was purified by silica gel column chromatography eluting with dichloromethane/methanol (100/1) to afford (R)-7-bromo-6-chloro-8-((2-hydroxy-3-methoxypropyl)thio)quinazoline-2,4(1H,3H)-dione (3.15 g, 80% yield) as a white solid. MS (ESI) m/z: 387.0 [M+H]$^+$.

(S)-10-bromo-9-chloro-3-(methoxymethyl)-2H-[1,4]thiazino[2,3,4-ij]quinazoline-5,7(3H,6H)-dione (4)

To a mixture of (R)-7-bromo-6-chloro-8-((2-hydroxy-3-methoxypropyl)thio)quinazoline-2,4(1H,3H)-dione (3.15 g, 8.16 mmol) and triphenylphosphoranylidene (4.28 g, 16.32 mmol) in tetrahydrofuran (160 mL) was added diethyl azodicarboxylate (2.84 g, 16.32 mmol) at 0° C. The mixture was stirred at 0° C. for 45 min. After completion, the mixture was poured into ice-water (300 mL) and extracted with ethyl acetate (3×500 mL). After concentration, the residue was purified by Flash chromatography column (C18, acetonitrile/water=30% to 95% as gradient) to afford (S)-10-bromo-9-chloro-3-(methoxymethyl)-2H-[1,4]thiazino[2,3,4-ij]quinazoline-5,7(3H,6H)-dione (1.84 g, 60% yield) as a white solid. MS (ESI) m/z: 378.0 [M+H]$^+$.

(2R,5S)-tert-butyl 4-((S)-10-bromo-9-chloro-3-(methoxymethyl)-5-oxo-3,5-dihydro-2H-[1,4]thiazino[2,3,4-ij]quinazolin-7-yl)-2,5-dimethylpiperazine-1-carboxylate (5)

To a mixture of (S)-10-bromo-9-chloro-3-(methoxymethyl)-2H-[1,4]thiazino[2,3,4-ij]quinazoline-5,7(3H,6H)-dione (1.84 g, 4.88 mmol) and potassium carbonate (6.73 g, 48.8 mmol) in acetonitrile (100 mL) was added 4-methylbenzenesulfonic anhydride (3.18 g, 9.76 mmol) at 0° C. The mixture was stirred at 0° C. for 30 min and at 30° C. for 1 hour. After completion, (2R,5S)-tert-butyl 2,5-dimethylpiperazine-1-carboxylate (2.09 g, 9.76 mmol) was added into the reaction solution. The reaction mixture was stirred at 0° C. for 1 hour. After completion, the mixture was poured into ice-water (300 mL) and extracted with ethyl acetate (3×200 mL). After concentration, the residue was purified by Flash chromatography column (C18, acetonitrile/water=20% to 95%) to afford (2R,5S)-tert-butyl 4-((S)-10-bromo-9- chloro-3-(methoxymethyl)-5-oxo-3,5-dihydro-2H-[1,4]thi-azino[2,3,4-ij]quinazolin-7-yl)-2,5-dimethylpiperazine-1-carboxylate (1.56 g, 56% yield) as a pale-white solid. MS (ESI) m z: 575.1 [M+H]+.

(2R,5S)-tert-butyl 4-((3S)-9-chloro-10-(5-chloro-2, 4-difluorophenyl)-3-(methoxymethyl)-5-oxo-3,5-dihydro-2H-[1,4]thiazino[2,3,4-ij]quinazolin-7-yl)-2, 5-dimethylpiperazine-1-carboxylate (6)

To a solution of (2R,5S)-tert-butyl 4-((S)-10-bromo-9-chloro-3-(methoxymethyl)-5-oxo-3,5-dihydro-2H-[1,4]thi-azino[2,3,4-ij]quinazolin-7-yl)-2,5-dimethylpiperazine-1-carboxylate (250 mg, 0.44 mmol) in 1,4-dioxane (8 mL) and water (1 mL) were added tripotassium phosphate (373 mg, 1.76 mmol), 2-(5-chloro-2,4-difluorophenyl)-4,4,5,5-te-tramethyl-1,3,2-dioxaborolane (724 mg, 2.64 mmol), and [1'1-bis(diphenylphosphino)ferrocene] dichloro palladiuM (II) (29 mg, 0.04 mmol). The mixture was stirred at 85° C. under nitrogen atmosphere for 10 hours. After completion, the mixture was diluted with tetrahydrofuran (300 mL) and filtered. After concentration, the residue was purified by silica gel column chromatography eluting with a gradient of dichloromethane/methanol 100/1 to 30/1 to afford (2R,5S)-tert-butyl 4-((3S)-9-chloro-10-(5-chloro-2,4-difluorophe-nyl)-3-(methoxymethyl)-5-oxo-3,5-dihydro-2H-[1,4]thi-azino[2,3,4-ij]quinazolin-7-yl)-2,5-dimethylpiperazine-1-carboxylate (260 mg, crude) as a yellow solid. MS (ESI) m/z: 641.6 [M+H]+.

(3S)-9-chloro-10-(5-chloro-2,4-difluorophenyl)-7-((2S,5R)-2,5-dimethylpiperazin-1-yl)-3-(methoxym-ethyl)-2H-[1,4]thiazino[2,3,4-ij]quinazolin-5(3H)-one (7)

To a cooled mixture of (2R,5S)-tert-butyl 4-((3S)-9-chloro-10-(5-chloro-2,4-difluorophenyl)-3-(methoxym-ethyl)-5-oxo-3,5-dihydro-2H-[1,4]thiazino[2,3,4-ij]qui-nazolin-7-yl)-2,5-dimethylpiperazine-1-carboxylate (260 mg, 0.44 mmol) in dichloromethane (5 ml) was added trifluoroacetic acid (2 mL) at 0° C. The reaction solution was stirred at room temperature for 1 h. After completion, the mixture was concentrated, the residue was purified by column using a mixture of dichloromethane/methanol (15:1) to afford (3S)-9-chloro-10-(5-chloro-2,4-difluorophenyl)-7-((2S,5R)-2,5-dimethylpiperazin-1-yl)-3-(methoxymethyl)-2H-[1,4]thiazino[2,3,4-ij]quinazolin-5(3H)-one (160 mg, crude) as a yellow-brown solid. MS (ESI) m/z: 541.1 [M+H]+.

(3S)-7-((2S,5R)-4-acryloyl-2,5-dimethylpiperazin-1-yl)-9-chloro-10-(5-chloro-2,4-difluorophenyl)-3-(methoxymethyl)-2H-[1,4]thiazino[2,3,4-ij]quinazo-lin-5(3H)-one (8)

To a mixture of (3S)-9-chloro-10-(5-chloro-2,4-difluoro-phenyl)-7-((2S,5R)-2,5-dimethylpiperazin-1-yl)-3-(methoxymethyl)-2H-[1,4]thiazino[2,3,4-ij]quinazolin-5 (3H)-one (130 mg, 0.24 mmol) and triethyl amine (49 mg, 0.48 mmol) in dichloromethane (5 ml) was added acrylic anhydride (45 mg, 0.36 mmol) at 0° C. The mixture was stirred at 0° C. for 1 h. After completion, the mixture was poured into ice-water (50 mL) and extracted with ethyl acetate (3×20 mL). After concentration, the residue was purified by preparative High Performance Liquid Chroma-tography (20% to 95% acetonitrile in water) to afford (3S)-7-((2S,5R)-4-acryloyl-2,5-dimethylpiperazin-1-yl)-9-chloro-10-(5-chloro-2,4-difluorophenyl)-3-(methoxym-ethyl)-2H-[1,4]thiazino[2,3,4-ij]quinazolin-5(3H)-one (50 mg, 35% yield) as a white solid. 1H NMR (400 MHz, CDCl3) δ 7.55-7.54 (m, 1H), 7.33-7.29 (m, 1H), 7.11-7.06 (m, 1H), 6.66-6.50 (m, 1H), 6.37 (t, J=15.6 Hz, 1H), 5.77 (t, J=7.6 Hz, 1H), 5.51-5.44 (m, 1H), 5.04-4.99 (m, 0.6H), 4.85-4.69 (m, 1H), 4.42-4.30 (m, 1.4H), 4.07-4.01 (m, 0.5H), 3.80-3.57 (m, 4H), 3.41-3.33 (m, 4.5H), 3.06-3.01 (m, 1H), 1.42-1.33 (m, 6H). MS (ESI) m/z: 595.1 [M+H]+.

BB. Example 498

(3S)-7-((2S,5R)-4-acryloyl-2,5-dimethylpiperazin-1-yl)-10-(2,4-difluorophenyl)-3-((2-methoxyethoxy) methyl)-9-(trifluoromethyl)-2H-[1,4]thiazino[2,3,4-ij]quinazolin-5(3H)-one

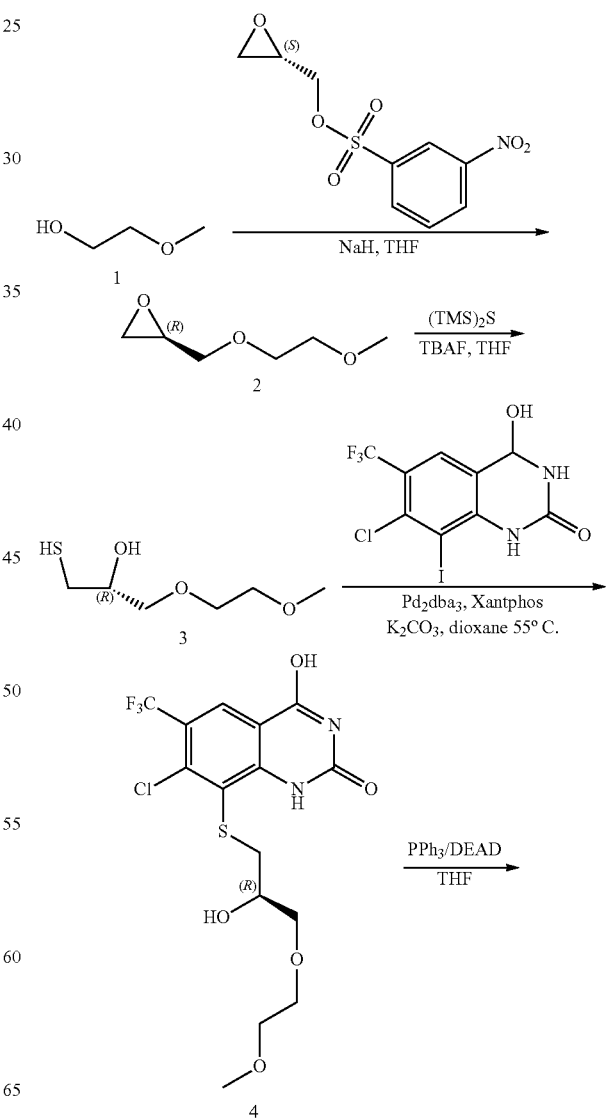

1029

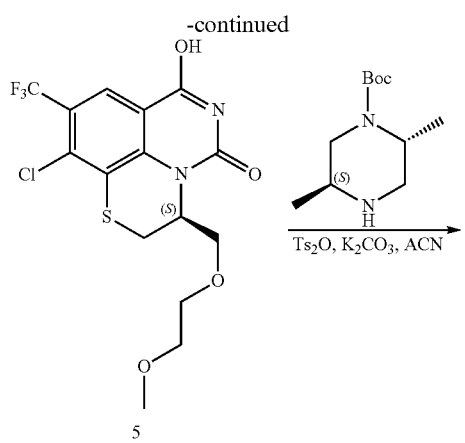

5

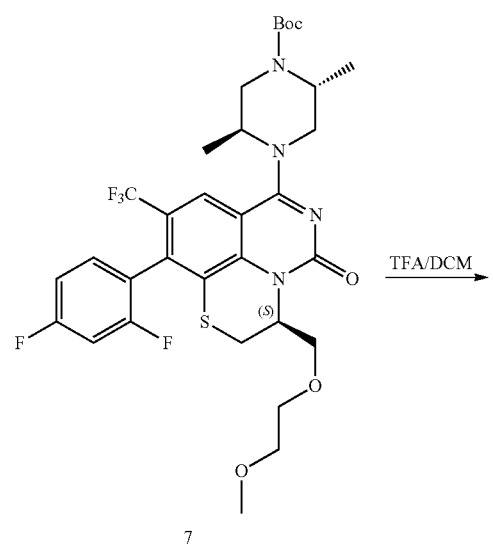

6

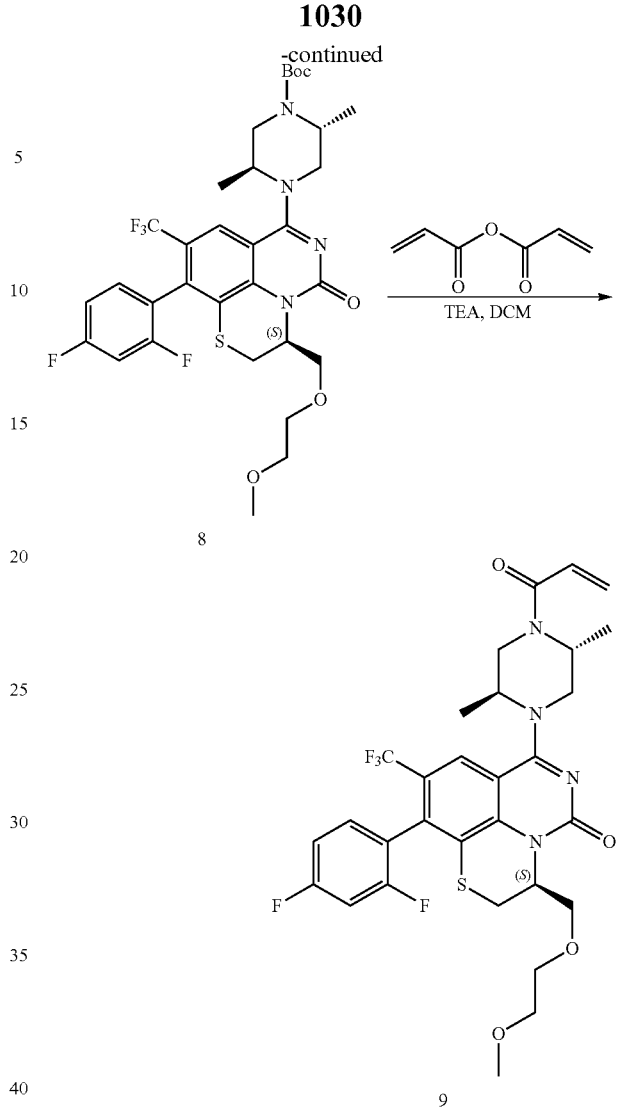

8

9

(R)-2-((2-methoxyethoxy)methyl)oxirane (2)

To a mixture of 2-methoxyethanol (40.00 g, 525.66 mmol) in tetrahydro-furan (3200 mL) was added sodium hydride (60% dispersed in mineral oil, 37.8 g, 946.20 mmol). The mixture was stirred at 0° C. for 1 hour. Then (S)-oxiran-2-ylmethyl 3-nitrobenzenesulfonate (40.00 g, 525.66 mmol) was added to the above solution, the mixture was stirred at room temperature for 3 hours. After completion, the mixture was poured into water (3200 mL), extracted with ethyl acetate (3×1000 mL). The combined organic phase was washed with brine (1000 mL) and dried over anhydrous sodium sulfate. After filtration and concentration, the residue was purified by silica gel column with petroleum ether to afford (R)-2-((2-methoxyethoxy)methyl) oxirane (27.00 g, crude) as colorless oil.

$^1$H NMR (400 MHz, CDCl$_3$) δ 3.82-3.77 (m, 1H), 3.71-3.64 (m, 2H), 3.58-3.54 (m, 2H), 3.46-3.38 (m, 4H), 3.18-3.16 (m, 1H), 2.81-2.78 (m, 1H), 2.62-2.59 (m, 1H).

(R)-1-mercapto-3-(2-methoxyethoxy)propan-2-ol (3)

To a mixture of (R)-2-((2-methoxyethoxy)methyl)oxirane (27.00 g, 204.3 mmol) in tetrahydrofuran (300 mL) was added 1,1,1,3,3,3-hexamethyldisilathiane (40.10 g, 224.7 mmol) and tetrabutylammonium fluoride (1.0 M in tetrahydrofuran, 15.17 mL, 224.7 mmol) at 0° C. The mixture was stirred at room temperature for 2 hours. After completion, the mixture was poured into water (300 mL), extracted with ethyl acetate (3×200 mL). The combined organic phase was washed with brine (300 mL) and dried over anhydrous sodium sulfate. After filtration and concentration, the residue was purified by silica gel column eluting with a mixture of petroleum ether/ethyl acetate (3/1) to afford (R)-1-mercapto-3-(2-methoxyethoxy)propan-2-ol (7.2 g, 21% yield) as a colorless oil.

$^1$H NMR (400 MHz, CDCl$_3$) δ 3.86-3.83 (m, 1H), 3.69-3.65 (m, 2H), 3.57-3.51 (m, 3H), 3.40-3.39 (m, 3H), 3.08-2.98 (m, 1H), 2.70-2.63 (m, 2H), 1.53 (t, J=1.2 Hz, 1H).

(R)-7-chloro-4-hydroxy-8-((2-hydroxy-3-(2-methoxyethoxy)propyl)thio)-6-(trifluoromethyl)quinazolin-2(1H)-one (4)

To a solution of 7-chloro-8-iodo-6-(trifluoromethyl)quinazoline-2,4(1H, 3H)-dione (4.00 g, 10.24 mmol) in dioxane (100 mL) were added potassium carbonate (4.25 g, 30.73 mmol), (R)-7-chloro-4-hydroxy-8-((2-hydroxy-3-(2-methoxyethoxy)propyl)thio)-6-(trifluoromethyl)quinazolin-2(1H)-one (2.55 g, 15.37 mmol), 4,5-bis(diphenyl-phosphino)-9,9-dimethylxanthene (0.89 g, 1.54 mmol) and tris (dibenzylideneacetone) dipalladium (0.94 g, 1.02 mmol). The mixture was stirred at 55° C. under nitrogen atmosphere for 18 hours. After completion, the mixture was diluted with tetrahydrofuran (300 mL) and filtered. After concentration, the residue was purified by silica gel column chromatography eluting with a gradient of dichloromethane/methanol (100/1 to 8/1) to afford the title product (S)-10-chloro-7-hydroxy-3-((2-methoxyethoxy) methyl)-9-(trifluoromethyl)-2H-[1,4]thiazino[2,3,4-ij]quinazolin-5(3H)-one (2.15 g, 49% yield) as a white solid. MS (ESI) m/z: 429.0 [M+H]$^+$.

(S)-10-chloro-7-hydroxy-3-((2-methoxyethoxy)methyl)-9-(trifluoromethyl)-2H-[1,4]thiazino[2,3,4-ij]quinazolin-5(3H)-one (5)

To a mixture of (S)-10-chloro-7-hydroxy-3-((2-methoxyethoxy)methyl)-9-(trifluoromethyl)-2H-[1,4]thiazino[2,3,4-ij]quinazolin-5(3H)-one (2.09 g, 4.88 mmol) and triphenylphosphoranylidene (5.12 g, 19.51 mmol) in tetrahydrofuran (700 ml) was added 2,5-dichloro-2,5-dimethylhexane (7.16 g, 19.51 mmol) at 0° C. The mixture was stirred at 0° C. for 45 min. After completion, the mixture was poured into ice-water (1500 mL) and extracted with ethyl acetate (3×500 mL). After concentration, the residue was purified by Flash chromatography column (C18, acetonitrile/water=30% to 95%) to afford (S)-10-chloro-7-hydroxy-3-((2-methoxyethoxy) methyl)-9-(trifluoromethyl)-2H-[1,4] thiazino[2,3,4-ij] quinazolin-5(3H)-one (1.58 g, 79% yield) as a white solid. MS (ESI) m/z: 411.0 [M+H]$^+$.

(2R,5S)-tert-butyl 4-((S)-10-chloro-3-((2-methoxyethoxy)methyl)-5-oxo-9-(trifluoromethyl)-3,5-dihydro-2H-[1,4]thiazino[2,3,4-ij]quinazolin-7-yl)-2,5-dimethylpiperazine-1-carboxylate (6)

To a mixture of (S)-10-chloro-7-hydroxy-3-((2-methoxyethoxy) methyl)-9-(trifluoromethyl)-2H-[1,4]thiazino[2,3,4-ij]quinazolin-5(3H)-one (1.58 g, 3.85 mmol) and potassium carbonate (5.32 g, 38.49 mmol) in acetonitrile (100 mL) was added 4-methylbenzenesulfonic anhydride (3.77 g, 11.55 mmol) at 0° C. The mixture was stirred at 0° C. for 30 min and at 30° C. for 1 hour. After completion, (2R,5S)-tert-butyl 2,5-dimethylpiperazine-1-carboxylate (3.30 g, 15.40 mmol) was added into the reaction solution. The reaction mixture was stirred at 0° C. for 1 hour. After completion, the mixture was poured into ice-water (300 mL) and extracted with ethyl acetate (3×200 mL). After concentration, the residue was purified by Flash chromatography column (C18, acetonitrile/water=20% to 95%) to afford (2R,5S)-tert-butyl 4-((S)-10-chloro-3-((2-methoxyethoxy)methyl)-5-oxo-9-(trifluoromethyl)-3,5-dihydro-2H-[1,4]thiazino[2,3,4-ij] quinazolin-7-yl)-2,5-dimethylpiperazine-1-carboxylate (1.97 g, 85% yield) as a yellow solid. MS (ESI) m/z: 607.1[M+H]$^+$.

(2R, 5S)-tert-butyl 4-((3S)-10-(2,4-difluorophenyl)-3-((2-methoxyethoxy) methyl)-5-oxo-9-(trifluoromethyl)-3,5-dihydro-2H-[1,4]thiazino[2,3,4-ij]quinazolin-7-yl)-2,5-dimethylpiperazine-1-carboxylate (7)

To a solution of (2R,5S)-tert-butyl 4-((S)-10-chloro-3-((2-methoxyethoxy) methyl)-5-oxo-9-(trifluoromethyl)-3,5-dihydro-2H-[1,4]thiazino[2,3,4-ij]quinazolin-7-yl)-2,5-dimethylpiperazine-1-carboxylate (350 mg, 0.58 mmol) in 1,4-dioxane (6 mL) and water (1 mL) were added tripotassium phosphate (734 mg, 3.46 mmol), (2,4-difluorophenyl) boronic acid (456 mg, 2.89 mmol), and chloro(2-dicyclohexylphosphino-2', 6'-diisopropoxy-1,1'-biphenyl)[2-(2'-amino-1,1'-biphenyl)]palladium(II) (45 mg, 0.058 mmol). The mixture was stirred at 85° C. under nitrogen atmosphere for 4 hours. After completion, the mixture was diluted with tetrahydrofuran (300 mL) and filtered. After concentration, the residue was purified by silica gel column chromatography using a gradient of dichloromethane/methanol (100/1 to 8/1) to afford (2R,5S)-tert-butyl 4-((3S)-10-(2,4-difluorophenyl)-3-((2-methoxyethoxy) methyl)-5-oxo-9-(trifluoromethyl)-3,5-dihydro-2H-[1,4]thiazino[2,3,4-ij]quinazolin-7-yl)-2,5-dimethylpiperazine-1-carboxylate (2.15 g, 49% yield) as a white solid. MS (ESI) m/z: 685.1 [M+H]$^+$.

(3S)-10-(2,4-difluorophenyl)-7-((2S,5R)-2,5-dimethylpiperazin-1-yl)-3-((2-methoxyethoxy)methyl)-9-(trifluoromethyl)-2H-[1,4]thiazino[2,3,4-ij]quinazolin-5(3H)-one (8)

To a cooled mixture of (2R,5S)-tert-butyl 4-((3S)-10-(2, 4-difluorophenyl)-3-((2-methoxyethoxy)methyl)-5-oxo-9-(trifluoromethyl)-3,5-dihydro-2H-[1,4]thiazino[2,3,4-ij]quinazolin-7-yl)-2,5-dimethylpiperazine-1-carboxylate (410 mg, 0.58 mmol) in dichloromethane (5 ml) was added trifluoroacetic acid (5 mL) at 0° C. The reaction solution was stirred at room temperature for 1 hour. After completion, the mixture was concentrated, the residue was purified by column eluting with dichloromethane/methanol (5/1) to afford (3S)-10-(2,4-difluorophenyl)-7-((2S, 5R)-2,5-dimethylpiperazin-1-yl)-3-((2-methoxyethoxy)methyl)-9-(trifluoromethyl)-2H-[1,4]thiazino[2,3,4-ij]quinazolin-5(3H)-one (701 mg, crude) as a yellow-brown solid. MS (ESI) m/z: 585.1 [M+H]$^+$.

(3S)-7-((2S,5R)-4-acryloyl-2,5-dimethylpiperazin-1-yl)-10-(2,4-difluorophenyl)-3-((2-methoxyethoxy) methyl)-9-(trifluoromethyl)-2H-[1,4]thiazino[2,3,4-ij]quinazolin-5(3H)-one (9)

To a mixture of (3S)-10-(2,4-difluorophenyl)-7-((2S, 5R)-2,5-dimethylpiperazin-1-yl)-3-((2-methoxyethoxy)methyl)-

9-(trifluoromethyl)-2H-[1,4]thiazino[2,3,4-ij]quinazolin-5 (3H)-one (655 mg, 0.54 mmol) and triethyl amine (164 mg, 1.62 mmol) in dichloromethane (10 ml) was added acrylic anhydride (68 mg, 0.54 mmol) at 0° C. The mixture was stirred at 0° C. for 1 hour. After completion, the mixture was poured into ice-water (50 mL) and extracted with ethyl acetate (3×20 mL). After concentration, the residue was purified by preparative High Performance Liquid Chromatography (20% to 95% acetonitrile in water) to afford (3S)-7-((2S,5R)-4-acryloyl-2,5-dimethylpiperazin-1-yl)-10-(2,4-difluorophenyl)-3-((2-methoxyethoxy) methyl)-9-(trifluoromethyl)-2H-[1,4]thiazino[2,3,4-ij]quinazolin-5(3H)-one (113 mg, 33% yield) as a white solid. MS (ESI) m/z: 639.1 [M+H]$^+$.

$^1$H NMR (400 MHz, CDCl$_3$) δ 7.87-7.83 (m, 1H), 7.19-7.15 (m, 1H), 7.03-6.95 (m, 2H), 6.67-6.51 (m, 1H), 6.37 (t, J=14.4 Hz, 1H), 5.78 (t, J=9.2 Hz, 1H), 5.50-5.36 (m, 1H), 5.14-5.00 (m, 0.6H), 4.78-4.66 (m, 1H), 4.45-4.41 (m, 1H), 4.41-4.34 (m, 0.4H), 4.16-4.08 (m, 0.6H), 3.78-3.63 (m, 6H), 3.52 (t, J=4.8 Hz, 2H), 3.41-3.38 (m, 1H), 3.35 (s, 3H), 3.26-3.22 (m, 0.4H), 3.05-2.95 (m, 1H), 1.50-1.44 (m, 6H).

CC. Example 500

(3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one

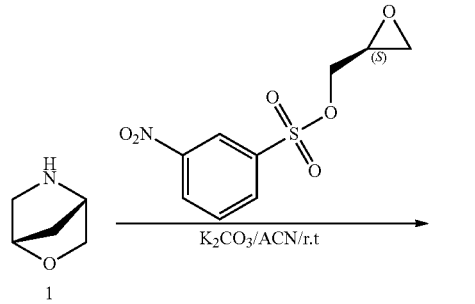

1

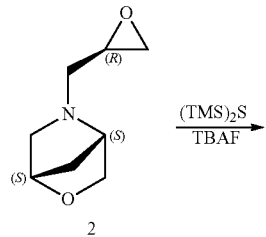

2

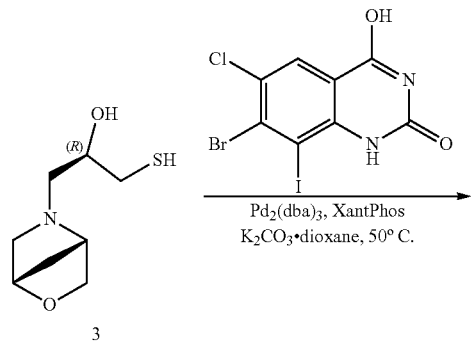

3

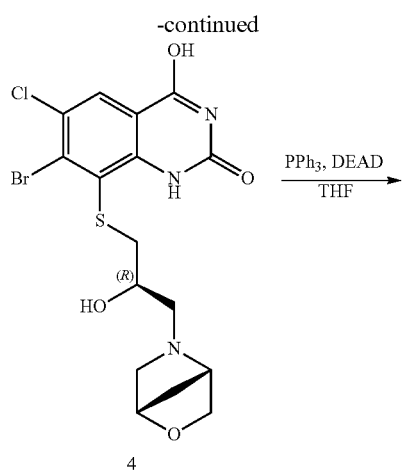

4

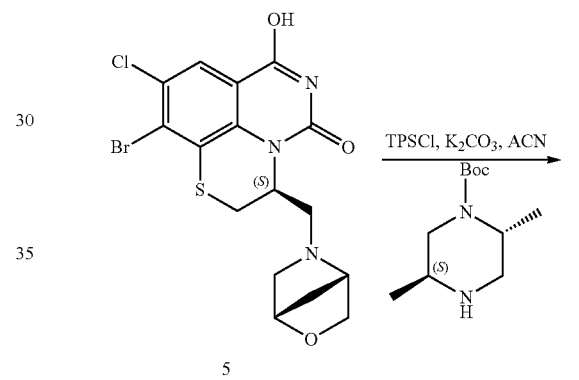

5

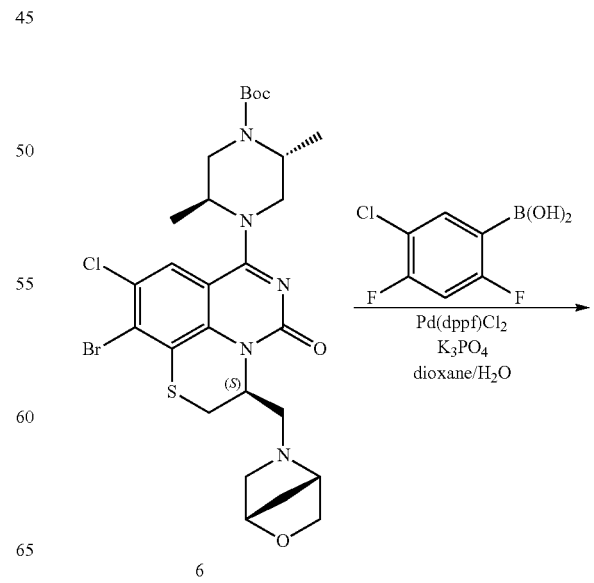

6

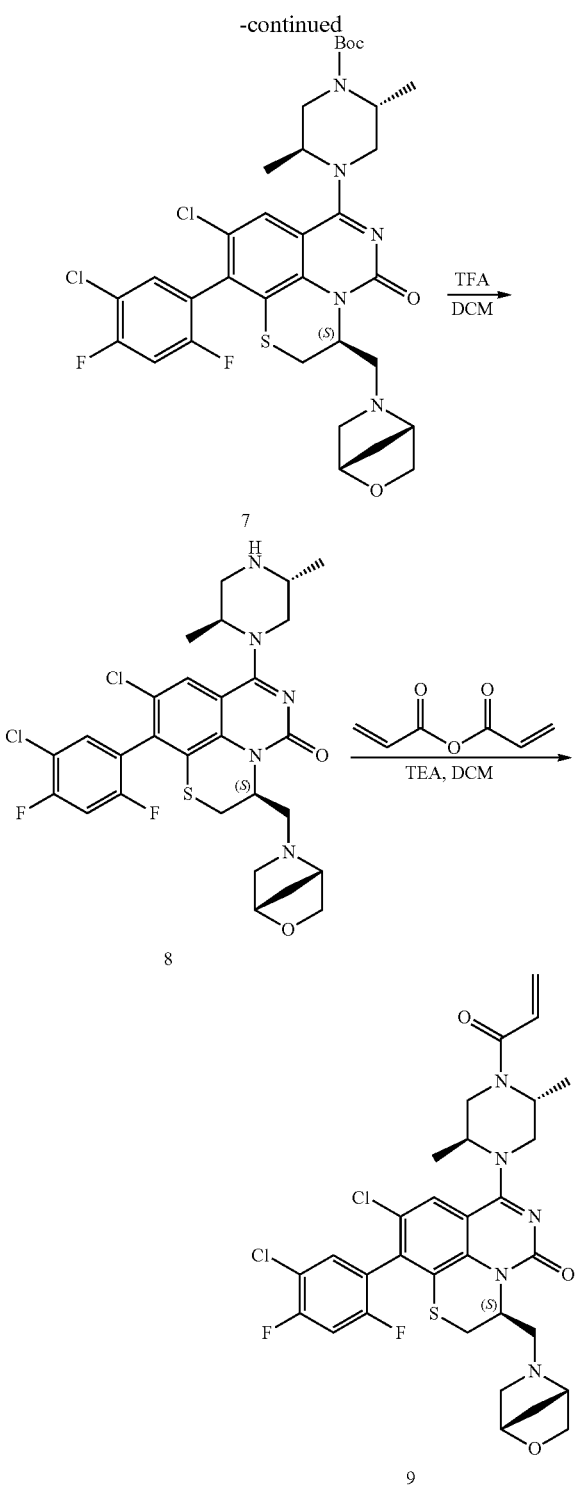

(1S,4S)-5-((R)-oxiran-2-ylmethyl)-2-oxa-5-azabicyclo[2.2.1]heptanes (2)

To a mixture of (S)-oxiran-2-ylmethyl 3-nitrobenzenesulfonate (38.2 g, 147.5 mmol) and (1S,4S)-2-oxa-5-azabicyclo[2.2.1]heptane (20.0 g, 147.5 mmol) in acetonitrile (300 mL) was added potassium carbonate (61 g, 442.5 mmol) at 0° C. under nitrogen atmosphere. The mixture was stirred at 0° C. for 16 hours. After completion, the mixture was concentrated and the residue was purified by silica gel column eluting with a mixture of dichloromethane/methanol (20/1) to afford the product (15.0 g, 66% yield) as a yellow oil. MS (ESI) m/z: 156.1 [M+H]⁺.

(R)-1-((1S,4S)-2-oxa-5-azabicyclo[2.2.1]heptan-5-yl)-3-mercaptopropan-2-ol (3)

To a mixture of (1S,4S)-5-((R)-oxiran-2-ylmethyl)-2-oxa-5-azabicyclo[2.2.1]heptane (6 g, 38.7 mmol) in tetrahydrofuran (60 mL) were added 1,1,1,3,3,3-hexamethyldisilathiane (8.9 g, 50.3 mmol) and tetrabutylammonium fluoride (1.0 M in tetrahydrofuran, 11.6 mL, 11.6 mmol) at 0° C. The mixture was stirred at room temperature for 2 hours. After completion, the mixture was poured into water (60 mL), extracted with ethyl acetate (3×100 mL). The organic phase was washed with brine (200 mL) and dried over anhydrous sodium sulfate. After filtration and concentration, the residue was purified by silica gel column eluting with a mixture of dichloromethane/methanol (50/1) to afford (R)-1-((1S,4S)-2-oxa-5-azabicyclo[2.2.1]heptan-5-yl)-3-mercaptopropan-2-ol (2.6 g, 35% yield) as a colorless oil. MS (ESI) m/z: 190.1 [M+H]⁺.

8-(((R)-3-((1S,4S)-2-oxa-5-azabicyclo[2.2.1]heptan-5-yl)-2-hydroxypropyl)thio)-7-bromo-6-chloro-4-hydroxyquinazolin-2(1H)-one (4)

To a solution of 7-bromo-6-chloro-4-hydroxy-8-iodoquinazolin-2(1H)-one (1.00 g, 2.5 mmol) in dioxane (30 mL) were added potassium carbonate (1.38 g, 10.0 mmol), (R)-1-((1S,4S)-2-oxa-5-azabicyclo[2.2.1]heptan-5-yl)-3-mercaptopropan-2-ol (742.5 mg, 3.75 mmol), 4,5-bis(diphenylphosphino)-9,9-dimethylxanthene (289 mg, 0.5 mmol) and tris(dibenzylideneacetone) dipalladium (421 mg, 0.46 mmol). The mixture was stirred at 55° C. under nitrogen atmosphere for 16 hours. After completion, the mixture was diluted with tetrahydrofuran (100 mL) and filtered. The filtrate was concentrated and the residue was purified by silica gel column chromatography using a gradient of dichloromethane/methanol (100/1 to 20/1) to afford 8-(((R)-3-((1S,4S)-2-oxa-5-azabicyclo[2.2.1]heptan-5-yl)-2-hydroxypropyl)thio)-7-bromo-6-chloro-4-hydroxyquinazolin-2(1H)-one (560 mg, 48% yield) as a yellow solid. MS (ESI) m/z: 462.1 [M+H]⁺.

(S)-3-((1S,4S)-2-oxa-5-azabicyclo[2.2.1]heptan-5-ylmethyl)-10-bromo-9-chloro-7-hydroxy-2H-[1,4]thiazino[2,3,4-ij]quinazolin-5(3H)-one (5)

To a mixture of 8-(((R)-3-((1S,4S)-2-oxa-5-azabicyclo[2.2.1]heptan-5-yl)-2-hydroxypropyl)thio)-7-bromo-6-chloro-4-hydroxyquinazolin-2(1H)-one (560 mg, 1.21 mmol) and triphenylphosphine (579 mg, 1.5 mmol) in tetrahydrofuran (200 mL) was added diethyl azodicarboxylate (810 mg, 1.5 mmol) at 0° C. The mixture was stirred at 0° C. for 45 min. After completion, the mixture was poured into ice-water (50 mL) and extracted with ethyl acetate (3×50 mL). The mixture was concentrated and the residue was purified by flash chromatography column (C18, acetonitrile/water=30% to 95%) to afford (S)-3-((1S,4S)-2-oxa-5-azabicyclo[2.2.1]heptan-5-ylmethyl)-10-bromo-9-chloro-7-hydroxy-2H-[1,4]thiazino[2,3,4-ij]quinazolin-5(3H)-one (500 mg, 85% yield) as a white solid. MS (ESI): m/z: 444.3 [M+H]⁺.

(2R,5S)-tert-butyl 4-((S)-3-((1S,4S)-2-oxa-5-azabi-cyclo[2.2.1]heptan-5-ylmethyl)-10-bromo-9-chloro-5-oxo-3,5-dihydro-2H-[1,4]thiazino[2,3,4-ij]qui-nazolin-7-yl)-2,5-dimethylpiperazine-1-carboxylate (6)

To a mixture of (S)-3-((1R,4S)-2-oxa-5-azabicyclo[2.2.1]heptan-5-ylmethyl)-9-bromo-10-chloro-7-hydroxy-2H-[1,4]thiazino[2,3,4-ij]quinazolin-5(3H)-one (500 mg, 1.12 mmol) and potassium carbonate (1.5 g, 11.2 mmol) in acetonitrile (20 mL) was added benzenesulphonyl chloride (678 mg, 2.24 mmol) at 25° C. The mixture was stirred at 25° C. for 1 hour. Then (2R,5S)-tert-butyl 2,5-dimethylpip-erazine-1-carboxylate (720 mg, 3.36 mmol) was added and the resulting mixture was stirred at 25° C. for 1 hour. After completion, the mixture was poured into ice-water (30 mL) and extracted with ethyl acetate (3×30 mL). After concen-tration, the residue was purified by Flash chromatography column (C18, acetonitrile/water=20% to 95%) to afford (2R,5S)-tert-butyl 4-((S)-3-((1S,4S)-2-oxa-5-azabicyclo[2.2.1]heptan-5-ylmethyl)-10-bromo-9-chloro-5-oxo-3,5-dihydro-2H-[1,4]thiazino[2,3,4-ij]quinazolin-7-yl)-2,5-dim-ethylpiperazine-1-carboxylate (233 mg, 33% yield) as a yellow solid. MS (ESI) m/z: 640.6[M+H]$^+$.

(2R,5S)-tert-butyl 4-((3S)-3-((1S,4S)-2-oxa-5-azabi-cyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (7)

To a solution of (2R,5S)-tert-butyl 4-((S)-3-((1S,4S)-2-oxa-5-azabicyclo[2.2.1]heptan-5-ylmethyl)-10-bromo-9-chloro-5-oxo-3,5-dihydro-2H-[1,4]thiazino[2,3,4-ij]qui-nazolin-7-yl)-2,5-dimethylpiperazine-1-carboxylate (233 mg, 0.36 mmol) in 1,4-dioxane (5 mL) and water (1 mL), tripotassium phosphate (230 mg, 1.08 mmol), (5-chloro-2,4-difluorophenyl)boronic acid (794 mg, 2.88 mmol), and [1,1'-bis(diphenylphosphino)ferrocene]dichloropalladium (II) (53 mg, 0.072 mmol) were added. The mixture was stirred at 85° C. under nitrogen atmosphere for 4 hours. After completion, the mixture was diluted with tetrahydrofuran (50 mL) and the insoluble solid was removed by filtration. The mixture was concentrated and the residue was purified by silica gel column chromatography (dichloromethane/methanol=100/1 to 30/1 as gradient) to afford (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (180 mg, 75% yield) as a yellow oil. MS (ESI) m/z: 708.7 [M+H]$^+$.

(2R,5S)-tert-butyl 4-((3S)-3-((1S,4S)-2-oxa-5-azabi-cyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (8)

To a cooled mixture of (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (180 mg, 0.25 mmol) in dichloromethane (5 mL) at 0° C. was added trifluoroacetic acid (1 mL). The reaction solution was stirred at room temperature for 1 hour. After completion, the mixture was concentrated and the residue was purified by silica gel column chromatography using a mixture of dichlorometh-ane/methanol (15/1) to afford (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (120 mg, 85% yield) as a yellow solid. MS (ESI) m/z: 608.5[M+H]$^+$.

$^1$H NMR (400 MHz, CDCl$_3$) δ 7.65-7.64 (m, 1H), 7.32-7.26 (m, 1H), 7.12-7.06 (m, 1H), 5.37-5.27 (m, 1H), 4.40-4.37 (m, 1H), 4.19-4.18 (m, 1H), 3.92-3.88 (m, 1H), 3.72-3.55 (m, 4H), 3.47-3.45 (m, 2H), 3.34-3.30 (m, 2H), 3.04-2.92 (m, 4H), 2.89-2.78 (m, 3H), 1.80-1.69 (m, 3H), 1.45-1.26 (m, 3H).

(3S)-3-((1S,4S)-2-oxa-5-azabicyclo[2.2.1]heptan-5-ylmethyl)-7-((2S,5R)-4-acryloyl-2,5-dimethylpiper-azin-1-yl)-9-chloro-10-(5-chloro-2,4-difluorophe-nyl)-2H-[1,4]thiazino[2,3,4-ij]quinazolin-5(3H)-one (9)

To a mixture of (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thi-azino[2,3,4-ij]quinazolin-7-yl)-2,5-dimethylpiperazine-1-carboxylate (120 mg, 0.20 mmol) and triethylamine (41 mg, 0.40 mmol) in dichloromethane (5 mL) was added acrylic anhydride (25 mg, 0.20 mmol) at 0° C. The mixture was stirred at 0° C. for 1 hour. After completion, the mixture was poured into ice-water (15 mL) and extracted with ethyl acetate (3×15 mL). After concentration, the residue was purified by preparative high performance liquid chromatog-raphy (20% to 95% acetonitrile in water) to afford (3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one (48 mg, 37% yield) as a yellow solid. MS (ESI) m/z: 662.1 [M+H]$^+$. $^1$H NMR (400 MHz, CDCl$_3$) δ 7.54-7.52 (m, 1H), 7.32-7.25 (m, 1H), 7.12-7.06 (m, 1H), 6.66-6.50 (m, 1H), 6.41-6.33 (m, 1H), 5.79-5.75 (m, 1H), 5.28-5.24 (m, 1H), 5.01-4.70 (m, 2H), 4.40-4.26 (m, 2H), 4.02-3.90 (m, 2H), 3.69-3.55 (m, 4H), 3.46-3.29 (m, 1H), 3.03-2.86 (m, 5H), 1.77-1.65 (m, 2H), 1.52-1.33 (m, 6H).

DD. Example 518

(3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one

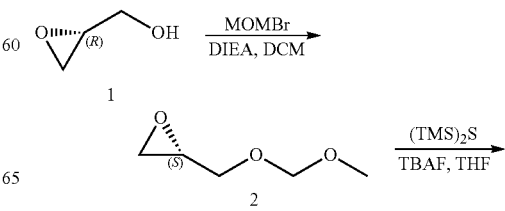

1039
-continued
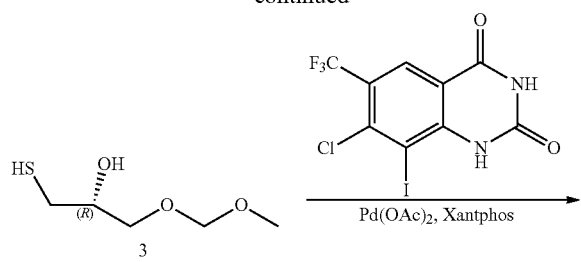
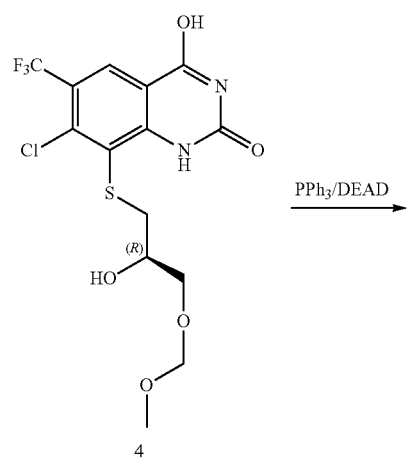
1040
-continued
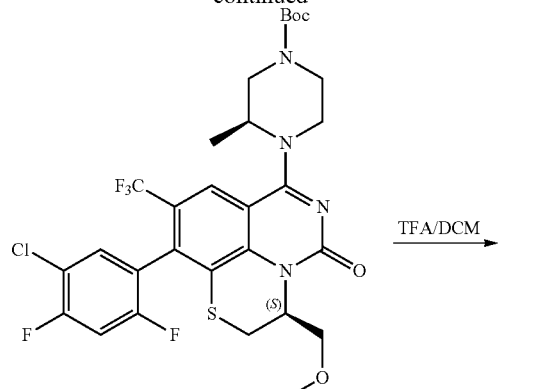
(S)-2-((methoxymethoxy)methyl)oxirane (2)
To a mixture of (R)-oxiran-2-ylmethanol (15 g, 202.7 mmol) and N,N-diisopropylethylamine (52.3 g, 405.4 mmol) in dichloromethane (200 mL) was added bromo(methoxy)methane (32.7 g, 263.5 mmol) at 0° C. The mixture was allowed to warm to room temperature and stirred for 5 hours. After completion, the mixture was poured into dichloromethane (300 mL), washed with water (3×200 mL). The organic phase was washed with brine (100 mL) and dried over anhydrous sodium sulfate. After filtration and concentration, the residue was purified by silica gel column with petroleum ether to afford (S)-2-((methoxymethoxy)methyl)oxirane (25.00 g, crude) as colorless oil; $^1$H NMR (400 MHz, CDCl$_3$) δ 4.66 (d, J=1.2 Hz, 2H), 3.79 (dd, J=11.6 Hz, 3.2 Hz, 1H), 3.51 (dd, J=11.6 Hz, 2.0 Hz, 1H), 3.38 (s, 3H), 3.20-3.16 (m, 1H), 2.83-2.80 (m, 1H), 2.64 (dd, J=5.2 Hz, 2.8 Hz, 1H).

(R)-1-mercapto-3-(methoxymethoxy)propan-2-ol (3)

To a mixture of (S)-2-((methoxymethoxy)methyl)oxirane (10 g, 84.7 mmol) in tetrahydrofuran (250 mL) was added 1,1,1,3,3,3-hexamethyldisilathiane (16.63 g, 93.2 mmol) and tetrabutylammonium fluoride (1.0 M in tetrahydrofuran, 25 mL, 25 mmol) at 0° C. The mixture was stirred at room temperature for 2 hours. After completion, the mixture concentrated under reduced pressure, the residue was purified by silica gel column eluting with petroleum ether/ethyl acetate=4/1 to afford (R)-1-mercapto-3-(methoxymethoxy)propan-2-ol (2 g, 16% yield) as a colorless oil. $^1$H NMR (400 MHz, CDCl$_3$) δ 4.66 (s, 2H), 3.85-3.82 (m, 1H), 3.69-3.60 (m, 2H), 3.39 (s, 3H), 2.88 (brs, 1H), 2.71-2.65 (m, 2H), 1.51 (t, J=8.8 Hz, 1H).

(R)-7-chloro-4-hydroxy-8-((2-hydroxy-3-(methoxymethoxy)propyl)thio)-6-(trifluoromethyl)quinazolin-2(1H)-one (4)

To a solution of 7-chloro-8-iodo-6-(trifluoromethyl)quinazoline-2,4(1H,3H)-dione (1.86 g, 4.77 mmol) in dioxane (40 mL) were added potassium carbonate (1.32 g, 9.54 mmol), (R)-1-mercapto-3-(methoxymethoxy)propan-2-ol (1.09 g, 7.15 mmol), 4,5-bis(diphenyl-phosphino)-9,9-dimethylxanthene (413 mg, 0.72 mmol) and Tris(dibenzylideneacetone) dipalladium (439 g, 0.48 mmol). The mixture was stirred at 60° C. under nitrogen atmosphere for 18 hours. After completion, the mixture was concentrated under reduced pressure. The residue was purified by silica gel column chromatography eluting with dichloromethane/methanol=60/1 to afford (R)-7-chloro-4-hydroxy-8-((2-hydroxy-3-(methoxymethoxy)propyl)thio)-6-(trifluoromethyl)quinazolin-2(1H)-one (1.33 g, 67% yield) as pale yellow solid. MS (ESI) m/z: 415.0 [M+H]$^+$.

(S)-10-chloro-7-hydroxy-3-((methoxymethoxy)methyl)-9-(trifluoromethyl)-2H-[1,4]thiazino[2,3,4-ij]quinazolin-5(3H)-one (5)

To a mixture of (R)-7-chloro-4-hydroxy-8-((2-hydroxy-3-(methoxymethoxy)propyl)thio)-6-(trifluoromethyl)quinazolin-2(1H)-one (1.33 g, 3.21 mmol) and triphenylphosphoranylidene (3.37 g, 12.85 mmol) in tetrahydrofuran (500 ml) was added 1,2-bis[(4-chlorophenyl)methyl] ester (4.71 g, 12.85 mmol) at 0° C. The mixture was stirred at 0° C. for 45 min. After completion, the mixture was poured into ice-water (200 mL) and extracted with ethyl acetate (200 mL×3). Concentrated and the residue was purified by C18 with gradient of 30-95% acetonitrile in water to afford (S)-10-chloro-7-hydroxy-3-((methoxymethoxy)methyl)-9-(trifluoromethyl)-2H-[1,4]thiazino[2,3,4-ij]quinazolin-5(3H)-one (1.1 g, 87% yield) as a pale yellow solid. MS (ESI) m/z: 397.0 [M+H]$^+$.

(S)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (6)

To a mixture of (S)-10-chloro-7-hydroxy-3-((methoxymethoxy)methyl)-9-(trifluoromethyl)-2H-[1,4]thiazino[2,3,4-ij]quinazolin-5(3H)-one (1.1 g, 2.78 mmol) and potassium carbonate (3.84 g, 27.8 mmol) in acetonitrile (50 mL) was added 4-methylbenzenesulfonic anhydride (1.81 g, 5.56 mmol) at 0° C. The mixture was stirred at room temperature for 4 hours. After completion, (S)-tert-butyl 3-methylpiperazine-1-carboxylate (1.95 g, 8.33 mmol) was added into the reaction solution. The reaction mixture was stirred at 0° C. for 1 hour. After completion, the mixture was poured into ice-water (200 mL) and extracted with ethyl acetate (100 mL×3).After concentration, the residue was purified by C18 column with gradient of 20-95% acetonitrile in water to afford (S)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (1 g, 59% yield) as a pale yellow solid. MS (ESI) m/z: 613.1 [M+H]$^+$.

(3S)-tert-butyl 4-((3S)-10-(5-chloro-2,4-difluorophenyl)-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (7)

To a solution of (S)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (250 mg, 0.408 mmol) in 1,4-dioxane (6 mL) and water (1 mL) were added tripotassium phosphate (260 mg, 1.224 mmol), (5-chloro-2,4-difluorophenyl)boronic acid (560 mg, 2.04 mmol), and Chloro(2-dicyclohexylphosphino-2', 6'-diisopropoxy-1,1'-biphenyl)[2-(2'-amino-1,1'-biphenyl)]palladium(II) (32 mg, 0.04 mmol). The mixture was stirred at 80° C. under nitrogen atmosphere for 4 hours. After completion, the mixture was concentrated under reduced pressure, the residue was purified by silica gel column chromatography eluting with dichloromethane/methanol=50/1 to afford (3S)-tert-butyl 4-((3S)-10-(5-chloro-2,4-difluorophenyl)-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (398 mg, crude) as a yellow solid. MS (ESI) m/z: 725.7 [M+H]$^+$.

(3S)-10-(5-chloro-2,4-difluorophenyl)-3-((methoxymethoxy)methyl)-7-((S)-2-methylpiperazin-1-yl)-9-(trifluoromethyl)-2H-[1,4]thiazino[2,3,4-ij]quinazolin-5(3H)-one (8)

To a mixture of (3S)-tert-butyl 4-((3S)-10-(5-chloro-2,4-difluorophenyl)-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (398 mg, 0.55 mmol) in methanol (15 ml) was added palladium on charcoal (10%) (148 mg). The reaction solution was stirred at room temperature under hydrogen atmosphere for 1 hour. After completion, the mixture was filtered and concentrated, the residue was purified by column (dichloromethane/methanol=5:1) to afford (3S)-10-(2,4-difluorophenyl)-7-((2S, 5R)-2,5-dimethylpiperazin-1-yl)-3-((2-methoxyethoxy)methyl)-9-(trifluoromethyl)-2H-[1,4]thiazino[2,3,4-ij]quinazolin-5(3H)-one (701 mg, impure) as a yellow-brown solid. MS (ESI) m/z: 591.5[M+H]$^+$.

(3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one (9)

To a mixture of (3S)-10-(2,4-difluorophenyl)-7-((2S, 5R)-2,5-dimethylpiperazin-1-yl)-3-((2-methoxyethoxy)methyl)-

9-(trifluoromethyl)-2H-[1,4]thiazino[2,3,4-ij]quinazolin-5 (3H)-one (272 mg, 0.46 mmol) and triethyl amine (93 mg, 0.92 mmol) in dichloromethane (5 ml) was added acrylic anhydride (70 mg, 0.55 mmol) at 0° C. The mixture was stirred at 0° C. for 1 hour. After completion, the mixture was poured into ice-water (30 mL) and extracted with dichloromethane (30 mL×3). After concentration, the residue was purified by preparative High Performance Liquid Chromatography with gradient of 20% to 95% acetonitrile in water to afford (3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one (73.6 mg, 25% yield) as a white solid. MS (ESI) m/z: 645.2 [M+H]$^+$.

$^1$H NMR (400 MHz, CDCl$_3$) δ 7.78 (s, 1H), 7.31-7.24 (m, 1H), 7.10-7.04 (m, 1H), 6.67-6.50 (m, 1H), 6.38 (dd, J=16.8 Hz, 2.0 Hz, 1H), 5.79 (d, J=10.4 Hz, 1H), 5.50-5.38 (m, 1H), 4.80-4.62 (m, 3H), 4.59-4.26 (m, 2H), 4.06-3.92 (m, 0.5H), 3.90-3.74 (m, 2.5H), 3.67-3.47 (m, 1.5H), 3.46-3.33 (m, 4.5H), 3.17-2.96 (m, 2H), 1.61-1.44 (m, 3H).

EE. Example 531

8'-((2S,5R)-4-Acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one

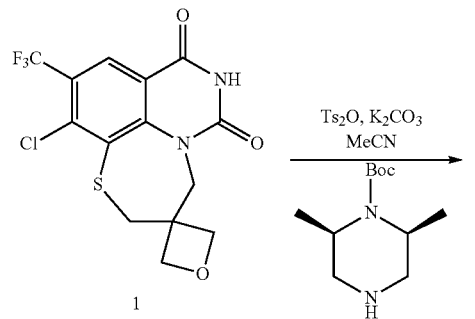

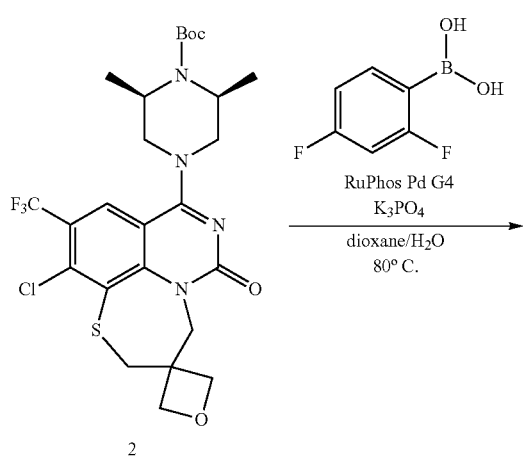

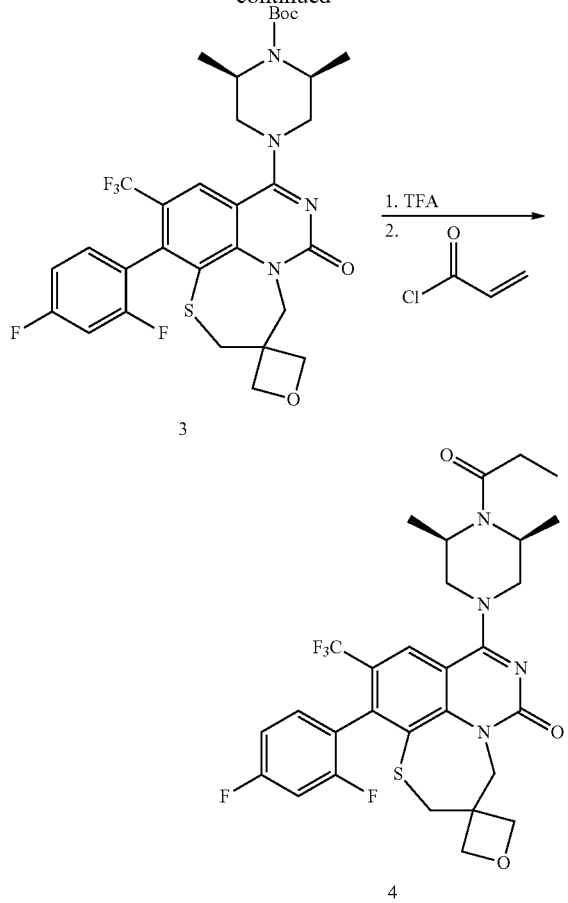

tert-Butyl (2S,6R)-4-(11'-chloro-6'-oxo-10'-(trifluoromethyl)-2'H,4'H,6'H-spiro[oxetane-3,3'-[1,4]thiazepino[2,3,4-ij]quinazolin]-8'-yl)-2,6-dimethylpiperazine-1-carboxylate (2)

Compound 1 (30 mg, 0.08 mmol, 1 equiv) was dissolved in MeCN (1.6 mL, 0.05 M) under a N$_2$ atmosphere in a 5 mL microwave vial. Potassium carbonate (33 mg, 0.24 mmol, 3 equiv) was added to the reaction mixture and the reaction mixture was briefly sonicated. p-Toluenesulfonic anhydride (52 mg, 0.16 mmol, 2 equiv) was added to the vial at room temperature. The reaction mixture was stirred for 21 hours and reached 65% conversion (determined by LC-MS). Next, tert-butyl (2R,6S)-2,6-dimethylpiperazine-1-carboxylate (34 mg, 0.16 mmol, 2 equiv) and K$_2$CO$_3$ (22 mg, 0.16 mmol, 2 equiv) were added to the vial and stirred for 30 min at room temperature. The intermediate was determined to be fully consumed by LC-MS and the solvent was removed by rotary evaporation. The mixture was transferred with CH$_2$Cl$_2$ to a separatory funnel, washed with saturated aqueous NH$_4$Cl (20 mL), extracted with CH$_2$Cl$_2$ (2×50 mL), dried over Na$_2$SO$_4$, and filtered. The solvent was removed by rotary evaporation. The crude material was partially purified by flash column chromatography using an Isolera One Biotage instrument (0-6% MeOH/CH$_2$Cl$_2$, 10 g column, 0% (5 CV), 0-6% (15 CV), 6% (5 CV)), to provide compound 2 (44 mg, impure) as a yellow solid. This impure material was used as is in the subsequent step: TLC (5% MeOH/CH$_2$Cl$_2$) R$_f$=0.43; LRMS-ESI (m/z) [M+H]$^+$ calculated for C$_{25}$H$_{31}$ClF$_3$N$_4$O$_4$S 575.17, found 575.2.

tert-Butyl (2S,6R)-4-(11'-(2,4-difluorophenyl)-6'-oxo-10'-(trifluoromethyl)-2'H,4'H,6'H-spiro[oxetane-3,3'-[1,4]thiazepino[2,3,4-ij]quinazolin]-8'-yl)-2,6-dimethylpiperazine-1-carboxylate (3)

Compound 2 (44 mg, impure ~0.08 mmol, 1 equiv) was dissolved in 1,4-dioxane and H₂O (1.3 mL, 0.3 mL, respectively, 0.05 M). The resulting mixture was purged with N₂ for 30 min prior to the addition of RuPhos Pd G4 (6.8 mg, 0.008 mmol, 10 mol %), K₃PO₄ (51 mg, 0.24 mmol, 3 equiv), and (2,4-difluorophenyl)boronic acid (63 mg, 0.4 mmol, 5 equiv). The microwave vial was fitted with a crimp-top cap, bubbled with N₂ for an additional 5 min, and placed on a heated block at 80° C. The resulting reaction mixture was homogenous and orange. After 1 h, the vial was removed from the heating block, allowed to cool, and the solvent was removed by rotary evaporation (full conversion determined by LC-MS). The crude material was partially purified by flash column chromatography using an Isolera One Biotage instrument (0-6% MeOH/CH₂Cl₂, 10 g column, 0% (5 CV), 0-6% (15 CV), 6% (5 CV)) to afford the desired product (3) as a brown oil (38 mg). The material was used as is in the subsequent step: TLC (3% MeOH/CH₂Cl₂) R$_f$=0.19; LRMS-ESI (m/z) [M+H]⁺ calculated for C₃₁H₃₄F₅N₄O₄S 653.22, found 653.3.

8'-((3S,5R)-4-Acryloyl-3,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one (4)

Standard deBoc and acrylation conditions: 0.054 mmol scale, 8.7 mg off-white solid, 27% yield:
¹H NMR (400 MHz, MeOH-d₄) δ 8.16 (s, 1H), 7.31 (q, J=7.6 Hz, 1H), 7.11 (t, J=8.6 Hz, 2H), 6.84 (dd, J=16.7, 10.6 Hz, 1H), 6.29 (dd, J=16.7, 2.0 Hz, 1H), 5.80 (dd, J=10.5, 2.0 Hz, 1H), 5.37-4.95 (m, 2H), 4.87-4.50 (m, 4H), 4.43 (dd, J=6.3, 1.6 Hz, 2H), 4.25 (d, J=13.5 Hz, 2H), 3.65-3.36 (m, 4H), 1.52 (d, J=6.6 Hz, 3H), 1.48 (d, J=6.8 Hz, 3H); LRMS-ESI (m/z) [M+H]⁺ calculated for C₂₉H₂₈F₅N₄O₃S 607.18, found 607.3.

FF. Example 588

8'-((2S,5R)-4-Acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one The title compound was synthesized using similar procedures described for Example 531.
¹H NMR (400 MHz, MeOH-d₄) δ 7.97 (d, J=2.7 Hz, 1H), 7.30 (dq, J=13.7, 7.6 Hz, 1H), 7.11 (t, J=8.3 Hz, 2H), 6.90-6.72 (m, 1H), 6.28 (ddd, J=16.7, 5.6, 2.0 Hz, 1H), 5.80 (ddd, J=9.7, 7.2, 2.0 Hz, 1H), 4.87-4.60 (m, 3H), 4.55-4.36 (m, 3H), 4.34-3.69 (m, 4H), 3.62-3.40 (m, 3H), 1.49-1.25 (m, 6H); LRMS-ESI (m/z) [M+H]⁺ calculated for C₂₉H₂₈F₅N₄O₃S 607.18, found 607.2.

GG. Example 589

8'-(4-Acryloylpiperazin-1-yl-2,2,3,3,5,5,6,6-d₈)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one

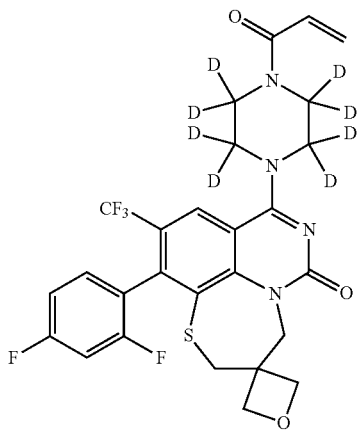 [SMILES: [2H]C1([2H])N(C(=O)C=C)C([2H])([2H])C([2H])([2H])N(c2nc(=O)n3c4c(c(-c5ccc(F)cc5F)c(C(F)(F)F)cc24)SCC2(COC2)C3)C1([2H])[2H]]

The title compound was synthesized via similar methods described for Example 531.
¹H NMR (400 MHz, MeOH-d₄) δ 8.00 (s, 1H), 7.30 (q, J=7.7 Hz, 1H), 7.11 (t, J=8.7 Hz, 2H), 6.80 (dd, J=16.7, 10.6 Hz, 1H), 6.27 (dd, J=16.7, 1.9 Hz, 1H), 5.80 (dd, J=10.6, 2.0 Hz, 1H), 4.82-4.54 (m, 2H), 4.43 (d, J=5.5 Hz, 2H), 3.61-3.46 (m, 2H), 3.23-3.11 (m, 2H); LRMS-ESI (m/z) [M+H]⁺ calculated for C₂₇H₁₆D₈F₅N₄O₃S 587.20, found 587.2.

HH. Examples 546 and 547

(3S,10S)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one and (3S,10R)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one

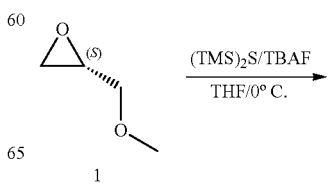

-continued
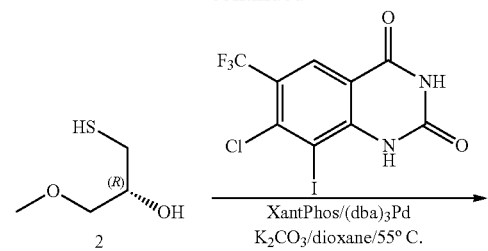
2
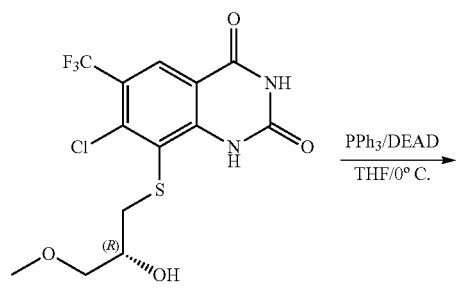
3
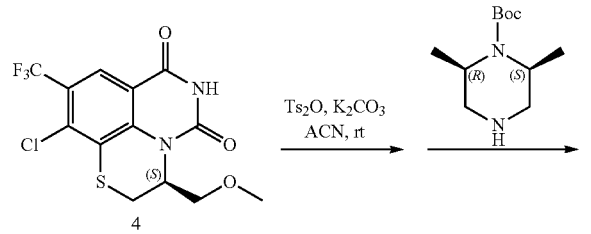
4
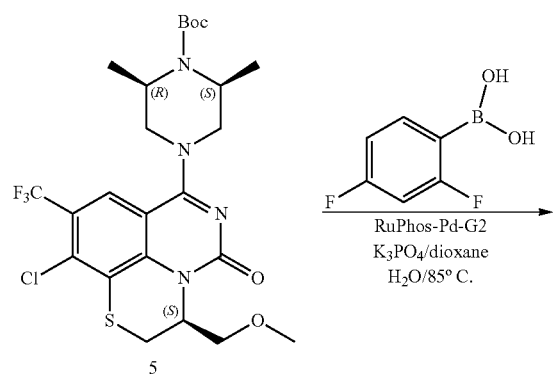
5
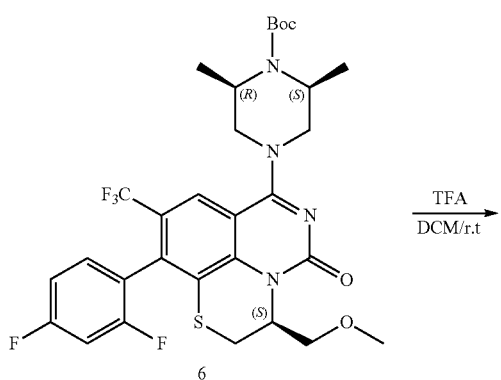
6
-continued
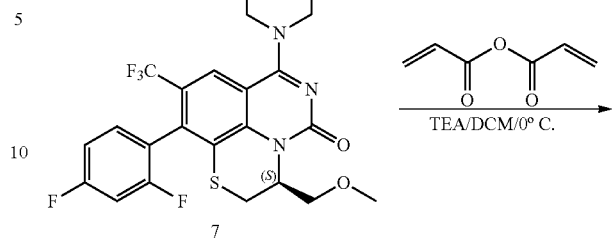
7
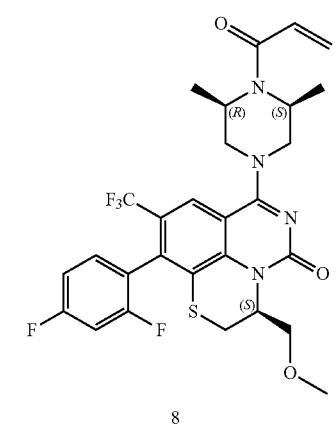
8
8
P1

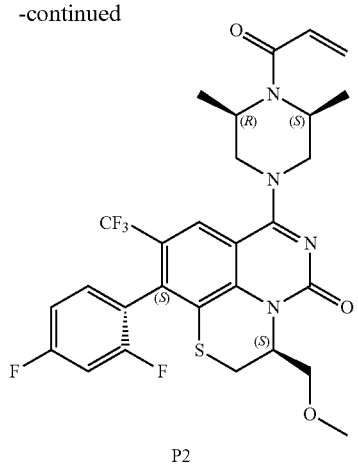

P2

(R)-1-mercapto-3-methoxypropan-2-ol (2)

To a mixture of (S)-2-(methoxymethyl)oxirane (10.00 g, 113.6 mmol) in tetrahydrofuran (150 mL) was added 1,1,1,3,3,3-hexamethyldisilathiane (30.33 g, 170.4 mmol) and tetrabutylammonium fluoride (1.0 M in tetrahydrofuran, 34.1 mL, 34.1 mmol) at 0° C. The mixture was stirred at room temperature for 2 hours. After completion, the mixture was poured into water (300 mL), extracted with ethyl acetate (3×200 mL). The combined organic phase was washed with brine (300 mL) and dried over anhydrous sodium sulfate. After filtration and concentration, the residue was purified by silica gel column eluting with petroleum ether/ethyl acetate (3/1) to afford (R)-1-mercapto-3-methoxypropan-2-ol (17.0 g, crude) as a colorless oil.

$^1$H NMR (300 MHz, CDCl$_3$) δ 3.86-3.82 (m, 1H), 3.49-3.46 (m, 1H), 3.41-3.37 (m, 4H), 2.71-2.64 (m, 1H), 1.55-1.50 (m, 1H).

(R)-7-chloro-8-((2-hydroxy-3-methoxypropyl)thio)-6-(trifluoromethyl)quinazoline-2,4(1H,3H)-dione (3)

To a solution of 7-chloro-8-iodo-6-(trifluoromethyl)quinazoline-2,4(1H,3H)-dione (4.00 g, 10.24 mmol) in dioxane (100 mL) were added potassium carbonate (4.25 g, 30.73 mmol), (R)-1-mercapto-3-methoxypropan-2-ol (2.50 g, 20.48 mmol), 4,5-bis(diphenyl-phosphino)-9,9-dimethylxanthene (0.89 g, 1.54 mmol) and tris(dibenzylideneacetone) dipalladium (0.94 g, 1.02 mmol). The mixture was stirred at 55° C. under nitrogen atmosphere for 18 hours. After completion, the mixture was diluted with tetrahydrofuran (300 mL) and filtered. After concentration, the residue was purified by silica gel column chromatography with a gradient of dichloromethane/methanol=100/1 to 30/1 to afford (R)-7-chloro-8-((2-hydroxy-3-methoxypropyl)thio)-6-(trifluoromethyl)quinazoline-2,4(1H,3H)-dione (3.15 g, 80% yield) as a white solid. MS (ESI) m/z: 385.0 [M+H]$^+$.

(S)-10-chloro-3-(methoxymethyl)-9-(trifluoromethyl)-2H-[1,4]thiazino[2,3,4-ij]quinazoline-5,7(3H,6H)-dione (4)

To a mixture of (R)-7-chloro-8-((2-hydroxy-3-methoxypropyl)thio)-6-(trifluoromethyl)quinazoline-2,4(1H,3H)-dione (3.15 g, 8.20 mmol) and triphenylphosphoranylidene (4.29 g, 16.40 mmol) in tetrahydrofuran (160 mL) was added diethyl azodicarboxylate (2.85 g, 16.40 mmol) at 0° C. The mixture was stirred at 0° C. for 45 min. After completion, the mixture was poured into ice-water (300 mL) and extracted with ethyl acetate (500 mL×3). After concentration, the residue was purified by Flash chromatography column (C18, acetonitrile/water=30% to 95%) to afford (S)-10-chloro-3-(methoxymethyl)-9-(trifluoromethyl)-2H-[1,4]thiazino[2,3,4-ij]quinazoline-5,7(3H,6H)-dione (2.10 g, 70% yield) as a white solid. MS (ESI): m/z: 367.0 [M+H]$^+$.

(2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (5)

To a mixture of (S)-10-chloro-3-(methoxymethyl)-9-(trifluoromethyl)-2H-[1,4]thiazino[2,3,4-ij]quinazoline-5,7(3H,6H)-dione (200 mg, 0.55 mmol) and potassium carbonate (759 mg, 5.50 mmol) in acetonitrile (25 mL) was added 4-methylbenzenesulfonic anhydride (534 mg, 1.65 mmol) at 0° C. The mixture was stirred at 0° C. for 30 min and 30° C. for 1 hour. After completion, (2S,6R)-tert-butyl 2,6-dimethylpiperazine-1-carboxylate (353 mg, 1.65 mmol) was added into the reaction solution. The reaction mixture was stirred at 0° C. for 1 hour. After completion, the mixture was poured into ice-water (300 mL) and extracted with ethyl acetate (3×200 mL). After concentration, the residue was purified by Flash chromatography column (C18, acetonitrile/water=20% to 95%) to afford (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (230 mg, 74% yield) as a pale-white solid. MS (ESI) m/z: 563.5[M+H]$^+$.

(2S,6R)-tert-butyl 4-((3S)-10-(2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a solution of (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (230 mg, 0.41 mmol) in 1,4-dioxane (8 mL) and water (1 mL) were added tripotassium phosphate (348 mg, 1.64 mmol), (2,4-difluorophenyl)boronic acid (385 mg, 2.45 mmol), and Chloro(2-dicyclohexylphosphino-2',6'-diisopropoxy-1,1'-biphenyl)[2-(2'-amino-1,1'-biphenyl)] palladium(II) (64 mg, 0.08 mmol). The mixture was stirred at 85° C. under nitrogen atmosphere for 4 hours. After completion, the mixture was diluted with tetrahydrofuran (300 mL) and filtered. Then After concentration, the residue was purified by silica gel column chromatography with a gradient of dichloromethane/methanol (100/1 to 30/1) to afford (2S,6R)-tert-butyl 4-((3S)-10-(2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (220 mg, crude) as a yellow solid. MS (ESI) m/z: 641.6 [M+H]$^+$.

(3S)-10-(2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (7)

To a mixture of (2S,6R)-tert-butyl 4-((3S)-10-(2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6- dimethylpiperazine-1-carboxylate (220 mg, 0.34 mmol) in dichloromethane (5 ml) was added trifluoroacetic acid (2 mL) at 0° C. The reaction solution was stirred at room temperature for 1 hour. After completion, the mixture was concentrated. The residue was purified by column chromatography (eluting with dichloromethane/methanol (15:1) to afford (3S)-10-(2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (140 mg, 76% yield) as a yellow solid. MS (ESI) m/z: 541.6[M+H]⁺.

(3S)-7-((3S,5R)-4-acryloyl-3,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one (8)

To a mixture of (3S)-10-(2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (120 mg, 0.22 mmol) and triethyl amine (44 mg, 0.44 mmol) in dichloromethane (5 ml) was added acrylic anhydride (42 mg, 0.33 mmol) at 0° C. The mixture was stirred at 0° C. for 1 hour. After completion, the mixture was poured into ice-water (50 mL) and extracted with ethyl acetate (20 mL×3). The organic layer was dried over Na₂SO₄ and filtered. After concentration, the residue was purified by preparative High Performance Liquid Chromatography (20% to 95% acetonitrile in water) to afford (3S)-7-((3S,5R)-4-acryloyl-3,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one (100 mg, 76% yield) as a white solid. $^1$H NMR (400 MHz, CDCl₃) δ 8.07 (s, 1H), 7.17 (q, J=8.0 Hz, 1H), 7.06-6.93 (m, 2H), 6.62 (dd, J=10.4 Hz, 16.8 Hz, 1H), 6.40 (dd, J=2.0 Hz, 16.8 Hz, 1H), 5.77 (dd, J=2.0 Hz, 10.4 Hz, 1H), 5.48-5.41 (m, 1H), 4.79-4.53 (m, 2H), 4.21-4.16 (m, 2H), 3.69-3.59 (m, 2H), 3.37-3.30 (m, 6H), 3.05-2.99 (m, 1H), 1.62 (d, J=6.8 Hz, 3H), 1.47 (d, J=6.8 Hz, 3H). MS (ESI) m/z: 595.6 [M+H]⁺.

The above racemate (72 mg) was dissolved in EtOH (5 mL) and separated by chiral supercritical fluid chromatography (separation condition: Column: Chiralpak AD-H 5 μm 20×250 mm; Mobile Phase: CO₂:EtOH=70:30 at 25 mL/min; Temp: 25° C.; Wavelength: 254 nm) to afford two atropisomers of the title compounds P1 (30.0 mg, 41% yield, 100% de), and P2 (35.0 mg, 48% yield, 100% de); Chiral HPLC Analytical: on CHIRALPAK® AD-H was using 5 μm 4.6×250 mm column, Mobile Phase: CO₂:EtOH=70:30 at 2.5 mL/min; Temp: 25° C.; Wavelength: 254 nm).

P1: $^1$H NMR (400 MHz, CDCl₃) δ 8.07 (s, 1H), 7.18 (q, J=8.0 Hz, 1H), 7.05-6.93 (m, 2H), 6.62 (dd, J=6.0 Hz, 16.4 Hz, 1H), 6.40 (dd, J=1.6 Hz, 16.4 Hz, 1H), 5.77 (dd, J=1.6 Hz, 10.4 Hz, 1H), 5.48-5.45 (m, 1H), 4.70-4.60 (m, 1H), 4.22-4.17 (m, 2H), 3.74-3.60 (m, 3H), 3.39-3.31 (m, 6H), 3.03-2.99 (m, 1H), 1.63-1.61 (m, 3H), 1.47 (d, J=7.2 Hz, 3H); Chiral SFC fraction 1: d.e.=100%, Rt=4.14 min.

P2: $^1$H NMR (400 MHz, CDCl₃) δ 8.07 (s, 1H), 7.18 (q, J=7.6 Hz, 1H), 7.04-6.94 (m, 2H), 6.62 (dd, J=10.0 Hz, 16.8 Hz, 1H), 6.40 (dd, J=2.0 Hz, 16.8 Hz, 1H), 5.77 (dd, J=2.0 Hz, 10.8 Hz, 1H), 5.46-5.42 (m, 1H), 4.73-4.61 (m, 1H), 4.21-4.16 (m, 2H), 3.74-3.64 (m, 3H), 3.40-3.30 (m, 6H), 3.03 (dd, J=2.4 Hz, 13.2 Hz, 1H), 1.63-1.61 (m, 3H), 1.47 (d, J=7.2 Hz, 3H); Chiral SFC fraction 1: d.e.=100%, Rt=4.29 min.

II. Example 560

(3S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one

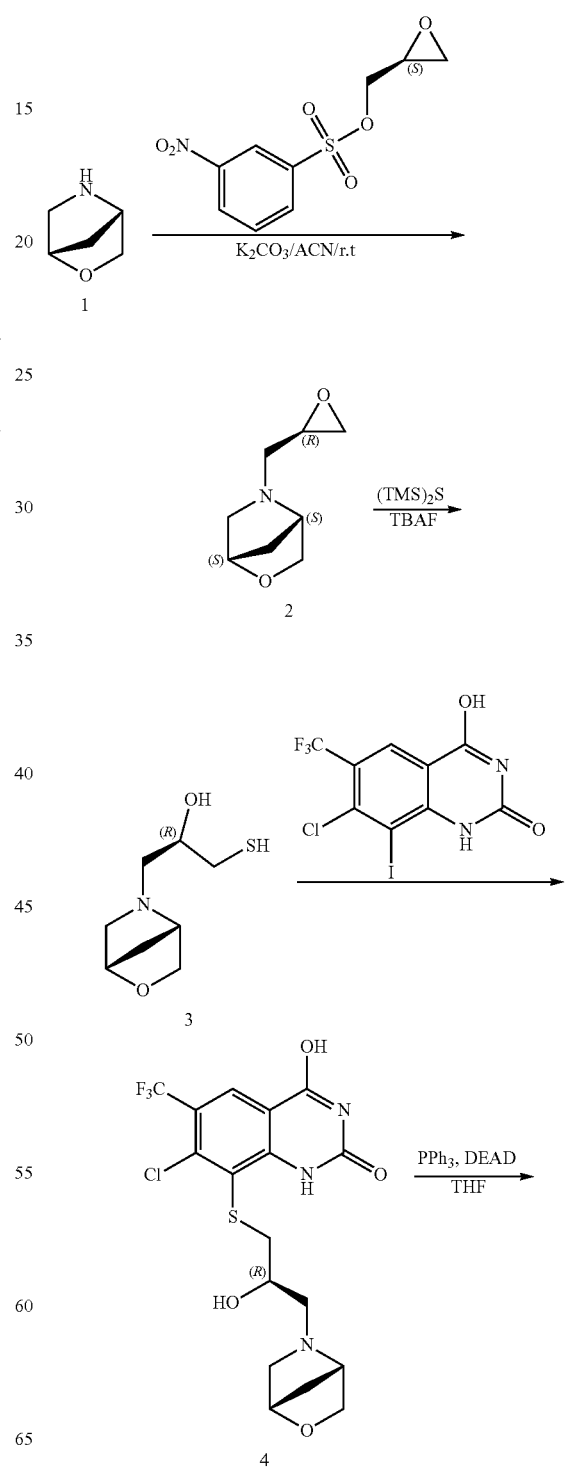

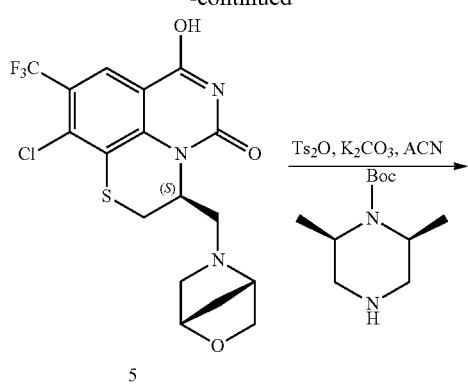

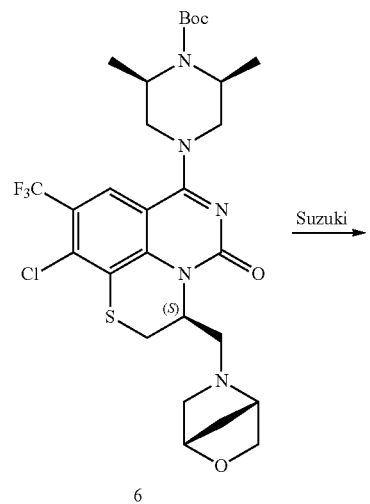

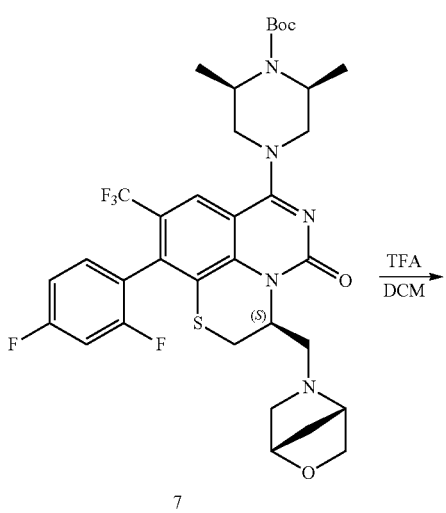

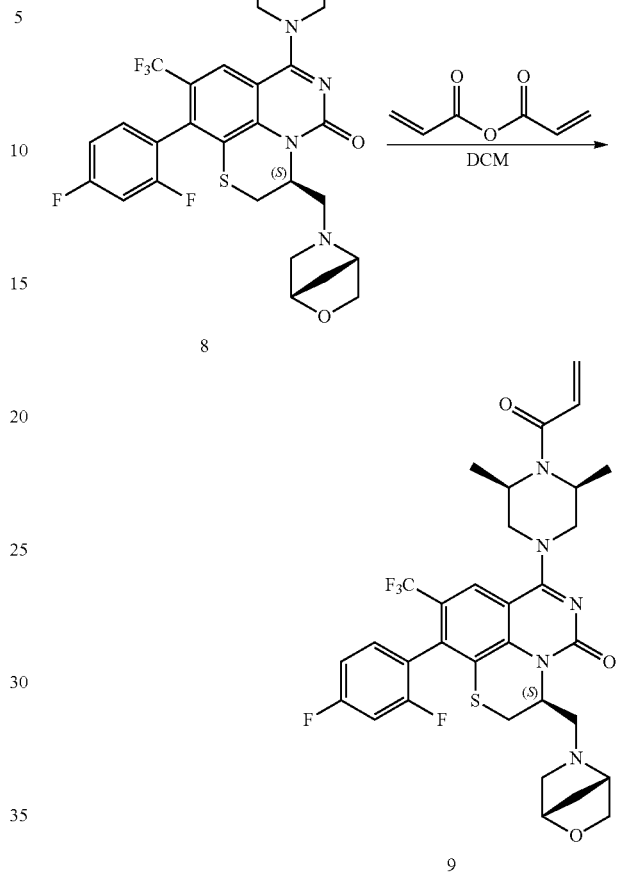

(1S,4S)-5-((R)-oxiran-2-ylmethyl)-2-oxa-5-azabicyclo[2.2.1]heptanes (2)

To a mixture of (S)-oxiran-2-ylmethyl 3-nitrobenzenesulfonate (38.2 g, 147.5 mmol), (1S,4S)-2-oxa-5-azabicyclo[2.2.1]heptane (20.0 g, 147.5 mmol) in acetonitrile (300 mL) was added potassium carbonate (61 g, 442.5 mmol) at 0° C. under nitrogen atmosphere. The mixture was stirred under nitrogen atmosphere at room temperature for 16 hours. After completion, the mixture was concentrated. The residue was purified by silica gel column eluting with dichloromethane/methanol (20/1) to afford the product (15.0 g, 66% yield) as a yellow oil. MS (ESI) m/z: 156.1 [M+H]$^+$.

(R)-1-((1S,4S)-2-oxa-5-azabicyclo[2.2.1]heptan-5-yl)-3-mercaptopropan-2-ol (3)

To a mixture of (1S,4S)-5-((R)-oxiran-2-ylmethyl)-2-oxa-5-azabicyclo[2.2.1]heptane (6 g, 38.7 mmol) in tetrahydrofuran (60 mL) were added 1,1,1,3,3,3-hexamethyldisilathiane (8.9 g, 50.3 mmol) and tetrabutylammonium fluoride (1.0 M in tetrahydrofuran, 11.6 mL, 11.6 mmol) at 0° C. The mixture was stirred at room temperature for 2 hours. After completion, the mixture was poured into water (60 mL), extracted with ethyl acetate (3×100 mL). The organic phase was washed with brine (200 mL) and dried over anhydrous sodium sulfate. After filtration and concentration, the residue was purified by silica gel column eluting with dichloromethane/methanol (50/1) to afford (R)-1-((1S,4S)-2-oxa-5-azabicyclo[2.2.1]heptan-5-yl)-3-mercaptopropan-2-ol (2.6 g, 35% yield) as a colorless oil. MS (ESI) m/z: 190.1 [M+H]$^+$.

8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (4)

To a solution of 7-chloro-4-hydroxy-8-iodo-6-(trifluoromethyl)quinazolin-2(1H)-one (4.00 g, 9.10 mmol) in dioxane (100 mL) were added potassium carbonate (3.70 g, 27.3 mmol), (R)-1-((1S,4S)-2-oxa-5-azabicyclo[2.2.1]heptan-5-yl)-3-mercaptopropan-2-ol (2.57 g, 13.6 mmol), 4,5-bis(diphenyl-phosphino)-9,9-dimethylxanthene (1.05 g, 1.82 mmol) and tris(dibenzylideneacetone) dipalladium (0.823 g, 0.91 mmol). The mixture was stirred at 55° C. under nitrogen atmosphere for 8 hours. After completion, the mixture was diluted with tetrahydrofuran (200 mL) and filtered. The filtrate was concentrated and the residue was purified by silica gel column chromatography (dichloromethane/methanol=100/1 to 20/1 as gradient) to afford 8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (4.00 g, 97% yield) as a yellow solid. MS (ESI) m/z: 452.5 [M+H]$^+$.

(S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (5)

To a mixture of 8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (3.50 g, 7.70 mmol) and triphenylphosphine (3.00 g, 11.6 mmol) in tetrahydrofuran (50 mL) was added diethyl azodicarboxylate (2.60 g, 15.4 mmol) at 0° C. The mixture was stirred at 0° C. for 45 min. After completion, the mixture was poured into ice-water (200 mL) and extracted with ethyl acetate (200 mL×3). After concentration, the residue was purified by flash chromatography column (C18, acetonitrile/water=30% to 95%) to afford (S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (3.14 g, 70% yield) as a white solid. MS (ESI) m/z: 434.4 [M+H]$^+$.

(2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (700 mg, 1.60 mmol) and potassium carbonate (2.20 g, 16.0 mmol) in acetonitrile (20 mL) was added 4-methylbenzenesulfonic anhydride (782 mg, 2.40 mmol) at 25° C. The mixture was stirred at 25° C. for 3 hours. (2R,6S)-tert-butyl 2,6-dimethylpiperazine-1-carboxylate (684 mg, 3.20 mmol) was added into the reaction solution. The reaction mixture was stirred at 25° C. for 1 hour. After completion, the mixture was poured into ice-water (50 mL) and extracted with ethyl acetate (3×50 mL). The mixture was concentrated and the residue was purified by flash chromatography column (C18, acetonitrile/water=20% to 95%) to afford (2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (800 mg, 80% yield) as a yellow solid. MS (ESI) m/z: 630.6 [M+H]$^+$.

(2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (300 mg, 0.476 mmol) in 1,4-dioxane (10 mL) and water (2 mL) were added tripotassium phosphate (404 mg, 1.90 mmol), (2,4-difluorophenyl)boronic acid (602 mg, 3.81 mmol), and chloro(2-dicyclohexylphosphino-2', 6'-diisopropoxy-1,1'-biphenyl)[2-(2'-amino-1,1'-biphenyl)]palladium(II) (74 mg, 0.095 mmol). The mixture was stirred at 85° C. under nitrogen atmosphere for 4 hours. After completion, the mixture was diluted with tetrahydrofuran (50 mL) and filtered. The filtrate was concentrated and the residue was purified by silica gel column chromatography with gradient of dichloromethane/methanol=100/1 to 30/1 to afford (2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (252 mg, 75% yield) as a yellow solid. MS (ESI) m/z: 708.4[M+H]$^+$.

(3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (8)

To a mixture of (2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (252 mg, 0.36 mmol) in dichloromethane (5 mL) was added trifluoroacetic acid (1 mL) at 0° C. The reaction solution was stirred at room temperature for 1 hour. After completion, the mixture was concentrated and the residue was purified by silica gel column chromatography eluting with dichloromethane/methanol (15:1) to afford (3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (185 mg, 85% yield) as a yellow solid. MS (ESI) m/z: 608.1[M+H]$^+$.

(3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (9)

To a mixture of (3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (160 mg, 0.26 mmol) and triethyl amine (40 mg, 0.39 mmol) in dichloromethane (5 mL) was added acrylic anhydride (40 mg, 0.31 mmol) at 0° C. The mixture was stirred at 0° C. for 1 hour.

After completion, the mixture was poured into ice-water (50 mL) and extracted with ethyl acetate (3×20 mL). The mixture was concentrated and the residue was purified by preparative high performance liquid chromatography (20% to 95% acetonitrile in water) to afford (3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (103 mg, 59% yield) as a white solid.

$^1$H NMR (400 MHz, CDCl$_3$) δ 8.07 (s, 1H), 7.21-7.14 (m, 1H), 7.06-6.93 (m, 2H), 6.66-6.59 (m, 1H), 6.43-6.38 (m, 1H), 5.77 (d, J=12.0 Hz, 1H), 5.28-5.24 (m, 1H), 4.74-4.60 (m, 2H), 4.43-4.37 (m, 1H), 4.19 (d, J=13.6 Hz, 2H), 3.91-3.84 (m, 1H), 3.69-3.31 (m, 5.5H), 2.99-2.85 (m, 4.5H), 1.75-1.66 (m, 2H), 1.60-1.58 (m, 3H), 1.49-1.41 (m, 3H). MS (ESI) m/z: 662.1 [M+H]$^+$.

JJ. Example 576 and 577

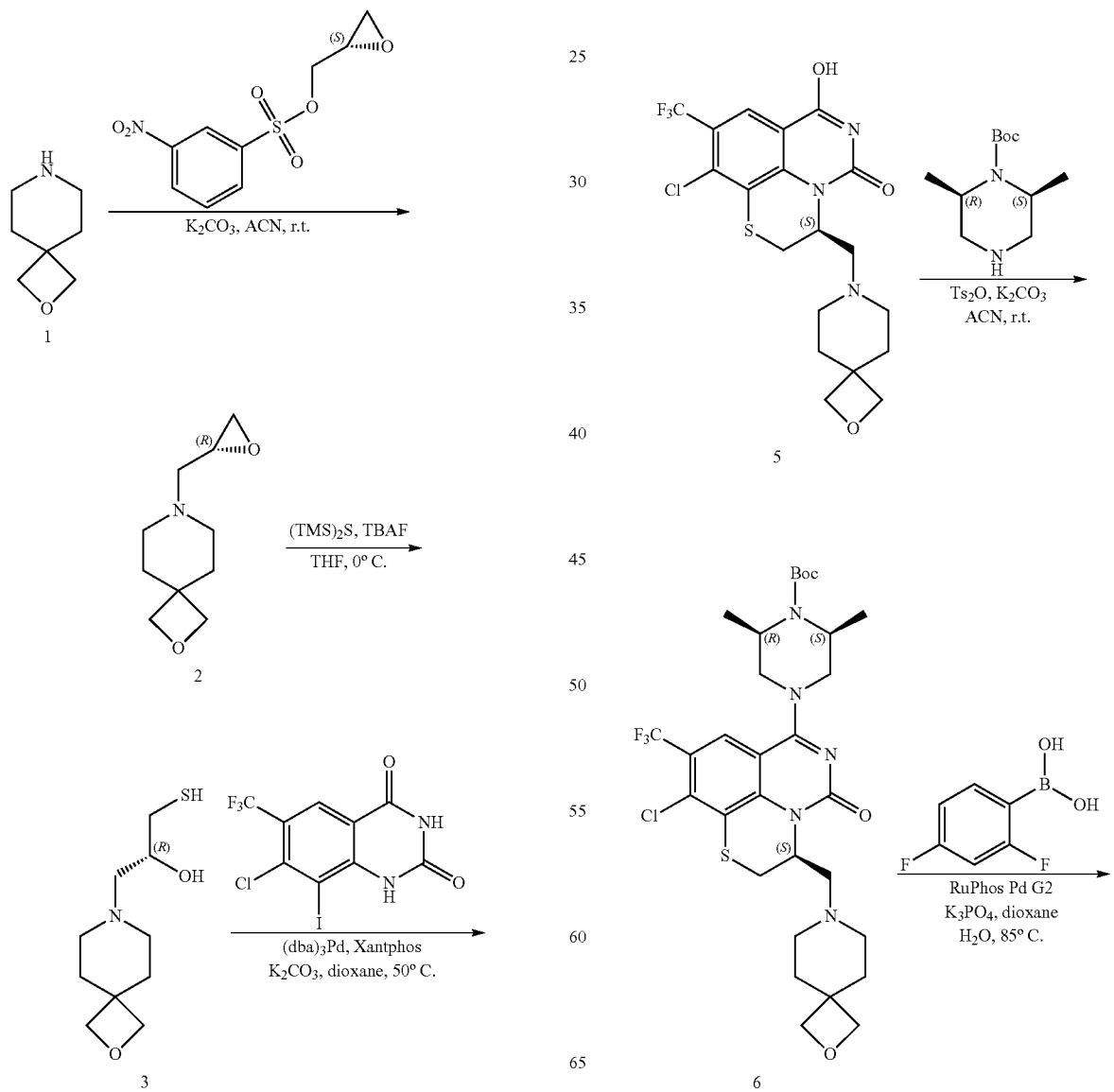

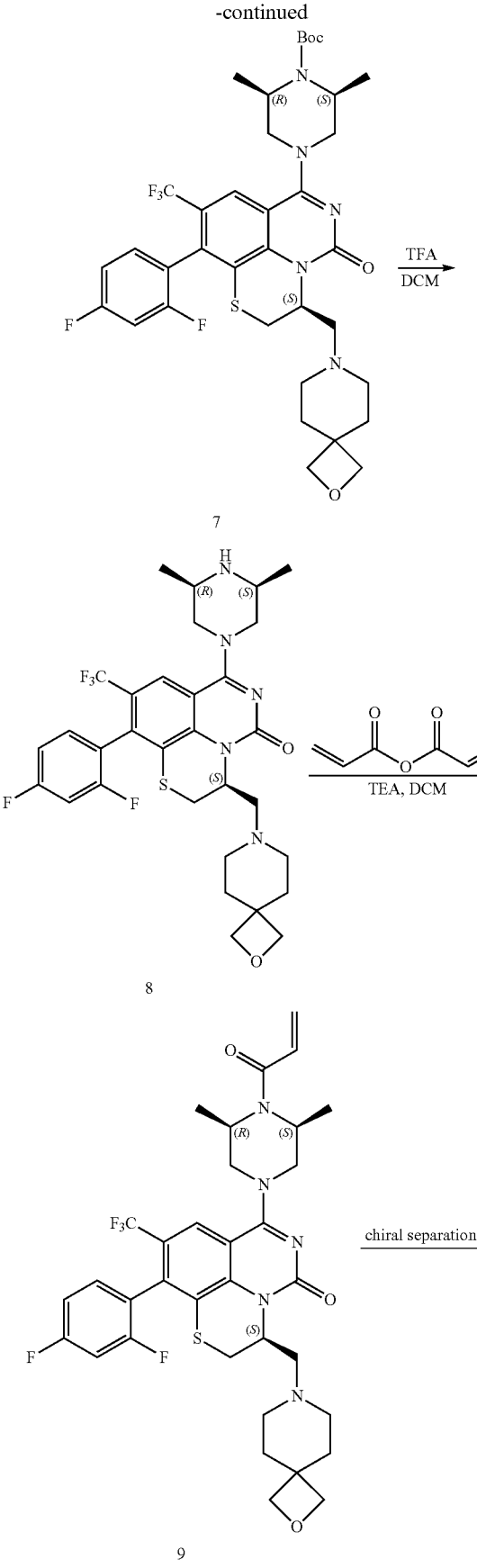

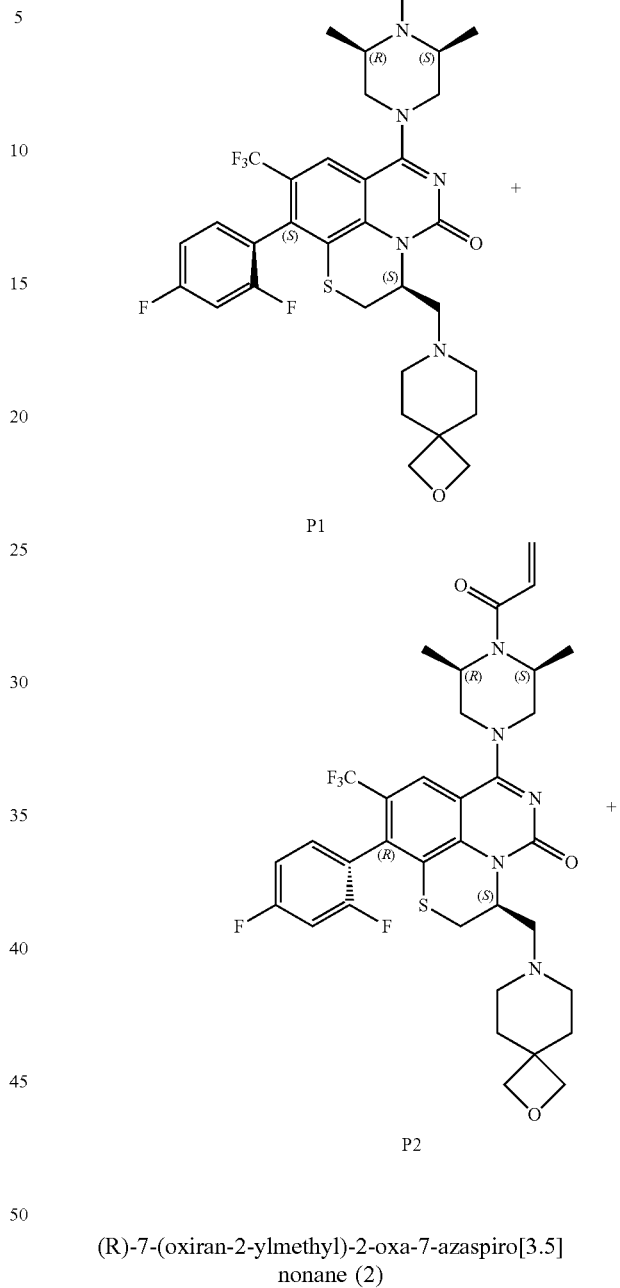

(R)-7-(oxiran-2-ylmethyl)-2-oxa-7-azaspiro[3.5]nonane (2)

To a mixture of (S)-oxiran-2-ylmethyl 3-nitrobenzenesulfonate (5.9 g, 22.8 mmol), 2-oxa-7-azaspiro[3.5]nonane oxalate (4.5 g, 20.7 mmol) in acetonitrile (60 mL) was added potassium carbonate (14.3 g, 103.6 mmol) at 0° C. The mixture was stirred under nitrogen atmosphere at room temperature for 16 hours. After completion, the mixture was concentrated and the residue was purified by silica gel column eluting with dichloromethane/methanol (20/1) to afford (R)-7-(oxiran-2-ylmethyl)-2-oxa-7-azaspiro[3.5]nonane (3.45 g, 91% yield) as a brown oil. MS (ESI) m/z: 180.1 [M+H]+.

(R)-1-mercapto-3-(2-oxa-7-azaspiro[3.5]nonan-7-yl)propan-2-ol (3)

To a mixture of (R)-7-(oxiran-2-ylmethyl)-2-oxa-7-azaspiro[3.5]nonane (3.74 g, 20.4 mmol) in tetrahydrofuran (70 mL) was added 1,1,1,3,3,3-hexamethyldisilathiane (5.45 g, 30.6 mmol) and tetrabutylammonium fluoride (1.0 M in tetrahydrofuran, 6.1 mL, 6.1 mmol) at 0° C. The mixture was stirred at room temperature for 6 hours. After completion, the mixture was concentrated and the residue was purified by silica gel column eluting with dichloromethane/methanol (20/1) to afford (R)-1-mercapto-3-(2-oxa-7-azaspiro[3.5]nonan-7-yl)propan-2-ol (3.47 g, 78% yield) as a brown oil. MS (ESI) m/z: 218.2 [M+H]$^+$.

(R)-7-chloro-4-hydroxy-8-((2-hydroxy-3-(2-oxa-7-azaspiro[3.5]nonan-7-yl)propyl)thio)-6-(trifluoromethyl)quinazolin-2(1H)-one (4)

To a solution of 7-chloro-8-iodo-6-(trifluoromethyl)quinazoline-2,4(1H,3H)-dione (2.0 g, 4.59 mmol) in dioxane (50 mL) were added potassium carbonate (2.5 g, 18.36 mmol), (R)-1-mercapto-3-(2-oxa-7-azaspiro[3.5]nonan-7-yl)propan-2-ol (1.5 g, 6.88 mmol), 4,5-bis(diphenyl-phosphino)-9,9-dimethylxanthene (526 mg, 0.9 mmol) and tris (dibenzylideneacetone) dipalladium (421 mg, 0.45 mmol). The mixture was stirred at 50° C. under nitrogen atmosphere for 16 hours. After completion, the mixture was concentrated and the residue was purified by flash chromatography column (C18, acetonitrile/water=30% to 95%) to afford (R)-7-chloro-4-hydroxy-8-((2-hydroxy-3-(2-oxa-7-azaspiro[3.5]nonan-7-yl)propyl)thio)-6-(trifluoromethyl)quinazolin-2(1H)-one (2.16 g, 98% yield) as a yellow solid. MS (ESI) m/z: 480.4 [M+H]$^+$.

(S)-3-(2-oxa-7-azaspiro[3.5]nonan-7-ylmethyl)-10-chloro-7-hydroxy-9-(trifluoromethyl)-2H-[1,4]thiazino[2,3,4-ij]quinazolin-5(3H)-one (5)

To a mixture of (R)-7-chloro-4-hydroxy-8-((2-hydroxy-3-(2-oxa-7-azaspiro[3.5]nonan-7-yl)propyl)thio)-6-(trifluoromethyl)quinazolin-2(1H)-one (2.16 g, 4.5 mmol) and triphenylphosphoranylidene (1.77 g, 6.75 mmol) in tetrahydrofuran (800 mL) was added diethyl azodicarboxylate (1.18 g, 6.75 mmol). The mixture was stirred at room temperature for 2 hours. After completion, the mixture was poured into ice-water (100 mL) and extracted with ethyl acetate (100 mL×3). The organic layer was dried over Na$_2$SO$_4$. After concentration, the residue was purified by flash chromatography column (C18, acetonitrile/water=20% to 95%) to afford (S)-3-(2-oxa-7-azaspiro[3.5]nonan-7-ylmethyl)-10-chloro-7-hydroxy-9-(trifluoromethyl)-2H-[1,4]thiazino[2,3,4-ij]quinazolin-5(3H)-one (1.45 g, 70% yield) as a white solid. MS (ESI) m/z: 462.1 [M+H]$^+$.

(2S,6R)-tert-butyl 4-((S)-3-(2-oxa-7-azaspiro[3.5]nonan-7-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-3-(2-oxa-7-azaspiro[3.5]nonan-7-ylmethyl)-10-chloro-7-hydroxy-9-(trifluoromethyl)-2H-[1,4]thiazino[2,3,4-ij]quinazolin-5(3H)-one (700 mg, 1.52 mmol) and potassium carbonate (2.1 g, 15.2 mmol) in acetonitrile (60 mL) was added 4-methylbenzenesulfonic anhydride (992 mg, 3.04 mmol) at 0° C. The mixture was stirred at 0° C. for 30 minute and at room temperature for 2 hours. After completion, (2S,6R)-tert-butyl 2,6-dimethylpiperazine-1-carboxylate (977 mg, 4.56 mmol) was added into the reaction solution. The mixture was stirred at room temperature for 1 hour. After completion, the mixture was poured into ice-water (50 mL) and extracted with ethyl acetate (3×50 mL). After concentration, the residue was purified by Flash chromatography column (C18, acetonitrile/water=20% to 95%) to afford (2S,6R)-tert-butyl 4-((S)-3-(2-oxa-7-azaspiro[3.5]nonan-7-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (710 mg, 71% yield) as a yellow solid. MS (ESI) m/z: 658.7[M+H]$^+$.

(2S,6R)-tert-butyl 4-((3S)-3-(2-oxa-7-azaspiro[3.5]nonan-7-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a mixture of (2S,6R)-tert-butyl 4-((S)-3-(2-oxa-7-azaspiro[3.5]nonan-7-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (200 mg, 0.30 mmol) and tripotassium orthophosphate (194 mg, 0.91 mmol) in 1,4-dioxane (5 mL) and water (1 mL) was added Chloro(2-dicyclohexylphosphino-2', 6'-diisopropoxy-1,1'-biphenyl)[2-(2'-amino-1,1'-biphenyl)]palladium(II) (24 mg, 0.03 mmol) and (2,4-difluorophenyl)boronic acid (480 mg, 3.04 mmol). The mixture was stirred at 80° C. for 4 hours. After completion, the mixture was purified by silica gel column eluting with dichloromethane/methanol (20/1) to afford the (2S,6R)-tert-butyl 4-((3S)-3-(2-oxa-7-azaspiro[3.5]nonan-7-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (215 mg, 96% yield) as a yellow solid. MS (ESI) m/z: 736.9 [M+H]$^+$.

(3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (8)

To a mixture of (3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (215 mg, 0.29 mmol) in dichloromethane (3 mL) was added trifluoroacetic acid (1 mL). The mixture was stirred at room temperature for 2 hours. After completion, the mixture was concentrated and the residue was purified by silica gel column eluting with dichloromethane/methanol (20/1) to afford the (3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (120 mg, 65% yield) as a yellow solid. MS (ESI) m/z: 636.7[M+H]$^+$.

(3S)-3-(2-oxa-7-azaspiro[3.5]nonan-7-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (9)

To a mixture of (3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (100 mg, 0.16 mmol) and triethylamine (32 mg, 0.32 mmol) in dichloromethane (8 mL) was added acrylic anhydride (20.1 mg, 0.16 mmol) at 0° C. The mixture was stirred at 0° C. for 2 hours. After completion, the mixture was purified by preparative high performance liquid chromatography (20% to 95% acetonitrile in water as gradient) to afford the product (50 mg, 46% yield) as a light yellow solid. MS (ESI) m/z: 690.1 [M+H]$^+$.

The above racemate (50 mg, 0.07 mmol) was dissolved in ethanol (5 mL) and separated by chiral supercritical fluid chromatography (separation condition: Column: AD-H 5 µm 20*250 mm; Mobile Phase: CO2:IPA=60:40 at 15 mL/min; Temp: 25° C.; Wavelength: 254 nm) to afford two atropisomers of the title compounds (P1: 15.6 mg with 100% de and P2: 18.4 mg with 100% de); Chiral SFC Analytical condition: on AD-H was using 5 µm 4.6×250 mm column, Mobile Phase: CO$_2$:IPA=60:40 at 1 mL/min; Temp: 25° C.; Wavelength: 254 nm).

P1: $^1$H NMR (400 MHz, CDCl$_3$) δ 8.06 (s, 1H), 7.21-7.15 (m, 1H), 7.06-6.94 (m, 2H), 6.65-6.59 (m, 1H), 6.43-6.38 (m, 1H), 5.79-5.76 (dd, J=10.4 Hz, 1.6 Hz, 1H), 5.37-5.35 (m, 1H), 4.72-4.65 (m, 2H), 4.46-4.32 (m, 4H), 4.20-4.17 (m, 2H), 3.48-3.30 (m, 3H), 3.00-2.96 (m, 1H), 2.76-2.66 (m, 1H), 2.65-2.51 (m, 2H), 2.47-2.28 (m, 3H), 1.82-1.81 (m, 4H), 1.61-1.60 (m, 3H), 1.48-1.47 (m, 3H); Chiral SFC fraction 1: d.e.=100%, Rt=5.82 min.

P2: $^1$H NMR (400 MHz, CDCl$_3$) δ 8.06 (s, 1H), 7.23-7.14 (m, 1H), 7.04-6.95 (m, 2H), 6.65-6.59 (m, 1H), 6.42-6.38 (m, 1H), 5.78-5.76 (dd, J=10.4 Hz, 1.6 Hz, 1H), 5.32-5.31 (m, 1H), 4.66-4.57 (m, 2H), 4.44-4.32 (m, 4H), 4.20-4.16 (m, 2H), 3.44-3.30 (m, 3H), 3.07-2.98 (m, 1H), 2.76-2.71 (m, 1H), 2.68-2.52 (m, 2H), 2.49-2.27 (m, 3H), 1.80-1.71 (m, 4H), 1.62-1.60 (m, 3H), 1.49-1.42 (m, 3H); Chiral SFC fraction 2: d.e.=99.8%, Rt=6.76 min.

KK. Example 580 and 581

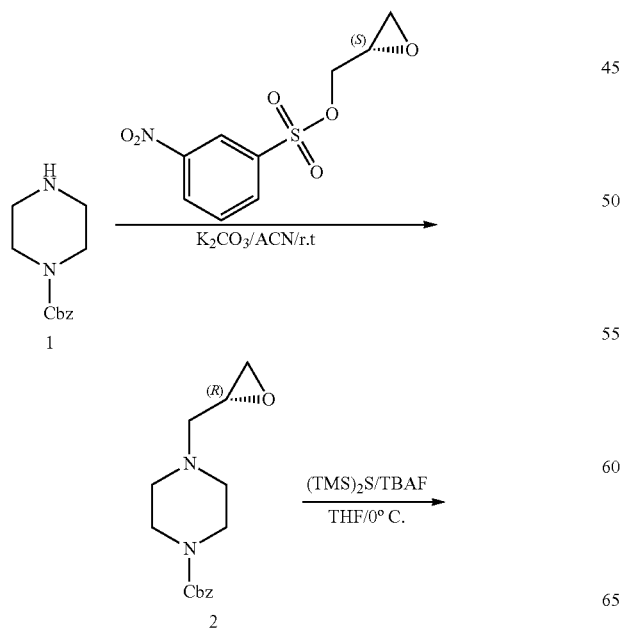

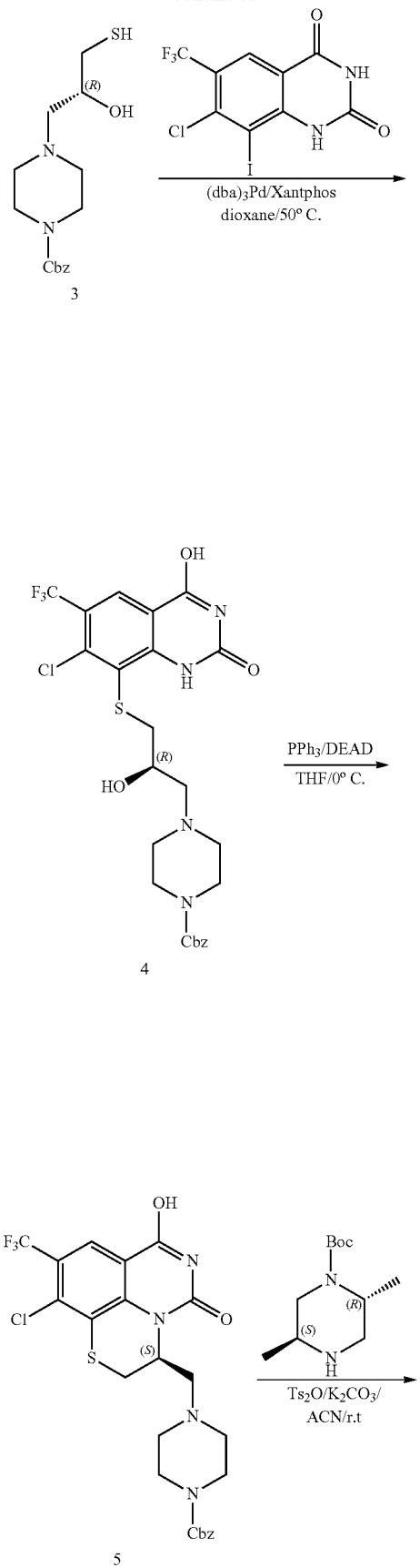

1065
-continued
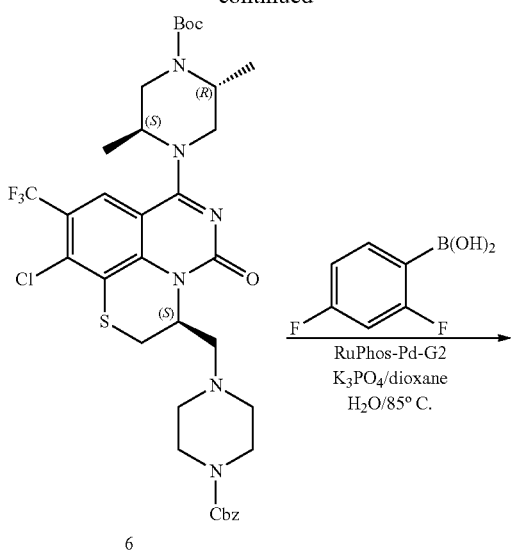
6
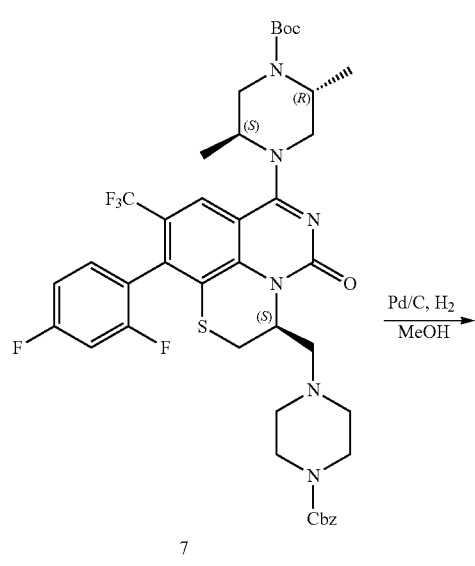
7
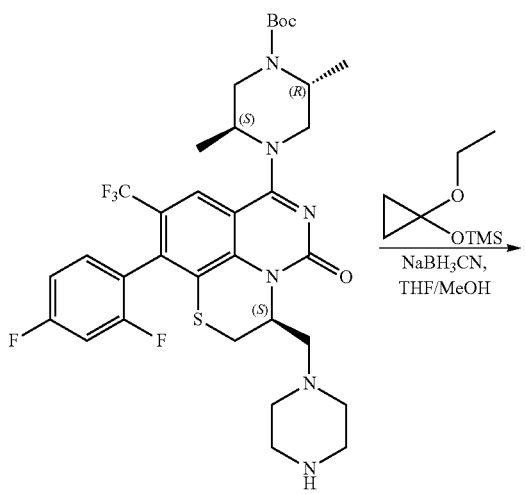
8
1066
-continued
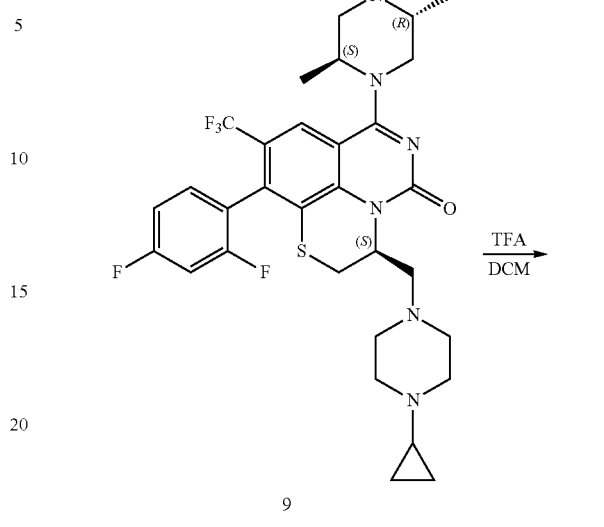
9
10
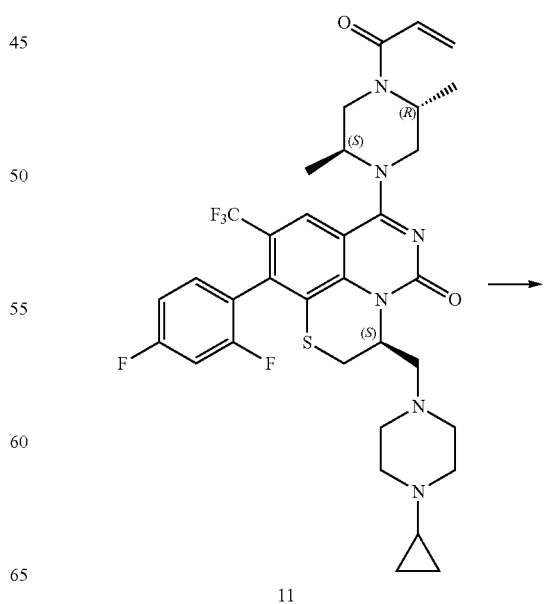
11

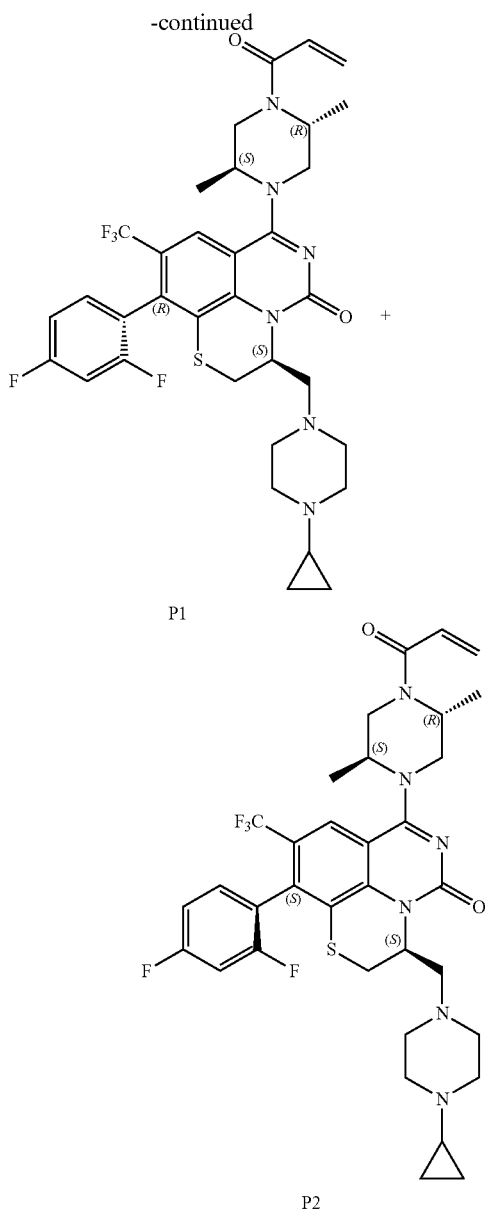

P1

P2

(R)-benzyl 4-(oxiran-2-ylmethyl)piperazine-1-carboxylate (2)

To a mixture of (S)-oxiran-2-ylmethyl 3-nitrobenzenesulfonate (25.0 g, 96.5 mmol) and benzyl piperazine-1-carboxylate (19.3 g, 75.8 mmol) in acetonitrile (150 mL) was added potassium carbonate (24.0 g, 176 mmol) at 0° C. The mixture was stirred under nitrogen atmosphere at room temperature for 22 hours. After completion, the mixture was concentrated and the residue was purified by silica gel column eluting with dichloromethane/methanol (50/1) to afford (R)-benzyl 4-(oxiran-2-ylmethyl)piperazine-1-carboxylate (24.5 g, crude) as a light yellow oil. MS (ESI) m/z: 277.4 [M+H]+.

(R)-benzyl 4-(3-hydroxy-2-mercaptopropyl)piperazine-1-carboxylate (3)

To a mixture of (R)-benzyl 4-(oxiran-2-ylmethyl)piperazine-1-carboxylate (24.5 g, 88.7 mmol) in tetrahydrofuran (300 mL) were added 1,1,1,3,3,3-hexamethyldisilathiane (17.4 g, 97.5 mmol) and tetrabutylammonium fluoride (1.0 M in tetrahydrofuran, 26.7 mL, 26.7 mmol) at 0° C. The mixture was stirred at room temperature for 2 hours. After completion, the mixture was poured into water (300 mL), extracted with ethyl acetate (3×200 mL). The organic phase was washed with brine (300 mL) and dried over anhydrous sodium sulfate. After filtration and concentration, the residue was purified by silica gel column eluting with dichloromethane/methanol (50/1) to afford (R)-benzyl 4-(3-hydroxy-2-mercaptopropyl)piperazine-1-carboxylate (20.8 g, 76% yield) as a colorless oil. $^1$H NMR (400 MHz, CDCl$_3$) δ 7.36-7.31 (m, 5H), 5.13 (s, 2H), 3.80-3.78 (m, 1H), 3.54-3.50 (m, 4H), 3.39 (s, 1H), 2.66-2.57 (m, 4H), 2.46-2.40 (m, 4H), 1.57-1.52 (m, 1H). MS (ESI) m/z: 311.5 [M+H]+.

(R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (4)

To a solution of 7-chloro-8-iodo-6-(trifluoromethyl)quinazoline-2,4(1H,3H)-dione (5.00 g, 12.8 mmol) in dioxane (128 mL) were added potassium carbonate (5.29 g, 38.4 mmol), (R)-benzyl 4-(2-hydroxy-3-mercaptopropyl)piperazine-1-carboxylate (3.97 g, 12.8 mmol), 4,5-bis(diphenylphosphino)-9,9-dimethylxanthene (1.47 g, 2.56 mmol) and tris(dibenzylideneacetone) dipalladium (1.20 g, 1.28 mmol). The mixture was stirred at 55° C. under nitrogen atmosphere for 8 hours. After completion, the mixture was diluted with tetrahydrofuran (300 mL) and filtered. The filtrate was concentrated and the residue was purified by silica gel column chromatography with a gradient of dichloromethane/methanol=100/1 to 20/1 to afford (R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (5.70 g, 78% yield) as a yellow solid. MS (ESI) m/z: 573.5 [M+H]+.

(S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (5)

To a mixture of (R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (4.66 g, 8.1 mmol) and triphenylphosphine (4.26 g, 16.2 mmol) in tetrahydrofuran (81 mL) was added diethyl azodicarboxylate (2.81 g, 16.2 mmol) at 0° C. The mixture was stirred at 0° C. for 45 min. After completion, the mixture was poured into ice-water (300 mL) and extracted with ethyl acetate (3×200 mL). After concentration, the residue was purified by flash chromatography column (C18, acetonitrile/water=30% to 95%) to afford (S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (3.14 g, 70% yield) as a white solid. MS (ESI) m/z: 555.5 [M+H]+.

(2R,5S)-tert-butyl 4-((S)-3-((4-((benzyloxy)carbonyl)piperazin-1-yl)methyl)-10-chloro-5-oxo-9-(trifluoromethyl)-3,5-dihydro-2H-[1,4]thiazino[2,3,4-ij]quinazolin-7-yl)-2,5-dimethylpiperazine-1-carboxylate (6)

To a mixture of (S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (1.77 g, 3.19 mmol) and potassium carbonate (4.40 g, 3.19 mmol)

in acetonitrile (106 mL) was added 4-methylbenzenesulfonic anhydride (2.08 g, 6.38 mmol) at 25° C. The mixture was stirred at 25° C. for 3 hours. After completion, (2R,5S)-tert-butyl 2,5-dimethylpiperazine-1-carboxylate (1.36 g, 6.38 mmol) was added into the reaction solution. The reaction mixture was stirred at 25° C. for 1 hour. After completion, the mixture was poured into ice-water (300 mL) and extracted with ethyl acetate (200 mL×3). After concentration, the residue was purified by flash chromatography column (C18, acetonitrile/water=20% to 95%) to afford (2R,5S)-tert-butyl 4-((S)-3-((4-((benzyloxy)carbonyl)piperazin-1-yl)methyl)-10-chloro-5-oxo-9-(trifluoromethyl)-3,5-dihydro-2H-[1,4]thiazino[2,3,4-ij]quinazolin-7-yl)-2,5-dimethylpiperazine-1-carboxylate (1.43 g, 60% yield) as a pale-white solid. MS (ESI) m/z: 751.1 [M+H]$^+$.

(2R,5S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (7)

To a solution of (2R,5S)-tert-butyl 4-((S)-3-((4-((benzyloxy)carbonyl)piperazin-1-yl)methyl)-10-chloro-5-oxo-9-(trifluoromethyl)-3,5-dihydro-2H-[1,4]thiazino[2,3,4-ij]quinazolin-7-yl)-2,5-dimethylpiperazine-1-carboxylate (1 g, 1.3 mmol) in 1,4-dioxane (15 mL) and water (3 mL) were added tripotassium phosphate (1.1 g, 5.2 mmol), (2,4-difluorophenyl)boronic acid (1.67 g, 10.6 mmol) and Chloro (2-dicyclohexylphosphino-2', 6'-diisopropoxy-1,1'-biphenyl)[2-(2'-amino-1,1'-biphenyl)]palladium(II) (202 mg, 0.26 mmol). The mixture was stirred at 85° C. under nitrogen atmosphere for 4 hours. After completion, the mixture was diluted with tetrahydrofuran (300 mL) and filtered. The filtrate was concentrated and the residue was purified by silica gel column chromatography with a gradient of dichloromethane/methanol=100/1 to 30/1 to afford (2R,5S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (1.00 g, 93% yield) as a yellow solid. MS (ESI) m/z: 829.5 [M+H]$^+$.

(2R,5S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-2,5-dimethylpiperazine-1-carboxylate (8)

To a mixture of (2R,5S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (1.00 g, 1.20 mmol) in ethanol (15 ml) was added Pd/C (0.300 g, 30% w/w). The mixture was stirred at room temperature under hydrogen atmosphere for 1 hour. After completion, the mixture was filtered and concentrated. The residue was purified by silica gel column chromatography eluting with dichloromethane/methanol (15/1) to afford (2R,5S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-2,5-dimethylpiperazine-1-carboxylate (600 mg, 71% yield) as a yellow solid. MS (ESI) m/z: 695.7[M+H]$^+$.

(2R,5S)-tert-butyl 4-((3S)-3-((4-cyclopropylpiperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (9)

To a mixture of (2R,5S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-2,5-dimethylpiperazine-1-carboxylate (400 mg, 0.57 mmol) and sodium cyanoborohydride (359 mg, 5.70 mmol) in tetrahydrofuran (5 mL) and methanol (5 mL) was added (1-ethoxycyclopropoxy)trimethylsilane (991 mg, 5.70 mmol) at 25° C. under nitrogen atmosphere. The reaction solution was heated to 85° C. for 12 hours. After completion, the mixture was filtered and concentrated. the residue was purified by silica gel column chromatography eluting with dichloromethane/methanol (30/1) to afford (2R,5S)-tert-butyl 4-((3S)-3-((4-cyclopropylpiperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (300 mg, 71% yield) as a yellow solid. MS (ESI) m/z: 735.9[M+H]$^+$.

(3S)-3-((4-cyclopropylpiperazin-1-yl)methyl)-10-(2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (10)

To a cooled mixture of (2R,5S)-tert-butyl 4-((3S)-3-((4-cyclopropylpiperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (300 mg, 0.40 mmol) in dichloromethane (5 mL) was added trifluoroacetic acid (1 mL) at 0° C. The reaction solution was stirred at room temperature for 1 hour. After completion, the mixture was concentrated and the residue was purified by silica gel column chromatography eluting with dichloromethane/methanol (15/1) to afford (3S)-3-((4-cyclopropylpiperazin-1-yl)methyl)-10-(2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (200 mg, 78% yield) as a yellow solid. MS (ESI) m/z: 635.8[M+H]$^+$.

(3S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2H-[1,4]thiazino[2,3,4-ij]quinazolin-5(3H)-one (11)

To a mixture of (3S)-3-((4-cyclopropylpiperazin-1-yl)methyl)-10-(2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (180 mg, 0.28 mmol) and triethyl amine (56 mg, 0.56 mmol) in dichloromethane (5 mL) was added acrylic anhydride (70 mg, 0.56 mmol) at 0° C. The mixture was stirred at 0° C. for 1 hour. After completion, the mixture was poured into ice-water (50 mL) and extracted with ethyl acetate (3×20 mL). After concentration, the residue was purified by preparative high performance liquid chromatography (20% to 95% acetonitrile in water) to afford (3S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2H-[1,4]thiazino[2,3,4-ij]quinazolin-5(3H)-one (130 mg, 67% yield) as a white solid. MS (ESI) m/z: 689.8 [M+H]$^+$.

The above racemate (130 mg) was dissolved with EtOH (10 mL) and separated by chiral supercritical fluid chromatography (separation condition: Column: Chiralpak AD-H, 5 μm 20×250 mm; Mobile Phase: CO$_2$:EtOH=60:40 at 25 mL/min; Temp: 25° C.; Wavelength: 254 nm) to afford two atropisomers of the title compounds (P1: 54.0 mg with 100% de and P2: 76.0 mg with 100% de); Chiral SFC Analytical condition: on CHIRALPAK® AD-H was using 5 μm 4.6×

250 mm column, Mobile Phase: CO$_2$:EtOH=60:40 at 2.5 mL/min; Temp: 25° C.; Wavelength: 254 nm).

P1: $^1$H NMR (400 MHz, CDCl$_3$) δ 7.87 (d, J=6.0, 1H), 7.31-7.27 (m, 1H), 7.16-7.10 (m, 2H), 6.73-6.55 (m, 1H), 6.46-6.37 (m, 1H), 5.84-5.79 (m, 1H), 5.44 (s, 1H), 5.13-4.70 (m, 1.5H), 4.47-4.36 (m, 1H), 4.11-3.70 (m, 3H), 3.52-3.32 (m, 1.5H), 3.11-3.03 (m, 1H), 2.84-2.55 (m, 10H), 1.52-1.43 (m, 7H), 0.57-0.42 (m, 4H); Chiral SFC fraction 1: e.e. =100%, Rt=4.96 min.

P2: $^1$H NMR (400 MHz, CDCl$_3$) δ 7.87 (s, 1H), 7.28-7.19 (m, 1H), 7.09-6.98 (m, 2H), 6.72-6.54 (m, 1H), 6.46-6.37 (m, 1H), 5.86-5.79 (m, 1H), 5.42-5.35 (m, 1H), 5.12-4.68 (m, 1.5H), 4.52-4.33 (m, 1H), 4.19-3.67 (m, 3H), 3.51-3.27 (m, 1.5H), 3.10-3.05 (m, 1H), 2.87-2.51 (m, 10H), 1.52-1.29 (m, 7H), 0.59-0.44 (m, 4H); Chiral SFC fraction 2: e.e. =99.9%, Rt=5.50 min.

Example 417: 7-(9-acryloyl-7,9-diazaspiro[bicyclo[3.3.1]nonane-3,3'-oxetan]-7-yl)-10-(2,4-difluorophenyl)-9-(trifluoromethyl)-2,3-dihydro-5H-[1,4]thiazino[2,3,4-ij]quinazolin-5-one

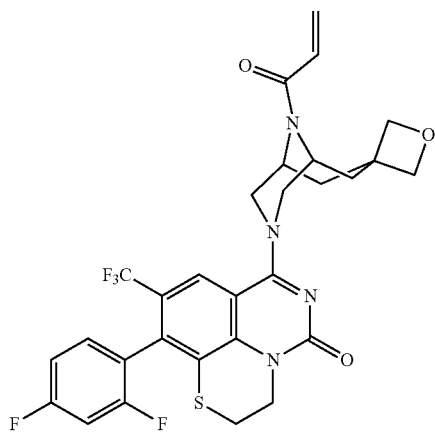 [SMILES: C=CC(=O)N1C2CN(c3nc(=O)n4c5c(c(-c6ccc(F)cc6F)c(C(F)(F)F)cc35)SCC4)CC1CC1(COC1)C2]

The title compound was prepared analogously to Example 84 where 10-(2,4-difluorophenyl)-7-(7,9-diazaspiro[bicyclo[3.3.1]nonane-3,3'-oxetan]-7-yl)-9-(trifluoromethyl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 10% yield as a white solid.

m/z (ESI, +ve)=605.2 (M+H)$^+$.

$^1$H NMR (400 MHz, DMSO-d6) δ 7.89 (s, 1H), 7.48-7.43 (m, 1H), 7.32-7.25 (m, 2H), 6.38-6.34 (m, 1H), 6.20-6.14 (m, 1H), 5.99-5.97 (m, 1H), 4.55-4.43 (m, 2H), 4.33-4.27 (m, 3H), 4.12-4.04 (m, 3H), 3.65-3.52 (m, 3H), 3.19-3.14 (m, 2H), 2.14-2.12 (m, 3H), 1.66-1.57 (m, 2H).

Step 1: (1R,5S)-Diethyl-9-benzyl-3-(phenylsulfonyl)-3,9-diazabicyclo[3.3.1]nonane-7,7-dicarboxylate

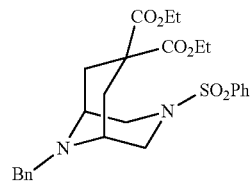

A solution of (1R,5S)-4-(benzenesulfonyl)-2,6-bis(chloromethyl)-1-(1-methylphenyl)piperazine (2 g, 4.8 mmol), 1,3-diethyl propanedioate (800 mg, 5 mmol), tetrabutylammonium bromide (160 mg, 0.5 mmol) and potassium carbonate (1.93 g, 14 mmol) in DMF (20 mL) was stirred at 100° C. for 16 hours. The solution was cooled to room temperature, diluted with water and extracted with ethyl acetate three times. The combined organic layers were washed with brine, dried over sodium sulfate, filtered and concentrated under reduced pressure to obtain a residue that was purified by silica gel chromatography (0-20% ethyl acetate in hexanes) to afford the title compound in 99% yield as colorless oil.

m/z (ESI, +ve)=501.2 (M+H)$^+$.

Step 2: (1R,5S)-(9-benzyl-3-(phenylsulfonyl)-3,9-diazabicyclo[3.3.1]nonane-7,7-diyl)dimethanol

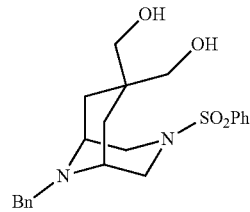

To a solution of (1R,5S)-diethyl 9-benzyl-3-(phenylsulfonyl)-3,9-diazabicyclo[3.3.1]nonane-7,7-dicarboxylate (900 mg, 1.79 mmol) in THF (10 mL) was added lithium aluminum hydride (250 mg, 6.58 mmol) and the mixture was stirred at 0° C. for 2 hours. The reaction was quenched with 15% aqueous NaOH (1 mL), dried over magnesium sulfate and filtered. The filtrate was concentrated under reduced pressure to afford the title compound (700 mg) as colorless oil.

m/z (ESI, +ve)=417.2 (M+H)$^+$.

Step 3: (1R,5S)-9-benzyl-7-(phenylsulfonyl)-7,9-diazaspiro[bicyclo[3.3.1]nonane-3,3'-oxetane]

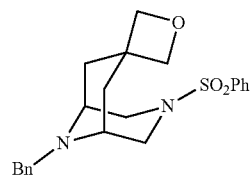

A solution of (1R,5S)-(9-benzyl-3-(phenylsulfonyl)-3,9-diazabicyclo[3.3.1]nonane-7,7-diyl)dimethanol (660 mg, 1.58 mmol), tosyl chloride (383 mg, 2.01 mmol) and triethyl amine (0.8 mL, 5.74 mmol) in toluene (5 mL) was stirred at 100° C. for 2 hours. The solution was cooled down to room temperature and concentrated under reduced pressure to obtain a residue that was purified by reverse phase chromatography to afford the title compound (410 mg) as colorless oil.

m/z (ESI, +ve)=399.1 (M+H)⁺.

Step 4: (1R,5S)-7,9-dibenzyl-7,9-diazaspiro[bicyclo[3.3.1]nonane-3,3'-oxetane]

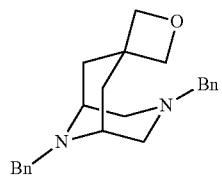 [SMILES: c1ccc(CN2CC3CC4(COC4)CC(C2)N3Cc2ccccc2)cc1]

To a solution of 9-benzyl-7-(phenylsulfonyl)-7,9-diazaspiro[bicyclo[3.3.1]nonane-3,3'-oxetane] (1.36 g, 3.40 mmol) in THF (15 mL) at −78° C. was added KPPh₂ (0.5 M solution in THF, 17 mL, 8.5 mmol) dropwise. The mixture was stirred at −78° C. for 3 hours. The reaction was quenched with 1M aqueous HCl (9 mL) and the aqueous phase was separated and concentrated under reduced pressure. The residue was taken up in acetonitrile (15 mL) and potassium carbonate (1.4 g, 10.14 mmol) and benzyl bromide (822 mg, 5.10 mmol) were added. The resulting mixture was stirred at room temperature for 16 hours. The solids were removed by filtration and the filtrate was concentrated and purified by reverse phase chromatography to afford the title compound (1.1 g) as colorless oil.

m/z (ESI, +ve)=349.2 (M+H)⁺.

Step 5: (1R,5S)-7,9-diazaspiro[bicyclo[3.3.1]nonane-3,3'-oxetane]

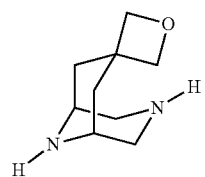 [SMILES: C1NCC2CC3(COC3)CC1N2]

A mixture of (1R,5S)-7,9-dibenzyl-7,9-diazaspiro[bicyclo[3.3.1]nonane-3,3'-oxetane] (1.1 g, 4.26 mol) and 10% palladium on activated carbon (2 g) in methanol/ammonium hydroxide (10/1 mL) was stirred at 25° C. for 16 h under hydrogen atmosphere. The mixture was filtered through celite and the filtrate was concentrated to afford (1R,5S)-7,9-diazaspiro[bicyclo[3.3.1]nonane-3,3'-oxetane] (700 mg, 50%) as colorless oil.

m/z (ESI, +ve)=169.2 (M+H)⁺.

Step 6: 10-(2,4-difluorophenyl)-7-(7,9-diazaspiro[bicyclo[3.3.1]nonane-3,3'-oxetan]-7-yl)-9-(trifluoromethyl)-2,3-dihydro-5H-[1,4]thiazino[2,3,4-ij]quinazolin-5-one

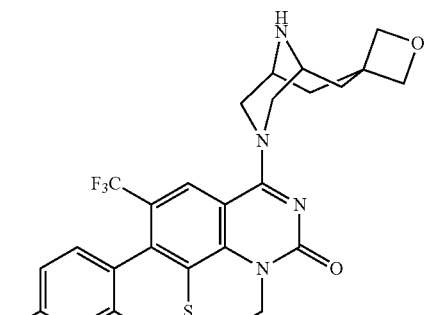

To a solution of 10-(2,4-difluorophenyl)-9-(trifluoromethyl)-2,3-dihydro-5H-[1,4]thiazino[2,3,4-ij]quinazoline-5,7(6H)-dione (100 mg, 0.25 mmol) and N,N-diisopropylethylamine (0.55 mL, 3.08 mmol) in toluene (1 mL), was added POCl₃ (1 mL) and the reaction mixture was stirred at 120° C. for 1.5 hours. The solution was concentrated to obtain a residue that was dissolved in dichloroethane (1.5 mL) and a solution of (1R,5S)-7,9-diazaspiro[bicyclo[3.3.1]nonane-3,3'-oxetane] (400 mg) and diisopropylethylamine (0.55 mL, 3.08 mmol) in DMF (1.5 mL) was added at 0° C. under nitrogen atmosphere. The mixture was stirred at 0° C. for 1 hours. The crude reaction mixture was purified by reverse phase chromatography to afford the title compound (25 mg) as a yellow solid.

m/z (ESI, +ve)=551.1 (M+H)⁺.

Example 418: 10-(2,4-difluorophenyl)-7-(9-(2-fluoroacryloyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one

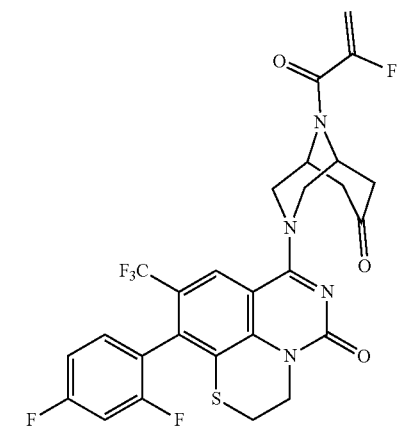 [SMILES: C=C(F)C(=O)N1C2CC(=O)CC1CN(c1nc(=O)n3c4c(c(-c5ccc(F)cc5F)c(C(F)(F)F)cc14)SCC3)C2]

To a solution of 2-fluoroacrylic acid (34 mg, 0.38 mmol) in DMF (3 mL) were added N,N,N',N'-tetramethyl-O-(7-azabenzotriazol-1-yl)uronium (160 mg, 0.42 mmol) and N,N-diisopropylethylamine (99 mg, 0.76 mmol). After 5 minutes, 10-(2,4-difluorophenyl)-7-(7-oxo-3,9-diazabicyclo

[3.3.1]nonan-3-yl)-9-(trifluoromethyl)-2,3-dihydro-5H-[1,4]thiazino[2,3,4-ij]quinazolin-5-one (100 mg, 0.19 mmol) was added and stirring was continued at room temperature for two additional hours. The solvent was removed under reduced pressure to afford a residue that was purified by preparative HPLC. The title compound was isolated n 12% yield as a light yellow solid.

m/z (ESI, +ve)=595.1 (M+H)⁺.

¹H NMR (400 MHz, DMSO-d6) δ 7.77 (s, 1H), 7.50-7.45 (m, 1H), 7.40-7.34 (m 1H), 7.30-7.25 (m, 1H), 5.47 (s, 1H), 5.48-5.27 (m, 1H), 5.29-5.18 (m, 1H), 5.10-5.06 (m, 1H), 4.86-4.79 (m, 2H), 4.39-4.30 (m, 1H), 4.20-3.96 (m, 3H), 3.123-3.13 (m, 4H), 2.98-2.89 (m, 2H).

Example 420: (E)-10-(2,4-difluorophenyl)-7-(9-(4-(dimethylamino)but-2-enoyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one

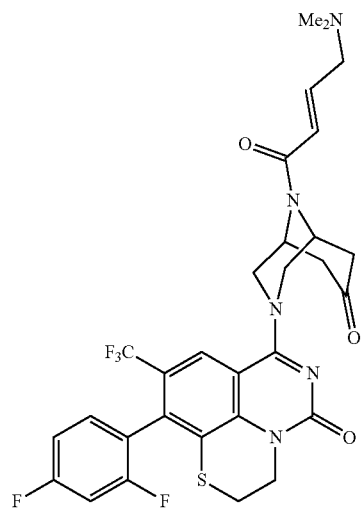 [SMILES: CN(C)C/C=C/C(=O)N1C2CC(=O)CC1CN(c1nc(=O)n3c4c(c(-c5ccc(F)cc5F)c(C(F)(F)F)cc14)SCC3)C2]

To a solution of (E)-4-(dimethylamino)but-2-enoic acid (148 mg, 1.146 mmol) in DMF (3 mL), N,N,N',N'-tetramethyl-O-(7-azabenzotriazol-1-yl)uronium (457 mg, 1.20 mmol) and N,N-diisopropylethylamine (247 mg, 1.91 mmol) were added. After 5 minutes, 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (100 mg, 0.19 mmol) was added over the reaction mixture and stirring was continued for another 2 hours. The solvent was removed under reduced pressure obtaining a residue that was purified by preparative HPLC to afford the title compound (2.7 mg, 2%) as a white solid.

m/z (ESI, +ve)=634.2 (M+H)⁺.

¹H NMR (400 MHz, DMSO-d6) δ 7.77 (s, 1H), 7.51-7.46 (m, 1H), 7.43-7.33 (m, 1H), 7.32-7.24 (m, 1H), 6.75 (s, 1H), 5.15 (s, 1H), 4.92 (s, 1H), 4.41-4.25 (m, 2H), 4.17-3.90 (m, 4H), 3.27-3.02 (m, 5H), 2.89-2.69 (m, 4H), 2.46-2.37 (m, 3H), 2.18 (s, 3H).

Example 431: (3S)-8-((S)-4-acryloyl-2-methylpiperazin-1-yl)-11-(2,4-difluorophenyl)-3-hydroxy-10-(trifluoromethyl)-3,4-dihydro-2H,6H-[1,4]thiazepino[2,3,4-ij]quinazolin-6-one

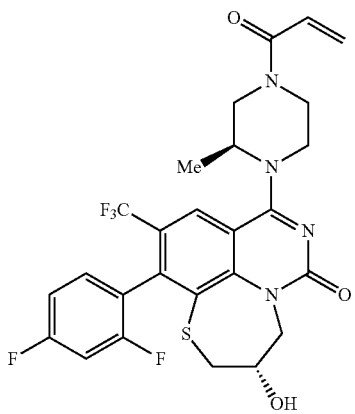 [SMILES: C=CC(=O)N1CCN(c2nc(=O)n3c4c(c(-c5ccc(F)cc5F)c(C(F)(F)F)cc24)SC[C@@H](O)C3)[C@@H](C)C1]

To a mixture of (3S)-11-(2,4-difluorophenyl)-3-hydroxy-8-((S)-2-methylpiperazin-1-yl)-10-(trifluoromethyl)-3,4-dihydro-2H,6H-[1,4]thiazepino[2,3,4-ij]quinazolin-6-one (50 mg, 0.09 mmol) and N,N-diisopropylethylamine (25 mg, 0.19 mmol) in dichloromethane (2 mL), was added prop-2-enoyl prop-2-enoate (19 mg, 0.15 mmol). The reaction mixture was stirred at room temperature for 1 hour. The mixture was concentrated under reduced pressure affording a residue that was purified by preparative HPLC. The title compound was isolated in 4% yield as a white solid.

m/z (ESI, +ve)=567.2 (M+H)⁺.

¹H NMR (400 MHz, methanol-d4) δ 7.92 (s, 1H), 7.31-7.26 (m, 1H), 7.12-7.06 (m, 2H), 6.87-6.75 (m, 1H), 6.29-6.25 (m, 1H), 5.81 (d, J=12.0 Hz, 1H), 4.41-4.33 (m, 2H), 4.18-4.11 (m, 1H), 4.04-3.99 (m, 1H), 3.77-3.37 (m, 6H), 3.22-2.92 (m, 2H), 1.44-1.34 (m, 3H).

Step 1: (R)-3-(tritylthio)propane-1,2-diol

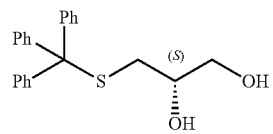

Potassium tert-butoxide (18.3 g, 0.18 mol) was added over a solution of triphenylmethyl mercaptan (25 g, 0.091 mol) and (2R)-3-chloropropane-1,2-diol (10 g, 0.091 mol) in DMF (200 mL) at room temperature. The mixture was stirred for 16 hours and after that time it was quenched with water. The resulting mixture was extracted with ethyl acetate three times and the organic layers were combined and washed with brine, dried over sodium sulfate and filtered. Evaporation of volatiles under reduced pressure afforded a residue that was purified by column chromatography on silica gel (0-50% ethyl acetate in hexanes). The title compound was isolated in 66% yield as yellow oil.

m/z (ESI, +ve)=373.1 (M+Na)⁺.

Step 2: (S)-1-((tert-butyldimethylsilyl)oxy)-3-(tritylthio)propan-2-ol

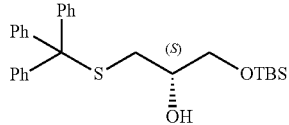

Imidazole (9.71 g, 0.14 mol) and tert-butyldimethylsilyl chloride (9.47 g, 0.063 mol) were added over a solution of (2S)-3-[(triphenylmethyl)sulfanyl] propane-1,2-diol (20 g, 0.057 mol) in DMF (250 mL) at room temperature. After 16 hours, the reaction was quenched by addition of water. The mixture was extracted with ethyl acetate three times and the combined organic layers were washed with brine, dried over sodium sulfate and filtered to afford a residue that was purified by silica gel chromatography (0-15% ethyl acetate in hexanes) to afford the title compound in 60% yield as a yellow oil.

m/z (ESI, +ve)=487.2 (M+Na)$^+$.

Step 3: (S)-(2-(benzyloxy)-3-(tritylthio)propoxy)(tert-butyl)dimethylsilane

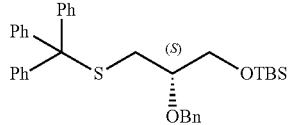

Sodium hydride (2.2 g, 0.090 mol) was added to a mixture of tert-butyl[(2S)-2-hydroxy-3-[(triphenylmethyl)sulfanyl] propoxy] dimethylsilane (28 g, 0.060 mol) in THF (200 mL) at 0° C. The mixture was stirred at 0° C. for 30 minutes and benzyl bromide (11.3 g, 0.066 mol) was added. The resulting solution was stirred at room temperature for 16 hours. The reaction was cooled down to 0° C. and quenched by the addition of saturated aqueous ammonium chloride (100 mL) followed by extraction with ethyl acetate. The combined organic layers were washed with brine, dried over sodium sulfate and filtered. Elimination of volatiles by reduced pressure and purification of the resulting residue by column chromatography on silica gel (0-10% ethyl acetate in hexanes) afforded the title compound in 71% yield as colorless oil.

m/z (ESI, +ve)=577.2 (M+Na)$^+$.

Step 4: (S)-2-(benzyloxy)-3-mercaptopropan-1-ol

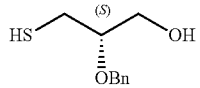

To a mixture of [(2S)-2-(benzyloxy)-3-[(triphenylmethyl) sulfanyl] propoxy](tert-butyl) dimethylsilane (26.5 g, 0.0478 mol) in dichloromethane/TFA (40 mL, 3:1 ratio) at 0° C., was added triethylsilane (16.7 g, 0.14 mol). The mixture was stirred at room temperature for 20 min and after that time the volatiles were removed under reduced pressure at 40° C. The resulting residue was redissolved with saturated sodium bicarbonate and extracted three times with ethyl acetate. The combined organic layers were washed with brine, dried over sodium sulfate and filtered. The crude solution was concentrated under reduced pressure and the resulting crude material purified by column chromatography on silica gel (0-12% methanol in dichloromethane) to afford the title compound in 22% yield as colorless oil.

Step 5: 8-(((S)-2-(benzyloxy)-3-hydroxypropyl)thio)-7-(2,4-difluorophenyl)-6-(trifluoromethyl)quinazoline-2,4(1H,3H)-dione

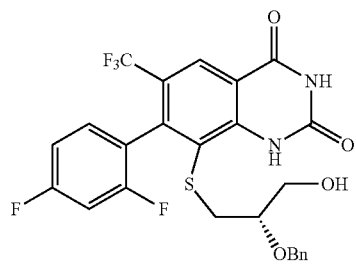 [SMILES: O=c1[nH]c(=O)c2cc(C(F)(F)F)c(-c3ccc(F)cc3F)c(SC[C@H](CO)OCc3ccccc3)c2[nH]1]

The title compound was prepared analogously to Example 100, step 9 where (S)-2-(benzyloxy)-3-mercaptopropan-1-ol was substituted in place of 2-mercaptoethan-1-ol. The title compound was isolated in 53% yield as a white solid.

m/z (ESI, +ve)=539.1 (M+H)$^+$.

Step 6: (3S)-3-(benzyloxy)-11-(2,4-difluorophenyl)-10-(trifluoromethyl)-3,4-dihydro-2H,6H-[1,4]thiazepino[2,3,4-ij]quinazoline-6,8(7H)-dione

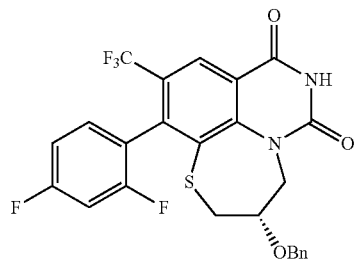 [SMILES: O=c1[nH]c(=O)n2c3c(c(-c4ccc(F)cc4F)c(C(F)(F)F)cc13)SC[C@@H](OCc1ccccc1)C2]

The title compound was prepared analogously to Example 100, step 10 where 8-(((S)-2-(benzyloxy)-3-hydroxypropyl)thio)-7-(2,4-difluorophenyl)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione. The title compound was isolated in 65% yield as a yellow solid.

m/z (ESI, +ve)=421.0 (M+H)$^+$.

Step 7: tert-butyl (3S)-4-((3S)-3-(benzyloxy)-11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate

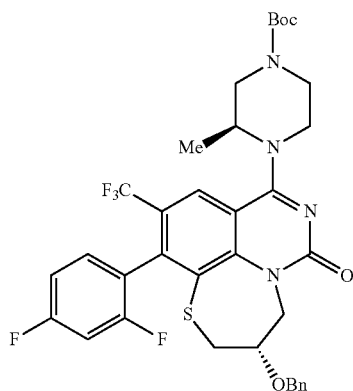 [SMILES: C[C@H]1CN(C(=O)OC(C)(C)C)CCN1c1nc(=O)n2c3c(c(-c4ccc(F)cc4F)c(C(F)(F)F)cc13)SC[C@@H](OCc1ccccc1)C2]

The title compound was prepared analogously to Example 100, step 21 where (3S)-3-(benzyloxy)-11-(2,4-difluorophenyl)-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 73% yield as a yellow solid m/z (ESI, +ve)=703.2 (M+H)+.

Step 8: (3S)-11-(2,4-difluorophenyl)-3-hydroxy-8-((S)-2-methylpiperazin-1-yl)-10-(trifluoromethyl)-3,4-dihydro-2H,6H-[1,4]thiazepino[2,3,4-ij]quinazolin-6-one

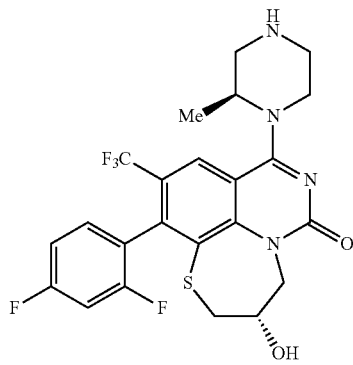 [SMILES: C[C@H]1CNCCN1c1nc(=O)n2c3c(c(-c4ccc(F)cc4F)c(C(F)(F)F)cc13)SC[C@@H](O)C2]

A 1M solution of boron tribromide in dichloromethane (1.1 mL) was added over a solution of tert-butyl (3S)-4-((3S)-3-(benzyloxy)-11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate (200 mg, 0.28 mmol) in dichloromethane (20 mL) precooled to −70° C. The reaction mixture was stirred at −70° C. for 1 hour and quenched by the addition of saturated sodium bicarbonate. The insoluble materials were removed by filtration and the filtrate was concentrated under reduced pressure to afford a residue that was purified by HPLC. The title compound was isolated in 61% yield as a yellow solid.

m/z (ESI, +ve)=513.1(M+H)+.

Example 439: (E)-7-(9-(4,4-difluorobut-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one

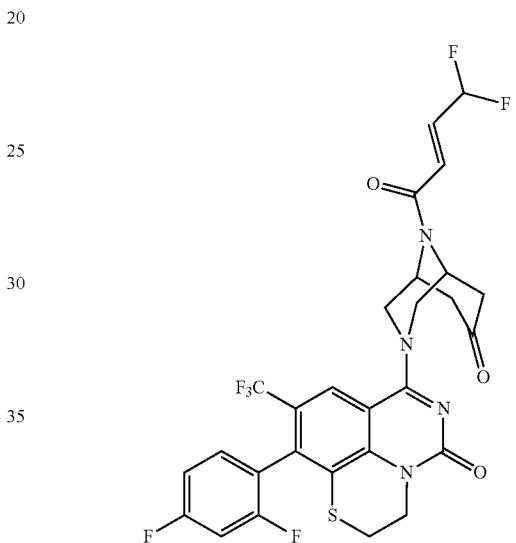

To a solution of (E)-4,4-difluorobut-2-enoic acid (63 mg, 0.516 mmol) in dichloromethane (3 mL), N,N,N',N'-tetramethylchloroformamidinium hexafluorophosphate (58 mg, 0.21 mmol) and N-methylimidazole (47 mg, 0.57 mmol) were added. After 5 minutes, 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (90 mg, 0.17 mmol) was added and the reaction mixture was stirred at room temperature for 2 hours. The solvent was removed under reduced pressure to afford a residue that was purified by preparative HPLC. The title compound was isolated in 4% yield as a white solid.

m/z (ESI, +ve)=627.1 (M+H)+.

$^1$H NMR (400 MHz, DMSO-d6) δ 7.77 (s, 1H), 7.50-7.46 (m, 1H), 7.38-7.35 (m, 1H), 7.31-7.24 (m, 1H), 6.81-6.46 (m, 3H), 5.17 (s, 1H), 4.88 (s, 1H), 4.37-4. 33 (m, 1H), 4.31-4.21 (m, 1H), 4.18-3.94 (m, 3H), 3.32-3.10 (m, 5H), 2.97-2.74 (m, 2H).

Example 440: (E)-10-(2,4-difluorophenyl)-7-(7-oxo-9-(4,4,4-trifluorobut-2-enoyl)-3,9-diazabicyclo[3.3.1]nonan-3-yl)-9-(trifluoromethyl)-2,3-dihydro-5H-[1,4]thiazino[2,3,4-ij]quinazolin-5-one

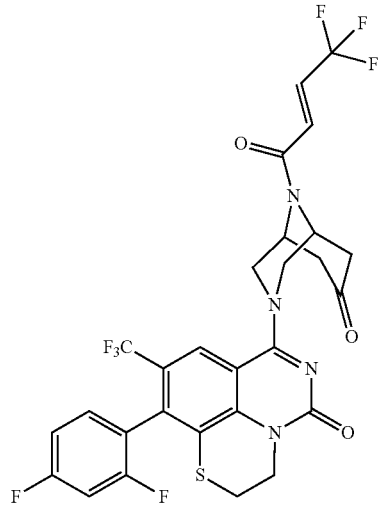 [SMILES: O=C1CC2CN(c3nc(=O)n4c5c(c(-c6ccc(F)cc6F)c(C(F)(F)F)cc35)SCC4)CC(C1)N2C(=O)/C=C/C(F)(F)F]

To a solution of (2E)-4,4,4-trifluorobut-2-enoic acid (43 mg, 0.31 mmol) in dichloromethane (1 mL) were added oxalyl chloride (59 mg, 0.45 mmol) and 2 drops of DMF. The reaction mixture was stirred at room temperature for 30 minutes and after that time a solution of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (80 mg, 0.15 mmol) and triethylamine (93 mg, 0.92 mmol) in dichloromethane (1 mL) was added. The mixture stirred at room temperature for 1 hour. The solvent was removed under reduced pressure to afford a residue that was purified by preparative HPLC. The title compound was isolated in 4% yield as a white solid.
m/z (ESI, +ve)=645.1 (M+H)$^+$.
$^1$H NMR (400 MHz, DMSO-d6) δ 7.77 (s, 1H), 7.59-7.43 (m, 2H), 7.37 (s, 1H), 7.30-7.26 (m, 1H), 6.93-6.89 (m, 1H), 5.17 (m, 1H), 4.92 (m, 1H), 4.33-4.17 (m, 2H), 4.17-3.97 (m, 3H), 3.30-3.14 (m, 5H), 3.09-2.96 (m, 1H), 2.79-2.72 (m, 1H).

Example 442: (2S)-7-((S)-4-acryloyl-2-methylpiperazin-1-yl)-10-(2,4-difluorophenyl)-2-((dimethylamino)methyl)-9-(trifluoromethyl)-2,3-dihydro-5H-[1,4]thiazino[2,3,4-ij]quinazolin-5-one

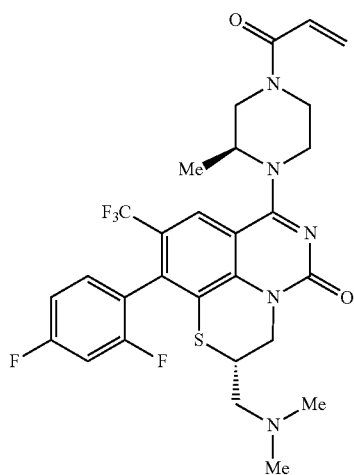 [SMILES: C=CC(=O)N1CCN(c2nc(=O)n3c4c(c(-c5ccc(F)cc5F)c(C(F)(F)F)cc24)S[C@@H](CN(C)C)C3)[C@@H](C)C1]

Over a solution of (2S)-10-(2,4-difluorophenyl)-2-((dimethylamino)methyl)-7-((S)-2-methylpiperazin-1-yl)-9-(trifluoromethyl)-2,3-dihydro-5H-[1,4]thiazino[2,3,4-ij]quinazolin-5-one (38 mg) in acetonitrile (2 mL), triethylamine (0.11 mL) and acryloyl chloride (0.014 mL) were added. The mixture was stirred at room temperature for 30 minutes and at that time quenched by the addition of water. The mixture was extracted with ethyl acetate, dried over sodium sulfate and concentrated to afford a residue that was purified by HPLC. The title compound was isolated as a white solid in 49% yield m/z (ESI, +ve)=594.2 (M+H)$^+$.

Step 1: tert-Butyl (3S)-4-((3S)-11-(2,4-difluorophenyl)-3-hydroxy-6-oxo-10-(trifluoromethyl)-3,4-dihydro-2H,6H-[1,4]thiazepino[2,3,4-ij]quinazolin-8-yl)-3-methylpiperazine-1-carboxylate

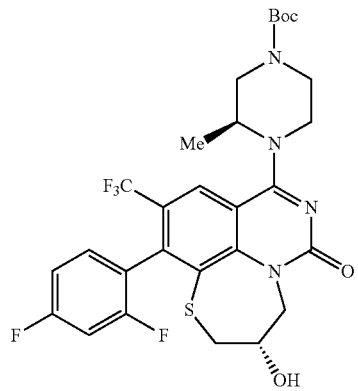 [SMILES: C[C@H]1CN(C(=O)OC(C)(C)C)CCN1c1nc(=O)n2c3c(c(-c4ccc(F)cc4F)c(C(F)(F)F)cc13)SC[C@@H](O)C2]

A solution of tert-butyl (3S)-4-((3S)-3-(benzyloxy)-11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate (100 mg) in 2 mL of isopropanol was hydrogenated at atmospheric pressure in the presence of 75 mg of 10% palladium on activated carbon. After 12 hours, the reaction was filtered through celite and the volatiles removed under reduced pressure to afford a solid that was hydrogenated for a second time in 2 mL of isopropanol and 75 mg of 10% palladium on activated carbon. The reaction was filtered through celite and the volatiles removed under reduced pressure to afford the title compound as an orange solid.

m/z (ESI, +ve)=613.2 (M+H)$^+$.

Step 2: tert-butyl (3S)-4-((3S)-11-(2,4-difluorophenyl)-3-((methylsulfonyl)oxy)-6-oxo-10-(trifluoromethyl)-3,4-dihydro-2H,6H-[1,4]thiazepino[2,3,4-ij]quinazolin-8-yl)-3-methylpiperazine-1-carboxylate

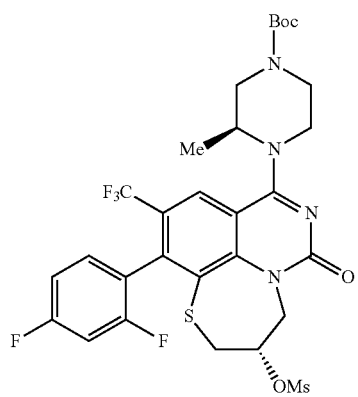

Over a solution of tert-Butyl (3S)-4-((3S)-11-(2,4-difluorophenyl)-3-hydroxy-6-oxo-10-(trifluoromethyl)-3,4-dihydro-2H,6H-[1,4]thiazepino[2,3,4-ij]quinazolin-8-yl)-3-methylpiperazine-1-carboxylate (368 mg) in dichloromethane (6 mL) at room temperature, N,N-diisopropylethylamine (0.50 mL) and methanesulfonyl chloride (0.12 mL) were added. The reaction was stirred for 3 hours, diluted with dichloromethane and washed with water. The organic layer was dried with sodium sulfate and concentrated under reduced pressure to afford an orange solid that was used in the next step without further purification.

m/z (ESI, +ve)=691.2 (M+H)⁺.

Step 3: tert-Butyl (3S)-4-((2R)-10-(2,4-difluorophenyl)-2-((dimethylamino)methyl)-5-oxo-9-(trifluoromethyl)-2,3-dihydro-5H-[1,4]thiazino[2,3,4-ij]quinazolin-7-yl)-3-methylpiperazine-1-carboxylate

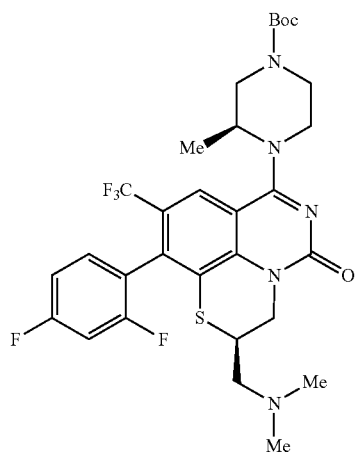 [SMILES: C[C@H]1CN(C(=O)OC(C)(C)C)CCN1c1nc(=O)n2c3c(c(-c4ccc(F)cc4F)c(C(F)(F)F)cc13)S[C@H](CN(C)C)C2]

tert-Butyl (3S)-4-((3S)-11-(2,4-difluorophenyl)-3-((methylsulfonyl)oxy)-6-oxo-10-(trifluoromethyl)-3,4-dihydro-2H,6H-[1,4]thiazepino[2,3,4-ij]quinazolin-8-yl)-3-methylpiperazine-1-carboxylate obtained in the previous step was taken up in 0.5 M solution of N-methylamine in dioxane (2 mL) and heated at 100° C. in microwave reactor for two hours. The volatiles were removed under reduced pressure and the crude residue purified by chromatography in silica gel (0-10% methanol in ethyl acetate) to afford the title compound in 32% yield as a orange oil.

m/z (ESI, +ve)=640.2 (M+H)⁺.

Step 4: (2R)-10-(2,4-difluorophenyl)-2-((dimethylamino)methyl)-7-((S)-2-methylpiperazin-1-yl)-9-(trifluoromethyl)-2,3-dihydro-5H-[1,4]thiazino[2,3,4-ij]quinazolin-5-one

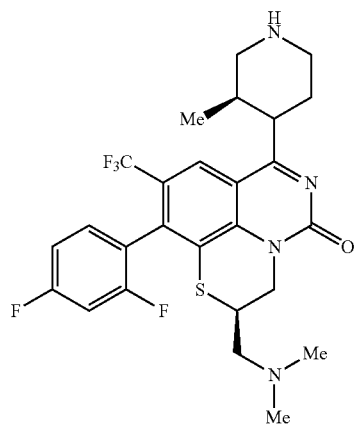 [SMILES: C[C@H]1CNCCC1c1nc(=O)n2c3c(c(-c4ccc(F)cc4F)c(C(F)(F)F)cc13)S[C@H](CN(C)C)C2]

Over a solution of tert-butyl (3S)-4-((2R)-10-(2,4-difluorophenyl)-2-((dimethylamino)methyl)-5-oxo-9-(trifluoromethyl)-2,3-dihydro-5H-[1,4]thiazino[2,3,4-ij]quinazolin-7-yl)-3-methylpiperazine-1-carboxylate (37 mg) in dichloromethane (1 mL), TFA (0.2 mL) was added. The mixture was stirred at room temperature for 4 hours and at that time all volatiles were removed under reduced pressure to afford a solid that was used in the next step without further purification.

m/z (ESI, +ve)=539.2 (M+H)⁺.

Example 450: 8-((S)-4-acryloyl-2-methylpiperazin-1-yl)-11-(2,4-difluorophenyl)-10-(trifluoromethyl)-3,4-dihydro-2H,6H-[1,4]thiazepino[2,3,4-ij]quinazolin-6-one

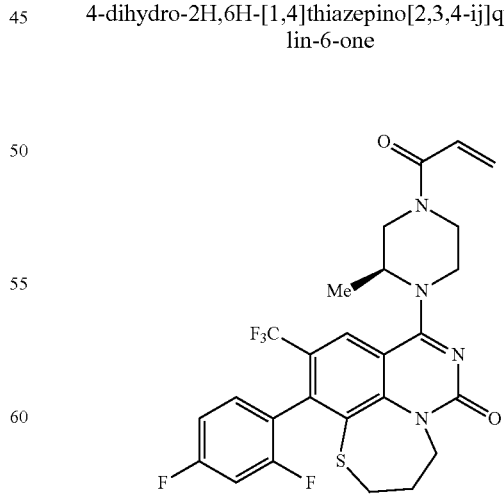

The title compound was prepared analogously to Example 84 where 11-(2,4-difluorophenyl)-8-((S)-2-methylpiperazin-1-yl)-10-(trifluoromethyl)-3,4-dihydro-2H,6H-[1,4]

thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 51% yield as a yellow solid m/z (ESI, +ve)=551.1 (M+H)$^+$.

$^1$H NMR (400 MHz, DMSO-d6) δ 7.81 (d, J=4.0 Hz, 1H), 7.50-7.33 (m, 2H), 7.26-7.23 (m, 1H), 6.91-6.75 (m, 1H), 6.21-6.15 (m, 1H), 5.74 (d, J=8 Hz, 1H), 4.57-4.47 (m, 3H), 4.42-4.24 (m, 1H), 4.10-3.98 (m, 2H), 3.62-3.48 (m, 1H), 3.46-2.92 (m, 4H), 2.11-1.86 (m, 2H), 1.33-1.28 (m, 3H).

Step 1: 7-(2,4-difluorophenyl)-8-((3-hydroxypropyl)thio)-6-(trifluoromethyl)quinazoline-2,4(1H,3H)-dione

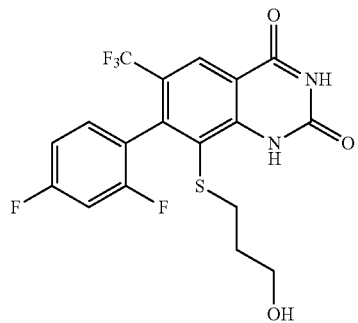

The title compound was prepared analogously to Example 100, step 9 where 3-mercaptopropan-1-ol was substituted in place of 2-mercaptoethan-1-ol in 56% yield as a white solid m/z (ESI, +ve)=433.1 (M+H)$^+$.

Step 2: 11-(2,4-difluorophenyl)-10-(trifluoromethyl)-3,4-dihydro-2H,6H-[1,4]thiazepino[2,3,4-ij]quinazoline-6,8(7H)-dione

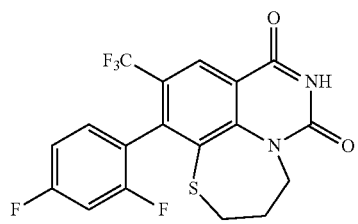

The title compound was prepared analogously to Example 100, step 10 where 7-(2,4-difluorophenyl)-8-((3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 52% yield as a white solid m/z (ESI, +ve)=415.1 (M+H)$^+$.

Step 3: tert-butyl (3S)-4-(11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate

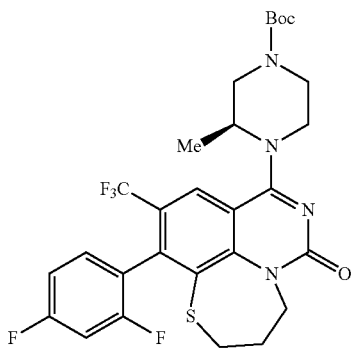 [SMILES: C[C@H]1CN(C(=O)OC(C)(C)C)CCN1c1nc(=O)n2c3c(c(-c4ccc(F)cc4F)c(C(F)(F)F)cc13)SCCC2]

The title compound was prepared analogously to Example 100, step 21 where 11-(2,4-difluorophenyl)-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 85% yield as a yellow solid.

m/z (ESI, +ve)=597.1 (M+H)$^+$.

Step 4: 11-(2,4-difluorophenyl)-8-((S)-2-methylpiperazin-1-yl)-10-(trifluoromethyl)-3,4-dihydro-2H,6H-[1,4]thiazepino[2,3,4-ij]quinazolin-6-one

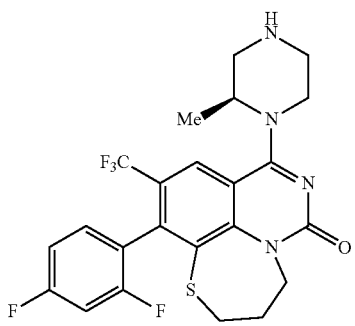 [SMILES: C[C@H]1CNCCN1c1nc(=O)n2c3c(c(-c4ccc(F)cc4F)c(C(F)(F)F)cc13)SCCC2]

The title compound was prepared analogously to Example 102, step 4, where (3S)-4-(11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow oil.

m/z (ESI, +ve)=497.1 (M+H)+.

Example 451: 11-(2,4-difluorophenyl)-8-(9-(2-fluoroacryloyl)-7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one

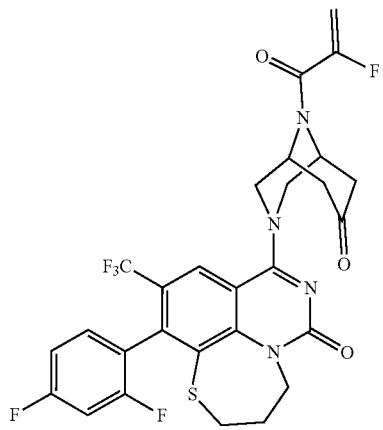 [SMILES: C=C(F)C(=O)N1C2CC(=O)CC1CN(c1nc(=O)n3c4c(c(-c5ccc(F)cc5F)c(C(F)(F)F)cc14)SCCC3)C2]

To a solution of 2-fluoroacrylic acid (34 mg, 0.38 mmol) in DMF (3 mL), N,N,N',N'-tetramethyl-O-(7-azabenzotriazol-1-yl)uronium (160 mg, 0.42 mmol) and N,N-diisopropylethylamine (99 mg, 0.76 mmol) were added. After 5 minutes, 11-(2,4-difluorophenyl)-8-(7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one (120 mg, 0.19 mmol) was added and the resulting solution stirred at room temperature for another 2 hours. The solvent was removed under reduced pressure to afford a residue that was purified by preparative HPLC. The title compound was isolated in 15% as a light yellow solid.

m/z (ESI, +ve)=609.1 (M+H)$^+$.

$^1$H NMR (400 MHz, DMSO-d6) δ7.77 (s, 1H), 7.44-7.36 (m, 2H), 7.28-7.24 (m, 1H), 5.47 (s, 1H), 5.38 (dd, J=24.0 Hz, 4.0 Hz, 1H), 5.06 (s, 1H), 4.79 (s, 1H), 4.55-4.45 (m, 2H), 4.16-4.01 (m, 2H), 3.32-3.06 (m, 4H), 3.00-2.73 (m, 2H), 2.55-2.52 (m, 2H), 2.14-1.89 (m, 2H).

Step 1: 11-(2,4-difluorophenyl)-8-(7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one

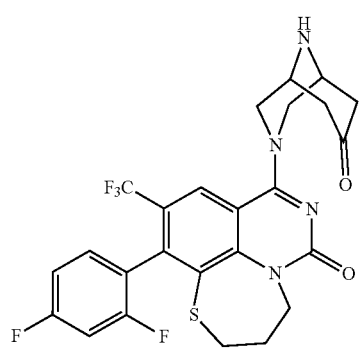 [SMILES: O=C1CC2CN(c3nc(=O)n4c5c(c(-c6ccc(F)cc6F)c(C(F)(F)F)cc35)SCCC4)CC(C1)N2]

The title compound was prepared analogously to Example 101, step 7 where 11-(2,4-difluorophenyl)-10-(trifluoromethyl)-3,4-dihydro-2H,6H-[1,4]thiazepino[2,3,4-ij]quinazoline-6,8(7H)-dione was substituted in place of 10-(2,4-difluorophenyl)-9-(trifluoromethyl)-2,3-dihydro-5H-[1,4]thiazino[2,3,4-ij]quinazoline-5,7(6H)-dione. The title compound was isolated in 8% yield as a pale yellow solid.

m/z (ESI, +ve)=537.0 (M+H)$^+$.

$^1$H NMR (400 MHz, DMSO-d6) δ 7.77 (s, 1H), 7.44-7.40 (m, 2H), 7.27-7.23 (m, 1H), 4.50-4.44 (m, 2H), 3.87-3.83 (m, 2H), 3.65 (s, 2H), 3.27-3.13 (m, 4H), 2.76-2.67 (m, 2H), 2.43-2.34 (m, 2H), 2.08-1.96 (m, 2H), 1.23 (s, 1H).

Example 452: (E)-7-(9-(but-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one

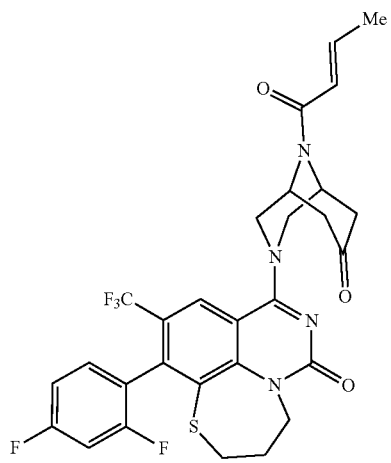 [SMILES: C/C=C/C(=O)N1C2CC(=O)CC1CN(c1nc(=O)n3c4c(c(-c5ccc(F)cc5F)c(C(F)(F)F)cc14)SCCC3)C2]

To a solution of (E)-but-2-enoic acid (13 mg, 0.15 mmol) in acetonitrile (2 mL) were added N,N,N',N'-tetramethylchloroformamidinium hexafluorophosphate (38 mg, 0.14 mmol) and N-methylimidazole (33 mg, 0.40 mmol). After 5 minutes, 10-(2,4-difluorophenyl)-7-(oxo-3,9-diazabicyclo[3.3.1]nonan-3-yl)-9-(trifluoromethyl)-2,3-dihydro-5H-[1,4]thiazino[2,3,4-ij]quinazolin-5-one (60 mg, 0.11 mmol) was added. The reaction mixture was stirred at room temperature for 2 hours. The solvent was removed under reduced pressure to afford a residue that was purified by preparative HPLC. The title compound was isolated in 5% yield as a white solid.

m/z (ESI, +ve)=591.1 (M+H)$^+$.

$^1$H NMR (400 MHz, DMSO-d6) δ 7.78 (s, 1H), 7.48-7.47 (m, 1H), 7.38-7.37 (m, 1H), 7.30-7.28 (m, 1H), 6.87-6.80 (m, 1H), 6.68-6.64 (m, 1H), 5.76 (s, 1H), 5.15 (s, 1H), 4.95 (s, 1H), 4.32-4.24 (m, 2H), 4.16-3.97 (m, 3H), 3.21-3.18 (m, 4H), 2.84-2.69 (m, 2H), 1.91-1.89 (m, 3H).

Example 453: 7-(9-(but-2-ynoyl)-7-oxo-3,9-diazabicyclo[3.3.1]nonan-3-yl)-10-(2,4-difluorophenyl)-9-(trifluoromethyl)-2,3-dihydro-5H-[1,4]thiazino [2,3,4-ij]quinazolin-5-one

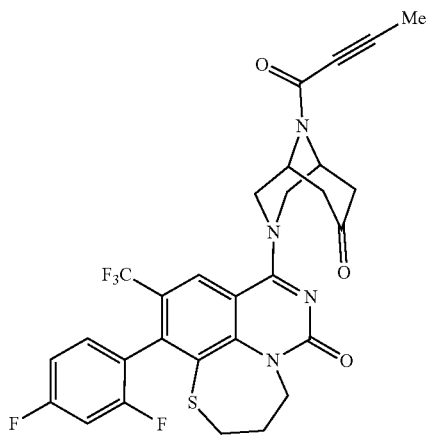 [SMILES: CC#CC(=O)N1C2CC(=O)CC1CN(c1nc(=O)n3c4c(c(-c5ccc(F)cc5F)c(C(F)(F)F)cc14)SCCC3)C2]

The title compound was prepared analogously to Example 452, where but-2-ynoic acid was substituted in place of (E)-but-2-enoic acid. The title compound was isolated in 18% yield as a white solid m/z (ESI, +ve)=589.1 (M+H)⁺.

¹H NMR (400 MHz, DMSO-d6) δ 7.76 (s, 1H), 7.50-7.46 (m, 1H), 7.38-7.34 (m, 1H), 7.30-7.26 (m, 1H), 5.05 (s, 2H), 4.31-4.30 (m, 1H), 4.13-4.04 (m, 3H), 3.30-3.07 (m, 5H), 2.87-2.76 (m, 3H), 2.09-2.05 (m, 3H).

Example 454: (3S)-8-((S)-4-acryloyl-2-methylpiperazin-1-yl)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazolin-6-one

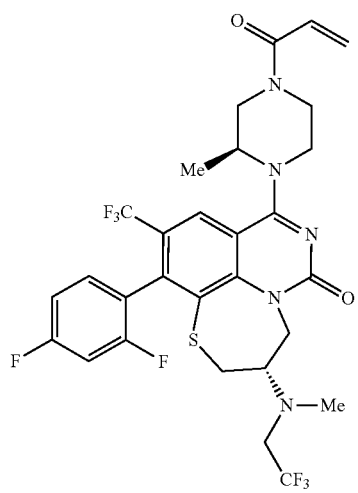 [SMILES: C=CC(=O)N1CCN(c2nc(=O)n3c4c(c(-c5ccc(F)cc5F)c(C(F)(F)F)cc24)SC[C@@H](N(C)CC(F)(F)F)C3)[C@@H](C)C1]

To a stirred solution of (3S)-11-(2,4-difluorophenyl)-3-(methyl(2,2,2-trifluoroethyl)amino)-8-((S)-2-methylpiperazin-1-yl)-10-(trifluoromethyl)-3,4-dihydro-2H,6H-[1,4]thiazepino[2,3,4-ij]quinazolin-6-one (8.5 mg, 0.01 mmol) at 0° C. in acetonitrile (2 mL), N,N-diisopropylethylamine (21 uL, 0.12 mmol) and prop-2-enoyl chloride (2.87 uL, 0.040 mmol) were added. The reaction was stirred for 5 minutes at 0° C., diluted with ethyl acetate and washed with water and brine. The organic layer was dried with sodium sulfate and concentrated to afford a yellow residue that was purified by silica (0-5% methanol in dichloromethane) isolating the title compound as a light yellow solid in 90% yield.

m/z (ESI, +ve)=662.2

¹H NMR (400 MHz, CDCl3) δ 7.75 (d, J=12.1 Hz, 1H), 7.15 (q, J=7.8 Hz, 1H), 7.07-6.77 (m, 2H), 6.71-6.47 (m, 1H), 6.39 (dd, J=16.8, 1.9 Hz, 1H), 5.79 (dd, J=10.4, 1.9 Hz, 1H), 5.10-4.58 (m, 2H), 4.58-4.08 (m, 2H), 4.07-3.71 (m, 2H), 3.67-3.37 (m, 2H), 3.22-2.99 (m, 2H), 2.90 (t, J=8.5 Hz, 1H), 2.75 (dd, J=13.3, 7.7 Hz, 1H), 2.47 (d, J=3.9 Hz, 2H), 1.60-1.35 (m, 3H), 1.35-1.10 (m, 3H).

Step 1: (R)-1-(benzyloxy)-3-(tritylthio)propan-2-ol

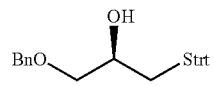

To a vigorously stirred solution of triphenylmethanethiol (7.0 g, 25.33 mmol) and (2R)-2-(benzyloxymethyl)oxirane (2.99 mL, 19.49 mmol) in THF (100 mL) at 0° C., sodium hydride (29 mmol) was added in three portions over five minutes. The reaction was left in an ice bath to slowly warm to room temperature overnight. The reaction was diluted with ethyl acetate (200 mL) and washed with water (×2) and brine. The organic layer was collected, dried with sodium sulfate, and concentrated to afford a tan oil. This oil was purified via column chromatography (5-50% ethyl acetate in hexanes) isolating the title compound in 71% yield a colorless oil.

¹H NMR (400 MHz, CDCl3) δ 7.26-7.23 (m, 5H), 7.23-6.96 (m, 15H), 4.28 (s, 2H), 3.35 (qd, J=6.6, 3.6 Hz, 1H), 3.23-3.05 (m, 2H), 2.31-2.15 (m, 2H).

Step 2: (R)-1-(benzyloxy)-3-(tritylthio)propan-2-yl methanesulfonate

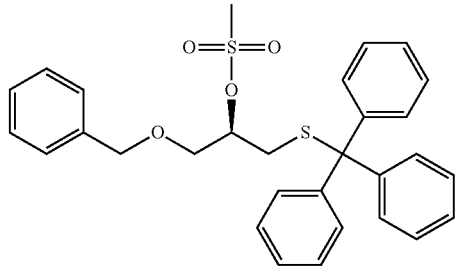 [SMILES: CS(=O)(=O)O[C@H](COCc1ccccc1)CSC(c1ccccc1)(c1ccccc1)c1ccccc1]

To a stirred solution of (R)-1-(benzyloxy)-3-(tritylthio) propan-2-ol (3.5 g, 7.94 mmol) and triethylamine (23.8 mmol) in acetonitrile (100 mL) cooled down to 0° C., methanesulfonyl chloride (2.13 mL) was added. The reaction was stirred at 0° C. for 30 minutes and let it warm up to ambient temperature afterwards. After 2 hours, the reaction was diluted with ethyl acetate, washed with water and brine and the organic layer dried over sodium sulfate and concentrated to afford a brown oil. This oil was purified via column chromatography (5-40% ethyl acetate in hexanes) isolating the title compound in 91% yield as a thick colorless oil.

$^1$H NMR (400 MHz, CDCl3) δ 7.45-7.42 (m, 5H), 7.34-7.24 (m, 15H), 4.52-4.41 (m, 2H), 4.33 (qd, J=6.4, 4.8 Hz, 1H), 3.55-3.43 (m, 2H), 2.95 (s, 3H), 2.64 (qd, J=13.4, 6.5 Hz, 2H).

Step 3: (S)-1-(benzyloxy)-N-methyl-N-(2,2,2-trifluoroethyl)-3-(tritylthio)propan-2-amine

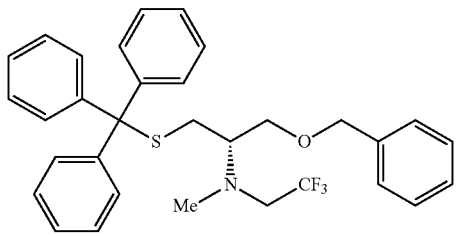 [SMILES: CN(CC(F)(F)F)[C@@H](COCc1ccccc1)CSC(c1ccccc1)(c1ccccc1)c1ccccc1]

To a stirred solution of (R)-1-(benzyloxy)-3-(tritylthio)propan-2-yl methanesulfonate (1 g, 1.93 mmol) and DMA (6.4 mL) in a 20 mL microwave vial was added 2,2,2-trifluoro-N-methyl-ethanamine (5.45 mL, 38.56 mmol). The vial was capped and heated at 50° C. for 13 hours. The crude reaction mixture was concentrated to afford light yellow oil. This crude oil was purified via chromatography (5-45% ethyl acetate in hexanes) isolating the title compound in 24% yield as a colorless oil.

$^1$H NMR (400 MHz, CDCl3) δ 7.44 (dd, J=7.7, 1.8 Hz, 5H), 7.25-7.07 (m, 15H), 4.40-4.28 (m, 2H), 3.31 (ddd, J=37.9, 9.5, 4.0 Hz, 2H), 2.71-2.49 (m, 3H), 2.32-2.24 (m, 1H), 2.17-2.00 (m, 4H).

Step 4: (S)-3-(benzyloxy)-2-(methyl(2,2,2-trifluoroethyl)amino)propane-1-thiol

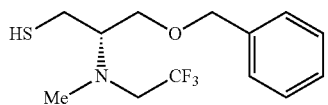 [SMILES: CN(CC(F)(F)F)[C@H](CS)COCc1ccccc1]

(S)-1-(benzyloxy)-N-methyl-N-(2,2,2-trifluoroethyl)-3-(tritylthio)propan-2-amine (150 mg, 0.28 mmol) was dissolved in a mixture of dichloromethane (1 mL) and TFA (1 mL) and treated with triethylsilane (1.12 g, 9.64 mmol) at ambient temperature. The reaction was stirred for 2 hours. The crude reaction mixture was concentrated under reduced pressure to afford the title compound that was used in the next step without further purification.

Step 5: 8-(((S)-3-(benzyloxy)-2-(methyl(2,2,2-trifluoroethyl)amino)propyl)thio)-7-(2,4-difluorophenyl)-6-(trifluoromethyl)quinazoline-2,4(1H,3H)-dione

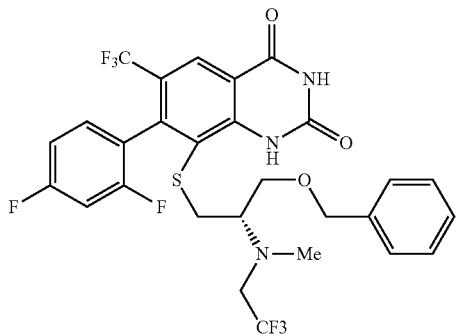 [SMILES: CN(CC(F)(F)F)[C@@H](COCc1ccccc1)CSc1c(-c2ccc(F)cc2F)c(C(F)(F)F)cc2c(=O)[nH]c(=O)[nH]c12]

A mixture of (S)-3-(benzyloxy)-2-(methyl(2,2,2-trifluoroethyl)amino)propane-1-thiol (65.8 mg, 0.22 mmol), potassium carbonate (62.mg, 0.45 mmol), ethylene glycol (0.1 mL), isopropanol (0.68 mL), and 7-(2,4-difluorophenyl)-8-iodo-6-(trifluoromethyl)-1H-quinazoline-2,4-dione (70 mg, 0.15 mmol) was degassed by bubbling nitrogen gas for 5 minutes. Copper iodide was then added (2.85 mg, 0.0100 mmol) and the mixture degassed again for another 3 minutes. The reaction was heated at 85° C. overnight. The reaction was cooled to ambient temperature, diluted with ethyl acetate, and washed with water and brine. The organic layer was dried with sodium sulfate and concentrated to afford a crude oil that was purified by silica gel chromatography (0-10% methanol in ethyl acetate) to afford the title compound in 95% yield as a white solid.

m/z (ESI, +ve)=634.2, RT: 5.25 min

Step 6: 7-(2,4-difluorophenyl)-8-(((S)-3-hydroxy-2-(methyl(2,2,2-trifluoroethyl)amino)propyl)thio)-6-(trifluoromethyl)quinazoline-2,4(1H,3H)-dione

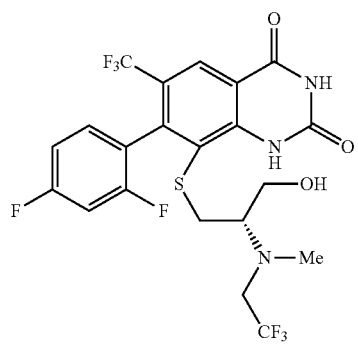 [SMILES: CN(CC(F)(F)F)[C@@H](CO)CSc1c(-c2ccc(F)cc2F)c(C(F)(F)F)cc2c(=O)[nH]c(=O)[nH]c12]

A solution of 8-(((S)-3-(benzyloxy)-2-(methyl(2,2,2-trifluoroethyl)amino)propyl)thio)-7-(2,4-difluorophenyl)-6-(trifluoromethyl)quinazoline-2,4(1H,3H)-dione (90 .mg, 0.14 mmol) and 30 mg of 10% palladium on carbon in isopropanol was hydrogenated for 18 hours. The reaction was filtered through celite and concentrated to afford the title compound as a semisolid in 82% yield.

m/z (ESI, +ve)=544.1

Step 7: (3S)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazoline-6,8(7H)-dione

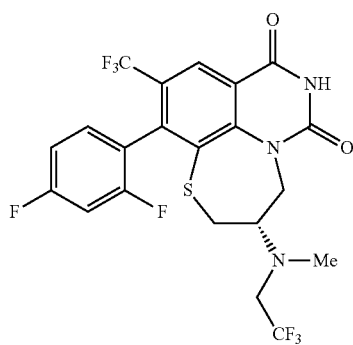 [SMILES: CN(CC(F)(F)F)[C@@H]1CSc2c(-c3ccc(F)cc3F)c(C(F)(F)F)cc3c(=O)[nH]c(=O)n(c23)C1]

A solution of triphenylphosphine (76 mg, 0.29 mmol) and (4-chlorophenyl)methyl (NE)-N-[(4-chlorophenyl)methoxycarbonylimino]carbamate (106 mg, 0.29 mmol) in 2 mL of THF was stirred at −10° C. for 10 minutes. To this mixture, a solution of 7-(2,4-difluorophenyl)-8-(((S)-3-hydroxy-2-(methyl(2,2,2-trifluoroethyl)amino)propyl)thio)-6-(trifluoromethyl)quinazoline-2,4(1H,3H)-dione (63 mg, 0.12 mmol) in 2 mL THF was added dropwise over 3 minutes. The reaction was stirred for 1 hour at 0° C. An additional equivalent of (4-chlorophenyl)methyl (NE)-N-[(4-chlorophenyl)methoxycarbonylimino]carbamate and triphenylphosphine in 0.5 mL of THF were added and the mixture stirred for another 30 min. The reaction was diluted with ethyl acetate and washed with water and brine. The organic layer was dried with sodium sulfate and concentrated to a residue that was purified by column chromatography (10-60% ethyl acetate in hexanes) to afford the title compound as a white solid in 82% yield.

m/z (ESI, +ve)=526.1

Step 8: tert-butyl (3S)-4-((3S)-11-(2,4-difluorophenyl)-3-(methyl(2,2,2-trifluoroethyl)amino)-6-oxo-10-(trifluoromethyl)-3,4-dihydro-2H,6H-[1,4]thiazepino[2,3,4-ij]quinazolin-8-yl)-3-methylpiperazine-1-carboxylate

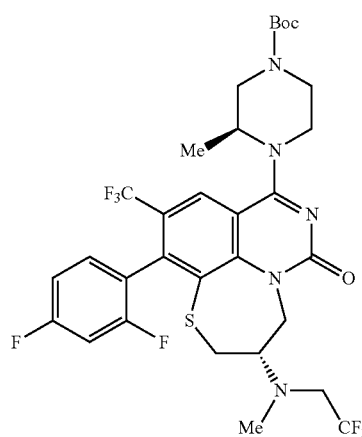

The title compound was prepared analogously to Example 100, step 21 where (3S)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 12% yield as a white solid m/z (ESI, +ve)=708.3 (M+H)⁺.

Step 9: (3S)-11-(2,4-difluorophenyl)-3-(methyl(2,2,2-trifluoroethyl)amino)-8-((S)-2-methylpiperazin-1-yl)-10-(trifluoromethyl)-3,4-dihydro-2H,6H-[1,4]thiazepino[2,3,4-ij]quinazolin-6-one

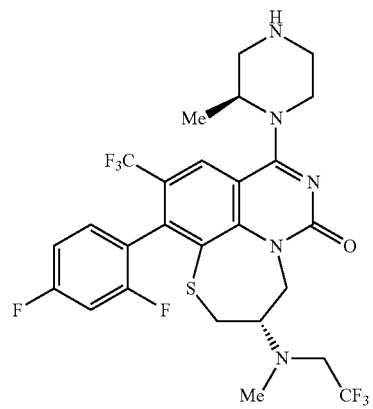 [SMILES: C[C@H]1CNCCN1c1nc(=O)n2c3c(c(-c4ccc(F)cc4F)c(C(F)(F)F)cc13)SC[C@@H](N(C)CC(F)(F)F)C2]

The title compound was prepared analogously to Example 102, step 4, where tert-butyl (3S)-4-((3S)-11-(2,4-difluorophenyl)-3-(methyl(2,2,2-trifluoroethyl)amino)-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a colorless oil Mass Spectrum (ESI) m/z=608.2 (M+H)⁺.

Example 464: (3S)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

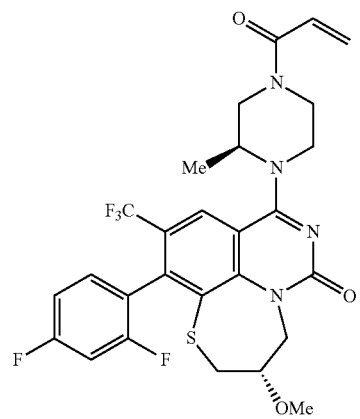 [SMILES: C=CC(=O)N1CCN(c2nc(=O)n3c4c(c(-c5ccc(F)cc5F)c(C(F)(F)F)cc24)SC[C@@H](OC)C3)[C@@H](C)C1]

The title compound was prepared analogously to Example 84 where (3S)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 41% yield as a yellow solid m/z (ESI, +ve)=581.1 (M+H)$^+$.

$^1$H NMR (400 MHz, DMSO-d6) δ 7.80 (d, J=8.0 Hz, 1H), 7.50-7.33 (m, 2H), 7.28-7.24 (m, 1H), 6.87-6.78 (m, 1H), 6.20-6.16 (m, 1H), 5.80-5.69 (m, 1H), 4.67-4.44 (m, 4H), 4.26-4.24 (m, 1H), 4.17-4.13 (m, 1H), 4.01-3.97 (m, 1H), 3.86-3.82 (m, 1H), 3.55-3. (m, 2H), 3.36-3.31 (m, 3H), 3.24-3.07 (m, 1H), 3.01 (s, 1H), 1.26-1.20 (m, 3H).

Step 1: (S)-3-(tritylthio)propane-1,2-diol

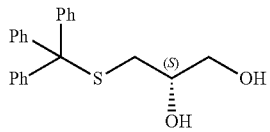

Potassium tert-butoxide (18.3 g, 0.18 mol) was added over a solution of triphenylmethyl mercaptan (25 g, 0.091 mol) and (2S)-3-chloropropane-1,2-diol (10 g, 0.091 mol) in DMF (200 mL) at 25° C. The mixture was stirred at room temperature for 16 hours and after that time it was quenched with water. The resulting mixture was extracted with ethyl acetate three times and the organic layers were combined and washed with brine, dried over sodium sulfate and filtered. Evaporation of volatiles under reduced pressure afforded a residue that was purified by column chromatography on silica gel (0-50% ethyl acetate in hexanes). The title compound was isolated in 66% yield as yellow oil.

m/z (ESI, +ve)=373.1 (M+Na).

Step 2: (S)-1-((tert-butyldimethylsilyl)oxy)-3-(tritylthio)propan-2-ol

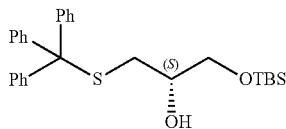

Imidazole (9.71 g, 0.14 mol) and tert-butyldimethylsilyl chloride (9.47 g, 0.063 mol) were added over a solution of (2S)-3-[(triphenylmethyl)sulfanyl] propane-1,2-diol (20 g, 0.057 mol) in DMF (250 mL) at room temperature. After 16 hours, the reaction was quenched by the addition of water. The mixture was extracted with ethyl acetate three times and the combined organic layers were washed with brine, dried over sodium sulfate and filtered to afford a residue that was purified by silica gel chromatography (0-15% ethyl acetate in hexanes). The title compound was isolated in 60% yield as a yellow oil.

m/z (ESI, +ve)=487.2 (M+Na)$^+$.

Step 3: (S)-tert-butyl(2-methoxy-3-(tritylthio)propoxy)dimethylsilane

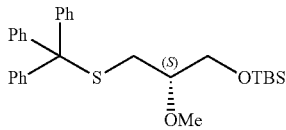

To a solution of tert-butyl[(2S)-2-hydroxy-3-[(triphenylmethyl)sulfanyl]propoxy]dimethylsilane (21 g, 0.045 mol) in THF (200 mL) at 0° C., sodium hydride (1.62 g, 0.068 mol) was added. After 30 minutes at 0° C., iodomethane (9.62 g, 0.067 mol) was added and stirring was prolonged for another 3.5 hours. The reaction was quenched by addition of water and extracted with ethyl acetate three times. The combined organic layers were washed with brine, dried over sodium sulfate and filtered to afford a residue that was purified by silica gel chromatography. The tile compound was isolated in 86% yield as a colorless oil.

m/z (ESI, +ve)=501.2 (M+Na)$^+$.

Step 4: (S)-3-Mercapto-2-methoxypropan-1-ol

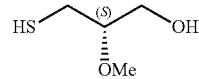

To a solution of tert-butyl[(2S)-2-methoxy-3-[(triphenylmethyl)sulfanyl]propoxy]dimethylsilane (18.7 g, 0.039 mol) in 180 mL of dichloromethane/TFA (3:1 ratio) at room temperature, was added triethylsilane (9.06 g, 0.078 mol). The mixture was stirred at room temperature for 30 minutes. The reaction was quenched by addition of water and extracted with dichloromethane three times. The combined organic layers were washed with brine, dried over sodium sulfate and filtered to afford a residue that was purified by silica gel chromatography. The tile compound was isolated in 90% yield as a colorless oil.

Step 5: 7-(2,4-difluorophenyl)-8-(((S)-3-hydroxy-2-methoxypropyl)thio)-6-(trifluoromethyl)quinazoline-2,4(1H,3H)-dione

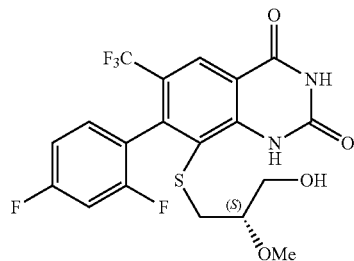

The title compound was prepared analogously to Example 100, step 9 where (S)-3-mercapto-2-methoxypropan-1-ol was substituted in place of 2-mercaptoethan-1-ol in 73% yield as a yellow solid m/z (ESI, +ve)=463.1 (M+H)$^+$.

Step 4: (3S)-11-(2,4-difluorophenyl)-3-methoxy-10-(trifluoromethyl)-3,4-dihydro-2H,6H-[1,4]thiazepino[2,3,4-ij]quinazoline-6,8(7H)-dione

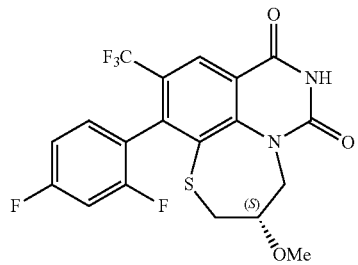

The title compound was prepared analogously to Example 100, step 10 where 7-(2,4-difluorophenyl)-8-(((S)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 65% yield as a yellow solid m/z (ESI, +ve)=445.1 (M+H)$^+$.

Step 5: tert-butyl (3S)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

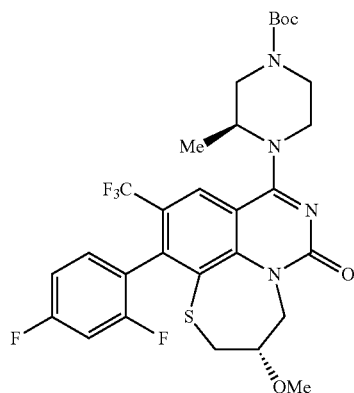 [SMILES: CO[C@@H]1CSc2c(-c3ccc(F)cc3F)c(C(F)(F)F)cc3c(N4CCN(C(=O)OC(C)(C)C)C[C@@H]4C)nc(=O)n(c23)C1]

The title compound was prepared analogously to Example 100, step 21 where (3S)-11-(2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 56% yield as a yellow solid m/z (ESI, +ve)=627.1 (M+H)$^+$.

Step 6: (3S)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

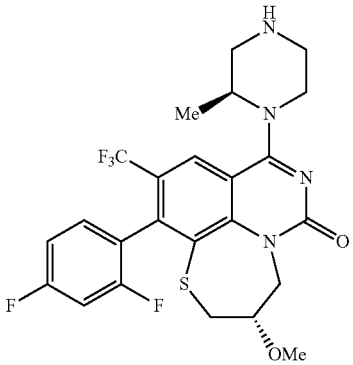 [SMILES: CO[C@@H]1CSc2c(-c3ccc(F)cc3F)c(C(F)(F)F)cc3c(N4CCNC[C@@H]4C)nc(=O)n(c23)C1]

The title compound was prepared analogously to Example 102, step 4, where tert-butyl (3S)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 95% yield as a yellow solid m/z (ESI, +ve)=527.0 (M+H)$^+$.

Example 465: (3R)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

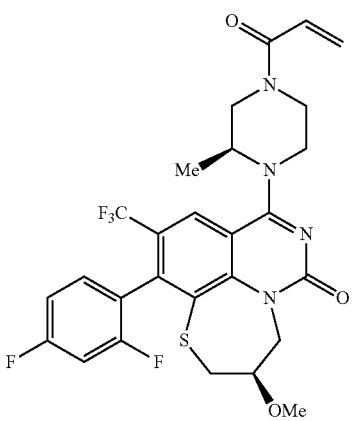 [SMILES: C=CC(=O)N1CCN(c2nc(=O)n3c4c(c(-c5ccc(F)cc5F)c(C(F)(F)F)cc24)SC[C@H](OC)C3)[C@@H](C)C1]

The title compound was prepared analogously to Example 84 where (3R)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 10% yield as a yellow solid m/z (ESI, +ve)=581.1 (M+H)$^+$.

¹H NMR (400 MHz, DMSO-d6) δ 7.81 (d, J=4.0 Hz, 1H), 7.51-7.36 (m, 2H), 7.28-7.24 (m, 1H), 6.89-6.76 (m, 1H), 6.20-6.15 (m, 1H), 5.76-5.70 (m, 1H), 4.53-4.21 (m, 3H), 4.17-3.95 (m, 2H), 3.84 (s, 1H), 3.68-3.42 (m, 3H), 3.35 (s, 3H), 3.21-3.07 (m, 2H), 3.01-2.91 (m, 1H), 1.32-1.27 (m, 3H).

Step 1: (R)-3-(tritylthio)propane-1,2-diol

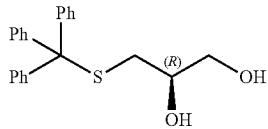

Potassium tert-butoxide (18.3 g, 0.18 mol) was added to a solution of triphenylmethyl mercaptan (25 g, 0.091 mol) and (2R)-3-chloropropane-1,2-diol (10 g, 0.091 mol) in DMF (200 mL) at room temperature. The mixture was stirred for 16 hours and stopped by the addition of water. The resulting mixture was extracted with ethyl acetate three times and the organic layers were combined and washed with brine, dried over sodium sulfate and filtered. Evaporation of volatiles under reduced pressure afforded a residue that was purified by column chromatography on silica gel (0-50% ethyl acetate in hexanes). The title compound was isolated in 51% yield as a yellow oil.

m/z (ESI, +ve)=373.1 (M+Na)⁺.

Step 2: (R)-1-((tert-butyldimethylsilyl)oxy)-3-(tritylthio)propan-2-ol

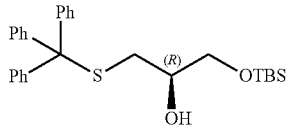

The titled compound was prepared analogously to example 464, step 2, where (2R)-3-[(triphenylmethyl)sulfanyl] propane-1,2-diol was substituted in place of (2s)-3-[(triphenylmethyl)sulfanyl] propane-1,2-diol. The title compound was isolated in 80% yield as a yellow oil.

m/z (ESI, +ve)=487.2 (M+Na)⁺.

Step 3: (R)-tert-butyl(2-methoxy-3-(tritylthio)propoxy)dimethylsilane

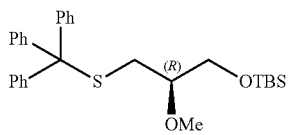

The titled compound was prepared analogously to example 464, step 3 where tert-butyl[(2R)-2-hydroxy-3-[(triphenylmethyl)sulfanyl]propoxy]dimethylsilane was substituted in place of tert-butyl[(2S)-2-hydroxy-3-[(triphenylmethyl)sulfanyl]propoxy]dimethylsilane. The title compound was isolated in 90% yield as a colorless oil.

m/z (ESI, +ve)=501.2 (M+Na)⁺.

Step 4: (R)-3-Mercapto-2-methoxypropan-1-ol

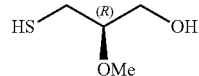

The titled compound was prepared analogously to example 464, step 4, where (R)-tert-butyl(2-methoxy-3-(tritylthio)propoxy)dimethylsilane was substituted for tert-butyl[(2S)-2-methoxy-3-[(triphenylmethyl)sulfanyl]propoxy]dimethylsilane. The title compound was isolated in 85% as a colorless oil.

Step 5: 7-(2,4-difluorophenyl)-8-(((R)-3-hydroxy-2-methoxypropyl)thio)-6-(trifluoromethyl)quinazoline-2,4(1H,3H)-dione

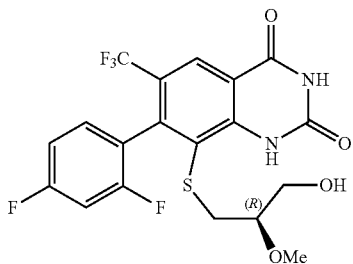

The title compound was prepared analogously to Example 100, step 9 where (R)-3-mercapto-2-methoxypropan-1-ol was substituted in place of 2-mercaptoethan-1-ol. The title compound was isolated in 54% yield as a yellow oil.

m/z (ESI, +ve)=463.0 (M+H)⁺.

¹H NMR (400 MHz, DMSO-d6) δ 11.87 (s, 1H), 10.42 (d, J=18.4 Hz, 1H), 8.28 (s, 1H), 7.49-7.33 (m, 2H), 7.25-7.19 (m, 1H), 4.84 (s, 1H), 3.40-3.35 (m, 2H), 3.28 (d, J=10.8 Hz, 3H), 3.25-3.19 (m, 1H), 2.68-2.65 (m, 1H), 2.35-2.31 (m, 1H).

Step 6: (3R)-11-(2,4-difluorophenyl)-3-methoxy-10-(trifluoromethyl)-3,4-dihydro-2H,6H-[1,4]thiazepino[2,3,4-ij]quinazoline-6,8(7H)-dione

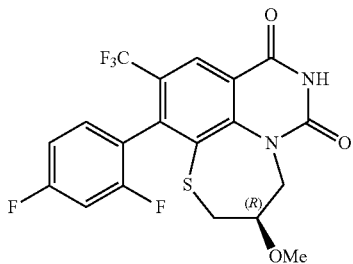

The title compound was prepared analogously to Example 100, step 10, where 7-(2,4-difluorophenyl)-8-(((R)-3-hydroxy-2-methoxypropyl)thio)-6-(trifluoromethyl)quinazoline-2,4(1H,3H)-dione was substituted in place of 7-(2,4- difluorophenyl)-8-((2-hydroxyethyl)thio)-6-(trifluoromethyl)quinazoline-2,4(1H,3H)-dione. The title compound was isolated in 56% yield as a white solid
m/z (ESI, +ve)=445.0 (M+H)+.

$^1$H NMR (400 MHz, DMSO-d6) δ 11.94 (d, J=4.0 Hz, 1H), 8.11 (d, J=7.2 Hz, 1H), 7.47-7.24 (m, 3H), 4.39-4.17 (m, 2H), 3.87-3.78 (m, 1H), 3.67-3.58 (m, 1H), 3.31 (d, J=8.8 Hz, 3H), 3.21-3.15 (m, 1H).

Step 7: tert-butyl (3S)-4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

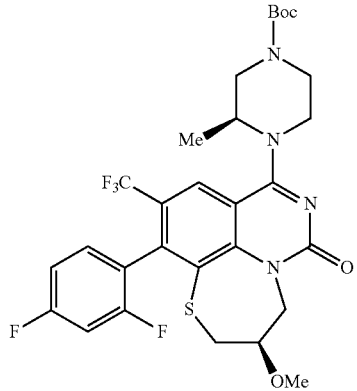 [SMILES: CO[C@H]1CSc2c(-c3ccc(F)cc3F)c(C(F)(F)F)cc3c(N4CCN(C(=O)OC(C)(C)C)C[C@@H]4C)nc(=O)n(c23)C1]

The title compound was prepared analogously to Example 100, step 21 where (3R)-11-(2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 95% yield as a yellow solid
m/z (ESI, +ve)=627.2 (M+H)+.

Step 8: (3R)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

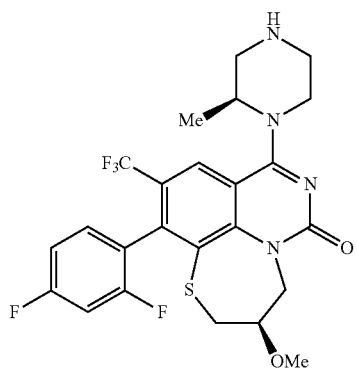 [SMILES: CO[C@H]1CSc2c(-c3ccc(F)cc3F)c(C(F)(F)F)cc3c(N4CCNC[C@@H]4C)nc(=O)n(c23)C1]

The title compound was prepared analogously to Example 102, step 4, where tert-butyl (3S)-4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 95% yield as a yellow solid
m/z (ESI, +ve)=527.2 (M+H)+.

Example 486: 8-(9-acryloyl-7-oxo-3,9-diazabicyclo[3.3.1]nonan-3-yl)-11-(2,4-difluorophenyl)-10-(trifluoromethyl)-3,4-dihydro-2H,6H-[1,4]thiazepino[2,3,4-ij]quinazolin-6-one

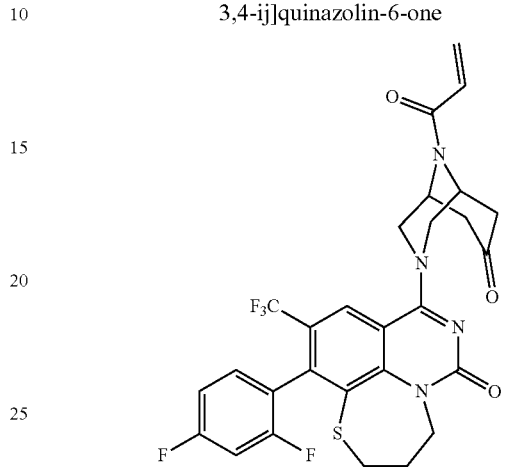

The title compound was prepared analogously to Example 84 where 11-(2,4-difluorophenyl)-8-(7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 5% yield as a yellow solid
m/z (ESI, +ve)=591.2 (M+H)+.

$^1$H NMR (400 MHz, DMSO-d6) δ 7.88-7.78 (m, 1H), 7.47-7.39 (m, 2H), 7.28-7.24 (m, 1H), 6.98-6.67 (m, 1H), 6.29-6.06 (m, 1H), 5.85-5.70 (m, 1H), 5.16 (s, 1H), 4.93 (s, 1H), 4.75 (s, 1H), 4.54-4.49 (m, 2H), 4.06-3.96 (m, 1H), 3.23-3.06 (m, 4H), 2.87-2.72 (m, 2H), 2.45-2.41 (m, 2H), 2.06-1.97 (m, 2H).

Example 487: (3S)-8-((S)-4-acryloyl-2-methylpiperazin-1-yl)-10-chloro-11-(2,4-difluorophenyl)-3-methoxy-3,4-dihydro-2H,6H-[1,4]thiazepino[2,3,4-ij]quinazolin-6-one

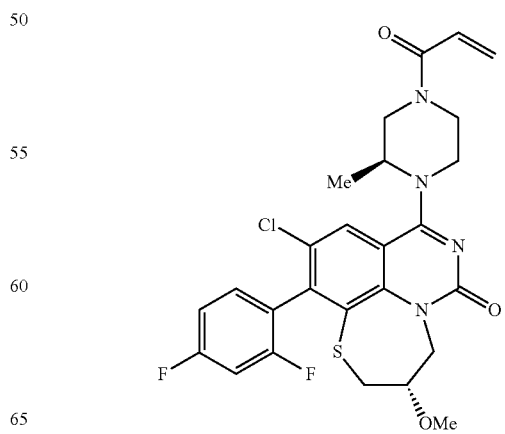

The title compound was prepared analogously to Example 84 where (3S)-10-chloro-11-(2,4-difluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 66% yield as a yellow solid.

m/z (ESI, +ve)=547.1 (M+H)$^+$.

$^1$H NMR (400 MHz, DMSO-d6) δ 7.64 (d, J=12.0 Hz, 1H), 7.49-7.44 (m, 2H), 7.30-7.25 (m, 1H), 6.86-6.77 (m, 1H), 6.21-6.15 (m, 1H), 5.76-5.73 (m, 1H), 4.69-4.20 (m, 4H), 4.18-4.03 (m, 1H), 3.96 (s, 1H), 3.88-3.80 (m, 1H), 3.64-3.38 (m, 3H), 3.35 (s, 3H), 3.11-2.97 (m, 2H), 1.31-1.24 (m, 3H).

Step 1: 6-chloro-7-(2,4-difluorophenyl)-8-(((S)-3-hydroxy-2-methoxypropyl)thio)quinazoline-2,4(1H,3H)-dione

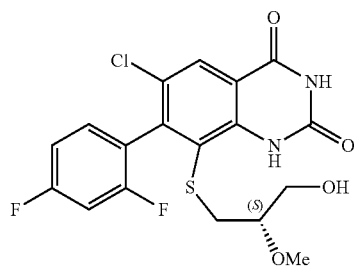

The title compound was prepared analogously to Example 100, step 9 where (S)-3-mercapto-2-methoxypropan-1-ol was substituted in place of 2-mercaptoethan-1-ol in 81% yield as a yellow solid m/z (ESI, +ve)=429.1 (M+H)$^+$.

Step 2: (3S)-10-chloro-11-(2,4-difluorophenyl)-3-methoxy-3,4-dihydro-2H,6H-[1,4]thiazepino[2,3,4-ij]quinazoline-6,8(7H)-dione

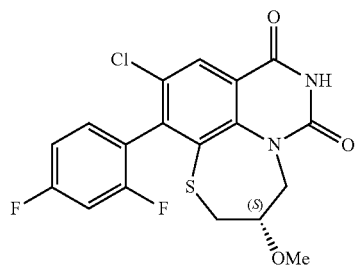

The title compound was prepared analogously to Example 100, step 10 where 6-chloro-7-(2,4-difluorophenyl)-8-(((S)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 74% yield as a yellow solid m/z (ESI, +ve)=411.0 (M+H)$^+$.

Step 3: tert-butyl (3S)-4-((3S)-10-chloro-11-(2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate

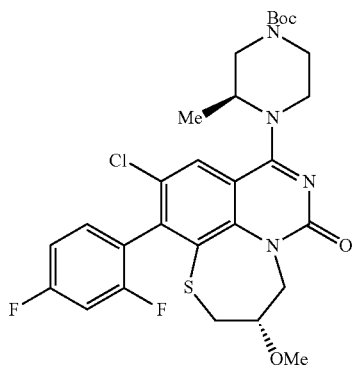 [SMILES: CO[C@@H]1CSc2c(-c3ccc(F)cc3F)c(Cl)cc3c(N4CCN(C(=O)OC(C)(C)C)C[C@@H]4C)nc(=O)n(c23)C1]

The title compound was prepared analogously to Example 100, step 21 where (3S)-10-chloro-11-(2,4-difluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid m/z (ESI, +ve)=593.2 (M+H)$^+$.

Step 4: (3S)-10-chloro-11-(2,4-difluorophenyl)-3-methoxy-8-((S)-2-methylpiperazin-1-yl)-3,4-dihydro-2H,6H-[1,4]thiazepino[2,3,4-ij]quinazolin-6-one

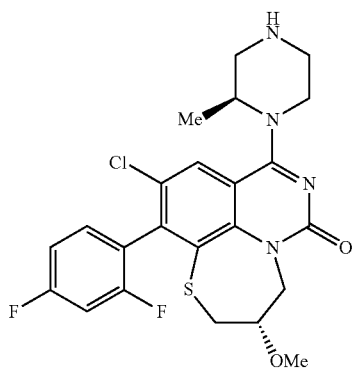 [SMILES: CO[C@@H]1CSc2c(-c3ccc(F)cc3F)c(Cl)cc3c(N4CCNC[C@@H]4C)nc(=O)n(c23)C1]

The title compound was prepared analogously to Example 102, step 4, where tert-butyl (3S)-4-((3S)-10-chloro-11-(2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 67% yield as a yellow solid m/z (ESI, +ve)=493.1 (M+H)$^+$.

Example 488: (3R)-8-((S)-4-acryloyl-2-methylpiper-azin-1-yl)-10-chloro-11-(2,4-difluorophenyl)-3-methoxy-3,4-dihydro-2H,6H-[1,4]thiazepino[2,3,4-ij]quinazolin-6-one

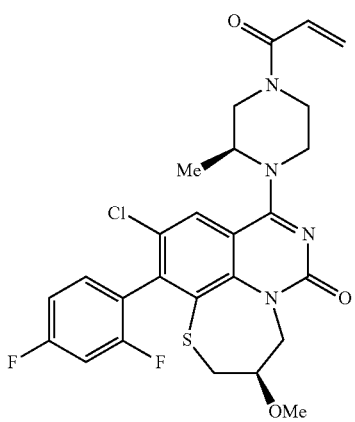 [SMILES: C=CC(=O)N1CCN(c2nc(=O)n3c4c(c(-c5ccc(F)cc5F)c(Cl)cc24)SC[C@H](OC)C3)[C@@H](C)C1]

The title compound was prepared analogously to Example 84 where (3R)-10-chloro-11-(2,4-difluorophenyl)-3-methoxy-8-((S)-2-methylpiperazin-1-yl)-3,4-dihydro-2H, 6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 22% yield as a yellow solid.

m/z (ESI, +ve)=547.1 (M+H)$^+$.

$^1$H NMR (400 MHz, DMSO-d6) δ 7.67 (d, J=16.0 Hz, 1H), 7.51-7.38 (m, 2H), 7.29-7.24 (m, 1H), 6.91-6.75 (m, 1H), 6.18 (dd, J=16.0, 4.0 Hz, 1H), 5.74 (dd, J=12.0, 4.0 Hz, 1H), 4.78-4.56 (m, 2H), 4.45-4.34 (m, 2H), 4.29-4.07 (m, 1H), 4.03-3.79 (m, 3H), 3.71-3.49 (m, 2H), 3.46-3.35 (m, 3H), 3.17-3.07 (m, 1H), 2.99-2.88 (m, 1H), 1.29-1.20 (m, 3H).

Step 1: 6-chloro-7-(2,4-difluorophenyl)-8-(((R)-3-hydroxy-2-methoxypropyl)thio)quinazoline-2,4(1H,3H)-dione

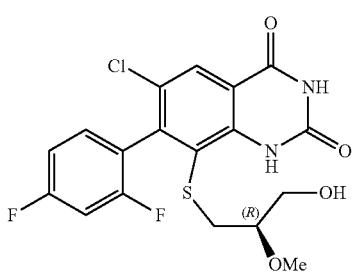

The title compound was prepared analogously to Example 100, step 9 where 6-chloro-7-(2,4-difluorophenyl)-8-iodo-quinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4 (1H,3H)-dione and 2-mercaptoethan-1-ol in 49% yield as a yellow solid m/z (ESI, +ve)=429.0 (M+H)$^+$.

$^1$H NMR (400 MHz, DMSO-d6) δ 11.75 (s, 1H), 10.16 (d, J=12 Hz, 1H), 8.05 (s, 1H), 7.48-7.34 (m, 2H), 7.29-7.23 (m, 1H), 4.79 (s, 1H), 3.25 (d, J=6.4 Hz, 3H), 3.22-3.14 (m, 1H), 2.84-2.77 (m, 1H), 2.73-2.64 (m, 1H), 2.57-2.52 (m, 1H), 2.47-2.34 (m, 1H).

Step 2: (3R)-10-chloro-11-(2,4-difluorophenyl)-3-methoxy-3,4-dihydro-2H,6H-[1,4]thiazepino[2,3,4-ij]quinazoline-6,8(7H)-dione

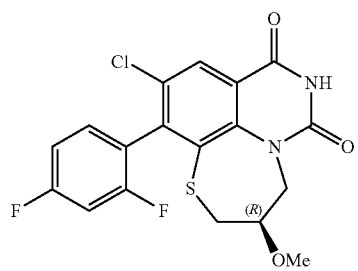

The title compound was prepared analogously to Example 100, step 10 where 6-chloro-7-(2,4-difluorophenyl)-8-(((R)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4 (1H,3H)-dione in 90% yield as a white solid m/z (ESI, +ve)=411.0 (M+H)$^+$.

$^1$H NMR (400 MHz, DMSO-d6) δ 11.81 (d, J=4.8 Hz, 1H), 7.87 (d, J=8.8 Hz, 1H), 7.52-7.32 (m, 2H), 7.28-7.19 (m, 1H), 4.35-2.25 (m, 1H), 3.86-3.79 (m, 1H), 3.58 (d, J=13.8 Hz, 1H), 3.31 (d, J=10.0 Hz, 3H), 3.18-3.06 (m, 2H).

Step 3: tert-butyl (3S)-4-((3R)-10-chloro-11-(2,4-difluorophenyl)-3-methoxy-6-oxo-3,4-dihydro-2H, 6H-[1,4]thiazepino[2,3,4-ij]quinazolin-8-yl)-3-methylpiperazine-1-carboxylate

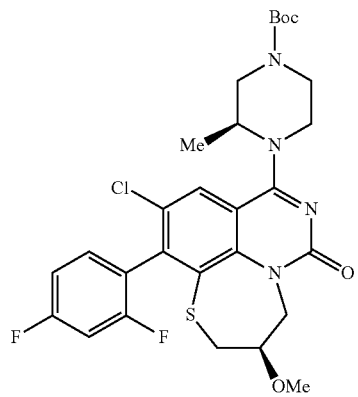 [SMILES: CO[C@H]1CSc2c(-c3ccc(F)cc3F)c(Cl)cc3c(N4CCN(C(=O)OC(C)(C)C)C[C@@H]4C)nc(=O)n(c23)C1]

The title compound was prepared analogously to Example 100, step 21 where (3R)-10-chloro-11-(2,4-difluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 88% yield as a yellow solid m/z (ESI, +ve)=593.2 (M+H)$^+$.

Step 4: (3R)-10-chloro-11-(2,4-difluorophenyl)-3-methoxy-8-((S)-2-methylpiperazin-1-yl)-3,4-dihydro-2H,6H-[1,4]thiazepino[2,3,4-ij]quinazolin-6-one

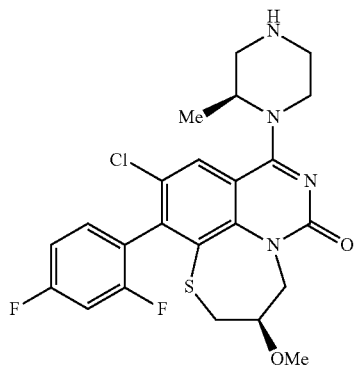 [SMILES: CO[C@H]1CSc2c(-c3ccc(F)cc3F)c(Cl)cc3c(N4CCNC[C@@H]4C)nc(=O)n(c23)C1]

The title compound was prepared analogously to Example 102, step 4, where tert-butyl (3S)-4-((3R)-10-chloro-11-(2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 81% yield as a yellow oil m/z (ESI, +ve)=493.1 (M+H)+.

Example 489: (3S)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

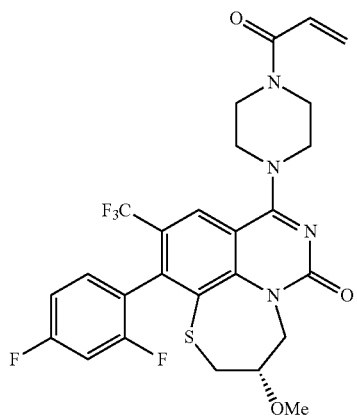 [SMILES: C=CC(=O)N1CCN(c2nc(=O)n3c4c(c(-c5ccc(F)cc5F)c(C(F)(F)F)cc24)SC[C@@H](OC)C3)CC1]

The title compound was prepared analogously to Example 84 where (3S)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 6% yield as a yellow solid.

m/z (ESI, +ve)=567.1 (M+H)+.
¹H NMR (400 MHz, DMSO-d6) δ 7.89 (s, 1H), 7.44-7.42 (m, 2H), 7.28-7.24 (m, 1H), 6.85-6.78 (m, 1H), 6.17 (d, J=16.0 Hz 1H), 5.75-5.72 (m, 1H), 4.50-4.47 (m, 1H), 3.79-3.73 (m, 8H), 3.45-3.43 (m, 1H), 3.35 (s, 3H), 3.20-3.11 (m, 1H), 2.53-2.51 (m, 2H).

Step 1: (3S)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

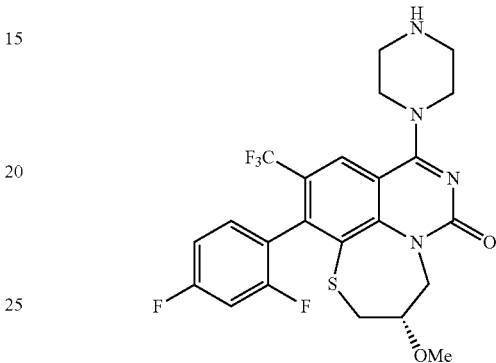

The title compound was prepared analogously to Example 102, step 4, where (3S)-11-(2,4-difluorophenyl)-3-methoxy-10-(trifluoromethyl)-3,4-dihydro-2H,6H-[1,4]thiazepino[2,3,4-ij]quinazoline-6,8(7H)-dione was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow oil m/z (ESI, +ve)=513.1 (M+H)+.

Example 490: (3R)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

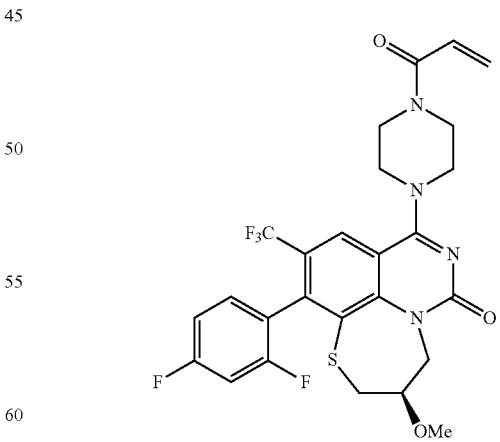

The title compound was prepared analogously to Example 84 where (3R)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3- thia-7,9-diazabicyclo[3.3.1]nonan-7-yl)-2,3-dihydro-5H-[1,4]thiazino[2,3,4-ij]quinazolin-5-one. The title compound was isolated in 26% yield as a yellow solid m/z (ESI, +ve)=567.0 (M+H)⁺.

¹H NMR (400 MHz, DMSO-d6) δ 7.89 (s, 1H), 7.48-7.37 (m, 2H), 7.26 (t, J=12.0 Hz, 1H), 6.82 (dd, J=20.0, 12.0 Hz, 1H), 6.17 (dd, J=16.0, 4.0 Hz, 1H), 5.74 (dd, J=12.0, 4.0 Hz, 1H), 4.50-4.46 (m, 1H), 3.95-3.62 (m, 9H), 3.52-3.40 (m, 3H), 3.20-3.11 (m, 1H), 2.57-2.55 (m, 2H).

Step 1: tert-butyl 4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

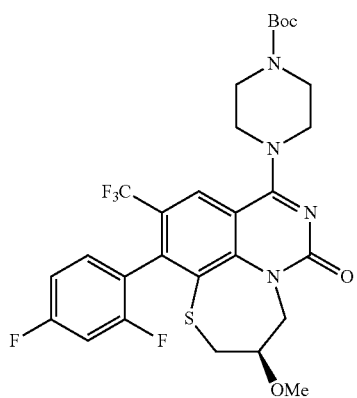 [SMILES: CO[C@H]1CSc2c(-c3ccc(F)cc3F)c(C(F)(F)F)cc3c(N4CCN(C(=O)OC(C)(C)C)CC4)nc(=O)n(c23)C1]

The title compound was prepared analogously to Example 100, step 21 where (3R)-11-(2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 97% yield as a yellow solid m/z (ESI, +ve)=613.1 (M+H)⁺.

Step 2: (3R)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

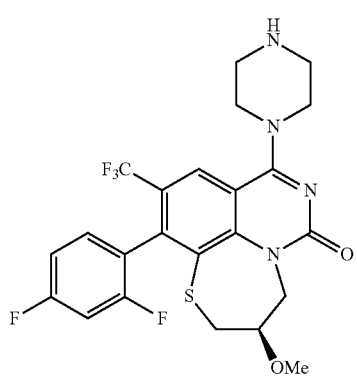 [SMILES: CO[C@H]1CSc2c(-c3ccc(F)cc3F)c(C(F)(F)F)cc3c(N4CCNCC4)nc(=O)n(c23)C1]

The title compound was prepared analogously to Example 102, step 4, where tert-butyl 4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 86% yield as a yellow oil.

m/z (ESI, +ve)=513.1 (M+H)⁺.

Example 503: (3S)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

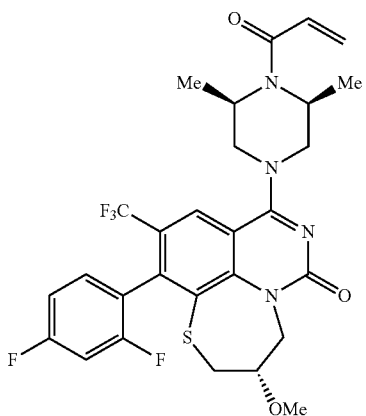 [SMILES: C=CC(=O)N1[C@H](C)CN(c2nc(=O)n3c4c(c(-c5ccc(F)cc5F)c(C(F)(F)F)cc24)SC[C@@H](OC)C3)C[C@@H]1C]

The title compound was prepared analogously to Example 84 where (3S)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 32% yield as a yellow solid.

m/z (ESI, +ve)=595.2 (M+H)⁺.

¹H NMR (400 MHz, DMSO-d6) δ 8.04 (s, 1H), 7.47-7.39 (m, 2H), 7.2 (m, 1H), 6.81 (dd, J=16.0, 8.0 Hz, 1H), 6.19 (d, J=16.0 Hz, 1H), 5.74 (d, J=8.0 Hz, 1H), 4.59 (m, 2H), 4.49-4.47 (m, 1H), 4.06 (d, J=12 Hz, 2H), 3.86 (s, 1H), 3.46 (s, 1H), 3.35 (s, 2H), 3.31-3.06 (m, 4H), 2.52 (s, 1H), 1.51-1.25 (m, 6H).

1111

Step 1: tert-butyl (2S,6R)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate

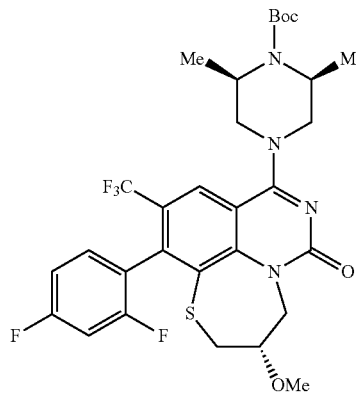

The title compound was prepared analogously to Example 100, step 21 where (3S)-11-(2,4-difluorophenyl)-8-hydroxy-3-methoxy-10-(trifluoromethyl)-3,4-dihydro-2H,6H-[1,4]thiazepino[2,3,4-ij]quinazolin-6-one and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid m/z (ESI, +ve)=541.1 (M+H)$^+$.

Step 2: (3S)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

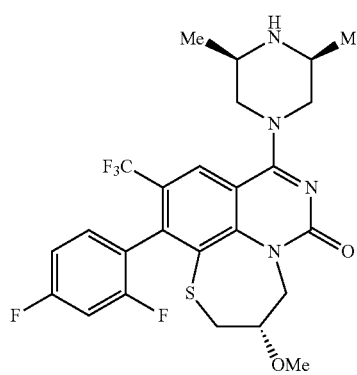

The title compound was prepared analogously to Example 102, step 4, where tert-butyl (2S,6R)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 32% yield as a yellow solid

1112

Example 504: (3S)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one

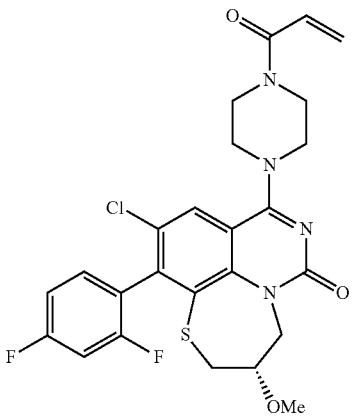 [SMILES: C=CC(=O)N1CCN(c2nc(=O)n3c4c(c(-c5ccc(F)cc5F)c(Cl)cc24)SC[C@@H](OC)C3)CC1]

The title compound was prepared analogously to Example 84 where (3S)-10-chloro-11-(2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 39% yield as a yellow solid m/z (ESI, +ve)=532.1 (M+H)$^+$.

$^1$H NMR (400 MHz, DMSO-d6) δ 7.74 (s, 1H), 7.48-7.44 (m, 2H), 7.29-7.25 (m, 1H), 6.82 (dd, J=16.0, 8.0 Hz, 1H), 6.17 (d, J=16.0 Hz, 1H), 5.74 (d, J=8.0 Hz, 1H), 4.49-4.40 (m, 1H), 3.90-3.64 (m, 8H), 3.44-3.40 (m, 1H), 3.35 (s, 3H), 3.31-3.29 (m, 1H), 3.17-3.08 (m, 1H), 2.52 (m, 1H).

Step 1: tert-butyl 4-((3S)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate

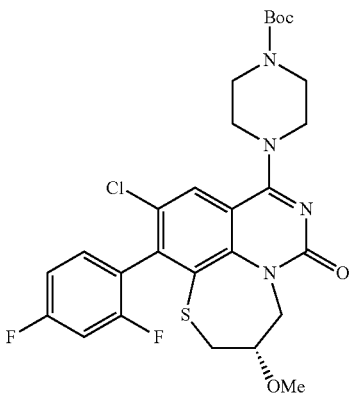 [SMILES: CO[C@@H]1CSc2c(-c3ccc(F)cc3F)c(Cl)cc3c(N4CCN(C(=O)OC(C)(C)C)CC4)nc(=O)n(c23)C1]

The title compound was prepared analogously to Example 100, step 21 where (3S)-10-chloro-11-(2,4-difluorophenyl)-8-hydroxy-3-methoxy-3,4-dihydro-2H,6H-[1,4]thiazepino[2,3,4-ij]quinazolin-6-one and tert-butyl piperazine-1-carboxylate were substituted in place of 10-(2,4- difluorophenyl)-9-(trifluoromethyl)-2,3-dihydro-5H-[1,4]
thiazino[2,3,4-ij]quinazoline-5,7(6H)-dione and
octahydrothieno[3,4-b]pyrazine 6,6-dioxide. The title compound was isolated in 89% yield as a yellow solid
m/z (ESI, +ve)=579.1 (M+H)+.

Step 2: (3S)-10-chloro-11-(2,4-difluorophenyl)-3-methoxy-8-(piperazin-1-yl)-3,4-dihydro-2H,6H-[1,4]thiazepino[2,3,4-ij]quinazolin-6-one

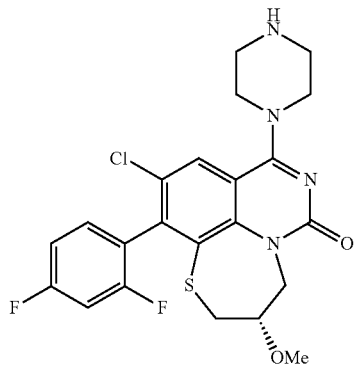 [SMILES: CO[C@@H]1CSc2c(-c3ccc(F)cc3F)c(Cl)cc3c(N4CCNCC4)nc(=O)n(c23)C1]

The title compound was prepared analogously to Example 102, step 4, where tert-butyl 4-((3S)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 89% yield as a yellow solid
m/z (ESI, +ve)=479.1 (M+H)+.

Example 505: (3S)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one

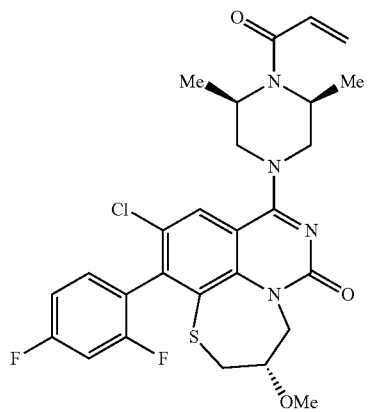 [SMILES: C=CC(=O)N1[C@H](C)CN(c2nc(=O)n3c4c(c(-c5ccc(F)cc5F)c(Cl)cc24)SC[C@@H](OC)C3)C[C@@H]1C]

The title compound was prepared analogously to Example 84 where (3S)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 16% yield as a yellow solid
m/z (ESI, +ve)=561.1(M+H)+.

¹H NMR (400 MHz, DMSO-d6) δ 7.81 (s, 1H), 7.50-7.41 (m, 2H), 7.30-7.25 (m, 1H), 6.84-6.77 (m, 1H), 6.21-6.16 (m, 1H), 5.75-5.72 (m, 1H), 4.56 (s, 2H), 4.46-4.43 (m, 1H), 4.08-4.03 (m, 2H), 3.87-3.86 (m, 1H), 3.46-3.43 (m, 2H), 3.35-3.28 (m, 3H), 3.17-3.10 (m, 1H), 2.52-2.51 (m, 2H), 1.43-1.34 (m, 6H).

Step 1: (3S)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

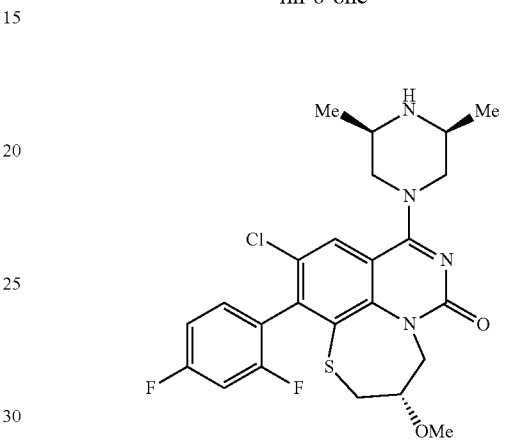

The title compound was prepared analogously to Example 100, step 21 where (3S)-10-chloro-11-(2,4-difluorophenyl)-8-hydroxy-3-methoxy-3,4-dihydro-2H,6H-[1,4]thiazepino[2,3,4-ij]quinazolin-6-one and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 89% yield as a yellow solid
m/z (ESI, +ve)=507.1 (M+H)+.

Example 507: (2S)-7-((S)-4-acryloyl-2-methylpiperazin-1-yl)-10-(2,4-difluorophenyl)-2-(methoxymethyl)-9-(trifluoromethyl)-2,3-dihydro-5H-[1,4]thiazino[2,3,4-ij]quinazolin-5-one

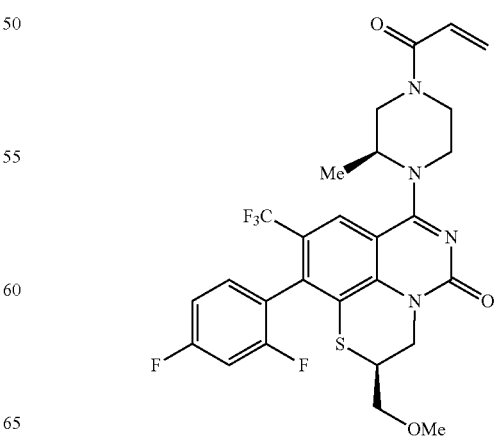

Over a solution of (2S)-10-(2,4-difluorophenyl)-2-(methoxymethyl)-7-((S)-2-methylpiperazin-1-yl)-9-(trifluoromethyl)-2,3-dihydro-5H-[1,4]thiazino[2,3,4-ij]quinazolin-5-one (32 mg) in acetonitrile (1 mL), triethylamine (0.11 mL) and acryloyl chloride (0.014 mL) were added. The mixture was stirred at room temperature for 30 minutes and at that time quenched by the addition of water. The mixture was extracted with ethyl acetate, dried over sodium sulfate and concentrated to afford a residue that was purified by HPLC. The title compound was isolated as a white solid in 32% yield m/z (ESI, +ve)=581.2 (M+H)$^+$.

Step 1: tert-butyl (3S)-4-((2S)-10-(2,4-difluorophenyl)-2-(((methylsulfonyl)oxy)methyl)-5-oxo-9-(trifluoromethyl)-2,3-dihydro-5H-[1,4]thiazino[2,3,4-ij]quinazolin-7-yl)-3-methylpiperazine-1-carboxylate

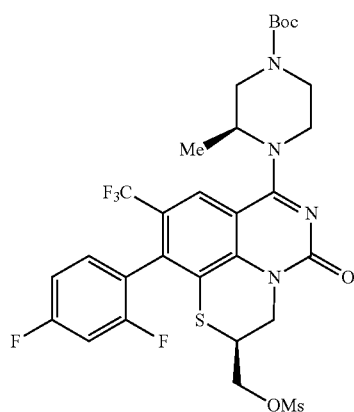

Over a solution of tert-butyl (3S)-4-((3S)-11-(2,4-difluorophenyl)-3-hydroxy-6-oxo-10-(trifluoromethyl)-3,4-dihydro-2H,6H-[1,4]thiazepino[2,3,4-ij]quinazolin-8-yl)-3-methylpiperazine-1-carboxylate (391 mg) in 3 mL of dichloroethane at room temperature, N,N-diisopropylethylamine (1.0 mL) and methanesulfonyl chloride (0.34 mL) were added and the mixture heated at 80° C. for three hours. The reaction was cooled down to room temperature and diluted with dichloromethane and water. The organic layer was separated and the aqueous layer extracted with dichloromethane twice. Evaporation of volatiles under reduced pressure afforded a crude residue that was purified by silica gel chromatography (0-3% methanol in ethyl acetate). The title compound was isolated in 43% yield.

m/z (ESI, +ve)=691.2 (M+H)$^+$.

Step 2: tert-Butyl (3S)-4-((2S)-10-(2,4-difluorophenyl)-2-(methoxymethyl)-5-oxo-9-(trifluoromethyl)-2,3-dihydro-5H-[1,4]thiazino[2,3,4-ij]quinazolin-7-yl)-3-methylpiperazine-1-carboxylate

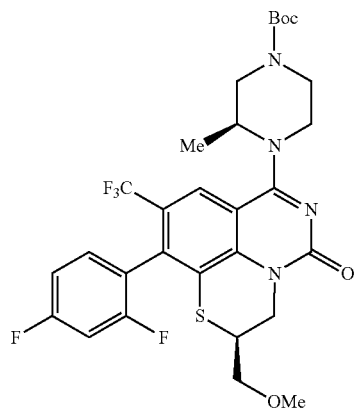 [SMILES: C[C@H]1CN(C(=O)OC(C)(C)C)CCN1c1nc(=O)n2c3c(c(-c4ccc(F)cc4F)c(C(F)(F)F)cc13)S[C@H](COS(C)(=O)=O)C2]

tert-butyl (3S)-4-((2S)-10-(2,4-difluorophenyl)-2-(((methylsulfonyl)oxy)methyl)-5-oxo-9-(trifluoromethyl)-2,3-dihydro-5H-[1,4]thiazino[2,3,4-ij]quinazolin-7-yl)-3-methylpiperazine-1-carboxylate (95 mg) was dissolved in methanol (2 mL) and heated at 70° C. for three hours. The methanol was removed under reduced pressure and the crude material purified by chromatography in silica gel to afford the title compound in 43% yield as an orange solid.

m/z (ESI, +ve)=627.2 (M+H)$^+$.

Step 3: (2S)-10-(2,4-difluorophenyl)-2-(methoxymethyl)-7-((S)-2-methylpiperazin-1-yl)-9-(trifluoromethyl)-2,3-dihydro-5H-[1,4]thiazino[2,3,4-ij]quinazolin-5-one

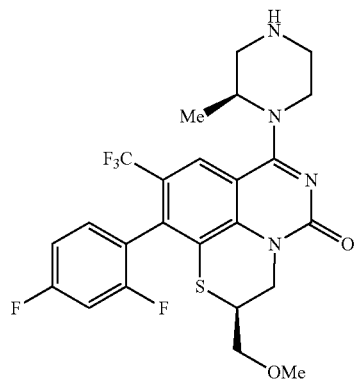 [SMILES: COC[C@@H]1Cn2c(=O)nc(N3CCNC[C@@H]3C)c3cc(C(F)(F)F)c(-c4ccc(F)cc4F)c(c32)S1]

Over a solution of tert-butyl (3S)-4-((2S)-10-(2,4-difluorophenyl)-2-(methoxymethyl)-5-oxo-9-(trifluoromethyl)-2,3-dihydro-5H-[1,4]thiazino[2,3,4-ij]quinazolin-7-yl)-3-methylpiperazine-1-carboxylate (37 mg) in dichloromethane (1 mL), TFA (0.2 mL) was added. The mixture was stirred at room temperature for 4 hours and at that time all volatiles were removed under reduced pressure to afford a solid that was used in the next step without further purification.

m/z (ESI, +ve)=627.2 (M+H)$^+$.

Example 524: (3R)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

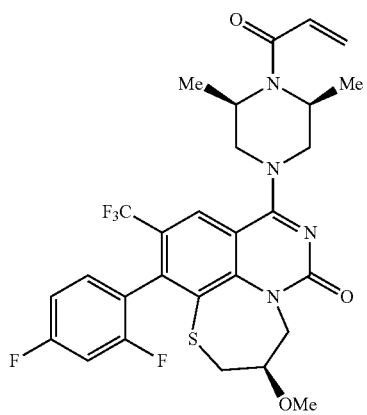 [SMILES: C=CC(=O)N1[C@H](C)CN(c2nc(=O)n3c4c(c(-c5ccc(F)cc5F)c(C(F)(F)F)cc24)SC[C@H](OC)C3)C[C@@H]1C]

The title compound was prepared analogously to Example 84 where (3R)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 25% yield as a white solid m/z (ESI, +ve)=595.0 (M+H)⁺.

¹H NMR (400 MHz, DMSO-d6) δ 8.04 (s, 1H), 7.52-7.39 (m, 2H), 7.30-7.23 (m, 1H), 6.81 (dd, J=16.0, 8.0 Hz, 1H), 6.19 (dd, J=16.0, 2.0 Hz, 1H), 5.74 (dd, J=16.0, 2.0 Hz, 1H), 4.78-4.40 (m, 4H), 4.17-4.09 (m, 2H), 3.86-3.81 (m, 1H), 3.57-3.35 (m, 4H), 3.29-3.09 (m, 3H), 1.52-1.26 (m, 6H).

Step 1: (3R)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

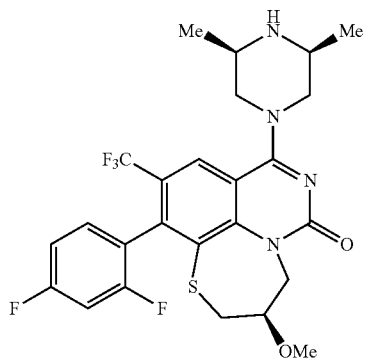 [SMILES: CO[C@H]1CSc2c(-c3ccc(F)cc3F)c(C(F)(F)F)cc3c(N4C[C@@H](C)N[C@@H](C)C4)nc(=O)n(c23)C1]

The title compound was prepared analogously to Example 100, step 21 where (3R)-11-(2,4-difluorophenyl)-8-hydroxy-3-methoxy-10-(trifluoromethyl)-3,4-dihydro-2H,6H-[1,4]thiazepino[2,3,4-ij]quinazolin-6-one and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid m/z (ESI, +ve)=541.1 (M+H)⁺.

Example 525: (3R)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one

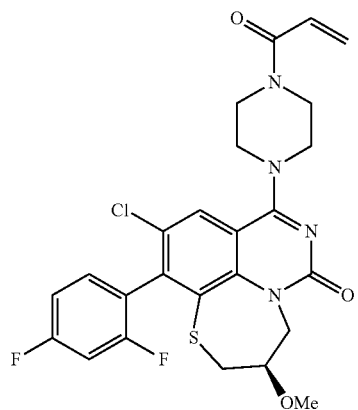 [SMILES: C=CC(=O)N1CCN(c2nc(=O)n3c4c(c(-c5ccc(F)cc5F)c(Cl)cc24)SC[C@H](OC)C3)CC1]

The title compound was prepared analogously to Example 84 where (3R)-10-chloro-11-(2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 19% yield as a yellow solid m/z (ESI, +ve)=533.0 (M+H)⁺.

¹H NMR (400 MHz, DMSO-d6) δ 7.74 (s, 1H), 7.50-7.43 (m, 2H), 7.30-7.25 (m, 1H), 6.82 (dd, J=16.0, 8.0 Hz, 1H), 6.19 (dd, J=16.0, 2.0 Hz, 1H), 5.74 (dd, J=16.0, 2.0 Hz, 1H), 4.49-4.41 (m, 1H), 3.90-3.63 (m, 9H), 3.46-3.35 (m, 2H), 3.32-3.26 (m, 3H), 3.17-3.08 (m, 1H).

Step 1: tert-butyl 4-((3R)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate

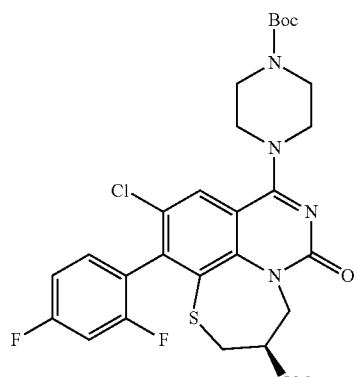

The title compound was prepared analogously to Example 100, step 21 where (3R)-10-chloro-11-(2,4-difluorophenyl)-8-hydroxy-3-methoxy-3,4-dihydro-2H,6H-[1,4]thiazepino[2,3,4-ij]quinazolin-6-one and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 72% yield as a yellow solid
m/z (ESI, +ve)=579.0 (M+H)⁺.

Step 2: (3R)-10-chloro-11-(2,4-difluorophenyl)-3-methoxy-8-(piperazin-1-yl)-3,4-dihydro-2H,6H-[1,4]thiazepino[2,3,4-ij]quinazolin-6-one

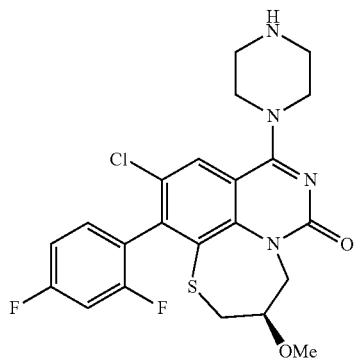 [SMILES: CO[C@H]1CSc2c(-c3ccc(F)cc3F)c(Cl)cc3c(N4CCNCC4)nc(=O)n(c23)C1]

The title compound was prepared analogously to Example 102, step 4, where tert-butyl 4-((3R)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 89% yield as a yellow solid
m/z (ESI, +ve)=479.1 (M+H)⁺.

Example 526: (3R)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one

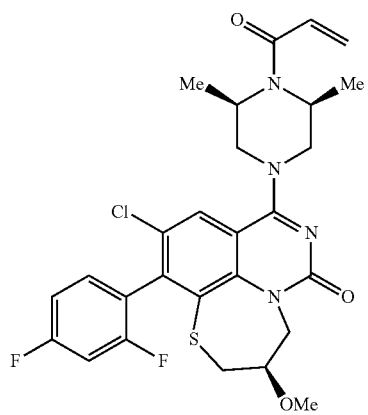 [SMILES: C=CC(=O)N1[C@H](C)CN(c2nc(=O)n3c4c(c(-c5ccc(F)cc5F)c(Cl)cc24)SC[C@H](OC)C3)C[C@@H]1C]

The title compound was prepared analogously to Example 84 where (3R)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 24% yield as a yellow solid
m/z (ESI, +ve)=561.1 (M+H)⁺.
¹H NMR (400 MHz, DMSO-d6) δ 7.81 (s, 1H), 7.50-7.45 (m, 2H), 7.30-7.25 (m, 1H), 6.80 (dd, J=16.0, 8.0 Hz, 1H), 6.19 (dd, J=16.0, 2.0 Hz, 1H), 5.74 (dd, J=16.0, 2.0 Hz, 1H), 4.68-4.39 (m, 4H), 4.14-3.97 (m, 2H), 3.88-3.86 (m, 1H), 3.50-3.35 (m, 3H), 3.30-3.06 (m, 4H), 1.47-1.17 (m, 6H).

Step 1: (3R)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

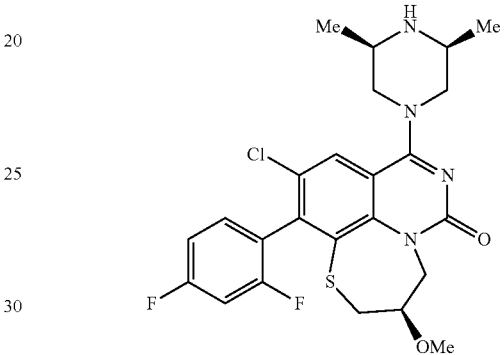

The title compound was prepared analogously to Example 100, step 21 where (3R)-10-chloro-11-(2,4-difluorophenyl)-8-hydroxy-3-methoxy-3,4-dihydro-2H,6H-[1,4]thiazepino[2,3,4-ij]quinazolin-6-one and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 610% yield as a yellow solid
m/z (ESI, +ve)=507.1 (M+H)⁺.

Example 527: (R)-8-((S)-4-acryloyl-2-methylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

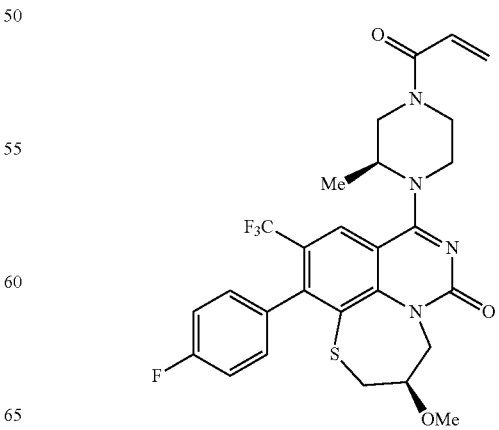

The title compound was prepared analogously to Example 84 where (R)-11-(4-fluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 9% yield as a yellow solid m/z (ESI, +ve)=563.2 (M+H)$^+$.

$^1$H NMR (400 MHz, DMSO) δ 7.78 (s, 1H), 7.35-7.34 (m, 4H), 6.90-6.78 (m, 1H), 6.18 (6.21-6.15, 1H), 5.76-5.73 (m, 1H), 4.64-4.60 (m, 1H), 4.53-4.49 (m, 1H), 4.42-4.38 (m, 1H), 4.30-4.25 (m, 1H), 4.12-3.99 (m, 2H), 3.81-3.80 (m, 1H), 3.56-3.54 (m, 2H), 3.33 (s, 3H), 3.13-2.97 (m, 3H), 1.30 (s, 3H).

Step 1: Methyl 3-amino-4'-fluoro-[1,1'-biphenyl]-4-carboxylate

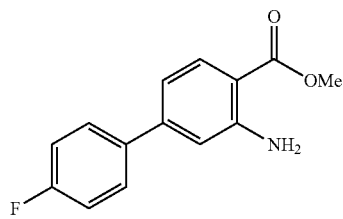 [SMILES: COC(=O)c1ccc(-c2ccc(F)cc2)cc1N]

The title compound was synthesized analogously to example 100, step 1 where 4-fluorophenylboronic acid was substituted in place of (2,4-difluorophenyl)boronic acid. The title compound was isolated in 99% yield as a brown solid m/z (ESI, +ve)=246.1 (M+H)$^+$.

Step 2: Methyl 5-amino-4'-fluoro-2-iodo-[1,1'-biphenyl]-4-carboxylate

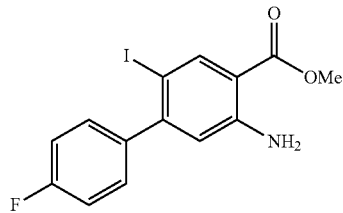 [SMILES: COC(=O)c1cc(I)c(-c2ccc(F)cc2)cc1N]

The title compound was synthesized analogously to example 100, step 2 where Methyl 3-amino-4'-fluoro-[1,1'-biphenyl]-4-carboxylate was substituted in place of methyl 3-amino-2',4'-difluoro-[1,1'-biphenyl]-4-carboxylate. The title compound was isolated in 90% yield as a brown solid m/z (ESI, +ve)=372.0 (M+H)$^+$.

Step 3: Methyl 5-acetamido-4'-fluoro-2-iodo-[1,1'-biphenyl]-4-carboxylate

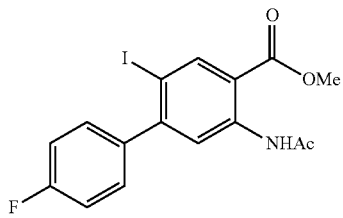 [SMILES: COC(=O)c1cc(I)c(-c2ccc(F)cc2)cc1NC(C)=O]

The title compound was synthesized analogously to example 100, step 3 where methyl 5-amino-4'-fluoro-2-iodo-[1,1'-biphenyl]-4-carboxylate was substituted in place of 2-amino-4-(2,4-difluorophenyl)-5-iodobenzoate. The title compound was isolated in 98% yield as a brown solid m/z (ESI, +ve)=414.0 (M+H)$^+$.

Step 4: Methyl 5-acetamido-4'-fluoro-2-(trifluoromethyl)-[1,1'-biphenyl]-4-carboxylate

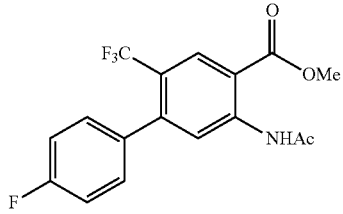 [SMILES: COC(=O)c1cc(C(F)(F)F)c(-c2ccc(F)cc2)cc1NC(C)=O]

The title compound was synthesized analogously to example 100, step 4 where methyl 5-acetamido-4'-fluoro-2-iodo-[1,1'-biphenyl]-4-carboxylate was substituted in place of methyl 4-(2,4-difluorophenyl)-2-acetamido-5-iodobenzoate. The title compound was isolated in 62% yield as a brown solid m/z (ESI, +ve)=356.1 (M+H)$^+$.

Step 5: Methyl 5-amino-4'-fluoro-2-(trifluoromethyl)-[1,1'-biphenyl]-4-carboxylate

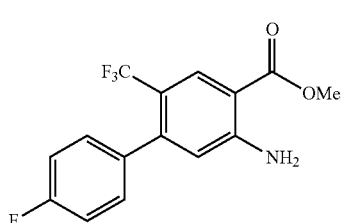

The title compound was synthesized analogously to example 100, step 5 where methyl 5-acetamido-4'-fluoro-2-(trifluoromethyl)-[1,1'-biphenyl]-4-carboxylate was substituted in place of methyl 5-acetamido-2',4'-difluoro-2-(trifluoromethyl)-[1,1'-biphenyl]-4-carboxylate. The title compound was isolated in 87% yield as a white solid m/z (ESI, +ve)=314.1 (M+H)$^+$.

Step 6: Methyl 3-amino-4'-fluoro-2-iodo-6-(trifluoromethyl)-[1,1'-biphenyl]-4-carboxylate

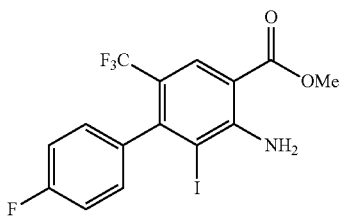 [SMILES: COC(=O)c1cc(C(F)(F)F)c(-c2ccc(F)cc2)c(I)c1N]

The title compound was synthesized analogously to example 100, step 6 where methyl 5-amino-4'-fluoro-2-(trifluoromethyl)-[1,1'-biphenyl]-4-carboxylate was substituted in place of methyl 5-amino-2',4'-difluoro-2-(trifluoromethyl)-[1,1'-biphenyl]-4-carboxylate. The title compound was isolated in 74% yield as a white solid
m/z (ESI, +ve)=440.0 (M+H)$^+$.

Step 7: 3-Amino-4'-fluoro-2-iodo-6-(trifluoromethyl)-[1,1'-biphenyl]-4-carboxylic acid

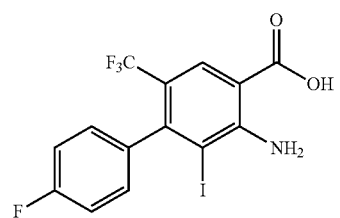 [SMILES: Nc1c(C(=O)O)cc(C(F)(F)F)c(-c2ccc(F)cc2)c1I]

The title compound was synthesized analogously to example 100, step 7 where methyl 3-amino-4'-fluoro-2-iodo-6-(trifluoromethyl)-[1,1'-biphenyl]-4-carboxylate was substituted in place of methyl 3-amino-2',4'-difluoro-2-iodo-6-(trifluoromethyl)-[1,1'-biphenyl]-4-carboxylate. The title compound was isolated in 94% yield as a white solid
$^1$H NMR (400 MHz, DMSO-d6) δ8.18 (s, 1H), 7.29 (t, 2H), 7.16 (m, 2H).

Step 8: 7-(4-fluorophenyl)-8-iodo-6-(trifluoromethyl)quinazoline-2,4(1H,3H)-dione

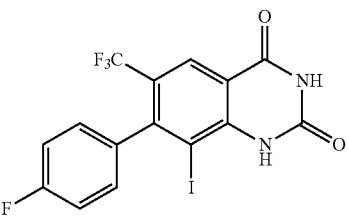 [SMILES: O=c1[nH]c(=O)c2cc(C(F)(F)F)c(-c3ccc(F)cc3)c(I)c2[nH]1]

The title compound was synthesized analogously to example 100, step 8 where 3-Amino-4'-fluoro-2-iodo-6-(trifluoromethyl)-[1,1'-biphenyl]-4-carboxylic acid was substituted in place of 3-amino-2',4'-difluoro-2-iodo-6-(trifluoromethyl)-[1,1'-biphenyl]-4-carboxylic acid. The title compound was isolated in 70% yield as a white solid.
m/z (ESI, +ve)=451.0 (M+H)$^+$.

$^1$H NMR (400 MHz, DMSO-d6) δ 11.89 (s, 1H), 9.75 (s, 1H), 8.23 (s, 1H), 7.41-7.31 (m, 2H), 7.21-7.11 (m, 2H).

Step 9: (R)-7-(4-fluorophenyl)-8-((3-hydroxy-2-methoxypropyl)thio)-6-(trifluoromethyl)quinazoline-2,4(1H,3H)-dione

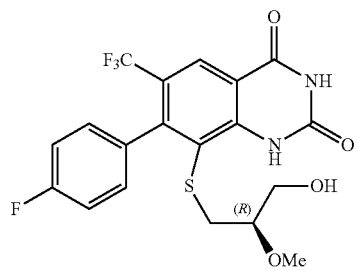

The title compound was synthesized analogously to example 100, step 9 where 7-(4-fluorophenyl)-8-iodo-6-(trifluoromethyl)quinazoline-2,4(1H,3H)-dione and (R)-3-mercapto-2-methoxypropan-1-ol was substituted in place of 7-(2,4-difluorophenyl)-8-iodo-6-(trifluoromethyl)quinazoline-2,4(1H,3H)-dione and 2-mercaptoethan-1-ol. The title compound was isolated in 58% yield as a white solid.

m/z (ESI, +ve)=445.1 (M+H)$^+$.

Step 10: (R)-11-(4-fluorophenyl)-3-methoxy-10-(trifluoromethyl)-3,4-dihydro-2H,6H-[1,4]thiazepino[2,3,4-ij]quinazoline-6,8(7H)-dione

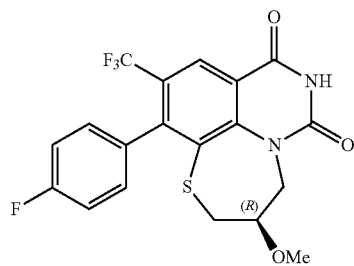

The title compound was prepared analogously to Example 100, step 10 where (R)-7-(4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 53% yield as a yellow solid m/z (ESI, +ve)=427.0 (M+H)$^+$.

Step 11: tert-butyl (S)-4-((R)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

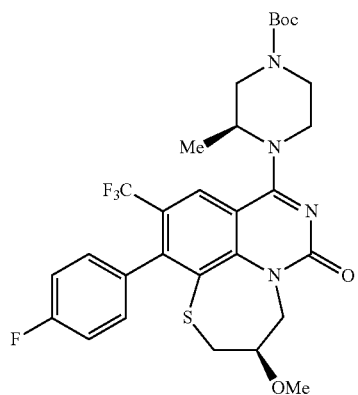 [SMILES: CO[C@H]1CSc2c(-c3ccc(F)cc3)c(C(F)(F)F)cc3c(N4CCN(C(=O)OC(C)(C)C)C[C@@H]4C)nc(=O)n(c23)C1]

The title compound was prepared analogously to Example 100, step 21 where (R)-11-(4-fluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 76% yield as a yellow solid m/z (ESI, +ve)=609.2 (M+H)+.

Step 12: (R)-11-(4-fluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

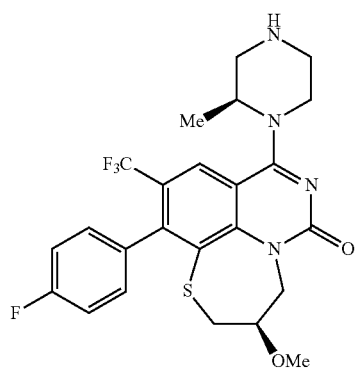 [SMILES: CO[C@H]1CSc2c(-c3ccc(F)cc3)c(C(F)(F)F)cc3c(N4CCNC[C@@H]4C)nc(=O)n(c23)C1]

The title compound was prepared analogously to Example 102, step 4, where tert-butyl (S)-4-((R)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 84% yield as a yellow solid m/z (ESI, +ve)=509.1 (M+H)+.

Example 528: (R)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one

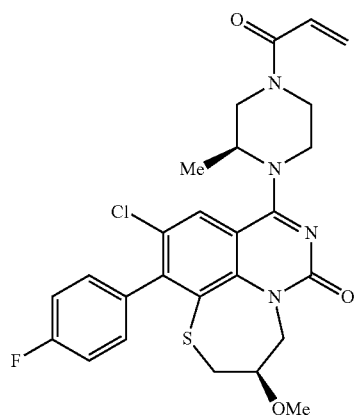 [SMILES: C=CC(=O)N1CCN(c2nc(=O)n3c4c(c(-c5ccc(F)cc5)c(Cl)cc24)SC[C@H](OC)C3)[C@@H](C)C1]

The title compound was prepared analogously to Example 84 where (R)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 9% yield as a yellow solid m/z (ESI, +ve)=529.2 (M+H)+.

1H NMR (400 MHz, DMSO-d6) δ 7.64 (s, 1H), 7.42-7.28 (m, 4H), 6.91-6.76 (m, 1H), 6.18 (dd, J=16.0 Hz, 8.0 Hz, 1H), 5.74 (d, J=8.0 Hz, 1H), 4.73-4.58 (m, 1H), 4.49-4.34 (m, 2H), 4.29-4.20 (m, 0.5H), 4.16-4.07 (m, 0.5H), 4.06-3.89 (m, 2H), 3.88-3.80 (m, 1H), 3.68-3.47 (m, 2H), 3.33 (s, 4H), 3.19-3.13 (m, 0.5H), 3.13-3.03 (m, 1H), 3.00-2.89 (m, 0.5H), 1.27-1.23 (m, 3H).

Step 1: Methyl 5-amino-2-chloro-4'-fluoro-[1,1'-biphenyl]-4-carboxylate

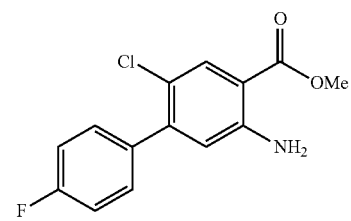 [SMILES: COC(=O)c1cc(Cl)c(-c2ccc(F)cc2)cc1N]

The title compound was prepared analogously to Example 84, step 15 where 4-fluorophenylboronic acid was substituted in place of (2,4-difluorophenyl)boronic acid. The title compound was isolated in 57% yield as a yellow solid m/z (ESI, +ve)=280.1 (M+H)+.

Step 2: Methyl 3-amino-6-chloro-4'-fluoro-2-iodo-[1,1'-biphenyl]-4-carboxylate

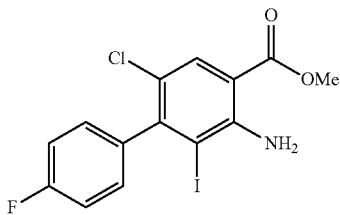 [SMILES: COC(=O)c1cc(Cl)c(-c2ccc(F)cc2)c(I)c1N]

The title compound was prepared analogously to Example 84, step 16 where Methyl 5-amino-2-chloro-4'-fluoro-[1,1'-biphenyl]-4-carboxylate was substituted in place of methyl 5-amino-2-chloro-2',4'-difluoro-[1,1'-biphenyl]-4-carboxylate. The title compound was isolated in 85% yield as a white solid m/z (ESI, +ve)=405.9 (M+H)⁺.

Step 3: 3-Amino-6-chloro-4'-fluoro-2-iodo-[1,1'-biphenyl]-4-carboxylic acid

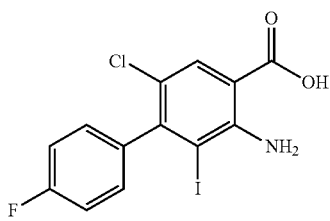 [SMILES: Nc1c(C(=O)O)cc(Cl)c(-c2ccc(F)cc2)c1I]

The title compound was prepared analogously to Example 84, step 17 where methyl 3-amino-6-chloro-4'-fluoro-2-iodo-[1,1'-biphenyl]-4-carboxylate was substituted in place of methyl 3-amino-6-chloro-2',4'-difluoro-2-iodo-[1,1'-biphenyl]-4-carboxylate. The title compound was isolated in 95% yield as a yellow solid m/z (ESI, +ve)=391.9 (M+H)⁺.

Step 4: 6-Chloro-7-(4-fluorophenyl)-8-iodoquinazoline-2,4(1H,3H)-dione

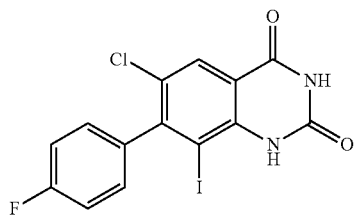 [SMILES: O=c1[nH]c(=O)c2cc(Cl)c(-c3ccc(F)cc3)c(I)c2[nH]1]

The title compound was prepared analogously to Example 84, step 18 where 3-amino-6-chloro-4'-fluoro-2-iodo-[1,1'-biphenyl]-4-carboxylic acid was substituted in place of 3-amino-6-chloro-2',4'-difluoro-2-iodo-[1,1'-biphenyl]-4-carboxylic acid. The title compound was isolated in 60% yield as a yellow solid m/z (ESI, +ve)=416.9 (M+H)⁺.

¹H NMR (400 MHz, DMSO-d6) δ=11.76 (s, 1H), 9.47 (s, 1H), 8.00 (s, 1H), 7.45-7.31 (m, 2H), 7.29-7.16 (m, 2H).

Step 5: (R)-6-chloro-7-(4-fluorophenyl)-8-((3-hydroxy-2-methoxypropyl)thio)quinazoline-2,4(1H,3H)-dione

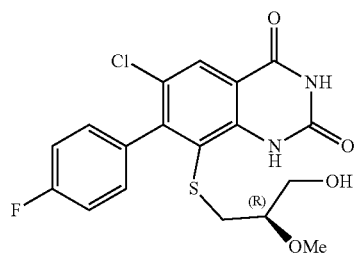

The title compound was prepared analogously to Example 100, step 9 where 6-Chloro-7-(4-fluorophenyl)-8-iodoquinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 60% yield as a white solid m/z (ESI, +ve)=411(M+H)⁺.

Step 6: (R)-10-chloro-11-(4-fluorophenyl)-3-methoxy-3,4-dihydro-2H,6H-[1,4]thiazepino[2,3,4-ij]quinazoline-6,8(7H)-dione

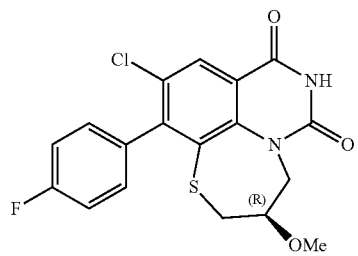

The title compound was prepared analogously to Example 100, step 10 where (R)-6-chloro-7-(4-fluorophenyl)-8-((3-hydroxy-2-methoxypropyl)thio)quinazoline-2,4(1H,3H)-dione
was substituted in place of 7-(2,4-difluorophenyl)-8-((2-hydroxyethyl)thio)-6-(trifluoromethyl)quinazoline-2,4(1H,3H)-dione in 90% yield as a yellow solid m/z (ESI, +ve)=393.0 (M+H)⁺.

Step 7: tert-butyl (S)-4-((R)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate

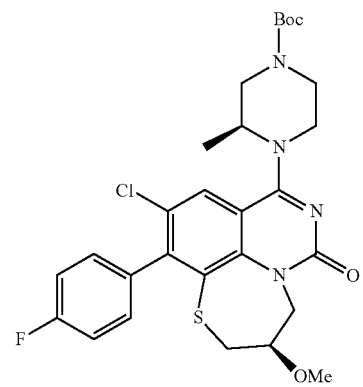 [SMILES: CO[C@H]1CSc2c(-c3ccc(F)cc3)c(Cl)cc3c(N4CCN(C(=O)OC(C)(C)C)C[C@@H]4C)nc(=O)n(c23)C1]

The title compound was prepared analogously to Example 100, step 21 where (R)-10-chloro-11-(4-fluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid m/z (ESI, +ve)=575.2 (M+H)$^+$.

Step 8: (R)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one

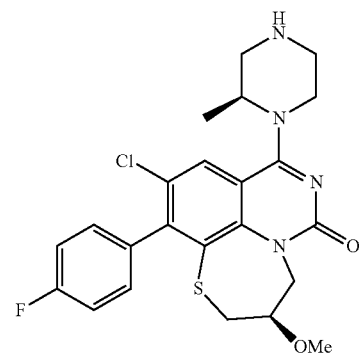 [SMILES: CO[C@H]1CSc2c(-c3ccc(F)cc3)c(Cl)cc3c(N4CCNC[C@@H]4C)nc(=O)n(c23)C1]

The title compound was prepared analogously to Example 102, step 4, where tert-butyl (S)-4-((R)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 67% yield as a yellow solid m/z (ESI, +ve)=475.1 (M+H)$^+$.

Example 529: (3S)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

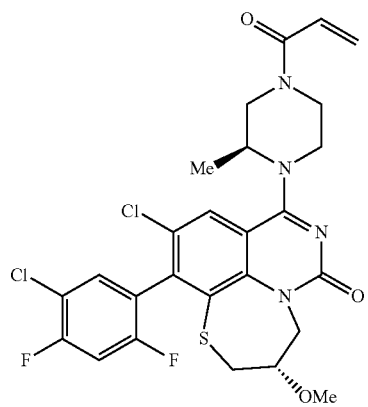 [SMILES: C=CC(=O)N1CCN(c2nc(=O)n3c4c(c(-c5cc(Cl)c(F)cc5F)c(Cl)cc24)SC[C@@H](OC)C3)[C@@H](C)C1]

The title compound was prepared analogously to Example 84 where (3S)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 14% yield as a yellow solid m/z (ESI, +ve)=580.0 (M+H)$^+$.

$^1$H NMR (400 MHz, DMSO-d6) δ7.84-7.77 (m, 2H), 7.68-7.64 (m, 1H), 6.93-6.74 (m, 1H), 6.20-6.16 (m, 1H), 5.76-5.72 (m, 1H), 4.62-4.40 (m, 3H), 4.30-4.02 (m, 2H), 4.02-3.82 (m, 2H), 3.65-3.40 (m, 2H), 3.38-3.33 (m, 4H), 3.24-2.91 (m, 2H), 1.31-1.24 (m, 3H).

Step 1: Methyl 2-amino-5-chloro-4-(4,4,5,5-tetramethyl-1,3,2-dioxaborolan-2-yl)benzoate To a mixture of methyl 2-amino-4-bromo-5-chlorobenzoate (40 g, 0.1512 mol) in dioxane (200 mL), bis(pinacolato)diboron (57.6 g, 0.2268 mol), Pd(dppf)Cl$_2$ (5.52 g, 0.0076 mol) and potassium acetate (44.12 g, 0.4536 mol) were added. The mixture was stirred at 100° C. for 16 hours and the solids removed by filtration. Evaporation of volatiles under reduced pressure afforded a residue that was purified by silica gel chromatography. The title compound was isolated in 74% yield as a yellow solid.

m/z (ESI, +ve)=312.1 (M+H)$^+$.

Step 2: Methyl 5-amino-2,5'-dichloro-2',4'-difluoro-[1,1'-biphenyl]-4-carboxylate

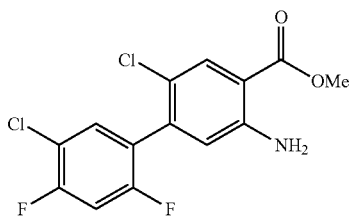 [SMILES: COC(=O)c1cc(Cl)c(-c2cc(Cl)c(F)cc2F)cc1N]

To a mixture of methyl 2-amino-5-chloro-4-(4,4,5,5-tetramethyl-1,3,2-dioxaborolan-2-yl)benzoate (25.5 g, 0.0818 mol) in 300 mL of dioxane/water (5:1 ratio) was added 1-bromo-5-chloro-2,4-difluorobenzene (15.5 g, 0.0682 mol), cesium carbonate (66.66 g, 0.2046 mol) and Pd(dppf)Cl$_2$ (2.5 g, 0.0034 mol). The resulting mixture was stirred at 100° C. for 1.5 hours and after that time the solids were removed by filtration. The reaction mixture was diluted with water and extracted with ethyl acetate three times. The combined organic layers were washed with brine, dried over sodium sulfate and concentrated under reduced pressure to afford a residue that was purified by silica gel chromatography. A second purification by chromatography on C18 column using acetonitrile in water (0-100%) as mobile phase afforded the title compound in 90% yield as a yellow oil.

m/z (ESI, +ve)=332.0 (M+H)$^+$.

Step 3: Methyl 3-amino-5',6-dichloro-2',4'-difluoro-2-iodo-[1,1'-biphenyl]-4-carboxylate

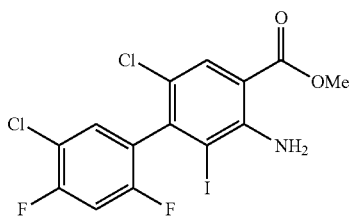 [SMILES: COC(=O)c1cc(Cl)c(-c2cc(Cl)c(F)cc2F)c(I)c1N]

The title compound was prepared analogously to Example 84, step 16 where methyl 5-amino-2,5'-dichloro-2',4'-difluoro-[1,1'-biphenyl]-4-carboxylate was substituted in place of methyl 5-amino-2-chloro-2',4'-difluoro-[1,1'-biphenyl]-4-carboxylate. The title compound was isolated in 80% yield as a white solid.

m/z (ESI, +ve)=457.9 (M+H)$^+$.

Step 4: 3-Amino-5',6-dichloro-2',4'-difluoro-2-iodo-[1,1'-biphenyl]-4-carboxylic acid

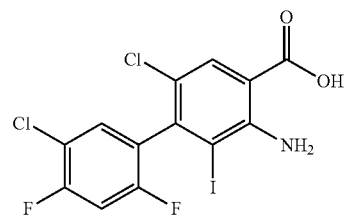 [SMILES: Nc1c(C(=O)O)cc(Cl)c(-c2cc(Cl)c(F)cc2F)c1I]

The title compound was prepared analogously to Example 84, step 17 where Methyl 3-amino-5',6-dichloro-2',4'-difluoro-2-iodo-[1,1'-biphenyl]-4-carboxylate was substituted in place of methyl 3-amino-6-chloro-2',4'-difluoro-2-iodo-[1,1'-biphenyl]-4-carboxylate. The title compound was isolated in 95% yield as a yellow solid m/z (ESI, +ve)=443.9 (M+H)$^+$.

Step 5: 6-chloro-7-(5-chloro-2,4-difluorophenyl)-8-iodoquinazoline-2,4(1H,3H)-dione

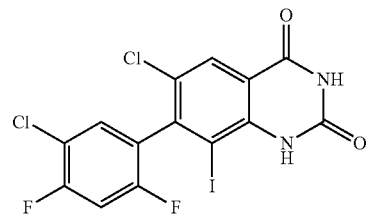 [SMILES: O=c1[nH]c(=O)c2cc(Cl)c(-c3cc(Cl)c(F)cc3F)c(I)c2[nH]1]

The title compound was prepared analogously to Example 84, step 18 where 3-Amino-5',6-dichloro-2',4'-difluoro-2-iodo-[1,1'-biphenyl]-4-carboxylic acid was substituted in place of 3-amino-6-chloro-2',4'-difluoro-2-iodo-[1,1'-biphenyl]-4-carboxylic acid. The title compound was isolated in 86% yield as a yellow solid m/z (ESI, +ve)=468.9 (M+H)$^+$.

$^1$H NMR (400 MHz, DMSO-d6) δ=11.79 (s, 1H), 11.17 (s, 1H), 8.05 (s, 1H), 7.8 (t, J=8.0 Hz, 1H), 7.72 (t, J=8.0 Hz, 1H).

Step 6: 6-chloro-7-(5-chloro-2,4-difluorophenyl)-8-(((S)-3-hydroxy-2-methoxypropyl)thio)quinazoline-2,4(1H,3H)-dione

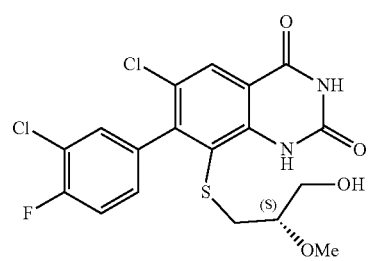

The title compound was prepared analogously to Example 100, step 9 where 6-chloro-7-(5-chloro-2,4-difluorophenyl)-8-iodoquinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol in 61% yield as a yellow solid m/z (ESI, +ve)=463.0 (M+H)$^+$.

Step 7: (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione

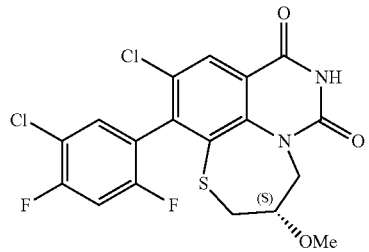

The title compound was prepared analogously to Example 100, step 10 where 6-chloro-7-(5-chloro-2,4-difluorophenyl)-8-(((S)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 60% yield as a yellow solid m/z (ESI, +ve)=445.0 (M+H)$^+$.

Step 8: tert-butyl (3S)-4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate

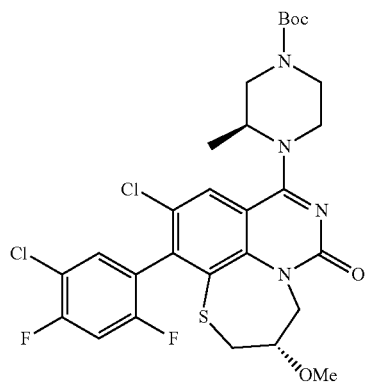 [SMILES: CO[C@@H]1CSc2c(-c3cc(Cl)c(F)cc3F)c(Cl)cc3c(N4CCN(C(=O)OC(C)(C)C)C[C@@H]4C)nc(=O)n(c23)C1]

The title compound was prepared analogously to Example 100, step 21 where (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 73% yield as a yellow solid m/z (ESI, +ve)=627.1 (M+H)$^+$.

Step 9: (3S)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one

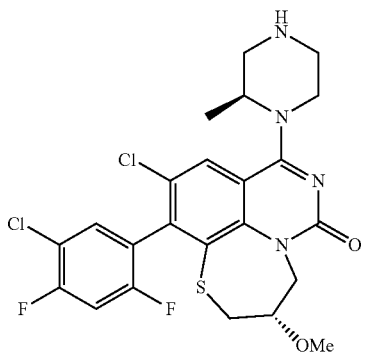 [SMILES: CO[C@@H]1CSc2c(-c3cc(Cl)c(F)cc3F)c(Cl)cc3c(N4CCNC[C@@H]4C)nc(=O)n(c23)C1]

The title compound was prepared analogously to Example 102, step 4, where tert-butyl (3S)-4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 74% yield as a yellow solid m/z (ESI, +ve)=527.0 (M+H)$^+$.

Example 530: (3S)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

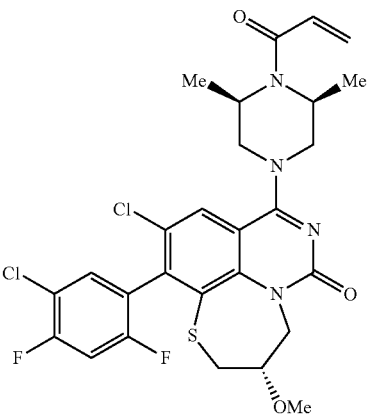 [SMILES: C=CC(=O)N1[C@H](C)CN(c2nc(=O)n3c4c(c(-c5cc(Cl)c(F)cc5F)c(Cl)cc24)SC[C@@H](OC)C3)C[C@@H]1C]

The title compound was prepared analogously to Example 84 where (3S)-10-chloro-11-(5-chloro-2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 37% yield as a yellow solid m/z (ESI, +ve)=595.1 (M+H)$^+$.

$^1$H NMR (400 MHz, DMSO-d6) δ 7.93-7.67 (m, 3H), 6.80 (dd, J=16.0 Hz, 8.0 Hz, 1H), 6.19 (d, J=16.0 Hz, 1H), 5.74 (d, J=8.0 Hz, 1H), 4.56 (s, 2H), 4.48-4.44 (m, 2H), 4.09-4.00 (m, 2H), 3.88 (s, 1H), 3.54-3.37 (m, 1H), 3.35 (s, 3H), 3.28 (s, 2H), 3.18-3.16 (d, J=12.0 Hz, 1H), 1.50-1.24 (m, 6H).

Step 1: (3S)-10-chloro-11-(5-chloro-2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

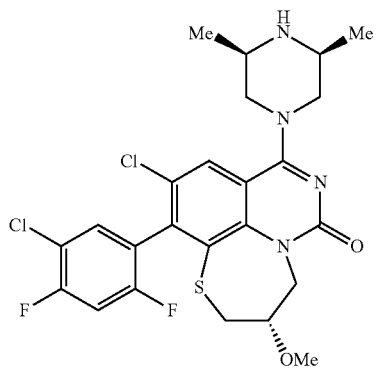 [SMILES: CO[C@@H]1CSc2c(-c3cc(Cl)c(F)cc3F)c(Cl)cc3c(N4C[C@@H](C)N[C@@H](C)C4)nc(=O)n(c23)C1]

The title compound was prepared analogously to Example 100, step 21 where (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 61% yield as a yellow solid
m/z (ESI, +ve)=541.0 (M+H)+.

Example 532: (S)-8-((S)-4-acryloyl-2-methylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

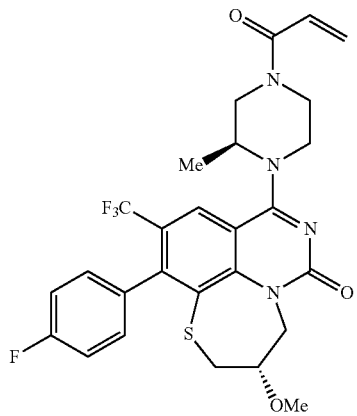 [SMILES: C=CC(=O)N1CCN(c2nc(=O)n3c4c(c(-c5ccc(F)cc5)c(C(F)(F)F)cc24)SC[C@@H](OC)C3)[C@@H](C)C1]

The title compound was prepared analogously to Example 84 where (S)-11-(4-fluorophenyl)-3-methoxy-8-((S)-2-methylpiperazin-1-yl)-10-(trifluoromethyl)-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 30% yield as a white solid
m/z (ESI, +ve)=563.1 (M+H)+.

1H NMR (400 MHz, DMSO-d6) δ 7.78 (s, 1H), 7.34 (d, J=8.0 Hz, 4H), 6.92-6.76 (m, 1H), 6.18 (dd, J=16.0, 8.0 Hz, 1H), 5.74 (dd, J=12.0, 4.0 Hz, 1H), 4.70-4.39 (m, 3H), 4.28-4.24 (m, 1H), 4.16-3.97 (m, 2H), 3.83-3.79 (m, 1H), 3.56-3.51 (m, 2H), 3.34 (s, 3H), 3.13-2.98 (m, 3H), 1.33-1.29 (m, 3H).

Step 1: (S)-7-(4-fluorophenyl)-8-((3-hydroxy-2-methoxypropyl)thio)-6-(trifluoromethyl)quinazoline-2,4(1H,3H)-dione

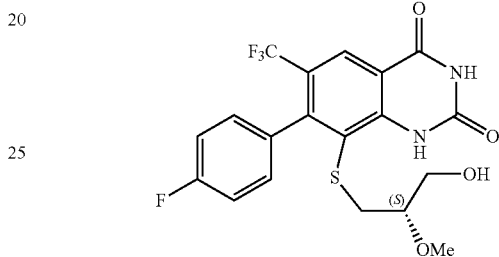

The title compound was prepared analogously to Example 100, step 9 where 7-(4-fluorophenyl)-8-iodo-6-(trifluoromethyl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 50% yield as a yellow solid
m/z (ESI, +ve)=445.0 (M+H)+.

Step 2: (S)-11-(4-fluorophenyl)-3-methoxy-10-(trifluoromethyl)-3,4-dihydro-2H,6H-[1,4]thiazepino[2,3,4-ij]quinazoline-6,8(7H)-dione

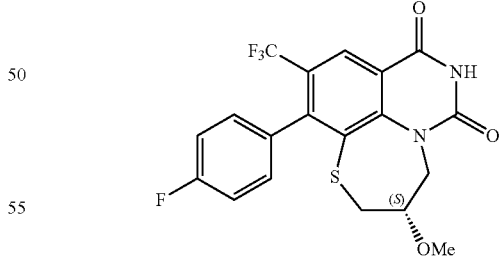

The title compound was prepared analogously to Example 100, step 10 where (S)-7-(4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 66% yield as a yellow solid
m/z (ESI, +ve)=427.1 (M+H)+.

Step 3: tert-butyl (S)-4-((S)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

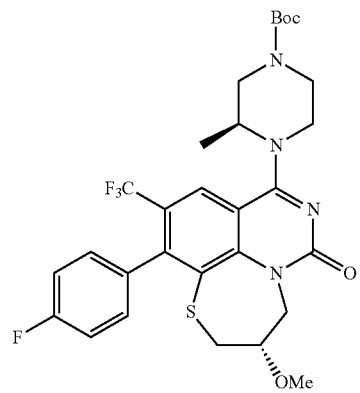 [SMILES: CO[C@@H]1CSc2c(-c3ccc(F)cc3)c(C(F)(F)F)cc3c(N4CCN(C(=O)OC(C)(C)C)C[C@@H]4C)nc(=O)n(c23)C1]

The title compound was prepared analogously to Example 100, step 21 where (S)-11-(4-fluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 59% yield as a yellow solid m/z (ESI, +ve)=609.2 (M+H)⁺.

Step 4: (S)-11-(4-fluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

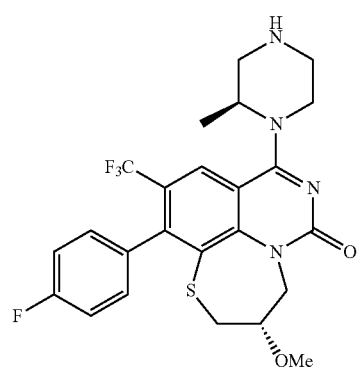 [SMILES: CO[C@@H]1CSc2c(-c3ccc(F)cc3)c(C(F)(F)F)cc3c(N4CCNC[C@@H]4C)nc(=O)n(c23)C1]

The title compound was prepared analogously to Example 102, step 4, where tert-butyl (S)-4-((S)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 86% yield as a yellow solid m/z (ESI, +ve)=509.1 (M+H)⁺.

Example 533: (3R)-8-((S)-4-acryloyl-2-methylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

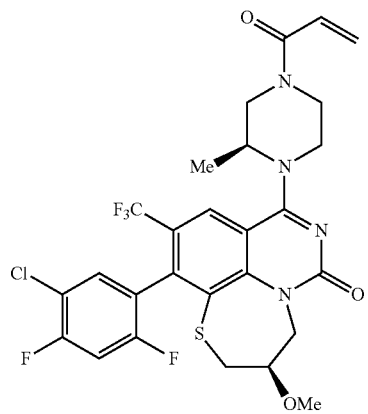 [SMILES: C=CC(=O)N1CCN(c2nc(=O)n3c4c(c(-c5cc(Cl)c(F)cc5F)c(C(F)(F)F)cc24)SC[C@H](OC)C3)[C@@H](C)C1]

The title compound was prepared analogously to Example 84 where (3R)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 34% yield as a yellow solid m/z (ESI, +ve)=615.0 (M+H)⁺.

¹H NMR (400 MHz, DMSO-d6) δ=7.83-7.66 (m, 3H), 6.91-6.74 (m, 1H), 6.19 (dd, J=16.0, 4.0 Hz, 1H), 5.74 (dd, J=16.0, 4.0 Hz, 1H), 4.80-4.31 (m, 4H), 4.17 (m, 3H), 3.85 (s, 1H), 3.54 (s, 2H), 3.37-3.32 (m, 3H), 3.22-3.18 (m, 2H), 1.33-1.28 (m, 3H).

Step 1: methyl 3-amino-5'-chloro-2',4'-difluoro-[1,1'-biphenyl]-4-carboxylate

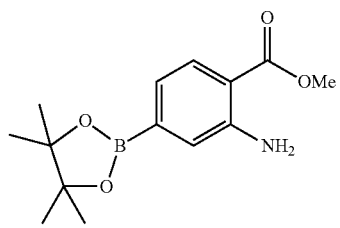 [SMILES: COC(=O)c1ccc(B2OC(C)(C)C(C)(C)O2)cc1N]

A mixture of methyl 2-amino-4-bromobenzoate (30 g, 0.130 mol), 4,4,4',4',5,5,5',5'-octamethyl-2,2'-bi(1,3,2-dioxaborolane) (50 g, 0.197 mol), Pd(dppf)Cl₂ (9.5 g, 13 mmol) and KOAc (38 g, 0.388 mol) in 1,4-dioxane (400 mL) was stirred at 100° C. for 16 hours. After that time, the mixture was filtered and the filtrate was concentrated under reduced pressure to afford a residue that was purified by silica gel column with ethyl acetate in hexanes (0-10%). The title compound was isolated in quantitative yield as a white solid.

m/z (ESI, +ve)=278.2 (M+H)⁺.

¹H NMR (400 MHz, DMSO-d6) δ=7.68 (d, J=8.0 Hz, 1H), 7.18 (s, 1H), 6.79 (d, J=8.0 Hz, 1H), 6.63 (s, 2H), 3.79 (s, 3H), 1.29 (s, 12H).

Step 2: methyl 3-amino-5'-chloro-2',4'-difluoro-[1,1'-biphenyl]-4-carboxylate

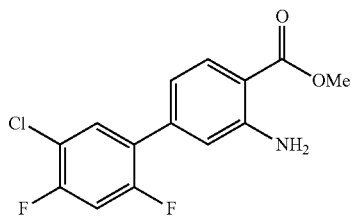 [SMILES: COC(=O)c1ccc(-c2cc(Cl)c(F)cc2F)cc1N]

A mixture of methyl 2-amino-4-(4,4,5,5-tetramethyl-1,3,2-dioxaborolan-2-yl)benzoate (36 g, 0.121 mol), 1-bromo-5-chloro-2,4-difluorobenzene (27 g, 0.119 mol), Pd(dppf)Cl₂ (17 g, 23.3 mmol) and Cs₂CO₃ (116 g, 0.356 mol) in 1,4-dioxane-water (300:60 mL) was stirred at 100° C. for 2 hours. The solution was cooled down to room temperature and filtered. The filtrate was concentrated under reduced pressure to afford a residue that was purified by silica gel chromatography with ethyl acetate in hexanes (0-8%). The title compound was isolated as a white solid in 83% yield.

m/z (ESI, +ve)=298.0 (M+H)⁺.

¹H NMR (400 MHz, DMSO-d6) δ=7.79-7.74 (m, 2H), 7.70-7.65 (m, 1H), 6.96 (s, 1H), 6.77 (s, 2H), 6.71-6.68 (m, 1H), 3.81 (s, 3H).

Step 3: methyl 5-amino-5'-chloro-2',4'-difluoro-2-iodo-[1,1'-biphenyl]-4-carboxylate

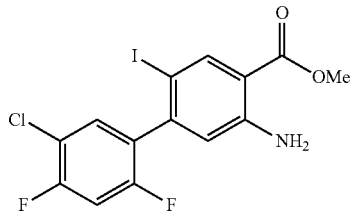 [SMILES: COC(=O)c1cc(I)c(-c2cc(Cl)c(F)cc2F)cc1N]

N-Iodosuccinamide (30 g, 0.133 mol) was added to a solution of methyl 3-amino-5'-chloro-2',4'-difluoro-[1,1'-biphenyl]-4-carboxylate (38 g, 0.128 mol) in DMF (200 mL) at room temperature. The mixture was stirred for 36 hours and after that time ethyl acetate (1 L) was added. The organic mixture was washed with sequentially washed with aqueous Na₂S₂O₃, water and brine. The organic layer was dried over sodium sulfate and filtered to afford a residue that was purified by silica gel chromatography (ethyl acetate in hexanes). The title compound was isolated in 87% yield as a yellow solid.

m/z (ESI, +ve)=423.9 (M+H)⁺.

¹H NMR (400 MHz, DMSO-d6) δ=8.15 (s, 1H), 7.68-7.61 (m, 2H), 6.87 (s, 2H), 6.81 (s, 1H), 3.83 (s, 3H).

Step 4: methyl 5-acetamido-5'-chloro-2',4'-difluoro-2-iodo-[1,1'-biphenyl]-4-carboxylate

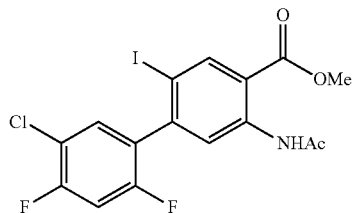 [SMILES: COC(=O)c1cc(I)c(-c2cc(Cl)c(F)cc2F)cc1NC(C)=O]

To a solution of methyl 5-amino-5'-chloro-2',4'-difluoro-2-iodo-[1,1'-biphenyl]-4-carboxylate (47 g, 0.111 mol) in AcOH (200 mL), acetic anhydride (14.5 g, 0.144 mol) was added and the resulting mixture was stirred at 100° C. for 2 hours. The reaction was cooled to room temperature and quenched by the addition of water (200 mL) inducing the precipitation of the desired final product. This solid was filtered and dried under reduced pressure to afford the title compound in 99% yield as an off-white solid.

m/z (ESI, +ve)=465.9 (M+H)⁺.

¹H NMR (400 MHz, DMSO-d6) δ=10.52 (s, 1H), 8.36 (s, 1H), 8.18 (s, 1H), 7.75-7.66 (m, 2H), 3.83 (s, 3H), 2.12 (s, 3H).

Step 5: methyl 5-acetamido-5'-chloro-2',4'-difluoro-2-(trifluoromethyl)-[1,1'-biphenyl]-4-carboxylate

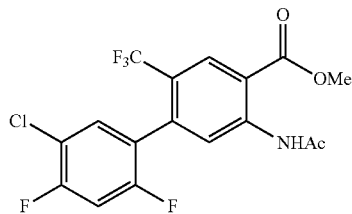 [SMILES: COC(=O)c1cc(C(F)(F)F)c(-c2cc(Cl)c(F)cc2F)cc1NC(C)=O]

To a solution of methyl 5-acetamido-5'-chloro-2',4'-difluoro-2-iodo-[1,1'-biphenyl]-4-carboxylate (10 g, 21.5 mmol), CuI (5.7 g, 30.0 mmol) and TBAI (4 g, 10.8 mmol) in HMPA (50 mL) at 90° C., was added methyl 2,2-difluoro-2-(fluorosulfonyl)acetate (41.2 g, 214.6 mmol). The mixture was stirred at 90° C. for 16 hours and after being cooled down to room temperature, water was added followed by filtration of the solids. The aqueous filtrate was extracted with ethyl acetate three times and the combined organic layers washed with water, brine and dried over sodium sulfate. Filtration and evaporation of volatiles under reduced pressure afforded a residue that was purified by silica gel chromatography (0-15% ethyl acetate in hexanes). The tile compound was isolated in 82% yield as a yellow solid.

m/z (ESI, +ve)=408.0 (M+H)⁺.

¹H NMR (400 MHz, DMSO-d6) δ=10.81 (s, 1H), 8.34 (s, 1H), 8.26 (s, 1H), 7.78-7.61 (m, 2H), 3.93 (s, 3H), 2.18 (s, 3H).

Step 6: methyl 5-amino-5'-chloro-2',4'-difluoro-2-(trifluoromethyl)-[1,1'-biphenyl]-4-carboxylate

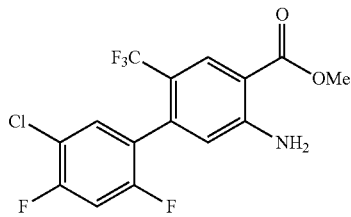 [SMILES: COC(=O)c1cc(C(F)(F)F)c(-c2cc(Cl)c(F)cc2F)cc1N]

The title compound was synthesized analogously to example 100, step 5 where methyl 5-acetamido-5'-chloro-2',4'-difluoro-2-(trifluoromethyl)-[1,1'-biphenyl]-4-carboxylate was substituted in place of methyl 5-acetamido-2',4'-difluoro-2-(trifluoromethyl)-[1,1'-biphenyl]-4-carboxylate. The title compound was isolated in 92% yield as a white solid
m/z (ESI, +ve)=366.0 (M+H)$^+$.

Step 7: methyl 3-amino-5'-chloro-2',4'-difluoro-2-iodo-6-(trifluoromethyl)-[1,1'-biphenyl]-4-carboxylate

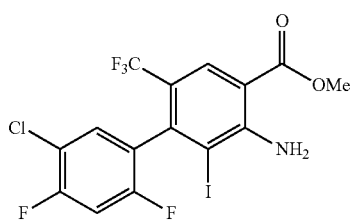 [SMILES: COC(=O)c1cc(C(F)(F)F)c(-c2cc(Cl)c(F)cc2F)c(I)c1N]

The title compound was synthesized analogously to example 100, step 6 where methyl 5-amino-5'-chloro-2',4'-difluoro-2-(trifluoromethyl)-[1,1'-biphenyl]-4-carboxylate was substituted in place of methyl 5-amino-2',4'-difluoro-2-(trifluoromethyl)-[1,1'-biphenyl]-4-carboxylate. The title compound was isolated in 86% yield as a white solid
m/z (ESI, +ve)=491.9 (M+H)$^+$.
$^1$H NMR (400 MHz, DMSO-d6) δ=8.19 (s, 1H), 7.76-7.73 (m, 1H), 7.67-7.63 (m, 1H), 7.48-7.44 (m, 2H), 3.90 (s, 3H).

Step 8: 3-amino-5'-chloro-2',4'-difluoro-2-iodo-6-(trifluoromethyl)-[1,1'-biphenyl]-4-carboxylic acid

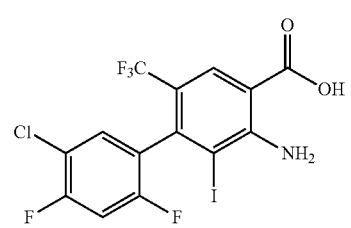

The title compound was synthesized analogously to example 100, step 7 where methyl 3-amino-5'-chloro-2',4'-difluoro-2-iodo-6-(trifluoromethyl)-[1,1'-biphenyl]-4-carboxylate was substituted in place of methyl 3-amino-2',4'-difluoro-2-iodo-6-(trifluoromethyl)-[1,1'-biphenyl]-4-carboxylate. The title compound was isolated in 99% yield as a white solid
m/z (ESI, +ve)=477.8 (M+H)$^+$.
$^1$H NMR (400 MHz, DMSO-d6) δ=13.60 (s, 1H), 8.19 (s, 1H), 7.77-7.72 (m, 1H), 7.67-7.63 (m, 1H), 7.57-7.48 (m, 2H).

Step 9: 7-(5-chloro-2,4-difluorophenyl)-8-iodo-6-(trifluoromethyl)quinazoline-2,4(1H,3H)-dione

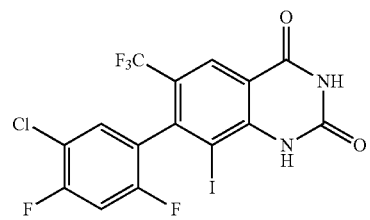 [SMILES: O=c1[nH]c(=O)c2cc(C(F)(F)F)c(-c3cc(Cl)c(F)cc3F)c(I)c2[nH]1]

The title compound was synthesized analogously to example 100, step 8 where 3-Amino-4'-fluoro-2-iodo-6-(trifluoromethyl)-[1,1'-biphenyl]-4-carboxylic acid was substituted in place of 3-amino-2',4'-difluoro-2-iodo-6-(trifluoromethyl)-[1,1'-biphenyl]-4-carboxylic acid. The title compound was isolated in 57% yield as a white solid.
m/z (ESI, +ve)=502.9 (M+H)$^+$.
$^1$H NMR (400 MHz, DMSO-d6) δ=11.93 (s, 1H), 9.99 (s, 1H), 8.27 (s, 1H), 7.83-7.78 (m, 1H), 7.72-7.68 (m, 1H).

Step 11: 7-(5-chloro-2,4-difluorophenyl)-8-(((R)-3-hydroxy-2-methoxypropyl)thio)-6-(trifluoromethyl)quinazoline-2,4(1H,3H)-dione

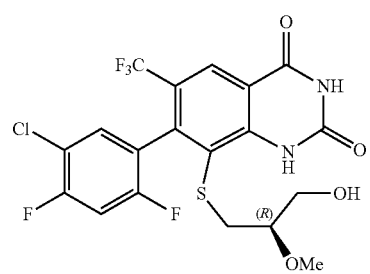

The title compound was synthesized analogously to example 100, step 9 where 7-(5-chloro-2,4-difluorophenyl)-8-iodo-6-(trifluoromethyl)quinazoline-2,4(1H,3H)-dione and (R)-3-mercapto-2-methoxypropan-1-ol was substituted in place of 7-(2,4-difluorophenyl)-8-iodo-6-(trifluoromethyl)quinazoline-2,4(1H,3H)-dione and 2-mercaptoethan-1-ol. The title compound was isolated in 70% yield as a white solid.
m/z (ESI, +ve)=497.0 (M+H)$^+$.

Step 12: (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione

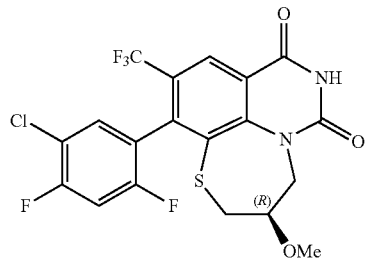

The title compound was prepared analogously to Example 100, step 10 where 7-(5-chloro-2,4-difluorophenyl)-8-(((R)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 55% yield as a yellow solid Step 13: tert-butyl (3S)-4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

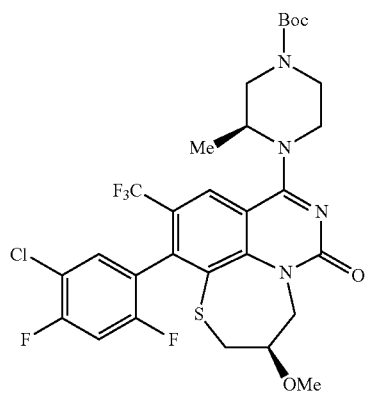 [SMILES: CO[C@H]1CSc2c(-c3cc(Cl)c(F)cc3F)c(C(F)(F)F)cc3c(N4CCN(C(=O)OC(C)(C)C)C[C@@H]4C)nc(=O)n(c23)C1]

The title compound was prepared analogously to Example 100, step 21 where (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 61% yield as a yellow solid m/z (ESI, +ve)=661.0 (M+H)⁺.

Step 14: (3R)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

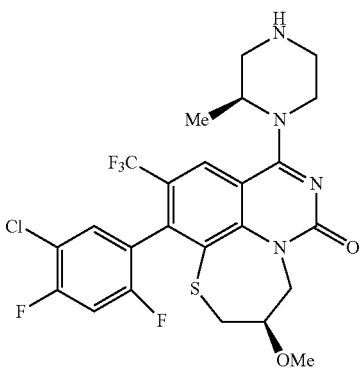 [SMILES: CO[C@H]1CSc2c(-c3cc(Cl)c(F)cc3F)c(C(F)(F)F)cc3c(N4CCNC[C@@H]4C)nc(=O)n(c23)C1]

The title compound was prepared analogously to Example 102, step 4, where tert-butyl (3S)-4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated as a yellow oil m/z (ESI, +ve)=561.0 (M+H)⁺.

Example 534: (3R)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

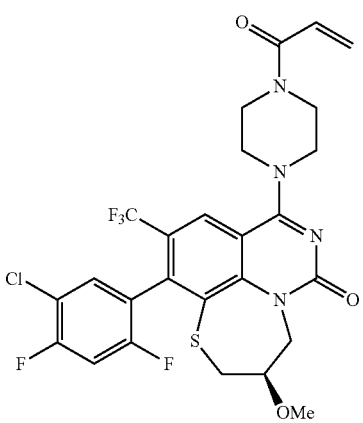 [SMILES: C=CC(=O)N1CCN(c2nc(=O)n3c4c(c(-c5cc(Cl)c(F)cc5F)c(C(F)(F)F)cc24)SC[C@H](OC)C3)CC1]

The title compound was prepared analogously to Example 84 where (3R)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 27% yield as a yellow solid m/z (ESI, +ve)=601.0 (M+H)⁺.

¹H NMR (400 MHz, DMSO-d6) δ=7.90 (s, 1H), 7.80-7.76 (m, 2H), 6.82 (dd, J=16.0, 8.0 Hz, 1H), 6.17 (dd, J=16.0, 4.0 Hz, 1H), 5.74 (dd, J=16.0, 4.0 Hz, 1H), 4.51-4.47 (m, 1H), 3.84-3.80 (m, 9H), 3.47-3.43 (m, 1H), 3.40-3.35 (m, 3H), 3.22-3.18 (m, 2H).

Step 1: tert-butyl 4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

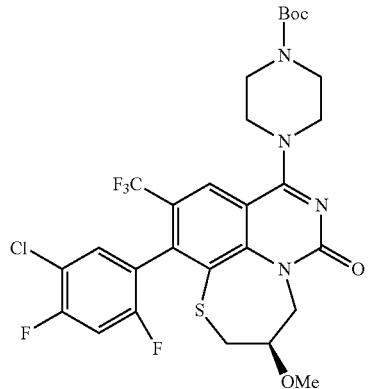 [SMILES: CO[C@H]1CSc2c(-c3cc(Cl)c(F)cc3F)c(C(F)(F)F)cc3c(N4CCN(C(=O)OC(C)(C)C)CC4)nc(=O)n(c23)C1]

The title compound was prepared analogously to Example 100, step 21 (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 68% yield as a yellow solid
m/z (ESI, +ve)=647.1 (M+H)⁺.

Step 2: (3R)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

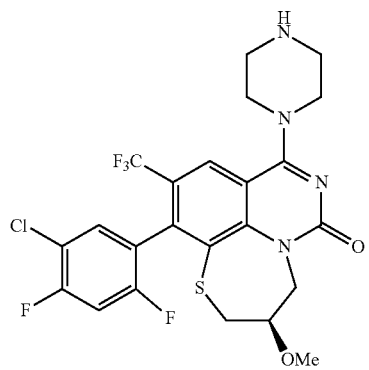 [SMILES: CO[C@H]1CSc2c(-c3cc(Cl)c(F)cc3F)c(C(F)(F)F)cc3c(N4CCNCC4)nc(=O)n(c23)C1]

The title compound was prepared analogously to Example 102, step 4, where tert-butyl 4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 70% yield as a yellow solid
m/z (ESI, +ve)=547.0 (M+H)⁺.

Example 535: (3R)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

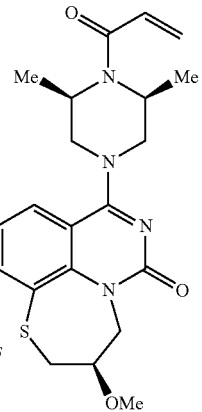

The title compound was prepared analogously to Example 84 where (3R)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 32% yield as a yellow solid
m/z (ESI, +ve)=629.0 (M+H)⁺.
¹H NMR (400 MHz, DMSO-d6) δ=8.04 (s, 1H), 7.87-7.69 (m, 2H), 6.81 (dd, J=16.0, 8.0 Hz, 1H), 6.19 (dd, J=16.0, 4.0 Hz, 1H), 5.74 (dd, J=16.0, 4.0 Hz, 1H), 4.67-4.46 (m, 3H), 4.08-4.04 (m, 2H), 3.88-3.84 (m, 1H), 3.49-3.44 (m, 1H), 3.35 (s, 3H), 3.32-3.21 (m, 3H), 3.17 (s, 1H), 1.53-1.27 (m, 6H).

Step 1: (3R)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

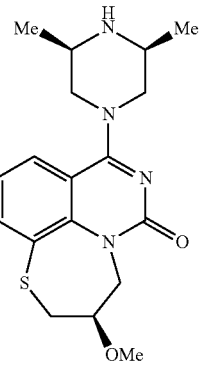

The title compound was prepared analogously to Example 100, step 21 where (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 63% yield as a yellow solid
m/z (ESI, +ve)=575.0 (M+H)+.

Example 536: (S)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one

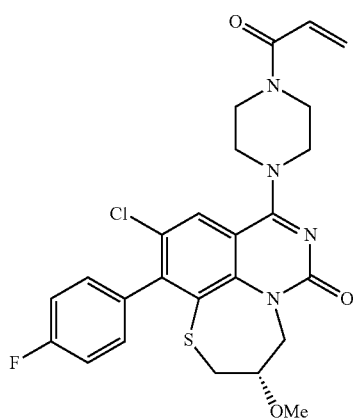 [SMILES: C=CC(=O)N1CCN(c2nc(=O)n3c4c(c(-c5ccc(F)cc5)c(Cl)cc24)SC[C@@H](OC)C3)CC1]

The title compound was prepared analogously to Example 84 where (S)-10-chloro-11-(4-fluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 27% yield as a yellow solid
m/z (ESI, +ve)=515.0 (M+H)+.
1H NMR (400 MHz, DMSO-d6) δ 7.72 (s, 1H), 7.41-7.30 (m, 4H), 6.83 (dd, J=16.0, 8.0 Hz, 1H), 6.17 (dd, J=16.0, 4.0 Hz, 1H), 5.74 (dd, J=16.0, 4.0 Hz, 1H), 4.49-4.44 (m, 1H), 3.80-3.76 (m, 10H), 3.35-3.31 (m, 3H), 3.32-3.28 (m, 1H), 3.10-3.06 (m, 1H).

Step 1: (S)-6-chloro-7-(4-fluorophenyl)-8-((3-hydroxy-2-methoxypropyl)thio)quinazoline-2,4(1H,3H)-dione

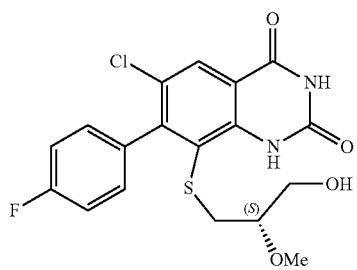

The title compound was prepared analogously to Example 100, step 9 where 6-Chloro-7-(4-fluorophenyl)-8-iodoquinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 76% yield as a yellow solid
m/z (ESI, +ve)=411.0 (M+H)+.

Step 2: (S)-10-chloro-11-(4-fluorophenyl)-3-methoxy-3,4-dihydro-2H,6H-[1,4]thiazepino[2,3,4-ij]quinazoline-6,8(7H)-dione

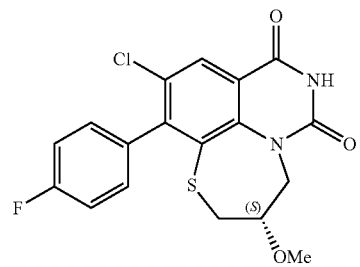

The title compound was prepared analogously to Example 100, step 10 where (S)-6-chloro-7-(4-fluorophenyl)-8-((3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 61% yield as a yellow solid
m/z (ESI, +ve)=393.0 (M+H)+.

Step 3: tert-butyl (S)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate

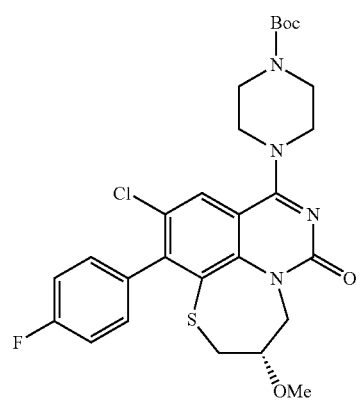 [SMILES: CO[C@@H]1CSc2c(-c3ccc(F)cc3)c(Cl)cc3c(N4CCN(C(=O)OC(C)(C)C)CC4)nc(=O)n(c23)C1]

The title compound was prepared analogously to Example 100, step 21 where (S)-10-chloro-11-(4-fluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 66% yield as a yellow solid
m/z (ESI, +ve)=561.2 (M+H)+.

Step 4: (S)-10-chloro-11-(4-fluorophenyl)-3-methoxy-8-(piperazin-1-yl)-3,4-dihydro-2H,6H-[1,4]thiazepino[2,3,4-ij]quinazolin-6-one

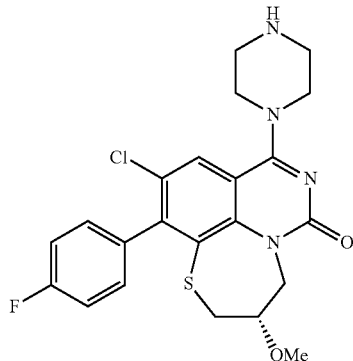 [SMILES: CO[C@@H]1CSc2c(-c3ccc(F)cc3)c(Cl)cc3c(N4CCNCC4)nc(=O)n(c23)C1]

The title compound was prepared analogously to Example 102, step 4, where tert-butyl (S)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 79% yield as a yellow solid m/z (ESI, +ve)=461.0 (M+H)⁺.

Example 537: (S)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one

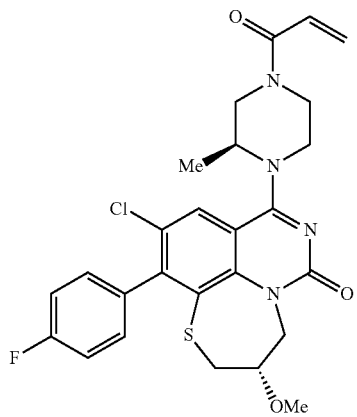 [SMILES: C=CC(=O)N1CCN(c2nc(=O)n3c4c(c(-c5ccc(F)cc5)c(Cl)cc24)SC[C@@H](OC)C3)[C@@H](C)C1]

The title compound was prepared analogously to Example 84 where (S)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 31% yield as a yellow solid m/z (ESI, +ve)=529.1 (M+H)⁺.

¹H NMR (400 MHz, DMSO-d6) δ 7.62 (s, 1H), 7.36 (d, J=8.0 Hz, 4H), 6.92-6.76 (m, 1H), 6.18 (dd, J=16.0, 4.0 Hz, 1H), 5.74 (dd, J=16.0, 4.0 Hz, 1H), 4.59-4.55 (m, 1H), 4.46-4.42 (m, 2H), 4.33-3.90 (m, 3H), 3.88-3.78 (m, 1H), 3.57-3.53 (m, 2H), 3.33 (s, 3H), 3.25-2.84 (m, 3H), 1.29-1.25 (m, 3H).

Step 1: tert-butyl (S)-4-((S)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate

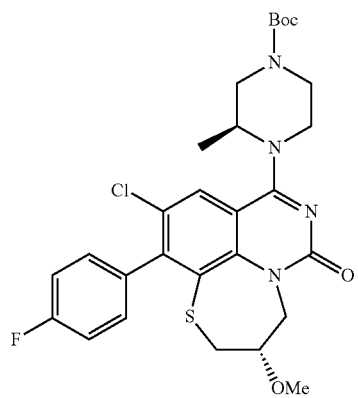 [SMILES: CO[C@@H]1CSc2c(-c3ccc(F)cc3)c(Cl)cc3c(N4CCN(C(=O)OC(C)(C)C)C[C@@H]4C)nc(=O)n(c23)C1]

The title compound was prepared analogously to Example 100, step 21 where (S)-10-chloro-11-(4-fluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 68% yield as a yellow solid m/z (ESI, +ve)=575.1 (M+H)⁺.

Step 2: (S)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one

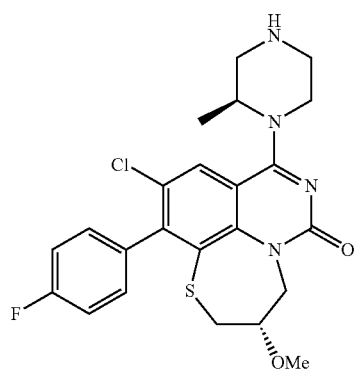 [SMILES: CO[C@@H]1CSc2c(-c3ccc(F)cc3)c(Cl)cc3c(N4CCNC[C@@H]4C)nc(=O)n(c23)C1]

The title compound was prepared analogously to Example 102, step 4, where tert-butyl (S)-4-((S)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H, 6H-[1,4]thiazepino[2,3,4-ij]quinazolin-8-yl)-3-methylpiperazine-1-carboxylate. The title compound was isolated in 76% yield as a yellow solid m/z (ESI, +ve)=475.1 (M+H)+.

Example 538: (3R)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

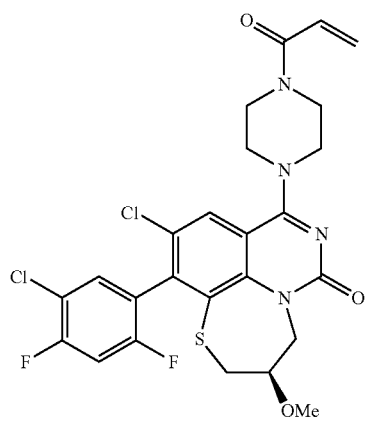 [SMILES: C=CC(=O)N1CCN(c2nc(=O)n3c4c(c(-c5cc(Cl)c(F)cc5F)c(Cl)cc24)SC[C@H](OC)C3)CC1]

The title compound was prepared analogously to Example 84 where (3R)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 36% yield as a yellow solid m/z (ESI, +ve)=567.0 (M+H)+.
1H NMR (400 MHz, DMSO-d6) δ 7.90-7.76 (m, 3H), 6.82 (dd, J=16.0, 8.0 Hz, 1H), 6.17 (dd, J=16.0, 4.0 Hz, 1H), 5.74 (dd, J=16.0, 4.0 Hz, 1H), 4.52-4.36 (m, 1H), 3.91-3.61 (m, 8H), 3.53-3.45 (m, 3H), 3.35-3.30 (m, 3H), 3.20-3.09 (m, 1H).

Step 1: 6-chloro-7-(5-chloro-2,4-difluorophenyl)-8-(((R)-3-hydroxy-2-methoxypropyl)thio)quinazoline-2,4(1H,3H)-dione

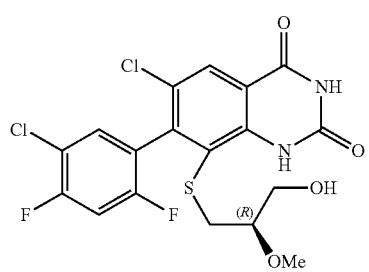

The title compound was prepared analogously to Example 100, step 9 where 6-chloro-7-(5-chloro-2,4-difluorophenyl)-8-iodoquinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol in 50% yield as a yellow solid m/z (ESI, +ve)=463.0 (M+H)+.

Step 2: (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione

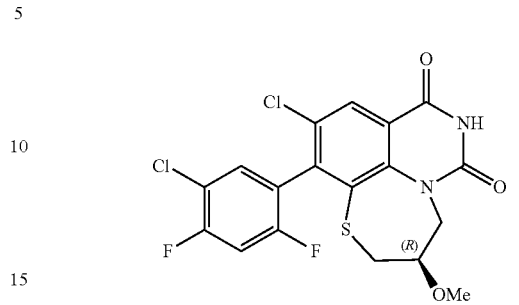

The title compound was prepared analogously to Example 100, step 10 where 6-chloro-7-(5-chloro-2,4-difluorophenyl)-8-(((R)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 65% yield as a yellow solid m/z (ESI, +ve)=445.0 (M+H)+.

Step 3: tert-butyl 4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate

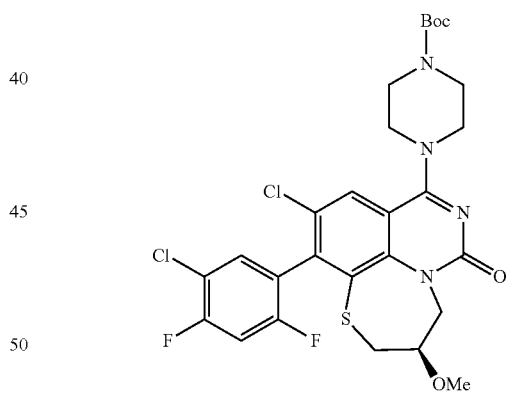

The title compound was prepared analogously to Example 100, step 21 where (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 78% yield as a yellow solid m/z (ESI, +ve)=613.2 (M+H)+.

Step 4: (3R)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one

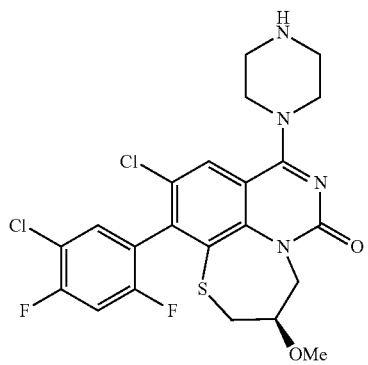 [SMILES: CO[C@H]1CSc2c(-c3cc(Cl)c(F)cc3F)c(Cl)cc3c(N4CCNCC4)nc(=O)n(c23)C1]

The title compound was prepared analogously to Example 102, step 4, where tert-butyl 4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow solid m/z (ESI, +ve)=513.0 (M+H)⁺.

Example 539: (3S)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

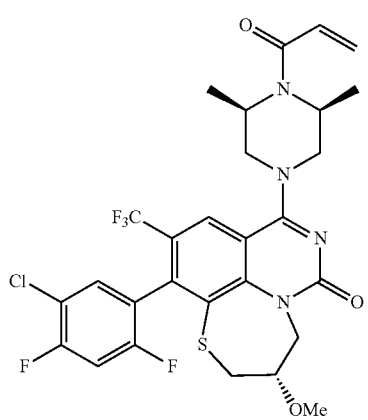 [SMILES: C=CC(=O)N1[C@H](C)CN(c2nc(=O)n3c4c(c(-c5cc(Cl)c(F)cc5F)c(C(F)(F)F)cc24)SC[C@@H](OC)C3)C[C@@H]1C]

The title compound was prepared analogously to Example 84 where (3S)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one
was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 33% yield as a yellow solid m/z (ESI, +ve)=629.1 (M+H)⁺.

¹H NMR (400 MHz, DMSO-d6) δ 8.04 (s, 1H), 7.80-7.72 (m, 2H), 6.81 (dd, J=16.0, 8.0 Hz, 1H), 6.19 (dd, J=16.0, 4.0 Hz, 1H), 5.74 (dd, J=16.0, 4.0 Hz, 1H), 4.80-4.30 (m, 4H), 4.15-3.98 (m, 2H), 3.92-3.80 (m, 1H), 3.61-3.40 (m, 1H), 3.35 (s, 3H), 3.30-3.12 (m, 3H), 1.43-1.20 (m, 6H).

Step 1: 7-(5-chloro-2,4-difluorophenyl)-8-(((S)-3-hydroxy-2-methoxypropyl)thio)-6-(trifluoromethyl)quinazoline-2,4(1H,3H)-dione

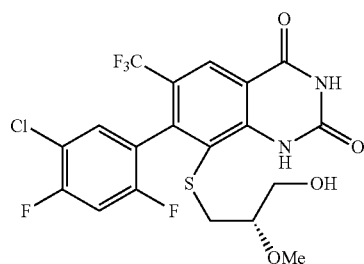 [SMILES: CO[C@@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione and (S)-2-methoxybutane-1-thiol was substituted in place of 7-(2,4-difluorophenyl)-8-iodo-6-(trifluoromethyl)quinazoline-2,4(1H,3H)-dione and 2-mercaptoethan-1-ol. The title compound was isolated in 49% yield as a white solid.

m/z (ESI, +ve)=497.0 (M+H)⁺.

Step 2: (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione

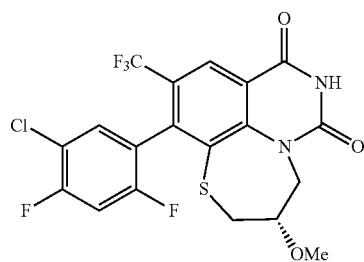 [SMILES: CO[C@@H]1CSc2c(-c3cc(Cl)c(F)cc3F)c(C(F)(F)F)cc3c(=O)[nH]c(=O)n(c23)C1]

The title compound was prepared analogously to Example 100, step 10 where 7-(5-chloro-2,4-difluorophenyl)-8-(((S)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 53% yield as a yellow solid m/z (ESI, +ve)=478.9 (M+H)⁺.

Step 3: (3S)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

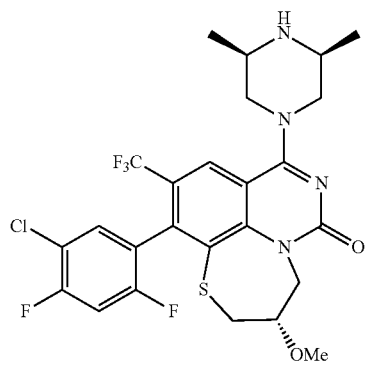 [SMILES: CO[C@@H]1CSc2c(-c3cc(Cl)c(F)cc3F)c(C(F)(F)F)cc3c(N4C[C@@H](C)N[C@@H](C)C4)nc(=O)n(c23)C1]

The title compound was prepared analogously to Example 100, step 21 where ((3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 74% yield as a yellow solid m/z (ESI, +ve)=575.0 (M+H)⁺.

Example 540: (R)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one

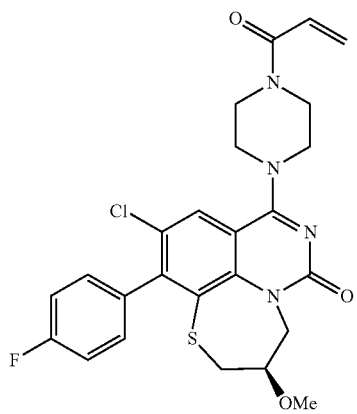 [SMILES: C=CC(=O)N1CCN(c2nc(=O)n3c4c(c(-c5ccc(F)cc5)c(Cl)cc24)SC[C@H](OC)C3)CC1]

The title compound was prepared analogously to Example 84 where (R)-10-chloro-11-(4-fluorophenyl)-3-methoxy-8-(piperazin-1-yl)-3,4-dihydro-2H,6H-[1,4]thiazepino[2,3,4-ij]quinazolin-6-one. The title compound was isolated in 32% yield as a yellow solid m/z (ESI, +ve)=515.1 (M+H)⁺.

¹H NMR (400 MHz, DMSO-d6) δ 7.72 (s, 1H), 7.45-7.28 (m, 4H), 6.83 (dd, J=16.0, 8.0 Hz, 1H), 6.17 (dd, J=16.0, 4.0 Hz, 1H), 5.74 (dd, J=16.0, 4.0 Hz, 1H), 4.49-4.45 (m, 1H), 3.86-3.66 (m, 8H), 3.34-3.29 (m, 6H), 3.10-3.06 (m, 1H).

Step 1: tert-butyl (R)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate

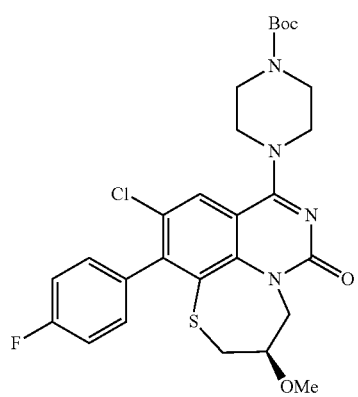 [SMILES: CO[C@H]1CSc2c(-c3ccc(F)cc3)c(Cl)cc3c(N4CCN(C(=O)OC(C)(C)C)CC4)nc(=O)n(c23)C1]

The title compound was prepared analogously to Example 100, step 21 where (R)-10-chloro-11-(4-fluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid m/z (ESI, +ve)=561.1 (M+H)⁺.

Step 2: (R)-10-chloro-11-(4-fluorophenyl)-3-methoxy-8-(piperazin-1-yl)-3,4-dihydro-2H,6H-[1,4]thiazepino[2,3,4-ij]quinazolin-6-one

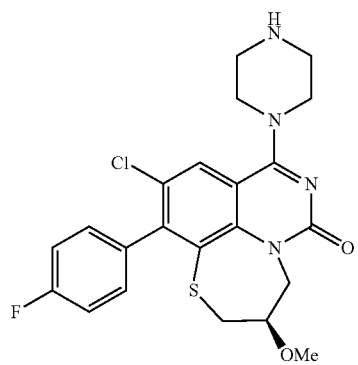 [SMILES: CO[C@H]1CSc2c(-c3ccc(F)cc3)c(Cl)cc3c(N4CCNCC4)nc(=O)n(c23)C1]

The title compound was prepared analogously to Example 102, step 4, where tert-butyl (R)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 88% yield as a yellow solid m/z (ESI, +ve)=461.1 (M+H)⁺.

Example 541: (3R)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

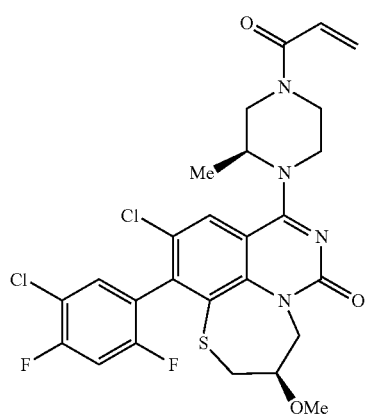 [SMILES: C=CC(=O)N1CCN(c2nc(=O)n3c4c(c(-c5cc(Cl)c(F)cc5F)c(Cl)cc24)SC[C@H](OC)C3)[C@@H](C)C1]

The title compound was prepared analogously to Example 84 where (3R)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 33% yield as a yellow solid m/z (ESI, +ve)=581.1 (M+H)$^+$.

$^1$H NMR (400 MHz, DMSO-d6) δ 7.85-7.74 (m, 2H), 7.72-7.65 (m, 1H), 6.92-6.78 (m, 1H), 6.23-6.18 (dd, J=16.0, 4.0 Hz, 1H), 5.76-5.72 (dd, J=16.0, 4.0 Hz, 1H), 4.85-4.52 (m, 2H), 4.48-4.37 (m, 2H), 4.30-4.09 (m, 1H), 4.05-3.96 (m, 1H), 3.94-3.84 (m, 1H), 3.78-3.43 (m, 3H), 3.42-3.34 (m, 3H), 3.25-3.17 (m, 1H), 3.08-2.86 (m, 1H), 1.31-1.15 (m, 3H).

Step 1: tert-butyl (3S)-4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate

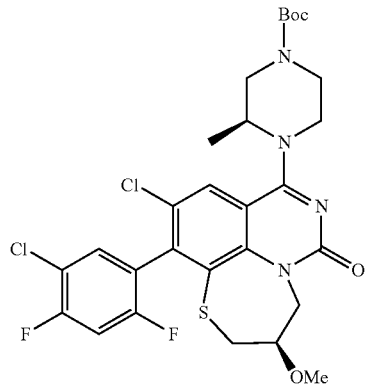 [SMILES: CO[C@H]1CSc2c(-c3cc(Cl)c(F)cc3F)c(Cl)cc3c(N4CCN(C(=O)OC(C)(C)C)C[C@@H]4C)nc(=O)n(c23)C1]

The title compound was prepared analogously to Example 100, step 21 where (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 65% yield as a yellow solid m/z (ESI, +ve)=627.1 (M+H)$^+$.

Step 2: (3R)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one

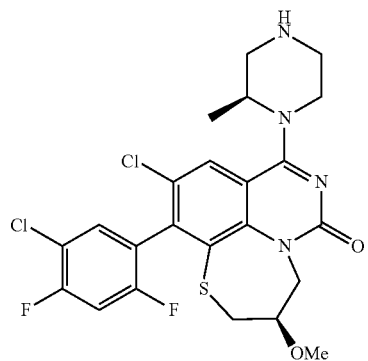 [SMILES: CO[C@H]1CSc2c(-c3cc(Cl)c(F)cc3F)c(Cl)cc3c(N4CCNC[C@@H]4C)nc(=O)n(c23)C1]

The title compound was prepared analogously to Example 102, step 4, where tert-butyl (3S)-4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a yellow solid m/z (ESI, +ve)=527.0 (M+H)$^+$.

Example 542: (3R)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

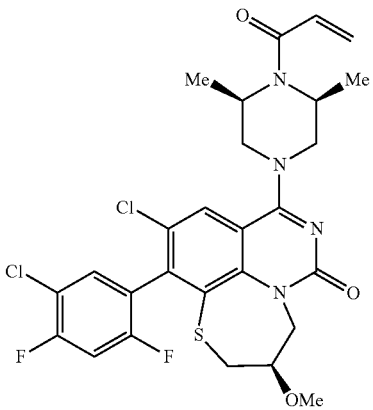 [SMILES: C=CC(=O)N1[C@H](C)CN(c2nc(=O)n3c4c(c(-c5cc(Cl)c(F)cc5F)c(Cl)cc24)SC[C@H](OC)C3)C[C@@H]1C]

The title compound was prepared analogously to Example 84 where (3R)-10-chloro-11-(5-chloro-2,4-difluorophenyl)-

8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 22% yield as a yellow solid m/z (ESI, +ve)=595.1 (M+H)+.

$^1$H NMR (400 MHz, DMSO-d6) δ 7.84-7.73 (m, 3H), 6.80 (dd, J=16.0, 8.0 Hz, 1H), 6.19 (dd, J=16.0, 4.0 Hz, 1H), 5.74 (dd, J=16.0, 4.0 Hz, 1H), 4.65-4.36 (m, 4H), 4.09-3.98 (m, 2H), 3.92-3.83 (m, 1H), 3.52-3.45 (m, 1H), 3.39-3.34 (m, 3H), 3.32-3.27 (m, 2H), 3.19-3.10 (m, 1H), 1.46-1.29 (m, 6H).

Step 1: (3R)-10-chloro-11-(5-chloro-2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

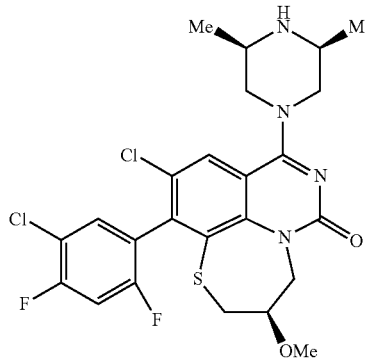

The title compound was prepared analogously to Example 100, step 21 where (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 76% yield as a yellow solid m/z (ESI, +ve)=541.1 (M+H)+.

Example 543: (3S)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

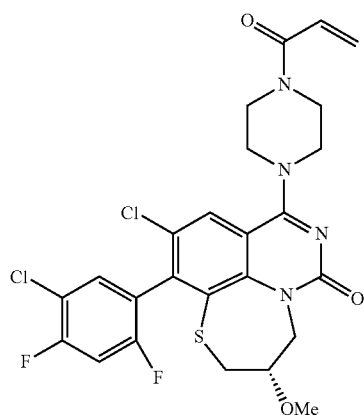 [SMILES: C=CC(=O)N1CCN(c2nc(=O)n3c4c(c(-c5cc(Cl)c(F)cc5F)c(Cl)cc24)SC[C@@H](OC)C3)CC1]

The title compound was prepared analogously to Example 84 where (3S)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 22% yield as a yellow solid m/z (ESI, +ve)=567.1 (M+H)+.

$^1$H NMR (400 MHz, DMSO-d6) δ 7.87-7.72 (m, 3H), 6.82 (dd, J=16.0, 8.0 Hz, 1H), 6.17 (dd, J=16.0, 4.0 Hz 1H), 5.74 (dd, J=16.0, 4.0 Hz, 1H), 4.48-4.44 (m, 1H), 3.91-3.63 (m, 9H), 3.48-3.44 (m, 1H), 3.32 (s, 4H), 3.21-3.09 (m, 1H).

Step 1: 6-chloro-7-(5-chloro-2,4-difluorophenyl)-8-(((S)-3-hydroxy-2-methoxypropyl)thio)quinazoline-2,4(1H,3H)-dione

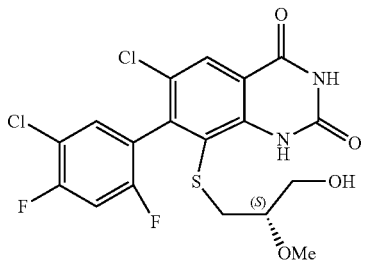

The title compound was prepared analogously to Example 100, step 9 where 6-chloro-7-(5-chloro-2,4-difluorophenyl)-8-iodoquinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol in 61% yield as a yellow solid m/z (ESI, +ve)=462.9 (M+H)+.

Step 2: (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione

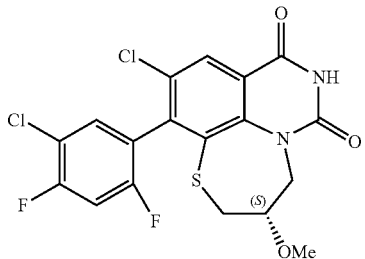

The title compound was prepared analogously to Example 100, step 10 where 6-chloro-7-(5-chloro-2,4-difluorophenyl)-8-(((S)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 58% yield as a yellow solid m/z (ESI, +ve)=445.0 (M+H)+.

1161

Step 3: tert-butyl 4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate

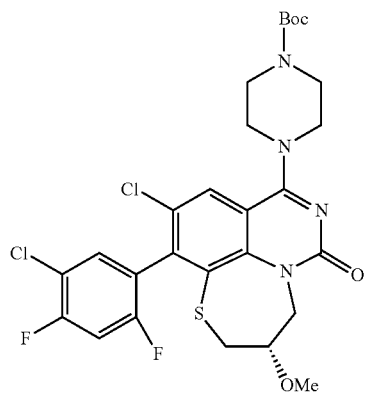 [SMILES: CO[C@@H]1CSc2c(-c3cc(Cl)c(F)cc3F)c(Cl)cc3c(N4CCN(C(=O)OC(C)(C)C)CC4)nc(=O)n(c23)C1]

The title compound was prepared analogously to Example 100, step 21 where (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 89% yield as a yellow solid m/z (ESI, +ve)=613.1 (M+H)$^+$.

Step 4: (3S)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one

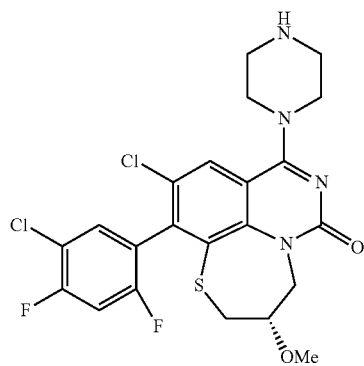 [SMILES: CO[C@@H]1CSc2c(-c3cc(Cl)c(F)cc3F)c(Cl)cc3c(N4CCNCC4)nc(=O)n(c23)C1]

The title compound was prepared analogously to Example 102, step 4, where tert-butyl 4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 75% yield as a yellow solid m/z (ESI, +ve)=513.0 (M+H)$^+$.

1162

Example 582: (3S)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

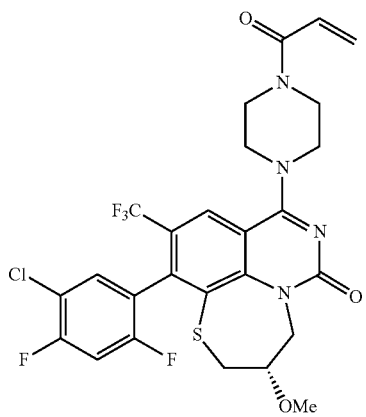 [SMILES: C=CC(=O)N1CCN(c2nc(=O)n3c4c(c(-c5cc(Cl)c(F)cc5F)c(C(F)(F)F)cc24)SC[C@@H](OC)C3)CC1]

The title compound was prepared analogously to Example 84 where (3S)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 13% yield as a yellow solid m/z (ESI, +ve)=601.1 (M+H)$^+$.

$^1$H NMR (400 MHz, DMSO-d6) δ 7.90 (s, 1H), 7.80-7.75 (m, 2H), 6.82 (dd, J=16.0, 8.0 Hz, 1H), 6.17 (dd, J=16.0, 4.0 Hz, 1H), 5.74 (dd, J=16.0, 4.0 Hz, 1H), 4.50-4.48 (m, 1H), 3.84-3.74 (m, 8H), 3.51-3.35 (m, 4H), 3.27-3.18 (m, 3H).

Step 1: tert-butyl 4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

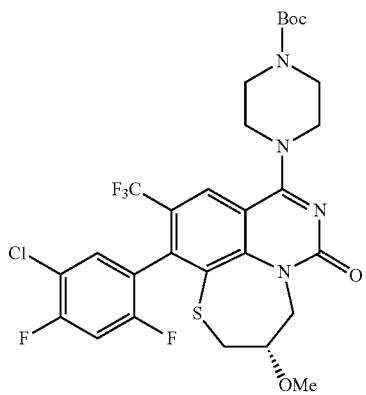 [SMILES: CO[C@@H]1CSc2c(-c3cc(Cl)c(F)cc3F)c(C(F)(F)F)cc3c(N4CCN(C(=O)OC(C)(C)C)CC4)nc(=O)n(c23)C1]

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2, 4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 70% yield as a yellow solid
m/z (ESI, +ve)=647.0 (M+H)+.

Step 2: (3S)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

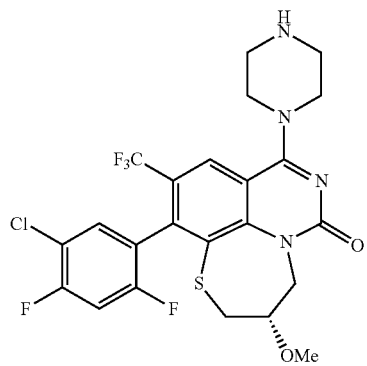 [SMILES: CO[C@@H]1CSc2c(-c3cc(Cl)c(F)cc3F)c(C(F)(F)F)cc3c(N4CCNCC4)nc(=O)n(c23)C1]

The title compound was prepared analogously to Example 102, step 4, where tert-butyl 4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 91% yield as a yellow solid
m/z (ESI, +ve)=547.1 (M+H)+.

Example 583: (3S)-8-((S)-4-acryloyl-2-methylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

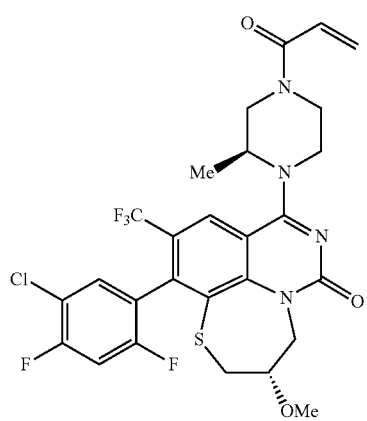 [SMILES: C=CC(=O)N1CCN(c2nc(=O)n3c4c(c(-c5cc(Cl)c(F)cc5F)c(C(F)(F)F)cc24)SC[C@@H](OC)C3)[C@@H](C)C1]

The title compound was prepared analogously to Example 84 where (3S)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 41% yield as a yellow solid
m/z (ESI, +ve)=615.1 (M+H)+.
1H NMR (400 MHz, DMSO-d6) δ 7.80-7.77 (m, 3H), 6.87-6.83 (m, 1H), 6.19 (dd, J=16.0, 4.0 Hz, 1H), 5.74 (dd, J=16.0, 4.0 Hz, 1H), 4.67-4.63 (m, 1H), 4.49-4.41 (m, 2H), 4.28-4.15 (m, 2H), 3.99-3.85 (m, 2H), 3.59-3.36 (m, 5H), 3.27-3.02 (m, 3H), 1.31 (dd, J=16.0, 4.0 Hz, 3H).

Step 1: (3S)-4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

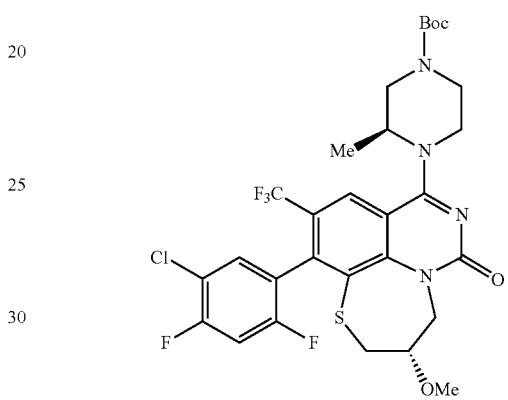

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid
m/z (ESI, +ve)=661.1 (M+H)+.

Step 2: (3S)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

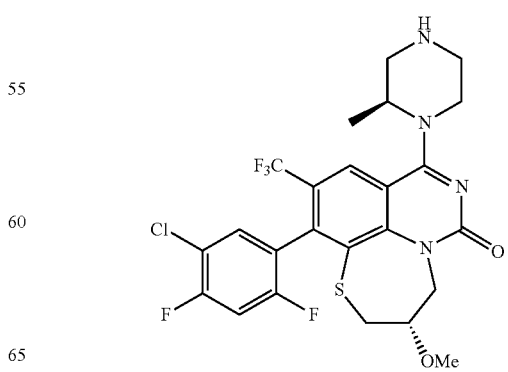

The title compound was prepared analogously to Example 102, step 4, where (3S)-4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 90% yield as a yellow solid
m/z (ESI, +ve)=561.1 (M+H)+.

Example 584: (R)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

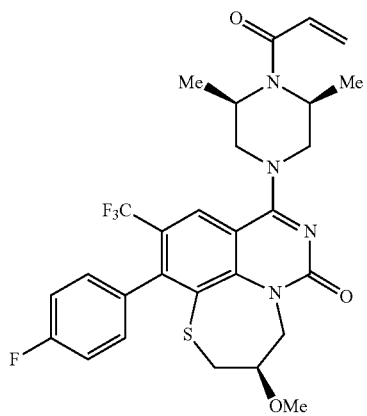 [SMILES: C=CC(=O)N1[C@H](C)CN(c2nc(=O)n3c4c(c(-c5ccc(F)cc5)c(C(F)(F)F)cc24)SC[C@H](OC)C3)C[C@@H]1C]

The title compound was prepared analogously to Example 84 where (R)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 39% yield as a yellow solid
m/z (ESI, +ve)=577.2 (M+H)+.
$^1$H NMR (400 MHz, DMSO-d6) δ 8.01 (s, 1H), 7.36-7.32 (m, 4H), 6.81 (dd, J=16.0, 8.0 Hz, 1H), 6.19 (dd, J=16.0, 4.0 Hz, 1H), 5.74 (dd, J=12.0, 4.0 Hz, 1H), 4.65-4.44 (m, 3H), 4.09-4.05 (m, 2H), 3.84-3.80 (m, 1H), 3.35-3.30 (m, 5H), 3.28-3.24 (m, 2H), 3.11-3.07 (m, 1H), 1.40 (s, 6H).

Step 1: (R)-7-(4-fluorophenyl)-8-((3-hydroxy-2-methoxypropyl)thio)-6-(trifluoromethyl)quinazoline-2,4(1H,3H)-dione

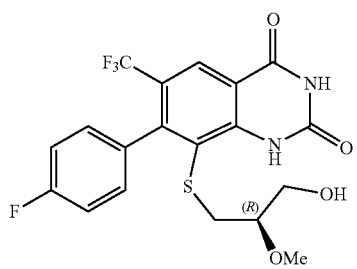

The title compound was prepared analogously to Example 100, step 9 where 7-(4-fluorophenyl)-8-iodo-6-(trifluoromethyl)quinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4 (1H,3H)-dione and 2-mercaptoethan-1-ol. The title compound was isolated in 90% yield as a yellow solid
m/z (ESI, +ve)=445.1 (M+H)+.

Step 2: (R)-11-(4-fluorophenyl)-3-methoxy-10-(trifluoromethyl)-3,4-dihydro-2H,6H-[1,4]thiazepino[2,3,4-ij]quinazoline-6,8(7H)-dione

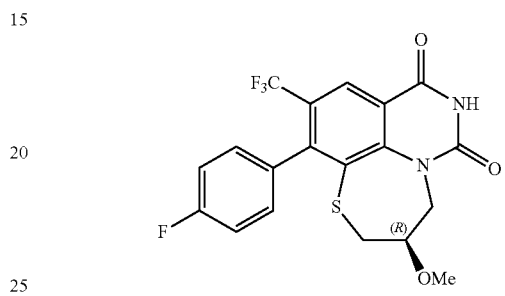

The title compound was prepared analogously to Example 100, step 10 where (R)-7-(4-fluorophenyl)-8-((3-hydroxy-2-methoxypropyl)thio)-6-(trifluoromethyl)quinazoline-2,4 (1H,3H)-dione was substituted in place of 7-(2,4-difluorophenyl)-8-((2-hydroxyethyl)thio)-6-(trifluoromethyl)quinazoline-2,4(1H,3H)-dione in 82% yield as a yellow solid
m/z (ESI, +ve)=427.1 (M+H)+.

Step 3: (R)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

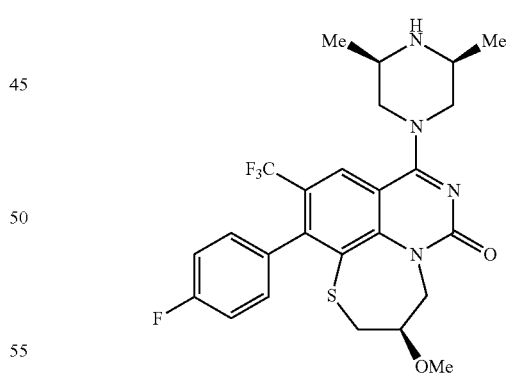

The title compound was prepared analogously to Example 100, step 21 where (R)-11-(4-fluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 73% yield as a yellow solid
m/z (ESI, +ve)=523.2 (M+H)+.

Example 585: (S)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

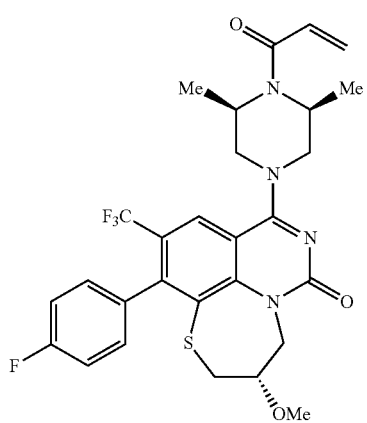 [SMILES: C=CC(=O)N1[C@H](C)CN(c2nc(=O)n3c4c(c(-c5ccc(F)cc5)c(C(F)(F)F)cc24)SC[C@@H](OC)C3)C[C@@H]1C]

The title compound was prepared analogously to Example 84 where (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 47% yield as a white solid
m/z (ESI, +ve)=577.1 (M+H)⁺.
¹H NMR (400 MHz, DMSO-d6) δ=8.02 (s, 1H), 7.36-7.34 (m, 4H), 6.82 (dd, J=16.0, 8.0 Hz, 1H), 6.19 (dd, J=16.0, 4.0 Hz, 1H), 5.74 (dd, J=16.0, 4.0 Hz, 1H), 4.59-4.48 (m, 3H), 4.09-4.05 (m, 2H), 3.84-3.82 (m, 1H), 3.33-3.32 (m, 5H), 3.28-3.24 (m, 2H), 3.12-3.08 (m, 1H), 1.40 (m, 6H).

Step 1: (S)-7-(4-fluorophenyl)-8-((3-hydroxy-2-methoxypropyl)thio)-6-(trifluoromethyl)quinazoline-2,4(1H,3H)-dione

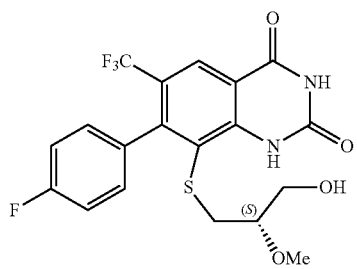

The title compound was prepared analogously to Example 100, step 9 where (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 90% yield as a yellow solid
m/z (ESI, +ve)=445.1 (M+H)⁺.

Step 2: (S)-11-(4-fluorophenyl)-3-methoxy-10-(trifluoromethyl)-3,4-dihydro-2H,6H-[1,4]thiazepino[2,3,4-ij]quinazoline-6,8(7H)-dione

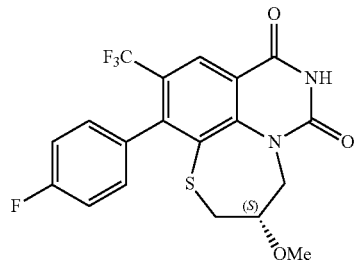

The title compound was prepared analogously to Example 100, step 10 where (S)-7-(4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 72% yield as a yellow solid
m/z (ESI, +ve)=427.1 (M+H)⁺.

Step 3: (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

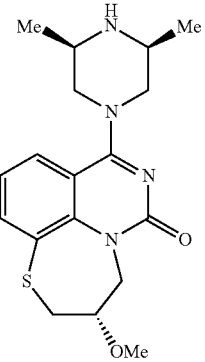

The title compound was prepared analogously to Example 100, step 21 where (S)-11-(4-fluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 53% yield as a yellow solid
m/z (ESI, +ve)=523.1 (M+H)⁺.

Example 586: (3R)-8-((3S,5R)-4-acryloyl-3,5-dimethylpiperazin-1-yl)-11-(2,4-difluorophenyl)-3-(dimethylamino)-10-(trifluoromethyl)-3,4-dihydro-2H,6H-[1,4]thiazepino[2,3,4-ij]quinazolin-6-one

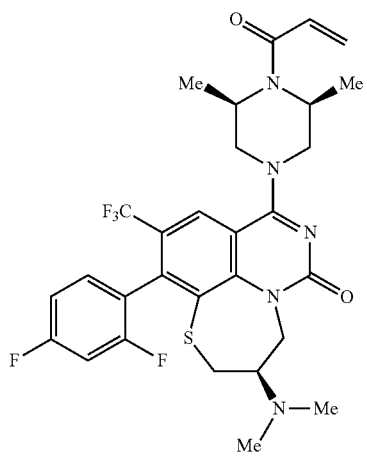 [SMILES: C=CC(=O)N1[C@H](C)CN(c2nc(=O)n3c4c(c(-c5ccc(F)cc5F)c(C(F)(F)F)cc24)SC[C@H](N(C)C)C3)C[C@@H]1C]

The title compound was prepared analogously to Example 454, where (12R)-8-(2,4-difluorophenyl)-12-(dimethylamino)-4-[(3S,5R)-3,5-dimethylpiperazin-1-yl]-7-(trifluoromethyl)-10-thia-1,3-diazatricyclo[7.4.1.0⁵,¹⁴]tetradeca-3,5(14),6,8-tetraen-2-one was substituted in place of (3S)-11-(2,4-difluorophenyl)-3-(methyl(2,2,2-trifluoroethyl)amino)-8-((S)-2-methylpiperazin-1-yl)-10-(trifluoromethyl)-3,4-dihydro-2H,6H-[1,4]thiazepino[2,3,4-ij]quinazolin-6-one. The title compound was isolated in 35% yield as a white solid m/z (ESI, +ve)=608.2

1H NMR (400 MHz, MeOD): δ 8.12 (d, J=2.1 Hz, 1H), 7.34-7.24 (m, 1H), 7.13 (ddt, J=10.8, 8.4, 2.9 Hz, 2H), 6.84 (dd, J=16.7, 10.6 Hz, 1H), 6.29 (dd, J=16.6, 2.1 Hz, 1H), 5.80 (dd, J=10.6, 2.0 Hz, 1H), 4.76 (dd, J=13.7, 2.5 Hz, 1H), 4.64-4.57 (m, 1H), 4.40-4.27 (m, 2H), 3.79-3.71 (m, 1H), 3.65-3.58 (m, 1H), 3.53-3.41 (m, 2H), 3.21-3.10 (m, 1H), 2.64-2.48 (m, 2H), 2.23 (d, J=1.9 Hz, 6H), 1.54 (dd, J=14.0, 7.0 Hz, 3H), 1.44 (dd, J=13.2, 6.9 Hz, 3H).

Step 1:
(2S)-1-benzyloxy-3-tritylsulfanyl-propan-2-ol

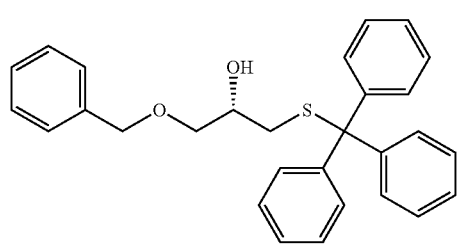 [SMILES: O[C@@H](COCc1ccccc1)CSC(c1ccccc1)(c1ccccc1)c1ccccc1]

The title compound was prepared analogously to Example 454, step 1, where (2S)-2-(benzyloxymethyl)oxirane was substituted in place of (2R)-2-(benzyloxymethyl)oxirane. The title compound was isolated in 95% yield as a colorless oil 1H NMR (400 MHz, DMSO) δ 7.38-7.19 (m, 20H), 5.04 (s, 1H), 4.39 (s, 2H), 3.54 (q, J=5.9 Hz, 1H), 3.25 (ddd, J=31.3, 9.8, 5.4 Hz, 2H), 2.33-2.15 (m, 2H).

Step 2: [(1S)-1-(benzyloxymethyl)-2-tritylsulfanyl-ethyl] methanesulfonate

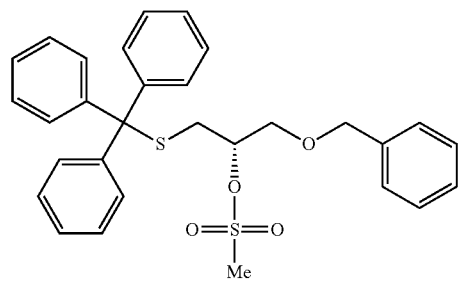 [SMILES: CS(=O)(=O)O[C@@H](COCc1ccccc1)CSC(c1ccccc1)(c1ccccc1)c1ccccc1]

The title compound was prepared analogously to Example 454, step 2, where (2S)-2-(benzyloxymethyl)oxirane was substituted in place of (2R)-2-(benzyloxymethyl)oxirane. The title compound was isolated in 52% yield as a colorless oil 1H NMR (400 MHz, CDCl3) δ 7.45-7.42 (m, 5H), 7.34-7.24 (m, 15H), 4.52-4.41 (m, 2H), 4.33 (qd, J=6.4, 4.8 Hz, 1H), 3.55-3.43 (m, 2H), 2.95 (s, 3H), 2.64 (qd, J=13.4, 6.5 Hz, 2H).

Step 3: (2R)-1-benzyloxy-N,N-dimethyl-3-tritylsulfanyl-propan-2-amine

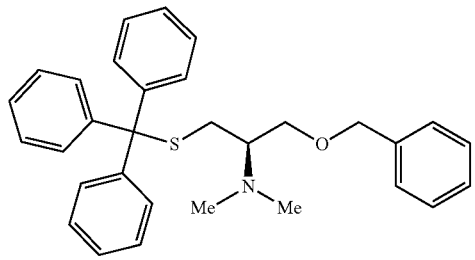 [SMILES: CN(C)[C@H](COCc1ccccc1)CSC(c1ccccc1)(c1ccccc1)c1ccccc1]

The title compound was prepared analogously to Example 454, step 3, where [(1S)-1-(benzyloxymethyl)-2-tritylsulfanyl-ethyl] methanesulfonate was substituted in place of (R)-1-(benzyloxy)-3-(tritylthio)propan-2-yl methanesulfonate. The title compound was isolated in 9% yield as a pale yellow oil m/z (ESI, +ve)=468.2

Step 4:
(2R)-3-Benzyloxy-2-(dimethylamino)propane-1-thiol

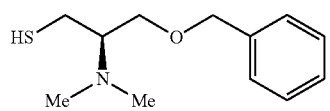 [SMILES: CN(C)[C@@H](CS)COCc1ccccc1]

The title compound was prepared analogously to Example 454, step 4, where (2R)-1-benzyloxy-N,N-dimethyl-3-tritylsulfanyl-propan-2-amine was substituted in place of (S)-1-(benzyloxy)-N-methyl-N-(2,2,2-trifluoroethyl)-3-(tritylthio)propan-2-amine. The title compound was immediately used in the next step without further purification Step 5: 8-[(2R)-3-benzyloxy-2-(dimethylamino)propyl]sulfanyl-7-(2,4-difluorophenyl)-6-(trifluoromethyl)-1H-quinazoline-2,4-dione

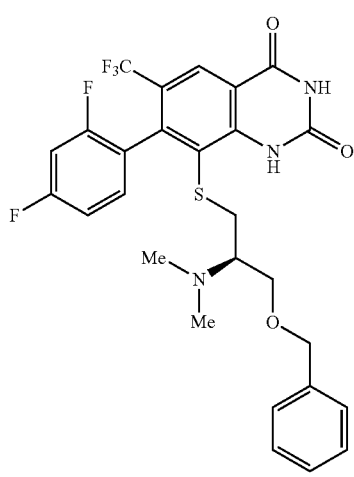 [SMILES: CN(C)[C@H](COCc1ccccc1)CSc1c(-c2ccc(F)cc2F)c(C(F)(F)F)cc2c(=O)[nH]c(=O)[nH]c12]

The title compound was prepared analogously to Example 454, step 5, where (2R)-3-Benzyloxy-2-(dimethylamino)propane-1-thiol was substituted in place of (2R)-3-benzyloxy-2-(dimethylamino)propane-1-thiol. The title compound was isolated in 71% yield as a yellow semisolid
m/z (ESI, +ve)=566.1

Step 6: 7-(2,4-difluorophenyl)-8-[(2R)-2-(dimethylamino)-3-hydroxy-propyl]sulfanyl-6-(trifluoromethyl)-1H-quinazoline-2,4-dione

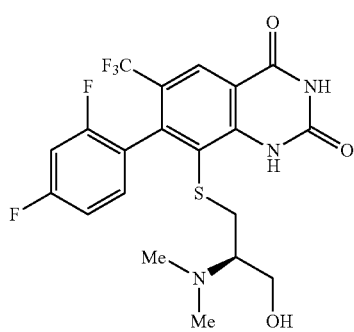 [SMILES: CN(C)[C@H](CO)CSc1c(-c2ccc(F)cc2F)c(C(F)(F)F)cc2c(=O)[nH]c(=O)[nH]c12]

To a solution of 8-[(2R)-3-benzyloxy-2-(dimethylamino)propyl]sulfanyl-7-(2,4-difluorophenyl)-6-(trifluoromethyl)-1H-quinazoline-2,4-dione (45 mg, 0.08 mmol) in dichloromethane (1 mL) precooled at −78° C. (1 mL), 0.16 mL of boron tribromide (1M in dichloromethane) was added dropwise. The reaction was stirred at −78° C. for 1 hour and after that time quenched by the addition of methanol (3 mL) and a small scoop of sodium sulfite powder. The reaction was stirred at room temperature for 10 minutes and diluted with 5 additional mL of methanol. The solids were separated by filtration and the filtrate concentrated under reduced pressure to afford the title compound which was used in the next step without further purification.
m/z (ESI, +ve)=476.1

Step 7: (12R)-8-(2,4-difluorophenyl)-12-(dimethylamino)-7-(trifluoromethyl)-10-thia-1,3-diazatricyclo[7.4.1.05,14]tetradeca-5(14),6,8-triene-2,4-dione

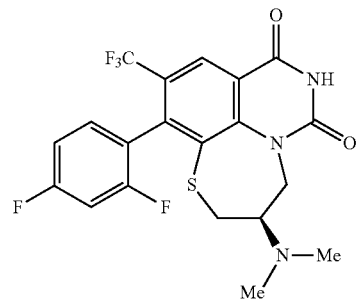 [SMILES: CN(C)[C@H]1CSc2c(-c3ccc(F)cc3F)c(C(F)(F)F)cc3c(=O)[nH]c(=O)n(c23)C1]

The title compound was prepared analogously to Example 454, step 7, where 7-(2,4-difluorophenyl)-8-[(2R)-2-(dimethylamino)-3-hydroxy-propyl]sulfanyl-6-(trifluoromethyl)-1H-quinazoline-2,4-dione was substituted in place of 7-(2,4-difluorophenyl)-8-(((S)-3-hydroxy-2-(methyl(2,2,2-trifluoroethyl)amino)propyl)thio)-6-(trifluoromethyl)quinazoline-2,4(1H,3H)-dione. The title compound was isolated in 82% yield as a white solid
m/z (ESI, +ve)=458.2

Step 8: tert-butyl (2S,6R)-4-[(12R)-8-(2,4-difluorophenyl)-12-(dimethylamino)-2-oxo-7-(trifluoromethyl)-10-thia-1,3-diazatricyclo[7.4.1.05,14]tetradeca-3,5,7,9(14)-tetraen-4-yl]-2,6-dimethyl-piperazine-1-carboxylate

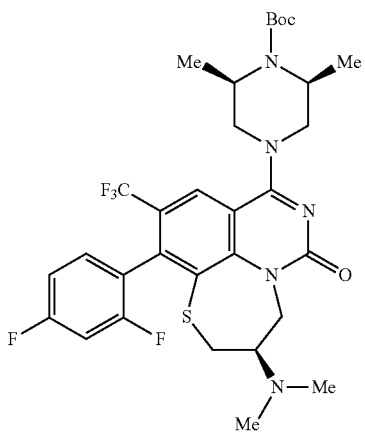 [SMILES: C[C@@H]1CN(c2nc(=O)n3c4c(c(-c5ccc(F)cc5F)c(C(F)(F)F)cc24)SC[C@H](N(C)C)C3)C[C@H](C)N1C(=O)OC(C)(C)C]

The title compound was prepared analogously to Example 100, step 21 where (12R)-8-(2,4-difluorophenyl)-12-(dimethylamino)-7-(trifluoromethyl)-10-thia-1,3-diazatricyclo[7.4.1.05,14]tetradeca-5(14),6,8-triene-2,4-dione and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 31% yield as a tan solid
m/z (ESI, +ve)=654.2

Step 9: (12R)-8-(2,4-difluorophenyl)-12-(dimethylamino)-4-[(3S,5R)-3,5-dimethylpiperazin-1-yl]-7-(trifluoromethyl)-10-thia-1,3-diazatricyclo[7.4.1.05,14]tetradeca-3,5(14),6,8-tetraen-2-one

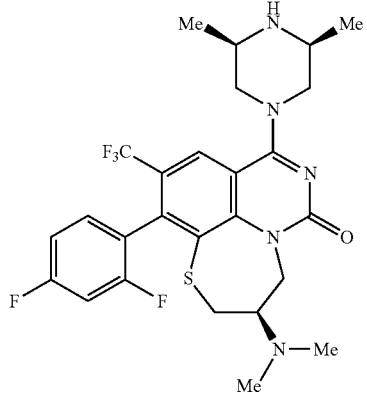 [SMILES: C[C@@H]1CN(c2nc(=O)n3c4c(c(-c5ccc(F)cc5F)c(C(F)(F)F)cc24)SC[C@H](N(C)C)C3)C[C@H](C)N1]

The title compound was prepared analogously to Example 102, step 4, where tert-butyl (2S,6R)-4-[(12R)-8-(2,4-difluorophenyl)-12-(dimethylamino)-2-oxo-7-(trifluoromethyl)-10-thia-1,3-diazatricyclo[7.4.1.05,14]tetradeca-3,5,7,9(14)-tetraen-4-yl]-2,6-dimethyl-piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a brown solid m/z (ESI, +ve)=554.2.

Select CAF data (see Example 7 below for assay) for various compounds are tabulated below:

| Example Number | IUPAC Name | MW | % CAF @ 10 uM, 1 h |
|---|---|---|---|
| 408 | 7-((S)-4-acryloyl-2-methylpiperazin-1-yl)-9-chloro-10-(5-fluoro-1H-indazol-4-yl)-2,3-dihydro-5H-[1,4]thiazino[2,3,4-ij]quinazolin-5-one | 525 | 39.3 |
| 409 | 7-((S)-4-acryloyl-2-methylpiperazin-1-yl)-9-chloro-10-(2,4,5-trifluorophenyl)-2,3-dihydro-5H-[1,4]thiazino[2,3,4-ij]quinazolin-5-one | 520.95 | 94 |
| 410 | (S)-7-((S)-4-acryloyl-2-methylpiperazin-1-yl)-9-chloro-3-((4-ethylpiperazin-1-yl)methyl)-10-(4-fluorophenyl)-2,3-dihydro-5H-[1,4]thiazino[2,3,4-ij]quinazolin-5-one | 611.17 | 83.9 |
| 411 | (3S)-7-((S)-4-acryloyl-2-methylpiperazin-1-yl)-9-chloro-10-(2,4-difluorophenyl)-3-((4-methylpiperazin-1-yl)methyl)-2,3-dihydro-5H-[1,4]thiazino[2,3,4-ij]quinazolin-5-one | 615.14 | 93.3 |
| 412 | (3S)-7-((S)-4-acryloyl-2-methylpiperazin-1-yl)-9-chloro-10-(5-chloro-2,4-difluorophenyl)-3-((4-ethylpiperazin-1-yl)methyl)-2,3-dihydro-5H-[1,4]thiazino[2,3,4-ij]quinazolin-5-one | 663.61 | 73.6 |
| 413 | (3S)-7-((S)-4-acryloyl-2-methylpiperazin-1-yl)-9-chloro-10-(2,4-difluorophenyl)-3-((1-ethylpiperidin-4-yl)methyl)-2,3-dihydro-5H-[1,4]thiazino[2,3,4-ij]quinazolin-5-one | 628.18 | 86.6 |
| 414 | (3S)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 664.16 | 92 |
| 415 | (3S)-7-((S)-4-acryloyl-2-methylpiperazin-1-yl)-9-chloro-10-(2,4-difluorophenyl)-3-((1-(oxetan-3-yl)piperidin-4-yl)methyl)-2,3-dihydro-5H-[1,4]thiazino[2,3,4-ij]quinazolin-5-one | 656.19 | 85.4 |
| 416 | (3S)-7-((S)-4-acryloyl-2-methylpiperazin-1-yl)-9-chloro-3-((4-ethylpiperazin-1-yl)methyl)-10-(2,4,5-trifluorophenyl)-2,3-dihydro-5H-[1,4]thiazino[2,3,4-ij]quinazolin-5-one | 647.15 | 91.2 |
| 417 | 7-(9-acryloyl-7,9-diazaspiro[bicyclo[3.3.1]nonane-3,3'-oxetan]-7-yl)-10-(2,4-difluorophenyl)-9-(trifluoromethyl)-2,3-dihydro-5H-[1,4]thiazino[2,3,4-ij]quinazolin-5-one | 604.59 | 2 |
| 418 | 10-(2,4-difluorophenyl)-7-(9-(2-fluoroacryloyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one | 594.53 | 58 |
| 419 | 7-((S)-4-acryloyl-2-methylpiperazin-1-yl)-9-chloro-10-(7-fluoro-1H-indazol-4-yl)-2,3-dihydro-5H-[1,4]thiazino[2,3,4-ij]quinazolin-5-one | 525 | 54.3 |

| Example Number | IUPAC Name | MW | % CAF @ 10 uM, 1 h |
|---|---|---|---|
| 420 | (E)-10-(2,4-difluorophenyl)-7-(9-(4-(dimethylamino)but-2-enoyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one | 633.63 | 93 |
| 421 | (3S)-7-((S)-4-acryloyl-2-methylpiperazin-1-yl)-9-chloro-3-((1-(oxetan-3-yl)piperidin-4-yl)methyl)-10-(2,4,5-trifluorophenyl)-2,3-dihydro-5H-[1,4]thiazino[2,3,4-ij]quinazolin-5-one | 674.18 | 85.1 |
| 422 | (3S)-7-((S)-4-acryloyl-2-methylpiperazin-1-yl)-9-chloro-3-((4-cyclopropylpiperazin-1-yl)methyl)-10-(2,4-difluorophenyl)-2,3-dihydro-5H-[1,4]thiazino[2,3,4-ij]quinazolin-5-one | 641.17 | 84.2 |
| 423 | (3S)-7-((S)-4-acryloyl-2-methylpiperazin-1-yl)-9-chloro-10-(2,4-difluorophenyl)-3-((1-methylpiperidin-4-yl)methyl)-2,3-dihydro-5H-[1,4]thiazino[2,3,4-ij]quinazolin-5-one | 614.15 | 34.1 |
| 424 | (R)-7-((S)-4-acryloyl-2-methylpiperazin-1-yl)-9-chloro-3-((1-ethylpiperidin-4-yl)methyl)-10-(2,4,6-trifluorophenyl)-2,3-dihydro-5H-[1,4]thiazino[2,3,4-ij]quinazolin-5-one | 646.17 | 13.9 |
| 425 | (S)-7-((S)-4-acryloyl-2-methylpiperazin-1-yl)-10-(4-fluorophenyl)-3-((1-(oxetan-3-yl)piperidin-4-yl)methyl)-9-(trifluoromethyl)-2,3-dihydro-5H-[1,4]thiazino[2,3,4-ij]quinazolin-5-one | 671.75 | 94.7 |
| 426 | (3S)-7-((S)-4-acryloyl-2-methylpiperazin-1-yl)-9-chloro-10-(5-chloro-2,4-difluorophenyl)-3-41-(oxetan-3-yl)piperidin-4-yl)methyl)-2,3-dihydro-5H-[1,4]thiazino[2,3,4-ij]quinazolin-5-one | 690.63 | 82.8 |
| 427 | 7-((S)-4-acryloyl-2-methylpiperazin-1-yl)-9-chloro-10-(2-chloro-4-fluorophenyl)-2,3-dihydro-5H-[1,4]thiazino[2,3,4-ij]quinazolin-5-one | 519.42 | 63.5 |
| 428 | (S)-7-((S)-4-acryloyl-2-methylpiperazin-1-yl)-3-((1-(2,2-difluoroethyl)piperidin-4-yl)methyl)-10-(4-fluorophenyl)-9-(trifluoromethyl)-2,3-dihydro-5H-[1,4]thiazino[2,3,4-ij]quinazolin-5-one | 679.72 | 79.6 |
| 429 | (3S)-7-((S)-4-acryloyl-2-methylpiperazin-1-yl)-3-((1-(2,2-difluoroethyl)piperidin-4-yl)methyl)-10-(2,4-difluorophenyl)-9-(trifluoromethyl)-2,3-dihydro-5H-[1,4]thiazino[2,3,4-ij]quinazolin-5-one 1,1-dioxide | 729.71 | 61 |
| 430 | (S)-7-((S)-4-acryloyl-2-methylpiperazin-1-yl)-10-(4-fluorophenyl)-9-(trifluoromethyl)-3-43-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 722.68 | 90.9 |
| 431 | (3S)-8-((S)-4-acryloyl-2-methylpiperazin-1-yl)-11-(2,4-difluorophenyl)-3-hydroxy-10-(trifluoromethyl)-3,4-dihydro-2H,6H-[1,4]thiazepino[2,3,4-ij]quinazolin-6-one | 566.54 | 90 |
| 432 | (3R)-7-((S)-4-acryloyl-2-methylpiperazin-1-yl)-9-chloro-10-(2,4-difluorophenyl)-3-(((1-ethylazetidin-3-yl)oxy)methyl)-2,3-dihydro-5H-[1,4]thiazino[2,3,4-ij]quinazolin-5-one | 616.12 | 2.6 |
| 433 | 7'-((S)-4-acryloyl-2-methylpiperazin-1-yl)-9'-chloro-10'-(2,4-difluorophenyl)-3'H,5'H-spiro[cyclopropane-1,2'-[1,4]thiazino[2,3,4-ij]quinazolin]-5'-one | 529 | 25.3 |
| 434 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2,3-dihydro-5H-[1,4]thiazino[2,3,4-ij]quinazolin-5-one 1,1-dioxide | 693.73 | 51.5 |
| 435 | (3S)-7-((S)-4-acryloyl-2-methylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 580.57 | 95.8 |
| 436 | (3S)-7-((S)-4-acryloyl-2-methylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one 1,1-dioxide | 612.57 | 72.5 |

-continued

| Example Number | IUPAC Name | MW | % CAF @ 10 uM, 1 h |
|---|---|---|---|
| 437 | (3S)-7-((S)-4-acryloyl-2-methylpiperazin-1-yl)-10-(2,4-difluorophenyl)-3-((tetrahydro-2H-pyran-4-yl)methyl)-9-(trifluoromethyl)-2,3-dihydro-5H-[1,4]thiazino[2,3,4-ij]quinazolin-5-one | 634.66 | 95.7 |
| 438 | (3S)-7-((S)-4-acryloyl-2-methylpiperazin-1-yl)-9-chloro-10-(2,4-difluorophenyl)-3-((tetrahydro-2H-pyran-4-yl)methyl)-2,3-dihydro-5H-[1,4]thiazino[2,3,4-ij]quinazolin-5-one | 601.11 | 92.8 |
| 439 | (E)-7-(9-(4,4-difluorobut-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one | 626.55 | 97 |
| 440 | (E)-10-(2,4-difluorophenyl)-7-(7-oxo-9-(4,4,4-trifluorobut-2-enoyl)-3,9-diazabicyclo[3.3.1]nonan-3-yl)-9-(trifluoromethyl)-2,3-dihydro-5H-[1,4]thiazino[2,3,4-ij]quinazolin-5-one | 644.54 | 96 |
| 441 | 7-((S)-4-acryloyl-2-methylpiperazin-1-yl)-9-chloro-10-(5-fluoroquinolin-8-yl)-2,3-dihydro-5H-[1,4]thiazino[2,3,4-ij]quinazolin-5-one | 536.02 | 78.5 |
| 442 | (2S)-7-((S)-4-acryloyl-2-methylpiperazin-1-yl)-10-(2,4-difluorophenyl)-2-((dimethylamino)methyl)-9-(trifluoromethyl)-2,3-dihydro-5H-[1,4]thiazino[2,3,4-ij]quinazolin-5-one | 593.61 | 87 |
| 443 | (3S)-7-((2S,5R)-4-acryloyl-2,5-dimethylpiperazin-1-yl)-3-((4-(2,2-difluoroethyl)piperazin-1-yl)methyl)-9-(trifluoromethyl)-10-(2,4,5-trifluorophenyl)-2,3-dihydro-5H-[1,4]thiazino[2,3,4-ij]quinazolin-5-one | 730.71 | 48.2 |
| 444 | (S)-7-((S)-4-acryloyl-2-methylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 689.13 | 24.1 |
| 445 | (S)-7-((2S,5R)-4-acryloyl-2,5-dimethylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 703.15 | 68.2 |
| 446 | (3R)-7-((S)-4-acryloyl-2-methylpiperazin-1-yl)-9-chloro-10-(5-chloro-2,4-difluorophenyl)-3-((methoxymethoxy)methyl)-2,3-dihydro-5H-[1,4]thiazino[2,3,4-ij]quinazolin-5-one | 611.49 | 38 |
| 447 | (3S)-7-((S)-4-acryloyl-2-methylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 741.56 | 63.3 |
| 448 | (3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 755.59 | 55 |
| 449 | (3S)-3-((2-oxa-7-azaspiro[3.5]nonan-7-yl)methyl)-7-((2S,5R)-4-acryloyl-2,5-dimethylpiperazin-1-yl)-9-chloro-10-(5-chloro-2,4-difluorophenyl)-2,3-dihydro-5H-[1,4]thiazino[2,3,4-ij]quinazolin-5-one | 690.63 | 51.6 |
| 450 | 8-((S)-4-acryloyl-2-methylpiperazin-1-yl)-11-(2,4-difluorophenyl)-10-(trifluoromethyl)-3,4-dihydro-2H,6H-[1,4]thiazepino[2,3,4-ij]quinazolin-6-one | 550.54 | 61 |
| 451 | 11-(2,4-difluorophenyl)-8-(9-(2-fluoroacryloyl)-7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one | 608.55 | 61 |
| 452 | (E)-7-(9-(but-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one | 590.56 | 63 |
| 453 | 7-(9-(but-2-ynoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one | | 37 |
| 454 | (3S)-8-((S)-4-acryloyl-2-methylpiperazin-1-yl)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazolin-6-one | 661.61 | 61 |

| Example Number | IUPAC Name | MW | % CAF @ 10 uM, 1 h |
|---|---|---|---|
| 455 | (S)-8-(4-acryloyl-2-methylpiperazin-1-yl)-10-(trifluoromethyl)-11-(2,4,6-trifluorophenyl)-3,4-dihydro-2H,6H-[1,4]thiazepino[2,3,4-ij]quinazolin-6-one | 534.98 | 21 |
| 456 | (3S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 676.6 | 77.6 |
| 457 | (3S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 699.59 | 76.8 |
| 458 | (3S)-7-((S)-4-acryloyl-2-methylpiperazin-1-yl)-9-chloro-10-(5-chloro-2,4-difluorophenyl)-3-((4-cyclopropylpiperazin-1-yl)methyl)-2,3-dihydro-5H-[1,4]thiazino[2,3,4-ij]quinazolin-5-one | 675.62 | 55.6 |
| 459 | (3S)-7-((S)-4-acryloyl-2-methylpiperazin-1-yl)-9-chloro-3-((3-(trifluoromethyl)-5,6-dihydro-[1,2,4]triazolo[4,3-a]pyrazin-7(8H)-yl)methyl)-10-(2,4,5-trifluorophenyl)-2,3-dihydro-5H-[1,4]thiazino[2,3,4-ij]quinazolin-5-one | 739.13 | 82.2 |
| 460 | (3S)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 674.18 | 79.7 |
| 461 | (3S)-7-((2S,5R)-4-acryloyl-2,5-dimethylpiperazin-1-yl)-9-chloro-10-(5-chloro-2,4-difluorophenyl)-3-((1-(2,2-difluoroethyl)piperidin-4-yl)methyl)-2,3-dihydro-5H-[1,4]thiazino[2,3,4-ij]quinazolin-5-one | 712.63 | 79.5 |
| 462 | (S)-3-((2-oxa-7-azaspiro[3.5]nonan-7-yl)methyl)-7-((S)-4-acryloyl-2-methylpiperazin-1-yl)-9-chloro-10-(4-fluorophenyl)-2,3-dihydro-5H-[1,4]thiazino[2,3,4-ij]quinazolin-5-one | 624.17 | 87.8 |
| 463 | (3S)-7-((S)-4-acryloyl-2-methylpiperazin-1-yl)-9-chloro-3-43-(trifluoromethyl)-5,6-dihydro-[1,2,41triazolo[4,3-a]pyrazin-7(8H)-yl)methyl)-10-(2,4,5-trifluorophenyl)-2,3-dihydro-5H-[1,4]thiazino[2,3,4-ij]quinazolin-5-one | 725.11 | 69 |
| 464 | (3S)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 580.57 | 95 |
| 465 | (3R)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 580.57 | 96 |
| 466 | (3R)-7-((S)-4-acryloyl-2-methylpiperazin-1-yl)-9-chloro-3-((methoxymethoxy)methyl)-10-(2,4,5-trifluorophenyl)-2,3-dihydro-5H-[1,4]thiazino[2,3,4-ij]quinazolin-5-one | 595.03 | 22.6 |
| 467 | (3S)-7-((2S,5R)-4-acryloyl-2,5-dimethylpiperazin-1-yl)-9-chloro-10-(5-chloro-2,4-difluorophenyl)-3-((1-cyclopropylpiperidin-4-yl)methyl)-2,3-dihydro-5H-1,4]thiazino[2,3,4-ij]quinazolin-5-one | 688.66 | 44.3 |
| 468 | (3S)-7-((2S,5R)-4-acryloyl-2,5-dimethylpiperazin-1-yl)-9-chloro-10-(2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 721.14 | 68.6 |
| 469 | (3S)-3-((2-oxa-7-azaspiro[3.5]nonan-7-yl)methyl)-7-((S)-4-acryloyl-2-methylpiperazin-1-yl)-9-chloro-10-(2,4,5-trifluorophenyl)-2,3-dihydro-5H-[1,4]thiazino[2,3,4-ij]quinazolin-5-one | 660.15 | 57.8 |
| 470 | (3R)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 645.04 | 35 |
| 471 | (3R)-7-((S)-4-acryloyl-2-methylpiperazin-1-yl)-3-((methoxymethoxy)methyl)-9-(trifluoromethyl)-10-(2,4,5-trifluorophenyl)-2,3-dihydro-5H-[1,4]thiazino[2,3,4-ij]quinazolin-5-one | 628.59 | 23.9 |

| Example Number | IUPAC Name | MW | % CAF @ 10 uM, 1 h |
|---|---|---|---|
| 472 | (3S)-3-((2-oxa-7-azaspiro[3.5]nonan-7-yl)methyl)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 642.16 | 72.3 |
| 473 | (S)-3-42-oxa-7-azaspiro[3.5]nonan-7-yl)methyl)-7-((2S,5R)-4-acryloyl-2,5-dimethylpiperazin-1-yl)-9-chloro-10-(4-fluorophenyl)-2,3-dihydro-5H-[1,4]thiazino[2,3,4-ij]quinazolin-5-one | 638.2 | 65.8 |
| 474 | (3S)-7-((S)-4-acryloyl-2-methylpiperazin-1-yl)-9-chloro-10-(5-fluoroquinolin-8-yl)-3-(methoxymethyl)-2,3-dihydro-5H-[1,4]thiazino[2,3,4-ij]quinazolin-5-one | 580.07 | 73.3 |
| 475 | (3S)-7-((2S,5R)-4-acryloyl-2,5-dimethylpiperazin-1-yl)-9-chloro-3-((1-cyclopropylpiperidin-4-yl)methyl)-10-(2,4,5-trifluorophenyl)-2,3-dihydro-5H-[1,4]thiazino[2,3,4-ij]quinazolin-5-one | 672.2 | 49.8 |
| 476 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4,5-trifluorophenyl)-2,3-dihydro-5H-[1,4]thiazino[2,3,4-ij]quinazolin-5-one | 696.17 | 53.8 |
| 477 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4-difluorophenyl)-2,3-dihydro-5H-[1,4]thiazino[2,3,4-ij]quinazolin-5-one | 678.18 | 63.5 |
| 478 | (3S)-7-((2S,5R)-4-acryloyl-2,5-dimethylpiperazin-1-yl)-9-chloro-3-((1-cyclopropylpiperidin-4-yl)methyl)-10-(2,4-difluorophenyl)-2,3-dihydro-5H-[1,4]thiazino[2,3,4-ij]quinazolin-5-one | 654.21 | 70.7 |
| 479 | (3R)-7-((S)-4-acryloyl-2-methylpiperazin-1-yl)-9-chloro-10-(2,4-difluorophenyl)-3-((methoxymethoxy)methyl)-2,3-dihydro-5H-[1,4]thiazino[2,3,4-ij]quinazolin-5-one | 577.04 | 42 |
| 480 | (3S)-7-((S)-4-acryloyl-2-methylpiperazin-1-yl)-9-chloro-3-((4-(2,2-difluoroethyl)piperazin-1-yl)methyl)-10-(2,4,5-trifluorophenyl)-2,3-dihydro-5H-[1,4]thiazino[2,3,4-ij]quinazolin-5-one | 683.13 | 61.2 |
| 481 | (S)-7-((2S,5R)-4-acryloyl-2,5-dimethylpiperazin-1-yl)-3-((1-(2,2-difluoroethyDazetidin-3-yl)methyl)-10-(4-fluorophenyl)-9-(trifluoromethyl)-2,3-dihydro-5H-[1,4]thiazino[2,3,4-ij]quinazolin-5-one | 665.69 | 59.4 |
| 482 | (3S,10S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 676.6 | 90 |
| 483 | (3S,10R)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 676.6 | 15.7 |
| 484 | (3S,10S)-3-42-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 674.18 | 77.9 |
| 485 | (3S,10R)-3-42-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 674.18 | 45 |
| 486 | 8-(9-acryloyl-7-oxo-3,9-diazabicyclo[3.3.1]nonan-3-yl)-11-(2,4-difluorophenyl)-10-(trifluoromethyl)-3,4-dihydro-2H,6H-[1,4]thiazepino[2,3,4-ij]quinazolin-6-one | 590.56 | 95 |
| 487 | (3S)-8-((S)-4-acryloyl-2-methylpiperazin-1-yl)-10-chloro-11-(2,4-difluorophenyl)-3-methoxy-3,4-dihydro-2H,6H-[1,4]thiazepino[2,3,4-ij]quinazolin-6-one | 547.02 | 96 |
| 488 | (3R)-8-((S)-4-acryloyl-2-methylpiperazin-1-yl)-10-chloro-11-(2,4-difluorophenyl)-3-methoxy-3,4-dihydro-2H,6H-[1,4]thiazepino[2,3,4-ij]quinazolin-6-one | 547.02 | 96 |
| 489 | (3S)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 566.54 | 96 |

-continued

| Example Number | IUPAC Name | MW | % CAF @ 10 uM, 1 h |
|---|---|---|---|
| 490 | (3R)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 566.54 | |
| 491 | (3S)-7-((2S,5R)-4-acryloyl-2,5-dimethylpiperazin-1-yl)-3-(methoxymethyl)-9-(trifluoromethyl)-10-(2,4,5-trifluorophenyl)-2,3-dihydro-5H-[1,4]thiazino[2,3,4-ij]quinazolin-5-one | 612.59 | 60 |
| 492 | (3S)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 63.2 |
| 493 | (3S)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 78.6 |
| 494 | (3S)-7-((2S,5R)-4-acryloyl-2,5-dimethylpiperazin-1-yl)-9-chloro-10-(2,4-difluorophenyl)-3-(methoxymethyl)-2,3-dihydro-5H-[1,4]thiazino[2,3,4-ij]quinazolin-5-one | 561.04 | 68.7 |
| 495 | (3S)-7-((2S,5R)-4-acryloyl-2,5-dimethylpiperazin-1-yl)-9-chloro-10-(5-chloro-2,4-difluorophenyl)-3-((4-(2,2-difluoroethyl)piperazin-1-yl)methyl)-2,3-dihydro-5H-[1,4]thiazino[2,3,4-ij]quinazolin-5-one | 713.62 | 50.8 |
| 496 | (3S)-7-((2S,5R)-4-acryloyl-2,5-dimethylpiperazin-1-yl)-9-chloro-10-(5-chloro-2,4-difluorophenyl)-3-(methoxymethyl)-2,3-dihydro-5H-[1,4]thiazino[2,3,4-ij]quinazolin-5-one | 595.49 | 65.3 |
| 497 | (S)-7-((2S,5R)-4-acryloyl-2,5-dimethylpiperazin-1-yl)-10-(4-fluorophenyl)-3-(methoxymethyl)-9-(trifluoromethyl)-2,3-dihydro-5H-[1,4]thiazino[2,3,4-ij]quinazolin-5-one | 576.61 | 85.1 |
| 498 | (3S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 638.65 | 81.2 |
| 499 | (3S)-7-((2S,5R)-4-acryloyl-2,5-dimethylpiperazin-1-yl)-9-chloro-10-(5-chloro-2,4-difluorophenyl)-3-((4-cyclopropylpiperazin-1-yl)methyl)-2,3-dihydro-5H-[1,4]thiazino[2,3,4-ij]quinazolin-5-one | 689.65 | 28 |
| 500 | (3S)-3-(((1S,4S)-2-oxa-5-azabicyclo[2.2.1]heptan-5-yl)methyl)-7-((2S,5R)-4-acryloyl-2,5-dimethylpiperazin-1-yl)-9-chloro-10-(5-chloro-2,4-difluorophenyl)-2,3-dihydro-5H-[1,4]thiazino[2,3,4-ij]quinazolin-5-one | 662.58 | 50.6 |
| 501 | (3S)-7-((2S,5R)-4-acryloyl-2,5-dimethylpiperazin-1-yl)-9-chloro-10-(2,4-difluorophenyl)-3-((2-methoxyethoxy)methyl)-2,3-dihydro-5H-[1,4]thiazino[2,3,4-ij]quinazolin-5-one | 605.1 | 66.8 |
| 502 | (3S)-7-((2S,5R)-4-acryloyl-2,5-dimethylpiperazin-1-yl)-9-chloro-10-(5-chloro-2,4-difluorophenyl)-3-((2-methoxyethoxy)methyl)-2,3-dihydro-5H-[1,4]thiazino[2,3,4-ij]quinazolin-5-one | 639.54 | 65.1 |
| 503 | (3S)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 594.6 | 96 |
| 504 | (3S)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one | 532.99 | 96 |
| 505 | (3S)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one | 561.04 | 95 |
| 506 | (3S)-7-((3S,5R)-4-acryloyl-3,5-dimethylpiperazin-1-yl)-9-chloro-3-(methoxymethyl)-10-(2,4,5-trifluorophenyl)-2,3-dihydro-5H-[1,4]thiazino[2,3,4-ij]quinazolin-5-one | 579.03 | 17.5 |
| 507 | (2S)-7-((S)-4-acryloyl-2-methylpiperazin-1-yl)-10-(2,4-difluorophenyl)-2-(methoxymethyl)-9-(trifluoromethyl)-2,3-dihydro-5H-[1,4]thiazino[2,3,4-ij]quinazolin-5-one | 580.57 | 71 |

| Example Number | IUPAC Name | MW | % CAF @ 10 uM, 1 h |
|---|---|---|---|
| 508 | (3S,10S)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 92 |
| 509 | (3S,10R)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 96.5 |
| 510 | (3S,10S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 638.65 | 72.9 |
| 511 | (3S,10R)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 638.65 | 80.6 |
| 512 | S)-7-((2S,5R)-4-acryloyl-2,5-dimethylpiperazin-1-yl)-10-(4-fluorophenyl)-3-((2-methoxyethoxy)methyl)-9-(trifluoromethyl)-2,3-dihydro-5H-[1,4]thiazino[2,3,4-ij]quinazolin-5-one | 620.66 | 66.1 |
| 513 | (3S)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 96.2 |
| 514 | (3S)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 566.54 | 96.1 |
| 515 | (S)-7-((2S,5R)-4-acryloyl-2,5-dimethylpiperazin-1-yl)-9-chloro-3-((4-(2,2-difluoroethyl)piperazin-1-yl)methyl)-10-(4-fluorophenyl)-2,3-dihydro-5H-[1,4]thiazino[2,3,4-ij]quinazolin-5-one | 661.18 | 55.1 |
| 516 | (S)-7-((S)-4-acryloyl-2-methylpiperazin-1-yl)-10-(4-fluorophenyl)-3-((methoxymethoxy)methyl)-9-(trifluoromethyl)-2,3-dihydro-5H-[1,4]thiazino[2,3,4-ij]quinazolin-5-one | 592.6 | 74.4 |
| 517 | (S)-7-((2S,5R)-4-acryloyl-2,5-dimethylpiperazin-1-yl)-9-chloro-3-((4-cyclopropylpiperazin-1-yl)methyl)-10-(4-fluorophenyl)-2,3-dihydro-5H-[1,4]thiazino[2,3,4-ij]quinazolin-5-one | 637.21 | 59.5 |
| 518 | (3S)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 645.04 | |
| 519 | (3S)-3-(((1S,4S)-2-oxa-5-azabicyclo[2.2.1]heptan-5-yl)methyl)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one | 628.13 | 61.3 |
| 520 | (3S)-7-((S)-4-acryloyl-2-methylpiperazin-1-yl)-9-chloro-3-((4-cyclopropylpiperazin-1-yl)methyl)-10-(2,4,5-trifluorophenyl)-2,3-dihydro-5H-[1,4]thiazino[2,3,4-ij]quinazolin-5-one | 659.16 | 51.1 |
| 521 | (3S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2,3-dihydro-5H-[1,4]thiazino[2,3,4-ij]quinazolin-5-one | 747.17 | 40.6 |
| 522 | (3S)-7-((S)-4-acryloyl-2-methylpiperazin-1-yl)-3-((methoxymethoxy)methyl)-9-(trifluoromethyl)-10-(2,4,5-trifluorophenyl)-2,3-dihydro-5H-[1,4]thiazino[2,3,4-ij]quinazolin-5-one | 628.59 | 72.4 |
| 523 | (3S)-7-(9-acryloyl-7,7-difluoro-3,9-diazabicyclo[3.3.1]nonan-3-yl)-10-(2,4-difluorophenyl)-3-(methoxymethyl)-9-(trifluoromethyl)-2,3-dihydro-5H-[1,4]thiazino[2,3,4-ij]quinazolin-5-one | 642.59 | 68.9 |
| 524 | (3R)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 594.6 | 95 |

-continued

| Example Number | IUPAC Name | MW | % CAF @ 10 uM, 1 h |
|---|---|---|---|
| 525 | (3R)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one | 532.99 | 86 |
| 526 | (3R)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one | 561.04 | 93 |
| 527 | (R)-8-((S)-4-acryloyl-2-methylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one | 562.58 | 97 |
| 528 | (R)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one | 529.03 | 98 |
| 529 | (3S)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | 581.46 | 95 |
| 530 | (3S)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | 595.49 | 92 |
| 531 | 8'-((3S,5R)-4-acryloyl-3,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 606.61 | 88.6 |
| 532 | (S)-8-((S)-4-acryloyl-2-methylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one | 562.58 | 97 |
| 533 | (3R)-8-((S)-4-acryloyl-2-methylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 615.01 | 96 |
| 534 | (3R)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 600.99 | 97 |
| 535 | (3R)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 629.04 | 96 |
| 536 | (S)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one | 515 | 97 |
| 537 | (S)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one | 529.03 | 96 |
| 538 | (3R)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | 567.43 | 97 |
| 539 | (3S)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | | 96 |
| 540 | (R)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one | | 98 |
| 541 | (3R)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | | 96 |
| 542 | (3R)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | | 96 |
| 543 | (3S)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | | 97 |

-continued

| Example Number | IUPAC Name | MW | % CAF @ 10 uM, 1 h |
|---|---|---|---|
| 544 | (3S,10S)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 48.8 |
| 545 | (3S,10R)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 94.1 |
| 546 | (3S,10S)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 94.3 |
| 547 | (3S,10R)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 96.7 |
| 548 | (3S,10R)-7-((S)-4-acryloyl-2-methylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one | 610.6 | 95.7 |
| 549 | (3S,10S)-7-((S)-4-acryloyl-2-methylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one | 610.6 | 80.2 |
| 550 | (3S)-7-((2S,5R)-4-acryloyl-2,5-dimethylpiperazin-1-yl)-9-chloro-3-((4-(2,2-difluoroethyl)piperazin-1-yl)methyl)-10-(2,4-difluorophenyl)-2,3-dihydro-5H-[1,4]thiazino[2,3,4-ij]quinazolin-5-one | 679.17 | 91.6 |
| 551 | (3S)-7-((2S,5R)-4-acryloyl-2,5-dimethylpiperazin-1-yl)-9-chloro-3-((4-cyclopropylpiperazin-1-yl)methyl)-10-(2,4-difluorophenyl)-2,3-dihydro-5H-[1,4]thiazino[2,3,4-ij]quinazolin-5-one | 655.2 | 53.4 |
| 552 | (3S,10R)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 645.04 | 62.2 |
| 553 | (3S,10S)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 645.04 | 37 |
| 554 | (3S,10S)-7-((2S,5R)-4-acryloyl-2,5-dimethylpiperazin-1-yl)-10-(5-chloro-2,4-difluorophenyl)-3-((2-methoxyethoxy)methyl)-9-(trifluoromethyl)-2,3-dihydro-5H-[1,4]thiazino[2,3,4-ij]quinazolin-5-one | 673.09 | 11.3 |
| 555 | (3S,10R)-7-((2S,5R)-4-acryloyl-2,5-dimethylpiperazin-1-yl)-10-(5-chloro-2,4-difluorophenyl)-3-((2-methoxyethoxy)methyl)-9-(trifluoromethyl)-2,3-dihydro-5H-[1,4]thiazino[2,3,4-ij]quinazolin-5-one | 673.09 | 67.6 |
| 556 | (3S,10R)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2,3-dihydro-5H-[1,4]thiazino[2,3,4-ij]quinazolin-5-one | 747.17 | 73.1 |
| 557 | (3S,10S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2,3-dihydro-5H-[1,4]thiazino[2,3,4-ij]quinazolin-5-one | 747.17 | 21.2 |
| 558 | (S)-7-((2S,5R)-4-acryloyl-2,5-dimethylpiperazin-1-yl)-9-chloro-10-(4-fluorophenyl)-3-((2-methoxyethoxy)methyl)-2,3-dihydro-5H-[1,4]thiazino[2,3,4-ij]quinazolin-5-one | 587.11 | 64.3 |
| 559 | (3S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 83.8 |

-continued

| Example Number | IUPAC Name | MW | % CAF @ 10 uM, 1 h |
|---|---|---|---|
| 560 | (3S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one | 661.69 | 95.6 |
| 561 | 2-(4-(((3S)-7-((2S,5R)-4-acryloyl-2,5-dimethylpiperazin-1-yl)-10-(2,4-difluorophenyl)-5-oxo-9-(trifluoromethyl)-2,3-dihydro-5H-[1,4]thiazino[2,3,4-ij]quinazolin-3-yl)methyl)piperazin-1-yl)acetonitrile | 687.73 | 10.4 |
| 562 | (3S)-7-((2S,5R)-4-acryloyl-2,5-dimethylpiperazin-1-yl)-3-((4-(2,2-difluoroethyl)piperazin-1-yl)methyl)-10-(2,4-difluorophenyl)-9-(trifluoromethyl)-2,3-dihydro-5H-[1,4]thiazino[2,3,4-ij]quinazolin-5-one | 712.72 | 83.6 |
| 563 | (3S,10R)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 93.9 |
| 564 | (3S,10S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 80.8 |
| 565 | (3S,10S)-3-42-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one | 724.18 | 48.3 |
| 566 | (3S,10R)-3-42-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one | 724.18 | 77.7 |
| 567 | (3S)-7-((3S,5R)-4-acryloyl-3,5-dimethylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 659.07 | 64.4 |
| 568 | (3S)-7-((3S,5R)-4-acryloyl-3,5-dimethylpiperazin-1-yl)-10-(5-chloro-2,4-difluorophenyl)-3-(hydroxymethyl)-9-(trifluoromethyl)-2,3-dihydro-5H-[1,4]thiazino[2,3,4-ij]quinazolin-5-one | 615.01 | 52.3 |
| 569 | (3S,10R)-7-((2S,5R)-4-acryloyl-2,5-dimethylpiperazin-1-yl)-9-chloro-3-((4-(2,2-difluoroethyl)piperazin-1-yl)methyl)-10-(1-methyl-1H-indazol-7-yl)-2,3-dihydro-5H-[1,4]thiazino[2,3,4-ij]quinazolin-5-one | 697.24 | 93.4 |
| 570 | (3S,10S)-7-((2S,5R)-4-acryloyl-2,5-dimethylpiperazin-1-yl)-9-chloro-3-((4-(2,2-difluoroethyl)piperazin-1-yl)methyl)-10-(1-methyl-1H-indazol-7-yl)-2,3-dihydro-5H-[1,4]thiazino[2,3,4-ij]quinazolin-5-one | 697.24 | 0 |
| 571 | (3S)-7-(9-acryloyl-7-oxo-3,9-diazabicyclo[3.3.1]nonan-3-yl)-10-(2,4-difluorophenyl)-3-(methoxymethyl)-9-(trifluoromethyl)-2,3-dihydro-5H-[1,4]thiazino[2,3,4-ij]quinazolin-5-one | 620.59 | 95.2 |
| 572 | (3S)-7-(4-acryloylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 600.99 | 93.6 |
| 573 | (S)-7-((2S,5R)-4-acryloyl-2,5-dimethylpiperazin-1-yl)-9-chloro-10-(4-fluorophenyl)-3-(methoxymethyl)-2,3-dihydro-5H-[1,4]thiazino[2,3,4-ij]quinazolin-5-one | 543.05 | 76.4 |
| 574 | (S)-7-((2S,5R)-4-acryloyl-2,5-dimethylpiperazin-1-yl)-3-((4-(2,2-difluoroethyl)piperazin-1-yl)methyl)-10-(4-fluorophenyl)-9-(trifluoromethyl)-2,3-dihydro-5H-[1,4]thiazino[2,3,4-ij]quinazolin-5-one | 694.73 | 83.2 |

| Example Number | IUPAC Name | MW | % CAF @ 10 uM, 1 h |
|---|---|---|---|
| 575 | 2-(4-(((3S)-7-((2S,5R)-4-acryloyl-2,5-dimethylpiperazin-1-yl)-10-(2,4-difluorophenyl)-5-oxo-9-(trifluoromethyl)-2,3-dihydro-5H-[1,4]thiazino[2,3,4-ij]quinazolin-3-yl)methyl)piperazin-1-yl)acetamide | 705.74 | 89.5 |
| 576 | (3S,10S)-3-42-oxa-7-azaspiro[3.5]nonan-7-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one | 689.74 | 80.5 |
| 577 | (3S,10R)-3-((2-oxa-7-azaspiro[3.5]nonan-7-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one | 689.74 | 74.8 |
| 578 | (3S,10R)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 566.54 | 98 |
| 579 | (3S,10S)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 566.54 | 96.9 |
| 580 | (3S,10S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 688.75 | 91.5 |
| 581 | (3S,10R)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 688.75 | 97.4 |
| 582 | (3S)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 600.99 | 88 |
| 583 | (3S)-8-((S)-4-acryloyl-2-methylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 615.01 | 91 |
| 584 | (R)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one | 576.61 | 97 |
| 585 | (S)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one | 576.61 | 97 |
| 586 | (3R)-8-((3S,5R)-4-acryloyl-3,5-dimethylpiperazin-1-yl)-11-(2,4-difluorophenyl)-3-(dimethylamino)-10-(trifluoromethyl)-3,4-dihydro-2H,6H-[1,4]thiazepino[2,3,4-ij]quinazolin-6-one | 607.64 | 40 |
| 587 | (3S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2,3-dihydro-5H-[1,4]thiazino[2,3,4-ij]quinazolin-5-one | | 58.9 |
| 588 | 8'-((2S,5R)-4-acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 607.18 | 95.9 |
| 589 | 8'-(4-acryloylpiperazin-1-yl-2,2,3,3,5,5,6,6-d8)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 587.2 | 92.9 |

In embodiments, there also provided the following further compounds:

1197                                     1198
-continued                               -continued
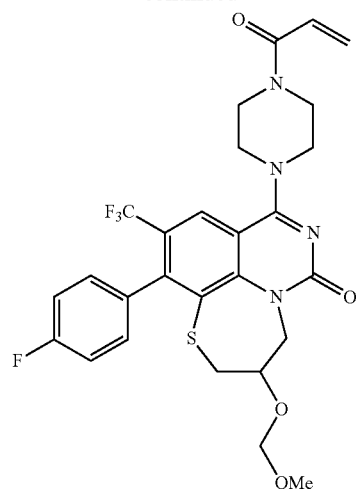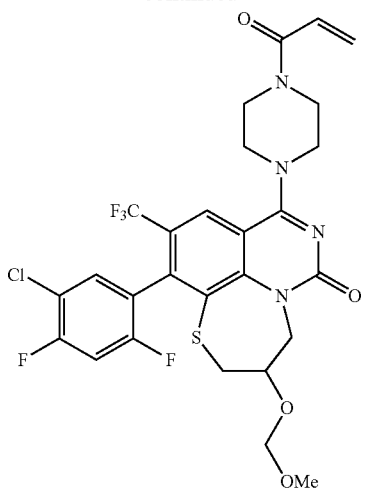
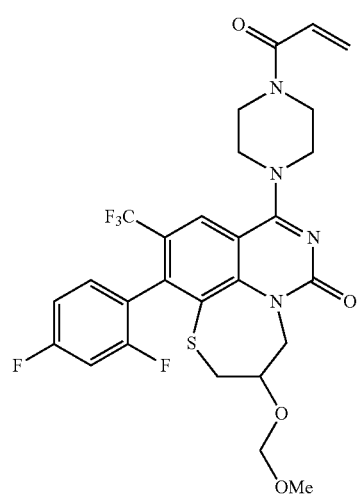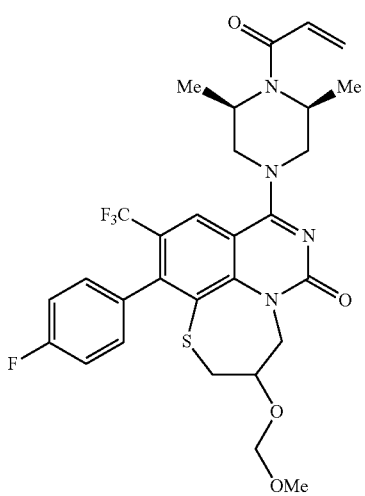
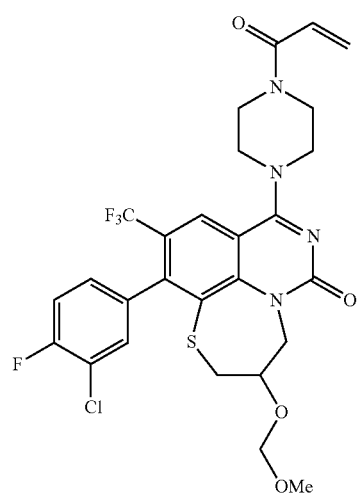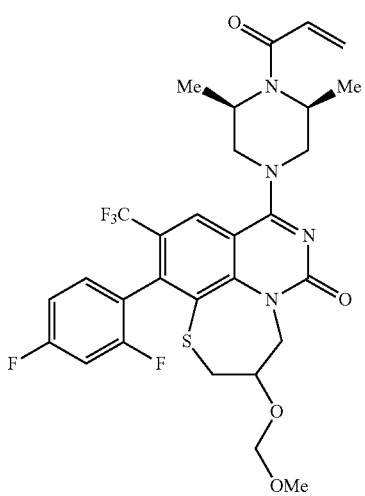

1199
-continued
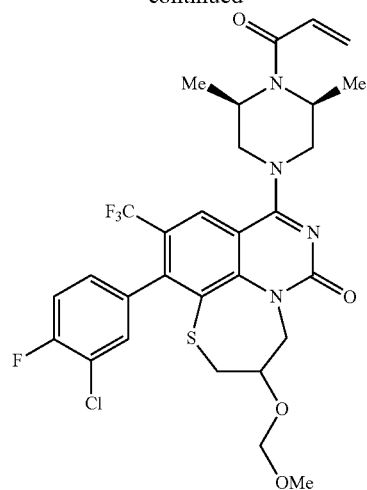
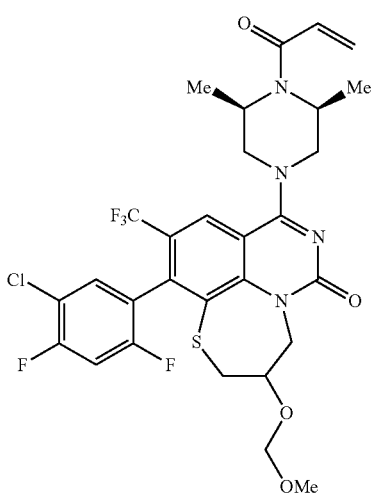
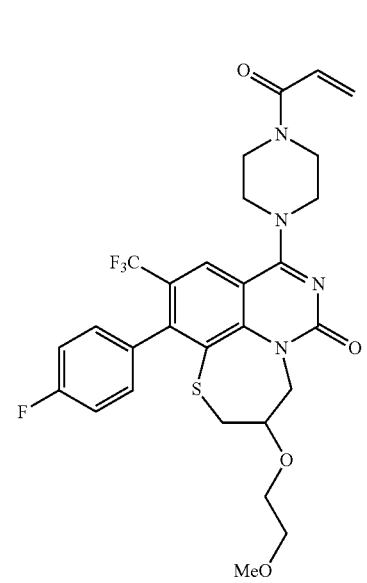
1200
-continued
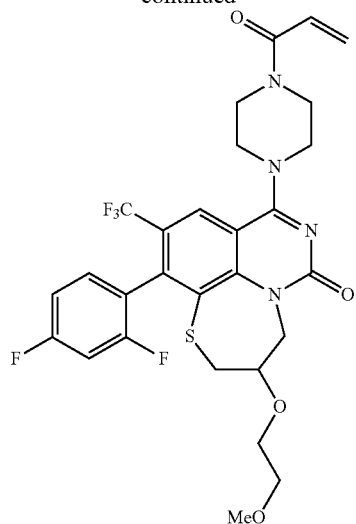
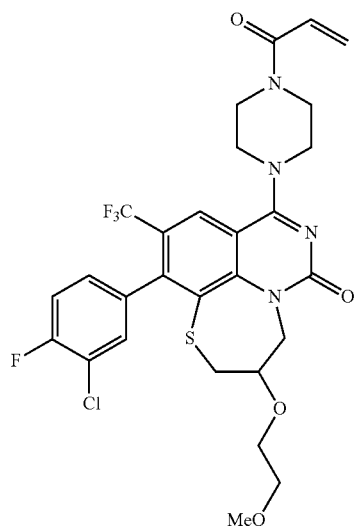
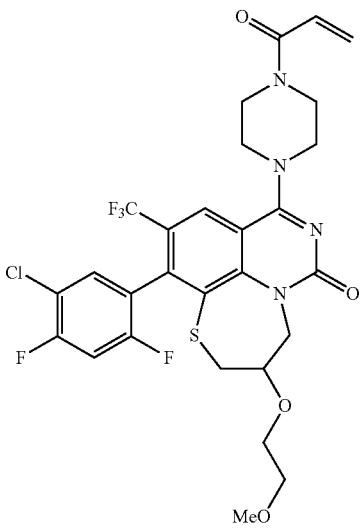

1201
-continued
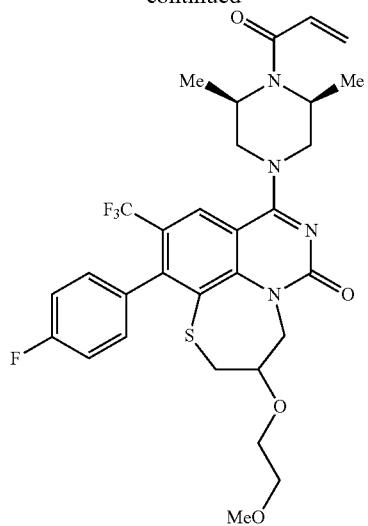
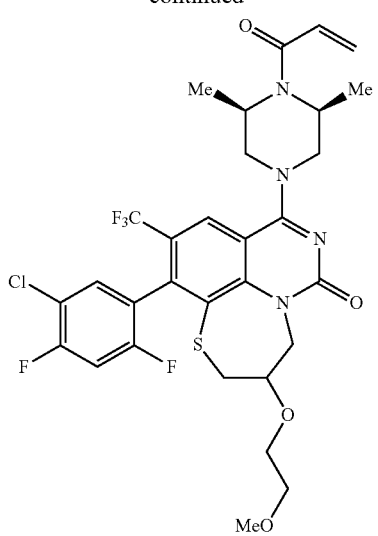
1202
-continued
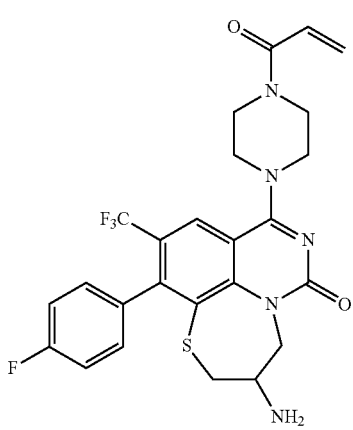
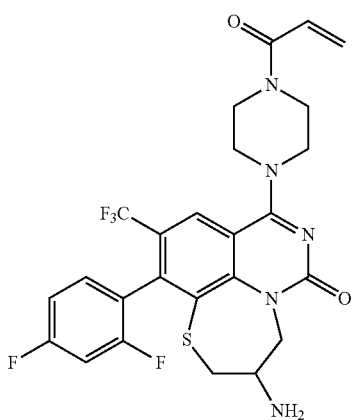

1203
-continued
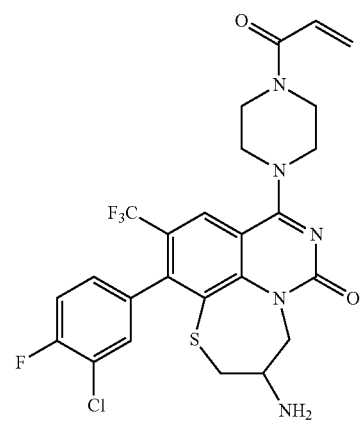
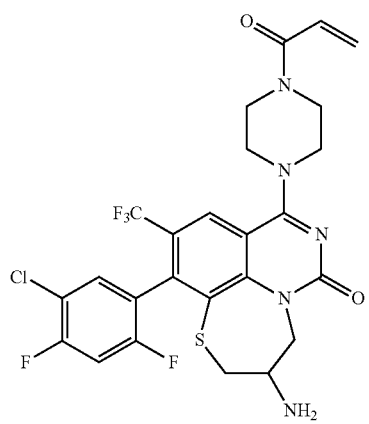
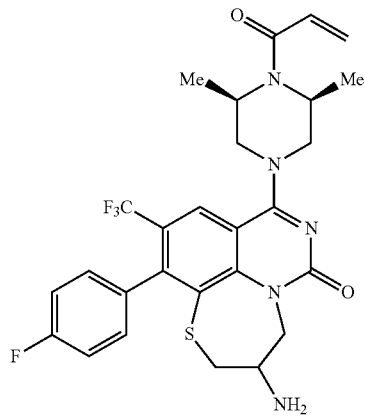
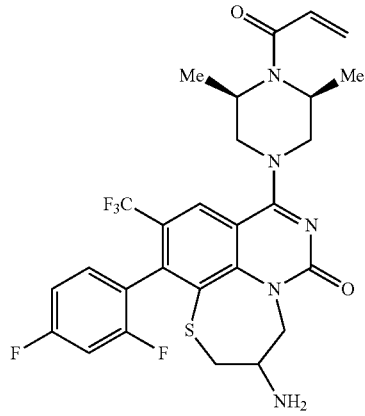
1204
-continued
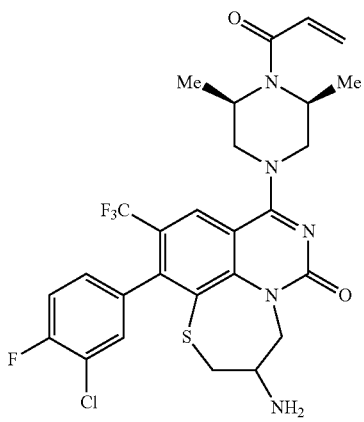
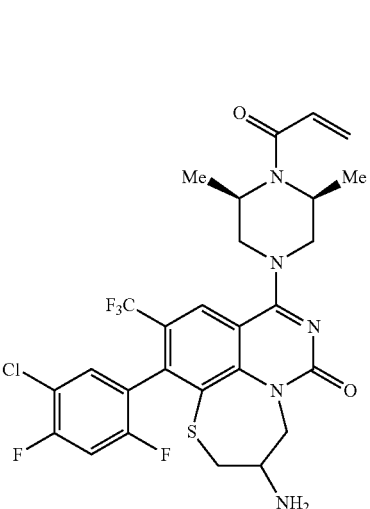
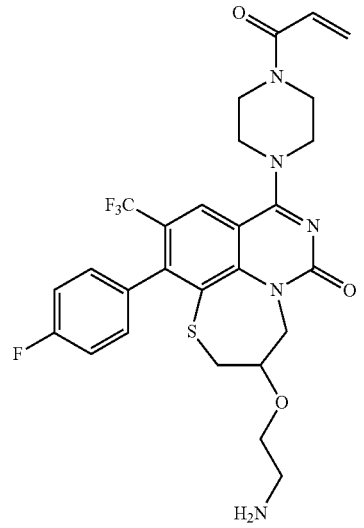

1205
-continued
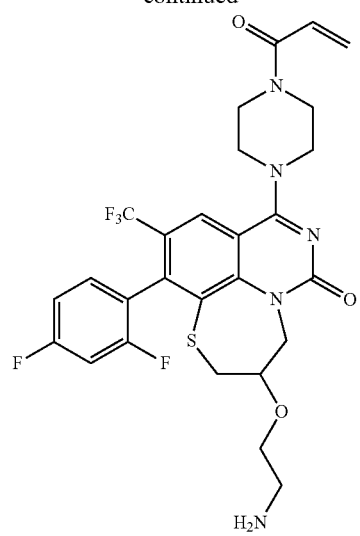
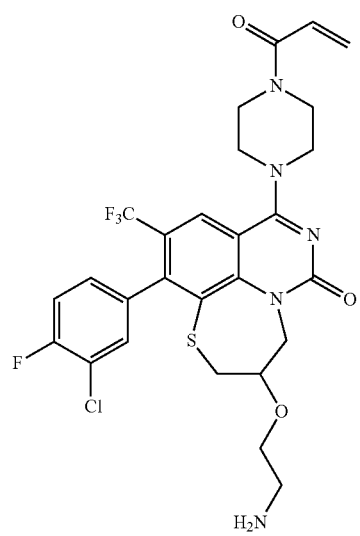
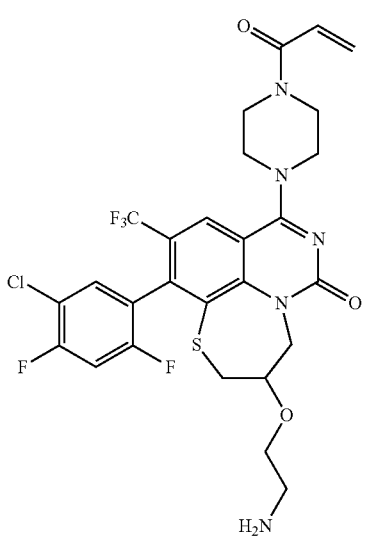
1206
-continued
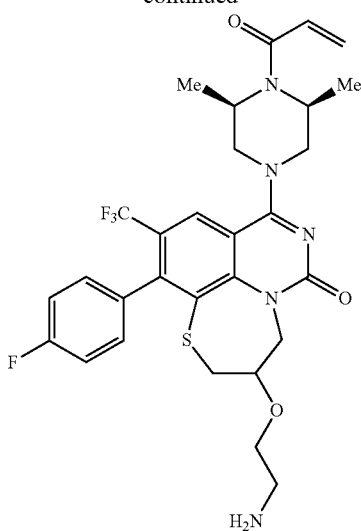
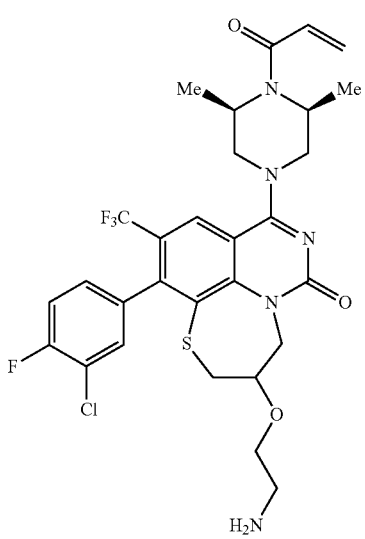
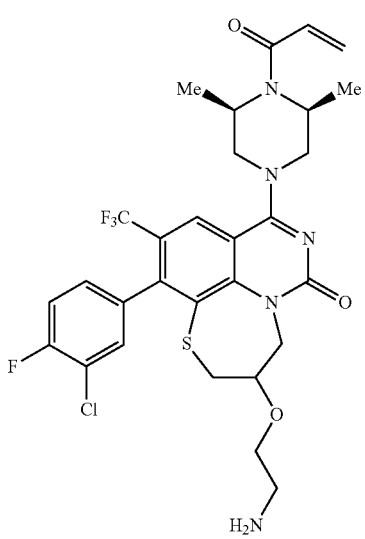

1207
-continued
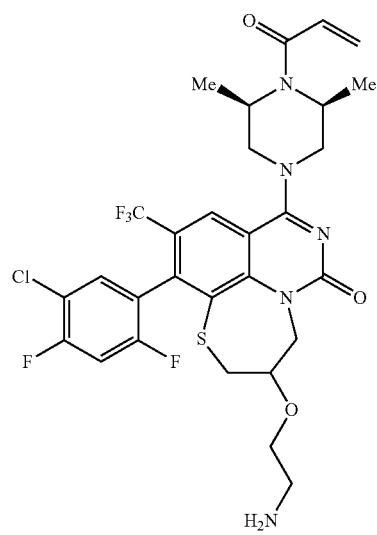
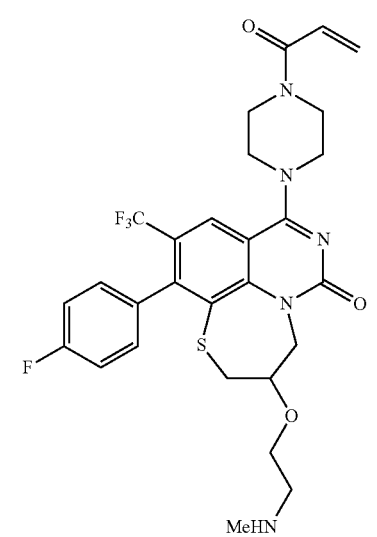
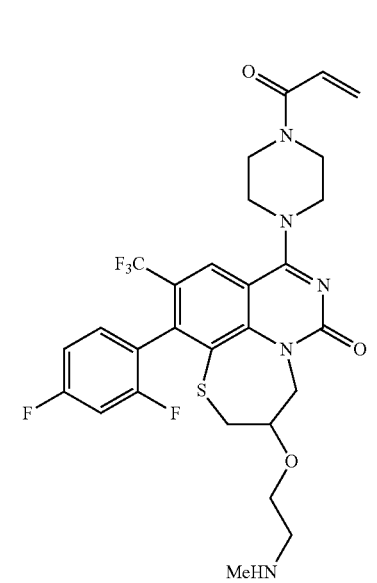
1208
-continued
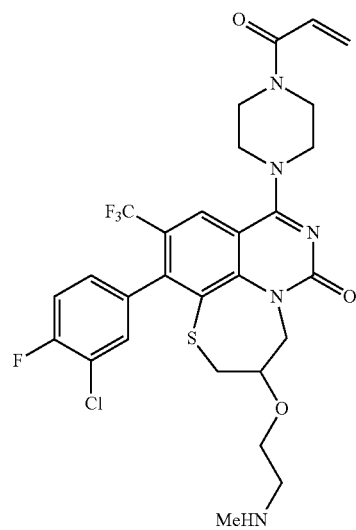
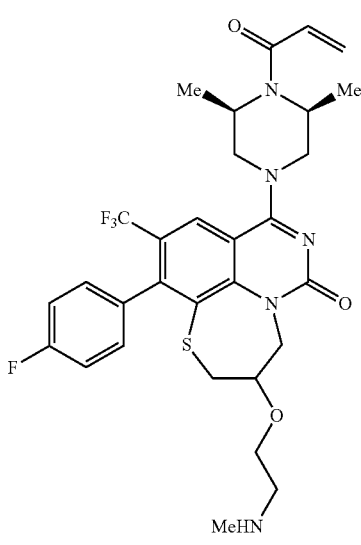
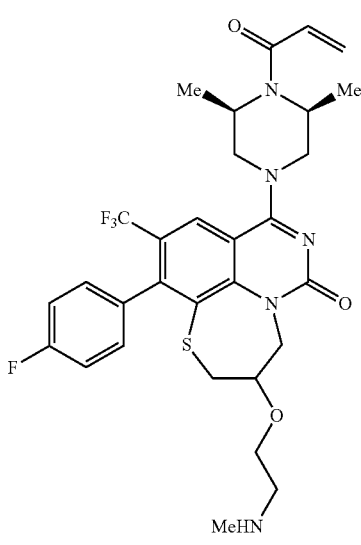

1209
-continued
1210
-continued
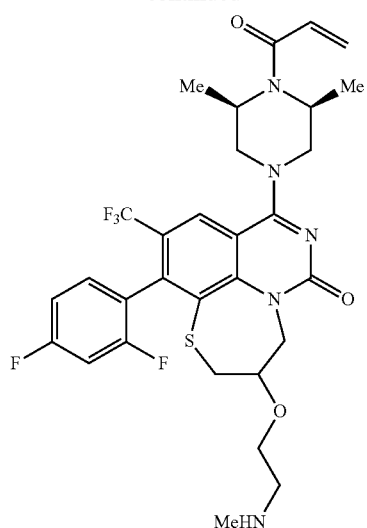
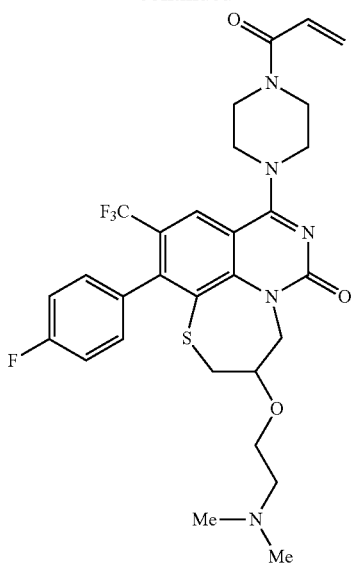

1211
-continued
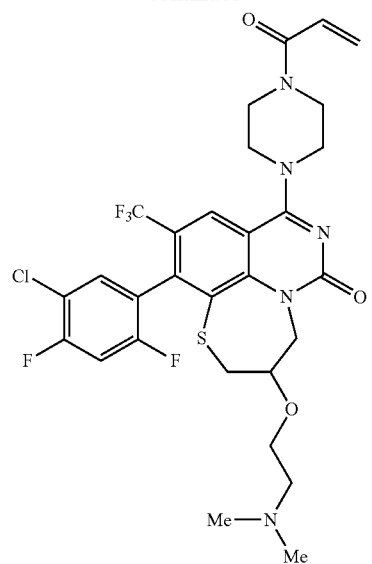
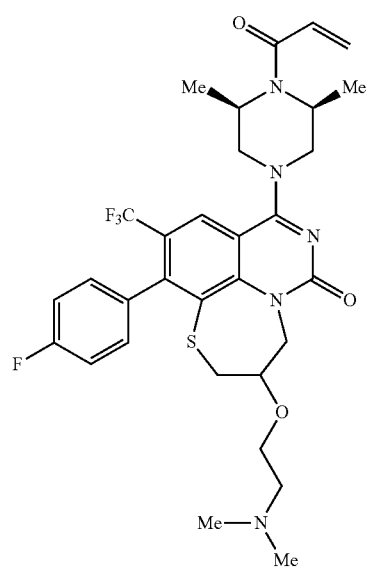
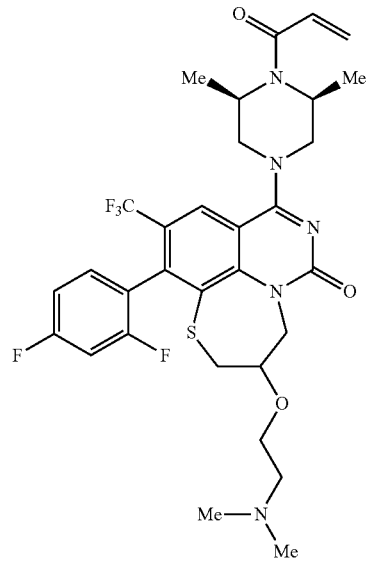
1212
-continued
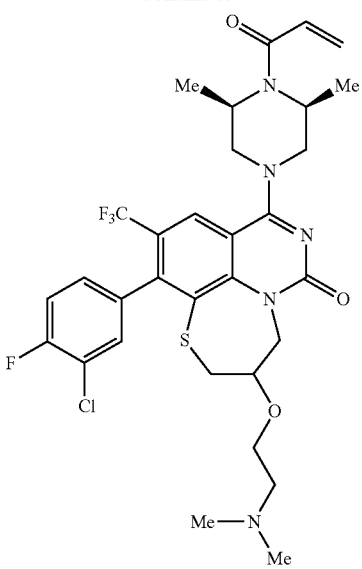
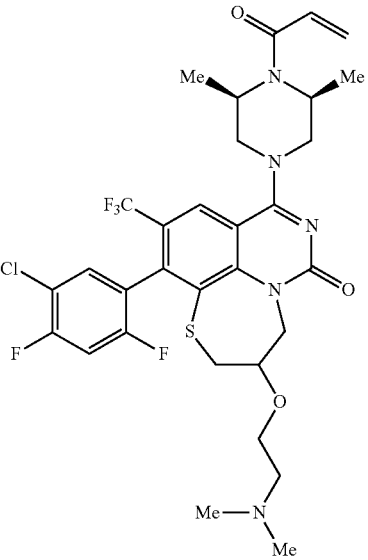
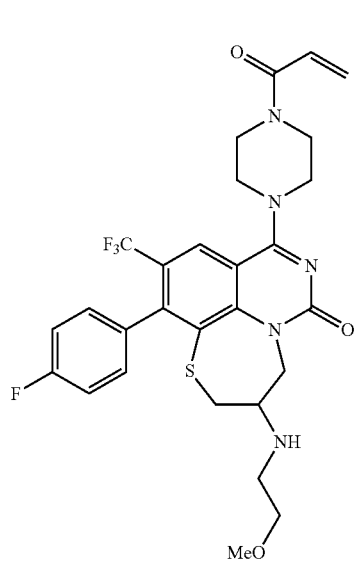

1213
-continued
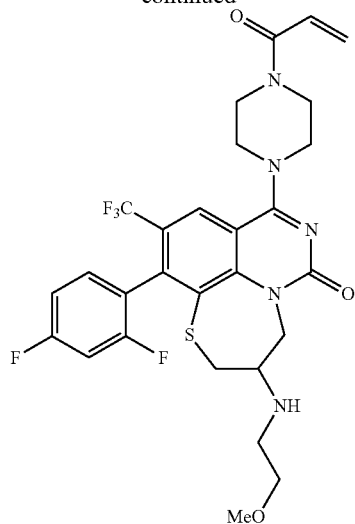
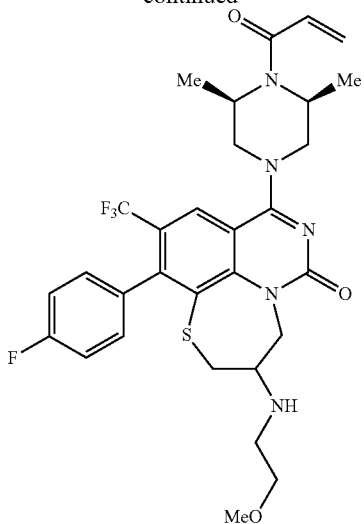
1214
-continued
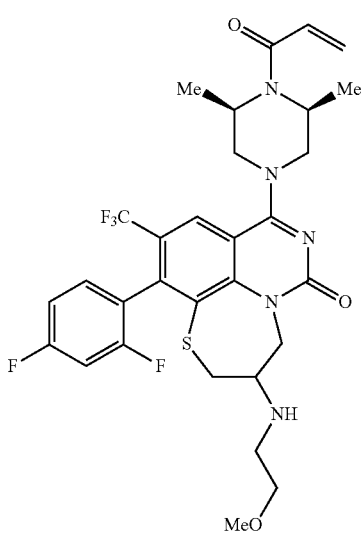
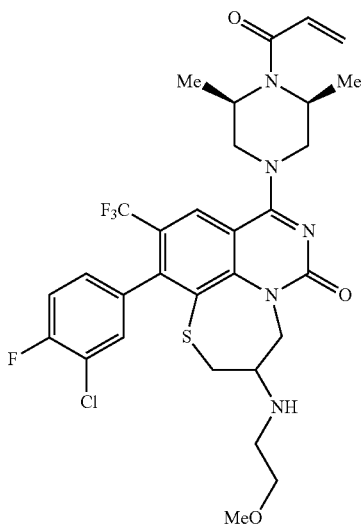

1215
-continued
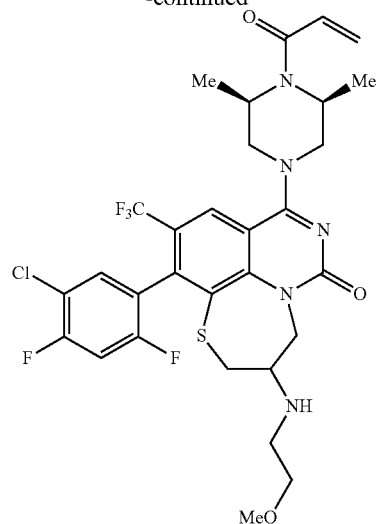
1216
-continued
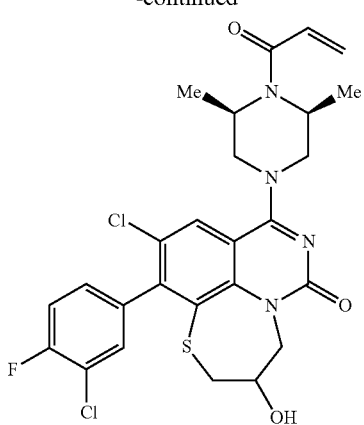
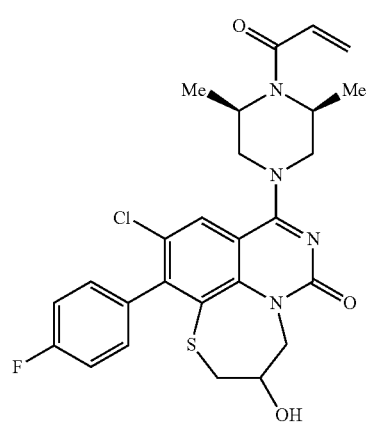
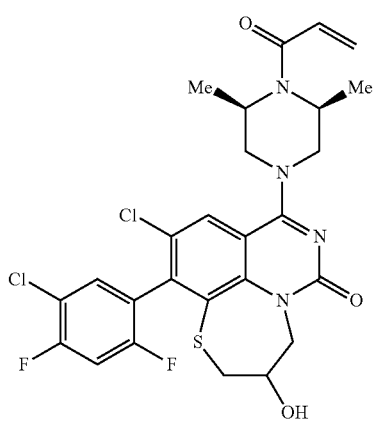
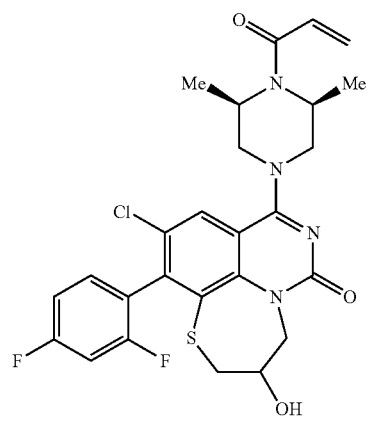
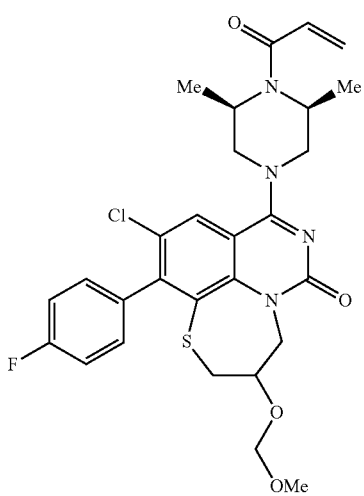

1217
-continued
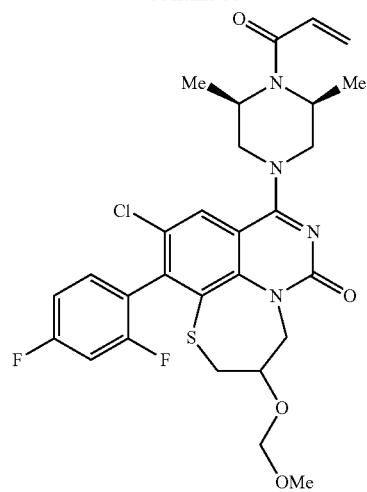
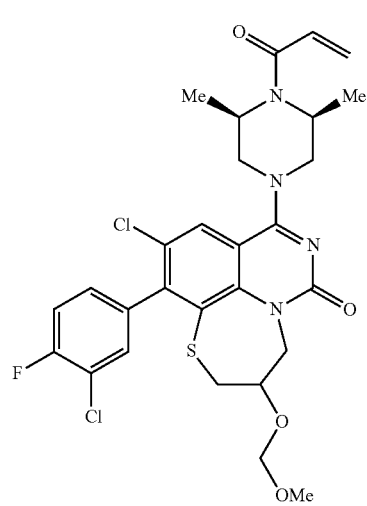
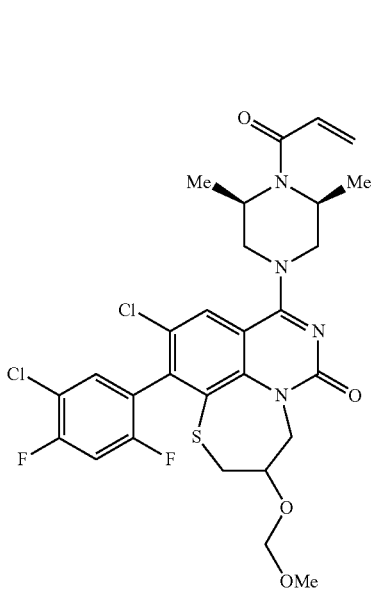
1218
-continued
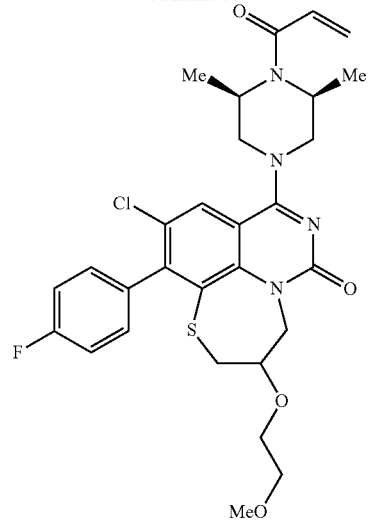
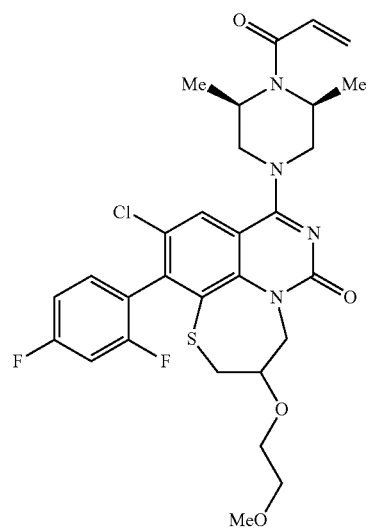
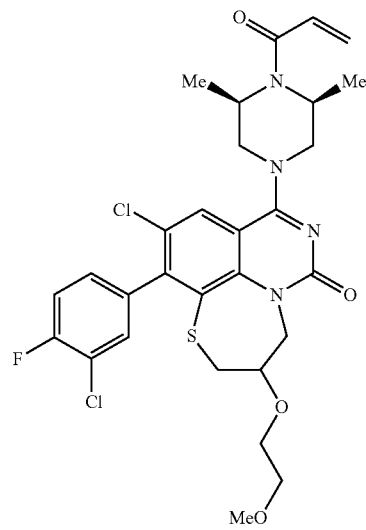

1219
-continued
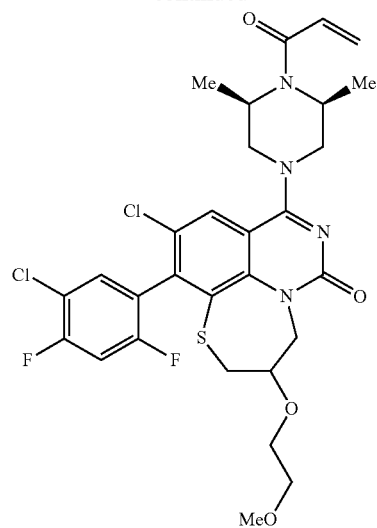
1220
-continued
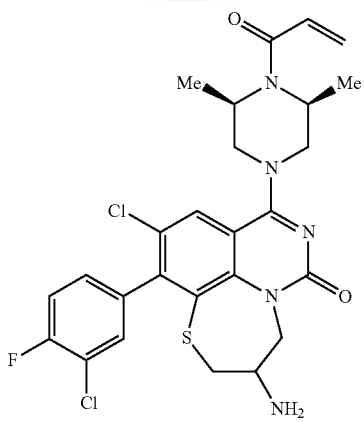
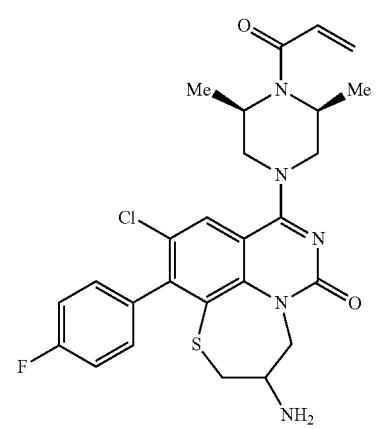
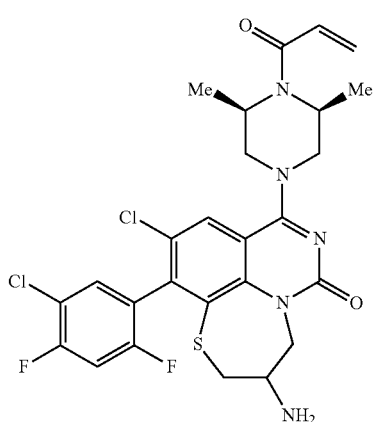
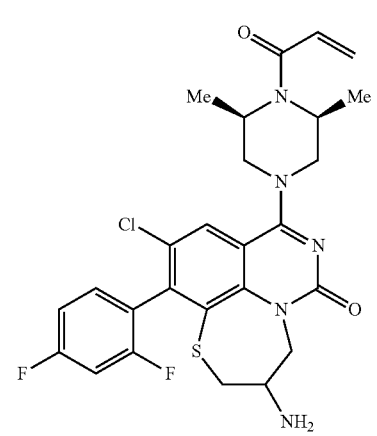
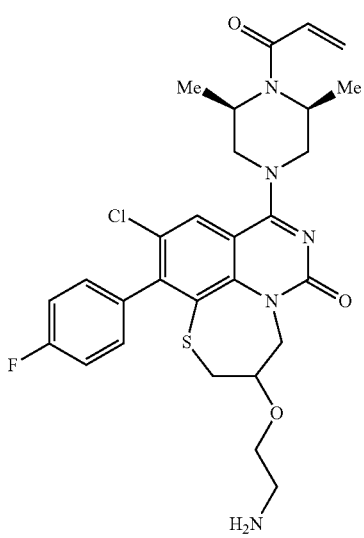

1221
-continued
1222
-continued
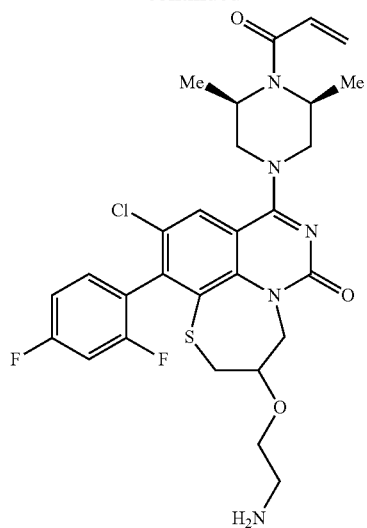
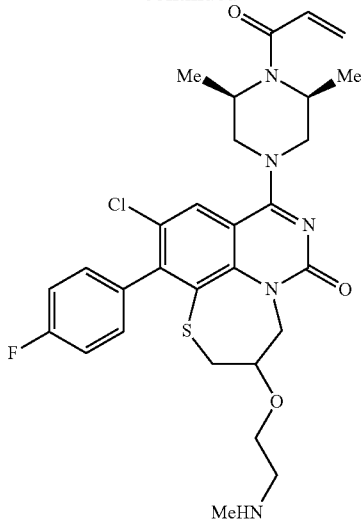

1223
-continued
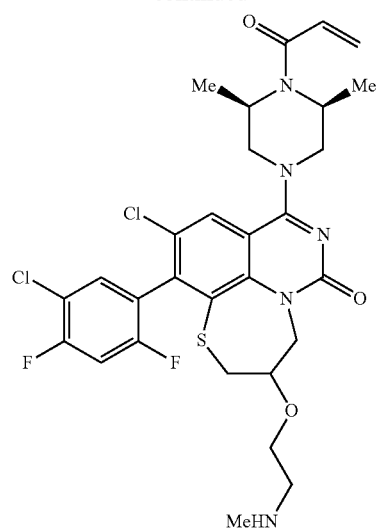
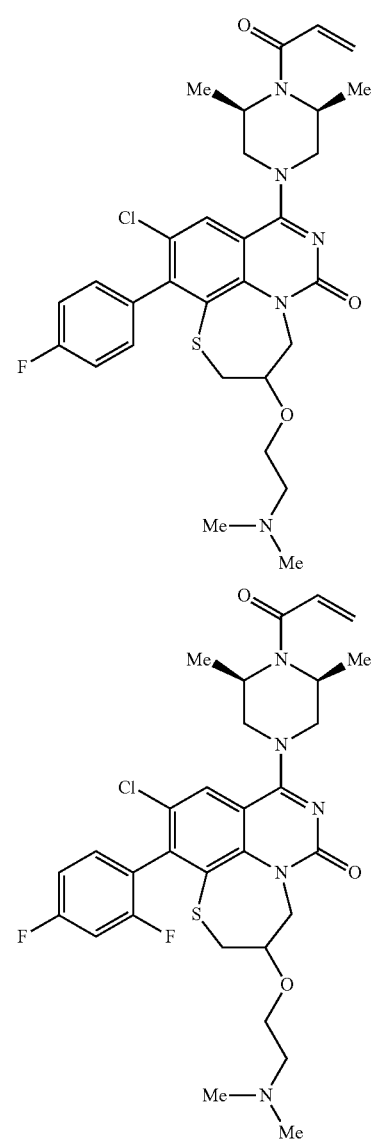
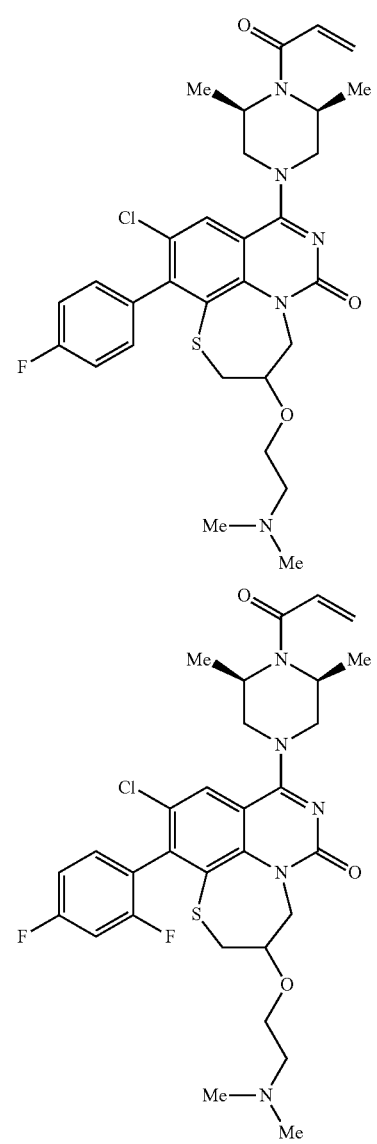
1224
-continued
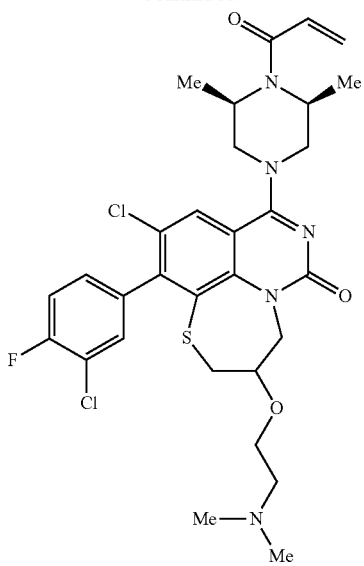
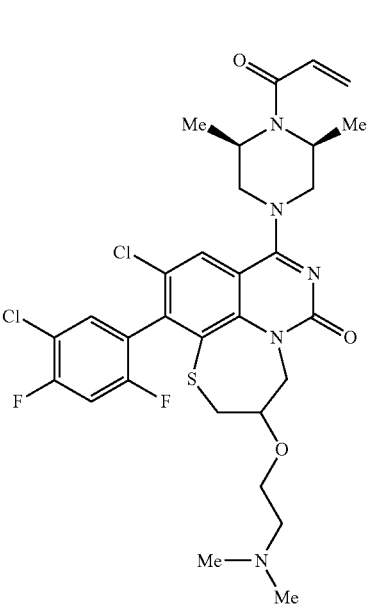
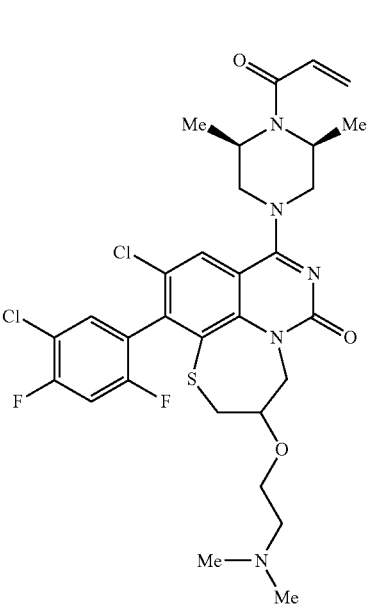

1225
-continued
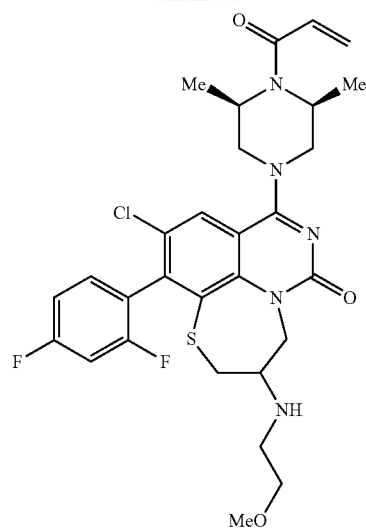
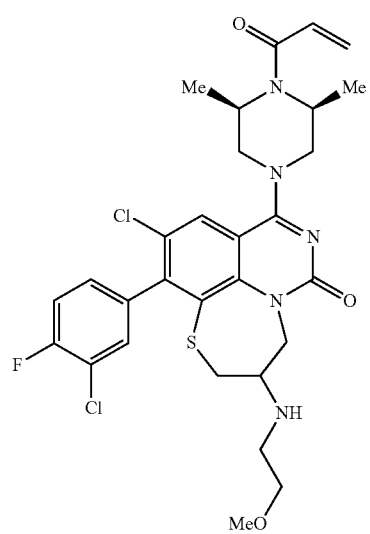
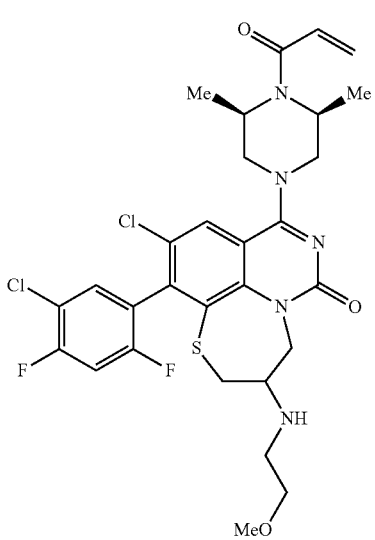
1226
-continued
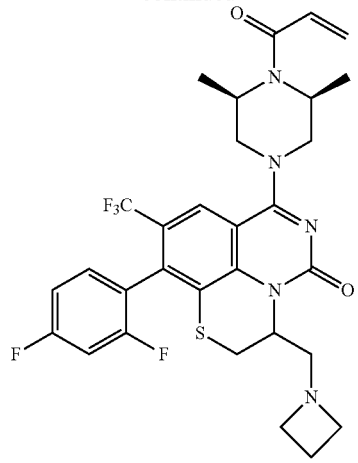
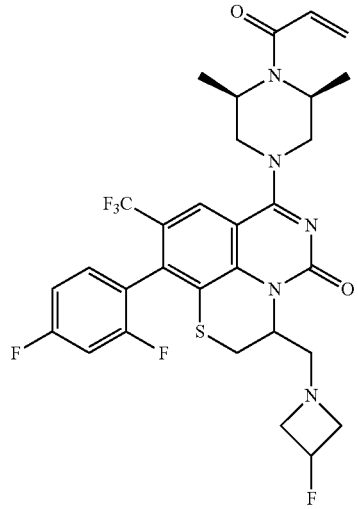
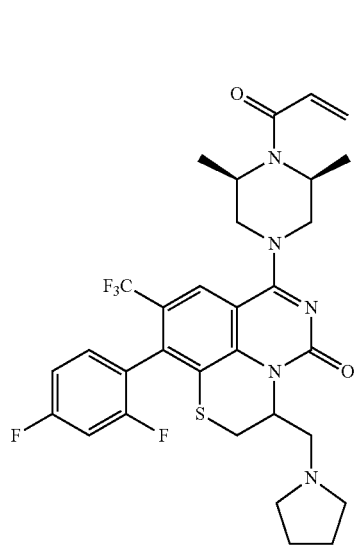

1227
-continued
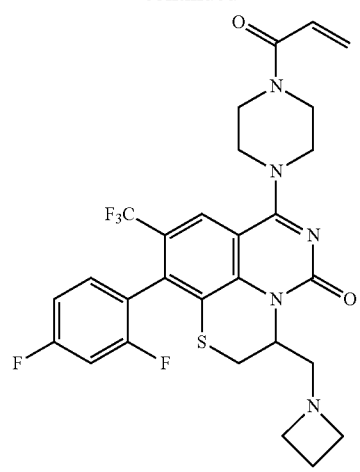
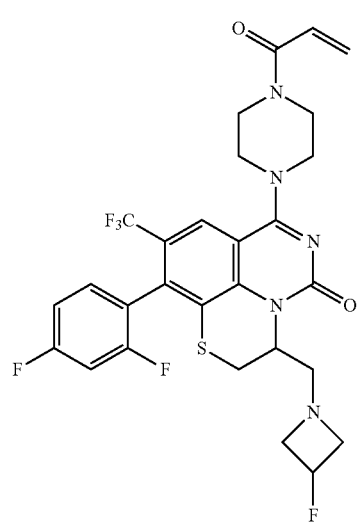
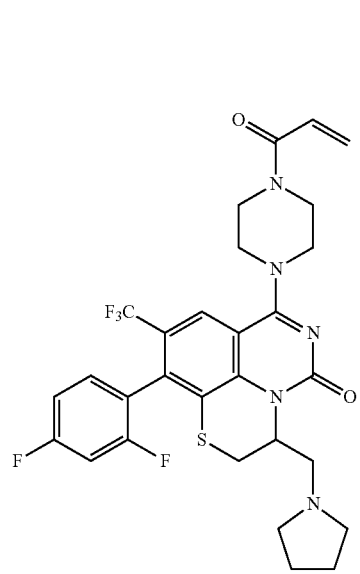
1228
-continued
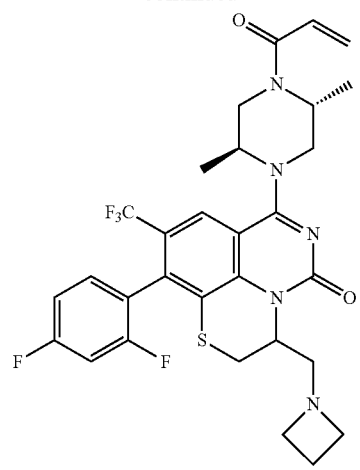
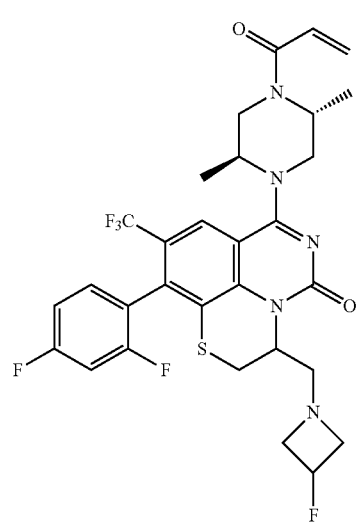
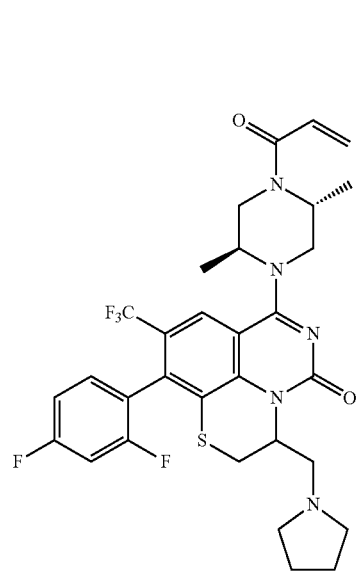

1229
-continued
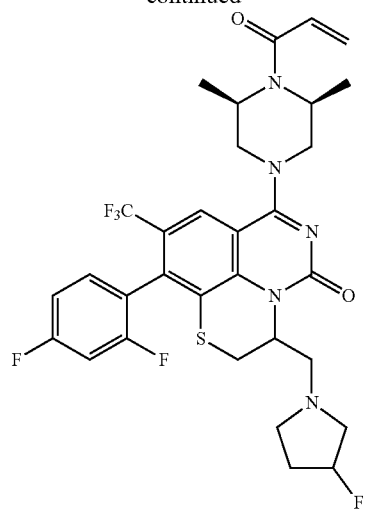
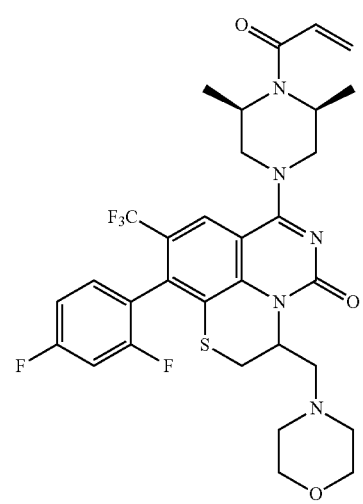
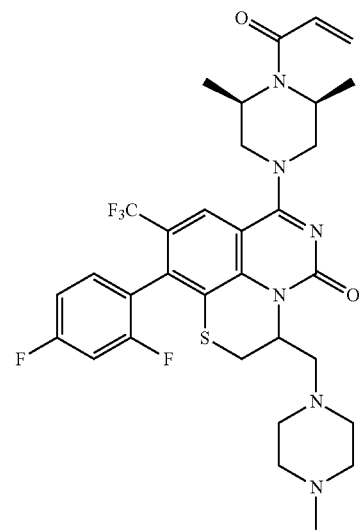
1230
-continued
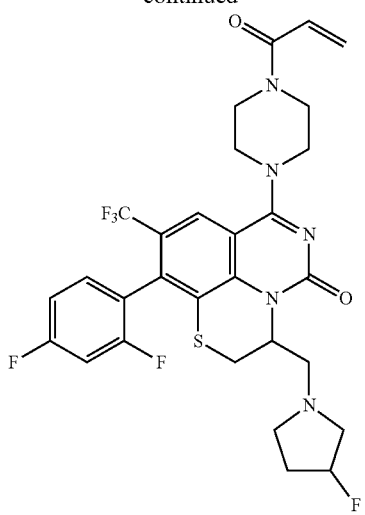
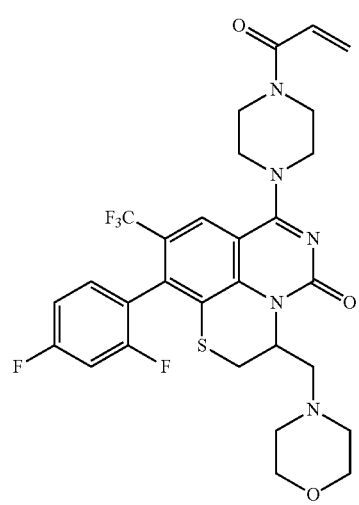
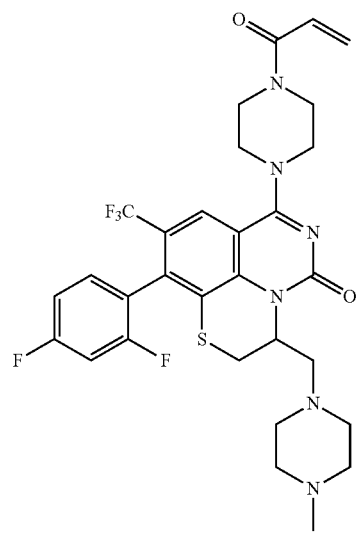

1231
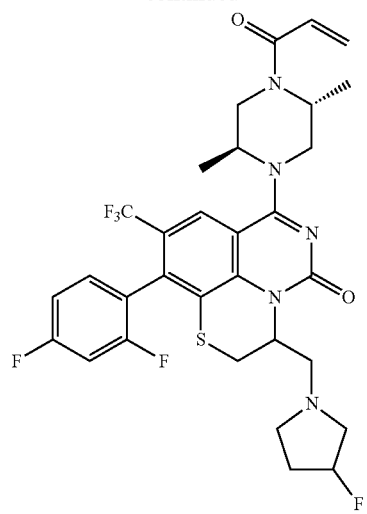
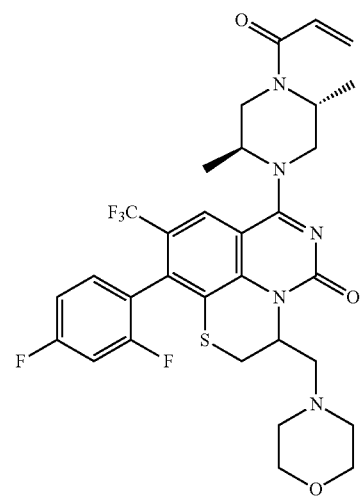
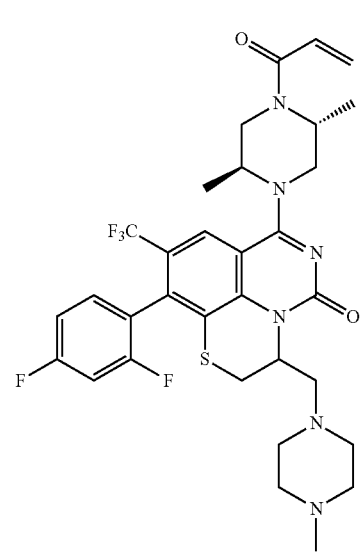 [SMILES: C=CC(=O)N1C[C@H](C)N(c2nc(=O)n3c4c(c(-c5ccc(F)cc5F)c(C(F)(F)F)cc24)SCC3CN2CCN(C)CC2)C[C@H]1C]
1232
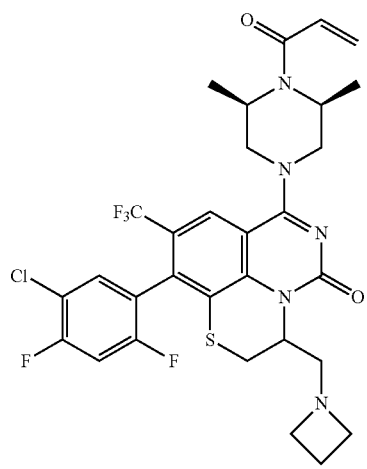
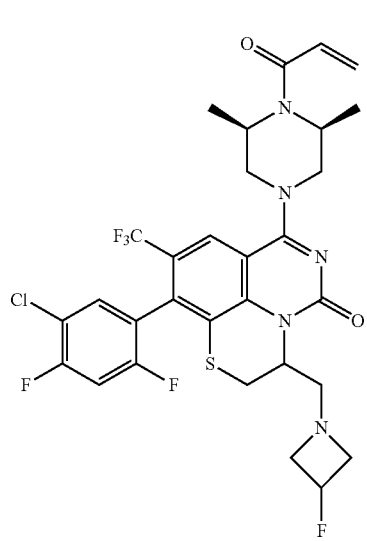
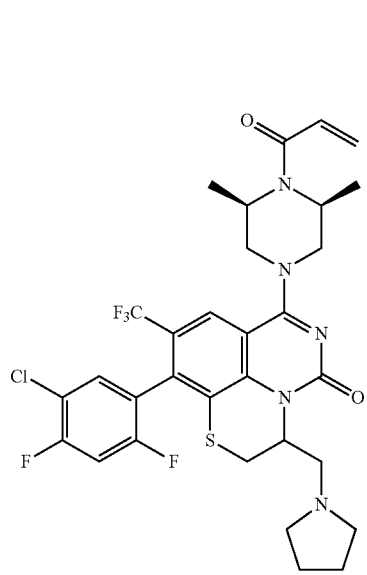

1233
-continued
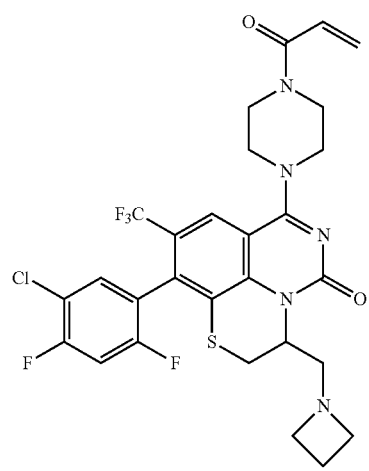
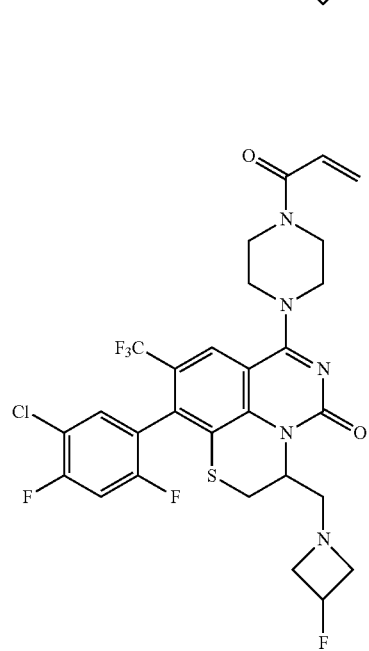
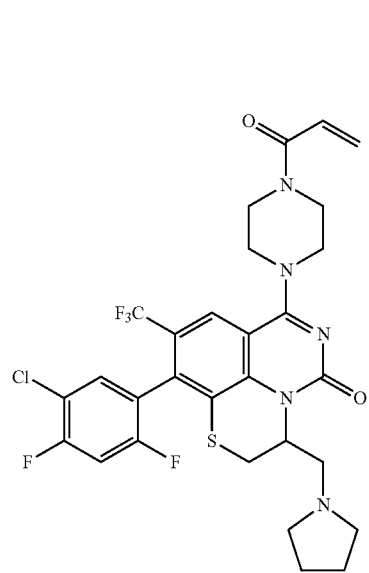
1234
-continued
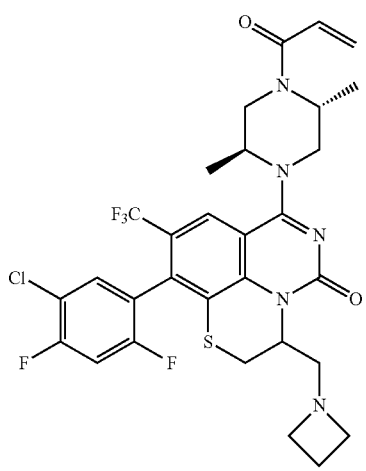
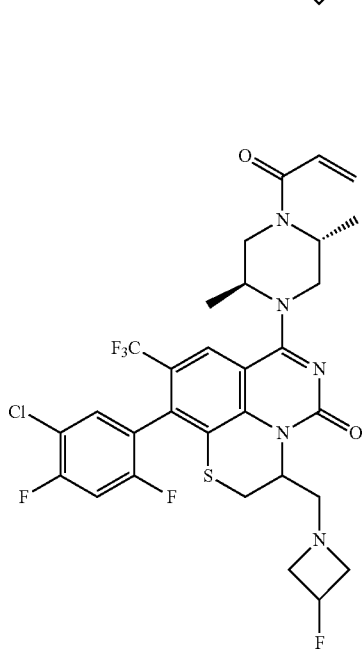
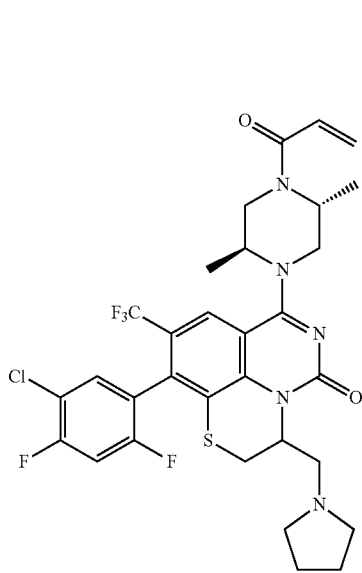

1235
-continued
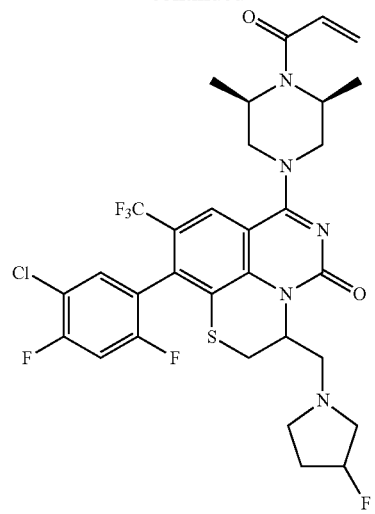
1236
-continued
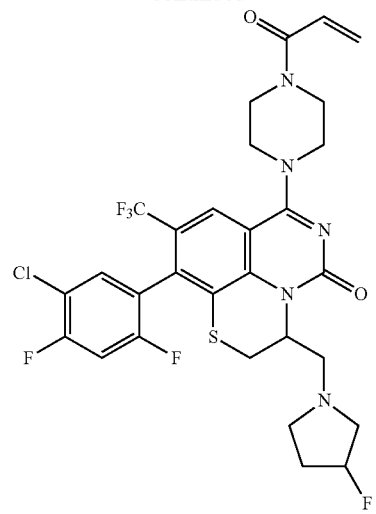
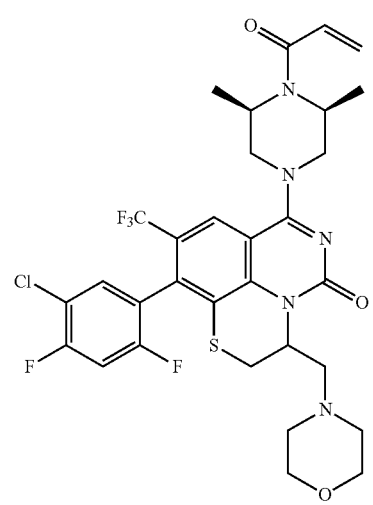
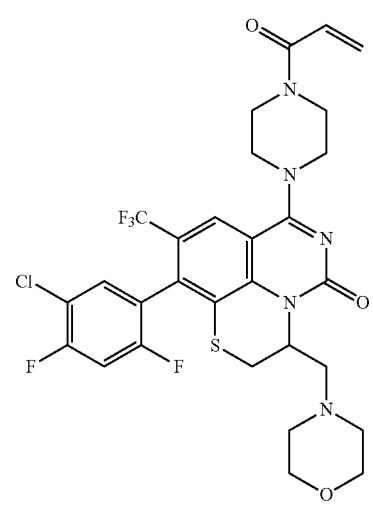
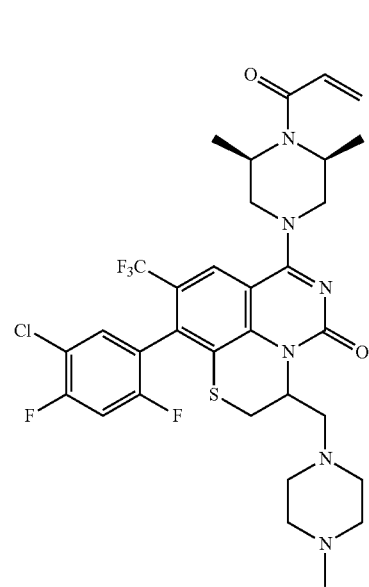
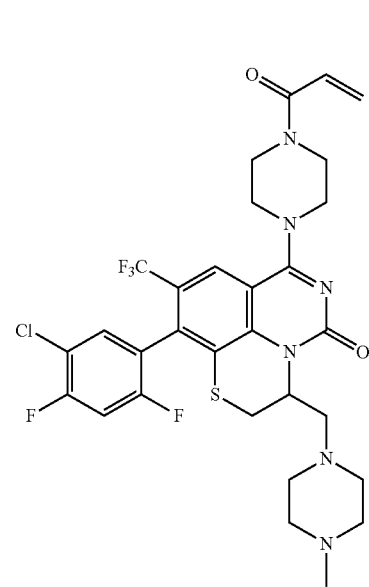

1237
-continued
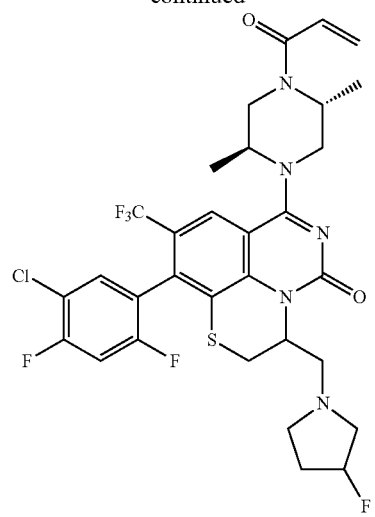
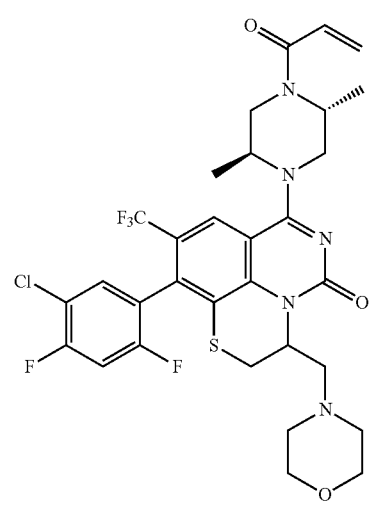
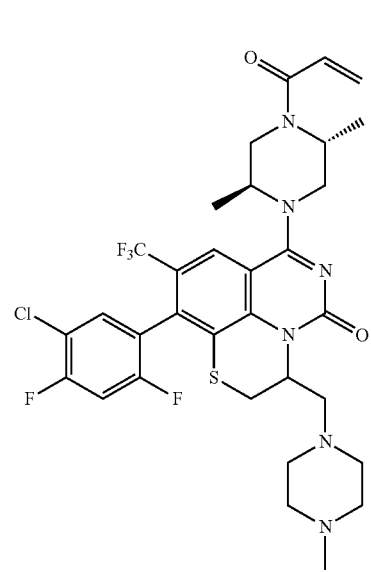
1238
-continued
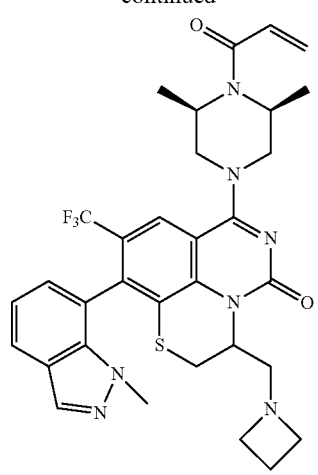
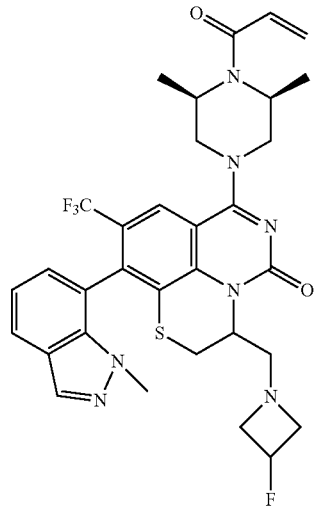
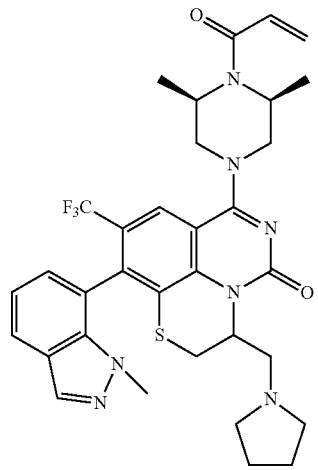

1239
-continued
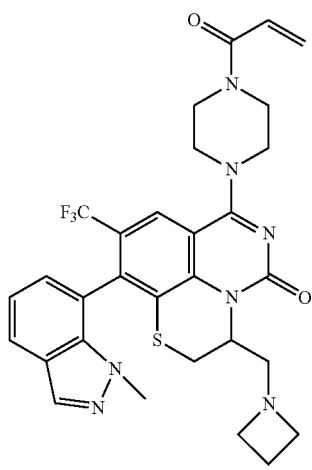
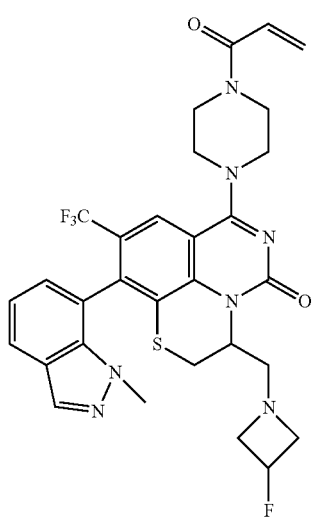
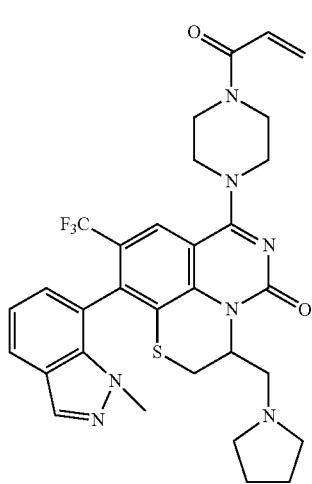
1240
-continued
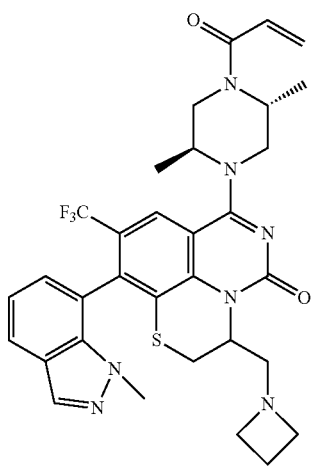
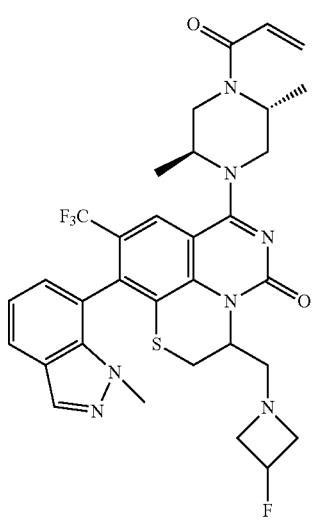
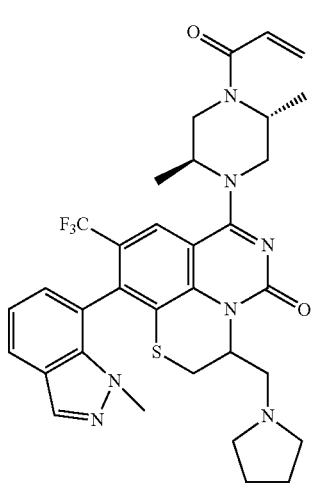

1241
-continued
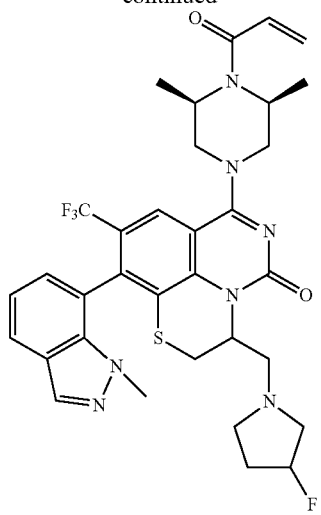
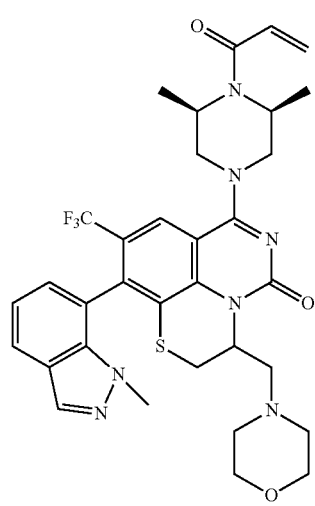
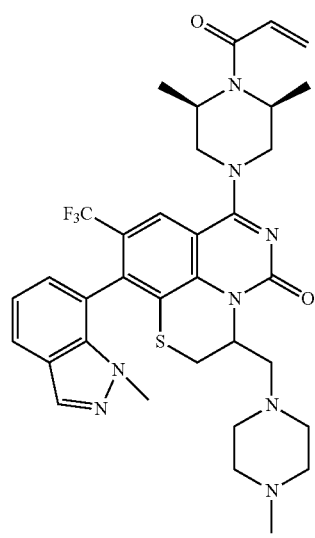
1242
-continued
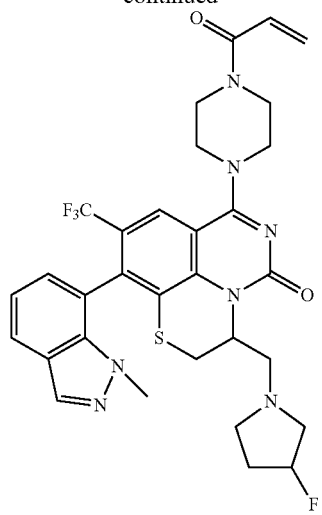
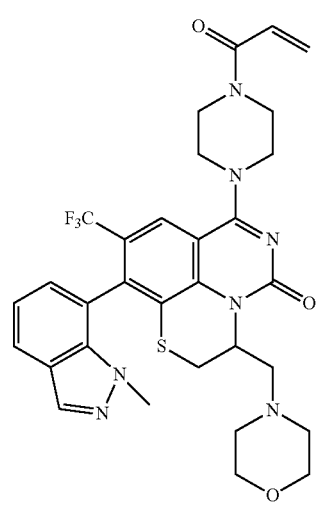
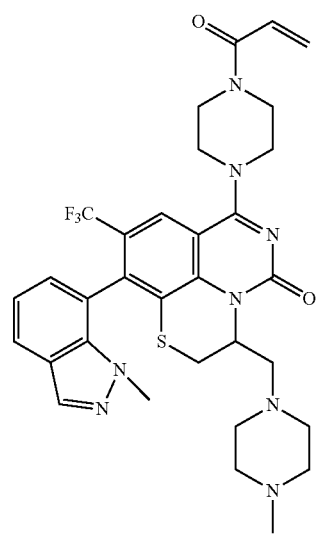

1243
-continued
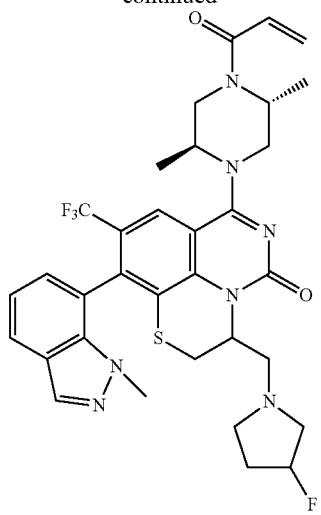
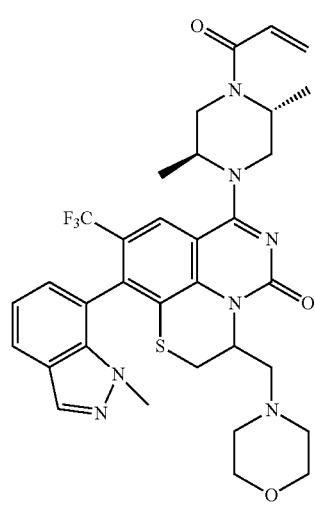
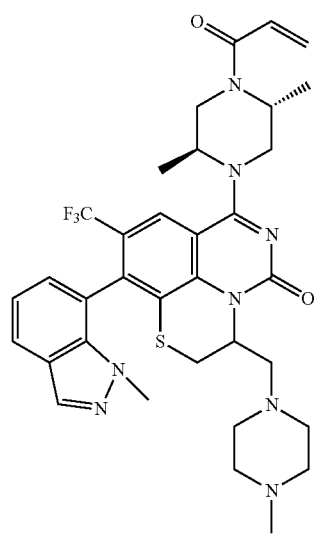
1244
-continued
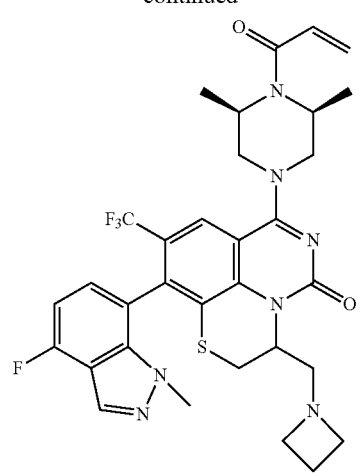
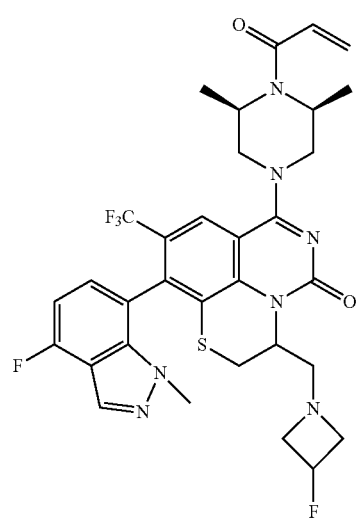
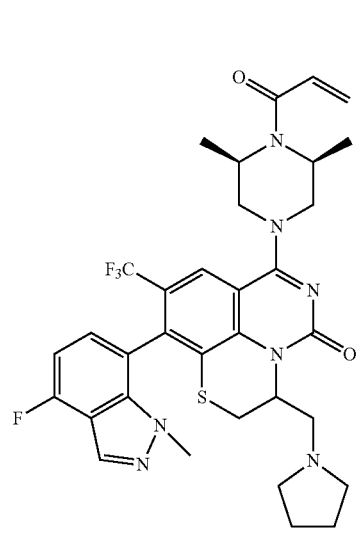

1245
-continued
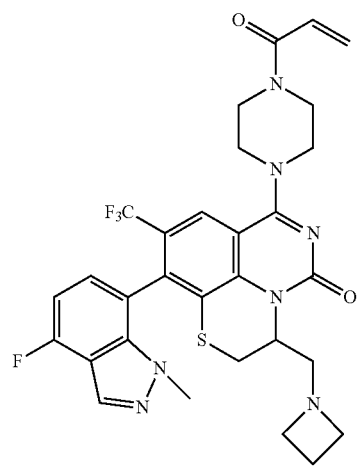
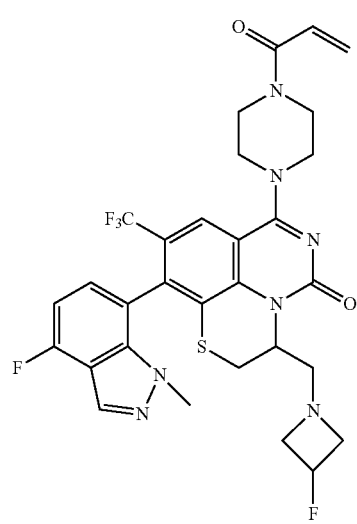
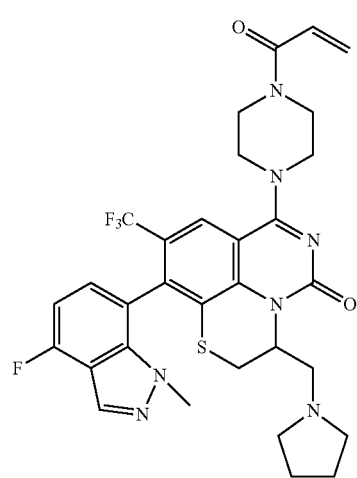
1246
-continued
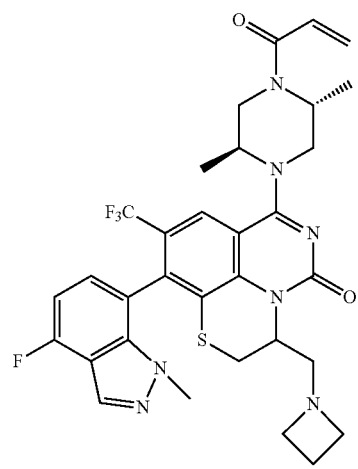
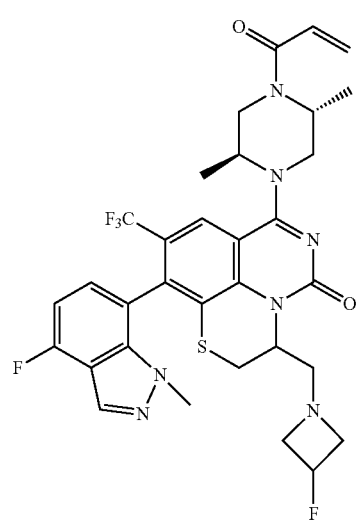
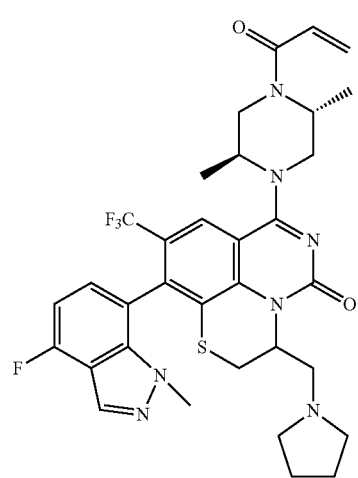

1247
-continued
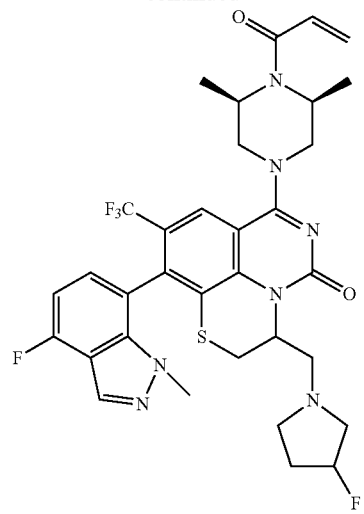
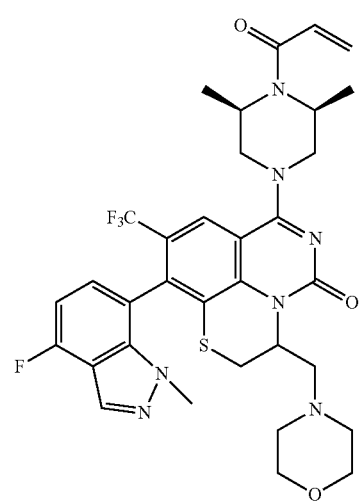
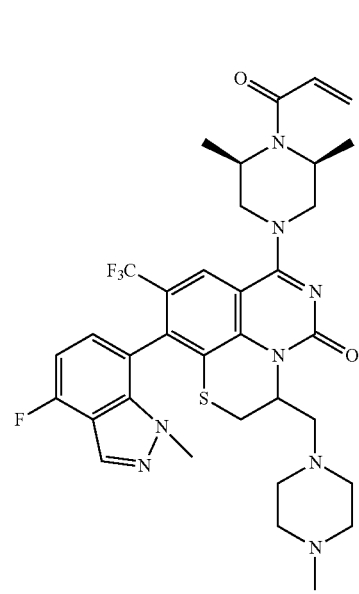
1248
-continued
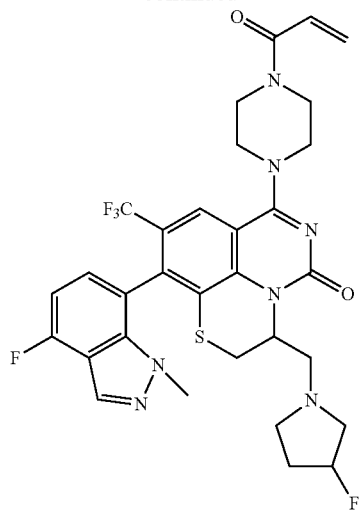
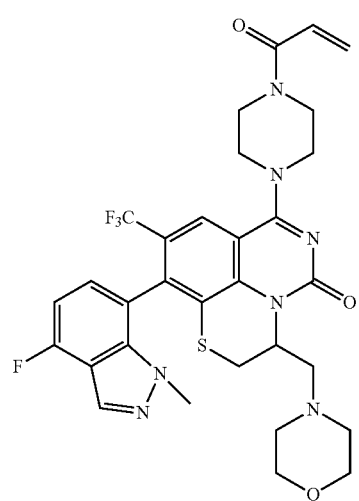
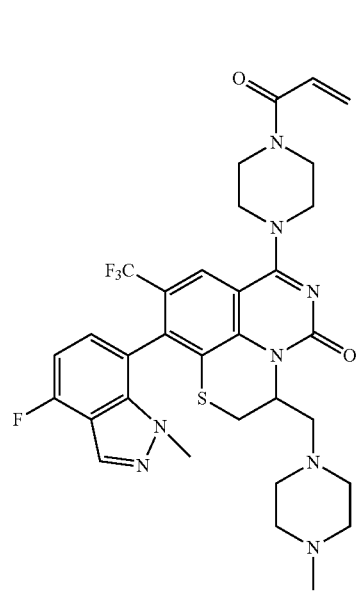

1249
-continued
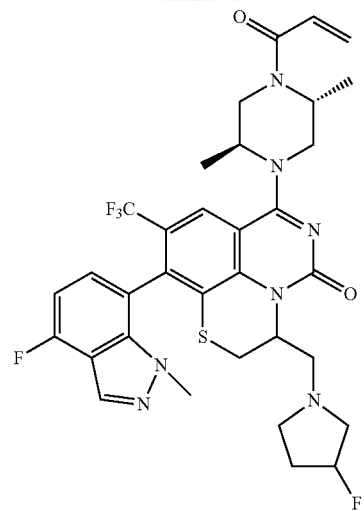
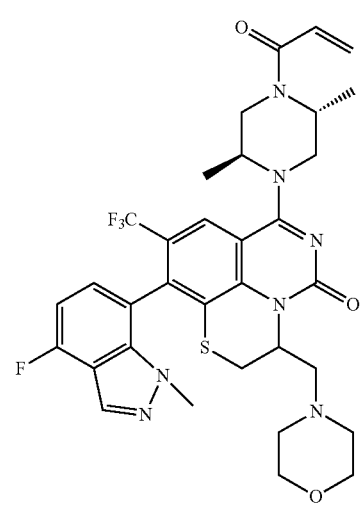
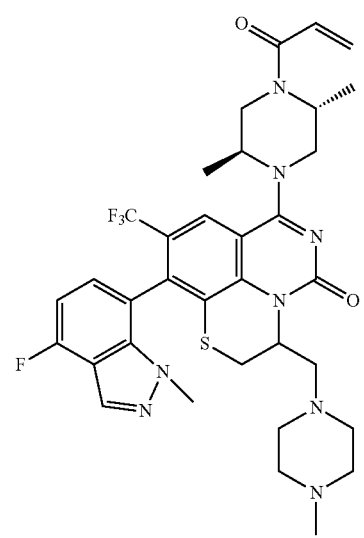
1250
-continued
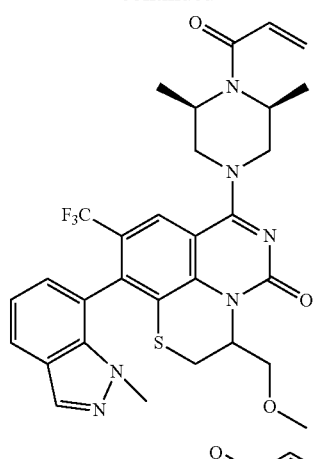
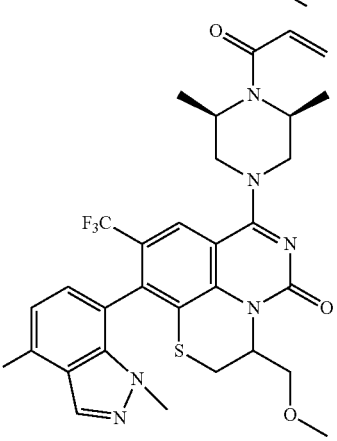
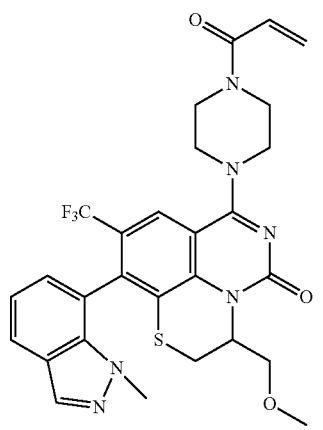
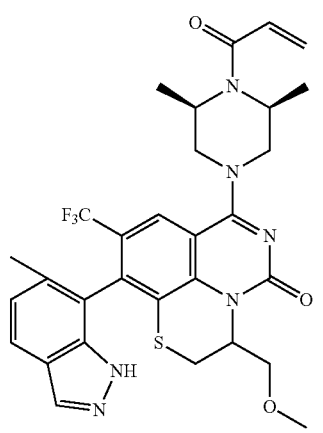

1251
-continued
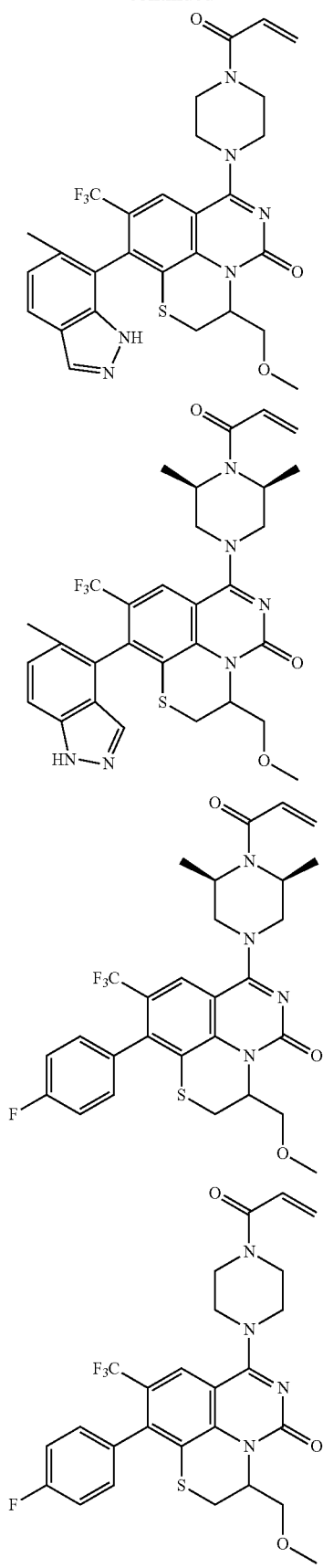
1252
-continued
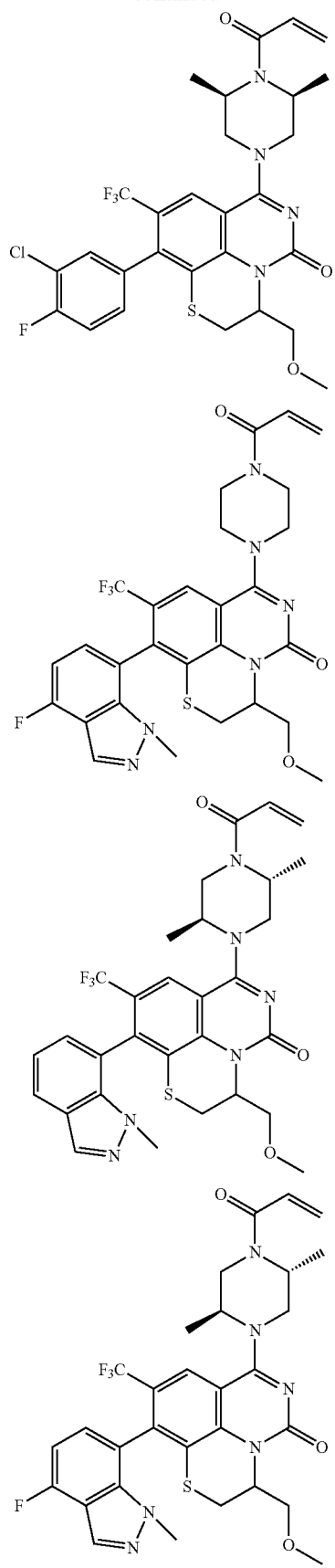

1253
-continued
1254
-continued
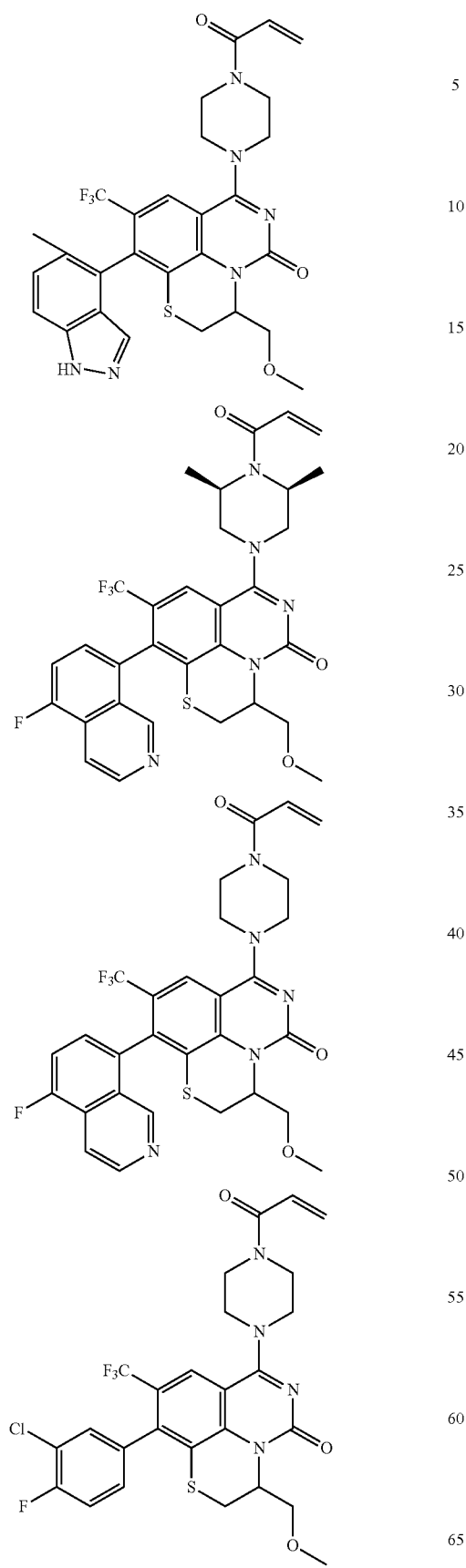
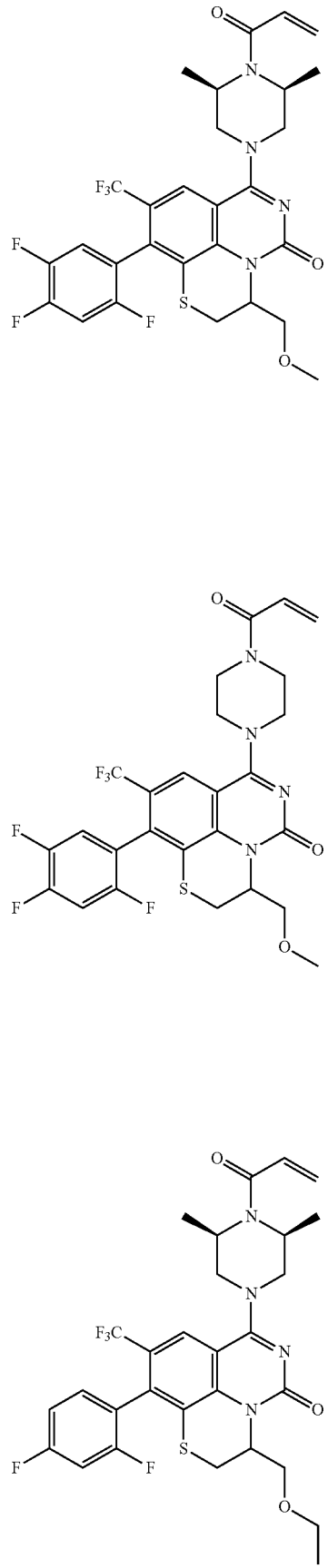

1255
-continued
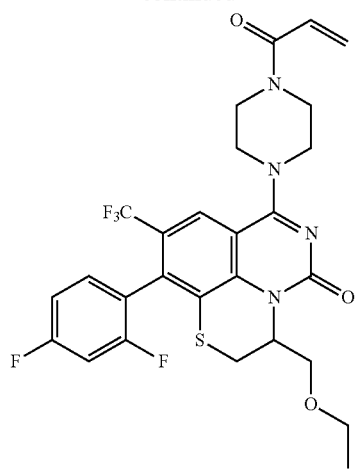
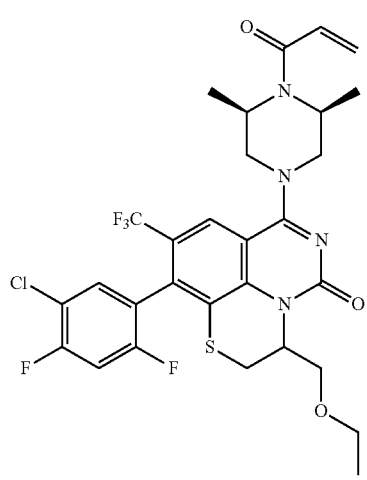
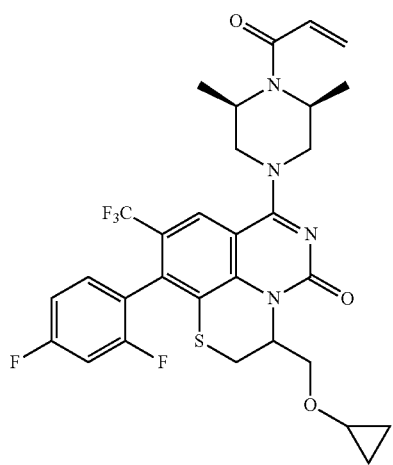
1256
-continued
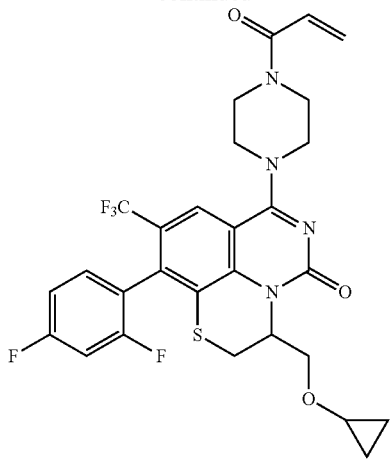
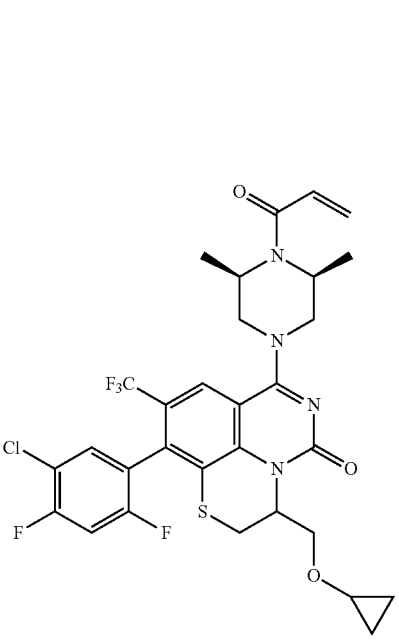
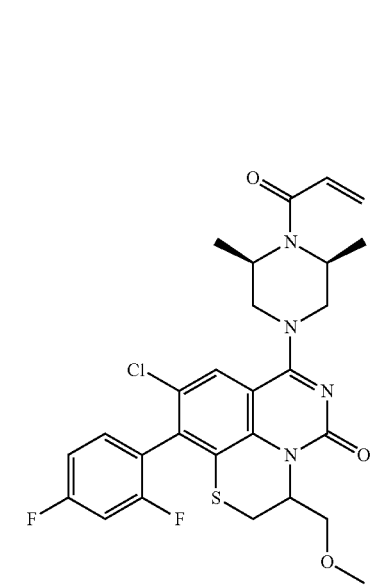

1257
-continued
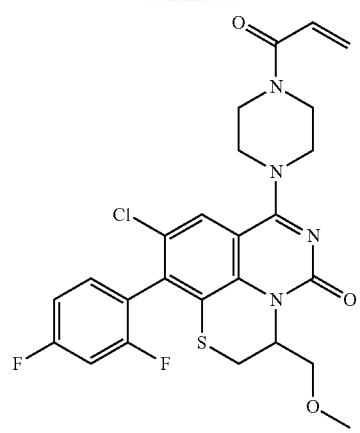
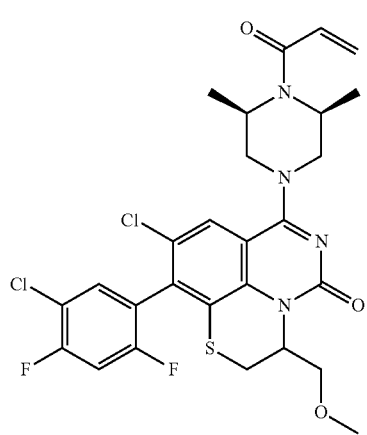
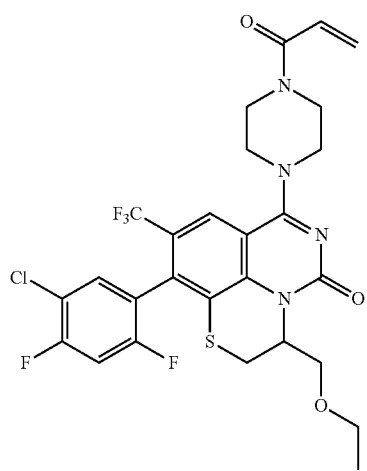
1258
-continued
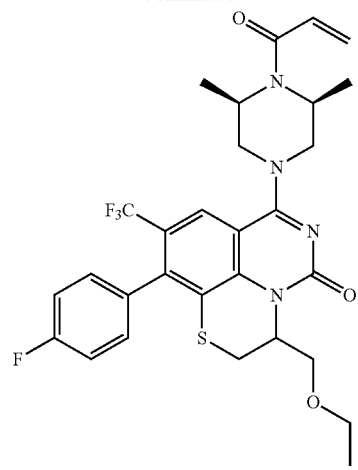
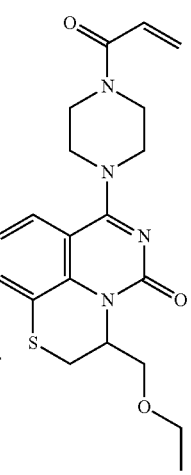
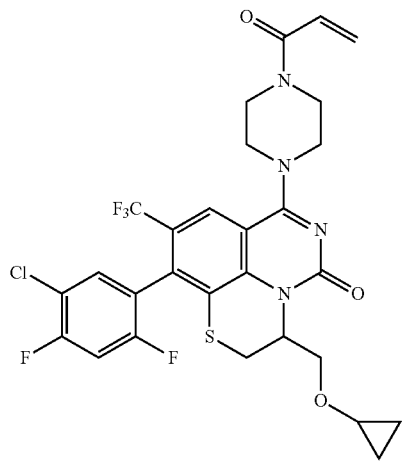

1259
-continued
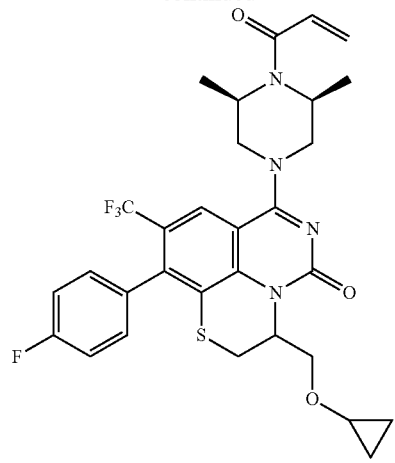
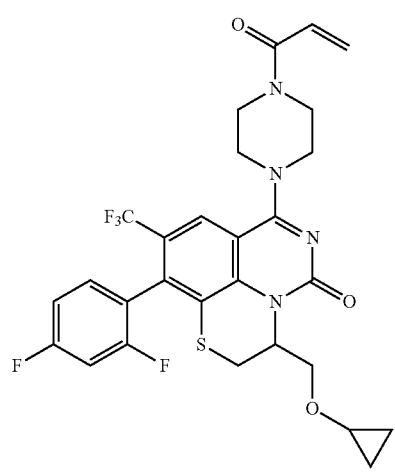
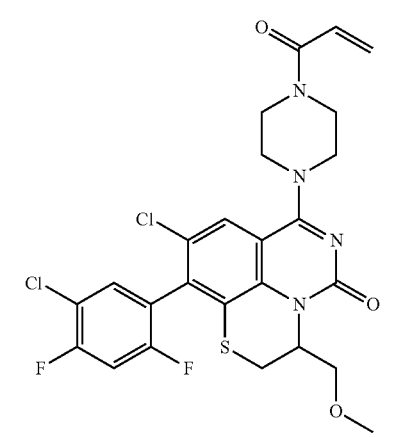
1260
-continued
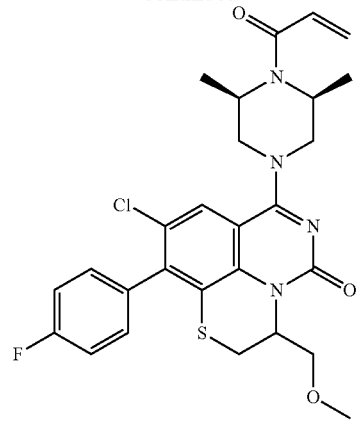
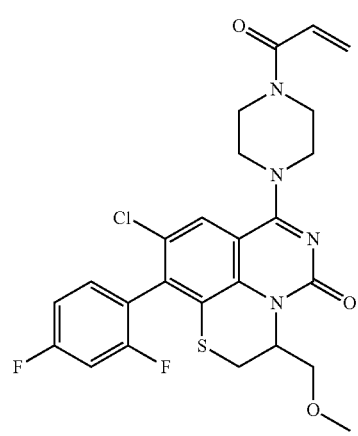
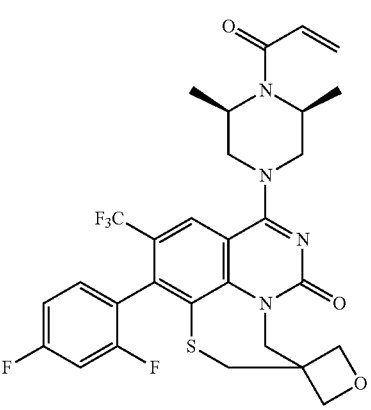
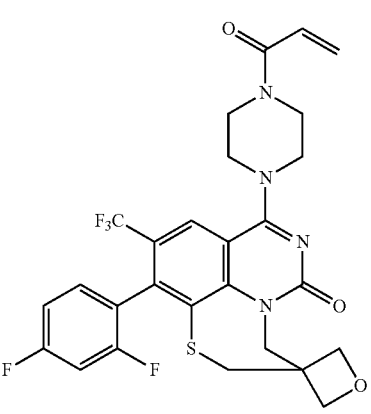

1261
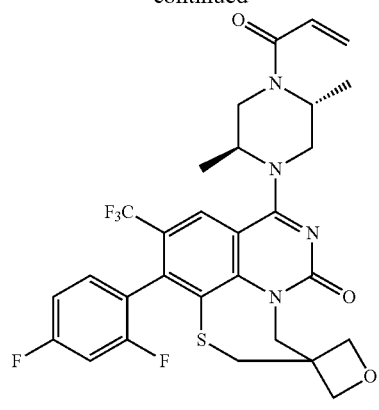
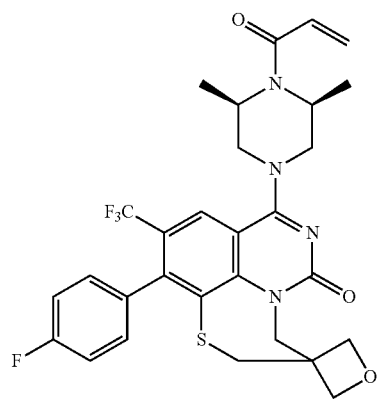
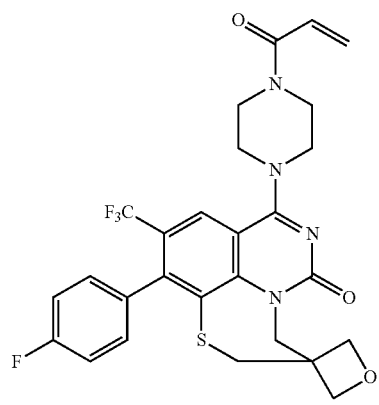
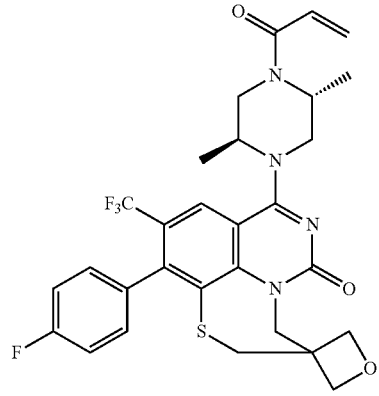
1262
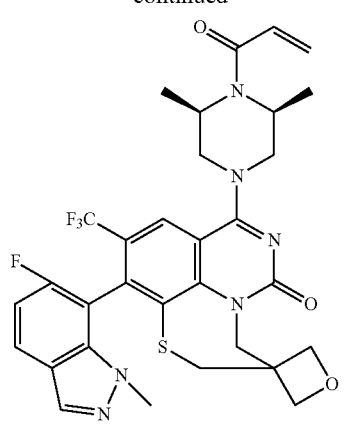
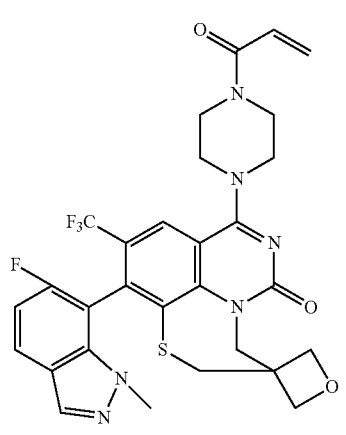
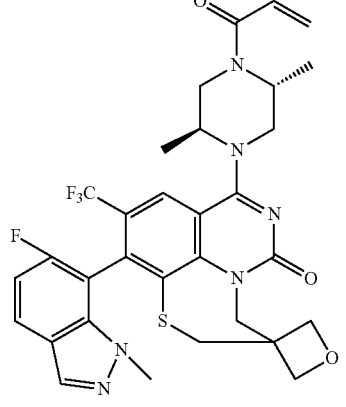
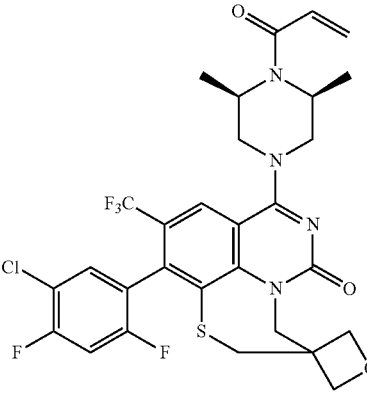

1263
-continued
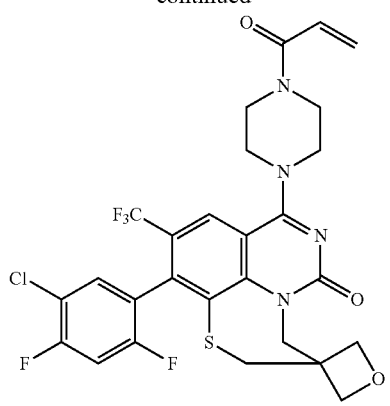
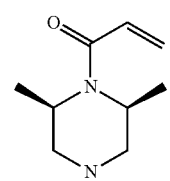
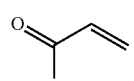
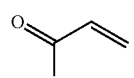
1264
-continued
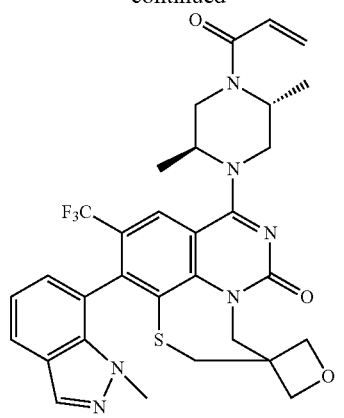
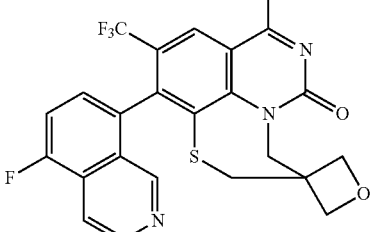
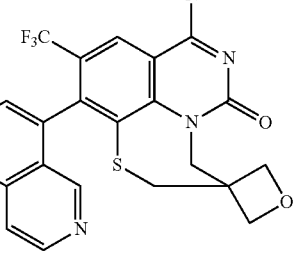
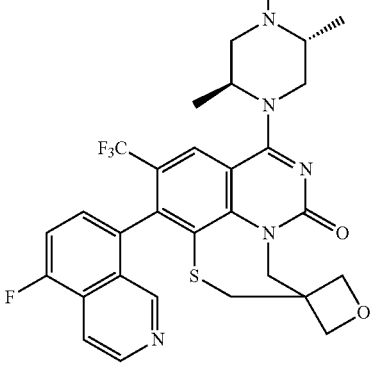

1265
-continued
1266
-continued
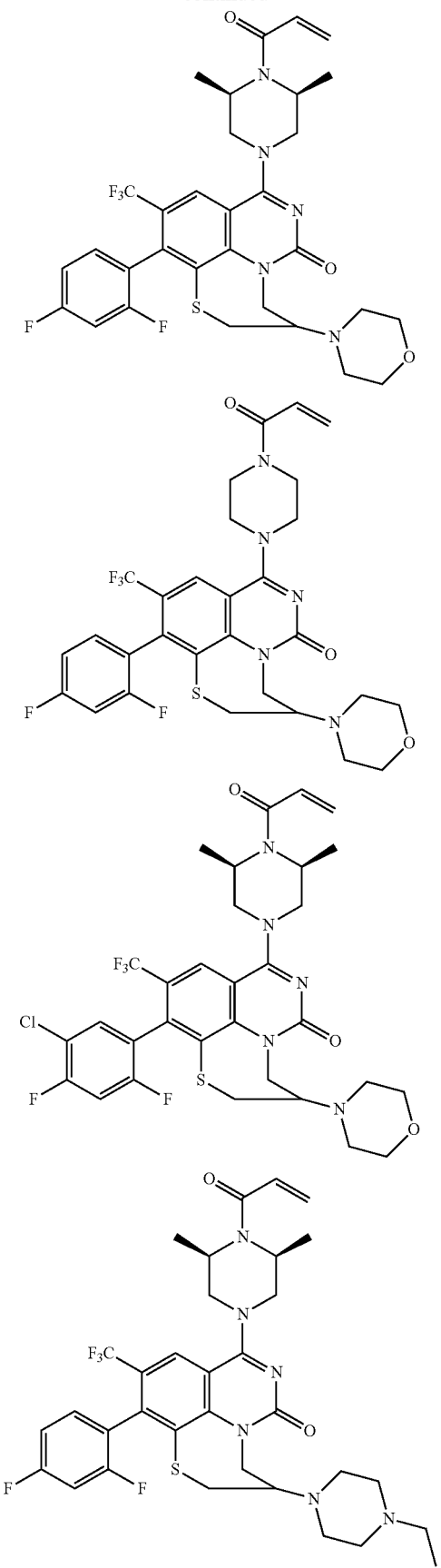
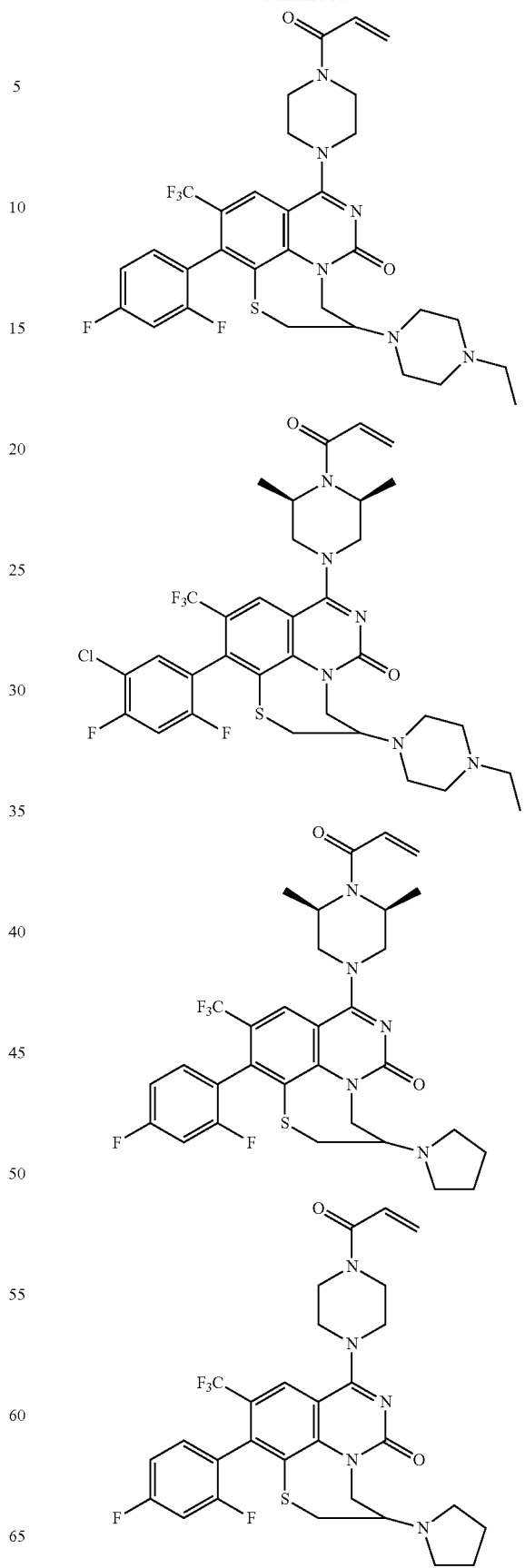

1267
-continued
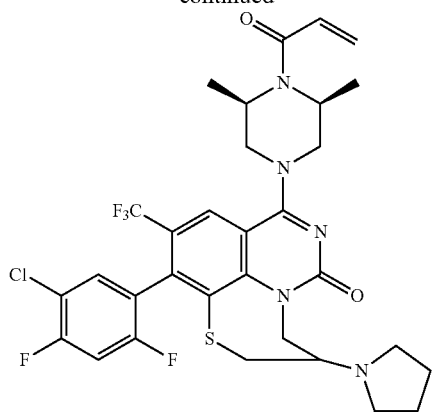
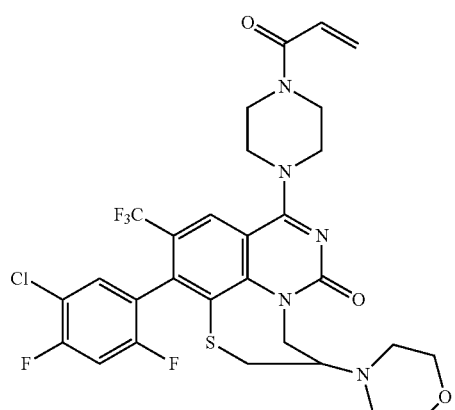
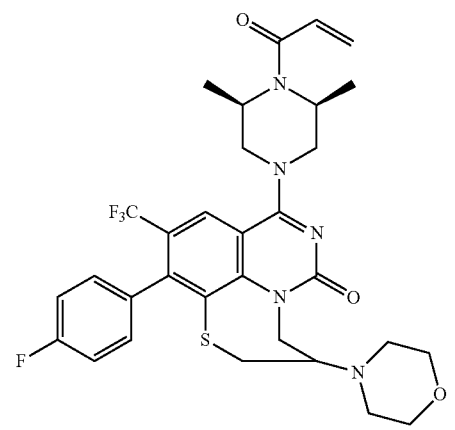
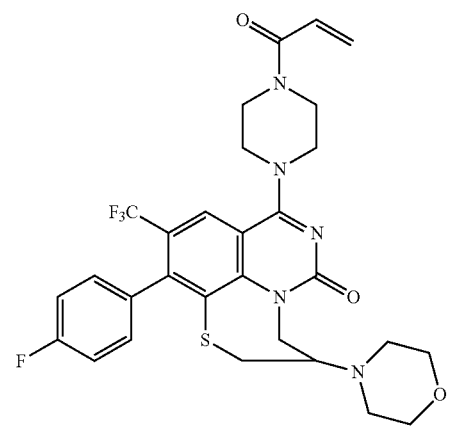
1268
-continued
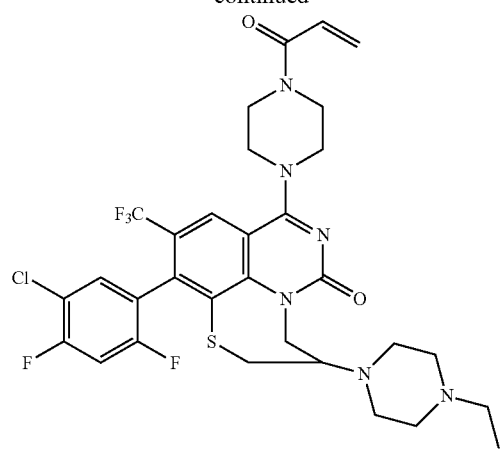
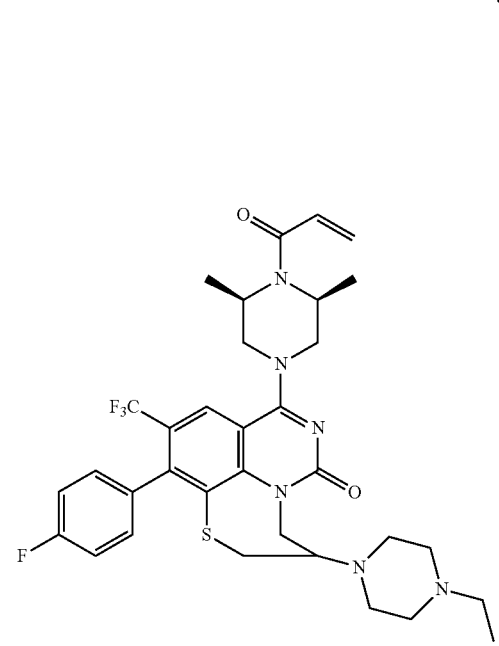
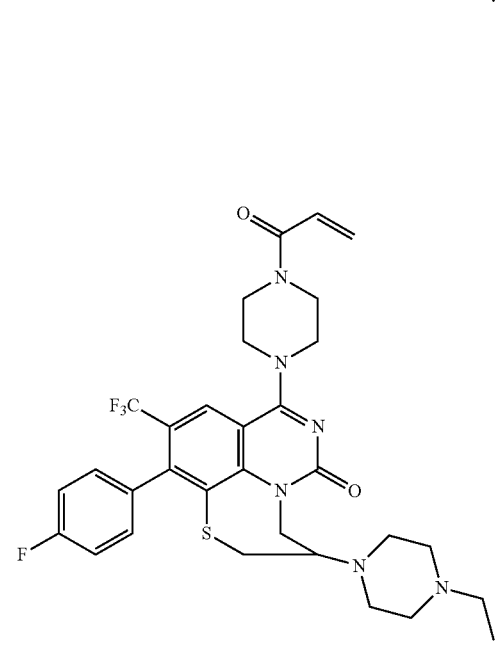

1269
-continued

1270
-continued

1271
-continued
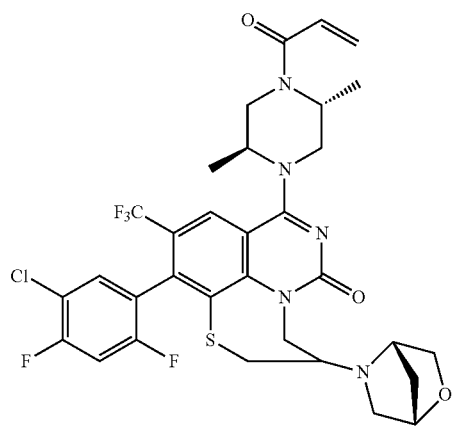
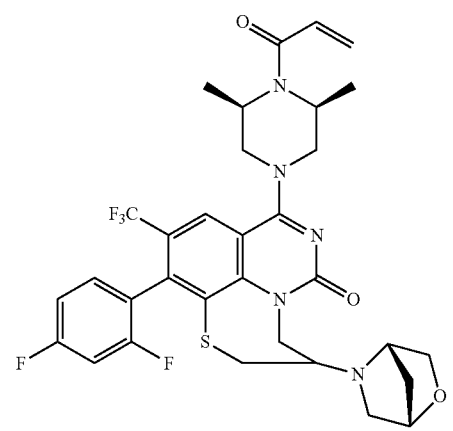
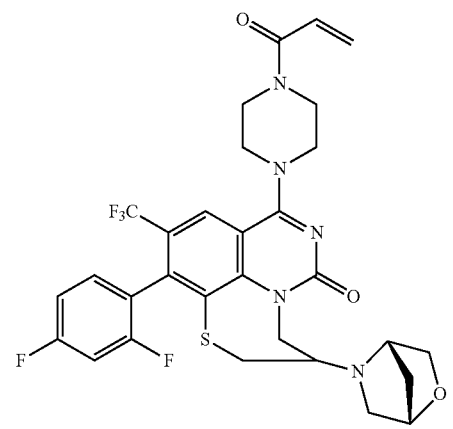
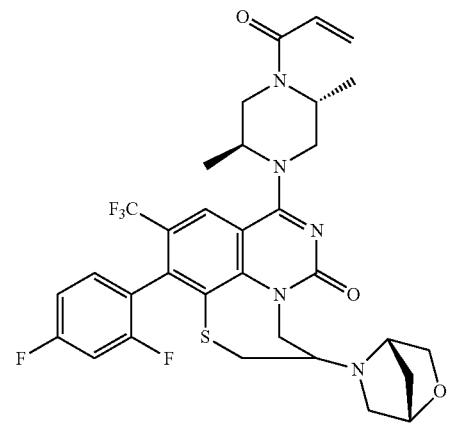
1272
-continued
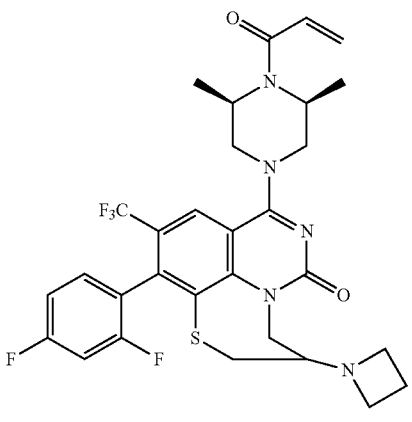
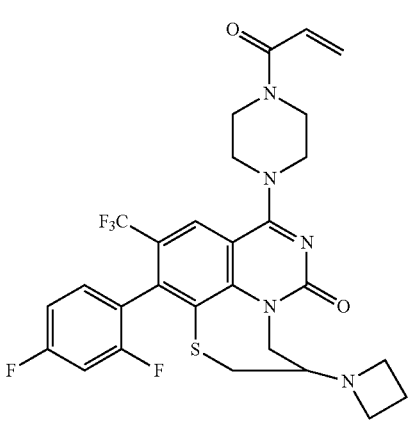
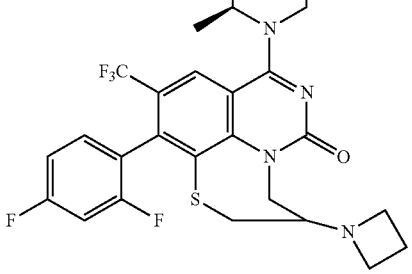
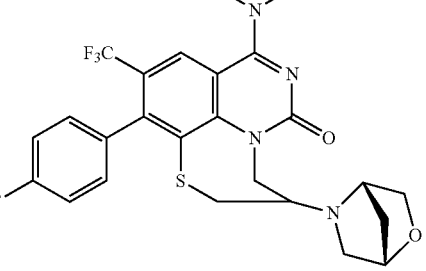

1273
-continued

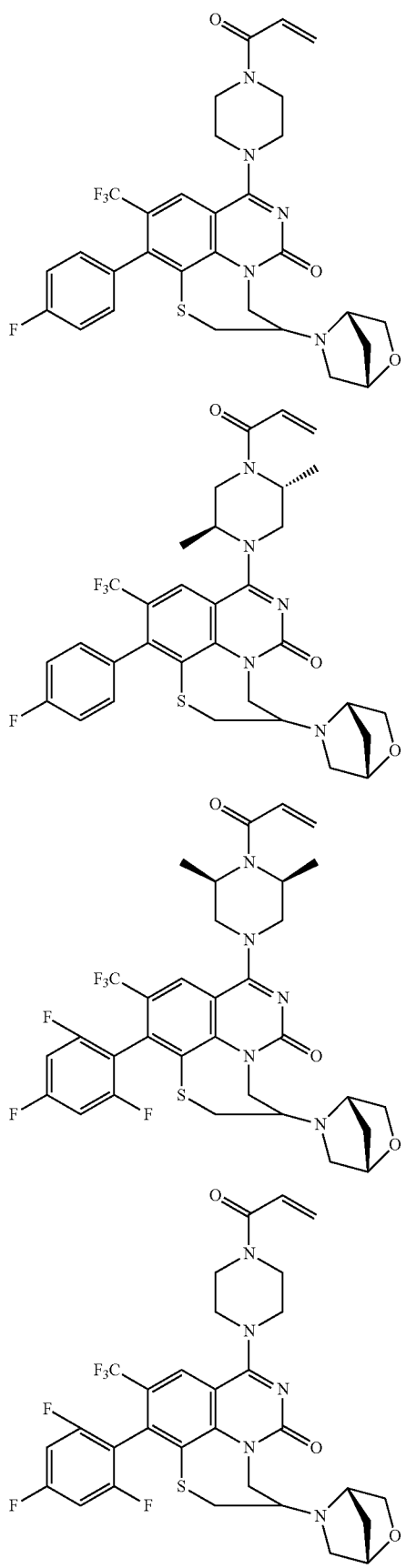

1274
-continued

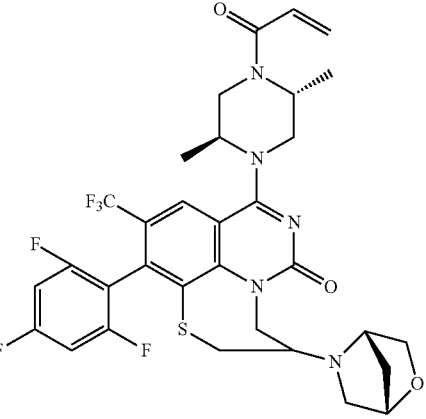

It will be appreciated by those skilled in the art that the compounds above possess chiral centers as well potential axial asymmetry, i.e., atropisomers. Each of the compounds may be provided as a mixture of diastereomers or in any diastereomerically pure form.

LL. Example 7 CAF Assay

This Example provides a protocol for assessing covalent adduct formation (CAF) between the compounds shown in Tables 1 to 4 above and KRAS.

In vitro covalent adduct formation assay: Covalent adduct formation (CAF) reactions between Cys12 of the KRAS 4B G12C protein and some of the compounds of Tables 1 to 4 were measured in vitro using liquid chromatography-mass spectrometry (LC-MS).

Recombinant Human KRAS 4B protein containing the G12C mutation was used in compound screening experiments. This protein contained 188 amino acids in total, including an N-terminal 6-Histidine tag, followed by a Tobacco Etch Virus (TEV) tag, followed by residues 1-169 of the native KRAS 4B sequence. The exact mass of the protein was 21,310 Da as determined by mass spectrometry. The full amino acid sequence is shown below:

```
                                    (SEQ ID NO.: 4)
MAHHHHHHAG GAENLYFQSM TEYKLVVVGA CGVGKSALTI

QLIQNHFVDE YDPTIEDSYR KQVVIDGETC LLDILDTAGQ

EEYSAMRDQY MRTGEGFLCV FAINNTKSFE DIHHYREQIK

RVKDSEDVPM VLVGNKCDLP SRTVDTKQAQ DLARSYGIPF

IETSAKTRQG VDDAFYTLVR EIRKHKEK
```

In an alternative screen, the assay can be conducted using a KRAS 4b G12C protein having 170 amino acids, a mass of 19,336 Da, and the amino acid sequence

```
                                    (SEQ ID NO.: 5)
SMTEYKLVVVGA CGVGKSALTI QLIQNHFVDE YDPTIEDSYR

KQVVIDGETC LLDILDTAGQ EEYSAMRDQY MRTGEGFLCV

FAINNTKSFE DIHHYREQIK RVKDSEDVPM VLVGNKCDLP

SRTVDTKQAQ DLARSYGIPF IETSAKTRQG VDDAFYTLVR

EIRKHKEK.
```

The recombinant protein was expressed in *E. coli* BL21 cells and purified using affinity chromatography via a Ni-NTA column. Protein stocks were nucleotide-exchanged to >95% GDP, concentrated to 4 mg/mL, and stored at −80° C. in storage buffer (50 mM HEPES pH 7.4, 50 mM NaCl, 5 mM MgCl2, 1 mM DTT). Pure KRAS 4B G12C protein was diluted to a concentration of 5 μM in Tris Buffered Saline, pH 7.4. The compounds were dissolved in DMSO and added to the diluted protein to make a 10 μM concentration. The total DMSO concentration in the reaction was 4%. The reaction was mixed by pipetting and incubated at 22° C. for one hour. Aliquots of the reaction were taken over time and diluted 2:1 in 0.1% formic acid. The intact mass of the protein samples was measured by LC-MS using a QExactive+ mass spectrometer (Thermo Scientific). An amount of 500 ng total protein was injected onto a C8 reverse phase column, eluted with a seven-minute gradient of 30%-90% acetonitrile/0.1% formic acid, and analyzed for intact mass by the mass spectrometer. Adducts identified were confirmed to be within 1 Dalton of the expected mass, and the relative ratios of free:adduct protein were used to quantify the percentage of protein bound by the compound. CAF reactions were run in duplicate, with a typical variability of ±5%.

What is claimed is:

1. A compound of Formula (XXIX) or pharmaceutically acceptable salt thereof:

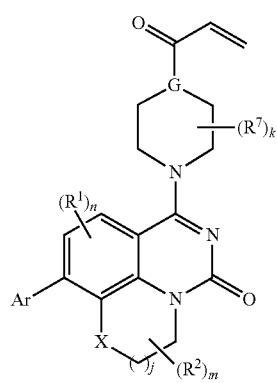

(XXIX)

wherein:

X is $S(O)_p$, wherein p is an integer from 0 to 2;

j is an integer from 0 to 2;

G is selected from the group consisting of N, CH, and

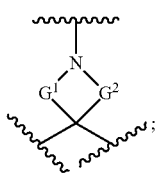

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

n is an integer from 0 to 2;

$R^2$ is selected from the group consisting of alkyl, alkylamino, dialkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aralkyl, heteroaryl, heteroarylalkyl, heterocyclyl, heterocyclylalkyl any of which are optionally substituted;

wherein when j is 1, the heterocyclylalkyl is selected from:

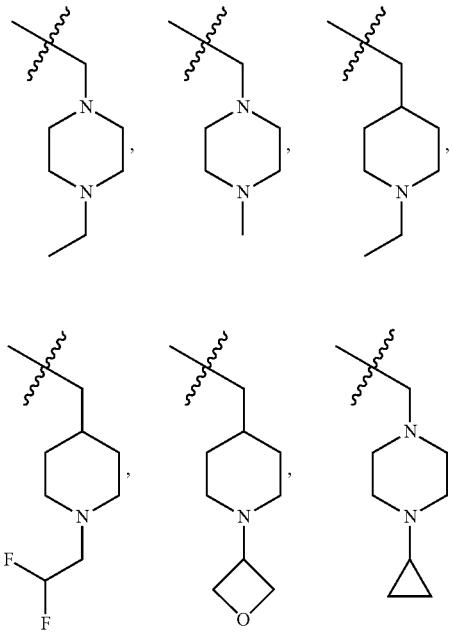

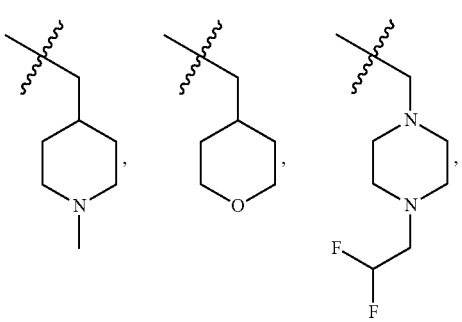

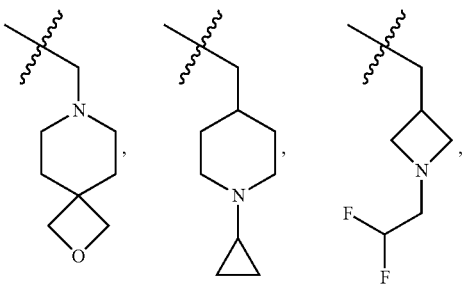

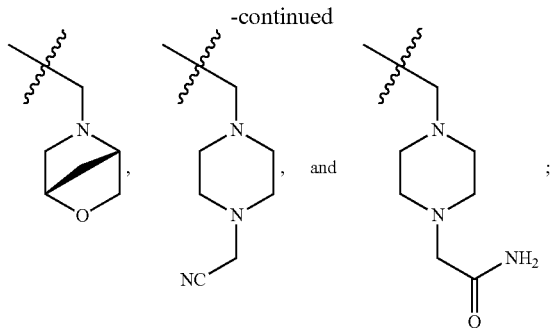

m is an integer from 0 to 6;

each $R^7$ is independently selected from an alkyl group selected from methyl, ethyl, and propyl, any of which are optionally substituted with one or more fluorine atoms, —$CH_2(CH_3)C$=$CF_2$, cyano, propargyl, —$CH_2C(O)V$, wherein V is selected from methyl, OH, $NHR^i$ wherein $R^i$ is hydrogen or alkyl; or any two $R^7$ may combine to form a fused-ring, spiro or bridging bicycle, wherein any one fused-ring or bridging atom is O, S, S=O, $SO_2$, or $NR^j$, wherein $R^j$ is H, methyl or trifluoromethyl;

k is an integer from 0 to 4; and, wherein the acrylyl moiety linked to G is optionally substituted.

2. The compound of claim 1, wherein X is S.

3. The compound of claim 1, wherein m is 0 or 1.

4. A pharmaceutical composition comprising a compound of claim 1 or a pharmaceutically acceptable salt thereof and a pharmaceutically acceptable carrier or diluent.

* * * * *

SEQUENCE LISTING

<160> NUMBER OF SEQ ID NOS: 5

<210> SEQ ID NO 1
<211> LENGTH: 169
<212> TYPE: PRT
<213> ORGANISM: Artificial Sequence
<220> FEATURE:
<223> OTHER INFORMATION: Synthetic polypeptide

<400> SEQUENCE: 1

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys
                165

<210> SEQ ID NO 2
<211> LENGTH: 188
<212> TYPE: PRT
<213> ORGANISM: Artificial Sequence
<220> FEATURE:
<223> OTHER INFORMATION: Synthetic polypeptide

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

-continued

```
Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 3
<211> LENGTH: 188
<212> TYPE: PRT
<213> ORGANISM: Artificial Sequence
<220> FEATURE:
<223> OTHER INFORMATION: Synthetic polypeptide

<400> SEQUENCE: 3

Met Thr Glu Tyr Lys Leu Val Val Val Gly Ala Gly Gly Val Gly Lys
 1                   5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 4
<211> LENGTH: 188
<212> TYPE: PRT
<213> ORGANISM: Artificial Sequence
```

```
<220> FEATURE:
<223> OTHER INFORMATION: Synthetic polypeptide

<400> SEQUENCE: 4

Met Ala His His His His His Ala Gly Gly Ala Glu Asn Leu Tyr
1               5                   10                  15

Phe Gln Ser Met Thr Glu Tyr Lys Leu Val Val Gly Ala Cys Gly
                20                  25                  30

Val Gly Lys Ser Ala Leu Thr Ile Gln Leu Ile Gln Asn His Phe Val
            35                  40                  45

Asp Glu Tyr Asp Pro Thr Ile Glu Asp Ser Tyr Arg Lys Gln Val Val
        50                  55                  60

Ile Asp Gly Glu Thr Cys Leu Leu Asp Ile Leu Asp Thr Ala Gly Gln
65                  70                  75                  80

Glu Glu Tyr Ser Ala Met Arg Asp Gln Tyr Met Arg Thr Gly Glu Gly
                85                  90                  95

Phe Leu Cys Val Phe Ala Ile Asn Asn Thr Lys Ser Phe Glu Asp Ile
            100                 105                 110

His His Tyr Arg Glu Gln Ile Lys Arg Val Lys Asp Ser Glu Asp Val
        115                 120                 125

Pro Met Val Leu Val Gly Asn Lys Cys Asp Leu Pro Ser Arg Thr Val
    130                 135                 140

Asp Thr Lys Gln Ala Gln Asp Leu Ala Arg Ser Tyr Gly Ile Pro Phe
145                 150                 155                 160

Ile Glu Thr Ser Ala Lys Thr Arg Gln Gly Val Asp Asp Ala Phe Tyr
                165                 170                 175

Thr Leu Val Arg Glu Ile Arg Lys His Lys Glu Lys
                180                 185

<210> SEQ ID NO 5
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 5

Ser Met Thr Glu Tyr Lys Leu Val Val Gly Ala Cys Gly Val Gly
1               5                   10                  15

Lys Ser Ala Leu Thr Ile Gln Leu Ile Gln Asn His Phe Val Asp Glu
                20                  25                  30

Tyr Asp Pro Thr Ile Glu Asp Ser Tyr Arg Lys Gln Val Val Ile Asp
            35                  40                  45

Gly Glu Thr Cys Leu Leu Asp Ile Leu Asp Thr Ala Gly Gln Glu Glu
        50                  55                  60

Tyr Ser Ala Met Arg Asp Gln Tyr Met Arg Thr Gly Glu Gly Phe Leu
65                  70                  75                  80

Cys Val Phe Ala Ile Asn Asn Thr Lys Ser Phe Glu Asp Ile His His
                85                  90                  95

Tyr Arg Glu Gln Ile Lys Arg Val Lys Asp Ser Glu Asp Val Pro Met
            100                 105                 110

Val Leu Val Gly Asn Lys Cys Asp Leu Pro Ser Arg Thr Val Asp Thr
        115                 120                 125
```

```
Lys Gln Ala Gln Asp Leu Ala Arg Ser Tyr Gly Ile Pro Phe Ile Glu
    130             135                 140
Thr Ser Ala Lys Thr Arg Gln Gly Val Asp Asp Ala Phe Tyr Thr Leu
145             150                 155                 160
Val Arg Glu Ile Arg Lys His Lys Glu Lys
                165         170
```